(12) United States Patent
Kurata et al.

(10) Patent No.: US 6,329,405 B1
(45) Date of Patent: Dec. 11, 2001

(54) CYCLOBUTENE DERIVATIVES, THEIR PREPARATION AND THEIR THERAPEUTIC USES

(75) Inventors: Hitoshi Kurata, Tokyo; Takafumi Kohama, Kiyose; Keita Kono, Kawasaki; Ken Kitayama, Yokohama, all of (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 09/620,741

(22) Filed: Jul. 20, 2000

(30) Foreign Application Priority Data

Jul. 22, 1999 (JP) .................................................. 11-207169

(51) Int. Cl.[7] .......................... C07D 213/02; A61K 31/41
(52) U.S. Cl. .......................... 514/357; 546/329; 564/305; 514/646
(58) Field of Search .................................. 514/357, 646; 546/329; 564/305

(56) References Cited

U.S. PATENT DOCUMENTS 4,526,973    7/1985    Algieri et al. ........................ 514/352

FOREIGN PATENT DOCUMENTS

| 0 623 597 A | 11/1994 | (EP) . |
| 11-199570 A | 7/1999 | (JP) . |
| WO 93/25517 | 12/1993 | (WO) . |
| WO98/02413 | 1/1998 | (WO) . |
| WO 98/56757 | 12/1998 | (WO) . |

OTHER PUBLICATIONS

The PPP Project Investigators, "Design, Rationale, and Baseline Characteristics of the Prospective Pravastatin Pooling (PPP) Project . . .", *The American Journal of Cardiology*, vol. 76, pp. 899–905 (Nov. 1, 1995).

M.S. Brown et al, "A Receptor–Mediated Pathway for Cholesterol Homeostasis", *Science*, vol. 232, pp. 34–47 (Apr. 1986).

J. Shepherd et al, Cholestyramine Promotes Receptor–Mediated Low–Density–Lipoprotein Catabolism, *The New England Journal of Medicine*, vol. 302, No. 22, pp. 1219–1222 (May 1980).

M.H. Wong et al, "Expression Cloning and Characterization of the Hamster Ileal Sodium–dependent Bile Acid Transporter", *The Journal Of Biological Chemistry*, vol. 269, No. 2, pp. 1340–1347 (1994).

G. Wess et al, "Specific Inhibitors of Ileal Bile Acid Transport", *Journal Of Medicinal Chemistry*, vol. 37, No. 7, pp. 873–875 (Apr. 1, 1994).

*Primary Examiner*—Zinna Northington Davis
(74) *Attorney, Agent, or Firm*—Frishauf, Holtz, Goodman, Langer & Chick, P.C.

(57) ABSTRACT

Compounds of formula (I):

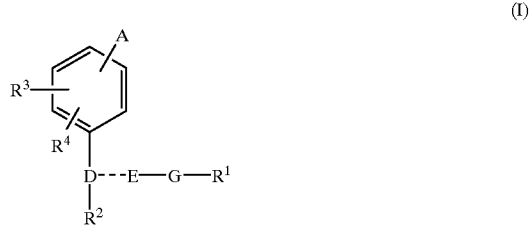

(I)

{wherein: $R^1$ and $R^2$ each represents a variety of organic groups; $R^3$ and $R^4$ each represents hydrogen or a variety of organic groups; A represents a group of formula (A-1):

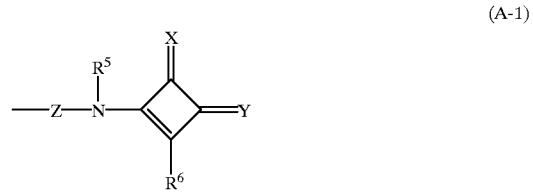

(A-1)

[wherein: $R^5$ represents hydrogen, hydroxy or alkyl, $R^6$ represents hydroxy, alkoxy, alkylthio or an amine residue, X and Y each represents oxygen or sulfur, and Z represents a direct single bond between the nitrogen atom shown and the benzene ring shown in formula (I), or an alkylene group], G represents a single bond, alkylene or substituted alkylene; the broken line represents a single or double bond; when the broken line represents a double bond, D represents a carbon atom; and E represents an =N—O— group; when the broken line represents a single bond, D represents a CH group or a nitrogen atom, and E represents an oxygen atom, a sulfur atom, an —NH— group or a —CO— group}; and pharmaceutically acceptable salts, esters or other derivatives thereof have the ability to inhibit an ileal bile transporter and so may be used to treat or prevent hypercholesterolemia.

63 Claims, No Drawings

CYCLOBUTENE DERIVATIVES, THEIR PREPARATION AND THEIR THERAPEUTIC USES

BACKGROUND OF THE INVENTION

The present invention relates to a series of novel cyclobutene derivatives having excellent inhibitory activity against an ileal bile acid transporter.

Hyperlipemia is one of three major risk factors in the causation of ischemic heart disease. It is widely accepted that reducing high blood cholesterol levels is particularly useful for the treatment or prevention of ischemic heart disease. Commercially available remedies for hyperlipemia at present include HMG-CoA reductase inhibitors and anion exchange resins, and these are used for treating or preventing hyperlipemia or arteriosclerosis [Am. J. Cardiol., 76, 899–905 (1995)].

HMG-CoA reductase inhibitors not only inhibit cholesterol synthesis but also increase LDL (low density lipoprotein) receptors in the liver, which increases the uptake of blood cholesterol and accelerates its excretion into bile [Science, 232, 34 (1986)]. Because these compounds are widely recognized to be both useful and safe, they have been used for a large number of patients.

Anion exchange resins, on the other hand, adsorb bile acid and disturb the re-absorption of bile acid in the intestines, thereby promoting the intrahepatic conversion of cholesterol to bile acid, which is a mechanism by which cholesterol may be removed from the blood. As a result, they are effective for reducing blood cholesterol levels [N. Engl. J. Med., 302, 1210–1222 (1980)]. Cholestyramine is such an anion exchange resin and has already been used in practice for this purpose. Because this compound is not readily absorbed by the body, it is the treatment of choice for infantile hyperlipemia where higher standards of safety are required. However, a large quantity of cholestyramine must be administered in one dose and moreover, being a resin, it has an unpleasant mouthfeel, which often discourages patients from using it regularly. Furthermore, it interferes with the absorption of fat from the gastro-intestinal tract and results in a reduced absorption of fat-soluble vitamins, and may inhibit or reduce the absorption of minerals. It may also delay or reduce the absorption of other drugs, particularly acidic ones, which are administered concurrently. Thus, although it is effective, a drug having a similar activity but without these disadvantages would be desirable.

In recent years, a protein which acts on the first step of the re-absorption of bile acid into the ileum, that is an ileal bile acid transporter, has been cloned [Wong M. H. et al., J. Biol. Chem., 269, 1340–1347 (1994)]. It has been suggested that similar pharmacological effects to those of cholestyramine could be achieved by the inhibition of this ileal bile acid transporter, and attempts have been made to find such an inhibitor [Wess G. et al, J. Med. Chem., 37, 873–875 (1994)].

The following prior art is thought relevant to the present invention:

(1) Japanese Laid-Open Publication No. Hei 6-509820 (WO93/25517)

This discloses compounds having the following formula (Z-1):

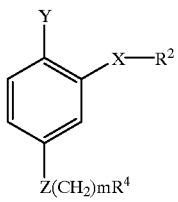

in which: Z represents a group of formula —N(R$^3$)CO—, where R$^3$ represents an aryl group; X represents a group of formula —N(R$^5$)—, where R$^5$ represents a hydrogen atom or an alkyl group; R$^2$ represents a cycloalkyl or cycloalkenyl group which may optionally be substituted, and R$^4$ represents an aryl or heteroaryl group.

Of the compounds of formula (I) according to the present invention, those in which D represents a nitrogen atom and in which E represents a —CO— group have a similar structure to the compounds of formula (Z-1), but they differ in that the cyclobutenyl portion of A in the compound of formula (I) has two oxo or thioxo groups as essential substituents, while the cycloalkenyl group defined in R$^2$ of the compound of formula (Z-1) contains neither an oxo nor a thioxo group.

Moreover, this prior art does not specifically disclose any compound having an analogous structure to the compounds of formula (I) of the present invention and, of the compounds disclosed, the closest to the compounds the present invention is only the following compound:

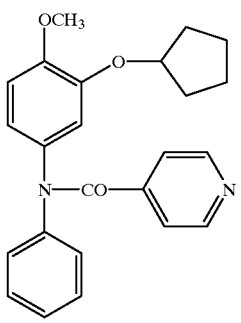

Finally, the compounds of formula (Z-1) are disclosed as selective phosphodiesterase IV inhibitors. There is no suggestion that they may have ileal bile acid transporter inhibitory action.

(2) Japanese Patent Application Kokai No. Hei 7-309837 (EP623597A) and Japanese Patent Application Kokai No. Hei 8-175994

These publications disclose compounds of formula (Z-2):

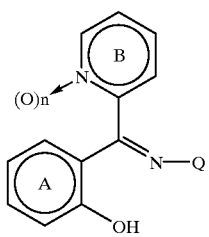

[in which, Ring A and Ring B each represents a benzene ring which may be substituted further, and Q represents a group of formula —OQ¹ (in which, Q¹ represents an aliphatic hydrocarbon group which may be substituted)].

Of the compounds of formula (I) of the present invention, the closest structurally to the compounds of formula (Z-2) are those wherein, in the compounds of the present invention, the broken line represents a double bond, D represents a carbon atom and E represents a group of formula =N—O—. The compounds of the present invention and those of the prior art differ in that the former contains an oxo- or thioxo-substituted cyclobutenylamino group as a substituent A of the benzene ring, while there is no disclosure of a cyclobutenylamino group as a substituent of the benzene ring in the prior compounds.

Moreover, this prior art does not specifically disclose any compound having an analogous structure to the compounds of formula (I) of the present invention and, of the compounds disclosed, the closest to the compounds the present invention is only the following compound:

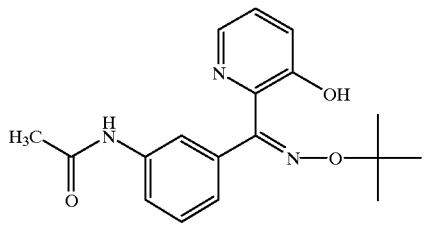

Finally, in these publications, the compounds of formula (Z-2) are disclosed as calcium channel opening agents and lipometabolism-improving agents, respectively. There is no suggestion that they may have ileal bile acid transporter inhibitory action.

(3) Japanese Laid-Open Publication No. Hei 11-60548 (WO98/56757)

This discloses compounds having the following formula (Z-3) as ileal bile acid transporter inhibitor:

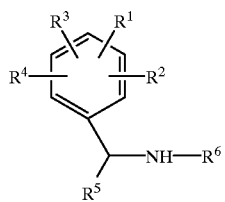

(Z-3)

in which: $R^1$ represents an $C_6$–$C_{10}$ aryl group which be substituted by from one to three of substituents α or a tetrazolyl group which may optionally be substituted by from one to three of substituents β; $R^2$, $R^3$ and $R^4$ represents a hydrogen group; $R^5$ represents an $C_6$–$C_{10}$ aryl group which may optionally be substituted by from one to three of substituents β; and $R^6$ represents $C_7$–$C_{10}$ aralkyl group which may optionally be substituted by from one to three of substituents γ.

Of the compounds of formula (I) according to the present invention, the closest structurally to the compounds of formula (Z-3) are those wherein, in the compounds of the present invention, D represents a carbon atom, in which in which E represents a —NH— group and the broken line represents a single bond have a similar structure to the compounds of formula (Z-3), but they differ in that the former contains an oxo- or thioxo-substituted cyclobutenylamino group as a substituent A of the benzene ring, while there is no disclosure of a cyclobutenylamino group as a substituent of the benzene ring in the prior compounds.

Moreover, this prior art does not specifically disclose any compound having an analogous structure to the compounds of formula (I) of the present invention and, of the compounds disclosed, the closest to the compounds the present invention is only the following compound:

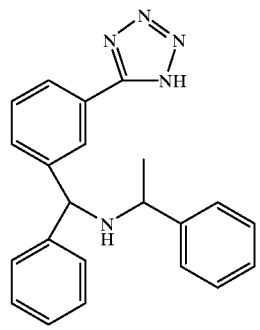

(4) Japanese Patent Application Kokai No. Hei 11-199570

This publication discloses compounds of formula (Z-4):

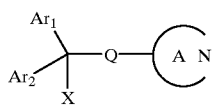

(Z-4)

[in which, $Ar_1$ and $Ar_2$ each represents an aromatic group which may optionally be substituted further, and Q represents a chain aliphatic hydrocarbon bivalent group which may be interposed with a bivalent group selected from O, S and a imino group; X represents a hydrogen group; and Ring A represents a nitrogenous 5 to 7-membered cyclic group which may optionally be substituted further.].

Of the compounds of formula (I) of the present invention, the closest structurally to the compounds of formula (Z-4) are those wherein, in the compounds of the present invention, the broken line represents a single bond, D represents a carbon atom and E represents a —NH— group. The compounds of the present invention and those of the prior art differ in that the former contains an oxo- or thioxo-substituted cyclobutenylamino group as a substituent A of the benzene ring, while there is no disclosure of a cyclobutenylamino group as a substituent of $Ar_1$ or $Ar_2$ in the prior compounds.

Moreover, this prior art does not specifically disclose any compound having an analogous structure to the compounds of formula (I) of the present invention.

Finally, the compounds of formula (Z-4) are disclosed as neurodegeneration inhibitor. There is no suggestion that they may have ileal bile acid transporter inhibitory action.

We have now discovered a series of novel cyclobutene derivatives that have excellent inhibitory action against the ileal bile acid transporter and can thus be used to reduce or maintain the level of cholesterol in the mammalian body.

Thus, the present invention consists in cyclobutenyl derivatives of formula (I):

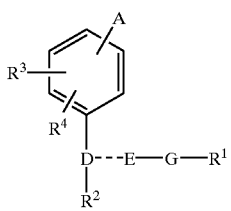

(I)

wherein:
R¹ represents a cycloalkyl group, an aryl group, a heterocyclic group, a cycloalkyl group substituted by at least one of substituents α and β, defined below, an aryl group substituted by at least one of substituents α and β, defined below, or a heterocyclic group substituted by at least one of substituents α and β, defined below;

R² represents a cycloalkyl group, an aryl group, a heterocyclic group, a cycloalkyl group substituted by at least one of substituents α, defined below, an aryl group substituted by at least one of substituents α, defined below, or a heterocyclic group substituted by at least one of substituents α, defined below;

R³ and R⁴ are the same as or different from each other and each represents a hydrogen atom or one of substituents α, defined below;

A represents a group of formula (A-1):

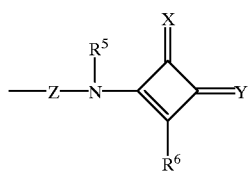

(A-1)

wherein:
R⁵ represents a hydrogen atom, a hydroxy group or a lower alkyl group,

R⁶ represents a hydroxy group, a lower alkoxy group, a lower alkylthio group or an amine residue, X and Y are the same as or different from each other and each represents an oxygen atom or a sulfur atom, and Z represents a direct single bond between the nitrogen atom shown and the benzene ring shown in formula (I), or an alkylene group having from 1 to 6 carbon atoms, G represents a single bond, an alkylene group having from 1 to 6 carbon atoms or an alkylene group having from 1 to 6 carbon atoms and substituted by at least one of substituents γ, defined below;

the broken line represents a single or double bond;
when the broken line represents a double bond,
D represents a carbon atom; and
E represents an =N—O— group;
when the broken line represents a single bond,
D represents a CH group or a nitrogen atom, and
E represents an oxygen atom, a sulfur atom, an —NH— group or a —CO— group;

said substituents α are selected from halogen atoms, hydroxy groups, cyano groups, nitro groups, lower alkyl groups, lower haloalkyl groups, lower alkoxy groups, lower alkylthio groups, amino groups, lower monoalkylamino groups and di(lower alkyl)amino groups.

said substituents β are selected from carboxy groups, lower alkoxycarbonyl groups, carbamoyl groups, lower monoalkylcarbamoyl groups, di(lower alkyl) carbamoyl groups, nitro groups, cycloalkyl groups, aryl groups, aryloxy groups, aralkyloxy groups, arylthio groups and cycloalkyl, aryl, aryloxy, aralkyloxy and arylthio groups each substituted by at least one of substituents α, defined above;

said substituents γ are selected from hydroxy groups, oxo groups, cycloalkyl groups, aryl groups, heterocyclic groups, cycloalkyl groups substituted by at least one of substituents α and β, defined above, aryl groups substituted by at least one of substituents α and β, defined above, and heterocyclic groups substituted by at least one of substituents α and β, defined above;

said cycloalkyl groups preferably have from 3 to 10 ring carbon atoms and are optionally fused to an aryl group, as defined below;

said aryl groups are preferably aromatic carbocyclic groups having from 6 to 10 ring carbon atoms;

said heterocyclic groups preferably have from 5 to 7 ring atoms, of which from 1 to 3 are hetero-atoms selected from the group consisting of sulfur, oxygen and nitrogen atoms, and are optionally fused to an aryl group, as defined above;

and pharmaceutically acceptable salts, esters or other derivatives thereof.

Where R¹, R², substituent β or substituent γ represents a cycloalkyl group or a substituted cycloalkyl group, this may be any saturated cycloalkyl group having from 3 to 10 carbon atoms. Such cycloalkyl groups may, if desired, be fused to an aryl group, as defined below, such as a benzene ring. Examples of such groups include the cyclopropyl, cyclobutyl, cyclopentyl, cyclohexyl, cycloheptyl, norbornyl, adamantyl and indanyl groups. Of these, we prefer the cycloalkyl groups having 5 or 6 carbon atoms, of which the cyclohexyl group is most preferred. Where R¹ or substituent γ represents such a cycloalkyl group, it may be unsubstituted or it may have one or more, preferably from 1 to 5, of substituents α or β, defined above. Where R² or substituent β represents such a cycloalkyl group, it may be unsubstituted or it may have one or more, preferably from 1 to 3, of substituents α, defined above.

Where R¹, R², substituent , or substituent γ represents an aryl group, this may be a substituted or unsubstituted aromatic hydrocarbon group having from 6 to 10 ring carbon atoms, and examples include the phenyl, indenyl and naphthyl groups. In the case of R¹, the phenyl and naphthyl groups are preferred, and the phenyl and 1-naphthyl groups are most preferred. In the case of R², the phenyl and naphthyl groups are preferred and the phenyl group is most preferred. Where R¹ or substituent γ represents such an aryl group, it may be unsubstituted or it may have one or more, preferably from 1 to 5, of substituents α or β, defined above. Where R² or substituent β represents such an aryl group, it may be unsubstituted or it may have one or more, preferably from 1 to 3, of substituents α, defined above.

Where R¹, R² or substituent γ represents a heterocyclic group, this has from 5 to 7 ring atoms, of which from 1 to 3 are hetero-atoms selected from the group consisting of sulfur, oxygen and nitrogen atoms. Where there are 3 hetero-atoms, we prefer that 1, 2, or 3 of these are nitrogen atoms, and that, correspondingly, 2, 1, or 0 of these are sulfur and/or oxygen atoms. Where there are 2 hetero-atoms, we prefer that 1 or 2 of these are nitrogen atoms, and that, correspondingly, 1 or 0 of these are sulfur and/or oxygen atoms. Examples of such groups include the aromatic heterocyclic groups, such as the furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl and pyrazinyl groups. Alternatively, the heterocyclic group may be a partially or wholly saturated analog of these groups, such as the morpholinyl, thiomorpholinyl, pyrrolidinyl, pyrrolinyl, imidazolidinyl, imidazolinyl, pyrazolidinyl, pyrazolinyl, piperidyl and piperazinyl groups.

Such heterocyclic groups may, if desired, be fused to an aryl group, as defined below, such as a benzene ring. Examples of such fused ring groups include the benzothienyl, benzothiazolyl, benzooxazolyl, isobenzofuranyl, chromenyl, xanthenyl, phenoxathienyl, indolizinyl, isoindolyl, indolyl, indazolyl, purinyl, quinolizinyl, isoquinolyl, quinolyl, phthalazinyl, naphthyridinyl, quinoxalinyl, quinazolinyl, carbazolyl, carbolinyl, acridinyl and isoindolinyl groups. Of these, the 5- or 6-membered aromatic heterocyclic groups and 5- or 6-membered aromatic heterocyclic groups fused with a benzene ring are preferred, the thienyl, furyl, pyrrolyl, thiazolyl, oxazolyl, imidazolyl and pyridyl groups and the thienyl, furyl, pyrrolyl, thiazolyl, oxazolyl, imidazolyl and pyridyl groups each fused with a benzene ring being more preferred, the thienyl and pyridyl groups being still more preferred and the 2-thienyl and 4-pyridyl groups being most preferred.

Where $R^1$ or substituent γ represents such a heterocyclic group, it may be unsubstituted or it may have one or more, preferably from 1 to 5, of substituents α or β defined above. Where $R^2$ represents such a heterocyclic group, it may be unsubstituted or it may have one or more, preferably from 1 to 3, of substituents α, defined above.

Where $R^5$ or substituent a represents a lower alkyl group, this may be a straight or branched alkyl group preferably having from 1 to 6 carbon atoms, and examples include the methyl, ethyl, propyl, isopropyl, butyl, isobutyl, sec-butyl, t-butyl, pentyl, isopentyl, 2-methylbutyl, neopentyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl groups, of which the alkyl groups having from 1 to 4 carbon atoms are preferred, the alkyl groups having 1 or 2 carbon atoms are more preferred and the methyl group is most preferred.

Where $R^6$ or substituent α represents a lower alkoxy group, this may be a straight or branched alkoxy group preferably having from 1 to 6 carbon atoms, and the alkyl part of this group may be any of the alkyl groups exemplified above. Examples include the methoxy, ethoxy, propoxy, isopropoxy, butoxy, isobutoxy, sec-butoxy, t-butoxy, pentyloxy, isopentyloxy, 2-methylbutoxy, neopentyloxy, hexyloxy, 4-methylpentyloxy, 3-methylpentyloxy, 2-methylpentyloxy, 3,3-dimethylbutoxy, 2,2-dimethylbutoxy, 1,1-dimethylbutoxy, 1,2-dimethylbutoxy, 1,3-dimethylbutoxy and 2,3-dimethylbutoxy groups, of which the alkoxy groups having from 1 to 4 carbon atoms are preferred, the alkoxy groups having 1 or 2 carbon atoms groups are more preferred and the methoxy group is most preferred.

Where $R^6$ or substituent α represents a lower alkylthio group, this may be a straight or branched alkylthio group preferably having from 1 to 6 carbon atoms, and the alkyl part of this group may be any of the alkyl groups exemplified above. Examples include the methylthio, ethylthio, propylthio, isopropylthio, butylthio, isobutylthio, sec-butylthio, t-butylthio, pentylthio, isopentylthio, 2-methylbutylthio, neopentylthio, hexylthio, 4-methylpentylthio, 3-methylpentylthio, 2-methylpentylthio, 3,3-dimethylbutylthio, 2,2-dimethylbutylthio, 1,1-dimethylbutylthio, 1,2-dimethylbutylthio, 1,3-dimethylbutylthio and 2,3-dimethylbutylthio groups, of which the alkylthio groups having from 1 to 4 carbon atoms are preferred, the alkylthio groups having 1 or 2 carbon atoms are more preferred and the methylthio group is most preferred.

Where $R^6$ represents an amine residue, this is a substituted or unsubstituted amino group or a cyclic amino (nitrogen-containing heterocyclic) group. Examples include amino groups, hydroxyamino groups, lower monoalkylamino groups, di(lower alkyl)amino groups, amino groups substituted by 1 or 2 lower alkoxy groups, amino groups substituted by 1 or 2 of the cycloalkyl groups described above, amino groups substituted by 1 or 2 lower sulfoalkyl groups, amino groups substituted by 1 or 2 carboxy- or lower-alkoxycarbonyl-substituted lower alkyl groups, saturated cyclic amine residues having a nitrogen atom in the ring, aryl- or aralkyl-amino groups in which the nitrogen atom may be further substituted by a lower alkyl group, and heteroarylamino groups in which the nitrogen atom may be further substituted by a lower alkyl group. Of these, the amino groups, hydroxyamino groups, lower monoalkylamino groups, di(lower alkyl)amino groups, amino groups substituted by 1 or 2 lower sulfoalkyl groups and amino groups substituted by 1 or 2 carboxy- or lower-alkoxycarbonyl-substituted lower alkyl groups are preferred, the amino groups, hydroxyamino groups, lower monoalkylamino groups and di(lower alkyl)amino groups are more preferred, and the amino groups and hydroxyamino groups are most preferred.

Examples of such lower monoalkylamino groups include any in which an alkyl group, as defined and exemplified above, is a substituent on an amino group, for example the methylamino, ethylamino, propylamino, isopropylamino, butylamino, isobutylamino, sec-butylamino, t-butylamino, pentylamino, isopentylamino, 2-methylbutylamino, neopentylamino, 1-ethylpropylamino, hexylamino, isohexylamino, 4-methylpentylamino, 3-methylpentylamino, 2-methylpentylamino, 1-methylpentylamino, 3,3-dimethylbutylamino, 2,2-dimethylbutylamino, 1,1-dimethylbutylamino, 1,2-dimethylbutylamino, 1,3-dimethylbutylamino, 2,3-dimethylbutylamino and 2-ethylbutylamino groups.

Examples of such di(lower alkyl)amino groups include any in which two alkyl groups, as defined and exemplified above, are substituents on an amino group, for example the dimethylamino, diethylamino, N-ethyl-N-methylamino, dipropylamino, dibutylamino, dipentylamino and dihexylamino groups.

Examples of such amino group substituted by 1 or 2 lower alkoxy groups include those in which an amino group is substituted by one or two alkoxy groups, as defined and exemplified above, for example, the methoxyamino, ethoxyamino, propoxyamino, isopropoxyamino, butoxyamino, isobutoxyamino, sec-butoxyamino, t-butoxyamino, pentyloxyamino, isopentyloxyamino, 2-methylbutoxyamino, neopentyloxyamino, hexyloxyamino, dimethoxyamino and diethoxyamino groups.

Examples of such amino groups substituted by 1 or 2 cycloalkyl groups include those in which an amino group is substituted by one or two of the cycloalkyl groups defined and exemplified above, for example the cyclopentylamino, cyclohexylamino, dicyclopentylamino and dicyclohexylamino groups.

Examples of such amino groups substituted by 1 or 2 lower sulfoalkyl groups include groups in which the alkyl part is any of the alkyl groups defined and exemplified above, for example the sulfomethylamino, 2-sulfoethylamino, 3-sulfopropylamino, 4-sulfobutylamino, 5-sulfopentylamino and 6-sulfohexylamino groups.

Examples of such amino groups substituted by 1 or 2 carboxy- or lower-alkoxycarbonyl-substituted lower alkyl groups include those in which the alkyl and alkoxy parts are as defined and exemplified above, and examples include the carboxymethylamino, 2-carboxyethylamino, 3-carboxypropylamino, 4-carboxybutylamino, 5-carboxypentylamino, 6-carboxyhexylamino, methoxycarboxymethylamino, ethoxycarboxymethylamino, 2-methoxycarboxyethylamino, 2-ethoxycarboxyethylamino, 3-methoxycarboxypropylamino, 3-ethoxycarboxypropylamino, 4-methoxycarboxybutylamino, 5-methoxycarboxypentylamino and 6-methoxycarboxyhexylamino groups;

Examples of such saturated cyclic amine residues having a nitrogen atom in the ring include the pyrrolidino, piperidino, piperazino, N-methylpiperazino, morpholino and thiomorpholino groups.

Examples of such aryl- or aralkyl-amino groups in which the nitrogen atom may be further substituted by a lower alkyl group include those in which the aryl, aralkyl and alkyl parts are as defined and exemplified above, for example the anilino, benzzylamino, N-methylanilino and N-methylbenzylamino groups.

Examples of such heteroarylamino groups in which the nitrogen atom may be further substituted by a lower alkyl group (the alkyl part being as defined and exemplified above) include the pyridylamino, N-methylpyridylamino and N-ethylpyridylamino groups.

Where Z or G represents an alkylene group having from 1 to 6 carbon atoms, this may be a straight or branched chain group, and, in the case of G, may be substituted or unsubstituted. Examples of such groups include the substituted and unsubstituted methylene, methylmethylene, ethylene, ethylmethylene, dimethylmethylene, propylene, trimethylene, 1-methylethylene, tetramethylene, 1-methyltrimethylene, 2-methyltnmethylene, 3-methyltrimethylene, 1-methylpropylene, 1,1-dimethylethylene, pentamethylene, 1-methyltetramethylene, 2-methyltetramethylene, 3-methyltetramethylene, 4-methyltetram ethylene, 1,1-dimethyltrimethylene, 2,2-dimethyltrimethylene, 3,3-dimethyltrimethylene, hexamethylene, 1-methylpentamethylene, 2-methylpentamethylene, 3-methylpentamethylene, 4-methylpentamethylene, 5-methylpentamethylene, 1,1-dimethyltetramethylene, 2,2-dimethyltetram ethylene, 3,3-dimethyltetramethylene and 4,4-dimethyltetramethylene groups. In the case of Z, those alkylene groups having from 1 to 4 carbon atoms are preferred, of which the alkylene groups having 1 or 2 carbon atoms are more preferred and the methylene group is most preferred. In the case of G, those alkylene groups having from 1 to 4 carbon atoms are preferred, the methylene, methylmethylene and ethylmethylene groups being more preferred and the methylmethylene group being most preferred.

Where substituent α is a halogen atom, this may be, for example, a fluorine, chlorine, bromine or iodine atom, of which the fluorine and chlorine atoms are preferred and the fluorine atom is most preferred.

Where substituent α is a lower haloalkyl group, this is a lower alkyl group, as defined and exemplified above, substituted by a halogen atom. Examples include the trifluoromethyl, trichloromethyl, difluoromethyl, dichloromethyl, dibromomethyl, fluoromethyl, 2,2,2-trifluoroethyl, 2,2,2-trichloroethyl, 2-bromoethyl, 2-chloroethyl, 2-fluoroethyl, 2-iodoethyl, 3-chloropropyl, 4-fluorobutyl, 6-iodohexyl and 2,2-dibromoethyl groups, of which those haloalkyl groups having from 1 to 4 carbon atoms are preferred, the haloalkyl groups having 1 or 2 carbon atoms being more preferred and the trifluoromethyl group being most preferred.

Where substituent α is a lower monoalkylamino group, this may be as defined and exemplified above in relation to the groups which may be represented by $R^6$. Of these, the monoalkylamino groups having from 1 to 4 carbon atoms are preferred, the monoalkylamino groups having 1 or 2 carbon atoms are more preferred and the methylamino group is most preferred.

Where substituent α is a di(lower alkyl)amino group, this may be as defined and exemplified above in relation to the groups which may be represented by $R^6$. Of these, the dialkylamino groups having from 1 to 4 carbon atoms in each alkyl group are preferred, the dialkylamino groups having 1 or 2 carbon atoms in each alkyl group are more preferred and the dimethylamino group is most preferred.

Where substituent β is a lower alkoxycarbonyl group, this may be any of the lower alkoxy groups defined and exemplified above bound to a carbonyl group. Examples include straight or branched chain alkoxycarbonyl groups having from 1 to 6 carbon atoms, such as the methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl, isopentyloxycarbonyl, 2-methylbutoxycarbonyl, neopentyloxycarbonyl, hexyloxycarbonyl, 4-methylpentyloxycarbonyl, 3-methylpentyloxycarbonyl, 2-methylpentyloxycarbonyl, 3,3-dimethylbutoxycarbonyl, 2,2-dimethylbutoxycarbonyl, 1,1-dimethylbutoxycarbonyl, 1,2-dimethylbutoxycarbonyl, 1,3-dimethylbutoxycarbonyl and 2,3-dimethylbutoxycarbonyl groups, of which the alkoxycarbonyl groups having from 1 to 4 carbon atoms in the alkoxy part are preferred, the alkoxycarbonyl groups having 1 or 2 carbon atoms in the alkoxy part are more preferred and the methoxycarbonyl group is most preferred.

Where substituent β is a lower monoalkylcarbamoyl group, this may be any of the lower alkyl groups defined and exemplified above bound to a carbamoyl group. Examples include the methylcarbamoyl, ethylcarbamoyl, propylcarbamoyl, isopropylcarbamoyl, butylcarbamoyl, isobutylcarbamoyl, sec-butylcarbamoyl, t-butylcarbamoyl, pentylcarbamoyl, isopentylcarbamnoyl, 2-methylbutylcarbamoyl, neopentylcarbamoyl, 1-ethylpropylcarbamoyl and hexylcarbamoyl groups, of which the monoalkylcarbamoyl groups having from 1 to 4 carbon atoms in the alkyl part are preferred, the methylcarbamoyl and ethylcarbamoyl groups are more preferred, and the methylcarbamoyl group is most preferred.

Where substituent β is a di(lower alkyl)carbamoyl group, each alkyl group preferably has from 1 to 6 carbon atoms, and these may be straight or branched chain groups, as defined and exemplified above. The two alkyl groups may be the same as or different from each other. Examples include the dimethylcarbamoyl, diethylcarbamoyl, N-ethyl-N-methylcarbamoyl, dipropylcarbamoyl, dibutylcarbamoyl, dipentylcarbamoyl and dihexylcarbamoyl groups, of which the dialkylcarbamoyl groups having from 1 to 4 carbon atoms are preferred, the dialkylcarbamoyl groups having 1 or 2 carbon atoms are more preferred, and the dimethylcarbamoyl group is most preferred.

Where substituent β is an aryloxy group, this may be unsubstituted or it may be substituted by from 1 to 3 of substituents α, as defined and exemplified above. Examples include phenoxy, 1-indenyloxy, 2-indenyloxy, 1-naphthyloxy and 2-naphthyloxy groups, of which the phenoxy group is preferred.

Where substituent β is an aralkyloxy group, the aryl part of this may be any of the aryl groups defined and exemplified above, and the alkoxy part may likewise be as defined and exemplified above. Example sinclude aralkyloxy groups having from 7 to 16 carbon atoms, such as the benzyloxy, α-naphthylmethoxy, β-naphthylmethoxy, indenylmethoxy, diphenylmethoxy, triphenylmethoxy, 1-phenethyloxy, 2-phenethyloxy, 1-naphthylethoxy, 2-naphthylethoxy, 1-phenylpropoxy, 2-phenylpropoxy, 3-phenylpropoxy, 1-naphthylpropoxy, 2-naphthylpropoxy, 3-naphthylpropoxy, 1-phenylbutoxy, 2-phenylbutoxy, 3-phenylbutoxy, 4-phenylbutoxy, 1-naphthylbutoxy, 2-naphthylbutoxy, 3-naphthylbutoxy, 4-naphthylbutoxy, 1-phenylpentyloxy, 2-phenylpentyloxy, 3-phenylpentyloxy, 4-phenylpentyloxy, 5-phenylpentyloxy, 1-naphthylpentyloxy, 2-naphthylpentyloxy, 3-naphthylpentyloxy, 4-naphthylpentyloxy, 5-naphthylpentyloxy, 1-phenylhexyloxy, 2-phenylhexyloxy, 3-phenylhexyloxy, 4-phenylhexyloxy. 5-phenylhexyloxy, 6-phenylhexyloxy, 1-naphthylhexyloxy, 2-naphthylhexyloxy, 3-naphthylhexyloxy, 4-naphthylhexyloxy, 5-naphthylhexyloxy and 6-naphthylhexyloxy groups, of which the benzyloxy group is preferred.

Where substituent β is an arylthio group, the aryl part may be as defined and exemplified above, and may be unsubstituted or may have from 1 to 3 of substituents α. Examples include the phenylthio, 1-indenylthio, 2-indenylthio, 3-indenylthio, 1-naphthylthio and 2-naphthylthio groups, of which the phenylthio group is preferred.

Specific examples of cycloalkyl groups substituted by from 1 to 3 of substituents α in the definition of $R^2$ include the 2-fluorocyclopropyl, 2-chlorocyclopropyl, 2- or 3-fluorocyclopentyl, 2- or 3-chlorocyclopentyl, 2-, 3- or 4-fluorocyclohexyl, 2-, 3- or 4-chlorocyclohexyl, 2-, 3- or 4-bromocyclohexyl, 2-, 3- or 4-iodocyclohexyl, 2-hydroxycyclopropyl, 2- or 3-hydroxycyclopentyl, 2-, 3- or 4-hydroxycyclohexyl, 2-methylcyclopropyl, 2-ethylcyclopropyl, 2- or 3-methylcyclopentyl, 2- or 3-ethylcyclopentyl, 2-, 3- or 4-methylcyclohexyl, 2-, 3- or 4-ethylcyclohexyl, 2-trifluoromethylcyclopropyl, 2- or 3-trifluoromethylcyclopentyl, 2-, 3- or 4-trifluoromethylcyclohexyl, 2-methoxycyclopropyl, 2- or 3-methoxycyclopentyl, 2-, 3- or 4-methoxycyclohexyl, 2-, 3- or 4-ethoxycyclohexyl, 2-methylthiocyclopropyl, 2- or 3-methylthiocyclopentyl, 2-, 3- or 4-methylthiocyclohexyl, 2-, 3- or 4-ethylthiocyclohexyl, 2-, 3- or 4-formyloxycyclohexyl, 2-, 3- or 4-acetoxycyclohexyl, 2-, 3- or 4-propionyloxycyclohexyl, 2-, 3- or 4-benzoyloxycyclohexyl, 2-aminocyclopropyl, 2- or 3-aminocyclopentyl, 2-, 3- or 4-aminocyclohexyl, 2-methylaminocyclopropyl, 2- or 3-methylaminocyclopentyl, 2-, 3- or 4-methylaminocyclohexyl, 2-dimethylaminocyclopropyl, 2- or 3-dimethylaminocyclopentyl, 2-, 3- or 4-dimethylaminocyclohexyl, 3,4-difluorocyclohexyl, 3,4-dichlorocyclohexyl, 2,3-dimethoxycyclohexyl, 3,4-dimethoxycyclohexyl, 3,5-dimethoxycyclohexyl and 3,4,5-trimethoxycyclohexyl groups. Of these, we prefer cyclopentyl and cyclohexyl groups having from 1 to 3 substituents (the substituent preferably being selected from halogen atoms, hydroxy groups, lower alkyl groups, lower haloalkyl groups and lower alkoxy groups) are preferred and the cyclohexyl group substituted by one substituent (the substituent preferably being selected from halogen atoms, hydroxy groups, lower alkyl groups, lower haloalkyl groups and lower alkoxy groups) is most preferred.

Specific examples of aryl groups substituted by from 1 to 3 of substituents α in the definition of $R^2$ include the 2-, 3- or 4-fluorophenyl, 2-, 3- or 4-chlorophenyl, 2-, 3- or bromophenyl, 2-, 3- or 4-iodophenyl, 2-, 3- or 4-hydroxyphenyl, 2-, 3- or 4-methylphenyl, 2-, 3- or 4-ethylphenyl, 2-, 3- or 4-trifluoromethylphenyl, 2-, 3- or 4-methoxyphenyl, 2-, 3- or 4-ethoxyphenyl, 2-, 3- or 4-propoxyphenyl, 2-, 3- or 4-isopropoxyphenyl, 2-, 3- or 4-methylthiophenyl, 2-, 3- or 4-ethylthiophenyl, 2-, 3- or 4-formyloxyphenyl, 2-, 3- or 4-acetoxyphenyl, 2-, 3- or 4-propionyloxyphenyl, 2-, 3- or 4-benzoyloxyphenyl, 2-, 3- or 4-aminophenyl, 2-, 3- or 4-methylaminophenyl, 2-, 3- or 4-dimethylaminophenyl, 3,4-difluorophenyl, 3,4-dichlorophenyl, 3,4-dibromophenyl, 3,5-difluorophenyl, 3,5-dichlorophenyl, 3,5-dibromophenyl, 2,3,4-trifluorophenyl, 2,3,4-trichlorophenyl, 3,4,5-trifluorophenyl, 3,4,5-trichlorophenyl, 2,3-dimethylphenyl, 3,4-dimethylphenyl, 3,5-dimethylphenyl, 2,3-dimethoxyphenyl, 3,4-dimethoxyphenyl, 3,5-dimethoxyphenyl, 3,4,5-trimethoxyphenyl, 3-fluoro-4-methoxyphenyl, 4-methyl-2-methoxyphenyl, 6-fluoro-4-methyl-2-methoxyphenyl, 5-fluoroinden-3-yl, 5-fluoroinden-3-yl, 5-methylinden-3-yl, 5-methoxyinden-3-yl, 5-fluoroinden-2-yl, 5-chloroinden-2-yl, 5-methylinden-2-yl, 5-methoxyinden-2-yl, 5-fluoronaphthalen-2-yl, 5-chloronaphthalen-2-yl, 5-methylnaphthalen-2-yl, 5-methoxynaphthalen-2-yl, 5-fluoronaphthalen-1-yl, 5-chloronaphthalen-1-yl, 5-methylnaphthalen-1-yl and 5-methoxynaphthalen-1-yl groups. Of these, we prefer those aryl groups substituted by from 1 to 3 of the following substituents: halogen atoms, hydroxy groups, lower alkyl groups, lower haloalkyl groups and lower alkoxy groups. More preferred are the aryl groups substituted by one of the following substituents: halogen atoms, hydroxy groups, lower alkyl groups, lower haloalkyl groups and lower alkoxy groups. The 4-fluorophenyl, 4-chlorophenyl, 4-methylphenyl and 4-methoxyphenyl groups are most preferred.

Specific examples of heterocyclic groups substituted by from 1 to 3 of substituents α in the definition of $R^2$ include the 3-, 4- or 5-fluorofuran-2-yl, 2-, 4- or 5-fluorofuran-3-yl, 3-, 4- or 5-hydroxyfuran-2-yl, 2-, 4- or 5-hydroxyfuran-3-yl, 3-, 4- or 5-methylfuran-2-yl, 2-, 4- or 5-methylfuran-3-yl, 3-, 4- or 5-methoxyfuran-2-yl, 2-, 4- or 5-methoxyfuran-3-yl, 3-, 4- or 5-methylthiofuran-2-yl, 2-, 4- or 5-methylthiofuran-3-yl, 4- or 5-acetoxyfuran-2-yl, 2-, 4- or 5-acetoxyfuran-3-yl, 4- or 5-formyloxyfuran-2-yl, 2-, 4- or 5-formyloxyfuran-3-yl, 4- or 5-benzoyloxyfuran-2-yl, 2-, 4- or 5-benzoyloxyfuran-3-yl, 3-, 4- or 5-fluorothiophen-2-yl, 3-, 4- or 5-bromothiophen-2-yl, 3-, 4- or 5-hydroxythiophen-2-yl, 3-, 4- or 5-methylthiophen-2-yl, 2-, 4- or 5-methylthiophen-3-yl, 3-, 4- or 5-ethylthiophen-2-yl, 2-, 4- or 5-ethylthiophen-3-yl, 3-, 4- or 5-methoxythiophen-2-yl, 2-, 4- or 5-methoxythiophen-3-yl, 3-, 4- or 5-methylthiothiophen-2-yl, 2-, 4- or 5-methylthiothiophen-3-yl, 3-, 4- or 5-acetoxythiophen-2-yl, 2-, 4- or 5-acetoxythiophen-3-yl, 3-, 4- or 5-formyloxythiophen-2-yl, 2-, 4- or 5-formyloxythiophen-3-yl, 3-, 4- or 5-benzoyloxythiophen-2-yl, 2-, 4- or 5-benzoyloxythiophen-3-yl, 3- or 4-fluorothiazol-5-yl, 3- or 4-hydroxythiazol-5-yl, 3- or 4-methylthiazol-5-yl, 3-, 4- or 5-fluorobenzothiophen-2-yl, 2-, 4- or 5-fluorobenzothiophen-3-yl, 3-, 4- or 5-bromobenzothiophen-2-yl, 2-, 4- or 5-bromobenzothiophen-3-yl, 3-, 4- or 5-hydroxybenzothiophen-2-yl, 2-, 4- or 5-hydroxybenzothiophen-3-yl, 3-, 4- or 5-methylbenzothiophen-2-yl, 2-, 4- or 5-methylbenzothiophen-3-yl, 3-, 4- or 5-methoxybenzothiophen-2-yl, 2-, 4- or 5-methoxybenzothiophen-3-yl, 4-, 5-, 6- or 7-methylbenzothiazol-2-yl, 2- or 4-fluoropyridin-3-yl, 2- or 3-fluoropyridin-4-yl, 2- or 4-hydroxypyridin-3-yl, 2- or 3-hydroxypyridin-4-yl, 2- or 4-methylpyridin-3-yl, 2- or 3-methylpyridin-4-yl, 2- or 4-methoxypyridin-4-yl, 2- or 3-methoxypyridin-4-yl, 2- or 4-methylthiopyridin-3-yl, 2- or 3-methylthiopyridin-4-yl, 2- or 4-acetoxypyridin-3-yl, 2- or 3-acetoxypyridin-4-yl, 2- or 4-formyloxypyridin-3-yl, 2- or 3-formyloxypyridin-4-yl, 2- or 4-benzoyloxypyridin-3-yl, and 2- or 3-benzoyloxypyridin-4-yl groups. Of these, we prefer the heterocyclic groups substituted by from 1 to 3 of the following substituents: halogen atoms, hydroxy groups, lower alkyl groups, lower haloalkyl groups and lower alkoxy groups. The heterocyclic groups substituted by one of the following substituents: halogen atoms, hydroxy groups, lower alkyl groups, lower haloalkyl groups and lower alkoxy groups are more preferred. Still more preferred are the 5- or 6-membered aromatic heterocyclic groups substituted by one of the following substituents: halogen atoms, hydroxy groups, lower alkyl groups, lower haloalkyl groups and lower alkoxy groups. The most preferred such groups are the thiophen and pyridin groups substituted by one of the following substituents: halogen atoms, hydroxy groups, lower alkyl groups and lower alkoxy groups.

Specific examples of the cycloalkyl groups substituted by from 1 to 5 of substituents α and β in the definition of $R^1$ include those defined and exemplified above in relation to $R^2$, and additionally the following: 2-carboxycyclopropyl, 2- or 3-carboxycyclopentyl, 2-, 3- or 4-carboxycyclohexyl, 2-methoxycarbonylcyclopropyl, 2- or 3-methoxycarbonylcyclopentyl, 2-, 3- or 4-methoxycarbonylcyclohexyl, 2-, 3- or 4-carbamoylcyclohexyl, 2-, 3- or 4-dimethylcarbamoylcyclohexyl, 2-nitrocyclopropyl, 2- or 3-nitrocyclopentyl, 2-, 3- or 4-nitrocyclohexyl, 2- or 3-cyclohexylcyclopentyl, 2-, 3- or 4-cyclohexylcyclohexyl, 2-phenylcyclopropyl, 2- or 3-phenylcyclopentyl, 2-, 3- or 4-phenylcyclohexyl, 2-phenoxycyclopropyl, 2- or 3-phenoxycyclopentyl, 2-, 3- or 4-phenoxycyclohexyl, 2-benzyloxycyclopropyl, 2- or 3-benzyloxycyclopentyl, 2-, 3- or 4-benzyloxycyclohexyl, 2-phenylthiocyclopropyl, 2- or 3-phenylthiocyclopentyl, and 2-, 3-or 4-phenylthiocyclohexyl groups. Of these, the cycloalkyl groups substituted by from 1 to 3 substituents are preferred and cyclohexyl groups substituted by one substituent are more preferred.

Specific examples of the aryl groups substituted by from 1 to 5 of substituents α and β in the definition of $R^1$ include those groups substituted by from 1 to 3 of substituents α defined and exemplified above in relation to $R^2$, and additionally 2-, 3- or 4-carboxyphenyl, 2-, 3- or 4-methoxycarbonylphenyl, 2-, 3- or 4-ethoxycarbonylphenyl, 2-, 3- or 4-carbamoylphenyl, 2-, 3- or 4-methylcarbamoylphenyl, 2-, 3- or 4-dimethylcarbamoylphenyl, 2-, 3- or 4-nitrophenyl, 2-, 3- or 4-cyclopentylphenyl, 2-, 3- or 4-cyclohexylphenyl, 2-, 3- or 4-phenoxyphenyl, 2-, 3- or 4-diphenyl, 2-, 3- or 4-benzyloxyphenyl, 3,4-dibenzyloxyphenyl, 3,5-dibenzyloxyphenyl, 2-, 3- or 4-phenylthiophenyl, 5-nitroinden-3-yl, 5-cyclohexylinden-3-yl, 5-phenylinden-3-yl, 5-phenoxyinden-3-yl, 5-benzyloxyinden-3-yl, 5-phenylthioinden-3-yl, 5-nitroinden-2-yl, 5-cyclohexylinden-2-yl, 5-phenylinden-2-yl, 5-phenoxyinden-2-yl, 5-benzyloxyinden-2-yl, 5-phenylthioinden-2-yl, 5-nitronaphthalen-2-yl, 5-cyclohexylnaphthalen-2-yl, 5-phenylnaphthalen-2-yl, 5-phenoxynaphthalen-2-yl, 5-benzyloxynaphthalen-2-yl, 5-phenylthionaphthalen-2-yl, 5-nitronaphthalen-1-yl, 5-cyclohexylnaphthalen-1-yl, 5-phenylnaphthalen-1-yl, 5-phenoxynaphthalen-1-yl, 5-benzyloxynaphthalen-1-yl and 5-phenylthionaphthalen-1-yl groups. Of these, we prefer those aryl groups substituted by from 1 to 3 of substituents α and β. More preferred are the aryl groups substituted by from 1 to 3 of the following substituents: substituents α, nitro groups, cycloalkyl groups, aryl groups, aryloxy groups, aralkyloxy groups, arylthio groups and cycloalkyl, aryl, aryloxy, aralkyloxy and arylthio groups each substituted by from 1 to 3 of substituents α. Still more preferred are the aryl groups substituted by from 1 to 3 of the following substituents: halogen atoms, hydroxy groups, lower alkyl groups, lower haloalkyl groups, lower alkoxy groups and nitro groups. Even more preferred are the 3-fluorophenyl, 4-fluorophenyl, 3-chlorophenyl, 4-chlorophenyl, 3,4-difluorophenyl, 3,5-difluorophenyl, 3,4-dichlorophenyl, 3,5-dichlorophenyl, 3-hydroxyphenyl, 4-hydroxyphenyl, 3-methylphenyl, 4-methylphenyl, 3,4-dimethylphenyl, 3-methoxyphenyl, 4-methoxyphenyl, 3,4-dimethoxyphenyl, 3,4,5-trimethoxyphenyl and 3,4,5-trifluorophenyl groups. The most preferred are the 3-fluorophenyl, 3-chlorophenyl, 3,4-difluorophenyl, 3,5-difluorophenyl, 3,4-dichlorophenyl and 3,5-difluorophenyl groups.

Specific examples of the heterocyclic groups substituted by from 1 to 5 of substituents α and β in the definition of $R^1$ include the heterocyclic groups substituted by from 1 to 3 of substituents α defined and exemplified above in relation to $R^2$, and additionally the 3-, 4- or 5-nitrothiophen-2-yl, 3-, 4- or 5-phenylthiophen-2-yl, 2-, 4- or 5-nitrothiophen-3-yl, 2-, 4- or 5-phenylthiophen-3-yl, 1-, 2- or 3-hydroxypyridin-4-yl, 1-, 2- or 3-nitropyridin-4-yl, 1-, 2- or 3-phenylpyridin-4-yl groups. Of these, we prefer the heterocyclic groups substituted by from 1 to 3 of the following substituents: halogen atoms, hydroxy groups, lower alkyl groups, lower haloalkyl groups, lower alkoxy groups and nitro groups. More preferred are the heterocyclic groups substituted by one of the following substituents: halogen atoms, hydroxy groups, lower alkyl groups, lower haloalkyl groups, lower alkoxy groups and nitro groups. Still more preferred are the thiophen and pyridin groups substituted by one of the following substituents: halogen atoms, hydroxy groups, lower alkyl groups, lower haloalkyl groups, lower alkoxy groups and nitro groups.

Where G represents a substituted alkylene group having from 1 to 6 carbon atoms, examples include the hydroxymethylene, oxomethylene, cyclopentylmethylene, cyclohexylmethylene, phenylmethylene, 1-naphthylmethylene, 2-naphthylmethylene, 4-fluorophenylmethylene, 4-chlorophenylmethylene, 4-hydroxyphenylmethylene, 4-methylphenylmethylene, 1-naphthylmethylene, 2-naphthylmethylene, 2-thienylmethylene, 4-pyridylmethylene, 1-hydroxyethylene, 1-oxoethylene, 1-cyclopentylethylene, 1-cyclohexylethylene, 1-phenylethylene, 1-(1-naphthyl)ethylene, 1-(9-naphthyl)ethylene, 1-(4-fluorophenyl)ethylene, 1-(4-chlorophenyl)ethylene, 1-(4-hydroxyphenyl)

ethylene, 1-(4-methylphenyl)ethylene, 1-(1-naphthyl)ethylene, 1-(2-naphthyl)ethylene, 1-(2-thienyl)ethylene, 1-(4-pyridyl)ethylene, 2-hydroxyethylene, 2-oxoethylene, 2-cyclopentylethylene, 2-cyclohexylethylene, 2-phenylethylene, 2-(1-naphthyl)ethylene, 2-(2-naphthyl)ethylene, 2-(4-fluorophenyl)ethylene, 2-(4-chlorophenyl)ethylene, 2-(4-hydroxyphenyl)ethylene, 2-(4-methylphenyl)ethylene, 2-(1-naphthyl)ethylene, 2-(2-naphthyl)ethylene, 2-(2-thienyl)ethylene, 2-(4-pyridyl)ethylene, 1-hydroxy-2-methylethylene, 2-methyl-1-oxoethylene, 1-cyclopentyl-2-methylethylene, 1-cyclohexyl-2-methylethylene, 2-methyl-1-phenylethylene, 2-methyl-1-(1-naphthyl)ethylene, 2-methyl-1-(2-naphthyl)ethylene, 1-(4-fluorophenyl)-2-methylethylene, 1-(4-chlorophenyl)-2-methylethylene, 1-(4-hydroxyphenyl)-2-methylethylene, 1-(4-methylphenyl)-2-methylethylene, 2-methyl-1-(1-naphthyl)ethylene, 2-methyl-1-(2-naphthyl)ethylene, 2-methyl-1-(2-thienyl)ethylene, 2-methyl-1-(4-pyridyl)ethylene, 1-hydroxytrimethylene, 1-oxotrimethylene, 1-cyclopentyltrimethylene, 1-cyclohexyltrimethylene, 1-phenyltrimethylene, 1-(1-naphthyl)trimethylene, 1-(2-naphthyl)trimethylene, 1-(4-fluorophenyl)trimethylene, 1-(4-chlorophenyl)trimethylene, 1-(4-hydroxyphenyl)trimethylene, 1-(4-methylphenyl)trimethylene, 1-(1-naphthyl)trimethylene, 1-(2-naphthyl)trimethylene, 1-(2-thienyl)trimethylene, 1-(4-pyridyl)trimethylene, 3-hydroxytrimethylene, 3-oxotrimethylene, 3-cyclopentyltrimethylene, 3-cyclohexyltrimethylene, 3-phenyltrimethylene, 3-(1-naphthyl)trimethylene, 3-(2-naphthyl)trimethylene, 3-(4-fluorophenyl)trimethylene, 3-(4-chlorophenyl)trimethylene, 3-(4-hydroxyphenyl)trimethylene, 3-(4-methylphenyl)trimethylene, 3-(1-naphthyl)trimethylene, 3-(2-naphthyl)trimethylene, 3-(2-thienyl)trimethylene and 3-(4-pyridyl)trimethylene groups, of which the those alkylene groups having from 1 to 6 carbon atoms and having a hydroxy, oxo or aryl substituent are preferred. More preferre are those alkylene groups having from 1 to 4 carbon atoms and having a hydroxy, oxo or aryl substituent. The most preferred are the hydroxy-, oxo- and aryl-substituted methylene and ethylene groups.

Of these, the following classes of compounds of the present invention are preferred:

(A) compounds of formula (Ia) or (Ib):

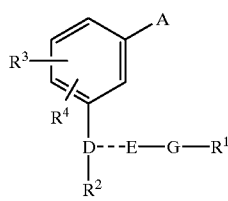

(Ia)

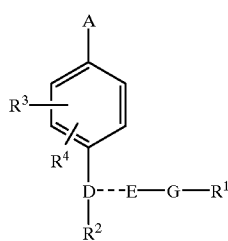

(Ib)

wherein $R^1$, $R^2$, $R^3$, $R^4$, A, D, E and G are as defined above, especially compounds of formula (Ia).

(B) compounds wherein Z represents a single bond or an alkylene group having 1 or 2 carbon atoms.

(C) compounds wherein $R^5$ represents a hydrogen atom or a lower alkyl group.

(D) compounds wherein $R^6$ represents a hydroxy group or an amine residue.

(E) compounds wherein X and Y each represents an oxygen atom.

(F) compounds wherein D represents a CH group or a nitrogen atom.

(G) compounds wherein E represents an oxygen atom, a sulfur atom or an —NH— group.

(H) compounds wherein G represents a substituted or unsubstituted alkylene group having from 1 to 6 carbon atoms.

(I) compounds wherein $R^1$ represents a cycloalkyl group, an aryl group, a heterocyclic group, an aryl group substituted by from 1 to 3 substituents selected from substituents α and β, defined above, or a heterocyclic group substituted by from 1 to 3 substituents selected from substituents α and β, defined above.

(J) compounds wherein $R^2$ represents a cycloalkyl group, an aryl group, a heterocyclic group, an aryl group substituted by from 1 to 3 substituents selected from substituents α, defined above, or a heterocyclic group substituted by from 1 to 3 substituents selected from substituents α, defined above.

(K) compounds wherein $R^3$ and $R^4$ are the same as or different from each other and each represents a hydrogen atom, a hydroxy group, a halogen atom, a lower alkoxy group, an amino group or a di(lower alkyl) amino group.

Especially preferred are those compounds in which Z is as defined in (B) above, $R^5$ is as defined in (C) above, $R^6$ is as defined in (D) above, X and Y are as defined in (E) above, D is as defined in (F) above, E is as defined in (G) above, G is as defined in (H) above, $R^1$ is as defined in (I) above, $R^2$ is as defined in (J) above, and $R^3$ and $R^4$ are as defined in (K) above, and more especially those compounds of formula (Ia) or (Ib) and most especially those compounds of formula (Ia).

(L) compounds wherein Z represents a single bond or a methylene group.

(M) compounds wherein $R^5$ represents a hydrogen atom or a methyl group.

(N) compounds wherein $R^6$ represents a hydroxy group, an amino group or a hydroxyamino group.

(O) compounds wherein D represents a CH group.

(P) compounds wherein E represents an —NH— group.

(Q) compounds wherein G represents a substituted or unsubstituted alkylene group having from 1 to 6 carbon atoms, said substituent being a hydroxy group, an oxo group, an aryl group or an aryl group substituted by from 1 to 3 substituents selected from substituents α, defined above.

(R) compounds wherein $R^1$ represents an aryl group, a 5- or 6-membered aromatic heterocyclic group which may be fused with a benzene ring, an aryl group substituted by from 1 to 3 substituents selected from substituents α and β, defined above, or a 5- or 6-membered aromatic heterocyclic group which is substituted by from 1 to 3 substituents selected from substituents α and β, defined above, and which may be fused with a benzene ring, (S) compounds wherein $R^2$ represents an aryl group, a 5- or 6-membered aromatic heterocyclic group which may be fused with a benzene ring, or a 5- or 6-membered aromatic heterocyclic group which may be fused with an aryl group substituted by from 1 to 3 substituents or a benzene ring (said substituent being a halogen atom, a hydroxy group, a lower alkyl group, a lower haloalkyl group or a lower alkoxy group).

(T) compounds wherein $R^3$ and $R^4$ are the same as or different from each other and each represents a hydrogen atom, a hydroxy group or a lower alkoxy group.

Especially preferred are those compounds in which Z is as defined in (L) above, $R^5$ is as defined in (M) above, $R^6$ is as defined in (N) above, X and Y are as defined in (E) above, D is as defined in (O) above, E is as defined in (P) above, G is as defined in (Q) above, $R^1$ is as defined in (R) above, $R^2$ is as defined in (S) above, and $R^3$ and $R^4$ are as defined in (T) above, and more especially those compounds of formula (Ia) or (Ib) and most especially those compounds of formula (Ia).

(U) compounds wherein Z represents a single bond.

(V) compounds wherein $R^5$ represents a hydrogen atom.

(W) compounds wherein $R^6$ represents a hydroxy group.

(X) compounds wherein G represents an alkylene group having from 1 to 6 carbon atoms.

(Y) compounds wherein $R^1$ represents an aryl group, a 5- or 6-membered aromatic heterocyclic group which may be fused with a benzene ring, or a 5- or 6-membered aromatic heterocyclic group which has been substituted by an aryl group substituted by from 1 to 3 substituents and which may be fused with a benzene ring (the substituent being selected from substituents α, defined above, nitro groups, cycloalkyl groups, aryl groups, aryloxy groups, aralkyloxy groups, arylthio groups and cycloalkyl, aryl, aryloxy, aralkyloxy and arylthio groups each substituted by from 1 to 3 substituents selected from substituents α, defined above).

(Z) compounds wherein $R^2$ represents an aryl group, a thienyl group, a furyl group, a pyrrolyl group, a thiazolyl group, an oxazolyl group, an imidazolyl group, a pyridyl group, a thienyl, furyl, pyrrolyl, thiazolyl, oxazolyl, imidazolyl or pyridyl group fused with a benzene ring or an aryl group substituted by a substituent (said substituent being a halogen atom, a hydroxy group, a lower alkyl group, a lower haloalkyl group or a lower alkoxy group).

(AA) compounds wherein $R^3$ and $R^4$ each represents a hydrogen atom.

Especially preferred are those compounds in which Z is as defined in (U) above, $R^5$ is as defined in (V) above, $R^6$ is as defined in (W) above, X and Y are as defined in (E) above, D is as defined in (O) above, E is as defined in (P) above, G is as defined in (X) above, $R^1$ is as defined in (Y) above, $R^2$ is as defined in (Z) above, and $R^3$ and $R^4$ are as defined in (AA) above, and more especially those compounds of formula (Ia) or (Ib) and most especially those compounds of formula (Ia).

(AB) compounds wherein $R^6$ represents a hydroxy group.

(AC) compounds wherein G represents an alkylene group having from 1 to 4 carbon atoms.

(AD) compounds wherein $R^1$ represents an aryl group, a 5- or 6-membered aromatic heterocyclic group which may be fused with a benzene ring, or a 5- or 6-membered aromatic heterocyclic group which has been substituted by an aryl group substituted by from 1 to 3 substituents and which may be fused with a benzene ring (the substituent being selected from halogen atoms, hydroxy groups, lower alkyl groups, lower haloalkyl groups, lower alkoxy groups, nitro groups, cycloalkyl groups, aryl groups, aryloxy groups and arylthio groups), (AE) compounds wherein $R^2$ represents an aryl group having from 6 to 10 carbon atoms, a 2-thienyl group, a 4-pyridyl group or an aryl group having from 6 to 10 carbon atoms substituted by a substituent (said substituent being a halogen atom, a hydroxy group, a lower alkyl group, a lower haloalkyl group or a lower alkoxy group, Especially preferred are those compounds in which Z is as defined in (U) above, $R^5$ is as defined in (V) above, $R^6$ is as defined in (AB) above, X and Y are as defined in (E) above, D is as defined in (O) above, E is as defined in (P) above, G is as defined in (AC) above, $R^1$ is as defined in (AD) above, $R^2$ is as defined in (AE) above, and $R^3$ and $R^4$ are as defined in (AA) above, and more especially those compounds of formula (Ia) or (Ib) and most especially those compounds of formula (Ia).

(AF) compounds wherein G represents a methylene, methylmethylene or ethylmethylene group.

(AG) compounds wherein $R^1$ represents an aryl group having from 6 to 10 carbon atoms, a thienyl group, a furyl group, a pyrrolyl group, a thiazolyl group, an oxazolyl group, an imidazolyl group, a pyridyl group, a thienyl, furyl, pyrrolyl, thiazolyl, oxazolyl, imidazolyl or pyridyl group fused with a benzene ring, or an aryl group having from 6 to 10 carbon atoms substituted by from 1 to 3 substituents (the substituent being selected from halogen atoms, hydroxy groups, lower alkyl groups, lower haloalkyl groups, lower alkoxy groups and nitro groups).

(AH) compounds wherein $R^2$ represents a phenyl group or a phenyl group substituted by a substituent (said substituent being a halogen atom, a hydroxy group, a lower alkyl group, a lower haloalkyl group or a lower alkoxy group).

Especially preferred are those compounds in which Z is as defined in (U) above, $R^5$ is as defined in (V) above, $R^6$ is as defined in (AB) above, X and Y are as defined in (E) above, D is as defined in (O) above, E is as defined in (P) above, G is as defined in (AF) above, $R^1$ is as defined in (AG) above, $R^2$ is as defined in (AH) above, and $R^3$ and $R^4$ are as defined in (AA) above, and more especially those compounds of formula (Ia) or (Ib) and most especially those compounds of formula (Ia).

(AI) compounds wherein G represents a methylmethylene group, (AJ) compounds wherein $R^1$ represents a phenyl, 1-naphthyl, 2-naphthyl, 3-fluorophenyl, 4-fluorophenyl, 3-chlorophenyl, 4-chlorophenyl, 3,4-difluorophenyl, 3,5-difluorophenyl, 3,4-dichlorophenyl, 3,5-dichlorophenyl, 3-hydroxyphenyl, 4-hydroxyphenyl, 3-methylphenyl, 4-methylphenyl, 3,4-dimethylphenyl, 3-methoxyphenyl, 4-methoxyphenyl, 3,4-dimethoxyphenyl, 3,4,5-trimethoxyphenyl, 3,4,5-trifluorophenyl, thienyl or pyridyl group.

(AK) compounds wherein $R^2$ represents a phenyl, 4-fluorophenyl, 4-chlorophenyl, 4-methylphenyl or 4-methoxyphenyl group.

Especially preferred are those compounds in which Z is as defined in (U) above, $R^5$ is as defined in (V) above, $R^6$ is as defined in (AB) above, X and Y are as defined in (E) above, D is as defined in (O) above, E is as defined in (P) above, G is as defined in (AI) above, $R^1$ is as defined in (AJ) above, $R^2$ is as defined in (AK) above, and $R^3$ and $R^4$ are as defined in (AA) above, and more especially those compounds of formula (Ia) or (Ib) and most especially those compounds of formula (Ia).

(AL) compounds wherein $R^1$ represents a phenyl, 3-fluorophenyl, 3-chlorophenyl, 3,4-difluorophenyl, 3,5-difluorophenyl, 3,4-dichlorophenyl, 3,5-dichlorophenyl, 1-naphthyl, 2-thienyl or 4-pyridyl group.

Especially preferred are those compounds in which Z is as defined in (U) above, $R^5$ is as defined in (V) above, $R^6$ is as defined in (AB) above, X and Y are as defined in (E) above, D is as defined in (O) above, E is as defined in (P) above, G is as defined in (AF) above, $R^1$ is as defined in (AL) above, $R^2$ is as defined in (AH) above, and $R^3$ and $R^4$ are as defined in (AA) above, and more especially those compounds of formula (Ia) or (Ib) and most especially those compounds of formula (Ia).

Particularly preferred compounds are:

3-amino-4-<3-{(4-methoxyphenyl)-[1-(3,4-difluorophenyl)ethylamino]methyl}phenylamino>-3-cyclobutene-1,2-dione, 3-amino-4-{3-[(4-fluorophenyl)-(1-phenylethylamino)methyl]phenylamino}-3-cyclobutene-1,2-dione, 3-amino-4-{3-[(4-methoxyphenyl)-(1-phenylethylamino)methyl]phenylamino}-3-cyclobutene-1,2-dione, 3-amino-4-{3-[4-pyridyl-(1-phenylethylamino)methyl]phenylamino}-3-cyclobutene-1,2-dione, 3-amino-4-<3-{(4-methoxyphenyl)-[1-(3-fluorophenyl)ethylamino]methyl}phenylamino>-3-cyclobutene-1,2-dione, 3-amino-4-<3-{(4-fluorophenyl)-[1-(3,4-difluorophenyl)ethylamino]methyl}phenylamino>-3-cyclobutene-1,2-dione, 3-amino-4-<3-{(4-methoxyphenyl)-[1-(3,4-difluorophenyl)ethylamino]methyl}phenylamino>-3-cyclobutene-1,2-dione, 3-amino-4-<3-{4-pyridyl-[1-(3,4-difluorophenyl)ethylamino]methyl}phenylamino>-3-cyclobutene-1,2-dione, 3-amino-4-<3-{phenyl-[1-(3,5-difluorophenyl)ethylamino]methyl}phenylamino>-3-cyclobutene-1,2-dione, 3-amino-4-<3-{(4-fluorophenyl)-[1-(3,5-difluorophenyl)ethylamino]methyl}phenylamino>-3-cyclobutene-1,2-dione, 3-amino-4-<3-{(4-methoxyphenyl)-[1-(3,5-difluorophenyl)ethylamino]methyl}phenylamino>-3-cyclobutene-1,2-dione, 3-amino-4-<3-{(4-methoxyphenyl)-[1-(4-pyridyl)ethylamino]methyl}phenylamino>-3-cyclobutene-1,2-dione, 3-amino-4-<3-{(4-methoxyphenyl)-[1-(3,4-difluorophenyl)ethylamino]methyl}phenylamino>-3-cyclobutene-1,2-dione, 4-<3-{[1-(3,4-difluorophenyl)ethylamino]-(4-methoxyphenyl)methyl}phenylamino>-3-hydroxy-3-cyclobutene-1,2-dione, 4-<3-{[1-(3,5-difluorophenyl)ethylamino]-(4-methoxyphenyl)methyl}phenylamino>-3-hydroxy-3-cyclobutene-1,2-dione, 4-<3-{[1-(3,5-difluorophenyl)ethylamino]-(4-fluorophenyl)methyl}phenylamino>-3-hydroxy-3-cyclobutene-1,2-dione, 3-<3-{[1-(3,4-difluorophenyl)ethylamino]-(4-fluorophenyl)methyl}phenylamino>-4-hydroxy-3-cyclobutene-1,2-dione, 3-<3-{[1-(3-fluorophenyl)ethylamino]-(4-methoxyphenyl)methyl}phenylamino>-4-hydroxy-3-cyclobutene-1,2-dione, 3-<3-{(4-fluorophenyl)-[1-(3-fluorophenyl)ethylamino]methyl}phenylamino>-4-hydroxy-3-cyclobutene-1,2-dione, 4-<3-{(4-chlorophenyl)-[1-(3-fluorophenyl)ethylamino]methyl}phenylamino>-3-hydroxy-3-cyclobutene-1,2-dione, 4-<3-{(4-chlorophenyl)-[1-(3,5-difluorophenyl)ethylamino]methyl}phenylamino>-3-hydroxy-3-cyclobutene-1,2-dione, 4-<3-{(4-chlorophenyl)-[1-(3,4-difluorophenyl)ethylamino]methyl}phenylamino>-3-hydroxy-3-cyclobutene-1,2-dione, 3-<3-{[1-(3,4-difluorophenylamino)ethylamino]-(p-tolyl)methyl}phenylamino>-4-hydroxy-3-cyclobutene-1,2-dione, 4-<3-{[1-(3,5-difluorophenyl)ethylamino]-(4-methylphenyl)methyl}phenylamino>-3-hydroxy-3-cyclobutene-1,2-dione, 3-hydroxy-4-<3-{(4-methoxyphenyl)-[1-(naphthalen-1-yl)ethylamino]methyl}phenylamino>-cycylobut-3-ene-1,2-dione, 3-<3-{(4-chlorophenyl)-[1-phenylethylamino]methyl}phenylamino>-4-hydroxy-3-cyclobutene-1,2-dione, 3-<3-{[4-(p-tolyl)-[1-(3-fluorophenyl)ethylamino]methyl}phenylamino>-4-hydroxy-3-cyclobutene-1,2-dione hydrochloride, 3-hydroxy-4-<3-{[1-(3-fluorophenyl)ethylamino]phenylmethyl}phenylamino>-3-cyclobutene-1,2-dione, 3-hydroxy-4-<3-{[1-(3,4-difluorophenyl)ethylamino]phenylmethyl}phenylamino>-3-cyclobutene-1,2-dione, 3-hydroxy-4-<3-{[1-(3,5-difluorophenyl)ethylamino]phenylmethyl}phenylamino>-3-cyclobutene-1,2-dione, 3-<3-{(4-fluorophenyl)-[1-(naphthalen-1-yl)ethylamino]methyl}phenylamino>-4-hydroxy-3-cyclobutene-1,2-dione, 3-<3-{(4-chlorophenyl)-[1-(naphthalen-1-yl)ethylamino]methyl}phenylamino>-4-hydroxy-3-cyclobutene-1,2-dione, 3-<3-{(4-fluorophenyl)-[1-phenylethylamino]methyl}phenylamino>-4-hydroxy-3-cyclobutene-1,2-dione, 3-hydroxy-4-<3-{[1-(1-naphthyl)ethylamino]phenylmethyl}phenylamino>-3-cyclobutene-1,2-dione, 3-hydroxy-4-<3-{[-(1-naphthyl)ethylamino]-p-tolylmethyl}phenylamino>-3-cyclobutene-1,2-dione; and 3-hydroxy-4-<3-{[1-phenylethylamino]-(4-methoxyphenyl)methyl}phenylamino>-3-cyclobutene-1,2-dione.

Where the compounds of formula (I) contain a basic group, such as amino group, they can form salts with acids; where they contain an acidic group, they can form salts with bases. There is no particular restriction on the nature of the acid or base used to form such salts, provided that, where the compounds are intended for use as pharmaceuticals, the resulting salt is pharmaceutically acceptable, which, as is well understood in the art, means that the compound is not significantly less active or unacceptably less active and is not significantly more toxic or unacceptably more toxic than the original compound of formula (I). Where the compound of the invention is intended for non-pharmaceutical purposes, for example as an intermediate in the preparation of other, and possibly more active, compounds, even this restriction need not apply.

Examples of salts which may be formed with a basic group include: inorganic acid salts, for example, hydrohalic acid salts (such as hydrofluoric acid salts, hydrochloric acid salts, hydrobromic acid salts and hydroiodic acid salts), nitric acid salts, perchloric acid salts, sulfuric acid salts and phosphoric acid salts; organic acid salts, for example, lower alkanesulfonic acid salts (such as methanesulfonic acid salts, trifluoromethanesulfonic acid salts and ethanesulfonic acid salts), arylsulfonic acid salts (such as benzenesulfonic acid salts and p-toluenesulfonic acid salts), acetic acid salts, malic acid salts, fumaric acid salts, succinic acid salts, citric acid salts, ascorbic acid salts, tartaric acid salts, oxalic acid salts and maleic acid salts; and amino acid salts (such as glycine salts, lysine salts, arginine salts, ornithine salts, glutamic acid salts and aspartic acid salts). Of these, the hydrohalic acid salts are most preferred.

Examples of salts which may be formed with an acidic group include: alkali metal salts (such as sodium salts, potassium salts and lithium salts), alkaline earth metal salts (such as calcium salts and magnesium salts), other metal salts (such as aluminum salts and iron salts); amine salts, for example, inorganic salts such as ammonium salts and organic salts [such as t-octylamine salts, dibenzylamine salts, morpholine salts, glucosamine salts, phenylglycine alkyl ester salts, ethylene diamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzylphenethylamine salts, piperazine salts, tetramethylammonium salts and tris(hydroxymethyl) aminomethane salts]; and amino acid salts (such as glycine salts, lysine salts, arginine salts, ornithine salts, glutamic acid salts and aspartic acid salts).

Since the compounds of formula (I) contain in their molecules asymmetric carbon atoms, they may exist in the form of various isomers. In the present invention, all of these isomers and mixtures thereof are represented by the same formula, that is, formula (I), and these isomers and mixtures of these isomers at any ratio are all embraced by the present invention.

Where the part of the molecule of the compound of formula (I) of formula —G—R$^1$ has the formula:

this contains an asymmetric carbon atom to which the groups R$^0$ and R$^1$ are attached. Where R$^0$ represents a methyl group and R$^1$ represents an optionally substituted phenyl group, we prefer those compounds in the R-configuration.

When the compound of formula (I) is allowed to stand in the air or is recrystallized, it may absorb water or may have adsorbed water attached thereto, thereby forming a hydrate. Such hydrates are also embraced by the present invention.

Where the compounds of formula (I) contain an acidic group or certain basic groups, they may form esters. Examples of such esters include esters with a hydroxy group and esters with a carboxy group. The ester residue may be an ordinary protecting group or a protecting group which can be cleaved in vivo by a biological method such as hydrolysis.

The term "ordinary protecting group" means a protecting group which can be cleaved by a chemical method such as hydrogenolysis, hydrolysis, electrolysis or photolysis.

Preferred examples of such ordinary protecting groups for an ester of a hydroxy group include:

lower aliphatic acyl groups, for example:
  alkanoyl groups, such as the formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, icosanoyl and henicosanoyl groups;
  halogenated alkylcarbonyl groups, such as the chloroacetyl, dichloroacetyl, trichloroacetyl, and trifluoroacetyl groups;
  alkoxyalkylcarbonyl groups, such as the methoxyacetyl group; and
  unsaturated alkylcarbonyl groups, such as the acryloyl, propioloyl, methacryloyl, crotonoyl, isocrotonoyl and (E)-2-methyl-2-butenoyl groups;
  more preferably, the lower aliphatic acyl groups having from 1 to 6 carbon atoms;

aromatic acyl groups, for example:
  arylcarbonyl groups, such as the benzoyl, α-naphthoyl and β-naphthoyl groups;
  halogenated arylcarbonyl groups, such as the 2-bromobenzoyl and 4-chlorobenzoyol groups;
  lower alkylated arylcarbonyl groups, such as the 2,4,6-trimethylbenzoyl and 4-toluoyl groups;
  lower alkoxylated arylcarbonyl groups, such as the 4-anisoyl group;
  nitrated arylcarbonyl groups, such as the 4-nitrobenzoyl and 2-nitrobenzoyl groups;
  lower alkoxycarbonylated arylcarbonyl groups, such as the 2-(methoxycarbonyl)benzoyl group; and
  arylated arylcarbonyl groups, such as the 4-phenylbenzoyl group;

alkoxycarbonyl groups, for example:
  lower alkoxycarbonyl groups, such as the methoxycarbonyl, ethoxycarbonyl, propoxycarbonyl, butoxycarbonyl, sec-butoxycarbonyl, t-butoxycarbonyl and isobutoxycarbonyl groups; and
  halogen- or tri(lower alkyl)silyl-substituted lower alkoxycarbonyl groups, such as the 2,2,2-trichloroethoxycarbonyl and 2-trimethylsilylethoxycarbonyl groups;

tetrahydropyranyl or tetrahydrothiopyranyl groups, such as:
  tetrahydropyran-2-yl, 3-bromotetrahydropyran-2-yl, 4-methoxytetrahydropyran-4-yl, tetrahydrothiopyran-2-yl, and 4-methoxytetrahydrothiopyran-4-yl groups;

tetrahydrofuranyl or tetrahydrothiofuranyl groups, such as:

tetrahydrofuran-2-yl and tetrahydrothiofuran-2-yl groups;

silyl groups, for example:
: tri(lower alkyl)silyl groups, such as the trimethylsilyl, triethylsilyl, isopropyldimethylsilyl, t-butyldimethylsilyl, methyldiisopropylsilyl, methyldi-t-butylsilyl and triisopropylsilyl groups; and
: tri(lower alkyl)silyl groups substituted by 1 or 2 aryl groups, such as the diphenylmethylsilyl, diphenylbutylsilyl, diphenylisopropylsilyl and phenyldiisopropylsilyl groups;

alkoxymethyl groups, for example:
: lower alkoxymethyl groups, such as the methoxymethyl, 1,1-dimethyl-1-methoxymethyl, ethoxymethyl, propoxymethyl, isopropoxymethyl, butoxymethyl and t-butoxymethyl groups;
: lower alkoxylated lower alkoxymethyl groups, such as the 2-methoxyethoxymethyl group; and
: halo(lower alkoxy)methyl groups, such as the 2,2,2-trichloroethoxymethyl and bis(2-chloroethoxy) methyl groups;

substituted ethyl groups, for example:
: lower alkoxylated ethyl groups, such as the 1-ethoxyethyl and 1-(isopropoxy)ethyl groups; and
: halogenated ethyl groups, such as the 2,2,2-trichloroethyl group;

aralkyl groups, for example:
: lower alkyl groups substituted by from 1 to 3 aryl groups, such as the benzyl, α-naphthylmethyl, β-naphthylmethyl, diphenylmethyl, triphenylmethyl, α-naphthyldiphenylmethyl and 9-anthrylmethyl groups; and
: lower alkyl groups substituted by from 1 to 3 substituted aryl groups, where one or more of the aryl groups is substituted by one or more lower alkyl, lower alkoxy, nitro, halogen or cyano substituents, such as the 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl and 4-cyanobenzyl groups;

alkenyloxycarbonyl groups:
: such as the vinyloxycarbonyl and aryloxycarbonyl groups; and aralkyloxycarbonyl groups in which the aryl ring may be substituted by 1 or 2 lower alkoxy or nitro groups:
: such as the benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups.

Preferred examples of such ordinary protecting groups for an ester of a carboxy group include:
: lower alkyl groups, such as those defined and exemplified above;
: lower alkenyl groups, such as the vinyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl and 5-hexenyl groups;
: lower alkynyl groups, such as the ethynyl, 2-propynyl, 1-methyl-2-propynyl, 2-methyl-2-propynyl, 2-ethyl-2-propynyl, 2-butynyl, 1-methyl-2-butynyl, 2-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 2-methyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl and 5-hexynyl groups;
: lower haloalkyl groups, such as those defined and exemplified above;
: lower hydroxyalkyl groups, such as the 2-hydroxyethyl, 2,3-dihydroxypropyl, 3-hydroxypropyl, 3,4-dihydroxybutyl and 4-hydroxybutyl groups;
: lower aliphatic acyl-lower alkyl groups, such as the acetylmethyl group;
: aralkyl groups, such as those defined and exemplified above; and
: silyl groups, such as those defined and exemplified above.

The term "protecting group which can be cleaved in vivo by a biological method such as hydrolysis" means a protecting group which is cleaved in vivo by a biological method such as hydrolysis and forms a free acid or salt thereof. Whether a compound is such a derivative or not can be determined by administering it by intravenous injection to an experimental animal, such as a rat or mouse, and then studying the body fluids of the animal to determine whether or not the compound or a pharmaceutically acceptable salt thereof can be detected.

Preferred examples of such protecting groups which can be cleaved in vivo and which can form esters with hydroxy groups include:
: lower carbonyloxyalkyl groups, for example:
  : 1-(acyloxy)-lower alkyl groups, e.g.:
    : 1-(lower aliphatic acyloxy)-lower alkyl groups, such as the formyloxymethyl, acetoxymethyl, dimethylaminoacetoxymethyl, propionyloxymethyl, butyryloxymethyl, pivaloyloxymethyl, valeryloxymethyl, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 1-formyloxypropyl, 1-acetoxypropyl, 1-propionyloxypropyl, 1-butyryloxypropyl, 1-pivaloyloxypropyl, 1-valeryloxypropyl, 1-isovaleryloxypropyl, 1-hexanoyloxypropyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypentyl, 1-pivaloyloxypentyl and 1-pivaloyloxyhexyl groups;
    : 1-(cycloalkylcarbonyloxy)-lower alkyl groups, such as the cyclopentylcarbonyloxymethyl, cyclohexylcarbonyloxymethyl, 1-cyclopentylcarbonyloxyethyl, 1-cyclohexylcarbonyloxyethyl, 1-cyclopentylcarbonyloxypropyl, 1-cyclohexylcarbonyloxypropyl, 1-cyclopentylcarbonyloxybutyl and 1-cyclohexylcarbonyloxybutyl groups; and
    : 1-(aromatic acyloxy)-lower alkyl groups, such as the benzoyloxymethyl group;

(lower alkoxycarbonyloxy)alkyl groups, such as the methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, pentyloxycarbonyloxymethyl, hexyloxycarbonyloxymethyl, cyclohexyloxycarbonyloxymethyl, cyclohexyloxycarbonyloxy(cyclohexyl)methyl, 1-(methoxycarbonyloxy)ethyl, 1-(ethoxycarbonyloxy)ethyl, 1-(propoxycarbonyloxy)ethyl, 1-(isopropoxycarbonyloxy)ethyl, 1-(butoxycarbonyloxy)ethyl, 1-(isobutoxycarbonyloxy)ethyl, 1-(t-butoxycarbonyloxy)ethyl, 1-(pentyloxycarbonyloxy)ethyl, 1-(hexyloxycarbonyloxy)ethyl, 1-(cyclopentyloxycarbonyloxy)ethyl, 1-(cyclopentyloxycarbonyloxy)propyl, 1-(cyclohexyloxycarbonyloxy)propyl, 1-(cyclopentyloxycarbonyloxy)butyl, 1-(cyclohexyloxycarbonyloxy)butyl, 1-(cyclohexyloxycarbonyloxy)ethyl, 1-(ethoxycarbonyloxy)propyl, 1-(methoxycarbonyloxy)propyl, 1-(ethoxycarbonyloxy)propyl, 1-(propoxycarbonyloxy)propyl, 1-(isopropoxycarbonyloxy)propyl, 1-(butoxycarbonyloxy)propyl, 1-(isobutoxycarbonyloxy)propyl, 1-(pentyloxycarbonyloxy)propyl, 1-(hexyloxycarbonyloxy)propyl, 1-(methoxycarbonyloxy)butyl, 1-(ethoxycarbonyloxy)butyl, 1-(propoxycarbonyloxy)butyl, 1-(isopropoxycarbonyloxy)butyl, 1-(butoxycarbonyloxy)butyl, 1-(isobutoxycarbonyloxy)butyl, 1-(methoxycarbonyloxy)pentyl, 1-(ethoxycarbonyloxy)pentyl, 1-(methoxycarbonyloxy)hexyl and 1-(ethoxycarbonyloxy)hexyl groups;

oxodioxolenylmethyl groups, such as the (5-phenyl-2-oxo-1,3-dioxolen-4-yl)methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-fluorophenyl)-2-oxo-1,3-dioxolen-4-yl] methyl, [5-(4-chlorophenyl)-2-oxo-1,3-dioxolen-4-yl]methyl, (2-oxo-1,3-dioxolen-4-yl)methyl, (5-methyl-2-oxo-1,3-dioxolen-4-yl)methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl)methyl, and (5-butyl-2-oxo-1,3-dioxolen-4-yl)methyl groups;

phthalidyl groups, such as the phthalidyl, dimethylphthalidyl and dimethoxyphthalidyl groups;

lower aliphatic acyl groups, such as those defined and exemplified above;

aromatic acyl groups, such as those defined and exemplified above;

half ester salt residues of succinic acid;

phosphoric acid ester salt residues;

ester forming residues such as amino acid;

carbamoyl groups;

carbamoyl groups substituted by 1 or 2 lower alkyl groups; and 1-(acyloxy)alkyloxycarbonyl groups, such as the pivaloyloxymethoxycarbonyl group;

of these, the carbonyloxyalkyl groups are preferred.

Preferred examples of such protecting groups which can be cleaved in vivo and which can form esters with carboxy groups include:

alkoxyalkyl groups, for example:
  lower alkoxy(lower alkyl) groups, such as the methoxyethyl, 1-ethoxyethyl, 1-methyl-1-methoxyethyl, 1-(isopropoxy)ethyl, 2-methoxyethyl, 2-ethoxyethyl, 1,1-dimethyl-1-methoxyethyl, ethoxymethyl, propoxymethyl, isopropoxymethyl, butoxymethyl and t-butoxymethyl groups; and
  (lower alkoxylated)-(lower alkoxy)(lower alkyl) groups, such as the 2-methoxyethoxymethyl group;

aryloxy-lower alkyl groups, such as the phenoxymethyl group; and halogenated (lower alkoxy)(lower alkyl) groups, such as the 2,2,2-trichloroethoxymethyl and bis(2-chloroethoxy)methyl groups;

lower alkoxycarbonyl-lower alkyl groups, such as the methoxycarbonylmethyl group;

lower cyanoalkyl groups, such as the cyanomethyl and 2-cyanoethyl groups;

lower alkyl-thiomethyl groups, such as the methylthiomethyl and ethylthiomethyl groups;

arylthiomethyl groups, such as the phenylthiomethyl and naphthylthiomethyl groups;

lower alkylsulfonyl-lower alkyl groups which may be substituted by a halogen atom, such as the 2-methanesulfonylethyl and 2-trifluoromethanesulfonylethyl groups;

arylsulfonyl-lower alkyl groups, such as the 2-benzenesulfonylethyl and 2-toluenesulfonylethyl groups;

1-(acyloxy)-lower alkyl groups; phthalidyl groups, aryl groups, and lower alkyl groups as defined and exemplified above;

carboxyalkyl groups, such as the carboxymethyl group; and amide forming residues of an amino acid, such as phenylalanine.

When the compound of formula (I) of the present invention contains an amino and/or carboxy group, it can be converted into derivatives other than the above-described pharmaceutically acceptable salts or the above-described esters. Examples of such other derivatives include amide derivatives.

Specific examples of the compounds of the present invention represented by the formula (I) include the compounds described in the following Tables 1 to 6. It should however be borne in mind that the present invention is not limited to or by these compounds. The compounds shown in Tables 1 to 6 have the structural formulae (I-1) to (I-6), respectively.

In Tables 1 to 6, the substituents of $R^1$, $R^2$ and A are the following groups.

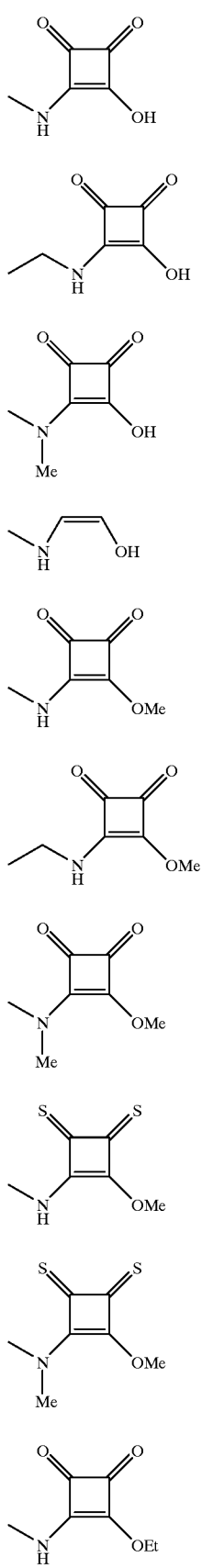
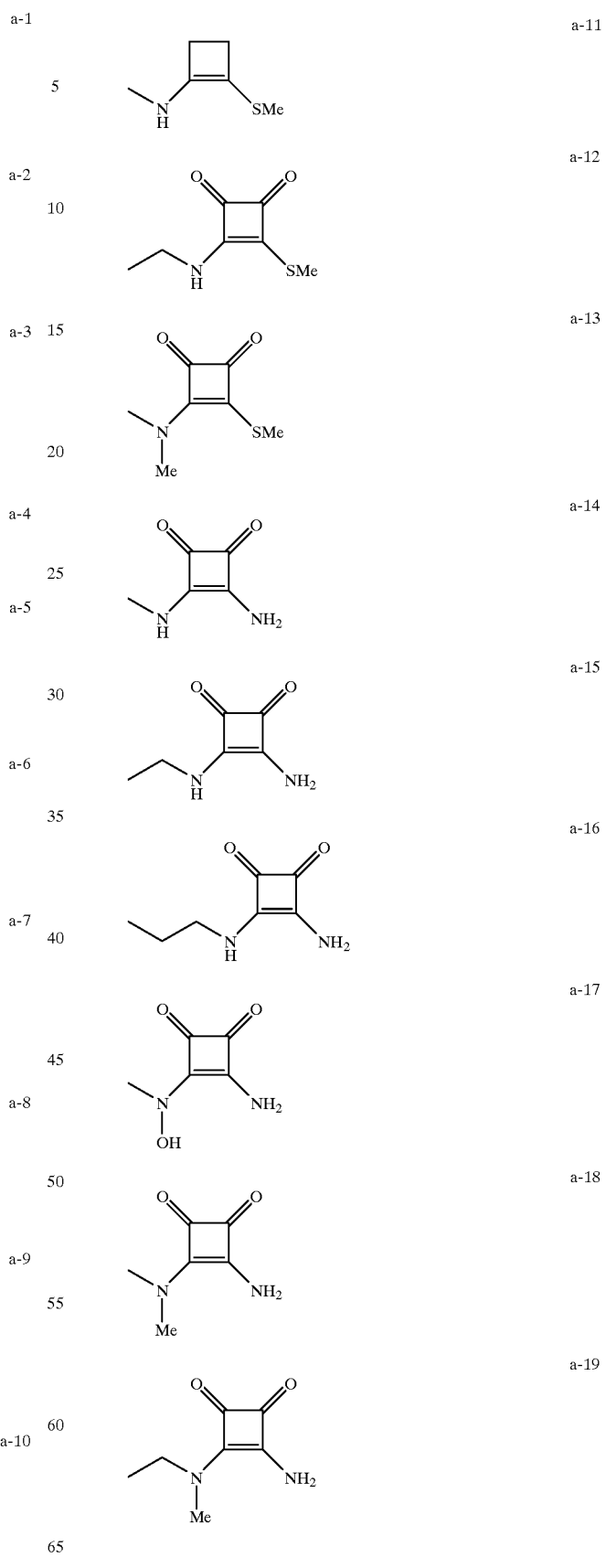

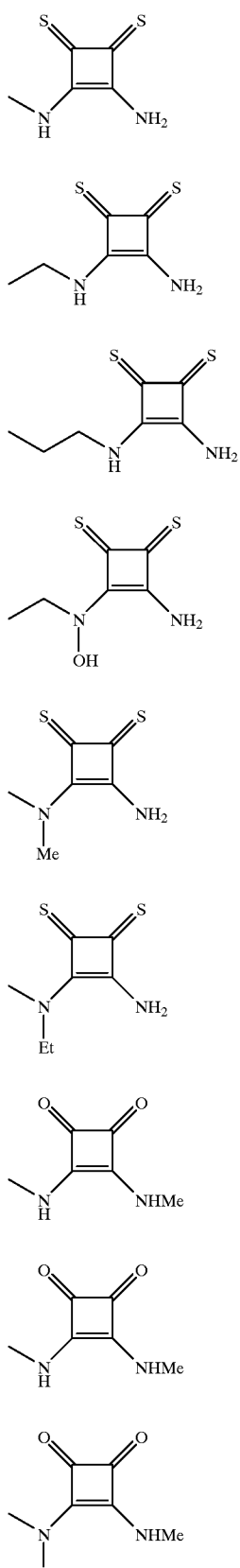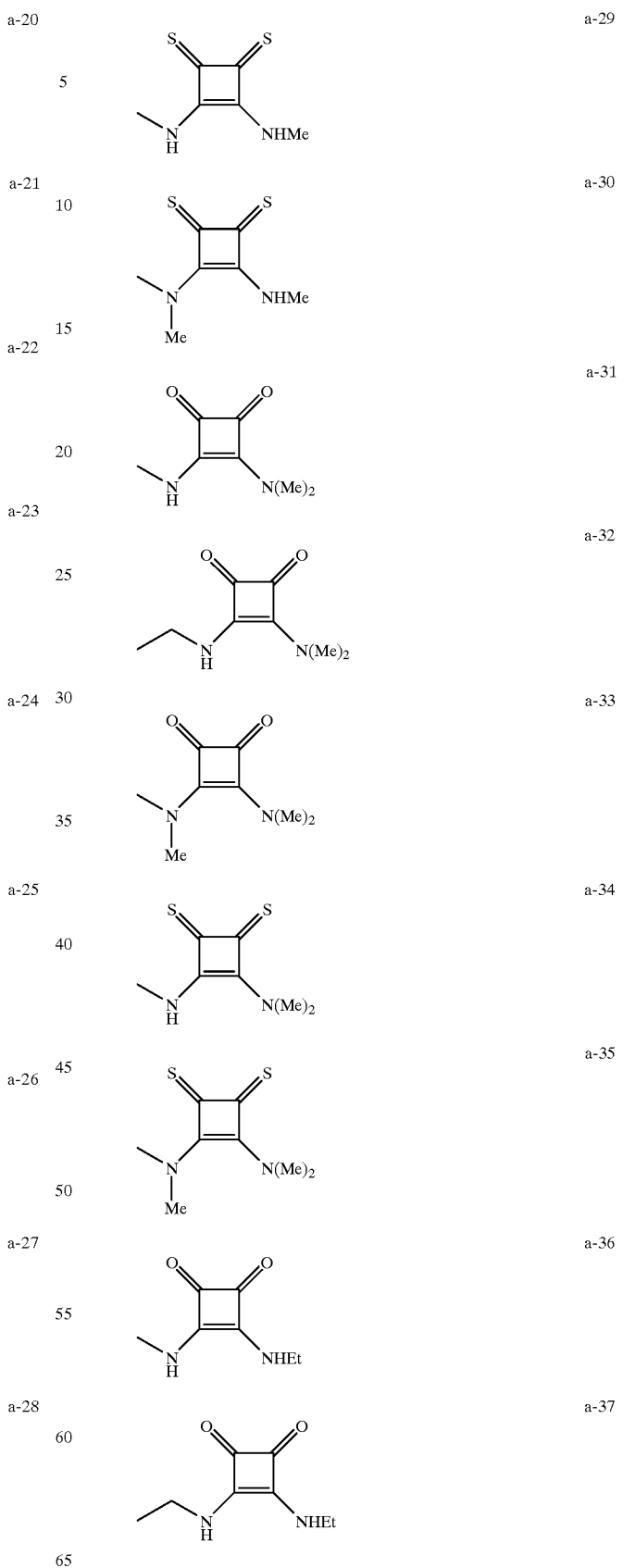

| | |
|---|---|
| a-38 | a-47 |
| a-39 | a-48 |
| a-40 | a-49 |
| a-41 | a-50 |
| a-42 | b-1 |
| a-43 | b-2 |
| a-44 | b-3 |
| a-45 | b-4 |
| a-46 | b-5 |
| | b-6 |
| | b-7 |
| | b-8 |

-continued
b-9 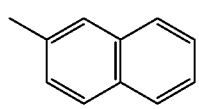
b-10 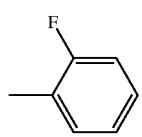
b-11 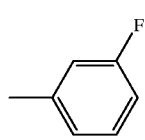
b-12 
b-13 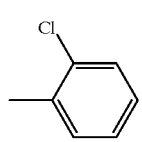
b-14 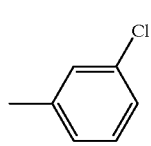
b-15 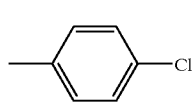
b-16 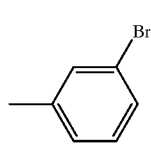
b-17 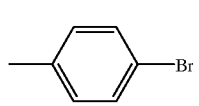
b-18 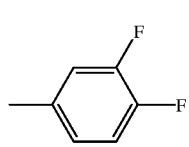
b-19 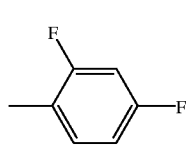
-continued
b-20 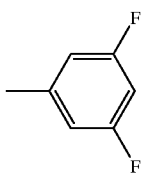
b-21 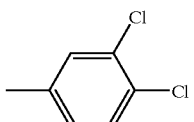
b-22 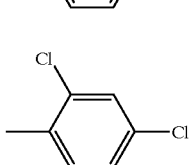
b-23 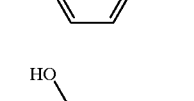
b-24 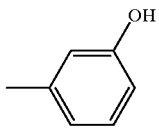
b-25 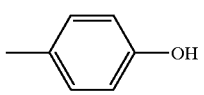
b-26 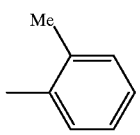
b-27 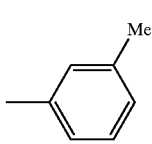
b-28 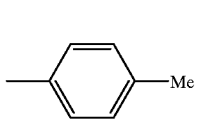
b-29 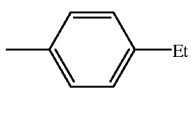
b-30 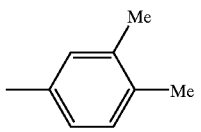

-continued
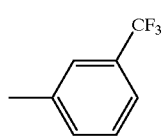 
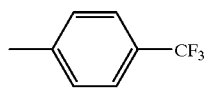
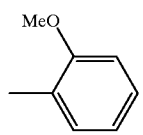
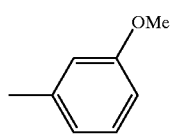
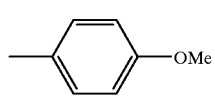
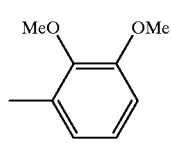
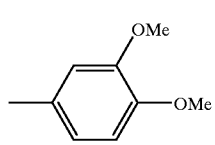
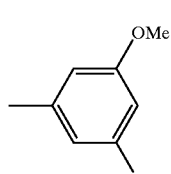
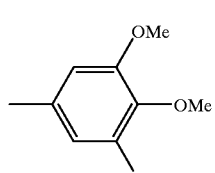
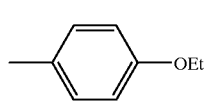
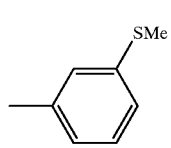
-continued
b-31 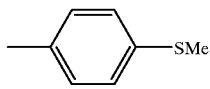
b-32 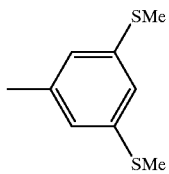
b-33 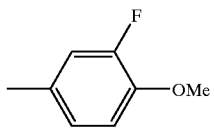
b-34 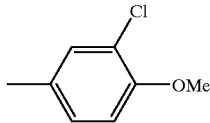
b-35 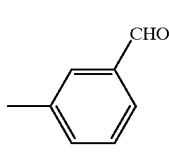
b-36 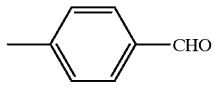
b-37 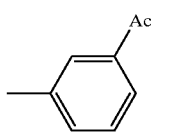
b-38 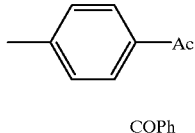
b-39 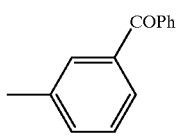
b-40 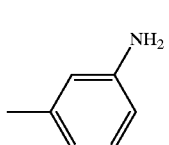
b-41 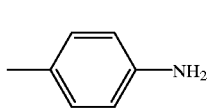
b-42
b-43
b-44
b-45
b-46
b-47
b-48
b-49
b-50
b-51
b-52
b-53

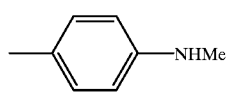 b-54
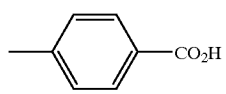 b-55
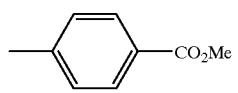 b-56
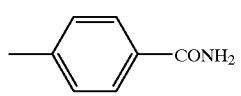 b-57
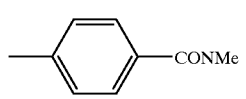 b-58
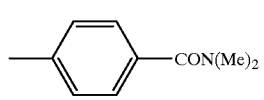 b-59
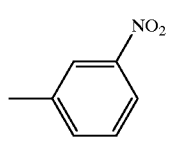 b-60
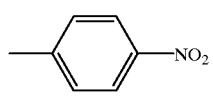 b-61
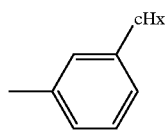 b-62
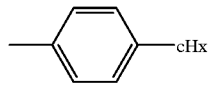 b-63
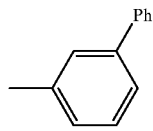 b-64
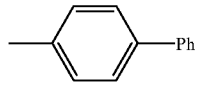 b-65
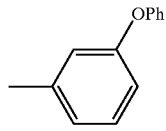 b-66
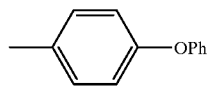 b-67
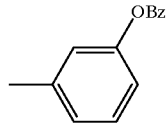 b-68
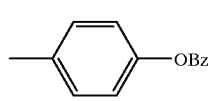 b-69
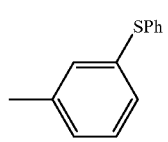 b-70
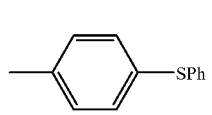 b-71
 b-72
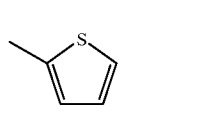 b-73
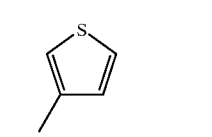 b-74
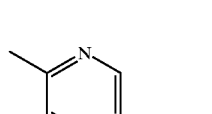 b-75
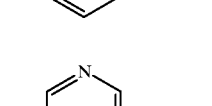 b-76
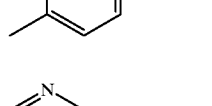 b-77
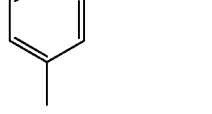 b-78
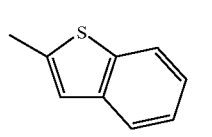

b-79 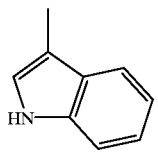
b-80 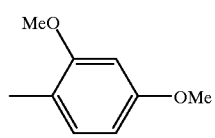
b-81 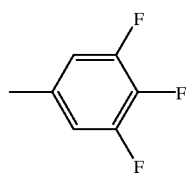
b-82 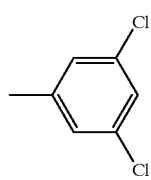
b-83 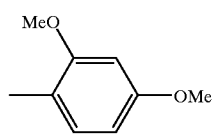
b-84 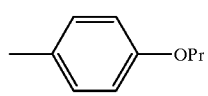
b-85 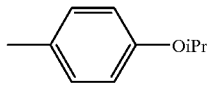
b-86 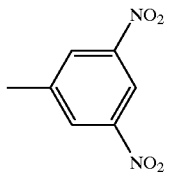
b-87 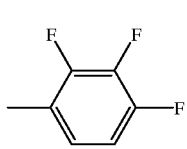
b-88 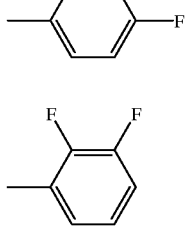
The following abbreviations are used in the Tables and in the above groups:
| | |
|---|---|
| Ac | acetyl group |
| Bz | benzyl group |
| cHx | cyclohexyl group |
| Et | ethyl group |
| Me | methyl group |
| Ph | phenyl group |
| Pr | propyl group |
| iPr | isopropyl group |
| Sub. No.: | substituent number |

TABLE 1

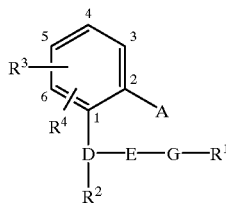

(I-1)

| Cpd. No. | R¹ Sub. No. | R² Sub. No. | R³ | R⁴ | A Sub. No. | D | E | G |
|---|---|---|---|---|---|---|---|---|
| 1-1 | (b-7) | (b-7) | H | H | (a-1) | —CH— | —NH— | —CH(Me)— |
| 1-2 | (b-7) | (b-35) | H | H | (a-1) | —CH— | —NH— | —CH(Me)— |
| 1-3 | (b-11) | (b-7) | H | H | (a-1) | —CH— | —NH— | —CH(Me)— |
| 1-4 | (b-11) | (b-35) | H | H | (a-1) | —CH— | —NH— | —CH(Me)— |
| 1-5 | (b-12) | (b-35) | H | H | (a-1) | —CH— | —NH— | —CH(Me)— |
| 1-6 | (b-15) | (b-35) | H | H | (a-1) | —CH— | —NH— | —CH(Me)— |
| 1-7 | (b-18) | (b-7) | H | H | (a-1) | —CH— | —NH— | —CH(Me)— |
| 1-8 | (b-18) | (b-35) | H | H | (a-1) | —CH— | —NH— | —CH(Me)— |
| 1-9 | (b-19) | (b-35) | H | H | (a-1) | —CH— | —NH— | —CH(Me)— |
| 1-10 | (b-20) | (b-7) | H | H | (a-1) | —CH— | —NH— | —CH(Me)— |
| 1-11 | (b-20) | (b-35) | H | H | (a-1) | —CH— | —NH— | —CH(Me)— |
| 1-12 | (b-21) | (b-35) | H | H | (a-1) | —CH— | —NH— | —CH(Me)— |
| 1-13 | (b-24) | (b-35) | H | H | (a-1) | —CH— | —NH— | —CH(Me)— |
| 1-14 | (b-25) | (b-35) | H | H | (a-1) | —CH— | —NH— | —CH(Me)— |
| 1-15 | (b-72) | (b-35) | H | H | (a-1) | —CH— | —NH— | —CH(Me)— |
| 1-16 | (b-73) | (b-7) | H | H | (a-1) | —CH— | —NH— | —CH(Me)— |
| 1-17 | (b-73) | (b-35) | H | H | (a-1) | —CH— | —NH— | —CH(Me)— |
| 1-18 | (b-74) | (b-35) | H | H | (a-1) | —CH— | —NH— | —CH(Me)— |
| 1-19 | (b-76) | (b-35) | H | H | (a-1) | —CH— | —NH— | —CH(Me)— |
| 1-20 | (b-77) | (b-7) | H | H | (a-1) | —CH— | —NH— | —CH(Me)— |
| 1-21 | (b-77) | (b-35) | H | H | (a-1) | —CH— | —NH— | —CH(Me)— |
| 1-22 | (b-11) | (b-35) | H | H | (a-2) | —CH— | —NH— | —CH(Me)— |
| 1-23 | (b-18) | (b-35) | H | H | (a-2) | —CH— | —NH— | —CH(Me)— |
| 1-24 | (b-20) | (b-35) | H | H | (a-2) | —CH— | —NH— | —CH(Me)— |
| 1-25 | (b-7) | (b-35) | H | H | (a-3) | —CH— | —NH— | —CH(Me)— |
| 1-26 | (b-11) | (b-35) | H | H | (a-3) | —CH— | —NH— | —CH(Me)— |
| 1-27 | (b-18) | (b-35) | H | H | (a-3) | —CH— | —NH— | —CH(Me)— |
| 1-28 | (b-20) | (b-35) | H | H | (a-3) | —CH— | —NH— | —CH(Me)— |
| 1-29 | (b-73) | (b-35) | H | H | (a-3) | —CH— | —NH— | —CH(Me)— |
| 1-30 | (b-77) | (b-35) | H | H | (a-3) | —CH— | —NH— | —CH(Me)— |
| 1-31 | (b-11) | (b-35) | H | H | (a-4) | —CH— | —NH— | —CH(Me)— |
| 1-32 | (b-18) | (b-35) | H | H | (a-4) | —CH— | —NH— | —CH(Me)— |
| 1-33 | (b-20) | (b-35) | H | H | (a-4) | —CH— | —NH— | —CH(Me)— |
| 1-34 | (b-7) | (b-7) | H | H | (a-5) | —CH— | —NH— | —CH(Me)— |
| 1-35 | (b-7) | (b-35) | H | H | (a-5) | —CH— | —NH— | —CH(Me)— |
| 1-36 | (b-11) | (b-7) | H | H | (a-5) | —CH— | —NH— | —CH(Me)— |
| 1-37 | (b-11) | (b-35) | H | H | (a-5) | —CH— | —NH— | —CH(Me)— |
| 1-38 | (b-12) | (b-35) | H | H | (a-5) | —CH— | —NH— | —CH(Me)— |
| 1-39 | (b-15) | (b-35) | H | H | (a-5) | —CH— | —NH— | —CH(Me)— |
| 1-40 | (b-18) | (b-7) | H | H | (a-5) | —CH— | —NH— | —CH(Me)— |
| 1-41 | (b-18) | (b-35) | H | H | (a-5) | —CH— | —NH— | —CH(Me)— |
| 1-42 | (b-19) | (b-35) | H | H | (a-5) | —CH— | —NH— | —CH(Me)— |
| 1-43 | (b-20) | (b-7) | H | H | (a-5) | —CH— | —NH— | —CH(Me)— |
| 1-44 | (b-20) | (b-35) | H | H | (a-5) | —CH— | —NH— | —CH(Me)— |
| 1-45 | (b-21) | (b-35) | H | H | (a-5) | —CH— | —NH— | —CH(Me)— |
| 1-46 | (b-24) | (b-35) | H | H | (a-5) | —CH— | —NH— | —CH(Me)— |
| 1-47 | (b-25) | (b-35) | H | H | (a-5) | —CH— | —NH— | —CH(Me)— |
| 1-48 | (b-72) | (b-35) | H | H | (a-5) | —CH— | —NH— | —CH(Me)— |
| 1-49 | (b-73) | (b-7) | H | H | (a-5) | —CH— | —NH— | —CH(Me)— |
| 1-50 | (b-73) | (b-35) | H | H | (a-5) | —CH— | —NH— | —CH(Me)— |
| 1-51 | (b-74) | (b-35) | H | H | (a-5) | —CH— | —NH— | —CH(Me)— |
| 1-52 | (b-76) | (b-35) | H | H | (a-5) | —CH— | —NH— | —CH(Me)— |
| 1-53 | (b-77) | (b-7) | H | H | (a-5) | —CH— | —NH— | —CH(Me)— |
| 1-54 | (b-77) | (b-35) | H | H | (a-5) | —CH— | —NH— | —CH(Me)— |
| 1-55 | (b-11) | (b-35) | H | H | (a-6) | —CH— | —NH— | —CH(Me)— |
| 1-56 | (b-18) | (b-35) | H | H | (a-6) | —CH— | —NH— | —CH(Me)— |
| 1-57 | (b-20) | (b-35) | H | H | (a-6) | —CH— | —NH— | —CH(Me)— |
| 1-58 | (b-7) | (b-35) | H | H | (a-7) | —CH— | —NH— | —CH(Me)— |
| 1-59 | (b-11) | (b-35) | H | H | (a-7) | —CH— | —NH— | —CH(Me)— |
| 1-60 | (b-18) | (b-35) | H | H | (a-7) | —CH— | —NH— | —CH(Me)— |
| 1-61 | (b-20) | (b-35) | H | H | (a-7) | —CH— | —NH— | —CH(Me)— |
| 1-62 | (b-73) | (b-35) | H | H | (a-7) | —CH— | —NH— | —CH(Me)— |
| 1-63 | (b-77) | (b-35) | H | H | (a-7) | —CH— | —NH— | —CH(Me)— |
| 1-64 | (b-11) | (b-35) | H | H | (a-8) | —CH— | —NH— | —CH(Me)— |
| 1-65 | (b-18) | (b-35) | H | H | (a-8) | —CH— | —NH— | —CH(Me)— |

TABLE 1-continued (I-1)

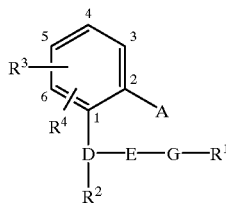

| Cpd. No. | R¹ Sub. No. | R² Sub. No. | R³ | R⁴ | A Sub. No. | D | E | G |
|---|---|---|---|---|---|---|---|---|
| 1-66 | (b-20) | (b-35) | H | H | (a-8) | —CH— | —NH— | —CH(Me)— |
| 1-67 | (b-11) | (b-35) | H | H | (a-11) | —CH— | —NH— | —CH(Me)— |
| 1-68 | (b-18) | (b-35) | H | H | (a-11) | —CH— | —NH— | —CH(Me)— |
| 1-69 | (b-20) | (b-35) | H | H | (a-11) | —CH— | —NH— | —CH(Me)— |
| 1-70 | (b-2) | (b-35) | H | H | (a-14) | —CH— | —NH— | —CH(Me)— |
| 1-71 | (b-7) | (b-7) | H | H | (a-14) | —CH— | —NH— | —CH(Me)— |
| 1-72 | (b-7) | (b-7) | H | H | (a-14) | —CH— | —NH— | —COCH(Me)— |
| 1-73 | (b-7) | (b-35) | H | H | (a-14) | —CH— | —NH— | —CH(Me)— |
| 1-74 | (b-7) | (b-35) | H | H | (a-14) | —CH— | —NH— | —COCH(Me)— |
| 1-75 | (b-8) | (b-35) | H | H | (a-14) | —CH— | —NH— | —CH(Me)— |
| 1-76 | (b-11) | (b-7) | H | H | (a-14) | —CH— | —NH— | —CH(Me)— |
| 1-77 | (b-11) | (b-7) | H | H | (a-14) | —CH— | —NH— | —COCH(Me)— |
| 1-78 | (b-11) | (b-35) | H | H | (a-14) | —CH— | —NH— | —CH(Me)— |
| 1-79 | (b-11) | (b-35) | H | H | (a-14) | —CH— | —NH— | —COCH(Me)— |
| 1-80 | (b-12) | (b-7) | H | H | (a-14) | —CH— | —NH— | —CH(Me)— |
| 1-81 | (b-12) | (b-35) | H | H | (a-14) | —CH— | —NH— | —CH(Me)— |
| 1-82 | (b-15) | (b-7) | H | H | (a-14) | —CH— | —NH— | —CH(Me)— |
| 1-83 | (b-15) | (b-35) | H | H | (a-14) | —CH— | —NH— | —CH(Me)— |
| 1-84 | (b-18) | (b-7) | H | H | (a-14) | —CH— | —NH— | —CH(Me)— |
| 1-85 | (b-18) | (b-7) | H | H | (a-14) | —CH— | —NH— | —COCH(Me)— |
| 1-86 | (b-18) | (b-35) | H | H | (a-14) | —CH— | —NH— | —CH(Me)— |
| 1-87 | (b-18) | (b-35) | H | H | (a-14) | —CH— | —NH— | —COCH(Me)— |
| 1-88 | (b-19) | (b-7) | H | H | (a-14) | —CH— | —NH— | —CH(Me)— |
| 1-89 | (b-19) | (b-35) | H | H | (a-14) | —CH— | —NH— | —CH(Me)— |
| 1-90 | (b-20) | (b-7) | H | H | (a-14) | —CH— | —NH— | —CH(Me)— |
| 1-91 | (b-20) | (b-7) | H | H | (a-14) | —CH— | —NH— | —COCH(Me)— |
| 1-92 | (b-20) | (b-35) | H | H | (a-14) | —CH— | —NH— | —CH(Me)— |
| 1-93 | (b-20) | (b-35) | H | H | (a-14) | —CH— | —NH— | —COCH(Me)— |
| 1-94 | (b-21) | (b-7) | H | H | (a-14) | —CH— | —NH— | —CH(Me)— |
| 1-95 | (b-21) | (b-35) | H | H | (a-14) | —CH— | —NH— | —CH(Me)— |
| 1-96 | (b-24) | (b-7) | H | H | (a-14) | —CH— | —NH— | —CH(Me)— |
| 1-97 | (b-24) | (b-35) | H | H | (a-14) | —CH— | —NH— | —CH(Me)— |
| 1-98 | (b-25) | (b-7) | H | H | (a-14) | —CH— | —NH— | —CH(Me)— |
| 1-99 | (b-25) | (b-35) | H | H | (a-14) | —CH— | —NH— | —CH(Me)— |
| 1-100 | (b-72) | (b-7) | H | H | (a-14) | —CH— | —NH— | —CH(Me)— |
| 1-101 | (b-72) | (b-35) | H | H | (a-14) | —CH— | —NH— | —CH(Me)— |
| 1-102 | (b-73) | (b-7) | H | H | (a-14) | —CH— | —NH— | —CH(Me)— |
| 1-103 | (b-73) | (b-7) | H | H | (a-14) | —CH— | —NH— | —COCH(Me)— |
| 1-104 | (b-73) | (b-35) | H | H | (a-14) | —CH— | —NH— | —CH(Me)— |
| 1-105 | (b-73) | (b-35) | H | H | (a-14) | —CH— | —NH— | —COCH(Me)— |
| 1-106 | (b-74) | (b-7) | H | H | (a-14) | —CH— | —NH— | —CH(Me)— |
| 1-107 | (b-74) | (b-35) | H | H | (a-14) | —CH— | —NH— | —CH(Me)— |
| 1-108 | (b-76) | (b-7) | H | H | (a-14) | —CH— | —NH— | —CH(Me)— |
| 1-109 | (b-76) | (b-35) | H | H | (a-14) | —CH— | —NH— | —CH(Me)— |
| 1-110 | (b-77) | (b-7) | H | H | (a-14) | —CH— | —NH— | —CH(Me)— |
| 1-111 | (b-77) | (b-7) | H | H | (a-14) | —CH— | —NH— | —COCH(Me)— |
| 1-112 | (b-77) | (b-35) | H | H | (a-14) | —CH— | —NH— | —CH(Me)— |
| 1-113 | (b-77) | (b-35) | H | H | (a-14) | —CH— | —NH— | —COCH(Me)— |
| 1-114 | (b-7) | (b-7) | H | H | (a-15) | —CH— | —NH— | —CH(Me)— |
| 1-115 | (b-7) | (b-35) | H | H | (a-15) | —CH— | —NH— | —CH(Me)— |
| 1-116 | (b-11) | (b-7) | H | H | (a-15) | —CH— | —NH— | —CH(Me)— |
| 1-117 | (b-11) | (b-35) | H | H | (a-15) | —CH— | —NH— | —CH(Me)— |
| 1-118 | (b-12) | (b-35) | H | H | (a-15) | —CH— | —NH— | —CH(Me)— |
| 1-119 | (b-15) | (b-35) | H | H | (a-15) | —CH— | —NH— | —CH(Me)— |
| 1-120 | (b-18) | (b-7) | H | H | (a-15) | —CH— | —NH— | —CH(Me)— |
| 1-121 | (b-18) | (b-35) | H | H | (a-15) | —CH— | —NH— | —CH(Me)— |
| 1-122 | (b-19) | (b-35) | H | H | (a-15) | —CH— | —NH— | —CH(Me)— |
| 1-123 | (b-20) | (b-7) | H | H | (a-15) | —CH— | —NH— | —CH(Me)— |
| 1-124 | (b-20) | (b-35) | H | H | (a-15) | —CH— | —NH— | —CH(Me)— |
| 1-125 | (b-21) | (b-35) | H | H | (a-15) | —CH— | —NH— | —CH(Me)— |
| 1-126 | (b-24) | (b-35) | H | H | (a-15) | —CH— | —NH— | —CH(Me)— |
| 1-127 | (b-25) | (b-35) | H | H | (a-15) | —CH— | —NH— | —CH(Me)— |
| 1-128 | (b-72) | (b-35) | H | H | (a-15) | —CH— | —NH— | —CH(Me)— |
| 1-129 | (b-73) | (b-7) | H | H | (a-15) | —CH— | —NH— | —CH(Me)— |
| 1-130 | (b-73) | (b-35) | H | H | (a-15) | —CH— | —NH— | —CH(Me)— |

TABLE 1-continued

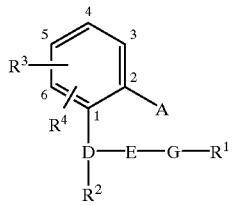

(I-1)

| Cpd. No. | R¹ Sub. No. | R² Sub. No. | R³ | R⁴ | A Sub. No. | D | E | G |
|---|---|---|---|---|---|---|---|---|
| 1-131 | (b-74) | (b-35) | H | H | (a-15) | —CH— | —NH— | —CH(Me)— |
| 1-132 | (b-76) | (b-35) | H | H | (a-15) | —CH— | —NH— | —CH(Me)— |
| 1-133 | (b-77) | (b-7) | H | H | (a-15) | —CH— | —NH— | —CH(Me)— |
| 1-134 | (b-77) | (b-35) | H | H | (a-15) | —CH— | —NH— | —CH(Me)— |
| 1-135 | (b-7) | (b-7) | H | H | (a-18) | —CH— | —NH— | —CH(Me)— |
| 1-136 | (b-7) | (b-35) | H | H | (a-18) | —CH— | —NH— | —CH(Me)— |
| 1-137 | (b-11) | (b-7) | H | H | (a-18) | —CH— | —NH— | —CH(Me)— |
| 1-138 | (b-11) | (b-35) | H | H | (a-18) | —CH— | —NH— | —CH(Me)— |
| 1-139 | (b-12) | (b-35) | H | H | (a-18) | —CH— | —NH— | —CH(Me)— |
| 1-140 | (b-15) | (b-35) | H | H | (a-18) | —CH— | —NH— | —CH(Me)— |
| 1-141 | (b-18) | (b-7) | H | H | (a-18) | —CH— | —NH— | —CH(Me)— |
| 1-142 | (b-18) | (b-35) | H | H | (a-18) | —CH— | —NH— | —CH(Me)— |
| 1-143 | (b-19) | (b-35) | H | H | (a-18) | —CH— | —NH— | —CH(Me)— |
| 1-144 | (b-20) | (b-7) | H | H | (a-18) | —CH— | —NH— | —CH(Me)— |
| 1-145 | (b-20) | (b-35) | H | H | (a-18) | —CH— | —NH— | —CH(Me)— |
| 1-146 | (b-21) | (b-35) | H | H | (a-18) | —CH— | —NH— | —CH(Me)— |
| 1-147 | (b-24) | (b-35) | H | H | (a-18) | —CH— | —NH— | —CH(Me)— |
| 1-148 | (b-25) | (b-35) | H | H | (a-18) | —CH— | —NH— | —CH(Me)— |
| 1-149 | (b-72) | (b-35) | H | H | (a-18) | —CH— | —NH— | —CH(Me)— |
| 1-150 | (b-73) | (b-7) | H | H | (a-18) | —CH— | —NH— | —CH(Me)— |
| 1-151 | (b-73) | (b-35) | H | H | (a-18) | —CH— | —NH— | —CH(Me)— |
| 1-152 | (b-74) | (b-35) | H | H | (a-18) | —CH— | —NH— | —CH(Me)— |
| 1-153 | (b-76) | (b-35) | H | H | (a-18) | —CH— | —NH— | —CH(Me)— |
| 1-154 | (b-77) | (b-7) | H | H | (a-18) | —CH— | —NH— | —CH(Me)— |
| 1-155 | (b-77) | (b-35) | H | H | (a-18) | —CH— | —NH— | —CH(Me)— |
| 1-156 | (b-7) | (b-35) | H | H | (a-19) | —CH— | —NH— | —CH(Me)— |
| 1-157 | (b-11) | (b-35) | H | H | (a-19) | —CH— | —NH— | —CH(Me)— |
| 1-158 | (b-18) | (b-35) | H | H | (a-19) | —CH— | —NH— | —CH(Me)— |
| 1-159 | (b-20) | (b-35) | H | H | (a-19) | —CH— | —NH— | —CH(Me)— |
| 1-160 | (b-73) | (b-35) | H | H | (a-19) | —CH— | —NH— | —CH(Me)— |
| 1-161 | (b-77) | (b-35) | H | H | (a-19) | —CH— | —NH— | —CH(Me)— |
| 1-162 | (b-7) | (b-7) | H | H | (a-20) | —CH— | —NH— | —CH(Me)— |
| 1-163 | (b-7) | (b-35) | H | H | (a-20) | —CH— | —NH— | —CH(Me)— |
| 1-164 | (b-11) | (b-7) | H | H | (a-20) | —CH— | —NH— | —CH(Me)— |
| 1-165 | (b-11) | (b-35) | H | H | (a-20) | —CH— | —NH— | —CH(Me)— |
| 1-166 | (b-12) | (b-35) | H | H | (a-20) | —CH— | —NH— | —CH(Me)— |
| 1-167 | (b-15) | (b-35) | H | H | (a-20) | —CH— | —NH— | —CH(Me)— |
| 1-168 | (b-18) | (b-7) | H | H | (a-20) | —CH— | —NH— | —CH(Me)— |
| 1-169 | (b-18) | (b-35) | H | H | (a-20) | —CH— | —NH— | —CH(Me)— |
| 1-170 | (b-19) | (b-35) | H | H | (a-20) | —CH— | —NH— | —CH(Me)— |
| 1-171 | (b-20) | (b-7) | H | H | (a-20) | —CH— | —NH— | —CH(Me)— |
| 1-172 | (b-20) | (b-35) | H | H | (a-20) | —CH— | —NH— | —CH(Me)— |
| 1-173 | (b-21) | (b-35) | H | H | (a-20) | —CH— | —NH— | —CH(Me)— |
| 1-174 | (b-24) | (b-35) | H | H | (a-20) | —CH— | —NH— | —CH(Me)— |
| 1-175 | (b-25) | (b-35) | H | H | (a-20) | —CH— | —NH— | —CH(Me)— |
| 1-176 | (b-72) | (b-35) | H | H | (a-20) | —CH— | —NH— | —CH(Me)— |
| 1-177 | (b-73) | (b-7) | H | H | (a-20) | —CH— | —NH— | —CH(Me)— |
| 1-178 | (b-73) | (b-35) | H | H | (a-20) | —CH— | —NH— | —CH(Me)— |
| 1-179 | (b-74) | (b-35) | H | H | (a-20) | —CH— | —NH— | —CH(Me)— |
| 1-180 | (b-76) | (b-35) | H | H | (a-20) | —CH— | —NH— | —CH(Me)— |
| 1-181 | (b-77) | (b-7) | H | H | (a-20) | —CH— | —NH— | —CH(Me)— |
| 1-182 | (b-77) | (b-35) | H | H | (a-20) | —CH— | —NH— | —CH(Me)— |
| 1-183 | (b-11) | (b-35) | H | H | (a-21) | —CH— | —NH— | —CH(Me)— |
| 1-184 | (b-18) | (b-35) | H | H | (a-21) | —CH— | —NH— | —CH(Me)— |
| 1-185 | (b-20) | (b-35) | H | H | (a-21) | —CH— | —NH— | —CH(Me)— |
| 1-186 | (b-7) | (b-35) | H | H | (a-24) | —CH— | —NH— | —CH(Me)— |
| 1-187 | (b-11) | (b-35) | H | H | (a-24) | —CH— | —NH— | —CH(Me)— |
| 1-188 | (b-18) | (b-35) | H | H | (a-24) | —CH— | —NH— | —CH(Me)— |
| 1-189 | (b-20) | (b-35) | H | H | (a-24) | —CH— | —NH— | —CH(Me)— |
| 1-190 | (b-73) | (b-35) | H | H | (a-24) | —CH— | —NH— | —CH(Me)— |
| 1-191 | (b-77) | (b-35) | H | H | (a-24) | —CH— | —NH— | —CH(Me)— |
| 1-192 | (b-7) | (b-7) | H | H | (a-26) | —CH— | —NH— | —CH(Me)— |
| 1-193 | (b-7) | (b-35) | H | H | (a-26) | —CH— | —NH— | —CH(Me)— |
| 1-194 | (b-11) | (b-7) | H | H | (a-26) | —CH— | —NH— | —CH(Me)— |
| 1-195 | (b-11) | (b-35) | H | H | (a-26) | —CH— | —NH— | —CH(Me)— |

TABLE 1-continued

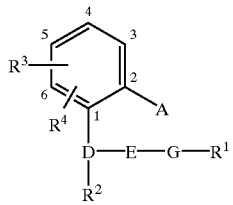

(I-1)

| Cpd. No. | R¹ Sub. No. | R² Sub. No. | R³ | R⁴ | A Sub. No. | D | E | G |
|---|---|---|---|---|---|---|---|---|
| 1-196 | (b-12) | (b-35) | H | H | (a-26) | —CH— | —NH— | —CH(Me)— |
| 1-197 | (b-15) | (b-35) | H | H | (a-26) | —CH— | —NH— | —CH(Me)— |
| 1-198 | (b-18) | (b-7) | H | H | (a-26) | —CH— | —NH— | —CH(Me)— |
| 1-199 | (b-18) | (b-35) | H | H | (a-26) | —CH— | —NH— | —CH(Me)— |
| 1-200 | (b-19) | (b-35) | H | H | (a-26) | —CH— | —NH— | —CH(Me)— |
| 1-201 | (b-20) | (b-7) | H | H | (a-26) | —CH— | —NH— | —CH(Me)— |
| 1-202 | (b-20) | (b-35) | H | H | (a-26) | —CH— | —NH— | —CH(Me)— |
| 1-203 | (b-21) | (b-35) | H | H | (a-26) | —CH— | —NH— | —CH(Me)— |
| 1-204 | (b-24) | (b-35) | H | H | (a-26) | —CH— | —NH— | —CH(Me)— |
| 1-205 | (b-25) | (b-35) | H | H | (a-26) | —CH— | —NH— | —CH(Me)— |
| 1-206 | (b-72) | (b-35) | H | H | (a-26) | —CH— | —NH— | —CH(Me)— |
| 1-207 | (b-73) | (b-7) | H | H | (a-26) | —CH— | —NH— | —CH(Me)— |
| 1-208 | (b-73) | (b-35) | H | H | (a-26) | —CH— | —NH— | —CH(Me)— |
| 1-209 | (b-74) | (b-35) | H | H | (a-26) | —CH— | —NH— | —CH(Me)— |
| 1-210 | (b-76) | (b-35) | H | H | (a-26) | —CH— | —NH— | —CH(Me)— |
| 1-211 | (b-77) | (b-7) | H | H | (a-26) | —CH— | —NH— | —CH(Me)— |
| 1-212 | (b-77) | (b-35) | H | H | (a-26) | —CH— | —NH— | —CH(Me)— |
| 1-213 | (b-11) | (b-35) | H | H | (a-27) | —CH— | —NH— | —CH(Me)— |
| 1-214 | (b-18) | (b-35) | H | H | (a-27) | —CH— | —NH— | —CH(Me)— |
| 1-215 | (b-20) | (b-35) | H | H | (a-27) | —CH— | —NH— | —CH(Me)— |
| 1-216 | (b-7) | (b-35) | H | H | (a-28) | —CH— | —NH— | —CH(Me)— |
| 1-217 | (b-11) | (b-35) | H | H | (a-28) | —CH— | —NH— | —CH(Me)— |
| 1-218 | (b-18) | (b-35) | H | H | (a-28) | —CH— | —NH— | —CH(Me)— |
| 1-219 | (b-20) | (b-35) | H | H | (a-28) | —CH— | —NH— | —CH(Me)— |
| 1-220 | (b-73) | (b-35) | H | H | (a-28) | —CH— | —NH— | —CH(Me)— |
| 1-221 | (b-77) | (b-35) | H | H | (a-28) | —CH— | —NH— | —CH(Me)— |
| 1-222 | (b-11) | (b-35) | H | H | (a-29) | —CH— | —NH— | —CH(Me)— |
| 1-223 | (b-18) | (b-35) | H | H | (a-29) | —CH— | —NH— | —CH(Me)— |
| 1-224 | (b-20) | (b-35) | H | H | (a-29) | —CH— | —NH— | —CH(Me)— |
| 1-225 | (b-7) | (b-7) | H | H | (a-31) | —CH— | —NH— | —CH(Me)— |
| 1-226 | (b-7) | (b-35) | H | H | (a-31) | —CH— | —NH— | —CH(Me)— |
| 1-227 | (b-11) | (b-7) | H | H | (a-31) | —CH— | —NH— | —CH(Me)— |
| 1-228 | (b-11) | (b-35) | H | H | (a-31) | —CH— | —NH— | —CH(Me)— |
| 1-229 | (b-12) | (b-35) | H | H | (a-31) | —CH— | —NH— | —CH(Me)— |
| 1-230 | (b-15) | (b-35) | H | H | (a-31) | —CH— | —NH— | —CH(Me)— |
| 1-231 | (b-18) | (b-7) | H | H | (a-31) | —CH— | —NH— | —CH(Me)— |
| 1-232 | (b-18) | (b-35) | H | H | (a-31) | —CH— | —NH— | —CH(Me)— |
| 1-233 | (b-19) | (b-35) | H | H | (a-31) | —CH— | —NH— | —CH(Me)— |
| 1-234 | (b-20) | (b-7) | H | H | (a-31) | —CH— | —NH— | —CH(Me)— |
| 1-235 | (b-20) | (b-35) | H | H | (a-31) | —CH— | —NH— | —CH(Me)— |
| 1-236 | (b-21) | (b-35) | H | H | (a-31) | —CH— | —NH— | —CH(Me)— |
| 1-237 | (b-24) | (b-35) | H | H | (a-31) | —CH— | —NH— | —CH(Me)— |
| 1-238 | (b-25) | (b-35) | H | H | (a-31) | —CH— | —NH— | —CH(Me)— |
| 1-239 | (b-72) | (b-35) | H | H | (a-31) | —CH— | —NH— | —CH(Me)— |
| 1-240 | (b-73) | (b-7) | H | H | (a-31) | —CH— | —NH— | —CH(Me)— |
| 1-241 | (b-73) | (b-35) | H | H | (a-31) | —CH— | —NH— | —CH(Me)— |
| 1-242 | (b-74) | (b-35) | H | H | (a-31) | —CH— | —NH— | —CH(Me)— |
| 1-243 | (b-76) | (b-35) | H | H | (a-31) | —CH— | —NH— | —CH(Me)— |
| 1-244 | (b-77) | (b-7) | H | H | (a-31) | —CH— | —NH— | —CH(Me)— |
| 1-245 | (b-77) | (b-35) | H | H | (a-31) | —CH— | —NH— | —CH(Me)— |
| 1-246 | (b-11) | (b-35) | H | H | (a-32) | —CH— | —NH— | —CH(Me)— |
| 1-247 | (b-18) | (b-35) | H | H | (a-32) | —CH— | —NH— | —CH(Me)— |
| 1-248 | (b-20) | (b-35) | H | H | (a-32) | —CH— | —NH— | —CH(Me)— |
| 1-249 | (b-7) | (b-35) | H | H | (a-33) | —CH— | —NH— | —CH(Me)— |
| 1-250 | (b-11) | (b-35) | H | H | (a-33) | —CH— | —NH— | —CH(Me)— |
| 1-251 | (b-18) | (b-35) | H | H | (a-33) | —CH— | —NH— | —CH(Me)— |
| 1-252 | (b-20) | (b-35) | H | H | (a-33) | —CH— | —NH— | —CH(Me)— |
| 1-253 | (b-73) | (b-35) | H | H | (a-33) | —CH— | —NH— | —CH(Me)— |
| 1-254 | (b-77) | (b-35) | H | H | (a-33) | —CH— | —NH— | —CH(Me)— |
| 1-255 | (b-11) | (b-35) | H | H | (a-34) | —CH— | —NH— | —CH(Me)— |
| 1-256 | (b-18) | (b-35) | H | H | (a-34) | —CH— | —NH— | —CH(Me)— |
| 1-257 | (b-20) | (b-35) | H | H | (a-34) | —CH— | —NH— | —CH(Me)— |
| 1-258 | (b-11) | (b-35) | H | H | (a-36) | —CH— | —NH— | —CH(Me)— |
| 1-259 | (b-18) | (b-35) | H | H | (a-36) | —CH— | —NH— | —CH(Me)— |
| 1-260 | (b-20) | (b-35) | H | H | (a-36) | —CH— | —NH— | —CH(Me)— |

TABLE 1-continued

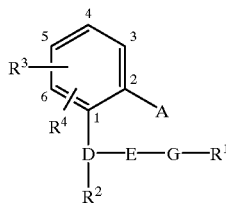
(I-1)

| Cpd. No. | R¹ Sub. No. | R² Sub. No. | R³ | R⁴ | A Sub. No. | D | E | G |
|---|---|---|---|---|---|---|---|---|
| 1-261 | (b-11) | (b-35) | H | H | (a-39) | —CH— | —NH— | —CH(Me)— |
| 1-262 | (b-18) | (b-35) | H | H | (a-39) | —CH— | —NH— | —CH(Me)— |
| 1-263 | (b-20) | (b-35) | H | H | (a-39) | —CH— | —NH— | —CH(Me)— |
| 1-264 | (b-7) | (b-7) | H | H | (a-43) | —CH— | —NH— | —CH(Me)— |
| 1-265 | (b-7) | (b-35) | H | H | (a-43) | —CH— | —NH— | —CH(Me)— |
| 1-266 | (b-11) | (b-7) | H | H | (a-43) | —CH— | —NH— | —CH(Me)— |
| 1-267 | (b-11) | (b-35) | H | H | (a-43) | —CH— | —NH— | —CH(Me)— |
| 1-268 | (b-12) | (b-35) | H | H | (a-43) | —CH— | —NH— | —CH(Me)— |
| 1-269 | (b-15) | (b-35) | H | H | (a-43) | —CH— | —NH— | —CH(Me)— |
| 1-270 | (b-18) | (b-7) | H | H | (a-43) | —CH— | —NH— | —CH(Me)— |
| 1-271 | (b-18) | (b-35) | H | H | (a-43) | —CH— | —NH— | —CH(Me)— |
| 1-272 | (b-19) | (b-35) | H | H | (a-43) | —CH— | —NH— | —CH(Me)— |
| 1-273 | (b-20) | (b-7) | H | H | (a-43) | —CH— | —NH— | —CH(Me)— |
| 1-274 | (b-20) | (b-35) | H | H | (a-43) | —CH— | —NH— | —CH(Me)— |
| 1-275 | (b-21) | (b-35) | H | H | (a-43) | —CH— | —NH— | —CH(Me)— |
| 1-276 | (b-24) | (b-35) | H | H | (a-43) | —CH— | —NH— | —CH(Me)— |
| 1-277 | (b-25) | (b-35) | H | H | (a-43) | —CH— | —NH— | —CH(Me)— |
| 1-278 | (b-72) | (b-35) | H | H | (a-43) | —CH— | —NH— | —CH(Me)— |
| 1-279 | (b-73) | (b-7) | H | H | (a-43) | —CH— | —NH— | —CH(Me)— |
| 1-280 | (b-73) | (b-35) | H | H | (a-43) | —CH— | —NH— | —CH(Me)— |
| 1-281 | (b-74) | (b-35) | H | H | (a-43) | —CH— | —NH— | —CH(Me)— |
| 1-282 | (b-76) | (b-35) | H | H | (a-43) | —CH— | —NH— | —CH(Me)— |
| 1-283 | (b-77) | (b-7) | H | H | (a-43) | —CH— | —NH— | —CH(Me)— |
| 1-284 | (b-77) | (b-35) | H | H | (a-43) | —CH— | —NH— | —CH(Me)— |
| 1-285 | (b-11) | (b-35) | H | H | (a-44) | —CH— | —NH— | —CH(Me)— |
| 1-286 | (b-18) | (b-35) | H | H | (a-44) | —CH— | —NH— | —CH(Me)— |
| 1-287 | (b-20) | (b-35) | H | H | (a-44) | —CH— | —NH— | —CH(Me)— |
| 1-288 | (b-7) | (b-35) | H | H | (a-45) | —CH— | —NH— | —CH(Me)— |
| 1-289 | (b-11) | (b-35) | H | H | (a-45) | —CH— | —NH— | —CH(Me)— |
| 1-290 | (b-18) | (b-35) | H | H | (a-45) | —CH— | —NH— | —CH(Me)— |
| 1-291 | (b-20) | (b-35) | H | H | (a-45) | —CH— | —NH— | —CH(Me)— |
| 1-292 | (b-73) | (b-35) | H | H | (a-45) | —CH— | —NH— | —CH(Me)— |
| 1-293 | (b-77) | (b-35) | H | H | (a-45) | —CH— | —NH— | —CH(Me)— |
| 1-294 | (b-11) | (b-35) | H | H | (a-46) | —CH— | —NH— | —CH(Me)— |
| 1-295 | (b-18) | (b-35) | H | H | (a-46) | —CH— | —NH— | —CH(Me)— |
| 1-296 | (b-20) | (b-35) | H | H | (a-46) | —CH— | —NH— | —CH(Me)— |

TABLE 2

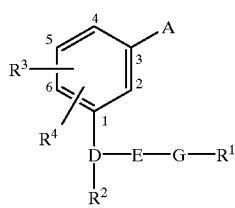
(I-2)

| Cpd. No. | R¹ Sub. No | R² Sub. No | R³ | R⁴ | A Sub. No | D | E | G |
|---|---|---|---|---|---|---|---|---|
| 2-1 | (b-2) | (b-7) | H | H | (a-1) | —CH— | —NH— | —CH(Me)— |
| 2-2 | (b-2) | (b-35) | H | H | (a-1) | —CH— | —NH— | —CH(Me)— |
| 2-3 | (b-7) | (b-7) | H | H | (a-1) | —CH— | —NH— | —CH(Me)— |
| 2-4 | (b-7) | (b-7) | H | H | (a-1) | —CH— | —NH— | —COCH(Me)— |
| 2-5 | (b-7) | (b-12) | H | H | (a-1) | —CH— | —NH— | —CH(Me)— |
| 2-6 | (b-7) | (b-15) | H | H | (a-1) | —CH— | —NH— | —CH(Me)— |
| 2-7 | (b-7) | (b-34) | H | H | (a-1) | —CH— | —NH— | —CH(Me)— |
| 2-8 | (b-7) | (b-35) | H | H | (a-1) | —CH— | —NH— | —CH(Me)— |
| 2-9 | (b-7) | (b-35) | H | H | (a-1) | —CH— | —NH— | —COCH(Me)— |

TABLE 2-continued (I-2)

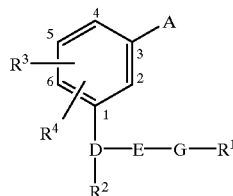

| Cpd. No. | R¹ Sub. No | R² Sub. No | R³ | R⁴ | A Sub. No | D | E | G |
|---|---|---|---|---|---|---|---|---|
| 2-10 | (b-7) | (b-37) | H | H | (a-1) | —CH— | —NH— | —CH(Me)— |
| 2-11 | (b-7) | (b-73) | H | H | (a-1) | —CH— | —NH— | —CH(Me)— |
| 2-12 | (b-7) | (b-77) | H | H | (a-1) | —CH— | —NH— | —CH(Me)— |
| 2-13 | (b-8) | (b-35) | H | H | (a-1) | —CH— | —NH— | —CH(Me)— |
| 2-14 | (b-9) | (b-35) | H | H | (a-1) | —CH— | —NH— | —CH(Me)— |
| 2-15 | (b-10) | (b-35) | H | H | (a-1) | —CH— | —NH— | —CH(Me)— |
| 2-16 | (b-11) | (b-7) | H | H | (a-1) | —CH— | —NH— | —CH(Me)— |
| 2-17 | (b-11) | (b-7) | H | H | (a-1) | —CH— | —NH— | —COCH(Me)— |
| 2-18 | (b-11) | (b-12) | H | H | (a-1) | —CH— | —NH— | —CH(Me)— |
| 2-19 | (b-11) | (b-15) | H | H | (a-1) | —CH— | —NH— | —CH(Me)— |
| 2-20 | (b-11) | (b-34) | H | H | (a-1) | —CH— | —NH— | —CH(Me)— |
| 2-21 | (b-11) | (b-35) | H | H | (a-1) | —CH— | —NH— | —CH(Me)— |
| 2-22 | (b-11) | (b-35) | H | H | (a-1) | —CH— | —NH— | —COCH(Me)— |
| 2-23 | (b-11) | (b-37) | H | H | (a-1) | —CH— | —NH— | —CH(Me)— |
| 2-24 | (b-11) | (b-73) | H | H | (a-1) | —CH— | —NH— | —CH(Me)— |
| 2-25 | (b-11) | (b-77) | H | H | (a-1) | —CH— | —NH— | —CH(Me)— |
| 2-26 | (b-12) | (b-7) | H | H | (a-1) | —CH— | —NH— | —CH(Me)— |
| 2-27 | (b-12) | (b-7) | H | H | (a-1) | —CH— | —NH— | —COCH(Me)— |
| 2-28 | (b-12) | (b-35) | H | H | (a-1) | —CH— | —NH— | —CH(Me)— |
| 2-29 | (b-12) | (b-35) | H | H | (a-1) | —CH— | —NH— | —COCH(Me)— |
| 2-30 | (b-13) | (b-35) | H | H | (a-1) | —CH— | —NH— | —CH(Me)— |
| 2-31 | (b-14) | (b-35) | H | H | (a-1) | —CH— | —NH— | —CH(Me)— |
| 2-32 | (b-15) | (b-7) | H | H | (a-1) | —CH— | —NH— | —CH(Me)— |
| 2-33 | (b-15) | (b-7) | H | H | (a-1) | —CH— | —NH— | —COCH(Me)— |
| 2-34 | (b-15) | (b-35) | H | H | (a-1) | —CH— | —NH— | —CH(Me)— |
| 2-35 | (b-15) | (b-35) | H | H | (a-1) | —CH— | —NH— | —COCH(Me)— |
| 2-36 | (b-17) | (b-35) | H | H | (a-1) | —CH— | —NH— | —CH(Me)— |
| 2-37 | (b-18) | (b-7) | H | H | (a-1) | —CH— | —NH— | —CH(Me)— |
| 2-38 | (b-18) | (b-7) | H | H | (a-1) | —CH— | —NH— | —COCH(Me)— |
| 2-39 | (b-18) | (b-12) | H | H | (a-1) | —CH— | —NH— | —CH(Me)— |
| 2-40 | (b-18) | (b-15) | H | H | (a-1) | —CH— | —NH— | —CH(Me)— |
| 2-41 | (b-18) | (b-34) | H | H | (a-1) | —CH— | —NH— | —CH(Me)— |
| 2-42 | (b-18) | (b-35) | H | H | (a-1) | —CH— | —NH— | —CH(Me)— |
| 2-43 | (b-18) | (b-35) | H | H | (a-1) | —CH— | —NH— | —COCH(Me)— |
| 2-44 | (b-18) | (b-37) | H | H | (a-1) | —CH— | —NH— | —CH(Me)— |
| 2-45 | (b-18) | (b-73) | H | H | (a-1) | —CH— | —NH— | —CH(Me)— |
| 2-46 | (b-18) | (b-77) | H | H | (a-1) | —CH— | —NH— | —CH(Me)— |
| 2-47 | (b-19) | (b-7) | H | H | (a-1) | —CH— | —NH— | —CH(Me)— |
| 2-48 | (b-19) | (b-7) | H | H | (a-1) | —CH— | —NH— | —COCH(Me)— |
| 2-49 | (b-19) | (b-35) | H | H | (a-1) | —CH— | —NH— | —CH(Me)— |
| 2-50 | (b-19) | (b-35) | H | H | (a-1) | —CH— | —NH— | —COCH(Me)— |
| 2-51 | (b-20) | (b-7) | H | H | (a-1) | —CH— | —NH— | —CH(Me)— |
| 2-52 | (b-20) | (b-7) | H | H | (a-1) | —CH— | —NH— | —COCH(Me)— |
| 2-53 | (b-20) | (b-12) | H | H | (a-1) | —CH— | —NH— | —CH(Me)— |
| 2-54 | (b-20) | (b-15) | H | H | (a-1) | —CH— | —NH— | —CH(Me)— |
| 2-55 | (b-20) | (b-34) | H | H | (a-1) | —CH— | —NH— | —CH(Me)— |
| 2-56 | (b-20) | (b-35) | H | H | (a-1) | —CH— | —NH— | —CH(Me)— |
| 2-57 | (b-20) | (b-35) | H | H | (a-1) | —CH— | —NH— | —COCH(Me)— |
| 2-58 | (b-20) | (b-37) | H | H | (a-1) | —CH— | —NH— | —CH(Me)— |
| 2-59 | (b-20) | (b-73) | H | H | (a-1) | —CH— | —NH— | —CH(Me)— |
| 2-60 | (b-20) | (b-77) | H | H | (a-1) | —CH— | —NH— | —CH(Me)— |
| 2-61 | (b-21) | (b-7) | H | H | (a-1) | —CH— | —NH— | —CH(Me)— |
| 2-62 | (b-21) | (b-7) | H | H | (a-1) | —CH— | —NH— | —COCH(Me)— |
| 2-63 | (b-21) | (b-35) | H | H | (a-1) | —CH— | —NH— | —CH(Me)— |
| 2-64 | (b-21) | (b-35) | H | H | (a-1) | —CH— | —NH— | —COCH(Me)— |
| 2-65 | (b-23) | (b-35) | H | H | (a-1) | —CH— | —NH— | —CH(Me)— |
| 2-66 | (b-24) | (b-7) | H | H | (a-1) | —CH— | —NH— | —CH(Me)— |
| 2-67 | (b-24) | (b-7) | H | H | (a-1) | —CH— | —NH— | —COCH(Me)— |
| 2-68 | (b-24) | (b-35) | H | H | (a-1) | —CH— | —NH— | —CH(Me)— |
| 2-69 | (b-24) | (b-35) | H | H | (a-1) | —CH— | —NH— | —COCH(Me)— |
| 2-70 | (b-25) | (b-7) | H | H | (a-1) | —CH— | —NH— | —CH(Me)— |
| 2-71 | (b-25) | (b-7) | H | H | (a-1) | —CH— | —NH— | —COCH(Me)— |
| 2-72 | (b-25) | (b-35) | H | H | (a-1) | —CH— | —NH— | —CH(Me)— |
| 2-73 | (b-25) | (b-35) | H | H | (a-1) | —CH— | —NH— | —COCH(Me)— |

TABLE 2-continued

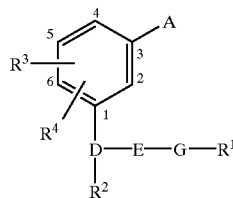

(I-2)

| Cpd. No. | R¹ Sub. No | R² Sub. No | R³ | R⁴ | A Sub. No | D | E | G |
|---|---|---|---|---|---|---|---|---|
| 2-74 | (b-35) | (b-35) | H | H | (a-1) | —CH— | —NH— | —CH(Me)— |
| 2-75 | (b-72) | (b-7) | H | H | (a-1) | —CH— | —NH— | —CH(Me)— |
| 2-76 | (b-72) | (b-7) | H | H | (a-1) | —CH— | —NH— | —COCH(Me)— |
| 2-77 | (b-72) | (b-35) | H | H | (a-1) | —CH— | —NH— | —CH(Me)— |
| 2-78 | (b-72) | (b-35) | H | H | (a-1) | —CH— | —NH— | —COCH(Me)— |
| 2-79 | (b-73) | (b-7) | H | H | (a-1) | —CH— | —NH— | —CH(Me)— |
| 2-80 | (b-73) | (b-7) | H | H | (a-1) | —CH— | —NH— | —COCH(Me)— |
| 2-81 | (b-73) | (b-12) | H | H | (a-1) | —CH— | —NH— | —CH(Me)— |
| 2-82 | (b-73) | (b-15) | H | H | (a-1) | —CH— | —NH— | —CH(Me)— |
| 2-83 | (b-73) | (b-34) | H | H | (a-1) | —CH— | —NH— | —CH(Me)— |
| 2-84 | (b-73) | (b-35) | H | H | (a-1) | —CH— | —NH— | —CH(Me)— |
| 2-85 | (b-73) | (b-35) | H | H | (a-1) | —CH— | —NH— | —COCH(Me)— |
| 2-86 | (b-73) | (b-37) | H | H | (a-1) | —CH— | —NH— | —CH(Me)— |
| 2-87 | (b-73) | (b-73) | H | H | (a-1) | —CH— | —NH— | —CH(Me)— |
| 2-88 | (b-73) | (b-77) | H | H | (a-1) | —CH— | —NH— | —CH(Me)— |
| 2-89 | (b-74) | (b-7) | H | H | (a-1) | —CH— | —NH— | —CH(Me)— |
| 2-90 | (b-74) | (b-7) | H | H | (a-1) | —CH— | —NH— | —COCH(Me)— |
| 2-91 | (b-74) | (b-35) | H | H | (a-1) | —CH— | —NH— | —CH(Me)— |
| 2-92 | (b-74) | (b-35) | H | H | (a-1) | —CH— | —NH— | —COCH(Me)— |
| 2-93 | (b-75) | (b-35) | H | H | (a-1) | —CH— | —NH— | —CH(Me)— |
| 2-94 | (b-76) | (b-7) | H | H | (a-1) | —CH— | —NH— | —CH(Me)— |
| 2-95 | (b-76) | (b-7) | H | H | (a-1) | —CH— | —NH— | —COCH(Me)— |
| 2-96 | (b-76) | (b-35) | H | H | (a-1) | —CH— | —NH— | —CH(Me)— |
| 2-97 | (b-76) | (b-35) | H | H | (a-1) | —CH— | —NH— | —COCH(Me)— |
| 2-98 | (b-77) | (b-7) | H | H | (a-1) | —CH— | —NH— | —CH(Me)— |
| 2-99 | (b-77) | (b-7) | H | H | (a-1) | —CH— | —NH— | —COCH(Me)— |
| 2-100 | (b-77) | (b-12) | H | H | (a-1) | —CH— | —NH— | —CH(Me)— |
| 2-101 | (b-77) | (b-15) | H | H | (a-1) | —CH— | —NH— | —CH(Me)— |
| 2-102 | (b-77) | (b-34) | H | H | (a-1) | —CH— | —NH— | —CH(Me)— |
| 2-103 | (b-77) | (b-35) | H | H | (a-1) | —CH— | —NH— | —CH(Me)— |
| 2-104 | (b-77) | (b-35) | H | H | (a-1) | —CH— | —NH— | —COCH(Me)— |
| 2-105 | (b-77) | (b-37) | H | H | (a-1) | —CH— | —NH— | —CH(Me)— |
| 2-106 | (b-77) | (b-73) | H | H | (a-1) | —CH— | —NH— | —CH(Me)— |
| 2-107 | (b-77) | (b-77) | H | H | (a-1) | —CH— | —NH— | —CH(Me)— |
| 2-108 | (b-78) | (b-35) | H | H | (a-1) | —CH— | —NH— | —CH(Me)— |
| 2-109 | (b-79) | (b-35) | H | H | (a-1) | —CH— | —NH— | —CH(Me)— |
| 2-110 | (b-7) | (b-7) | H | H | (a-2) | —CH— | —NH— | —CH(Me)— |
| 2-111 | (b-7) | (b-35) | H | H | (a-2) | —CH— | —NH— | —CH(Me)— |
| 2-112 | (b-11) | (b-7) | H | H | (a-2) | —CH— | —NH— | —CH(Me)— |
| 2-113 | (b-11) | (b-35) | H | H | (a-2) | —CH— | —NH— | —CH(Me)— |
| 2-114 | (b-12) | (b-35) | H | H | (a-2) | —CH— | —NH— | —CH(Me)— |
| 2-115 | (b-15) | (b-35) | H | H | (a-2) | —CH— | —NH— | —CH(Me)— |
| 2-116 | (b-18) | (b-7) | H | H | (a-2) | —CH— | —NH— | —CH(Me)— |
| 2-117 | (b-18) | (b-35) | H | H | (a-2) | —CH— | —NH— | —CH(Me)— |
| 2-118 | (b-19) | (b-35) | H | H | (a-2) | —CH— | —NH— | —CH(Me)— |
| 2-119 | (b-20) | (b-7) | H | H | (a-2) | —CH— | —NH— | —CH(Me)— |
| 2-120 | (b-20) | (b-35) | H | H | (a-2) | —CH— | —NH— | —CH(Me)— |
| 2-121 | (b-21) | (b-35) | H | H | (a-2) | —CH— | —NH— | —CH(Me)— |
| 2-122 | (b-24) | (b-35) | H | H | (a-2) | —CH— | —NH— | —CH(Me)— |
| 2-123 | (b-25) | (b-35) | H | H | (a-2) | —CH— | —NH— | —CH(Me)— |
| 2-124 | (b-72) | (b-35) | H | H | (a-2) | —CH— | —NH— | —CH(Me)— |
| 2-125 | (b-73) | (b-7) | H | H | (a-2) | —CH— | —NH— | —CH(Me)— |
| 2-126 | (b-73) | (b-35) | H | H | (a-2) | —CH— | —NH— | —CH(Me)— |
| 2-127 | (b-74) | (b-35) | H | H | (a-2) | —CH— | —NH— | —CH(Me)— |
| 2-128 | (b-76) | (b-35) | H | H | (a-2) | —CH— | —NH— | —CH(Me)— |
| 2-129 | (b-77) | (b-7) | H | H | (a-2) | —CH— | —NH— | —CH(Me)— |
| 2-130 | (b-77) | (b-35) | H | H | (a-2) | —CH— | —NH— | —CH(Me)— |
| 2-131 | (b-2) | (b-35) | H | H | (a-3) | —CH— | —NH— | —CH(Me)— |
| 2-132 | (b-7) | (b-7) | H | H | (a-3) | —CH— | —NH— | —CH(Me)— |
| 2-133 | (b-7) | (b-7) | H | H | (a-3) | —CH— | —NH— | —COCH(Me)— |
| 2-134 | (b-7) | (b-35) | H | H | (a-3) | —CH— | —NH— | —CH(Me)— |
| 2-135 | (b-7) | (b-35) | H | H | (a-3) | —CH— | —NH— | —COCH(Me)— |
| 2-136 | (b-8) | (b-35) | H | H | (a-3) | —CH— | —NH— | —CH(Me)— |
| 2-137 | (b-11) | (b-7) | H | H | (a-3) | —CH— | —NH— | —CH(Me)— |

TABLE 2-continued

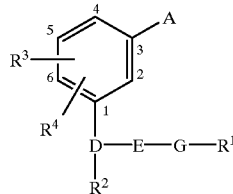

(I-2)

| Cpd. No. | R¹ Sub. No | R² Sub. No | R³ | R⁴ | A Sub. No | D | E | G |
|---|---|---|---|---|---|---|---|---|
| 2-138 | (b-11) | (b-7) | H | H | (a-3) | —CH— | —NH— | —COCH(Me)— |
| 2-139 | (b-11) | (b-35) | H | H | (a-3) | —CH— | —NH— | —CH(Me)— |
| 2-140 | (b-11) | (b-35) | H | H | (a-3) | —CH— | —NH— | —COCH(Me)— |
| 2-141 | (b-12) | (b-7) | H | H | (a-3) | —CH— | —NH— | —CH(Me)— |
| 2-142 | (b-12) | (b-35) | H | H | (a-3) | —CH— | —NH— | —CH(Me)— |
| 2-143 | (b-15) | (b-7) | H | H | (a-3) | —CH— | —NH— | —CH(Me)— |
| 2-144 | (b-15) | (b-35) | H | H | (a-3) | —CH— | —NH— | —CH(Me)— |
| 2-145 | (b-18) | (b-7) | H | H | (a-3) | —CH— | —NH— | —CH(Me)— |
| 2-146 | (b-18) | (b-7) | H | H | (a-3) | —CH— | —NH— | —COCH(Me)— |
| 2-147 | (b-18) | (b-35) | H | H | (a-3) | —CH— | —NH— | —CH(Me)— |
| 2-148 | (b-18) | (b-35) | H | H | (a-3) | —CH— | —NH— | —COCH(Me)— |
| 2-149 | (b-19) | (b-7) | H | H | (a-3) | —CH— | —NH— | —CH(Me)— |
| 2-150 | (b-19) | (b-35) | H | H | (a-3) | —CH— | —NH— | —CH(Me)— |
| 2-151 | (b-20) | (b-7) | H | H | (a-3) | —CH— | —NH— | —CH(Me)— |
| 2-152 | (b-20) | (b-7) | H | H | (a-3) | —CH— | —NH— | —COCH(Me)— |
| 2-153 | (b-20) | (b-35) | H | H | (a-3) | —CH— | —NH— | —CH(Me)— |
| 2-154 | (b-20) | (b-35) | H | H | (a-3) | —CH— | —NH— | —COCH(Me)— |
| 2-155 | (b-21) | (b-7) | H | H | (a-3) | —CH— | —NH— | —CH(Me)— |
| 2-156 | (b-21) | (b-35) | H | H | (a-3) | —CH— | —NH— | —CH(Me)— |
| 2-157 | (b-24) | (b-7) | H | H | (a-3) | —CH— | —NH— | —CH(Me)— |
| 2-158 | (b-24) | (b-35) | H | H | (a-3) | —CH— | —NH— | —CH(Me)— |
| 2-159 | (b-25) | (b-7) | H | H | (a-3) | —CH— | —NH— | —CH(Me)— |
| 2-160 | (b-25) | (b-35) | H | H | (a-3) | —CH— | —NH— | —CH(Me)— |
| 2-161 | (b-72) | (b-7) | H | H | (a-3) | —CH— | —NH— | —CH(Me)— |
| 2-162 | (b-72) | (b-35) | H | H | (a-3) | —CH— | —NH— | —CH(Me)— |
| 2-163 | (b-73) | (b-7) | H | H | (a-3) | —CH— | —NH— | —CH(Me)— |
| 2-164 | (b-73) | (b-7) | H | H | (a-3) | —CH— | —NH— | —COCH(Me)— |
| 2-165 | (b-73) | (b-35) | H | H | (a-3) | —CH— | —NH— | —CH(Me)— |
| 2-166 | (b-73) | (b-35) | H | H | (a-3) | —CH— | —NH— | —COCH(Me)— |
| 2-167 | (b-74) | (b-7) | H | H | (a-3) | —CH— | —NH— | —CH(Me)— |
| 2-168 | (b-74) | (b-35) | H | H | (a-3) | —CH— | —NH— | —CH(Me)— |
| 2-169 | (b-76) | (b-7) | H | H | (a-3) | —CH— | —NH— | —CH(Me)— |
| 2-170 | (b-76) | (b-35) | H | H | (a-3) | —CH— | —NH— | —CH(Me)— |
| 2-171 | (b-77) | (b-7) | H | H | (a-3) | —CH— | —NH— | —CH(Me)— |
| 2-172 | (b-77) | (b-7) | H | H | (a-3) | —CH— | —NH— | —COCH(Me)— |
| 2-173 | (b-77) | (b-35) | H | H | (a-3) | —CH— | —NH— | —CH(Me)— |
| 2-174 | (b-77) | (b-35) | H | H | (a-3) | —CH— | —NH— | —COCH(Me)— |
| 2-175 | (b-7) | (b-7) | H | H | (a-4) | —CH— | —NH— | —CH(Me)— |
| 2-176 | (b-7) | (b-35) | H | H | (a-4) | —CH— | —NH— | —CH(Me)— |
| 2-177 | (b-11) | (b-7) | H | H | (a-4) | —CH— | —NH— | —CH(Me)— |
| 2-178 | (b-11) | (b-35) | H | H | (a-4) | —CH— | —NH— | —CH(Me)— |
| 2-179 | (b-12) | (b-35) | H | H | (a-4) | —CH— | —NH— | —CH(Me)— |
| 2-180 | (b-15) | (b-35) | H | H | (a-4) | —CH— | —NH— | —CH(Me)— |
| 2-181 | (b-18) | (b-7) | H | H | (a-4) | —CH— | —NH— | —CH(Me)— |
| 2-182 | (b-18) | (b-35) | H | H | (a-4) | —CH— | —NH— | —CH(Me)— |
| 2-183 | (b-19) | (b-35) | H | H | (a-4) | —CH— | —NH— | —CH(Me)— |
| 2-184 | (b-20) | (b-7) | H | H | (a-4) | —CH— | —NH— | —CH(Me)— |
| 2-185 | (b-20) | (b-35) | H | H | (a-4) | —CH— | —NH— | —CH(Me)— |
| 2-186 | (b-21) | (b-35) | H | H | (a-4) | —CH— | —NH— | —CH(Me)— |
| 2-187 | (b-24) | (b-35) | H | H | (a-4) | —CH— | —NH— | —CH(Me)— |
| 2-188 | (b-25) | (b-35) | H | H | (a-4) | —CH— | —NH— | —CH(Me)— |
| 2-189 | (b-72) | (b-35) | H | H | (a-4) | —CH— | —NH— | —CH(Me)— |
| 2-190 | (b-73) | (b-7) | H | H | (a-4) | —CH— | —NH— | —CH(Me)— |
| 2-191 | (b-73) | (b-35) | H | H | (a-4) | —CH— | —NH— | —CH(Me)— |
| 2-192 | (b-74) | (b-35) | H | H | (a-4) | —CH— | —NH— | —CH(Me)— |
| 2-193 | (b-76) | (b-35) | H | H | (a-4) | —CH— | —NH— | —CH(Me)— |
| 2-194 | (b-77) | (b-7) | H | H | (a-4) | —CH— | —NH— | —CH(Me)— |
| 2-195 | (b-77) | (b-35) | H | H | (a-4) | —CH— | —NH— | —CH(Me)— |
| 2-196 | (b-2) | (b-7) | H | H | (a-5) | —CH— | —NH— | —CH(Me)— |
| 2-197 | (b-2) | (b-35) | H | H | (a-5) | —CH— | —NH— | —CH(Me)— |
| 2-198 | (b-7) | (b-7) | H | H | (a-5) | —CH— | —NH— | —CH(Me)— |
| 2-199 | (b-7) | (b-7) | H | H | (a-5) | —CH— | —NH— | —COCH(Me)— |
| 2-200 | (b-7) | (b-12) | H | H | (a-5) | —CH— | —NH— | —CH(Me)— |
| 2-201 | (b-7) | (b-15) | H | H | (a-5) | —CH— | —NH— | —CH(Me)— |

TABLE 2-continued

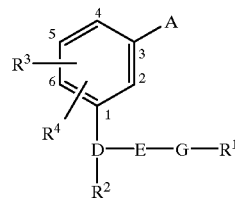

(I-2)

| Cpd. No. | R$^1$ Sub. No | R$^2$ Sub. No | R$^3$ | R$^4$ | A Sub. No | D | E | G |
|---|---|---|---|---|---|---|---|---|
| 2-202 | (b-7) | (b-34) | H | H | (a-5) | —CH— | —NH— | —CH(Me)— |
| 2-203 | (b-7) | (b-35) | H | H | (a-5) | —CH— | —NH— | —CH(Me)— |
| 2-204 | (b-7) | (b-35) | H | H | (a-5) | —CH— | —NH— | —COCH(Me)— |
| 2-205 | (b-7) | (b-37) | H | H | (a-5) | —CH— | —NH— | —CH(Me)— |
| 2-206 | (b-7) | (b-73) | H | H | (a-5) | —CH— | —NH— | —CH(Me)— |
| 2-207 | (b-7) | (b-77) | H | H | (a-5) | —CH— | —NH— | —CH(Me)— |
| 2-208 | (b-8) | (b-35) | H | H | (a-5) | —CH— | —NH— | —CH(Me)— |
| 2-209 | (b-9) | (b-35) | H | H | (a-5) | —CH— | —NH— | —CH(Me)— |
| 2-210 | (b-10) | (b-35) | H | H | (a-5) | —CH— | —NH— | —CH(Me)— |
| 2-211 | (b-11) | (b-7) | H | H | (a-5) | —CH— | —NH— | —CH(Me)— |
| 2-212 | (b-11) | (b-7) | H | H | (a-5) | —CH— | —NH— | —COCH(Me)— |
| 2-213 | (b-11) | (b-12) | H | H | (a-5) | —CH— | —NH— | —CH(Me)— |
| 2-214 | (b-11) | (b-15) | H | H | (a-5) | —CH— | —NH— | —CH(Me)— |
| 2-215 | (b-11) | (b-34) | H | H | (a-5) | —CH— | —NH— | —CH(Me)— |
| 2-216 | (b-11) | (b-35) | H | H | (a-5) | —CH— | —NH— | —CH(Me)— |
| 2-217 | (b-11) | (b-35) | H | H | (a-5) | —CH— | —NH— | —COCH(Me)— |
| 2-218 | (b-11) | (b-37) | H | H | (a-5) | —CH— | —NH— | —CH(Me)— |
| 2-219 | (b-11) | (b-73) | H | H | (a-5) | —CH— | —NH— | —CH(Me)— |
| 2-220 | (b-11) | (b-77) | H | H | (a-5) | —CH— | —NH— | —CH(Me)— |
| 2-221 | (b-12) | (b-7) | H | H | (a-5) | —CH— | —NH— | —CH(Me)— |
| 2-222 | (b-12) | (b-7) | H | H | (a-5) | —CH— | —NH— | —COCH(Me)— |
| 2-223 | (b-12) | (b-35) | H | H | (a-5) | —CH— | —NH— | —CH(Me)— |
| 2-224 | (b-12) | (b-35) | H | H | (a-5) | —CH— | —NH— | —COCH(Me)— |
| 2-225 | (b-13) | (b-35) | H | H | (a-5) | —CH— | —NH— | —CH(Me)— |
| 2-226 | (b-14) | (b-35) | H | H | (a-5) | —CH— | —NH— | —CH(Me)— |
| 2-227 | (b-15) | (b-7) | H | H | (a-5) | —CH— | —NH— | —CH(Me)— |
| 2-228 | (b-15) | (b-7) | H | H | (a-5) | —CH— | —NH— | —COCH(Me)— |
| 2-229 | (b-15) | (b-35) | H | H | (a-5) | —CH— | —NH— | —CH(Me)— |
| 2-230 | (b-15) | (b-35) | H | H | (a-5) | —CH— | —NH— | —COCH(Me)— |
| 2-231 | (b-17) | (b-35) | H | H | (a-5) | —CH— | —NH— | —CH(Me)— |
| 2-232 | (b-18) | (b-7) | H | H | (a-5) | —CH— | —NH— | —CH(Me)— |
| 2-233 | (b-18) | (b-7) | H | H | (a-5) | —CH— | —NH— | —COCH(Me)— |
| 2-234 | (b-18) | (b-12) | H | H | (a-5) | —CH— | —NH— | —CH(Me)— |
| 2-235 | (b-18) | (b-15) | H | H | (a-5) | —CH— | —NH— | —CH(Me)— |
| 2-236 | (b-18) | (b-34) | H | H | (a-5) | —CH— | —NH— | —CH(Me)— |
| 2-237 | (b-18) | (b-35) | H | H | (a-5) | —CH— | —NH— | —CH(Me)— |
| 2-238 | (b-18) | (b-35) | H | H | (a-5) | —CH— | —NH— | —COCH(Me)— |
| 2-239 | (b-18) | (b-37) | H | H | (a-5) | —CH— | —NH— | —CH(Me)— |
| 2-240 | (b-18) | (b-73) | H | H | (a-5) | —CH— | —NH— | —CH(Me)— |
| 2-241 | (b-18) | (b-77) | H | H | (a-5) | —CH— | —NH— | —CH(Me)— |
| 2-242 | (b-19) | (b-7) | H | H | (a-5) | —CH— | —NH— | —CH(Me)— |
| 2-243 | (b-19) | (b-7) | H | H | (a-5) | —CH— | —NH— | —COCH(Me)— |
| 2-244 | (b-19) | (b-35) | H | H | (a-5) | —CH— | —NH— | —CH(Me)— |
| 2-245 | (b-19) | (b-35) | H | H | (a-5) | —CH— | —NH— | —COCH(Me)— |
| 2-246 | (b-20) | (b-7) | H | H | (a-5) | —CH— | —NH— | —CH(Me)— |
| 2-247 | (b-20) | (b-7) | H | H | (a-5) | —CH— | —NH— | —COCH(Me)— |
| 2-248 | (b-20) | (b-12) | H | H | (a-5) | —CH— | —NH— | —CH(Me)— |
| 2-249 | (b-20) | (b-15) | H | H | (a-5) | —CH— | —NH— | —CH(Me)— |
| 2-250 | (b-20) | (b-34) | H | H | (a-5) | —CH— | —NH— | —CH(Me)— |
| 2-251 | (b-20) | (b-35) | H | H | (a-5) | —CH— | —NH— | —CH(Me)— |
| 2-252 | (b-20) | (b-35) | H | H | (a-5) | —CH— | —NH— | —COCH(Me)— |
| 2-253 | (b-20) | (b-37) | H | H | (a-5) | —CH— | —NH— | —CH(Me)— |
| 2-254 | (b-20) | (b-73) | H | H | (a-5) | —CH— | —NH— | —CH(Me)— |
| 2-255 | (b-20) | (b-77) | H | H | (a-5) | —CH— | —NH— | —CH(Me)— |
| 2-256 | (b-21) | (b-7) | H | H | (a-5) | —CH— | —NH— | —CH(Me)— |
| 2-257 | (b-21) | (b-7) | H | H | (a-5) | —CH— | —NH— | —COCH(Me)— |
| 2-258 | (b-21) | (b-35) | H | H | (a-5) | —CH— | —NH— | —CH(Me)— |
| 2-259 | (b-21) | (b-35) | H | H | (a-5) | —CH— | —NH— | —COCH(Me)— |
| 2-260 | (b-23) | (b-35) | H | H | (a-5) | —CH— | —NH— | —CH(Me)— |
| 2-261 | (b-24) | (b-7) | H | H | (a-5) | —CH— | —NH— | —CH(Me)— |
| 2-262 | (b-24) | (b-7) | H | H | (a-5) | —CH— | —NH— | —COCH(Me)— |
| 2-263 | (b-24) | (b-35) | H | H | (a-5) | —CH— | —NH— | —CH(Me)— |
| 2-264 | (b-24) | (b-35) | H | H | (a-5) | —CH— | —NH— | —COCH(Me)— |
| 2-265 | (b-25) | (b-7) | H | H | (a-5) | —CH— | —NH— | —CH(Me)— |

TABLE 2-continued

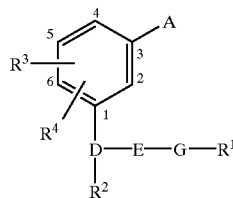

(I-2)

| Cpd. No. | R¹ Sub. No | R² Sub. No | R³ | R⁴ | A Sub. No | D | E | G |
|---|---|---|---|---|---|---|---|---|
| 2-266 | (b-25) | (b-7) | H | H | (a-5) | —CH— | —NH— | —COCH(Me)— |
| 2-267 | (b-25) | (b-35) | H | H | (a-5) | —CH— | —NH— | —CH(Me)— |
| 2-268 | (b-25) | (b-35) | H | H | (a-5) | —CH— | —NH— | —COCH(Me)— |
| 2-269 | (b-35) | (b-35) | H | H | (a-5) | —CH— | —NH— | —CH(Me)— |
| 2-270 | (b-72) | (b-7) | H | H | (a-5) | —CH— | —NH— | —CH(Me)— |
| 2-271 | (b-72) | (b-7) | H | H | (a-5) | —CH— | —NH— | —COCH(Me)— |
| 2-272 | (b-72) | (b-35) | H | H | (a-5) | —CH— | —NH— | —CH(Me)— |
| 2-273 | (b-72) | (b-35) | H | H | (a-5) | —CH— | —NH— | —COCH(Me)— |
| 2-274 | (b-73) | (b-7) | H | H | (a-5) | —CH— | —NH— | —CH(Me)— |
| 2-275 | (b-73) | (b-7) | H | H | (a-5) | —CH— | —NH— | —COCH(Me)— |
| 2-276 | (b-73) | (b-12) | H | H | (a-5) | —CH— | —NH— | —CH(Me)— |
| 2-277 | (b-73) | (b-15) | H | H | (a-5) | —CH— | —NH— | —CH(Me)— |
| 2-278 | (b-73) | (b-34) | H | H | (a-5) | —CH— | —NH— | —CH(Me)— |
| 2-279 | (b-73) | (b-35) | H | H | (a-5) | —CH— | —NH— | —CH(Me)— |
| 2-280 | (b-73) | (b-35) | H | H | (a-5) | —CH— | —NH— | —COCH(Me)— |
| 2-281 | (b-73) | (b-37) | H | H | (a-5) | —CH— | —NH— | —CH(Me)— |
| 2-282 | (b-73) | (b-73) | H | H | (a-5) | —CH— | —NH— | —CH(Me)— |
| 2-283 | (b-73) | (b-77) | H | H | (a-5) | —CH— | —NH— | —CH(Me)— |
| 2-284 | (b-74) | (b-7) | H | H | (a-5) | —CH— | —NH— | —CH(Me)— |
| 2-285 | (b-74) | (b-7) | H | H | (a-5) | —CH— | —NH— | —COCH(Me)— |
| 2-286 | (b-74) | (b-35) | H | H | (a-5) | —CH— | —NH— | —CH(Me)— |
| 2-287 | (b-74) | (b-35) | H | H | (a-5) | —CH— | —NH— | —COCH(Me)— |
| 2-288 | (b-75) | (b-35) | H | H | (a-5) | —CH— | —NH— | —CH(Me)— |
| 2-289 | (b-76) | (b-7) | H | H | (a-5) | —CH— | —NH— | —CH(Me)— |
| 2-290 | (b-76) | (b-7) | H | H | (a-5) | —CH— | —NH— | —COCH(Me)— |
| 2-291 | (b-76) | (b-35) | H | H | (a-5) | —CH— | —NH— | —CH(Me)— |
| 2-292 | (b-76) | (b-35) | H | H | (a-5) | —CH— | —NH— | —COCH(Me)— |
| 2-293 | (b-77) | (b-7) | H | H | (a-5) | —CH— | —NH— | —CH(Me)— |
| 2-294 | (b-77) | (b-7) | H | H | (a-5) | —CH— | —NH— | —COCH(Me)— |
| 2-295 | (b-77) | (b-12) | H | H | (a-5) | —CH— | —NH— | —CH(Me)— |
| 2-296 | (b-77) | (b-15) | H | H | (a-5) | —CH— | —NH— | —CH(Me)— |
| 2-297 | (b-77) | (b-34) | H | H | (a-5) | —CH— | —NH— | —CH(Me)— |
| 2-298 | (b-77) | (b-35) | H | H | (a-5) | —CH— | —NH— | —CH(Me)— |
| 2-299 | (b-77) | (b-35) | H | H | (a-5) | —CH— | —NH— | —COCH(Me)— |
| 2-300 | (b-77) | (b-37) | H | H | (a-5) | —CH— | —NH— | —CH(Me)— |
| 2-301 | (b-77) | (b-73) | H | H | (a-5) | —CH— | —NH— | —CH(Me)— |
| 2-302 | (b-77) | (b-77) | H | H | (a-5) | —CH— | —NH— | —CH(Me)— |
| 2-303 | (b-78) | (b-35) | H | H | (a-5) | —CH— | —NH— | —CH(Me)— |
| 2-304 | (b-79) | (b-35) | H | H | (a-5) | —CH— | —NH— | —CH(Me)— |
| 2-305 | (b-7) | (b-7) | H | H | (a-6) | —CH— | —NH— | —CH(Me)— |
| 2-306 | (b-7) | (b-35) | H | H | (a-6) | —CH— | —NH— | —CH(Me)— |
| 2-307 | (b-11) | (b-7) | H | H | (a-6) | —CH— | —NH— | —CH(Me)— |
| 2-308 | (b-11) | (b-35) | H | H | (a-6) | —CH— | —NH— | —CH(Me)— |
| 2-309 | (b-12) | (b-35) | H | H | (a-6) | —CH— | —NH— | —CH(Me)— |
| 2-310 | (b-15) | (b-35) | H | H | (a-6) | —CH— | —NH— | —CH(Me)— |
| 2-311 | (b-18) | (b-7) | H | H | (a-6) | —CH— | —NH— | —CH(Me)— |
| 2-312 | (b-18) | (b-35) | H | H | (a-6) | —CH— | —NH— | —CH(Me)— |
| 2-313 | (b-19) | (b-35) | H | H | (a-6) | —CH— | —NH— | —CH(Me)— |
| 2-314 | (b-20) | (b-7) | H | H | (a-6) | —CH— | —NH— | —CH(Me)— |
| 2-315 | (b-20) | (b-35) | H | H | (a-6) | —CH— | —NH— | —CH(Me)— |
| 2-316 | (b-21) | (b-35) | H | H | (a-6) | —CH— | —NH— | —CH(Me)— |
| 2-317 | (b-24) | (b-35) | H | H | (a-6) | —CH— | —NH— | —CH(Me)— |
| 2-318 | (b-25) | (b-35) | H | H | (a-6) | —CH— | —NH— | —CH(Me)— |
| 2-319 | (b-72) | (b-35) | H | H | (a-6) | —CH— | —NH— | —CH(Me)— |
| 2-320 | (b-73) | (b-7) | H | H | (a-6) | —CH— | —NH— | —CH(Me)— |
| 2-321 | (b-73) | (b-35) | H | H | (a-6) | —CH— | —NH— | —CH(Me)— |
| 2-322 | (b-74) | (b-35) | H | H | (a-6) | —CH— | —NH— | —CH(Me)— |
| 2-323 | (b-76) | (b-35) | H | H | (a-6) | —CH— | —NH— | —CH(Me)— |
| 2-324 | (b-77) | (b-7) | H | H | (a-6) | —CH— | —NH— | —CH(Me)— |
| 2-325 | (b-77) | (b-35) | H | H | (a-6) | —CH— | —NH— | —CH(Me)— |
| 2-326 | (b-2) | (b-35) | H | H | (a-7) | —CH— | —NH— | —CH(Me)— |
| 2-327 | (b-7) | (b-7) | H | H | (a-7) | —CH— | —NH— | —CH(Me)— |
| 2-328 | (b-7) | (b-7) | H | H | (a-7) | —CH— | —NH— | —COCH(Me)— |
| 2-329 | (b-7) | (b-35) | H | H | (a-7) | —CH— | —NH— | —CH(Me)— |

TABLE 2-continued

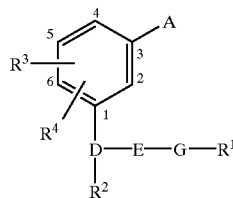

(I-2)

| Cpd. No. | R¹ Sub. No | R² Sub. No | R³ | R⁴ | A Sub. No | D | E | G |
|---|---|---|---|---|---|---|---|---|
| 2-330 | (b-7) | (b-35) | H | H | (a-7) | —CH— | —NH— | —COCH(Me)— |
| 2-331 | (b-8) | (b-35) | H | H | (a-7) | —CH— | —NH— | —CH(Me)— |
| 2-332 | (b-11) | (b-7) | H | H | (a-7) | —CH— | —NH— | —CH(Me)— |
| 2-333 | (b-11) | (b-7) | H | H | (a-7) | —CH— | —NH— | —COCH(Me)— |
| 2-334 | (b-11) | (b-35) | H | H | (a-7) | —CH— | —NH— | —CH(Me)— |
| 2-335 | (b-11) | (b-35) | H | H | (a-7) | —CH— | —NH— | —COCH(Me)— |
| 2-336 | (b-12) | (b-7) | H | H | (a-7) | —CH— | —NH— | —CH(Me)— |
| 2-337 | (b-12) | (b-35) | H | H | (a-7) | —CH— | —NH— | —CH(Me)— |
| 2-338 | (b-15) | (b-7) | H | H | (a-7) | —CH— | —NH— | —CH(Me)— |
| 2-339 | (b-15) | (b-35) | H | H | (a-7) | —CH— | —NH— | —CH(Me)— |
| 2-340 | (b-18) | (b-7) | H | H | (a-7) | —CH— | —NH— | —CH(Me)— |
| 2-341 | (b-18) | (b-7) | H | H | (a-7) | —CH— | —NH— | —COCH(Me)— |
| 2-342 | (b-18) | (b-35) | H | H | (a-7) | —CH— | —NH— | —CH(Me)— |
| 2-343 | (b-18) | (b-35) | H | H | (a-7) | —CH— | —NH— | —COCH(Me)— |
| 2-344 | (b-19) | (b-7) | H | H | (a-7) | —CH— | —NH— | —CH(Me)— |
| 2-345 | (b-19) | (b-35) | H | H | (a-7) | —CH— | —NH— | —CH(Me)— |
| 2-346 | (b-20) | (b-7) | H | H | (a-7) | —CH— | —NH— | —CH(Me)— |
| 2-347 | (b-20) | (b-7) | H | H | (a-7) | —CH— | —NH— | —COCH(Me)— |
| 2-348 | (b-20) | (b-35) | H | H | (a-7) | —CH— | —NH— | —CH(Me)— |
| 2-349 | (b-20) | (b-35) | H | H | (a-7) | —CH— | —NH— | —COCH(Me)— |
| 2-350 | (b-21) | (b-7) | H | H | (a-7) | —CH— | —NH— | —CH(Me)— |
| 2-351 | (b-21) | (b-35) | H | H | (a-7) | —CH— | —NH— | —CH(Me)— |
| 2-352 | (b-24) | (b-7) | H | H | (a-7) | —CH— | —NH— | —CH(Me)— |
| 2-353 | (b-24) | (b-35) | H | H | (a-7) | —CH— | —NH— | —CH(Me)— |
| 2-354 | (b-25) | (b-7) | H | H | (a-7) | —CH— | —NH— | —CH(Me)— |
| 2-355 | (b-25) | (b-35) | H | H | (a-7) | —CH— | —NH— | —CH(Me)— |
| 2-356 | (b-72) | (b-7) | H | H | (a-7) | —CH— | —NH— | —CH(Me)— |
| 2-357 | (b-72) | (b-35) | H | H | (a-7) | —CH— | —NH— | —CH(Me)— |
| 2-358 | (b-73) | (b-7) | H | H | (a-7) | —CH— | —NH— | —CH(Me)— |
| 2-359 | (b-73) | (b-7) | H | H | (a-7) | —CH— | —NH— | —COCH(Me)— |
| 2-360 | (b-73) | (b-35) | H | H | (a-7) | —CH— | —NH— | —CH(Me)— |
| 2-361 | (b-73) | (b-35) | H | H | (a-7) | —CH— | —NH— | —COCH(Me)— |
| 2-362 | (b-74) | (b-7) | H | H | (a-7) | —CH— | —NH— | —CH(Me)— |
| 2-363 | (b-74) | (b-35) | H | H | (a-7) | —CH— | —NH— | —CH(Me)— |
| 2-364 | (b-76) | (b-7) | H | H | (a-7) | —CH— | —NH— | —CH(Me)— |
| 2-365 | (b-76) | (b-35) | H | H | (a-7) | —CH— | —NH— | —CH(Me)— |
| 2-366 | (b-77) | (b-7) | H | H | (a-7) | —CH— | —NH— | —CH(Me)— |
| 2-367 | (b-77) | (b-7) | H | H | (a-7) | —CH— | —NH— | —COCH(Me)— |
| 2-368 | (b-77) | (b-35) | H | H | (a-7) | —CH— | —NH— | —CH(Me)— |
| 2-369 | (b-77) | (b-35) | H | H | (a-7) | —CH— | —NH— | —COCH(Me)— |
| 2-370 | (b-7) | (b-7) | H | H | (a-8) | —CH— | —NH— | —CH(Me)— |
| 2-371 | (b-7) | (b-35) | H | H | (a-8) | —CH— | —NH— | —CH(Me)— |
| 2-372 | (b-11) | (b-7) | H | H | (a-8) | —CH— | —NH— | —CH(Me)— |
| 2-373 | (b-11) | (b-35) | H | H | (a-8) | —CH— | —NH— | —CH(Me)— |
| 2-374 | (b-12) | (b-35) | H | H | (a-8) | —CH— | —NH— | —CH(Me)— |
| 2-375 | (b-15) | (b-35) | H | H | (a-8) | —CH— | —NH— | —CH(Me)— |
| 2-376 | (b-18) | (b-7) | H | H | (a-8) | —CH— | —NH— | —CH(Me)— |
| 2-377 | (b-18) | (b-35) | H | H | (a-8) | —CH— | —NH— | —CH(Me)— |
| 2-378 | (b-19) | (b-35) | H | H | (a-8) | —CH— | —NH— | —CH(Me)— |
| 2-379 | (b-20) | (b-7) | H | H | (a-8) | —CH— | —NH— | —CH(Me)— |
| 2-380 | (b-20) | (b-35) | H | H | (a-8) | —CH— | —NH— | —CH(Me)— |
| 2-381 | (b-21) | (b-35) | H | H | (a-8) | —CH— | —NH— | —CH(Me)— |
| 2-382 | (b-24) | (b-35) | H | H | (a-8) | —CH— | —NH— | —CH(Me)— |
| 2-383 | (b-25) | (b-35) | H | H | (a-8) | —CH— | —NH— | —CH(Me)— |
| 2-384 | (b-72) | (b-35) | H | H | (a-8) | —CH— | —NH— | —CH(Me)— |
| 2-385 | (b-73) | (b-7) | H | H | (a-8) | —CH— | —NH— | —CH(Me)— |
| 2-386 | (b-73) | (b-35) | H | H | (a-8) | —CH— | —NH— | —CH(Me)— |
| 2-387 | (b-74) | (b-35) | H | H | (a-8) | —CH— | —NH— | —CH(Me)— |
| 2-388 | (b-76) | (b-35) | H | H | (a-8) | —CH— | —NH— | —CH(Me)— |
| 2-389 | (b-77) | (b-7) | H | H | (a-8) | —CH— | —NH— | —CH(Me)— |
| 2-390 | (b-77) | (b-35) | H | H | (a-8) | —CH— | —NH— | —CH(Me)— |
| 2-391 | (b-7) | (b-35) | H | H | (a-9) | —CH— | —NH— | —CH(Me)— |
| 2-392 | (b-11) | (b-35) | H | H | (a-9) | —CH— | —NH— | —CH(Me)— |
| 2-393 | (b-18) | (b-35) | H | H | (a-9) | —CH— | —NH— | —CH(Me)— |

TABLE 2-continued

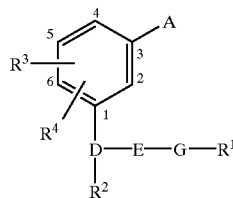

(I-2)

| Cpd. No. | R$^1$ Sub. No | R$^2$ Sub. No | R$^3$ | R$^4$ | A Sub. No | D | E | G |
|---|---|---|---|---|---|---|---|---|
| 2-394 | (b-7) | (b-35) | H | H | (a-10) | —CH— | —NH— | —CH(Me)— |
| 2-395 | (b-11) | (b-35) | H | H | (a-10) | —CH— | —NH— | —CH(Me)— |
| 2-396 | (b-18) | (b-35) | H | H | (a-10) | —CH— | —NH— | —CH(Me)— |
| 2-397 | (b-20) | (b-35) | H | H | (a-10) | —CH— | —NH— | —CH(Me)— |
| 2-398 | (b-73) | (b-35) | H | H | (a-10) | —CH— | —NH— | —CH(Me)— |
| 2-399 | (b-77) | (b-35) | H | H | (a-10) | —CH— | —NH— | —CH(Me)— |
| 2-400 | (b-7) | (b-7) | H | H | (a-11) | —CH— | —NH— | —CH(Me)— |
| 2-401 | (b-7) | (b-35) | H | H | (a-11) | —CH— | —NH— | —CH(Me)— |
| 2-402 | (b-11) | (b-7) | H | H | (a-11) | —CH— | —NH— | —CH(Me)— |
| 2-403 | (b-11) | (b-35) | H | H | (a-11) | —CH— | —NH— | —CH(Me)— |
| 2-404 | (b-12) | (b-35) | H | H | (a-11) | —CH— | —NH— | —CH(Me)— |
| 2-405 | (b-15) | (b-35) | H | H | (a-11) | —CH— | —NH— | —CH(Me)— |
| 2-406 | (b-18) | (b-7) | H | H | (a-11) | —CH— | —NH— | —CH(Me)— |
| 2-407 | (b-18) | (b-35) | H | H | (a-11) | —CH— | —NH— | —CH(Me)— |
| 2-408 | (b-19) | (b-35) | H | H | (a-11) | —CH— | —NH— | —CH(Me)— |
| 2-409 | (b-20) | (b-7) | H | H | (a-11) | —CH— | —NH— | —CH(Me)— |
| 2-410 | (b-20) | (b-35) | H | H | (a-11) | —CH— | —NH— | —CH(Me)— |
| 2-411 | (b-21) | (b-35) | H | H | (a-11) | —CH— | —NH— | —CH(Me)— |
| 2-412 | (b-24) | (b-35) | H | H | (a-11) | —CH— | —NH— | —CH(Me)— |
| 2-413 | (b-25) | (b-35) | H | H | (a-11) | —CH— | —NH— | —CH(Me)— |
| 2-414 | (b-72) | (b-35) | H | H | (a-11) | —CH— | —NH— | —CH(Me)— |
| 2-415 | (b-73) | (b-7) | H | H | (a-11) | —CH— | —NH— | —CH(Me)— |
| 2-416 | (b-73) | (b-35) | H | H | (a-11) | —CH— | —NH— | —CH(Me)— |
| 2-417 | (b-74) | (b-35) | H | H | (a-11) | —CH— | —NH— | —CH(Me)— |
| 2-418 | (b-76) | (b-35) | H | H | (a-11) | —CH— | —NH— | —CH(Me)— |
| 2-419 | (b-77) | (b-7) | H | H | (a-11) | —CH— | —NH— | —CH(Me)— |
| 2-420 | (b-77) | (b-35) | H | H | (a-11) | —CH— | —NH— | —CH(Me)— |
| 2-421 | (b-7) | (b-35) | H | H | (a-12) | —CH— | —NH— | —CH(Me)— |
| 2-422 | (b-11) | (b-35) | H | H | (a-12) | —CH— | —NH— | —CH(Me)— |
| 2-423 | (b-18) | (b-35) | H | H | (a-12) | —CH— | —NH— | —CH(Me)— |
| 2-424 | (b-20) | (b-35) | H | H | (a-12) | —CH— | —NH— | —CH(Me)— |
| 2-425 | (b-73) | (b-35) | H | H | (a-12) | —CH— | —NH— | —CH(Me)— |
| 2-426 | (b-77) | (b-35) | H | H | (a-12) | —CH— | —NH— | —CH(Me)— |
| 2-427 | (b-7) | (b-35) | H | H | (a-13) | —CH— | —NH— | —CH(Me)— |
| 2-428 | (b-11) | (b-35) | H | H | (a-13) | —CH— | —NH— | —CH(Me)— |
| 2-429 | (b-18) | (b-35) | H | H | (a-13) | —CH— | —NH— | —CH(Me)— |
| 2-430 | (b-1) | (b-35) | H | H | (a-14) | —CH— | —NH— | —CH(Me)— |
| 2-431 | (b-2) | (b-7) | H | H | (a-14) | —CH— | —NH— | —CH(Me)— |
| 2-432 | (b-2) | (b-7) | H | H | (a-14) | —CH— | —NH— | —COCH(Me)— |
| 2-433 | (b-2) | (b-12) | H | H | (a-14) | —CH— | —NH— | —CH(Me)— |
| 2-434 | (b-2) | (b-15) | H | H | (a-14) | —CH— | —NH— | —CH(Me)— |
| 2-435 | (b-2) | (b-34) | H | H | (a-14) | —CH— | —NH— | —CH(Me)— |
| 2-436 | (b-2) | (b-35) | H | H | (a-14) | —CH— | —NH— | —CH(Me)— |
| 2-437 | (b-2) | (b-35) | H | H | (a-14) | —CH— | —NH— | —(CH$_2$)$_2$— |
| 2-438 | (b-2) | (b-37) | H | H | (a-14) | —CH— | —NH— | —CH(Me)— |
| 2-439 | (b-2) | (b-73) | H | H | (a-14) | —CH— | —NH— | —CH(Me)— |
| 2-440 | (b-2) | (b-77) | H | H | (a-14) | —CH— | —NH— | —CH(Me)— |
| 2-441 | (b-3) | (b-35) | H | H | (a-14) | —CH— | —NH— | —CH(Me)— |
| 2-442 | (b-4) | (b-35) | H | H | (a-14) | —CH— | —NH— | —CH(Me)— |
| 2-443 | (b-5) | (b-35) | H | H | (a-14) | —CH— | —NH— | —CH(Me)— |
| 2-444 | (b-6) | (b-35) | H | H | (a-14) | —CH— | —NH— | —CH(Me)— |
| 2-445 | (b-7) | (b-1) | H | H | (a-14) | —CH— | —NH— | —CH(Me)— |
| 2-446 | (b-7) | (b-2) | H | H | (a-14) | —CH— | —NH— | —CH(Me)— |
| 2-447 | (b-7) | (b-7) | H | H | (a-14) | —CH— | —NH— | single bond |
| 2-448 | (b-7) | (b-7) | H | H | (a-14) | —CH— | —NH— | —CH$_2$— |
| 2-449 | (b-7) | (b-7) | H | H | (a-14) | —CH— | —NH— | —(CH$_2$)$_2$— |
| 2-450 | (b-7) | (b-7) | H | H | (a-14) | —CH— | —NH— | —CH(Me)— |
| 2-451 | (b-7) | (b-7) | H | H | (a-14) | —CH— | —NH— | —CH(Et)— |
| 2-452 | (b-7) | (b-7) | H | H | (a-14) | —CH— | —NH— | —(CH$_2$)3— |
| 2-453 | (b-7) | (b-7) | H | H | (a-14) | —CH— | —NH— | —CH$_2$CH(Me)— |
| 2-454 | (b-7) | (b-7) | H | H | (a-14) | —CH— | —NH— | —CH$_2$CH(OH)— |
| 2-455 | (b-7) | (b-7) | H | H | (a-14) | —CH— | —NH— | —CH$_2$C(=O)— |
| 2-456 | (b-7) | (b-7) | H | H | (a-14) | —CH— | —NH— | —CH$_2$C(Ph)— |
| 2-457 | (b-7) | (b-7) | H | H | (a-14) | —CH— | —NH— | —(CH$_2$)$_2$CH(Me)— |

TABLE 2-continued

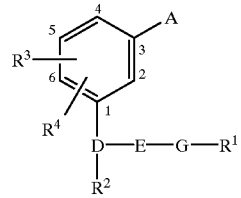

(I-2)

| Cpd. No. | R¹ Sub. No | R² Sub. No | R³ | R⁴ | A Sub. No | D | E | G |
|---|---|---|---|---|---|---|---|---|
| 2-458 | (b-7) | (b-7) | H | H | (a-14) | —CH— | —NH— | —(CH₂)₂CH(OH)— |
| 2-459 | (b-7) | (b-7) | H | H | (a-14) | —CH— | —NH— | —(CH₂)₂C(=O)— |
| 2-460 | (b-7) | (b-7) | H | H | (a-14) | —CH— | —NH— | —(CH₂)₂C(Ph)— |
| 2-461 | (b-7) | (b-7) | H | H | (a-14) | —CH— | —NH— | —CO— |
| 2-462 | (b-7) | (b-7) | H | H | (a-14) | —CH— | —NH— | —COCH₂— |
| 2-463 | (b-7) | (b-7) | H | H | (a-14) | —CH— | —NH— | —CO(CH₂)₂— |
| 2-464 | (b-7) | (b-7) | H | H | (a-14) | —CH— | —NH— | —COCH(Me)— |
| 2-465 | (b-7) | (b-7) | H | H | (a-14) | —CH— | —NH— | —COCH(Et)— |
| 2-466 | (b-7) | (b-7) | H | H | (a-14) | —CH— | —NH— | —CO(CH₂)₃— |
| 2-467 | (b-7) | (b-7) | H | H | (a-14) | —CH— | —NH— | —COCH₂CH(Me)— |
| 2-468 | (b-7) | (b-7) | H | H | (a-14) | —CH— | —O— | —CH₂— |
| 2-469 | (b-7) | (b-7) | H | H | (a-14) | —CH— | —O— | —(CH₂)₂— |
| 2-470 | (b-7) | (b-7) | H | H | (a-14) | —CH— | —O— | —CH(Me)— |
| 2-471 | (b-7) | (b-7) | H | H | (a-14) | —CH— | —S— | —CH₂— |
| 2-472 | (b-7) | (b-7) | H | H | (a-14) | —CH— | —S— | —(CH₂)₂— |
| 2-473 | (b-7) | (b-7) | H | H | (a-14) | —CH— | —S— | —CH(Me)— |
| 2-474 | (b-7) | (b-7) | 4-F | H | (a-14) | —CH— | —NH— | —CH(Me)— |
| 2-475 | (b-7) | (b-7) | 6-F | H | (a-14) | —CH— | —NH— | —CH(Me)— |
| 2-476 | (b-7) | (b-7) | 4-Cl | H | (a-14) | —CH— | —NH— | -CH(Me)- |
| 2-477 | (b-7) | (b-7) | 5-Cl | H | (a-14) | —CH— | —NH— | -CH(Me)- |
| 2-478 | (b-7) | (b-7) | 6-Cl | H | (a-14) | —CH— | —NH— | -CH(Me)- |
| 2-479 | (b-7) | (b-7) | 4-OH | H | (a-14) | —CH— | —NH— | -CH(Me)- |
| 2-480 | (b-7) | (b-7) | 5-OH | H | (a-14) | —CH— | —NH— | -CH(Me)- |
| 2-481 | (b-7) | (b-7) | 6-OH | H | (a-14) | —CH— | —NH— | -CH(Me)- |
| 2-482 | (b-7) | (b-7) | H | H | (a-14) | N | —CO— | —CH₂— |
| 2-483 | (b-7) | (b-7) | H | H | (a-14) | N | —CO— | —(CH₂)₂— |
| 2-484 | (b-7) | (b-7) | H | H | (a-14) | N | —CO— | —CH(Me)— |
| 2-485 | (b-7) | (b-8) | H | H | (a-14) | —CH— | —NH— | —CH(Me)— |
| 2-486 | (b-7) | (b-10) | H | H | (a-14) | —CH— | —NH— | —CH(Me)— |
| 2-487 | (b-7) | (b-11) | H | H | (a-14) | —CH— | —NH— | —CH(Me)— |
| 2-488 | (b-7) | (b-11) | H | H | (a-14) | —CH— | —NH— | —COCH(Me)— |
| 2-489 | (b-7) | (b-11) | H | H | (a-14) | —CH— | —O— | —CH(Me)— |
| 2-490 | (b-7) | (b-11) | H | H | (a-14) | —CH— | —S— | —CH(Me)— |
| 2-491 | (b-7) | (b-12) | H | H | (a-14) | —CH— | —NH— | —(CH₂)₂— |
| 2-492 | (b-7) | (b-12) | H | H | (a-14) | —CH— | —NH— | —CH(Me)— |
| 2-493 | (b-7) | (b-12) | H | H | (a-14) | —CH— | —NH— | —CH₂CH(Me)— |
| 2-494 | (b-7) | (b-12) | H | H | (a-14) | —CH— | —NH— | —CO(CH₂)₂— |
| 2-495 | (b-7) | (b-12) | H | H | (a-14) | —CH— | —NH— | —COCH(Me)— |
| 2-496 | (b-7) | (b-12) | H | H | (a-14) | —CH— | —O— | —CH(Me)— |
| 2-497 | (b-7) | (b-12) | H | H | (a-14) | —CH— | —S— | —CH(Me)— |
| 2-498 | (b-7) | (b-12) | 6-Cl | H | (a-14) | —CH— | —NH— | —CH(Me)— |
| 2-499 | (b-7) | (b-12) | 4-OH | H | (a-14) | —CH— | —NH— | —CH(Me)— |
| 2-500 | (b-7) | (b-12) | 6-OH | H | (a-14) | —CH— | —NH— | —CH(Me)— |
| 2-501 | (b-7) | (b-12) | 4-MeO | H | (a-14) | —CH— | —NH— | —CH(Me)— |
| 2-502 | (b-7) | (b-12) | 4-MeO | 5-MeO | (a-14) | —CH— | —NH— | —CH(Me)— |
| 2-503 | (b-7) | (b-12) | H | H | (a-14) | N | —CO— | —CH(Me)— |
| 2-504 | (b-7) | (b-13) | H | H | (a-14) | —CH— | —NH— | —CH(Me)— |
| 2-505 | (b-7) | (b-14) | H | H | (a-14) | —CH— | —NH— | —CH(Me)— |
| 2-506 | (b-7) | (b-14) | H | H | (a-14) | —CH— | —NH— | —COCH(Me)— |
| 2-507 | (b-7) | (b-14) | H | H | (a-14) | —CH— | —O— | —CH(Me)— |
| 2-508 | (b-7) | (b-14) | H | H | (a-14) | —CH— | —S— | —CH(Me)— |
| 2-509 | (b-7) | (b-15) | H | H | (a-14) | —CH— | —NH— | —(CH₂)₂— |
| 2-510 | (b-7) | (b-15) | H | H | (a-14) | —CH— | —NH— | —CH(Me)— |
| 2-511 | (b-7) | (b-15) | H | H | (a-14) | —CH— | —NH— | —CH₂CH(Me)— |
| 2-512 | (b-7) | (b-15) | H | H | (a-14) | —CH— | —NH— | —CO(CH₂)₂— |
| 2-513 | (b-7) | (b-15) | H | H | (a-14) | —CH— | —NH— | —COCH(Me)— |
| 2-514 | (b-7) | (b-15) | H | H | (a-14) | —CH— | —O— | —CH(Me)— |
| 2-515 | (b-7) | (b-15) | H | H | (a-14) | —CH— | —S— | —CH(Me)— |
| 2-516 | (b-7) | (b-15) | 6-Cl | H | (a-14) | —CH— | —NH— | —CH(Me)— |
| 2-517 | (b-7) | (b-15) | 4-OH | H | (a-14) | —CH— | —NH— | —CH(Me)— |
| 2-518 | (b-7) | (b-15) | 6-OH | H | (a-14) | —CH— | —NH— | —CH(Me)— |
| 2-519 | (b-7) | (b-15) | H | H | (a-14) | N | —CO— | —CH(Me)— |
| 2-520 | (b-7) | (b-16) | H | H | (a-14) | —CH— | —NH— | —CH(Me)— |
| 2-521 | (b-7) | (b-17) | H | H | (a-14) | —CH— | —NH— | —CH(Me)— |

TABLE 2-continued

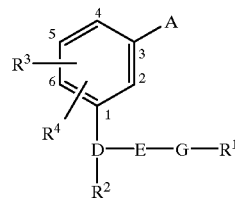

(I-2)

| Cpd. No. | R$^1$ Sub. No | R$^2$ Sub. No | R$^3$ | R$^4$ | A Sub. No | D | E | G |
|---|---|---|---|---|---|---|---|---|
| 2-522 | (b-7) | (b-17) | H | H | (a-14) | —CH— | —NH— | —COCH(Me)— |
| 2-523 | (b-7) | (b-17) | H | H | (a-14) | —CH— | —O— | —CH(Me)— |
| 2-524 | (b-7) | (b-17) | H | H | (a-14) | —CH— | —S— | —CH(Me)— |
| 2-525 | (b-7) | (b-23) | H | H | (a-14) | —CH— | —NH— | —CH(Me)— |
| 2-526 | (b-7) | (b-24) | H | H | (a-14) | —CH— | —NH— | —CH(Me)— |
| 2-527 | (b-7) | (b-25) | H | H | (a-14) | —CH— | —NH— | —CH(Me)— |
| 2-528 | (b-7) | (b-25) | H | H | (a-14) | —CH— | —NH— | —COCH(Me)— |
| 2-529 | (b-7) | (b-25) | H | H | (a-14) | —CH— | —O— | —CH(Me)— |
| 2-530 | (b-7) | (b-25) | H | H | (a-14) | —CH— | —S— | —CH(Me)— |
| 2-531 | (b-7) | (b-27) | H | H | (a-14) | —CH— | —NH— | —CH(Me)— |
| 2-532 | (b-7) | (b-28) | H | H | (a-14) | —CH— | —NH— | —CH(Me)— |
| 2-533 | (b-7) | (b-30) | H | H | (a-14) | —CH— | —NH— | —CH(Me)— |
| 2-534 | (b-7) | (b-31) | H | H | (a-14) | —CH— | —NH— | —CH(Me)— |
| 2-535 | (b-7) | (b-32) | H | H | (a-14) | —CH— | —NH— | —CH(Me)— |
| 2-536 | (b-7) | (b-33) | H | H | (a-14) | —CH— | —NH— | —CH(Me)— |
| 2-537 | (b-7) | (b-33) | H | H | (a-14) | —CH— | —NH— | —COCH(Me)— |
| 2-538 | (b-7) | (b-33) | H | H | (a-14) | —CH— | —O— | —CH(Me)— |
| 2-539 | (b-7) | (b-33) | H | H | (a-14) | —CH— | —S— | —CH(Me)— |
| 2-540 | (b-7) | (b-34) | H | H | (a-14) | —CH— | —NH— | —(CH$_2$)$_2$— |
| 2-541 | (b-7) | (b-34) | H | H | (a-14) | —CH— | —NH— | —CH(Me)— |
| 2-542 | (b-7) | (b-34) | H | H | (a-14) | —CH— | —NH— | —CH$_2$CH(Me)— |
| 2-543 | (b-7) | (b-34) | H | H | (a-14) | —CH— | —NH— | —CO(CH$_2$)$_2$— |
| 2-544 | (b-7) | (b-34) | H | H | (a-14) | —CH— | —NH— | —COCH(Me)— |
| 2-545 | (b-7) | (b-34) | H | H | (a-14) | —CH— | —O— | —CH(Me)— |
| 2-546 | (b-7) | (b-34) | H | H | (a-14) | —CH— | —S— | —CH(Me)— |
| 2-547 | (b-7) | (b-34) | 6-Cl | H | (a-14) | —CH— | —NH— | —CH(Me)— |
| 2-548 | (b-7) | (b-34) | 4-OH | H | (a-14) | —CH— | —NH— | —CH(Me)— |
| 2-549 | (b-7) | (b-34) | 6-OH | H | (a-14) | —CH— | —NH— | —CH(Me)— |
| 2-550 | (b-7) | (b-34) | H | H | (a-14) | N | —CO— | —CH(Me)— |
| 2-551 | (b-7) | (b-35) | H | H | (a-14) | —CH— | —NH— | single bond |
| 2-552 | (b-7) | (b-35) | H | H | (a-14) | —CH— | —NH— | —CH$_2$— |
| 2-553 | (b-7) | (b-35) | H | H | (a-14) | —CH— | —NH— | —(CH$_2$)$_2$— |
| 2-554 | (b-7) | (b-35) | H | H | (a-14) | —CH— | —NH— | —CH(Me)— |
| 2-555 | (b-7) | (b-35) | H | H | (a-14) | —CH— | —NH— | —CH(Et)— |
| 2-556 | (b-7) | (b-35) | H | H | (a-14) | —CH— | —NH— | —(CH$_2$)$_3$— |
| 2-557 | (b-7) | (b-35) | H | H | (a-14) | —CH— | —NH— | —CH$_2$CH(Me)— |
| 2-558 | (b-7) | (b-35) | H | H | (a-14) | —CH— | —NH— | —CH$_2$CH(OH)— |
| 2-559 | (b-7) | (b-35) | H | H | (a-14) | —CH— | —NH— | —CH$_2$C(=O)— |
| 2-560 | (b-7) | (b-35) | H | H | (a-14) | —CH— | —NH— | —CH$_2$C(Ph)— |
| 2-561 | (b-7) | (b-35) | H | H | (a-14) | —CH— | —NH— | —(CH$_2$)$_2$CH(Me)— |
| 2-562 | (b-7) | (b-35) | H | H | (a-14) | —CH— | —NH— | —(CH$_2$)$_2$CH(OH)— |
| 2-563 | (b-7) | (b-35) | H | H | (a-14) | —CH— | —NH— | —(CH$_2$)$_2$C(=O)— |
| 2-564 | (b-7) | (b-35) | H | H | (a-14) | —CH— | —NH— | —(CH$_2$)$_2$C(Ph)— |
| 2-565 | (b-7) | (b-35) | H | H | (a-14) | —CH— | —NH— | —CO— |
| 2-566 | (b-7) | (b-35) | H | H | (a-14) | —CH— | —NH— | —COCH$_2$— |
| 2-567 | (b-7) | (b-35) | H | H | (a-14) | —CH— | —NH— | —CO(CH$_2$)$_2$— |
| 2-568 | (b-7) | (b-35) | H | H | (a-14) | —CH— | —NH— | —COCH(Me)— |
| 2-569 | (b-7) | (b-35) | H | H | (a-14) | —CH— | —NH— | —COCH(Et)— |
| 2-570 | (b-7) | (b-35) | H | H | (a-14) | —CH— | —NH— | —CO(CH$_2$)$_3$— |
| 2-571 | (b-7) | (b-35) | H | H | (a-14) | —CH— | —NH— | —COCH$_2$CH(Me)— |
| 2-572 | (b-7) | (b-35) | H | H | (a-14) | —CH— | —O— | —CH$_2$— |
| 2-573 | (b-7) | (b-35) | H | H | (a-14) | —CH— | —O— | —(CH$_2$)$_2$— |
| 2-574 | (b-7) | (b-35) | H | H | (a-14) | —CH— | —O— | —CH(Me)— |
| 2-575 | (b-7) | (b-35) | H | H | (a-14) | —CH— | —S— | —CH$_2$— |
| 2-576 | (b-7) | (b-35) | H | H | (a-14) | —CH— | —S— | —(CH$_2$)$_2$— |
| 2-577 | (b-7) | (b-35) | H | H | (a-14) | —CH— | —S— | —CH(Me)— |
| 2-578 | (b-7) | (b-35) | 4-F | H | (a-14) | —CH— | —NH— | —CH(Me)— |
| 2-579 | (b-7) | (b-35) | 6-F | H | (a-14) | —CH— | —NH— | —CH(Me)— |
| 2-580 | (b-7) | (b-35) | 4-Cl | H | (a-14) | —CH— | —NH— | —CH(Me)— |
| 2-581 | (b-7) | (b-35) | 5-Cl | H | (a-14) | —CH— | —NH— | —CH(Me)— |
| 2-582 | (b-7) | (b-35) | 6-Cl | H | (a-14) | —CH— | —NH— | —CH(Me)— |
| 2-583 | (b-7) | (b-35) | 4-OH | H | (a-14) | —CH— | —NH— | —CH(Me)— |
| 2-584 | (b-7) | (b-35) | 5-OH | H | (a-14) | —CH— | —NH— | —CH(Me)— |
| 2-585 | (b-7) | (b-35) | 6-OH | H | (a-14) | —CH— | —NH— | —CH(Me)— |

TABLE 2-continued (I-2)

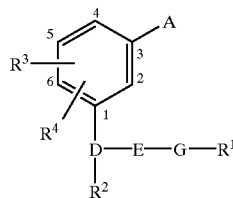

| Cpd. No. | R¹ Sub. No | R² Sub. No | R³ | R⁴ | A Sub. No | D | E | G |
|---|---|---|---|---|---|---|---|---|
| 2-586 | (b-7) | (b-35) | H | H | (a-14) | N | —CO— | —CH₂— |
| 2-587 | (b-7) | (b-35) | H | H | (a-14) | N | —CO— | —(CH₂)₂— |
| 2-588 | (b-7) | (b-35) | H | H | (a-14) | N | —CO— | —CH(Me)— |
| 2-589 | (b-7) | (b-37) | H | H | (a-14) | —CH— | —NH— | single bond |
| 2-590 | (b-7) | (b-37) | H | H | (a-14) | —CH— | —NH— | —CH₂— |
| 2-591 | (b-7) | (b-37) | H | H | (a-14) | —CH— | —NH— | —(CH₂)₂— |
| 2-592 | (b-7) | (b-37) | H | H | (a-14) | —CH— | —NH— | —CH(Me)— |
| 2-593 | (b-7) | (b-37) | H | H | (a-14) | —CH— | —NH— | —CH(Et)— |
| 2-594 | (b-7) | (b-37) | H | H | (a-14) | —CH— | —NH— | —(CH₂)₃— |
| 2-595 | (b-7) | (b-37) | H | H | (a-14) | —CH— | —NH— | —CH₂CH(Me)— |
| 2-596 | (b-7) | (b-37) | H | H | (a-14) | —CH— | —NH— | —CH₂CH(OH)— |
| 2-597 | (b-7) | (b-37) | H | H | (a-14) | —CH— | —NH— | —CH₂C(=O)— |
| 2-598 | (b-7) | (b-37) | H | H | (a-14) | —CH— | —NH— | —CH₂C(Ph)— |
| 2-599 | (b-7) | (b-37) | H | H | (a-14) | —CH— | —NH— | —(CH₂)₂CH(Me)— |
| 2-600 | (b-7) | (b-37) | H | H | (a-14) | —CH— | —NH— | —(CH₂)₂CH(OH)— |
| 2-601 | (b-7) | (b-37) | H | H | (a-14) | —CH— | —NH— | —(CH₂)₂C(=O)— |
| 2-602 | (b-7) | (b-37) | H | H | (a-14) | —CH— | —NH— | —(CH₂)₂C(Ph)— |
| 2-603 | (b-7) | (b-37) | H | H | (a-14) | —CH— | —NH— | —CO— |
| 2-604 | (b-7) | (b-37) | H | H | (a-14) | —CH— | —NH— | —COCH₂— |
| 2-605 | (b-7) | (b-37) | H | H | (a-14) | —CH— | —NH— | —CO(CH₂)₂— |
| 2-606 | (b-7) | (b-37) | H | H | (a-14) | —CH— | —NH— | —COCH(Me)— |
| 2-607 | (b-7) | (b-37) | H | H | (a-14) | —CH— | —NH— | COCH(Et)— |
| 2-608 | (b-7) | (b-37) | H | H | (a-14) | —CH— | —NH— | —CO(CH₂)₃— |
| 2-609 | (b-7) | (b-37) | H | H | (a-14) | —CH— | —NH— | —COCH₂CH(Me)— |
| 2-610 | (b-7) | (b-37) | H | H | (a-14) | —CH— | —O— | —CH₂— |
| 2-611 | (b-7) | (b-37) | H | H | (a-14) | —CH— | —O— | —(CH₂)₂— |
| 2-612 | (b-7) | (b-37) | H | H | (a-14) | —CH— | —O— | —CH(Me)— |
| 2-613 | (b-7) | (b-37) | H | H | (a-14) | —CH— | —S— | —CH₂— |
| 2-614 | (b-7) | (b-37) | H | H | (a-14) | —CH— | —S— | —(CH₂)₂— |
| 2-615 | (b-7) | (b-37) | H | H | (a-14) | —CH— | —S— | —CH(Me)— |
| 2-616 | (b-7) | (b-37) | 4-F | H | (a-14) | —CH— | —NH— | —CH(Me)— |
| 2-617 | (b-7) | (b-37) | 6-F | H | (a-14) | —CH— | —NH— | —CH(Me)— |
| 2-618 | (b-7) | (b-37) | 4-Cl | H | (a-14) | —CH— | —NH— | —CH(Me)— |
| 2-619 | (b-7) | (b-37) | 5-Cl | H | (a-14) | —CH— | —NH— | —CH(Me)— |
| 2-620 | (b-7) | (b-37) | 6-Cl | H | (a-14) | —CH— | —NH— | —CH(Me)— |
| 2-621 | (b-7) | (b-37) | 4-OH | H | (a-14) | —CH— | —NH— | —CH(Me)— |
| 2-622 | (b-7) | (b-37) | 5-OH | H | (a-14) | —CH— | —NH— | —CH(Me)— |
| 2-623 | (b-7) | (b-37) | 6-OH | H | (a-14) | —CH— | —NH— | —CH(Me)— |
| 2-624 | (b-7) | (b-37) | H | H | (a-14) | N | —CO— | —CH₂— |
| 2-625 | (b-7) | (b-37) | H | H | (a-14) | N | —CO— | —(CH₂)₂— |
| 2-626 | (b-7) | (b-37) | H | H | (a-14) | N | —CO— | —CH(Me)— |
| 2-627 | (b-7) | (b-38) | H | H | (a-14) | —CH— | —NH— | —CH(Me)— |
| 2-628 | (b-7) | (b-41) | H | H | (a-14) | —CH— | —NH— | —CH(Me)— |
| 2-629 | (b-7) | (b-42) | H | H | (a-14) | —CH— | —NH— | —CH(Me)— |
| 2-630 | (b-7) | (b-42) | H | H | (a-14) | —CH— | —NH— | —COCH(Me)— |
| 2-631 | (b-7) | (b-42) | H | H | (a-14) | —CH— | —O— | —CH(Me)— |
| 2-632 | (b-7) | (b-42) | H | H | (a-14) | —CH— | —S— | —CH(Me)— |
| 2-633 | (b-7) | (b-43) | H | H | (a-14) | —CH— | —NH— | —CH(Me)— |
| 2-634 | (b-7) | (b-72) | H | H | (a-14) | —CH— | —NH— | —(CH₂)₂— |
| 2-635 | (b-7) | (b-72) | H | H | (a-14) | —CH— | —NH— | —CH(Me)— |
| 2-636 | (b-7) | (b-72) | H | H | (a-14) | —CH— | —NH— | —CH₂CH(Me)— |
| 2-637 | (b-7) | (b-72) | H | H | (a-14) | —CH— | —NH— | —COCH(Me)— |
| 2-638 | (b-7) | (b-72) | H | H | (a-14) | —CH— | —O— | —CH(Me)— |
| 2-639 | (b-7) | (b-72) | H | H | (a-14) | —CH— | —S— | —CH(Me)— |
| 2-640 | (b-7) | (b-72) | 6-Cl | H | (a-14) | —CH— | —NH— | —CH(Me)— |
| 2-641 | (b-7) | (b-72) | 4-OH | H | (a-14) | —CH— | —NH— | —CH(Me)— |
| 2-642 | (b-7) | (b-72) | 6-OH | H | (a-14) | —CH— | —NH— | —CH(Me)— |
| 2-643 | (b-7) | (b-73) | H | H | (a-14) | —CH— | —NH— | single bond |
| 2-644 | (b-7) | (b-73) | H | H | (a-14) | —CH— | —NH— | —CH₂— |
| 2-645 | (b-7) | (b-73) | H | H | (a-14) | —CH— | —NH— | —(CH₂)₂— |
| 2-646 | (b-7) | (b-73) | H | H | (a-14) | —CH— | —NH— | —CH(Me)— |
| 2-647 | (b-7) | (b-73) | H | H | (a-14) | —CH— | —NH— | —CH(Et)— |
| 2-648 | (b-7) | (b-73) | H | H | (a-14) | —CH— | —NH— | —(CH₂)₃— |
| 2-649 | (b-7) | (b-73) | H | H | (a-14) | —CH— | —NH— | —CH₂CH(Me)— |

TABLE 2-continued

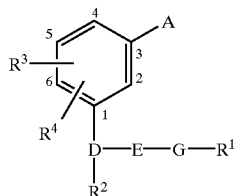

(I-2)

| Cpd. No. | R¹ Sub. No | R² Sub. No | R³ | R⁴ | A Sub. No | D | E | G |
|---|---|---|---|---|---|---|---|---|
| 2-650 | (b-7) | (b-73) | H | H | (a-14) | —CH— | —NH— | —CH₂CH(OH)— |
| 2-651 | (b-7) | (b-73) | H | H | (a-14) | —CH— | —NH— | —CH₂C(=O)— |
| 2-652 | (b-7) | (b-73) | H | H | (a-14) | —CH— | —NH— | —CH₂C(Ph)— |
| 2-653 | (b-7) | (b-73) | H | H | (a-14) | —CH— | —NH— | —(CH₂)₂CH(Me)— |
| 2-654 | (b-7) | (b-73) | H | H | (a-14) | —CH— | —NH— | —(CH₂)₂CH(OH)— |
| 2-655 | (b-7) | (b-73) | H | H | (a-14) | —CH— | —NH— | —(CH₂)₂C(=O)— |
| 2-656 | (b-7) | (b-73) | H | H | (a-14) | —CH— | —NH— | —(CH₂)₂C(Ph)— |
| 2-657 | (b-7) | (b-73) | H | H | (a-14) | —CH— | —NH— | —CO— |
| 2-658 | (b-7) | (b-73) | H | H | (a-14) | —CH— | —NH— | —COCH₂— |
| 2-659 | (b-7) | (b-73) | H | H | (a-14) | —CH— | —NH— | —CO(CH₂)₂— |
| 2-660 | (b-7) | (b-73) | H | H | (a-14) | —CH— | —NH— | —COCH(Me)— |
| 2-661 | (b-7) | (b-73) | H | H | (a-14) | —CH— | —NH— | —COCH(Et)— |
| 2-662 | (b-7) | (b-73) | H | H | (a-14) | —CH— | —NH— | —CO(CH₂)₃— |
| 2-663 | (b-7) | (b-73) | H | H | (a-14) | —CH— | —NH— | —COCH₂CH(Me)— |
| 2-664 | (b-7) | (b-73) | H | H | (a-14) | —CH— | —O— | —CH₂— |
| 2-665 | (b-7) | (b-73) | H | H | (a-14) | —CH— | —O— | —(CH₂)₂— |
| 2-666 | (b-7) | (b-73) | H | H | (a-14) | —CH— | —O— | —CH(Me)— |
| 2-667 | (b-7) | (b-73) | H | H | (a-14) | —CH— | —S— | —CH₂— |
| 2-668 | (b-7) | (b-73) | H | H | (a-14) | —CH— | —S— | —(CH₂)₂— |
| 2-669 | (b-7) | (b-73) | H | H | (a-14) | —CH— | —S— | —CH(Me)— |
| 2-670 | (b-7) | (b-73) | 4-F | H | (a-14) | —CH— | —NH— | —CH(Me)— |
| 2-671 | (b-7) | (b-73) | 6-F | H | (a-14) | —CH— | —NH— | —CH(Me)— |
| 2-672 | (b-7) | (b-73) | 4-Cl | H | (a-14) | —CH— | —NH— | —CH(Me)— |
| 2-673 | (b-7) | (b-73) | 5-Cl | H | (a-14) | —CH— | —NH— | —CH(Me)— |
| 2-674 | (b-7) | (b-73) | 6-Cl | H | (a-14) | —CH— | —NH— | —CH(Me)— |
| 2-675 | (b-7) | (b-73) | 4-OH | H | (a-14) | —CH— | —NH— | —CH(Me)— |
| 2-676 | (b-7) | (b-73) | 5-OH | H | (a-14) | —CH— | —NH— | —CH(Me)— |
| 2-677 | (b-7) | (b-73) | 6-OH | H | (a-14) | —CH— | —NH— | —CH(Me)— |
| 2-678 | (b-7) | (b-73) | H | H | (a-14) | N | —CO— | —CH₂— |
| 2-679 | (b-7) | (b-73) | H | H | (a-14) | N | —CO— | —(CH₂)₂— |
| 2-680 | (b-7) | (b-73) | H | H | (a-14) | N | —CO— | —CH(Me)— |
| 2-681 | (b-7) | (b-74) | H | H | (a-14) | —CH— | —NH— | —CH(Me)— |
| 2-682 | (b-7) | (b-74) | H | H | (a-14) | —CH— | —NH— | —COCH(Me)— |
| 2-683 | (b-7) | (b-74) | H | H | (a-14) | —CH— | —O— | —CH(Me)— |
| 2-684 | (b-7) | (b-74) | H | H | (a-14) | —CH— | —S— | —CH(Me)— |
| 2-685 | (b-7) | (b-75) | H | H | (a-14) | —CH— | —NH— | —CH(Me)— |
| 2-686 | (b-7) | (b-76) | H | H | (a-14) | —CH— | —NH— | —CH(Me)— |
| 2-687 | (b-7) | (b-76) | H | H | (a-14) | —CH— | —NH— | —COCH(Me)— |
| 2-688 | (b-7) | (b-76) | H | H | (a-14) | —CH— | —O— | —CH(Me)— |
| 2-689 | (b-7) | (b-76) | H | H | (a-14) | —CH— | —S— | —CH(Me)— |
| 2-690 | (b-7) | (b-77) | H | H | (a-14) | —CH— | —NH— | —(CH₂)₂— |
| 2-691 | (b-7) | (b-77) | H | H | (a-14) | —CH— | —NH— | —CH(Me)— |
| 2-692 | (b-7) | (b-77) | H | H | (a-14) | —CH— | —NH— | —CH₂CH(Me)— |
| 2-693 | (b-7) | (b-77) | H | H | (a-14) | —CH— | —NH— | —CO(CH₂)₂— |
| 2-694 | (b-7) | (b-77) | H | H | (a-14) | —CH— | —NH— | —COCH(Me)— |
| 2-695 | (b-7) | (b-77) | H | H | (a-14) | —CH— | —O— | —CH(Me)— |
| 2-696 | (b-7) | (b-77) | H | H | (a-14) | —CH— | —S— | —CH(Me)— |
| 2-697 | (b-7) | (b-77) | 6-Cl | H | (a-14) | —CH— | —NH— | —CH(Me)— |
| 2-698 | (b-7) | (b-77) | 4-OH | H | (a-14) | —CH— | —NH— | —CH(Me)— |
| 2-699 | (b-7) | (b-77) | 6-OH | H | (a-14) | —CH— | —NH— | —CH(Me)— |
| 2-700 | (b-7) | (b-77) | H | H | (a-14) | N | —CO— | —CH(Me)— |
| 2-701 | (b-7) | (b-78) | H | H | (a-14) | —CH— | —NH— | —CH(Me)— |
| 2-702 | (b-8) | (b-7) | H | H | (a-14) | —CH— | —NH— | —CH(Me)— |
| 2-703 | (b-8) | (b-35) | H | H | (a-14) | —CH— | —NH— | —CH(Me)— |
| 2-704 | (b-9) | (b-7) | H | H | (a-14) | —CH— | —NH— | —CH(Me)— |
| 2-705 | (b-9) | (b-35) | H | H | (a-14) | —CH— | —NH— | —CH(Me)— |
| 2-706 | (b-10) | (b-7) | H | H | (a-14) | —CH— | —NH— | —CH(Me)— |
| 2-707 | (b-10) | (b-35) | H | H | (a-14) | —CH— | —NH— | —CH(Me)— |
| 2-708 | (b-11) | (b-1) | H | H | (a-14) | —CH— | —NH— | —CH(Me)— |
| 2-709 | (b-11) | (b-2) | H | H | (a-14) | —CH— | —NH— | —CH(Me)— |
| 2-710 | (b-11) | (b-7) | H | H | (a-14) | —CH— | —NH— | single bond |
| 2-711 | (b-11) | (b-7) | H | H | (a-14) | —CH— | —NH— | —CH₂— |
| 2-712 | (b-11) | (b-7) | H | H | (a-14) | —CH— | —NH— | —(CH₂)₂— |
| 2-713 | (b-11) | (b-7) | H | H | (a-14) | —CH— | —NH— | —CH(Me)— |

TABLE 2-continued

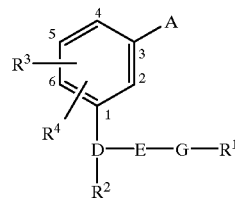

(I-2)

| Cpd. No. | R¹ Sub. No | R² Sub. No | R³ | R⁴ | A Sub. No | D | E | G |
|---|---|---|---|---|---|---|---|---|
| 2-714 | (b-11) | (b-7) | H | H | (a-14) | —CH— | —NH— | —CH(Et)— |
| 2-715 | (b-11) | (b-7) | H | H | (a-14) | —CH— | —NH— | —(CH₂)₃— |
| 2-716 | (b-11) | (b-7) | H | H | (a-14) | —CH— | —NH— | —CH₂CH(Me)— |
| 2-717 | (b-11) | (b-7) | H | H | (a-14) | —CH— | —NH— | —CH₂CH(OH)— |
| 2-718 | (b-11) | (b-7) | H | H | (a-14) | —CH— | —NH— | —CH₂C(=O)— |
| 2-719 | (b-11) | (b-7) | H | H | (a-14) | —CH— | —NH— | —CH₂C(Ph)— |
| 2-720 | (b-11) | (b-7) | H | H | (a-14) | —CH— | —NH— | —(CH₂)₂CH(Me)— |
| 2-721 | (b-11) | (b-7) | H | H | (a-14) | —CH— | —NH— | —(CH₂)₂CH(OH)— |
| 2-722 | (b-11) | (b-7) | H | H | (a-14) | —CH— | —NH— | —(CH₂)₂C(=O)— |
| 2-723 | (b-11) | (b-7) | H | H | (a-14) | —CH— | —NH— | —(CH₂)₂C(Ph)— |
| 2-724 | (b-11) | (b-7) | H | H | (a-14) | —CH— | —NH— | —CO— |
| 2-725 | (b-11) | (b-7) | H | H | (a-14) | —CH— | —NH— | —COCH₂— |
| 2-726 | (b-11) | (b-7) | H | H | (a-14) | —CH— | —NH— | —CO(CH₂)₂— |
| 2-727 | (b-11) | (b-7) | H | H | (a-14) | —CH— | —NH— | —COCH(Me)— |
| 2-728 | (b-11) | (b-7) | H | H | (a-14) | —CH— | —NH— | —COCH(Et)— |
| 2-729 | (b-11) | (b-7) | H | H | (a-14) | —CH— | —NH— | —CO(CH₂)₃— |
| 2-730 | (b-11) | (b-7) | H | H | (a-14) | —CH— | —NH— | —COCH₂CH(Me)— |
| 2-731 | (b-11) | (b-7) | H | H | (a-14) | —CH— | —O— | —CH₂— |
| 2-732 | (b-11) | (b-7) | H | H | (a-14) | —CH— | —O— | —(CH₂)₂— |
| 2-733 | (b-11) | (b-7) | H | H | (a-14) | —CH— | —O— | —CH(Me)— |
| 2-734 | (b-11) | (b-7) | H | H | (a-14) | —CH— | —S— | —CH₂— |
| 2-735 | (b-11) | (b-7) | H | H | (a-14) | —CH— | —S— | —(CH₂)₂— |
| 2-736 | (b-11) | (b-7) | H | H | (a-14) | —CH— | —S— | —CH(Me)— |
| 2-737 | (b-11) | (b-7) | 4-F | H | (a-14) | —CH— | —NH— | —CH(Me)— |
| 2-738 | (b-11) | (b-7) | 6-F | H | (a-14) | —CH— | —NH— | —CH(Me)— |
| 2-739 | (b-11) | (b-7) | 4-Cl | H | (a-14) | —CH— | —NH— | —CH(Me)— |
| 2-740 | (b-11) | (b-7) | 5-Cl | H | (a-14) | —CH— | —NH— | —CH(Me)— |
| 2-741 | (b-11) | (b-7) | 6-Cl | H | (a-14) | —CH— | —NH— | —CH(Me)— |
| 2-742 | (b-11) | (b-7) | 4-OH | H | (a-14) | —CH— | —NH— | —CH(Me)— |
| 2-743 | (b-11) | (b-7) | 5-OH | H | (a-14) | —CH— | —NH— | —CH(Me)— |
| 2-744 | (b-11) | (b-7) | 6-OH | H | (a-14) | —CH— | —NH— | —CH(Me)— |
| 2-745 | (b-11) | (b-7) | H | H | (a-14) | N | —CO— | —CH₂— |
| 2-746 | (b-11) | (b-7) | H | H | (a-14) | N | —CO— | —(CH₂)₂— |
| 2-747 | (b-11) | (b-7) | H | H | (a-14) | N | —CO— | —CH(Me)— |
| 2-748 | (b-11) | (b-8) | H | H | (a-14) | —CH— | —NH— | —CH(Me)— |
| 2-749 | (b-11) | (b-10) | H | H | (a-14) | —CH— | —NH— | —CH(Me)— |
| 2-750 | (b-11) | (b-11) | H | H | (a-14) | —CH— | —NH— | —CH(Me)— |
| 2-751 | (b-11) | (b-11) | H | H | (a-14) | —CH— | —NH— | —COCH(Me)— |
| 2-752 | (b-11) | (b-11) | H | H | (a-14) | —CH— | —O— | —CH(Me)— |
| 2-753 | (b-11) | (b-11) | H | H | (a-14) | —CH— | —S— | —CH(Me)— |
| 2-754 | (b-11) | (b-12) | H | H | (a-14) | —CH— | —NH— | —(CH₂)₂— |
| 2-755 | (b-11) | (b-12) | H | H | (a-14) | —CH— | —NH— | —CH(Me)— |
| 2-756 | (b-11) | (b-12) | H | H | (a-14) | —CH— | —NH— | —CH₂CH(Me)— |
| 2-757 | (b-11) | (b-12) | H | H | (a-14) | —CH— | —NH— | —CO(CH₂)₂— |
| 2-758 | (b-11) | (b-12) | H | H | (a-14) | —CH— | —NH— | —COCH(Me)— |
| 2-759 | (b-11) | (b-12) | H | H | (a-14) | —CH— | —O— | —CH(Me)— |
| 2-760 | (b-11) | (b-12) | H | H | (a-14) | —CH— | —S— | —CH(Me)— |
| 2-761 | (b-11) | (b-12) | 6-Cl | H | (a-14) | —CH— | —NH— | —CH(Me)— |
| 2-762 | (b-11) | (b-12) | 4-OH | H | (a-14) | —CH— | —NH— | —CH(Me)— |
| 2-763 | (b-11) | (b-12) | 6-OH | H | (a-14) | —CH— | —NH— | —CH(Me)— |
| 2-764 | (b-11) | (b-12) | H | H | (a-14) | N | —CO— | —CH(Me)— |
| 2-765 | (b-11) | (b-13) | H | H | (a-14) | —CH— | —NH— | —CH(Me)— |
| 2-766 | (b-11) | (b-14) | H | H | (a-14) | —CH— | —NH— | —CH(Me)— |
| 2-767 | (b-11) | (b-14) | H | H | (a-14) | —CH— | —NH— | —COCH(Me)— |
| 2-768 | (b-11) | (b-14) | H | H | (a-14) | —CH— | —O— | —CH(Me)— |
| 2-769 | (b-11) | (b-14) | H | H | (a-14) | —CH— | —S— | —CH(Me)— |
| 2-770 | (b-11) | (b-15) | H | H | (a-14) | —CH— | —NH— | —(CH₂)₂— |
| 2-771 | (b-11) | (b-15) | H | H | (a-14) | —CH— | —NH— | —CH(Me)— |
| 2-772 | (b-11) | (b-15) | H | H | (a-14) | —CH— | —NH— | —CH₂CH(Me)— |
| 2-773 | (b-11) | (b-15) | H | H | (a-14) | —CH— | —NH— | —CO(CH₂)₂— |
| 2-774 | (b-11) | (b-15) | H | H | (a-14) | —CH— | —NH— | —COCH(Me)— |
| 2-775 | (b-11) | (b-15) | H | H | (a-14) | —CH— | —O— | —CH(Me)— |
| 2-776 | (b-11) | (b-15) | H | H | (a-14) | —CH— | —S— | —CH(Me)— |
| 2-777 | (b-11) | (b-15) | 6-Cl | H | (a-14) | —CH— | —NH— | —CH(Me)— |

TABLE 2-continued

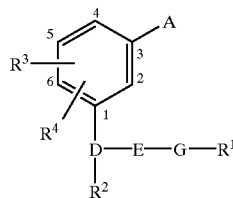

(I-2)

| Cpd. No. | R¹ Sub. No | R² Sub. No | R³ | R⁴ | A Sub. No | D | E | G |
|---|---|---|---|---|---|---|---|---|
| 2-778 | (b-11) | (b-15) | 4-OH | H | (a-14) | —CH— | —NH— | —CH(Me)— |
| 2-779 | (b-11) | (b-15) | 6-OH | H | (a-14) | —CH— | —NH— | —CH(Me)— |
| 2-780 | (b-11) | (b-15) | H | H | (a-14) | N | —CO— | —CH(Me)— |
| 2-781 | (b-11) | (b-16) | H | H | (a-14) | —CH— | —NH— | —CH(Me)— |
| 2-782 | (b-11) | (b-17) | H | H | (a-14) | —CH— | —NH— | —CH(Me)— |
| 2-783 | (b-11) | (b-17) | H | H | (a-14) | —CH— | —NH— | —COCH(Me)— |
| 2-784 | (b-11) | (b-17) | H | H | (a-14) | —CH— | —O— | —CH(Me)— |
| 2-785 | (b-11) | (b-17) | H | H | (a-14) | —CH— | —S— | —CH(Me)— |
| 2-786 | (b-11) | (b-23) | H | H | (a-14) | —CH— | —NH— | —CH(Me)— |
| 2-787 | (b-11) | (b-24) | H | H | (a-14) | —CH— | —NH— | —CH(Me)— |
| 2-788 | (b-11) | (b-25) | H | H | (a-14) | —CH— | —NH— | —CH(Me)— |
| 2-789 | (b-11) | (b-25) | H | H | (a-14) | —CH— | —NH— | —COCH(Me)— |
| 2-790 | (b-11) | (b-25) | H | H | (a-14) | —CH— | —O— | —CH(Me)— |
| 2-791 | (b-11) | (b-25) | H | H | (a-14) | —CH— | —S— | —CH(Me)— |
| 2-792 | (b-11) | (b-27) | H | H | (a-14) | —CH— | —NH— | —CH(Me)— |
| 2-793 | (b-11) | (b-28) | H | H | (a-14) | —CH— | —NH— | —CH(Me)— |
| 2-794 | (b-11) | (b-30) | H | H | (a-14) | —CH— | —NH— | —CH(Me)— |
| 2-795 | (b-11) | (b-31) | H | H | (a-14) | —CH— | —NH— | —CH(Me)— |
| 2-796 | (b-11) | (b-32) | H | H | (a-14) | —CH— | —NH— | —CH(Me)— |
| 2-797 | (b-11) | (b-33) | H | H | (a-14) | —CH— | —NH— | —CH(Me)— |
| 2-798 | (b-11) | (b-33) | H | H | (a-14) | —CH— | —NH— | —COCH(Me)— |
| 2-799 | (b-11) | (b-33) | H | H | (a-14) | —CH— | —O— | —CH(Me)— |
| 2-800 | (b-11) | (b-33) | H | H | (a-14) | —CH— | —S— | —CH(Me)— |
| 2-801 | (b-11) | (b-34) | H | H | (a-14) | —CH— | —NH— | —(CH₂)₂— |
| 2-802 | (b-11) | (b-34) | H | H | (a-14) | —CH— | —NH— | —CH(Me)— |
| 2-803 | (b-11) | (b-34) | H | H | (a-14) | —CH— | —NH— | —CH₂CH(Me)— |
| 2-804 | (b-11) | (b-34) | H | H | (a-14) | —CH— | —NH— | —CO(CH₂)₂— |
| 2-805 | (b-11) | (b-34) | H | H | (a-14) | —CH— | —NH— | —COCH(Me)— |
| 2-806 | (b-11) | (b-34) | H | H | (a-14) | —CH— | —O— | —CH(Me)— |
| 2-807 | (b-11) | (b-34) | H | H | (a-14) | —CH— | —S— | —CH(Me)— |
| 2-808 | (b-11) | (b-34) | 6-Cl | H | (a-14) | —CH— | —NH— | —CH(Me)— |
| 2-809 | (b-11) | (b-34) | 4-OH | H | (a-14) | —CH— | —NH— | —CH(Me)— |
| 2-810 | (b-11) | (b-34) | 6-OH | H | (a-14) | —CH— | —NH— | —CH(Me)— |
| 2-811 | (b-11) | (b-34) | H | H | (a-14) | N | —CO— | —CH(Me)— |
| 2-812 | (b-11) | (b-35) | H | H | (a-14) | —CH— | —NH— | single bond |
| 2-813 | (b-11) | (b-35) | H | H | (a-14) | —CH— | —NH— | —CH₂— |
| 2-814 | (b-11) | (b-35) | H | H | (a-14) | —CH— | —NH— | —(CH₂)₂— |
| 2-815 | (b-11) | (b-35) | H | H | (a-14) | —CH— | —NH— | —CH(Me)— |
| 2-816 | (b-11) | (b-35) | H | H | (a-14) | —CH— | —NH— | —CH(Et)— |
| 2-817 | (b-11) | (b-35) | H | H | (a-14) | —CH— | —NH— | —(CH₂)₃— |
| 2-818 | (b-11) | (b-35) | H | H | (a-14) | —CH— | —NH— | —CH₂CH(Me)— |
| 2-819 | (b-11) | (b-35) | H | H | (a-14) | —CH— | —NH— | —CH₂CH(OH)— |
| 2-820 | (b-11) | (b-35) | H | H | (a-14) | —CH— | —NH— | —CH₂C(=O)— |
| 2-821 | (b-11) | (b-35) | H | H | (a-14) | —CH— | —NH— | —CH₂C(Ph)— |
| 2-822 | (b-11) | (b-35) | H | H | (a-14) | —CH— | —NH— | —(CH₂)₂CH(Me)— |
| 2-823 | (b-11) | (b-35) | H | H | (a-14) | —CH— | —NH— | —(CH₂)₂CH(OH)— |
| 2-824 | (b-11) | (b-35) | H | H | (a-14) | —CH— | —NH— | —(CH₂)₂C(=O)— |
| 2-825 | (b-11) | (b-35) | H | H | (a-14) | —CH— | —NH— | —(CH₂)₂C(Ph)— |
| 2-826 | (b-11) | (b-35) | H | H | (a-14) | —CH— | —NH— | —CO— |
| 2-827 | (b-11) | (b-35) | H | H | (a-14) | —CH— | —NH— | —COCH₂— |
| 2-828 | (b-11) | (b-35) | H | H | (a-14) | —CH— | —NH— | —CO(CH₂)₂— |
| 2-829 | (b-11) | (b-35) | H | H | (a-14) | —CH— | —NH— | —COCH(Me)— |
| 2-830 | (b-11) | (b-35) | H | H | (a-14) | —CH— | —NH— | —COCH(Et)— |
| 2-831 | (b-11) | (b-35) | H | H | (a-14) | —CH— | —NH— | —CO(CH₂)₃— |
| 2-832 | (b-11) | (b-35) | H | H | (a-14) | —CH— | —NH— | —COCH₂CH(Me)— |
| 2-833 | (b-11) | (b-35) | H | H | (a-14) | —CH— | —O— | —CH₂— |
| 2-834 | (b-11) | (b-35) | H | H | (a-14) | —CH— | —O— | —(CH₂)₂— |
| 2-835 | (b-11) | (b-35) | H | H | (a-14) | —CH— | —O— | —CH(Me)— |
| 2-836 | (b-11) | (b-35) | H | H | (a-14) | —CH— | —S— | —CH₂— |
| 2-837 | (b-11) | (b-35) | H | H | (a-14) | —CH— | —S— | —(CH₂)₂— |
| 2-838 | (b-11) | (b-35) | H | H | (a-14) | —CH— | —S— | —CH(Me)— |
| 2-839 | (b-11) | (b-35) | 4-F | H | (a-14) | —CH— | —NH— | —CH(Me)— |
| 2-840 | (b-11) | (b-35) | 6-F | H | (a-14) | —CH— | —NH— | —CH(Me)— |
| 2-841 | (b-11) | (b-35) | 4-Cl | H | (a-14) | —CH— | —NH— | —CH(Me)— |

TABLE 2-continued

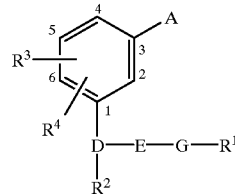

(I-2)

| Cpd. No. | R¹ Sub. No | R² Sub. No | R³ | R⁴ | A Sub. No | D | E | G |
|---|---|---|---|---|---|---|---|---|
| 2-842 | (b-11) | (b-35) | 5-Cl | H | (a-14) | —CH— | —NH— | —CH(Me)— |
| 2-843 | (b-11) | (b-35) | 6-Cl | H | (a-14) | —CH— | —NH— | —CH(Me)— |
| 2-844 | (b-11) | (b-35) | 4-OH | H | (a-14) | —CH— | —NH— | —CH(Me)— |
| 2-845 | (b-11) | (b-35) | 5-OH | H | (a-14) | —CH— | —NH— | —CH(Me)— |
| 2-846 | (b-11) | (b-35) | 6-OH | H | (a-14) | —CH— | —NH— | —CH(Me)— |
| 2-847 | (b-11) | (b-35) | H | H | (a-14) | N | —CO— | —CH$_2$— |
| 2-848 | (b-11) | (b-35) | H | H | (a-14) | N | —CO— | —(CH$_2$)$_2$— |
| 2-849 | (b-11) | (b-35) | H | H | (a-14) | N | —CO— | —CH(Me)— |
| 2-850 | (b-11) | (b-37) | H | H | (a-14) | —CH— | —NH— | single bond |
| 2-851 | (b-11) | (b-37) | H | H | (a-14) | —CH— | —NH— | —CH$_2$— |
| 2-852 | (b-11) | (b-37) | H | H | (a-14) | —CH— | —NH— | —(CH$_2$)$_2$— |
| 2-853 | (b-11) | (b037) | H | H | (a-14) | —CH— | —NH— | —CH(Me)— |
| 2-854 | (b-11) | (b-37) | H | H | (a-14) | —CH— | —NH— | —CH(Et)— |
| 2-855 | (b-11) | (b-37) | H | H | (a-14) | —CH— | —NH— | —(CH$_2$)$_3$— |
| 2-856 | (b-11) | (b-37) | H | H | (a-14) | —CH— | —NH— | —CH$_2$CH(Me)— |
| 2-857 | (b-11) | (b-37) | H | H | (a-14) | —CH— | —NH— | —CH$_2$CH(OH)— |
| 2-858 | (b-11) | (b-37) | H | H | (a-14) | —CH— | —NH— | —CH$_2$C(=O)— |
| 2-859 | (b-11) | (b-37) | H | H | (a-14) | —CH— | —NH— | —CH$_2$C(Ph)— |
| 2-860 | (b-11) | (b-37) | H | H | (a-14) | —CH— | —NH— | —(CH$_2$)$_2$CH(Me)— |
| 2-861 | (b-11) | (b-37) | H | H | (a-14) | —CH— | —NH— | —(CH$_2$)$_2$CH(OH)— |
| 2-862 | (b-11) | (b-37) | H | H | (a-14) | —CH— | —NH— | —(CH$_2$)$_2$C(=O)— |
| 2-863 | (b-11) | (b-37) | H | H | (a-14) | —CH— | —NH— | —(CH$_2$)$_2$C(Ph)— |
| 2-864 | (b-11) | (b-37) | H | H | (a-14) | —CH— | —NH— | —CO— |
| 2-865 | (b-11) | (b-37) | H | H | (a-14) | —CH— | —NH— | —COCH$_2$— |
| 2-866 | (b-11) | (b-37) | H | H | (a-14) | —CH— | —NH— | —CO(CH$_2$)$_2$— |
| 2-867 | (b-11) | (b-37) | H | H | (a-14) | —CH— | —NH— | —COCH(Me)— |
| 2-868 | (b-11) | (b-37) | H | H | (a-14) | —CH— | —NH— | —COCH(Et)— |
| 2-869 | (b-11) | (b-37) | H | H | (a-14) | —CH— | —NH— | —CO(CH$_2$)$_3$— |
| 2-870 | (b-11) | (b-37) | H | H | (a-14) | —CH— | —NH— | —COCH$_2$CH(Me)— |
| 2-871 | (b-11) | (b-37) | H | H | (a-14) | —CH— | —O— | —CH$_2$— |
| 2-872 | (b-11) | (b-37) | H | H | (a-14) | —CH— | —O— | —(CH$_2$)$_2$— |
| 2-873 | (b-11) | (b-37) | H | H | (a-14) | —CH— | —O— | —CH(Me)— |
| 2-874 | (b-11) | (b-37) | H | H | (a-14) | —CH— | —S— | —CH$_2$— |
| 2-875 | (b-11) | (b-37) | H | H | (a-14) | —CH— | —S— | —(CH$_2$)$_2$— |
| 2-876 | (b-11) | (b-37) | H | H | (a-14) | —CH— | —S— | —CH(Me)— |
| 2-877 | (b-11) | (b-37) | 4-F | H | (a-14) | —CH— | —NH— | —CH(Me)— |
| 2-878 | (b-11) | (b-37) | 6-F | H | (a-14) | —CH— | —NH— | —CH(Me)— |
| 2-879 | (b-11) | (b-37) | 4-Cl | H | (a-14) | —CH— | —NH— | —CH(Me)— |
| 2-880 | (b-11) | (b-37) | 5-Cl | H | (a-14) | —CH— | —NH— | —CH(Me)— |
| 2-881 | (b-11) | (b-37) | 6-Cl | H | (a-14) | —CH— | —NH— | —CH(Me)— |
| 2-882 | (b-11) | (b-37) | 4-OH | H | (a-14) | —CH— | —NH— | —CH(Me)— |
| 2-883 | (b-11) | (b-37) | 5-OH | H | (a-14) | —CH— | —NH— | —CH(Me)— |
| 2-884 | (b-11) | (b-37) | 6-OH | H | (a-14) | —CH— | —NH— | —CH(Me)— |
| 2-885 | (b-11) | (b-37) | H | H | (a-14) | N | —CO— | —CH$_2$— |
| 2-886 | (b-11) | (b-37) | H | H | (a-14) | N | —CO— | —(CH$_2$)$_2$— |
| 2-887 | (b-11) | (b-37) | H | H | (a-14) | N | —CO— | —CH(Me)— |
| 2-888 | (b-11) | (b-38) | H | H | (a-14) | —CH— | —NH— | —CH(Me)— |
| 2-889 | (b-11) | (b-41) | H | H | (a-14) | —CH— | —NH— | —CH(Me)— |
| 2-890 | (b-11) | (b-42) | H | H | (a-14) | —CH— | —NH— | —CH(Me)— |
| 2-891 | (b-11) | (b-42) | H | H | (a-14) | —CH— | —NH— | —COCH(Me)— |
| 2-892 | (b-11) | (b-42) | H | H | (a-14) | —CH— | —O— | —CH(Me)— |
| 2-893 | (b-11) | (b-42) | H | H | (a-14) | —CH— | —S— | —CH(Me)— |
| 2-894 | (b-11) | (b-43) | H | H | (a-14) | —CH— | —NH— | —CH(Me)— |
| 2-895 | (b-11) | (b-72) | H | H | (a-14) | —CH— | —NH— | —(CH$_2$)$_2$— |
| 2-896 | (b-11) | (b-72) | H | H | (a-14) | —CH— | —NH— | —CH(Me)— |
| 2-897 | (b-11) | (b-72) | H | H | (a-14) | —CH— | —NH— | CH$_2$CH(Me)— |
| 2-898 | (b-11) | (b-72) | H | H | (a-14) | —CH— | —NH— | —COCH(Me)— |
| 2-899 | (b-11) | (b-72) | H | H | (a-14) | —CH— | —O— | —CH(Me)— |
| 2-900 | (b-11) | (b-72) | H | H | (a-14) | —CH— | —S— | —CH(Me)— |
| 2-901 | (b-11) | (b-72) | 6-Cl | H | (a-14) | —CH— | —NH— | —CH(Me)— |
| 2-902 | (b-11) | (b-72) | 4-OH | H | (a-14) | —CH— | —NH— | —CH(Me)— |
| 2-903 | (b-11) | (b-72) | 6-OH | H | (a-14) | —CH— | —NH— | —CH(Me)— |
| 2-904 | (b-11) | (b-73) | H | H | (a-14) | —CH— | —NH— | single bond |
| 2-905 | (b-11) | (b-73) | H | H | (a-14) | —CH— | —NH— | —CH$_2$— |

TABLE 2-continued

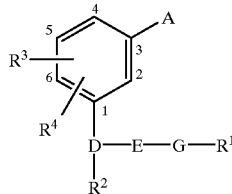

(I-2)

| Cpd. No. | R¹ Sub. No | R² Sub. No | R³ | R⁴ | A Sub. No | D | E | G |
|---|---|---|---|---|---|---|---|---|
| 2-906 | (b-11) | (b-73) | H | H | (a-14) | —CH— | —NH— | —(CH₂)₂— |
| 2-907 | (b-11) | (b-73) | H | H | (a-14) | —CH— | —NH— | —CH(Me)— |
| 2-908 | (b-11) | (b-73) | H | H | (a-14) | —CH— | —NH— | —CH(Et)— |
| 2-909 | (b-11) | (b-73) | H | H | (a-14) | —CH— | —NH— | —(CH₂)₃— |
| 2-910 | (b-11) | (b-73) | H | H | (a-14) | —CH— | —NH— | —CH₂CH(Me)— |
| 2-911 | (b-11) | (b-73) | H | H | (a-14) | —CH— | —NH— | —CH₂CH(OH)— |
| 2-912 | (b-11) | (b-73) | H | H | (a-14) | —CH— | —NH— | —CH₂C(=O)— |
| 2-913 | (b-11) | (b-73) | H | H | (a-14) | —CH— | —NH— | —CH₂C(Ph)— |
| 2-914 | (b-11) | (b-73) | H | H | (a-14) | —CH— | —NH— | —(CH₂)₂CH(Me)— |
| 2-915 | (b-11) | (b-73) | H | H | (a-14) | —CH— | —NH— | —(CH₂)₂CH(OH)— |
| 2-916 | (b-11) | (b-73) | H | H | (a-14) | —CH— | —NH— | —(CH₂)₂C(=O)— |
| 2-917 | (b-11) | (b-73) | H | H | (a-14) | —CH— | —NH— | —(CH₂)₂C(Ph)— |
| 2-918 | (b-11) | (b-73) | H | H | (a-14) | —CH— | —NH— | —CO— |
| 2-919 | (b-11) | (b-73) | H | H | (a-14) | —CH— | —NH— | —COCH₂— |
| 2-920 | (b-11) | (b-73) | H | H | (a-14) | —CH— | —NH— | —CO(CH₂)₂— |
| 2-921 | (b-11) | (b-73) | H | H | (a-14) | —CH— | —NH— | —COCH(Me)— |
| 2-922 | (b-11) | (b-73) | H | H | (a-14) | —CH— | —NH— | —COCH(Et)— |
| 2-923 | (b-11) | (b-73) | H | H | (a-14) | —CH— | —NH— | —CO(CH₂)₃— |
| 2-924 | (b-11) | (b-73) | H | H | (a-14) | —CH— | —NH— | —COCH₂CH(Me)— |
| 2-925 | (b-11) | (b-73). | H | H | (a-14) | —CH— | —O— | —CH₂— |
| 2-926 | (b-11) | (b-73) | H | H | (a-14) | —CH— | —O— | —(CH₂)₂— |
| 2-927 | (b-11) | (b-73) | H | H | (a-14) | —CH— | —O— | —CH(Me)— |
| 2-928 | (b-11) | (b-73) | H | H | (a-14) | —CH— | —S— | —CH₂— |
| 2-929 | (b-11) | (b-73) | H | H | (a-14) | —CH— | —S— | —(CH₂)₂— |
| 2-930 | (b-11) | (b-73) | H | H | (a-14) | —CH— | —S— | —CH(Me)— |
| 2-931 | (b-11) | (b-73) | 4-F | H | (a-14) | —CH— | —NH— | —CH(Me)— |
| 2-932 | (b-11) | (b-73) | 6-F | H | (a-14) | —CH— | —NH— | —CH(Me)— |
| 2-933 | (b-11) | (b-73) | 4-Cl | H | (a-14) | —CH— | —NH— | —CH(Me)— |
| 2-934 | (b-11) | (b-73) | 5-Cl | H | (a-14) | —CH— | —NH— | —CH(Me)— |
| 2-935 | (b-11) | (b-73) | 6-Cl | H | (a-14) | —CH— | —NH— | —CH(Me)— |
| 2-936 | (b-11) | (b-73) | 4-OH | H | (a-14) | —CH— | —NH— | —CH(Me)— |
| 2-937 | (b-11) | (b-73) | 5-OH | H | (a-14) | —CH— | —NH— | —CH(Me)— |
| 2-938 | (b-11) | (b-73) | 6-OH | H | (a-14) | —CH— | —NH— | —CH(Me)— |
| 2-939 | (b-11) | (b-73) | H | H | (a-14) | N | —CO— | —CH₂— |
| 2-940 | (b-11) | (b-73) | H | H | (a-14) | N | —CO— | —(CH₂)₂— |
| 2-941 | (b-11) | (b-73) | H | H | (a-14) | N | —CO— | —CH(Me)— |
| 2-942 | (b-11) | (b-74) | H | H | (a-14) | —CH— | —NH— | —CH(Me)— |
| 2-943 | (b-11) | (b-74) | H | H | (a-14) | —CH— | —NH— | —COCH(Me)— |
| 2-944 | (b-11) | (b-74) | H | H | (a-14) | —CH— | —O— | —CH(Me)— |
| 2-945 | (b-11) | (b-74) | H | H | (a-14) | —CH— | —S— | —CH(Me)— |
| 2-946 | (b-11) | (b-75) | H | H | (a-14) | —CH— | —NH— | —CH(Me)— |
| 2-947 | (b-11) | (b-76) | H | H | (a-14) | —CH— | —NH— | —CH(Me)— |
| 2-948 | (b-11) | (b-76) | H | H | (a-14) | —CH— | —NH— | —COCH(Me)— |
| 2-949 | (b-11) | (b-76) | H | H | (a-14) | —CH— | —O— | —CH(Me)— |
| 2-950 | (b-11) | (b-76) | H | H | (a-14) | —CH— | —S— | —CH(Me)— |
| 2-951 | (b-11) | (b-77) | H | H | (a-14) | —CH— | —NH— | —(CH₂)₂— |
| 2-952 | (b-11) | (b-77) | H | H | (a-14) | —CH— | —NH— | —CH(Me)— |
| 2-953 | (b-11) | (b-77) | H | H | (a-14) | —CH— | —NH— | —CH₂CH(Me)— |
| 2-954 | (b-11) | (b-77) | H | H | (a-14) | —CH— | —NH— | —CO(CH₂)₂— |
| 2-955 | (b-11) | (b-77) | H | H | (a-14) | —CH— | —NH— | —COCH(Me)— |
| 2-956 | (b-11) | (b-77) | H | H | (a-14) | —CH— | —O— | —CH(Me)— |
| 2-957 | (b-11) | (b-77) | H | H | (a-14) | —CH— | —S— | —CH(Me)— |
| 2-958 | (b-11) | (b-77) | 6-Cl | H | (a-14) | —CH— | —NH— | —CH(Me)— |
| 2-959 | (b-11) | (b-77) | 4-OH | H | (a-14) | —CH— | —NH— | —CH(Me)— |
| 2-960 | (b-11) | (b-77) | 6-OH | H | (a-14) | —CH— | —NH— | —CH(Me)— |
| 2-961 | (b-11) | (b-77) | H | H | (a-14) | N | —CO— | —CH(Me)— |
| 2-962 | (b-11) | (b-78) | H | H | (a-14) | —CH— | —NH— | —CH(Me)— |
| 2-963 | (b-12) | (b-7) | H | H | (a-14) | —CH— | —NH— | —CH(Me)— |
| 2-964 | (b-12) | (b-7) | H | H | (a-14) | —CH— | —NH— | —COCH(Me)— |
| 2-965 | (b-12) | (b-12) | H | H | (a-14) | —CH— | —NH— | —CH(Me)— |
| 2-966 | (b-12) | (b-15) | H | H | (a-14) | —CH— | —NH— | —CH(Me)— |
| 2-967 | (b-12) | (b-34) | H | H | (a-14) | —CH— | —NH— | —CH(Me)— |
| 2-968 | (b-12) | (b-35) | H | H | (a-14) | —CH— | —NH— | —CH(Me)— |
| 2-969 | (b-12) | (b-35) | H | H | (a-14) | —CH— | —NH— | —CO— |

TABLE 2-continued

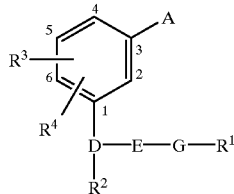

(I-2)

| Cpd. No. | R¹ Sub. No | R² Sub. No | R³ | R⁴ | A Sub. No | D | E | G |
|---|---|---|---|---|---|---|---|---|
| 2-970 | (b-12) | (b-35) | H | H | (a-14) | —CH— | —NH— | —COCH(Me)— |
| 2-971 | (b-12) | (b-37) | H | H | (a-14) | —CH— | —NH— | —CH(Me)— |
| 2-972 | (b-12) | (b-73) | H | H | (a-14) | —CH— | —NH— | —CH(Me)— |
| 2-973 | (b-12) | (b-77) | H | H | (a-14) | —CH— | —NH— | —CH(Me)— |
| 2-974 | (b-13) | (b-7) | H | H | (a-14) | —CH— | —NH— | —CH(Me)— |
| 2-975 | (b-13) | (b-7) | H | H | (a-14) | —CH— | —NH— | —COCH(Me)— |
| 2-976 | (b-13) | (b-35) | H | H | (a-14) | —CH— | —NH— | —CH(Me)— |
| 2-977 | (b-13) | (b-35) | H | H | (a-14) | —CH— | —NH— | —COCH(Me)— |
| 2-978 | (b-14) | (b-1) | H | H | (a-14) | —CH— | —NH— | —CH(Me)— |
| 2-979 | (b-14) | (b-2) | H | H | (a-14) | —CH— | —NH— | —CH(Me)— |
| 2-980 | (b-14) | (b-7) | H | H | (a-14) | —CH— | —NH— | single bond |
| 2-981 | (b-14) | (b-7) | H | H | (a-14) | —CH— | —NH— | —CH₂— |
| 2-982 | (b-14) | (b-7) | H | H | (a-14) | —CH— | —NH— | —(CH₂)₂— |
| 2-983 | (b-14) | (b-7) | H | H | (a-14) | —CH— | —NH— | —CH(Me)— |
| 2-984 | (b-14) | (b-7) | H | H | (a-14) | —CH— | —NH— | —CH(Et)— |
| 2-985 | (b-14) | (b-7) | H | H | (a-14) | —CH— | —NH— | —(CH₂)₃— |
| 2-986 | (b-14) | (b-7) | H | H | (a-14) | —CH— | —NH— | —CH₂CH(Me)— |
| 2-987 | (b-14) | (b-7) | H | H | (a-14) | —CH— | —NH— | —CH₂CH(OH)— |
| 2-988 | (b-14) | (b-7) | H | H | (a-14) | —CH— | —NH— | —CH₂C(=O)— |
| 2-989 | (b-14) | (b-7) | H | H | (a-14) | —CH— | —NH— | —CH₂C(Ph)— |
| 2-990 | (b-14) | (b-7) | H | H | (a-14) | —CH— | —NH— | —(CH₂)₂CH(Me)— |
| 2-991 | (b-14) | (b-7) | H | H | (a-14) | —CH— | —NH— | —(CH₂)₂CH(OH)— |
| 2-992 | (b-14) | (b-7) | H | H | (a-14) | —CH— | —NH— | —(CH₂)₂C(=O)— |
| 2-993 | (b-14) | (b-7) | H | H | (a-14) | —CH— | —NH— | —(CH₂)₂C(Ph)— |
| 2-994 | (b-14) | (b-7) | H | H | (a-14) | —CH— | —NH— | —CO— |
| 2-995 | (b-14) | (b-7) | H | H | (a-14) | —CH— | —NH— | —COCH₂— |
| 2-996 | (b-14) | (b-7) | H | H | (a-14) | —CH— | —NH— | —CO(CH₂)₂— |
| 2-997 | (b-14) | (b-7) | H | H | (a-14) | —CH— | —NH— | —COCH(Me)— |
| 2-998 | (b-14) | (b-7) | H | H | (a-14) | —CH— | —NH— | —COCH(Et)— |
| 2-999 | (b-14) | (b-7) | H | H | (a-14) | —CH— | —NH— | —CO(CH₂)₃— |
| 2-1000 | (b-14) | (b-7) | H | H | (a-14) | —CH— | —NH— | —COCH₂CH(Me)— |
| 2-1001 | (b-14) | (b-7) | H | H | (a-14) | —CH— | —O— | —CH₂— |
| 2-1002 | (b-14) | (b-7) | H | H | (a-14) | —CH— | —O— | —(CH₂)₂— |
| 2-1003 | (b-14) | (b-7) | H | H | (a-14) | —CH— | —O— | —CH(Me)— |
| 2-1004 | (b-14) | (b-7) | H | H | (a-14) | —CH— | —S— | —CH₂— |
| 2-1005 | (b-14) | (b-7) | H | H | (a-14) | —CH— | —S— | —(CH₂)₂— |
| 2-1006 | (b-14) | (b-7) | H | H | (a-14) | —CH— | —S— | —CH(Me)— |
| 2-1007 | (b-14) | (b-7) | 4-F | H | (a-14) | —CH— | —NH— | —CH(Me)— |
| 2-1008 | (b-14) | (b-7) | 6-F | H | (a-14) | —CH— | —NH— | —CH(Me)— |
| 2-1009 | (b-14) | (b-7) | 4-Cl | H | (a-14) | —CH— | —NH— | —CH(Me)— |
| 2-1010 | (b-14) | (b-7) | 5-Cl | H | (a-14) | —CH— | —NH— | —CH(Me)— |
| 2-1011 | (b-14) | (b-7) | 6-Cl | H | (a-14) | —CH— | —NH— | —CH(Me)— |
| 2-1012 | (b-14) | (b-7) | 4-OH | H | (a-14) | —CH— | —NH— | —CH(Me)— |
| 2-1013 | (b-14) | (b-7) | 5-OH | H | (a-14) | —CH— | —NH— | —CH(Me)— |
| 2-1014 | (b-14) | (b-7) | 6-OH | H | (a-14) | —CH— | —NH— | —CH(Me)— |
| 2-1015 | (b-14) | (b-7) | H | H | (a-14) | N | —CO— | —CH₂— |
| 2-1016 | (b-14) | (b-7) | H | H | (a-14) | N | —CO— | —(CH₂)₂— |
| 2-1017 | (b-14) | (b-7) | H | H | (a-14) | N | —CO— | —CH(Me)— |
| 2-1018 | (b-14) | (b-8) | H | H | (a-14) | —CH— | —NH— | —CH(Me)— |
| 2-1019 | (b-14) | (b-10) | H | H | (a-14) | —CH— | —NH— | —CH(Me)— |
| 2-1020 | (b-14) | (b-11) | H | H | (a-14) | —CH— | —NH— | —CH(Me)— |
| 2-1021 | (b-14) | (b-11) | H | H | (a-14) | —CH— | —NH— | —COCH(Me)— |
| 2-1022 | (b-14) | (b-11) | H | H | (a-14) | —CH— | —O— | —CH(Me)— |
| 2-1023 | (b-14) | (b-11) | H | H | (a-14) | —CH— | —S— | —CH(Me)— |
| 2-1024 | (b-14) | (b-12) | H | H | (a-14) | —CH— | —NH— | —(CH₂)₂— |
| 2-1025 | (b-14) | (b-12) | H | H | (a-14) | —CH— | —NH— | —CH(Me)— |
| 2-1026 | (b-14) | (b-12) | H | H | (a-14) | —CH— | —NH— | —CH₂CH(Me)— |
| 2-1027 | (b-14) | (b-12) | H | H | (a-14) | —CH— | —NH— | —CO(CH₂)₂— |
| 2-1028 | (b-14) | (b-12) | H | H | (a-14) | —CH— | —NH— | —COCH(Me)— |
| 2-1029 | (b-14) | (b-12) | H | H | (a-14) | —CH— | —O— | —CH(Me)— |
| 2-1030 | (b-14) | (b-12) | H | H | (a-14) | —CH— | —S— | —CH(Me)— |
| 2-1031 | (b-14) | (b-12) | 6-Cl | H | (a-14) | —CH— | —NH— | —CH(Me)— |
| 2-1032 | (b-14) | (b-12) | 4-OH | H | (a-14) | —CH— | —NH— | —CH(Me)— |
| 2-1033 | (b-14) | (b-12) | 6-OH | H | (a-14) | —CH— | —NH— | —CH(Me)— |

TABLE 2-continued

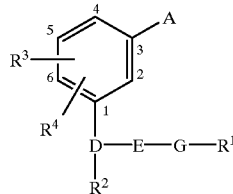

(I-2)

| Cpd. No. | R$^1$ Sub. No | R$^2$ Sub. No | R$^3$ | R$^4$ | A Sub. No | D | E | G |
|---|---|---|---|---|---|---|---|---|
| 2-1034 | (b-14) | (b-12) | H | H | (a-14) | N | —CO— | —CH(Me)— |
| 2-1035 | (b-14) | (b-13) | H | H | (a-14) | —CH— | —NH— | —CH(Me)— |
| 2-1036 | (b-14) | (b-14) | H | H | (a-14) | —CH— | —NH— | —CH(Me)— |
| 2-1037 | (b-14) | (b-14) | H | H | (a-14) | —CH— | —NH— | —COCH(Me)— |
| 2-1038 | (b-14) | (b-14) | H | H | (a-14) | —CH— | —O— | —CH(Me)— |
| 2-1039 | (b-14) | (b-14) | H | H | (a-14) | —CH— | —S— | —CH(Me)— |
| 2-1040 | (b-14) | (b-15) | H | H | (a-14) | —CH— | —NH— | —(CH$_2$)$_2$— |
| 2-1041 | (b-14) | (b-15) | H | H | (a-14) | —CH— | —NH— | —CH(Me)— |
| 2-1042 | (b-14) | (b-15) | H | H | (a-14) | —CH— | —NH— | —CH$_2$CH(Me)— |
| 2-1043 | (b-14) | (b-15) | H | H | (a-14) | —CH— | —NH— | —CO(CH$_2$)$_2$— |
| 2-1044 | (b-14) | (b-15) | H | H | (a-14) | —CH— | —NH— | —COCH(Me)— |
| 2-1045 | (b-14) | (b-15) | H | H | (a-14) | —CH— | —O— | —CH(Me)— |
| 2-1046 | (b-14) | (b-15) | H | H | (a-14) | —CH— | —S— | —CH(Me)— |
| 2-1047 | (b-14) | (b-15) | 6-Cl | H | (a-14) | —CH— | —NH— | —CH(Me)— |
| 2-1048 | (b-14) | (b-15) | 4-OH | H | (a-14) | —CH— | —NH— | —CH(Me)— |
| 2-1049 | (b-14) | (b-15) | 6-OH | H | (a-14) | —CH— | —NH— | —CH(Me)— |
| 2-1050 | (b-14) | (b-15) | H | H | (a-14) | N | —CO— | —CH(Me)— |
| 2-1051 | (b-14) | (b-16) | H | H | (a-14) | —CH— | —NH— | —CH(Me)— |
| 2-1052 | (b-14) | (b-17) | H | H | (a-14) | —CH— | —NH— | —CH(Me)— |
| 2-1053 | (b-14) | (b-17) | H | H | (a-14) | —CH— | —NH— | —COCH(Me)— |
| 2-1054 | (b-14) | (b-17) | H | H | (a-14) | —CH— | —O— | —CH(Me)— |
| 2-1055 | (b-14) | (b-17) | H | H | (a-14) | —CH— | —S— | —CH(Me)— |
| 2-1056 | (b-14) | (b-23) | H | H | (a-14) | —CH— | —NH— | —CH(Me)— |
| 2-1057 | (b-14) | (b-24) | H | H | (a-14) | —CH— | —NH— | —CH(Me)— |
| 2-1058 | (b-14) | (b-25) | H | H | (a-14) | —CH— | —NH— | —CH(Me)— |
| 2-1059 | (b-14) | (b-25) | H | H | (a-14) | —CH— | —NH— | —COCH(Me)— |
| 2-1060 | (b-14) | (b-25) | H | H | (a-14) | —CH— | —O— | —CH(Me)— |
| 2-1061 | (b-14) | (b-25) | H | H | (a-14) | —CH— | —S— | —CH(Me)— |
| 2-1062 | (b-14) | (b-27) | H | H | (a-14) | —CH— | —NH— | —CH(Me)— |
| 2-1063 | (b-14) | (b-28) | H | H | (a-14) | —CH— | —NH— | —CH(Me)— |
| 2-1064 | (b-14) | (b-30) | H | H | (a-14) | —CH— | —NH— | —CH(Me)— |
| 2-1065 | (b-14) | (b-31) | H | H | (a-14) | —CH— | —NH— | —CH(Me)— |
| 2-1066 | (b-14) | (b-32) | H | H | (a-14) | —CH— | —NH— | —CH(Me)— |
| 2-1067 | (b-14) | (b-33) | H | H | (a-14) | —CH— | —NH— | —CH(Me)— |
| 2-1068 | (b-14) | (b-33) | H | H | (a-14) | —CH— | —NH— | —COCH(Me)— |
| 2-1069 | (b-14) | (b-33) | H | H | (a-14) | —CH— | —O— | —CH(Me)— |
| 2-1070 | (b-14) | (b-33) | H | H | (a-14) | —CH— | —S— | —CH(Me)— |
| 2-1071 | (b-14) | (b-34) | H | H | (a-14) | —CH— | —NH— | —(CH$_2$)$_2$— |
| 2-1072 | (b-14) | (b-34) | H | H | (a-14) | —CH— | —NH— | —CH(Me)— |
| 2-1073 | (b-14) | (b-34) | H | H | (a-14) | —CH— | —NH— | —CH$_2$CH(Me)— |
| 2-1074 | (b-14) | (b-34) | H | H | (a-14) | —CH— | —NH— | —CO(CH$_2$)$_2$— |
| 2-1075 | (b-14) | (b-34) | H | H | (a-14) | —CH— | —NH— | —COCH(Me)— |
| 2-1076 | (b-14) | (b-34) | H | H | (a-14) | —CH— | —O— | —CH(Me)— |
| 2-1077 | (b-14) | (b-34) | H | H | (a-14) | —CH— | —S— | —CH(Me)— |
| 2-1078 | (b-14) | (b-34) | 6-Cl | H | (a-14) | —CH— | —NH— | —CH(Me)— |
| 2-1079 | (b-14) | (b-34) | 4-OH | H | (a-14) | —CH— | —NH— | —CH(Me)— |
| 2-1080 | (b-14) | (b-34) | 6-OH | H | (a-14) | —CH— | —NH— | —CH(Me)— |
| 2-1081 | (b-14) | (b-34) | H | H | (a-14) | N | —CO— | —CH(Me)— |
| 2-1082 | (b-14) | (b-35) | H | H | (a-14) | —CH— | —NH— | single bond |
| 2-1083 | (b-14) | (b-35) | H | H | (a-14) | —CH— | —NH— | —CH$_2$— |
| 2-1084 | (b-14) | (b-35) | H | H | (a-14) | —CH— | —NH— | —(CH$_2$)$_2$— |
| 2-1085 | (b-14) | (b-35) | H | H | (a-14) | —CH— | —NH— | —CH(Me)— |
| 2-1086 | (b-14) | (b-35) | H | H | (a-14) | —CH— | —NH— | —CH(Et)— |
| 2-1087 | (b-14) | (b-35) | H | H | (a-14) | —CH— | —NH— | —(CH$_2$)$_3$— |
| 2-1088 | (b-14) | (b-35) | H | H | (a-14) | —CH— | —NH— | —CH$_2$CH(Me)— |
| 2-1089 | (b-14) | (b-35) | H | H | (a-14) | —CH— | —NH— | —CH$_2$CH(OH)— |
| 2-1090 | (b-14) | (b-35) | H | H | (a-14) | —CH— | —NH— | —CH$_2$C(=O)— |
| 2-1091 | (b-14) | (b-35) | H | H | (a-14) | —CH— | —NH— | —CH$_2$C(Ph)— |
| 2-1092 | (b-14) | (b-35) | H | H | (a-14) | —CH— | —NH— | —(CH$_2$)$_2$CH(Me)— |
| 2-1093 | (b-14) | (b-35) | H | H | (a-14) | —CH— | —NH— | —(CH$_2$)$_2$CH(OH)— |
| 2-1094 | (b-14) | (b-35) | H | H | (a-14) | —CH— | —NH— | —(CH$_2$)$_2$C(=O)— |
| 2-1095 | (b-14) | (b-35) | H | H | (a-14) | —CH— | —NH— | —(CH$_2$)$_2$C(Ph)— |
| 2-1096 | (b-14) | (b-35) | H | H | (a-14) | —CH— | —NH— | —CO— |
| 2-1097 | (b-14) | (b-35) | H | H | (a-14) | —CH— | —NH— | —COCH$_2$— |

TABLE 2-continued

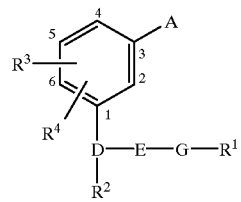

(I-2)

| Cpd. No. | R¹ Sub. No | R² Sub. No | R³ | R⁴ | A Sub. No | D | E | G |
|---|---|---|---|---|---|---|---|---|
| 2-1098 | (b-14) | (b-35) | H | H | (a-14) | —CH— | —NH— | —CO(CH₂)₂— |
| 2-1099 | (b-14) | (b-35) | H | H | (a-14) | —CH— | —NH— | —COCH(Me)— |
| 2-1100 | (b-14) | (b-35) | H | H | (a-14) | —CH— | —NH— | —COCH(Et)— |
| 2-1101 | (b-14) | (b-35) | H | H | (a-14) | —CH— | —NH— | —CO(CH₂)₃— |
| 2-1102 | (b-14) | (b-35) | H | H | (a-14) | —CH— | —NH— | —COCH₂CH(Me)— |
| 2-1103 | (b-14) | (b-35) | H | H | (a-14) | —CH— | —O— | —CH₂— |
| 2-1104 | (b-14) | (b-35) | H | H | (a-14) | —CH— | —O— | —(CH₂)₂— |
| 2-1105 | (b-14) | (b-35) | H | H | (a-14) | —CH— | —O— | —CH(Me)— |
| 2-1106 | (b-14) | (b-35) | H | H | (a-14) | —CH— | —S— | —CH₂— |
| 2-1107 | (b-14) | (b-35) | H | H | (a-14) | —CH— | —S— | —(CH₂)₂— |
| 2-1108 | (b-14) | (b-35) | H | H | (a-14) | —CH— | —S— | —CH(Me)— |
| 2-1109 | (b-14) | (b-35) | 4-F | H | (a-14) | —CH— | —NH— | —CH(Me)— |
| 2-1110 | (b-14) | (b-35) | 6-F | H | (a-14) | —CH— | —NH— | —CH(Me)— |
| 2-1111 | (b-14) | (b-35) | 4-Cl | H | (a-14) | —CH— | —NH— | —CH(Me)— |
| 2-1112 | (b-14) | (b-35) | 5-Cl | H | (a-14) | —CH— | —NH— | —CH(Me)— |
| 2-1113 | (b-14) | (b-35) | 6-Cl | H | (a-14) | —CH— | —NH— | —CH(Me)— |
| 2-1114 | (b-14) | (b-35) | 4-OH | H | (a-14) | —CH— | —NH— | —CH(Me)— |
| 2-1115 | (b-14) | (b-35) | 5-OH | H | (a-14) | —CH— | —NH— | —CH(Me)— |
| 2-1116 | (b-14) | (b-35) | 6-OH | H | (a-14) | —CH— | —NH— | —CH(Me)— |
| 2-1117 | (b-14) | (b-35) | H | H | (a-14) | N | —CO— | —CH₂— |
| 2-1118 | (b-14) | (b-35) | H | H | (a-14) | N | —CO— | —(CH₂)₂— |
| 2-1119 | (b-14) | (b-35) | H | H | (a-14) | N | —CO— | —CH(Me)— |
| 2-1120 | (b-14) | (b-37) | H | H | (a-14) | —CH— | —NH— | single bond |
| 2-1121 | (b-14) | (b-37) | H | H | (a-14) | —CH— | —NH— | —CH₂— |
| 2-1122 | (b-14) | (b-37) | H | H | (a-14) | —CH— | —NH— | —(CH₂)₂— |
| 2-1123 | (b-14) | (b-37) | H | H | (a-14) | —CH— | —NH— | —CH(Me)— |
| 2-1124 | (b-14) | (b-37) | H | H | (a-14) | —CH— | —NH— | —CH(Et)— |
| 2-1125 | (b-14) | (b-37) | H | H | (a-14) | —CH— | —NH— | —(CH₂)₃— |
| 2-1126 | (b-14) | (b-37) | H | H | (a-14) | —CH— | —NH— | —CH₂CH(Me)— |
| 2-1127 | (b-14) | (b-37) | H | H | (a-14) | —CH— | —NH— | —CH₂CH(OH)— |
| 2-1128 | (b-14) | (b-37) | H | H | (a-14) | —CH— | —NH— | —CH₂C(=O)— |
| 2-1129 | (b-14) | (b-37) | H | H | (a-14) | —CH— | —NH— | —CH₂C(Ph)— |
| 2-1130 | (b-14) | (b-37) | H | H | (a-14) | —CH— | —NH— | —(CH₂)₂CH(Me)— |
| 2-1131 | (b-14) | (b-37) | H | H | (a-14) | —CH— | —NH— | —(CH₂)₂CH(OH)— |
| 2-1132 | (b-14) | (b-37) | H | H | (a-14) | —CH— | —NH— | —(CH₂)₂C(=O)— |
| 2-1133 | (b-14) | (b-37) | H | H | (a-14) | —CH— | —NH— | —(CH₂)₂C(Ph)— |
| 2-1134 | (b-14) | (b-37) | H | H | (a-14) | —CH— | —NH— | —CO— |
| 2-1135 | (b-14) | (b-37) | H | H | (a-14) | —CH— | —NH— | —COCH₂— |
| 2-1136 | (b-14) | (b-37) | H | H | (a-14) | —CH— | —NH— | —CO(CH₂)₂— |
| 2-1137 | (b-14) | (b-37) | H | H | (a-14) | —CH— | —NH— | —COCH(Me)— |
| 2-1138 | (b-14) | (b-37) | H | H | (a-14) | —CH— | —NH— | —COCH(Et)— |
| 2-1139 | (b-14) | (b-37) | H | H | (a-14) | —CH— | —NH— | —CO(CH₂)₃— |
| 2-1140 | (b-14) | (b-37) | H | H | (a-14) | —CH— | —NH— | —COCH₂CH(Me)— |
| 2-1141 | (b-14) | (b-37) | H | H | (a-14) | —CH— | —O— | —CH₂— |
| 2-1142 | (b-14) | (b-37) | H | H | (a-14) | —CH— | —O— | —(CH₂)₂— |
| 2-1143 | (b-14) | (b-37) | H | H | (a-14) | —CH— | —O— | —CH(Me)— |
| 2-1144 | (b-14) | (b-37) | H | H | (a-14) | —CH— | —S— | —CH₂— |
| 2-1145 | (b-14) | (b-37) | H | H | (a-14) | —CH— | —S— | —(CH₂)₂— |
| 2-1146 | (b-14) | (b-37) | H | H | (a-14) | —CH— | —S— | —CH(Me)— |
| 2-1147 | (b-14) | (b-37) | 4-F | H | (a-14) | —CH— | —NH— | —CH(Me)— |
| 2-1148 | (b-14) | (b-37) | 6-F | H | (a-14) | —CH— | —NH— | —CH(Me)— |
| 2-1149 | (b-14) | (b-37) | 4-Cl | H | (a-14) | —CH— | —NH— | —CH(Me)— |
| 2-1150 | (b-14) | (b-37) | 5-Cl | H | (a-14) | —CH— | —NH— | —CH(Me)— |
| 2-1151 | (b-14) | (b-37) | 6-Cl | H | (a-14) | —CH— | —NH— | —CH(Me)— |
| 2-1152 | (b-14) | (b-37) | 4-OH | H | (a-14) | —CH— | —NH— | —CH(Me)— |
| 2-1153 | (b-14) | (b-37) | 5-OH | H | (a-14) | —CH— | —NH— | —CH(Me)— |
| 2-1154 | (b-14) | (b-37) | 6-OH | H | (a-14) | —CH— | —NH— | —CH(Me)— |
| 2-1155 | (b-14) | (b-37) | H | H | (a-14) | N | —CO— | —CH₂— |
| 2-1156 | (b-14) | (b-37) | H | H | (a-14) | N | —CO— | —(CH₂)₂— |
| 2-1157 | (b-14) | (b-37) | H | H | (a-14) | N | —CO— | —CH(Me)— |
| 2-1158 | (b-14) | (b-38) | H | H | (a-14) | —CH— | —NH— | —CH(Me)— |
| 2-1159 | (b-14) | (b-41) | H | H | (a-14) | —CH— | —NH— | —CH(Me)— |
| 2-1160 | (b-14) | (b-42) | H | H | (a-14) | —CH— | —NH— | —CH(Me)— |
| 2-1161 | (b-14) | (b-42) | H | H | (a-14) | —CH— | —NH— | —COCH(Me)— |

TABLE 2-continued

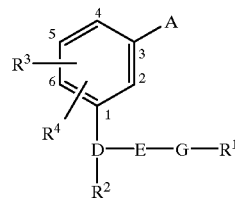

(I-2)

| Cpd. No. | R¹ Sub. No | R² Sub. No | R³ | R⁴ | A Sub. No | D | E | G |
|---|---|---|---|---|---|---|---|---|
| 2-1162 | (b-14) | (b-42) | H | H | (a-14) | —CH— | —O— | —CH(Me)— |
| 2-1163 | (b-14) | (b-42) | H | H | (a-14) | —CH— | —S— | —CH(Me)— |
| 2-1164 | (b-14) | (b-43) | H | H | (a-14) | —CH— | —NH— | —CH(Me)— |
| 2-1165 | (b-14) | (b-72) | H | H | (a-14) | —CH— | —NH— | —(CH₂)₂— |
| 2-1166 | (b-14) | (b-72) | H | H | (a-14) | —CH— | —NH— | —CH(Me)— |
| 2-1167 | (b-14) | (b-72) | H | H | (a-14) | —CH— | —NH— | —CH₂CH(Me)— |
| 2-1168 | (b-14) | (b-72) | H | H | (a-14) | —CH— | —NH— | —COCH(Me)— |
| 2-1169 | (b-14) | (b-72) | H | H | (a-14) | —CH— | —O— | —CH(Me)— |
| 2-1170 | (b-14) | (b-72) | H | H | (a-14) | —CH— | —S— | —CH(Me)— |
| 2-1171 | (b-14) | (b-72) | 6-Cl | H | (a-14) | —CH— | —NH— | —CH(Me)— |
| 2-1172 | (b-14) | (b-72) | 4-OH | H | (a-14) | —CH— | —NH— | —CH(Me)— |
| 2-1173 | (b-14) | (b-72) | 6-OH | H | (a-14) | —CH— | —NH— | —CH(Me)— |
| 2-1174 | (b-14) | (b-73) | H | H | (a-14) | —CH— | —NH— | single bond |
| 2-1175 | (b-14) | (b-73) | H | H | (a-14) | —CH— | —NH— | —CH₂— |
| 2-1176 | (b-14) | (b-73) | H | H | (a-14) | —CH— | —NH— | —(CH₂)₂— |
| 2-1177 | (b-14) | (b-73) | H | H | (a-14) | —CH— | —NH— | —CH(Me)— |
| 2-1178 | (b-14) | (b-73) | H | H | (a-14) | —CH— | —NH— | —CH(Et)— |
| 2-1179 | (b-14) | (b-73) | H | H | (a-14) | —CH— | —NH— | —(CH₂)₃— |
| 2-1180 | (b-14) | (b-73) | H | H | (a-14) | —CH— | —NH— | —CH₂CH(Me)— |
| 2-1181 | (b-14) | (b-73) | H | H | (a-14) | —CH— | —NH— | —CH₂CH(OH)— |
| 2-1182 | (b-14) | (b-73) | H | H | (a-14) | —CH— | —NH— | —CH₂C(=O)— |
| 2-1183 | (b-14) | (b-73) | H | H | (a-14) | —CH— | —NH— | —CH₂C(Ph)— |
| 2-1184 | (b-14) | (b-73) | H | H | (a-14) | —CH— | —NH— | —(CH₂)₂CH(Me)— |
| 2-1185 | (b-14) | (b-73) | H | H | (a-14) | —CH— | —NH— | —(CH₂)₂CH(OH)— |
| 2-1186 | (b-14) | (b-73) | H | H | (a-14) | —CH— | —NH— | —(CH₂)₂C(=O)— |
| 2-1187 | (b-14) | (b-73) | H | H | (a-14) | —CH— | —NH— | —(CH₂)₂C(Ph)— |
| 2-1188 | (b-14) | (b-73) | H | H | (a-14) | —CH— | —NH— | —CO— |
| 2-1189 | (b-14) | (b-73) | H | H | (a-14) | —CH— | —NH— | —COCH₂— |
| 2-1190 | (b-14) | (b-73) | H | H | (a-14) | —CH— | —NH— | —CO(CH₂)₂— |
| 2-1191 | (b-14) | (b-73) | H | H | (a-14) | —CH— | —NH— | —COCH(Me)— |
| 2-1192 | (b-14) | (b-73) | H | H | (a-14) | —CH— | —NH— | —COCH(Et)— |
| 2-1193 | (b-14) | (b-73) | H | H | (a-14) | —CH— | —NH— | —CO(CH₂)₃— |
| 2-1194 | (b-14) | (b-73) | H | H | (a-14) | —CH— | —NH— | —COCH₂CH(Me)— |
| 2-1195 | (b-14) | (b-73) | H | H | (a-14) | —CH— | —O— | —CH₂— |
| 2-1196 | (b-14) | (b-73) | H | H | (a-14) | —CH— | —O— | —(CH₂)₂— |
| 2-1197 | (b-14) | (b-73) | H | H | (a-14) | —CH— | —O— | —CH(Me)— |
| 2-1198 | (b-14) | (b-73) | H | H | (a-14) | —CH— | —S— | —CH₂— |
| 2-1199 | (b-14) | (b-73) | H | H | (a-14) | —CH— | —S— | —(CH₂)₂— |
| 2-1200 | (b-14) | (b-73) | H | H | (a-14) | —CH— | —S— | —CH(Me)— |
| 2-1201 | (b-14) | (b-73) | 4-F | H | (a-14) | —CH— | —NH— | —CH(Me)— |
| 2-1202 | (b-14) | (b-73) | 6-F | H | (a-14) | —CH— | —NH— | —CH(Me)— |
| 2-1203 | (b-14) | (b-73) | 4-Cl | H | (a-14) | —CH— | —NH— | —CH(Me)— |
| 2-1204 | (b-14) | (b-73) | 5-Cl | H | (a-14) | —CH— | —NH— | —CH(Me)— |
| 2-1205 | (b-14) | (b-73) | 6-Cl | H | (a-14) | —CH— | —NH— | —CH(Me)— |
| 2-1206 | (b-14) | (b-73) | 4 OH | H | (a-14) | —CH— | —NH— | —CH(Me)— |
| 2-1207 | (b-14) | (b-73) | 5-OH | H | (a-14) | —CH— | —NH— | —CH(Me)— |
| 2-1208 | (b-14) | (b-73) | 6-OH | H | (a-14) | —CH— | —NH— | —CH(Me)— |
| 2-1209 | (b-14) | (b-73) | H | H | (a-14) | N | —CO— | —CH₂— |
| 2-1210 | (b-14) | (b-73) | H | H | (a-14) | N | —CO— | —(CH₂)₂— |
| 2-1211 | (b-14) | (b-73) | H | H | (a-14) | N | —CO— | —CH(Me)— |
| 2-1212 | (b-14) | (b-74) | H | H | (a-14) | —CH— | —NH— | —CH(Me)— |
| 2-1213 | (b-14) | (b-74) | H | H | (a-14) | —CH— | —NH— | —COCH(Me)— |
| 2-1214 | (b-14) | (b-74) | H | H | (a-14) | —CH— | —O— | —CH(Me)— |
| 2-1215 | (b-14) | (b-74) | H | H | (a-14) | —CH— | —S— | —CH(Me)— |
| 2-1216 | (b-14) | (b-75) | H | H | (a-14) | —CH— | —NH— | —CH(Me)— |
| 2-1217 | (b-14) | (b-76) | H | H | (a-14) | —CH— | —NH— | —CH(Me)— |
| 2-1218 | (b-14) | (b-76) | H | H | (a-14) | —CH— | —NH— | —COCH(Me)— |
| 2-1219 | (b-14) | (b-76) | H | H | (a-14) | —CH— | —O— | —CH(Me)— |
| 2-1220 | (b-14) | (b-76) | H | H | (a-14) | —CH— | —S— | —CH(Me)— |
| 2-1221 | (b-14) | (b-77) | H | H | (a-14) | —CH— | —NH— | —(CH₂)₂— |
| 2-1222 | (b-14) | (b-77) | H | H | (a-14) | —CH— | —NH— | —CH(Me)— |
| 2-1223 | (b-14) | (b-77) | H | H | (a-14) | —CH— | —NH— | —CH₂CH(Me)— |
| 2-1224 | (b-14) | (b-77) | H | H | (a-14) | —CH— | —NH— | —CO(CH₂)₂— |
| 2-1225 | (b-14) | (b-77) | H | H | (a-14) | —CH— | —NH— | —COCH(Me)— |

TABLE 2-continued

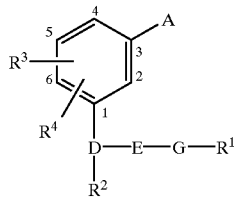

(I-2)

| Cpd. No. | R¹ Sub. No | R² Sub. No | R³ | R⁴ | A Sub. No | D | E | G |
|---|---|---|---|---|---|---|---|---|
| 2-1226 | (b-14) | (b-77) | H | H | (a-14) | —CH— | —O— | —CH(Me)— |
| 2-1227 | (b-14) | (b-77) | H | H | (a-14) | —CH— | —S— | —CH(Me)— |
| 2-1228 | (b-14) | (b-77) | 6-Cl | H | (a-14) | —CH— | —NH— | —CH(Me)— |
| 2-1229 | (b-14) | (b-77) | 4-OH | H | (a-14) | —CH— | —NH— | —CH(Me)— |
| 2-1230 | (b-14) | (b-77) | 6-OH | H | (a-14) | —CH— | —NH— | —CH(Me)— |
| 2-1231 | (b-14) | (b-77) | H | H | (a-14) | N | —CO— | —CH(Me)— |
| 2-1232 | (b-14) | (b-78) | H | H | (a-14) | —CH— | —NH— | —CH(Me)— |
| 2-1233 | (b-15) | (b-1) | H | H | (a-14) | —CH— | —NH— | —CH(Me)— |
| 2-1234 | (b-15) | (b-2) | H | H | (a-14) | —CH— | —NH— | —CH(Me)— |
| 2-1235 | (b-15) | (b-3) | H | H | (a-14) | —CH— | —NH— | —CH(Me)— |
| 2-1236 | (b-15) | (b-4) | H | H | (a-14) | —CH— | —NH— | —CH(Me)— |
| 2-1237 | (b-15) | (b-5) | H | H | (a-14) | —CH— | —NH— | —CH(Me)— |
| 2-1238 | (b-15) | (b-7) | H | H | (a-14) | —CH— | —NH— | —CH(Me)— |
| 2-1239 | (b-15) | (b-7) | H | H | (a-14) | —CH— | —NH— | —COCH(Me)— |
| 2-1240 | (b-15) | (b-12) | H | H | (a-14) | —CH— | —NH— | —CH(Me)— |
| 2-1241 | (b-15) | (b-15) | H | H | (a-14) | —CH— | —NH— | —CH(Me)— |
| 2-1242 | (b-15) | (b-34) | H | H | (a-14) | —CH— | —NH— | —CH(Me)— |
| 2-1243 | (b-15) | (b-35) | H | H | (a-14) | —CH— | —NH— | —CH(Me)— |
| 2-1244 | (b-15) | (b-35) | H | H | (a-14) | —CH— | —NH— | —COCH(Me)— |
| 2-1245 | (b-15) | (b-37) | H | H | (a-14) | —CH— | —NH— | —CH(Me)— |
| 2-1246 | (b-15) | (b-73) | H | H | (a-14) | —CH— | —NH— | —CH(Me)— |
| 2-1247 | (b-15) | (b-77) | H | H | (a-14) | —CH— | —NH— | —CH(Me)— |
| 2-1248 | (b-16) | (b-35) | H | H | (a-14) | —CH— | —NH— | —CH(Me)— |
| 2-1249 | (b-17) | (b-7) | H | H | (a-14) | —CH— | —NH— | —CH(Me)— |
| 2-1250 | (b-17) | (b-35) | H | H | (a-14) | —CH— | —NH— | —CH(Me)— |
| 2-1251 | (b-18) | (b-1) | H | H | (a-14) | —CH— | —NH— | —CH(Me)— |
| 2-1252 | (b-18) | (b-2) | H | H | (a-14) | —CH— | —NH— | —CH(Me)— |
| 2-1253 | (b-18) | (b-7) | H | H | (a-14) | —CH— | —NH— | single bond |
| 2-1254 | (b-18) | (b-7) | H | H | (a-14) | —CH— | —NH— | —CH₂— |
| 2-1255 | (b-18) | (b-7) | H | H | (a-14) | —CH— | —NH— | —(CH₂)₂— |
| 2-1256 | (b-18) | (b-7) | H | H | (a-14) | —CH— | —NH— | —CH(Me)— |
| 2-1257 | (b-18) | (b-7) | H | H | (a-14) | —CH— | —NH— | —CH(Et)— |
| 2-1258 | (b-18) | (b-7) | H | H | (a-14) | —CH— | —NH— | —(CH₂)₃— |
| 2-1259 | (b-18) | (b-7) | H | H | (a-14) | —CH— | —NH— | —CH₂CH(Me)— |
| 2-1260 | (b-18) | (b-7) | H | H | (a-14) | —CH— | —NH— | —CH₂CH(Et)— |
| 2-1261 | (b-18) | (b-7) | H | H | (a-14) | —CH— | —NH— | —CH₂CH(OH)— |
| 2-1262 | (b-18) | (b-7) | H | H | (a-14) | —CH— | —NH— | —CH₂C(=O)— |
| 2-1263 | (b-18) | (b-7) | H | H | (a-14) | —CH— | —NH— | —CH₂C(Ph)— |
| 2-1264 | (b-18) | (b-7) | H | H | (a-14) | —CH— | —NH— | —(CH₂)₂CH(Me)— |
| 2-1265 | (b-18) | (b-7) | H | H | (a-14) | —CH— | —NH— | —(CH₂)₂CH(OH)— |
| 2-1266 | (b-18) | (b-7) | H | H | (a-14) | —CH— | —NH— | —(CH₂)₂C(=O)— |
| 2-1267 | (b-18) | (b-7) | H | H | (a-14) | —CH— | —NH— | —(CH₂)₂C(Ph)— |
| 2-1268 | (b-18) | (b-7) | H | H | (a-14) | —CH— | —NH— | —CO— |
| 2-1269 | (b-18) | (b-7) | H | H | (a-14) | —CH— | —NH— | —COCH₂— |
| 2-1270 | (b-18) | (b-7) | H | H | (a-14) | —CH— | —NH— | —CO(CH₂)₂— |
| 2-1271 | (b-18) | (b-7) | H | H | (a-14) | —CH— | —NH— | —COCH(Me)— |
| 2-1272 | (b-18) | (b-7) | H | H | (a-14) | —CH— | —NH— | —COCH(Et)— |
| 2-1273 | (b-18) | (b-7) | H | H | (a-14) | —CH— | —NH— | —CO(CH₂)₃— |
| 2-1274 | (b-18) | (b-7) | H | H | (a-14) | —CH— | —NH— | —COCH₂CH(Me)— |
| 2-1275 | (b-18) | (b-7) | H | H | (a-14) | —CH— | —O— | —CH₂— |
| 2-1276 | (b-18) | (b-7) | H | H | (a-14) | —CH— | —O— | —(CH₂)₂— |
| 2-1277 | (b-18) | (b-7) | H | H | (a-14) | —CH— | —O— | —CH(Me)— |
| 2-1278 | (b-18) | (b-7) | H | H | (a-14) | —CH— | —S— | —CH₂— |
| 2-1279 | (b-18) | (b-7) | H | H | (a-14) | —CH— | —S— | —(CH₂)₂— |
| 2-1280 | (b-18) | (b-7) | H | H | (a-14) | —CH— | —S— | —CH(Me)— |
| 2-1281 | (b-18) | (b-7) | 4-F | H | (a-14) | —CH— | —NH— | —CH(Me)— |
| 2-1282 | (b-18) | (b-7) | 6-F | H | (a-14) | —CH— | —NH— | —CH(Me)— |
| 2-1283 | (b-18) | (b-7) | 4-Cl | H | (a-14) | —CH— | —NH— | —CH(Me)— |
| 2-1284 | (b-18) | (b-7) | 5-Cl | H | (a-14) | —CH— | —NH— | —CH(Me)— |
| 2-1285 | (b-18) | (b-7) | 6-Cl | H | (a-14) | —CH— | —NH— | —CH(Me)— |
| 2-1286 | (b-18) | (b-7) | 4-OH | H | (a-14) | —CH— | —NH— | —CH(Me)— |
| 2-1287 | (b-18) | (b-7) | 5-OH | H | (a-14) | —CH— | —NH— | —CH(Me)— |
| 2-1288 | (b-18) | (b-7) | 6-OH | H | (a-14) | —CH— | —NH— | —CH(Me)— |
| 2-1289 | (b-18) | (b-7) | H | H | (a-14) | N | —CO— | —CH₂— |

TABLE 2-continued

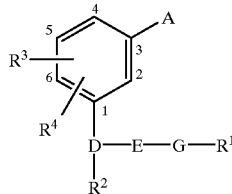

(I-2)

| Cpd. No. | R¹ Sub. No | R² Sub. No | R³ | R⁴ | A Sub. No | D | E | G |
|---|---|---|---|---|---|---|---|---|
| 2-1290 | (b-18) | (b-7) | H | H | (a-14) | N | —CO— | —(CH₂)₂— |
| 2-1291 | (b-18) | (b-7) | H | H | (a-14) | N | —CO— | —CH(Me)— |
| 2-1292 | (b-18) | (b-8) | H | H | (a-14) | —CH— | —NH— | —CH(Me)— |
| 2-1293 | (b-18) | (b-10) | H | H | (a-14) | —CH— | —NH— | —CH(Me)— |
| 2-1294 | (b-18) | (b-11) | H | H | (a-14) | —CH— | —NH— | —CH(Me)— |
| 2-1295 | (b-18) | (b-11) | H | H | (a-14) | —CH— | —NH— | —COCH(Me)— |
| 2-1296 | (b-18) | (b-11) | H | H | (a-14) | —CH— | —O— | —CH(Me)— |
| 2-1297 | (b-18) | (b-11) | H | H | (a-14) | —CH— | —S— | —CH(Me)— |
| 2-1298 | (b-18) | (b-12) | H | H | (a-14) | —CH— | —NH— | —(CH₂)₂— |
| 2-1299 | (b-18) | (b-12) | H | H | (a-14) | —CH— | —NH— | —CH(Me)— |
| 2-1300 | (b-18) | (b-12) | H | H | (a-14) | —CH— | —NH— | —CH₂CH(Me)— |
| 2-1301 | (b-18) | (b-12) | H | H | (a-14) | —CH— | —NH— | —CO(CH₂)₂— |
| 2-1302 | (b-18) | (b-12) | H | H | (a-14) | —CH— | —NH— | —COCH(Me)— |
| 2-1303 | (b-18) | (b-12) | H | H | (a-14) | —CH— | —O— | —CH(Me)— |
| 2-1304 | (b-18) | (b-12) | H | H | (a-14) | —CH— | —S— | —CH(Me)— |
| 2-1305 | (b-18) | (b-12) | 6-Cl | H | (a-14) | —CH— | —NH— | —CH(Me)— |
| 2-1306 | (b-18) | (b-12) | 4-OH | H | (a-14) | —CH— | —NH— | —CH(Me)— |
| 2-1307 | (b-18) | (b-12) | 6-OH | H | (a-14) | —CH— | —NH— | —CH(Me)— |
| 2-1308 | (b-18) | (b-12) | H | H | (a-14) | N | —CO— | —CH(Me)— |
| 2-1309 | (b-18) | (b-13) | H | H | (a-14) | —CH— | —NH— | —CH(Me)— |
| 2-1310 | (b-18) | (b-14) | H | H | (a-14) | —CH— | —NH— | —CH(Me)— |
| 2-1311 | (b-18) | (b-14) | H | H | (a-14) | —CH— | —NH— | —COCH(Me)— |
| 2-1312 | (b-18) | (b-14) | H | H | (a-14) | —CH— | —O— | —CH(Me)— |
| 2-1313 | (b-18) | (b-14) | H | H | (a-14) | —CH— | —S— | —CH(Me)— |
| 2-1314 | (b-18) | (b-15) | H | H | (a-14) | —CH— | —NH— | —(CH₂)₂— |
| 2-1315 | (b-18) | (b-15) | H | H | (a-14) | —CH— | —NH— | —CH(Me)— |
| 2-1316 | (b-18) | (b-15) | H | H | (a-14) | —CH— | —NH— | —CH₂CH(Me)— |
| 2-1317 | (b-18) | (b-15) | H | H | (a-14) | —CH— | —NH— | —CO(CH₂)₂— |
| 2-1318 | (b-18) | (b-15) | H | H | (a-14) | —CH— | —NH— | —COCH(Me)— |
| 2-1319 | (b-18) | (b-15) | H | H | (a-14) | —CH— | —O— | —CH(Me)— |
| 2-1320 | (b-18) | (b-15) | H | H | (a-14) | —CH— | —S— | —CH(Me)— |
| 2-1321 | (b-18) | (b-15) | 6-Cl | H | (a-14) | —CH— | —NH— | —CH(Me)— |
| 2-1322 | (b-18) | (b-15) | 4-OH | H | (a-14) | —CH— | —NH— | —CH(Me)— |
| 2-1323 | (b-18) | (b-15) | 6-OH | H | (a-14) | —CH— | —NH— | —CH(Me)— |
| 2-1324 | (b-18) | (b-15) | H | H | (a-14) | N | —CO— | —CH(Me)— |
| 2-1325 | (b-18) | (b-16) | H | H | (a-14) | —CH— | —NH— | —CH(Me)— |
| 2-1326 | (b-18) | (b-17) | H | H | (a-14) | —CH— | —NH— | —CH(Me)— |
| 2-1327 | (b-18) | (b-17) | H | H | (a-14) | —CH— | —NH— | —COCH(Me)— |
| 2-1328 | (b-18) | (b-17) | H | H | (a-14) | —CH— | —O— | —CH(Me)— |
| 2-1329 | (b-18) | (b-17) | H | H | (a-14) | —CH— | —S— | —CH(Me)— |
| 2-1330 | (b-18) | (b-23) | H | H | (a-14) | —CH— | —NH— | —CH(Me)— |
| 2-1331 | (b-18) | (b-24) | H | H | (a-14) | —CH— | —NH— | —CH(Me)— |
| 2-1332 | (b-18) | (b-25) | H | H | (a-14) | —CH— | —NH— | —CH(Me)— |
| 2-1333 | (b-18) | (b-25) | H | H | (a-14) | —CH— | —NH— | —COCH(Me)— |
| 2-1334 | (b-18) | (b-25) | H | H | (a-14) | —CH— | —O— | —CH(Me)— |
| 2-1335 | (b-18) | (b-25) | H | H | (a-14) | —CH— | —S— | —CH(Me)— |
| 2-1336 | (b-18) | (b-27) | H | H | (a-14) | —CH— | —NH— | —CH(Me)— |
| 2-1337 | (b-18) | (b-28) | H | H | (a-14) | —CH— | —NH— | —CH(Me)— |
| 2-1338 | (b-18) | (b-30) | H | H | (a-14) | —CH— | —NH— | —CH(Me)— |
| 2-1339 | (b-18) | (b-31) | H | H | (a-14) | —CH— | —NH— | —CH(Me)— |
| 2-1340 | (b-18) | (b-32) | H | H | (a-14) | —CH— | —NH— | —CH(Me)— |
| 2-1341 | (b-18) | (b-33) | H | H | (a-14) | —CH— | —NH— | —CH(Me)— |
| 2-1342 | (b-18) | (b-33) | H | H | (a-14) | —CH— | —NH— | —COCH(Me)— |
| 2-1343 | (b-18) | (b-33) | H | H | (a-14) | —CH— | —O— | —CH(Me)— |
| 2-1344 | (b-18) | (b-33) | H | H | (a-14) | —CH— | —S— | —CH(Me)— |
| 2-1345 | (b-18) | (b-34) | H | H | (a-14) | —CH— | —NH— | —(CH₂)₂— |
| 2-1346 | (b-18) | (b-34) | H | H | (a-14) | —CH— | —NH— | —CH(Me)— |
| 2-1347 | (b-18) | (b-34) | H | H | (a-14) | —CH— | —NH— | —CH₂CH(Me)— |
| 2-1348 | (b-18) | (b-34) | H | H | (a-14) | —CH— | —NH— | —CO(CH₂)₂— |
| 2-1349 | (b-18) | (b-34) | H | H | (a-14) | —CH— | —NH— | —COCH(Me)— |
| 2-1350 | (b-18) | (b-34) | H | H | (a-14) | —CH— | —O— | —CH(Me)— |
| 2-1351 | (b-18) | (b-34) | H | H | (a-14) | —CH— | —S— | —CH(Me)— |
| 2-1352 | (b-18) | (b-34) | 6-Cl | H | (a-14) | —CH— | —NH— | —CH(Me)— |
| 2-1353 | (b-18) | (b-34) | 4-OH | H | (a-14) | —CH— | —NH— | —CH(Me)— |

TABLE 2-continued (I-2)

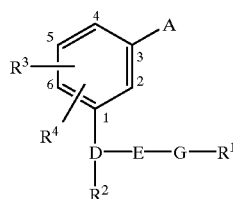

| Cpd. No. | R¹ Sub. No | R² Sub. No | R³ | R⁴ | A Sub. No | D | E | G |
|---|---|---|---|---|---|---|---|---|
| 2-1354 | (b-18) | (b-34) | 6-OH | H | (a-14) | —CH— | —NH— | —CH(Me)— |
| 2-1355 | (b-18) | (b-34) | H | H | (a-14) | N | —CO— | —CH(Me)— |
| 2-1356 | (b-18) | (b-35) | H | H | (a-14) | —CH— | —NH— | single bond |
| 2-1357 | (b-18) | (b-35) | H | H | (a-14) | —CH— | —NH— | —CH₂— |
| 2-1358 | (b-18) | (b-35) | H | H | (a-14) | —CH— | —NH— | —(CH₂)₂— |
| 2-1359 | (b-18) | (b-35) | H | H | (a-14) | —CH— | —NH— | —CH(Me)— |
| 2-1360 | (b-18) | (b-35) | H | H | (a-14) | —CH— | —NH— | —CH(Et)— |
| 2-1361 | (b-18) | (b-35) | H | H | (a-14) | —CH— | —NH— | —(CH₂)₃— |
| 2-1362 | (b-18) | (b-35) | H | H | (a-14) | —CH— | —NH— | —CH₂CH(Me)— |
| 2-1363 | (b-18) | (b-35) | H | H | (a-14) | —CH— | —NH— | —CH₂CH(OH)— |
| 2-1364 | (b-18) | (b-35) | H | H | (a-14) | —CH— | —NH— | —CH₂C(=O)— |
| 2-1365 | (b-18) | (b-35) | H | H | (a-14) | —CH— | —NH— | —CH₂C(Ph)— |
| 2-1366 | (b-18) | (b-35) | H | H | (a-14) | —CH— | —NH— | —(CH₂)₂CH(Me)— |
| 2-1367 | (b-18) | (b-35) | H | H | (a-14) | —CH— | —NH— | —(CH₂)₂CH(OH)— |
| 2-1368 | (b-18) | (b-35) | H | H | (a-14) | —CH— | —NH— | —(CH₂)₂C(=O)— |
| 2-1369 | (b-18) | (b-35) | H | H | (a-14) | —CH— | —NH— | —(CH₂)₂C(Ph)— |
| 2-1370 | (b-18) | (b-35) | H | H | (a-14) | —CH— | —NH— | —CO— |
| 2-1371 | (b-18) | (b-35) | H | H | (a-14) | —CH— | —NH— | —COCH₂— |
| 2-1372 | (b-18) | (b-35) | H | H | (a-14) | —CH— | —NH— | —CO(CH₂)₂— |
| 2-1373 | (b-18) | (b-35) | H | H | (a-14) | —CH— | —NH— | —COCH(Me)— |
| 2-1374 | (b-18) | (b-35) | H | H | (a-14) | —CH— | —NH— | —COCH(Et)— |
| 2-1375 | (b-18) | (b-35) | H | H | (a-14) | —CH— | —NH— | —CO(CH₂)₃— |
| 2-1376 | (b-18) | (b-35) | H | H | (a-14) | —CH— | —NH— | —COCH₂CH(Me)— |
| 2-1377 | (b-18) | (b-35) | H | H | (a-14) | —CH— | —O— | —CH₂— |
| 2-1378 | (b-18) | (b-35) | H | H | (a-14) | —CH— | —O— | —(CH₂)₂— |
| 2-1379 | (b-18) | (b-35) | H | H | (a-14) | —CH— | —O— | —CH(Me)— |
| 2-1380 | (b-18) | (b-35) | H | H | (a-14) | —CH— | —S— | —CH₂— |
| 2-1381 | (b-18) | (b-35) | H | H | (a-14) | —CH— | —S— | —(CH₂)₂— |
| 2-1382 | (b-18) | (b-35) | H | H | (a-14) | —CH— | —S— | —CH(Me)— |
| 2-1383 | (b-18) | (b-35) | 4-F | H | (a-14) | —CH— | —NH— | —CH(Me)— |
| 2-1384 | (b-18) | (b-35) | 6-F | H | (a-14) | —CH— | —NH— | —CH(Me)— |
| 2-1385 | (b-18) | (b-35) | 4-Cl | H | (a-14) | —CH— | —NH— | —CH(Me)— |
| 2-1386 | (b-18) | (b-35) | 5-Cl | H | (a-14) | —CH— | —NH— | —CH(Me)— |
| 2-1387 | (b-18) | (b-35) | 6-Cl | H | (a-14) | —CH— | —NH— | —CH(Me)— |
| 2-1388 | (b-18) | (b-35) | 4-OH | H | (a-14) | —CH— | —NH— | —CH(Me)— |
| 2-1389 | (b-18) | (b-35) | 5-OH | H | (a-14) | —CH— | —NH— | —CH(Me)— |
| 2-1390 | (b-18) | (b-35) | 6-OH | H | (a-14) | —CH— | —NH— | —CH(Me)— |
| 2-1391 | (b-18) | (b-35) | H | H | (a-14) | N | —CO— | —CH₂— |
| 2-1392 | (b-18) | (b-35) | H | H | (a-14) | N | —CO— | —(CH₂)₂— |
| 2-1393 | (b-18) | (b-35) | H | H | (a-14) | N | —CO— | —CH(Me)— |
| 2-1394 | (b-18) | (b-37) | H | H | (a-14) | —CH— | —NH— | single bond |
| 2-1395 | (b-18) | (b-37) | H | H | (a-14) | —CH— | —NH— | —CH₂— |
| 2-1396 | (b-18) | (b-37) | H | H | (a-14) | —CH— | —NH— | —(CH₂)₂— |
| 2-1397 | (b-18) | (b-37) | H | H | (a-14) | —CH— | —NH— | —CH(Me)— |
| 2-1398 | (b-18) | (b-37) | H | H | (a-14) | —CH— | —NH— | —CH(Et)— |
| 2-1399 | (b-18) | (b-37) | H | H | (a-14) | —CH— | —NH— | —(CH₂)₃— |
| 2-1400 | (b-18) | (b-37) | H | H | (a-14) | —CH— | —NH— | —CH₂CH(Me)— |
| 2-1401 | (b-18) | (b-37) | H | H | (a-14) | —CH— | —NH— | —CH₂CH(OH)— |
| 2-1402 | (b-18) | (b-37) | H | H | (a-14) | —CH— | —NH— | —CH₂C(=O)— |
| 2-1403 | (b-18) | (b-37) | H | H | (a-14) | —CH— | —NH— | —CH₂C(Ph)— |
| 2-1404 | (b-18) | (b-37) | H | H | (a-14) | —CH— | —NH— | —(CH₂)₂CH(Me)— |
| 2-1405 | (b-18) | (b-37) | H | H | (a-14) | —CH— | —NH— | —(CH₂)₂CH(OH)— |
| 2-1406 | (b-18) | (b-37) | H | H | (a-14) | —CH— | —NH— | —(CH₂)₂C(=O)— |
| 2-1407 | (b-18) | (b-37) | H | H | (a-14) | —CH— | —NH— | —(CH₂)₂C(Ph)— |
| 2-1408 | (b-18) | (b-37) | H | H | (a-14) | —CH— | —NH— | —CO— |
| 2-1409 | (b-18) | (b-37) | H | H | (a-14) | —CH— | —NH— | —COCH₂— |
| 2-1410 | (b-18) | (b-37) | H | H | (a-14) | —CH— | —NH— | —CO(CH₂)₂— |
| 2-1411 | (b-18) | (b-37) | H | H | (a-14) | —CH— | —NH— | —COCH(Me)— |
| 2-1412 | (b-18) | (b-37) | H | H | (a-14) | —CH— | —NH— | —COCH(Et)— |
| 2-1413 | (b-18) | (b-37) | H | H | (a-14) | —CH— | —NH— | —CO(CH₂)₃— |
| 2-1414 | (b-18) | (b-37) | H | H | (a-14) | —CH— | —NH— | —COCH₂CH(Me)— |
| 2-1415 | (b-18) | (b-37) | H | H | (a-14) | —CH— | —O— | —CH₂— |
| 2-1416 | (b-18) | (b-37) | H | H | (a-14) | —CH— | —O— | —(CH₂)₂— |
| 2-1417 | (b-18) | (b-37) | H | H | (a-14) | —CH— | —O— | —CH(Me)— |

TABLE 2-continued

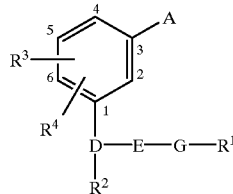

(I-2)

| Cpd. No. | $R^1$ Sub. No | $R^2$ Sub. No | $R^3$ | $R^4$ | A Sub. No | D | E | G |
|---|---|---|---|---|---|---|---|---|
| 2-1418 | (b-18) | (b-37) | H | H | (a-14) | —CH— | —S— | —CH$_2$— |
| 2-1419 | (b-18) | (b-37) | H | H | (a-14) | —CH— | —S— | —(CH$_2$)$_2$— |
| 2-1420 | (b-18) | (b-37) | H | H | (a-14) | —CH— | —S— | —CH(Me)— |
| 2-1421 | (b-18) | (b-37) | 4-F | H | (a-14) | —CH— | —NH— | —CH(Me)— |
| 2-1422 | (b-18) | (b-37) | 6-F | H | (a-14) | —CH— | —NH— | —CH(Me)— |
| 2-1423 | (b-18) | (b-37) | 4-Cl | H | (a-14) | —CH— | —NH— | —CH(Me)— |
| 2-1424 | (b-18) | (b-37) | 5-Cl | H | (a-14) | —CH— | —NH— | —CH(Me)— |
| 2-1425 | (b-18) | (b-37) | 6-Cl | H | (a-14) | —CH— | —NH— | —CH(Me)— |
| 2-1426 | (b-18) | (b-37) | 4-OH | H | (a-14) | —CH— | —NH— | —CH(Me)— |
| 2-1427 | (b-18) | (b-37) | 5-OH | H | (a-14) | —CH— | —NH— | —CH(Me)— |
| 2-1428 | (b-18) | (b-37) | 6-OH | H | (a-14) | —CH— | —NH— | —CH(Me)— |
| 2-1429 | (b-18) | (b-37) | H | H | (a-14) | N | —CO— | —CH$_2$— |
| 2-1430 | (b-18) | (b-37) | H | H | (a-14) | N | —CO— | —(CH$_2$)$_2$— |
| 2-1431 | (b-18) | (b-37) | H | H | (a-14) | N | —CO— | —CH(Me)— |
| 2-1432 | (b-18) | (b-38) | H | H | (a-14) | —CH— | —NH— | —CH(Me)— |
| 2-1433 | (b-18) | (b-41) | H | H | (a-14) | —CH— | —NH— | —CH(Me)— |
| 2-1434 | (b-18) | (b-42) | H | H | (a-14) | —CH— | —NH— | —CH(Me)— |
| 2-1435 | (b-18) | (b-42) | H | H | (a-14) | —CH— | —NH— | —COCH(Me)— |
| 2-1436 | (b-18) | (b-42) | H | H | (a-14) | —CH— | —O— | —CH(Me)— |
| 2-1437 | (b-18) | (b-42) | H | H | (a-14) | —CH— | —S— | —CH(Me)— |
| 2-1438 | (b-18) | (b-43) | H | H | (a-14) | —CH— | —NH— | —CH(Me)— |
| 2-1439 | (b-18) | (b-72) | H | H | (a-14) | —CH— | —NH— | —(CH$_2$)$_2$— |
| 2-1440 | (b-18) | (b-72) | H | H | (a-14) | —CH— | —NH— | —CH(Me)— |
| 2-1441 | (b-18) | (b-72) | H | H | (a-14) | —CH— | —NH— | —CH$_2$CH(Me)— |
| 2-1442 | (b-18) | (b-72) | H | H | (a-14) | —CH— | —NH— | —COCH(Me)— |
| 2-1443 | (b-18) | (b-72) | H | H | (a-14) | —CH— | —O— | —CH(Me)— |
| 2-1444 | (b-18) | (b-72) | H | H | (a-14) | —CH— | —S— | —CH(Me)— |
| 2-1445 | (b-18) | (b-72) | 6-Cl | H | (a-14) | —CH— | —NH— | —CH(Me)— |
| 2-1446 | (b-18) | (b-72) | 4-OH | H | (a-14) | —CH— | —NH— | —CH(Me)— |
| 2-1447 | (b-18) | (b-72) | 6-OH | H | (a-14) | —CH— | —NH— | —CH(Me)— |
| 2-1448 | (b-18) | (b-73) | H | H | (a-14) | —CH— | —NH— | single bond |
| 2-1449 | (b-18) | (b-73) | H | H | (a-14) | —CH— | —NH— | —CH$_2$— |
| 2-1450 | (b-18) | (b-73) | H | H | (a-14) | —CH— | —NH— | —(CH$_2$)$_2$— |
| 2-1451 | (b-18) | (b-73) | H | H | (a-14) | —CH— | —NH— | —CH(Me)— |
| 2-1452 | (b-18) | (b-73) | H | H | (a-14) | —CH— | —NH— | —CH(Et)— |
| 2-1453 | (b-18) | (b-73) | H | H | (a-14) | —CH— | —NH— | —(CH$_2$)$_3$— |
| 2-1454 | (b-18) | (b-73) | H | H | (a-14) | —CH— | —NH— | —CH$_2$CH(Me)— |
| 2-1455 | (b-18) | (b-73) | H | H | (a-14) | —CH— | —NH— | —CH$_2$CH(OH)— |
| 2-1456 | (b-18) | (b-73) | H | H | (a-14) | —CH— | —NH— | —CH$_2$C(=O)— |
| 2-1457 | (b-18) | (b-73) | H | H | (a-14) | —CH— | —NH— | —CH$_2$C(Ph)— |
| 2-1458 | (b-18) | (b-73) | H | H | (a-14) | —CH— | —NH— | —(CH$_2$)$_2$CH(Me)— |
| 2-1459 | (b-18) | (b-73) | H | H | (a-14) | —CH— | —NH— | —(CH$_2$)$_2$CH(OH)— |
| 2-1460 | (b-18) | (b-73) | H | H | (a-14) | —CH— | —NH— | —(CH$_2$)$_2$C(=O)— |
| 2-1461 | (b-18) | (b-73) | H | H | (a-14) | —CH— | —NH— | —(CH$_2$)$_2$C(Ph)— |
| 2-1462 | (b-18) | (b-73) | H | H | (a-14) | —CH— | —NH— | —CO— |
| 2-1463 | (b-18) | (b-73) | H | H | (a-14) | —CH— | —NH— | —COCH$_2$— |
| 2-1464 | (b-18) | (b-73) | H | H | (a-14) | —CH— | —NH— | —CO(CH$_2$)$_2$— |
| 2-1465 | (b-18) | (b-73) | H | H | (a-14) | —CH— | —NH— | —COCH(Me)— |
| 2-1466 | (b-18) | (b-73) | H | H | (a-14) | —CH— | —NH— | —COCH(Et)— |
| 2-1467 | (b-18) | (b-73) | H | H | (a-14) | —CH— | —NH— | —CO(CH$_2$)$_3$— |
| 2-1468 | (b-18) | (b-73) | H | H | (a-14) | —CH— | —NH— | —COCH$_2$CH(Me)— |
| 2-1469 | (b-18) | (b-73) | H | H | (a-14) | —CH— | —O— | —CH$_2$— |
| 2-1470 | (b-18) | (b-73) | H | H | (a-14) | —CH— | —O— | —(CH$_2$)$_2$— |
| 2-1471 | (b-18) | (b-73) | H | H | (a-14) | —CH— | —O— | —CH(Me)— |
| 2-1472 | (b-18) | (b-73) | H | H | (a-14) | —CH— | —S— | —CH$_2$— |
| 2-1473 | (b-18) | (b-73) | H | H | (a-14) | —CH— | —S— | —(CH$_2$)$_2$— |
| 2-1474 | (b-18) | (b-73) | H | H | (a-14) | —CH— | —S— | —CH(Me)— |
| 2-1475 | (b-18) | (b-73) | 4-F | H | (a-14) | —CH— | —NH— | —CH(Me)— |
| 2-1476 | (b-18) | (b-73) | 6-F | H | (a-14) | —CH— | —NH— | —CH(Me)— |
| 2-1477 | (b-18) | (b-73) | 4-Cl | H | (a-14) | —CH— | —NH— | —CH(Me)— |
| 2-1478 | (b-18) | (b-73) | 5-Cl | H | (a-14) | —CH— | —NH— | —CH(Me)— |
| 2-1479 | (b-18) | (b-73) | 6-Cl | H | (a-14) | —CH— | —NH— | —CH(Me)— |
| 2-1480 | (b-18) | (b-73) | 4-OH | H | (a-14) | —CH— | —NH— | —CH(Me)— |
| 2-1481 | (b-18) | (b-73) | 5-OH | H | (a-14) | —CH— | —NH— | —CH(Me)— |

TABLE 2-continued

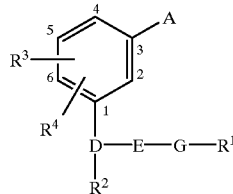

(I-2)

| Cpd. No. | R¹ Sub. No | R² Sub. No | R³ | R⁴ | A Sub. No | D | E | G |
|---|---|---|---|---|---|---|---|---|
| 2-1482 | (b-18) | (b-73) | 6-OH | H | (a-14) | —CH— | —NH— | —CH(Me)— |
| 2-1483 | (b-18) | (b-73) | H | H | (a-14) | N | —CO— | —CH₂— |
| 2-1484 | (b-18) | (b-73) | H | H | (a-14) | N | —CO— | —(CH₂)₂— |
| 2-1485 | (b-18) | (b-73) | H | H | (a-14) | N | —CO— | —CH(Me)— |
| 2-1486 | (b-18) | (b-74) | H | H | (a-14) | —CH— | —NH— | —CH(Me)— |
| 2-1487 | (b-18) | (b-74) | H | H | (a-14) | —CH— | —NH— | —COCH(Me)— |
| 2-1488 | (b-18) | (b-74) | H | H | (a-14) | —CH— | —O— | —CH(Me)— |
| 2-1489 | (b-18) | (b-74) | H | H | (a-14) | —CH— | —S— | —CH(Me)— |
| 2-1490 | (b-18) | (b-75) | H | H | (a-14) | —CH— | —NH— | —CH(Me)— |
| 2-1491 | (b-18) | (b-76) | H | H | (a-14) | —CH— | —NH— | —CH(Me)— |
| 2-1492 | (b-18) | (b-76) | H | H | (a-14) | —CH— | —NH— | —COCH(Me)— |
| 2-1493 | (b-18) | (b-76) | H | H | (a-14) | —CH— | —O— | —CH(Me)— |
| 2-1494 | (b-18) | (b-76) | H | H | (a-14) | —CH— | —S— | —CH(Me)— |
| 2-1495 | (b-18) | (b-77) | H | H | (a-14) | —CH— | —NH— | —(CH₂)₂— |
| 2-1496 | (b-18) | (b-77) | H | H | (a-14) | —CH— | —NH— | —CH(Me)— |
| 2-1497 | (b-18) | (b-77) | H | H | (a-14) | —CH— | —NH— | —CH₂CH(Me)— |
| 2-1498 | (b-18) | (b-77) | H | H | (a-14) | —CH— | —NH— | —CO(CH₂)₂— |
| 2-1499 | (b-18) | (b-77) | H | H | (a-14) | —CH— | —NH— | —COCH(Me)— |
| 2-1500 | (b-18) | (b-77) | H | H | (a-14) | —CH— | —O— | —CH(Me)— |
| 2-1501 | (b-18) | (b-77) | H | H | (a-14) | —CH— | —S— | —CH(Me)— |
| 2-1502 | (b-18) | (b-77) | 6-Cl | H | (a-14) | —CH— | —NH— | —CH(Me)— |
| 2-1503 | (b-18) | (b-77) | 4-OH | H | (a-14) | —CH— | —NH— | —CH(Me)— |
| 2-1504 | (b-18) | (b-77) | 6-OH | H | (a-14) | —CH— | —NH— | —CH(Me)— |
| 2-1505 | (b-18) | (b-77) | H | H | (a-14) | N | —CO— | —CH(Me)— |
| 2-1506 | (b-18) | (b-78) | H | H | (a-14) | —CH— | —NH— | —CH(Me)— |
| 2-1507 | (b-19) | (b-7) | H | H | (a-14) | —CH— | —NH— | —CH(Me)— |
| 2-1508 | (b-19) | (b-7) | H | H | (a-14) | —CH— | —NH— | —COCH(Me)— |
| 2-1509 | (b-19) | (b-12) | H | H | (a-14) | —CH— | —NH— | —CH(Me)— |
| 2-1510 | (b-19) | (b-15) | H | H | (a-14) | —CH— | —NH— | —CH(Me)— |
| 2-1511 | (b-19) | (b-34) | H | H | (a-14) | —CH— | —NH— | —CH(Me)— |
| 2-1512 | (b-19) | (b-35) | H | H | (a-14) | —CH— | —NH— | —CH(Me)— |
| 2-1513 | (b-19) | (b-35) | H | H | (a-14) | —CH— | —NH— | —COCH(Me)— |
| 2-1514 | (b-19) | (b-37) | H | H | (a-14) | —CH— | —NH— | —CH(Me)— |
| 2-1515 | (b-19) | (b-73) | H | H | (a-14) | —CH— | —NH— | —CH(Me)— |
| 2-1516 | (b-19) | (b-77) | H | H | (a-14) | —CH— | —NH— | —CH(Me)— |
| 2-1517 | (b-19) | (b-77) | H | H | (a-14) | —CH— | —NH— | —COCH(Me)— |
| 2-1518 | (b-20) | (b-1) | H | H | (a-14) | —CH— | —NH— | —CH(Me)— |
| 2-1519 | (b-20) | (b-2) | H | H | (a-14) | —CH— | —NH— | —CH(Me)— |
| 2-1520 | (b-20) | (b-7) | H | H | (a-14) | —CH— | —NH— | single bond |
| 2-1521 | (b-20) | (b-7) | H | H | (a-14) | —CH— | —NH— | —CH₂— |
| 2-1522 | (b-20) | (b-7) | H | H | (a-14) | —CH— | —NH— | —(CH₂)₂— |
| 2-1523 | (b-20) | (b-7) | H | H | (a-14) | —CH— | —NH— | —CH(Me)— |
| 2-1524 | (b-20) | (b-7) | H | H | (a-14) | —CH— | —NH— | —CH(Et)— |
| 2-1525 | (b-20) | (b-7) | H | H | (a-14) | —CH— | —NH— | —(CH₂)₃— |
| 2-1526 | (b-20) | (b-7) | H | H | (a-14) | —CH— | —NH— | —CH₂CH(Me)— |
| 2-1527 | (b-20) | (b-7) | H | H | (a-14) | —CH— | —NH— | —CH₂CH(OH)— |
| 2-1528 | (b-20) | (b-7) | H | H | (a-14) | —CH— | —NH— | —CH₂C(=O)— |
| 2-1529 | (b-20) | (b-7) | H | H | (a-14) | —CH— | —NH— | —CH₂C(Ph)— |
| 2-1530 | (b-20) | (b-7) | H | H | (a-14) | —CH— | —NH— | —(CH₂)₂CH(Me)— |
| 2-1531 | (b-20) | (b-7) | H | H | (a-14) | —CH— | —NH— | —(CH₂)₂CH(OH)— |
| 2-1532 | (b-20) | (b-7) | H | H | (a-14) | —CH— | —NH— | —(CH₂)₂C(=O)— |
| 2-1533 | (b-20) | (b-7) | H | H | (a-14) | —CH— | —NH— | —(CH₂)₂C(Ph)— |
| 2-1534 | (b-20) | (b-7) | H | H | (a-14) | —CH— | —NH— | —CO— |
| 2-1535 | (b-20) | (b-7) | H | H | (a-14) | —CH— | —NH— | —COCH₂— |
| 2-1536 | (b-20) | (b-7) | H | H | (a-14) | —CH— | —NH— | —CO(CH₂)₂— |
| 2-1537 | (b-20) | (b-7) | H | H | (a-14) | —CH— | —NH— | —COCH(Me)— |
| 2-1538 | (b-20) | (b-7) | H | H | (a-14) | —CH— | —NH— | —COCH(Et)— |
| 2-1539 | (b-20) | (b-7) | H | H | (a-14) | —CH— | —NH— | —CO(CH₂)₃— |
| 2-1540 | (b-20) | (b-7) | H | H | (a-14) | —CH— | —NH— | —COCH₂CH(Me)— |
| 2-1541 | (b-20) | (b-7) | H | H | (a-14) | —CH— | —O— | —CH₂— |
| 2-1542 | (b-20) | (b-7) | H | H | (a-14) | —CH— | —O— | —(CH₂)₂— |
| 2-1543 | (b-20) | (b-7) | H | H | (a-14) | —CH— | —O— | —CH(Me)— |
| 2-1544 | (b-20) | (b-7) | H | H | (a-14) | —CH— | —S— | —CH₂— |
| 2-1545 | (b-20) | (b-7) | H | H | (a-14) | —CH— | —S— | —(CH₂)₂— |

TABLE 2-continued

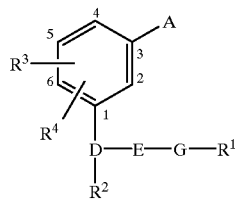

(I-2)

| Cpd. No. | R¹ Sub. No | R² Sub. No | R³ | R⁴ | A Sub. No | D | E | G |
|---|---|---|---|---|---|---|---|---|
| 2-1546 | (b-20) | (b-7) | H | H | (a-14) | —CH— | —S— | —CH(Me)— |
| 2-1547 | (b-20) | (b-7) | 4-F | H | (a-14) | —CH— | —NH— | —CH(Me)— |
| 2-1548 | (b-20) | (b-7) | 6-F | H | (a-14) | —CH— | —NH— | —CH(Me)— |
| 2-1549 | (b-20) | (b-7) | 4-Cl | H | (a-14) | —CH— | —NH— | —CH(Me)— |
| 2-1550 | (b-20) | (b-7) | 5-Cl | H | (a-14) | —CH— | —NH— | —CH(Me)— |
| 2-1551 | (b-20) | (b-7) | 6-Cl | H | (a-14) | —CH— | —NH— | —CH(Me)— |
| 2-1552 | (b-20) | (b-7) | 4-OH | H | (a-14) | —CH— | —NH— | —CH(Me)— |
| 2-1553 | (b-20) | (b-7) | 5-OH | H | (a-14) | —CH— | —NH— | —CH(Me)— |
| 2-1554 | (b-20) | (b-7) | 6-OH | H | (a-14) | —CH— | —NH— | —CH(Me)— |
| 2-1555 | (b-20) | (b-7) | H | H | (a-14) | N | —CO— | —CH₂— |
| 2-1556 | (b-20) | (b-7) | H | H | (a-14) | N | —CO— | —(CH₂)₂— |
| 2-1557 | (b-20) | (b-7) | H | H | (a-14) | N | —CO— | —CH(Me)— |
| 2-1558 | (b-20) | (b-8) | H | H | (a-14) | —CH— | —NH— | —CH(Me)— |
| 2-1559 | (b-20) | (b-10) | H | H | (a-14) | —CH— | —NH— | —CH(Me)— |
| 2-1560 | (b-20) | (b-11) | H | H | (a-14) | —CH— | —NH— | —CH(Me)— |
| 2-1561 | (b-20) | (b-11) | H | H | (a-14) | —CH— | —NH— | —COCH(Me)— |
| 2-1562 | (b-20) | (b-11) | H | H | (a-14) | —CH— | —O— | —CH(Me)— |
| 2-1563 | (b-20) | (b-11) | H | H | (a-14) | —CH— | —S— | —CH(Me)— |
| 2-1564 | (b-20) | (b-12) | H | H | (a-14) | —CH— | —NH— | —(CH₂)₂— |
| 2-1565 | (b-20) | (b-12) | H | H | (a-14) | —CH— | —NH— | —CH(Me)— |
| 2-1566 | (b-20) | (b-12) | H | H | (a-14) | —CH— | —NH— | —CH₂CH(Me)— |
| 2-1567 | (b-20) | (b-12) | H | H | (a-14) | —CH— | —NH— | —CO(CH₂)₂— |
| 2-1568 | (b-20) | (b-12) | H | H | (a-14) | —CH— | —NH— | —COCH(Me)— |
| 2-1569 | (b-20) | (b-12) | H | H | (a-14) | —CH— | —O— | —CH(Me)— |
| 2-1570 | (b-20) | (b-12) | H | H | (a-14) | —CH— | —S— | —CH(Me)— |
| 2-1571 | (b-20) | (b-12) | 6-Cl | H | (a-14) | —CH— | —NH— | —CH(Me)— |
| 2-1572 | (b-20) | (b-12) | 4-OH | H | (a-14) | —CH— | —NH— | —CH(Me)— |
| 2-1573 | (b-20) | (b-12) | 6-OH | H | (a-14) | —CH— | —NH— | —CH(Me)— |
| 2-1574 | (b-20) | (b-12) | H | H | (a-14) | N | —CO— | —CH(Me)— |
| 2-1575 | (b-20) | (b-13) | H | H | (a-14) | —CH— | —NH— | —CH(Me)— |
| 2-1576 | (b-20) | (b-14) | H | H | (a-14) | —CH— | —NH— | —CH(Me)— |
| 2-1577 | (b-20) | (b-14) | H | H | (a-14) | —CH— | —NH— | —COCH(Me)— |
| 2-1578 | (b-20) | (b-14) | H | H | (a-14) | —CH— | —O— | —CH(Me)— |
| 2-1579 | (b-20) | (b-14) | H | H | (a-14) | —CH— | —S— | —CH(Me)— |
| 2-1580 | (b-20) | (b-15) | H | H | (a-14) | —CH— | —NH— | —(CH₂)₂— |
| 2-1581 | (b-20) | (b-15) | H | H | (a-14) | —CH— | —NH— | —CH(Me)— |
| 2-1582 | (b-20) | (b-15) | H | H | (a-14) | —CH— | —NH— | —CH₂CH(Me)— |
| 2-1583 | (b-20) | (b-15) | H | H | (a-14) | —CH— | —NH— | —CO(CH₂)₂— |
| 2-1584 | (b-20) | (b-15) | H | H | (a-14) | —CH— | —NH— | —COCH(Me)— |
| 2-1585 | (b-20) | (b-15) | H | H | (a-14) | —CH— | —O— | —CH(Me)— |
| 2-1586 | (b-20) | (b-15) | H | H | (a-14) | —CH— | —S— | —CH(Me)— |
| 2-1587 | (b-20) | (b-15) | 6-Cl | H | (a-14) | —CH— | —NH— | —CH(Me)— |
| 2-1588 | (b-20) | (b-15) | 4-OH | H | (a-14) | —CH— | —NH— | —CH(Me)— |
| 2-1589 | (b-20) | (b-15) | 6-OH | H | (a-14) | —CH— | —NH— | —CH(Me)— |
| 2-1590 | (b-20) | (b-15) | H | H | (a-14) | N | —CO— | —CH(Me)— |
| 2-1591 | (b-20) | (b-16) | H | H | (a-14) | —CH— | —NH— | —CH(Me)— |
| 2-1592 | (b-20) | (b-17) | H | H | (a-14) | —CH— | —NH— | —CH(Me)— |
| 2-1593 | (b-20) | (b-17) | H | H | (a-14) | —CH— | —NH— | —COCH(Me)— |
| 2-1594 | (b-20) | (b-17) | H | H | (a-14) | —CH— | —O— | —CH(Me)— |
| 2-1595 | (b-20) | (b-17) | H | H | (a-14) | —CH— | —S— | —CH(Me)— |
| 2-1596 | (b-20) | (b-23) | H | H | (a-14) | —CH— | —NH— | —CH(Me)— |
| 2-1597 | (b-20) | (b-24) | H | H | (a-14) | —CH— | —NH— | —CH(Me)— |
| 2-1598 | (b-20) | (b-25) | H | H | (a-14) | —CH— | —NH— | —CH(Me)— |
| 2-1599 | (b-20) | (b-25) | H | H | (a-14) | —CH— | —NH— | —COCH(Me)— |
| 2-1600 | (b-20) | (b-25) | H | H | (a-14) | —CH— | —O— | —CH(Me)— |
| 2-1601 | (b-20) | (b-25) | H | H | (a-14) | —CH— | —S— | —CH(Me)— |
| 2-1602 | (b-20) | (b-27) | H | H | (a-14) | —CH— | —NH— | —CH(Me)— |
| 2-1603 | (b-20) | (b-28) | H | H | (a-14) | —CH— | —NH— | —CH(Me)— |
| 2-1604 | (b-20) | (b-30) | H | H | (a-14) | —CH— | —NH— | —CH(Me)— |
| 2-1605 | (b-20) | (b-31) | H | H | (a-14) | —CH— | —NH— | —CH(Me)— |
| 2-1606 | (b-20) | (b-32) | H | H | (a-14) | —CH— | —NH— | —CH(Me)— |
| 2-1607 | (b-20) | (b-33) | H | H | (a-14) | —CH— | —NH— | —CH(Me)— |
| 2-1608 | (b-20) | (b-33) | H | H | (a-14) | —CH— | —NH— | —COCH(Me)— |
| 2-1609 | (b-20) | (b-33) | H | H | (a-14) | —CH— | —O— | —CH(Me)— |

TABLE 2-continued

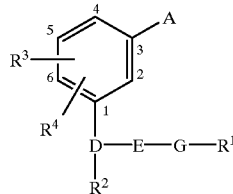

(I-2)

| Cpd. No. | R¹ Sub. No | R² Sub. No | R³ | R⁴ | A Sub. No | D | E | G |
|---|---|---|---|---|---|---|---|---|
| 2-1610 | (b-20) | (b-33) | H | H | (a-14) | —CH— | —S— | —CH(Me)— |
| 2-1611 | (b-20) | (b-34) | H | H | (a-14) | —CH— | —NH— | —(CH$_2$)$_2$— |
| 2-1612 | (b-20) | (b-34) | H | H | (a-14) | —CH— | —NH— | —CH(Me)— |
| 2-1613 | (b-20) | (b-34) | H | H | (a-14) | —CH— | —NH— | —CH$_2$CH(Me)— |
| 2-1614 | (b-20) | (b-34) | H | H | (a-14) | —CH— | —NH— | —CO(CH$_2$)$_2$— |
| 2-1615 | (b-20) | (b-34) | H | H | (a-14) | —CH— | —NH— | —COCH(Me)— |
| 2-1616 | (b-20) | (b-34) | H | H | (a-14) | —CH— | —O— | —CH(Me)— |
| 2-1617 | (b-20) | (b-34) | H | H | (a-14) | —CH— | —S— | —CH(Me)— |
| 2-1618 | (b-20) | (b-34) | 6-Cl | H | (a-14) | —CH— | —NH— | —CH(Me)— |
| 2-1619 | (b-20) | (b-34) | 4-OH | H | (a-14) | —CH— | —NH— | —CH(Me)— |
| 2-1620 | (b-20) | (b-34) | 6-OH | H | (a-14) | —CH— | —NH— | —CH(Me)— |
| 2-1621 | (b-20) | (b-34) | H | H | (a-14) | N | —CO— | —CH(Me)— |
| 2-1622 | (b-20) | (b-35) | H | H | (a-14) | —CH— | —NH— | single bond |
| 2-1623 | (b-20) | (b-35) | H | H | (a-14) | —CH— | —NH— | —CH$_2$— |
| 2-1624 | (b-20) | (b-35) | H | H | (a-14) | —CH— | —NH— | —(CH$_2$)$_2$— |
| 2-1625 | (b-20) | (b-35) | H | H | (a-14) | —CH— | —NH— | —CH(Me)— |
| 2-1626 | (b-20) | (b-35) | H | H | (a-14) | —CH— | —NH— | —CH(Et)— |
| 2-1627 | (b-20) | (b-35) | H | H | (a-14) | —CH— | —NH— | —(CH$_2$)$_3$— |
| 2-1628 | (b-20) | (b-35) | H | H | (a-14) | —CH— | —NH— | —CH$_2$CH(Me)— |
| 2-1629 | (b-20) | (b-35) | H | H | (a-14) | —CH— | —NH— | —CH$_2$CH(OH)— |
| 2-1630 | (b-20) | (b-35) | H | H | (a-14) | —CH— | —NH— | —CH$_2$C(=O)— |
| 2-1631 | (b-20) | (b-35) | H | H | (a-14) | —CH— | —NH— | —CH$_2$C(Ph)— |
| 2-1632 | (b-20) | (b-35) | H | H | (a-14) | —CH— | —NH— | —(CH$_2$)$_2$CH(Me)— |
| 2-1633 | (b-20) | (b-35) | H | H | (a-14) | —CH— | —NH— | —(CH$_2$)$_2$CH(OH)— |
| 2-1634 | (b-20) | (b-35) | H | H | (a-14) | —CH— | —NH— | —(CH$_2$)$_2$C(=O)— |
| 2-1635 | (b-20) | (b-35) | H | H | (a-14) | —CH— | —NH— | —(CH$_2$)$_2$C(Ph)— |
| 2-1636 | (b-20) | (b-35) | H | H | (a-14) | —CH— | —NH— | —CO— |
| 2-1637 | (b-20) | (b-35) | H | H | (a-14) | —CH— | —NH— | —COCH$_2$— |
| 2-1638 | (b-20) | (b-35) | H | H | (a-14) | —CH— | —NH— | —CO(CH$_2$)$_2$— |
| 2-1639 | (b-20) | (b-35) | H | H | (a-14) | —CH— | —NH— | —COCH(Me)— |
| 2-1640 | (b-20) | (b-35) | H | H | (a-14) | —CH— | —NH— | —COCH(Et)— |
| 2-1641 | (b-20) | (b-35) | H | H | (a-14) | —CH— | —NH— | —CO(CH$_2$)$_3$— |
| 2-1642 | (b-20) | (b-35) | H | H | (a-14) | —CH— | —NH— | —COCH$_2$CH(Me)— |
| 2-1643 | (b-20) | (b-35) | H | H | (a-14) | —CH— | —O— | —CH$_2$— |
| 2-1644 | (b-20) | (b-35) | H | H | (a-14) | —CH— | —O— | —(CH$_2$)$_2$— |
| 2-1645 | (b-20) | (b-35) | H | H | (a-14) | —CH— | —O— | —CH(Me)— |
| 2-1646 | (b-20) | (b-35) | H | H | (a-14) | —CH— | —S— | —CH$_2$— |
| 2-1647 | (b-20) | (b-35) | H | H | (a-14) | —CH— | —S— | —(CH$_2$)$_2$— |
| 2-1648 | (b-20) | (b-35) | H | H | (a-14) | —CH— | —S— | —CH(Me)— |
| 2-1649 | (b-20) | (b-35) | 4-F | H | (a-14) | —CH— | —NH— | —CH(Me)— |
| 2-1650 | (b-20) | (b-35) | 6-F | H | (a-14) | —CH— | —NH— | —CH(Me)— |
| 2-1651 | (b-20) | (b-35) | 4-Cl | H | (a-14) | —CH— | —NH— | —CH(Me)— |
| 2-1652 | (b-20) | (b-35) | 5-Cl | H | (a-14) | —CH— | —NH— | —CH(Me)— |
| 2-1653 | (b-20) | (b-35) | 6-Cl | H | (a-14) | —CH— | —NH— | —CH(Me)— |
| 2-1654 | (b-20) | (b-35) | 4-OH | H | (a-14) | —CH— | —NH— | —CH(Me)— |
| 2-1655 | (b-20) | (b-35) | 5-OH | H | (a-14) | —CH— | —NH— | —CH(Me)— |
| 2-1666 | (b-20) | (b-35) | 6-OH | H | (a-14) | —CH— | —NH— | —CH(Me)— |
| 2-1667 | (b-20) | (b-35) | H | H | (a-14) | N | —CO— | —CH$_2$— |
| 2-1668 | (b-20) | (b-35) | H | H | (a-14) | N | —CO— | —(CH$_2$)$_2$— |
| 2-1669 | (b-20) | (b-35) | H | H | (a-14) | N | —CO— | —CH(Me)— |
| 2-1670 | (b-20) | (b-37) | H | H | (a-14) | —CH— | —NH— | single bond |
| 2-1671 | (b-20) | (b-37) | H | H | (a-14) | —CH— | —NH— | —CH$_2$— |
| 2-1672 | (b-20) | (b-37) | H | H | (a-14) | —CH— | —NH— | —(CH$_2$)$_2$— |
| 2-1673 | (b-20) | (b-37) | H | H | (a-14) | —CH— | —NH— | —CH(Me)— |
| 2-1674 | (b-20) | (b-37) | H | H | (a-14) | —CH— | —NH— | —CH(Et)— |
| 2-1675 | (b-20) | (b-37) | H | H | (a-14) | —CH— | —NH— | —(CH$_2$)$_3$— |
| 2-1676 | (b-20) | (b-37) | H | H | (a-14) | —CH— | —NH— | —CH$_2$CH(Me)— |
| 2-1677 | (b-20) | (b-37) | H | H | (a-14) | —CH— | —NH— | —CH$_2$CH(OH)— |
| 2-1678 | (b-20) | (b-37) | H | H | (a-14) | —CH— | —NH— | —CH$_2$C(=O)— |
| 2-1679 | (b-20) | (b-37) | H | H | (a-14) | —CH— | —NH— | —CH$_2$C(Ph)— |
| 2-1680 | (b-20) | (b-37) | H | H | (a-14) | —CH— | —NH— | —(CH$_2$)$_2$CH(Me)— |
| 2-1681 | (b-20) | (b-37) | H | H | (a-14) | —CH— | —NH— | —(CH$_2$)$_2$CH(OH)— |
| 2-1682 | (b-20) | (b-37) | H | H | (a-14) | —CH— | —NH— | —(CH$_2$)$_2$C(=O)— |
| 2-1683 | (b-20) | (b-37) | H | H | (a-14) | —CH— | —NH— | —(CH$_2$)$_2$C(Ph)— |

TABLE 2-continued

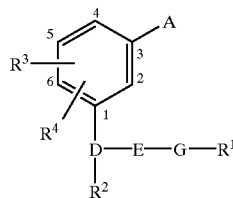

(I-2)

| Cpd. No. | $R^1$ Sub. No | $R^2$ Sub. No | $R^3$ | $R^4$ | A Sub. No | D | E | G |
|---|---|---|---|---|---|---|---|---|
| 2-1684 | (b-20) | (b-37) | H | H | (a-14) | —CH— | —NH— | —CO— |
| 2-1685 | (b-20) | (b-37) | H | H | (a-14) | —CH— | —NH— | —COCH$_2$— |
| 2-1686 | (b-20) | (b-37) | H | H | (a-14) | —CH— | —NH— | —CO(CH$_2$)$_2$— |
| 2-1687 | (b-20) | (b-37) | H | H | (a-14) | —CH— | —NH— | —COCH(Me)— |
| 2-1688 | (b-20) | (b-37) | H | H | (a-14) | —CH— | —NH— | —COCH(Et)— |
| 2-1689 | (b-20) | (b-37) | H | H | (a-14) | —CH— | —NH— | —CO(CH$_2$)$_3$— |
| 2-1690 | (b-20) | (b-37) | H | H | (a-14) | —CH— | —NH— | —COCH$_2$CH(Me)— |
| 2-1691 | (b-20) | (b-37) | H | H | (a-14) | —CH— | —O— | —CH$_2$— |
| 2-1692 | (b-20) | (b-37) | H | H | (a-14) | —CH— | —O— | —(CH$_2$)$_2$— |
| 2-1693 | (b-20) | (b-37) | H | H | (a-14) | —CH— | —O— | —CH(Me)— |
| 2-1694 | (b-20) | (b-37) | H | H | (a-14) | —CH— | —S— | —CH$_2$— |
| 2-1695 | (b-20) | (b-37) | H | H | (a-14) | —CH— | —S— | —(CH$_2$)$_2$— |
| 2-1696 | (b-20) | (b-37) | H | H | (a-14) | —CH— | —S— | —CH(Me)— |
| 2-1697 | (b-20) | (b-37) | 4-F | H | (a-14) | —CH— | —NH— | —CH(Me)— |
| 2-1698 | (b-20) | (b-37) | 6-F | H | (a-14) | —CH— | —NH— | —CH(Me)— |
| 2-1699 | (b-20) | (b-37) | 4-Cl | H | (a-14) | —CH— | —NH— | —CH(Me)— |
| 2-1700 | (b-20) | (b-37) | 5-Cl | H | (a-14) | —CH— | —NH— | —CH(Me)— |
| 2-1701 | (b-20) | (b-37) | 6-Cl | H | (a-14) | —CH— | —NH— | —CH(Me)— |
| 2-1702 | (b-20) | (b-37) | 4-OH | H | (a-14) | —CH— | —NH— | —CH(Me)— |
| 2-1703 | (b-20) | (b-37) | 5-OH | H | (a-14) | —CH— | —NH— | —CH(Me)— |
| 2-1704 | (b-20) | (b-37) | 6-OH | H | (a-14) | —CH— | —NH— | —CH(Me)— |
| 2-1705 | (b-20) | (b-37) | H | H | (a-14) | N | —CO— | —CH$_2$— |
| 2-1706 | (b-20) | (b-37) | H | H | (a-14) | N | —CO— | —(CH$_2$)$_2$— |
| 2-1707 | (b-20) | (b-37) | H | H | (a-14) | N | —CO— | —CH(Me)— |
| 2-1708 | (b-20) | (b-38) | H | H | (a-14) | —CH— | —NH— | —CH(Me)— |
| 2-1709 | (b-20) | (b-41) | H | H | (a-14) | —CH— | —NH— | —CH(Me)— |
| 2-1710 | (b-20) | (b-42) | H | H | (a-14) | —CH— | —NH— | —CH(Me)— |
| 2-1711 | (b-20) | (b-42) | H | H | (a-14) | —CH— | —NH— | —COCH(Me)— |
| 2-1712 | (b-20) | (b-42) | H | H | (a-14) | —CH— | —O— | —CH(Me)— |
| 2-1713 | (b-20) | (b-42) | H | H | (a-14) | —CH— | —S— | —CH(Me)— |
| 2-1714 | (b-20) | (b-43) | H | H | (a-14) | —CH— | —NH— | —CH(Me)— |
| 2-1715 | (b-20) | (b-72) | H | H | (a-14) | —CH— | —NH— | —(CH$_2$)$_2$— |
| 2-1716 | (b-20) | (b-72) | H | H | (a-14) | —CH— | —NH— | —CH(Me)— |
| 2-1717 | (b-20) | (b-72) | H | H | (a-14) | —CH— | —NH— | —CH$_2$CH(Me)— |
| 2-1718 | (b-20) | (b-72) | H | H | (a-14) | —CH— | —NH— | —COCH(Me)— |
| 2-1719 | (b-20) | (b-72) | H | H | (a-14) | —CH— | —O— | —CH(Me)— |
| 2-1720 | (b-20) | (b-72) | H | H | (a-14) | —CH— | —S— | —CH(Me)— |
| 2-1721 | (b-20) | (b-72) | 6-Cl | H | (a-14) | —CH— | —NH— | —CH(Me)— |
| 2-1722 | (b-20) | (b-72) | 4-OH | H | (a-14) | —CH— | —NH— | —CH(Me)— |
| 2-1723 | (b-20) | (b-72) | 6-OH | H | (a-14) | —CH— | —NH— | —CH(Me)— |
| 2-1724 | (b-20) | (b-73) | H | H | (a-14) | —CH— | —NH— | single bond |
| 2-1725 | (b-20) | (b-73) | H | H | (a-14) | —CH— | —NH— | —CH$_2$— |
| 2-1726 | (b-20) | (b-73) | H | H | (a-14) | —CH— | —NH— | —(CH$_2$)$_2$— |
| 2-1727 | (b-20) | (b-73) | H | H | (a-14) | —CH— | —NH— | —CH(Me)— |
| 2-1728 | (b-20) | (b-73) | H | H | (a-14) | —CH— | —NH— | —CH(Et)— |
| 2-1729 | (b-20) | (b-73) | H | H | (a-14) | —CH— | —NH— | —(CH$_2$)$_3$— |
| 2-1730 | (b-20) | (b-73) | H | H | (a-14) | —CH— | —NH— | —CH$_2$CH(Me)— |
| 2-1731 | (b-20) | (b-73) | H | H | (a-14) | —CH— | —NH— | —CH$_2$CH(OH)— |
| 2-1732 | (b-20) | (b-73) | H | H | (a-14) | —CH— | —NH— | —CH$_2$C(=O)— |
| 2-1733 | (b-20) | (b-73) | H | H | (a-14) | —CH— | —NH— | —CH$_2$C(Ph)— |
| 2-1734 | (b-20) | (b-73) | H | H | (a-14) | —CH— | —NH— | —(CH$_2$)$_2$CH(Me)— |
| 2-1735 | (b-20) | (b-73) | H | H | (a-14) | —CH— | —NH— | —(CH$_2$)$_2$CH(OH)— |
| 2-1736 | (b-20) | (b-73) | H | H | (a-14) | —CH— | —NH— | —(CH$_2$)$_2$C(=O)— |
| 2-1737 | (b-20) | (b-73) | H | H | (a-14) | —CH— | —NH— | —(CH$_2$)$_2$C(Ph)— |
| 2-1738 | (b-20) | (b-73) | H | H | (a-14) | —CH— | —NH— | —CO— |
| 2-1739 | (b-20) | (b-73) | H | H | (a-14) | —CH— | —NH— | —COCH$_2$— |
| 2-1740 | (b-20) | (b-73) | H | H | (a-14) | —CH— | —NH— | —CO(CH$_2$)$_2$— |
| 2-1741 | (b-20) | (b-73) | H | H | (a-14) | —CH— | —NH— | —COCH(Me)— |
| 2-1742 | (b-20) | (b-73) | H | H | (a-14) | —CH— | —NH— | —COCH(Et)— |
| 2-1743 | (b-20) | (b-73) | H | H | (a-14) | —CH— | —NH— | —CO(CH$_2$)$_3$— |
| 2-1744 | (b-20) | (b-73) | H | H | (a-14) | —CH— | —NH— | —COCH$_2$CH(Me)— |
| 2-1745 | (b-20) | (b-73) | H | H | (a-14) | —CH— | —O— | —CH$_2$— |
| 2-1746 | (b-20) | (b-73) | H | H | (a-14) | —CH— | —O— | —(CH$_2$)$_2$— |
| 2-1747 | (b-20) | (b-73) | H | H | (a-14) | —CH— | —O— | —CH(Me)— |

TABLE 2-continued

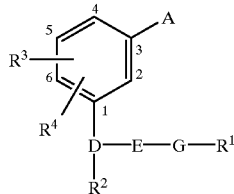

(I-2)

| Cpd. No. | R¹ Sub. No | R² Sub. No | R³ | R⁴ | A Sub. No | D | E | G |
|---|---|---|---|---|---|---|---|---|
| 2-1748 | (b-20) | (b-73) | H | H | (a-14) | —CH— | —S— | —CH₂— |
| 2-1749 | (b-20) | (b-73) | H | H | (a-14) | —CH— | —S— | —(CH₂)₂— |
| 2-1750 | (b-20) | (b-73) | H | H | (a-14) | —CH— | —S— | —CH(Me)— |
| 2-1751 | (b-20) | (b-73) | 4-F | H | (a-14) | —CH— | —NH— | —CH(Me)— |
| 2-1752 | (b-20) | (b-73) | 6-F | H | (a-14) | —CH— | —NH— | —CH(Me)— |
| 2-1753 | (b-20) | (b-73) | 4-Cl | H | (a-14) | —CH— | —NH— | —CH(Me)— |
| 2-1754 | (b-20) | (b-73) | 5-Cl | H | (a-14) | —CH— | —NH— | —CH(Me)— |
| 2-1755 | (b-20) | (b-73) | 6-Cl | H | (a-14) | —CH— | —NH— | —CH(Me)— |
| 2-1756 | (b-20) | (b-73) | 4-OH | H | (a-14) | —CH— | —NH— | —CH(Me)— |
| 2-1757 | (b-20) | (b-73) | 5-OH | H | (a-14) | —CH— | —NH— | —CH(Me)— |
| 2-1758 | (b-20) | (b-73) | 6-OH | H | (a-14) | —CH— | —NH— | —CH(Me)— |
| 2-1759 | (b-20) | (b-73) | H | H | (a-14) | N | —CO— | —CH₂— |
| 2-1760 | (b-20) | (b-73) | H | H | (a-14) | N | —CO— | —(CH₂)₂— |
| 2-1761 | (b-20) | (b-73) | H | H | (a-14) | N | —CO— | —CH(Me)— |
| 2-1762 | (b-20) | (b-74) | H | H | (a-14) | —CH— | —NH— | —CH(Me)— |
| 2-1763 | (b-20) | (b-74) | H | H | (a-14) | —CH— | —NH— | —COCH(Me)— |
| 2-1764 | (b-20) | (b-74) | H | H | (a-14) | —CH— | —O— | —CH(Me)— |
| 2-1765 | (b-20) | (b-74) | H | H | (a-14) | —CH— | —S— | —CH(Me)— |
| 2-1766 | (b-20) | (b-75) | H | H | (a-14) | —CH— | —NH— | —CH(Me)— |
| 2-1767 | (b-20) | (b-76) | H | H | (a-14) | —CH— | —NH— | —CH(Me)— |
| 2-1768 | (b-20) | (b-76) | H | H | (a-14) | —CH— | —NH— | —COCH(Me)— |
| 2-1769 | (b-20) | (b-76) | H | H | (a-14) | —CH— | —O— | —CH(Me)— |
| 2-1770 | (b-20) | (b-76) | H | H | (a-14) | —CH— | —S— | —CH(Me)— |
| 2-1771 | (b-20) | (b-77) | H | H | (a-14) | —CH— | —NH— | —(CH₂)₂— |
| 2-1772 | (b-20) | (b-77) | H | H | (a-14) | —CH— | —NH— | —CH(Me)— |
| 2-1773 | (b-20) | (b-77) | H | H | (a-14) | —CH— | —NH— | —CH₂CH(Me)— |
| 2-1774 | (b-20) | (b-77) | H | H | (a-14) | —CH— | —NH— | —CO(CH₂)₂— |
| 2-1775 | (b-20) | (b-77) | H | H | (a-14) | —CH— | —NH— | —COCH(Me)— |
| 2-1776 | (b-20) | (b-77) | H | H | (a-14) | —CH— | —O— | —CH(Me)— |
| 2-1777 | (b-20) | (b-77) | H | H | (a-14) | —CH— | —S— | —CH(Me)— |
| 2-1778 | (b-20) | (b-77) | 6-Cl | H | (a-14) | —CH— | —NH— | —CH(Me)— |
| 2-1779 | (b-20) | (b-77) | 4-OH | H | (a-14) | —CH— | —NH— | —CH(Me)— |
| 2-1780 | (b-20) | (b-77) | 6-OH | H | (a-14) | —CH— | —NH— | —CH(Me)— |
| 2-1781 | (b-20) | (b-77) | H | H | (a-14) | N | —CO— | —CH(Me)— |
| 2-1782 | (b-20) | (b-78) | H | H | (a-14) | —CH— | —NH— | —CH(Me)— |
| 2-1783 | (b-21) | (b-1) | H | H | (a-14) | —CH— | —NH— | —CH(Me)— |
| 2-1784 | (b-21) | (b-2) | H | H | (a-14) | —CH— | —NH— | —CH(Me)— |
| 2-1785 | (b-21) | (b-3) | H | H | (a-14) | —CH— | —NH— | —CH(Me)— |
| 2-1786 | (b-21) | (b-4) | H | H | (a-14) | —CH— | —NH— | —CH(Me)— |
| 2-1787 | (b-21) | (b-5) | H | H | (a-14) | —CH— | —NH— | —CH(Me)— |
| 2-1788 | (b-21) | (b-7) | H | H | (a-14) | —CH— | —NH— | —CH(Me)— |
| 2-1789 | (b-21) | (b-7) | H | H | (a-14) | —CH— | —NH— | —COCH(Me)— |
| 2-1790 | (b-21) | (b-12) | H | H | (a-14) | —CH— | —NH— | —CH(Me)— |
| 2-1791 | (b-21) | (b-15) | H | H | (a-14) | —CH— | —NH— | —CH(Me)— |
| 2-1792 | (b-21) | (b-34) | H | H | (a-14) | —CH— | —NH— | —CH(Me)— |
| 2-1793 | (b-21) | (b-35) | H | H | (a-14) | —CH— | —NH— | —CH(Me)— |
| 2-1794 | (b-21) | (b-35) | H | H | (a-14) | —CH— | —NH— | —COCH(Me)— |
| 2-1795 | (b-21) | (b-37) | H | H | (a-14) | —CH— | —NH— | —CH(Me)— |
| 2-1796 | (b-21) | (b-73) | H | H | (a-14) | —CH— | —NH— | —CH(Me)— |
| 2-1797 | (b-21) | (b-77) | H | H | (a-14) | —CH— | —NH— | —CH(Me)— |
| 2-1798 | (b-22) | (b-35) | H | H | (a-14) | —CH— | —NH— | —CH(Me)— |
| 2-1799 | (b-23) | (b-7) | H | H | (a-14) | —CH— | —NH— | —CH(Me)— |
| 2-1800 | (b-23) | (b-35) | H | H | (a-14) | —CH— | —NH— | —CH(Me)— |
| 2-1801 | (b-24) | (b-7) | H | H | (a-14) | —CH— | —NH— | —CH(Me)— |
| 2-1802 | (b-24) | (b-7) | H | H | (a-14) | —CH— | —NH— | —COCH(Me)— |
| 2-1803 | (b-24) | (b-12) | H | H | (a-14) | —CH— | —NH— | —CH(Me)— |
| 2-1804 | (b-24) | (b-15) | H | H | (a-14) | —CH— | —NH— | —CH(Me)— |
| 2-1805 | (b-24) | (b-34) | H | H | (a-14) | —CH— | —NH— | —CH(Me)— |
| 2-1806 | (b-24) | (b-35) | H | H | (a-14) | —CH— | —NH— | —CH(Me)— |
| 2-1807 | (b-24) | (b-35) | H | H | (a-14) | —CH— | —NH— | —COCH(Me)— |
| 2-1808 | (b-24) | (b-37) | H | H | (a-14) | —CH— | —NH— | —CH(Me)— |
| 2-1809 | (b-24) | (b-73) | H | H | (a-14) | —CH— | —NH— | —CH(Me)— |
| 2-1810 | (b-24) | (b-77) | H | H | (a-14) | —CH— | —NH— | —CH(Me)— |
| 2-1811 | (b-25) | (b-7) | H | H | (a-14) | —CH— | —NH— | —CH(Me)— |

TABLE 2-continued

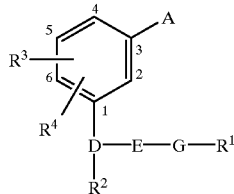

(I-2)

| Cpd. No. | R¹ Sub. No | R² Sub. No | R³ | R⁴ | A Sub. No | D | E | G |
|---|---|---|---|---|---|---|---|---|
| 2-1812 | (b-25) | (b-7) | H | H | (a-14) | —CH— | —NH— | —COCH(Me)— |
| 2-1813 | (b-25) | (b-12) | H | H | (a-14) | —CH— | —NH— | —CH(Me)— |
| 2-1814 | (b-25) | (b-15) | H | H | (a-14) | —CH— | —NH— | —CH(Me)— |
| 2-1815 | (b-25) | (b-34) | H | H | (a-14) | —CH— | —NH— | —CH(Me)— |
| 2-1816 | (b-25) | (b-35) | H | H | (a-14) | —CH— | —NH— | —CH(Me)— |
| 2-1817 | (b-25) | (b-35) | H | H | (a-14) | —CH— | —NH— | —COCH(Me)— |
| 2-1818 | (b-25) | (b-37) | H | H | (a-14) | —CH— | —NH— | —CH(Me)— |
| 2-1819 | (b-25) | (b-73) | H | H | (a-14) | —CH— | —NH— | —CH(Me)— |
| 2-1820 | (b-25) | (b-77) | H | H | (a-14) | —CH— | —NH— | —CH(Me)— |
| 2-1821 | (b-26) | (b-35) | H | H | (a-14) | —CH— | —NH— | —CH(Me)— |
| 2-1822 | (b-27) | (b-35) | H | H | (a-14) | —CH— | —NH— | —CH(Me)— |
| 2-1823 | (b-28) | (b-35) | H | H | (a-14) | —CH— | —NH— | —CH(Me)— |
| 2-1824 | (b-29) | (b-35) | H | H | (a-14) | —CH— | —NH— | —CH(Me)— |
| 2-1825 | (b-30) | (b-35) | H | H | (a-14) | —CH— | —NH— | —CH(Me)— |
| 2-1826 | (b-31) | (b-35) | H | H | (a-14) | —CH— | —NH— | —CH(Me)— |
| 2-1827 | (b-32) | (b-35) | H | H | (a-14) | —CH— | —NH— | —CH(Me)— |
| 2-1828 | (b-33) | (b-35) | H | H | (a-14) | —CH— | —NH— | —CH(Me)— |
| 2-1829 | (b-34) | (b-35) | H | H | (a-14) | —CH— | —NH— | —CH(Me)— |
| 2-1830 | (b-35) | (b-7) | H | H | (a-14) | —CH— | —NH— | —CH(Me)— |
| 2-1831 | (b-35) | (b-35) | H | H | (a-14) | —CH— | —NH— | —CH(Me)— |
| 2-1832 | (b-36) | (b-35) | H | H | (a-14) | —CH— | —NH— | —CH(Me)— |
| 2-1833 | (b-37) | (b-35) | H | H | (a-14) | —CH— | —NH— | —CH(Me)— |
| 2-1834 | (b-38) | (b-35) | H | H | (a-14) | —CH— | —NH— | —CH(Me)— |
| 2-1835 | (b-39) | (b-35) | H | H | (a-14) | —CH— | —NH— | —CH(Me)— |
| 2-1836 | (b-40) | (b-35) | H | H | (a-14) | —CH— | —NH— | —CH(Me)— |
| 2-1837 | (b-41) | (b-35) | H | H | (a-14) | —CH— | —NH— | —CH(Me)— |
| 2-1838 | (b-42) | (b-35) | H | H | (a-14) | —CH— | —NH— | —CH(Me)— |
| 2-1839 | (b-43) | (b-35) | H | H | (a-14) | —CH— | —NH— | —CH(Me)— |
| 2-1840 | (b-44) | (b-35) | H | H | (a-14) | —CH— | —NH— | —CH(Me)— |
| 2-1841 | (b-45) | (b-35) | H | H | (a-14) | —CH— | —NH— | —CH(Me)— |
| 2-1842 | (b-46) | (b-35) | H | H | (a-14) | —CH— | —NH— | —CH(Me)— |
| 2-1843 | (b-47) | (b-35) | H | H | (a-14) | —CH— | —NH— | —CH(Me)— |
| 2-1844 | (b-48) | (b-35) | H | H | (a-14) | —CH— | —NH— | —CH(Me)— |
| 2-1845 | (b-49) | (b-35) | H | H | (a-14) | —CH— | —NH— | —CH(Me)— |
| 2-1846 | (b-50) | (b-35) | H | H | (a-14) | —CH— | —NH— | —CH(Me)— |
| 2-1847 | (b-51) | (b-35) | H | H | (a-14) | —CH— | —NH— | —CH(Me)— |
| 2-1848 | (b-52) | (b-35) | H | H | (a-14) | —CH— | —NH— | —CH(Me)— |
| 2-1849 | (b-53) | (b-35) | H | H | (a-14) | —CH— | —NH— | —CH(Me)— |
| 2-1850 | (b-54) | (b-35) | H | H | (a-14) | —CH— | —NH— | —CH(Me)— |
| 2-1851 | (b-55) | (b-35) | H | H | (a-14) | —CH— | —NH— | —CH(Me)— |
| 2-1852 | (b-56) | (b-35) | H | H | (a-14) | —CH— | —NH— | —CH(Me)— |
| 2-1853 | (b-57) | (b-35) | H | H | (a-14) | —CH— | —NH— | —CH(Me)— |
| 2-1854 | (b-58) | (b-35) | H | H | (a-14) | —CH— | —NH— | —CH(Me)— |
| 2-1855 | (b-59) | (b-35) | H | H | (a-14) | —CH— | —NH— | —CH(Me)— |
| 2-1856 | (b-60) | (b-35) | H | H | (a-14) | —CH— | —NH— | —CH(Me)— |
| 2-1857 | (b-61) | (b-35) | H | H | (a-14) | —CH— | —NH— | —CH(Me)— |
| 2-1858 | (b-62) | (b-35) | H | H | (a-14) | —CH— | —NH— | —CH(Me)— |
| 2-1859 | (b-63) | (b-35) | H | H | (a-14) | —CH— | —NH— | —CH(Me)— |
| 2-1860 | (b-64) | (b-35) | H | H | (a-14) | —CH— | —NH— | —CH(Me)— |
| 2-1861 | (b-65) | (b-35) | H | H | (a-14) | —CH— | —NH— | —CH(Me)— |
| 2-1862 | (b-66) | (b-35) | H | H | (a-14) | —CH— | —NH— | —CH(Me)— |
| 2-1863 | (b-67) | (b-35) | H | H | (a-14) | —CH— | —NH— | —CH(Me)— |
| 2-1864 | (b-68) | (b-35) | H | H | (a-14) | —CH— | —NH— | —CH(Me)— |
| 2-1865 | (b-69) | (b-35) | H | H | (a-14) | —CH— | —NH— | —CH(Me)— |
| 2-1866 | (b-70) | (b-35) | H | H | (a-14) | —CH— | —NH— | —CH(Me)— |
| 2-1867 | (b-71) | (b-35) | H | H | (a-14) | —CH— | —NH— | —CH(Me)— |
| 2-1868 | (b-72) | (b-7) | H | H | (a-14) | —CH— | —NH— | —CH(Me)— |
| 2-1869 | (b-72) | (b-7) | H | H | (a-14) | —CH— | —NH— | —COCH(Me)— |
| 2-1870 | (b-72) | (b-12) | H | H | (a-14) | —CH— | —NH— | —CH(Me)— |
| 2-1871 | (b-72) | (b-15) | H | H | (a-14) | —CH— | —NH— | —CH(Me)— |
| 2-1872 | (b-72) | (b-34) | H | H | (a-14) | —CH— | —NH— | —CH(Me)— |
| 2-1873 | (b-72) | (b-35) | H | H | (a-14) | —CH— | —NH— | —CH(Me)— |
| 2-1874 | (b-72) | (b-35) | H | H | (a-14) | —CH— | —NH— | —COCH(Me)— |
| 2-1875 | (b-72) | (b-37) | H | H | (a-14) | —CH— | —NH— | —CH(Me)— |

TABLE 2-continued

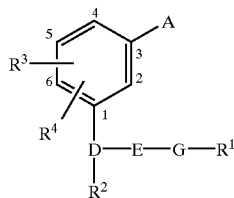

(I-2)

| Cpd. No. | R$^1$ Sub. No | R$^2$ Sub. No | R$^3$ | R$^4$ | A Sub. No | D | E | G |
|---|---|---|---|---|---|---|---|---|
| 2-1876 | (b-72) | (b-73) | H | H | (a-14) | —CH— | —NH— | —CH(Me)— |
| 2-1877 | (b-72) | (b-77) | H | H | (a-14) | —CH— | —NH— | —CH(Me)— |
| 2-1878 | (b-73) | (b-7) | H | H | (a-14) | —CH— | —NH— | —CH(Me)— |
| 2-1879 | (b-73) | (b-7) | H | H | (a-14) | —CH— | —NH— | —COCH(Me)— |
| 2-1880 | (b-73) | (b-7) | H | H | (a-14) | —CH— | —O— | —CH(Me)— |
| 2-1881 | (b-73) | (b-7) | H | H | (a-14) | —CH— | —S— | —CH(Me)— |
| 2-1882 | (b-73) | (b-11) | H | H | (a-14) | —CH— | —NH— | —CH(Me)— |
| 2-1883 | (b-73) | (b-12) | H | H | (a-14) | —CH— | —NH— | —CH(Me)— |
| 2-1884 | (b-73) | (b-12) | H | H | (a-14) | —CH— | —NH— | —COCH(Me)— |
| 2-1885 | (b-73) | (b-12) | H | H | (a-14) | —CH— | —O— | —CH(Me)— |
| 2-1886 | (b-73) | (b-12) | H | H | (a-14) | —CH— | —S— | —CH(Me)— |
| 2-1887 | (b-73) | (b-14) | H | H | (a-14) | —CH— | —NH— | —CH(Me)— |
| 2-1888 | (b-73) | (b-15) | H | H | (a-14) | —CH— | —NH— | —CH(Me)— |
| 2-1889 | (b-73) | (b-15) | H | H | (a-14) | —CH— | —NH— | —COCH(Me)— |
| 2-1890 | (b-73) | (b-15) | H | H | (a-14) | —CH— | —O— | —CH(Me)— |
| 2-1891 | (b-73) | (b-15) | H | H | (a-14) | —CH— | —S— | —CH(Me)— |
| 2-1892 | (b-73) | (b-17) | H | H | (a-14) | —CH— | —NH— | —CH(Me)— |
| 2-1893 | (b-73) | (b-25) | H | H | (a-14) | —CH— | —NH— | —CH(Me)— |
| 2-1894 | (b-73) | (b-33) | H | H | (a-14) | —CH— | —NH— | —CH(Me)— |
| 2-1895 | (b-73) | (b-34) | H | H | (a-14) | —CH— | —NH— | —CH(Me)— |
| 2-1896 | (b-73) | (b-34) | H | H | (a-14) | —CH— | —NH— | —COCH(Me)— |
| 2-1897 | (b-73) | (b-34) | H | H | (a-14) | —CH— | —O— | —CH(Me)— |
| 2-1898 | (b-73) | (b-34) | H | H | (a-14) | —CH— | —S— | —CH(Me)— |
| 2-1899 | (b-73) | (b-35) | H | H | (a-14) | —CH— | —NH— | —CH(Me)— |
| 2-1900 | (b-73) | (b-35) | H | H | (a-14) | —CH— | —NH— | —COCH(Me)— |
| 2-1901 | (b-73) | (b-35) | H | H | (a-14) | —CH— | —O— | —CH(Me)— |
| 2-1902 | (b-73) | (b-35) | H | H | (a-14) | —CH— | —S— | —CH(Me)— |
| 2-1903 | (b-73) | (b-37) | H | H | (a-14) | —CH— | —NH— | —CH(Me)— |
| 2-1904 | (b-73) | (b-37) | H | H | (a-14) | —CH— | —NH— | —COCH(Me)— |
| 2-1905 | (b-73) | (b-37) | H | H | (a-14) | —CH— | —O— | —CH(Me)— |
| 2-1906 | (b-73) | (b-37) | H | H | (a-14) | —CH— | —S— | —CH(Me)— |
| 2-1907 | (b-73) | (b-42) | H | H | (a-14) | —CH— | —NH— | —CH(Me)— |
| 2-1908 | (b-73) | (b-72) | H | H | (a-14) | —CH— | —NH— | —CH(Me)— |
| 2-1909 | (b-73) | (b-73) | H | H | (a-14) | —CH— | —NH— | —CH(Me)— |
| 2-1910 | (b-73) | (b-73) | H | H | (a-14) | —CH— | —NH— | —COCH(Me)— |
| 2-1911 | (b-73) | (b-73) | H | H | (a-14) | —CH— | —O— | —CH(Me)— |
| 2-1912 | (b-73) | (b-73) | H | H | (a-14) | —CH— | —S— | —CH(Me)— |
| 2-1913 | (b-73) | (b-74) | H | H | (a-14) | —CH— | —NH— | —CH(Me)— |
| 2-1914 | (b-73) | (b-76) | H | H | (a-14) | —CH— | —NH— | —CH(Me)— |
| 2-1915 | (b-73) | (b-77) | H | H | (a-14) | —CH— | —NH— | —CH(Me)— |
| 2-1916 | (b-73) | (b-77) | H | H | (a-14) | —CH— | —NH— | —COCH(Me)— |
| 2-1917 | (b-73) | (b-77) | H | H | (a-14) | —CH— | —O— | —CH(Me)— |
| 2-1918 | (b-73) | (b-77) | H | H | (a-14) | —CH— | —S— | —CH(Me)— |
| 2-1919 | (b-74) | (b-7) | H | H | (a-14) | —CH— | —NH— | —CH(Me)— |
| 2-1920 | (b-74) | (b-7) | H | H | (a-14) | —CH— | —NH— | —COCH(Me)— |
| 2-1921 | (b-74) | (b-12) | H | H | (a-14) | —CH— | —NH— | —CH(Me)— |
| 2-1922 | (b-74) | (b-15) | H | H | (a-14) | —CH— | —NH— | —CH(Me)— |
| 2-1923 | (b-74) | (b-34) | H | H | (a-14) | —CH— | —NH— | —CH(Me)— |
| 2-1924 | (b-74) | (b-35) | H | H | (a-14) | —CH— | —NH— | —CH(Me)— |
| 2-1925 | (b-74) | (b-35) | H | H | (a-14) | —CH— | —NH— | —COCH(Me)— |
| 2-1926 | (b-74) | (b-37) | H | H | (a-14) | —CH— | —NH— | —CH(Me)— |
| 2-1927 | (b-74) | (b-73) | H | H | (a-14) | —CH— | —NH— | —CH(Me)— |
| 2-1928 | (b-74) | (b-77) | H | H | (a-14) | —CH— | —NH— | —CH(Me)— |
| 2-1929 | (b-75) | (b-7) | H | H | (a-14) | —CH— | —NH— | —CH(Me)— |
| 2-1930 | (b-75) | (b-35) | H | H | (a-14) | —CH— | —NH— | —CH(Me)— |
| 2-1931 | (b-76) | (b-7) | H | H | (a-14) | —CH— | —NH— | —CH(Me)— |
| 2-1932 | (b-76) | (b-7) | H | H | (a-14) | —CH— | —NH— | —COCH(Me)— |
| 2-1933 | (b-76) | (b-12) | H | H | (a-14) | —CH— | —NH— | —CH(Me)— |
| 2-1934 | (b-76) | (b-15) | H | H | (a-14) | —CH— | —NH— | —CH(Me)— |
| 2-1935 | (b-76) | (b-34) | H | H | (a-14) | —CH— | —NH— | —CH(Me)— |
| 2-1936 | (b-76) | (b-35) | H | H | (a-14) | —CH— | —NH— | —CH(Me)— |
| 2-1937 | (b-76) | (b-35) | H | H | (a-14) | —CH— | —NH— | —COCH(Me)— |
| 2-1938 | (b-76) | (b-37) | H | H | (a-14) | —CH— | —NH— | —CH(Me)— |
| 2-1939 | (b-76) | (b-73) | H | H | (a-14) | —CH— | —NH— | —CH(Me)— |

TABLE 2-continued

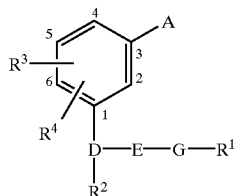

(I-2)

| Cpd. No. | R¹ Sub. No | R² Sub. No | R³ | R⁴ | A Sub. No | D | E | G |
|---|---|---|---|---|---|---|---|---|
| 2-1940 | (b-76) | (b-77) | H | H | (a-14) | —CH— | —NH— | —CH(Me)— |
| 2-1941 | (b-77) | (b-7) | H | H | (a-14) | —CH— | —NH— | —CH(Me)— |
| 2-1942 | (b-77) | (b-7) | H | H | (a-14) | —CH— | —NH— | —COCH(Me)— |
| 2-1943 | (b-77) | (b-7) | H | H | (a-14) | —CH— | —O— | —CH(Me)— |
| 2-1944 | (b-77) | (b-7) | H | H | (a-14) | —CH— | —S— | —CH(Me)— |
| 2-1945 | (b-77) | (b-11) | H | H | (a-14) | —CH— | —NH— | —CH(Me)— |
| 2-1946 | (b-77) | (b-12) | H | H | (a-14) | —CH— | —NH— | —CH(Me)— |
| 2-1947 | (b-77) | (b-12) | H | H | (a-14) | —CH— | —NH— | —COCH(Me)— |
| 2-1948 | (b-77) | (b-12) | H | H | (a-14) | —CH— | —O— | —CH(Me)— |
| 2-1949 | (b-77) | (b-12) | H | H | (a-14) | —CH— | —S— | —CH(Me)— |
| 2-1950 | (b-77) | (b-14) | H | H | (a-14) | —CH— | —NH— | —CH(Me)— |
| 2-1951 | (b-77) | (b-15) | H | H | (a-14) | —CH— | —NH— | —CH(Me)— |
| 2-1952 | (b-77) | (b-15) | H | H | (a-14) | —CH— | —NH— | —COCH(Me)— |
| 2-1953 | (b-77) | (b-15) | H | H | (a-14) | —CH— | —O— | —CH(Me)— |
| 2-1954 | (b-77) | (b-15) | H | H | (a-14) | —CH— | —S— | —CH(Me)— |
| 2-1955 | (b-77) | (b-17) | H | H | (a-14) | —CH— | —NH— | —CH(Me)— |
| 2-1956 | (b-77) | (b-25) | H | H | (a-14) | —CH— | —NH— | —CH(Me)— |
| 2-1957 | (b-77) | (b-33) | H | H | (a-14) | —CH— | —NH— | —CH(Me)— |
| 2-1958 | (b-77) | (b-34) | H | H | (a-14) | —CH— | —NH— | —CH(Me)— |
| 2-1959 | (b-77) | (b-34) | H | H | (a-14) | —CH— | —NH— | —COCH(Me)— |
| 2-1960 | (b-77) | (b-34) | H | H | (a-14) | —CH— | —O— | —CH(Me)— |
| 2-1961 | (b-77) | (b-34) | H | H | (a-14) | —CH— | —S— | —CH(Me)— |
| 2-1962 | (b-77) | (b-35) | H | H | (a-14) | —CH— | —NH— | —CH(Me)— |
| 2-1963 | (b-77) | (b-35) | H | H | (a-14) | —CH— | —NH— | —COCH(Me)— |
| 2-1964 | (b-77) | (b-35) | H | H | (a-14) | —CH— | —O— | —CH(Me)— |
| 2-1965 | (b-77) | (b-35) | H | H | (a-14) | —CH— | —S— | —CH(Me)— |
| 2-1966 | (b-77) | (b-37) | H | H | (a-14) | —CH— | —NH— | —CH(Me)— |
| 2-1967 | (b-77) | (b-37) | H | H | (a-14) | —CH— | —NH— | —COCH(Me)— |
| 2-1968 | (b-77) | (b-37) | H | H | (a-14) | —CH— | —O— | —CH(Me)— |
| 2-1969 | (b-77) | (b-37) | H | H | (a-14) | —CH— | —S— | —CH(Me)— |
| 2-1970 | (b-77) | (b-42) | H | H | (a-14) | —CH— | —NH— | —CH(Me)— |
| 2-1971 | (b-77) | (b-72) | H | H | (a-14) | —CH— | —NH— | —CH(Me)— |
| 2-1972 | (b-77) | (b-73) | H | H | (a-14) | —CH— | —NH— | —CH(Me)— |
| 2-1973 | (b-77) | (b-73) | H | H | (a-14) | —CH— | —NH— | —COCH(Me)— |
| 2-1974 | (b-77) | (b-73) | H | H | (a-14) | —CH— | —O— | —CH(Me)— |
| 2-1975 | (b-77) | (b-73) | H | H | (a-14) | —CH— | —S— | —CH(Me)— |
| 2-1976 | (b-77) | (b-74) | H | H | (a-14) | —CH— | —NH— | —CH(Me)— |
| 2-1977 | (b-77) | (b-76) | H | H | (a-14) | —CH— | —NH— | —CH(Me)— |
| 2-1978 | (b-77) | (b-77) | H | H | (a-14) | —CH— | —NH— | —CH(Me)— |
| 2-1979 | (b-77) | (b-77) | H | H | (a-14) | —CH— | —NH— | —COCH(Me)— |
| 2-1980 | (b-77) | (b-77) | H | H | (a-14) | —CH— | —O— | —CH(Me)— |
| 2-1981 | (b-77) | (b-77) | H | H | (a-14) | —CH— | —S— | —CH(Me)— |
| 2-1982 | (b-78) | (b-7) | H | H | (a-14) | —CH— | —NH— | —CH(Me)— |
| 2-1983 | (b-78) | (b-35) | H | H | (a-14) | —CH— | —NH— | —CH(Me)— |
| 2-1984 | (b-79) | (b-7) | H | H | (a-14) | —CH— | —NH— | —CH(Me)— |
| 2-1985 | (b-79) | (b-35) | H | H | (a-14) | —CH— | —NH— | —(CH₂)₂— |
| 2-1986 | (b-2) | (b-7) | H | H | (a-15) | —CH— | NH— | —CH(Me)— |
| 2-1987 | (b-2) | (b-35) | H | H | (a-15) | —CH— | —NH— | —CH(Me)— |
| 2-1988 | (b-7) | (b-7) | H | H | (a-15) | —CH— | —NH— | —CH(Me)— |
| 2-1989 | (b-7) | (b-7) | H | H | (a-15) | —CH— | —NH— | —COCH(Me)— |
| 2-1990 | (b-7) | (b-12) | H | H | (a-15) | —CH— | —NH— | —CH(Me)— |
| 2-1991 | (b-7) | (b-15) | H | H | (a-15) | —CH— | —NH— | —CH(Me)— |
| 2-1992 | (b-7) | (b-34) | H | H | (a-15) | —CH— | —NH— | —CH(Me)— |
| 2-1993 | (b-7) | (b-35) | H | H | (a-15) | —CH— | —NH— | —CH(Me)— |
| 2-1994 | (b-7) | (b-35) | H | H | (a-15) | —CH— | —NH— | —COCH(Me)— |
| 2-1995 | (b-7) | (b-37) | H | H | (a-15) | —CH— | —NH— | —CH(Me)— |
| 2-1996 | (b-7) | (b-73) | H | H | (a-15) | —CH— | —NH— | —CH(Me)— |
| 2-1997 | (b-7) | (b-77) | H | H | (a-15) | —CH— | —NH— | —CH(Me)— |
| 2-1998 | (b-8) | (b-35) | H | H | (a-15) | —CH— | —NH— | —CH(Me)— |
| 2-1999 | (b-9) | (b-35) | H | H | (a-15) | —CH— | —NH— | —CH(Me)— |
| 2-2000 | (b-10) | (b-35) | H | H | (a-15) | —CH— | —NH— | —CH(Me)— |
| 2-2001 | (b-11) | (b-7) | H | H | (a-15) | —CH— | —NH— | —CH(Me)— |
| 2-2002 | (b-11) | (b-7) | H | H | (a-15) | —CH— | —NH— | —COCH(Me)— |
| 2-2003 | (b-11) | (b-12) | H | H | (a-15) | —CH— | —NH— | —CH(Me)— |

TABLE 2-continued

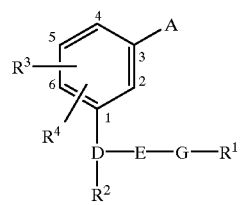

(I-2)

| Cpd. No. | R¹ Sub. No | R² Sub. No | R³ | R⁴ | A Sub. No | D | E | G |
|---|---|---|---|---|---|---|---|---|
| 2-2004 | (b-11) | (b-15) | H | H | (a-15) | —CH— | —NH— | —CH(Me)— |
| 2-2005 | (b-11) | (b-34) | H | H | (a-15) | —CH— | —NH— | —CH(Me)— |
| 2-2006 | (b-11) | (b-35) | H | H | (a-15) | —CH— | —NH— | —CH(Me)— |
| 2-2007 | (b-11) | (b-35) | H | H | (a-15) | —CH— | —NH— | —COCH(Me)— |
| 2-2008 | (b-11) | (b-37) | H | H | (a-15) | —CH— | —NH— | —CH(Me)— |
| 2-2009 | (b-11) | (b-73) | H | H | (a-15) | —CH— | —NH— | —CH(Me)— |
| 2-2010 | (b-11) | (b-77) | H | H | (a-15) | —CH— | —NH— | —CH(Me)— |
| 2-2011 | (b-12) | (b-7) | H | H | (a-15) | —CH— | —NH— | —CH(Me)— |
| 2-2012 | (b-12) | (b-7) | H | H | (a-15) | —CH— | —NH— | —COCH(Me)— |
| 2-2013 | (b-12) | (b-35) | H | H | (a-15) | —CH— | —NH— | —CH(Me)— |
| 2-2014 | (b-12) | (b-35) | H | H | (a-15) | —CH— | —NH— | —COCH(Me)— |
| 2-2015 | (b-13) | (b-35) | H | H | (a-15) | —CH— | —NH— | —CH(Me)— |
| 2-2016 | (b-14) | (b-35) | H | H | (a-15) | —CH— | —NH— | —CH(Me)— |
| 2-2017 | (b-15) | (b-7) | H | H | (a-15) | —CH— | —NH— | —CH(Me)— |
| 2-2018 | (b-15) | (b-7) | H | H | (a-15) | —CH— | —NH— | —COCH(Me)— |
| 2-2019 | (b-15) | (b-35) | H | H | (a-15) | —CH— | —NH— | —CH(Me)— |
| 2-2020 | (b-15) | (b-35) | H | H | (a-15) | —CH— | —NH— | —COCH(Me)— |
| 2-2021 | (b-17) | (b-35) | H | H | (a-15) | —CH— | —NH— | —CH(Me)— |
| 2-2022 | (b-18) | (b-7) | H | H | (a-15) | —CH— | —NH— | —CH(Me)— |
| 2-2023 | (b-18) | (b-7) | H | H | (a-15) | —CH— | —NH— | —COCH(Me)— |
| 2-2024 | (b-18) | (b-12) | H | H | (a-15) | —CH— | —NH— | —CH(Me)— |
| 2-2025 | (b-18) | (b-15) | H | H | (a-15) | —CH— | —NH— | —CH(Me)— |
| 2-2026 | (b-18) | (b-34) | H | H | (a-15) | —CH— | —NH— | —CH(Me)— |
| 2-2027 | (b-18) | (b-35) | H | H | (a-15) | —CH— | —NH— | —CH(Me)— |
| 2-2028 | (b-18) | (b-35) | H | H | (a-15) | —CH— | —NH— | —COCH(Me)— |
| 2-2029 | (b-18) | (b-37) | H | H | (a-15) | —CH— | —NH— | —CH(Me)— |
| 2-2030 | (b-18) | (b-73) | H | H | (a-15) | —CH— | —NH— | —CH(Me)— |
| 2-2031 | (b-18) | (b-77) | H | H | (a-15) | —CH— | —NH— | —CH(Me)— |
| 2-2032 | (b-19) | (b-7) | H | H | (a-15) | —CH— | —NH— | —CH(Me)— |
| 2-2033 | (b-19) | (b-7) | H | H | (a-15) | —CH— | —NH— | —COCH(Me)— |
| 2-2034 | (b-19) | (b-35) | H | H | (a-15) | —CH— | —NH— | —CH(Me)— |
| 2-2035 | (b-19) | (b-35) | H | H | (a-15) | —CH— | —NH— | —COCH(Me)— |
| 2-2036 | (b-20) | (b-7) | H | H | (a-15) | —CH— | —NH— | —CH(Me)— |
| 2-2037 | (b-20) | (b-7) | H | H | (a-15) | —CH— | —NH— | —COCH(Me)— |
| 2-2038 | (b-20) | (b-12) | H | H | (a-15) | —CH— | —NH— | —CH(Me)— |
| 2-2039 | (b-20) | (b-15) | H | H | (a-15) | —CH— | —NH— | —CH(Me)— |
| 2-2040 | (b-20) | (b-34) | H | H | (a-15) | —CH— | —NH— | —CH(Me)— |
| 2-2041 | (b-20) | (b-35) | H | H | (a-15) | —CH— | —NH— | —CH(Me)— |
| 2-2042 | (b-20) | (b-35) | H | H | (a-15) | —CH— | —NH— | —COCH(Me)— |
| 2-2043 | (b-20) | (b-37) | H | H | (a-15) | —CH— | —NH— | —CH(Me)— |
| 2-2044 | (b-20) | (b-73) | H | H | (a-15) | —CH— | —NH— | —CH(Me)— |
| 2-2045 | (b-20) | (b-77) | H | H | (a-15) | —CH— | —NH— | —CH(Me)— |
| 2-2046 | (b-21) | (b-7) | H | H | (a-15) | —CH— | —NH— | —CH(Me)— |
| 2-2047 | (b-21) | (b-7) | H | H | (a-15) | —CH— | —NH— | —COCH(Me)— |
| 2-2048 | (b-21) | (b-35) | H | H | (a-15) | —CH— | —NH— | —CH(Me)— |
| 2-2049 | (b-21) | (b-35) | H | H | (a-15) | —CH— | —NH— | —COCH(Me)— |
| 2-2050 | (b-23) | (b-35) | H | H | (a-15) | —CH— | —NH— | —CH(Me)— |
| 2-2051 | (b-24) | (b-7) | H | H | (a-15) | —CH— | —NH— | —CH(Me)— |
| 2-2052 | (b-24) | (b-7) | H | H | (a-15) | —CH— | —NH— | —COCH(Me)— |
| 2-2053 | (b-24) | (b-35) | H | H | (a-15) | —CH— | —NH— | —CH(Me)— |
| 2-2054 | (b-24) | (b-35) | H | H | (a-15) | —CH— | —NH— | —COCH(Me)— |
| 2-2055 | (b-25) | (b-7) | H | H | (a-15) | —CH— | —NH— | —CH(Me)— |
| 2-2056 | (b-25) | (b-7) | H | H | (a-15) | —CH— | —NH— | —COCH(Me)— |
| 2-2057 | (b-25) | (b-35) | H | H | (a-15) | —CH— | —NH— | —CH(Me)— |
| 2-2058 | (b-25) | (b-35) | H | H | (a-15) | —CH— | —NH— | —COCH(Me)— |
| 2-2059 | (b-35) | (b-35) | H | H | (a-15) | —CH— | —NH— | —CH(Me)— |
| 2-2060 | (b-72) | (b-7) | H | H | (a-15) | —CH— | —NH— | —CH(Me)— |
| 2-2061 | (b-72) | (b-7) | H | H | (a-15) | —CH— | —NH— | —COCH(Me)— |
| 2-2062 | (b-72) | (b-35) | H | H | (a-15) | —CH— | —NH— | —CH(Me)— |
| 2-2063 | (b-72) | (b-35) | H | H | (a-15) | —CH— | —NH— | —COCH(Me)— |
| 2-2064 | (b-73) | (b-7) | H | H | (a-15) | —CH— | —NH— | —CH(Me)— |
| 2-2065 | (b-73) | (b-7) | H | H | (a-15) | —CH— | —NH— | —COCH(Me)— |
| 2-2066 | (b-73) | (b-12) | H | H | (a-15) | —CH— | —NH— | —CH(Me)— |
| 2-2067 | (b-73) | (b-15) | H | H | (a-15) | —CH— | —NH— | —CH(Me)— |

TABLE 2-continued (I-2)

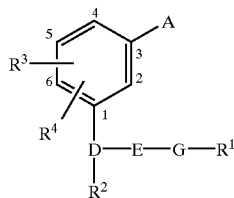

| Cpd. No. | R¹ Sub. No | R² Sub. No | R³ | R⁴ | A Sub. No | D | E | G |
|---|---|---|---|---|---|---|---|---|
| 2-2068 | (b-73) | (b-34) | H | H | (a-15) | —CH— | —NH— | —CH(Me)— |
| 2-2069 | (b-73) | (b-35) | H | H | (a-15) | —CH— | —NH— | —CH(Me)— |
| 2-2070 | (b-73) | (b-35) | H | H | (a-15) | —CH— | —NH— | —COCH(Me)— |
| 2-2071 | (b-73) | (b-37) | H | H | (a-15) | —CH— | —NH— | —CH(Me)— |
| 2-2072 | (b-73) | (b-73) | H | H | (a-15) | —CH— | —NH— | —CH(Me)— |
| 2-2073 | (b-73) | (b-77) | H | H | (a-15) | —CH— | —NH— | —CH(Me)— |
| 2-2074 | (b-74) | (b-7) | H | H | (a-15) | —CH— | —NH— | —CH(Me)— |
| 2-2075 | (b-74) | (b-7) | H | H | (a-15) | —CH— | —NH— | —COCH(Me)— |
| 2-2076 | (b-74) | (b-35) | H | H | (a-15) | —CH— | —NH— | —CH(Me)— |
| 2-2077 | (b-74) | (b-35) | H | H | (a-15) | —CH— | —NH— | —COCH(Me)— |
| 2-2078 | (b-75) | (b-35) | H | H | (a-15) | —CH— | —NH— | —CH(Me)— |
| 2-2079 | (b-76) | (b-7) | H | H | (a-15) | —CH— | —NH— | —CH(Me)— |
| 2-2080 | (b-76) | (b-7) | H | H | (a-15) | —CH— | —NH— | —COCH(Me)— |
| 2-2081 | (b-76) | (b-35) | H | H | (a-15) | —CH— | —NH— | —CH(Me)— |
| 2-2082 | (b-76) | (b-35) | H | H | (a-15) | —CH— | —NH— | —COCH(Me)— |
| 2-2083 | (b-77) | (b-7) | H | H | (a-15) | —CH— | —NH— | —CH(Me)— |
| 2-2084 | (b-77) | (b-7) | H | H | (a-15) | —CH— | —NH— | —COCH(Me)— |
| 2-2085 | (b-77) | (b-12) | H | H | (a-15) | —CH— | —NH— | —CH(Me)— |
| 2-2086 | (b-77) | (b-15) | H | H | (a-15) | —CH— | —NH— | —CH(Me)— |
| 2-2087 | (b-77) | (b-34) | H | H | (a-15) | —CH— | —NH— | —CH(Me)— |
| 2-2088 | (b-77) | (b-35) | H | H | (a-15) | —CH— | —NH— | —CH(Me)— |
| 2-2089 | (b-77) | (b-35) | H | H | (a-15) | —CH— | —NH— | —COCH(Me)— |
| 2-2090 | (b-77) | (b-37) | H | H | (a-15) | —CH— | —NH— | —CH(Me)— |
| 2-2091 | (b-77) | (b-73) | H | H | (a-15) | —CH— | —NH— | —CH(Me)— |
| 2-2092 | (b-77) | (b-77) | H | H | (a-15) | —CH— | —NH— | —CH(Me)— |
| 2-2093 | (b-78) | (b-35) | H | H | (a-15) | —CH— | —NH— | —CH(Me)— |
| 2-2094 | (b-79) | (b-35) | H | H | (a-15) | —CH— | —NH— | —CH(Me)— |
| 2-2095 | (b-7) | (b-35) | H | H | (a-16) | —CH— | —NH— | —CH(Me)— |
| 2-2096 | (b-11) | (b-35) | H | H | (a-16) | —CH— | —NH— | —CH(Me)— |
| 2-2097 | (b-18) | (b-35) | H | H | (a-16) | —CH— | —NH— | —CH(Me)— |
| 2-2098 | (b-7) | (b-35) | H | H | (a-17) | —CH— | —NH— | —CH(Me)— |
| 2-2099 | (b-11) | (b-35) | H | H | (a-17) | —CH— | —NH— | —CH(Me)— |
| 2-2100 | (b-18) | (b-35) | H | H | (a-17) | —CH— | —NH— | —CH(Me)— |
| 2-2101 | (b-2) | (b-7) | H | H | (a-18) | —CH— | —NH— | —CH(Me)— |
| 2-2102 | (b-2) | (b-35) | H | H | (a-18) | —CH— | —NH— | —CH(Me)— |
| 2-2103 | (b-7) | (b-7) | H | H | (a-18) | —CH— | —NH— | —CH(Me)— |
| 2-2104 | (b-7) | (b-7) | H | H | (a-18) | —CH— | —NH— | —COCH(Me)— |
| 2-2105 | (b-7) | (b-12) | H | H | (a-18) | —CH— | —NH— | —CH(Me)— |
| 2-2106 | (b-7) | (b-15) | H | H | (a-18) | —CH— | —NH— | —CH(Me)— |
| 2-2107 | (b-7) | (b-34) | H | H | (a-18) | —CH— | —NH— | —CH(Me)— |
| 2-2108 | (b-7) | (b-35) | H | H | (a-18) | —CH— | —NH— | —CH(Me)— |
| 2-2109 | (b-7) | (b-35) | H | H | (a-18) | —CH— | —NH— | —COCH(Me)— |
| 2-2110 | (b-7) | (b-37) | H | H | (a-18) | —CH— | —NH— | —CH(Me)— |
| 2-2111 | (b-7) | (b-73) | H | H | (a-18) | —CH— | —NH— | —CH(Me)— |
| 2-2112 | (b-7) | (b-77) | H | H | (a-18) | —CH— | —NH— | —CH(Me)— |
| 2-2113 | (b-8) | (b-35) | H | H | (a-18) | —CH— | —NH— | —CH(Me)— |
| 2-2114 | (b-9) | (b-35) | H | H | (a-18) | —CH— | —NH— | —CH(Me)— |
| 2-2115 | (b-10) | (b-35) | H | H | (a-18) | —CH— | —NH— | —CH(Me)— |
| 2-2116 | (b-11) | (b-7) | H | H | (a-18) | —CH— | —NH— | —CH(Me)— |
| 2-2117 | (b-11) | (b-7) | H | H | (a-18) | —CH— | —NH— | —COCH(Me)— |
| 2-2118 | (b-11) | (b-12) | H | H | (a-18) | —CH— | —NH— | —CH(Me)— |
| 2-2119 | (b-11) | (b-15) | H | H | (a-18) | —CH— | —NH— | —CH(Me)— |
| 2-2120 | (b-11) | (b-34) | H | H | (a-18) | —CH— | —NH— | —CH(Me)— |
| 2-2121 | (b-11) | (b-35) | H | H | (a-18) | —CH— | —NH— | —CH(Me)— |
| 2-2122 | (b-11) | (b-35) | H | H | (a-18) | —CH— | —NH— | —COCH(Me)— |
| 2-2123 | (b-11) | (b-37) | H | H | (a-18) | —CH— | —NH— | —CH(Me)— |
| 2-2124 | (b-11) | (b-73) | H | H | (a-18) | —CH— | —NH— | —CH(Me)— |
| 2-2125 | (b-11) | (b-77) | H | H | (a-18) | —CH— | —NH— | —CH(Me)— |
| 2-2126 | (b-12) | (b-7) | H | H | (a-18) | —CH— | —NH— | —CH(Me)— |
| 2-2127 | (b-12) | (b-7) | H | H | (a-18) | —CH— | —NH— | —COCH(Me)— |
| 2-2128 | (b-12) | (b-35) | H | H | (a-18) | —CH— | —NH— | —CH(Me)— |
| 2-2129 | (b-12) | (b-35) | H | H | (a-18) | —CH— | —NH— | —COCH(Me)— |
| 2-2130 | (b-13) | (b-35) | H | H | (a-18) | —CH— | —NH— | —CH(Me)— |
| 2-2131 | (b-14) | (b-35) | H | H | (a-18) | —CH— | —NH— | —CH(Me)— |

TABLE 2-continued

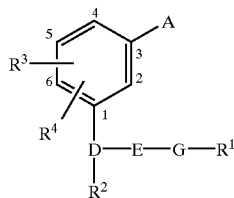

(I-2)

| Cpd. No. | R$^1$ Sub. No | R$^2$ Sub. No | R$^3$ | R$^4$ | A Sub. No | D | E | G |
|---|---|---|---|---|---|---|---|---|
| 2-2132 | (b-15) | (b-7) | H | H | (a-18) | —CH— | —NH— | —CH(Me)— |
| 2-2133 | (b-15) | (b-7) | H | H | (a-18) | —CH— | —NH— | —COCH(Me)— |
| 2-2134 | (b-15) | (b-35) | H | H | (a-18) | —CH— | —NH— | —CH(Me)— |
| 2-2135 | (b-15) | (b-35) | H | H | (a-18) | —CH— | —NH— | —COCH(Me)— |
| 2-2136 | (b-17) | (b-35) | H | H | (a-18) | —CH— | —NH— | —CH(Me)— |
| 2-2137 | (b-18) | (b-7) | H | H | (a-18) | —CH— | —NH— | —CH(Me)— |
| 2-2138 | (b-18) | (b-7) | H | H | (a-18) | —CH— | —NH— | —COCH(Me)— |
| 2-2139 | (b-18) | (b-12) | H | H | (a-18) | —CH— | —NH— | —CH(Me)— |
| 2-2140 | (b-18) | (b-15) | H | H | (a-18) | —CH— | —NH— | —CH(Me)— |
| 2-2141 | (b-18) | (b-34) | H | H | (a-18) | —CH— | —NH— | —CH(Me)— |
| 2-2142 | (b-18) | (b-35) | H | H | (a-18) | —CH— | —NH— | —CH(Me)— |
| 2-2143 | (b-18) | (b-35) | H | H | (a-18) | —CH— | —NH— | —COCH(Me)— |
| 2-2144 | (b-18) | (b-37) | H | H | (a-18) | —CH— | —NH— | —CH(Me)— |
| 2-2145 | (b-18) | (b-73) | H | H | (a-18) | —CH— | —NH— | —CH(Me)— |
| 2-2146 | (b-18) | (b-77) | H | H | (a-18) | —CH— | —NH— | —CH(Me)— |
| 2-2147 | (b-19) | (b-7) | H | H | (a-18) | —CH— | —NH— | —CH(Me)— |
| 2-2148 | (b-19) | (b-7) | H | H | (a-18) | —CH— | —NH— | —COCH(Me)— |
| 2-2149 | (b-19) | (b-35) | H | H | (a-18) | —CH— | —NH— | —CH(Me)— |
| 2-2150 | (b-19) | (b-35) | H | H | (a-18) | —CH— | —NH— | —COCH(Me)— |
| 2-2151 | (b-20) | (b-7) | H | H | (a-18) | —CH— | —NH— | —CH(Me)— |
| 2-2152 | (b-20) | (b-7) | H | H | (a-18) | —CH— | —NH— | —COCH(Me)— |
| 2-2153 | (b-20) | (b-12) | H | H | (a-18) | —CH— | —NH— | —CH(Me)— |
| 2-2154 | (b-20) | (b-15) | H | H | (a-18) | —CH— | —NH— | —CH(Me)— |
| 2-2155 | (b-20) | (b-34) | H | H | (a-18) | —CH— | —NH— | —CH(Me)— |
| 2-2156 | (b-20) | (b-35) | H | H | (a-18) | —CH— | —NH— | —CH(Me)— |
| 2-2157 | (b-20) | (b-35) | H | H | (a-18) | —CH— | —NH— | —COCH(Me)— |
| 2-2158 | (b-20) | (b-37) | H | H | (a-18) | —CH— | —NH— | —CH(Me)— |
| 2-2159 | (b-20) | (b-73) | H | H | (a-18) | —CH— | —NH— | —CH(Me)— |
| 2-2160 | (b-20) | (b-77) | H | H | (a-18) | —CH— | —NH— | —CH(Me)— |
| 2-2161 | (b-21) | (b-7) | H | H | (a-18) | —CH— | —NH— | —CH(Me)— |
| 2-2162 | (b-21) | (b-7) | H | H | (a-18) | —CH— | —NH— | —COCH(Me)— |
| 2-2163 | (b-21) | (b-35) | H | H | (a-18) | —CH— | —NH— | —CH(Me)— |
| 2-2164 | (b-21) | (b-35) | H | H | (a-18) | —CH— | —NH— | —COCH(Me)— |
| 2-2165 | (b-23) | (b-35) | H | H | (a-18) | —CH— | —NH— | —CH(Me)— |
| 2-2166 | (b-24) | (b-7) | H | H | (a-18) | —CH— | —NH— | —CH(Me)— |
| 2-2167 | (b-24) | (b-7) | H | H | (a-18) | —CH— | —NH— | —COCH(Me)— |
| 2-2168 | (b-24) | (b-35) | H | H | (a-18) | —CH— | —NH— | —CH(Me)— |
| 2-2169 | (b-24) | (b-35) | H | H | (a-18) | —CH— | —NH— | —COCH(Me)— |
| 2-2170 | (b-25) | (b-7) | H | H | (a-18) | —CH— | —NH— | —CH(Me)— |
| 2-2171 | (b-25) | (b-7) | H | H | (a-18) | —CH— | —NH— | —COCH(Me)— |
| 2-2172 | (b-25) | (b-35) | H | H | (a-18) | —CH— | —NH— | —CH(Me)— |
| 2-2173 | (b-25) | (b-35) | H | H | (a-18) | —CH— | —NH— | —COCH(Me)— |
| 2-2174 | (b-35) | (b-35) | H | H | (a-18) | —CH— | —NH— | —CH(Me)— |
| 2-2175 | (b-72) | (b-7) | H | H | (a-18) | —CH— | —NH— | —CH(Me)— |
| 2-2176 | (b-72) | (b-7) | H | H | (a-18) | —CH— | —NH— | —COCH(Me)— |
| 2-2177 | (b-72) | (b-35) | H | H | (a-18) | —CH— | —NH— | —CH(Me)— |
| 2-2178 | (b-72) | (b-35) | H | H | (a-18) | —CH— | —NH— | —COCH(Me)— |
| 2-2179 | (b-73) | (b-7) | H | H | (a-18) | —CH— | —NH— | —CH(Me)— |
| 2-2180 | (b-73) | (b-7) | H | H | (a-18) | —CH— | —NH— | —COCH(Me)— |
| 2-2181 | (b-73) | (b-12) | H | H | (a-18) | —CH— | —NH— | —CH(Me)— |
| 2-2182 | (b-73) | (b-15) | H | H | (a-18) | —CH— | —NH— | —CH(Me)— |
| 2-2183 | (b-73) | (b-34) | H | H | (a-18) | —CH— | —NH— | —CH(Me)— |
| 2-2184 | (b-73) | (b-35) | H | H | (a-18) | —CH— | —NH— | —CH(Me)— |
| 2-2185 | (b-73) | (b-35) | H | H | (a-18) | —CH— | —NH— | —COCH(Me)— |
| 2-2186 | (b-73) | (b-37) | H | H | (a-18) | —CH— | —NH— | —CH(Me)— |
| 2-2187 | (b-73) | (b-73) | H | H | (a-18) | —CH— | —NH— | —CH(Me)— |
| 2-2188 | (b-73) | (b-77) | H | H | (a-18) | —CH— | —NH— | —CH(Me)— |
| 2-2189 | (b-74) | (b-7) | H | H | (a-18) | —CH— | —NH— | —CH(Me)— |
| 2-2190 | (b-74) | (b-7) | H | H | (a-18) | —CH— | —NH— | —COCH(Me)— |
| 2-2191 | (b-74) | (b-35) | H | H | (a-18) | —CH— | —NH— | —CH(Me)— |
| 2-2192 | (b-74) | (b-35) | H | H | (a-18) | —CH— | —NH— | —COCH(Me)— |
| 2-2193 | (b-75) | (b-35) | H | H | (a-18) | —CH— | —NH— | —CH(Me)— |
| 2-2194 | (b-76) | (b-7) | H | H | (a-18) | —CH— | —NH— | —CH(Me)— |
| 2-2195 | (b-76) | (b-7) | H | H | (a-18) | —CH— | —NH— | —COCH(Me)— |

TABLE 2-continued

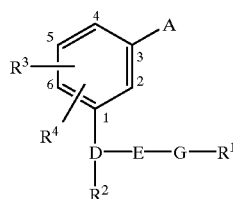

(I-2)

| Cpd. No. | R¹ Sub. No | R² Sub. No | R³ | R⁴ | A Sub. No | D | E | G |
|---|---|---|---|---|---|---|---|---|
| 2-2196 | (b-76) | (b-35) | H | H | (a-18) | —CH— | —NH— | —CH(Me)— |
| 2-2197 | (b-76) | (b-35) | H | H | (a-18) | —CH— | —NH— | —COCH(Me)— |
| 2-2198 | (b-77) | (b-7) | H | H | (a-18) | —CH— | —NH— | —CH(Me)— |
| 2-2199 | (b-77) | (b-7) | H | H | (a-18) | —CH— | —NH— | —COCH(Me)— |
| 2-2200 | (b-77) | (b-12) | H | H | (a-18) | —CH— | —NH— | —CH(Me)— |
| 2-2201 | (b-77) | (b-15) | H | H | (a-18) | —CH— | —NH— | —CH(Me)— |
| 2-2202 | (b-77) | (b-34) | H | H | (a-18) | —CH— | —NH— | —CH(Me)— |
| 2-2203 | (b-77) | (b-35) | H | H | (a-18) | —CH— | —NH— | —CH(Me)— |
| 2-2204 | (b-77) | (b-35) | H | H | (a-18) | —CH— | —NH— | —COCH(Me)— |
| 2-2205 | (b-77) | (b-37) | H | H | (a-18) | —CH— | —NH— | —CH(Me)— |
| 2-2206 | (b-77) | (b-73) | H | H | (a-18) | —CH— | —NH— | —CH(Me)— |
| 2-2207 | (b-77) | (b-77) | H | H | (a-18) | —CH— | —NH— | —CH(Me)— |
| 2-2208 | (b-78) | (b-35) | H | H | (a-18) | —CH— | —NH— | —CH(Me)— |
| 2-2209 | (b-79) | (b-35) | H | H | (a-18) | —CH— | —NH— | —CH(Me)— |
| 2-2210 | (b-2) | (b-35) | H | H | (a-19) | —CH— | —NH— | —CH(Me)— |
| 2-2211 | (b-7) | (b-7) | H | H | (a-19) | —CH— | —NH— | —CH(Me)— |
| 2-2212 | (b-7) | (b-7) | H | H | (a-19) | —CH— | —NH— | —COCH(Me)— |
| 2-2213 | (b-7) | (b-35) | H | H | (a-19) | —CH— | —NH— | —CH(Me)— |
| 2-2214 | (b-7) | (b-35) | H | H | (a-19) | —CH— | —NH— | —COCH(Me)— |
| 2-2215 | (b-8) | (b-35) | H | H | (a-19) | —CH— | —NH— | —CH(Me)— |
| 2-2216 | (b-11) | (b-7) | H | H | (a-19) | —CH— | —NH— | —CH(Me)— |
| 2-2217 | (b-11) | (b-7) | H | H | (a-19) | —CH— | —NH— | —COCH(Me)— |
| 2-2218 | (b-11) | (b-35) | H | H | (a-19) | —CH— | —NH— | —CH(Me)— |
| 2-2219 | (b-11) | (b-35) | H | H | (a-19) | —CH— | —NH— | —COCH(Me)— |
| 2-2220 | (b-12) | (b-7) | H | H | (a-19) | —CH— | —NH— | —CH(Me)— |
| 2-2221 | (b-12) | (b-35) | H | H | (a-19) | —CH— | —NH— | —CH(Me)— |
| 2-2222 | (b-15) | (b-7) | H | H | (a-19) | —CH— | —NH— | —CH(Me)— |
| 2-2223 | (b-15) | (b-35) | H | H | (a-19) | —CH— | —NH— | —CH(Me)— |
| 2-2224 | (b-18) | (b-7) | H | H | (a-19) | —CH— | —NH— | —CH(Me)— |
| 2-2225 | (b-18) | (b-7) | H | H | (a-19) | —CH— | —NH— | —COCH(Me)— |
| 2-2226 | (b-18) | (b-35) | H | H | (a-19) | —CH— | —NH— | —CH(Me)— |
| 2-2227 | (b-18) | (b-35) | H | H | (a-19) | —CH— | —NH— | —COCH(Me)— |
| 2-2228 | (b-19) | (b-7) | H | H | (a-19) | —CH— | —NH— | —CH(Me)— |
| 2-2229 | (b-19) | (b-35) | H | H | (a-19) | —CH— | —NH— | —CH(Me)— |
| 2-2230 | (b-20) | (b-7) | H | H | (a-19) | —CH— | —NH— | —CH(Me)— |
| 2-2231 | (b-20) | (b-7) | H | H | (a-19) | —CH— | —NH— | —COCH(Me)— |
| 2-2232 | (b-20) | (b-35) | H | H | (a-19) | —CH— | —NH— | —CH(Me)— |
| 2-2233 | (b-20) | (b-35) | H | H | (a-19) | —CH— | —NH— | —COCH(Me)— |
| 2-2234 | (b-21) | (b-7) | H | H | (a-19) | —CH— | —NH— | —CH(Me)— |
| 2-2235 | (b-21) | (b-35) | H | H | (a-19) | —CH— | —NH— | —CH(Me)— |
| 2-2236 | (b-24) | (b-7) | H | H | (a-19) | —CH— | —NH— | —CH(Me)— |
| 2-2237 | (b-24) | (b-35) | H | H | (a-19) | —CH— | —NH— | —CH(Me)— |
| 2-2238 | (b-25) | (b-7) | H | H | (a-19) | —CH— | —NH— | —CH(Me)— |
| 2-2239 | (b-25) | (b-35) | H | H | (a-19) | —CH— | —NH— | —CH(Me)— |
| 2-2240 | (b-72) | (b-7) | H | H | (a-19) | —CH— | —NH— | —CH(Me)— |
| 2-2241 | (b-72) | (b-35) | H | H | (a-19) | —CH— | —NH— | —CH(Me)— |
| 2-2242 | (b-73) | (b-7) | H | H | (a-19) | —CH— | —NH— | —CH(Me)— |
| 2-2243 | (b-73) | (b-7) | H | H | (a-19) | —CH— | —NH— | —COCH(Me)— |
| 2-2244 | (b-73) | (b-35) | H | H | (a-19) | —CH— | —NH— | —CH(Me)— |
| 2-2245 | (b-73) | (b-35) | H | H | (a-19) | —CH— | —NH— | —COCH(Me)— |
| 2-2246 | (b-74) | (b-7) | H | H | (a-19) | —CH— | —NH— | —CH(Me)— |
| 2-2247 | (b-74) | (b-35) | H | H | (a-19) | —CH— | —NH— | —CH(Me)— |
| 2-2248 | (b-76) | (b-7) | H | H | (a-19) | —CH— | —NH— | —CH(Me)— |
| 2-2249 | (b-76) | (b-35) | H | H | (a-19) | —CH— | —NH— | —CH(Me)— |
| 2-2250 | (b-77) | (b-7) | H | H | (a-19) | —CH— | —NH— | —CH(Me)— |
| 2-2251 | (b-77) | (b-7) | H | H | (a-19) | —CH— | —NH— | —COCH(Me)— |
| 2-2252 | (b 77) | (b-35) | H | H | (a-19) | —CH— | —NH— | —CH(Me)— |
| 2-2253 | (b 77) | (b-35) | H | H | (a-19) | —CH— | —NH— | —COCH(Me)— |
| 2-2254 | (b-2) | (b-7) | H | H | (a-20) | —CH— | —NH— | —CH(Me)— |
| 2-2255 | (b-2) | (b-35) | H | H | (a-20) | —CH— | —NH— | —CH(Me)— |
| 2-2256 | (b-7) | (b-7) | H | H | (a-20) | —CH— | —NH— | —CH(Me)— |
| 2-2257 | (b-7) | (b-7) | H | H | (a-20) | —CH— | —NH— | —COCH(Me)— |
| 2-2258 | (b-7) | (b-12) | H | H | (a-20) | —CH— | —NH— | —CH(Me)— |
| 2-2259 | (b-7) | (b-15) | H | H | (a-20) | —CH— | —NH— | —CH(Me)— |

TABLE 2-continued

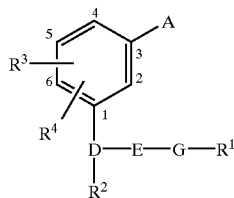

(I-2)

| Cpd. No. | R¹ Sub. No | R² Sub. No | R³ | R⁴ | A Sub. No | D | E | G |
|---|---|---|---|---|---|---|---|---|
| 2-2260 | (b-7) | (b-34) | H | H | (a-20) | —CH— | —NH— | —CH(Me)— |
| 2-2261 | (b-7) | (b-35) | H | H | (a-20) | —CH— | —NH— | —CH(Me)— |
| 2-2262 | (b-7) | (b-35) | H | H | (a-20) | —CH— | —NH— | —COCH(Me)— |
| 2-2263 | (b-7) | (b-37) | H | H | (a-20) | —CH— | —NH— | —CH(Me)— |
| 2-2264 | (b-7) | (b-73) | H | H | (a-20) | —CH— | —NH— | —CH(Me)— |
| 2-2265 | (b-7) | (b-77) | H | H | (a-20) | —CH— | —NH— | —CH(Me)— |
| 2-2266 | (b-8) | (b-35) | H | H | (a-20) | —CH— | —NH— | —CH(Me)— |
| 2-2267 | (b-9) | (b-35) | H | H | (a-20) | —CH— | —NH— | —CH(Me)— |
| 2-2268 | (b-10) | (b-35) | H | H | (a-20) | —CH— | —NH— | —CH(Me)— |
| 2-2269 | (b-11) | (b-7) | H | H | (a-20) | —CH— | —NH— | —CH(Me)— |
| 2-2270 | (b-11) | (b-7) | H | H | (a-20) | —CH— | —NH— | —COCH(Me)— |
| 2-2271 | (b-11) | (b-12) | H | H | (a-20) | —CH— | —NH— | —CH(Me)— |
| 2-2272 | (b-11) | (b-15) | H | H | (a-20) | —CH— | —NH— | —CH(Me)— |
| 2-2273 | (b-11) | (b-34) | H | H | (a-20) | —CH— | —NH— | —CH(Me)— |
| 2-2274 | (b-11) | (b-35) | H | H | (a-20) | —CH— | —NH— | —CH(Me)— |
| 2-2275 | (b-11) | (b-35) | H | H | (a-20) | —CH— | —NH— | —COCH(Me)— |
| 2-2276 | (b-11) | (b-37) | H | H | (a-20) | —CH— | —NH— | —CH(Me)— |
| 2-2277 | (b-11) | (b-73) | H | H | (a-20) | —CH— | —NH— | —CH(Me)— |
| 2-2278 | (b-11) | (b-77) | H | H | (a-20) | —CH— | —NH— | —CH(Me)— |
| 2-2279 | (b-12) | (b-7) | H | H | (a-20) | —CH— | —NH— | —CH(Me)— |
| 2-2280 | (b-12) | (b-7) | H | H | (a-20) | —CH— | —NH— | —COCH(Me)— |
| 2-2281 | (b-12) | (b-35) | H | H | (a-20) | —CH— | —NH— | —CH(Me)— |
| 2-2282 | (b-12) | (b-35) | H | H | (a-20) | —CH— | —NH— | —COCH(Me)— |
| 2-2283 | (b-13) | (b-35) | H | H | (a-20) | —CH— | —NH— | —CH(Me)— |
| 2-2284 | (b-14) | (b-35) | H | H | (a-20) | —CH— | —NH— | —CH(Me)— |
| 2-2285 | (b-15) | (b-7) | H | H | (a-20) | —CH— | —NH— | —CH(Me)— |
| 2-2286 | (b-15) | (b-7) | H | H | (a-20) | —CH— | —NH— | —COCH(Me)— |
| 2-2287 | (b-15) | (b-35) | H | H | (a-20) | —CH— | —NH— | —CH(Me)— |
| 2-2288 | (b-15) | (b-35) | H | H | (a-20) | —CH— | —NH— | —COCH(Me)— |
| 2-2289 | (b-17) | (b-35) | H | H | (a-20) | —CH— | —NH— | —CH(Me)— |
| 2-2290 | (b-18) | (b-7) | H | H | (a-20) | —CH— | —NH— | —CH(Me)— |
| 2-2291 | (b-18) | (b-7) | H | H | (a-20) | —CH— | —NH— | —COCH(Me)— |
| 2-2292 | (b-18) | (b-12) | H | H | (a-20) | —CH— | —NH— | —CH(Me)— |
| 2-2293 | (b-18) | (b-15) | H | H | (a-20) | —CH— | —NH— | —CH(Me)— |
| 2-2294 | (b-18) | (b-34) | H | H | (a-20) | —CH— | —NH— | —CH(Me)— |
| 2-2295 | (b-18) | (b-35) | H | H | (a-20) | —CH— | —NH— | —CH(Me)— |
| 2-2296 | (b-18) | (b-35) | H | H | (a-20) | —CH— | —NH— | —COCH(Me)— |
| 2-2297 | (b-18) | (b-37) | H | H | (a-20) | —CH— | —NH— | —CH(Me)— |
| 2-2298 | (b-18) | (b-73) | H | H | (a-20) | —CH— | —NH— | —CH(Me)— |
| 2-2299 | (b-18) | (b-77) | H | H | (a-20) | —CH— | —NH— | —CH(Me)— |
| 2-2300 | (b-19) | (b-7) | H | H | (a-20) | —CH— | —NH— | —CH(Me)— |
| 2-2301 | (b-19) | (b-7) | H | H | (a-20) | —CH— | —NH— | —COCH(Me)— |
| 2-2302 | (b-19) | (b-35) | H | H | (a-20) | —CH— | —NH— | —CH(Me)— |
| 2-2303 | (b-19) | (b-35) | H | H | (a-20) | —CH— | —NH— | —COCH(Me)— |
| 2-2304 | (b-20) | (b-7) | H | H | (a-20) | —CH— | —NH— | —CH(Me)— |
| 2-2305 | (b-20) | (b-7) | H | H | (a-20) | —CH— | —NH— | —COCH(Me)— |
| 2-2306 | (b-20) | (b-12) | H | H | (a-20) | —CH— | —NH— | —CH(Me)— |
| 2-2307 | (b-20) | (b-15) | H | H | (a-20) | —CH— | —NH— | —CH(Me)— |
| 2-2308 | (b-20) | (b-34) | H | H | (a-20) | —CH— | —NH— | —CH(Me)— |
| 2-2309 | (b-20) | (b-35) | H | H | (a-20) | —CH— | —NH— | —CH(Me)— |
| 2-2310 | (b-20) | (b-35) | H | H | (a-20) | —CH— | —NH— | —COCH(Me)— |
| 2-2311 | (b-20) | (b-37) | H | H | (a-20) | —CH— | —NH— | —CH(Me)— |
| 2-2312 | (b-20) | (b-73) | H | H | (a-20) | —CH— | —NH— | —CH(Me)— |
| 2-2313 | (b-20) | (b-77) | H | H | (a-20) | —CH— | —NH— | —CH(Me)— |
| 2-2314 | (b-21) | (b-7) | H | H | (a-20) | —CH— | —NH— | —CH(Me)— |
| 2-2315 | (b-21) | (b-7) | H | H | (a-20) | —CH— | —NH— | —COCH(Me)— |
| 2-2316 | (b-21) | (b-35) | H | H | (a-20) | —CH— | —NH— | —CH(Me)— |
| 2-2317 | (b-21) | (b-35) | H | H | (a-20) | —CH— | —NH— | —COCH(Me)— |
| 2-2318 | (b-23) | (b-35) | H | H | (a-20) | —CH— | —NH— | —CH(Me)— |
| 2-2319 | (b-24) | (b-7) | H | H | (a-20) | —CH— | —NH— | —CH(Me)— |
| 2-2320 | (b-24) | (b-7) | H | H | (a-20) | —CH— | —NH— | —COCH(Me)— |
| 2-2321 | (b-24) | (b-35) | H | H | (a-20) | —CH— | —NH— | —CH(Me)— |
| 2-2322 | (b-24) | (b-35) | H | H | (a-20) | —CH— | —NH— | —COCH(Me)— |
| 2-2323 | (b-25) | (b-7) | H | H | (a-20) | —CH— | —NH— | —CH(Me)— |

TABLE 2-continued

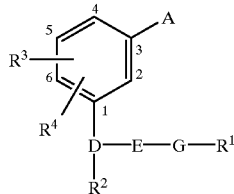

(I-2)

| Cpd. No. | R¹ Sub. No | R² Sub. No | R³ | R⁴ | A Sub. No | D | E | G |
|---|---|---|---|---|---|---|---|---|
| 2-2324 | (b-25) | (b-7) | H | H | (a-20) | —CH— | —NH— | —COCH(Me)— |
| 2-2325 | (b-25) | (b-35) | H | H | (a-20) | —CH— | —NH— | —CH(Me)— |
| 2-2326 | (b-25) | (b-35) | H | H | (a-20) | —CH— | —NH— | —COCH(Me)— |
| 2-2327 | (b-35) | (b-35) | H | H | (a-20) | —CH— | —NH— | —CH(Me)— |
| 2-2328 | (b-72) | (b-7) | H | H | (a-20) | —CH— | —NH— | —CH(Me)— |
| 2-2329 | (b-72) | (b-7) | H | H | (a-20) | —CH— | —NH— | —COCH(Me)— |
| 2-2330 | (b-72) | (b-35) | H | H | (a-20) | —CH— | —NH— | —CH(Me)— |
| 2-2331 | (b-72) | (b-35) | H | H | (a-20) | —CH— | —NH— | —COCH(Me)— |
| 2-2332 | (b-73) | (b-7) | H | H | (a-20) | —CH— | —NH— | —CH(Me)— |
| 2-2333 | (b-73) | (b-7) | H | H | (a-20) | —CH— | —NH— | —COCH(Me)— |
| 2-2334 | (b-73) | (b-12) | H | H | (a-20) | —CH— | —NH— | —CH(Me)— |
| 2-2335 | (b-73) | (b-15) | H | H | (a-20) | —CH— | —NH— | —CH(Me)— |
| 2-2336 | (b-73) | (b-34) | H | H | (a-20) | —CH— | —NH— | —CH(Me)— |
| 2-2337 | (b-73) | (b-35) | H | H | (a-20) | —CH— | —NH— | —CH(Me)— |
| 2-2338 | (b-73) | (b-35) | H | H | (a-20) | —CH— | —NH— | —COCH(Me)— |
| 2-2339 | (b-73) | (b-37) | H | H | (a-20) | —CH— | —NH— | —CH(Me)— |
| 2-2340 | (b-73) | (b-73) | H | H | (a-20) | —CH— | —NH— | —CH(Me)— |
| 2-2341 | (b-73) | (b-77) | H | H | (a-20) | —CH— | —NH— | —CH(Me)— |
| 2-2342 | (b-74) | (b-7) | H | H | (a-20) | —CH— | —NH— | —CH(Me)— |
| 2-2343 | (b-74) | (b-7) | H | H | (a-20) | —CH— | —NH— | —COCH(Me)— |
| 2-2344 | (b-74) | (b-35) | H | H | (a-20) | —CH— | —NH— | —CH(Me)— |
| 2-2345 | (b-74) | (b-35) | H | H | (a-20) | —CH— | —NH— | —COCH(Me)— |
| 2-2346 | (b-75) | (b-35) | H | H | (a-20) | —CH— | —NH— | —CH(Me)— |
| 2-2347 | (b-76) | (b-7) | H | H | (a-20) | —CH— | —NH— | —CH(Me)— |
| 2-2348 | (b-76) | (b-7) | H | H | (a-20) | —CH— | —NH— | —COCH(Me)— |
| 2-2349 | (b-76) | (b-35) | H | H | (a-20) | —CH— | —NH— | —CH(Me)— |
| 2-2350 | (b-76) | (b-35) | H | H | (a-20) | —CH— | —NH— | —COCH(Me)— |
| 2-2351 | (b-77) | (b-7) | H | H | (a-20) | —CH— | —NH— | —CH(Me)— |
| 2-2352 | (b-77) | (b-7) | H | H | (a-20) | —CH— | —NH— | —COCH(Me)— |
| 2-2353 | (b-77) | (b-12) | H | H | (a-20) | —CH— | —NH— | —CH(Me)— |
| 2-2354 | (b-77) | (b-15) | H | H | (a-20) | —CH— | —NH— | —CH(Me)— |
| 2-2355 | (b-77) | (b-34) | H | H | (a-20) | —CH— | —NH— | —CH(Me)— |
| 2-2356 | (b-77) | (b-35) | H | H | (a-20) | —CH— | —NH— | —CH(Me)— |
| 2-2357 | (b-77) | (b-35) | H | H | (a-20) | —CH— | —NH— | —COCH(Me)— |
| 2-2358 | (b-77) | (b-37) | H | H | (a-20) | —CH— | —NH— | —CH(Me)— |
| 2-2359 | (b-77) | (b-73) | H | H | (a-20) | —CH— | —NH— | —CH(Me)— |
| 2-2360 | (b-77) | (b-77) | H | H | (a-20) | —CH— | —NH— | —CH(Me)— |
| 2-2361 | (b-78) | (b-35) | H | H | (a-20) | —CH— | —NH— | —CH(Me)— |
| 2-2362 | (b-79) | (b-35) | H | H | (a-20) | —CH— | —NH— | —CH(Me)— |
| 2-2363 | (b-7) | (b-7) | H | H | (a-21) | —CH— | —NH— | —CH(Me)— |
| 2-2364 | (b-7) | (b-35) | H | H | (a-21) | —CH— | —NH— | —CH(Me)— |
| 2-2365 | (b-11) | (b-7) | H | H | (a-21) | —CH— | —NH— | —CH(Me)— |
| 2-2366 | (b-11) | (b-35) | H | H | (a-21) | —CH— | —NH— | —CH(Me)— |
| 2-2367 | (b-12) | (b-35) | H | H | (a-21) | —CH— | —NH— | —CH(Me)— |
| 2-2368 | (b-15) | (b-35) | H | H | (a-21) | —CH— | —NH— | —CH(Me)— |
| 2-2369 | (b-18) | (b-7) | H | H | (a-21) | —CH— | —NH— | —CH(Me)— |
| 2-2370 | (b-18) | (b-35) | H | H | (a-21) | —CH— | —NH— | —CH(Me)— |
| 2-2371 | (b-19) | (b-35) | H | H | (a-21) | —CH— | —NH— | —CH(Me)— |
| 2-2372 | (b-20) | (b-7) | H | H | (a-21) | —CH— | —NH— | —CH(Me)— |
| 2-2373 | (b-20) | (b-35) | H | H | (a-21) | —CH— | —NH— | —CH(Me)— |
| 2-2374 | (b-21) | (b-35) | H | H | (a-21) | —CH— | —NH— | —CH(Me)— |
| 2-2375 | (b-24) | (b-35) | H | H | (a-21) | —CH— | —NH— | —CH(Me)— |
| 2-2376 | (b-25) | (b-35) | H | H | (a-21) | —CH— | —NH— | —CH(Me)— |
| 2-2377 | (b-72) | (b-35) | H | H | (a-21) | —CH— | —NH— | —CH(Me)— |
| 2-2378 | (b-73) | (b-7) | H | H | (a-21) | —CH— | —NH— | —CH(Me)— |
| 2-2379 | (b-73) | (b-35) | H | H | (a-21) | —CH— | —NH— | —CH(Me)— |
| 2-2380 | (b-74) | (b-35) | H | H | (a-21) | —CH— | —NH— | —CH(Me)— |
| 2-2381 | (b-76) | (b-35) | H | H | (a-21) | —CH— | —NH— | —CH(Me)— |
| 2-2382 | (b-77) | (b-7) | H | H | (a-21) | —CH— | —NH— | —CH(Me)— |
| 2-2383 | (b-77) | (b-35) | H | H | (a-21) | —CH— | —NH— | —CH(Me)— |
| 2-2384 | (b-7) | (b-35) | H | H | (a-22) | —CH— | —NH— | —CH(Me)— |
| 2-2385 | (b-11) | (b-35) | H | H | (a-22) | —CH— | —NH— | —CH(Me)— |
| 2-2386 | (b-18) | (b-35) | H | H | (a-22) | —CH— | —NH— | —CH(Me)— |
| 2-2387 | (b-7) | (b-35) | H | H | (a-23) | —CH— | —NH— | —CH(Me)— |

TABLE 2-continued

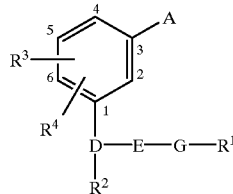

(I-2)

| Cpd. No. | R¹ Sub. No | R² Sub. No | R³ | R⁴ | A Sub. No | D | E | G |
|---|---|---|---|---|---|---|---|---|
| 2-2388 | (b-11) | (b-35) | H | H | (a-23) | —CH— | —NH— | —CH(Me)— |
| 2-2389 | (b-18) | (b-35) | H | H | (a-23) | —CH— | —NH— | —CH(Me)— |
| 2-2390 | (b-2) | (b-35) | H | H | (a-24) | —CH— | —NH— | —CH(Me)— |
| 2-2391 | (b-7) | (b-7) | H | H | (a-24) | —CH— | —NH— | —CH(Me)— |
| 2-2392 | (b-7) | (b-7) | H | H | (a-24) | —CH— | —NH— | —COCH(Me)— |
| 2-2393 | (b-7) | (b-35) | H | H | (a-24) | —CH— | —NH— | —CH(Me)— |
| 2-2394 | (b-7) | (b-35) | H | H | (a-24) | —CH— | —NH— | —COCH(Me)— |
| 2-2395 | (b-8) | (b-35) | H | H | (a-24) | —CH— | —NH— | —CH(Me)— |
| 2-2396 | (b-11) | (b-7) | H | H | (a-24) | —CH— | —NH— | —CH(Me)— |
| 2-2397 | (b-11) | (b-7) | H | H | (a-24) | —CH— | —NH— | —COCH(Me)— |
| 2-2398 | (b-11) | (b-35) | H | H | (a-24) | —CH— | —NH— | —CH(Me)— |
| 2-2399 | (b-11) | (b-35) | H | H | (a-24) | —CH— | —NH— | —COCH(Me)— |
| 2-2400 | (b-12) | (b-7) | H | H | (a-24) | —CH— | —NH— | —CH(Me)— |
| 2-2401 | (b-12) | (b-35) | H | H | (a-24) | —CH— | —NH— | —CH(Me)— |
| 2-2402 | (b-15) | (b-7) | H | H | (a-24) | —CH— | —NH— | —CH(Me)— |
| 2-2403 | (b-15) | (b-35) | H | H | (a-24) | —CH— | —NH— | —CH(Me)— |
| 2-2404 | (b-18) | (b-7) | H | H | (a-24) | —CH— | —NH— | —CH(Me)— |
| 2-2405 | (b-18) | (b-7) | H | H | (a-24) | —CH— | —NH— | —COCH(Me)— |
| 2-2406 | (b-18) | (b-35) | H | H | (a-24) | —CH— | —NH— | —CH(Me)— |
| 2-2407 | (b-18) | (b-35) | H | H | (a-24) | —CH— | —NH— | —COCH(Me)— |
| 2-2408 | (b-19) | (b-7) | H | H | (a-24) | —CH— | —NH— | —CH(Me)— |
| 2-2409 | (b-19) | (b-35) | H | H | (a-24) | —CH— | —NH— | —CH(Me)— |
| 2-2410 | (b-20) | (b-7) | H | H | (a-24) | —CH— | —NH— | —CH(Me)— |
| 2-2411 | (b-20) | (b-7) | H | H | (a-24) | —CH— | —NH— | —COCH(Me)— |
| 2-2412 | (b-20) | (b-35) | H | H | (a-24) | —CH— | —NH— | —CH(Me)— |
| 2-2413 | (b-20) | (b-35) | H | H | (a-24) | —CH— | —NH— | —COCH(Me)— |
| 2-2414 | (b-21) | (b-7) | H | H | (a-24) | —CH— | —NH— | —CH(Me)— |
| 2-2415 | (b-21) | (b-35) | H | H | (a-24) | —CH— | —NH— | —CH(Me)— |
| 2-2416 | (b-24) | (b-7) | H | H | (a-24) | —CH— | —NH— | —CH(Me)— |
| 2-2417 | (b-24) | (b-35) | H | H | (a-24) | —CH— | —NH— | —CH(Me)— |
| 2-2418 | (b-25) | (b-7) | H | H | (a-24) | —CH— | —NH— | —CH(Me)— |
| 2-2419 | (b-25) | (b-35) | H | H | (a-24) | —CH— | —NH— | —CH(Me)— |
| 2-2420 | (b-72) | (b-7) | H | H | (a-24) | —CH— | —NH— | —CH(Me)— |
| 2-2421 | (b-72) | (b-35) | H | H | (a-24) | —CH— | —NH— | —CH(Me)— |
| 2-2422 | (b-73) | (b-7) | H | H | (a-24) | —CH— | —NH— | —CH(Me)— |
| 2-2423 | (b-73) | (b-7) | H | H | (a-24) | —CH— | —NH— | —COCH(Me)— |
| 2-2424 | (b-73) | (b-35) | H | H | (a-24) | —CH— | —NH— | —CH(Me)— |
| 2-2425 | (b-73) | (b-35) | H | H | (a-24) | —CH— | —NH— | —COCH(Me)— |
| 2-2426 | (b-74) | (b-7) | H | H | (a-24) | —CH— | —NH— | —CH(Me)— |
| 2-2427 | (b-74) | (b-35) | H | H | (a-24) | —CH— | —NH— | —CH(Me)— |
| 2-2428 | (b-76) | (b-7) | H | H | (a-24) | —CH— | —NH— | —CH(Me)— |
| 2-2429 | (b-76) | (b-35) | H | H | (a-24) | —CH— | —NH— | —CH(Me)— |
| 2-2430 | (b-77) | (b-7) | H | H | (a-24) | —CH— | —NH— | —CH(Me)— |
| 2-2431 | (b-77) | (b-7) | H | H | (a-24) | —CH— | —NH— | —COCH(Me)— |
| 2-2432 | (b-77) | (b-35) | H | H | (a-24) | —CH— | —NH— | —CH(Me)— |
| 2-2433 | (b-77) | (b-35) | H | H | (a-24) | —CH— | —NH— | —COCH(Me)— |
| 2-2434 | (b-7) | (b-35) | H | H | (a-25) | —CH— | —NH— | —CH(Me)— |
| 2-2435 | (b-11) | (b-35) | H | H | (a-25) | —CH— | —NH— | —CH(Me)— |
| 2-2436 | (b-18) | (b-35) | H | H | (a-25) | —CH— | —NH— | —CH(Me)— |
| 2-2437 | (b-2) | (b-7) | H | H | (a-26) | —CH— | —NH— | —CH(Me)— |
| 2-2438 | (b-2) | (b-35) | H | H | (a-26) | —CH— | —NH— | —CH(Me)— |
| 2-2439 | (b-7) | (b-7) | H | H | (a-26) | —CH— | —NH— | —CH(Me)— |
| 2-2440 | (b-7) | (b-7) | H | H | (a-26) | —CH— | —NH— | —COCH(Me)— |
| 2-2441 | (b-7) | (b-12) | H | H | (a-26) | —CH— | —NH— | —CH(Me)— |
| 2-2442 | (b-7) | (b-15) | H | H | (a-26) | —CH— | —NH— | —CH(Me)— |
| 2-2443 | (b-7) | (b-34) | H | H | (a-26) | —CH— | —NH— | —CH(Me)— |
| 2-2444 | (b-7) | (b-35) | H | H | (a-26) | —CH— | —NH— | —CH(Me)— |
| 2-2445 | (b-7) | (b-35) | H | H | (a-26) | —CH— | —NH— | —COCH(Me)— |
| 2-2446 | (b-7) | (b-37) | H | H | (a-26) | —CH— | —NH— | —CH(Me)— |
| 2-2447 | (b-7) | (b-73) | H | H | (a-26) | —CH— | —NH— | —CH(Me)— |
| 2-2448 | (b-7) | (b-77) | H | H | (a-26) | —CH— | —NH— | —CH(Me)— |
| 2-2449 | (b-8) | (b-35) | H | H | (a-26) | —CH— | —NH— | —CH(Me)— |
| 2-2450 | (b-9) | (b-35) | H | H | (a-26) | —CH— | —NH— | —CH(Me)— |
| 2-2451 | (b-10) | (b-35) | H | H | (a-26) | —CH— | —NH— | —CH(Me)— |

TABLE 2-continued

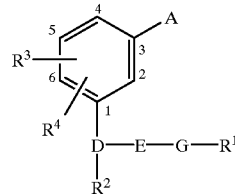

(I-2)

| Cpd. No. | R¹ Sub. No | R² Sub. No | R³ | R⁴ | A Sub. No | D | E | G |
|---|---|---|---|---|---|---|---|---|
| 2-2452 | (b-11) | (b-7) | H | H | (a-26) | —CH— | —NH— | —CH(Me)— |
| 2-2453 | (b-11) | (b-7) | H | H | (a-26) | —CH— | —NH— | —COCH(Me)— |
| 2-2454 | (b-11) | (b-12) | H | H | (a-26) | —CH— | —NH— | —CH(Me)— |
| 2-2455 | (b-11) | (b-15) | H | H | (a-26) | —CH— | —NH— | —CH(Me)— |
| 2-2456 | (b-11) | (b-34) | H | H | (a-26) | —CH— | —NH— | —CH(Me)— |
| 2-2457 | (b-11) | (b-35) | H | H | (a-26) | —CH— | —NH— | —CH(Me)— |
| 2-2458 | (b-11) | (b-35) | H | H | (a-26) | —CH— | —NH— | —COCH(Me)— |
| 2-2459 | (b-11) | (b-37) | H | H | (a-26) | —CH— | —NH— | —CH(Me)— |
| 2-2460 | (b-11) | (b-73) | H | H | (a-26) | —CH— | —NH— | —CH(Me)— |
| 2-2461 | (b-11) | (b-77) | H | H | (a-26) | —CH— | —NH— | —CH(Me)— |
| 2-2462 | (b-12) | (b-7) | H | H | (a-26) | —CH— | —NH— | —CH(Me)— |
| 2-2463 | (b-12) | (b-7) | H | H | (a-26) | —CH— | —NH— | —COCH(Me)— |
| 2-2464 | (b-12) | (b-35) | H | H | (a-26) | —CH— | —NH— | —CH(Me)— |
| 2-2465 | (b-12) | (b-35) | H | H | (a-26) | —CH— | —NH— | —COCH(Me)— |
| 2-2466 | (b-13) | (b-35) | H | H | (a-26) | —CH— | —NH— | —CH(Me)— |
| 2-2467 | (b-14) | (b-35) | H | H | (a-26) | —CH— | —NH— | —CH(Me)— |
| 2-2468 | (b-15) | (b-7) | H | H | (a-26) | —CH— | —NH— | —CH(Me)— |
| 2-2469 | (b-15) | (b-7) | H | H | (a-26) | —CH— | —NH— | —COCH(Me)— |
| 2-2470 | (b-15) | (b-35) | H | H | (a-26) | —CH— | —NH— | —CH(Me)— |
| 2-2471 | (b-15) | (b-35) | H | H | (a-26) | —CH— | —NH— | —COCH(Me)— |
| 2-2472 | (b-17) | (b-35) | H | H | (a-26) | —CH— | —NH— | —CH(Me)— |
| 2-2473 | (b-18) | (b-7) | H | H | (a-26) | —CH— | —NH— | —CH(Me)— |
| 2-2474 | (b-18) | (b-7) | H | H | (a-26) | —CH— | —NH— | —COCH(Me)— |
| 2-2475 | (b-18) | (b-12) | H | H | (a-26) | —CH— | —NH— | —CH(Me)— |
| 2-2476 | (b-18) | (b-15) | H | H | (a-26) | —CH— | —NH— | —CH(Me)— |
| 2-2477 | (b-18) | (b-34) | H | H | (a-26) | —CH— | —NH— | —CH(Me)— |
| 2-2478 | (b-18) | (b-35) | H | H | (a-26) | —CH— | —NH— | —CH(Me)— |
| 2-2479 | (b-18) | (b-35) | H | H | (a-26) | —CH— | —NH— | —COCH(Me)— |
| 2-2480 | (b-18) | (b-37) | H | H | (a-26) | —CH— | —NH— | —CH(Me)— |
| 2-2481 | (b-18) | (b-73) | H | H | (a-26) | —CH— | —NH— | —CH(Me)— |
| 2-2482 | (b-18) | (b-77) | H | H | (a-26) | —CH— | —NH— | —CH(Me)— |
| 2-2483 | (b-19) | (b-7) | H | H | (a-26) | —CH— | —NH— | —CH(Me)— |
| 2-2484 | (b-19) | (b-7) | H | H | (a-26) | —CH— | —NH— | —COCH(Me)— |
| 2-2485 | (b-19) | (b-35) | H | H | (a-26) | —CH— | —NH— | —CH(Me)— |
| 2-2486 | (b-19) | (b-35) | H | H | (a-26) | —CH— | —NH— | —COCH(Me)— |
| 2-2487 | (b-20) | (b-7) | H | H | (a-26) | —CH— | —NH— | —CH(Me)— |
| 2-2488 | (b-20) | (b-7) | H | H | (a-26) | —CH— | —NH— | —COCH(Me)— |
| 2-2489 | (b-20) | (b-12) | H | H | (a-26) | —CH— | —NH— | —CH(Me)— |
| 2-2490 | (b-20) | (b-15) | H | H | (a-26) | —CH— | —NH— | —CH(Me)— |
| 2-2491 | (b-20) | (b-34) | H | H | (a-26) | —CH— | —NH— | —CH(Me)— |
| 2-2492 | (b-20) | (b-35) | H | H | (a-26) | —CH— | —NH— | —CH(Me)— |
| 2-2493 | (b-20) | (b-35) | H | H | (a-26) | —CH— | —NH— | —COCH(Me)— |
| 2-2494 | (b-20) | (b-37) | H | H | (a-26) | —CH— | —NH— | —CH(Me)— |
| 2-2495 | (b-20) | (b-73) | H | H | (a-26) | —CH— | —NH— | —CH(Me)— |
| 2-2496 | (b-20) | (b-77) | H | H | (a-26) | —CH— | —NH— | —CH(Me)— |
| 2-2497 | (b-21) | (b-7) | H | H | (a-26) | —CH— | —NH— | —CH(Me)— |
| 2-2498 | (b-21) | (b-7) | H | H | (a-26) | —CH— | —NH— | —COCH(Me)— |
| 2-2499 | (b-21) | (b-35) | H | H | (a-26) | —CH— | —NH— | —CH(Me)— |
| 2-2500 | (b-21) | (b-35) | H | H | (a-26) | —CH— | —NH— | —COCH(Me)— |
| 2-2501 | (b-23) | (b-35) | H | H | (a-26) | —CH— | —NH— | —CH(Me)— |
| 2-2502 | (b-24) | (b-7) | H | H | (a-26) | —CH— | —NH— | —CH(Me)— |
| 2-2503 | (b-24) | (b-7) | H | H | (a-26) | —CH— | —NH— | —COCH(Me)— |
| 2-2504 | (b-24) | (b-35) | H | H | (a-26) | —CH— | —NH— | —CH(Me)— |
| 2-2505 | (b-24) | (b-35) | H | H | (a-26) | —CH— | —NH— | —COCH(Me)— |
| 2-2506 | (b-25) | (b-7) | H | H | (a-26) | —CH— | —NH— | —CH(Me)— |
| 2-2507 | (b-25) | (b-7) | H | H | (a-26) | —CH— | —NH— | —COCH(Me)— |
| 2-2508 | (b-25) | (b-35) | H | H | (a-26) | —CH— | —NH— | —CH(Me)— |
| 2-2509 | (b-25) | (b-35) | H | H | (a-26) | —CH— | —NH— | —COCH(Me)— |
| 2-2510 | (b-35) | (b-35) | H | H | (a-26) | —CH— | —NH— | —CH(Me)— |
| 2-2511 | (b-72) | (b-7) | H | H | (a-26) | —CH— | —NH— | —CH(Me)— |
| 2-2512 | (b-72) | (b-7) | H | H | (a-26) | —CH— | —NH— | —COCH(Me)— |
| 2-2513 | (b-72) | (b-35) | H | H | (a-26) | —CH— | —NH— | —CH(Me)— |
| 2-2514 | (b-72) | (b-35) | H | H | (a-26) | —CH— | —NH— | —COCH(Me)— |
| 2-2515 | (b-73) | (b-7) | H | H | (a-26) | —CH— | —NH— | —CH(Me)— |

TABLE 2-continued

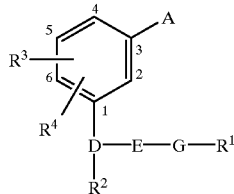

(I-2)

| Cpd. No. | R¹ Sub. No | R² Sub. No | R³ | R⁴ | A Sub. No | D | E | G |
|---|---|---|---|---|---|---|---|---|
| 2-2516 | (b-73) | (b-7) | H | H | (a-26) | —CH— | —NH— | —COCH(Me)— |
| 2-2517 | (b-73) | (b-12) | H | H | (a-26) | —CH— | —NH— | —CH(Me)— |
| 2-2518 | (b-73) | (b-15) | H | H | (a-26) | —CH— | —NH— | —CH(Me)— |
| 2-2519 | (b-73) | (b-34) | H | H | (a-26) | —CH— | —NH— | —CH(Me)— |
| 2-2520 | (b-73) | (b-35) | H | H | (a-26) | —CH— | —NH— | —CH(Me)— |
| 2-2521 | (b-73) | (b-35) | H | H | (a-26) | —CH— | —NH— | —COCH(Me)— |
| 2-2522 | (b-73) | (b-37) | H | H | (a-26) | —CH— | —NH— | —CH(Me)— |
| 2-2523 | (b-73) | (b-73) | H | H | (a-26) | —CH— | —NH— | —CH(Me)— |
| 2-2524 | (b-73) | (b-77) | H | H | (a-26) | —CH— | —NH— | —CH(Me)— |
| 2-2525 | (b-74) | (b-7) | H | H | (a-26) | —CH— | —NH— | —CH(Me)— |
| 2-2526 | (b-74) | (b-7) | H | H | (a-26) | —CH— | —NH— | —COCH(Me)— |
| 2-2527 | (b-74) | (b-35) | H | H | (a-26) | —CH— | —NH— | —CH(Me)— |
| 2-2528 | (b-74) | (b-35) | H | H | (a-26) | —CH— | —NH— | —COCH(Me)— |
| 2-2529 | (b-75) | (b-35) | H | H | (a-26) | —CH— | —NH— | —CH(Me)— |
| 2-2530 | (b-76) | (b-7) | H | H | (a-26) | —CH— | —NH— | —CH(Me)— |
| 2-2531 | (b 76) | (b-7) | H | H | (a-26) | —CH— | —NH— | —COCH(Me)— |
| 2-2532 | (b-76) | (b-35) | H | H | (a-26) | —CH— | —NH— | —CH(Me)— |
| 2-2533 | (b-76) | (b-35) | H | H | (a-26) | —CH— | —NH— | —COCH(Me)— |
| 2-2534 | (b-77) | (b-7) | H | H | (a-26) | —CH— | —NH— | —CH(Me)— |
| 2-2535 | (b-77) | (b-7) | H | H | (a-26) | —CH— | —NH— | —COCH(Me)— |
| 2-2536 | (b-77) | (b-12) | H | H | (a-26) | —CH— | —NH— | —CH(Me)— |
| 2-2537 | (b-77) | (b-15) | H | H | (a-26) | —CH— | —NH— | —CH(Me)— |
| 2-2538 | (b-77) | (b-34) | H | H | (a-26) | —CH— | —NH— | —CH(Me)— |
| 2-2539 | (b-77) | (b-35) | H | H | (a-26) | —CH— | —NH— | —CH(Me)— |
| 2-2540 | (b-77) | (b-35) | H | H | (a-26) | —CH— | —NH— | —COCH(Me)— |
| 2-2541 | (b-77) | (b-37) | H | H | (a-26) | —CH— | —NH— | —CH(Me)— |
| 2-2542 | (b-77) | (b-73) | H | H | (a-26) | —CH— | —NH— | —CH(Me)— |
| 2-2543 | (b-77) | (b-77) | H | H | (a-26) | —CH— | —NH— | —CH(Me)— |
| 2-2544 | (b-78) | (b-35) | H | H | (a-26) | —CH— | —NH— | —CH(Me)— |
| 2-2545 | (b-79) | (b-35) | H | H | (a-26) | —CH— | —NH— | —CH(Me)— |
| 2-2546 | (b-7) | (b-7) | H | H | (a-27) | —CH— | —NH— | —CH(Me)— |
| 2-2547 | (b-7) | (b-35) | H | H | (a-27) | —CH— | —NH— | —CH(Me)— |
| 2-2548 | (b-11) | (b-7) | H | H | (a-27) | —CH— | —NH— | —CH(Me)— |
| 2-2549 | (b-11) | (b-35) | H | H | (a-27) | —CH— | —NH— | —CH(Me)— |
| 2-2550 | (b-12) | (b-35) | H | H | (a-27) | —CH— | —NH— | —CH(Me)— |
| 2-2551 | (b-15) | (b-35) | H | H | (a-27) | —CH— | —NH— | —CH(Me)— |
| 2-2552 | (b-18) | (b-7) | H | H | (a-27) | —CH— | —NH— | —CH(Me)— |
| 2-2553 | (b-18) | (b-35) | H | H | (a-27) | —CH— | —NH— | —CH(Me)— |
| 2-2554 | (b-19) | (b-35) | H | H | (a-27) | —CH— | —NH— | —CH(Me)— |
| 2-2555 | (b-20) | (b-7) | H | H | (a-27) | —CH— | —NH— | —CH(Me)— |
| 2-2556 | (b-20) | (b-35) | H | H | (a-27) | —CH— | —NH— | —CH(Me)— |
| 2-2557 | (b-21) | (b-35) | H | H | (a-27) | —CH— | —NH— | —CH(Me)— |
| 2-2558 | (b-24) | (b-35) | H | H | (a-27) | —CH— | —NH— | —CH(Me)— |
| 2-2559 | (b-25) | (b-35) | H | H | (a-27) | —CH— | —NH— | —CH(Me)— |
| 2-2560 | (b-72) | (b-35) | H | H | (a-27) | —CH— | —NH— | —CH(Me)— |
| 2-2561 | (b-73) | (b-7) | H | H | (a-27) | —CH— | —NH— | —CH(Me)— |
| 2-2562 | (b-73) | (b-35) | H | H | (a-27) | —CH— | —NH— | —CH(Me)— |
| 2-2563 | (b-74) | (b-35) | H | H | (a-27) | —CH— | —NH— | —CH(Me)— |
| 2-2564 | (b-76) | (b-35) | H | H | (a-27) | —CH— | —NH— | —CH(Me)— |
| 2-2565 | (b-77) | (b-7) | H | H | (a-27) | —CH— | —NH— | —CH(Me)— |
| 2-2566 | (b-77) | (b-35) | H | H | (a-27) | —CH— | —NH— | —CH(Me)— |
| 2-2567 | (b-2) | (b-35) | H | H | (a-28) | —CH— | —NH— | —CH(Me)— |
| 2-2568 | (b-7) | (b-7) | H | H | (a-28) | —CH— | —NH— | —CH(Me)— |
| 2-2569 | (b-7) | (b-7) | H | H | (a-28) | —CH— | —NH— | —COCH(Me)— |
| 2-2570 | (b-7) | (b-35) | H | H | (a-28) | —CH— | —NH— | —CH(Me)— |
| 2-2571 | (b-7) | (b-35) | H | H | (a-28) | —CH— | —NH— | —COCH(Me)— |
| 2-2572 | (b-8) | (b-35) | H | H | (a-28) | —CH— | —NH— | —CH(Me)— |
| 2-2573 | (b-11) | (b-7) | H | H | (a-28) | —CH— | —NH— | —CH(Me)— |
| 2-2574 | (b-11) | (b-7) | H | H | (a-28) | —CH— | —NH— | —COCH(Me)— |
| 2-2575 | (b-11) | (b-35) | H | H | (a-28) | —CH— | —NH— | —CH(Me)— |
| 2-2576 | (b-11) | (b-35) | H | H | (a-28) | —CH— | —NH— | —COCH(Me)— |
| 2-2577 | (b-12) | (b-7) | H | H | (a-28) | —CH— | —NH— | —CH(Me)— |
| 2-2578 | (b-12) | (b-35) | H | H | (a-28) | —CH— | —NH— | —CH(Me)— |
| 2-2579 | (b-15) | (b-7) | H | H | (a-28) | —CH— | —NH— | —CH(Me)— |

TABLE 2-continued

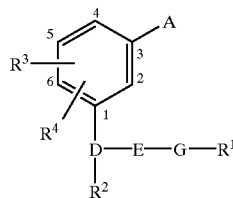

(I-2)

| Cpd. No. | R¹ Sub. No | R² Sub. No | R³ | R⁴ | A Sub. No | D | E | G |
|---|---|---|---|---|---|---|---|---|
| 2-2580 | (b-15) | (b-35) | H | H | (a-28) | —CH— | —NH— | —CH(Me)— |
| 2-2581 | (b-18) | (b-7) | H | H | (a-28) | —CH— | —NH— | —CH(Me)— |
| 2-2582 | (b-18) | (b-7) | H | H | (a-28) | —CH— | —NH— | —COCH(Me)— |
| 2-2583 | (b-18) | (b-35) | H | H | (a-28) | —CH— | —NH— | —CH(Me)— |
| 2-2584 | (b-l8) | (b-35) | H | H | (a-28) | —CH— | —NH— | —COCH(Me)— |
| 2-2585 | (b-19) | (b-7) | H | H | (a-28) | —CH— | —NH— | —CH(Me)— |
| 2-2586 | (b-19) | (b-35) | H | H | (a-28) | —CH— | —NH— | —CH(Me)— |
| 2-2587 | (b-20) | (b-7) | H | H | (a-28) | —CH— | —NH— | —CH(Me)— |
| 2-2588 | (b-20) | (b-7) | H | H | (a-28) | —CH— | —NH— | —COCH(Me)— |
| 2-2589 | (b-20) | (b-35) | H | H | (a-28) | —CH— | —NH— | —CH(Me)— |
| 2-2590 | (b-20) | (b-35) | H | H | (a-28) | —CH— | —NH— | —COCH(Me)— |
| 2-2591 | (b-21) | (b-7) | H | H | (a-28) | —CH— | —NH— | —CH(Me)— |
| 2-2592 | (b-21) | (b-35) | H | H | (a-28) | —CH— | —NH— | —CH(Me)— |
| 2-2593 | (b-24) | (b-7) | H | H | (a-28) | —CH— | —NH— | —CH(Me)— |
| 2-2594 | (b-24) | (b-35) | H | H | (a-28) | —CH— | —NH— | —CH(Me)— |
| 2-2595 | (b-25) | (b-7) | H | H | (a-28) | —CH— | —NH— | —CH(Me)— |
| 2-2596 | (b-25) | (b-35) | H | H | (a-28) | —CH— | —NH— | —CH(Me)— |
| 2-2597 | (b-72) | (b-7) | H | H | (a-28) | —CH— | —NH— | —CH(Me)— |
| 2-2598 | (b-72) | (b-35) | H | H | (a-28) | —CH— | —NH— | —CH(Me)— |
| 2-2599 | (b-73) | (b-7) | H | H | (a-28) | —CH— | —NH— | —CH(Me)— |
| 2-2600 | (b-73) | (b-7) | H | H | (a-28) | —CH— | —NH— | —COCH(Me)— |
| 2-2601 | (b-73) | (b-35) | H | H | (a-28) | —CH— | —NH— | —CH(Me)— |
| 2-2602 | (b-73) | (b-35) | H | H | (a-28) | —CH— | —NH— | —COCH(Me)— |
| 2-2603 | (b-74) | (b-7) | H | H | (a-28) | —CH— | —NH— | —CH(Me)— |
| 2-2604 | (b-74) | (b-35) | H | H | (a-28) | —CH— | —NH— | —CH(Me)— |
| 2-2605 | (b-76) | (b-7) | H | H | (a-28) | —CH— | —NH— | —CH(Me)— |
| 2-2606 | (b-76) | (b-35) | H | H | (a-28) | —CH— | —NH— | —CH(Me)— |
| 2-2607 | (b-77) | (b-7) | H | H | (a-28) | —CH— | —NH— | —CH(Me)— |
| 2-2608 | (b-77) | (b-7) | H | H | (a-28) | —CH— | —NH— | —COCH(Me)— |
| 2-2609 | (b-77) | (b-35) | H | H | (a-28) | —CH— | —NH— | —CH(Me)— |
| 2-2610 | (b-77) | (b-35) | H | H | (a-28) | —CH— | —NH— | —COCH(Me)— |
| 2-2611 | (b-7) | (b-7) | H | H | (a-29) | —CH— | —NH— | —CH(Me)— |
| 2-2612 | (b-7) | (b-35) | H | H | (a-29) | —CH— | —NH— | —CH(Me)— |
| 2-2613 | (b-11) | (b-7) | H | H | (a-29) | —CH— | —NH— | —CH(Me)— |
| 2-2614 | (b-11) | (b-35) | H | H | (a-29) | —CH— | —NH— | —CH(Me)— |
| 2-2615 | (b-12) | (b-35) | H | H | (a-29) | —CH— | —NH— | —CH(Me)— |
| 2-2616 | (b-15) | (b-35) | H | H | (a-29) | —CH— | —NH— | —CH(Me)— |
| 2-2617 | (b-18) | (b-7) | H | H | (a-29) | —CH— | —NH— | —CH(Me)— |
| 2-2618 | (b-18) | (b-35) | H | H | (a-29) | —CH— | —NH— | —CH(Me)— |
| 2-2619 | (b-19) | (b-35) | H | H | (a-29) | —CH— | —NH— | —CH(Me)— |
| 2-2620 | (b-20) | (b-7) | H | H | (a-29) | —CH— | —NH— | —CH(Me)— |
| 2-2621 | (b-20) | (b-35) | H | H | (a-29) | —CH— | —NH— | —CH(Me)— |
| 2-2622 | (b-21) | (b-35) | H | H | (a-29) | —CH— | —NH— | —CH(Me)— |
| 2-2623 | (b-24) | (b-35) | H | H | (a-29) | —CH— | —NH— | —CH(Me)— |
| 2-2624 | (b-25) | (b-35) | H | H | (a-29) | —CH— | —NH— | —CH(Me)— |
| 2-2625 | (b-72) | (b-35) | H | H | (a-29) | —CH— | —NH— | —CH(Me)— |
| 2-2626 | (b-73) | (b-7) | H | H | (a-29) | —CH— | —NH— | —CH(Me)— |
| 2-2627 | (b-73) | (b-35) | H | H | (a-29) | —CH— | —NH— | —CH(Me)— |
| 2-2628 | (b-74) | (b-35) | H | H | (a-29) | —CH— | —NH— | —CH(Me)— |
| 2-2629 | (b-76) | (b-35) | H | H | (a-29) | —CH— | —NH— | —CH(Me)— |
| 2-2630 | (b-77) | (b-7) | H | H | (a-29) | —CH— | —NH— | —CH(Me)— |
| 2-2631 | (b-77) | (b-35) | H | H | (a-29) | —CH— | —NH— | —CH(Me)— |
| 2-2632 | (b-7) | (b-35) | H | H | (a-30) | —CH— | —NH— | —CH(Me)— |
| 2-2633 | (b-11) | (b-35) | H | H | (a-30) | —CH— | —NH— | —CH(Me)— |
| 2-2634 | (b-18) | (b-35) | H | H | (a-30) | —CH— | —NH— | —CH(Me)— |
| 2-2635 | (b-2) | (b-7) | H | H | (a-31) | —CH— | —NH— | —CH(Me)— |
| 2-2636 | (b-2) | (b-35) | H | H | (a-31) | —CH— | —NH— | —CH(Me)— |
| 2-2637 | (b-7) | (b-7) | H | H | (a-31) | —CH— | —NH— | —CH(Me)— |
| 2-2638 | (b-7) | (b-7) | H | H | (a-31) | —CH— | —NH— | —COCH(Me)— |
| 2-2639 | (b-7) | (b-12) | H | H | (a-31) | —CH— | —NH— | —CH(Me)— |
| 2-2640 | (b-7) | (b-15) | H | H | (a-31) | —CH— | —NH— | —CH(Me)— |
| 2-2641 | (b-7) | (b-34) | H | H | (a-31) | —CH— | —NH— | —CH(Me)— |
| 2-2642 | (b-7) | (b-35) | H | H | (a-31) | —CH— | —NH— | —CH(Me)— |
| 2-2643 | (b-7) | (b-35) | H | H | (a-31) | —CH— | —NH— | —COCH(Me)— |

TABLE 2-continued

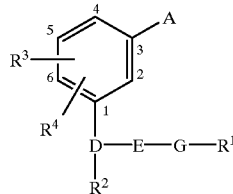

(I-2)

| Cpd. No. | R$^1$ Sub. No | R$^2$ Sub. No | R$^3$ | R$^4$ | A Sub. No | D | E | G |
|---|---|---|---|---|---|---|---|---|
| 2-2644 | (b-7) | (b-37) | H | H | (a-31) | —CH— | —NH— | —CH(Me)— |
| 2-2645 | (b-7) | (b-73) | H | H | (a-31) | —CH— | —NH— | —CH(Me)— |
| 2-2646 | (b-7) | (b-77) | H | H | (a-31) | —CH— | —NH— | —CH(Me)— |
| 2-2647 | (b-8) | (b-35) | H | H | (a-31) | —CH— | —NH— | —CH(Me)— |
| 2-2648 | (b-9) | (b-35) | H | H | (a-31) | —CH— | —NH— | —CH(Me)— |
| 2-2649 | (b-10) | (b-35) | H | H | (a-31) | —CH— | —NH— | —CH(Me)— |
| 2-2650 | (b-11) | (b-7) | H | H | (a-31) | —CH— | —NH— | —CH(Me)— |
| 2-2651 | (b-11) | (b-7) | H | H | (a-31) | —CH— | —NH— | —COCH(Me)— |
| 2-2652 | (b-11) | (b-12) | H | H | (a-31) | —CH— | —NH— | —CH(Me)— |
| 2-2653 | (b-11) | (b-15) | H | H | (a-31) | —CH— | —NH— | —CH(Me)— |
| 2-2654 | (b-11) | (b-34) | H | H | (a-31) | —CH— | —NH— | —CH(Me)— |
| 2-2655 | (b-11) | (b-35) | H | H | (a-31) | —CH— | —NH— | —CH(Me)— |
| 2-2656 | (b-11) | (b-35) | H | H | (a-31) | —CH— | —NH— | —COCH(Me)— |
| 2-2657 | (b-11) | (b-37) | H | H | (a-31) | —CH— | —NH— | —CH(Me)— |
| 2-2658 | (b-11) | (b-73) | H | H | (a-31) | —CH— | —NH— | —CH(Me)— |
| 2-2659 | (b-11) | (b-77) | H | H | (a-31) | —CH— | —NH— | —CH(Me)— |
| 2-2660 | (b-12) | (b-7) | H | H | (a-31) | —CH— | —NH— | —CH(Me)— |
| 2-2661 | (b-12) | (b-7) | H | H | (a-31) | —CH— | —NH— | —COCH(Me)— |
| 2-2662 | (b-12) | (b-35) | H | H | (a-31) | —CH— | —NH— | —CH(Me)— |
| 2-2663 | (b-12) | (b-35) | H | H | (a-31) | —CH— | —NH— | —COCH(Me)— |
| 2-2664 | (b-13) | (b-35) | H | H | (a-31) | —CH— | —NH— | —CH(Me)— |
| 2-2665 | (b-14) | (b-35) | H | H | (a-31) | —CH— | —NH— | —CH(Me)— |
| 2-2666 | (b-15) | (b-7) | H | H | (a-31) | —CH— | —NH— | —CH(Me)— |
| 2-2667 | (b-15) | (b-7) | H | H | (a-31) | —CH— | —NH— | —COCH(Me)— |
| 2-2668 | (b-15) | (b-35) | H | H | (a-31) | —CH— | —NH— | —CH(Me)— |
| 2-2669 | (b-15) | (b-35) | H | H | (a-31) | —CH— | —NH— | —COCH(Me)— |
| 2-2670 | (b-17) | (b-35) | H | H | (a-31) | —CH— | —NH— | —CH(Me)— |
| 2-2671 | (b-18) | (b-7) | H | H | (a-31) | —CH— | —NH— | —CH(Me)— |
| 2-2672 | (b-18) | (b-7) | H | H | (a-31) | —CH— | —NH— | —COCH(Me)— |
| 2-2673 | (b-18) | (b-12) | H | H | (a-31) | —CH— | —NH— | —CH(Me)— |
| 2-2674 | (b-18) | (b-15) | H | H | (a-31) | —CH— | —NH— | —CH(Me)— |
| 2-2675 | (b-18) | (b-34) | H | H | (a-31) | —CH— | —NH— | —CH(Me)— |
| 2-2676 | (b-18) | (b-35) | H | H | (a-31) | —CH— | —NH— | —CH(Me)— |
| 2-2677 | (b-18) | (b-35) | H | H | (a-31) | —CH— | —NH— | —COCH(Me)— |
| 2-2678 | (b-18) | (b-37) | H | H | (a-31) | —CH— | —NH— | —CH(Me)— |
| 2-2679 | (b-18) | (b-73) | H | H | (a-31) | —CH— | —NH— | —CH(Me)— |
| 2-2680 | (b-18) | (b-77) | H | H | (a-31) | —CH— | —NH— | —CH(Me)— |
| 2-2681 | (b-19) | (b-7) | H | H | (a-31) | —CH— | —NH— | —CH(Me)— |
| 2-2682 | (b-19) | (b-7) | H | H | (a-31) | —CH— | —NH— | —COCH(Me)— |
| 2-2683 | (b-19) | (b-35) | H | H | (a-31) | —CH— | —NH— | —CH(Me)— |
| 2-2684 | (b-19) | (b-35) | H | H | (a-31) | —CH— | —NH— | —COCH(Me)— |
| 2-2685 | (b-20) | (b-7) | H | H | (a-31) | —CH— | —NH— | —CH(Me)— |
| 2-2686 | (b-20) | (b-7) | H | H | (a-31) | —CH— | —NH— | —COCH(Me)— |
| 2-2687 | (b-20) | (b-12) | H | H | (a-31) | —CH— | —NH— | —CH(Me)— |
| 2-2688 | (b-20) | (b-15) | H | H | (a-31) | —CH— | —NH— | —CH(Me)— |
| 2-2689 | (b-20) | (b-34) | H | H | (a-31) | —CH— | —NH— | —CH(Me)— |
| 2-2690 | (b-20) | (b-35) | H | H | (a-31) | —CH— | —NH— | —CH(Me)— |
| 2-2691 | (b-20) | (b-35) | H | H | (a-31) | —CH— | —NH— | —COCH(Me)— |
| 2-2692 | (b-20) | (b-37) | H | H | (a-31) | —CH— | —NH— | —CH(Me)— |
| 2-2693 | (b-20) | (b-73) | H | H | (a-31) | —CH— | —NH— | —CH(Me)— |
| 2-2694 | (b-20) | (b-77) | H | H | (a-31) | —CH— | —NH— | —CH(Me)— |
| 2-2695 | (b-21) | (b-7) | H | H | (a-31) | —CH— | —NH— | —CH(Me)— |
| 2-2696 | (b-21) | (b-7) | H | H | (a-31) | —CH— | —NH— | —COCH(Me)— |
| 2-2697 | (b-21) | (b-35) | H | H | (a-31) | —CH— | —NH— | —CH(Me)— |
| 2-2698 | (b-21) | (b-35) | H | H | (a-31) | —CH— | —NH— | —COCH(Me)— |
| 2-2699 | (b-23) | (b-35) | H | H | (a-31) | —CH— | —NH— | —CH(Me)— |
| 2-2700 | (b-24) | (b-7) | H | H | (a-31) | —CH— | —NH— | —CH(Me)— |
| 2-2701 | (b-24) | (b-7) | H | H | (a-31) | —CH— | —NH— | —COCH(Me)— |
| 2-2702 | (b-24) | (b-35) | H | H | (a-31) | —CH— | —NH— | —CH(Me)— |
| 2-2703 | (b-24) | (b-35) | H | H | (a-31) | —CH— | —NH— | —COCH(Me)— |
| 2-2704 | (b-25) | (b-7) | H | H | (a-31) | —CH— | —NH— | —CH(Me)— |
| 2-2705 | (b-25) | (b-7) | H | H | (a-31) | —CH— | —NH— | —COCH(Me)— |
| 2-2706 | (b-25) | (b-35) | H | H | (a-31) | —CH— | —NH— | —CH(Me)— |
| 2-2707 | (b-25) | (b-35) | H | H | (a-31) | —CH— | —NH— | —COCH(Me)— |

TABLE 2-continued

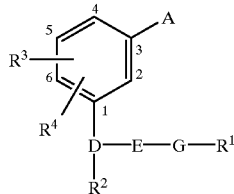

(I-2)

| Cpd. No. | R$^1$ Sub. No | R$^2$ Sub. No | R$^3$ | R$^4$ | A Sub. No | D | E | G |
|---|---|---|---|---|---|---|---|---|
| 2-2708 | (b-35) | (b-35) | H | H | (a-31) | —CH— | —NH— | —CH(Me)— |
| 2-2709 | (b-72) | (b-7) | H | H | (a-31) | —CH— | —NH— | —CH(Me)— |
| 2-2710 | (b-72) | (b-7) | H | H | (a-31) | —CH— | —NH— | —COCH(Me)— |
| 2-2711 | (b-72) | (b-35) | H | H | (a-31) | —CH— | —NH— | —CH(Me)— |
| 2-2712 | (b-72) | (b-35) | H | H | (a-31) | —CH— | —NH— | —COCH(Me)— |
| 2-2713 | (b-73) | (b-7) | H | H | (a-31) | —CH— | —NH— | —CH(Me)— |
| 2-2714 | (b-73) | (b-7) | H | H | (a-31) | —CH— | —NH— | —COCH(Me)— |
| 2-2715 | (b-73) | (b-12) | H | H | (a-31) | —CH— | —NH— | —CH(Me)— |
| 2-2716 | (b-73) | (b-15) | H | H | (a-31) | —CH— | —NH— | —CH(Me)— |
| 2-2717 | (b-73) | (b-34) | H | H | (a-31) | —CH— | —NH— | —CH(Me)— |
| 2-2718 | (b-73) | (b-35) | H | H | (a-31) | —CH— | —NH— | —CH(Me)— |
| 2-2719 | (b-73) | (b-35) | H | H | (a-31) | —CH— | —NH— | —COCH(Me)— |
| 2-2720 | (b-73) | (b-37) | H | H | (a-31) | —CH— | —NH— | —CH(Me)— |
| 2-2721 | (b-73) | (b-73) | H | H | (a-31) | —CH— | —NH— | —CH(Me)— |
| 2-2722 | (b-73) | (b-77) | H | H | (a-31) | —CH— | —NH— | —CH(Me)— |
| 2-2723 | (b-74) | (b-7) | H | H | (a-31) | —CH— | —NH— | —CH(Me)— |
| 2-2724 | (b-74) | (b-7) | H | H | (a-31) | —CH— | —NH— | —COCH(Me)— |
| 2-2725 | (b-74) | (b-35) | H | H | (a-31) | —CH— | —NH— | —CH(Me)— |
| 2-2726 | (b-74) | (b-35) | H | H | (a-31) | —CH— | —NH— | —COCH(Me)— |
| 2-2727 | (b-75) | (b-35) | H | H | (a-31) | —CH— | —NH— | —CH(Me)— |
| 2-2728 | (b-76) | (b-7) | H | H | (a-31) | —CH— | —NH— | —CH(Me)— |
| 2-2729 | (b-76) | (b-7) | H | H | (a-31) | —CH— | —NH— | —COCH(Me)— |
| 2-2730 | (b-76) | (b-35) | H | H | (a-31) | —CH— | —NH— | —CH(Me)— |
| 2-2731 | (b-76) | (b-35) | H | H | (a-31) | —CH— | —NH— | —COCH(Me)— |
| 2-2732 | (b-77) | (b-7) | H | H | (a-31) | —CH— | —NH— | —CH(Me)— |
| 2-2733 | (b-77) | (b-7) | H | H | (a-31) | —CH— | —NH— | —COCH(Me)— |
| 2-2734 | (b-77) | (b-12) | H | H | (a-31) | —CH— | —NH— | —CH(Me)— |
| 2-2735 | (b-77) | (b-15) | H | H | (a-31) | —CH— | —NH— | —CH(Me)— |
| 2-2736 | (b-77) | (b-34) | H | H | (a-31) | —CH— | —NH— | —CH(Me)— |
| 2-2737 | (b-77) | (b-35) | H | H | (a-31) | —CH— | —NH— | —CH(Me)— |
| 2-2738 | (b-77) | (b-35) | H | H | (a-31) | —CH— | —NH— | —COCH(Me)— |
| 2-2739 | (b-77) | (b-37) | H | H | (a-31) | —CH— | —NH— | —CH(Me)— |
| 2-2740 | (b-77) | (b-73) | H | H | (a-31) | —CH— | —NH— | —CH(Me)— |
| 2-2741 | (b-77) | (b-77) | H | H | (a-31) | —CH— | —NH— | —CH(Me)— |
| 2-2742 | (b-78) | (b-35) | H | H | (a-31) | —CH— | —NH— | —CH(Me)— |
| 2-2743 | (b-79) | (b-35) | H | H | (a-31) | —CH— | —NH— | —CH(Me)— |
| 2-2744 | (b-7) | (b-7) | H | H | (a-32) | —CH— | —NH— | —CH(Me)— |
| 2-2745 | (b-7) | (b-35) | H | H | (a-32) | —CH— | —NH— | —CH(Me)— |
| 2-2746 | (b-11) | (b-7) | H | H | (a-32) | —CH— | —NH— | —CH(Me)— |
| 2-2747 | (b-11) | (b-35) | H | H | (a-32) | —CH— | —NH— | —CH(Me)— |
| 2-2748 | (b-12) | (b-35) | H | H | (a-32) | —CH— | —NH— | —CH(Me)— |
| 2-2749 | (b-15) | (b-35) | H | H | (a-32) | —CH— | —NH— | —CH(Me)— |
| 2-2750 | (b-18) | (b-7) | H | H | (a-32) | —CH— | —NH— | —CH(Me)— |
| 2-2751 | (b-18) | (b-35) | H | H | (a-32) | —CH— | —NH— | —CH(Me)— |
| 2-2752 | (b-19) | (b-35) | H | H | (a-32) | —CH— | —NH— | —CH(Me)— |
| 2-2753 | (b-20) | (b-7) | H | H | (a-32) | —CH— | —NH— | —CH(Me)— |
| 2-2754 | (b-20) | (b-35) | H | H | (a-32) | —CH— | —NH— | —CH(Me)— |
| 2-2755 | (b-21) | (b-35) | H | H | (a-32) | —CH— | —NH— | —CH(Me)— |
| 2-2756 | (b-24) | (b-35) | H | H | (a-32) | —CH— | —NH— | —CH(Me)— |
| 2-2757 | (b-25) | (b-35) | H | H | (a-32) | —CH— | —NH— | —CH(Me)— |
| 2-2758 | (b-72) | (b-35) | H | H | (a-32) | —CH— | —NH— | —CH(Me)— |
| 2-2759 | (b-73) | (b-7) | H | H | (a-32) | —CH— | —NH— | —CH(Me)— |
| 2-2760 | (b-73) | (b-35) | H | H | (a-32) | —CH— | —NH— | —CH(Me)— |
| 2-2761 | (b-74) | (b-35) | H | H | (a-32) | —CH— | —NH— | —CH(Me)— |
| 2-2762 | (b-76) | (b-35) | H | H | (a-32) | —CH— | —NH— | —CH(Me)— |
| 2-2763 | (b-77) | (b-7) | H | H | (a-32) | —CH— | —NH— | —CH(Me)— |
| 2-2764 | (b-77) | (b-35) | H | H | (a-32) | —CH— | —NH— | —CH(Me)— |
| 2-2765 | (b-2) | (b-35) | H | H | (a-33) | —CH— | —NH— | —CH(Me)— |
| 2-2766 | (b-7) | (b-7) | H | H | (a-33) | —CH— | —NH— | —CH(Me)— |
| 2-2767 | (b-7) | (b-7) | H | H | (a-33) | —CH— | —NH— | —COCH(Me)— |
| 2-2768 | (b-7) | (b-35) | H | H | (a-33) | —CH— | —NH— | —CH(Me)— |
| 2-2769 | (b-7) | (b-35) | H | H | (a-33) | —CH— | —NH— | —COCH(Me)— |
| 2-2770 | (b-8) | (b-35) | H | H | (a-33) | —CH— | —NH— | —CH(Me)— |
| 2-2771 | (b-11) | (b-7) | H | H | (a-33) | —CH— | —NH— | —CH(Me)— |

TABLE 2-continued

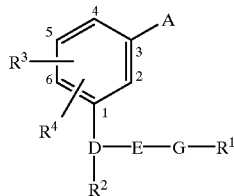

(I-2)

| Cpd. No. | R¹ Sub. No | R² Sub. No | R³ | R⁴ | A Sub. No | D | E | G |
|---|---|---|---|---|---|---|---|---|
| 2-2772 | (b-11) | (b-7) | H | H | (a-33) | —CH— | —NH— | —COCH(Me)— |
| 2-2773 | (b-11) | (b-35) | H | H | (a-33) | —CH— | —NH— | —CH(Me)— |
| 2-2774 | (b-11) | (b-35) | H | H | (a-33) | —CH— | —NH— | —COCH(Me)— |
| 2-2775 | (b-12) | (b-7) | H | H | (a-33) | —CH— | —NH— | —CH(Me)— |
| 2-2776 | (b-12) | (b-35) | H | H | (a-33) | —CH— | —NH— | —CH(Me)— |
| 2-2777 | (b-15) | (b-7) | H | H | (a-33) | —CH— | —NH— | —CH(Me)— |
| 2-2778 | (b-15) | (b-35) | H | H | (a-33) | —CH— | —NH— | —CH(Me)— |
| 2-2779 | (b-18) | (b-7) | H | H | (a-33) | —CH— | —NH— | —CH(Me)— |
| 2-2780 | (b-18) | (b-7) | H | H | (a-33) | —CH— | —NH— | —COCH(Me)— |
| 2-2781 | (b-18) | (b-35) | H | H | (a-33) | —CH— | —NH— | —CH(Me)— |
| 2-2782 | (b-18) | (b-35) | H | H | (a-33) | —CH— | —NH— | —COCH(Me)— |
| 2-2783 | (b-19) | (b-7) | H | H | (a-33) | —CH— | —NH— | —CH(Me)— |
| 2-2784 | (b-19) | (b-35) | H | H | (a-33) | —CH— | —NH— | —CH(Me)— |
| 2-2785 | (b-20) | (b-7) | H | H | (a-33) | —CH— | —NH— | —CH(Me)— |
| 2-2786 | (b-20) | (b-7) | H | H | (a-33) | —CH— | —NH— | —COCH(Me)— |
| 2-2787 | (b-20) | (b-35) | H | H | (a-33) | —CH— | —NH— | —CH(Me)— |
| 2-2788 | (b-20) | (b-35) | H | H | (a-33) | —CH— | —NH— | —COCH(Me)— |
| 2-2789 | (b-21) | (b-7) | H | H | (a-33) | —CH— | —NH— | —CH(Me)— |
| 2-2790 | (b-21) | (b-35) | H | H | (a-33) | —CH— | —NH— | —CH(Me)— |
| 2-2791 | (b-24) | (b-7) | H | H | (a-33) | —CH— | —NH— | —CH(Me)— |
| 2-2792 | (b-24) | (b-35) | H | H | (a-33) | —CH— | —NH— | —CH(Me)— |
| 2-2793 | (b-25) | (b-7) | H | H | (a-33) | —CH— | —NH— | —CH(Me)— |
| 2-2794 | (b-25) | (b-35) | H | H | (a-33) | —CH— | —NH— | —CH(Me)— |
| 2-2795 | (b-72) | (b-7) | H | H | (a-33) | —CH— | —NH— | —CH(Me)— |
| 2-2796 | (b-72) | (b-35) | H | H | (a-33) | —CH— | —NH— | —CH(Me)— |
| 2-2797 | (b-73) | (b-7) | H | H | (a-33) | —CH— | —NH— | —CH(Me)— |
| 2-2798 | (b-73) | (b-7) | H | H | (a-33) | —CH— | —NH— | —COCH(Me)— |
| 2-2799 | (b-73) | (b-35) | H | H | (a-33) | —CH— | —NH— | —CH(Me)— |
| 2-2800 | (b-73) | (b-35) | H | H | (a-33) | —CH— | —NH— | —COCH(Me)— |
| 2-2801 | (b-74) | (b-7) | H | H | (a-33) | —CH— | —NH— | —CH(Me)— |
| 2-2802 | (b-74) | (b-35) | H | H | (a-33) | —CH— | —NH— | —CH(Me)— |
| 2-2803 | (b-76) | (b-7) | H | H | (a-33) | —CH— | —NH— | —CH(Me)— |
| 2-2804 | (b-76) | (b-35) | H | H | (a-33) | —CH— | —NH— | —CH(Me)— |
| 2-2805 | (b-77) | (b-7) | H | H | (a-33) | —CH— | —NH— | —CH(Me)— |
| 2-2806 | (b-77) | (b-7) | H | H | (a-33) | —CH— | —NH— | —COCH(Me)— |
| 2-2807 | (b-77) | (b-35) | H | H | (a-33) | —CH— | —NH— | —CH(Me)— |
| 2-2808 | (b-77) | (b-35) | H | H | (a-33) | —CH— | —NH— | —COCH(Me)— |
| 2-2809 | (b-7) | (b-7) | H | H | (a-34) | —CH— | —NH— | —CH(Me)— |
| 2-2810 | (b-7) | (b-35) | H | H | (a-34) | —CH— | —NH— | —CH(Me)— |
| 2-2811 | (b-11) | (b-7) | H | H | (a-34) | —CH— | —NH— | —CH(Me)— |
| 2-2812 | (b-11) | (b-35) | H | H | (a-34) | —CH— | —NH— | —CH(Me)— |
| 2-2813 | (b-12) | (b-35) | H | H | (a-34) | —CH— | —NH— | —CH(Me)— |
| 2-2814 | (b-15) | (b-35) | H | H | (a-34) | —CH— | —NH— | —CH(Me)— |
| 2-2815 | (b-18) | (b-7) | H | H | (a-34) | —CH— | —NH— | —CH(Me)— |
| 2-2816 | (b-18) | (b-35) | H | H | (a-34) | —CH— | —NH— | —CH(Me)— |
| 2-2817 | (b-19) | (b-35) | H | H | (a-34) | —CH— | —NH— | —CH(Me)— |
| 2-2818 | (b-20) | (b-7) | H | H | (a-34) | —CH— | —NH— | —CH(Me)— |
| 2-2819 | (b-20) | (b-35) | H | H | (a-34) | —CH— | —NH— | —CH(Me)— |
| 2-2820 | (b-21) | (b-35) | H | H | (a-34) | —CH— | —NH— | —CH(Me)— |
| 2-2821 | (b-24) | (b-35) | H | H | (a-34) | —CH— | —NH— | —CH(Me)— |
| 2-2822 | (b-25) | (b-35) | H | H | (a-34) | —CH— | —NH— | —CH(Me)— |
| 2-2823 | (b-72) | (b-35) | H | H | (a-34) | —CH— | —NH— | —CH(Me)— |
| 2-2824 | (b-73) | (b-7) | H | H | (a-34) | —CH— | —NH— | —CH(Me)— |
| 2-2825 | (b-73) | (b-35) | H | H | (a-34) | —CH— | —NH— | —CH(Me)— |
| 2-2826 | (b-74) | (b-35) | H | H | (a-34) | —CH— | —NH— | —CH(Me)— |
| 2-2827 | (b-76) | (b-35) | H | H | (a-34) | —CH— | —NH— | —CH(Me)— |
| 2-2828 | (b-77) | (b-7) | H | H | (a-34) | —CH— | —NH— | —CH(Me)— |
| 2-2829 | (b-77) | (b-35) | H | H | (a-34) | —CH— | —NH— | —CH(Me)— |
| 2-2830 | (b-7) | (b-35) | H | H | (a-35) | —CH— | —NH— | —CH(Me)— |
| 2-2831 | (b-11) | (b-35) | H | H | (a-35) | —CH— | —NH— | —CH(Me)— |
| 2-2832 | (b-18) | (b-35) | H | H | (a-35) | —CH— | —NH— | —CH(Me)— |
| 2-2833 | (b-7) | (b-7) | H | H | (a-36) | —CH— | —NH— | —CH(Me)— |
| 2-2834 | (b-7) | (b-35) | H | H | (a-36) | —CH— | —NH— | —CH(Me)— |
| 2-2835 | (b-11) | (b-7) | H | H | (a-36) | —CH— | —NH— | —CH(Me)— |

TABLE 2-continued

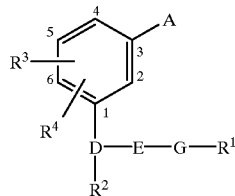

(I-2)

| Cpd. No. | R¹ Sub. No | R² Sub. No | R³ | R⁴ | A Sub. No | D | E | G |
|---|---|---|---|---|---|---|---|---|
| 2-2836 | (b-11) | (b-35) | H | H | (a-36) | —CH— | —NH— | —CH(Me)— |
| 2-2837 | (b-12) | (b-35) | H | H | (a-36) | —CH— | —NH— | —CH(Me)— |
| 2-2838 | (b-15) | (b-35) | H | H | (a-36) | —CH— | —NH— | —CH(Me)— |
| 2-2839 | (b-18) | (b-7) | H | H | (a-36) | —CH— | —NH— | —CH(Me)— |
| 2-2840 | (b-18) | (b-35) | H | H | (a-36) | —CH— | —NH— | —CH(Me)— |
| 2-2841 | (b-19) | (b-35) | H | H | (a-36) | —CH— | —NH— | —CH(Me)— |
| 2-2842 | (b-20) | (b-7) | H | H | (a-36) | —CH— | —NH— | —CH(Me)— |
| 2-2843 | (b-20) | (b-35) | H | H | (a-36) | —CH— | —NH— | —CH(Me)— |
| 2-2844 | (b-21) | (b-35) | H | H | (a-36) | —CH— | —NH— | —CH(Me)— |
| 2-2845 | (b-24) | (b-35) | H | H | (a-36) | —CH— | —NH— | —CH(Me)— |
| 2-2846 | (b-25) | (b-35) | H | H | (a-36) | —CH— | —NH— | —CH(Me)— |
| 2-2847 | (b-72) | (b-35) | H | H | (a-36) | —CH— | —NH— | —CH(Me)— |
| 2-2848 | (b-73) | (b-7) | H | H | (a-36) | —CH— | —NH— | —CH(Me)— |
| 2-2849 | (b-73) | (b-35) | H | H | (a-36) | —CH— | —NH— | —CH(Me)— |
| 2-2850 | (b-74) | (b-35) | H | H | (a-36) | —CH— | —NH— | —CH(Me)— |
| 2-2851 | (b-76) | (b-35) | H | H | (a-36) | —CH— | —NH— | —CH(Me)— |
| 2-2852 | (b-77) | (b-7) | H | H | (a-36) | —CH— | —NH— | —CH(Me)— |
| 2-2853 | (b-77) | (b-35) | H | H | (a-36) | —CH— | —NH— | —CH(Me)— |
| 2-2854 | (b-7) | (b-35) | H | H | (a-37) | —CH— | —NH— | —CH(Me)— |
| 2-2855 | (b-11) | (b-35) | H | H | (a-37) | —CH— | —NH— | —CH(Me)— |
| 2-2856 | (b-18) | (b-35) | H | H | (a-37) | —CH— | —NH— | —CH(Me)— |
| 2-2857 | (b-7) | (b-35) | H | H | (a-38) | —CH— | —NH— | —CH(Me)— |
| 2-2858 | (b-11) | (b-35) | H | H | (a-38) | —CH— | —NH— | —CH(Me)— |
| 2-2859 | (b-18) | (b-35) | H | H | (a-38) | —CH— | —NH— | —CH(Me)— |
| 2-2860 | (b-20) | (b-35) | H | H | (a-38) | —CH— | —NH— | —CH(Me)— |
| 2-2861 | (b-73) | (b-35) | H | H | (a-38) | —CH— | —NH— | —CH(Me)— |
| 2-2862 | (b-77) | (b-35) | H | H | (a-38) | —CH— | —NH— | —CH(Me)— |
| 2-2863 | (b-7) | (b-7) | H | H | (a-39) | —CH— | —NH— | —CH(Me)— |
| 2-2864 | (b-7) | (b-35) | H | H | (a-39) | —CH— | —NH— | —CH(Me)— |
| 2-2865 | (b-11) | (b-7) | H | H | (a-39) | —CH— | —NH— | —CH(Me)— |
| 2-2866 | (b-11) | (b-35) | H | H | (a-39) | —CH— | —NH— | —CH(Me)— |
| 2-2867 | (b-12) | (b-35) | H | H | (a-39) | —CH— | —NH— | —CH(Me)— |
| 2-2868 | (b-15) | (b-35) | H | H | (a-39) | —CH— | —NH— | —CH(Me)— |
| 2-2869 | (b-18) | (b-7) | H | H | (a-39) | —CH— | —NH— | —CH(Me)— |
| 2-2870 | (b-18) | (b-35) | H | H | (a-39) | —CH— | —NH— | —CH(Me)— |
| 2-2871 | (b-19) | (b-35) | H | H | (a-39) | —CH— | —NH— | —CH(Me)— |
| 2-2872 | (b-20) | (b-7) | H | H | (a-39) | —CH— | —NH— | —CH(Me)— |
| 2-2873 | (b-20) | (b-35) | H | H | (a-39) | —CH— | —NH— | —CH(Me)— |
| 2-2874 | (b-21) | (b-35) | H | H | (a-39) | —CH— | —NH— | —CH(Me)— |
| 2-2875 | (b-24) | (b-35) | H | H | (a-39) | —CH— | —NH— | —CH(Me)— |
| 2-2876 | (b-25) | (b-35) | H | H | (a-39) | —CH— | —NH— | —CH(Me)— |
| 2-2877 | (b-72) | (b-35) | H | H | (a-39) | —CH— | —NH— | —CH(Me)— |
| 2-2878 | (b-73) | (b-7) | H | H | (a-39) | —CH— | —NH— | —CH(Me)— |
| 2-2879 | (b-73) | (b-35) | H | H | (a-39) | —CH— | —NH— | —CH(Me)— |
| 2-2880 | (b-74) | (b-35) | H | H | (a-39) | —CH— | —NH— | —CH(Me)— |
| 2-2881 | (b-76) | (b-35) | H | H | (a-39) | —CH— | —NH— | —CH(Me)— |
| 2-2882 | (b-77) | (b-7) | H | H | (a-39) | —CH— | —NH— | —CH(Me)— |
| 2-2883 | (b-77) | (b-35) | H | H | (a-39) | —CH— | —NH— | —CH(Me)— |
| 2-2884 | (b-7) | (b-35) | H | H | (a-40) | —CH— | —NH— | —CH(Me)— |
| 2-2885 | (b-11) | (b-35) | H | H | (a-40) | —CH— | —NH— | —CH(Me)— |
| 2-2886 | (b-18) | (b-35) | H | H | (a-40) | —CH— | —NH— | —CH(Me)— |
| 2-2887 | (b-7) | (b-35) | H | H | (a-41) | —CH— | —NH— | —CH(Me)— |
| 2-2888 | (b-11) | (b-35) | H | H | (a-41) | —CH— | —NH— | —CH(Me)— |
| 2-2889 | (b-18) | (b-35) | H | H | (a-41) | —CH— | —NH— | —CH(Me)— |
| 2-2890 | (b-20) | (b-35) | H | H | (a-41) | —CH— | —NH— | —CH(Me)— |
| 2-2891 | (b-73) | (b-35) | H | H | (a-41) | —CH— | —NH— | —CH(Me)— |
| 2-2892 | (b-77) | (b-35) | H | H | (a-41) | —CH— | —NH— | —CH(Me)— |
| 2-2893 | (b-7) | (b-35) | H | H | (a-42) | —CH— | —NH— | —CH(Me)— |
| 2-2894 | (b-11) | (b-35) | H | H | (a-42) | —CH— | —NH— | —CH(Me)— |
| 2-2895 | (b-18) | (b-35) | H | H | (a-42) | —CH— | —NH— | —CH(Me)— |
| 2-2896 | (b-2) | (b-7) | H | H | (a-43) | —CH— | —NH— | —CH(Me)— |
| 2-2897 | (b-2) | (b-35) | H | H | (a-43) | —CH— | —NH— | —CH(Me)— |
| 2-2898 | (b-7) | (b-7) | H | H | (a-43) | —CH— | —NH— | —CH(Me)— |
| 2-2899 | (b-7) | (b-7) | H | H | (a-43) | —CH— | —NH— | —COCH(Me)— |

TABLE 2-continued

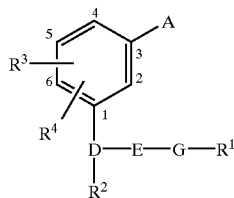

(I-2)

| Cpd. No. | R¹ Sub. No | R² Sub. No | R³ | R⁴ | A Sub. No | D | E | G |
|---|---|---|---|---|---|---|---|---|
| 2-2900 | (b-7) | (b-12) | H | H | (a-43) | —CH— | —NH— | —CH(Me)— |
| 2-2901 | (b-7) | (b-15) | H | H | (a-43) | —CH— | —NH— | —CH(Me)— |
| 2-2902 | (b-7) | (b-34) | H | H | (a-43) | —CH— | —NH— | —CH(Me)— |
| 2-2903 | (b-7) | (b-35) | H | H | (a-43) | —CH— | —NH— | —CH(Me)— |
| 2-2904 | (b-7) | (b-35) | H | H | (a-43) | —CH— | —NH— | —COCH(Me)— |
| 2-2905 | (b-7) | (b-37) | H | H | (a-43) | —CH— | —NH— | —CH(Me)— |
| 2-2906 | (b-7) | (b-73) | H | H | (a-43) | —CH— | —NH— | —CH(Me)— |
| 2-2907 | (b-7) | (b-77) | H | H | (a-43) | —CH— | —NH— | —CH(Me)— |
| 2-2908 | (b-8) | (b-35) | H | H | (a-43) | —CH— | —NH— | —CH(Me)— |
| 2-2909 | (b-9) | (b-35) | H | H | (a-43) | —CH— | —NH— | —CH(Me)— |
| 2-2910 | (b-10) | (b-35) | H | H | (a-43) | —CH— | —NH— | —CH(Me)— |
| 2-2911 | (b-11) | (b-7) | H | H | (a-43) | —CH— | —NH— | —CH(Me)— |
| 2-2912 | (b-11) | (b-7) | H | H | (a-43) | —CH— | —NH— | —COCH(Me)— |
| 2-2913 | (b-11) | (b-12) | H | H | (a-43) | —CH— | —NH— | —CH(Me)— |
| 2-2914 | (b-11) | (b-15) | H | H | (a-43) | —CH— | —NH— | —CH(Me)— |
| 2-2915 | (b-11) | (b-34) | H | H | (a-43) | —CH— | —NH— | —CH(Me)— |
| 2-2916 | (b-11) | (b-35) | H | H | (a-43) | —CH— | —NH— | —CH(Me)— |
| 2-2917 | (b-11) | (b-35) | H | H | (a-43) | —CH— | —NH— | —COCH(Me)— |
| 2-2918 | (b-11) | (b-37) | H | H | (a-43) | —CH— | —NH— | —CH(Me)— |
| 2-2919 | (b-11) | (b-73) | H | H | (a-43) | —CH— | —NH— | —CH(Me)— |
| 2-2920 | (b-11) | (b-77) | H | H | (a-43) | —CH— | —NH— | —CH(Me)— |
| 2-2921 | (b-12) | (b-7) | H | H | (a-43) | —CH— | —NH— | —CH(Me)— |
| 2-2922 | (b-12) | (b-7) | H | H | (a-43) | —CH— | —NH— | —COCH(Me)— |
| 2-2923 | (b-12) | (b-35) | H | H | (a-43) | —CH— | —NH— | —CH(Me)— |
| 2-2924 | (b-12) | (b-35) | H | H | (a-43) | —CH— | —NH— | —COCH(Me)— |
| 2-2925 | (b-13) | (b-35) | H | H | (a-43) | —CH— | —NH— | —CH(Me)— |
| 2-2926 | (b-14) | (b-35) | H | H | (a-43) | —CH— | —NH— | —CH(Me)— |
| 2-2927 | (b-15) | (b-7) | H | H | (a-43) | —CH— | —NH— | —CH(Me)— |
| 2-2928 | (b-15) | (b-7) | H | H | (a-43) | —CH— | —NH— | —COCH(Me)— |
| 2-2929 | (b-15) | (b-35) | H | H | (a-43) | —CH— | —NH— | —CH(Me)— |
| 2-2930 | (b-15) | (b-35) | H | H | (a-43) | —CH— | —NH— | —COCH(Me)— |
| 2-2931 | (b-17) | (b-35) | H | H | (a-43) | —CH— | —NH— | —CH(Me)— |
| 2-2932 | (b-18) | (b-7) | H | H | (a-43) | —CH— | —NH— | —CH(Me)— |
| 2-2933 | (b-18) | (b-7) | H | H | (a-43) | —CH— | —NH— | —COCH(Me)— |
| 2-2934 | (b-18) | (b-12) | H | H | (a-43) | —CH— | —NH— | —CH(Me)— |
| 2-2935 | (b-18) | (b-15) | H | H | (a-43) | —CH— | —NH— | —CH(Me)— |
| 2-2936 | (b-18) | (b-34) | H | H | (a-43) | —CH— | —NH— | —CH(Me)— |
| 2-2937 | (b-18) | (b-35) | H | H | (a-43) | —CH— | —NH— | —CH(Me)— |
| 2-2938 | (b-18) | (b-35) | H | H | (a-43) | —CH— | —NH— | —COCH(Me)— |
| 2-2939 | (b-18) | (b-37) | H | H | (a-43) | —CH— | —NH— | —CH(Me)— |
| 2-2940 | (b-18) | (b-73) | H | H | (a-43) | —CH— | —NH— | —CH(Me)— |
| 2-2941 | (b-18) | (b-77) | H | H | (a-43) | —CH— | —NH— | —CH(Me)— |
| 2-2942 | (b-19) | (b-7) | H | H | (a-43) | —CH— | —NH— | —CH(Me)— |
| 2-2943 | (b-19) | (b-7) | H | H | (a-43) | —CH— | —NH— | —COCH(Me)— |
| 2-2944 | (b-19) | (b-35) | H | H | (a-43) | —CH— | —NH— | —CH(Me)— |
| 2-2945 | (b-19) | (b-35) | H | H | (a-43) | —CH— | —NH— | —COCH(Me)— |
| 2-2946 | (b-20) | (b-7) | H | H | (a-43) | —CH— | —NH— | —CH(Me)— |
| 2-2947 | (b-20) | (b-7) | H | H | (a-43) | —CH— | —NH— | —COCH(Me)— |
| 2-2948 | (b-20) | (b-12) | H | H | (a-43) | —CH— | —NH— | —CH(Me)— |
| 2-2949 | (b-20) | (b-15) | H | H | (a-43) | —CH— | —NH— | —CH(Me)— |
| 2-2950 | (b-20) | (b-34) | H | H | (a-43) | —CH— | —NH— | —CH(Me)— |
| 2-2951 | (b-20) | (b-35) | H | H | (a-43) | —CH— | —NH— | —CH(Me)— |
| 2-2952 | (b-20) | (b-35) | H | H | (a-43) | —CH— | —NH— | —COCH(Me)— |
| 2-2953 | (b-20) | (b-37) | H | H | (a-43) | —CH— | —NH— | —CH(Me)— |
| 2-2954 | (b-20) | (b-73) | H | H | (a-43) | —CH— | —NH— | —CH(Me)— |
| 2-2955 | (b-20) | (b-77) | H | H | (a-43) | —CH— | —NH— | —CH(Me)— |
| 2-2956 | (b-21) | (b-7) | H | H | (a-43) | —CH— | —NH— | —CH(Me)— |
| 2-2957 | (b-21) | (b-7) | H | H | (a-43) | —CH— | —NH— | —COCH(Me)— |
| 2-2958 | (b-21) | (b-35) | H | H | (a-43) | —CH— | —NH— | —CH(Me)— |
| 2-2959 | (b-21) | (b-35) | H | H | (a-43) | —CH— | —NH— | —COCH(Me)— |
| 2-2960 | (b-23) | (b-35) | H | H | (a-43) | —CH— | —NH— | —CH(Me)— |
| 2-2961 | (b-24) | (b-7) | H | H | (a-43) | —CH— | —NH— | —CH(Me)— |
| 2-2962 | (b-24) | (b-7) | H | H | (a-43) | —CH— | —NH— | —COCH(Me)— |
| 2-2963 | (b-24) | (b-35) | H | H | (a-43) | —CH— | —NH— | —CH(Me)— |

TABLE 2-continued

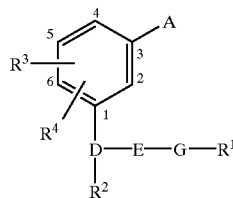

(I-2)

| Cpd. No. | R$^1$ Sub. No | R$^2$ Sub. No | R$^3$ | R$^4$ | A Sub. No | D | E | G |
|---|---|---|---|---|---|---|---|---|
| 2-2964 | (b-24) | (b-35) | H | H | (a-43) | —CH— | —NH— | —COCH(Me)— |
| 2-2965 | (b-25) | (b-7) | H | H | (a-43) | —CH— | —NH— | —CH(Me)— |
| 2-2966 | (b-25) | (b-7) | H | H | (a-43) | —CH— | —NH— | —COCH(Me)— |
| 2-2967 | (b-25) | (b-35) | H | H | (a-43) | —CH— | —NH— | —CH(Me)— |
| 2-2968 | (b-25) | (b-35) | H | H | (a-43) | —CH— | —NH— | —COCH(Me)— |
| 2-2969 | (b-35) | (b-35) | H | H | (a-43) | —CH— | —NH— | —CH(Me)— |
| 2-2960 | (b-72) | (b-7) | H | H | (a-43) | —CH— | —NH— | —CH(Me)— |
| 2-2961 | (b-72) | (b-7) | H | H | (a-43) | —CH— | —NH— | —COCH(Me)— |
| 2-2962 | (b-72) | (b-35) | H | H | (a-43) | —CH— | —NH— | —CH(Me)— |
| 2-2963 | (b-72) | (b-35) | H | H | (a-43) | —CH— | —NH— | —COCH(Me)— |
| 2-2964 | (b-73) | (b-7) | H | H | (a-43) | —CH— | —NH— | —CH(Me)— |
| 2-2965 | (b-73) | (b-7) | H | H | (a-43) | —CH— | —NH— | —COCH(Me)— |
| 2-2966 | (b-73) | (b-12) | H | H | (a-43) | —CH— | —NH— | —CH(Me)— |
| 2-2967 | (b-73) | (b-15) | H | H | (a-43) | —CH— | —NH— | —CH(Me)— |
| 2-2968 | (b-73) | (b-34) | H | H | (a-43) | —CH— | —NH— | —CH(Me)— |
| 2-2969 | (b-73) | (b-35) | H | H | (a-43) | —CH— | —NH— | —CH(Me)— |
| 2-2970 | (b-73) | (b-35) | H | H | (a-43) | —CH— | —NH— | —COCH(Me)— |
| 2-2971 | (b-73) | (b-37) | H | H | (a-43) | —CH— | —NH— | —CH(Me)— |
| 2-2972 | (b-73) | (b-73) | H | H | (a-43) | —CH— | —NH— | —CH(Me)— |
| 2-2973 | (b-73) | (b-77) | H | H | (a-43) | —CH— | —NH— | —CH(Me)— |
| 2-2974 | (b-74) | (b-7) | H | H | (a-43) | —CH— | —NH— | —CH(Me)— |
| 2-2975 | (b-74) | (b-7) | H | H | (a-43) | —CH— | —NH— | —COCH(Me)— |
| 2-2976 | (b-74) | (b-35) | H | H | (a-43) | —CH— | —NH— | —CH(Me)— |
| 2-2977 | (b-74) | (b-35) | H | H | (a-43) | —CH— | —NH— | —COCH(Me)— |
| 2-2978 | (b-75) | (b-35) | H | H | (a-43) | —CH— | —NH— | —CH(Me)— |
| 2-2979 | (b-76) | (b-7) | H | H | (a-43) | —CH— | —NH— | —CH(Me)— |
| 2-2980 | (b-76) | (b-7) | H | H | (a-43) | —CH— | —NH— | —COCH(Me)— |
| 2-2981 | (b-76) | (b-35) | H | H | (a-43) | —CH— | —NH— | —CH(Me)— |
| 2-2982 | (b-76) | (b-35) | H | H | (a-43) | —CH— | —NH— | —COCH(Me)— |
| 2-2983 | (b-77) | (b-7) | H | H | (a-43) | —CH— | —NH— | —CH(Me)— |
| 2-2984 | (b-77) | (b-7) | H | H | (a-43) | —CH— | —NH— | —COCH(Me)— |
| 2-2985 | (b-77) | (b-12) | H | H | (a-43) | —CH— | —NH— | —CH(Me)— |
| 2-2986 | (b-77) | (b-15) | H | H | (a-43) | —CH— | —NH— | —CH(Me)— |
| 2-2987 | (b-77) | (b-34) | H | H | (a-43) | —CH— | —NH— | —CH(Me)— |
| 2-2988 | (b-77) | (b-35) | H | H | (a-43) | —CH— | —NH— | —CH(Me)— |
| 2-2989 | (b-77) | (b-35) | H | H | (a-43) | —CH— | —NH— | —COCH(Me)— |
| 2-2990 | (b-77) | (b-37) | H | H | (a-43) | —CH— | —NH— | —CH(Me)— |
| 2-2991 | (b-77) | (b-73) | H | H | (a-43) | —CH— | —NH— | —CH(Me)— |
| 2-2992 | (b-77) | (b-77) | H | H | (a-43) | —CH— | —NH— | —CH(Me)— |
| 2-2993 | (b-78) | (b-35) | H | H | (a-43) | —CH— | —NH— | —CH(Me)— |
| 2-2994 | (b-79) | (b-35) | H | H | (a-43) | —CH— | —NH— | —CH(Me)— |
| 2-2995 | (b-7) | (b-7) | H | H | (a-44) | —CH— | —NH— | —CH(Me)— |
| 2-2996 | (b-7) | (b-35) | H | H | (a-44) | —CH— | —NH— | —CH(Me)— |
| 2-2997 | (b-11) | (b-7) | H | H | (a-44) | —CH— | —NH— | —CH(Me)— |
| 2-2998 | (b-11) | (b-35) | H | H | (a-44) | —CH— | —NH— | —CH(Me)— |
| 2-2999 | (b-12) | (b-35) | H | H | (a-44) | —CH— | —NH— | —CH(Me)— |
| 2-3000 | (b-15) | (b-35) | H | H | (a-44) | —CH— | —NH— | —CH(Me)— |
| 2-3001 | (b-18) | (b-7) | H | H | (a-44) | —CH— | —NH— | —CH(Me)— |
| 2-3002 | (b-18) | (b-35) | H | H | (a-44) | —CH— | —NH— | —CH(Me)— |
| 2-3003 | (b-19) | (b-35) | H | H | (a-44) | —CH— | —NH— | —CH(Me)— |
| 2-3004 | (b-20) | (b-7) | H | H | (a-44) | —CH— | —NH— | —CH(Me)— |
| 2-3005 | (b-20) | (b-35) | H | H | (a-44) | —CH— | —NH— | —CH(Me)— |
| 2-3006 | (b-21) | (b-35) | H | H | (a-44) | —CH— | —NH— | —CH(Me)— |
| 2-3007 | (b-24) | (b-35) | H | H | (a-44) | —CH— | —NH— | —CH(Me)— |
| 2-3008 | (b-25) | (b-35) | H | H | (a-44) | —CH— | —NH— | —CH(Me)— |
| 2-3009 | (b-72) | (b-35) | H | H | (a-44) | —CH— | —NH— | —CH(Me)— |
| 2-3010 | (b-73) | (b-7) | H | H | (a-44) | —CH— | —NH— | —CH(Me)— |
| 2-3011 | (b-73) | (b-35) | H | H | (a-44) | —CH— | —NH— | —CH(Me)— |
| 2-3012 | (b-74) | (b-35) | H | H | (a-44) | —CH— | —NH— | —CH(Me)— |
| 2-3013 | (b-76) | (b-35) | H | H | (a-44) | —CH— | —NH— | —CH(Me)— |
| 2-3014 | (b-77) | (b-7) | H | H | (a-44) | —CH— | —NH— | —CH(Me)— |
| 2-3015 | (b-77) | (b-35) | H | H | (a-44) | —CH— | —NH— | —CH(Me)— |
| 2-3016 | (b-2) | (b-35) | H | H | (a-45) | —CH— | —NH— | —CH(Me)— |
| 2-3017 | (b-7) | (b-7) | H | H | (a-45) | —CH— | —NH— | —CH(Me)— |

TABLE 2-continued

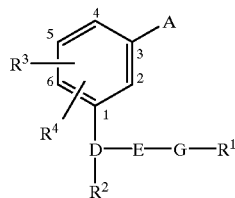

(I-2)

| Cpd. No. | R¹ Sub. No | R² Sub. No | R³ | R⁴ | A Sub. No | D | E | G |
|---|---|---|---|---|---|---|---|---|
| 2-3018 | (b-7) | (b-7) | H | H | (a-45) | —CH— | —NH— | —COCH(Me)— |
| 2-3019 | (b-7) | (b-35) | H | H | (a-45) | —CH— | —NH— | —CH(Me)— |
| 2-3020 | (b-7) | (b-35) | H | H | (a-45) | —CH— | —NH— | —COCH(Me)— |
| 2-3021 | (b-8) | (b-35) | H | H | (a-45) | —CH— | —NH— | —CH(Me)— |
| 2-3022 | (b-11) | (b-7) | H | H | (a-45) | —CH— | —NH— | —CH(Me)— |
| 2-3023 | (b-11) | (b-7) | H | H | (a-45) | —CH— | —NH— | —COCH(Me)— |
| 2-3024 | (b-11) | (b-35) | H | H | (a-45) | —CH— | —NH— | —CH(Me)— |
| 2-3025 | (b-11) | (b-35) | H | H | (a-45) | —CH— | —NH— | —COCH(Me)— |
| 2-3026 | (b-12) | (b-7) | H | H | (a-45) | —CH— | —NH— | —CH(Me)— |
| 2-3027 | (b-12) | (b-35) | H | H | (a-45) | —CH— | —NH— | —CH(Me)— |
| 2-3028 | (b-15) | (b-7) | H | H | (a-45) | —CH— | —NH— | —CH(Me)— |
| 2-3029 | (b-15) | (b-35) | H | H | (a-45) | —CH— | —NH— | —CH(Me)— |
| 2-3030 | (b-18) | (b-7) | H | H | (a-45) | —CH— | —NH— | —CH(Me)— |
| 2-3031 | (b-18) | (b-7) | H | H | (a-45) | —CH— | —NH— | —COCH(Me)— |
| 2-3032 | (b-18) | (b-35) | H | H | (a-45) | —CH— | —NH— | —CH(Me)— |
| 2-3033 | (b-18) | (b-35) | H | H | (a-45) | —CH— | —NH— | —COCH(Me)— |
| 2-3034 | (b-19) | (b-7) | H | H | (a-45) | —CH— | —NH— | —CH(Me)— |
| 2-3035 | (b-19) | (b-35) | H | H | (a-45) | —CH— | —NH— | —CH(Me)— |
| 2-3036 | (b-20) | (b-7) | H | H | (a-45) | —CH— | —NH— | —CH(Me)— |
| 2-3037 | (b-20) | (b-7) | H | H | (a-45) | —CH— | —NH— | —COCH(Me)— |
| 2-3038 | (b-20) | (b-35) | H | H | (a-45) | —CH— | —NH— | —CH(Me)— |
| 2-3039 | (b-20) | (b-35) | H | H | (a-45) | —CH— | —NH— | —COCH(Me)— |
| 2-3040 | (b-21) | (b-7) | H | H | (a-45) | —CH— | —NH— | —CH(Me)— |
| 2-3041 | (b-21) | (b-35) | H | H | (a-45) | —CH— | —NH— | —CH(Me)— |
| 2-3042 | (b-24) | (b-7) | H | H | (a-45) | —CH— | —NH— | —CH(Me)— |
| 2-3043 | (b-24) | (b-35) | H | H | (a-45) | —CH— | —NH— | —CH(Me)— |
| 2-3044 | (b-25) | (b-7) | H | H | (a-45) | —CH— | —NH— | —CH(Me)— |
| 2-3045 | (b-25) | (b-35) | H | H | (a-45) | —CH— | —NH— | —CH(Me)— |
| 2-3046 | (b-72) | (b-7) | H | H | (a-45) | —CH— | —NH— | —CH(Me)— |
| 2-3047 | (b-72) | (b-35) | H | H | (a-45) | —CH— | —NH— | —CH(Me)— |
| 2-3048 | (b-73) | (b-7) | H | H | (a-45) | —CH— | —NH— | —CH(Me)— |
| 2-3049 | (b-73) | (b-7) | H | H | (a-45) | —CH— | —NH— | —COCH(Me)— |
| 2-3050 | (b-73) | (b-35) | H | H | (a-45) | —CH— | —NH— | —CH(Me)— |
| 2-3051 | (b-73) | (b-35) | H | H | (a-45) | —CH— | —NH— | —COCH(Me)— |
| 2-3052 | (b-74) | (b-7) | H | H | (a-45) | —CH— | —NH— | —CH(Me)— |
| 2-3053 | (b-74) | (b-35) | H | H | (a-45) | —CH— | —NH— | —CH(Me)— |
| 2-3054 | (b-76) | (b-7) | H | H | (a-45) | —CH— | —NH— | —CH(Me)— |
| 2-3055 | (b-76) | (b-35) | H | H | (a-45) | —CH— | —NH— | —CH(Me)— |
| 2-3056 | (b-77) | (b-7) | H | H | (a-45) | —CH— | —NH— | —CH(Me)— |
| 2-3057 | (b-77) | (b-7) | H | H | (a-45) | —CH— | —NH— | —COCH(Me)— |
| 2-3058 | (b-77) | (b-35) | H | H | (a-45) | —CH— | —NH— | —CH(Me)— |
| 2-3059 | (b-77) | (b-35) | H | H | (a-45) | —CH— | —NH— | —COCH(Me)— |
| 2-3060 | (b-7) | (b-7) | H | H | (a-46) | —CH— | —NH— | —CH(Me)— |
| 2-3061 | (b-7) | (b-35) | H | H | (a-46) | —CH— | —NH— | —CH(Me)— |
| 2-3062 | (b-11) | (b-7) | H | H | (a-46) | —CH— | —NH— | —CH(Me)— |
| 2-3063 | (b-11) | (b-35) | H | H | (a-46) | —CH— | —NH— | —CH(Me)— |
| 2-3064 | (b-12) | (b-35) | H | H | (a-46) | —CH— | —NH— | —CH(Me)— |
| 2-3065 | (b-15) | (b-35) | H | H | (a-46) | —CH— | —NH— | —CH(Me)— |
| 2-3066 | (b-18) | (b-7) | H | H | (a-46) | —CH— | —NH— | —CH(Me)— |
| 2-3067 | (b-18) | (b-35) | H | H | (a-46) | —CH— | —NH— | —CH(Me)— |
| 2-3068 | (b-19) | (b-35) | H | H | (a-46) | —CH— | —NH— | —CH(Me)— |
| 2-3069 | (b-20) | (b-7) | H | H | (a-46) | —CH— | —NH— | —CH(Me)— |
| 2-3070 | (b-20) | (b-35) | H | H | (a-46) | —CH— | —NH— | —CH(Me)— |
| 2-3071 | (b-21) | (b-35) | H | H | (a-46) | —CH— | —NH— | —CH(Me)— |
| 2-3072 | (b-24) | (b-35) | H | H | (a-46) | —CH— | —NH— | —CH(Me)— |
| 2-3073 | (b-25) | (b-35) | H | H | (a-46) | —CH— | —NH— | —CH(Me)— |
| 2-3074 | (b-72) | (b-35) | H | H | (a-46) | —CH— | —NH— | —CH(Me)— |
| 2-3075 | (b-73) | (b-7) | H | H | (a-46) | —CH— | —NH— | —CH(Me)— |
| 2-3076 | (b-73) | (b-35) | H | H | (a-46) | —CH— | —NH— | —CH(Me)— |
| 2-3077 | (b-74) | (b-35) | H | H | (a-46) | —CH— | —NH— | —CH(Me)— |
| 2-3078 | (b-76) | (b-35) | H | H | (a-46) | —CH— | —NH— | —CH(Me)— |
| 2-3079 | (b-77) | (b-7) | H | H | (a-46) | —CH— | —NH— | —CH(Me)— |
| 2-3080 | (b-77) | (b-35) | H | H | (a-46) | —CH— | —NH— | —CH(Me)— |
| 2-3081 | (b-7) | (b-35) | H | H | (a-47) | —CH— | —NH— | —CH(Me)— |

TABLE 2-continued

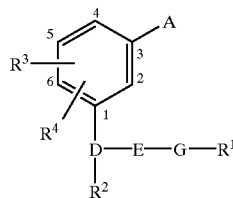

(I-2)

| Cpd. No. | R¹ Sub. No | R² Sub. No | R³ | R⁴ | A Sub. No | D | E | G |
|---|---|---|---|---|---|---|---|---|
| 2-3082 | (b-11) | (b-35) | H | H | (a-47) | —CH— | —NH— | —CH(Me)— |
| 2-3083 | (b-18) | (b-35) | H | H | (a-47) | —CH— | —NH— | —CH(Me)— |
| 2-3084 | (b-20) | (b-35) | H | H | (a-47) | —CH— | —NH— | —CH(Me)— |
| 2-3085 | (b-73) | (b-35) | H | H | (a-47) | —CH— | —NH— | —CH(Me)— |
| 2-3086 | (b-77) | (b-35) | H | H | (a-47) | —CH— | —NH— | —CH(Me)— |
| 2-3087 | (b-7) | (b-35) | H | H | (a-48) | —CH— | —NH— | —CH(Me)— |
| 2-3088 | (b-11) | (b-35) | H | H | (a-48) | —CH— | —NH— | —CH(Me)— |
| 2-3089 | (b-18) | (b-35) | H | H | (a-48) | —CH— | —NH— | —CH(Me)— |
| 2-3090 | (b-7) | (b-7) | H | H | (a-1) | —CH— | —NH— | —CH(Et)— |
| 2-3091 | (b-7) | (b-7) | H | H | (a-1) | —CH— | —NH— | —(CH₂)₃— |
| 2-3092 | (b-7) | (b-7) | H | H | (a-1) | —CH— | —NH— | —CH₂CH(Me)— |
| 2-3093 | (b-7) | (b-7) | H | H | (a-1) | —CH— | —NH— | —CH₂CH(OH)— |
| 2-3094 | (b-7) | (b-7) | H | H | (a-1) | —CH— | —NH— | —CH₂C(=O)— |
| 2-3095 | (b-7) | (b-7) | H | H | (a-1) | —CH— | —NH— | —CH₂C(Ph)— |
| 2-3096 | (b-7) | (b-7) | H | H | (a-1) | —CH— | —NH— | —CO— |
| 2-3097 | (b-7) | (b-7) | H | H | (a-1) | —CH— | —NH— | —COCH(Me)— |
| 2-3098 | (b-7) | (b-7) | H | H | (a-1) | —CH— | —O— | —CH(Me)— |
| 2-3099 | (b-7) | (b-7) | H | H | (a-1) | —CH— | —S— | —CH(Me)— |
| 2-3100 | (b-7) | (b-7) | 4-F | H | (a-1) | —CH— | —NH— | —CH(Me)— |
| 2-3101 | (b-7) | (b-7) | 6-F | H | (a-1) | —CH— | —NH— | —CH(Me)— |
| 2-3102 | (b-7) | (b-7) | 4-Cl | H | (a-1) | —CH— | —NH— | —CH(Me)— |
| 2-3103 | (b-7) | (b-7) | 6-Cl | H | (a-1) | —CH— | —NH— | —CH(Me)— |
| 2-3104 | (b-7) | (b-7) | 4-MeO | H | (a-1) | —CH— | —NH— | —CH(Me)— |
| 2-3105 | (b-7) | (b-7) | 6-MeO | H | (a-1) | —CH— | —NH— | —CH(Me)— |
| 2-3106 | (b-7) | (b-7) | H | H | (a-1) | N | —CO— | —CH(Me)— |
| 2-3107 | (b-7) | (b-8) | H | H | (a-1) | —CH— | —NH— | —CH(Me)— |
| 2-3108 | (b-7) | (b-10) | H | H | (a-1) | —CH— | —NH— | —CH(Me)— |
| 2-3109 | (b-7) | (b-11) | H | H | (a-1) | —CH— | —NH— | —CH(Me)— |
| 2-3110 | (b-7) | (b-12) | H | H | (a-1) | —CH— | —NH— | —(CH₂)₂— |
| 2-3111 | (b-7) | (b-12) | H | H | (a-1) | —CH— | —NH— | —CH(Et)— |
| 2-3112 | (b-7) | (b-13) | H | H | (a-1) | —CH— | —NH— | —CH(Me)— |
| 2-3113 | (b-7) | (b-14) | H | H | (a-1) | —CH— | —NH— | —CH(Me)— |
| 2-3114 | (b-7) | (b-15) | H | H | (a-1) | —CH— | —NH— | —(CH₂)₂— |
| 2-3115 | (b-7) | (b-15) | H | H | (a-1) | —CH— | —NH— | —CH(Me)— |
| 2-3116 | (b-7) | (b-15) | H | H | (a-1) | —CH— | —NH— | —CH₂CH(Me)— |
| 2-3117 | (b-7) | (b-16) | H | H | (a-1) | —CH— | —NH— | —CH(Me)— |
| 2-3118 | (b-7) | (b-17) | H | H | (a-1) | —CH— | —NH— | —CH(Me)— |
| 2-3119 | (b-7) | (b-23) | H | H | (a-1) | —CH— | —NH— | —CH(Me)— |
| 2-3120 | (b-7) | (b-24) | H | H | (a-1) | —CH— | —NH— | —CH(Me)— |
| 2-3121 | (b-7) | (b-25) | H | H | (a-1) | —CH— | —NH— | —CH(Me)— |
| 2-3122 | (b-7) | (b-27) | H | H | (a-1) | —CH— | —NH— | —CH(Me)— |
| 2-3123 | (b-7) | (b-28) | H | H | (a-1) | —CH— | —NH— | —CH(Me)— |
| 2-3124 | (b-7) | (b-30) | H | H | (a-1) | —CH— | —NH— | —CH(Me)— |
| 2-3125 | (b-7) | (b-31) | H | H | (a-1) | —CH— | —NH— | —CH(Me)— |
| 2-3126 | (b-7) | (b-32) | H | H | (a-1) | —CH— | —NH— | —CH(Me)— |
| 2-3127 | (b-7) | (b-33) | H | H | (a-1) | —CH— | —NH— | —CH(Me)— |
| 2-3128 | (b-7) | (b-34) | 6-MeO | H | (a-1) | —CH— | —NH— | —CH(Me)— |
| 2-3129 | (b-7) | (b-34) | H | H | (a-1) | —CH— | —O— | —CH(Me)— |
| 2-3130 | (b-7) | (b-34) | H | H | (a-1) | —CH— | —S— | —CH(Me)— |
| 2-3131 | (b-7) | (b-34) | H | H | (a-1) | N | —CO— | —CH(Me)— |
| 2-3132 | (b-7) | (b-35) | H | H | (a-1) | —CH— | —NH— | single bond |
| 2-3133 | (b-7) | (b-35) | H | H | (a-1) | —CH— | —NH— | —CH₂— |
| 2-3134 | (b-7) | (b-35) | H | H | (a-1) | —CH— | —NH— | —(CH₂)₂— |
| 2-3135 | (b-7) | (b-35) | H | H | (a-1) | —CH— | —NH— | —CH(Et)— |
| 2-3136 | (b-7) | (b-35) | H | H | (a-1) | —CH— | —NH— | —C(Me)₂— |
| 2-3137 | (b-7) | (b-35) | H | H | (a-1) | —CH— | —NH— | —CH₂CH(Me)— |
| 2-3138 | (b-7) | (b-35) | H | H | (a-1) | —CH— | —NH— | —CH₂CH(OH)— |
| 2-3139 | (b-7) | (b-35) | H | H | (a-1) | —CH— | —NH— | —CH₂C(=O)— |
| 2-3140 | (b-7) | (b-35) | H | H | (a-1) | —CH— | —NH— | —CH₂C(Ph)— |
| 2-3141 | (b-7) | (b-35) | H | H | (a-1) | —CH— | —NH— | —CO— |
| 2-3142 | (b-7) | (b-35) | H | H | (a-1) | —CH— | —NH— | —COCH₂— |
| 2-3143 | (b-7) | (b-35) | H | H | (a-1) | —CH— | —O— | —CH(Me)— |
| 2-3144 | (b-7) | (b-35) | H | H | (a-1) | —CH— | —S— | —CH(Me)— |
| 2-3145 | (b-7) | (b-35) | 4-F | H | (a-1) | —CH— | —NH— | —CH(Me)— |

TABLE 2-continued

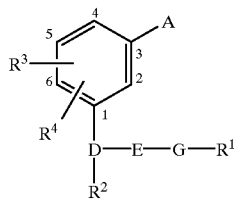

(I-2)

| Cpd. No. | R¹ Sub. No | R² Sub. No | R³ | R⁴ | A Sub. No | D | E | G |
|---|---|---|---|---|---|---|---|---|
| 2-3146 | (b-7) | (b-35) | 6-F | H | (a-1) | —CH— | —NH— | —CH(Me)— |
| 2-3147 | (b-7) | (b-35) | 4-Cl | H | (a-1) | —CH— | —NH— | —CH(Me)— |
| 2-3148 | (b-7) | (b-35) | 6-Cl | H | (a-1) | —CH— | —NH— | —CH(Me)— |
| 2-3149 | (b-7) | (b-35) | 4-MeO | H | (a-1) | —CH— | —NH— | —CH(Me)— |
| 2-3150 | (b-7) | (b-35) | 6-MeO | H | (a-1) | —CH— | —NH— | —CH(Me)— |
| 2-3151 | (b-7) | (b-35) | H | H | (a-1) | N | —CO— | —CH(Me)— |
| 2-3152 | (b-7) | (b-37) | H | H | (a-1) | —CH— | —NH— | —CO— |
| 2-3153 | (b-7) | (b-37) | H | H | (a-1) | —CH— | —NH— | —COCH₂— |
| 2-3154 | (b-7) | (b-37) | H | H | (a-1) | —CH— | —O— | —CH(Me)— |
| 2-3155 | (b-7) | (b-37) | H | H | (a-1) | —CH— | —S— | —CH(Me)— |
| 2-3156 | (b-7) | (b-37) | H | H | (a-1) | N | —CO— | —CH(Me)— |
| 2-3157 | (b-7) | (b-38) | H | H | (a-1) | —CH— | —NH— | —CH(Me)— |
| 2-3158 | (b-7) | (b-41) | H | H | (a-1) | —CH— | —NH— | —CH(Me)— |
| 2-3159 | (b-7) | (b-42) | H | H | (a-1) | —CH— | —NH— | —CH(Me)— |
| 2-3160 | (b-7) | (b-43) | H | H | (a-1) | —CH— | —NH— | —CH(Me)— |
| 2-3161 | (b-8) | (b-7) | H | H | (a-1) | —CH— | —NH— | —CH(Me)— |
| 2-3162 | (b-8) | (b-12) | H | H | (a-1) | —CH— | —NH— | —CH(Me)— |
| 2-3163 | (b-8) | (b-15) | H | H | (a-1) | —CH— | —NH— | —CH(Me)— |
| 2-3164 | (b-8) | (b-28) | H | H | (a-1) | —CH— | —NH— | —CH(Me)— |
| 2-3165 | (b-8) | (b-35) | 6-MeO | H | (a-1) | —CH— | —NH— | —CH(Me)— |
| 2-3166 | (b-11) | (b-1) | H | H | (a-1) | —CH— | —NH— | —CH(Me)— |
| 2-3167 | (b-11) | (b-2) | H | H | (a-1) | —CH— | —NH— | —CH(Me)— |
| 2-3168 | (b-11) | (b-7) | H | H | (a-1) | —CH— | —NH— | single bond |
| 2-3169 | (b-11) | (b-7) | H | H | (a-1) | —CH— | —NH— | —CH₂— |
| 2-3170 | (b-11) | (b-7) | H | H | (a-1) | —CH— | —NH— | —(CH₂)₂— |
| 2-3171 | (b-11) | (b-7) | H | H | (a-1) | —CH— | —NH— | —CH(Et)— |
| 2-3172 | (b-11) | (b-7) | H | H | (a-1) | —CH— | —NH— | —(CH₂)₃— |
| 2-3173 | (b-11) | (b-7) | H | H | (a-1) | —CH— | —NH— | —CO— |
| 2-3174 | (b-11) | (b-7) | H | H | (a-1) | —CH— | —NH— | —COCH₂— |
| 2-3175 | (b-11) | (b-7) | H | H | (a-1) | —CH— | —O— | —CH(Me)— |
| 2-3176 | (b-11) | (b-7) | H | H | (a-1) | —CH— | —S— | —CH(Me)— |
| 2-3177 | (b-11) | (b-7) | H | H | (a-1) | N | —CO— | —CH(Me)— |
| 2-3178 | (b-11) | (b-8) | H | H | (a-1) | —CH— | —NH— | —CH(Me)— |
| 2-3179 | (b-11) | (b-10) | H | H | (a-1) | —CH— | —NH— | —CH(Me)— |
| 2-3180 | (b-11) | (b-11) | H | H | (a-1) | —CH— | —NH— | —CH(Me)— |
| 2-3181 | (b-11) | (b-12) | H | H | (a-1) | —CH— | —NH— | —COCH(Me)— |
| 2-3182 | (b-11) | (b-12) | H | H | (a-1) | —CH— | —O— | —CH(Me)— |
| 2-3183 | (b-11) | (b-12) | H | H | (a-1) | —CH— | —S— | —CH(Me)— |
| 2-3184 | (b-11) | (b-12) | H | H | (a-1) | N | —CO— | —CH(Me)— |
| 2-3185 | (b-11) | (b-13) | H | H | (a-1) | —CH— | —NH— | —CH(Me)— |
| 2-3186 | (b-11) | (b-14) | H | H | (a-1) | —CH— | —NH— | —CH(Me)— |
| 2-3187 | (b-11) | (b-15) | H | H | (a-1) | —CH— | —NH— | —COCH(Me)— |
| 2-3188 | (b-11) | (b-15) | H | H | (a-1) | —CH— | —O— | —CH(Me)— |
| 2-3189 | (b-11) | (b-15) | H | H | (a-1) | —CH— | —S— | —CH(Me)— |
| 2-3290 | (b-11) | (b-15) | H | H | (a-1) | N | —CO— | —CH(Me)— |
| 2-3291 | (b-11) | (b-16) | H | H | (a-1) | —CH— | —NH— | —CH(Me)— |
| 2-3292 | (b-11) | (b-17) | H | H | (a-1) | —CH— | —NH— | —CH(Me)— |
| 2-3293 | (b-11) | (b-23) | H | H | (a-1) | —CH— | —NH— | —CH(Me)— |
| 2-3294 | (b-11) | (b-24) | H | H | (a-1) | —CH— | —NH— | —CH(Me)— |
| 2-3295 | (b-11) | (b-25) | H | H | (a-l) | —CH— | —NH— | —CH(Me)— |
| 2-3296 | (b-11) | (b-27) | H | H | (a-1) | —CH— | —NH— | —CH(Me)— |
| 2-3297 | (b-11) | (b-28) | H | H | (a-1) | —CH— | —NH— | —CH(Me)— |
| 2-3298 | (b-11) | (b-30) | H | H | (a-1) | —CH— | —NH— | —CH(Me)— |
| 2-3299 | (b-11) | (b-31) | H | H | (a-1) | —CH— | —NH— | —CH(Me)— |
| 2-3200 | (b-11) | (b-32) | H | H | (a-1) | —CH— | —NH— | —CH(Me)— |
| 2-3201 | (b-11) | (b-33) | H | H | (a-1) | —CH— | —NH— | —CH(Me)— |
| 2-3202 | (b-11) | (b-34) | H | H | (a-1) | —CH— | —NH— | —COCH(Me)— |
| 2-3203 | (b-11) | (b-34) | H | H | (a-1) | —CH— | —O— | —CH(Me)— |
| 2-3204 | (b-11) | (b-34) | H | H | (a-1) | —CH— | —S— | —CH(Me)— |
| 2-3205 | (b-11) | (b-34) | H | H | (a-1) | N | —CO— | —CH(Me)— |
| 2-3206 | (b-11) | (b-35) | H | H | (a-1) | —CH— | —NH— | single bond |
| 2-3207 | (b-11) | (b-35) | H | H | (a-1) | —CH— | —NH— | —CH₂— |
| 2-3208 | (b-11) | (b-35) | H | H | (a-1) | —CH— | —NH— | —(CH₂)₂— |
| 2-3209 | (b-11) | (b-35) | H | H | (a-1) | —CH— | —NH— | —CH(Et)— |

TABLE 2-continued (I-2)

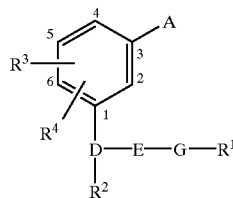

| Cpd. No. | R¹ Sub. No | R² Sub. No | R³ | R⁴ | A Sub. No | D | E | G |
|---|---|---|---|---|---|---|---|---|
| 2-3210 | (b-11) | (b-35) | H | H | (a-1) | —CH— | —NH— | —(CH₂)₃— |
| 2-3211 | (b-11) | (b-35) | H | H | (a-1) | —CH— | —NH— | —CH₂CH(Me)— |
| 2-3212 | (b-11) | (b-35) | H | H | (a-1) | —CH— | —NH— | —CH₂CH(OH)— |
| 2-3213 | (b-11) | (b-35) | H | H | (a-1) | —CH— | —NH— | —CH₂C(=O)— |
| 2-3214 | (b-11) | (b-35) | H | H | (a-1) | —CH— | —NH— | —CH₂C(Ph)— |
| 2-3215 | (b-11) | (b-35) | H | H | (a-1) | —CH— | —O— | —CH(Me)— |
| 2-3216 | (b-11) | (b-35) | H | H | (a-1) | —CH— | —S— | —CH(Me)— |
| 2-3217 | (b-11) | (b-35) | 4-F | H | (a-1) | —CH— | —NH— | —CH(Me)— |
| 2-3218 | (b-11) | (b-35) | 6-F | H | (a-1) | —CH— | —NH— | —CH(Me)— |
| 2-3219 | (b-11) | (b-35) | 4-Cl | H | (a-1) | —CH— | —NH— | —CH(Me)— |
| 2-3220 | (b-11) | (b-35) | 6-Cl | H | (a-1) | —CH— | —NH— | —CH(Me)— |
| 2-3221 | (b-11) | (b-35) | 4-MeO | H | (a-1) | —CH— | —NH— | —CH(Me)— |
| 2-3222 | (b-11) | (b-35) | 6-MeO | H | (a-1) | —CH— | —NH— | —CH(Me)— |
| 2-3223 | (b-11) | (b-35) | H | H | (a-1) | N | —CO— | —CH(Me)— |
| 2-3224 | (b-11) | (b-37) | H | H | (a-1) | —CH— | —NH— | single bond |
| 2-3225 | (b-11) | (b-37) | H | H | (a-1) | —CH— | —NH— | —CH₂— |
| 2-3226 | (b-11) | (b-37) | H | H | (a-1) | —CH— | —NH— | —(CH₂)₂— |
| 2-3227 | (b-11) | (b-37) | H | H | (a-1) | —CH— | —NH— | —CH(Et)— |
| 2-3228 | (b-11) | (b-37) | H | H | (a-1) | —CH— | —NH— | —(CH₂)₃— |
| 2-3229 | (b-11) | (b-37) | H | H | (a-1) | —CH— | —NH— | —CH₂CH(Me)— |
| 2-3230 | (b-11) | (b-37) | H | H | (a-1) | —CH— | —NH— | —CH₂CH(OH)— |
| 2-3231 | (b-11) | (b-37) | H | H | (a-1) | —CH— | —NH— | —CH₂C(=O)— |
| 2-3232 | (b-11) | (b-37) | H | H | (a-1) | —CH— | —NH— | —CH₂C(Ph)— |
| 2-3233 | (b-11) | (b-37) | H | H | (a-1) | —CH— | —NH— | —COCH(Me)— |
| 2-3234 | (b-11) | (b-37) | H | H | (a-1) | —CH— | —O— | —CH(Me)— |
| 2-3235 | (b-11) | (b-37) | H | H | (a-1) | —CH— | —S— | —CH(Me)— |
| 2-3236 | (b-11) | (b-37) | H | H | (a-1) | N | —CO— | —CH(Me)— |
| 2-3237 | (b-11) | (b-38) | H | H | (a-1) | —CH— | —NH— | —CH(Me)— |
| 2-3238 | (b-11) | (b-41) | H | H | (a-1) | —CH— | —NH— | —CH(Me)— |
| 2-3239 | (b-11) | (b-42) | H | H | (a-1) | —CH— | —NH— | —CH(Me)— |
| 2-3240 | (b-11) | (b-43) | H | H | (a-1) | —CH— | —NH— | —CH(Me)— |
| 2-3241 | (b-11) | (b-72) | H | H | (a-1) | —CH— | —NH— | —CH(Me)— |
| 2-3242 | (b-11) | (b-72) | 6-Cl | H | (a-1) | —CH— | —NH— | —CH(Me)— |
| 2-3243 | (b-11) | (b-72) | 4-MeO | H | (a-1) | —CH— | —NH— | —CH(Me)— |
| 2-3244 | (b-11) | (b-72) | 6-MeO | H | (a-1) | —CH— | —NH— | —CH(Me)— |
| 2-3245 | (b-11) | (b-73) | H | H | (a-1) | —CH— | —NH— | —COCH(Me)— |
| 2-3246 | (b-11) | (b-73) | H | H | (a-1) | —CH— | —O— | —CH(Me)— |
| 2-3247 | (b-11) | (b-73) | H | H | (a-1) | —CH— | —S— | —CH(Me)— |
| 2-3248 | (b-11) | (b-73) | 4-F | H | (a-1) | —CH— | —NH— | —CH(Me)— |
| 2-3249 | (b-11) | (b-73) | 6-F | H | (a-1) | —CH— | —NH— | —CH(Me)— |
| 2-3250 | (b-11) | (b-73) | 4-Cl | H | (a-1) | —CH— | —NH— | —CH(Me)— |
| 2-3251 | (b-11) | (b-73) | 6-Cl | H | (a-1) | —CH— | —NH— | —CH(Me)— |
| 2-3252 | (b-11) | (b-73) | 4-MeO | H | (a-1) | —CH— | —NH— | —CH(Me)— |
| 2-3253 | (b-11) | (b-73) | 6-MeO | H | (a-1) | —CH— | —NH— | —CH(Me)— |
| 2-3254 | (b-11) | (b-73) | H | H | (a-1) | N | —CO— | —CH(Me)— |
| 2-3255 | (b-11) | (b-74) | H | H | (a-1) | —CH— | —NH— | —CH(Me)— |
| 2-3256 | (b-11) | (b-76) | H | H | (a-1) | —CH— | —NH— | —CH(Me)— |
| 2-3257 | (b-11) | (b-77) | 6-F | H | (a-1) | —CH— | —NH— | —CH(Me)— |
| 2-3258 | (b-11) | (b-77) | 6-Cl | H | (a-1) | —CH— | —NH— | —CH(Me)— |
| 2-3259 | (b-11) | (b-77) | 4-MeO | H | (a-1) | —CH— | —NH— | —CH(Me)— |
| 2-3260 | (b-11) | (b-77) | 6-MeO | H | (a-1) | —CH— | —NH— | —CH(Me)— |
| 2-3261 | (b-14) | (b-7) | H | H | (a-1) | —CH— | —NH— | single bond |
| 2-3262 | (b-14) | (b-7) | H | H | (a-1) | —CH— | —NH— | —CH₂— |
| 2-3263 | (b-14) | (b-7) | H | H | (a-1) | —CH— | —NH— | —(CH₂)₂— |
| 2-3264 | (b-14) | (b-7) | H | H | (a-1) | —CH— | —NH— | —CH(Me)— |
| 2-3265 | (b-14) | (b-7) | H | H | (a-1) | —CH— | —NH— | —CH(Et)— |
| 2-3266 | (b-14) | (b-7) | H | H | (a-1) | —CH— | —NH— | —(CH₂)₃— |
| 2-3267 | (b-14) | (b-7) | H | H | (a-1) | —CH— | —NH— | —CH₂CH(Me)— |
| 2-3268 | (b-14) | (b-7) | H | H | (a-1) | —CH— | —NH— | —CH₂CH(OH)— |
| 2-3269 | (b-14) | (b-7) | H | H | (a-1) | —CH— | —NH— | —CH₂C(=O)— |
| 2-3270 | (b-14) | (b-7) | H | H | (a-1) | —CH— | —NH— | —CH₂C(Ph)— |
| 2-3271 | (b-14) | (b-7) | H | H | (a-1) | —CH— | —NH— | —COCH(Me)— |
| 2-3272 | (b-14) | (b-7) | H | H | (a-1) | —CH— | —O— | —CH(Me)₂— |
| 2-3273 | (b-14) | (b-7) | H | H | (a-1) | —CH— | —S— | —CH(Me)— |

TABLE 2-continued

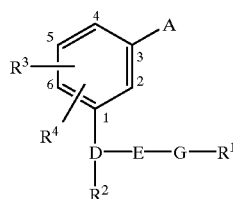

(I-2)

| Cpd. No. | $R^1$ Sub. No | $R^2$ Sub. No | $R^3$ | $R^4$ | A Sub. No | D | E | G |
|---|---|---|---|---|---|---|---|---|
| 2-3274 | (b-14) | (b-7) | 4-F | H | (a-1) | —CH— | —NH— | —CH(Me)— |
| 2-3275 | (b-14) | (b-7) | 6-F | H | (a-1) | —CH— | —NH— | —CH(Me)— |
| 2-3276 | (b-14) | (b-7) | 4-Cl | H | (a-1) | —CH— | —NH— | —CH(Me)— |
| 2-3277 | (b-14) | (b-7) | 6-Cl | H | (a-1) | —CH— | —NH— | —CH(Me)— |
| 2-3278 | (b-14) | (b-7) | 4-MeO | H | (a-1) | —CH— | —NH— | —CH(Me)— |
| 2-3279 | (b-14) | (b-7) | 6-MeO | H | (a-1) | —CH— | —NH— | —CH(Me)— |
| 2-3280 | (b-14) | (b-7) | H | H | (a-1) | N | —CO— | —CH(Me)— |
| 2-3281 | (b-14) | (b-11) | H | H | (a-1) | —CH— | —NH— | —CH(Me)— |
| 2-3282 | (b-14) | (b-12) | H | H | (a-1) | —CH— | —NH— | —CH(Me)— |
| 2-3283 | (b-14) | (b-12) | 6-Cl | H | (a-1) | —CH— | —NH— | —CH(Me)— |
| 2-3284 | (b-14) | (b-12) | 6-F | H | (a-1) | —CH— | —NH— | —CH(Me)— |
| 2-3285 | (b-14) | (b-12) | 6-MeO | H | (a-1) | —CH— | —NH— | —CH(Me)— |
| 2-3286 | (b-14) | (b-14) | H | H | (a-1) | —CH— | —NH— | —CH(Me)— |
| 2-3287 | (b-14) | (b-15) | H | H | (a-1) | —CH— | —NH— | —CH(Me)— |
| 2-3288 | (b-14) | (b-15) | 6-Cl | H | (a-1) | —CH— | —NH— | —CH(Me)— |
| 2-3289 | (b-14) | (b-15) | 6-F | H | (a-1) | —CH— | —NH— | —CH(Me)— |
| 2-3390 | (b-14) | (b-15) | 6-MeO | H | (a-1) | —CH— | —NH— | —CH(Me)— |
| 2-3391 | (b-14) | (b-17) | H | H | (a-1) | —CH— | —NH— | —CH(Me)— |
| 2-3392 | (b-14) | (b-25) | H | H | (a-1) | —CH— | —NH— | —CH(Me)— |
| 2-3393 | (b-14) | (b-33) | H | H | (a-1) | —CH— | —NH— | —CH(Me)— |
| 2-3394 | (b-14) | (b-34) | H | H | (a-1) | —CH— | —NH— | —CH(Me)— |
| 2-3395 | (b-14) | (b-34) | 6-Cl | H | (a-1) | —CH— | —NH— | —CH(Me)— |
| 2-3396 | (b-14) | (b-34) | 6-F | H | (a-1) | —CH— | —NH— | —CH(Me)— |
| 2-3397 | (b-14) | (b-34) | 6-MeO | H | (a-1) | —CH— | —NH— | —CH(Me)— |
| 2-3398 | (b-14) | (b-35) | H | H | (a-1) | —CH— | —NH— | single bond |
| 2-3399 | (b-14) | (b-35) | H | H | (a-1) | —CH— | —NH— | —CH$_2$— |
| 2-3300 | (b-14) | (b-35) | H | H | (a-1) | —CH— | —NH— | —(CH$_2$)$_2$— |
| 2-3301 | (b-14) | (b-35) | H | H | (a-1) | —CH— | —NH— | —CH(Et)— |
| 2-3302 | (b-14) | (b-35) | H | H | (a-1) | —CH— | —NH— | —(CH$_2$)$_3$— |
| 2-3303 | (b-14) | (b-35) | H | H | (a-1) | —CH— | —NH— | —CH$_2$CH(Me)— |
| 2-3304 | (b-14) | (b-35) | H | H | (a-1) | —CH— | —NH— | —COCH(Me)— |
| 2-3305 | (b-14) | (b-35) | H | H | (a-1) | —CH— | —O— | —CH(Me)— |
| 2-3306 | (b-14) | (b-35) | H | H | (a-1) | —CH— | —S— | —CH(Me)— |
| 2-3307 | (b-14) | (b-35) | 4-F | H | (a-1) | —CH— | —NH— | —CH(Me)— |
| 2-3308 | (b-14) | (b-35) | 6-F | H | (a-1) | —CH— | —NH— | —CH(Me)— |
| 2-3309 | (b-14) | (b-35) | 4-Cl | H | (a-1) | —CH— | —NH— | —CH(Me)— |
| 2-3310 | (b-14) | (b-35) | 6-Cl | H | (a-1) | —CH— | —NH— | —CH(Me)— |
| 2-3311 | (b-14) | (b-35) | 4-MeO | H | (a-1) | —CH— | —NH— | —CH(Me)— |
| 2-3312 | (b-14) | (b-35) | 6-MeO | H | (a-1) | —CH— | —NH— | —CH(Me)— |
| 2-3313 | (b-14) | (b-35) | H | H | (a-1) | N | —CO— | —CH(Me)— |
| 2-3314 | (b-14) | (b-37) | H | H | (a-1) | —CH— | —NH— | single bond |
| 2-3315 | (b-14) | (b-37) | H | H | (a-1) | —CH— | —NH— | —CH$_2$— |
| 2-3316 | (b-14) | (b-37) | H | H | (a-1) | —CH— | —NH— | —(CH$_2$)$_2$— |
| 2-3317 | (b-14) | (b-37) | H | H | (a-1) | —CH— | —NH— | —CH(Me)— |
| 2-3318 | (b-14) | (b-37) | H | H | (a-1) | —CH— | —NH— | —CH(Et)— |
| 2-3319 | (b-14) | (b-37) | H | H | (a-1) | —CH— | —NH— | —(CH$_2$)$_3$— |
| 2-3320 | (b-14) | (b-37) | H | H | (a-1) | —CH— | —NH— | —CH$_2$CH(Me)— |
| 2-3321 | (b-14) | (b-37) | H | H | (a-1) | —CH— | —NH— | —COCH(Me)— |
| 2-3322 | (b-14) | (b-37) | H | H | (a-1) | —CH— | —O— | —CH(Me)— |
| 2-3323 | (b-14) | (b-37) | H | H | (a-1) | —CH— | —S— | —CH(Me)— |
| 2-3324 | (b-14) | (b-37) | 4-F | H | (a-1) | —CH— | —NH— | —CH(Me)— |
| 2-3325 | (b-14) | (b-37) | 6-F | H | (a-1) | —CH— | —NH— | —CH(Me)— |
| 2-3326 | (b-14) | (b-37) | 4-Cl | H | (a-1) | —CH— | —NH— | —CH(Me)— |
| 2-3327 | (b-14) | (b-37) | 6-Cl | H | (a-1) | —CH— | —NH— | —CH(Me)— |
| 2-3328 | (b-14) | (b-37) | 4-MeO | H | (a-1) | —CH— | —NH— | —CH(Me)— |
| 2-3329 | (b-14) | (b-37) | 6-MeO | H | (a-1) | —CH— | —NH— | —CH(Me)— |
| 2-3330 | (b-14) | (b-37) | H | H | (a-1) | N | —CO— | —CH(Me)— |
| 2-3331 | (b-14) | (b-42) | H | H | (a-1) | —CH— | —NH— | —CH(Me)— |
| 2-3332 | (b-14) | (b-72) | H | H | (a-1) | —CH— | —NH— | —CH(Me)— |
| 2-3333 | (b-14) | (b-72) | 6-Cl | H | (a-1) | —CH— | —NH— | —CH(Me)— |
| 2-3334 | (b-14) | (b-72) | 6-F | H | (a-1) | —CH— | —NH— | —CH(Me)— |
| 2-3335 | (b-14) | (b-72) | 6-MeO | H | (a-1) | —CH— | —NH— | —CH(Me)— |
| 2-3336 | (b-14) | (b-73) | H | H | (a-1) | —CH— | —NH— | single bond |
| 2-3337 | (b-14) | (b-73) | H | H | (a-1) | —CH— | —NH— | —CH$_2$— |

TABLE 2-continued

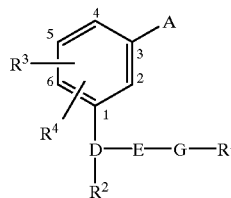

(I-2)

| Cpd. No. | R¹ Sub. No | R² Sub. No | R³ | R⁴ | A Sub. No | D | E | G |
|---|---|---|---|---|---|---|---|---|
| 2-3338 | (b-14) | (b-73) | H | H | (a-1) | —CH— | —NH— | —(CH$_2$)$_2$— |
| 2-3339 | (b-14) | (b-73) | H | H | (a-1) | —CH— | —NH— | —CH(Me)— |
| 2-3340 | (b-14) | (b-73) | H | H | (a-1) | —CH— | —NH— | —CH(Et)— |
| 2-3341 | (b-14) | (b-73) | H | H | (a-1) | —CH— | —NH— | —(CH$_2$)$_3$— |
| 2-3342 | (b-14) | (b-73) | H | H | (a-1) | —CH— | —NH— | —CH$_2$CH(Me)— |
| 2-3343 | (b-14) | (b-73) | H | H | (a-1) | —CH— | —NH— | —COCH(Me)— |
| 2-3344 | (b-14) | (b-73) | H | H | (a-1) | —CH— | —O— | —CH(Me)— |
| 2-3345 | (b-14) | (b-73) | H | H | (a-1) | —CH— | —S— | —CH(Me)— |
| 2-3346 | (b-14) | (b-73) | 4-F | H | (a-1) | —CH— | —NH— | —CH(Me)— |
| 2-3347 | (b-14) | (b-73) | 6-F | H | (a-1) | —CH— | —NH— | —CH(Me)— |
| 2-3348 | (b-14) | (b-73) | 4-Cl | H | (a-1) | —CH— | —NH— | —CH(Me)— |
| 2-3349 | (b-14) | (b-73) | 6-Cl | H | (a-1) | —CH— | —NH— | —CH(Me)— |
| 2-3350 | (b-14) | (b-73) | 4-MeO | H | (a-1) | —CH— | —NH— | —CH(Me)— |
| 2-3351 | (b-14) | (b-73) | 6-MeO | H | (a-1) | —CH— | —NH— | —CH(Me)— |
| 2-3352 | (b-14) | (b-73) | H | H | (a-1) | N | —CO— | —CH(Me)— |
| 2-3353 | (b-14) | (b-74) | H | H | (a-1) | —CH— | —NH— | —CH(Me)— |
| 2-3354 | (b-14) | (b-76) | H | H | (a-1) | —CH— | —NH— | —CH(Me)— |
| 2-3355 | (b-14) | (b-77) | H | H | (a-1) | —CH— | —NH— | —CH(Me)— |
| 2-3356 | (b-14) | (b-77) | 6-Cl | H | (a-1) | —CH— | —NH— | —CH(Me)— |
| 2-3357 | (b-14) | (b-77) | 6-F | H | (a-1) | —CH— | —NH— | —CH(Me)— |
| 2-3358 | (b-14) | (b-77) | 6-MeO | H | (a-1) | —CH— | —NH— | —CH(Me)— |
| 2-3359 | (b-18) | (b-7) | H | H | (a-1) | —CH— | —NH— | single bond |
| 2-3360 | (b-18) | (b-7) | H | H | (a-1) | —CH— | —NH— | —CH$_2$— |
| 2-3361 | (b-18) | (b-7) | H | H | (a-1) | —CH— | —NH— | —(CH$_2$)$_2$— |
| 2-3362 | (b-18) | (b-7) | H | H | (a-1) | —CH— | —NH— | —CH(Et)— |
| 2-3363 | (b-18) | (b-7) | H | H | (a-1) | —CH— | —NH— | —(CH$_2$)$_3$— |
| 2-3364 | (b-18) | (b-7) | H | H | (a-1) | —CH— | —NH— | —CH$_2$CH(Me)— |
| 2-3365 | (b-18) | (b-7) | H | H | (a-1) | —CH— | —NH— | —COCH(Me)— |
| 2-3366 | (b-18) | (b-7) | H | H | (a-1) | —CH— | —O— | —CH(Me)— |
| 2-3367 | (b-18) | (b-7) | H | H | (a-1) | —CH— | —S— | —CH(Me)— |
| 2-3368 | (b-18) | (b-7) | 4-F | H | (a-1) | —CH— | —NH— | —CH(Me)— |
| 2-3369 | (b-18) | (b-7) | 6-F | H | (a-1) | —CH— | —NH— | —CH(Me)— |
| 2-3370 | (b-18) | (b-7) | 4-Cl | H | (a-1) | —CH— | —NH— | —CH(Me)— |
| 2-3371 | (b-18) | (b-7) | 6-Cl | H | (a-1) | —CH— | —NH— | —CH(Me)— |
| 2-3372 | (b-18) | (b-7) | 4-MeO | H | (a-1) | —CH— | —NH— | —CH(Me)— |
| 2-3373 | (b-18) | (b-7) | 6-MeO | H | (a-1) | —CH— | —NH— | —CH(Me)— |
| 2-3374 | (b-18) | (b-7) | H | H | (a-1) | N | —CO— | —CH(Me)— |
| 2-3375 | (b-18) | (b-11) | H | H | (a-1) | —CH— | —NH— | —CH(Me)— |
| 2-3376 | (b-18) | (b-12) | 6-MeO | H | (a-1) | —CH— | —NH— | —CH(Me)— |
| 2-3377 | (b-18) | (b-12) | 4-MeO | 5-MeO | (a-1) | —CH— | —NH— | —CH(Me)— |
| 2-3378 | (b-18) | (b-12) | 4-MeO | H | (a-1) | —CH— | —NH— | —CH(Me)— |
| 2-3379 | (b-18) | (b-14) | H | H | (a-1) | —CH— | —NH— | —CH(Me)— |
| 2-3380 | (b-18) | (b-15) | 6-Cl | H | (a-1) | —CH— | —NH— | —CH(Me)— |
| 2-3381 | (b-18) | (b-15) | 6-F | H | (a-1) | —CH— | —NH— | —CH(Me)— |
| 2-3382 | (b-18) | (b-15) | 6-MeO | H | (a-1) | —CH— | —NH— | —CH(Me)— |
| 2-3383 | (b-18) | (b-17) | H | H | (a-1) | —CH— | —NH— | —CH(Me)— |
| 2-3384 | (b-18) | (b-25) | H | H | (a-1) | —CH— | —NH— | —CH(Me)— |
| 2-3385 | (b-18) | (b-27) | H | H | (a-1) | —CH— | —NH— | —CH(Me)— |
| 2-3386 | (b-18) | (b-28) | H | H | (a-1) | —CH— | —NH— | —CH(Me)— |
| 2-3387 | (b-18) | (b-33) | H | H | (a-1) | —CH— | —NH— | —CH(Me)— |
| 2-3388 | (b-18) | (b-34) | 6-Cl | H | (a-1) | —CH— | —NH— | —CH(Me)— |
| 2-3389 | (b-18) | (b-34) | 6-F | H | (a-1) | —CH— | —NH— | —CH(Me)— |
| 2-3490 | (b-18) | (b-34) | 6-MeO | H | (a-1) | —CH— | —NH— | —CH(Me)— |
| 2-3491 | (b-18) | (b-35) | H | H | (a-1) | —CH— | —NH— | single bond |
| 2-3492 | (b-18) | (b-35) | H | H | (a-1) | —CH— | —NH— | —CH$_2$— |
| 2-3493 | (b-18) | (b-35) | H | H | (a-1) | —CH— | —NH— | —(CH$_2$)$_2$— |
| 2-3494 | (b-18) | (b-35) | H | H | (a-1) | —CH— | —NH— | —CH(Et)— |
| 2-3495 | (b-18) | (b-35) | H | H | (a-1) | —CH— | —NH— | —(CH$_2$)$_3$— |
| 2-3496 | (b-18) | (b-35) | H | H | (a-1) | —CH— | —NH— | —CH$_2$CH(Me)— |
| 2-3497 | (b-18) | (b-35) | H | H | (a-1) | —CH— | —NH— | —COCH(Me)— |
| 2-3498 | (b-18) | (b-35) | H | H | (a-1) | —CH— | —O— | —CH(Me)— |
| 2-3499 | (b-18) | (b-35) | H | H | (a-1) | —CH— | —S— | —CH(Me)— |
| 2-3400 | (b-18) | (b-35) | 4-F | H | (a-1) | —CH— | —NH— | —CH(Me)— |
| 2-3401 | (b-18) | (b-35) | 6-F | H | (a-1) | —CH— | —NH— | —CH(Me)— |

TABLE 2-continued

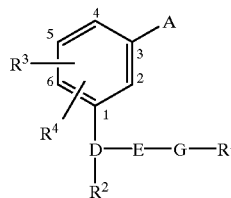

(I-2)

| Cpd. No. | R$^1$ Sub. No | R$^2$ Sub. No | R$^3$ | R$^4$ | A Sub. No | D | E | G |
|---|---|---|---|---|---|---|---|---|
| 2-3402 | (b-18) | (b-35) | 4-Cl | H | (a-1) | —CH— | —NH— | —CH(Me)— |
| 2-3403 | (b-18) | (b-35) | 6-Cl | H | (a-1) | —CH— | —NH— | —CH(Me)— |
| 2-3404 | (b-18) | (b-35) | 4-MeO | H | (a-1) | —CH— | —NH— | —CH(Me)— |
| 2-3405 | (b-18) | (b-35) | 6-MeO | H | (a-1) | —CH— | —NH— | —CH(Me)— |
| 2-3406 | (b-18) | (b-35) | 4-MeO | 5-MeO | (a-1) | —CH— | —NH— | —CH(Me)— |
| 2-3407 | (b-18) | (b-35) | H | H | (a-1) | N | —CO— | —CH(Me)— |
| 2-3408 | (b-18) | (b-37) | 4-F | H | (a-1) | —CH— | —NH— | —CH(Me)— |
| 2-3409 | (b-18) | (b-37) | 6-F | H | (a-1) | —CH— | —NH— | —CH(Me)— |
| 2-3410 | (b-18) | (b-37) | 4-Cl | H | (a-1) | —CH— | —NH— | —CH(Me)— |
| 2-3411 | (b-18) | (b-37) | 6-Cl | H | (a-1) | —CH— | —NH— | —CH(Me)— |
| 2-3412 | (b-18) | (b-37) | 4-MeO | H | (a-1) | —CH— | —NH— | —CH(Me)— |
| 2-3413 | (b-18) | (b-37) | 6-MeO | H | (a-1) | —CH— | —NH— | —CH(Me)— |
| 2-3414 | (b-18) | (b-42) | H | H | (a-1) | —CH— | —NH— | —CH(Me)— |
| 2-3415 | (b-18) | (b-72) | H | H | (a-1) | —CH— | —NH— | —CH(Me)— |
| 2-3416 | (b-18) | (b-73) | H | H | (a-1) | —CH— | —NH— | single bond |
| 2-3417 | (b-18) | (b-73) | H | H | (a-1) | —CH— | —NH— | —CH$_2$— |
| 2-3418 | (b-18) | (b-73) | H | H | (a-1) | —CH— | —NH— | —(CH$_2$)$_2$— |
| 2-3419 | (b-18) | (b-73) | H | H | (a-1) | —CH— | —NH— | —CH(Et)— |
| 2-3420 | (b-18) | (b-73) | H | H | (a-1) | —CH— | —NH— | —(CH$_2$)$_3$— |
| 2-3421 | (b-18) | (b-73) | H | H | (a-1) | —CH— | —NH— | —CH$_2$CH(Me)— |
| 2-3422 | (b-18) | (b-73) | H | H | (a-1) | —CH— | —NH— | —COCH(Me)— |
| 2-3423 | (b-18) | (b-73) | H | H | (a-1) | —CH— | —O— | —CH(Me)— |
| 2-3424 | (b-18) | (b-73) | H | H | (a-1) | —CH— | —S— | —CH(Me)— |
| 2-3425 | (b-18) | (b-73) | 4-F | H | (a-1) | —CH— | —NH— | —CH(Me)— |
| 2-3426 | (b-18) | (b-73) | 6-F | H | (a-1) | —CH— | —NH— | —CH(Me)— |
| 2-3427 | (b-18) | (b-73) | 4-Cl | H | (a-1) | —CH— | —NH— | —CH(Me)— |
| 2-3428 | (b-18) | (b-73) | 6-Cl | H | (a-1) | —CH— | —NH— | —CH(Me)— |
| 2-3429 | (b-18) | (b-73) | 4-MeO | H | (a-1) | —CH— | —NH— | —CH(Me)— |
| 2-3430 | (b-18) | (b-73) | 6-MeO | H | (a-1) | —CH— | —NH— | —CH(Me)— |
| 2-3431 | (b-18) | (b-73) | H | H | (a-1) | N | —CO— | —CH(Me)— |
| 2-3432 | (b-18) | (b-74) | H | H | (a-1) | —CH— | —NH— | —CH(Me)— |
| 2-3433 | (b-18) | (b-76) | H | H | (a-1) | —CH— | —NH— | —CH(Me)— |
| 2-3434 | (b-18) | (b-77) | 6-Cl | H | (a-1) | —CH— | —NH— | —CH(Me)— |
| 2-3435 | (b-18) | (b-77) | 6-F | H | (a-1) | —CH— | —NH— | —CH(Me)— |
| 2-3436 | (b-18) | (b-77) | 6-MeO | H | (a-1) | —CH— | —NH— | —CH(Me)— |
| 2-3437 | (b-18) | (b-78) | H | H | (a-1) | —CH— | —NH— | —CH(Me)— |
| 2-3438 | (b-18) | (b-80) | H | H | (a-1) | —CH— | —NH— | —CH(Me)— |
| 2-3439 | (b-18) | (b-83) | H | H | (a-1) | —CH— | —NH— | —CH(Me)— |
| 2-3440 | (b-19) | (b-77) | H | H | (a-1) | —CH— | —NH— | —CH(Me)— |
| 2-3441 | (b-20) | (b-7) | 4-F | H | (a-1) | —CH— | —NH— | —CH(Me)— |
| 2-3442 | (b-20) | (b-7) | 6-F | H | (a-1) | —CH— | —NH— | —CH(Me)— |
| 2-3443 | (b-20) | (b-7) | 4-Cl | H | (a-1) | —CH— | —NH— | —CH(Me)— |
| 2-3444 | (b-20) | (b-7) | 6-Cl | H | (a-1) | —CH— | —NH— | —CH(Me)— |
| 2-3445 | (b-20) | (b-7) | 4-MeO | H | (a-1) | —CH— | —NH— | —CH(Me)— |
| 2-3446 | (b-20) | (b-7) | 6-MeO | H | (a-1) | —CH— | —NH— | —CH(Me)— |
| 2-3447 | (b-20) | (b-11) | H | H | (a-1) | —CH— | —NH— | —CH(Me)— |
| 2-3448 | (b-20) | (b-12) | 6-Cl | H | (a-1) | —CH— | —NH— | —CH(Me)— |
| 2-3449 | (b-20) | (b-12) | 6-F | H | (a-1) | —CH— | —NH— | —CH(Me)— |
| 2-3450 | (b-20) | (b-12) | 6-MeO | H | (a-1) | —CH— | —NH— | —CH(Me)— |
| 2-3451 | (b-20) | (b-14) | H | H | (a-1) | —CH— | —NH— | —CH(Me)— |
| 2-3452 | (b-20) | (b-15) | 6-Cl | H | (a-1) | —CH— | —NH— | —CH(Me)— |
| 2-3453 | (b-20) | (b-15) | 6-MeO | H | (a-1) | —CH— | —NH— | —CH(Me)— |
| 2-3454 | (b-20) | (b-15) | 6-F | H | (a-1) | —CH— | —NH— | —CH(Me)— |
| 2-3455 | (b-20) | (b-17) | H | H | (a-1) | —CH— | —NH— | —CH(Me)— |
| 2-3456 | (b-20) | (b-25) | H | H | (a-1) | —CH— | —NH— | —CH(Me)— |
| 2-3457 | (b-20) | (b-28) | H | H | (a-1) | —CH— | —NH— | —CH(Me)— |
| 2-3458 | (b-20) | (b-33) | H | H | (a-1) | —CH— | —NH— | —CH(Me)— |
| 2-3459 | (b-20) | (b-34) | 6-Cl | H | (a-1) | —CH— | —NH— | —CH(Me)— |
| 2-3460 | (b-20) | (b-34) | 6-F | H | (a-1) | —CH— | —NH— | —CH(Me)— |
| 2-3461 | (b-20) | (b-34) | 6-MeO | H | (a-1) | —CH— | —NH— | —CH(Me)— |
| 2-3462 | (b-20) | (b-35) | H | H | (a-1) | —CH— | —NH— | single bond |
| 2-3463 | (b-20) | (b-35) | H | H | (a-1) | —CH— | —NH— | —CH$_2$— |
| 2-3464 | (b-20) | (b-35) | H | H | (a-1) | —CH— | —NH— | —(CH$_2$)$_2$— |
| 2-3465 | (b-20) | (b-35) | H | H | (a-1) | —CH— | —NH— | —CH(Et)— |

TABLE 2-continued (I-2)

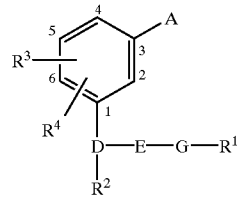

| Cpd. No. | R¹ Sub. No | R² Sub. No | R³ | R⁴ | A Sub. No | D | E | G |
|---|---|---|---|---|---|---|---|---|
| 2-3466 | (b-20) | (b-35) | H | H | (a-1) | —CH— | —NH— | —(CH₂)₃— |
| 2-3467 | (b-20) | (b-35) | H | H | (a-1) | —CH— | —NH— | —CH₂CH(Me)— |
| 2-3468 | (b-20) | (b-35) | H | H | (a-1) | —CH— | —NH— | —COCH(Et)— |
| 2-3469 | (b-20) | (b-35) | H | H | (a-1) | —CH— | —O— | —CH(Me)— |
| 2-3470 | (b-20) | (b-35) | H | H | (a-1) | —CH— | —S— | —CH(Me)— |
| 2-3471 | (b-20) | (b-35) | 4-F | H | (a-1) | —CH— | —NH— | —CH(Me)— |
| 2-3472 | (b-20) | (b-35) | 6-F | H | (a-1) | —CH— | —NH— | —CH(Me)— |
| 2-3473 | (b-20) | (b-35) | 4-Cl | H | (a-1) | —CH— | —NH— | —CH(Me)— |
| 2-3474 | (b-20) | (b-35) | 6-Cl | H | (a-1) | —CH— | —NH— | —CH(Me)— |
| 2-3475 | (b-20) | (b-35) | 4-MeO | H | (a-1) | —CH— | —NH— | —CH(Me)— |
| 2-3476 | (b-20) | (b-35) | 4-MeO | 5-MeO | (a-1) | —CH— | —NH— | —CH(Me)— |
| 2-3477 | (b-20) | (b-35) | 6-MeO | H | (a-1) | —CH— | —NH— | —CH(Me)— |
| 2-3478 | (b-20) | (b-35) | H | H | (a-1) | N | —CO— | —CH(Me)— |
| 2-3479 | (b-20) | (b-37) | 4-F | H | (a-1) | —CH— | —NH— | —CH(Me)— |
| 2-3480 | (b-20) | (b-37) | 6-F | H | (a-1) | —CH— | —NH— | —CH(Me)— |
| 2-3481 | (b-20) | (b-37) | 4-Cl | H | (a-1) | —CH— | —NH— | —CH(Me)— |
| 2-3482 | (b-20) | (b-37) | 6-Cl | H | (a-1) | —CH— | —NH— | —CH(Me)— |
| 2-3483 | (b-20) | (b-37) | 4-MeO | H | (a-1) | —CH— | —NH— | —CH(Me)— |
| 2-3484 | (b-20) | (b-37) | 6-MeO | H | (a-1) | —CH— | —NH— | —CH(Me)— |
| 2-3485 | (b-20) | (b-40) | H | H | (a-1) | —CH— | —NH— | —CH(Me)— |
| 2-3486 | (b-20) | (b-42) | H | H | (a-1) | —CH— | —NH— | —CH(Me)— |
| 2-3487 | (b-20) | (b-74) | H | H | (a-1) | —CH— | —NH— | —CH(Me)— |
| 2-3488 | (b-20) | (b-76) | H | H | (a-1) | —CH— | —NH— | —CH(Me)— |
| 2-3489 | (b-20) | (b-84) | H | H | (a-1) | —CH— | —NH— | —CH(Me)— |
| 2-3590 | (b-20) | (b-85) | H | H | (a-1) | —CH— | —NH— | —CH(Me)— |
| 2-3591 | (b-28) | (b-35) | H | H | (a-1) | —CH— | —NH— | —CH(Me)— |
| 2-3592 | (b-29) | (b-35) | H | H | (a-1) | —CH— | —NH— | —CH(Me)— |
| 2-3593 | (b-30) | (b-35) | H | H | (a-1) | —CH— | —NH— | —CH(Me)— |
| 2-3594 | (b-31) | (b-35) | H | H | (a-1) | —CH— | —NH— | —CH(Me)— |
| 2-3595 | (b-32) | (b-35) | H | H | (a-1) | —CH— | —NH— | —CH(Me)— |
| 2-3596 | (b-33) | (b-35) | H | H | (a-1) | —CH— | —NH— | —CH(Me)— |
| 2-3597 | (b-34) | (b-35) | H | H | (a-1) | —CH— | —NH— | —CH(Me)— |
| 2-3598 | (b-35) | (b-7) | H | H | (a-1) | —CH— | —NH— | —CH(Me)— |
| 2-3599 | (b-36) | (b-35) | H | H | (a-1) | —CH— | —NH— | —CH(Me)— |
| 2-3500 | (b-37) | (b-35) | H | H | (a-1) | —CH— | —NH— | —CH(Me)— |
| 2-3501 | (b-38) | (b-12) | H | H | (a-1) | —CH— | —NH— | —CH(Me)— |
| 2-3502 | (b-81) | (b-12) | H | H | (a-1) | —CH— | —NH— | —CH(Me)— |
| 2-3503 | (b-81) | (b-15) | H | H | (a-1) | —CH— | —NH— | —CH(Me)— |
| 2-3504 | (b-81) | (b-35) | H | H | (a-1) | —CH— | —NH— | —CH(Me)— |
| 2-3505 | (b-82) | (b-12) | H | H | (a-1) | —CH— | —NH— | —CH(Me)— |
| 2-3506 | (b-86) | (b-12) | H | H | (a-1) | —CH— | —NH— | —CH(Me)— |
| 2-3507 | (b-87) | (b-15) | H | H | (a-1) | —CH— | —NH— | —CH(Me)— |
| 2-3508 | (b-88) | (b-7) | H | H | (a-1) | —CH— | —NH— | —CH(Me)— |
| 2-3509 | (b-88) | (b-12) | H | H | (a-1) | —CH— | —NH— | —CH(Me)— |
| 2-3510 | (b-88) | (b-15) | H | H | (a-1) | —CH— | —NH— | —CH(Me)— |
| 2-3511 | (b-88) | (b-28) | H | H | (a-1) | —CH— | —NH— | —CH(Me)— |
| 2-3512 | (b-88) | (b-35) | H | H | (a-1) | —CH— | —NH— | —CH(Me)— |
| 2-3513 | (b-18) | (b-35) | H | H | (a-49) | —CH— | —NH— | —CH(Me)— |
| 2-3514 | (b-18) | (b-35) | H | H | (a-50) | —CH— | —NH— | —CH(Me)— |

TABLE 3

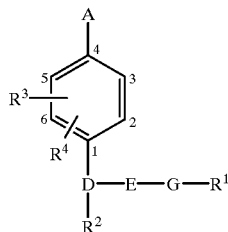

(I-3)

| Cpd. No. | R¹ Sub. No | R² Sub. No | R³ | R⁴ | A Sub. No. | D | E | G |
|---|---|---|---|---|---|---|---|---|
| 3-1 | (b-2) | (b-35) | H | H | (a-1) | —CH— | —NH— | —CH(Me)— |
| 3-2 | (b-7) | (b-7) | H | H | (a-1) | —CH— | —NH— | —CH(Me)— |
| 3-3 | (b-7) | (b-7) | H | H | (a-1) | —CH— | —NH— | —COCH(Me)— |
| 3-4 | (b-7) | (b-35) | H | H | (a-1) | —CH— | —NH— | —CH(Me)— |
| 3-5 | (b-7) | (b-35) | H | H | (a-1) | —CH— | —NH— | —COCH(Me)— |
| 3-6 | (b-8) | (b-35) | H | H | (a-1) | —CH— | —NH— | —CH(Me)— |
| 3-7 | (b-11) | (b-7) | H | H | (a-1) | —CH— | —NH— | —CH(Me)— |
| 3-8 | (b-11) | (b-7) | H | H | (a-1) | —CH— | —NH— | —COCH(Me)— |
| 3-9 | (b-11) | (b-35) | H | H | (a-1) | —CH— | —NH— | —CH(Me)— |
| 3-10 | (b-11) | (b-35) | H | H | (a-1) | —CH— | —NH— | —COCH(Me)— |
| 3-11 | (b-12) | (b-7) | H | H | (a-1) | —CH— | —NH— | —CH(Me)— |
| 3-12 | (b-12) | (b-35) | H | H | (a-1) | —CH— | —NH— | —CH(Me)— |
| 3-13 | (b-15) | (b-7) | H | H | (a-1) | —CH— | —NH— | —CH(Me)— |
| 3-14 | (b-15) | (b-35) | H | H | (a-1) | —CH— | —NH— | —CH(Me)— |
| 3-15 | (b-18) | (b-7) | H | H | (a-1) | —CH— | —NH— | —CH(Me)— |
| 3-16 | (b-18) | (b-7) | H | H | (a-1) | —CH— | —NH— | —COCH(Me)— |
| 3-17 | (b-18) | (b-35) | H | H | (a-1) | —CH— | —NH— | —CH(Me)— |
| 3-18 | (b-18) | (b-35) | H | H | (a-1) | —CH— | —NH— | —COCH(Me)— |
| 3-19 | (b-19) | (b-7) | H | H | (a-1) | —CH— | —NH— | —CH(Me)— |
| 3-20 | (b-19) | (b-35) | H | H | (a-1) | —CH— | —NH— | —CH(Me)— |
| 3-21 | (b-20) | (b-7) | H | H | (a-1) | —CH— | —NH— | —CH(Me)— |
| 3-22 | (b-20) | (b-7) | H | H | (a-1) | —CH— | —NH— | —COCH(Me)— |
| 3-23 | (b-20) | (b-35) | H | H | (a-1) | —CH— | —NH— | —CH(Me)— |
| 3-24 | (b-20) | (b-35) | H | H | (a-1) | —CH— | —NH— | —COCH(Me)— |
| 3-25 | (b-21) | (b-7) | H | H | (a-1) | —CH— | —NH— | —CH(Me)— |
| 3-26 | (b-21) | (b-35) | H | H | (a-1) | —CH— | —NH— | —CH(Me)— |
| 3-27 | (b-24) | (b-7) | H | H | (a-1) | —CH— | —NH— | —CH(Me)— |
| 3-28 | (b-24) | (b-35) | H | H | (a-1) | —CH— | —NH— | —CH(Me)— |
| 3-29 | (b-25) | (b-7) | H | H | (a-1) | —CH— | —NH— | —CH(Me)— |
| 3-30 | (b-25) | (b-35) | H | H | (a-1) | —CH— | —NH— | —CH(Me)— |
| 3-31 | (b-72) | (b-7) | H | H | (a-1) | —CH— | —NH— | —CH(Me)— |
| 3-32 | (b-72) | (b-35) | H | H | (a-1) | —CH— | —NH— | —CH(Me)— |
| 3-33 | (b-73) | (b-7) | H | H | (a-1) | —CH— | —NH— | —CH(Me)— |
| 3-34 | (b-73) | (b-7) | H | H | (a-1) | —CH— | —NH— | —COCH(Me)— |
| 3-35 | (b-73) | (b-35) | H | H | (a-1) | —CH— | —NH— | —CH(Me)— |
| 3-36 | (b-73) | (b-35) | H | H | (a-1) | —CH— | —NH— | —COCH(Me)— |
| 3-37 | (b-74) | (b-7) | H | H | (a-1) | —CH— | —NH— | —CH(Me)— |
| 3-38 | (b-74) | (b-35) | H | H | (a-1) | —CH— | —NH— | —CH(Me)— |
| 3-39 | (b-76) | (b-7) | H | H | (a-1) | —CH— | —NH— | —CH(Me)— |
| 3-40 | (b-76) | (b-35) | H | H | (a-1) | —CH— | —NH— | —CH(Me)— |
| 3-41 | (b-77) | (b-7) | H | H | (a-1) | —CH— | —NH— | —CH(Me)— |
| 3-42 | (b-77) | (b-7) | H | H | (a-1) | —CH— | —NH— | —COCH(Me)— |
| 3-43 | (b-77) | (b-35) | H | H | (a-1) | —CH— | —NH— | —CH(Me)— |
| 3-44 | (b-77) | (b-35) | H | H | (a-1) | —CH— | —NH— | —COCH(Me)— |
| 3-45 | (b-7) | (b-35) | H | H | (a-2) | —CH— | —NH— | —CH(Me)— |
| 3-46 | (b-11) | (b-35) | H | H | (a-2) | —CH— | —NH— | —CH(Me)— |
| 3-47 | (b-18) | (b-35) | H | H | (a-2) | —CH— | —NH— | —CH(Me)— |
| 3-48 | (b-20) | (b-35) | H | H | (a-2) | —CH— | —NH— | —CH(Me)— |
| 3-49 | (b-73) | (b-35) | H | H | (a-2) | —CH— | —NH— | —CH(Me)— |
| 3-50 | (b-77) | (b-35) | H | H | (a-2) | —CH— | —NH— | —CH(Me)— |
| 3-51 | (b-7) | (b-7) | H | H | (a-3) | —CH— | —NH— | —CH(Me)— |
| 3-52 | (b-7) | (b-35) | H | H | (a-3) | —CH— | —NH— | —CH(Me)— |
| 3-53 | (b-11) | (b-7) | H | H | (a-3) | —CH— | —NH— | —CH(Me)— |
| 3-54 | (b-11) | (b-35) | H | H | (a-3) | —CH— | —NH— | —CH(Me)— |
| 3-55 | (b-12) | (b-35) | H | H | (a-3) | —CH— | —NH— | —CH(Me)— |
| 3-56 | (b-15) | (b-35) | H | H | (a-3) | —CH— | —NH— | —CH(Me)— |
| 3-57 | (b-18) | (b-7) | H | H | (a-3) | —CH— | —NH— | —CH(Me)— |
| 3-58 | (b-18) | (b-35) | H | H | (a-3) | —CH— | —NH— | —CH(Me)— |
| 3-59 | (b-19) | (b-35) | H | H | (a-3) | —CH— | —NH— | —CH(Me)— |
| 3-60 | (b-20) | (b-7) | H | H | (a-3) | —CH— | —NH— | —CH(Me)— |
| 3-61 | (b-20) | (b-35) | H | H | (a-3) | —CH— | —NH— | —CH(Me)— |
| 3-62 | (b-21) | (b-35) | H | H | (a-3) | —CH— | —NH— | —CH(Me)— |

TABLE 3-continued (I-3)

| Cpd. No. | R¹ Sub. No | R² Sub. No | R³ | R⁴ | A Sub. No. | D | E | G |
|---|---|---|---|---|---|---|---|---|
| 3-63 | (b-24) | (b-35) | H | H | (a-3) | —CH— | —NH— | —CH(Me)— |
| 3-64 | (b-25) | (b-35) | H | H | (a-3) | —CH— | —NH— | —CH(Me)— |
| 3-65 | (b-72) | (b-35) | H | H | (a-3) | —CH— | —NH— | —CH(Me)— |
| 3-66 | (b-73) | (b-7) | H | H | (a-3) | —CH— | —NH— | —CH(Me)— |
| 3-67 | (b-73) | (b-35) | H | H | (a-3) | —CH— | —NH— | —CH(Me)— |
| 3-68 | (b-74) | (b-35) | H | H | (a-3) | —CH— | —NH— | —CH(Me)— |
| 3-69 | (b-76) | (b-35) | H | H | (a-3) | —CH— | —NH— | —CH(Me)— |
| 3-70 | (b-77) | (b-7) | H | H | (a-3) | —CH— | —NH— | —CH(Me)— |
| 3-71 | (b-77) | (b-35) | H | H | (a-3) | —CH— | —NH— | —CH(Me)— |
| 3-72 | (b-7) | (b-35) | H | H | (a-4) | —CH— | —NH— | —CH(Me)— |
| 3-73 | (b-11) | (b-35) | H | H | (a-4) | —CH— | —NH— | —CH(Me)— |
| 3-74 | (b-18) | (b-35) | H | H | (a-4) | —CH— | —NH— | —CH(Me)— |
| 3-75 | (b-20) | (b-35) | H | H | (a-4) | —CH— | —NH— | —CH(Me)— |
| 3-76 | (b-73) | (b-35) | H | H | (a-4) | —CH— | —NH— | —CH(Me)— |
| 3-77 | (b-77) | (b-35) | H | H | (a-4) | —CH— | —NH— | —CH(Me)— |
| 3-78 | (b-2) | (b-35) | H | H | (a-5) | —CH— | —NH— | —CH(Me)— |
| 3-79 | (b-7) | (b-7) | H | H | (a-5) | —CH— | —NH— | —CH(Me)— |
| 3-80 | (b-7) | (b-7) | H | H | (a-5) | —CH— | —NH— | —COCH(Me)— |
| 3-81 | (b-7) | (b-35) | H | H | (a-5) | —CH— | —NH— | —CH(Me)— |
| 3-82 | (b-7) | (b-35) | H | H | (a-5) | —CH— | —NH— | —COCH(Me)— |
| 3-83 | (b-8) | (b-35) | H | H | (a-5) | —CH— | —NH— | —CH(Me)— |
| 3-84 | (b-11) | (b-7) | H | H | (a-5) | —CH— | —NH— | —CH(Me)— |
| 3-85 | (b-11) | (b-7) | H | H | (a-5) | —CH— | —NH— | —COCH(Me)— |
| 3-86 | (b-11) | (b-35) | H | H | (a-5) | —CH— | —NH— | —CH(Me)— |
| 3-87 | (b-11) | (b-35) | H | H | (a-5) | —CH— | —NH— | —COCH(Me)— |
| 3-88 | (b-12) | (b-7) | H | H | (a-5) | —CH— | —NH— | —CH(Me)— |
| 3-89 | (b-12) | (b-35) | H | H | (a-5) | —CH— | —NH— | —CH(Me)— |
| 3-90 | (b-15) | (b-7) | H | H | (a-5) | —CH— | —NH— | —CH(Me)— |
| 3-91 | (b-15) | (b-35) | H | H | (a-5) | —CH— | —NH— | —CH(Me)— |
| 3-92 | (b-18) | (b-7) | H | H | (a-5) | —CH— | —NH— | —CH(Me)— |
| 3-93 | (b-18) | (b-7) | H | H | (a-5) | —CH— | —NH— | —COCH(Me)— |
| 3-94 | (b-18) | (b-35) | H | H | (a-5) | —CH— | —NH— | —CH(Me)— |
| 3-95 | (b-18) | (b-35) | H | H | (a-5) | —CH— | —NH— | —COCH(Me)— |
| 3-96 | (b-19) | (b-7) | H | H | (a-5) | —CH— | —NH— | —CH(Me)— |
| 3-97 | (b-19) | (b-35) | H | H | (a-5) | —CH— | —NH— | —CH(Me)— |
| 3-98 | (b-20) | (b-7) | H | H | (a-5) | —CH— | —NH— | —CH(Me)— |
| 3-99 | (b-20) | (b-7) | H | H | (a-5) | —CH— | —NH— | —COCH(Me)— |
| 3-100 | (b-20) | (b-35) | H | H | (a-5) | —CH— | —NH— | —CH(Me)— |
| 3-101 | (b-20) | (b-35) | H | H | (a-5) | —CH— | —NH— | —COCH(Me)— |
| 3-102 | (b-21) | (b-7) | H | H | (a-5) | —CH— | —NH— | —CH(Me)— |
| 3-103 | (b-21) | (b-35) | H | H | (a-5) | —CH— | —NH— | —CH(Me)— |
| 3-104 | (b-24) | (b-7) | H | H | (a-5) | —CH— | —NH— | —CH(Me)— |
| 3-105 | (b-24) | (b-35) | H | H | (a-5) | —CH— | —NH— | —CH(Me)— |
| 3-106 | (b-25) | (b-7) | H | H | (a-5) | —CH— | —NH— | —CH(Me)— |
| 3-107 | (b-25) | (b-35) | H | H | (a-5) | —CH— | —NH— | —CH(Me)— |
| 3-108 | (b-72) | (b-7) | H | H | (a-5) | —CH— | —NH— | —CH(Me)— |
| 3-109 | (b-72) | (b-35) | H | H | (a-5) | —CH— | —NH— | —CH(Me)— |
| 3-110 | (b-73) | (b-7) | H | H | (a-5) | —CH— | —NH— | —CH(Me)— |
| 3-111 | (b-73) | (b-7) | H | H | (a-5) | —CH— | —NH— | —COCH(Me)— |
| 3-112 | (b-73) | (b-35) | H | H | (a-5) | —CH— | —NH— | —CH(Me)— |
| 3-113 | (b-73) | (b-35) | H | H | (a-5) | —CH— | —NH— | —COCH(Me)— |
| 3-114 | (b-74) | (b-7) | H | H | (a-5) | —CH— | —NH— | —CH(Me)— |
| 3-115 | (b-74) | (b-35) | H | H | (a-5) | —CH— | —NH— | —CH(Me)— |
| 3-116 | (b-76) | (b-7) | H | H | (a-5) | —CH— | —NH— | —CH(Me)— |
| 3-117 | (b-76) | (b-35) | H | H | (a-5) | —CH— | —NH— | —CH(Me)— |
| 3-118 | (b-77) | (b-7) | H | H | (a-5) | —CH— | —NH— | —CH(Me)— |
| 3-119 | (b-77) | (b-7) | H | H | (a-5) | —CH— | —NH— | —COCH(Me)— |
| 3-120 | (b-77) | (b-35) | H | H | (a-5) | —CH— | —NH— | —CH(Me)— |
| 3-121 | (b-77) | (b-35) | H | H | (a-5) | —CH— | —NH— | —COCH(Me)— |
| 3-122 | (b-7) | (b-35) | H | H | (a-6) | —CH— | —NH— | —CH(Me)— |
| 3-123 | (b-11) | (b-35) | H | H | (a-6) | —CH— | —NH— | —CH(Me)— |
| 3-124 | (b-18) | (b-35) | H | H | (a-6) | —CH— | —NH— | —CH(Me)— |

TABLE 3-continued (I-3)

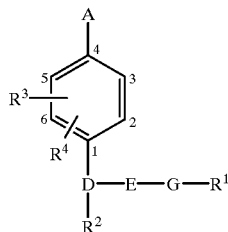

| Cpd. No. | R¹ Sub. No | R² Sub. No | R³ | R⁴ | A Sub. No. | D | E | G |
|---|---|---|---|---|---|---|---|---|
| 3-125 | (b-20) | (b-35) | H | H | (a-6) | —CH— | —NH— | —CH(Me)— |
| 3-126 | (b-73) | (b-35) | H | H | (a-6) | —CH— | —NH— | —CH(Me)— |
| 3-127 | (b-77) | (b-35) | H | H | (a-6) | —CH— | —NH— | —CH(Me)— |
| 3-128 | (b-7) | (b-7) | H | H | (a-7) | —CH— | —NH— | —CH(Me)— |
| 3-129 | (b-7) | (b-35) | H | H | (a-7) | —CH— | —NH— | —CH(Me)— |
| 3-130 | (b-11) | (b-7) | H | H | (a-7) | —CH— | —NH— | —CH(Me)— |
| 3-131 | (b-11) | (b-35) | H | H | (a-7) | —CH— | —NH— | —CH(Me)— |
| 3-132 | (b-12) | (b-35) | H | H | (a-7) | —CH— | —NH— | —CH(Me)— |
| 3-133 | (b-15) | (b-35) | H | H | (a-7) | —CH— | —NH— | —CH(Me)— |
| 3-134 | (b-18) | (b-7) | H | H | (a-7) | —CH— | —NH— | —CH(Me)— |
| 3-135 | (b-18) | (b-35) | H | H | (a-7) | —CH— | —NH— | —CH(Me)— |
| 3-136 | (b-19) | (b-35) | H | H | (a-7) | —CH— | —NH— | —CH(Me)— |
| 3-137 | (b-20) | (b-7) | H | H | (a-7) | —CH— | —NH— | —CH(Me)— |
| 3-138 | (b-20) | (b-35) | H | H | (a-7) | —CH— | —NH— | —CH(Me)— |
| 3-139 | (b-21) | (b-35) | H | H | (a-7) | —CH— | —NH— | —CH(Me)— |
| 3-140 | (b-24) | (b-35) | H | H | (a-7) | —CH— | —NH— | —CH(Me)— |
| 3-141 | (b-25) | (b-35) | H | H | (a-7) | —CH— | —NH— | —CH(Me)— |
| 3-142 | (b-72) | (b-35) | H | H | (a-7) | —CH— | —NH— | —CH(Me)— |
| 3-143 | (b-73) | (b-7) | H | H | (a-7) | —CH— | —NH— | —CH(Me)— |
| 3-144 | (b-73) | (b-35) | H | H | (a-7) | —CH— | —NH— | —CH(Me)— |
| 3-145 | (b-74) | (b-35) | H | H | (a-7) | —CH— | —NH— | —CH(Me)— |
| 3-146 | (b-76) | (b-35) | H | H | (a-7) | —CH— | —NH— | —CH(Me)— |
| 3-147 | (b-77) | (b-7) | H | H | (a-7) | —CH— | —NH— | —CH(Me)— |
| 3-148 | (b-77) | (b-35) | H | H | (a-7) | —CH— | —NH— | —CH(Me)— |
| 3-149 | (b-7) | (b-35) | H | H | (a-8) | —CH— | —NH— | —CH(Me)— |
| 3-150 | (b-11) | (b-35) | H | H | (a-8) | —CH— | —NH— | —CH(Me)— |
| 3-151 | (b-18) | (b-35) | H | H | (a-8) | —CH— | —NH— | —CH(Me)— |
| 3-152 | (b-20) | (b-35) | H | H | (a-8) | —CH— | —NH— | —CH(Me)— |
| 3-153 | (b-73) | (b-35) | H | H | (a-8) | —CH— | —NH— | —CH(Me)— |
| 3-154 | (b-77) | (b-35) | H | H | (a-8) | —CH— | —NH— | —CH(Me)— |
| 3-155 | (b-7) | (b-35) | H | H | (a-10) | —CH— | —NH— | —CH(Me)— |
| 3-156 | (b-11) | (b-35) | H | H | (a-10) | —CH— | —NH— | —CH(Me)— |
| 3-157 | (b-18) | (b-35) | H | H | (a-10) | —CH— | —NH— | —CH(Me)— |
| 3-158 | (b-7) | (b-35) | H | H | (a-11) | —CH— | —NH— | —CH(Me)— |
| 3-159 | (b-11) | (b-35) | H | H | (a-11) | —CH— | —NH— | —CH(Me)— |
| 3-160 | (b-18) | (b-35) | H | H | (a-11) | —CH— | —NH— | —CH(Me)— |
| 3-161 | (b-20) | (b-35) | H | H | (a-11) | —CH— | —NH— | —CH(Me)— |
| 3-162 | (b-73) | (b-35) | H | H | (a-11) | —CH— | —NH— | —CH(Me)— |
| 3-163 | (b-77) | (b-35) | H | H | (a-11) | —CH— | —NH— | —CH(Me)— |
| 3-164 | (b-7) | (b-35) | H | H | (a-12) | —CH— | —NH— | —CH(Me)— |
| 3-165 | (b-11) | (b-35) | H | H | (a-12) | —CH— | —NH— | —CH(Me)— |
| 3-166 | (b-18) | (b-35) | H | H | (a-12) | —CH— | —NH— | —CH(Me)— |
| 3-167 | (b-2) | (b-7) | H | H | (a-14) | —CH— | —NH— | —CH(Me)— |
| 3-168 | (b-2) | (b-35) | H | H | (a-14) | —CH— | —NH— | —CH(Me)— |
| 3-169 | (b-7) | (b-7) | H | H | (a-14) | —CH— | —NH— | —CH(Me)— |
| 3-170 | (b-7) | (b-7) | H | H | (a-14) | —CH— | —NH— | —COCH(Me)— |
| 3-171 | (b-7) | (b-12) | H | H | (a-14) | —CH— | —NH— | —CH(Me)— |
| 3-172 | (b-7) | (b-15) | H | H | (a-14) | —CH— | —NH— | —CH(Me)— |
| 3-173 | (b-7) | (b-34) | H | H | (a-14) | —CH— | —NH— | —CH(Me)— |
| 3-174 | (b-7) | (b-35) | H | H | (a-14) | —CH— | —NH— | —CH(Me)— |
| 3-175 | (b-7) | (b-35) | H | H | (a-14) | —CH— | —NH— | —COCH(Me)— |
| 3-176 | (b-7) | (b-37) | H | H | (a-14) | —CH— | —NH— | —CH(Me)— |
| 3-177 | (b-7) | (b-73) | H | H | (a-14) | —CH— | —NH— | —CH(Me)— |
| 3-178 | (b-7) | (b-77) | H | H | (a-14) | —CH— | —NH— | —CH(Me)— |
| 3-179 | (b-8) | (b-35) | H | H | (a-14) | —CH— | —NH— | —CH(Me)— |
| 3-180 | (b-9) | (b-35) | H | H | (a-14) | —CH— | —NH— | —CH(Me)— |
| 3-181 | (b-10) | (b-35) | H | H | (a-14) | —CH— | —NH— | —CH(Me)— |
| 3-182 | (b-10) | (b-7) | H | H | (a-14) | —CH— | —NH— | —CH(Me)— |
| 3-183 | (b-11) | (b-7) | H | H | (a-14) | —CH— | —NH— | —COCH(Me)— |
| 3-184 | (b-11) | (b-12) | H | H | (a-14) | —CH— | —NH— | —CH(Me)— |
| 3-185 | (b-11) | (b-15) | H | H | (a-14) | —CH— | —NH— | —CH(Me)— |
| 3-186 | (b-11) | (b-34) | H | H | (a-14) | —CH— | —NH— | —CH(Me)— |

TABLE 3-continued (I-3)

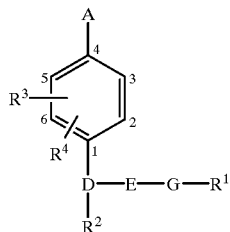

| Cpd. No. | R¹ Sub. No | R² Sub. No | R³ | R⁴ | A Sub. No. | D | E | G |
|---|---|---|---|---|---|---|---|---|
| 3-187 | (b-11) | (b-35) | H | H | (a-14) | —CH— | —NH— | —CH(Me)— |
| 3-188 | (b-11) | (b-35) | H | H | (a-14) | —CH— | —NH— | —COCH(Me)— |
| 3-189 | (b-11) | (b-37) | H | H | (a-14) | —CH— | —NH— | —CH(Me)— |
| 3-190 | (b-11) | (b-73) | H | H | (a-14) | —CH— | —NH— | —CH(Me)— |
| 3-191 | (b-11) | (b-77) | H | H | (a-14) | —CH— | —NH— | —CH(Me)— |
| 3-192 | (b-12) | (b-7) | H | H | (a-14) | —CH— | —NH— | —CH(Me)— |
| 3-193 | (b-12) | (b-7) | H | H | (a-14) | —CH— | —NH— | —COCH(Me)— |
| 3-194 | (b-12) | (b-35) | H | H | (a-14) | —CH— | —NH— | —CH(Me)— |
| 3-195 | (b-12) | (b-35) | H | H | (a-14) | —CH— | —NH— | —COCH(Me)— |
| 3-196 | (b-13) | (b-35) | H | H | (a-14) | —CH— | —NH— | —CH(Me)— |
| 3-197 | (b-14) | (b-35) | H | H | (a-14) | —CH— | —NH— | —CH(Me)— |
| 3-198 | (b-15) | (b-7) | H | H | (a-14) | —CH— | —NH— | —CH(Me)— |
| 3-199 | (b-15) | (b-7) | H | H | (a-14) | —CH— | —NH— | —COCH(Me)— |
| 3-200 | (b-15) | (b-35) | H | H | (a-14) | —CH— | —NH— | —CH(Me)— |
| 3-201 | (b-15) | (b-35) | H | H | (a-14) | —CH— | —NH— | —COCH(Me)— |
| 3-202 | (b-17) | (b-35) | H | H | (a-14) | —CH— | —NH— | —CH(Me)— |
| 3-203 | (b-18) | (b-7) | H | H | (a-14) | —CH— | —NH— | —CH(Me)— |
| 3-204 | (b-18) | (b-7) | H | H | (a-14) | —CH— | —NH— | —COCH(Me)— |
| 3-205 | (b-18) | (b-12) | H | H | (a-14) | —CH— | —NH— | —CH(Me)— |
| 3-206 | (b-18) | (b-15) | H | H | (a-14) | —CH— | —NH— | —CH(Me)— |
| 3-207 | (b-18) | (b-34) | H | H | (a-14) | —CH— | —NH— | —CH(Me)— |
| 3-208 | (b-18) | (b-35) | H | H | (a-14) | —CH— | —NH— | —CH(Me)— |
| 3-209 | (b-18) | (b-35) | H | H | (a-14) | —CH— | —NH— | —COCH(Me)— |
| 3-210 | (b-18) | (b-37) | H | H | (a-14) | —CH— | —NH— | —CH(Me)— |
| 3-211 | (b-18) | (b-73) | H | H | (a-14) | —CH— | —NH— | —CH(Me)— |
| 3-212 | (b-18) | (b-77) | H | H | (a-14) | —CH— | —NH— | —CH(Me)— |
| 3-213 | (b-19) | (b-7) | H | H | (a-14) | —CH— | —NH— | —CH(Me)— |
| 3-214 | (b-19) | (b-7) | H | H | (a-14) | —CH— | —NH— | —COCH(Me)— |
| 3-215 | (b-19) | (b-35) | H | H | (a-14) | —CH— | —NH— | —CH(Me)— |
| 3-216 | (b-19) | (b-35) | H | H | (a-14) | —CH— | —NH— | —COCH(Me)— |
| 3-217 | (b-20) | (b-7) | H | H | (a-14) | —CH— | —NH— | —CH(Me)— |
| 3-218 | (b-20) | (b-7) | H | H | (a-14) | —CH— | —NH— | —COCH(Me)— |
| 3-219 | (b-20) | (b-12) | H | H | (a-14) | —CH— | —NH— | —CH(Me)— |
| 3-220 | (b-20) | (b-15) | H | H | (a-14) | —CH— | —NH— | —CH(Me)— |
| 3-221 | (b-20) | (b-34) | H | H | (a-14) | —CH— | —NH— | —CH(Me)— |
| 3-222 | (b-20) | (b-35) | H | H | (a-14) | —CH— | —NH— | —CH(Me)— |
| 3-223 | (b-20) | (b-35) | H | H | (a-14) | —CH— | —NH— | —COCH(Me)— |
| 3-224 | (b-20) | (b-37) | H | H | (a-14) | —CH— | —NH— | —CH(Me)— |
| 3-225 | (b-20) | (b-73) | H | H | (a-14) | —CH— | —NH— | —CH(Me)— |
| 3-226 | (b-20) | (b-77) | H | H | (a-14) | —CH— | —NH— | —CH(Me)— |
| 3-227 | (b-21) | (b-7) | H | H | (a-14) | —CH— | —NH— | —CH(Me)— |
| 3-228 | (b-21) | (b-7) | H | H | (a-14) | —CH— | —NH— | —COCH(Me)— |
| 3-229 | (b-21) | (b-35) | H | H | (a-14) | —CH— | —NH— | —CH(Me)— |
| 3-230 | (b-21) | (b-35) | H | H | (a-14) | —CH— | —NH— | —COCH(Me)— |
| 3-231 | (b-23) | (b-35) | H | H | (a-14) | —CH— | —NH— | —CH(Me)— |
| 3-232 | (b-24) | (b-7) | H | H | (a-14) | —CH— | —NH— | —CH(Me)— |
| 3-233 | (b-24) | (b-7) | H | H | (a-14) | —CH— | —NH— | —COCH(Me)— |
| 3-234 | (b-24) | (b-35) | H | H | (a-14) | —CH— | —NH— | —CH(Me)— |
| 3-235 | (b-24) | (b-35) | H | H | (a-14) | —CH— | —NH— | —COCH(Me)— |
| 3-236 | (b-25) | (b-7) | H | H | (a-14) | —CH— | —NH— | —CH(Me)— |
| 3-237 | (b-25) | (b-7) | H | H | (a-14) | —CH— | —NH— | —COCH(Me)— |
| 3-238 | (b-25) | (b-35) | H | H | (a-14) | —CH— | —NH— | —CH(Me)— |
| 3-239 | (b-25) | (b-35) | H | H | (a-14) | —CH— | —NH— | —COCH(Me)— |
| 3-240 | (b-35) | (b-35) | H | H | (a-14) | —CH— | —NH— | —CH(Me)— |
| 3-241 | (b-72) | (b-7) | H | H | (a-14) | —CH— | —NH— | —CH(Me)— |
| 3-242 | (b-72) | (b-7) | H | H | (a-14) | —CH— | —NH— | —COCH(Me)— |
| 3-243 | (b-72) | (b-35) | H | H | (a-14) | —CH— | —NH— | —CH(Me)— |
| 3-244 | (b-72) | (b-35) | H | H | (a-14) | —CH— | —NH— | —COCH(Me)— |
| 3-245 | (b-73) | (b-7) | H | H | (a-14) | —CH— | —NH— | —CH(Me)— |
| 3-246 | (b-73) | (b-7) | H | H | (a-14) | —CH— | —NH— | —COCH(Me)— |
| 3-247 | (b-73) | (b-12) | H | H | (a-14) | —CH— | —NH— | —CH(Me)— |
| 3-248 | (b-73) | (b-15) | H | H | (a-14) | —CH— | —NH— | —CH(Me)— |

TABLE 3-continued

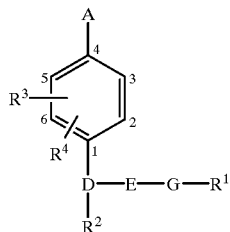

(I-3)

| Cpd. No. | R¹ Sub. No | R² Sub. No | R³ | R⁴ | A Sub. No. | D | E | G |
|---|---|---|---|---|---|---|---|---|
| 3-249 | (b-73) | (b-34) | H | H | (a-14) | —CH— | —NH— | —CH(Me)— |
| 3-250 | (b-73) | (b-35) | H | H | (a-14) | —CH— | —NH— | —CH(Me)— |
| 3-251 | (b-73) | (b-35) | H | H | (a-14) | —CH— | —NH— | —COCH(Me)— |
| 3-252 | (b-73) | (b-37) | H | H | (a-14) | —CH— | —NH— | —CH(Me)— |
| 3-253 | (b-73) | (b-73) | H | H | (a-14) | —CH— | —NH— | —CH(Me)— |
| 3-254 | (b-73) | (b-77) | H | H | (a-14) | —CH— | —NH— | —CH(Me)— |
| 3-255 | (b-74) | (b-7) | H | H | (a-14) | —CH— | —NH— | —CH(Me)— |
| 3-256 | (b-74) | (b-7) | H | H | (a-14) | —CH— | —NH— | —COCH(Me)— |
| 3-257 | (b-74) | (b-35) | H | H | (a-14) | —CH— | —NH— | —CH(Me)— |
| 3-258 | (b-74) | (b-35) | H | H | (a-14) | —CH— | —NH— | —COCH(Me)— |
| 3-259 | (b-75) | (b-35) | H | H | (a-14) | —CH— | —NH— | —CH(Me)— |
| 3-260 | (b-76) | (b-7) | H | H | (a-14) | —CH— | —NH— | —CH(Me)— |
| 3-261 | (b-76) | (b-7) | H | H | (a-14) | —CH— | —NH— | —COCH(Me)— |
| 3-262 | (b-76) | (b-35) | H | H | (a-14) | —CH— | —NH— | —CH(Me)— |
| 3-263 | (b-76) | (b-35) | H | H | (a-14) | —CH— | —NH— | —COCH(Me)— |
| 3-264 | (b-77) | (b-7) | H | H | (a-14) | —CH— | —NH— | —CH(Me)— |
| 3-265 | (b-77) | (b-7) | H | H | (a-14) | —CH— | —NH— | —COCH(Me)— |
| 3-266 | (b-77) | (b-12) | H | H | (a-14) | —CH— | —NH— | —CH(Me)— |
| 3-267 | (b-77) | (b-15) | H | H | (a-14) | —CH— | —NH— | —CH(Me)— |
| 3-268 | (b-77) | (b-34) | H | H | (a-14) | —CH— | —NH— | —CH(Me)— |
| 3-269 | (b-77) | (b-35) | H | H | (a-14) | —CH— | —NH— | —CH(Me)— |
| 3-270 | (b-77) | (b-35) | H | H | (a-14) | —CH— | —NH— | —COCH(Me)— |
| 3-271 | (b-77) | (b-37) | H | H | (a-14) | —CH— | —NH— | —CH(Me)— |
| 3-272 | (b-77) | (b-73) | H | H | (a-14) | —CH— | —NH— | —CH(Me)— |
| 3-273 | (b-77) | (b-77) | H | H | (a-14) | —CH— | —NH— | —CH(Me)— |
| 3-274 | (b-78) | (b-35) | H | H | (a-14) | —CH— | —NH— | —CH(Me)— |
| 3-275 | (b-79) | (b-35) | H | H | (a-14) | —CH— | —NH— | —CH(Me)— |
| 3-276 | (b-2) | (b-35) | H | H | (a-15) | —CH— | —NH— | —CH(Me)— |
| 3-277 | (b-7) | (b-7) | H | H | (a-15) | —CH— | —NH— | —CH(Me)— |
| 3-278 | (b-7) | (b-7) | H | H | (a-15) | —CH— | —NH— | —COCH(Me)— |
| 3-279 | (b-7) | (b-35) | H | H | (a-15) | —CH— | —NH— | —CH(Me)— |
| 3-280 | (b-7) | (b-35) | H | H | (a-15) | —CH— | —NH— | —COCH(Me)— |
| 3-281 | (b-8) | (b-35) | H | H | (a-15) | —CH— | —NH— | —CH(Me)— |
| 3-282 | (b-11) | (b-7) | H | H | (a-15) | —CH— | —NH— | —CH(Me)— |
| 3-283 | (b-11) | (b-7) | H | H | (a-15) | —CH— | —NH— | —COCH(Me)— |
| 3-284 | (b-11) | (b-35) | H | H | (a-15) | —CH— | —NH— | —CH(Me)— |
| 3-285 | (b-11) | (b-35) | H | H | (a-15) | —CH— | —NH— | —COCH(Me)— |
| 3-286 | (b-12) | (b-7) | H | H | (a-15) | —CH— | —NH— | —CH(Me)— |
| 3-287 | (b-12) | (b-35) | H | H | (a-15) | —CH— | —NH— | —CH(Me)— |
| 3-288 | (b-15) | (b-7) | H | H | (a-15) | —CH— | —NH— | —CH(Me)— |
| 3-289 | (b-15) | (b-35) | H | H | (a-15) | —CH— | —NH— | —CH(Me)— |
| 3-290 | (b-18) | (b-7) | H | H | (a-15) | —CH— | —NH— | —CH(Me)— |
| 3-291 | (b-18) | (b-7) | H | H | (a-15) | —CH— | —NH— | —COCH(Me)— |
| 3-292 | (b-18) | (b-35) | H | H | (a-15) | —CH— | —NH— | —CH(Me)— |
| 3-293 | (b-18) | (b-35) | H | H | (a-15) | —CH— | —NH— | —COCH(Me)— |
| 3-294 | (b-19) | (b-7) | H | H | (a-15) | —CH— | —NH— | —CH(Me)— |
| 3-295 | (b-19) | (b-35) | H | H | (a-15) | —CH— | —NH— | —CH(Me)— |
| 3-296 | (b-20) | (b-7) | H | H | (a-15) | —CH— | —NH— | —CH(Me)— |
| 3-297 | (b-20) | (b-7) | H | H | (a-15) | —CH— | —NH— | —COCH(Me)— |
| 3-298 | (b-20) | (b-35) | H | H | (a-15) | —CH— | —NH— | —CH(Me)— |
| 3-299 | (b-20) | (b-35) | H | H | (a-15) | —CH— | —NH— | —COCH(Me)— |
| 3-300 | (b-21) | (b-7) | H | H | (a-15) | —CH— | —NH— | —CH(Me)— |
| 3-301 | (b-21) | (b-35) | H | H | (a-15) | —CH— | —NH— | —CH(Me)— |
| 3-302 | (b-24) | (b-7) | H | H | (a-15) | —CH— | —NH— | —CH(Me)— |
| 3-303 | (b-24) | (b-35) | H | H | (a-15) | —CH— | —NH— | —CH(Me)— |
| 3-304 | (b-25) | (b-7) | H | H | (a-15) | —CH— | —NH— | —CH(Me)— |
| 3-305 | (b-25) | (b-35) | H | H | (a-15) | —CH— | —NH— | —CH(Me)— |
| 3-306 | (b-72) | (b-7) | H | H | (a-15) | —CH— | —NH— | —CH(Me)— |
| 3-307 | (b-72) | (b-35) | H | H | (a-15) | —CH— | —NH— | —CH(Me)— |
| 3-308 | (b-73) | (b-7) | H | H | (a-15) | —CH— | —NH— | —CH(Me)— |
| 3-309 | (b-73) | (b-7) | H | H | (a-15) | —CH— | —NH— | —COCH(Me)— |
| 3-310 | (b-73) | (b-35) | H | H | (a-15) | —CH— | —NH— | —CH(Me)— |

TABLE 3-continued (I-3)

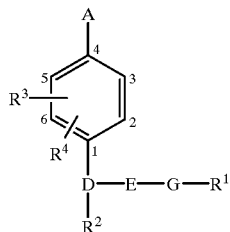

| Cpd. No. | R¹ Sub. No | R² Sub. No | R³ | R⁴ | A Sub. No. | D | E | G |
|---|---|---|---|---|---|---|---|---|
| 3-311 | (b-73) | (b-35) | H | H | (a-15) | —CH— | —NH— | —COCH(Me)— |
| 3-312 | (b-74) | (b-7) | H | H | (a-15) | —CH— | —NH— | —CH(Me)— |
| 3-313 | (b-74) | (b-35) | H | H | (a-15) | —CH— | —NH— | —CH(Me)— |
| 3-314 | (b-76) | (b-7) | H | H | (a-15) | —CH— | —NH— | —CH(Me)— |
| 3-315 | (b-76) | (b-35) | H | H | (a-15) | —CH— | —NH— | —CH(Me)— |
| 3-316 | (b-77) | (b-7) | H | H | (a-15) | —CH— | —NH— | —CH(Me)— |
| 3-317 | (b-77) | (b-7) | H | H | (a-15) | —CH— | —NH— | —COCH(Me)— |
| 3-318 | (b-77) | (b-35) | H | H | (a-15) | —CH— | —NH— | —CH(Me)— |
| 3-319 | (b-77) | (b-35) | H | H | (a-15) | —CH— | —NH— | —COCH(Me)— |
| 3-320 | (b-2) | (b-35) | H | H | (a-18) | —CH— | —NH— | —CH(Me)— |
| 3-321 | (b-7) | (b-7) | H | H | (a-18) | —CH— | —NH— | —CH(Me)— |
| 3-322 | (b-7) | (b-7) | H | H | (a-18) | —CH— | —NH— | —COCH(Me)— |
| 3-323 | (b-7) | (b-35) | H | H | (a-18) | —CH— | —NH— | —CH(Me)— |
| 3-324 | (b-7) | (b-35) | H | H | (a-18) | —CH— | —NH— | —COCH(Me)— |
| 3-325 | (b-8) | (b-35) | H | H | (a-18) | —CH— | —NH— | —CH(Me)— |
| 3-326 | (b-11) | (b-7) | H | H | (a-18) | —CH— | —NH— | —CH(Me)— |
| 3-327 | (b-11) | (b-7) | H | H | (a-18) | —CH— | —NH— | —COCH(Me)— |
| 3-328 | (b-11) | (b-35) | H | H | (a-18) | —CH— | —NH— | —CH(Me)— |
| 3-329 | (b-11) | (b-35) | H | H | (a-18) | —CH— | —NH— | —COCH(Me)— |
| 3-330 | (b-12) | (b-7) | H | H | (a-18) | —CH— | —NH— | —CH(Me)— |
| 3-331 | (b-12) | (b-35) | H | H | (a-18) | —CH— | —NH— | —CH(Me)— |
| 3-332 | (b-15) | (b-7) | H | H | (a-18) | —CH— | —NH— | —CH(Me)— |
| 3-333 | (b-15) | (b-35) | H | H | (a-18) | —CH— | —NH— | —CH(Me)— |
| 3-334 | (b-18) | (b-7) | H | H | (a-18) | —CH— | —NH— | —CH(Me)— |
| 3-335 | (b-18) | (b-7) | H | H | (a-18) | —CH— | —NH— | —COCH(Me)— |
| 3-336 | (b-18) | (b-35) | H | H | (a-18) | —CH— | —NH— | —CH(Me)— |
| 3-337 | (b-18) | (b-35) | H | H | (a-18) | —CH— | —NH— | —COCH(Me)— |
| 3-338 | (b-19) | (b-7) | H | H | (a-18) | —CH— | —NH— | —CH(Me)— |
| 3-339 | (b-19) | (b-35) | H | H | (a-18) | —CH— | —NH— | —CH(Me)— |
| 3-340 | (b-20) | (b-7) | H | H | (a-18) | —CH— | —NH— | —CH(Me)— |
| 3-341 | (b-20) | (b-7) | H | H | (a-18) | —CH— | —NH— | —COCH(Me)— |
| 3-342 | (b-20) | (b-35) | H | H | (a-18) | —CH— | —NH— | —CH(Me)— |
| 3-343 | (b-20) | (b-35) | H | H | (a-18) | —CH— | —NH— | —COCH(Me)— |
| 3-344 | (b-21) | (b-7) | H | H | (a-18) | —CH— | —NH— | —CH(Me)— |
| 3-345 | (b-21) | (b-35) | H | H | (a-18) | —CH— | —NH— | —CH(Me)— |
| 3-346 | (b-24) | (b-7) | H | H | (a-18) | —CH— | —NH— | —CH(Me)— |
| 3-347 | (b-24) | (b-35) | H | H | (a-18) | —CH— | —NH— | —CH(Me)— |
| 3-348 | (b-25) | (b-7) | H | H | (a-18) | —CH— | —NH— | —CH(Me)— |
| 3-349 | (b-25) | (b-35) | H | H | (a-18) | —CH— | —NH— | —CH(Me)— |
| 3-350 | (b-72) | (b-7) | H | H | (a-18) | —CH— | —NH— | —CH(Me)— |
| 3-351 | (b-72) | (b-35) | H | H | (a-18) | —CH— | —NH— | —CH(Me)— |
| 3-352 | (b-73) | (b-7) | H | H | (a-18) | —CH— | —NH— | —CH(Me)— |
| 3-353 | (b-73) | (b-7) | H | H | (a-18) | —CH— | —NH— | —COCH(Me)— |
| 3-354 | (b-73) | (b-35) | H | H | (a-18) | —CH— | —NH— | —CH(Me)— |
| 3-355 | (b-73) | (b-35) | H | H | (a-18) | —CH— | —NH— | —COCH(Me)— |
| 3-356 | (b-74) | (b-7) | H | H | (a-18) | —CH— | —NH— | —CH(Me)— |
| 3-357 | (b-74) | (b-35) | H | H | (a-18) | —CH— | —NH— | —CH(Me)— |
| 3-358 | (b-76) | (b-7) | H | H | (a-18) | —CH— | —NH— | —CH(Me)— |
| 3-359 | (b-76) | (b-35) | H | H | (a-18) | —CH— | —NH— | —CH(Me)— |
| 3-360 | (b-77) | (b-7) | H | H | (a-18) | —CH— | —NH— | —CH(Me)— |
| 3-361 | (b-77) | (b-7) | H | H | (a-18) | —CH— | —NH— | —COCH(Me)— |
| 3-362 | (b-77) | (b-35) | H | H | (a-18) | —CH— | —NH— | —CH(Me)— |
| 3-363 | (b-77) | (b-35) | H | H | (a-18) | —CH— | —NH— | —COCH(Me)— |
| 3-364 | (b-7) | (b-7) | H | H | (a-19) | —CH— | —NH— | —CH(Me)— |
| 3-365 | (b-7) | (b-35) | H | H | (a-19) | —CH— | —NH— | —CH(Me)— |
| 3-366 | (b-11) | (b-7) | H | H | (a-19) | —CH— | —NH— | —CH(Me)— |
| 3-367 | (b-11) | (b-35) | H | H | (a-19) | —CH— | —NH— | —CH(Me)— |
| 3-368 | (b-12) | (b-35) | H | H | (a-19) | —CH— | —NH— | —CH(Me)— |
| 3-369 | (b-15) | (b-35) | H | H | (a-19) | —CH— | —NH— | —CH(Me)— |
| 3-370 | (b-18) | (b-7) | H | H | (a-19) | —CH— | —NH— | —CH(Me)— |
| 3-371 | (b-18) | (b-35) | H | H | (a-19) | —CH— | —NH— | —CH(Me)— |
| 3-372 | (b-19) | (b-35) | H | H | (a-19) | —CH— | —NH— | —CH(Me)— |

TABLE 3-continued

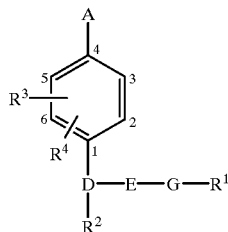

(I-3)

| Cpd. No. | R¹ Sub. No | R² Sub. No | R³ | R⁴ | A Sub. No. | D | E | G |
|---|---|---|---|---|---|---|---|---|
| 3-373 | (b-20) | (b-7) | H | H | (a-19) | —CH— | —NH— | —CH(Me)— |
| 3-374 | (b-20) | (b-35) | H | H | (a-19) | —CH— | —NH— | —CH(Me)— |
| 3-375 | (b-20) | (b-35) | H | H | (a-19) | —CH— | —NH— | —CH(Me)— |
| 3-376 | (b-24) | (b-35) | H | H | (a-19) | —CH— | —NH— | —CH(Me)— |
| 3-377 | (b-25) | (b-35) | H | H | (a-19) | —CH— | —NH— | —CH(Me)— |
| 3-378 | (b-72) | (b-35) | H | H | (a-19) | —CH— | —NH— | —CH(Me)— |
| 3-379 | (b-73) | (b-7) | H | H | (a-19) | —CH— | —NH— | —CH(Me)— |
| 3-380 | (b-73) | (b-35) | H | H | (a-19) | —CH— | —NH— | —CH(Me)— |
| 3-381 | (b-74) | (b-35) | H | H | (a-19) | —CH— | —NH— | —CH(Me)— |
| 3-382 | (b-76) | (b-35) | H | H | (a-19) | —CH— | —NH— | —CH(Me)— |
| 3-383 | (b-77) | (b-7) | H | H | (a-19) | —CH— | —NH— | —CH(Me)— |
| 3-384 | (b-77) | (b-35) | H | H | (a-19) | —CH— | —NH— | —CH(Me)— |
| 3-385 | (b-2) | (b-35) | H | H | (a-20) | —CH— | —NH— | —CH(Me)— |
| 3-386 | (b-7) | (b-7) | H | H | (a-20) | —CH— | —NH— | —CH(Me)— |
| 3-387 | (b-7) | (b-7) | H | H | (a-20) | —CH— | —NH— | —COCH(Me)— |
| 3-388 | (b-7) | (b-35) | H | H | (a-20) | —CH— | —NH— | —CH(Me)— |
| 3-389 | (b-7) | (b-35) | H | H | (a-20) | —CH— | —NH— | —COCH(Me)— |
| 3-390 | (b-8) | (b-35) | H | H | (a-20) | —CH— | —NH— | —CH(Me)— |
| 3-391 | (b-11) | (b-7) | H | H | (a-20) | —CH— | —NH— | —CH(Me)— |
| 3-392 | (b-11) | (b-7) | H | H | (a-20) | —CH— | —NH— | —COCH(Me)— |
| 3-393 | (b-11) | (b-35) | H | H | (a-20) | —CH— | —NH— | —CH(Me)— |
| 3-394 | (b-11) | (b-35) | H | H | (a-20) | —CH— | —NH— | —COCH(Me)— |
| 3-395 | (b-12) | (b-7) | H | H | (a-20) | —CH— | —NH— | —CH(Me)— |
| 3-396 | (b-12) | (b-35) | H | H | (a-20) | —CH— | —NH— | —CH(Me)— |
| 3-397 | (b-15) | (b-7) | H | H | (a-20) | —CH— | —NH— | —CH(Me)— |
| 3-398 | (b-15) | (b-35) | H | H | (a-20) | —CH— | —NH— | —CH(Me)— |
| 3-399 | (b-18) | (b-7) | H | H | (a-20) | —CH— | —NH— | —CH(Me)— |
| 3-400 | (b-18) | (b-7) | H | H | (a-20) | —CH— | —NH— | —COCH(Me)— |
| 3-401 | (b-18) | (b-35) | H | H | (a-20) | —CH— | —NH— | —CH(Me)— |
| 3-402 | (b-18) | (b-35) | H | H | (a-20) | —CH— | —NH— | —COCH(Me)— |
| 3-403 | (b-19) | (b-7) | H | H | (a-20) | —CH— | —NH— | —CH(Me)— |
| 3-404 | (b-19) | (b-35) | H | H | (a-20) | —CH— | —NH— | —CH(Me)— |
| 3-405 | (b-20) | (b-7) | H | H | (a-20) | —CH— | —NH— | —CH(Me)— |
| 3-406 | (b-20) | (b-7) | H | H | (a-20) | —CH— | —NH— | —COCH(Me)— |
| 3-407 | (b-20) | (b-35) | H | H | (a-20) | —CH— | —NH— | —CH(Me)— |
| 3-408 | (b-20) | (b-35) | H | H | (a-20) | —CH— | —NH— | —COCH(Me)— |
| 3-409 | (b-21) | (b-7) | H | H | (a-20) | —CH— | —NH— | —CH(Me)— |
| 3-410 | (b-21) | (b-35) | H | H | (a-20) | —CH— | —NH— | —CH(Me)— |
| 3-411 | (b-24) | (b-7) | H | H | (a-20) | —CH— | —NH— | —CH(Me)— |
| 3-412 | (b-24) | (b-35) | H | H | (a-20) | —CH— | —NH— | —CH(Me)— |
| 3-413 | (b-25) | (b-7) | H | H | (a-20) | —CH— | —NH— | —CH(Me)— |
| 3-414 | (b-25) | (b-35) | H | H | (a-20) | —CH— | —NH— | —CH(Me)— |
| 3-415 | (b-72) | (b-7) | H | H | (a-20) | —CH— | —NH— | —CH(Me)— |
| 3-416 | (b-72) | (b-35) | H | H | (a-20) | —CH— | —NH— | —CH(Me)— |
| 3-417 | (b-73) | (b-7) | H | H | (a-20) | —CH— | —NH— | —CH(Me)— |
| 3-418 | (b-73) | (b-7) | H | H | (a-20) | —CH— | —NH— | —COCH(Me)— |
| 3-419 | (b-73) | (b-35) | H | H | (a-20) | —CH— | —NH— | —CH(Me)— |
| 3-420 | (b-73) | (b-35) | H | H | (a-20) | —CH— | —NH— | —COCH(Me)— |
| 3-421 | (b-74) | (b-7) | H | H | (a-20) | —CH— | —NH— | —CH(Me)— |
| 3-422 | (b-74) | (b-35) | H | H | (a-20) | —CH— | —NH— | —CH(Me)— |
| 3-423 | (b-76) | (b-7) | H | H | (a-20) | —CH— | —NH— | —CH(Me)— |
| 3-424 | (b-76) | (b-35) | H | H | (a-20) | —CH— | —NH— | —CH(Me)— |
| 3-425 | (b-77) | (b-7) | H | H | (a-20) | —CH— | —NH— | —CH(Me)— |
| 3-426 | (b-77) | (b-7) | H | H | (a-20) | —CH— | —NH— | —COCH(Me)— |
| 3-427 | (b-77) | (b-35) | H | H | (a-20) | —CH— | —NH— | —CH(Me)— |
| 3-428 | (b-77) | (b-35) | H | H | (a-20) | —CH— | —NH— | —COCH(Me)— |
| 3-429 | (b-7) | (b-35) | H | H | (a-21) | —CH— | —NH— | —CH(Me)— |
| 3-430 | (b-11) | (b-35) | H | H | (a-21) | —CH— | —NH— | —CH(Me)— |
| 3-431 | (b-18) | (b-35) | H | H | (a-21) | —CH— | —NH— | —CH(Me)— |
| 3-432 | (b-20) | (b-35) | H | H | (a-21) | —CH— | —NH— | —CH(Me)— |
| 3-433 | (b-73) | (b-35) | H | H | (a-21) | —CH— | —NH— | —CH(Me)— |
| 3-434 | (b-77) | (b-35) | H | H | (a-21) | —CH— | —NH— | —CH(Me)— |

TABLE 3-continued

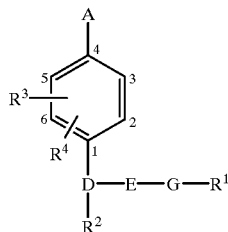

(I-3)

| Cpd. No. | R$^1$ Sub. No | R$^2$ Sub. No | R$^3$ | R$^4$ | A Sub. No. | D | E | G |
|---|---|---|---|---|---|---|---|---|
| 3-435 | (b-7) | (b-7) | H | H | (a-24) | —CH— | —NH— | —CH(Me)— |
| 3-436 | (b-7) | (b-35) | H | H | (a-24) | —CH— | —NH— | —CH(Me)— |
| 3-437 | (b-11) | (b-7) | H | H | (a-24) | —CH— | —NH— | —CH(Me)— |
| 3-438 | (b-11) | (b-35) | H | H | (a-24) | —CH— | —NH— | —CH(Me)— |
| 3-439 | (b-12) | (b-35) | H | H | (a-24) | —CH— | —NH— | —CH(Me)— |
| 3-440 | (b-15) | (b-35) | H | H | (a-24) | —CH— | —NH— | —CH(Me)— |
| 3-441 | (b-18) | (b-7) | H | H | (a-24) | —CH— | —NH— | —CH(Me)— |
| 3-442 | (b-18) | (b-35) | H | H | (a-24) | —CH— | —NH— | —CH(Me)— |
| 3-443 | (b-19) | (b-35) | H | H | (a-24) | —CH— | —NH— | —CH(Me)— |
| 3-444 | (b-20) | (b-7) | H | H | (a-24) | —CH— | —NH— | —CH(Me)— |
| 3-445 | (b-20) | (b-35) | H | H | (a-24) | —CH— | —NH— | —CH(Me)— |
| 3-446 | (b-21) | (b-35) | H | H | (a-24) | —CH— | —NH— | —CH(Me)— |
| 3-447 | (b-24) | (b-35) | H | H | (a-24) | —CH— | —NH— | —CH(Me)— |
| 3-448 | (b-25) | (b-35) | H | H | (a-24) | —CH— | —NH— | —CH(Me)— |
| 3-449 | (b-72) | (b-35) | H | H | (a-24) | —CH— | —NH— | —CH(Me)— |
| 3-450 | (b-73) | (b-7) | H | H | (a-24) | —CH— | —NH— | —CH(Me)— |
| 3-451 | (b-73) | (b-35) | H | H | (a-24) | —CH— | —NH— | —CH(Me)— |
| 3-452 | (b-74) | (b-35) | H | H | (a-24) | —CH— | —NH— | —CH(Me)— |
| 3-453 | (b-76) | (b-35) | H | H | (a-24) | —CH— | —NH— | —CH(Me)— |
| 3-454 | (b-77) | (b-7) | H | H | (a-24) | —CH— | —NH— | —CH(Me)— |
| 3-455 | (b-77) | (b-35) | H | H | (a-24) | —CH— | —NH— | —CH(Me)— |
| 3-456 | (b-2) | (b-35) | H | H | (a-26) | —CH— | —NH— | —CH(Me)— |
| 3-457 | (b-7) | (b-7) | H | H | (a-26) | —CH— | —NH— | —CH(Me)— |
| 3-458 | (b-7) | (b-7) | H | H | (a-26) | —CH— | —NH— | —COCH(Me)— |
| 3-459 | (b-7) | (b-35) | H | H | (a-26) | —CH— | —NH— | —CH(Me)— |
| 3-460 | (b-7) | (b-35) | H | H | (a-26) | —CH— | —NH— | —COCH(Me)— |
| 3-461 | (b-8) | (b-35) | H | H | (a-26) | —CH— | —NH— | —CH(Me)— |
| 3-462 | (b-11) | (b-7) | H | H | (a-26) | —CH— | —NH— | —CH(Me)— |
| 3-463 | (b-11) | (b-7) | H | H | (a-26) | —CH— | —NH— | —COCH(Me)— |
| 3-464 | (b-11) | (b-35) | H | H | (a-26) | —CH— | —NH— | —CH(Me)— |
| 3-465 | (b-11) | (b-35) | H | H | (a-26) | —CH— | —NH— | —COCH(Me)— |
| 3-466 | (b-12) | (b-7) | H | H | (a-26) | —CH— | —NH— | —CH(Me)— |
| 3-467 | (b-12) | (b-35) | H | H | (a-26) | —CH— | —NH— | —CH(Me)— |
| 3-468 | (b-15) | (b-7) | H | H | (a-26) | —CH— | —NH— | —CH(Me)— |
| 3-469 | (b-15) | (b-35) | H | H | (a-26) | —CH— | —NH— | —CH(Me)— |
| 3-470 | (b-18) | (b-7) | H | H | (a-26) | —CH— | —NH— | —CH(Me)— |
| 3-471 | (b-18) | (b-7) | H | H | (a-26) | —CH— | —NH— | —COCH(Me)— |
| 3-472 | (b-18) | (b-35) | H | H | (a-26) | —CH— | —NH— | —CH(Me)— |
| 3-473 | (b-18) | (b-35) | H | H | (a-26) | —CH— | —NH— | —COCH(Me)— |
| 3-474 | (b-19) | (b-7) | H | H | (a-26) | —CH— | —NH— | —CH(Me)— |
| 3-475 | (b-19) | (b-35) | H | H | (a-26) | —CH— | —NH— | —CH(Me)— |
| 3-476 | (b-20) | (b-7) | H | H | (a-26) | —CH— | —NH— | —CH(Me)— |
| 3-477 | (b-20) | (b-7) | H | H | (a-26) | —CH— | —NH— | —COCH(Me)— |
| 3-478 | (b-20) | (b-35) | H | H | (a-26) | —CH— | —NH— | —CH(Me)— |
| 3-479 | (b-20) | (b-35) | H | H | (a-26) | —CH— | —NH— | —COCH(Me)— |
| 3-480 | (b-21) | (b-7) | H | H | (a-26) | —CH— | —NH— | —CH(Me)— |
| 3-481 | (b-21) | (b-35) | H | H | (a-26) | —CH— | —NH— | —CH(Me)— |
| 3-482 | (b-24) | (b-7) | H | H | (a-26) | —CH— | —NH— | —CH(Me)— |
| 3-483 | (b-24) | (b-35) | H | H | (a-26) | —CH— | —NH— | —CH(Me)— |
| 3-484 | (b-25) | (b-7) | H | H | (a-26) | —CH— | —NH— | —CH(Me)— |
| 3-485 | (b-25) | (b-35) | H | H | (a-26) | —CH— | —NH— | —CH(Me)— |
| 3-486 | (b-72) | (b-7) | H | H | (a-26) | —CH— | —NH— | —CH(Me)— |
| 3-487 | (b-72) | (b-35) | H | H | (a-26) | —CH— | —NH— | —CH(Me)— |
| 3-488 | (b-73) | (b-7) | H | H | (a-26) | —CH— | —NH— | —CH(Me)— |
| 3-489 | (b-73) | (b-7) | H | H | (a-26) | —CH— | —NH— | —COCH(Me)— |
| 3-490 | (b-73) | (b-35) | H | H | (a-26) | —CH— | —NH— | —CH(Me)— |
| 3-491 | (b-73) | (b-35) | H | H | (a-26) | —CH— | —NH— | —COCH(Me)— |
| 3-492 | (b-74) | (b-7) | H | H | (a-26) | —CH— | —NH— | —CH(Me)— |
| 3-493 | (b-74) | (b-35) | H | H | (a-26) | —CH— | —NH— | —CH(Me)— |
| 3-494 | (b-76) | (b-7) | H | H | (a-26) | —CH— | —NH— | —CH(Me)— |
| 3-495 | (b-76) | (b-35) | H | H | (a-26) | —CH— | —NH— | —CH(Me)— |
| 3-496 | (b-77) | (b-7) | H | H | (a-26) | —CH— | —NH— | —CH(Me)— |

TABLE 3-continued (I-3)

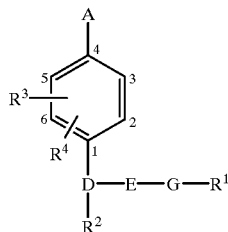

| Cpd. No. | R¹ Sub. No | R² Sub. No | R³ | R⁴ | A Sub. No. | D | E | G |
|---|---|---|---|---|---|---|---|---|
| 3-497 | (b-77) | (b-7) | H | H | (a-26) | —CH— | —NH— | —COCH(Me)— |
| 3-498 | (b-77) | (b-35) | H | H | (a-26) | —CH— | —NH— | —CH(Me)— |
| 3-499 | (b-77) | (b-35) | H | H | (a-26) | —CH— | —NH— | —COCH(Me)— |
| 3-500 | (b-7) | (b-35) | H | H | (a-27) | —CH— | —NH— | —CH(Me)— |
| 3-501 | (b-11) | (b-35) | H | H | (a-27) | —CH— | —NH— | —CH(Me)— |
| 3-502 | (b-l8) | (b-35) | H | H | (a-27) | —CH— | —NH— | —CH(Me)— |
| 3-503 | (b-20) | (b-35) | H | H | (a-27) | —CH— | —NH— | —CH(Me)— |
| 3-504 | (b-73) | (b-35) | H | H | (a-27) | —CH— | —NH— | —CH(Me)— |
| 3-505 | (b-77) | (b-35) | H | H | (a-27) | —CH— | —NH— | —CH(Me)— |
| 3-506 | (b-7) | (b-7) | H | H | (a-28) | —CH— | —NH— | —CH(Me)— |
| 3-507 | (b-7) | (b-35) | H | H | (a-28) | —CH— | —NH— | —CH(Me)— |
| 3-508 | (b-11) | (b-7) | H | H | (a-28) | —CH— | —NH— | —CH(Me)— |
| 3-509 | (b-11) | (b-35) | H | H | (a-28) | —CH— | —NH— | —CH(Me)— |
| 3-510 | (b-12) | (b-35) | H | H | (a-28) | —CH— | —NH— | —CH(Me)— |
| 3-511 | (b-15) | (b-35) | H | H | (a-28) | —CH— | —NH— | —CH(Me)— |
| 3-512 | (b-18) | (b-7) | H | H | (a-28) | —CH— | —NH— | —CH(Me)— |
| 3-513 | (b-18) | (b-35) | H | H | (a-28) | —CH— | —NH— | —CH(Me)— |
| 3-514 | (b-19) | (b-35) | H | H | (a-28) | —CH— | —NH— | —CH(Me)— |
| 3-515 | (b-20) | (b-7) | H | H | (a-28) | —CH— | —NH— | —CH(Me)— |
| 3-516 | (b-20) | (b-35) | H | H | (a-28) | —CH— | —NH— | —CH(Me)— |
| 3-517 | (b-21) | (b-35) | H | H | (a-28) | —CH— | —NH— | —CH(Me)— |
| 3-518 | (b-24) | (b-35) | H | H | (a-28) | —CH— | —NH— | —CH(Me)— |
| 3-519 | (b-25) | (b-35) | H | H | (a-28) | —CH— | —NH— | —CH(Me)— |
| 3-520 | (b-72) | (b-35) | H | H | (a-28) | —CH— | —NH— | —CH(Me)— |
| 3-521 | (b-73) | (b-7) | H | H | (a-28) | —CH— | —NH— | —CH(Me)— |
| 3-522 | (b-73) | (b-35) | H | H | (a-28) | —CH— | —NH— | —CH(Me)— |
| 3-523 | (b-74) | (b-35) | H | H | (a-28) | —CH— | —NH— | —CH(Me)— |
| 3-524 | (b-76) | (b-35) | H | H | (a-28) | —CH— | —NH— | —CH(Me)— |
| 3-525 | (b-77) | (b-7) | H | H | (a-28) | —CH— | —NH— | —CH(Me)— |
| 3-526 | (b-77) | (b-35) | H | H | (a-28) | —CH— | —NH— | —CH(Me)— |
| 3-527 | (b-7) | (b-35) | H | H | (a-29) | —CH— | —NH— | —CH(Me)— |
| 3-528 | (b-11) | (b-35) | H | H | (a-29) | —CH— | —NH— | —CH(Me)— |
| 3-529 | (b-18) | (b-35) | H | H | (a-29) | —CH— | —NH— | —CH(Me)— |
| 3-530 | (b-20) | (b-35) | H | H | (a-29) | —CH— | —NH— | —CH(Me)— |
| 3-531 | (b-73) | (b-35) | H | H | (a-29) | —CH— | —NH— | —CH(Me)— |
| 3-532 | (b-77) | (b-35) | H | H | (a-29) | —CH— | —NH— | —CH(Me)— |
| 3-533 | (b-2) | (b-35) | H | H | (a-31) | —CH— | —NH— | —CH(Me)— |
| 3-534 | (b-7) | (b-7) | H | H | (a-31) | —CH— | —NH— | —CH(Me)— |
| 3-535 | (b-7) | (b-7) | H | H | (a-31) | —CH— | —NH— | —COCH(Me)— |
| 3-536 | (b-7) | (b-35) | H | H | (a-31) | —CH— | —NH— | —CH(Me)— |
| 3-537 | (b-7) | (b-35) | H | H | (a-31) | —CH— | —NH— | —COCH(Me)— |
| 3-538 | (b-8) | (b-35) | H | H | (a-31) | —CH— | —NH— | —CH(Me)— |
| 3-539 | (b-11) | (b-7) | H | H | (a-31) | —CH— | —NH— | —CH(Me)— |
| 3-540 | (b-11) | (b-7) | H | H | (a-31) | —CH— | —NH— | —COCH(Me)— |
| 3-541 | (b-11) | (b-35) | H | H | (a-31) | —CH— | —NH— | —CH(Me)— |
| 3-542 | (b-11) | (b-35) | H | H | (a-31) | —CH— | —NH— | —COCH(Me)— |
| 3-543 | (b-12) | (b-7) | H | H | (a-31) | —CH— | —NH— | —CH(Me)— |
| 3-544 | (b-12) | (b-35) | H | H | (a-31) | —CH— | —NH— | —CH(Me)— |
| 3-545 | (b-15) | (b-7) | H | H | (a-31) | —CH— | —NH— | —CH(Me)— |
| 3-546 | (b-15) | (b-35) | H | H | (a-31) | —CH— | —NH— | —CH(Me)— |
| 3-547 | (b-18) | (b-7) | H | H | (a-31) | —CH— | —NH— | —CH(Me)— |
| 3-548 | (b-18) | (b-7) | H | H | (a-31) | —CH— | —NH— | —COCH(Me)— |
| 3-549 | (b-18) | (b-35) | H | H | (a-31) | —CH— | —NH— | —CH(Me)— |
| 3-550 | (b-18) | (b-35) | H | H | (a-31) | —CH— | —NH— | —COCH(Me)— |
| 3-551 | (b-19) | (b-7) | H | H | (a-31) | —CH— | —NH— | —CH(Me)— |
| 3-552 | (b-19) | (b-35) | H | H | (a-31) | —CH— | —NH— | —CH(Me)— |
| 3-553 | (b-20) | (b-7) | H | H | (a-31) | —CH— | —NH— | —CH(Me)— |
| 3-554 | (b-20) | (b-7) | H | H | (a-31) | —CH— | —NH— | —COCH(Me)— |
| 3-555 | (b-20) | (b-35) | H | H | (a-31) | —CH— | —NH— | —CH(Me)— |
| 3-556 | (b-20) | (b-35) | H | H | (a-31) | —CH— | —NH— | —COCH(Me)— |
| 3-557 | (b-21) | (b-7) | H | H | (a-31) | —CH— | —NH— | —CH(Me)— |
| 3-558 | (b-21) | (b-35) | H | H | (a-31) | —CH— | —NH— | —CH(Me)— |

TABLE 3-continued

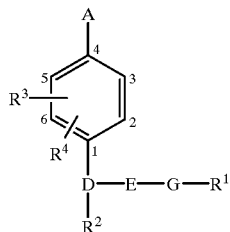

(I-3)

| Cpd. No. | R$^1$ Sub. No | R$^2$ Sub. No | R$^3$ | R$^4$ | A Sub. No. | D | E | G |
|---|---|---|---|---|---|---|---|---|
| 3-559 | (b-24) | (b-7) | H | H | (a-31) | —CH— | —NH— | —CH(Me)— |
| 3-560 | (b-24) | (b-35) | H | H | (a-31) | —CH— | —NH— | —CH(Me)— |
| 3-561 | (b-25) | (b-7) | H | H | (a-31) | —CH— | —NH— | —CH(Me)— |
| 3-562 | (b-25) | (b-35) | H | H | (a-31) | —CH— | —NH— | —CH(Me)— |
| 3-563 | (b-72) | (b-7) | H | H | (a-31) | —CH— | —NH— | —CH(Me)— |
| 3-564 | (b-72) | (b-35) | H | H | (a-31) | —CH— | —NH— | —CH(Me)— |
| 3-565 | (b-73) | (b-7) | H | H | (a-31) | —CH— | —NH— | —CH(Me)— |
| 3-566 | (b-73) | (b-7) | H | H | (a-31) | —CH— | —NH— | —COCH(Me)— |
| 3-567 | (b-73) | (b-35) | H | H | (a-31) | —CH— | —NH— | —CH(Me)— |
| 3-568 | (b-73) | (b-35) | H | H | (a-31) | —CH— | —NH— | —COCH(Me)— |
| 3-569 | (b-74) | (b-7) | H | H | (a-31) | —CH— | —NH— | —CH(Me)— |
| 3-570 | (b-74) | (b-35) | H | H | (a-31) | —CH— | —NH— | —CH(Me)— |
| 3-571 | (b-76) | (b-7) | H | H | (a-31) | —CH— | —NH— | —CH(Me)— |
| 3-572 | (b-76) | (b-35) | H | H | (a-31) | —CH— | —NH— | —CH(Me)— |
| 3-573 | (b-77) | (b-7) | H | H | (a-31) | —CH— | —NH— | —CH(Me)— |
| 3-574 | (b-77) | (b-7) | H | H | (a-31) | —CH— | —NH— | —COCH(Me)— |
| 3-575 | (b-77) | (b-35) | H | H | (a-31) | —CH— | —NH— | —CH(Me)— |
| 3-576 | (b-77) | (b-35) | H | H | (a-31) | —CH— | —NH— | —COCH(Me)— |
| 3-577 | (b-7) | (b-35) | H | H | (a-32) | —CH— | —NH— | —CH(Me)— |
| 3-578 | (b-11) | (b-35) | H | H | (a-32) | —CH— | —NH— | —CH(Me)— |
| 3-579 | (b-18) | (b-35) | H | H | (a-32) | —CH— | —NH— | —CH(Me)— |
| 3-580 | (b-20) | (b-35) | H | H | (a-32) | —CH— | —NH— | —CH(Me)— |
| 3-581 | (b-73) | (b-35) | H | H | (a-32) | —CH— | —NH— | —CH(Me)— |
| 3-582 | (b-77) | (b-35) | H | H | (a-32) | —CH— | —NH— | —CH(Me)— |
| 3-583 | (b-7) | (b-7) | H | H | (a-33) | —CH— | —NH— | —CH(Me)— |
| 3-584 | (b-7) | (b-35) | H | H | (a-33) | —CH— | —NH— | —CH(Me)— |
| 3-585 | (b-11) | (b-7) | H | H | (a-33) | —CH— | —NH— | —CH(Me)— |
| 3-586 | (b-11) | (b-35) | H | H | (a-33) | —CH— | —NH— | —CH(Me)— |
| 3-587 | (b-12) | (b-35) | H | H | (a-33) | —CH— | —NH— | —CH(Me)— |
| 3-588 | (b-15) | (b-35) | H | H | (a-33) | —CH— | —NH— | —CH(Me)— |
| 3-589 | (b-18) | (b-7) | H | H | (a-33) | —CH— | —NH— | —CH(Me)— |
| 3-590 | (b-18) | (b-35) | H | H | (a-33) | —CH— | —NH— | —CH(Me)— |
| 3-591 | (b-19) | (b-35) | H | H | (a-33) | —CH— | —NH— | —CH(Me)— |
| 3-592 | (b-20) | (b-7) | H | H | (a-33) | —CH— | —NH— | —CH(Me)— |
| 3-593 | (b-20) | (b-35) | H | H | (a-33) | —CH— | —NH— | —CH(Me)— |
| 3-594 | (b-21) | (b-35) | H | H | (a-33) | —CH— | —NH— | —CH(Me)— |
| 3-595 | (b-24) | (b-35) | H | H | (a-33) | —CH— | —NH— | —CH(Me)— |
| 3-596 | (b-25) | (b-35) | H | H | (a-33) | —CH— | —NH— | —CH(Me)— |
| 3-597 | (b-72) | (b-35) | H | H | (a-33) | —CH— | —NH— | —CH(Me)— |
| 3-598 | (b-73) | (b-7) | H | H | (a-33) | —CH— | —NH— | —CH(Me)— |
| 3-599 | (b-73) | (b-35) | H | H | (a-33) | —CH— | —NH— | —CH(Me)— |
| 3-600 | (b-74) | (b-35) | H | H | (a-33) | —CH— | —NH— | —CH(Me)— |
| 3-601 | (b-76) | (b-35) | H | H | (a-33) | —CH— | —NH— | —CH(Me)— |
| 3-602 | (b-77) | (b-7) | H | H | (a-33) | —CH— | —NH— | —CH(Me)— |
| 3-603 | (b-77) | (b-35) | H | H | (a-33) | —CH— | —NH— | —CH(Me)— |
| 3-604 | (b-7) | (b-35) | H | H | (a-34) | —CH— | —NH— | —CH(Me)— |
| 3-605 | (b-11) | (b-35) | H | H | (a-34) | —CH— | —NH— | —CH(Me)— |
| 3-606 | (b-18) | (b-35) | H | H | (a-34) | —CH— | —NH— | —CH(Me)— |
| 3-607 | (b-20) | (b-35) | H | H | (a-34) | —CH— | —NH— | —CH(Me)— |
| 3-608 | (b-73) | (b-35) | H | H | (a-34) | —CH— | —NH— | —CH(Me)— |
| 3-609 | (b-77) | (b-35) | H | H | (a-34) | —CH— | —NH— | —CH(Me)— |
| 3-610 | (b-7) | (b-35) | H | H | (a-36) | —CH— | —NH— | —CH(Me)— |
| 3-611 | (b-11) | (b-35) | H | H | (a-36) | —CH— | —NH— | —CH(Me)— |
| 3-612 | (b-18) | (b-35) | H | H | (a-36) | —CH— | —NH— | —CH(Me)— |
| 3-613 | (b-20) | (b-35) | H | H | (a-36) | —CH— | —NH— | —CH(Me)— |
| 3-614 | (b-73) | (b-35) | H | H | (a-36) | —CH— | —NH— | —CH(Me)— |
| 3-615 | (b-77) | (b-35) | H | H | (a-36) | —CH— | —NH— | —CH(Me)— |
| 3-616 | (b-7) | (b-35) | H | H | (a-38) | —CH— | —NH— | —CH(Me)— |
| 3-617 | (b-11) | (b-35) | H | H | (a-38) | —CH— | —NH— | —CH(Me)— |
| 3-618 | (b-18) | (b-35) | H | H | (a-38) | —CH— | —NH— | —CH(Me)— |
| 3-619 | (b-7) | (b-35) | H | H | (a-39) | —CH— | —NH— | —CH(Me)— |
| 3-620 | (b-11) | (b-35) | H | H | (a-39) | —CH— | —NH— | —CH(Me)— |

TABLE 3-continued

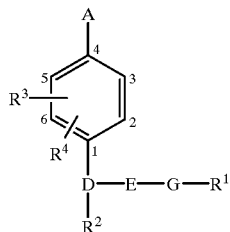

(I-3)

| Cpd. No. | R¹ Sub. No | R² Sub. No | R³ | R⁴ | A Sub. No. | D | E | G |
|---|---|---|---|---|---|---|---|---|
| 3-621 | (b-18) | (b-35) | H | H | (a-39) | —CH— | —NH— | —CH(Me)— |
| 3-622 | (b-20) | (b-35) | H | H | (a-39) | —CH— | —NH— | —CH(Me)— |
| 3-623 | (b-73) | (b-35) | H | H | (a-39) | —CH— | —NH— | —CH(Me)— |
| 3-624 | (b-77) | (b-35) | H | H | (a-39) | —CH— | —NH— | —CH(Me)— |
| 3-625 | (b-7) | (b-35) | H | H | (a-41) | —CH— | —NH— | —CH(Me)— |
| 3-626 | (b-11) | (b-35) | H | H | (a-41) | —CH— | —NH— | —CH(Me)— |
| 3-627 | (b-18) | (b-35) | H | H | (a-41) | —CH— | —NH— | —CH(Me)— |
| 3-628 | (b-2) | (b-35) | H | H | (a-43) | —CH— | —NH— | —CH(Me)— |
| 3-629 | (b-7) | (b-7) | H | H | (a-43) | —CH— | —NH— | —CH(Me)— |
| 3-630 | (b-7) | (b-7) | H | H | (a-43) | —CH— | —NH— | —COCH(Me)— |
| 3-631 | (b-7) | (b-35) | H | H | (a-43) | —CH— | —NH— | —CH(Me)— |
| 3-632 | (b-7) | (b-35) | H | H | (a-43) | —CH— | —NH— | —COCH(Me)— |
| 3-633 | (b-8) | (b-35) | H | H | (a-43) | —CH— | —NH— | —CH(Me)— |
| 3-634 | (b-11) | (b-7) | H | H | (a-43) | —CH— | —NH— | —CH(Me)— |
| 3-635 | (b-11) | (b-7) | H | H | (a-43) | —CH— | —NH— | —COCH(Me)— |
| 3-636 | (b-11) | (b-35) | H | H | (a-43) | —CH— | —NH— | —CH(Me)— |
| 3-637 | (b-11) | (b-35) | H | H | (a-43) | —CH— | —NH— | —COCH(Me)— |
| 3-638 | (b-12) | (b-7) | H | H | (a-43) | —CH— | —NH— | —CH(Me)— |
| 3-639 | (b-12) | (b-35) | H | H | (a-43) | —CH— | —NH— | —CH(Me)— |
| 3-640 | (b-15) | (b-7) | H | H | (a-43) | —CH— | —NH— | —CH(Me)— |
| 3-641 | (b-15) | (b-35) | H | H | (a-43) | —CH— | —NH— | —CH(Me)— |
| 3-642 | (b-18) | (b-7) | H | H | (a-43) | —CH— | —NH— | —CH(Me)— |
| 3-643 | (b-18) | (b-7) | H | H | (a-43) | —CH— | —NH— | —COCH(Me)— |
| 3-644 | (b-18) | (b-35) | H | H | (a-43) | —CH— | —NH— | —CH(Me)— |
| 3-645 | (b-18) | (b-35) | H | H | (a-43) | —CH— | —NH— | —COCH(Me)— |
| 3-646 | (b-19) | (b-7) | H | H | (a-43) | —CH— | —NH— | —CH(Me)— |
| 3-647 | (b-19) | (b-35) | H | H | (a-43) | —CH— | —NH— | —CH(Me)— |
| 3-648 | (b-20) | (b-7) | H | H | (a-43) | —CH— | —NH— | —CH(Me)— |
| 3-649 | (b-20) | (b-7) | H | H | (a-43) | —CH— | —NH— | —COCH(Me)— |
| 3-650 | (b-20) | (b-35) | H | H | (a-43) | —CH— | —NH— | —CH(Me)— |
| 3-651 | (b-20) | (b-35) | H | H | (a-43) | —CH— | —NH— | —COCH(Me)— |
| 3-652 | (b-21) | (b-7) | H | H | (a-43) | —CH— | —NH— | —CH(Me)— |
| 3-653 | (b-21) | (b-35) | H | H | (a-43) | —CH— | —NH— | —CH(Me)— |
| 3-654 | (b-24) | (b-7) | H | H | (a-43) | —CH— | —NH— | —CH(Me)— |
| 3-655 | (b-24) | (b-35) | H | H | (a-43) | —CH— | —NH— | —CH(Me)— |
| 3-656 | (b-25) | (b-7) | H | H | (a-43) | —CH— | —NH— | —CH(Me)— |
| 3-657 | (b-25) | (b-35) | H | H | (a-43) | —CH— | —NH— | —CH(Me)— |
| 3-658 | (b-72) | (b-7) | H | H | (a-43) | —CH— | —NH— | —CH(Me)— |
| 3-659 | (b-72) | (b-35) | H | H | (a-43) | —CH— | —NH— | —CH(Me)— |
| 3-660 | (b-73) | (b-7) | H | H | (a-43) | —CH— | —NH— | —CH(Me)— |
| 3-661 | (b-73) | (b-7) | H | H | (a-43) | —CH— | —NH— | —COCH(Me)— |
| 3-662 | (b-73) | (b-35) | H | H | (a-43) | —CH— | —NH— | —CH(Me)— |
| 3-663 | (b-73) | (b-35) | H | H | (a-43) | —CH— | —NH— | —COCH(Me)— |
| 3-664 | (b-74) | (b-7) | H | H | (a-43) | —CH— | —NH— | —CH(Me)— |
| 3-665 | (b-74) | (b-35) | H | H | (a-43) | —CH— | —NH— | —CH(Me)— |
| 3-666 | (b-76) | (b-7) | H | H | (a-43) | —CH— | —NH— | —CH(Me)— |
| 3-667 | (b-76) | (b-35) | H | H | (a-43) | —CH— | —NH— | —CH(Me)— |
| 3-668 | (b-77) | (b-7) | H | H | (a-43) | —CH— | —NH— | —CH(Me)— |
| 3-669 | (b-77) | (b-7) | H | H | (a-43) | —CH— | —NH— | —COCH(Me)— |
| 3-670 | (b-77) | (b-35) | H | H | (a-43) | —CH— | —NH— | —CH(Me)— |
| 3-671 | (b-77) | (b-35) | H | H | (a-43) | —CH— | —NH— | —COCH(Me)— |
| 3-672 | (b-7) | (b-35) | H | H | (a-44) | —CH— | —NH— | —CH(Me)— |
| 3-673 | (b-11) | (b-35) | H | H | (a-44) | —CH— | —NH— | —CH(Me)— |
| 3-674 | (b-18) | (b-35) | H | H | (a-44) | —CH— | —NH— | —CH(Me)— |
| 3-675 | (b-20) | (b-35) | H | H | (a-44) | —CH— | —NH— | —CH(Me)— |
| 3-676 | (b-73) | (b-35) | H | H | (a-44) | —CH— | —NH— | —CH(Me)— |
| 3-677 | (b-77) | (b-35) | H | H | (a-44) | —CH— | —NH— | —CH(Me)— |
| 3-678 | (b-7) | (b-7) | H | H | (a-45) | —CH— | —NH— | —CH(Me)— |
| 3-679 | (b-7) | (b-35) | H | H | (a-45) | —CH— | —NH— | —CH(Me)— |
| 3-680 | (b-11) | (b-7) | H | H | (a-45) | —CH— | —NH— | —CH(Me)— |
| 3-681 | (b-11) | (b-35) | H | H | (a-45) | —CH— | —NH— | —CH(Me)— |
| 3-682 | (b-12) | (b-35) | H | H | (a-45) | —CH— | —NH— | —CH(Me)— |

TABLE 3-continued (I-3)

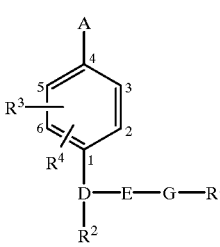

| Cpd. No. | R¹ Sub. No | R² Sub. No | R³ | R⁴ | A Sub. No. | D | E | G |
|---|---|---|---|---|---|---|---|---|
| 3-683 | (b-15) | (b-35) | H | H | (a-45) | —CH— | —NH— | —CH(Me)— |
| 3-684 | (b-18) | (b-7) | H | H | (a-45) | —CH— | —NH— | —CH(Me)— |
| 3-685 | (b-18) | (b-35) | H | H | (a-45) | —CH— | —NH— | —CH(Me)— |
| 3-686 | (b-19) | (b-35) | H | H | (a-45) | —CH— | —NH— | —CH(Me)— |
| 3-687 | (b-20) | (b-7) | H | H | (a-45) | —CH— | —NH— | —CH(Me)— |
| 3-688 | (b-20) | (b-35) | H | H | (a-45) | —CH— | —NH— | —CH(Me)— |
| 3-689 | (b-21) | (b-35) | H | H | (a-45) | —CH— | —NH— | —CH(Me)— |
| 3-690 | (b-24) | (b-35) | H | H | (a-45) | —CH— | —NH— | —CH(Me)— |
| 3-691 | (b-25) | (b-35) | H | H | (a-45) | —CH— | —NH— | —CH(Me)— |
| 3-692 | (b-72) | (b-35) | H | H | (a-45) | —CH— | —NH— | —CH(Me)— |
| 3-693 | (b-73) | (b-7) | H | H | (a-45) | —CH— | —NH— | —CH(Me)— |
| 3-694 | (b-73) | (b-35) | H | H | (a-45) | —CH— | —NH— | —CH(Me)— |
| 3-695 | (b-74) | (b-35) | H | H | (a-45) | —CH— | —NH— | —CH(Me)— |
| 3-696 | (b-76) | (b-35) | H | H | (a-45) | —CH— | —NH— | —CH(Me)— |
| 3-697 | (b-77) | (b-7) | H | H | (a-45) | —CH— | —NH— | —CH(Me)— |
| 3-698 | (b-77) | (b-35) | H | H | (a-45) | —CH— | —NH— | —CH(Me)— |
| 3-699 | (b-7) | (b-35) | H | H | (a-46) | —CH— | —NH— | —CH(Me)— |
| 3-700 | (b-11) | (b-35) | H | H | (a-46) | —CH— | —NH— | —CH(Me)— |
| 3-701 | (b-18) | (b-35) | H | H | (a-46) | —CH— | —NH— | —CH(Me)— |
| 3-702 | (b-20) | (b-35) | H | H | (a-46) | —CH— | —NH— | —CH(Me)— |
| 3-703 | (b-73) | (b-35) | H | H | (a-46) | —CH— | —NH— | —CH(Me)— |
| 3-704 | (b-77) | (b-35) | H | H | (a-46) | —CH— | —NH— | —CH(Me)— |
| 3-705 | (b-7) | (b-35) | H | H | (a-47) | —CH— | —NH— | —CH(Me)— |
| 3-706 | (b-11) | (b-35) | H | H | (a-47) | —CH— | —NH— | —CH(Me)— |
| 3-707 | (b-18) | (b-35) | H | H | (a-47) | —CH— | —NH— | —CH(Me)— |

TABLE 4

(I-4)

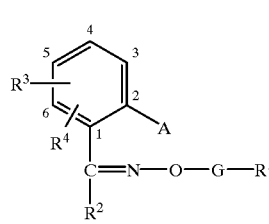

| Cpd. No. | R¹ Sub. No. | R² Sub. No. | R³ | R⁴ | A Sub. No. | G |
|---|---|---|---|---|---|---|
| 4-1 | (b-7) | (b-35) | H | H | (a-1) | —CH(Me)— |
| 4-2 | (b-11) | (b-35) | H | H | (a-1) | —CH(Me)— |
| 4-3 | (b-18) | (b-35) | H | H | (a-1) | —CH(Me)— |
| 4-4 | (b-20) | (b-35) | H | H | (a-1) | —CH(Me)— |
| 4-5 | (b-73) | (b-35) | H | H | (a-1) | —CH(Me)— |
| 4-6 | (b-77) | (b-35) | H | H | (a-1) | —CH(Me)— |
| 4-7 | (b-7) | (b-35) | H | H | (a-3) | —CH(Me)— |
| 4-8 | (b-11) | (b-35) | H | H | (a-3) | —CH(Me)— |
| 4-9 | (b-18) | (b-35) | H | H | (a-3) | —CH(Me)— |
| 4-10 | (b-7) | (b-35) | H | H | (a-5) | —CH(Me)— |
| 4-11 | (b-11) | (b-35) | H | H | (a-5) | —CH(Me)— |
| 4-12 | (b-18) | (b-35) | H | H | (a-5) | —CH(Me)— |
| 4-13 | (b-20) | (b-35) | H | H | (a-5) | —CH(Me)— |
| 4-14 | (b-73) | (b-35) | H | H | (a-5) | —CH(Me)— |
| 4-15 | (b-77) | (b-35) | H | H | (a-5) | —CH(Me)— |
| 4-16 | (b-7) | (b-35) | H | H | (a-7) | —CH(Me)— |
| 4-17 | (b-11) | (b-35) | H | H | (a-7) | —CH(Me)— |
| 4-18 | (b-18) | (b-35) | H | H | (a-7) | —CH(Me)— |

TABLE 4-continued

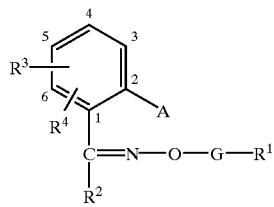

(I-4)

| Cpd. No. | $R^1$ Sub. No. | $R^2$ Sub. No. | $R^3$ | $R^4$ | A Sub. No. | G |
|---|---|---|---|---|---|---|
| 4-19 | (b-7) | (b-7) | H | H | (a-14) | —CH(Me)— |
| 4-20 | (b-7) | (b-35) | H | H | (a-14) | —CH(Me)— |
| 4-21 | (b-11) | (b-7) | H | H | (a-14) | —CH(Me)— |
| 4-22 | (b-11) | (b-35) | H | H | (a-14) | —CH(Me)— |
| 4-23 | (b-12) | (b-35) | H | H | (a-14) | —CH(Me)— |
| 4-24 | (b-15) | (b-35) | H | H | (a-14) | —CH(Me)— |
| 4-25 | (b-18) | (b-7) | H | H | (a-14) | —CH(Me)— |
| 4-26 | (b-18) | (b-35) | H | H | (a-14) | —CH(Me)— |
| 4-27 | (b-19) | (b-35) | H | H | (a-14) | —CH(Me)— |
| 4-28 | (b-20) | (b-7) | H | H | (a-14) | —CH(Me)— |
| 4-29 | (b-20) | (b-35) | H | H | (a-14) | —CH(Me)— |
| 4-30 | (b-21) | (b-35) | H | H | (a-14) | —CH(Me)— |
| 4-31 | (b-24) | (b-35) | H | H | (a-14) | —CH(Me)— |
| 4-32 | (b-25) | (b-35) | H | H | (a-14) | —CH(Me)— |
| 4-33 | (b-72) | (b-35) | H | H | (a-14) | —CH(Me)— |
| 4-34 | (b-73) | (b-7) | H | H | (a-14) | —CH(Me)— |
| 4-35 | (b-73) | (b-35) | H | H | (a-14) | —CH(Me)— |
| 4-36 | (b-74) | (b-35) | H | H | (a-14) | —CH(Me)— |
| 4-37 | (b-76) | (b-35) | H | H | (a-14) | —CH(Me)— |
| 4-38 | (b-77) | (b-7) | H | H | (a-14) | —CH(Me)— |
| 4-39 | (b-77) | (b-35) | H | H | (a-14) | —CH(Me)— |
| 4-40 | (b-7) | (b-35) | H | H | (a-15) | —CH(Me)— |
| 4-41 | (b-11) | (b-35) | H | H | (a-15) | —CH(Me)— |
| 4-42 | (b-18) | (b-35) | H | H | (a-15) | —CH(Me)— |
| 4-43 | (b-20) | (b-35) | H | H | (a-15) | —CH(Me)— |
| 4-44 | (b-73) | (b-35) | H | H | (a-15) | —CH(Me)— |
| 4-45 | (b-77) | (b-35) | H | H | (a-15) | —CH(Me)— |
| 4-46 | (b-7) | (b-35) | H | H | (a-18) | —CH(Me)— |
| 4-47 | (b-11) | (b-35) | H | H | (a-18) | —CH(Me)— |
| 4-48 | (b-18) | (b-35) | H | H | (a-18) | —CH(Me)— |
| 4-49 | (b-20) | (b-35) | H | H | (a-18) | —CH(Me)— |
| 4-50 | (b-73) | (b-35) | H | H | (a-18) | —CH(Me)— |
| 4-51 | (b-77) | (b-35) | H | H | (a-18) | —CH(Me)— |
| 4-52 | (b-7) | (b-35) | H | H | (a-19) | —CH(Me)— |
| 4-53 | (b-11) | (b-35) | H | H | (a-19) | —CH(Me)— |
| 4-54 | (b-18) | (b-35) | H | H | (a-19) | —CH(Me)— |
| 4-55 | (b-7) | (b-35) | H | H | (a-20) | —CH(Me)— |
| 4-56 | (b-11) | (b-35) | H | H | (a-20) | —CH(Me)— |
| 4-57 | (b-18) | (b-35) | H | H | (a-20) | —CH(Me)— |
| 4-58 | (b-20) | (b-35) | H | H | (a-20) | —CH(Me)— |
| 4-59 | (b-73) | (b-35) | H | H | (a-20) | —CH(Me)— |
| 4-60 | (b-77) | (b-35) | H | H | (a-20) | —CH(Me)— |
| 4-61 | (b-7) | (b-35) | H | H | (a-24) | —CH(Me)— |
| 4-62 | (b-11) | (b-35) | H | H | (a-24) | —CH(Me)— |
| 4-63 | (b-18) | (b-35) | H | H | (a-24) | —CH(Me)— |
| 4-64 | (b-7) | (b-35) | H | H | (a-26) | —CH(Me)— |
| 4-65 | (b-11) | (b-35) | H | H | (a-26) | —CH(Me)— |
| 4-66 | (b-18) | (b-35) | H | H | (a-26) | —CH(Me)— |
| 4-67 | (b-20) | (b-35) | H | H | (a-26) | —CH(Me)— |
| 4-68 | (b-73) | (b-35) | H | H | (a-26) | —CH(Me)— |
| 4-69 | (b-77) | (b-35) | H | H | (a-26) | —CH(Me)— |
| 4-70 | (b-7) | (b-35) | H | H | (a-28) | —CH(Me)— |
| 4-71 | (b-11) | (b-35) | H | H | (a-28) | —CH(Me)— |
| 4-72 | (b-18) | (b-35) | H | H | (a-28) | —CH(Me)— |
| 4-73 | (b-7) | (b-35) | H | H | (a-31) | —CH(Me)— |
| 4-74 | (b-11) | (b-35) | H | H | (a-31) | —CH(Me)— |
| 4-75 | (b-18) | (b-35) | H | H | (a-31) | —CH(Me)— |
| 4-76 | (b-20) | (b-35) | H | H | (a-31) | —CH(Me)— |
| 4-77 | (b-73) | (b-35) | H | H | (a-31) | —CH(Me)— |
| 4-78 | (b-77) | (b-35) | H | H | (a-31) | —CH(Me)— |
| 4-79 | (b-7) | (b-35) | H | H | (a-33) | —CH(Me)— |
| 4-80 | (b-11) | (b-35) | H | H | (a-33) | —CH(Me)— |
| 4-81 | (b-18) | (b-35) | H | H | (a-33) | —CH(Me)— |
| 4-82 | (b-7) | (b-35) | H | H | (a-43) | —CH(Me)— |
| 4-83 | (b-11) | (b-35) | H | H | (a-43) | —CH(Me)— |

TABLE 4-continued

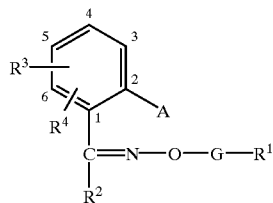

(I-4)

| Cpd. No. | R¹ Sub. No. | R² Sub. No. | R³ | R⁴ | A Sub. No. | G |
|---|---|---|---|---|---|---|
| 4-84 | (b-18) | (b-35) | H | H | (a-43) | —CH(Me)— |
| 4-85 | (b-20) | (b-35) | H | H | (a-43) | —CH(Me)— |
| 4-86 | (b-73) | (b-35) | H | H | (a-43) | —CH(Me)— |
| 4-87 | (b-77) | (b-35) | H | H | (a-43) | —CH(Me)— |
| 4-88 | (b-7) | (b-35) | H | H | (a-45) | —CH(Me)— |
| 4-89 | (b-11) | (b-35) | H | H | (a-45) | —CH(Me)— |
| 4-90 | (b-18) | (b-35) | H | H | (a-45) | —CH(Me)— |

TABLE 5

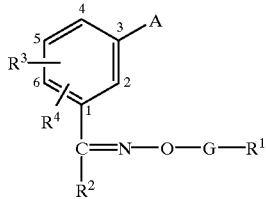

(I-5)

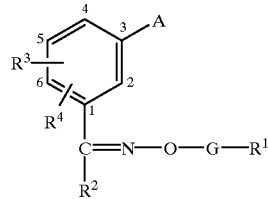

(I-5)

| Cpd. No. | R¹ Sub. No. | R² Sub. No. | R³ | R⁴ | A sub. No. | G |
|---|---|---|---|---|---|---|
| 5-1 | (b-2) | (b-35) | H | H | (a-1) | —CH(Me)— |
| 5-2 | (b-7) | (b-7) | H | H | (a-1) | —CH(Me)— |
| 5-3 | (b-7) | (b-7) | H | H | (a-1) | —COCH(Me)— |
| 5-4 | (b-7) | (b-35) | H | H | (a-1) | —CH₂— |
| 5-5 | (b-7) | (b-35) | H | H | (a-1) | —CH(Me)— |
| 5-6 | (b-8) | (b-35) | H | H | (a-1) | —CH(Me)— |
| 5-7 | (b-11) | (b-7) | H | H | (a-1) | —CH(Me)— |
| 5-8 | (b-11) | (b-7) | H | H | (a-1) | —COCH(Me)— |
| 5-9 | (b-11) | (b-35) | H | H | (a-1) | —CH(Me)— |
| 5-10 | (b-11) | (b-35) | H | H | (a-1) | —COCH(Me)— |
| 5-11 | (b-12) | (b-7) | H | H | (a-1) | —CH(Me)— |
| 5-12 | (b-12) | (b-35) | H | H | (a-1) | —CH(Me)— |
| 5-13 | (b-15) | (b-7) | H | H | (a-1) | —CH(Me)— |
| 5-14 | (b-15) | (b-35) | H | H | (a-1) | —CH(Me)— |
| 5-15 | (b-18) | (b-7) | H | H | (a-1) | —CH(Me)— |
| 5-16 | (b-18) | (b-7) | H | H | (a-1) | —COCH(Me)— |
| 5-17 | (b-18) | (b-35) | H | H | (a-1) | —CH(Me)— |
| 5-18 | (b-18) | (b-35) | H | H | (a-1) | —COCH(Me)— |
| 5-19 | (b-19) | (b-7) | H | H | (a-1) | —CH(Me)— |
| 5-20 | (b-19) | (b-35) | H | H | (a-1) | —CH(Me)— |
| 5-21 | (b-20) | (b-7) | H | H | (a-1) | —CH(Me)— |
| 5-22 | (b-20) | (b-7) | H | H | (a-1) | —COCH(Me)— |
| 5-23 | (b-20) | (b-35) | H | H | (a-1) | —CH(Me)— |
| 5-24 | (b-20) | (b-35) | H | H | (a-1) | —COCH(Me)— |
| 5-25 | (b-21) | (b-7) | H | H | (a-1) | —CH(Me)— |
| 5-26 | (b-21) | (b-35) | H | H | (a-1) | —CH(Me)— |
| 5-27 | (b-24) | (b-7) | H | H | (a-1) | —CH(Me)— |
| 5-28 | (b-24) | (b-35) | H | H | (a-1) | —CH(Me)— |
| 5-29 | (b-25) | (b-7) | H | H | (a-1) | —CH(Me)— |
| 5-30 | (b-25) | (b-35) | H | H | (a-1) | —CH(Me)— |
| 5-31 | (b-72) | (b-7) | H | H | (a-1) | —CH(Me)— |
| 5-32 | (b-72) | (b-35) | H | H | (a-1) | —CH(Me)— |
| 5-33 | (b-73) | (b-7) | H | H | (a-1) | —CH(Me)— |
| 5-34 | (b-73) | (b-7) | H | H | (a-1) | —COCH(Me)— |
| 5-35 | (b-73) | (b-35) | H | H | (a-1) | —CH(Me)— |
| 5-36 | (b-73) | (b-35) | H | H | (a-1) | —COCH(Me)— |
| 5-37 | (b-74) | (b-7) | H | H | (a-1) | —CH(Me)— |
| 5-38 | (b-74) | (b-35) | H | H | (a-1) | —CH(Me)— |
| 5-39 | (b-76) | (b-7) | H | H | (a-1) | —CH(Me)— |
| 5-40 | (b-76) | (b-35) | H | H | (a-1) | —CH(Me)— |
| 5-41 | (b-77) | (b-7) | H | H | (a-1) | —CH(Me)— |
| 5-42 | (b-77) | (b-7) | H | H | (a-1) | —COCH(Me)— |
| 5-43 | (b-77) | (b-35) | H | H | (a-1) | —CH(Me)— |
| 5-44 | (b-77) | (b-35) | H | H | (a-1) | —COCH(Me)— |
| 5-45 | (b-7) | (b-35) | H | H | (a-2) | —CH(Me)— |
| 5-46 | (b-11) | (b-35) | H | H | (a-2) | —CH(Me)— |
| 5-47 | (b-18) | (b-35) | H | H | (a-2) | —CH(Me)— |
| 5-48 | (b-20) | (b-35) | H | H | (a-2) | —CH(Me)— |
| 5-49 | (b-73) | (b-35) | H | H | (a-2) | —CH(Me)— |
| 5-50 | (b-77) | (b-35) | H | H | (a-2) | —CH(Me)— |
| 5-51 | (b-7) | (b-7) | H | H | (a-3) | —CH(Me)— |
| 5-52 | (b-7) | (b-35) | H | H | (a-3) | —CH(Me)— |
| 5-53 | (b-11) | (b-7) | H | H | (a-3) | —CH(Me)— |
| 5-54 | (b-11) | (b-35) | H | H | (a-3) | —CH(Me)— |
| 5-55 | (b-12) | (b-35) | H | H | (a-3) | —CH(Me)— |
| 5-56 | (b-15) | (b-35) | H | H | (a-3) | —CH(Me)— |
| 5-57 | (b-18) | (b-7) | H | H | (a-3) | —CH(Me)— |
| 5-58 | (b-18) | (b-35) | H | H | (a-3) | —CH(Me)— |
| 5-59 | (b-19) | (b-35) | H | H | (a-3) | —CH(Me)— |
| 5-60 | (b-20) | (b-7) | H | H | (a-3) | —CH(Me)— |
| 5-61 | (b-20) | (b-35) | H | H | (a-3) | —CH(Me)— |
| 5-62 | (b-21) | (b-35) | H | H | (a-3) | —CH(Me)— |
| 5-63 | (b-24) | (b-35) | H | H | (a-3) | —CH(Me)— |
| 5-64 | (b-25) | (b-35) | H | H | (a-3) | —CH(Me)— |
| 5-65 | (b-72) | (b-35) | H | H | (a-3) | —CH(Me)— |
| 5-66 | (b-73) | (b-7) | H | H | (a-3) | —CH(Me)— |
| 5-67 | (b-73) | (b-35) | H | H | (a-3) | —CH(Me)— |
| 5-68 | (b-74) | (b-35) | H | H | (a-3) | —CH(Me)— |
| 5-69 | (b-76) | (b-35) | H | H | (a-3) | —CH(Me)— |
| 5-70 | (b-77) | (b-7) | H | H | (a-3) | —CH(Me)— |
| 5-71 | (b-77) | (b-35) | H | H | (a-3) | —CH(Me)— |
| 5-72 | (b-7) | (b-35) | H | H | (a-4) | —CH(Me)— |
| 5-73 | (b-11) | (b-35) | H | H | (a-4) | —CH(Me)— |
| 5-74 | (b-18) | (b-35) | H | H | (a-4) | —CH(Me)— |

TABLE 5-continued (I-5)

![Structure with benzene ring numbered 1-6, substituents R³ at 5, R⁴ at 1, A at 3, and C(R²)=N-O-G-R¹ at position 1]

| Cpd. No. | R¹ Sub. No. | R² Sub. No. | R³ | R⁴ | A sub. No. | G |
|---|---|---|---|---|---|---|
| 5-75 | (b-20) | (b-35) | H | H | (a-4) | —CH(Me)— |
| 5-76 | (b-73) | (b-35) | H | H | (a-4) | —CH(Me)— |
| 5-77 | (b-77) | (b-35) | H | H | (a-4) | —CH(Me)— |
| 5-78 | (b-2) | (b-35) | H | H | (a-5) | —CH(Me)— |
| 5-79 | (b-7) | (b-7) | H | H | (a-5) | —CH(Me)— |
| 5-80 | (b-7) | (b-7) | H | H | (a-5) | —COCH(Me)— |
| 5-81 | (b-7) | (b-35) | H | H | (a-5) | —CH(Me)— |
| 5-82 | (b-7) | (b-35) | H | H | (a-5) | —COCH(Me)— |
| 5-83 | (b-8) | (b-35) | H | H | (a-5) | —CH(Me)— |
| 5-84 | (b-11) | (b-7) | H | H | (a-5) | —CH(Me)— |
| 5-85 | (b-11) | (b-7) | H | H | (a-5) | —COCH(Me)— |
| 5-86 | (b-11) | (b-35) | H | H | (a-5) | —CH(Me)— |
| 5-87 | (b-11) | (b-35) | H | H | (a-5) | —COCH(Me)— |
| 5-88 | (b-12) | (b-7) | H | H | (a-5) | —CH(Me)— |
| 5-89 | (b-12) | (b-35) | H | H | (a-5) | —CH(Me)— |
| 5-90 | (b-15) | (b-7) | H | H | (a-5) | —CH(Me)— |
| 5-91 | (b-15) | (b-35) | H | H | (a-5) | —CH(Me)— |
| 5-92 | (b-18) | (b-7) | H | H | (a-5) | —CH(Me)— |
| 5-93 | (b-18) | (b-7) | H | H | (a-5) | —COCH(Me)— |
| 5-94 | (b-18) | (b-35) | H | H | (a-5) | —CH(Me)— |
| 5-95 | (b-18) | (b-35) | H | H | (a-5) | —COCH(Me)— |
| 5-96 | (b-19) | (b-7) | H | H | (a-5) | —CH(Me)— |
| 5-97 | (b-19) | (b-35) | H | H | (a-5) | —CH(Me)— |
| 5-98 | (b-20) | (b-7) | H | H | (a-5) | —CH(Me)— |
| 5-99 | (b-20) | (b-7) | H | H | (a-5) | —COCH(Me)— |
| 5-100 | (b-20) | (b-35) | H | H | (a-5) | —CH(Me)— |
| 5-101 | (b-20) | (b-35) | H | H | (a-5) | —COCH(Me)— |
| 5-102 | (b-21) | (b-7) | H | H | (a-5) | —CH(Me)— |
| 5-103 | (b-21) | (b-35) | H | H | (a-5) | —CH(Me)— |
| 5-104 | (b-24) | (b-7) | H | H | (a-5) | —CH(Me)— |
| 5-105 | (b-24) | (b-35) | H | H | (a-5) | —CH(Me)— |
| 5-106 | (b-25) | (b-7) | H | H | (a-5) | —CH(Me)— |
| 5-107 | (b-25) | (b-35) | H | H | (a-5) | —CH(Me)— |
| 5-108 | (b-72) | (b-7) | H | H | (a-5) | —CH(Me)— |
| 5-109 | (b-72) | (b-35) | H | H | (a-5) | —CH(Me)— |
| 5-110 | (b-73) | (b-7) | H | H | (a-5) | —CH(Me)— |
| 5-111 | (b-73) | (b-7) | H | H | (a-5) | —COCH(Me)— |
| 5-112 | (b-73) | (b-35) | H | H | (a-5) | —CH(Me)— |
| 5-113 | (b-73) | (b-35) | H | H | (a-5) | —COCH(Me)— |
| 5-114 | (b-74) | (b-7) | H | H | (a-5) | —CH(Me)— |
| 5-115 | (b-74) | (b-35) | H | H | (a-5) | —CH(Me)— |
| 5-116 | (b-76) | (b-7) | H | H | (a-5) | —CH(Me)— |
| 5-117 | (b-76) | (b-35) | H | H | (a-5) | —CH(Me)— |
| 5-118 | (b-77) | (b-7) | H | H | (a-5) | —CH(Me)— |
| 5-119 | (b-77) | (b-7) | H | H | (a-5) | —COCH(Me)— |
| 5-120 | (b-77) | (b-35) | H | H | (a-5) | —CH(Me)— |
| 5-121 | (b-77) | (b-35) | H | H | (a-5) | —COCH(Me)— |
| 5-122 | (b-7) | (b-35) | H | H | (a-6) | —CH(Me)— |
| 5-123 | (b-11) | (b-35) | H | H | (a-6) | —CH(Me)— |
| 5-124 | (b-18) | (b-35) | H | H | (a-6) | —CH(Me)— |
| 5-125 | (b-20) | (b-35) | H | H | (a-6) | —CH(Me)— |
| 5-126 | (b-73) | (b-35) | H | H | (a-6) | —CH(Me)— |
| 5-127 | (b-77) | (b-35) | H | H | (a-6) | —CH(Me)— |
| 5-128 | (b-7) | (b-7) | H | H | (a-7) | —CH(Me)— |
| 5-129 | (b-7) | (b-35) | H | H | (a-7) | —CH(Me)— |
| 5-130 | (b-11) | (b-7) | H | H | (a-7) | —CH(Me)— |
| 5-131 | (b-11) | (b-35) | H | H | (a-7) | —CH(Me)— |
| 5-132 | (b-12) | (b-35) | H | H | (a-7) | —CH(Me)— |
| 5-133 | (b-15) | (b-35) | H | H | (a-7) | —CH(Me)— |
| 5-134 | (b-18) | (b-7) | H | H | (a-7) | —CH(Me)— |
| 5-135 | (b-18) | (b-35) | H | H | (a-7) | —CH(Me)— |
| 5-136 | (b-19) | (b-35) | H | H | (a-7) | —CH(Me)— |
| 5-137 | (b-20) | (b-7) | H | H | (a-7) | —CH(Me)— |
| 5-138 | (b-20) | (b-35) | H | H | (a-7) | —CH(Me)— |
| 5-139 | (b-21) | (b-35) | H | H | (a-7) | —CH(Me)— |
| 5-140 | (b-24) | (b-35) | H | H | (a-7) | —CH(Me)— |
| 5-141 | (b-25) | (b-35) | H | H | (a-7) | —CH(Me)— |
| 5-142 | (b-72) | (b-35) | H | H | (a-7) | —CH(Me)— |
| 5-143 | (b-73) | (b-7) | H | H | (a-7) | —CH(Me)— |
| 5-144 | (b-73) | (b-35) | H | H | (a-7) | —CH(Me)— |
| 5-145 | (b-74) | (b-35) | H | H | (a-7) | —CH(Me)— |
| 5-146 | (b-76) | (b-35) | H | H | (a-7) | —CH(Me)— |
| 5-147 | (b-77) | (b-7) | H | H | (a-7) | —CH(Me)— |
| 5-148 | (b-77) | (b-35) | H | H | (a-7) | —CH(Me)— |
| 5-149 | (b-7) | (b-35) | H | H | (a-8) | —CH(Me)— |
| 5-150 | (b-11) | (b-35) | H | H | (a-8) | —CH(Me)— |
| 5-151 | (b-18) | (b-35) | H | H | (a-8) | —CH(Me)— |
| 5-152 | (b-20) | (b-35) | H | H | (a-8) | —CH(Me)— |
| 5-153 | (b-73) | (b-35) | H | H | (a-8) | —CH(Me)— |
| 5-154 | (b-77) | (b-35) | H | H | (a-8) | —CH(Me)— |
| 5-155 | (b-7) | (b-35) | H | H | (a-10) | —CH(Me)— |
| 5-156 | (b-11) | (b-35) | H | H | (a-10) | —CH(Me)— |
| 5-157 | (b-18) | (b-35) | H | H | (a-10) | —CH(Me)— |
| 5-158 | (b-7) | (b-35) | H | H | (a-11) | —CH(Me)— |
| 5-159 | (b-11) | (b-35) | H | H | (a-11) | —CH(Me)— |
| 5-160 | (b-18) | (b-35) | H | H | (a-11) | —CH(Me)— |
| 5-161 | (b-20) | (b-35) | H | H | (a-11) | —CH(Me)— |
| 5-162 | (b-73) | (b-35) | H | H | (a-11) | —CH(Me)— |
| 5-163 | (b-77) | (b-35) | H | H | (a-11) | —CH(Me)— |
| 5-164 | (b-7) | (b-35) | H | H | (a-12) | —CH(Me)— |
| 5-165 | (b-11) | (b-35) | H | H | (a-12) | —CH(Me)— |
| 5-166 | (b-18) | (b-35) | H | H | (a-12) | —CH(Me)— |
| 5-167 | (b-2) | (b-7) | H | H | (a-14) | —CH(Me)— |
| 5-168 | (b-2) | (b-35) | H | H | (a-14) | —CH(Me)— |
| 5-169 | (b-7) | (b-7) | H | H | (a-14) | —CH(Me)— |
| 5-170 | (b-7) | (b-7) | H | H | (a-14) | —COCH(Me)— |
| 5-171 | (b-7) | (b-12) | H | H | (a-14) | —CH(Me)— |
| 5-172 | (b-7) | (b-15) | H | H | (a-14) | —CH(Me)— |
| 5-173 | (b-7) | (b-34) | H | H | (a-14) | —CH(Me)— |
| 5-174 | (b-7) | (b-35) | H | H | (a-14) | —CH(Me)— |
| 5-175 | (b-7) | (b-35) | H | H | (a-14) | —COCH(Me)— |
| 5-176 | (b-7) | (b-37) | H | H | (a-14) | —CH(Me)— |
| 5-177 | (b-7) | (b-73) | H | H | (a-14) | —CH(Me)— |
| 5-178 | (b-7) | (b-77) | H | H | (a-14) | —CH(Me)— |
| 5-179 | (b-8) | (b-35) | H | H | (a-14) | —CH(Me)— |
| 5-180 | (b-9) | (b-35) | H | H | (a-14) | —CH(Me)— |
| 5-181 | (b-10) | (b-35) | H | H | (a-14) | —CH(Me)— |
| 5-182 | (b-11) | (b-7) | H | H | (a-14) | —CH(Me)— |
| 5-183 | (b-11) | (b-7) | H | H | (a-14) | —COCH(Me)— |
| 5-184 | (b-11) | (b-12) | H | H | (a-14) | —CH(Me)— |
| 5-185 | (b-11) | (b-15) | H | H | (a-14) | —CH(Me)— |
| 5-186 | (b-11) | (b-34) | H | H | (a-14) | —CH(Me)— |
| 5-187 | (b-11) | (b-35) | H | H | (a-14) | —CH(Me)— |
| 5-188 | (b-11) | (b-35) | H | H | (a-14) | —COCH(Me)— |
| 5-189 | (b-11) | (b-37) | H | H | (a-14) | —CH(Me)— |
| 5-190 | (b-11) | (b-73) | H | H | (a-14) | —CH(Me)— |
| 5-191 | (b-11) | (b-77) | H | H | (a-14) | —CH(Me)— |
| 5-192 | (b-12) | (b-7) | H | H | (a-14) | —CH(Me)— |
| 5-193 | (b-12) | (b-7) | H | H | (a-14) | —COCH(Me)— |
| 5-194 | (b-12) | (b-35) | H | H | (a-14) | —CH(Me)— |
| 5-195 | (b-12) | (b-35) | H | H | (a-14) | —COCH(Me)— |
| 5-196 | (b-13) | (b-35) | H | H | (a-14) | —CH(Me)— |
| 5-197 | (b-14) | (b-35) | H | H | (a-14) | —CH(Me)— |
| 5-198 | (b-15) | (b-7) | H | H | (a-14) | —CH(Me)— |
| 5-199 | (b-15) | (b-7) | H | H | (a-14) | —COCH(Me)— |
| 5-200 | (b-15) | (b-35) | H | H | (a-14) | —CH(Me)— |
| 5-201 | (b-15) | (b-35) | H | H | (a-14) | —COCH(Me)— |
| 5-202 | (b-17) | (b-35) | H | H | (a-14) | —CH(Me)— |

TABLE 5-continued (I-5)

![Structure: benzene ring with positions 1-6, substituent A at position 3, R³ at position 5, R⁴ at position 1, and at position 1 also C(R²)=N—O—G—R¹]

| Cpd. No. | R¹ Sub. No. | R² Sub. No. | R³ | R⁴ | A sub. No. | G |
|---|---|---|---|---|---|---|
| 5-203 | (b-18) | (b-7) | H | H | (a-14) | —CH(Me)— |
| 5-204 | (b-18) | (b-7) | H | H | (a-14) | —COCH(Me)— |
| 5-205 | (b-18) | (b-12) | H | H | (a-14) | —CH(Me)— |
| 5-206 | (b-18) | (b-15) | H | H | (a-14) | —CH(Me)— |
| 5-207 | (b-18) | (b-34) | H | H | (a-14) | —CH(Me)— |
| 5-208 | (b-18) | (b-35) | H | H | (a-14) | —CH(Me)— |
| 5-209 | (b-18) | (b-35) | H | H | (a-14) | —COCH(Me)— |
| 5-210 | (b-18) | (b-37) | H | H | (a-14) | —CH(Me)— |
| 5-211 | (b-18) | (b-73) | H | H | (a-14) | —CH(Me)— |
| 5-212 | (b-18) | (b-77) | H | H | (a-14) | —CH(Me)— |
| 5-213 | (b-19) | (b-7) | H | H | (a-14) | —CH(Me)— |
| 5-214 | (b-19) | (b-7) | H | H | (a-14) | —COCH(Me)— |
| 5-215 | (b-19) | (b-35) | H | H | (a-14) | —CH(Me)— |
| 5-216 | (b-19) | (b-35) | H | H | (a-14) | —COCH(Me)— |
| 5-217 | (b-20) | (b-7) | H | H | (a-14) | —CH(Me)— |
| 5-218 | (b-20) | (b-7) | H | H | (a-14) | —COCH(Me)— |
| 5-219 | (b-20) | (b-12) | H | H | (a-14) | —CH(Me)— |
| 5-220 | (b-20) | (b-15) | H | H | (a-14) | —CH(Me)— |
| 5-221 | (b-20) | (b-34) | H | H | (a-14) | —CH(Me)— |
| 5-222 | (b-20) | (b-35) | H | H | (a-14) | —CH(Me)— |
| 5-223 | (b-20) | (b-35) | H | H | (a-14) | —COCH(Me)— |
| 5-224 | (b-20) | (b-37) | H | H | (a-14) | —CH(Me)— |
| 5-225 | (b-20) | (b-73) | H | H | (a-14) | —CH(Me)— |
| 5-226 | (b-20) | (b-77) | H | H | (a-14) | —CH(Me)— |
| 5-227 | (b-21) | (b-7) | H | H | (a-14) | —CH(Me)— |
| 5-228 | (b-21) | (b-7) | H | H | (a-14) | —COCH(Me)— |
| 5-229 | (b-21) | (b-35) | H | H | (a-14) | —CH(Me)— |
| 5-230 | (b-21) | (b-35) | H | H | (a-14) | —COCH(Me)— |
| 5-231 | (b-23) | (b-35) | H | H | (a-14) | —CH(Me)— |
| 5-232 | (b-24) | (b-7) | H | H | (a-14) | —CH(Me)— |
| 5-233 | (b-24) | (b-7) | H | H | (a-14) | —COCH(Me)— |
| 5-234 | (b-24) | (b-35) | H | H | (a-14) | —CH(Me)— |
| 5-235 | (b-24) | (b-35) | H | H | (a-14) | —COCH(Me)— |
| 5-236 | (b-25) | (b-7) | H | H | (a-14) | —CH(Me)— |
| 5-237 | (b-25) | (b-7) | H | H | (a-14) | —COCH(Me)— |
| 5-238 | (b-25) | (b-35) | H | H | (a-14) | —CH(Me)— |
| 5-239 | (b-25) | (b-35) | H | H | (a-14) | —COCH(Me)— |
| 5-240 | (b-35) | (b-35) | H | H | (a-14) | —CH(Me)— |
| 5-241 | (b-72) | (b-7) | H | H | (a-14) | —CH(Me)— |
| 5-242 | (b-72) | (b-7) | H | H | (a-14) | —COCH(Me)— |
| 5-243 | (b-72) | (b-35) | H | H | (a-14) | —CH(Me)— |
| 5-244 | (b-72) | (b-35) | H | H | (a-14) | —COCH(Me)— |
| 5-245 | (b-73) | (b-7) | H | H | (a-14) | —CH(Me)— |
| 5-246 | (b-73) | (b-7) | H | H | (a-14) | —COCH(Me)— |
| 5-247 | (b-73) | (b-12) | H | H | (a-14) | —CH(Me)— |
| 5-248 | (b-73) | (b-15) | H | H | (a-14) | —CH(Me)— |
| 5-249 | (b-73) | (b-34) | H | H | (a-14) | —CH(Me)— |
| 5-250 | (b-73) | (b-35) | H | H | (a-14) | —CH(Me)— |
| 5-251 | (b-73) | (b-35) | H | H | (a-14) | —COCH(Me)— |
| 5-252 | (b-73) | (b-37) | H | H | (a-14) | —CH(Me)— |
| 5-253 | (b-73) | (b-73) | H | H | (a-14) | —CH(Me)— |
| 5-254 | (b-73) | (b-77) | H | H | (a-14) | —CH(Me)— |
| 5-255 | (b-74) | (b-7) | H | H | (a-14) | —CH(Me)— |
| 5-256 | (b-74) | (b-7) | H | H | (a-14) | —COCH(Me)— |
| 5-257 | (b-74) | (b-35) | H | H | (a-14) | —CH(Me)— |
| 5-258 | (b-74) | (b-35) | H | H | (a-14) | —COCH(Me)— |
| 5-259 | (b-75) | (b-35) | H | H | (a-14) | —CH(Me)— |
| 5-260 | (b-76) | (b-7) | H | H | (a-14) | —CH(Me)— |
| 5-261 | (b-76) | (b-7) | H | H | (a-14) | —COCH(Me)— |
| 5-262 | (b-76) | (b-35) | H | H | (a-14) | —CH(Me)— |
| 5-263 | (b-76) | (b-35) | H | H | (a-14) | —COCH(Me)— |
| 5-264 | (b-77) | (b-7) | H | H | (a-14) | —CH(Me)— |
| 5-265 | (b-77) | (b-7) | H | H | (a-14) | —COCH(Me)— |
| 5-266 | (b-77) | (b-12) | H | H | (a-14) | —CH(Me)— |
| 5-267 | (b-77) | (b-15) | H | H | (a-14) | —CH(Me)— |
| 5-268 | (b-77) | (b-34) | H | H | (a-14) | —CH(Me)— |
| 5-269 | (b-77) | (b-35) | H | H | (a-14) | —CH(Me)— |
| 5-270 | (b-77) | (b-35) | H | H | (a-14) | —COCH(Me)— |
| 5-271 | (b-77) | (b-37) | H | H | (a-14) | —CH(Me)— |
| 5-272 | (b-77) | (b-73) | H | H | (a-14) | —CH(Me)— |
| 5-273 | (b-77) | (b-77) | H | H | (a-14) | —CH(Me)— |
| 5-274 | (b-78) | (b-35) | H | H | (a-14) | —CH(Me)— |
| 5-275 | (b-79) | (b-35) | H | H | (a-14) | —CH(Me)— |
| 5-276 | (b-2) | (b-35) | H | H | (a-15) | —CH(Me)— |
| 5-277 | (b-7) | (b-7) | H | H | (a-15) | —CH(Me)— |
| 5-278 | (b-7) | (b-7) | H | H | (a-15) | —COCH(Me)— |
| 5-279 | (b-7) | (b-35) | H | H | (a-15) | —CH(Me)— |
| 5-280 | (b-7) | (b-35) | H | H | (a-15) | —COCH(Me)— |
| 5-281 | (b-8) | (b-35) | H | H | (a-15) | —CH(Me)— |
| 5-282 | (b-11) | (b-7) | H | H | (a-15) | —CH(Me)— |
| 5-283 | (b-11) | (b-7) | H | H | (a-15) | —COCH(Me)— |
| 5-284 | (b-11) | (b-35) | H | H | (a-15) | —CH(Me)— |
| 5-285 | (b-11) | (b-35) | H | H | (a-15) | —COCH(Me)— |
| 5-286 | (b-12) | (b-7) | H | H | (a-15) | —CH(Me)— |
| 5-287 | (b-12) | (b-35) | H | H | (a-15) | —CH(Me)— |
| 5-288 | (b-15) | (b-7) | H | H | (a-15) | —CH(Me)— |
| 5-289 | (b-15) | (b-35) | H | H | (a-15) | —CH(Me)— |
| 5-290 | (b-18) | (b-7) | H | H | (a-15) | —CH(Me)— |
| 5-291 | (b-18) | (b-7) | H | H | (a-15) | —COCH(Me)— |
| 5-292 | (b-18) | (b-35) | H | H | (a-15) | —CH(Me)— |
| 5-293 | (b-18) | (b-35) | H | H | (a-15) | —COCH(Me)— |
| 5-294 | (b-19) | (b-7) | H | H | (a-15) | —CH(Me)— |
| 5-295 | (b-19) | (b-35) | H | H | (a-15) | —CH(Me)— |
| 5-296 | (b-20) | (b-7) | H | H | (a-15) | —CH(Me)— |
| 5-297 | (b-20) | (b-7) | H | H | (a-15) | —COCH(Me)— |
| 5-298 | (b-20) | (b-35) | H | H | (a-15) | —CH(Me)— |
| 5-299 | (b-20) | (b-35) | H | H | (a-15) | —COCH(Me)— |
| 5-300 | (b-21) | (b-7) | H | H | (a-15) | —CH(Me)— |
| 5-301 | (b-21) | (b-35) | H | H | (a-15) | —CH(Me)— |
| 5-302 | (b-24) | (b-7) | H | H | (a-15) | —CH(Me)— |
| 5-303 | (b-24) | (b-35) | H | H | (a-15) | —CH(Me)— |
| 5-304 | (b-25) | (b-7) | H | H | (a-15) | —CH(Me)— |
| 5-305 | (b-25) | (b-35) | H | H | (a-15) | —CH(Me)— |
| 5-306 | (b-72) | (b-7) | H | H | (a-15) | —CH(Me)— |
| 5-307 | (b-72) | (b-35) | H | H | (a-15) | —CH(Me)— |
| 5-308 | (b-73) | (b-7) | H | H | (a-15) | —CH(Me)— |
| 5-309 | (b-73) | (b-7) | H | H | (a-15) | —COCH(Me)— |
| 5-310 | (b-73) | (b-35) | H | H | (a-15) | —CH(Me)— |
| 5-311 | (b-73) | (b-35) | H | H | (a-15) | —COCH(Me)— |
| 5-312 | (b-74) | (b-7) | H | H | (a-15) | —CH(Me)— |
| 5-313 | (b-74) | (b-35) | H | H | (a-15) | —CH(Me)— |
| 5-314 | (b-76) | (b-7) | H | H | (a-15) | —CH(Me)— |
| 5-315 | (b-76) | (b-35) | H | H | (a-15) | —CH(Me)— |
| 5-316 | (b-77) | (b-7) | H | H | (a-15) | —CH(Me)— |
| 5-317 | (b-77) | (b-7) | H | H | (a-15) | —COCH(Me)— |
| 5-318 | (b-77) | (b-35) | H | H | (a-15) | —CH(Me)— |
| 5-319 | (b-77) | (b-35) | H | H | (a-15) | —COCH(Me)— |
| 5-320 | (b-2) | (b-35) | H | H | (a-18) | —CH(Me)— |
| 5-321 | (b-7) | (b-7) | H | H | (a-18) | —CH(Me)— |
| 5-322 | (b-7) | (b-7) | H | H | (a-18) | —COCH(Me)— |
| 5-323 | (b-7) | (b-35) | H | H | (a-18) | —CH(Me)— |
| 5-324 | (b-7) | (b-35) | H | H | (a-18) | —COCH(Me)— |
| 5-325 | (b-8) | (b-35) | H | H | (a-18) | —CH(Me)— |
| 5-326 | (b-11) | (b-7) | H | H | (a-18) | —CH(Me)— |
| 5-327 | (b-11) | (b-7) | H | H | (a-18) | —COCH(Me)— |
| 5-328 | (b-11) | (b-35) | H | H | (a-18) | —CH(Me)— |
| 5-329 | (b-11) | (b-35) | H | H | (a-18) | —COCH(Me)— |
| 5-330 | (b-12) | (b-7) | H | H | (a-18) | —CH(Me)— |

TABLE 5-continued (I-5)

| Cpd. No. | R¹ Sub. No. | R² Sub. No. | R³ | R⁴ | A sub. No. | G |
|---|---|---|---|---|---|---|
| 5-331 | (b-12) | (b-35) | H | H | (a-18) | —CH(Me)— |
| 5-332 | (b-15) | (b-7) | H | H | (a-18) | —CH(Me)— |
| 5-333 | (b-15) | (b-35) | H | H | (a-18) | —CH(Me)— |
| 5-334 | (b-18) | (b-7) | H | H | (a-18) | —CH(Me)— |
| 5-335 | (b-18) | (b-7) | H | H | (a-18) | —COCH(Me)— |
| 5-336 | (b-18) | (b-35) | H | H | (a-18) | —CH(Me)— |
| 5-337 | (b-18) | (b-35) | H | H | (a-18) | —COCH(Me)— |
| 5-338 | (b-19) | (b-7) | H | H | (a-18) | —CH(Me)— |
| 5-339 | (b-19) | (b-35) | H | H | (a-18) | —CH(Me)— |
| 5-340 | (b-20) | (b-7) | H | H | (a-18) | —CH(Me)— |
| 5-341 | (b-20) | (b-7) | H | H | (a-18) | —COCH(Me)— |
| 5-342 | (b-20) | (b-35) | H | H | (a-18) | —CH(Me)— |
| 5-343 | (b-20) | (b-35) | H | H | (a-18) | —COCH(Me)— |
| 5-344 | (b-21) | (b-7) | H | H | (a-18) | —CH(Me)— |
| 5-345 | (b-21) | (b-35) | H | H | (a-18) | —CH(Me)— |
| 5-346 | (b-24) | (b-7) | H | H | (a-18) | —CH(Me)— |
| 5-347 | (b-24) | (b-35) | H | H | (a-18) | —CH(Me)— |
| 5-348 | (b-25) | (b-7) | H | H | (a-18) | —CH(Me)— |
| 5-349 | (b-25) | (b-35) | H | H | (a-18) | —CH(Me)— |
| 5-350 | (b-72) | (b-7) | H | H | (a-18) | —CH(Me)— |
| 5-351 | (b-72) | (b-35) | H | H | (a-18) | —CH(Me)— |
| 5-352 | (b-73) | (b-7) | H | H | (a-18) | —CH(Me)— |
| 5-353 | (b-73) | (b-7) | H | H | (a-18) | —COCH(Me)— |
| 5-354 | (b-73) | (b-35) | H | H | (a-18) | —CH(Me)— |
| 5-355 | (b-73) | (b-35) | H | H | (a-18) | —COCH(Me)— |
| 5-356 | (b-74) | (b-7) | H | H | (a-18) | —CH(Me)— |
| 5-357 | (b-74) | (b-35) | H | H | (a-18) | —CH(Me)— |
| 5-358 | (b-76) | (b-7) | H | H | (a-18) | —CH(Me)— |
| 5-359 | (b-76) | (b-35) | H | H | (a-18) | —CH(Me)— |
| 5-360 | (b-77) | (b-7) | H | H | (a-18) | —CH(Me)— |
| 5-361 | (b-77) | (b-7) | H | H | (a-18) | —COCH(Me)— |
| 5-362 | (b-77) | (b-35) | H | H | (a-18) | —CH(Me)— |
| 5-363 | (b-77) | (b-35) | H | H | (a-18) | —COCH(Me)— |
| 5-364 | (b-7) | (b-7) | H | H | (a-19) | —CH(Me)— |
| 5-365 | (b-7) | (b-35) | H | H | (a-19) | —CH(Me)— |
| 5-366 | (b-11) | (b-7) | H | H | (a-19) | —CH(Me)— |
| 5-367 | (b-11) | (b-35) | H | H | (a-19) | —CH(Me)— |
| 5-368 | (b-12) | (b-35) | H | H | (a-19) | —CH(Me)— |
| 5-369 | (b-15) | (b-35) | H | H | (a-19) | —CH(Me)— |
| 5-370 | (b-18) | (b-7) | H | H | (a-19) | —CH(Me)— |
| 5-371 | (b-18) | (b-35) | H | H | (a-19) | —CH(Me)— |
| 5-372 | (b-19) | (b-35) | H | H | (a-19) | —CH(Me)— |
| 5-373 | (b-20) | (b-7) | H | H | (a-19) | —CH(Me)— |
| 5-374 | (b-20) | (b-35) | H | H | (a-19) | —CH(Me)— |
| 5-375 | (b-21) | (b-35) | H | H | (a-19) | —CH(Me)— |
| 5-376 | (b-24) | (b-35) | H | H | (a-19) | —CH(Me)— |
| 5-377 | (b-25) | (b-35) | H | H | (a-19) | —CH(Me)— |
| 5-378 | (b-72) | (b-35) | H | H | (a-19) | —CH(Me)— |
| 5-379 | (b-73) | (b-7) | H | H | (a-19) | —CH(Me)— |
| 5-380 | (b-73) | (b-35) | H | H | (a-19) | —CH(Me)— |
| 5-381 | (b-74) | (b-35) | H | H | (a-19) | —CH(Me)— |
| 5-382 | (b-76) | (b-35) | H | H | (a-19) | —CH(Me)— |
| 5-383 | (b-77) | (b-7) | H | H | (a-19) | —CH(Me)— |
| 5-384 | (b-77) | (b-35) | H | H | (a-19) | —CH(Me)— |
| 5-385 | (b-2) | (b-35) | H | H | (a-20) | —CH(Me)— |
| 5-386 | (b-7) | (b-7) | H | H | (a-20) | —CH(Me)— |
| 5-387 | (b-7) | (b-7) | H | H | (a-20) | —COCH(Me)— |
| 5-388 | (b-7) | (b-35) | H | H | (a-20) | —CH(Me)— |
| 5-389 | (b-7) | (b-35) | H | H | (a-20) | —COCH(Me)— |
| 5-390 | (b-8) | (b-35) | H | H | (a-20) | —CH(Me)— |
| 5-391 | (b-11) | (b-7) | H | H | (a-20) | —CH(Me)— |
| 5-392 | (b-11) | (b-7) | H | H | (a-20) | —COCH(Me)— |
| 5-393 | (b-11) | (b-35) | H | H | (a-20) | —CH(Me)— |
| 5-394 | (b-11) | (b-35) | H | H | (a-20) | —COCH(Me)— |
| 5-395 | (b-12) | (b-7) | H | H | (a-20) | —CH(Me)— |
| 5-396 | (b-12) | (b-35) | H | H | (a-20) | —CH(Me)— |
| 5-397 | (b-15) | (b-7) | H | H | (a-20) | —CH(Me)— |
| 5-398 | (b-15) | (b-35) | H | H | (a-20) | —CH(Me)— |
| 5-399 | (b-18) | (b-7) | H | H | (a-20) | —CH(Me)— |
| 5-400 | (b-18) | (b-7) | H | H | (a-20) | —COCH(Me)— |
| 5-401 | (b-18) | (b-35) | H | H | (a-20) | —CH(Me)— |
| 5-402 | (b-18) | (b-35) | H | H | (a-20) | —COCH(Me)— |
| 5-403 | (b-19) | (b-7) | H | H | (a-20) | —CH(Me)— |
| 5-404 | (b-19) | (b-35) | H | H | (a-20) | —CH(Me)— |
| 5-405 | (b-20) | (b-7) | H | H | (a-20) | —CH(Me)— |
| 5-406 | (b-20) | (b-7) | H | H | (a-20) | —COCH(Me)— |
| 5-407 | (b-20) | (b-35) | H | H | (a-20) | —CH(Me)— |
| 5-408 | (b-20) | (b-35) | H | H | (a-20) | —COCH(Me)— |
| 5-409 | (b-21) | (b-7) | H | H | (a-20) | —CH(Me)— |
| 5-410 | (b-21) | (b-35) | H | H | (a-20) | —CH(Me)— |
| 5-411 | (b-24) | (b-7) | H | H | (a-20) | —CH(Me)— |
| 5-412 | (b-24) | (b-35) | H | H | (a-20) | —CH(Me)— |
| 5-413 | (b-25) | (b-7) | H | H | (a-20) | —CH(Me)— |
| 5-414 | (b-25) | (b-35) | H | H | (a-20) | —CH(Me)— |
| 5-415 | (b-72) | (b-7) | H | H | (a-20) | —CH(Me)— |
| 5-416 | (b-72) | (b-35) | H | H | (a-20) | —CH(Me)— |
| 5-417 | (b-73) | (b-7) | H | H | (a-20) | —CH(Me)— |
| 5-418 | (b-73) | (b-7) | H | H | (a-20) | —COCH(Me)— |
| 5-419 | (b-73) | (b-35) | H | H | (a-20) | —CH(Me)— |
| 5-420 | (b-73) | (b-35) | H | H | (a-20) | —COCH(Me)— |
| 5-421 | (b-74) | (b-7) | H | H | (a-20) | —CH(Me)— |
| 5-422 | (b-74) | (b-35) | H | H | (a-20) | —CH(Me)— |
| 5-423 | (b-76) | (b-7) | H | H | (a-20) | —CH(Me)— |
| 5-424 | (b-76) | (b-35) | H | H | (a-20) | —CH(Me)— |
| 5-425 | (b-77) | (b-7) | H | H | (a-20) | —CH(Me)— |
| 5-426 | (b-77) | (b-7) | H | H | (a-20) | —COCH(Me)— |
| 5-427 | (b-77) | (b-35) | H | H | (a-20) | —CH(Me)— |
| 5-428 | (b-77) | (b-35) | H | H | (a-20) | —COCH(Me)— |
| 5-429 | (b-7) | (b-35) | H | H | (a-21) | —CH(Me)— |
| 5-430 | (b-11) | (b-35) | H | H | (a-21) | —CH(Me)— |
| 5-431 | (b-18) | (b-35) | H | H | (a-21) | —CH(Me)— |
| 5-432 | (b-20) | (b-35) | H | H | (a-21) | —CH(Me)— |
| 5-433 | (b-73) | (b-35) | H | H | (a-21) | —CH(Me)— |
| 5-434 | (b-77) | (b-35) | H | H | (a-21) | —CH(Me)— |
| 5-435 | (b-7) | (b-7) | H | H | (a-24) | —CH(Me)— |
| 5-436 | (b-7) | (b-35) | H | H | (a-24) | —CH(Me)— |
| 5-437 | (b-11) | (b-7) | H | H | (a-24) | —CH(Me)— |
| 5-438 | (b-11) | (b-35) | H | H | (a-24) | —CH(Me)— |
| 5-439 | (b-12) | (b-35) | H | H | (a-24) | —CH(Me)— |
| 5-440 | (b-15) | (b-35) | H | H | (a-24) | —CH(Me)— |
| 5-441 | (b-18) | (b-7) | H | H | (a-24) | —CH(Me)— |
| 5-442 | (b-18) | (b-35) | H | H | (a-24) | —CH(Me)— |
| 5-443 | (b-19) | (b-35) | H | H | (a-24) | —CH(Me)— |
| 5-444 | (b-20) | (b-7) | H | H | (a-24) | —CH(Me)— |
| 5-445 | (b-20) | (b-35) | H | H | (a-24) | —CH(Me)— |
| 5-446 | (b-21) | (b-35) | H | H | (a-24) | —CH(Me)— |
| 5-447 | (b-24) | (b-35) | H | H | (a-24) | —CH(Me)— |
| 5-448 | (b-25) | (b-35) | H | H | (a-24) | —CH(Me)— |
| 5-449 | (b-72) | (b-35) | H | H | (a-24) | —CH(Me)— |
| 5-450 | (b-73) | (b-7) | H | H | (a-24) | —CH(Me)— |
| 5-451 | (b-73) | (b-35) | H | H | (a-24) | —CH(Me)— |
| 5-452 | (b-74) | (b-35) | H | H | (a-24) | —CH(Me)— |
| 5-453 | (b-76) | (b-35) | H | H | (a-24) | —CH(Me)— |
| 5-454 | (b-77) | (b-7) | H | H | (a-24) | —CH(Me)— |
| 5-455 | (b-77) | (b-35) | H | H | (a-24) | —CH(Me)— |
| 5-456 | (b-2) | (b-35) | H | H | (a-26) | —CH(Me)— |
| 5-457 | (b-7) | (b-7) | H | H | (a-26) | —CH(Me)— |
| 5-458 | (b-7) | (b-7) | H | H | (a-26) | —COCH(Me)— |

TABLE 5-continued (I-5)

| Cpd. No. | R¹ Sub. No. | R² Sub. No. | R³ | R⁴ | A sub. No. | G |
|---|---|---|---|---|---|---|
| 5-459 | (b-7) | (b-35) | H | H | (a-26) | —CH(Me)— |
| 5-460 | (b-7) | (b-35) | H | H | (a-26) | —COCH(Me)— |
| 5-461 | (b-8) | (b-35) | H | H | (a-26) | —CH(Me)— |
| 5-462 | (b-11) | (b-7) | H | H | (a-26) | —CH(Me)— |
| 5-463 | (b-11) | (b-7) | H | H | (a-26) | —COCH(Me)— |
| 5-464 | (b-11) | (b-35) | H | H | (a-26) | —CH(Me)— |
| 5-465 | (b-11) | (b-35) | H | H | (a-26) | —COCH(Me)— |
| 5-466 | (b-12) | (b-7) | H | H | (a-26) | —CH(Me)— |
| 5-467 | (b-12) | (b-35) | H | H | (a-26) | —CH(Me)— |
| 5-468 | (b-15) | (b-7) | H | H | (a-26) | —CH(Me)— |
| 5-469 | (b-15) | (b-35) | H | H | (a-26) | —CH(Me)— |
| 5-470 | (b-18) | (b-7) | H | H | (a-26) | —CH(Me)— |
| 5-471 | (b-18) | (b-7) | H | H | (a-26) | —COCH(Me)— |
| 5-472 | (b-18) | (b-35) | H | H | (a-26) | —CH(Me)— |
| 5-473 | (b-18) | (b-35) | H | H | (a-26) | —COCH(Me)— |
| 5-474 | (b-19) | (b-7) | H | H | (a-26) | —CH(Me)— |
| 5-475 | (b-19) | (b-35) | H | H | (a-26) | —CH(Me)— |
| 5-476 | (b-20) | (b-7) | H | H | (a-26) | —CH(Me)— |
| 5-477 | (b-20) | (b-7) | H | H | (a-26) | —COCH(Me)— |
| 5-478 | (b-20) | (b-35) | H | H | (a-26) | —CH(Me)— |
| 5-479 | (b-20) | (b-35) | H | H | (a-26) | —COCH(Me)— |
| 5-480 | (b-21) | (b-7) | H | H | (a-26) | —CH(Me)— |
| 5-481 | (b-21) | (b-35) | H | H | (a-26) | —CH(Me)— |
| 5-482 | (b-24) | (b-7) | H | H | (a-26) | —CH(Me)— |
| 5-483 | (b-24) | (b-35) | H | H | (a-26) | —CH(Me)— |
| 5-484 | (b-25) | (b-7) | H | H | (a-26) | —CH(Me)— |
| 5-485 | (b-25) | (b-35) | H | H | (a-26) | —CH(Me)— |
| 5-486 | (b-72) | (b-7) | H | H | (a-26) | —CH(Me)— |
| 5-487 | (b-72) | (b-35) | H | H | (a-26) | —CH(Me)— |
| 5-488 | (b-73) | (b-7) | H | H | (a-26) | —CH(Me)— |
| 5-489 | (b-73) | (b-7) | H | H | (a-26) | —COCH(Me)— |
| 5-490 | (b-73) | (b-35) | H | H | (a-26) | —CH(Me)— |
| 5-491 | (b-73) | (b-35) | H | H | (a-26) | —COCH(Me)— |
| 5-492 | (b-74) | (b-7) | H | H | (a-26) | —CH(Me)— |
| 5-493 | (b-74) | (b-35) | H | H | (a-26) | —CH(Me)— |
| 5-494 | (b-76) | (b-7) | H | H | (a-26) | —CH(Me)— |
| 5-495 | (b-76) | (b-35) | H | H | (a-26) | —CH(Me)— |
| 5-496 | (b-77) | (b-7) | H | H | (a-26) | —CH(Me)— |
| 5-497 | (b-77) | (b-7) | H | H | (a-26) | —COCH(Me)— |
| 5-498 | (b-77) | (b-35) | H | H | (a-26) | —CH(Me)— |
| 5-499 | (b-77) | (b-35) | H | H | (a-26) | —COCH(Me)— |
| 5-500 | (b-7) | (b-35) | H | H | (a-27) | —CH(Me)— |
| 5-501 | (b-11) | (b-35) | H | H | (a-27) | —CH(Me)— |
| 5-502 | (b-18) | (b-35) | H | H | (a-27) | —CH(Me)— |
| 5-503 | (b-20) | (b-35) | H | H | (a-27) | —CH(Me)— |
| 5-504 | (b-73) | (b-35) | H | H | (a-27) | —CH(Me)— |
| 5-505 | (b-77) | (b-35) | H | H | (a-27) | —CH(Me)— |
| 5-506 | (b-7) | (b-7) | H | H | (a-28) | —CH(Me)— |
| 5-507 | (b-7) | (b-35) | H | H | (a-28) | —CH(Me)— |
| 5-508 | (b-11) | (b-7) | H | H | (a-28) | —CH(Me)— |
| 5-509 | (b-11) | (b-35) | H | H | (a-28) | —CH(Me)— |
| 5-510 | (b-12) | (b-35) | H | H | (a-28) | —CH(Me)— |
| 5-511 | (b-15) | (b-35) | H | H | (a-28) | —CH(Me)— |
| 5-512 | (b-18) | (b-7) | H | H | (a-28) | —CH(Me)— |
| 5-513 | (b-18) | (b-35) | H | H | (a-28) | —CH(Me)— |
| 5-514 | (b-19) | (b-35) | H | H | (a-28) | —CH(Me)— |
| 5-515 | (b-20) | (b-7) | H | H | (a-28) | —CH(Me)— |
| 5-516 | (b-20) | (b-35) | H | H | (a-28) | —CH(Me)— |
| 5-517 | (b-21) | (b-35) | H | H | (a-28) | —CH(Me)— |
| 5-518 | (b-24) | (b-35) | H | H | (a-28) | —CH(Me)— |
| 5-519 | (b-25) | (b-35) | H | H | (a-28) | —CH(Me)— |
| 5-520 | (b-72) | (b-35) | H | H | (a-28) | —CH(Me)— |
| 5-521 | (b-73) | (b-7) | H | H | (a-28) | —CH(Me)— |
| 5-522 | (b-73) | (b-35) | H | H | (a-28) | —CH(Me)— |
| 5-523 | (b-74) | (b-35) | H | H | (a-28) | —CH(Me)— |
| 5-524 | (b-76) | (b-35) | H | H | (a-28) | —CH(Me)— |
| 5-525 | (b-77) | (b-7) | H | H | (a-28) | —CH(Me)— |
| 5-526 | (b-77) | (b-35) | H | H | (a-28) | —CH(Me)— |
| 5-527 | (b-7) | (b-35) | H | H | (a-29) | —CH(Me)— |
| 5-528 | (b-11) | (b-35) | H | H | (a-29) | —CH(Me)— |
| 5-529 | (b-18) | (b-35) | H | H | (a-29) | —CH(Me)— |
| 5-530 | (b-20) | (b-35) | H | H | (a-29) | —CH(Me)— |
| 5-531 | (b-73) | (b-35) | H | H | (a-29) | —CH(Me)— |
| 5-532 | (b-77) | (b-35) | H | H | (a-29) | —CH(Me)— |
| 5-533 | (b-2) | (b-35) | H | H | (a-31) | —CH(Me)— |
| 5-534 | (b-7) | (b-7) | H | H | (a-31) | —CH(Me)— |
| 5-535 | (b-7) | (b-7) | H | H | (a-31) | —COCH(Me)— |
| 5-536 | (b-7) | (b-35) | H | H | (a-31) | —CH(Me)— |
| 5-537 | (b-7) | (b-35) | H | H | (a-31) | —COCH(Me)— |
| 5-538 | (b-8) | (b-35) | H | H | (a-31) | —CH(Me)— |
| 5-539 | (b-11) | (b-7) | H | H | (a-31) | —CH(Me)— |
| 5-540 | (b-11) | (b-7) | H | H | (a-31) | —COCH(Me)— |
| 5-541 | (b-11) | (b-35) | H | H | (a-31) | —CH(Me)— |
| 5-542 | (b-11) | (b-35) | H | H | (a-31) | —COCH(Me)— |
| 5-543 | (b-12) | (b-7) | H | H | (a-31) | —CH(Me)— |
| 5-544 | (b-12) | (b-35) | H | H | (a-31) | —CH(Me)— |
| 5-545 | (b-15) | (b-7) | H | H | (a-31) | —CH(Me)— |
| 5-546 | (b-15) | (b-35) | H | H | (a-31) | —CH(Me)— |
| 5-547 | (b-18) | (b-7) | H | H | (a-31) | —CH(Me)— |
| 5-548 | (b-18) | (b-7) | H | H | (a-31) | —COCH(Me)— |
| 5-549 | (b-18) | (b-35) | H | H | (a-31) | —CH(Me)— |
| 5-550 | (b-18) | (b-35) | H | H | (a-31) | —COCH(Me)— |
| 5-551 | (b-19) | (b-7) | H | H | (a-31) | —CH(Me)— |
| 5-552 | (b-19) | (b-35) | H | H | (a-31) | —CH(Me)— |
| 5-553 | (b-20) | (b-7) | H | H | (a-31) | —CH(Me)— |
| 5-554 | (b-20) | (b-7) | H | H | (a-31) | —COCH(Me)— |
| 5-555 | (b-20) | (b-35) | H | H | (a-31) | —CH(Me)— |
| 5-556 | (b-20) | (b-35) | H | H | (a-31) | —COCH(Me)— |
| 5-557 | (b-21) | (b-7) | H | H | (a-31) | —CH(Me)— |
| 5-558 | (b-21) | (b-35) | H | H | (a-31) | —CH(Me)— |
| 5-559 | (b-24) | (b-7) | H | H | (a-31) | —CH(Me)— |
| 5-560 | (b-24) | (b-35) | H | H | (a-31) | —CH(Me)— |
| 5-561 | (b-25) | (b-7) | H | H | (a-31) | —CH(Me)— |
| 5-562 | (b-25) | (b-35) | H | H | (a-31) | —CH(Me)— |
| 5-563 | (b-72) | (b-7) | H | H | (a-31) | —CH(Me)— |
| 5-564 | (b-72) | (b-35) | H | H | (a-31) | —CH(Me)— |
| 5-565 | (b-73) | (b-7) | H | H | (a-31) | —CH(Me)— |
| 5-566 | (b-73) | (b-7) | H | H | (a-31) | —COCH(Me)— |
| 5-567 | (b-73) | (b-35) | H | H | (a-31) | —CH(Me)— |
| 5-568 | (b-73) | (b-35) | H | H | (a-31) | —COCH(Me)— |
| 5-569 | (b-74) | (b-7) | H | H | (a-31) | —CH(Me)— |
| 5-570 | (b-74) | (b-35) | H | H | (a-31) | —CH(Me)— |
| 5-571 | (b-76) | (b-7) | H | H | (a-31) | —CH(Me)— |
| 5-572 | (b-76) | (b-35) | H | H | (a-31) | —CH(Me)— |
| 5-573 | (b-77) | (b-7) | H | H | (a-31) | —CH(Me)— |
| 5-574 | (b-77) | (b-7) | H | H | (a-31) | —COCH(Me)— |
| 5-575 | (b-77) | (b-35) | H | H | (a-31) | —CH(Me)— |
| 5-576 | (b-77) | (b-35) | H | H | (a-31) | —COCH(Me)— |
| 5-577 | (b-7) | (b-35) | H | H | (a-32) | —CH(Me)— |
| 5-578 | (b-11) | (b-35) | H | H | (a-32) | —CH(Me)— |
| 5-579 | (b-18) | (b-35) | H | H | (a-32) | —CH(Me)— |
| 5-580 | (b-20) | (b-35) | H | H | (a-32) | —CH(Me)— |
| 5-581 | (b-73) | (b-35) | H | H | (a-32) | —CH(Me)— |
| 5-582 | (b-77) | (b-35) | H | H | (a-32) | —CH(Me)— |
| 5-583 | (b-7) | (b-7) | H | H | (a-33) | —CH(Me)— |
| 5-584 | (b-7) | (b-35) | H | H | (a-33) | —CH(Me)— |
| 5-585 | (b-11) | (b-7) | H | H | (a-33) | —CH(Me)— |
| 5-586 | (b-11) | (b-35) | H | H | (a-33) | —CH(Me)— |

TABLE 5-continued (I-5)

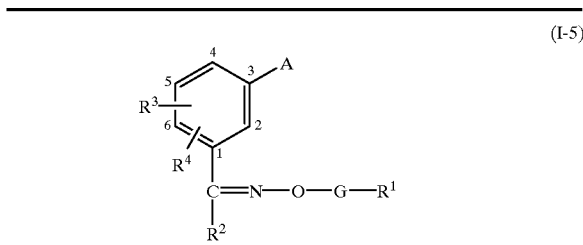

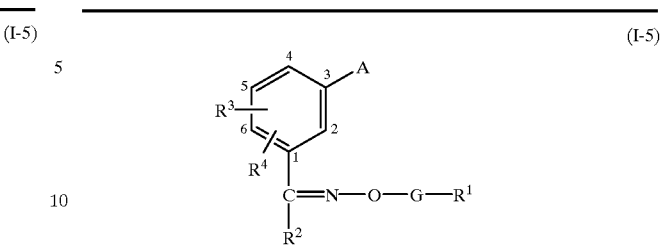

| Cpd. No. | R¹ Sub. No. | R² Sub. No. | R³ | R⁴ | A sub. No. | G |
|---|---|---|---|---|---|---|
| 5-587 | (b-12) | (b-35) | H | H | (a-33) | —CH(Me)— |
| 5-588 | (b-15) | (b-35) | H | H | (a-33) | —CH(Me)— |
| 5-589 | (b-18) | (b-7) | H | H | (a-33) | —CH(Me)— |
| 5-590 | (b-18) | (b-35) | H | H | (a-33) | —CH(Me)— |
| 5-591 | (b-19) | (b-35) | H | H | (a-33) | —CH(Me)— |
| 5-592 | (b-20) | (b-7) | H | H | (a-33) | —CH(Me)— |
| 5-593 | (b-20) | (b-35) | H | H | (a-33) | —CH(Me)— |
| 5-594 | (b-21) | (b-35) | H | H | (a-33) | —CH(Me)— |
| 5-595 | (b-24) | (b-35) | H | H | (a-33) | —CH(Me)— |
| 5-596 | (b-25) | (b-35) | H | H | (a-33) | —CH(Me)— |
| 5-597 | (b-72) | (b-35) | H | H | (a-33) | —CH(Me)— |
| 5-598 | (b-73) | (b-7) | H | H | (a-33) | —CH(Me)— |
| 5-599 | (b-73) | (b-35) | H | H | (a-33) | —CH(Me)— |
| 5-600 | (b-74) | (b-35) | H | H | (a-33) | —CH(Me)— |
| 5-601 | (b-76) | (b-35) | H | H | (a-33) | —CH(Me)— |
| 5-602 | (b-77) | (b-7) | H | H | (a-33) | —CH(Me)— |
| 5-603 | (b-77) | (b-35) | H | H | (a-33) | —CH(Me)— |
| 5-604 | (b-7) | (b-35) | H | H | (a-34) | —CH(Me)— |
| 5-605 | (b-11) | (b-35) | H | H | (a-34) | —CH(Me)— |
| 5-606 | (b-18) | (b-35) | H | H | (a-34) | —CH(Me)— |
| 5-607 | (b-20) | (b-35) | H | H | (a-34) | —CH(Me)— |
| 5-608 | (b-73) | (b-35) | H | H | (a-34) | —CH(Me)— |
| 5-609 | (b-77) | (b-35) | H | H | (a-34) | —CH(Me)— |
| 5-610 | (b-7) | (b-35) | H | H | (a-36) | —CH(Me)— |
| 5-611 | (b-11) | (b-35) | H | H | (a-36) | —CH(Me)— |
| 5-612 | (b-18) | (b-35) | H | H | (a-36) | —CH(Me)— |
| 5-613 | (b-20) | (b-35) | H | H | (a-36) | —CH(Me)— |
| 5-614 | (b-73) | (b-35) | H | H | (a-36) | —CH(Me)— |
| 5-615 | (b-77) | (b-35) | H | H | (a-36) | —CH(Me)— |
| 5-616 | (b-7) | (b-35) | H | H | (a-38) | —CH(Me)— |
| 5-617 | (b-11) | (b-35) | H | H | (a-38) | —CH(Me)— |
| 5-618 | (b-18) | (b-35) | H | H | (a-38) | —CH(Me)— |
| 5-619 | (b-7) | (b-35) | H | H | (a-39) | —CH(Me)— |
| 5-620 | (b-11) | (b-35) | H | H | (a-39) | —CH(Me)— |
| 5-621 | (b-18) | (b-35) | H | H | (a-39) | —CH(Me)— |
| 5-622 | (b-20) | (b-35) | H | H | (a-39) | —CH(Me)— |
| 5-623 | (b-73) | (b-35) | H | H | (a-39) | —CH(Me)— |
| 5-624 | (b-77) | (b-35) | H | H | (a-39) | —CH(Me)— |
| 5-625 | (b-7) | (b-35) | H | H | (a-41) | —CH(Me)— |
| 5-626 | (b-11) | (b-35) | H | H | (a-41) | —CH(Me)— |
| 5-627 | (b-18) | (b-35) | H | H | (a-41) | —CH(Me)— |
| 5-628 | (b-2) | (b-35) | H | H | (a-43) | —CH(Me)— |
| 5-629 | (b-7) | (b-7) | H | H | (a-43) | —CH(Me)— |
| 5-630 | (b-7) | (b-7) | H | H | (a-43) | —COCH(Me)— |
| 5-631 | (b-7) | (b-35) | H | H | (a-43) | —CH(Me)— |
| 5-632 | (b-7) | (b-35) | H | H | (a-43) | —COCH(Me)— |
| 5-633 | (b-8) | (b-35) | H | H | (a-43) | —CH(Me)— |
| 5-634 | (b-11) | (b-7) | H | H | (a-43) | —CH(Me)— |
| 5-635 | (b-11) | (b-7) | H | H | (a-43) | —COCH(Me)— |
| 5-636 | (b-11) | (b-35) | H | H | (a-43) | —CH(Me)— |
| 5-637 | (b-11) | (b-35) | H | H | (a-43) | —COCH(Me)— |
| 5-638 | (b-12) | (b-7) | H | H | (a-43) | —CH(Me)— |
| 5-639 | (b-12) | (b-35) | H | H | (a-43) | —CH(Me)— |
| 5-640 | (b-15) | (b-7) | H | H | (a-43) | —CH(Me)— |
| 5-641 | (b-15) | (b-35) | H | H | (a-43) | —CH(Me)— |
| 5-642 | (b-18) | (b-7) | H | H | (a-43) | —CH(Me)— |
| 5-643 | (b-18) | (b-7) | H | H | (a-43) | —COCH(Me)— |
| 5-644 | (b-18) | (b-35) | H | H | (a-43) | —CH(Me)— |
| 5-645 | (b-18) | (b-35) | H | H | (a-43) | —COCH(Me)— |
| 5-646 | (b-19) | (b-7) | H | H | (a-43) | —CH(Me)— |
| 5-647 | (b-19) | (b-35) | H | H | (a-43) | —CH(Me)— |
| 5-648 | (b-20) | (b-7) | H | H | (a-43) | —CH(Me)— |
| 5-649 | (b-20) | (b-7) | H | H | (a-43) | —COCH(Me)— |
| 5-650 | (b-20) | (b-35) | H | H | (a-43) | —CH(Me)— |
| 5-651 | (b-20) | (b-35) | H | H | (a-43) | —COCH(Me)— |
| 5-652 | (b-21) | (b-7) | H | H | (a-43) | —CH(Me)— |
| 5-653 | (b-21) | (b-35) | H | H | (a-43) | —CH(Me)— |
| 5-654 | (b-24) | (b-7) | H | H | (a-43) | —CH(Me)— |
| 5-655 | (b-24) | (b-35) | H | H | (a-43) | —CH(Me)— |
| 5-656 | (b-25) | (b-7) | H | H | (a-43) | —CH(Me)— |
| 5-657 | (b-25) | (b-35) | H | H | (a-43) | —CH(Me)— |
| 5-658 | (b-72) | (b-7) | H | H | (a-43) | —CH(Me)— |
| 5-659 | (b-72) | (b-35) | H | H | (a-43) | —CH(Me)— |
| 5-660 | (b-73) | (b-7) | H | H | (a-43) | —CH(Me)— |
| 5-661 | (b-73) | (b-7) | H | H | (a-43) | —COCH(Me)— |
| 5-662 | (b-73) | (b-35) | H | H | (a-43) | —CH(Me)— |
| 5-663 | (b-73) | (b-35) | H | H | (a-43) | —COCH(Me)— |
| 5-664 | (b-74) | (b-7) | H | H | (a-43) | —CH(Me)— |
| 5-665 | (b-74) | (b-35) | H | H | (a-43) | —CH(Me)— |
| 5-666 | (b-76) | (b-7) | H | H | (a-43) | —CH(Me)— |
| 5-667 | (b-76) | (b-35) | H | H | (a-43) | —CH(Me)— |
| 5-668 | (b-77) | (b-7) | H | H | (a-43) | —CH(Me)— |
| 5-669 | (b-77) | (b-7) | H | H | (a-43) | —COCH(Me)— |
| 5-670 | (b-77) | (b-35) | H | H | (a-43) | —CH(Me)— |
| 5-671 | (b-77) | (b-35) | H | H | (a-43) | —COCH(Me)— |
| 5-672 | (b-7) | (b-35) | H | H | (a-44) | —CH(Me)— |
| 5-673 | (b-11) | (b-35) | H | H | (a-44) | —CH(Me)— |
| 5-674 | (b-18) | (b-35) | H | H | (a-44) | —CH(Me)— |
| 5-675 | (b-20) | (b-35) | H | H | (a-44) | —CH(Me)— |
| 5-676 | (b-73) | (b-35) | H | H | (a-44) | —CH(Me)— |
| 5-677 | (b-77) | (b-35) | H | H | (a-44) | —CH(Me)— |
| 5-678 | (b-7) | (b-7) | H | H | (a-45) | —CH(Me)— |
| 5-679 | (b-7) | (b-35) | H | H | (a-45) | —CH(Me)— |
| 5-680 | (b-11) | (b-7) | H | H | (a-45) | —CH(Me)— |
| 5-681 | (b-11) | (b-35) | H | H | (a-45) | —CH(Me)— |
| 5-682 | (b-12) | (b-35) | H | H | (a-45) | —CH(Me)— |
| 5-683 | (b-15) | (b-35) | H | H | (a-45) | —CH(Me)— |
| 5-684 | (b-18) | (b-7) | H | H | (a-45) | —CH(Me)— |
| 5-685 | (b-18) | (b-35) | H | H | (a-45) | —CH(Me)— |
| 5-686 | (b-19) | (b-35) | H | H | (a-45) | —CH(Me)— |
| 5-687 | (b-20) | (b-7) | H | H | (a-45) | —CH(Me)— |
| 5-688 | (b-20) | (b-35) | H | H | (a-45) | —CH(Me)— |
| 5-689 | (b-21) | (b-35) | H | H | (a-45) | —CH(Me)— |
| 5-690 | (b-24) | (b-35) | H | H | (a-45) | —CH(Me)— |
| 5-691 | (b-25) | (b-35) | H | H | (a-45) | —CH(Me)— |
| 5-692 | (b-72) | (b-35) | H | H | (a-45) | —CH(Me)— |
| 5-693 | (b-73) | (b-7) | H | H | (a-45) | —CH(Me)— |
| 5-694 | (b-73) | (b-35) | H | H | (a-45) | —CH(Me)— |
| 5-695 | (b-74) | (b-35) | H | H | (a-45) | —CH(Me)— |
| 5-696 | (b-76) | (b-35) | H | H | (a-45) | —CH(Me)— |
| 5-697 | (b-77) | (b-7) | H | H | (a-45) | —CH(Me)— |
| 5-698 | (b-77) | (b-35) | H | H | (a-45) | —CH(Me)— |
| 5-699 | (b-7) | (b-35) | H | H | (a-46) | —CH(Me)— |
| 5-700 | (b-11) | (b-35) | H | H | (a-46) | —CH(Me)— |
| 5-701 | (b-18) | (b-35) | H | H | (a-46) | —CH(Me)— |
| 5-702 | (b-20) | (b-35) | H | H | (a-46) | —CH(Me)— |
| 5-703 | (b-73) | (b-35) | H | H | (a-46) | —CH(Me)— |
| 5-704 | (b-77) | (b-35) | H | H | (a-46) | —CH(Me)— |
| 5-705 | (b-7) | (b-35) | H | H | (a-47) | —CH(Me)— |
| 5-706 | (b-11) | (b-35) | H | H | (a-47) | —CH(Me)— |
| 5-707 | (b-18) | (b-35) | H | H | (a-47) | —CH(Me)— |

TABLE 6

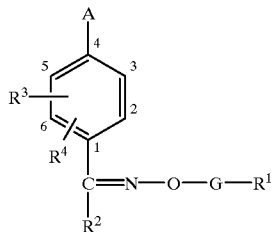

(I-6)

| Cpd. No. | R¹ Sub. No. | R² Sub. No. | R³ | R⁴ | A Sub. No. | G |
|---|---|---|---|---|---|---|
| 6-1 | (b-7) | (b-7) | H | H | (a-1) | —CH(Me)— |
| 6-2 | (b-7) | (b-35) | H | H | (a-1) | —CH(Me)— |
| 6-3 | (b-11) | (b-7) | H | H | (a-1) | —CH(Me)— |
| 6-4 | (b-11) | (b-35) | H | H | (a-1) | —CH(Me)— |
| 6-5 | (b-12) | (b-35) | H | H | (a-1) | —CH(Me)— |
| 6-6 | (b-15) | (b-35) | H | H | (a-1) | —CH(Me)— |
| 6-7 | (b-18) | (b-7) | H | H | (a-1) | —CH(Me)— |
| 6-8 | (b-18) | (b-35) | H | H | (a-1) | —CH(Me)— |
| 6-9 | (b-19) | (b-35) | H | H | (a-1) | —CH(Me)— |
| 6-10 | (b-20) | (b-7) | H | H | (a-1) | —CH(Me)— |
| 6-11 | (b-20) | (b-35) | H | H | (a-1) | —CH(Me)— |
| 6-12 | (b-21) | (b-35) | H | H | (a-1) | —CH(Me)— |
| 6-13 | (b-24) | (b-35) | H | H | (a-1) | —CH(Me)— |
| 6-14 | (b-25) | (b-35) | H | H | (a-1) | —CH(Me)— |
| 6-15 | (b-72) | (b-35) | H | H | (a-1) | —CH(Me)— |
| 6-16 | (b-73) | (b-7) | H | H | (a-1) | —CH(Me)— |
| 6-17 | (b-73) | (b-35) | H | H | (a-1) | —CH(Me)— |
| 6-18 | (b-74) | (b-35) | H | H | (a-1) | —CH(Me)— |
| 6-19 | (b-76) | (b-35) | H | H | (a-1) | —CH(Me)— |
| 6-20 | (b-77) | (b-7) | H | H | (a-1) | —CH(Me)— |
| 6-21 | (b-77) | (b-35) | H | H | (a-1) | —CH(Me)— |
| 6-22 | (b-11) | (b-35) | H | H | (a-2) | —CH(Me)— |
| 6-23 | (b-18) | (b-35) | H | H | (a-2) | —CH(Me)— |
| 6-24 | (b-20) | (b-35) | H | H | (a-2) | —CH(Me)— |
| 6-25 | (b-7) | (b-35) | H | H | (a-3) | —CH(Me)— |
| 6-26 | (b-11) | (b-35) | H | H | (a-3) | —CH(Me)— |
| 6-27 | (b-18) | (b-35) | H | H | (a-3) | —CH(Me)— |
| 6-28 | (b-20) | (b-35) | H | H | (a-3) | —CH(Me)— |
| 6-29 | (b-73) | (b-35) | H | H | (a-3) | —CH(Me)— |
| 6-30 | (b-77) | (b-35) | H | H | (a-3) | —CH(Me)— |
| 6-31 | (b-11) | (b-35) | H | H | (a-4) | —CH(Me)— |
| 6-32 | (b-18) | (b-35) | H | H | (a-4) | —CH(Me)— |
| 6-33 | (b-20) | (b-35) | H | H | (a-4) | —CH(Me)— |
| 6-34 | (b-7) | (b-7) | H | H | (a-5) | —CH(Me)— |
| 6-35 | (b-7) | (b-35) | H | H | (a-5) | —CH(Me)— |
| 6-36 | (b-11) | (b-7) | H | H | (a-5) | —CH(Me)— |
| 6-37 | (b-11) | (b-35) | H | H | (a-5) | —CH(Me)— |
| 6-38 | (b-12) | (b-35) | H | H | (a-5) | —CH(Me)— |
| 6-39 | (b-15) | (b-35) | H | H | (a-5) | —CH(Me)— |
| 6-40 | (b-18) | (b-7) | H | H | (a-5) | —CH(Me)— |
| 6-41 | (b-18) | (b-35) | H | H | (a-5) | —CH(Me)— |
| 6-42 | (b-19) | (b-35) | H | H | (a-5) | —CH(Me)— |
| 6-43 | (b-20) | (b-7) | H | H | (a-5) | —CH(Me)— |
| 6-44 | (b-20) | (b-35) | H | H | (a-5) | —CH(Me)— |
| 6-45 | (b-21) | (b-35) | H | H | (a-5) | —CH(Me)— |
| 6-46 | (b-24) | (b-35) | H | H | (a-5) | —CH(Me)— |
| 6-47 | (b-25) | (b-35) | H | H | (a-5) | —CH(Me)— |
| 6-48 | (b-72) | (b-35) | H | H | (a-5) | —CH(Me)— |
| 6-49 | (b-73) | (b-7) | H | H | (a-5) | —CH(Me)— |
| 6-50 | (b-73) | (b-35) | H | H | (a-5) | —CH(Me)— |
| 6-51 | (b-74) | (b-35) | H | H | (a-5) | —CH(Me)— |
| 6-52 | (b-76) | (b-35) | H | H | (a-5) | —CH(Me)— |
| 6-53 | (b-77) | (b-7) | H | H | (a-5) | —CH(Me)— |
| 6-54 | (b-77) | (b-35) | H | H | (a-5) | —CH(Me)— |
| 6-55 | (b-11) | (b-35) | H | H | (a-6) | —CH(Me)— |
| 6-56 | (b-18) | (b-35) | H | H | (a-6) | —CH(Me)— |
| 6-57 | (b-20) | (b-35) | H | H | (a-6) | —CH(Me)— |
| 6-58 | (b-7) | (b-35) | H | H | (a-7) | —CH(Me)— |
| 6-59 | (b-11) | (b-35) | H | H | (a-7) | —CH(Me)— |
| 6-60 | (b-18) | (b-35) | H | H | (a-7) | —CH(Me)— |
| 6-61 | (b-20) | (b-35) | H | H | (a-7) | —CH(Me)— |
| 6-62 | (b-73) | (b-35) | H | H | (a-7) | —CH(Me)— |
| 6-63 | (b-77) | (b-35) | H | H | (a-7) | —CH(Me)— |

TABLE 6-continued

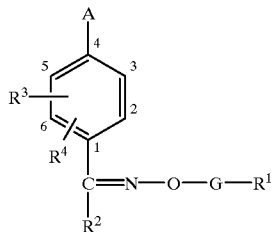

(I-6)

| Cpd. No. | R¹ Sub. No. | R² Sub. No. | R³ | R⁴ | A Sub. No. | G |
|---|---|---|---|---|---|---|
| 6-64 | (b-11) | (b-35) | H | H | (a-8) | —CH(Me)— |
| 6-65 | (b-18) | (b-35) | H | H | (a-8) | —CH(Me)— |
| 6-66 | (b-20) | (b-35) | H | H | (a-8) | —CH(Me)— |
| 6-67 | (b-11) | (b-35) | H | H | (a-11) | —CH(Me)— |
| 6-68 | (b-18) | (b-35) | H | H | (a-11) | —CH(Me)— |
| 6-69 | (b-20) | (b-35) | H | H | (a-11) | —CH(Me)— |
| 6-70 | (b-2) | (b-35) | H | H | (a-14) | —CH(Me)— |
| 6-71 | (b-7) | (b-7) | H | H | (a-14) | —CH(Me)— |
| 6-72 | (b-7) | (b-7) | H | H | (a-14) | —COCH(Me)— |
| 6-73 | (b-7) | (b-35) | H | H | (a-14) | —CH(Me)— |
| 6-74 | (b-7) | (b-35) | H | H | (a-14) | —COCH(Me)— |
| 6-75 | (b-8) | (b-35) | H | H | (a-14) | —CH(Me)— |
| 6-76 | (b-11) | (b-7) | H | H | (a-14) | —CH(Me)— |
| 6-77 | (b-11) | (b-7) | H | H | (a-14) | —COCH(Me)— |
| 6-78 | (b-11) | (b-35) | H | H | (a-14) | —CH(Me)— |
| 6-79 | (b-11) | (b-35) | H | H | (a-14) | —COCH(Me)— |
| 6-80 | (b-12) | (b-7) | H | H | (a-14) | —CH(Me)— |
| 6-81 | (b-12) | (b-35) | H | H | (a-14) | —CH(Me)— |
| 6-82 | (b-15) | (b-7) | H | H | (a-14) | —CH(Me)— |
| 6-83 | (b-15) | (b-35) | H | H | (a-14) | —CH(Me)— |
| 6-84 | (b-18) | (b-7) | H | H | (a-14) | —CH(Me)— |
| 6-85 | (b-18) | (b-7) | H | H | (a-14) | —COCH(Me)— |
| 6-86 | (b-18) | (b-35) | H | H | (a-14) | —CH(Me)— |
| 6-87 | (b-18) | (b-35) | H | H | (a-14) | —COCH(Me)— |
| 6-88 | (b-19) | (b-7) | H | H | (a-14) | —CH(Me)— |
| 6-89 | (b-19) | (b-35) | H | H | (a-14) | —CH(Me)— |
| 6-90 | (b-20) | (b-7) | H | H | (a-14) | —CH(Me)— |
| 6-91 | (b-20) | (b-7) | H | H | (a-14) | —COCH(Me)— |
| 6-92 | (b-20) | (b-35) | H | H | (a-14) | —CH(Me)— |
| 6-93 | (b-20) | (b-35) | H | H | (a-14) | —COCH(Me)— |
| 6-94 | (b-21) | (b-7) | H | H | (a-14) | —CH(Me)— |
| 6-95 | (b-21) | (b-35) | H | H | (a-14) | —CH(Me)— |
| 6-96 | (b-24) | (b-7) | H | H | (a-14) | —CH(Me)— |
| 6-97 | (b-24) | (b-35) | H | H | (a-14) | —CH(Me)— |
| 6-98 | (b-25) | (b-7) | H | H | (a-14) | —CH(Me)— |
| 6-99 | (b-25) | (b-35) | H | H | (a-14) | —CH(Me)— |
| 6-100 | (b-72) | (b-7) | H | H | (a-14) | —CH(Me)— |
| 6-101 | (b-72) | (b-35) | H | H | (a-14) | —CH(Me)— |
| 6-102 | (b-73) | (b-7) | H | H | (a-14) | —CH(Me)— |
| 6-103 | (b-73) | (b-7) | H | H | (a-14) | —COCH(Me)— |
| 6-104 | (b-73) | (b-35) | H | H | (a-14) | —CH(Me)— |
| 6-105 | (b-73) | (b-35) | H | H | (a-14) | —COCH(Me)— |
| 6-106 | (b-74) | (b-7) | H | H | (a-14) | —CH(Me)— |
| 6-107 | (b-74) | (b-35) | H | H | (a-14) | —CH(Me)— |
| 6-108 | (b-76) | (b-7) | H | H | (a-14) | —CH(Me)— |
| 6-109 | (b-76) | (b-35) | H | H | (a-14) | —CH(Me)— |
| 6-110 | (b-77) | (b-7) | H | H | (a-14) | —CH(Me)— |
| 6-111 | (b-77) | (b-7) | H | H | (a-14) | —COCH(Me)— |
| 6-112 | (b-77) | (b-35) | H | H | (a-14) | —CH(Me)— |
| 6-113 | (b-77) | (b-35) | H | H | (a-14) | —COCH(Me)— |
| 6-114 | (b-7) | (b-7) | H | H | (a-15) | —CH(Me)— |
| 6-115 | (b-7) | (b-35) | H | H | (a-15) | —CH(Me)— |
| 6-116 | (b-11) | (b-7) | H | H | (a-15) | —CH(Me)— |
| 6-117 | (b-11) | (b-35) | H | H | (a-15) | —CH(Me)— |
| 6-118 | (b-12) | (b-35) | H | H | (a-15) | —CH(Me)— |
| 6-119 | (b-15) | (b-35) | H | H | (a-15) | —CH(Me)— |
| 6-120 | (b-18) | (b-7) | H | H | (a-15) | —CH(Me)— |
| 6-121 | (b-18) | (b-35) | H | H | (a-15) | —CH(Me)— |
| 6-122 | (b-19) | (b-35) | H | H | (a-15) | —CH(Me)— |
| 6-123 | (b-20) | (b-7) | H | H | (a-15) | —CH(Me)— |
| 6-124 | (b-20) | (b-35) | H | H | (a-15) | —CH(Me)— |
| 6-125 | (b-21) | (b-35) | H | H | (a-15) | —CH(Me)— |
| 6-126 | (b-24) | (b-35) | H | H | (a-15) | —CH(Me)— |

TABLE 6-continued (I-6)

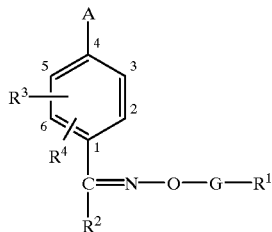

| Cpd. No. | R¹ Sub. No. | R² Sub. No. | R³ | R⁴ | A Sub. No. | G |
|---|---|---|---|---|---|---|
| 6-127 | (b-25) | (b-35) | H | H | (a-15) | —CH(Me)— |
| 6-128 | (b-72) | (b-35) | H | H | (a-15) | —CH(Me)— |
| 6-129 | (b-73) | (b-7) | H | H | (a-15) | —CH(Me)— |
| 6-130 | (b-73) | (b-35) | H | H | (a-15) | —CH(Me)— |
| 6-131 | (b-74) | (b-35) | H | H | (a-15) | —CH(Me)— |
| 6-132 | (b-76) | (b-35) | H | H | (a-15) | —CH(Me)— |
| 6-133 | (b-77) | (b-7) | H | H | (a-15) | —CH(Me)— |
| 6-134 | (b-77) | (b-35) | H | H | (a-15) | —CH(Me)— |
| 6-135 | (b-7) | (b-7) | H | H | (a-18) | —CH(Me)— |
| 6-136 | (b-7) | (b-35) | H | H | (a-18) | —CH(Me)— |
| 6-137 | (b-11) | (b-7) | H | H | (a-18) | —CH(Me)— |
| 6-138 | (b-11) | (b-35) | H | H | (a-18) | —CH(Me)— |
| 6-139 | (b-12) | (b-35) | H | H | (a-18) | —CH(Me)— |
| 6-140 | (b-15) | (b-35) | H | H | (a-18) | —CH(Me)— |
| 6-141 | (b-18) | (b-7) | H | H | (a-18) | —CH(Me)— |
| 6-142 | (b-18) | (b-35) | H | H | (a-18) | —CH(Me)— |
| 6-143 | (b-19) | (b-35) | H | H | (a-18) | —CH(Me)— |
| 6-144 | (b-20) | (b-7) | H | H | (a-18) | —CH(Me)— |
| 6-145 | (b-20) | (b-35) | H | H | (a-18) | —CH(Me)— |
| 6-146 | (b-21) | (b-35) | H | H | (a-18) | —CH(Me)— |
| 6-147 | (b-24) | (b-35) | H | H | (a-18) | —CH(Me)— |
| 6-148 | (b-25) | (b-35) | H | H | (a-18) | —CH(Me)— |
| 6-149 | (b-72) | (b-35) | H | H | (a-18) | —CH(Me)— |
| 6-150 | (b-73) | (b-7) | H | H | (a-18) | —CH(Me)— |
| 6-151 | (b-73) | (b-35) | H | H | (a-18) | —CH(Me)— |
| 6-152 | (b-74) | (b-35) | H | H | (a-18) | —CH(Me)— |
| 6-153 | (b-76) | (b-35) | H | H | (a-18) | —CH(Me)— |
| 6-154 | (b-77) | (b-7) | H | H | (a-18) | —CH(Me)— |
| 6-155 | (b-77) | (b-35) | H | H | (a-18) | —CH(Me)— |
| 6-156 | (b-7) | (b-35) | H | H | (a-19) | —CH(Me)— |
| 6-157 | (b-11) | (b-35) | H | H | (a-19) | —CH(Me)— |
| 6-158 | (b-18) | (b-35) | H | H | (a-19) | —CH(Me)— |
| 6-159 | (b-20) | (b-35) | H | H | (a-19) | —CH(Me)— |
| 6-160 | (b-73) | (b-35) | H | H | (a-19) | —CH(Me)— |
| 6-161 | (b-77) | (b-35) | H | H | (a-19) | —CH(Me)— |
| 6-162 | (b-7) | (b-7) | H | H | (a-20) | —CH(Me)— |
| 6-163 | (b-7) | (b-35) | H | H | (a-20) | —CH(Me)— |
| 6-164 | (b-11) | (b-7) | H | H | (a-20) | —CH(Me)— |
| 6-165 | (b-11) | (b-35) | H | H | (a-20) | —CH(Me)— |
| 6-166 | (b-12) | (b-35) | H | H | (a-20) | —CH(Me)— |
| 6-167 | (b-15) | (b-35) | H | H | (a-20) | —CH(Me)— |
| 6-168 | (b-18) | (b-7) | H | H | (a-20) | —CH(Me)— |
| 6-169 | (b-18) | (b-35) | H | H | (a-20) | —CH(Me)— |
| 6-170 | (b-19) | (b-35) | H | H | (a-20) | —CH(Me)— |
| 6-171 | (b-20) | (b-7) | H | H | (a-20) | —CH(Me)— |
| 6-172 | (b-20) | (b-35) | H | H | (a-20) | —CH(Me)— |
| 6-173 | (b-21) | (b-35) | H | H | (a-20) | —CH(Me)— |
| 6-174 | (b-24) | (b-35) | H | H | (a-20) | —CH(Me)— |
| 6-175 | (b-25) | (b-35) | H | H | (a-20) | —CH(Me)— |
| 6-176 | (b-72) | (b-35) | H | H | (a-20) | —CH(Me)— |
| 6-177 | (b-73) | (b-7) | H | H | (a-20) | —CH(Me)— |
| 6-178 | (b-73) | (b-35) | H | H | (a-20) | —CH(Me)— |
| 6-179 | (b-74) | (b-35) | H | H | (a-20) | —CH(Me)— |
| 6-180 | (b-76) | (b-35) | H | H | (a-20) | —CH(Me)— |
| 6-181 | (b-77) | (b-7) | H | H | (a-20) | —CH(Me)— |
| 6-182 | (b-77) | (b-35) | H | H | (a-20) | —CH(Me)— |
| 6-183 | (b-11) | (b-35) | H | H | (a-21) | —CH(Me)— |
| 6-184 | (b-18) | (b-35) | H | H | (a-21) | —CH(Me)— |
| 6-185 | (b-20) | (b-35) | H | H | (a-21) | —CH(Me)— |
| 6-186 | (b-7) | (b-35) | H | H | (a-24) | —CH(Me)— |
| 6-187 | (b-11) | (b-35) | H | H | (a-24) | —CH(Me)— |
| 6-188 | (b-18) | (b-35) | H | H | (a-24) | —CH(Me)— |
| 6-189 | (b-20) | (b-35) | H | H | (a-24) | —CH(Me)— |

TABLE 6-continued (I-6)

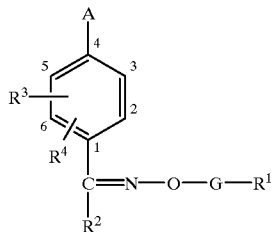

| Cpd. No. | R¹ Sub. No. | R² Sub. No. | R³ | R⁴ | A Sub. No. | G |
|---|---|---|---|---|---|---|
| 6-190 | (b-73) | (b-35) | H | H | (a-24) | —CH(Me)— |
| 6-191 | (b-77) | (b-35) | H | H | (a-24) | —CH(Me)— |
| 6-192 | (b-7) | (b-7) | H | H | (a-26) | —CH(Me)— |
| 6-193 | (b-7) | (b-35) | H | H | (a-26) | —CH(Me)— |
| 6-194 | (b-11) | (b-7) | H | H | (a-26) | —CH(Me)— |
| 6-195 | (b-11) | (b-35) | H | H | (a-26) | —CH(Me)— |
| 6-196 | (b-12) | (b-35) | H | H | (a-26) | —CH(Me)— |
| 6-197 | (b-15) | (b-35) | H | H | (a-26) | —CH(Me)— |
| 6-198 | (b-18) | (b-7) | H | H | (a-26) | —CH(Me)— |
| 6-199 | (b-18) | (b-35) | H | H | (a-26) | —CH(Me)— |
| 6-200 | (b-19) | (b-35) | H | H | (a-26) | —CH(Me)— |
| 6-201 | (b-20) | (b-7) | H | H | (a-26) | —CH(Me)— |
| 6-202 | (b-20) | (b-35) | H | H | (a-26) | —CH(Me)— |
| 6-203 | (b-21) | (b-35) | H | H | (a-26) | —CH(Me)— |
| 6-204 | (b-24) | (b-35) | H | H | (a-26) | —CH(Me)— |
| 6-205 | (b-25) | (b-35) | H | H | (a-26) | —CH(Me)— |
| 6-206 | (b-72) | (b-35) | H | H | (a-26) | —CH(Me)— |
| 6-207 | (b-73) | (b-7) | H | H | (a-26) | —CH(Me)— |
| 6-208 | (b-73) | (b-35) | H | H | (a-26) | —CH(Me)— |
| 6-209 | (b-74) | (b-35) | H | H | (a-26) | —CH(Me)— |
| 6-210 | (b-76) | (b-35) | H | H | (a-26) | —CH(Me)— |
| 6-211 | (b-77) | (b-7) | H | H | (a-26) | —CH(Me)— |
| 6-212 | (b-77) | (b-35) | H | H | (a-26) | —CH(Me)— |
| 6-213 | (b-11) | (b-35) | H | H | (a-27) | —CH(Me)— |
| 6-214 | (b-18) | (b-35) | H | H | (a-27) | —CH(Me)— |
| 6-215 | (b-20) | (b-35) | H | H | (a-27) | —CH(Me)— |
| 6-216 | (b-7) | (b-35) | H | H | (a-28) | —CH(Me)— |
| 6-217 | (b-11) | (b-35) | H | H | (a-28) | —CH(Me)— |
| 6-218 | (b-18) | (b-35) | H | H | (a-28) | —CH(Me)— |
| 6-219 | (b-20) | (b-35) | H | H | (a-28) | —CH(Me)— |
| 6-220 | (b-73) | (b-35) | H | H | (a-28) | —CH(Me)— |
| 6-221 | (b-77) | (b-35) | H | H | (a-28) | —CH(Me)— |
| 6-222 | (b-11) | (b-35) | H | H | (a-29) | —CH(Me)— |
| 6-223 | (b-18) | (b-35) | H | H | (a-29) | —CH(Me)— |
| 6-224 | (b-20) | (b-35) | H | H | (a-29) | —CH(Me)— |
| 6-225 | (b-7) | (b-7) | H | H | (a-31) | —CH(Me)— |
| 6-226 | (b-7) | (b-35) | H | H | (a-31) | —CH(Me)— |
| 6-227 | (b-11) | (b-7) | H | H | (a-31) | —CH(Me)— |
| 6-228 | (b-11) | (b-35) | H | H | (a-31) | —CH(Me)— |
| 6-229 | (b-12) | (b-35) | H | H | (a-31) | —CH(Me)— |
| 6-230 | (b-15) | (b-35) | H | H | (a-31) | —CH(Me)— |
| 6-231 | (b-18) | (b-7) | H | H | (a-31) | —CH(Me)— |
| 6-232 | (b-18) | (b-35) | H | H | (a-31) | —CH(Me)— |
| 6-233 | (b-19) | (b-35) | H | H | (a-31) | —CH(Me)— |
| 6-234 | (b-20) | (b-7) | H | H | (a-31) | —CH(Me)— |
| 6-235 | (b-20) | (b-35) | H | H | (a-31) | —CH(Me)— |
| 6-236 | (b-21) | (b-35) | H | H | (a-31) | —CH(Me)— |
| 6-237 | (b-24) | (b-35) | H | H | (a-31) | —CH(Me)— |
| 6-238 | (b-25) | (b-35) | H | H | (a-31) | —CH(Me)— |
| 6-239 | (b-72) | (b-35) | H | H | (a-31) | —CH(Me)— |
| 6-240 | (b-73) | (b-7) | H | H | (a-31) | —CH(Me)— |
| 6-241 | (b-73) | (b-35) | H | H | (a-31) | —CH(Me)— |
| 6-242 | (b-74) | (b-35) | H | H | (a-31) | —CH(Me)— |
| 6-243 | (b-76) | (b-35) | H | H | (a-31) | —CH(Me)— |
| 6-244 | (b-77) | (b-7) | H | H | (a-31) | —CH(Me)— |
| 6-245 | (b-77) | (b-35) | H | H | (a-31) | —CH(Me)— |
| 6-246 | (b-11) | (b-35) | H | H | (a-32) | —CH(Me)— |
| 6-247 | (b-18) | (b-35) | H | H | (a-32) | —CH(Me)— |
| 6-248 | (b-20) | (b-35) | H | H | (a-32) | —CH(Me)— |
| 6-249 | (b-7) | (b-35) | H | H | (a-33) | —CH(Me)— |
| 6-250 | (b-11) | (b-35) | H | H | (a-33) | —CH(Me)— |
| 6-251 | (b-18) | (b-35) | H | H | (a-33) | —CH(Me)— |
| 6-252 | (b-20) | (b-35) | H | H | (a-33) | —CH(Me)— |

TABLE 6-continued

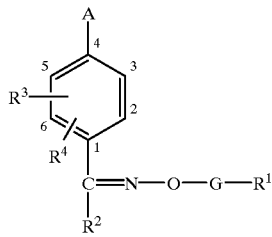

(I-6)

| Cpd. No. | R¹ Sub. No. | R² Sub. No. | R³ | R⁴ | A Sub. No. | G |
|---|---|---|---|---|---|---|
| 6-253 | (b-73) | (b-35) | H | H | (a-33) | —CH(Me)— |
| 6-254 | (b-77) | (b-35) | H | H | (a-33) | —CH(Me)— |
| 6-255 | (b-11) | (b-35) | H | H | (a-34) | —CH(Me)— |
| 6-256 | (b-18) | (b-35) | H | H | (a-34) | —CH(Me)— |
| 6-257 | (b-20) | (b-35) | H | H | (a-34) | —CH(Me)— |
| 6-258 | (b-11) | (b-35) | H | H | (a-36) | —CH(Me)— |
| 6-259 | (b-18) | (b-35) | H | H | (a-36) | —CH(Me)— |
| 6-260 | (b-20) | (b-35) | H | H | (a-36) | —CH(Me)— |
| 6-261 | (b-11) | (b-35) | H | H | (a-39) | —CH(Me)— |
| 6-262 | (b-18) | (b-35) | H | H | (a-39) | —CH(Me)— |
| 6-263 | (b-20) | (b-35) | H | H | (a-39) | —CH(Me)— |
| 6-264 | (b-7) | (b-7) | H | H | (a-43) | —CH(Me)— |
| 6-265 | (b-7) | (b-35) | H | H | (a-43) | —CH(Me)— |
| 6-266 | (b-11) | (b-7) | H | H | (a-43) | —CH(Me)— |
| 6-267 | (b-11) | (b-35) | H | H | (a-43) | —CH(Me)— |
| 6-268 | (b-12) | (b-35) | H | H | (a-43) | —CH(Me)— |
| 6-269 | (b-15) | (b-35) | H | H | (a-43) | —CH(Me)— |
| 6-270 | (b-18) | (b-7) | H | H | (a-43) | —CH(Me)— |
| 6-271 | (b-18) | (b-35) | H | H | (a-43) | —CH(Me)— |
| 6-272 | (b-19) | (b-35) | H | H | (a-43) | —CH(Me)— |
| 6-273 | (b-20) | (b-7) | H | H | (a-43) | —CH(Me)— |
| 6-274 | (b-20) | (b-35) | H | H | (a-43) | —CH(Me)— |
| 6-275 | (b-21) | (b-35) | H | H | (a-43) | —CH(Me)— |
| 6-276 | (b-24) | (b-35) | H | H | (a-43) | —CH(Me)— |
| 6-277 | (b-25) | (b-35) | H | H | (a-43) | —CH(Me)— |
| 6-278 | (b-72) | (b-35) | H | H | (a-43) | —CH(Me)— |
| 6-279 | (b-73) | (b-7) | H | H | (a-43) | —CH(Me)— |
| 6-280 | (b-73) | (b-35) | H | H | (a-43) | —CH(Me)— |
| 6-281 | (b-74) | (b-35) | H | H | (a-43) | —CH(Me)— |
| 6-282 | (b-76) | (b-35) | H | H | (a-43) | —CH(Me)— |
| 6-283 | (b-77) | (b-7) | H | H | (a-43) | —CH(Me)— |
| 6-284 | (b-77) | (b-35) | H | H | (a-43) | —CH(Me)— |
| 6-285 | (b-11) | (b-35) | H | H | (a-44) | —CH(Me)— |
| 6-286 | (b-18) | (b-35) | H | H | (a-44) | —CH(Me)— |
| 6-287 | (b-20) | (b-35) | H | H | (a-44) | —CH(Me)— |
| 6-288 | (b-7) | (b-35) | H | H | (a-45) | —CH(Me)— |
| 6-289 | (b-11) | (b-35) | H | H | (a-45) | —CH(Me)— |
| 6-290 | (b-18) | (b-35) | H | H | (a-45) | —CH(Me)— |
| 6-291 | (b-20) | (b-35) | H | H | (a-45) | —CH(Me)— |
| 6-292 | (b-73) | (b-35) | H | H | (a-45) | —CH(Me)— |
| 6-293 | (b-77) | (b-35) | H | H | (a-45) | —CH(Me)— |
| 6-294 | (b-11) | (b-35) | H | H | (a-46) | —CH(Me)— |
| 6-295 | (b-18) | (b-35) | H | H | (a-46) | —CH(Me)— |
| 6-296 | (b-20) | (b-35) | H | H | (a-46) | —CH(Me)— |

Of the compounds listed above, the following are preferred, that is to say, Compounds No.:

1-41, 1-78, 1-86, 1-92, 2–1-2-64, 2-74–2-86, 2-89-2-106, 2-116, 2-117, 2-237, 2-377, 2-403, 2-407, 2-450, 2-479, 2-480, 2-481, 2-492, 2-499, 2-500, 2-554, 2-574, 2-577, 2-583, 2-584, 2-585, 2-592, 2-691, 2-698, 2-699, 2-713, 2-755, 2-762, 2-763, 2-835, 2-838, 2-844, 2-845, 9-846, 2-815, 2-952, 2-1085, 2-1256, 2-1286, 2-1287, 2-1288, 2-1299, 2-1306, 2-1307, 2-1359, 2-1360, 2-1379, 2-1382, 2-1388, 2-1389, 2-1390, 2-1496, 2-1523, 2-1565, 2-1625, 2-1627, 2-1628, 2-1654, 2-1655, 2-1666, 2-1772, 2-1831, 2-1941, 2-1946, 2-1962, 2-2256, 2-2274, 2-2295, 2-2309, 2-3090–2-3514, 3-79, 3-94, 3-100, 2-169, 3-187, 3-208, 3-401, 5-94, 5-208 and 5-401;

More preferred compounds are Compounds No.:

2-2-2-58, 2-74, 2-81, 2-237, 2-450, 2-479, 2-480, 2-481, 2-492, 2-499, 2-500, 2-554, 2-583, 2-584, 2-585, 2-691, 2-713, 2-755, 2-762, 2-763, 2-835, 2-838, 2-844, 2-845, 2-846, 2-815, 2-952, 2-1085, 2-1256, 2-1286, 2-1287, 2-1288, 2-1299, 2-1306, 2-1307, 2-1359, 2-1360, 2-1379, 2-1382, 2-1388, 2-1389, 2-1390, 2-1496, 2-1523, 2-1565, 2-1625, 2-1627, 2-1628, 2-1654, 2-1655, 2-1666, 2-1772, 2-1831, 2-1941, 2-1962, 2-2274, 2-2295, 2-2309, 2-3108–2-3118, 2-3136, 2-3157–2-3165, 2-3178–2-3180, 2-3185, 2-3186, 2-3191–2-3201, 2-3217–2-3222, 2-3376–2-3390, 2-3400–2-3406, 2-3461, 2-3471–2-3477, 2-3479–2-3514, 3-79, 3-94, 3-100, 3-169, 3-187 and 3-208;

Still more preferred compounds are Compounds No.:

2-5, 2-6, 2-8, 2-13, 2-16, 2-18, 2-19, 2-21, 2-37, 2-39, 2-40, 2-42, 2-51, 2-53, 2-54, 2-56, 2-237, 2-450, 2-479, 2-480, 2-481, 2-492, 2-554, 2-583, 2-584, 2-585, 2-691, 2-713, 2-755, 2-815, 2-844, 2-845, 2-846, 2-1085, 2-1256, 2-1299, 2-1359, 2-1388, 2-1389, 2-1390, 2-1496, 2-1523, 2-1565, 2-1625, 2-1772, 2-1831, 2-1962, 2-2274, 2-2295, 2-2309, 2-3136, 2-3161, 2-3162, 2-3164, 2-3197, 2-3377, 2-3386, 2-3400, 2-3457, 2-3485, 2-3497, 2-3502, 2-3504, 3-94 and 3-208.

The most preferred compounds are Compounds No.:

2-5: 3-<3-{(4-Fluorophenyl)-[1-phenylethylamino]methyl}phenylamino>-4-hydroxy-3-cyclobutene-1,2-dione, 2-6: 3-<3-{(4-Chlorophenyl)-[1-phenylethylamino]methyl}phenylamino>-4-hydroxy-3-cyclobutene-1,2-dione, 2-8: 3-Hydroxy-4-<3-{[(R)-1-phenylethylamino]-(4-methoxyphenyl)methyl}phenylamino>-3-cyclobutene-1,2-dione, 2-13: 3-Hydroxy-4-<3-{(4-methoxyphenyl)-[1-(naphthalen-1-yl)ethylamino]methyl}phenylamino>-cycylobut-3-ene-1,2-dione, 2-16: 3-Hydroxy-4-<3-{[1-(3-fluorophenyl)ethylamino]phenylmethyl}phenylamino>-3-cyclobutene-1,2-dione, 2-18: 3-<3-{(4-Fluorophenyl)-[1-(3-fluorophenyl)ethylamino]methyl}phenylamino>-4-hydroxy-3-cyclobutene-1,2-dione, 2-19: 4-<3-{(4-Chlorophenyl)-[1-(3-fluorophenyl)ethylamino]methyl}phenylamino>-3-hydroxy-3-cyclobutene-1,2-dione, 2-21: 3-<3-{[1-(3-Fluorophenyl)ethylamino]-(4-methoxyphenyl)methyl}phenylamino>-4-hydroxy-3-cyclobutene-1,2-dione, 2-37: 3-Hydroxy-4-<3-{[1-(3,4-difluorophenyl)ethylamino]-phenylmethyl}phenylamino>-3-cyclobutene-1,2-dione, 2-39: 3-<3-{[1-(3,4-Difluorophenyl)ethylamino]-(4-fluorophenyl)methyl}phenylamino>-4-hydroxy-3-cyclobutene-1,2-dione, 2-40: 4-<3-{(4-Chlorophenyl)-[1-(3,4-difluorophenyl)ethylamino]methyl}phenylamino>-3-hydroxy-3-cyclobutene-1,2-dione, 2-42: 4-<3-{[1-(3,4-Difluorophenyl)ethylamino]-(4-methoxyphenyl)methyl}phenylamino>-3-hydroxy-3-cyclobutene-1,2-dione, 2-51: 3-Hydroxy-4-<3-{[1-(3,5-difluorophenyl)ethylamino]-phenylmethyl}phenylamino>-3-cyclobutene-1,2-dione, 2-53: 4-<3-{[1-(3,5-Difluorophenyl)ethylamino]-(4-fluorophenyl)methyl}phenylamino>-3-hydroxy-3-cyclobutene-1,2-dione, 2-54: 4-<3-{(4-Chlorophenyl)-[1-(3,5-difluorophenyl)ethylamino]methyl}phenylamino>-3-hydroxy-3-cyclobutene-1,2-dione, 2-56: 4-<3-{[1-(3,5-Difluorophenyl)ethylamino]-(4-methoxyphenyl)methyl}phenylamino>-3-hydroxy-3-cyclobutene-1,2-dione, 2-237: 3-Amino-4-<3-{(4-methoxyphenyl)-[1-(3,4-difluorophenyl)ethylamino]methyl}phenylamino>-3-cyclobuten-1,2-dione, 2-492: 3-Amino-4-{3-[(4-fluorophenyl)-(1-phenylethylamino)methyl]phenylamino}-3-cyclobutene-1,2-dione, 2-554: 3-Amino-4-{3-[(4-methoxyphenyl)-(1-phenylethylamino)methyl]phenylamino}-3-cyclobutene-1,2-dione, 2-691: 3-Amino-4-{3-[4-pyridyl-(1-phenylethylamino)methyl]phenylamino}-3-cyclobutene-1,2-dione, 2-815: 3-Amino-4-<3-{(4-methoxyphenyl)-[1-(3-fluorophenyl)ethylamino]methyl}phenylamino>-3-cyclobutene-1,2-dione, 2-1299: 3-Amino-4-<3-{(4-fluorophenyl)-[1-(3,4-difluorophenyl)ethylamino]methyl}phenylamino>-3-cyclobutene-1,2-dione, 2-1359: 3-Amino-4-<3-{(4-methoxyphenyl)-[1-(3,4-difluorophenyl)ethylamino]methyl}phenylamino>-3-cyclobutene-1,2-dione, 2-1496: 3-Amino-4-<3-{(4-pyridyl)-[1-(3,4-difluorophenyl)ethylamino]methyl}phenylamino>-3-cyclobutene-1,2-dione, 2-1523: 3-Amino-4-<3-{phenyl-[1-(3,5-difluorophenyl)ethylamino]methyl}phenylamino>-3-cyclobutene-1,2-dione, 2-1565: 3-Amino-4-<3-{(4-fluorophenyl)-[1-(3,5-difluorophenyl)ethylamino]methyl}phenylamino>-3-cyclobutene-1,2-dione, 2-1625: 3-Amino-4-<3-{(4-methoxyphenyl)-[1-(3,5-difluorophenyl)ethylamino]methyl}phenylamino>-3-cyclobutene-1,2-dione, 2-1962: 3-Amino-4-<3-{(4-methoxyphenyl)-[1-(4-pyridyl)ethylamino]methyl}phenylamino>-3-cyclobutene-1,2-dione, 2-2295: 3-Amino-4-<3-{(4-methoxyphenyl)-[1-(3,4-difluorophenyl)ethylamino]methyl}phenylamino>-3-cyclobutene-1,2-dione, 2-3136: 3-<3-{(4-Chlorophenyl)-[1-(naphthalen-1-yl)ethylamino]methyl}phenylamino>-4-hydroxy-3-cyclobutene-1,2-dione, 2-3161: 3-Hydroxy-4-<3-{[1-(1-naphthyl)ethylamino]-phenylmethyl}phenylamino>-3-cyclobutene-1,2-dione, 2-3162: 3-<3-{(4-Fluorophenyl)-[1-(naphthalen-1-yl)ethylamino]methyl}phenylamino>-4-hydroxy-3-cyclobutene-1,2-dione, 2-3164: 3-Hydroxy-4-<3-{[1-(1-naphthyl)ethylamino]-p-tolylmethyl}phenylamino>-3-cyclobutene-1,2-dione, 2-3197: 3-<3-{[4-(p-Tolyl)-[1-(3-fluorophenyl)ethylamino]methyl}phenylamino>-4-hydroxy-3-cyclobutene-1,2-dione hydrochloride, 2-3386: 3-<3-{[1-(3,4-Difluorophenylamino)ethylamino]-(p-toluyl)methyl}phenylamino>-4-hydroxy-3-cyclobutene-1,2-dione, and 2-3457: 4-<3-{[1-(3,5-Difluorophenyl)ethylamino]-(4-methylphenyl)methyl}phenylamino>-3-hydroxy-3-cyclobutene-1,2-dione.

The compounds of the present invention may be prepared by a variety of methods, well known in themselves. For example, they may be prepared by the following Processes A to G.

Process A

Process A is a process for the preparation of Compound (I), as shown in the following Reaction Scheme:

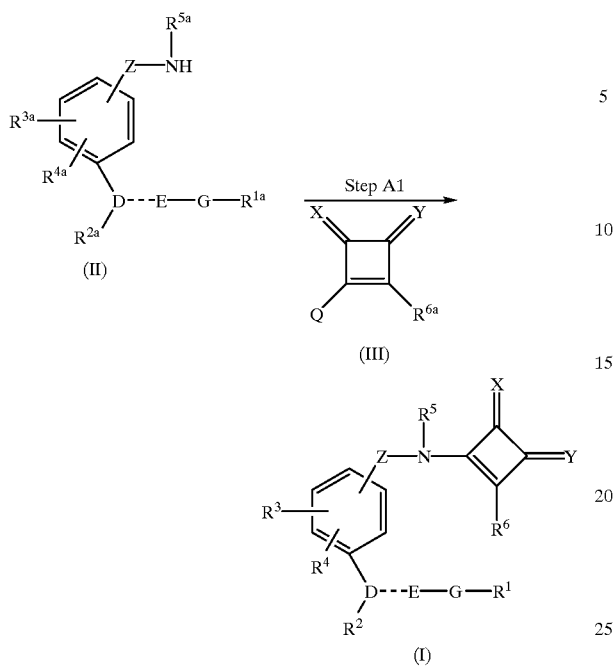

In the above reaction scheme:

$R^1$, $R^2$, $R^3$, $R^4$, $R^5$, $R^6$, D, E, G, X, Y, Z and the broken line have the same meanings as described above;

$R^{1a}$ has the same meanings as described above for $R^1$, with the proviso any amino, hydroxy and/or carboxy group contained as a substituent in $R^1$ may be protected;

$R^{2a}$, $R^{3a}$, $R^{4a}$ and $R^{6a}$ have the same meanings as described above for $R^2$, $R^3$, $R^4$ and $R^6$ with the proviso that the amino and/or hydroxy group contained as a substituent in $R^2$, $R^3$, $R^4$ and $R^6$ may be protected;

$R^{5a}$ has the same meaning as described above for $R^5$ with the proviso that the hydroxy group contained as a substituent in $R^5$ may be protected; and Q is any one group which can be eliminated in a nucleophilic reaction, and preferred examples include:
halogen atoms, such as the chlorine, bromine and iodine atoms;
lower alkoxy groups, such as the methoxy and ethoxy groups;
trihalomethoxy groups, such as the trichloromethoxy group;
lower alkanesulfonyloxy groups, such as the methanesulfonyloxy and ethanesulfonyloxy groups;
lower haloalkanesulfonyloxy groups, such as the trifluoromethanesulfonyloxy and pentafluoroethanesulfonyloxy groups; and
arylsulfonyloxy groups, such as the benzenesulfonyloxy, p-toluenesulfonyloxy and p-nitrobenzenesulfonyloxy groups;
of which the halogen atoms and lower alkoxy groups are most preferred.

There is no particular limitation on the nature of the protecting group for the amino group which may be protected in the definition of $R^{1a}$, $R^{2a}$, $R^{3a}$, $R^{4a}$ or $R^{6a}$, and any protecting group commonly used for amino or imino groups in organic synthetic chemistry may equally be used here. Preferred examples include:

aliphatic acyl groups, for example, lower aliphatic acyl groups (such as the formyl, acetyl, propionyl, butyryl, isobutyryl, valeryl, isovaleryl, pivaloyl, hexanoyl, acryloyl, methacryloyl and crotonoyl groups), lower haloalkylcarbonyl groups (such as the chloroacetyl, dichloroacetyl, trichloroacetyl and trifluoroacetyl groups), and lower-alkoxy-substituted (lower alkyl) carbonyl groups (such as the methoxyacetyl group);

aromatic acyl groups, for example, $C_{7-11}$ aromatic acyl groups (i.e. a group in which a carbonyl group is bound to an aryl group such as those defined and exemplified above), $C_{7-11}$ haloaromatic acyl groups (such as the 2-bromobenzoyl and 4-chlorobenzoyl groups), lower-alkyl-substituted $C_{7-11}$ aromatic acyl groups (such as the 2,4,6-trimethylbenzoyl and 4-toluoyl groups), lower-alkoxy-substituted $C_{7-11}$ aromatic acyl groups (such as the 4-anisoyl group), nitro-substituted $C_{7-11}$ aromatic acyl groups (such as the 4-nitrobenzoyl and 2-nitrobenzoyl groups), lower-alkoxycarbonyl-substituted $C_{7-11}$ aromatic acyl groups [such as the 2-(methoxycarbonyl)benzoyl group], and aryl-substituted $C_{7-11}$ aromatic acyl groups (such as the 4-phenylbenzoyl group);

alkoxycarbonyl groups, for example, those defined and exemplified above, and halogen- or tri(lower alkyl) silyl-substituted lower alkoxycarbonyl groups (such as the 2,2,2-trichloroethoxycarbonyl and 2-trimethylsilylethoxycarbonyl groups);

alkenyloxycarbonyl groups (such as the vinyloxycarbonyl and allyloxycarbonyl groups);

aralkyloxycarbonyl groups having an aryl ring which may be substituted by 1 or 2 lower alkoxy or nitro groups (such as the benzyloxycarbonyl, 4-methoxybenzyloxycarboyl, 3,4-dimethoxybenzyloxycarbonyl, 2-nitrobenzyloxycarbonyl and 4-nitrobenzyloxycarbonyl groups);

silyl groups, for example, tri(lower alkyl)silyl groups (such as the trimethylsilyl, triethylsilyl, isopropyldimethylsilyl, t-butyldimethylsilyl, methyldiisopropylsilyl, methyl-di-t-butylsilyl and tri-isopropylsilyl groups) and silyl groups each substituted by 3 substituents selected from aryl and lower alkyl groups (such as the diphenylmethylsilyl, diphenylbutylsilyl, diphenylisopropylsilyl and phenyldiisopropylsilyl groups);

aralkyl groups, for example, lower alkyl groups each substituted by from 1 to 3 aryl groups (such as the benzyl, phenethyl, 3-phenylpropyl, α-naphthylmethyl, β-naphthylmethyl, diphenylmethyl, triphenylmethyl, α-naphthyldiphenylmethyl and 9-anthrylmethyl groups), and lower alkyl groups each substituted by from 1 to 3 aryl groups having a lower-alkyl-, lower-alkoxy-, nitro-, halogen- or cyano-substituted aryl ring (such as the 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, 4-cyanobenzyl, 4-cyanobenzyldiphenylmethyl, bis(2-nitrophenyl)methyl, and piperonyl groups); and substituted methylene groups forming a Schiff base [such as N,N-dimethylaminomethylene, benzylidene, 4-methoxybenzylidene, 4-nitrobenzylidene, salicylidene, 5-chlorosalicylidene, diphenylmethylene and (5-chloro-2-hydroxyphenyl)phenylmethylene];

of which the lower aliphatic acyl groups, $C_{7-11}$ aromatic acyl groups and alkoxycarbonyl groups are preferred, the lower alkoxycarbonyl groups and the lower alkoxycarbonyl groups are more preferred and the acetyl group and the t-butoxycarbonyl group is most preferred.

There is no particular limitation on the nature of the protecting group for the hydroxy group which may be protected in the definitions of $R^{1a}$, $R^{2a}$, $R^{3a}$, $R^{4a}$, $R^{5a}$ and $R^{6a}$, and any protecting group for a hydroxy group commonly used in organic synthetic chemistry may equally be used here. The hydroxy-protecting groups defined and exemplified above in relation to esters of the compounds of the present invention may also be used in this reaction. Of these, the lower aliphatic acyl groups, $C_{7-11}$ aromatic acyl groups, lower alkoxycarbonyl groups and (lower alkoxy)methyl groups are preferred, the $C_{7-11}$ aromatic acyl groups and (lower alkoxy)methyl groups are more preferred and the benzoyl and methoxymethyl groups are most preferred.

There is no particular limitation on the nature of the protecting group for the carboxy group which may be protected in the definition of $R^{1a}$, and any carboxy-protecting group commonly used in the field of organic synthetic chemistry may equally be used here. The carboxy-protecting groups defined and exemplified above in relation to esters of the compounds of the present invention may also be used in this reaction. Of these, the lower alkyl and benzyl groups are preferred.

In step A1, the compound of formula (I) is prepared by reacting a compound of formula (II) with a compound of formula (III) in an inert solvent and then optionally removing the protecting group from any protected amino, hydroxy and/or carboxy group in $R^{1a}$, $R^{2a}$, $R^{3a}$, $R^{4a}$, $R^{5a}$ and $R^{6a}$.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene; halogenated hydrocarbons, such as chloroform, dichloromethane, 1,2-dichloroethane and carbon tetrachloride; esters, such as methyl acetate, ethyl acetate, propyl acetate, butyl acetate and diethyl carbonate; ethers, such as diethyl ether, diisopropyl ether, tetrahydrofuran, dioxane, dimethoxyethane, and diethylene glycol dimethyl ether; alcohols, such as methanol, ethanol, propanol, isopropanol, butanol, isobutanol, t-butanol, isoamyl alcohol, diethylene glycol, glycerin, octanol, cyclohexanol and methyl cellosolve; nitriles, such as acetonitrile and isobutyronitrile; amides, such as formamide, dimethylformamide, dimethylacetamide and hexamethylphosphoryl triamide; and water; and mixtures of any two or more of these solvents. Preferred are the alcohols (methanol is most preferred).

The reaction can take place over a wide range of temperatures, and the precise reaction temperature is not critical to the invention. The preferred reaction temperature will depend upon such factors as the nature of the solvent, and the catalyst, solvent, starting material or reagent used. However, in general, we find it convenient to carry out the reaction at a temperature of from −20° C. to 150° C. more preferably from 0 to 50° C. The time required for the reaction may also vary widely, depending on many factors, notably the reaction temperature and the nature of the catalyst, reagents and solvent employed. However, provided that the reaction is effected under the preferred conditions outlined above, a period of from 5 minutes to 24 hours, more preferably from 15 minutes to 12 hours, will usually suffice.

If desired, the compound of formula (I) wherein $R^6$ represents a lower alkoxy group may be reacted with ammo-nia or a compound of formula HR' (wherein R' represents an amine residue) in an inert solvent (preferably an alcohol or an ether) at a temperature from −20 to 150° C. (preferably from 0 to 50° C.) for a period of from 5 minutes to 24 hours (preferably from 15 minutes to 12 hours), to give a corresponding compound in which $R^6$ represents an amine residue.

If desired, the compound of formula (I) wherein $R^6$ represents a lower alkoxy group may be reacted with a compound of formula (IV):

$$H_2N\text{---}R"\qquad\qquad\qquad\qquad\qquad\qquad(IV)$$

wherein R" represents a lower sulfoalkyl group or a lower carboxyalkyl group in an inert solvent (preferably an alcohol or a mixture of an alcohol and water) in the presence of a base (preferably an organic amine) at a temperature of from −20 to 150° C. (preferably from 0 to 50° C.) for a period of from 5 minutes to 24 hours (preferably from 15 minutes to 12 hours), to obtain a compound in which $R^6$ represents an amino group substituted by a lower sulfoalkyl group or lower carboxyalkyl group.

If desired, the compound of formula (I) wherein $R^6$ represents a lower alkoxy group may be reacted with an acid in an inert solvent (preferably an alcohol or a halogenated hydrocarbon) at a temperature of from −20 to 150° C. (preferably from 0 to 50° C.) for a period of from 5 minutes to 24 hours (preferably from 15 minutes to 12 hours), to give the corresponding compound in which $R^6$ represents a hydroxy group.

The method employed to remove the protecting group from the amino, hydroxy or carboxy group will vary, depending on the nature of the protecting group, as is well known in the art. However, all of the protecting groups referred to herein may be removed by techniques well known in the field of organic synthetic chemistry, for example, as described by T. W. Green, "Protective Groups in Organic Synthesis", John Wiley & Sons: or J. F. W. McOmis, "Protective Groups in Organic Chemistry", Plenum Press, the disclosures of which are incorporated herein by reference.

When the protecting group for the amino group is a silyl group, it can usually be removed by treatment with a fluorine-anion-forming compound such as tetrabutyl ammonium fluoride, hydrofluoric acid, hydrofluoric acid-pyridine or potassium fluoride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, diusopropyl ether, tetrahydrofuran, dioxane, dimethoxyethane and diethylene glycol dimethyl ether.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0 to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 18 hours, will usually suffice.

When the protecting group for an amino group is an aliphatic acyl, aromatic acyl, alkoxycarbonyl or Schiff-baseforming substituted methylene group, it can be removed by treatment with an acid or base in the presence of an aqueous solvent.

There is no particular limitation on the nature of the acid to be used for this reaction, and any acid commonly employed in reactions of this type may equally be employed here. Examples of suitable acids include: inorganic acids, such as hydrobromic acid, hydrochloric acid, sulfuric acid, perchloric acid, phosphoric acid and nitric acid, of which hydrochloric acid is preferred.

There is no particular limitation on the nature of the base to be used for this reaction, and any base commonly employed in reactions of this type may equally be employed here, provided that it does not adversely affect another part of the molecule. Preferred examples include: alkali metal carbonates, such as lithium carbonate, sodium carbonate and potassium carbonate; alkali metal hydroxides, such as lithium hydroxide, sodium hydroxide and potassium hydroxide; metal alkoxides, such as lithium methoxide, sodium methoxide, sodium ethoxide and potassium-t-butoxidel; and ammonias, such as aqueous ammonia and concentrated ammonia-methanol.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent, and any such solvent commonly used in hydrolysis reactions may equally be employed here. Examples of suitable solvents include: alcohols, such as methanol, ethanol, propanol, isopropanol, butanol, isobutanol, t-butanol, isoamyl alcohol, diethylene glycol, glycerin, octanol, cyclohexanol and methyl cellosolve; ethers, such as diethyl ether, diusopropyl ether, tetrahydrofuran, dioxane, dimethoxyethane and diethylene glycol dimethyl ether; and water; and mixtures of any two or more of these solvents. Preferred are the ethers, dioxane being most preferred.

The reaction can take place over a wide range of temperatures, and the precise reaction temperature is not critical to the invention. The preferred reaction temperature will depend upon such factors as the nature of the solvent, and the starting material or reagent used. However, in general, in order to suppress side reactions, we find it convenient to carry out the reaction at a temperature of from 0 to 150° C. The time required for the reaction may also vary widely, depending on many factors, notably the reaction temperature and the nature of the reagents and solvent employed. However, provided that the reaction is effected under the preferred conditions outlined above, a period of from 1 to 10 hours, will usually suffice.

When an aralkyl or aralkyloxycarbonyl group is the protecting group for the amino group, it is usually preferably removed by bringing it into contact with a reducing agent in an inert solvent (preferably by catalytic reduction at standard temperature in the presence of a catalyst) or by using an oxidizing agent.

The reaction is normally and preferably effected in the presence of a solvent. There is no particular restriction on the nature of the solvent to be employed for the catalytic removal, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as toluene, benzene and xylene; esters, such as methyl acetate, ethyl acetate, propyl acetate, butyl acetate and diethyl carbonate; ethers, such as diethyl ether, dilsopropyl ether, tetrahydrofuran, dioxane, dimethoxyethane and diethylene glycol dimethyl ether; alcohols, such as methanol, ethanol, propanol, isopropanol, butanol, isobutanol, t-butanol, isoamyl alcohol, diethylene glycol, glycerin, octanol, cyclohexanol and methyl cellosolve; organic acids, such as acetic acid; and water; and mixtures of the above-described solvent with water. Preferred are the alcohols, ethers, organic acids and water, the alcohols and organic acids being most preferred.

There is no particular limitation on the nature of the catalyst to be used for the removal by catalytic reduction, and any such catalyst commonly used in reactions of this type may equally be employed here. Preferred examples include palladium on carbon, Raney-nickel, platinum oxide, platinum black, rhodium-aluminum oxide, triphenylphosphine-rhodium chloride and palladium-barium sulfate.

Although there is no particular limitation on the pressure, the reaction is usually carried out at from 1 to 10 atmospheric pressure.

The reaction can take place over a wide range of temperatures, and the precise reaction temperature is not critical to the invention. The preferred reaction temperature will depend upon such factors as the nature of the solvent, and the starting material, catalyst or reagent used. However, in general, we find it convenient to carry out the reaction at a temperature of from 0 to 100° C. The time required for the reaction may also vary widely, depending on many factors, notably the reaction temperature and the nature of the reagents and solvent employed. However, provided that the reaction is effected under the preferred conditions outlined above, a period of from 5 minutes to 24 hours, will usually suffice.

The oxidative removal reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water-containing organic solvents.

Examples of such organic solvents include: halogenated hydrocarbons, such as chloroform, dichloromethane, 1,2-dichloroethane and carbon tetrachloride; nitriles, such as acetonitrile; ethers, such as diethyl ether, diisopropyl ether, tetrahydrofuran, dioxane, dimethoxyethane and diethylene glycol dimethyl ether; ketones, such as acetone; amides, such as formamide, dimethylformamide, dimethylacetamide and hexamethylphosphoryl triamide; sulfoxides, such as dimethyl sulfoxide; and sulfolane. Preferred are the halogenated hydrocarbons, ethers and sulfoxides, the halogenated hydrocarbons and sulfoxides being most preferred.

There is likewise no particular limitation on the nature of the oxidizing agent to be employed in this reaction, and any oxidizing agent commonly used in oxidative removal reactions may equally be employed here. Preferred examples include potassium persulfate, sodium persulfate, ammonium cerium nitrate (CAN), and 2,3-dichloro-5,6-dicyano-p-benzoquinone (DDQ).

The reaction can take place over a wide range of temperatures, and the precise reaction temperature is not critical to the invention. The preferred reaction temperature will depend upon such factors as the nature of the solvent, and the starting material, catalyst or reagent used. However, in general, we find it convenient to carry out the reaction at a temperature of from 0 to 150° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, will usually suffice.

When the amino group is protected with an aralkyl group, it can be removed using an acid.

There is no particular limitation on the nature of the acid to be used for this reaction, and any acid commonly used in reactions of this type may equally be employed here. Examples include:

Brønsted acids, for example: inorganic acids, such as hydrochloric acid, hydrobromic acid, sulfuric acid, perchloric acid and phosphoric acid; and organic acids, such as acetic acid, formic acid, oxalic acid, methanesulfonic acid, p-toluenesulfonic acid, camphorsulfonic acid, trifluoroacetic acid and trifluoromethanesulfonic acid;

Lewis acids, such as zinc chloride, tin tetrachloride, boron trichloride, boron trifluoride and boron tribromide; and acid ion exchange resins, of which the inorganic or organic acids are preferred, hydrochloric acid, acetic acid or trifluoroacetic acid being most preferred.

The first stage of this reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene, halogenated hydrocarbons, such as chloroform, dichloromethane, 1,2-dichloroethane and carbon tetrachloride; esters, such as methyl acetate, ethyl acetate, propyl acetate, butyl acetate and diethyl carbonate; ethers, such as diethyl ether, diusopropyl ether, tetrahydrofuran, dioxane, dimethoxyethane and diethylene glycol dimethyl ether; alcohols, such as methanol, ethanol, propanol, isopropanol, butanol, isobutanol, t-butanol, isoamyl alcohol, diethylene glycol, glycerin, octanol, cyclohexanol and methyl cellosolve; amides, such as formamide, dimethylformamide, dimethylacetamide and hexamethylphosphoryl triamide; and water; and mixtures of any two or more of these solvents. Preferred are the ethers, alcohols and water, dioxane, tetrahydrofuran, ethanol and water being most preferred.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. to the boiling point of the reaction medium, preferably from 0 to 100° C. The time required for the reaction may also vary widely, depending on many factors, notably the reaction temperature and the nature of the reagents and solvent employed. However, provided that the reaction is effected under the preferred conditions outlined above, a period of from 15 minutes to 48 hours more preferably from 30 minutes to 20 hours, will usually suffice.

When the amino group is protected with an alkenyloxycarbonyl group, the protecting group may be removed by treatment with a base under similar conditions to those employed when the amino group is protected with the above-described aliphatic acyl group, aromatic acyl group, alkoxycarbonyl group or a Schiff-base forming substituted methylene group.

The aryloxycarbonyl group can be removed easily and with fewer side reactions by using palladium and triphenylphosphine or nickel tetracarbonyl.

When the hydroxy group is protected with a silyl group, the silyl group can usually be removed by treating the protected compound with a fluorine-anion-forming compound, such as tetrabutyl ammonium fluoride, hydrofluoric acid, hydrofluoric acid-pyridine or potassium fluoride; or by treating it with an inorganic acid, such as hydrochloric acid, hydrobromic acid, sulfuric acid, perchloric acid or phosphoric acid, or an organic acid, such as acetic acid, formic acid, oxalic acid, methanesulfonic acid, p-toluenesulfonic acid, camphor sulfonic acid, trifluoroacetic acid or trifluoromethanesulfonic acid.

Reaction using a fluorine anion may be accelerated by the addition of an organic acid such as formic acid, acetic acid or propionic acid.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: include ethers, such as diethyl ether, diisopropyl ether, tetrahydrofuran, dioxane, dimethoxyethane and diethylene glycol dimethyl ether; nitriles, such as acetonitrile and isobutyronitrile; organic acids, such as acetic acid; water; and mixtures of any two or more of these solvents.

The reaction can take place over a wide range of temperatures, and the precise reaction temperature is not critical to the invention. The preferred reaction temperature will depend upon such factors as the nature of the solvent, and the starting material, catalyst or reagent used. However, in general, we find it convenient to carry out the reaction at a temperature of from 0 to 100° C., more preferably from 10 to 50° C. The time required for the reaction may also vary widely, depending on many factors, notably the reaction temperature and the nature of the reagents and solvent employed. However, provided that the reaction is effected under the preferred conditions outlined above, a period of from 1 hour to 24 hours, will usually suffice.

When the hydroxy group is protected with an aralkyl or aralkyloxycarbonyl group, the protecting group can usually preferably be removed by bringing it into contact with a reducing agent in an inert solvent (preferably by catalytic reduction at standard temperature in the presence of a catalyst) or by oxidation with an oxidizing agent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as toluene, benzene and xylene; esters, such as ethyl acetate and propyl acetate; ethers, such as diethyl ether, diusopropyl ether, tetrahydrofuran, dioxane, dimethoxyethane and diethylene glycol dimethyl ether; alcohols, such as methanol, ethanol, propanol, isopropanol, butanol, isobutanol, t-butanol, isoamyl alcohol, diethylene glycol, glycerin, octanol, cyclohexanol and methyl cellosolve; amides, such as formamide, dimethylformamide, dimethylacetamide, N-methyl-2-pyrrolidone and hexamethylphosphoryl triamide; organic acids, such as formic acid and acetic acid; and water; and mixtures of any two or more of these solvents. Preferred are the alcohols, methanol being most preferred.

There is no particular limitation imposed on the nature of the catalyst to be used for the removal by catalytic reduction, and any catalyst commonly used in reactions of this type may equally be employed here. Examples of suitable catalysts include palladium on carbon, palladium-black, Raney-nickel, platinum oxide, platinum black, rhodium-aluminum oxide, triphenylphosphine-rhodium chloride and palladium-barium sulfate, of which the palladium on carbon is preferred.

Although there is no particular limitation imposed on the pressure, the reaction is usually carried out at from 1 to 10 times atmospheric pressure.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0 to 100° C., more preferably from 20 to 70° C. The time required for the reaction may also vary widely, depending on many factors, notably the reaction temperature and the nature of the reagents and solvent employed. However, provided that the reaction is effected under the preferred conditions outlined above, a period of from 5 minutes to 28 hours, more preferably from 1 to 24 hours, will usually suffice.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water-containing organic solvents.

Preferred examples of such organic solvents include: ketones, such as acetone, halogenated hydrocarbons, such as methylene chloride, chloroform and carbon tetrachloride; nitriles, such as acetonitrile; ethers, such as diethyl ether, tetrahydrofuran and dioxane; amides, such as dimethyl formamide, dimethyl acetamide and hexamethylphosphoryl triamide; and sulfoxides, such as dimethyl sulfoxide.

There is no particular limitation on the nature of the oxidizing agent to be used for the above-described reaction, and any oxidizing agent commonly used in reactions of this type may equally be employed here. Preferred examples include potassium persulfate, sodium persulfate, ammonium cerium nitrate (CAN) and 2,3-dichloro-5,6-dicyano-p-benzoquinone (DDQ).

The reaction can take place over a wide range of temperatures, and the precise reaction temperature is not critical to the invention. The preferred reaction temperature will depend upon such factors as the nature of the solvent, and the starting material, catalyst or reagent used. However, in general, we find it convenient to carry out the reaction at a temperature of from 0 to 150° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, will usually suffice.

Deprotection can also be carried out by reaction with an alkali metal, such as metal lithium or metal sodium at a relatively low temperature, for example from −78 to 0° C. in aqueous ammonia or in an alcohol, such as methanol, ethanol, propanol, isopropanol, butanol, isobutanol, t-butanol, isoamyl alcohol, diethylene glycol, glycerin, octanol, cyclohexanol or methyl cellosolve.

The protecting group can also be removed using aluminum chloride-sodium iodide or an alkyl silyl halide, such as trimethylsilyl iodide, in a solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, such as methylene chloride, chloroform or carbon tetrachloride; nitriles, such as acetonitrile; and mixtures of any two or more of these solvents.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0 to 50° C. The time required for the reaction may also vary widely, depending on many factors, notably the reaction temperature and the nature of the reagents and solvent employed. However, provided that the reaction is effected under the preferred conditions outlined above, a period of from 5 minutes to 72 hours, will usually suffice.

When the reaction substrate contains a sulfur atom, aluminum chloride-sodium iodide is preferably employed.

When the hydroxy group is protected with an aliphatic acyl, aromatic acyl or alkoxycarbonyl group. the protecting group can be removed by treatment with a base in a solvent.

There is no particular limitation is imposed on the nature of the base to be used in this reaction, and any base commonly used in reactions of this type may equally be employed here. Preferred examples include: alkali metal carbonates, such as lithium carbonate, sodium carbonate and potassium carbonate; alkali metal hydrogencarbonates, such as lithium hydrogencarbonate, sodium hydrogencarbonate or potassium hydrogencarbonate; alkali metal hydroxides, such as lithium hydroxide, sodium hydroxide and potassium hydroxide; metal alkoxides, such as lithium methoxide, sodium methoxide, sodium ethoxide and potassium-t-butoxide; and ammonias, such as aqueous ammonia and concentrated ammonia-methanol, of which the alkali metal hydroxides, metal alkoxides and ammonias are preferred, the alkali metal hydroxides and metal alkoxides being most preferred.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent, and any solvent commonly used in hydrolysis reactions may equally be employed here. Examples of suitable solvents include: ethers, such as diethyl ether, diusopropyl ether, tetrahydrofuran, dioxane, dimethoxyethane and diethylene glycol dimethyl ether; alcohols, such as methanol, ethanol, propanol, isopropanol, butanol, isobutanol, t-butanol, isoamyl alcohol, diethylene glycol, glycerin, octanol, cyclohexanol and methyl cellosolve; and water; and mixtures of any two or more of these solvents.

The reaction can take place over a wide range of temperatures, and the precise reaction temperature is not critical to the invention. The preferred reaction temperature will depend upon such factors as the nature of the solvent, and the starting material or reagent used. However, in general, in order to suppress side reactions, we find it convenient to carry out the reaction at a temperature of from −20 to 150° C. The time required for the reaction may also vary widely, depending on many factors, notably the reaction temperature and the nature of the reagents and solvent employed. However, provided that the reaction is effected under the preferred conditions outlined above, a period of from for 1 hour to 10 hours, will usually suffice.

When the hydroxy group is protected with an alkoxymethyl, tetrahydropyranyl, tetrahydrothiopyranyl, tetrahydrofuranyl, tetrahydrothiofuranyl or substituted ethyl group, deprotection is usually carried out by treatment with an acid in a solvent.

There is no particular limitation on the nature of the acid used in this reaction, and any acid commonly used in reactions of this type may equally be used here. Normally, a Brønsted acid or Lewis acid is used. Preferred examples include Bronsted acids, for example, hydrogen chloride, inorganic acids, such as hydrochloric acid, sulfuric acid and nitric acid, and organic acids, such as acetic acid, trifluoroacetic acid, methanesulfonic acid and p-toluenesulfonic acid; and Lewis acids, such as boron trifluoride. A strong acid ion exchange resin such as Dowex 50W can also be used.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene, halogenated hydrocarbons, such as methylene chloride, chloroform, carbon tetrachloride, dichloroethane, chlorobenzene and dichlorobenzene; esters, such as methyl formate, ethyl acetate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; alcohols, such as methanol, ethanol, propanol, isopropanol, butanol, isobutanol, t-butanol, isoamyl alcohol, diethylene glycol, glycerin, octanol, cyclohexanol and methyl cellosolve; ketones, such as acetone, methyl ethyl ketone, methyl isobutyl ketone, isophorone and cyclohexanone; and water; and mixtures of any two or more of these solvents. Preferred are the ethers, of which tetrahydrofuran is most preferred, or the alcohols, of which methanol is most preferred.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −10 to 200° C., more preferably from 0 to 150° C. The time required for the reaction may also vary widely, depending on many factors, notably the reaction temperature and the nature of the reagents and solvent employed. However, provided that the reaction is effected under the preferred conditions outlined above, a period of from 5 minutes to 48 hours, more preferably from 30 minutes to 10 hours, will usually suffice.

When the hydroxy group is protected with an alkenyloxycarbonyl group, deprotection may be carried out by treatment with a base under similar conditions to those employed when the hydroxy group is protected with an aliphatic acyl, aromatic acyl or alkoxycarbonyl group.

Particularly when the protecting group is an allyloxycarbonyl group, removal can be carried out more easily with fewer side reactions by using palladium, and triphenylphosphine, or bis(methyldiphenylphosphine)(1,5-cyclooctadiene)iridium (I)hexafluorophosphate.

When the carboxy group is protected with a lower alkyl group or a lower alkyl group substituted by 1 to 3 aryl groups which may be substituted by a lower alky, lower alkoxy, nitro, halogen or cyano group, deprotection can be carried out by treatment with a base under similar conditions to those employed when the hydroxy group is protected with an aliphatic acyl, aromatic acyl or alkoxycarbonyl group.

The removal of the protecting group of the amino, hydroxy and/or carboxy groups can be carried out in any desired order.

After completion of the reaction, the resulting compound of formula (I) may be collected from the reaction mixture in conventional manner. It may be recovered, for example, by neutralizing the reaction mixture as desired, removing any insoluble matter by filtration, adding a water-immiscible organic solvent such as ethyl acetate to separate an organic layer containing the compound, washing with water or the like, drying over anhydrous magnesium sulfate, anhydrous sodium sulfate or anhydrous sodium hydrogencarbonate and then distilling off the solvent. The resulting compound thus obtained can be separated and purified in a conventional manner by using commonly employed methods for the separation and purification of an organic compound, such as recrystallization or reprecipitation, in combination, making use of chromatography and eluting with a proper eluent.

Process B

In this process, a compound of formula (Ic), that is, a compound of formula (I) wherein D represents a —CH— group and E represents an —NH— group, a compound of formula (Id), that is, a compound of formula (I) wherein D represents a —CH— group and E represents an oxygen atom or sulfur atom; a compound of formula (Ie), that is, a compound of formula (I) wherein D represents a —CH— group, E represents —NH—, and G represents a —CO— $G_a$— group (wherein, $G_a$ represents a single bond or a $C_{1-5}$ alkylene group), a compound of formula (If), that is, a compound of formula (I) wherein D represents a carbon-containing group and E represents a =N—O— group and a compound of formula (Ig), that is, a compound of formula (I) wherein D represents a —CH— group and E represents a —CO— group, may be prepared.

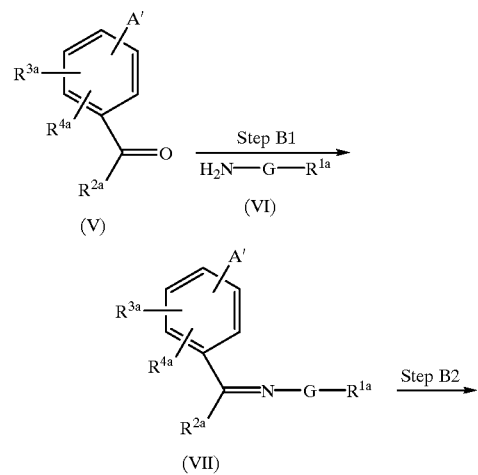

-continued
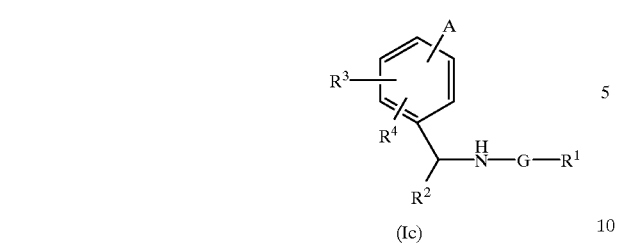
(Ic)
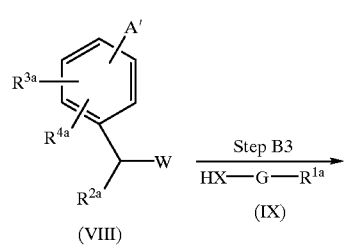
(VIII)
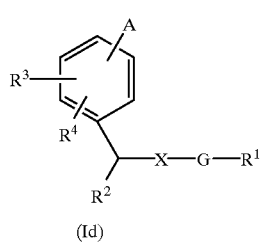
(Id)
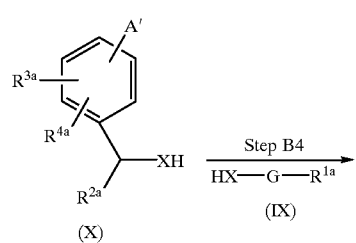
(X)
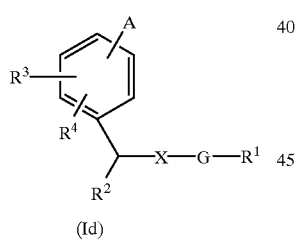
(Id)
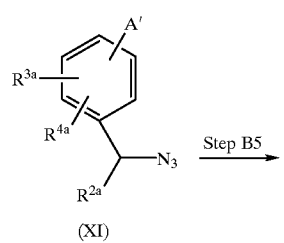
(XI)
-continued
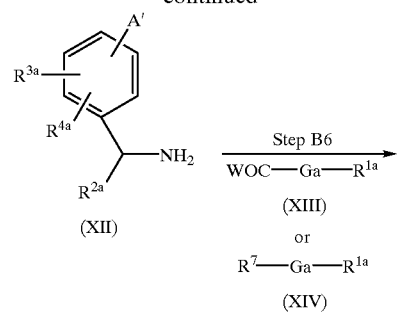
(XII)
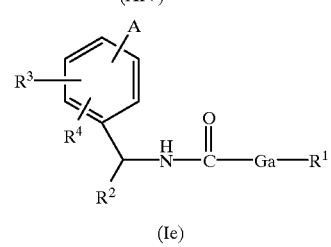
(Ie)
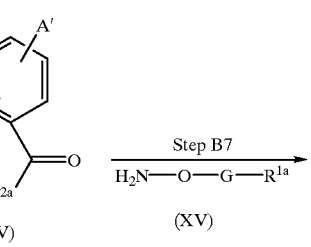
(V)
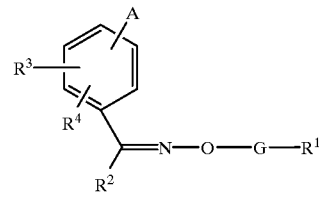
(If)
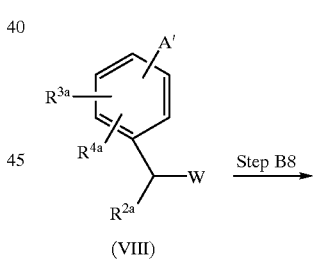
(VIII)
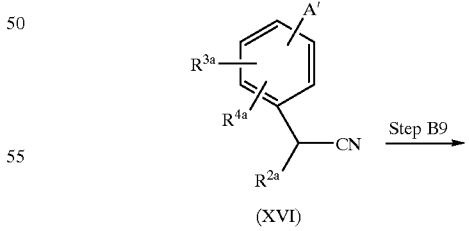
(XVI)

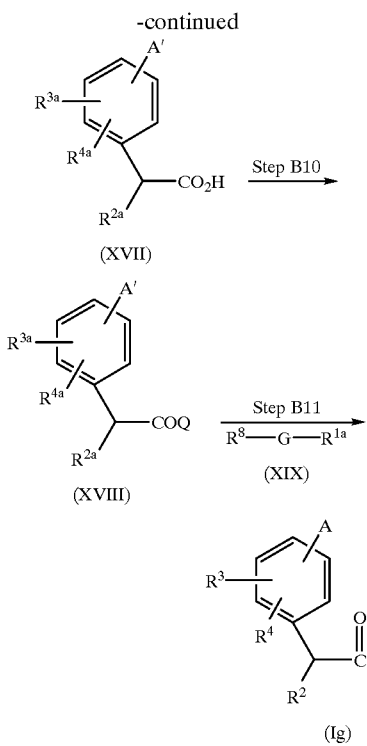

In the above formulae:

$R^1$, $R^{1a}$, $R^2$, $R^{2a}$, $R^3$, $R^{3a}$, $R^4$, $R^{4a}$, A, G, $G_a$ and Q have the same meanings as described above;

$R^7$ represents a formyl, carboxy or lower alkoxycarbonyl group;

$R^8$ represents a metal atom, such as lithium, magnesium, zinc, cadmium, tin or cerium;

A' has the same meaning as defined in A except that the amino and/or hydroxy group contained as a substituent in the definition of A may be protected;

X represents an oxygen or sulfur atom; and

W represents a halogen atom.

Step B1

In this step, a compound of formula (VII) is prepared by reacting a compound of formula (V) with a compound of formula (VI) or with an acid addition salt thereof (for example a mineral acid salt such as a hydrochloride, nitrate or sulfate) in an inert solvent. It may, for example, be carried out by condensing the compounds with heating in the presence of an organic sulfonic acid, such as p-toluenesulfonic acid, or by condensing the compounds in the presence of a Lewis acid, such as titanium tetrachloride, or of an acid ion exchange resin.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene, halogenated hydrocarbons, such as chloroform, dichloromethane, 1,2-dichloroethane and carbon tetrachloride; esters, such as methyl acetate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; alcohols, such as methanol, ethanol, propanol, isopropanol, butanol, isobutanol, t-butanol, isoamyl alcohol, diethylene glycol, glycerin, octanol, cyclohexanol and methyl cellosolve; amides, such as formamide, dimethylformamide, dimethylacetamide and hexamethylphosphoryl triamide; and water; and mixtures of any two or more of these solvents. Preferred are the hydrogenated hydrocarbons, dichloromethane being most preferred.

In the above-described reaction, when the compound (VI) is an acid addition salt, reaction can be effected by a base.

Examples of such bases include: alkali metal carbonates, such as lithium carbonate, sodium carbonate and potassium carbonate; alkali metal hydrogencarbonates, such as lithium hydrogencarbonate, sodium hydrogencarbonate and potassium hydrogencarbonate; alkali metal hydrides, such as lithium hydride, sodium hydride and potassium hydride; alkali metal hydroxides, such as lithium hydroxide, sodium hydroxide, and potassium hydroxide: metal alkoxides, such as lithium methoxide, sodium methoxide. sodium ethoxide and potassium t-butoxide; and organic amines, such as triethylamine, tributylamine, diisopropylethylamine, N-methylmorpholine, pyridine, 4-(N,N-dimethylamino) pyridine, N,N-dimethylaniline, N,N-diethylaniline, 1,5-diazabicyclo[4.3.0]nona-5-en, 1,4-diazabicyclo[2.2.2]octane (DABCO), 1,8-diazabicyclo[5.4.0]-7-undecene (DBU), of which the organic amines are preferred, triethylamine being most preferred.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene, halogenated hydrocarbons, such as chloroform, dichloromethane, 1,2-dichloroethane and carbon tetrachloride; acetic acid; esters, such as methyl acetate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; alcohols, such as methanol, ethanol, propanol, isopropanol, butanol, isobutanol, t-butanol, isoamyl alcohol, diethylene glycol, glycerin, octanol, cyclohexanol and methyl cellosolve; amides, such as formamide, dimethylformamide, dimethylacetamide and hexamethylphosphoryl triamide; and water; and mixtures of any two or more of these solvents. Preferred are the halogenated hydrocarbons, dichloromethane being most preferred.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. to 200° C. The time required for the reaction may also vary widely, depending on many factors, notably the reaction temperature and the nature of the reagents and solvent employed. However, provided that the reaction is effected under the preferred conditions outlined above, a period of from 15 minutes to 48 hours, more preferably from 1 to 30 hours, will usually suffice. Condensation in the presence of a Lewis acid is preferably conducted at from 10° C. to 40° C., while condensation under heat in the presence of an organic sulfonic acid is effected preferably at from 50 to 150° C.

After completion of the reaction, the resulting compound (VII) of the present reaction may be collected from the reaction mixture in a known manner. More specifically, the resulting compound can be obtained by neutralizing the reaction mixture if necessary, removing any insoluble matter by filtration, adding a water-immiscible organic solvent such as ethyl acetate to separate an organic layer containing the compound, washing, with water or the like, drying over anhydrous magnesium sulfate, anhydrous sodium sulfate or anhydrous sodium hydrogencarbonate and then distilling off the solvent. If necessary, the compound thus obtained can be separated and purified in a known manner by using commonly employed methods for the separation and purification of an organic compound, such as recrystallization and reprecipitation, in combination, making use of chromatography and eluting with a proper eluent.

Step B2

In this step a compound of formula (Ic) is prepared by reducing the compound of formula (VII) in an inert solvent and optionally removing the protecting group of the amino, hydroxy and/or carboxy group in $R^{1a}$, $R^{2a}$, $R^{3a}$, $R^{4a}$ and A'.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene, halogenated hydrocarbons, such as chloroform, dichloromethane, 1,2-dichloroethane and carbon tetrachloride; acetic acid, esters, such as methyl acetate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; alcohols, such as methanol, ethanol, propanol, isopropanol, butanol, isobutanol, t-butanol, isoamyl alcohol, diethylene glycol, glycerin, octanol, cyclohexanol and methyl cellosolve; amides, such as formamide, dimethylformamide, dimethylacetamide and hexamethylphosphoryl triamide; and water; and mixtures of any two or more of these solvents. Preferred are the esters, alcohols and ethers, acetic acid, ethanol and tetrahydrofuran being most preferred.

Examples of the reducing agents which may be used in this reaction include: alkali metal borohydrides, such as sodium borohydride, lithium borohydride and sodium cyanoborohydride; aluminum hydride compounds, such as diisobutylaluminum hydride, lithium aluminum hydride and lithium triethoxyaluminum hydride; Raney nickel; and boron. Of these, the alkali metal borohydrides are preferred, sodium cyanoborohydride being most preferred.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20 to 150° C., more preferably from 10 to 80° C. The time required for the reaction may also vary widely, depending on many factors, notably the reaction temperature and the nature of the reagents and solvent employed. However, provided that the reaction is effected under the preferred conditions outlined above, a period of from 15 minutes to 24 hours, more preferably from 30 minutes to 16 hours, will usually suffice.

The optional removal of the protecting croup of the amino, hydroxy and/or carboxy group in $R^{1a}$, $R^{2a}$, $R^{3a}$, $R^{4a}$ and A' may be carried out in a similar manner to that described above for removing the protecting group of the amino, hydroxy and/or carboxy group in Step A1 of Process A.

After completion of the reaction, the resulting compound of formula (Ic) of the present reaction may be collected from the reaction mixture in a known manner. For example, it may be recovered by neutralizing the reaction mixture as desired, removing any insoluble matter by filtration, adding a water-immiscible organic solvent such as ethyl acetate to separate an organic layer containing the compound, washing with water or the like, drying over anhydrous magnesium sulfate, anhydrous sodium sulfate or anhydrous sodium hydrogencarbonate and distilling off the solvent. If necessary, the compound thus obtained can be separated and purified in a known manner by using commonly employed methods for the separation and purification of an organic compound, such as recrystallization and reprecipitation, in combination, making use of chromatography and eluting with a proper eluent.

Step B3

In this step a compound of formula (Id) is prepared by reacting a compound of formula (VIII) with a base in the presence or absence (preferably in the presence) of an inert solvent, reacting the reaction mixture with a compound of formula (IX) and then optionally removing the protecting group from the amino, hydroxy and/or carboxy group in $R^{1a}$, $R^{2a}$, $R^{3a}$, $R^{4a}$ and A'.

Examples of the base which may be used in this reaction include those employed in Step B1 of Process B, of which the alkali metal hydrides are preferred, sodium hydride being most preferred.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene; ethers, such as diethyl ether, diisopropyl ether, tetrahydrofuran, dioxane, dimethoxyethane and diethylene glycol dimethyl ether; amides, such as dimethylformamide, dimethylacetamide and hexamethylphosphoryl triamide; and mixtures of any two or more of these solvents. Preferred are the amides, dimethylformamide being most preferred.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction with the compound of formula (VIII) at a temperature of from −50 to 200° C. more preferably from 0 to 120° C. The time required for the reaction may also vary widely, depending on many factors, notably the reaction temperature and the nature of the reagents and solvent employed. However, provided that the reaction with the compound of formula (VIII) is effected under the preferred conditions outlined above, a period of from 15 minutes to 24 hours more preferably from 1 hour to 10 hours, will usually suffice.

The temperature upon the subsequent reaction with the compound (IX) usually ranges from −20 to 200° C. more preferably from 0 to 150° C. The time for the subsequent reaction with the compound (IX) usually ranges from 15 minutes to 48 hours, more preferably from 30 minutes to 24 hours.

The optional removal of the protecting group from the amino, hydroxy and/or carboxy group in $R^{1a}$, $R^{2a}$, $R^{3a}$, $R^{4a}$ and A' may be carried out in a similar manner to that employed for the above-described removal of the amino, hydroxy and/or carboxy group in Step A1 of Process A.

After completion of the reaction, the resulting compound of formula (Id) of the present reaction may be collected from the reaction mixture in a conventional manner. For example, it may be recovered by neutralizing the reaction mixture as desired, removing any insoluble matter by filtration, adding a water-immiscible organic solvent such as ethyl acetate to separate an organic layer containing the compound, washing with water or the like, drying over anhydrous magnesium sulfate, anhydrous sodium sulfate or anhydrous sodium hydrogencarbonate and distilling off the solvent. If necessary, the compound thus obtained can be separated and purified in a conventional manner by using commonly employed methods for the separation and purification of an organic compound, such as recrystallization or reprecipitation, in combination, making use of chromatography and eluting with a proper eluent.

Step B4

In this step the compound of formula (Id) is prepared by an alternative route is prepared by converting the —XH— containing group of the compound of formula (X) into an leaving group Q in the presence or absence of a Lewis acid in an inert solvent, reacting with the compound of formula (IX) and optionally removing the protecting group of the amino, hydroxy and/or carboxy group in $R^{1a}$, $R^{2a}$, $R^{3a}$, $R^{4a}$ and A'.

Examples of the reagent for forming the leaving group Q include: halogenating agents, for example, sulfonyl halides, such as methanesulfonyl chloride and p-toluenesulfonyl chloride, thionyl halides, such as thionyl chloride, thionyl bromide and thionyl iodide, sulfuryl halides, such as sulfuryl chloride, sulfuryl bromide and sulfuryl iodide, phosphorous trihalides, such as phosphorous trichloride, phosphorus tribromide and phosphorus triiodide, phosphorus pentahalides, such as phosphorus pentachloride, phosphorus pentabromide and phosphorus pentaiodide, phosphorus oxyhalides, such as phosphorus oxychloride, phosphorus oxybromide and phosphorus oxyiodide; and rhenium reagents, such as methyltrioxorhenium (VII), of which the rhenium reagents are preferred.

Examples of the Lewis acid which may be used in this reaction include: zinc halides, such as zinc iodide and zinc chloride, tin halides, such as tin tetrachloride, boron halides, such as boron trichloride, boron trifluoride and boron tribromide, of which the zinc halides (particularly, zinc iodide) are preferred.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene, halogenated hydrocarbons, such as dichloromethane, 1,2-dichloroethane and carbon tetrachloride; ethers, such as diethyl ether, diisopropyl ether, tetrahydrofuran, dioxane, dimethoxyethane and diethylene glycol dimethyl ether; ketones, such as acetone; amides, such as formamide, dimethylformamide, dimethylacetamide and hexamethylphosphoryl triamide; sulfoxides, such as dimethyl sulfoxide; and sulfolane. Preferred are the aromatic hydrocarbons (particularly benzene).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20 to 100° C. more preferably from 0 to 50° C. The time required for the reaction may also vary widely, depending on many factors, notably the reaction temperature and the nature of the reagents and solvent employed. However, provided that the reaction is effected under the preferred conditions outlined above, a period of from 15 minutes to 150 hours more preferably from 30 minutes to 100 hours, will usually suffice.

The optional removal of the protecting group of the amino, hydroxy and/or carboxy group in $R^{1a}$, $R^{2a}$, $R^{3a}$, $R^{4a}$ and A' may be carried out in a similar manner to the method described above for the removal of a protecting group of the amino, hydroxy and/or carboxy group in Step A1 of Process A.

After completion of the reaction, the resulting compound of formula (Id) of the present reaction may be collected from the reaction mixture in a known manner. For example, it may be recovered by neutralizing the reaction mixture as desired, removing any insoluble matter by filtration, adding a water-immiscible organic solvent such as ethyl acetate to separate an organic layer containing the compound, washing with water or the like, drying over anhydrous magnesium sulfate, anhydrous sodium sulfate or anhydrous sodium hydrogencarbonate and distilling off the solvent. If necessary, the compound thus obtained can be separated and purified in a known manner by using commonly employed methods for the separation and purification of an organic compound, such as recrystallization and reprecipitation, in combination, making use of chromatography and eluting with a proper eluent.

Step B5

In this step a compound of formula (XII) is prepared by reducing a compound of formula (XI) using a reducing agent such as triphenylphosphine in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include inert solvents similar to those employed in Step B1 of Process B. Of these, the mixtures of water and an ether are preferred, a mixture of tetrahydrofuran and water being most preferred.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 20 to 150° C., more preferably from 50 to 100° C. The time required for the reaction may also vary widely, depending on many factors, notably the reaction temperature and the nature of the reagents and solvent employed. However, provided that the reaction is effected under the preferred conditions outlined above, a period of from 15 minutes to 24 hours, more preferably from 1 hour to 12 hours, will usually suffice.

After completion of the reaction, the resulting compound of formula (XII) of the present reaction may be collected from the reaction mixture in a known manner. For example, it may be recovered by neutralizing the reaction mixture as desired, removing any insoluble matter by filtration, adding a water-immiscible organic solvent such as ethyl acetate to separate an organic layer containing the compound, washing with water or the like, drying over anhydrous magnesium sulfate, anhydrous sodium sulfate or anhydrous sodium hydrogencarbonate and distilling off the solvent. If necessary, the compound thus obtained can be separated and purified in a known manner by using commonly employed methods for the separation and purification of an organic compound, such as recrystallization and reprecipitation, in combination, making use of chromatography and eluting with a proper eluent.

Step B6

In this step a compound of formula (Ie) is prepared by reacting the compound of formula (XII) or acid addition salt thereof with a compound of formula (XIII) in an inert solvent in the presence or absence (preferably in the presence) of a base and optionally removing the protecting group of the amino, hydroxy and/or carboxy group in $R^{1a}$, $R^{2a}$, $R^{3a}$, $R^{4a}$ and A'.

The reaction with the compound of formula (XIII) is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene, halogenated hydrocarbons, such as chloroform, dichloromethane, 1,2-dichloroethane and carbon tetrachloride; esters, such as methyl acetate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; alcohols, such as methanol, ethanol, propanol, isopropanol, butanol, isobutanol, t-butanol, isoamyl alcohol, diethylene glycol, glycerin, octanol, cyclohexanol and methyl cellosolve; amides, such as formamide, dimethylformamide, dimethylacetamide and hexamethylphosphoryl triamide; nitriles, such as acetonitrile; and water; and mixtures of any two or more of these solvents. Preferred are the nitriles.

Bases similar to those employed in Step B1 of Process B can be used for this reaction, of which the organic amines are preferred, triethylamine being most preferred.

The reaction with the compound of formula (XIII) can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20 to 150° C., more preferably from 0 to 100° C. The time required for the reaction may also vary widely, depending on many factors, notably the reaction temperature and the nature of the reagents and solvent employed. However, provided that the reaction is effected under the preferred conditions outlined above, a period of from 15 minutes to 24 hours, more preferably from 30 minutes to 16 hours, will usually suffice.

The compound of formula (Ie) can be prepared by alternative reaction by reacting the compound of formula (XII) or acid addition salt thereof with a compound of formula (XIV).

When $R^7$, in the compound of formula (XIV), represents a formyl group, the compound of formula (XIV) may be reacted with the compound of formula (XII) or acid addition salt thereof in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene; ethers, such as diethyl ether, diisopropyl ether, tetrahydrofuran, dioxane, dimethoxyethane and diethylene glycol dimethyl ether; alcohols, such as methanol, ethanol, propanol, isopropanol, butanol, isobutanol, t-butanol, isoamyl alcohol, diethylene glycol, glycerin, octanol, cyclohexanol and methyl cellosolve; amides, such as formamide, dimethylformamide, dimethylacetamide and hexamethylphosphoryl triamide; acids, such as acetic acid and propionic acid; sulfoxides, such as dimethyl sulfoxide; sulfolane; and mixtures of any two or more of these solvents. Preferred are the ethers, tetrahydrofuran being most preferred.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0 to 200° C., more preferably from 10 to 120° C. The time required for the reaction may also vary widely, depending on many factors, notably the reaction temperature and the nature of the reagents and solvent employed. However, provided that the reaction is effected under the preferred conditions outlined above, a period of from 1 hour to 50 hours, more preferably from 5 hours to 24 hours, will usually suffice.

When $R^7$, in the compound of formula (XIV), represents a carboxy group, the compound of formula (IXV) or reactive derivative thereof (acid halide, active ester or anhydride of mixed acids) may be reacted with the compound of formula (XII) or acid addition salt thereof.

The acid halide method is effected by reacting the compound of formula (XIV) with a halogenating agent (for example, oxalyl chloride, thionyl chloride, thionyl bromide, oxalic chloride, oxalic dichloride, phosphorus oxychloride, phosphorus trichloride, phosphorus pentachloride) to prepare its acid halide and then reacting the acid halide with the compound of formula (XII) or acid addition salt thereof in an inert solvent in the presence or absence (preferably in the presence) of a base.

Bases similar to those employed in Step B1 of Process B can be used in this reaction, of which the organic amines are preferred, pyridine being most preferred.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene, halogenated hydrocarbons, such as chloroform, dichloromethane, 1,2-dichloroethane and carbon tetrachloride; ethers, such as diethyl ether, diisopropyl ether, tetrahydrofuran, dioxane, dimethoxyethane and diethylene glycol dimethyl ether; ketones, such as acetone; amides, such as formamide, dimethylformamide, dimethylacetamide and hexamethylphosphoryl triamide; sulfoxides, such as dimethyl sulfoxide; and sulfolane. Preferred are the halogenated hydrocarbons, ethers and amides, dichloromethane, chloroform, tetrahydrofuran and dimethylformamide being most preferred.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20 to 150° C. in each of the reaction of the halogenating agent with the compound of formula (XIV) and the reaction of the resulting acid halide with the compound of formula (XII) or acid addition salt thereof, or from −10 to 100° C. in the reaction of the halogenating agent with the compound of formula (XIV), or from −20 to 100° C. in the reaction of the resulting acid halide with the compound of formula (XII) or acid addition salt thereof. The time required for the reaction may also vary widely, depending on many factors, notably the reaction temperature and the nature of the reagents and solvent employed. However, provided that the reaction is effected under the preferred conditions outlined above, a period of from 30 minutes to 80 hours, more preferably from 1 hour to 48 hours, in each of the reaction of the halogenating agent with the compound of formula (XIV) and the reaction of the resulting acid halide with the compound of formula (XII) or acid addition salt thereof, will usually suffice.

The active ester method may be carried out by reacting the compound of formula (XIV) with an active esterifying agent in an inert solvent to prepare its active ester and then reacting it with the compound of formula (XII) or acid addition salt thereof in an inert solvent in the presence or absence (preferably in the presence) of a base.

Examples of the active esterifying agent to be used in this reaction include N-hydroxy compounds, such as N-hydroxysuccinimide, 1-hydroxybenzotriazole and N-hydroxy-5-norbornene-2,3-dicarboxyimide; disulfide compounds, such as dipyridyl disulfide; carbodiimides, such as dicyclohexylcarbodiimide; carbonyldiimidazole; and triphenylphosphine. Active esterification is preferably conducted in the presence of such a condensing agent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene; halogenated hydrocarbons, such as dichloromethane, 1,2-dichloroethane and carbon tetrachloride; ethers, such as diethyl ether, diisopropyl ether, tetrahydrofuran, dioxane, dimethoxyethane and diethylene glycol dimethyl ether; ketones, such as acetone; amides, such as formamide, dimethylformamide, dimethylacetamide and hexamethylphosphoryl triamide; sulfoxides, such as dimethyl sulfoxide; and sulfolane. Preferred are the ethers and amides, dioxane, tetrahydrofuran and dimethylformamide being most preferred.

Bases similar to those employed in the above-described acid halide method can be used, for example, in this reaction.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −70 to 150° C., more preferably from −10° C. to 100° C., in the active esterification, and from −20 to 100° C., more preferably from 0 to 50° C., in the reaction of the active ester with the compound of formula (XII) or acid addition salt thereof. The time required for the reaction may also vary widely, depending on many factors, notably the reaction temperature and the nature of the reagents and solvent employed. However, provided that the reaction is effected under the preferred conditions outlined above, a period of from 30 minutes to 80 hours, more preferably from 1 hour to 48 hours, in each of the active esterification and the reaction of the active ester with the compound of formula (XII) or acid addition salt thereof, will usually suffice.

The mixed acid anhydride method is effected by reacting the compound of formula (XIV) with a mixed-acid-anhydride forming agent in an inert solvent in the presence or absence of a base (preferably in the presence) and then reacting the resulting mixed acid anhydride with the compound of formula (XII) or acid addition salt thereof in an inert solvent.

Bases similar to those employed in the above-described acid halide method can be used in this reaction, of which the organic amines are preferred, pyridine being most preferred.

Examples of the mixed-acid-anhydride forming agent which may be used in this reaction include: lower alkyl halocarbonates, such as ethyl chlorocarbonate and isobutyl chlorocarbonate, lower alkanoyl halides, such as pivaloyl chloride, and di(lower alkyl)- or diaryl-cyanophosphates, such as diethyl cyanophosphonate and diphenyl cyanophosphonate, of which the di(lower alkyl)- or diaryl-cyanophosphates are preferred, diethyl cyanophosphonate being most preferred.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene; halogenated hydrocarbons, such as dichloromethane, 1,2-dichloroethane and carbon tetrachloride; ethers, such as diethyl ether, diisopropyl ether, tetrahydrofuran, dioxane, dimethoxyethane and diethylene glycol dimethyl ether; ketones, such as acetone; amides, such as fornamide, dimethylformamide, dimethylacetamide and hexamethylphosphoryl triamide; sulfoxides, such as dimethyl sulfoxide; and sulfolane. Preferred are the ethers and amides, tetrahydrofuran and dimethylformamide being most preferred.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −50 to 100° C., more preferably from 0 to 60° C. The time required for the reaction may also vary widely, depending on many factors, notably the reaction temperature and the nature of the reagents and solvent employed. However, provided that the reaction is effected under the preferred conditions outlined above, a period of from 30 minutes to 72 hours, more preferably from 1 hour to 24 hours, will usually suffice.

The reaction of the mixed acid anhydride with the compound of formula (XII) or acid addition salt thereof may be carried out in an inert solvent in the presence or absence (preferably in the presence) of a base. Bases and inert solvents similar to those used in this reaction for preparing a mixed acid anhydride are used in this reaction.

The reaction of the mixed acid anhydride with the compound of formula (XII) or acid addition salt thereof can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −30 to 100° C., more preferably from 0 to 80° C. The time required for the reaction may also vary widely, depending on many factors, notably the reaction temperature and the nature of the reagents and solvent employed. However, provided that the reaction is effected under the preferred conditions outlined above, a period of from 5 minutes to 24 hours, more preferably from 30 minutes to 16 hours, will usually suffice.

In the present reaction, when a di(lower alkyl) cyanophosphoric acid or diarylcyanophosphoric acid is used, the compound of formula (XII) can also be reacted directly with the compound of formula (XIV) in the presence of a base.

When $R^7$, in the compound of formula (XIV), represents a lower alkoxycarbonyl group, the compound of formula (XIV) may be reacted with the compound of formula (XII) or acid addition salt thereof in the presence or absence (preferably in the absence) of an inert solvent, in the presence or absence (preferably in the absence) of a base.

Bases similar to those employed in Step B1 of Process B can be used for the reaction of the compound of formula (XII) or acid addition salt thereof with the compound of formula (XIV), of which the organic amines are preferred, pyridine being most preferred.

The reaction of the compound of formula (XII) or acid addition salt thereof with the compound of formula (XIV) is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene; ethers, such as diethyl ether, diisopropyl ether, tetrahydrofuran, dioxane, dimethoxyethane and diethylene glycol dimethyl ether; alcohols, such as methanol, ethanol, propanol, isopropanol, butanol, isobutanol, t-butanol, isoamyl alcohol, diethylene glycol, glycerin, octanol, cyclohexanol and methyl cellosolve; amides, such as formamide, dimethylformamide, dimethylacetamide and hexamethylphosphoryl triamide; and mixtures of any two or more of these solvents. Preferred are the ethers and amides, tetrahydrofuran, dioxane and dimethylformamide being most preferred.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0 to 200° C., more preferably from 50 to 150° C. The time required for the reaction may also vary widely, depending on many factors, notably the reaction temperature and the nature of the reagents and solvent employed. However, provided that the reaction is effected under the preferred conditions outlined above, a period of from 1 hour to 50 hours more preferably from 5 hours to 24 hours, will usually suffice.

The optional removal of the protecting group of the amino, hydroxy and/or carboxy group in $R^{1a}$, $R^{2a}$, $R^{3a}$, $R^{4a}$ and A' may be carried out in a similar manner to that in Step A1 of Process A.

After completion of the reaction, the resulting compound of formula (Ie) of the present reaction may be collected from the reaction mixture by known methods, for example, by neutralizing the reaction mixture as desired, removing any insoluble matter by filtration, adding a water-immiscible organic solvent such as ethyl acetate to separate an organic layer containing the compound, washing with water or the like, drying over anhydrous magnesium sulfate, anhydrous sodium sulfate or anhydrous sodium hydrogencarbonate and distilling off the solvent. If necessary, the compound thus obtained can be separated and purified by known methods by using commonly employed methods for the separation and purification of an organic compound, such as recrystallization and reprecipitation, in combination, making use of chromatography and eluting with a proper eluent.

Step B7

In this step the compound of formula (If) is prepared by reacting the compound of formula (V) with a compound of formula (XV) or acid addition salt thereof (for example, a mineral acid salt such as hydrochloride, nitrate or sulfate) in an inert solvent and then optionally removing the protecting group of the amino, hydroxy and/or carboxy group in $R^{1a}$, $R^{2a}$, $R^{3a}$, $R^{4a}$ and A'. The reaction of the compound of formula (V) with the compound of formula (XV) is effected, for example, by condensation under heat by using, as a catalyst, an organic sulfonic acid such as p-toluenesulfonic acid or by condensation using a Lewis acid such as titanium tetrachloride. The reaction of the compound of formula (V) with the compound of formula (XV) may be carried out in a similar manner to Step B1 of Process B, while the deprotection from the protected amino, hydroxy and/or carboxy group in $R^{1a}$, $R^{2a}$, $R^{3a}$, $R^{4a}$ and A' may be carried out in a similar manner to that of Step A1 of Process A.

After completion of the reaction, the resulting compound of formula (If) of the present reaction may be collected from the reaction mixture by known methods, for example, by neutralizing the reaction mixture as desired, removing any insoluble matter by filtration, adding a water-immiscible organic solvent such as ethyl acetate to separate an organic layer containing the compound, washing with water or the like, drying over anhydrous magnesium sulfate, anhydrous sodium sulfate or anhydrous sodium hydrogencarbonate and distilling off the solvent. If necessary, the compound thus obtained can be separated and purified by known methods by using commonly employed methods for the separation and purification of an organic compound, such as recrystallization and reprecipitation, in combination, making use of chromatography and eluting with a proper eluent.

Step B8

In this step a compound of formula (XVI) is prepared by reacting the compound of formula (VIII) with an alkali metal cyanide in an inert solvent.

Examples of the alkali metal cyanide to be used for this reaction include lithium cyanide, sodium cyanide and potassium cyanide.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as heptane, ligroin and petroleum ether; aromatic hydrocarbons, such as benzene, toluene and xylene; halogenated hydrocarbons, such as dichloromethane, 1,2-dichloroethane and carbon tetrachloride; ethers, such as diethyl ether, diisopropyl ether, tetrahydrofuran, dioxane, dimethoxyethane and diethylene glycol dimethyl ether; ketones, such as acetone; amides, such as formamide, dimethylformamide, dimethylacetamide and hexamethylphosphoryl triamide; sulfoxides, such as dimethyl sulfoxide; and sulfolane, of which the ethers are preferred (with the tetrahydrofuran being particularly preferred).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0 to 200° C., more preferably from 10 to 50° C. The time required for the reaction may also vary widely, depending on many factors, notably the reaction temperature and the nature of the reagents and solvent employed. However, provided that the reaction is effected under the preferred conditions outlined above, a period of from 15 minutes to 24 hours, more preferably from 30 minutes to 16 hours, will usually suffice.).

After completion of the reaction, the resulting compound of formula (XVI) of the present reaction may be collected from the reaction mixture by known methods, for example, by neutralizing the reaction mixture as desired, removing any insoluble matter by filtration, adding a water-immiscible organic solvent such as ethyl acetate to separate an organic layer containing the compound, washing with water or the like, drying over anhydrous magnesium sulfate, anhydrous sodium sulfate or anhydrous sodium hydrogencarbonate and distilling off the solvent. If necessary, the compound thus obtained can be separated and purified by known methods by using commonly employed methods for the separation and purification of an organic compound, such as recrystallization and reprecipitation, in combination, making use of chromatography and eluting with a proper eluent.

Step B9

In this step a compound of formula (XVII) is prepared by hydrolyzing the compound of formula (XVI) with an acid or alkali in an inert solvent.

Hydrolysis with an acid may be carried out by treatment with a aqueous mineral acid solution such as hydrochloric acid, aqueous sulfuric acid solution or aqueous nitric acid solution for 1 hour to 10 hours (preferably for from 3 hours to 7 hours) at room temperature to 100° C. (preferably from 50 to 100° C.).

Hydrolysis with an alkali may be carried out by treatment with from 1 to 10 equivalents (preferably from 1 to 5 equivalents) of an alkali metal hydroxide such as lithium hydroxide, sodium hydroxide or potassium hydroxide or an alkaline earth metal hydroxide such as calcium hydroxide or barium hydroxide in an inert solvent (preferably water, an alcohol such as methanol or ethanol, an ether such as tetrahydrofuran or dioxane or a mixture thereof) at a temperature of from 0 to 120° C. (preferably at from 20 to 100° C.) for a period of from 30 minutes to 48 hours (preferably for from 1 hour to 24 hours).

After completion of the reaction, the resulting compound of formula (XVII) of the present reaction may be collected from the reaction mixture by known methods, for example, by neutralizing the reaction mixture as desired, removing any insoluble matter by filtration, adding a water-immiscible organic solvent such as ethyl acetate to separate an organic layer containing the compound, washing with water or the like, drying over anhydrous magnesium sulfate, anhydrous sodium sulfate or anhydrous sodium hydrogencarbonate and distilling off the solvent. If necessary, the compound thus obtained can be separated and purified by known methods by using commonly employed methods for the separation and purification of an organic compound, such as recrystallization and reprecipitation, in combination, making use of chromatography and eluting with a proper eluent.

Step B10

In this step a compound of formula (XVIII) is prepared by converting the carboxy group of the compound of formula (XVII) into a group of formula —COQ in an inert solvent. This step may be conducted in a similar manner to that employed for the above-described conversion of the —XH— containing group of the compound of formula (X) into an leaving group Q in Step B4 of Process B.

Step B11

In this step a compound of formula (Ig) is prepared by reacting the compound of formula (XVIII) with a compound of formula (XIX) in an inert solvent in the presence or absence of a palladium catalyst and then optionally removing the protecting group of the amino, hydroxy and/or carboxy group in $R^{1a}$, $R^{2a}$, $R^{3a}$, $R^{4a}$, A'.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as heptane, ligroin and petroleum ether; aromatic hydrocarbons, such as benzene, toluene and xylene; halogenated hydrocarbons, such as dichloromethane, 1,2-dichloroethane and carbon tetrachloride; ethers, such as diethyl ether, diisopropyl ether. tetrahydrofuran, dioxane, dimethoxyethane and diethylene glycol dimethyl ether; ketones, such as acetone; amides, such as formamide, dimethylformamide, dimethylacetamide and hexamethylphosphoryl triamide; sulfoxides, such as dimethyl sulfoxide; and sulfolane, of which the ethers (particularly tetrahydrofuran) are preferred.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −80 to 50° C., more preferably from −50 to 0° C. The time required for the reaction may also vary widely, depending on many factors, notably the reaction temperature and the nature of the reagents and solvent employed. However, provided that the reaction is effected under the preferred conditions outlined above, a period of from 15 minutes to 24 hours, more preferably from 30 minutes to 12 hours, will usually suffice.

After completion of the reaction, the resulting compound of formula (Ig) of the present reaction may be collected from the reaction mixture by known methods, for example, by neutralizing the reaction mixture as desired, removing any insoluble matter by filtration, adding a water-immiscible organic solvent such as ethyl acetate to separate an organic layer containing the compound, washing with water or the like, drying over anhydrous magnesium sulfate, anhydrous sodium sulfate or anhydrous sodium hydrogencarbonate and distilling off the solvent. If necessary, the compound thus obtained can be separated and purified by known methods by using commonly employed methods for the separation and purification of an organic compound, such as recrystallization and reprecipitation, in combination, making use of chromatography and eluting with a proper eluent.

Process C

This is a process for preparing a compound of formula (Ih), that is, a compound of formula (I) wherein D represents a nitrogen atom, E represents an —NH— group and G represents a —CO—$G_a$— group, a compound of formula (Ii), that is, a compound of formula (I) wherein D represents a nitrogen atom, and E represents an oxygen or sulfur atom, a compound of formula (Ij), that is, a compound of formula (I) wherein D represents a nitrogen atom and E represents an —NH— group, a compound of formula (Ija), that is, a compound of formula (I) wherein D represents a nitrogen atom, E represents an —NH— group and G represents a $C_{1-6}$ alkylene group, and a compound of formula (Ik), that is, a compound of formula (I) wherein D represents a nitrogen atom, and E represents a —CO— group.

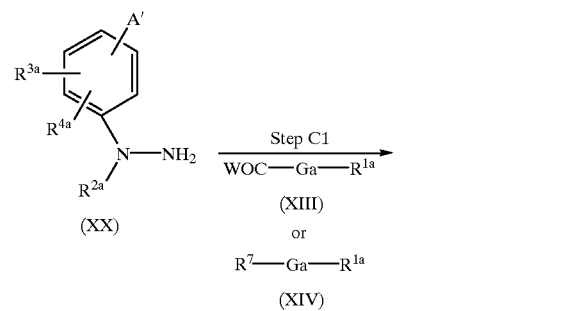

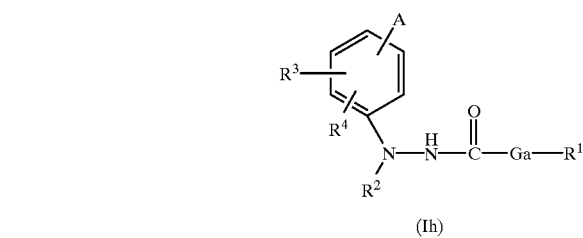

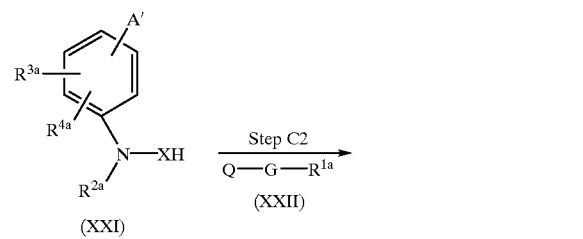

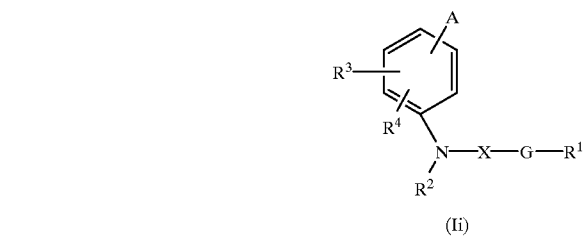

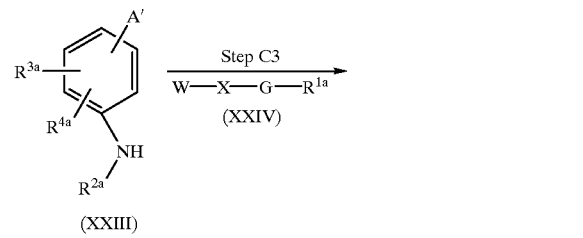

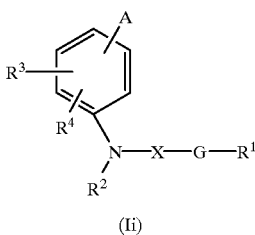

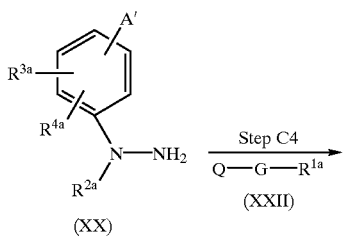

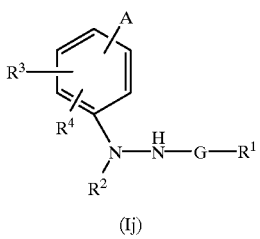

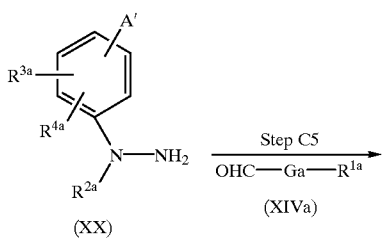

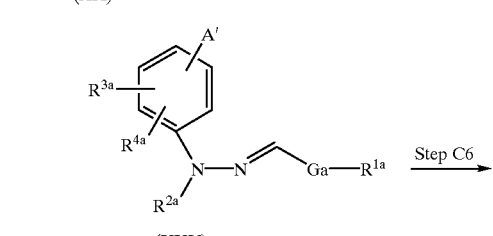

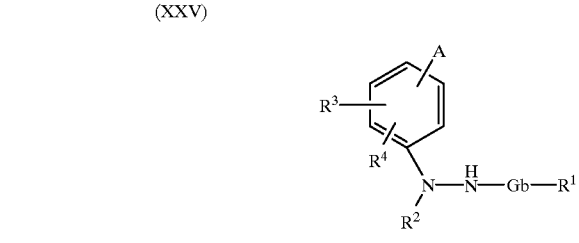

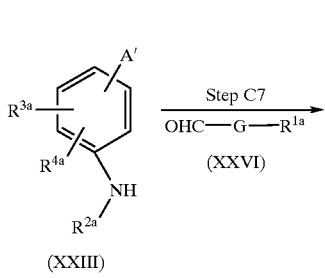

-continued

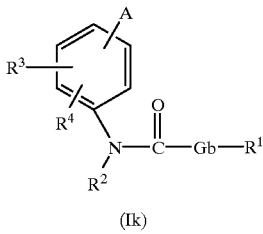

(Ik)

In the above reaction scheme:

$R^1, R^{1a}, R^2, R^{2a}, R^3, R^{3a}, R^4, R^{4a}, R^7, A, A', G, G_a, Q, X$ and W have the same meanings as described above; and $G_b$ represents a $C_{1-6}$ alkylene group.

Step C1

In this step the compound of formula (Ih) is prepared by reacting the compound of formula (XX) or acid addition salt (preferably hydrochloride) thereof with the compound of formula (XIII) or (XIV) in an inert solvent and then optionally removing the protecting group of the amino, hydroxy and/or carboxy group in $R^{1a}, R^{2a}, R^{3a}, R^{4a}$ and A'. This step may be carried out in a similar manner to that described in Step B6 of Process B.

Step C2

In this step the compound of formula (Ii) is prepare by reacting a compound of formula (XXI) with a compound of formula (XXII) in an inert solvent in the presence or absence (preferably in the presence) of a base and then optionally removing the protecting group of the amino, hydroxy and/or carboxy group in $R^{1a}, R^{2a}, R^{3a}, R^{4a}$ and A'. This step may be carried out in a similar manner to Step B4 of Process B.

Step C3

In this step there is provided an alternative method for preparing the compound of formula (Ii), which comprises reacting a compound of formula (XXIII) with a compound of formula (XXIV) in an inert solvent in the presence of an organic base (preferably triethylamine) and then optionally removing the protecting group of the amino, hydroxy and/or carboxy group in $R^{1a}, R^{2a}, R^{3a}, R^{4a}$ and A'. This step may be carried out in a similar manner to Step B3 of Process B.

Step C4

In this step the compound of formula (Ij) is prepared by reacting the compound of formula (XX) with the compound of formula (XXII) in an inert solvent in the presence or absence (preferably in the presence) of a base and then optionally removing the protecting group of the amino, hydroxy and/or carboxy group in $R^{1a}, R^{2a}, R^{3a}, R^{4a}$ and A'. This step may be carried out in a similar manner to Step A1 of Process A.

Step C5

In this step a compound of formula (XXV) is prepared by reacting a compound of formula (XIVa) with the compound of formula (XX) or acid addition salt thereof (for example, a mineral acid salt such as hydrochloride, nitrate or sulfate) in an inert solvent. This reaction may be effected, for example, by condensation under heat by using, as a catalyst, an organic sulfonic acid such as p-toluenesulfonic acid or condensation using a Lewis acid such as titanium tetrachloride. This step may be carried out in a similar manner to Step B1 of Process B.

Step C6

In this step the compound of formula (Ija) is prepared by reacting the compound of formula (XXV) with a reducing agent and then optionally removing the protecting group of the amino, hydroxy and/or carboxy group in $R^{1a}, R^{2a}, R^{3a}$, $R^{4a}$ and A'. This step may be carried out in a similar manner to Step B2 of Process B.

The compound of formula (Ija) can also be prepared by subjecting the compound of formula (XXV) to catalytic reduction and then optionally removing the protecting group or the amino, hydroxy and/or carboxy group in $R^{1a}, R^{2a}, R^{3a}, R^{4a}$ and A'.

The catalytic reduction reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as toluene, benzene and xylene; esters, such as methyl acetate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; alcohols, such as methanol, ethanol, propanol, isopropanol, butanol, isobutanol, t-butanol, isoamyl alcohol, diethylene glycol, glycerin, octanol, cyclohexanol and methyl cellosolve; organic acids, such as acetic acid; and water; and mixed solvents of the above-described solvent and water, of which the alcohols, ethers, organic acids and water are preferred, the alcohols and organic acids being most preferred.

There is no particular limitation on the nature of the catalyst to be used for the catalytic reduction, and any such catalyst commonly used in reactions of this type may equally be employed here. Preferred examples include palladium on carbon, Raney nickel, platinum oxide, platinum black, rhodium-aluminum oxide, triphenylphosphine-rhodium chloride, and palladium-barium sulfate, of which palladium on carbon is preferred.

Although no particular limitation is imposed on the pressure, it usually ranges from 1 to 10 times atmospheric pressures.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20 to 150° C., more preferably from 0 to 100° C. The time required for the reaction may also vary widely, depending on many factors, notably the reaction temperature and the nature of the reagents and solvent employed. However, provided that the reaction is effected under the preferred conditions outlined above, a period of from 15 minutes to 24 hours, more preferably from 30 minutes to 16 hours, will usually suffice.

The optional removal of the protecting group of the amino, hydroxy and/or carboxy group in $R^{1a}, R^{2a}, R^{3a}, R^{4a}$ and A' may be carried out in a similar manner to that employed in Step A1 of Process A.

After completion of the reaction, the resulting compound of formula (Ija) of the present reaction may be collected from the reaction mixture by known methods, for example, by neutralizing the reaction mixture as desired, removing any insoluble matter by filtration, adding a water-immiscible organic solvent such as ethyl acetate to separate an organic layer containing the compound, washing with water or the like, drying over anhydrous magnesium sulfate, anhydrous sodium sulfate or anhydrous sodium hydrogencarbonate and distilling off the solvent. If necessary, the compound thus obtained can be separated and purified by known methods by using commonly employed methods for the separation and purification of an organic compound, such as recrystallization and reprecipitation, in combination, making use of chromatography and eluting with a proper eluent.

Step C7

In this step the compound of formula (Ik) is prepared by reacting the compound of formula (XXVI) with the compound of formula (XXIII) or acid addition salt thereof (for example, a mineral acid salt such as hydrochloride, nitrate or sulfate) in an inert solvent and then optionally removing the protecting group of the amino, hydroxy and/or carboxy group in $R^{1a}$, $R^{2a}$, $R^{3a}$, $R^{4a}$ and A'. The reaction of the compound of formula (XXVI) with the compound of formula (XXIII) or acid addition salt thereof may be carried out in a similar manner to the reaction of the step B6 of Process B in the case where $R^7$ of the compound of formula (IXV) represents a formyl group. The optional removal of the protecting group of the amino, hydroxy and/or carboxy group in $R^{1a}$, $R^{2a}$, $R^{3a}$, $R^{4a}$ and A' may be carried out in a similar manner to that employed in Step A1 of Process A.

Each of the starting material compounds of formula (II), (III), (IV), (V), (VI), (VIII), (IX), (X), (XI), (XIII), (XIV), (XV), (XIX), (XX), (XXI), (XXII), (XXIII), (XXIV), (XXIVa) and (XXVI) is known, or may be prepared easily by known processes or by processes similar thereto [for example, J. Org. Chem., 56, 1445–1453 (1991), Organic Reaction, 5, 301–330 (1949), etc.].

Each of the starting material compounds of formula (II), (V), (VIII), (X), (XI), (XX), (XXI) and (XXIII) can also be prepared by the process described below.

Process D

In this process the compound of formula (II), the compound of formula (IIa), that is, a compound of formula (II) wherein $R^{5a}$ represents a hydrogen atom, and the compound of formula (IIb), that is, a compound of formula (II) wherein Z represents a $C_{1-6}$ alkylene group and $R^{5a}$ represents a hydrogen atom, are prepared.

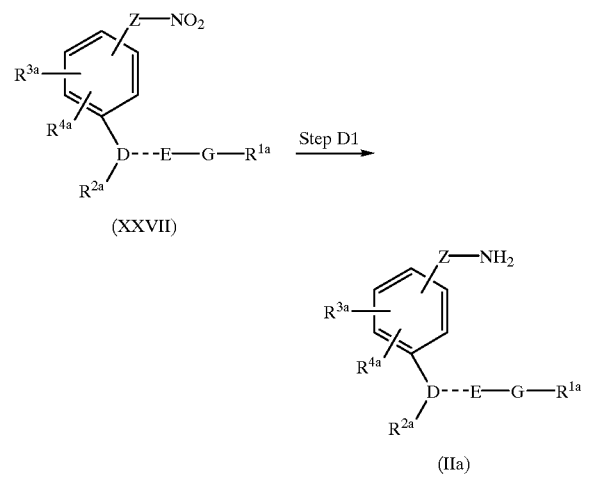

In the above reaction scheme:

$R^{1a}$, $R^{2a}$, $R^{3a}$, $R^{4a}$, $R^{5a}$, D, E, G, Z and Q have the same meanings as described above;

$Z_a$ represents a single bond or a $C_{1-5}$ alkylene group; and $Z_b$ represents a $C_{1-6}$ alkylene group.

Step D1

In this step the compound of formula (IIa) is prepared by reacting a compound of formula (XXVII) with a reducing agent (preferably sodium borohydride, sodium cyanoborohydride or lithium aluminum hydride) in an inert solvent (preferably an alcohol or an ether) at a temperature of from –20 to 150° C., preferably from 10 to 80° C., for a period of from 5 minutes to 24 hours, preferably for from 10 minutes to 16 hours.

This step can also be effected using a catalytic reduction method, a zinc-acetic acid method, which is a general reduction method of a nitro group, a tin-alcohol method or a tin-hydrochloric acid method.

Step D2

In this step the compound of formula (IIb) is prepared by reacting a compound of formula (XXVIII) with a reducing agent (preferably an aluminum hydride compound) in an inert solvent (preferably an alcohol or ether). This step may be carried out in a similar manner to Step D1 of Process D.

Step D3

In this step a compound of formula (XXX) is prepared by reacting the compound of formula (IIa) with a compound of formula (XXIX) in an inert solvent (preferably an amide) in the presence of a base (preferably an alkali metal hydrogencarbonate or organic amine). This step may be carried out in a similar manner to Step A1 of Process A.

Step D4

In this step the compound of formula (II) is prepared by reducing the compound of formula (XXX) in an inert solvent. This step may be carried out in a similar manner to Step D1 of Process D.

After completion of the reaction, the resulting compound of each of the reactions may be collected from the reaction mixture by known methods, for example, by neutralizing the reaction mixture as desired, removing any insoluble matter by filtration, adding a water-immiscible organic solvent such as ethyl acetate to separate an organic layer containing the compound, washing with water or the like, drying over anhydrous magnesium sulfate, anhydrous sodium sulfate or anhydrous sodium hydrogencarbonate and distilling off the solvent. If necessary, the compound thus obtained can be separated and purified by known methods by using commonly employed methods for the separation and purification of an organic compound, such as recrystallization and reprecipitation, in combination, making use of chromatography and eluting with a proper eluent.

Process E

This a process for preparing a compound of formula (XXXI):

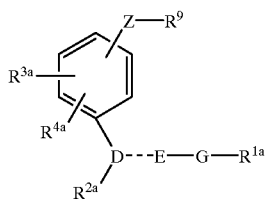

(XXXI)

[wherein $R^{1a}$, $R^{2a}$, $R^{3a}$, $R^{4a}$, D, E, G and Z have the same meanings as described above; and $R^9$ represents an amino, cyano or nitro group which may be protected], including the compounds of formula (XXVII), (XXVIII) and (IIa).

More specifically, in this process a compound of formula (XXXIa), that is, a compound of formula (XXXI) wherein D represents a —CH— group and E represents an —NH— group, a compound of formula (XXXIb), that is, a compound of formula (XXXI) wherein D represents a —CH— group and E represents an oxygen or sulfur atom, a compound of formula (XXXIc), that is, a compound of formula (XXXI) wherein D represents a —CH— group, E represents an —NH— group and G represents a —CO—$G_a$— group, a compound of formula (XXXId), that is, a compound of formula (XXXI) wherein D represents a carbon atom, E represents an =N—O— group, and a compound of formula (XXXIe), that is, a compound of formula (XXXI) wherein D represents a —CH— group and E represents a —CO— group, is prepared.

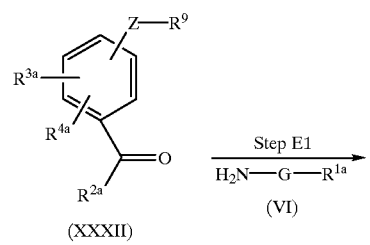

(XXXII)

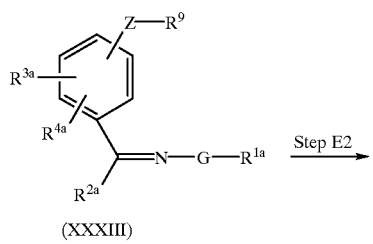

(XXXIII)

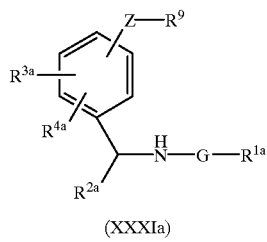

(XXXIa)

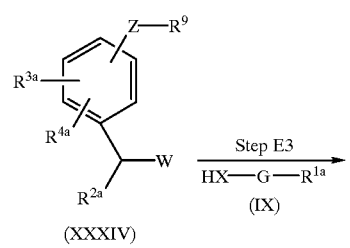

(XXXIV)

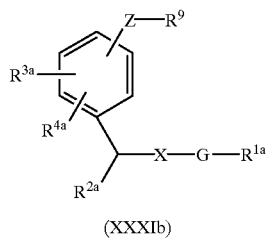

(XXXIb)

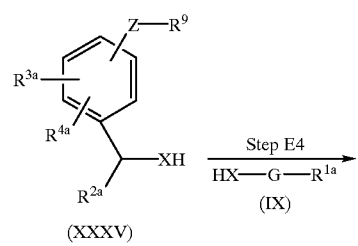

(XXXV)

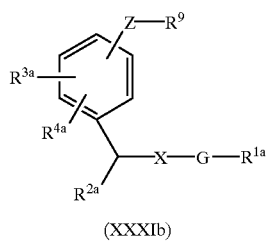

(XXXIb)

-continued
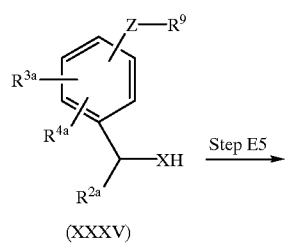
(XXXV)
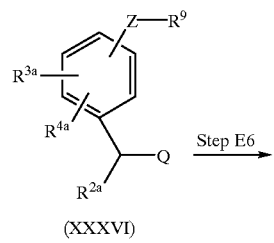
(XXXVI)
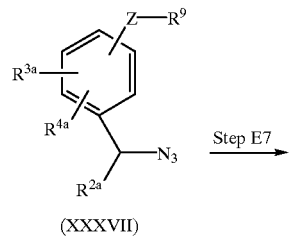
(XXXVII)
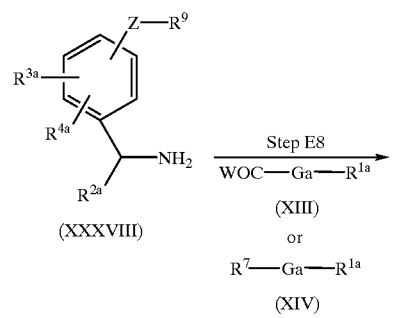
(XXXVIII)
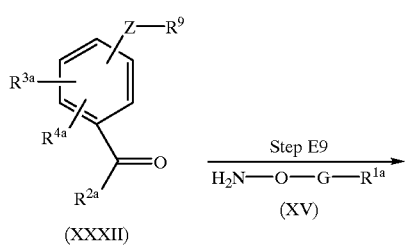
(XXXII)
-continued
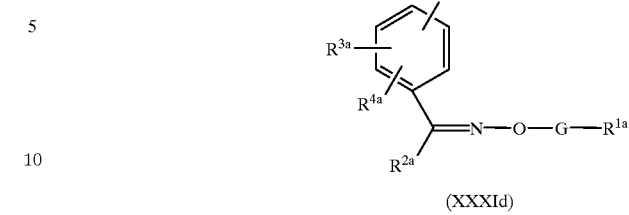
(XXXId)
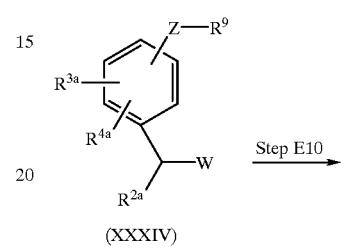
(XXXIV)
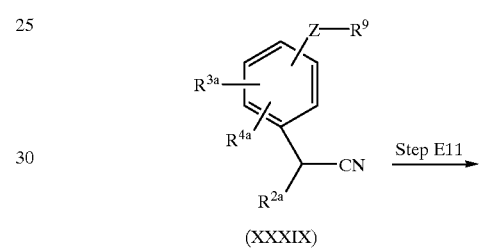
(XXXIX)
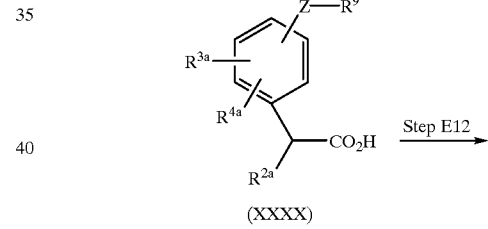
(XXXX)
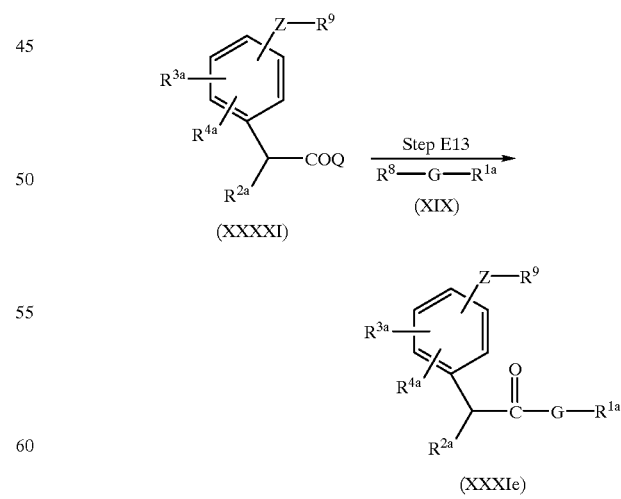
In this reaction scheme:
$R^{1a}, R^{2a}, R^{3a}, R^{4a}, R^7, R^8, R^9, G, G_a, Q, X, W$ and $Z$ have the same meanings as described above.
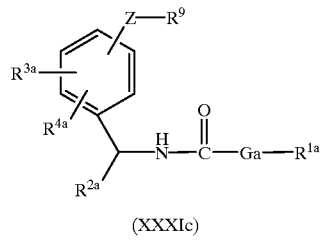
(XXXIc)

Step E1

In this step a compound of formula (XXXIII) is prepared by reacting a compound of formula (XXXII) with the compound of formula (VI) or acid addition salt thereof (for example, a mineral acid salt such as hydrochloride, nitrate or sulfate) in an inert solvent. This step may be carried out in a similar manner to Step B1 of Process B.

Step E2

In this step the compound of formula (XXXIa) is prepared by reducing the compound of formula (XXXIII) in an inert solvent. This step may be carried out in a similar manner to Step B2 of Process B.

Step E3

In this step the compound of formula (XXXIb) is prepared by reacting a compound of formula (XXXIV) with a base in the presence or absence (preferably in the presence) of an inert solvent and then reacting the reaction mixture with the compound of formula (IX). This step may be carried out in a similar manner to Step B3 of Process B.

Step E4

In this step there is provided an alternative method for preparing the compound of formula (XXXIb) is prepared by converting the —XH— containing group of a compound of formula (XXXV) into an leaving group Q in an inert solvent in the presence or absence of a Lewis acid and then reacting with the compound of formula (IX). This step may be carried out in a similar manner to Step B4 of Process B.

Step E5

In this step a compound of formula (XXXVI) is prepared by converting the —XH— containing group of a compound of formula (XXXV) into an leaving group Q in an inert solvent in the presence or absence of a base. This step may be carried out in a similar manner to Step B4 of Process B for the conversion of the —XH— containing group of the compound of formula (X) into an leaving group Q.

Step E6

In this step a compound of formula (XXXVII) is prepared by converting the compound of formula (XXXVI) into the corresponding azide in an inert solvent. The reaction is normally and preferably effected in the presence of a solvent. There is no particular restriction on the nature of the solvent to be employed, provided that it has no adverse effect on the reaction or on the reagents involved and that it can dissolve the reagents at least to some extent. Examples of suitable solvents include: aromatic hydrocarbons, such as benzene, toluene and xylene, halogenated hydrocarbons, such as methylene chloride and chloroform; ethers, such as ether, tetrahydrofuran, dioxane and dimethoxyethane; amides, such as formamide, dimethylformamide, dimethylacetamide and hexamethylphosphoryl triamide; and nitrites, such as acetonitrile. Preferred are the amides, dimethylformaamide being most preferred.

There is no particular limitation imposed on the reagent used in this reaction to form the azide, and any reagent commonly used for this purpose may equally be employed here. Examples include diaryl phosphoric azide derivatives, such as diphenylphosphoric azide, trialkylsilyl azides, such as trimethylsilyl azide and triethylsilyl azide, and alkali metal azide salts, such as sodium azide and potassium azide, of which the alkali metal azide salts are preferred, sodium azide being most preferred.

In this reaction, a catalyst may be used. Examples include trialkylsilyl triflates, such as trimethylsilyl triflate and triethylsilyl triflate and Lewis acids, such as trifluoroborane etherate, aluminum chloride and zinc chloride.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20 to 100° C., more preferably from 0 to 50° C. The time required for the reaction may also vary widely, depending on many factors, notably the reaction temperature and the nature of the reagents and solvent employed. However, provided that the reaction is effected under the preferred conditions outlined above, a period of from 15 minutes to 50 hours, more preferably from 30 minutes to 12 hours, will usually suffice.

Step E7

In this step a compound of formula (XXXVIII) is prepared by reducing the compound of formula (XXXVII) with a reducing agent such as triphenylphosphine in an inert solvent. This step may be carried out in a similar manner to Step B5 of Process B.

Step E8

In this step the compound of formula (XXXIc) is prepared by reacting the compound of formula (XXXVIII) with the compound of formula (XIII) or (XIV). This step may be carried out in a similar manner to Step B6 of Process B.

Step E9

In this step the compound of formula (XXXId) is prepared by reacting the compound of formula (XXXII) with the compound of formula (XV) or acid addition salt thereof (for example, a mineral acid salt such as hydrochloride, nitrate or sulfate). This step may be carried out in a similar manner to Step B7 of Process B.

Step E10

In this step a compound of formula (XXXIX) is prepared by reacting the compound of formula (XXXIV) with an alkali metal cyanide in an inert solvent. This step may be carried out in a similar manner to Step B8 of Process B.

Step E11

In this step a compound of formula (XXXX), which comprises hydrolyzing the compound of formula (XXXIX) with an acid or alkali in an inert solvent. This step may be carried out in a similar manner to Step B9 of Process B.

Step E12

In this step a compound of formula (XXXXI) is prepared by converting the carboxy group of the compound of formula (XXXX) into a —COQ group in an inert solvent. This step may be carried out in a similar manner to Step B10 of Process B.

Step E13

In this step a compound of formula (XXXIe) is prepared by reacting the compound of formula (XXXXI) with the compound of formula (XIX) in an inert solvent in the presence or absence of a palladium catalyst. This step may be carried out in a similar manner to Step B11 of Process B.

After completion of the reaction, the resulting compound of each of these reactions may be collected from the reaction mixture by known methods, for example, by neutralizing the reaction mixture as desired, removing any insoluble matter by filtration, adding a water-immiscible organic solvent such as ethyl acetate to separate an organic layer containing the compound, washing with water or the like, drying over anhydrous magnesium sulfate, anhydrous sodium sulfate or anhydrous sodium hydrogencarbonate and distilling off the solvent. If necessary, the compound thus obtained can be separated and purified by known methods by using commonly employed methods for the separation and purification of an organic compound, such as recrystallization and reprecipitation, in combination, making use of chromatography and eluting with a proper eluent.

Process F

This is a process for preparing a compound of formula (XXXIf), that is, a compound of formula (XXXI) wherein D represents a nitrogen atom, E represents an —NH— group and G represents a —CO—$G_a$— group, a compound of formula (XXXIg), that is, a compound of formula (XXXI) wherein D represents a nitrogen atom and E represents an oxygen or sulfur atom, a compound of formula (XXXIh), that is, a compound of formula (XXXI) wherein D represents a nitrogen atom and E represents an —NH— group, a compound of formula (XXXIha), that is, a compound of formula (XXXI) wherein D represents a nitrogen atom, E represents an —NH— group and G represents a $C_{1-6}$ alkylene group, and a compound of formula (XXXIi), that is, a compound of formula (XXXI) wherein D represents a nitrogen atom and E represents a —CO— group.

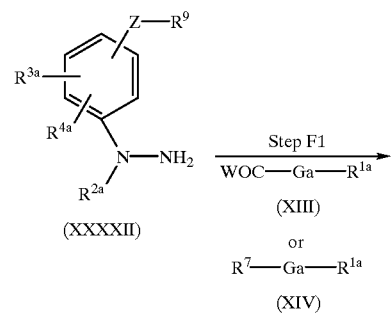

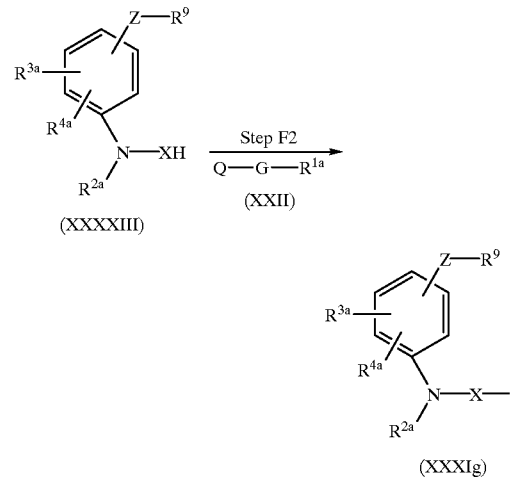

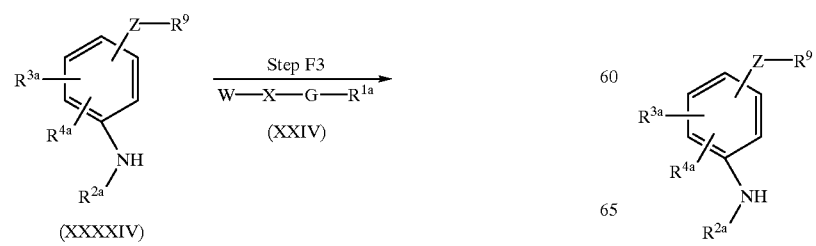

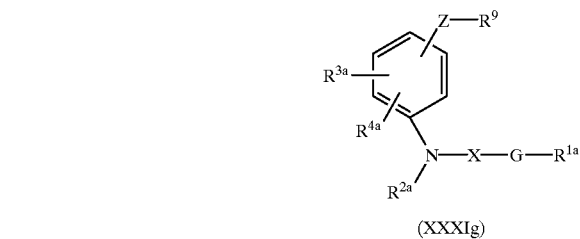

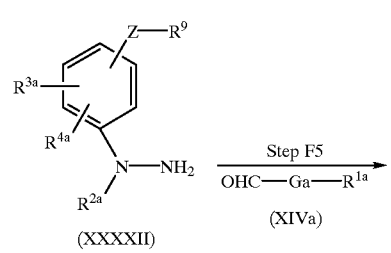

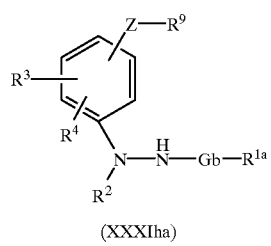

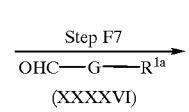

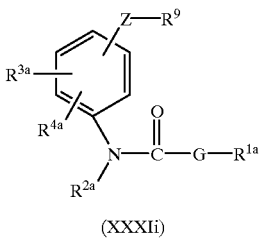

(XXXIi)

In this reaction scheme:
$R^{1a}, R^{2a}, R^{3a}, R^{4a}, R^7, R^9, G, G_a, G_b, Q, X, W$ and $Z$ have the same meanings as described above.

Step F1

In this step the compound of formula (XXXIf) is prepared by reacting the compound of formula (XXXXII) or acid addition salt thereof (preferably hydrochloride) with the compound of formula (XIII) or (XIV) in an inert solvent in the presence or absence (preferably in the presence) of a base. This step may be carried out in a similar manner to Step B6 of Process B.

Step F2

In this step the compound of formula (XXXIg) is prepared by reacting a compound of formula (XXXXIII) with the compound of formula (XXII) in an inert solvent in the presence or absence (preferably in the presence) of a base. This step may be carried out in a similar manner to Step B4 of Process B.

Step F3

In this there is provided an alternative method for preparing the compound of formula (XXXIg) by reacting a compound of formula (XXXXIV) with the compound of formula (XXIV) in an inert solvent in the presence of an organic base (preferably triethylamine). This step may be carried out in a similar manner to Step B3 of Process B.

Step F4

In this step the compound of formula (XXXIh) is prepared by reacting the compound of formula (XXXXII) with the compound of formula (XXII) in an inert solvent in the presence or absence (preferably in the presence) of a base. This step may be carried out in a similar manner to Step A1 of Process A.

Step F5

In this step a compound of formula (XXXXV) is prepared by reacting the compound of formula (XIVa) with the compound of formula (XXXXII) or acid addition salt thereof (for example, a mineral acid salt such as hydrochloride, nitrate or sulfate) in an inert solvent. This step may be carried out in a similar manner to Step B1 of Process B, for example, by condensation under heat by using, as a catalyst, an organic sulfonic acid such as p-toluenesulfonic acid, or condensation using a Lewis acid such as titanium tetrachloride.

Step F6

In this step the compound of formula (XXXIha) is prepared by reducing the compound of formula (XXXXV). This step may be carried out in a similar manner to Step C6 of Process C.

Step F7

In this step the compound of formula (XXXIi) is prepared by reacting a compound of formula (XXXXVI) with the compound of formula (XXXXIV) or acid addition salt thereof (for example, a mineral acid salt such as hydrochloride, nitrate or sulfate) in an inert solvent. This step may be carried out in a similar manner to Step B1 of Process B.

After completion of the reaction, the resulting compound of each of these reactions may be collected from the reaction mixture by known methods, for example, by neutralizing the reaction mixture as desired, removing any insoluble matter by filtration, adding a water-immiscible organic solvent such as ethyl acetate to separate an organic layer containing the compound, washing with water or the like, drying over anhydrous magnesium sulfate, anhydrous sodium sulfate or anhydrous sodium hydrogencarbonate and distilling off the solvent. If necessary, the compound thus obtained can be separated and purified by known methods by using commonly employed methods for the separation and purification of an organic compound, such as recrystallization and reprecipitation, in combination, making use of chromatography and eluting with a proper eluent.

The starting material compounds of formula (V), (VIII), (X) and (XI) can be prepared by reacting, instead of the compound of formula (II), a compound of formula (XXXXVII):

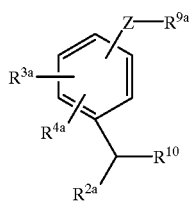

(XXXXVII)

[wherein:
$R^{3a}, R^{2a}, R^{4a}$ and Z have the same meanings as described above;
$R^{9a}$ has the same meaning as described above in $R^9$ except that the amino group which may be protected is an amino group; and
$R^{10}$ represents a halogen atom, azide or —XH-containing group (in which, X has the same meaning as described above) when the broken line means a single bond, while it represents an oxygen atom when a broken line means a double bond.]

with the compound of formula (III) in a similar manner to the process as described in Process A.

The starting material compounds of formula (XX), (XXI) and (XXIII) can be prepared by reacting, instead of the compound of formula (II), a compound of formula (XXXXVIII):

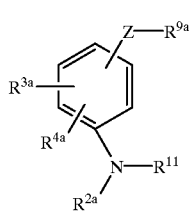

(XXXXVIII)

[wherein:
$R^{3a}, R^{2a}, R^{4a}, R^{9a}$ and Z have the same meanings as described above, and
$R^{11}$ represents a hydrogen atom, an amino group or an —XH-containing group (in which, X has the same meaning as described above)]

with the compound of formula (III) in a similar manner to the method described in Process A.

Process G

This is a process for preparing the compound of formula (XXXII).

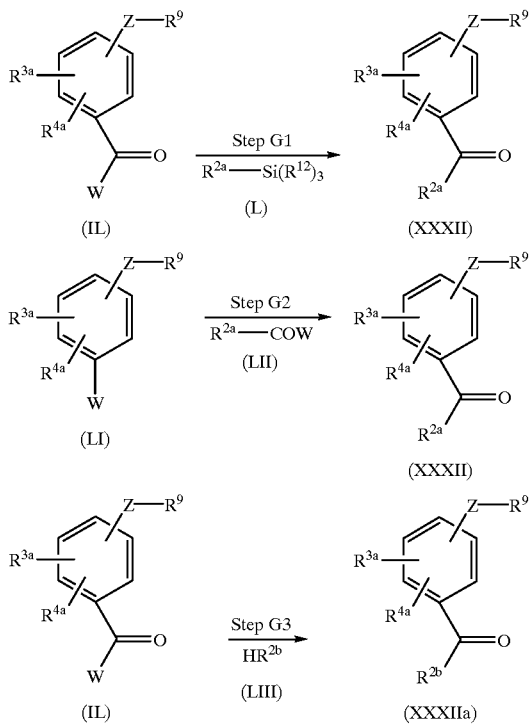

In this reaction scheme:

$R^{2a}$, $R^{3a}$, $R^{4a}$, $R^9$, W and Z have the same meanings as described above;

$R^{2b}$ represents a phenyl group or a phenyl group substituted by at least one of substituents α' (substituents α' has the same meaning as substituents α except that the amino and/or hydroxy group may be protected); and $R^{12}$ represents a lower alkyl group.

Step G1

In this step the compound of formula (XXXII) is prepared by reacting a compound of formula (IL) with a compound of formula (L) in an inert solvent (preferably a hydrocarbon such as hexane, cyclohexane, benzene, toluene or xylene) at a temperature of from −20 to 200° C. (preferably from 0 to 150° C.) for a period of from 15 minutes to 24 hours (preferably from 30 minutes to 16 hours).

Step G2

In this step there is provided an alternative method of preparing the compound of formula (XXXII) by reacting a compound of formula (LI) with a compound of formula (LII) in an inert solvent (preferably a hydrocarbon such as hexane, cyclohexane, benzene, toluene or xylene, or an ether such as diethyl ether, diisopropyl ether, tetrahydrofuran, dioxane, dimethoxyethane or diethylene glycol dimethyl ether) in the presence of a base (preferably an organolithium such as n-butyl lithium, t-butyl lithium or phenyl lithium) at a temperature of from −150 to 50° C. (preferably from −100 to 0° C.) for a period of from 15 minutes to 24 hours (preferably from 30 minutes to 16 hours). In order to remove the acid which is generated with the passage of the reaction, the reaction can also be carried out in the presence of an organic amine (preferably N,N,N',N'-tetramethylethylenediamine).

Step G3

In this step a compound of formula (XXXIIa) is prepared by reacting the compound of formula (IL) with a compound of formula (LIII) in an inert solvent (preferably a hydrocarbon such as hexane, cyclohexane, benzene, toluene or xylene) at a temperature of from −20 to 200° C. (preferably from 0 to 150° C.) for a period of from 15 minutes to 24 hours (preferably from 30 minutes to 20 hours).

Alternatively, this step may be carried out by condensing the compound of formula (IL) with the compound of formula (LIII) by using a Lewis acid (preferably aluminum chloride or zinc chloride) in an inert solvent (preferably a halogenated hydrocarbon such as dichloromethane, 1,2-dichloroethane or carbon tetrachloride, or a sulfoxide such as dimethyl sulfoxide) at a temperature of from 20° C. to 200° C. (preferably from 50 to 150° C.) for a period of from 15 minutes to 24 hours (preferably from 30 minutes to 16 hours).

After completion of the reaction, the resulting compound of each of these reactions may be collected from the reaction mixture by known methods, for example, by neutralizing the reaction mixture as desired, removing any insoluble matter by filtration, adding a water-immiscible organic solvent such as ethyl acetate to separate an organic layer containing the compound washing with water or the like, drying over anhydrous magnesium sulfate, anhydrous sodium sulfate or anhydrous sodium hydrogencarbonate and distilling off the solvent. If necessary, the compound thus obtained can be separated and purified by known methods by using commonly employed methods for the separation and purification of an organic compound, such as recrystallization and reprecipitation, in combination, making use of chromatography and eluting with a proper eluent.

The starting material compounds of formula (XXIX), (XXXIV), (XXXV), (XXXII), (XXXIII), (XXXIV), (XXXVI), (IL), (L), (LI), (LII) and (LIII) are known compounds or prepared easily by known methods or a method similar thereto [for example, Acta. Chim. Acad. Humg., 34, 75–76(1962), Chem. Ber., 28, 1625(1895), Chem. Abstr., 71, 123951j(1969), etc.]

Compounds of formula (I), pharmacologically acceptable salts and esters thereof according to the present invention have excellent inhibitory action against an ileal bile acid transporter.

When each of the compounds of the formula (I) and pharmacologically acceptable salts and esters thereof is employed as a remedy or preventive having the above-described action, it can be administered, as is or after mixed with a pharmacologically acceptable excipient or diluent, in an orally administrable form such as tablets, capsules, granules, powders or syrups or in a parenteral form such as injection or suppository.

These formulations can be prepared in a known manner by using carriers which may be and/or incorporate additives and diluents. Examples of such additives include excipients (for example, organic excipients, such as sugar derivatives, e.g. lactose, sucrose, dextrose, mannitol and sorbitol, starch derivatives, such as corn starch, potato starch, α-starch and dextrin, cellulose derivatives, such as crystalline cellulose, gum arabic, dextran, and pullulan; and inorganic excipients, for example, silicate derivatives, such as light silicic anhydride, synthetic aluminum silicate, calcium silicate and magnesium aluminate metasilicate, phosphates, such as calcium hydrogenophosphate, carbonates, such as calcium carbonate, and sulfates, such as calcium sulfate), lubricants (for example, stearic acid, metal salts of stearic acid such as calcium stearate and magnesium stearate, talc, colloidal silica, waxes, such as bee gum and spermaceti, boric acid, adipic acid, sulfates, such as sodium sulfate, glycol, fumaric acid, sodium benzoate, DL leucine, fatty acid sodium salts, lauryl sulfates, such as sodium lauryl sulfate and magnesium lauryl sulfate, silicic acids, such as silicic anhydride and silicic hydrate and the above-exemplified starch derivatives), binders (for example, hydroxypropyl cellulose, hydroxypropylmethyl cellulose, polyvinyl pyrrolidone, macrogol and compounds similar to those exemplified above as excipients) disintegrators (for example, cellulose derivatives, such as low-substitution degree hydroxypropyl cellulose, carboxymethyl cellulose, carboxymethyl cellulose calcium and internally crosslinked carboxymethyl cellulose sodium and chemically modified starchcelluloses, such as carboxymethyl starch, carboxymethyl starch sodium and crosslinked polyvinyl pyrrolidone), stabilizers (paraoxybenzoates, such as methyl paraben and propyl paraben, alcohols, such as chlorobutanol, benzyl alcohol and phenyl ethyl alcohol, benzalkonium chloride, phenols, such as phenol and cresol, thimerosal, dehydroacetic acid, and sorbic acid), corrigents (ordinarily-used sweeteners, acidifiers and perfumes), and diluents.

The daily dose may vary depending upon the symptoms, age, body weight or the like of the patient (human or other mammal), but is, per adult, 1 mg/once (preferably 10 mg/once) as the lower limit and 2000 mg/once (preferably 400 mg/once) as the upper limit in the case of oral administration, while it is 0.1 mg/once (preferably 1 mg/once) as the lower limit and 500 mg/once (preferably 300 mg/once) as the upper limit in the case of intravenous administration. The dose is desirably administered in 1 to 6 portions a day depending on the symptoms.

The invention is further illustrated by the following non-limiting Examples. In the Examples, DMSO-$d_6$ is hexadeuterated dimethyl sulfoxide.

EXAMPLE 1

3-Amino-4-<3-{phenyl-[(R)-1-phenylethylamino]
methyl}phenylamino>-3-cyclobutene-1,2-dione
(Compound No. 2-450)

(1a) N-[(3-Nitrophenyl)phenylmethyl]-N-[(R)-phenylethyl] amine

Triethylamine (7.3 ml) was added to a solution of 3-nitrobenzophenone (3 g) and (R)-1-phenylethylamine (3.4 ml) in anhydrous dichloromethane (60 ml). A solution of titanium tetrachloride (1.74 ml) in anhydrous dichloromethane (17 ml) was slowly added dropwise to the mixture in an ice bath. This mixture was stirred at ambient temperature for 2 hours. At the end of this time, ethyl acetate and an aqueous solution of sodium hydrogencarbonate were added to the reaction mixture. The mixture was then filtered through a Celite (trade mark) filter aid to remove the insoluble material, and the ethyl acetate layer was separated from the filtrate. The aqueous layer was extracted with ethyl acetate. The ethyl acetate layer and the extract were combined and washed with a saturated aqueous solution of sodium chloride. The organic layer was dried over anhydrous sodium sulfate and concentrated by evaporation under reduced pressure to afford the imine derivative (5.41 g) as a dark brown oil.

Sodium cyanoborohydride (3.3 g) and acetic acid (1.1 ml) were added to a solution of this oil in ethanol (100 ml). The reaction mixture was heated under reflux for 1 hour, after which it was concentrated by evaporation under reduced pressure. The residue was neutralized with an aqueous solution of sodium hydrogencarbonate and extracted with ethyl acetate three times. The combined ethyl acetate extracts were washed with a saturated aqueous solution of sodium chloride and dried over anhydrous sodium sulfate. The resulting solution was then concentrated by evaporation under reduced pressure. The residue was purified by chromatography through a silica gel column using a 19:1 by volume mixture of cyclohexane and ethyl acetate as eluant and on a Lobar column using a 19:1 by volume mixture of cyclohexane and ethyl acetate as eluant under medium pressure to afford isomer A of the title compound (1.43 g) as a yellow oil and isomer B of the title compound (1.12 g) as a yellow oil.

Isomer A

Nuclear Magnetic Resonance Spectrum (CDCl$_3$) δ ppm: 1.40 (3H, doublet, J=6.8 Hz); 3.62 (1H, quartet, J=6.8 Hz); 4.72 (1H, singlet); 7.18–7.40 (10H, multiplet); 7.48 (1H, triplet, J=8.0 Hz); 7.69 (1H, doublet, J=7.6 Hz); 8.10 (1H, doublet of doublets, J=2.0, 8.0 Hz); 8.27 (1H, doublet, J=2.0 Hz).

Isomer B

Nuclear Magnetic Resonance Spectrum (CDCl$_3$) δ ppm: 1.40 (3H, doublet, J=6.6 Hz); 3.69 (1H, quartet, J=6.6 Hz); 4.69 (1H, singlet); 7.24–7.40 (11H, multiplet); 7.59 (1H, doublet, J=8.0 Hz); 8.02 (1H, doublet of doublets, J=2.0, 8.0 Hz); 8.24 (1H, doublet, J=1.7 Hz).

(1b) 3-{Phenyl-[(R)-1-phenylethylamino]methyl}phenylamine

Nickel chloride hexahydrate (2.04 g) was added to a solution of 1.43 g of isomer A of N-[(3-nitrophenyl)-phenylmethyl]-N-[(R)-1-phenylethyl]amine [prepared as described in step (a) above] in methanol (30 ml). Sodium borohydride (650 mg) was added in several portions to the mixture in an ice bath, and the mixture was then stirred for 30 minutes. Acetone was added to the reaction mixture, and this mixture was stirred for 20 minutes. The solvent was evaporated from the mixture under reduced pressure. The residue was then partitioned between ethyl acetate and an aqueous solution of sodium hydrogencarbonate, and the aqueous layer was extracted with ethyl acetate two times. The ethyl acetate extracts were combined and washed with a saturated aqueous solution of sodium chloride. It was then dried over anhydrous sodium sulfate and concentrated by evaporation under reduced pressure. The residue was purified by chromatography through a silica gel column using a 3:1 by volume mixture of cyclohexane and ethyl acetate as the eluant, to afford isomer A of the title compound (1.24 g) as a pale yellow oil.

Isomer A

Nuclear Magnetic Resonance Spectrum (CDCl$_3$) δ ppm: 1.36 (3H, doublet, J=6.6 Hz); 3.72 (1H, quartet, J=6.6 Hz); 4.53 (1H, singlet); 6.57 (1H, doublet of doublets, J=2.5, 8.1 Hz); 6.67 (1H, doublet, J=2.0 Hz); 6.71 (1H, doublet, J=7.7 Hz); 7.10 (1H, triplet, J=7.7 Hz); 7.13–7.35 (10H, multiplet).

In a similar manner to that described in relation to isomer A of Example (1b), a solution of N-[(3-nitrophenyl)-phenylmethyl]-N-[(R)-1-phenylethyl]amine (isomer B, 1.71 g) in methanol (30 ml), nickel chloride hexahydrate (2.42 g) and sodium borohydride (772 mg) were reacted, to afford isomer B of the title compound (1.41 g) as a yellow oil.

Isomer B

Nuclear Magnetic Resonance Spectrum (CDCl$_3$) δ ppm: 1.35 (3H, doublet, J=6.7 Hz); 3.65 (1H, quartet, J=6.7 Hz); 4.53 (1H, singlet); 6.50 (1H, doublet of doublets, J=2.0, 8.0 Hz); 6.62 (1H, doublet, J=1.7 Hz); 6.66 (1H, doublet, J=7.7 Hz); 7.03 (1H, triplet. J=8.4 Hz); 7.21–7.35 (10H, multiplet).

(1c) 3-Methoxy-4-<3-{phenyl-[(R)-1-phenylethylamino]methyl}phenylamino>-3-cyclobutene-1,2-dione 3,4-Dimethoxy-3-cyclobutene-1,2-dione (1.17 g) was added a solution of 3-{phenyl-[(R)-phenylethylamino]methyl}phenylamine (isomer A, 1.24 g) [prepared as described in step (b) above] at ambient temperature. After stirring for 1 hour, the reaction mixture was concentrated by evaporation under reduced pressure. The residue was purified by chromatography through a silica gel column using a 1:1 by volume mixture of cyclohexane and ethyl acetate as the eluant, to afford isomer A of the title compound (1.21 g) as white foamy solid.

Isomer A

Nuclear Magnetic Resonance Spectrum (CDCl$_3$) δ ppm: 1.39 (3H, doublet, J=6.6 Hz); 3.67 (1H, quartet, J=6.6 Hz); 4.41 (3H, singlet); 4.63 (1H, singlet); 7.13–7.36 (14H, multiplet).

In a similar manner to that described in relation to isomer A in Example (1c), a solution of 3-{phenyl-[(R)-1-phenylethylamino]methyl}phenylamine (isomer B, 1.41 g) and 3,4-dimethoxy-3-cyclobutene-1,2-dione (796 mg) were reacted, to afford isomer B of the title compound (1.21 g) as white foams.

Isomer B

Nuclear Magnetic Resonance Spectrum (CDCl$_3$) δ ppm: 1.37 (3H, doublet, J=6.6 Hz); 3.66 (1H, quartet, J=6.6 Hz); 4.41 (3H, singlet); 4.61 (1H, singlet); 7.08 (1H, doublet, J=7.6 Hz); 7.22–7.37 (13H, multiplet).

(1d) 3-Amino-4-<3-{phenyl-[(R)-1-phenylethylamino]methyl}phenylamino>-3-cyclobutene-1,2-dione A solution of ammonia in ethanol (2N, 12 ml) was added to a solution of 3-methoxy-4-<3-{phenyl-[(R)-1-phenylethylamino]methyl}phenylamino>-3-cyclobutene-1,2-dione (isomer A, 1.21 g) [prepared as described in step (c) above] in ethanol (25 ml). The mixture was stirred at ambient temperature for 2 hours. At the end of this time, the solvent was evaporated from the reaction mixture under reduced pressure. The residue was suspended in ethyl acetate and filtered to afford isomer A of the title compound (574 mg) as a yellow solid.

Isomer A

Nuclear Magnetic Resonance Spectrum (DMSO-d$_6$) δ ppm: 1.31 (3H, doublet, J=6.6 Hz); 3.57 (1H, quartet, J=6.5 Hz); 4.49 (1H, singlet); 6.98 (1H, doublet, J=7.5 Hz); 7.15–7.43 (13H, multiplet). melting point: 189–191° C.; optical rotation [α]$_D$=−0.61 (c=1.0, EtOH).

In a similar manner to that described in relation to isomer A in Example (1d), a solution of 3-methoxy-4-<3-{phenyl-[(R)-1-phenylethylamino]methyl}phenylamino>-3-cyclobutene-1,2-dione (isomer B, 1.43 g) in ethanol (30 ml) and a solution of ammonia in ethanol (2N, 15 ml) were reacted, to afford isomer B of the title compound (546 mg) as a yellow solid.

Isomer B

Nuclear Magnetic Resonance Spectrum (DMSO-d$_6$) δ ppm: 1.29 (3H, doublet, J=6.7 Hz); 3.51 (1H, quartet, J=6.5 Hz); 4.46 (1H, singlet); 6.91 (1H, doublet, J=7.8 Hz); 7.18–7.35 (13H, multiplet). melting point: 196–198° C.; optical rotation [α]$_D$=+10.3 (c=1.0, EtOH).

EXAMPLE 2

3-Amino-4-<3-{phenyl-[(S)-1-phenylethylamino]methyl}phenylamino>-3-cyclobutene-1,2-dione (Compound No. 2-450)

In a similar manner to that described in Example 1, 3-nitrobenzophenone and (S)-1-phenylethyl amine were reacted, and the reaction mixture was purified to give isomer A (461 mg) and isomer B (431 mg) of the title compound.

Isomer A melting point: 177° C. (dec); optical rotation [α]$_D$=+1.0 (c=1.0, EtOH).

Isomer B melting point: 165° C. (dec); optical rotation [α]$_D$=−9.9 (c=1.0, EtOH).

EXAMPLE 3

3-Amino-4-{3-[(4-methoxyphenyl)-(3-phenylpropylamino)methyl]phenylamino}-3-cyclobutene-1,2-dione (Compound No. 2-556)

(3a) N-[(4-Methoxyphenyl)-(3-nitrophenyl)methyl]-N-(3-phenylpropyl)amine

Triethylamine (4.33 ml) was added to a solution of 3-nitro-4'-methoxybenzophenone (2 g) and 3-phenylpropylamine (2.22 ml) in anhydrous dichloromethane (20 ml). A solution of titanium tetrachloride (1.03 ml) in anhydrous dichloromethane (10 ml) was then slowly added dropwise to the mixture in an ice bath. This mixture was stirred at ambient temperature for 1 hour. Ethyl acetate and an aqueous solution of sodium 1hydrogencarbonate were added to the reaction mixture. This was filtered through a Celite (trade mark) filter aid to remove the insoluble material, and the ethyl acetate layer was separated from the filtrate. The aqueous layer was extracted with ethyl acetate. The ethyl acetate layer and extract were combined and washed with a saturated aqueous solution of sodium chloride. The organic layer was dried over anhydrous sodium sulfate and concentrated by evaporation under reduced pressure, to afford the imine derivative (3.26 g) as a dark brown oil.

In a similar manner to that described in Example (1a), a solution of this oil in ethanol (60 ml), sodium cyanoborohydride (1.96 g) and acetic acid (0.67 ml) were reacted, to give the title compound (2.79 g) as a yellow oil.

Nuclear Magnetic Resonance Spectrum (CDCl$_3$) δ ppm: 1.82–1.89 (2H, multiplet); 2.53–2.70 (4H, multiplet); 3.78 (3H, singlet); 4.84 (1H, singlet); 6.83–6.86 (2H, multiplet); 7.15–7.18 (3H, multiplet); 7.24–7.28 (4H, multiplet); 7.44 (1H, triplet, J=8.0 Hz); 7.72 (1H, doublet, J=7.5 Hz); 8.05 (1H, doublet, J=7.9 Hz); 8.29 (1H, doublet, J=1.9 Hz).

(3b) 3-[(4-Methoxyphenyl)-(3-phenylpropylamino)methyl]phenylamine

In a similar manner to that described in Example (1b), a solution of N-[(4-methoxyphenyl)-(3-nitrophenyl)methyl]-N-(3-phenylpropyl)amine (2.79 g) [prepared as described in step (a) above] in methanol (60 ml), nickel chloride hexahydrate (3.52 g) and sodium borohydride (1.12 g) were reacted, to afford the title compound (2.02 g) as a pale yellow oil.

Nuclear Magnetic Resonance Spectrum (CDCl$_3$) δ ppm: 1.79–1.87 (2H, multiplet); 2.57–2.71 (4H, multiplet); 3.77 (3H, singlet); 4.66 (1H, singlet); 6.52 (1H, doublet, J=8.1 Hz); 6.71 (1H, doublet, J=7.8 Hz); 6.76 (1H, doublet, J=7.8 Hz); 6.80–6.84 (2H, multiplet); 7.07 (1H, triplet, J=7.7 Hz); 7.15–7.18 (3H, multiplet); 7.24–7.30 (4H, multiplet).

(3c) 3-Methoxy-4-{3-[(4-methoxyphenyl)-(3-phenylpropylamino)methyl]phenylamino}-3-cyclobutene-1,2-dione In a similar manner to that described in Example (1c), a solution of 3-[(4-methoxyphenyl)-(3-phenylpropylamino)methyl]phenylamine (2.02 g) [prepared as described in step (b) above] in methanol (40 ml) and 3,4-dimethoxy-3-cyclobutene-1,2-dione were reacted, to afford the title compound (1.82 g) as yellow foamy solid.

Nuclear Magnetic Resonance Spectrum (CDCl$_3$) δ ppm: 1.84–1.89 (2H, multiplet); 2.58–2.68 (4H, multiplet); 3.77 (3H, singlet); 4.44 (3H, singlet); 4.77 (1H, broad singlet); 6.84 (2H, doublet, J=8.5 Hz); 7.09–7.29 (11H, multiplet).

(3d) 3-Amino-4-{3-[(4-methoxyphenyl)-(3-phenylpropylamino)methyl]phenylamino}-3-cyclobutene-1,2-dione In a similar manner to that described in Example (1d), 3-methoxy-4-{3-[(4-methoxyphenyl)-(3-phenylpropylamino)methyl]phenylamino}-3-cyclobutene-1,2-dione [prepared as described in step (c) above] and a solution of ammonia in ethanol (2N, 8 ml) were reacted, to afford the title compound (1.58 g) as a yellow solid.

Nuclear Magnetic Resonance Spectrum (DMSO-$d_6$) δ ppm: 1.72–1.79 (2H, multiplet); 2.50–2.51 (2H, multiplet); 2.61 (2H, triplet, J=7.7 Hz); 3.70 (3H, singlet); 4.70 (1H, broad singlet); 6.84 (2H, doublet, J=8.6 Hz); 7.03 (1H, doublet, J=7.6 Hz); 7.12–7.40 (10H, multiplet). melting point: 178–180° C.

EXAMPLE 4

3-Amino-4-{3-[(4-methoxyphenyl)-(2-phenylethylamino)methyl]phenylamino}-3-cyclobutene-1,2-dione (Compound No. 2-553)

(4a) N-[(4-Methoxyphenyl)-(3-nitrophenyl)methyl]-N-(2-phenylethyl)amine

Triethylamine (4.33 ml) was added to a solution of 3-nitro-4'-methoxybenzophenone (2 g) and 2-phenylethylamine (1.97 ml) in anhydrous dichloromethane (20 ml). A solution of titanium tetrachloride (1.03 ml) in anhydrous dichloromethane (10 ml) was then slowly added dropwise to the mixture in an ice bath. This mixture was stirred at ambient temperature for 1 hour. Ethyl acetate and an aqueous solution of sodium hydrogencarbonate were added to the reaction mixture, which was then filtered through a Celite (trade mark) filter aid to remove the insoluble material. The ethyl acetate layer was separated from the filtrate. The aqueous layer was extracted with ethyl acetate. The ethyl acetate layer and extract were combined and washed with a saturated aqueous solution of sodium chloride. The organic layer was dried over anhydrous sodium sulfate and concentrated by evaporation under reduced pressure, to afford the imine derivative (2.91 g) as an orange oil.

In a similar mamner to that described in Example (1a), a solution of this oil in ethanol (60 ml), sodium cyanoborohydride (1.96 g) and acetic acid (0.67 ml) were reacted, to afford the title compound (2.70 g) as a yellow oil.

Nuclear Magnetic Resonance Spectrum (CDCl$_3$) δ ppm: 2.75–2.90 (4H, multiplet); 3.77 (3H, singlet); 4.86 (1H, singlet); 5.82 (2H, doublet, J=8.7 Hz); 7.15–7.45 (8H, multiplet); 7.68 (1H, doublet, J=7.7 Hz); 8.04 (1H, doublet of doublets, J=2.0, 8.0 Hz); 8.26 (1H, triplet, J=2.0 Hz).

(4b) 3-[(4-Methoxyphenyl)-(2-phenylethylamino)methyl]phenylamine

In a similar manner to that described in Example (1b), a solution of N-[(4-methoxyphenyl)-(3-nitrophenyl)methyl]-N-(2-phenylethyl)amine (2.70 g) [prepared as described in step (a) above] in methanol (60 ml), nickel chloride hexahydrate (3.52 g) and sodium borohydride (1.12 g) were reacted, to afford the title compound (1.74 g) as a clear colorless oil.

Nuclear Magnetic Resonance Spectrum (CDCl$_3$) δ ppm: 2.80–2.86 (4H, multiplet); 3.76 (3H, singlet); 4.68 (1H, singlet); 6.51 (1H, doublet of doublets, J=3.1, 8.1 Hz); 6.65 (1H, singlet); 6.71 (1H, doublet, J=7.9 Hz); 6.80 (2H, doublet, J=8.7 Hz); 7.05 (1H, triplet, J=7.6 Hz); 7.15–7.40 (7H, multiplet).

(4c) 3-Methoxy-4-{3-[(4-methoxyphenyl)-(2-phenylethylamino)methyl]phenylamino]-3-cyclobutene-1,2-dione In a similar manner to that described in Example (1c), a solution of 3-[(4-methoxyphenyl)-(2-phenylethylamino) methyl]phenylamine (1.74 g) [prepared as described in step (b) above] in methanol (40 ml) and 3,4-dimethoxy-3-cyclobutene-1,2-dione (776 mg) were reacted, to afford the title compound (1.88 g) as yellow foamy solid.

Nuclear Magnetic Resonance Spectrum (CDCl$_3$) δ ppm: 2.70–3.00 (4H, multiplet); 3.75 (3H, singlet); 4.42 (3H, singlet); 4.46 (1H, singlet); 6.70–7.35 (13H, multiplet).

(4d) 3-Amino-4-{3-[(4-methoxyphenyl)-(2-phenylethylamino)methyl]phenylamino}-3-cyclobutene-1,2-dione In a similar manner to that described in Example (1d), 3-methoxy-4-{3-[(4-methoxyphenyl)-(2-phenylethylamino) methyl]phenylamino}-3-cyclobutene-1,2-dione (1.88 g) [prepared as described in step (c) above] and a solution of ammonia in ethanol (2N, 8.4 ml) were reacted, to give the title compound (1.66 g) as a yellow solid.

Nuclear Magnetic Resonance Spectrum (DMSO-$d_6$) δ ppm: 2.60–2.85 (4H, multiplet); 3.70 (3H, singlet); 4.78 (1H, singlet); 6.84 (2H, doublet, J=8.6 Hz); 7.00–7.45 (11H, multiplet). melting point: 174–176° C.

EXAMPLE 5

3-Amino-4-{3-[(4-methoxyphenyl)-(2-phenylpropylamino)methyl]phenylamino]-3-cyclobutene-1,2-dione (Compound No. 2-557)

(5a) N-[(4-Methoxyphenyl)-(3-nitrophenyl)methyl]-N-(2-phenylpropyl)amine

Triethylamine (4.33 ml) was added to a solution of 3-nitro-4'-methoxybenzophenone (2 g) and 2-phenylpropylamine (2.27 ml) in anhydrous dichloromethane (20 ml). A solution of titanium tetrachloride (1.03 ml) in anhydrous dichloromethane (10 ml) was slowly added dropwise to the mixture in an ice bath. This mixture was stirred at ambient temperature for 1 hour. At the end of this time, ethyl acetate and an aqueous solution of sodium hydrogencarbonate were added to the reaction mixture. This was filtered through a Celite (trade mark) filter aid to remove the insoluble material, and the ethyl acetate layer was separated from the filtrate. The aqueous layer was extracted with ethyl acetate. The ethyl acetate layer and extract were combined and washed with a saturated aqueous solution of sodium chloride. The organic layer was dried over anhydrous sodium sulfate and concentrated by evaporation under reduced pressure, to afford the imine derivative.

In a similar manner to that described in Example (1a), a solution of this oil in ethanol (60 ml), sodium cyanoborohydride (1.96 g) and acetic acid (0.67 ml) were reacted, to afford the title compound (3.17 g) as a yellow oil.

Nuclear Magnetic Resonance Spectrum (CDCl$_3$) δ ppm: 1.25–1.27 (3H, multiplet); 2.66–2.79 (2H, multiplet); 2.93–2.98 (1H, multiplet); 3.76 (3H, singlet); 4.78 and 4.80 (total 1H, each singlet); 6.78–6.83 (2H, multiplet); 7.14–7.44 (8H, multiplet); 7.61 and 7.67 (total 1H, each doublet, J=7.9 Hz); 8.01–8.05 (1H, multiplet); 8.18 and 8.24 (total 1H, each doublet, J=1.8, 1.9 Hz).

(5b) 3-[(4-Methoxyphenyl)-(2-phenylpropylamino)methyl]phenylamine

In a similar manner to that described in Example (1b), a solution of N-[(4-methoxyphenyl)-(3-nitrophenyl)methyl]-N-(2-phenylpropyl)amine (3.17 g) [prepared as described in step (a) above] in methanol (60 ml), nickel chloride hexahydrate (3.7 g) and sodium borohydride (1.18 g) were reacted, to afford the title compound (2.52 g) as a clear purple oil.

Nuclear Magnetic Resonance Spectrum (CDCl$_3$) δ ppm: 1.24 (3H, doublet, J=7.2 Hz); 2.71–2.74 (2H, multiplet); 2.92–2.97 (1H, multiplet); 3.75 (3H, singlet); 4.62 (1H, singlet); 6.48–6.81 (5H, multiplet); 7.00–7.05 (1H, multiplet); 7.15–7.31 (7H, multiplet).

(5c) 3-Methoxy-4-{3-[(4-methoxyphenyl)-(2-phenylpropylamino)methyl]phenylamino}-3-cyclobutene-1,2-dione In a similar manner to that described in Example (1c), a solution of 3-[(4-methoxyphenyl)-(2-phenylpropylamino) methyl]phenylamine (2.52 g) [prepared as described in step (b) above] in methanol (25 ml) and 3,4-dimethoxy-3-cyclobutene-1,2-dione (1.09 g) were reacted, to afford the title compound (2.35 g) as a pink foamy solid.

Nuclear Magnetic Resonance Spectrum (CDCl$_3$) δ ppm: 1.25 (3H, doublet, J=7.3 Hz); 2.69–2.79 (2H, broad); 2.94–3.02 (1H, broad); 3.75 (3H, singlet); 4.42 (3H, singlet); 4.73 (1H, broad singlet); 6.78–6.82 (2H, multiplet); 7.00–7.34 (11H, multiplet).

(5d) 3-Amino-4-{3-[(4-methoxyphenyl)-(2-phenylpropylamino)methyl]phenylamino}-3-cyclobutene-1,2-dione In a similar manner to that described in Example (1d), 3-methoxy-4-{3-[(4-methoxyphenyl)-(2-phenylpropylamino)methyl]phenylamino}-3-cyclobutene-1,2-dione (2.35 g) [prepared as described in step (c) above] and a solution of ammonia in ethanol (2N, 10.2 ml) were reacted, to give the title compound (1.87 g) as a yellow solid.

Nuclear Magnetic Resonance Spectrum (DMSO-d$_6$) δ ppm: 1.21 (3H, doublet, J=6.9 Hz); 2.54–2.65 (2H, multiplet); 2.88–2.95 (1H, multiplet); 3.686 and 3.694 (total 3H, each singlet); 4.69 and 4.70 (total 1H, each singlet); 6.82 (2H, triplet, J=8.5 Hz); 6.95–7.01 (1H, multiplet); 7.14–7.39 (10H, multiplet). melting point: 192–194° C.

EXAMPLE 6

3-Amino-4-{3-[(4-metboxyphenyl)-(3,3-diphenylpropylamino)methyl]phenylamino}-3-cyelobutene-1,2-dione (Compound No. 2-564)

(6a) N-[(4-Methoxyphenyl)-(3-nitrophenyl)methyl-N-(3,3-diphenylpropyl)amine

Triethylamine (4.33 ml) was added to a solution of 3-nitro-4'-methoxybenzophenone (2 g) and 3,3-diplienylpropylamine (2.09 ml) in anhydrous dichloromethane (20 ml). A solution of titanium tetrachloride (1.03 ml) in anhydrous dichloromethane (10 ml) was slowly added dropwise to the mixture in an ice bath. This mixture was then stinred at ambient temperature for 1 hour. At the end of this time, ethyl acetate and an aqueous solution of sodium hydrogencarbonate were added to the reaction mixture. This was filtered through a Celite (trade mark) filter aid to remove the insoluble material, and the ethyl acetate layer was separated from the filtrate. The aqueous layer was extracted with ethyl acetate. The ethyl acetate layer and extract were combined and washed with a saturated aqueous solution of sodium chloride. The organic layer was dried over anhydrous sodium sulfate and concentrated by evaporation under reduced pressure, to afford the imine derivative (3.62 g) as a brown oil.

In a similar manner to that described in Example (1a), a solution of this oil in ethanol (60 ml), sodium cyanoborohydride (1.96 g) and acetic acid (0.67 ml) were reacted, to afford the title compound (3.53 g) as an orange oil.

Nuclear Magnetic Resonance Spectrum (CDCl$_3$) δ ppm: 2.27 (2H, quartet, J=7.5 Hz); 2.45–2.65 (2H, multiplet); 3.77 (3H, singlet); 4.06 (1H, triplet, J=7.5 Hz); 4.76 (1H, singlet); 6.82 (2H, doublet, J=8.6 Hz); 7.10–7.35 (12H, multiplet); 7.39 (1H, triplet, J=8.0 Hz); 7.63 (1H, doublet, J=7.5 Hz); 8.00–8.05 (1H, multiplet); 8.23 (1H, triplet, J=1.6 Hz).

(6b) 3-[(4-Methoxyphenyl)-(3,3-diphenylpropylamino) methyl]phenylamine

In a similar manner to that described in Example (1b), a solution of N-[(4-methoxyphenyl)-(3-nitrophenyl)methyl]-N-(3,3-diphenylpropyl)amine (3.53 g) [prepared as described in step (a) above] in ethanol (70 ml), nickel chloride hexahydrate (3.71 g) and sodium borohydride (1.18 g) were reacted, to afford the title compound (2.67 g) as a yellow oil.

Nuclear Magnetic Resonance Spectrum (CDCl$_3$) δ ppm: 2.25 (2H, quartet, J=7.5 Hz); 2.50–2.60 (2H, multiplet); 3.76 (3H, singlet); 4.05 (1H, triplet, J=7.5 Hz); 4.59 (1H, singlet); 6.62 (1H, triplet, J=1.5 Hz); 6.48–6.51 (1H, multiplet); 6.68 (1H, doublet, J=7.7 Hz); 6.79 (2H, doublet, J=8.7 Hz); 7.03 (1H, triplet, J=7.8 Hz); 7.10–7.35 (12H, multiplet).

(6c) 3-Methoxy-4-{3-[(4-metloxyphenyl)-(3,3-diphenylpropylamino)methyl]phenylamino}-3-cyclobutene-1,2-dione In a similar manner to that described in Example (1c), a solution of 3-[(4-methoxyphenyl)-(3,3-diphenylpropylamino)methyl]phenylamine (1.99 g) [prepared as described in step (b) above] in methanol (40 ml) and 3,4-dimethoxy-3-cyclobutene-1,2-dione (701 mg) were reacted, to afford the title compound (1.86 g) as a pale yellow foamy solid.

Nuclear Magnetic Resonance Spectrum (CDCl$_3$) δ ppm: 2.35–2.45 (2H, multiplet); 2.60–2.70 (2H, multiplet); 3.76 (3H, singlet); 4.02 (1H, triplet, J=7.7 Hz); 4.41 (3H, singlet); 4.80 (1H, singlet); 6.82 (2H, doublet, J=8.6 Hz); 7.00–7.40 (16H, multiplet).

(6d) 3-Amino-4-{3-[(4-methoxyphenyl)-(3,3-diphenylpropylamino)methyl]phenylamino}-3-cyclobutene-1,2-dione In a similar maiser to that described in Example (1d), 3-methoxy-4-{3-[(4-methoxyphenyl)-(3,3-diphenylpropylamino)methyl]phenylamino}-3-cyclobutene-1,2-dione (1.86 g) [prepared as described in step (c) above] and a solution of ammonia in ethanol (2N, 7 ml) were reacted, to give the title compound (1.36 g) as a pale yellow solid.

Nuclear Magnetic Resonance Spectrum (DMSO-d$_6$) δ ppm: 2.10–2.70 (4H, multiplet); 3.70 (3H, singlet); 4.09 (1H, triplet, J=7.6 Hz); 4.70 (1H, broad); 6.70–7.50 (18H, multiplet). melting point: 132–134° C.

EXAMPLE 7

3-Amino-4-{3-[(4-methoxyphenyl)-(2,2-diphenylethylamino)methyl]phenylamino}-3-cyclobutene-1,2-dione (Compound No. 2-560)

(7a) N-[(4-Methoxyphenyl)-(3-nitrophenyl)methyl]-N-(2,2-diphenylethyl)amine

Triethylamine (3.22 ml) was added to a solution of 3-nitro-4'-methoxybenzophenone (1.5 g) and 2,2-diphenylethylamine (2.29 g) in anhydrous dichloromethane (15 ml). A solution of titanium tetrachloride (0.77 ml) in anhydrous dichloromethane (10 ml) was slowly added dropwise to the mixture in an ice bath. This mixture was stirred at ambient temperature for 1 hour. At the end of this time, ethyl acetate and an aqueous solution of sodium hydrogencarbonate were added to the reaction mixture. This was filtered through a Celite (trade mark) filter aid to remove the insoluble material, and the ethyl acetate layer was separated from the filtrate. The aqueous layer was extracted with ethyl acetate. The ethyl acetate layer and extract were combined and washed with a saturated aqueous solution of sodium chloride. The organic layer was dried over anhydrous sodium sulfate and concentrated by evaporation under reduced pressure, to afford the imine derivative (3.82 g) as an orange oil.

In a similar manner to that described in Example (1a), a solution of this oil in ethanol (60 ml), sodium cyanoborohydride (1.46 g) and acetic acid (0.5 ml) were reacted, to afford the title compound (2.54 g) as a yellow oil.

Nuclear Magnetic Resonance Spectrum (CDCl$_3$) δ ppm: 3.19–3.24 (2H, multiplet); 3.76 (3H, singlet); 4.22 (1H, triplet, J=7.5 Hz); 4.87 (1H, singlet); 6.81 (2H, doublet, J=8.7 Hz); 7.17–7.30 (12H, multiplet); 7.41 (1H, triplet, J=8.0 Hz); 7.64 (1H, doublet, J=7.5 Hz); 8.03 (1H, doublet, J=7.9 Hz); 8.22 (1H, doublet, J=1.9 Hz).

(7b) 3-[(4-Methoxyphenyl)-(2,2-diphenylethylamino) methyl]phenylamine

In a similar manner to that described in Example (1b), a solution of [(4-methoxyphenyl)-(3-nitrophenyl)methyl]-(2,2-diphenylethyl)amine (2.54 g) [prepared as described in step (a) above] in methanol (50 ml), nickel chloride hexahydrate (2.76 g) and sodium borohydride (878 mg) were reacted, to afford the title compound (2.02 g) as a clear colorless oil.

Nuclear Magnetic Resonance Spectrum (CDCl$_3$) δ ppm: 3.18 (2H, doublet, J=7.8 Hz); 3.75 (3H, singlet); 4.21 (1H, triplet, J=7.8 Hz); 4.69 (1H, singlet); 6.50 (1H, doublet, J=7.0 Hz); 6.58–6.59 (1H, multiplet); 6.67 (1H, doublet, J=7.5 Hz); 6.78 (2H, doublet, J=8.7 Hz); 7.03 (1H, triplet, J=7.7 Hz); 7.15–7.29 (12H, multiplet).

(7c) 3-Methoxy-4-{3-[(4-methoxyphenyl)-(2,2-diphenylethylamino)methyl]phenylamino}-3-cyclobutene-1,2-dione In a similar manner to that described in Example (1c), a solution of 3-[(4-methoxyphenyl)-(2,2-diphenylethylamino) methyl]phenylamine (2.02 g) [prepared as described in step (b) above] in methanol (40 ml) and 3,4-dimethoxy-3-cyclobutene-1,2-dione (731 mg) were reacted, to afford the title compound (1.35 g) as a white foamy solid.

Nuclear Magnetic Resonance Spectrum (CDCl$_3$) δ ppm: 3.12–3.17 (1H, multiplet); 3.21–3.26 (1H, multiplet); 3.76 (3H, singlet); 4.19 (1H, triplet, J=7.5 Hz); 4.38 (3H, singlet); 4.79 (1H, singlet); 6.80 (2H, doublet, J=8.7 Hz); 7.07–7.29 (16H, multiplet).

(7d) 3-Amino-4-{3-[(4-methoxyphenyl)-(2,2-diphenylethylamino)methyl]phenylamino}-3-cyclobutene-1,2-dione In a similar manner to that described in Example (1d), 3-methoxy-4-{3-[(4-methoxyphenyl)-(2,2-diphenylethylamino)methyl]phenylamino}-3-cyclobutene-1,2-dione (1.35 g) [prepared as described in step (c) above] and a solution of ammonia in ethanol (2N, 5.2 ml) were reacted, to give the title compound (1.36 g) as a pale yellow solid.

Nuclear Magnetic Resonance Spectrum (DMSO-d$_6$) δ ppm: 3.07 (2H, doublet, J=6.9 Hz); 3.69 (3H, singlet); 4.22 (1H, triplet, J=6.9 Hz); 4.79 (1H, broad singlet); 6.82 (2H, doublet, J=8.5 Hz); 6.98 (1H, doublet, J=7.7 Hz); 7.14–7.28 (14H, multiplet); 7.36 (1H, doublet, J=7.9 Hz). melting point: 193–194° C.

EXAMPLE 8

3-Amino-4-<3-{(4-methoxyphenyl)-[2-(3-fluorophenyl)ethylamino]methyl}phenylamino>-3-cyclobutene-1,2-dione (Compound No. 2-814)

(8a) N-[(4-Methoxyphenyl)-(3-nitrophenyl)methyl]-N-[2-(3-fluorophenyl)ethyl]amine Triethylamine (4.33 ml) was added to a solution of 3-nitro-4'-methoxybenzophenone (2.0 g) and 2-(3-fluorophenyl)ethylamine (2.04 ml) in anhydrous dichloromethane (20 ml). A solution of titanium tetrachloride (1.03 ml) in anhydrous dichloromethane (10 ml) was slowly added dropwise to the mixture in an ice bath. This mixture was stirred at ambient temperature for 1 hour. At the end of this time, ethyl acetate and an aqueous solution of sodium hydrogencarbonate were added to the reaction mixture. This was filtered through a Celite (trade mark) filter aid to remove the insoluble material, and the ethyl acetate layer was separated from the filtrate. The aqueous layer was extracted with ethyl acetate. The ethyl acetate layer and extract were combined and washed with a saturated aqueous solution of sodium chloride. The organic layer was dried over anhydrous sodium sulfate and concentrated by evaporation under reduced pressure, to afford the imine derivative (2.76 g) as an orange oil.

In a similar manner to that described in Example (1a), a solution of this oil in ethanol (60 ml), sodium cyanoborohydride (1.96 g) and acetic acid (0.67 ml) were reacted, to afford the title compound (2.51 g) as a yellow oil.

Nuclear Magnetic Resonance Spectrum (CDCl$_3$) δ ppm: 2.78–2.88 (4H, multiplet); 3.77 (3H, singlet); 4.85 (1H, singlet); 6.82–6.97 (5H, multiplet); 7.21–7.26 (3H, multiplet); 7.43 (1H, triplet, J=7.8 Hz); 7.68 (1H, doublet, J=7.8 Hz); 8.05 (1H, doublet, J=8.0 Hz); 8.25–8.26 (1H, multiplet).

(8b) 3-{(4-Methoxyphenyl)-[2-(3-fluorophenyl)ethylamino] methyl}phenylamine

In a similar manner to that described in Example (1b), a solution of N-[(4-methoxyphenyl)-(3-nitrophenyl)methyl]-N-[2-(3-fluorophenyl)ethyl]amine (2.51 g) [prepared as described in step (a) above] in methanol (50 ml), nickel chloride hexahydrate (3.14 g) and sodium borohydride (1.0 g) were reacted, to afford the title compound (1.94 g) as a yellow oil.

Nuclear Magnetic Resonance Spectrum (CDCl$_3$) δ ppm: 2.79–2.85 (4H, multiplet); 3.77 (3H, singlet); 4.67 (1H, singlet); 6.51 (1H, doublet, J=8.2 Hz); 6.66 (1H, doublet, J=1.9 Hz); 6.72 (1H, doublet, J=7.4 Hz); 6.81 (2H, doublet, J=8.7 Hz); 6.89 (2H, doublet, J=8.9 Hz); 6.96 (1H, doublet, J=7.8 Hz); 7.05 (1H, triplet, J=7.7 Hz); 7.19–7.26 (3H, multiplet).

(8c) 3-Methoxy-4-<3-{(4-methoxyphenyl)-[2-(3-fluorophenyl)ethylamino]methyl}phenylamino>-3-cyclobutene-1,2-dione In a similar manner to that described in Example (1c), a solution of 3-{(4-methoxyphenyl)-[2-(3-fluorophenyl) ethylamino]methyl}phenylamine (1.94 g) [prepared as described in step (b) above] in methanol (40 ml) and 3,4-dimethoxy-3-cyclobutene-1,2-dione (824 mg) were reacted, to afford the title compound (2.07 g) as a white foamy solid.

Nuclear Magnetic Resonance Spectrum (CDCl$_3$) δ ppm: 2.77–2.88 (4H, multiplet); 3.76 (3H, singlet); 4.44 (3H, singlet); 4.78 (1H, broad singlet); 6.79–6.97 (5H, multiplet); 7.03–7.28 (7H, multiplet).

(8d) 3-Amino-4-<3-{(4-methoxyphenyl)-[2-(3-fluorophenyl)ethylamino]methyl}phenylamino>-3-cyclobutene-1,2-dione In a similar manner to that described in Example (1d), 3-methoxy-4-<3-{(4-methoxyphenyl)-[2-(3-fluorophenyl) ethylamino]methyl}phenylamino>-3-cyclobutene-1,2-dione (2.07 g) [prepared as described in step (c) above] and a solution of ammonia in ethanol (2N, 9 ml) were reacted, to give the title compound (1.73 g) as a yellow solid.

Nuclear Magnetic Resonance Spectrum (DMSO-d$_6$) δ ppm: 2.67 (2H, broad singlet); 2.77–2.80 (2H, multiplet); 3.70 (3H, singlet); 4.76 (1H, broad singlet); 6.84 (2H, doublet J=8.5 Hz); 6.96–7.03 (4H, multiplet); 7.21–7.39 (6H, multiplet). melting point: 139–141° C.

EXAMPLE 9

3-Amino-4-<3-{(4-methoxyphenyl)-[1-(3,5-difluorophenyl)ethylamino]methyl}phenylamino)-3-cyclobutene-1,2-dione (Compound No. 2-1625)

(9a) N-[(4-Methoxyphenyl)-(3-nitrophenyl)methyl-N-[1-(3,5-difluorophenyl)ethyl)]amine Triethylamine (4.8 ml) was added to a solution of 3-nitro-4'-methoxybenzophenone (1.5 g) and 1-(3,5-difluorophenyl)ethylamine hydrochloride (2.26 g) in anhydrous dichloromethane (30 ml). A solution of titanium tetrachloride (0.77 ml) in anhydrous dichloromethane (10 ml) was slowly added dropwise to the mixture in an ice bath. This mixture was stirred at ambient temperature for 1 hour. At the end of this time, ethyl acetate and an aqueous solution of sodium hydrogencarbonate were added to the reaction mixture. This was filtered through a Celite (trade mark) filter aid to remove the insoluble material, and the ethyl acetate layer was separated from the filtrate. The aqueous layer was extracted with ethyl acetate. The ethyl acetate layer and extract were combined and washed with a saturated aqueous solution of sodium chloride. The organic layer was dried over anhydrous sodium sulfate and concentrated by evaporation under reduced pressure, to afford the imine derivative (3.12 g) as an orange oil.

In a similar manner to that described in Example (1a), a solution of this oil in ethanol (60 ml), sodium cyanoborohydride (1.46 g) and acetic acid (0.5 ml) were reacted, to afford the title compound (2.65 g) as a yellow oil.

Nuclear Magnetic Resonance Spectrum (CDCl$_3$) δ ppm: 1.34–1.38 (3H, multiplet); 3.58–3.70 (1H, multiplet); 3.76 and 3.82 (total 3H, each singlet); 4.63 and 4.69 (total 1H, each singlet); 6.65–7.93 (5H, multiplet); 7.15–7.20 (2H, multiplet); 7.38–7.68 (2H, multiplet); 8.02–8.28 (2H, multiplet).

(9b) 3-{(4-Methoxyphenyl)-[1-(3,5-difluorophenyl)ethylamino]methyl}phenylamine

In a similar manner to that described in Example (1b), a solution of N-[(4-methoxyphenyl)-(3-nitrophenyl)methyl]-N-[1-(3,5-difluorophenyl)ethyl]amine (2.65 g) [prepared as described in step (a) above] in methanol (50 ml), nickel chloride hexahydrate (3.16 g) and sodium borohydride (1.0 g) were reacted, to afford the title compound (2.24 g) as a pale orange oil.

Nuclear Magnetic Resonance Spectrum (CDCl$_3$) δ ppm: 1.31 (3H, doublet, J=6.6 Hz); 3.55–3.73 (1H, multiplet); 3.76 and 3.80 (total 3H, each singlet); 4.47 (1H, singlet); 6.50–7.26 (11H, multiplet).

(9c) 3-Methoxy-4-<3-{(4-methoxyphenyl)-[1-(3,5-difluorophenyl)ethylamino]methyl}phenylamino>-3-cyclobutene-1,2-dione In a similar manner to that described in Example (1c), a solution of 3-{(4-methoxyphenyl)-[1-(3,5-difluorophenyl)ethylamino]methyl}phenylamine (2.24 g) [prepared as described in step (b) above] in methanol (20 ml) and 3,4-dimethoxy-3-cyclobutene-1,2-dione (950 mg) were reacted, to afford the title compound (2.2 g) as a white foamy solid.

Nuclear Magnetic Resonance Spectrum (CDCl$_3$) δ ppm: 1.32–1.37 (3H, multiplet); 3.65 (1H, quartet, J=6.6 Hz); 3.76 and 3.81 (total 3H, each singlet); 4.44 (3H, singlet); 4.55 and 4.58 (total 1H, each singlet); 6.63–7.35 (11H, multiplet).

(9d) 3-Amino-4-<3-{(4-methoxyphenyl)-[1-(3,5-difluorophenyl)ethylamino]methyl}phenylamino>-3-cyclobutene-1,2-dione In a similar manner to that described in Example (1d), 3-methoxy-4-<3-{(4-methoxyphenyl)-[1-(3,5-difluorophenyl)ethylamino]methyl}phenylamino>-3-cyclobutene-1,2-dione (2.2 g) [prepared as described in step (c) above] and a solution of ammonia in ethanol (2N, 9.2 ml) were reacted, to give the title compound (1.86 g) as a yellow solid.

Nuclear Magnetic Resonance Spectrum (DMSO-d$_6$) δ ppm: 1.26–1.31 (3H, multiplet); 3.50–3.65 (1H, multiplet); 3.69 and 3.73 (total 3H, each singlet); 4.43 and 4.46 (total 1H, each singlet); 6.80–7.50 (11H, mnltiplet). melting point: 177–181° C.

EXAMPLE 10

3-Amino-4-<3-{(4-methoxyphenyl)-[1-(4-pyridyl)ethylamino]methyl}phenylamino>-3-cyclobutene-1,2-dione (Compound No. 2-1962)

(10a) N-[(4-Methoxyphenyl)-(3-nitrophenyl)methyl]-N-[1-(4-pyridyl)ethyl]amine

Triethylamine (4.33 ml) was added to a solution of 3-nitro-4'-methoxybenzophenone (2 g) and 1-(4-pyridyl)ethylamine (1.91 g) in anhydrous dichloromethane (40 ml). A solution of titanium tetrachloride (1.03 ml) in anhydrous dichloromethane (10 ml) was slowly added dropwise to the mixture in an ice bath. This mixture was stirred at ambient temperature for 1 hour. At the end of this time, ethyl acetate and an aqueous solution of sodium hydrogencarbonate were added to the reaction mixture. This was filtered through a Celite (trade mark) filter aid to remove the insoluble material, and the ethyl acetate layer was separated from the filtrate. The aqueous layer was extracted with ethyl acetate. The ethyl acetate layer and extract were combined and washed with a saturated aqueous solution of sodium chloride. The organic layer was dried over anhydrous sodium sulfate and concentrated by evaporation under reduced pressure, to afford the imine derivative (3.13 g) as an orange oil.

In a similar manner to that described in Example (1a), a solution of this oil in ethanol (60 ml), sodium cyanoborohydride (1.96 g) and acetic acid (0.7 ml) were reacted, to afford the title compound (2.41 g) as a yellow oil.

Nuclear Magnetic Resonance Spectrum (CDCl$_3$) δ ppm: 1.36–1.41 (3H, multiplet); 3.58–3.72 (1H, multiplet); 3.76 and 3.81 (total 3H, each singlet); 4.61 and 4.66 (total 1H, each singlet); 6.79–6.92 (2H, multiplet); 7.10–7.23 (4H, multiplet); 7.40 and 7.48 (total 1H, each triplet, J=7.9 Hz); 7.58 and 7.64 (total 1H, each doublet, J=7.9 Hz); 8.02–8.13 (1H, multiplet); 8.23–8.28 (1H, multiplet); 8.52–8.62 (2H, multiplet).

(10b) 3-{(4-Methoxyphenyl)-1-(4-pyridyl)ethylamino]methyl}phenylamine

In a similar manner to that described in Example (1b), a solution of N-[(4-methoxyphenyl)-(3-nitrophenyl)methyl]-N-[1-(4-pyridyl)ethyl]amine (2.41 g) [prepared as described in step (a) above] in ethanol (40 ml), nickel chloride hexahydrate (3.14 g) and sodium borohydride (1.0 g) were reacted, to afford the title compound (1.09 g) as a yellow oil.

Nuclear Magnetic Resonance Spectrum (CDCl$_3$) δ ppm: 1.34 (3H, doublet, J=6.6 Hz); 3.55–3.75 (1H, multiplet); 3.76 and 3.80 (total 3H, each singlet); 4.44 (1H, singlet); 6.50–7.25 (10H, multiplet); 8.52–8.60 (2H, multiplet).

(10c) 3-Methoxy-4-<3-{(4-methoxyphenyl)-[1-(4-pyridyl)ethylamino]methyl}phenylamino>-3-cyclobutene-1,2-dione In a similar manner to that described in Example (1c), a solution of 3-{(4-methoxyphenyl)-[1-(4-pyridyl)ethylamino]methyl}phenylamine (1.09 g) [prepared as described in step (b) above] in methanol (20 ml) and 3,4-dimethoxy-3-cyclobutene-1,2-dione (511 mg) were reacted, to afford the title compound (1.21 g) as a yellow foamy solid.

Nuclear Magnetic Resonance Spectrum (CDCl$_3$) δ ppm: 1.25–1.40 (3H, multiplet); 3.60–3.75 (1H, multiplet); 3.75 and 3.80 (total 3H, each singlet); 4.50–4.60 (1H, multiplet); 6.65–8.65 (12H, inultiplet).

(10d) 3-Amino-4-<3-{(4-methoxyphenyl)-[1-(4-pyridyl)ethylamino]methyl}phenylamino>-3-cyclobutene-1,2-dione In a similar manner to that described in Example (1d), a solution of 3-methoxy-4-<3-{(4-methoxyphenyl)-[1-(4-pyridyl)ethylamino]methyl}phenylamino>-3-cyclobutene-1,2-dione (1.21 g) [prepared as described in step (c) above] in ethanol (10 ml) and a solution of ammonia in ethanol (2N, 6 ml) were reacted, to give the title compound (1.0 g) as a yellow solid.

Nuclear Magnetic Resonance Spectrum (DMSO-$d_6$) δ ppm: 1.20–1.35 (3H, multiplet); 3.50–3.62 (1H, multiplet); 3.69 and 3.73 (total 3H, each singlet); 4.41 and 4.45 (total 1H, each singlet); 7.15–7.45 (7H, multiplet); 7.80–8.00 (3H miultiplet); 8.48–8.52 (2H, multiplet). melting point: 125° C. (dec).

EXAMPLE 11

3-Amino-4-<3-{(4-methoxyphenyl)-[1-(2-thienyl) ethylamino]methyl}phenylamino>-3-cyclobutene-1, 2-dione (Compound No. 2-1899)

(11a) N-[(4-Methoxyphenyl)-(3-nitrophenyl)methyl]-N-[1-(2-thienyl)ethyl)]amine

Triethylamine (4.6 ml) was added to a solution of 3-nitro-4'-methoxybenzophenone (1.41 g) and 1-(2-thienyl) ethylamine hydrochloride (1.78 g) in anhydrous dichloromethane (20 ml). A solution of titanium tetrachloride (0.73 ml) in anhydrous dichloromethane (10 ml) was slowly added dropwise to the mixture in an ice bath. This mixture was strired at ambient temperature for 1 hour. At the end of this time, ethyl acetate and an aqueous solution of sodium hydrogencarbonate were added to the reaction mixture. This was filtered through a Celite (trade mark) filter aid to remove the insoluble material, and the ethyl acetate layer was separated from the filtrate. The aqueous layer was extracted with ethyl acetate. The ethyl acetate layer and extract were combined and washed with a saturated aqueous solution of sodium chloride. The organic layer was dried over anhydrous sodium sulfate and concentrated by evaporation under reduced pressure, to afford the imine derivative (2.35 g) as a red oil.

In a similar manner to that described in Example (1a), a solution of this oil in ethanol (40 ml), sodium cyanoborohydride (1.38 g) and acetic acid (0.48 ml) were reacted, to afford the title compound (2.11 g) as a yellow oil.

Nuclear Magnetic Resonance Spectrum (CDCl$_3$) δ ppm: 1.45–1.52 (3H, multiplet); 3.76 and 3.81 (total 3H, each singlet); 3.87–4.01 (1H, multiplet); 4.84 and 4.86 (total 1H, each singlet); 6.75–7.00 (4H, multiplet); 7.15–7.30 (3H, multiplet); 7.41 and 7.49 (total 1H, triplet, J=8.0 Hz); 7.65 and 7.74 (total 1H, each doublet, J=7.4 Hz); 8.00–8.12 (1H, multiplet); 8.22–8.33 (1H, multiplet).

(11b) 3-{(4-Methoxyphenyl)-[1-(2-thienyl)ethylamino] methyl}phenylamine

In a similar manner to that described in Example (1b), a solution of N-[(4-methoxyphenyl)-(3-nitrophenyl)methyl]-N-[1-(2-thienyl)ethyl]amine (2.11 g) [prepared as described in step (a) above] in ethanol (40 ml), nickel chloride hexahydrate (2.71 g) and sodium borohydride (863 mg) were reacted, to afford the title compound (1.66 g) as a dark brown oil.

Nuclear Magnetic Resonance Spectrum (CDCl$_3$) δ ppm: 1.46 (3H, doublet, J=6.6 Hz); 3.75 and 3.80 (total 3H, each singlet); 3.90–4.02 (1H, niultiplet); 4.68 (1H, singlet); 6.47–7.30 (11H, multiplet).

(11c) 3-Methoxy-4-<3-{(4-methoxyphenyl)-[1-(2-thienyl) ethylamino]methyl}phenylamino>-3-cyclobutene-1,2-dione In a similar manner to that described in Example (1c), a solution of 3-{(4-methoxyphenyl)-[1-(2-thienyl) ethylamino]methyl}phenylamine (1.66 g) [prepared as described in step (b) above] in methanol (30 ml) and 3,4-dimethoxy-3-cyclobutene-1,2-dione (767 mg) were reacted, to afford the title compound (1.97 g) as a white foamy solid.

Nuclear Magnetic Resonance Spectrum (CDCl$_3$) δ ppm: 1.45–1.51 (3H, multiplet); 3.76 and 3.81 (total 3H, each singlet); 3.90–4.00 (1H, multiplet); 4.44 (3H, singlet); 4.76 and 4.78 (total 1H, each singlet); 6.78–7.35 (11H, multiplet).

(11d) 3-Amino-4-<3-{4-methoxyphenyl)-[1-(2-thienyl) ethylamino]methy}phenylamino>-3-cyclobutene-1,2-dione In a similar manner to that described in Example (1d), a solution 3-methoxy-4-<3-{(4-methoxyphenyl)-[ -(2-thienyl) ethylamino]methyl}phenylamino>-3-cyclobutene-1,2-dione (1.97 g) [prepared as described in step (c) above] in ethanol (40 ml) and a solution of ammonia in ethanol (2N, 10 ml) were reacted, to give the title compound (1.59 g) as a yellow solid.

Nuclear Magnetic Resonance Spectrum (DMSO-$d_6$) δ ppm: 1.35–1.45 (3H, multiplet); 3.69 and 3.73 (total 3H, each singlet); 3.75–3.90 (1H, multiplet); 4.63 and 4.66 (total 1H, each singlet); 6.80–7.50 (11H, multiplet). melting point: 178–180° C.

EXAMPLE 12

3-Amino-4-<3-{phenyl-[1-(3,5-difluorophenyl) ethylamino]methyl}phenylamino>-3-cyclobutene-1, 2-dione (Compound No. 2-1523)

(12a) N-[(3-nitrophenyl)-phenylmethyl]-N-[1-(3,5-difluorophenyl)ethyl)]amine

Triethylamine (7.3 ml) was added to a solution of 3-nitrobenzophenone (2.0 g) and 1-(3,5-difluorophenyl) ethylamine hydrochloride (3.41 g) in anhydrous dichloromethane (40 ml). A solution of titanium tetrachloride (1.16 ml) in anhydrous dichloromethane (11 ml) was slowly added dropwise to the mixture in an ice bath. This mixture was stirred at ambient temperature for 1 hour. At the end of this time, ethyl acetate and an aqueous solution of sodium hydrogencarbonate were added to the reaction mixture. This was filtered through a Celite (trade mark) filter aid to remove the insoluble material, and the ethyl acetate layer was separated from the filtrate. The aqueous layer was extracted with ethyl acetate. The ethyl acetate layer and extract were combined and washed with a saturated aqueous solution of sodium chloride. The organic layer was dried over anhydrous sodium sulfate and concentrated by evaporation under reduced pressure, to afford the imine derivative.

In a similar manner to that described in Example (1a), a solution of this oil in ethanol (60 ml), sodium cyanoborohydride (2.21 g) and acetic acid (0.76 ml) were reacted, and the reaction mixture was purified to afford isomer A (904 mg, as a colorless oil) and isomer B (897 mg, as a white solid) of the title compound.

Isomer A

Nuclear Magnetic Resonance Spectrum (CDCl$_3$) δ ppm: 1.37 (3H, doublet, J=6.6 Hz); 3.63 (1H, quartet, J=6.6 Hz); 4.73 (1H, singlet); 6.65–6.80 (3H, multiplet); 7.20–7.35 (5H, multiplet); 7.50 (1H, triplet, J=7.8 Hz); 7.66 (1H, doublet, J=7.4 Hz); 8.10–8.13 (1H, multiplet); 8.26–8.28 (1H, multiplet).

Isomer B

Nuclear Magnetic Resonance Spectrum (CDCl$_3$) δ ppm: 1.36 (3H, doublet, J=6.6 Hz); 3.67 (1H, quartet, J=6.6 Hz); 4.68 (1H, singlet); 6.65–6.85 (3H, multiplet); 7.20–7.45 (6H, multiplet); 7.61 (1H, doublet, J=7.4 Hz); 8.04 (1H, doublet of doublets, J=1.8, 7.8 Hz); 8.24 (1H, broad singlet). melting point: 119–121° C.

(12b) 3-{Phenyl-[1-(3,5-difluorophenyl)ethylamino] methyl}phenylamine

In a similar manner to that described in Example (1b), a solution of isomer A of [(3-nitrophenyl)phenylmethyl]-[1-(3,5-difluorophenyl)ethyl]amine (900 mg) [prepared as described in step (a) above] in methanol (20 ml), nickel chloride hexahydrate (1.14 g) and sodium borohydride (363 mg) were reacted, to afford isomer A of the title compound (739 mg) as a pale yellow oil.

Isomer A

Nuclear Magnetic Resonance Spectrum (CDCl$_3$) δ ppm: 1.32 (3H, doublet, J=6.6 Hz); 3.70 (1H, quartet, J=6.6 Hz); 4.51 (1H, singlet); 6.55–6.87 (6H, multiplet); 7.07–7.40 (6H, multiplet).

In a similar manner to that described in Example (1b), a solution of isomer B of [(3-nitrophenyl)-phenylmethyl]-[1-(3,5-difluorophenyl)ethyl]amine (890 mg) in methanol (20 ml), nickel chloride hexahydrate (1.14 g) and sodium borohydride (363 mg) were reacted, to afford isomer B of the title compound (791 mg) as a colorless oil.

Isomer B

Nuclear Magnetic Resonance Spectrum (CDCl$_3$) δ ppm: 1.32 (3H, doublet, J=6.7 Hz); 3.64 (1H, quartet, J=6.7 Hz); 4.52 (1H, singlet); 6.50–7.35 (12H, multiplet).

(12c) 3-Methoxy-4-<3-{phenyl-[1-(3,5-difluorophenyl)ethylamino]methyl}phenylamino>-3-cyclobutene-1,2-dione In a similar manner to that described in Example (1c), a solution of isomer A of 3-{phenyl-[1-(3,5-difluorophenyl)ethylamino]methyl}phenylamine (733 mg) [prepared as described in step (b) above] in methanol (10 ml) and 3,4-dimethoxy-3-cyclobutene-1,2-dione (341 mg) were reacted, to afford isomer A of the title compound (814 mg) as a white solid.

Isomer A

Nuclear Magnetic Resonance Spectrum (CDCl$_3$) δ ppm: 1.36 (3H, doublet, J=6.6 Hz); 3.66 (1H, quartet, J=6.6 Hz); 4.43 (3H, singlet); 4.62 (1H, singlet); 6.65–6.85 (3H, multiplet); 7.10–7.40 (9H, multiplet). melting point: 155–157° C.

In a similar manner to that described in Example (1c), a solution of isomer B of 3-{phenyl-[1-(3,5-difluorophenyl)ethylamino]methyl}phenylamine (785 mg) in methanol (10 ml) and 3,4-dimethoxy-3-cyclobutene-1,2-dione (355 mg) were reacted, to afford isomer B of the title compound (888 mg) as a white foamy solid.

Isomer B

Nuclear Magnetic Resonance Spectrum (CDCl$_3$) δ ppm: 1.34 (3H, doublet, J=6.6 Hz); 3.65 (1H, doublet, J=6.6 Hz); 4.43 (3H, singlet); 4.60 (1H, singlet); 6.65–7.40 (12H, multiplet).

(12d) 3-Amino-4-<3-{phenyl-[1-(3,5-difluorophenyl)ethylamino]methyl}phenylamino>-3-cyclobutene-1,2-dione In a similar manner to that described in Example (1d), a solution of isomer A of 3-methoxy-4-<3-{phenyl)-[1-(3,5-difluorophenyl)ethylamino]methyl}phenylamino>-3-cyclobutene-1,2-dione (810 mg) [prepared as described in step (c) above] in tetrahydrofuran (5 ml) and a solution of ammonia in ethanol (2N, 3.6 ml) were reacted, to give isomer A of the title compound (733 mg) as a yellow solid.

Isomer A

Nuclear Magnetic Resonance Spectrum (DMSO-d$_6$) δ ppm: 1.30 (3H, doublet, J=6.6 Hz); 3.61 (1H, quartets J=6.6 Hz); 4.50 (1H, singlet); 6.95–7.45 (12H, multiplet). melting point: 184° C. (dec).

In a similar manner to that described in Example (1d), a solution of isomer B of 3-methoxy-4-<3-{phenyl-[1-(3,5-difluorophenyl)ethylamino]methyl}phenylamino>-3-cyclobutene-1,2-dione (880 mg) in ethanol (5 ml) and a solution of ammonia in ethanol (2N, 4.0 ml) were reacted, to give isomer B of the title compound (708 mg) as a pale yellow solid.

Isomer B

Nuclear Magnetic Resonance Spectrum (DMSO-d$_6$) δ ppm: 1.28 (3H, doublet, J=6.6 Hz); 3.55 (1H, quartet, J=6.6 Hz); 4.49 (1H, singlet); 6.80–7.45 (12H, multiplet). melting point: 197° C. (dec).

EXAMPLE 13

3-Amino-4-<3-{(3,4-dimethylphenyl)-[(S)-1-phenylethylamino]methyl}phenylamino)-3-cyclobutene-1,2-dione (Compound No. 2-533)

(13a) N-[(3-Nitrophenyl)-(3,4-dimethylphenyl)methyl]-N-[(S)-1-phenylethyl)]amine Triethylamine (4.33 ml) was added to a solution of 3-nitro-3',4'-dimethylbenzophenone (2.0 g) and (S)-1-phenylethylamine (1.99 ml) in anhydrous dichloromethane (20 ml). A solution of titanium tetrachloride (1.03 ml) in anhydrous dichloromethane (10 ml) was slowly added dropwise to the mixture in an ice bath. This mixture was stirred at ambient temperature for 1 hour. At the end of this time, ethyl acetate and an aqueous solution of sodium hydrogencarbonate were added to the reaction mixture. This was filtered through a Celite (trade mark) filter aid to remove the insoluble material, and the ethyl acetate layer was separated from the filtrate. The aqueous layer was extracted with ethyl acetate. The ethyl acetate layer and extract were combined and washed with a saturated aqueous solution of sodium chloride. The organic layer was dried over anhydrous sodium sulfate and concentrated by evaporation under reduced pressure, to afford the imine derivative (2.92 g) as a yellow oil.

In a similar manner to that described in Example (1a), a solution of this oil in ethanol (60 ml), sodium cyanoborohydride (2.21 g) and acetic acid (0.76 ml) were reacted, and the reaction mixture was purified to afford isomer A (1.10 g) as a colorless oil and isomer B (1.19 g) as a pale yellow oil of the title compound.

Isomer A

Nuclear Magnetic Resonance Spectrum (CDCl$_3$) δ ppm: 1.39 (3H, doublet, J=6.7 Hz); 2.20 (6H, singlet); 3.60 (1H, quartet, J=6.7 Hz); 4.65 (1H, singlet); 6.97–7.37 (8H, multiplet); 7.46 (1H, triplet, J=7.9 Hz); 7.69 (1H, doublet, J=7.5 Hz); 8.08 (1H, doublet, J=8.0 Hz); 8.26–8.28 (1H, multiplet).

Isomer B

Nuclear Magnetic Resonance Spectrum (CDCl$_3$) δ ppm: 1.38 (3H, doublet, J=6.7 Hz); 2.25 (6H, singlet); 3.70 (1H, quartet, J=6.7 Hz); 4.63 (1H, singlet); 7.01–7.02 (2H, multiplet); 7.11 (1H, doublet, J=8.2 Hz); 7.22–7.38 (6H, multiplet); 7.59 (1H, doublet, J=7.4 Hz); 8.01 (1H, doublet, J=8.0 Hz); 8.23–8.24 (1H, multiplet).

(13b) 3-{(3,4-Dimethylphenyl)-[(S)-1-phenylethylamino]methyl}phenylamine

In a similar manner to that described in Example (1b), a solution of isomer A of N-[(3-nitrophenyl)-(3,4-dimethylphenyl)methyl]-N-[(S)-1-phenylethyl]amine (1.10 g) [prepared as described in step (a) above] in methanol (20 ml), nickel chloride hexahydrate (1.45 g) and sodium borohydride (469 mg) were reacted, to afford isomer A of the title compound (954 mg) as a yellow oil.

Isomer A

Nuclear Magnetic Resonance Spectrum (CDCl$_3$) δ ppm: 1.35 (3H, doublet, J=6.6 Hz); 2.19 (6H, singlet); 3.70 (1H, quartet, J=6.6 Hz); 4.47 (1H, singlet); 6.55 (1H, doublet, J=8.2 Hz); 6.68–6.69 (1H, multiplet); 6.71 (1H, doublet, J=7.7 Hz); 7.03 (1H, singlet); 7.09 (1H, triplet, .T=7.7 Hz); 7.22–7.34 (7H multiplet).

In a similar manner to that described in Example (1b), a solution of isomer B of N-[(3-nitrophenyl)-(3,4- dimethylphenyl)methyl]-N-[(S)-1-phenylethyl]amine (1.19 g) in methanol (20 ml), nickel chloride hexahydrate (1.57 g) and sodium borohydride (500 mg) were reacted, to afford isomer B of the title compound (849 mg) as a colorless oil.
Isomer B Nuclear Magnetic Resonance Spectrum (CDCl₃) δ ppm: 1.35 (3H, doublet, J=6.9 Hz); 2.23 (6H, singlet); 3.67 (1H, quartet, J=6.9 Hz); 4.47 (1H, singlet); 6.49 (1H, doublet, J=8.1 Hz); 6.62–6.63 (1H, multiplet); 6.66 (1H, doublet, J=7.6 Hz); 7.00–7.09 (4H, multiplet); 7.24–7.35 (5H, multiplet).

(13c) 3-Methoxy-4-<3-{(3,4-dimethylphenyl)-[(S)-1-phenylethylamino]methyl}phenylamino>-3-cyclobutene-1,2-dione In a similar manner to that described in Example (1c), a solution of isomer A of 3-{(3,4-dimethylphenyl)-[(S)-1-phenylethylamino]methyl}phenylamine (950 mg) [prepared as described in step (b) above] in methanol (15 ml) and 3,4-dimethoxy- 3-cyclobutene-1,2-dione (430 mL) wvere reacted, to afford isomer A of the title compound (976 mg) as a white foamy solid.
Isomer A Nuclear Magnetic Resonance Spectrum (CDCl₃) δ ppm: 1.38 (3H, doublet, J=6.6 Hz); 2.20 (6H, singlet); 3.65 (1H, quartet, J=6.6 Hz); 4.42 (3H, singlet); 4.56 (1H, singlet); 6.98–7.04 (3H, multiplet); 7.13–7.36 (9H, multiplet).

In a similar manner to that described in Example (1c), a solution of isomer B of 3-{(3,4-dimethylphenyl)-[(S)-1-phenylethylamino]methyl}phenylamine (845 mg) in methanol (15 ml) and 3,4-dimethoxy-3-cyclobutene-1,2-dione (382 mg) were reacted, to afford isomer B of the title compound (1.04 g) as a white foamy solid.
Isomer B Nuclear Magnetic Resonance Spectrum (CDCl₃) δ ppm: 1.36 (3H, doublet, J=6.6 Hz); 2.25 (6H, singlet); 3.68 (1H, quartet, J=6.6 Hz); 4.42 (3H, singlet); 4.55 (1H, singlet); 7.03–7.12 (5H, multiplet); 7.20–7.35 (7H, multiplet).

(13d) 3-Amino-4-<3-{(3,4-dimethylphenyl)-[(S)-1-phenylethylamino]methyl}phenylamino>-3-cyclobutene-1,2-dione In a similar manner to that described in Example (1d), a solution of isomer A of 3-methoxy-4-<3-{(3,4-dimethylphenyl)-[(S)-1-phenylethylamino]methyl}phenylamino>- 3-cyclobutene-1,2-dione (970 mg) [prepared as described in step (c) above] in ethanol (10 ml) and a solution of ammonia in ethanol (2N, 4.4 ml) were reacted, to give isomer A of the title compound (604 mg) as a yellow solid.
Isomer A Nuclear Magnetic Resonance Spectrum (DMSO-d₆) δ ppm: 1.30 (3H, doublet, J=6.6 Hz); 2.13 (3H, singlet); 2.14 (3H, singlet); 3.55 (1H, quartet, J=6.6 Hz); 4.42 (1H, singlet); 6.96 (1H, doublet, J=7.6 Hz); 6.99–7.03 (2H, multiplet); 7.08 (1H, singlet); 7.21–7.33 (7H, multiplet); 7.41 (1H, doublet, J=7.9 Hz). melting point: 182–185° C.

In a similar manner to that described in Example (1d), a solution of isomer B of 3-methoxy-4-<3-{(3,4-dimethylphenyl)-[(S)-1-phenylethylamino]methyl}phenylamino>-3-cyclobutene-1,2-dione (1.04 g) in ethanol (10 ml) and a solution of ammonia in ethanol (2N, 4.8 ml) were reacted, to give isomer B of the title compound (899 mg) as a yellow solid.
Isomer B Nuclear Magnetic Resonance Spectrum (DMSO-d₆) δ ppm: 1.27 (3H, doublet, J=6.6 Hz); 2.18 (3H, singlet); 2.19 (3H, singlet); 3.52 (1H, quartet, J=6.6 Hz); 4.39 (1H, singlet); 6.90 (1H, doublet, J=7.6 Hz); 7.03–7.08 (3H, multiplet); 7.17–7.33 (7H, multiplet); 7.43 (1H, doublet, J=8.0 Hz). melting point: 229–225° C.

EXAMPLE 14

3-Amino-4-<2-chloro-5-{phenyl-[(S)-1-phenylethylamino]methyl}phenylamino>-3-cyclobutene-1,2-dione hydrochloride (Compound No. 2-478)

(14a) N-[(4-Chloro-3-nitrophenyl)phenylmethyl]-N-[(S)-1-phenylethyl]amine

In a similar manner to that described in Example (1a), 4-chloro-3-nitrobenzophenone (2.0 g), (S)-1-phenylethylamine (1.94 ml), triethylamine (4.2 ml) and titanium tetrachloride (1.16 ml) were reacted, to afford the imine derivative.

In a similar manner to that described in Example (1a), the imine derivative, sodium cyanoborohydride (1.91 g) and acetic acid (0.65 ml) were reacted, to afford the title compound (2.89 g) as a yellow oil.

Nuclear Magnetic Resonance Spectrum (CDCl₃) δ ppm: 1.35–1.43 (3H, multiplet); 3.55–3.70 (1H, multiplet); 4.61 and 4.64 (total 1H, each singlet); 7.15–7.53 (12H, multiplet); 7.88–7.95 (1H, multiplet).

(14b) 2-Chloro-3-{phenyl-[(S)-1-phenylethylamino]methyl}phenylamine

In a similar manner to that described in Example (1b), N-[(4-chloro-3-nitrophenyl)phenylmethyl]-[(S)-1-phenylethyl]amine (2.89 g) [prepared as described in step (a) above], nickel chloride hexahydrate (3.76 g) and sodium borohydride (1.2 g) were reacted, to afford the title compound (2.36 g) as a pale yellow oil.

Nuclear Magnetic Resonance Spectrum (CDCl₃) δ ppm: 1.32–1.40 (3H, multiplet); 3.60–3.72 (1H, multiplet); 4.49 and 4.50 (total 1H, each singlet); 6.58–6.77 (2H, multiplet); 7.08–7.40 (11H, multiplet).

(14c) 3-Methoxy-4-<2-chloro-5-{phenyl-[(S)-1-phenylethylamino]methyl}phenylamino>-3-cyclobutene-1,2-dione In a similar manner to that described in Example (1c), 2-chloro-3-{phenyl-[(S)-1-phenylethylamino]methyl}phenylamine (2.36 g) [prepared as described in step (b) above] and 3,4-dimethoxy-3-cyclobutene-1,2-dione (1.05 g) were reacted, to afford the title compound (2.42 g) as a white foamy solid.

Nuclear Magnetic Resonance Spectrum (CDCl₃) δ ppm: 1.35–1.45 (3H, multiplet); 3.65 (1H, quartet, J=6.6 Hz); 4.36 and 4.39 (total 3H, each singlet); 4.60 and 4.61 (total 1H, each singlet); 7.00–7.40 (13H, multiplet).

(14d) 3-Amino-4-<2-chloro-5-{phenyl-[(S)-1-phenylethylamino]methyl}phenylamino>-3-cyclobutene-1,2-dione hydrochloride In a similar manner to that described in Example (1d), a solution of 3-methoxy-4-(2-chloro-5-{phenyl-[(S)-1-phenylethylamino]methyl}phenylamino)-3-cyclobutene-1,2-dione (2.42 g) [prepared as described in step (c) above] in ethanol (25 ml) and a solution of ammonia in ethanol (2N, 10.8 ml) were reacted. The reaction mixture was concentrated by evaporation under reduced pressure, and the crude product was dissolved in ethyl acetate (20 ml). A solution of hydrogen chloride in ethyl acetate (4N, 5.4 ml) was added to the solution, and the precipitate was suspended in diethyl etlher and filtered, to give the title compound (2.32 g) as a pale yellow solid.

Nuclear Magnetic Resonance Spectrum (DMSO-d₆) δ ppm: 1.68 (3H, doublet, J=6.3 Hz); 4.23 and 4.40 (total 1H, each broad); 5.00 and 5.30 (total 1H, each broad); 7.15–7.80 (13H, multiplet). melting point: 187–194° C.

EXAMPLE 15

3-Amino-4-<4-chloro-5-{phenyl-[(S)-1-phenylethylamino]methyl}phenylamino)-3-cycloblutene-1,2-dione (Compound No. 2-476)

(15a) N-[(2-Chloro-5-nitrophenyl)phenylmethyl-N-[(S)-1-phenylethyl]amine

In a similar maiuer to that described in Example (1a), 2-chloro-5-nitrobenzophenone (2.0 g), (S)-1-phenylethylamine (1.94 ml) triethylamine (4.2 ml) and titanium tetrachloride (1.0 ml) were reacted, to afford the imine derivative.

In a similar manner to that described in Example (1a), this imine derivative, sodium cyanoborohydride (1.91 g) and acetic acid (0.65 ml) were reacted, to afford the title compound (2.58 g) as an orange oil.

Nuclear Magnetic Resonance Spectrum (CDCl$_3$) δ ppm: 1.40–1.44 (3H, multiplet); 3.59 and 3.75 (total 1H, each quartet, J=6.6 Hz); 5.07 and 5.20 (total 1H, each singlet); 7.15–7.50 (11 H, multiplet); 7.90–7.95 and 8.04–8.09 (total 1H, each multiplet); 8.57 and 8.83 (total 1H, each doublet, J=2.8 Hz).

(15b) 4-Chloro-3-{phenyl-[(S)-1-phenylethylamino]methyl}phenylamine

In a similar manner to that described in Example (1b), N-[(2-chloro-5-nitrophenyl)phenylmethyl]-N-[(S)-1-phenylethyl]amine (2.58 g) [prepared as described in step (a) above], nickel chloride hexahydrate (3.33 g) and sodium borohydride (1.06 g) were reacted. The crude product was separated and purified by chromatography through a silica gel column using a 1:10 by volume mixture of ethyl acetate and toluene as the eluant, to afford isomer A (771 mg) as a colorless oil and isomer B (659 mg) as a pale yellow oil of the title compound.

Isomer A

Nuclear Magnetic Resonance Spectrum (CDCl$_3$) δ ppm: 1.38 (3H, doublet, J=6.7 Hz); 3.65–3.75 (1H, multiplet); 4.98 (1H, singlet); 6.53 (1H, doublet of doublets, J=2.8, 8.2 Hz); 7.02 (1H, doublet, J=2.9 Hz); 7.06 (1H, doublet, J=8.2 Hz); 7.15–7.37 (10H, multiplet).

Isomer B

Nuclear Magnetic Resonance Spectrum (CDCl$_3$) δ ppm: 1.39 (3H, doublet, J=6.6 Hz); 3.70 (1H, quartets J=6.6 Hz); 5.13 (1H, singlet); 6.45 (1H, doublet of doublets, J=2.8, 8.2 Hz); 6.82 (1H, doublet, J=2.8 Hz); 7.02 (1H, doublet, J=8.2 Hz); 7.20–7.45 (10H, multiplet).

(15c) 3-Methoxy-4-<4-chloro-5-{phenyl-[(S)-1-phenylethylamino]methyl}phenylamino>-3-cyclobutene-1,2-dione In a similar manner to that described in Example (1c), isomer A of 2-chloro-3-{phenyl-[(S)-1-phenylethylamino]methyl}phenylamine (765 mg) [prepared as described in step (b) above] and 3,4-dimethoxy-3-cyclobutene-1,2-dione (339 mg) were reacted, to afford isomer A of the title compound (800 mg) as a white foamy solid.

Isomer A

Nuclear Magnetic Resonance Spectrum (CDCl$_3$) δ ppm: 1.41 (3H, doublet, J=6.6 Hz); 3.63 (1H, quartet, J=6.6 Hz); 4.47 (3H, singlet); 5.07 (1H, singlet); 7.10–7.40 (12H, multiplet); 7.76 (1H, doublet, J=2.7 Hz).

In a similar manner to that described in Example (1c), isomer B of 2-chloro-3-{phenyl-[(S)-1-phenylethylamino]methyl}phenylamine (654 mg) and 3,4-dimethoxy-3-cyclobutene-1,2-dione (290 mg) were reacted, to afford isomer B of the title compound (246 mg) as a white foamy solid.

Isomer B

Nuclear Magnetic Resonance Spectrum (CDCl$_3$) δ ppm: 1.41 (3H, doublet, J=6.6 Hz); 3.69 (1H, quartet, J=6.6 Hz); 4.42 (3H, singlet); 5.19 (1H, singlet); 7.00–7.42 (12H, multiplet); 7.50 (1H, doublet, J=2.8 Hz).

(15d) 3-Amino-4-<4-chloro-5-{phenyl-[(S)-1-phenylethylamino]methyl}phenylamino>-3-cyclobutene-1,2-dione In a similar manner to that described in Example (1d), isomer A of 3-methoxy-4-<4-chloro-5-{phenyl-[(S)-1-phenylethylamino]methyl}phenylamino>-3-cyclobutene-1,2-dione (800 mg) [prepared as described in step (c) above] and a solution of ammonia in ethanol (2N, 3.6 ml) were reacted, to give isomer A of the title compound (620 mg) as a pale yellow solid.

Isomer A

Nuclear Magnetic Resonance Spectrum (DMSO-d$_6$) δ ppm: 1.33 (3H, doublet, J=6.6 Hz); 3.55 (1H, quartet, J=6.6 Hz); 4.88 (1H, singlet); 7.15–7.35 (11, multiplet); 7.45–7.55 (1H, multiplet); 7.85 (1H, doublet, J=2.5 Hz). melting point: 177–179° C.

In a similar manner to that described in Example (1d), isomer B of 3-methoxy-4-<4-chloro-5-{phenyl-[(S)-1-phenylethylamino]methyl}phenylamino>-3-cyclobutene-1, 2-dione (246 mg) and a solution of ammonia in ethanol (2N, 1.2 ml) were reacted, to give isomer B of the title compound (133 mg) as a pale yellow solid.

Isomer B

Nuclear Magnetic Resonance Spectrum (DMSO-d$_6$) δ ppm: 1.29 (3H, doublet, J=6.6 Hz); 3.52 (1H, quartet, J=6.6 Hz); 4.91 (1H, singlet); 7.20–7.40 (11H, multiplet); 7.48–7.55 (1H, multiplet); 7.66 (1H, doublet, J=2.7 Hz). melting point: 210–212° C.

EXAMPLE 16

3-Amino-4-<2-methoxy-5-{(4-fluorophenyl)-[(S)-1-phenylethylamino]methyl}phenylamino>-3-cyclobutene-1,2-dione (Compound No.2-501)

(16a) N-[(4-Methoxy-3-nitrophenyl)-(4-fluorophenyl)methyl-N-](S)-1-phenylethyliamine In a similar manner to that described in Example (1a), 4-methoxy-3-nitro-4'-fluorobenzophenone (2.0), (S)-1-phenylethylamine (1.98 ml) triethylamine (4.3 ml) and titanium tetrachloride (1.03 nil) were reacted, to afford the imine derivative (2.96 g) as a yellow oil .

In a similar manner to that described in Example (1a), this imine derivative, sodium cyanoboroiiydride (1.96 g) and acetic acid (0.67 ml) were reacted, to afford isomer A (678 mg) as a yellow oil and isomer B (1.31 g) as a white solid of the title compound.

Isomer A

Nuclear Magnetic Resonance Spectrum (CDCl$_3$) δ ppm: 1.38 (3H, doublet, J=6.6 Hz); 3.62 (1H, quartet, J=6.6 Hz); 3.75 (3H, multiplet); 4.93 (1H, singlet); 6.85–6.96 (3H, multiplet); 7.15–7.37 (7H, multiplet); 8.18 (1H, doublet of doublets, J=2.9, 8.9 Hz); 8.54 (1H, doublet, J=2.9 Hz).

Isomer B

Nuclear Magnetic Resonance Spectrum (CDCl$_3$) δ ppm: 1.38 (3H, doublet, J=6.6 Hz); 3.63 (1H, quartet, J=6.6 Hz); 3.77 (3H, multiplet); 4.97 (1H, singlet); 6.79 (1H, doublet, J=9.1 Hz); 7.00 (2H, triplet, J=8.6 Hz); 7.17–7.35 (7H, multiplet); 8.09 (1H, doublet of doublets, J=2.9, 9.3 Hz); 8.36 (1H, doublet, J=2.9 Hz).

(16b) 2-Methoxy-5-{(4-fluorophenyl)-[(S)-1-phenylethylamino]methyl}phenylamine

In a similar manner to that described in Example (1b), isomer A of N-[(4-methoxy-3-nitrophenyl)-(4-fluorophenyl)methyl]-N-[(S)-1-phenylethyl]amine (670 mg) [prepared as described in step (a) above], nickel chloride hexahydrate (856 mg) and sodium borohydride (272 mg) were reacted, to afford isomer A (584 mg) of the title compound as a yellow oil.

Isomer A

Nuclear Magnetic Resonance Spectrum (CDCl$_3$) δ ppm: 1.34 (3H, doublet, J=6.6 Hz); 3.56 (3H, singlet); 3.69 (1H, quartet, J=6.6 Hz); 4.78 (1H, singlet); 6.58 (1H, doublet of doublets, J=2.9, 8.6 Hz); 6.69–6.73 (2H, multiplet); 6.89 (2H, triplet, J=8.7 Hz); 7.20–7.35 (7H, multiplet).

In a similar manner to that described in Example (1b), isomer B of N-[(4-methoxy-3-nitrophenyl)-(4-fluorophenyl) methyl]-N-[(S)-1-phenylethyl]amine (1.4 g), nickel chloride hexahydrate (1.76 g) and sodium borohydride (560 mg) were reacted, to afford isomer B (844 mg) of the title compound as a colorless oil.

Isomer B

Nuclear Magnetic Resonance Spectrum (CDCl$_3$) δ ppm: 1.35 (3H, doublet, J=6.6 Hz); 3.58 (3H, sing let); 3.63 (1H, quartet, J=6.6 Hz); 4.94 (1H, singlet); 6.49–6.65 (3H, multiplet); 6.95–7.01 (2H, multiplet); 7.20–7.40 (7H, multiplet).

(16c) 3-Methoxy-4-<2-methoxy-5-{(4-fluorophenyl)-[(S)-1-phenylethylamino]methyl}phenylamino>-3-cyclobutene-1,2-dione In a similar manner to that described in Example (1c), isomer A of 2-methoxy-5-{(4-fluorophenyl-[(S)-1-phenylethylamino]methyl}phenylamine (635 mg) [prepared as described in step (b) above] and 3,4-dimethoxy-3-cyclobutene-1,2-dione (254 mg) were reacted, to afford isomer A (635 mg) of the title compound as a white foamy solid.

Isomer A

Nuclear Magnetic Resonance Spectrum (CDCl$_3$) δ ppm: 1.37 (3H, doublet, J=6.6 Hz); 3.60–3.70 (1H, multiplet); 3.66 (3H, singlet); 4.42 (3H, singlet); 4.94 (1H, singlet); 6.83 (1H, doublet, J=8.7 Hz); 6.91 (2H, triplet, J=8.7 Hz); 7.10–7.45 (9H, multiplet).

In a similar manner to that described in Example (1c), isomer B of 2-methoxy-5-{(4-fluorophenyl)-[(S)-1-phenylethylamino]methyl}phenylamine (840 mg) and 3,4-dimethoxy-3-cyclobutene-1,2-dione (358 mg) were reacted, to afford isomer B (811 mg) of the title compound as a pale yellow foamy solid.

Isomer B

Nuclear Magnetic Resonance Spectrum (CDCl$_3$) δ ppm: 1.37 (3H, doublet, J=6.6 Hz); 3.62 (1H, quartet, J=6.6 Hz); 3.68 (3H, singlet); 4.39 (3H, singlet); 4.99 (1H, singlet); 6.76 (1H, doublet, J=8.7 Hz); 6.97–7.40 (11H, multiplet).

(16d) 3-Amino-4-<2-methoxy-5-{(4-fluorophenyl)-[(S)-1-phenylethylamino]methyl}phenylamino>-3-cyclobutene-1,2-dione In a similar manner to that described in Example (1d), isomer A of 3-methoxy-4-<2-methoxy-5-{(4-fluorophenyl)-[(S)-1-phenylethylamino]methyl}phenylamino>-3-cyclobutene-1,2-dione (630 mg) [prepared as described in step (c) above] and a solution of ammonia in ethanol (2N, 2.8 ml) were reacted, to give isomer A of the title compound (491 mg) as a yellow solid.

Isomer A

Nuclear Magnetic Resonance Spectrum (DMSO-d$_6$) δ ppm: 1.26 (3H, doublet, J=6.3 Hz); 3.42–3.52 (1H, multiplet); 3.59 (3H, singlet); 4.83 (1H, singlet); 6.87 (1H, doublet, J=8.6 Hz); 7.05–7.45 (11H, multiplet). melting point: 189–192° C.

In a similar manner to that described in Example (1d), isomer B of 3-methoxy-4-<2-methoxy-5-{(4-fluorophenyl)-[(S)-1-phenylethylamino]methyl}phenylamino)-3-cyclobutene-1,2-dione (805 mg) and a solution of ammonia in ethanol (2N, 3.4 ml) were reacted, to give isomer A of the title compound (700 mg) as a yellow solid.

Isomer B

Nuclear Magnetic Resonance Spectrum (DMSO-d$_6$) δ ppm: 1.29 (3H, doublet, J=6.5 Hz); 3.55–3.65 (1H, multiplet); 3.58 (3H, singlet); 4.85 (1H, singlet); 6.94 (1H, doublet, J=8.8 Hz); 7.05 (2H, triplet J=8.8 Hz); 7.20–7.42 (8H, multiplet); 7.53 (1H, doublet, J=2.6 Hz). melting point: 196–198° C.

EXAMPLE 17

3-Amino-4-<2,3-dimethoxy-5-{(4-fluorophenyl)-[(S)-1-phenylethylamino]methyl}phenylamino>-3-cyclobutene-1,2-dione (Compound No. 2-502)

(17a) N-[(3,4-Dimethoxy-5-nitrophenyl)-(4-fluorophenyl)methyl]-N-[(S)-1-phenylethyl]amine In a similar manner to that described in Example (1a), 3,4-dimethoxy-5-nitro-4'-fluorobenzophenone (2.0 g), (S)-1-phenylethylamine (1.68 ml) triethylamine (3.66 ml) and titanium tetrachloride (0.87 ml) were reacted, to afford the imine derivative.

In a similar manner to that described in Example (1a), this imine derivative, sodium cyanoborohydride (1.67 g) and acetic acid (0.57 ml) were reacted, to afford the title compound (2.73 g) as an orange oil.

Nuclear Magnetic Resonance Spectrum (CDCl$_3$) δ ppm: 1.35–1.40 (3H, multiplet); 3.58–3.65 (1H, multiplet); 3.80 and 3.88 (total 3H, each singlet); 3.91 and 3.97 (total 3H, each singlet); 4.56 (1H, singlet); 6.93–7.40 (11H, multiplet).

(17b) 2,3-Dimethoxy-5-{(4-fluorophenyl)-[(S)-1-phenylethylamino]methyl}phenylamine In a similar manner to that described in Example (15b), N-[(3,4-dimethoxy-5-nitrophenyl)-(4-fluorophenyl)methyl]-N-[(S)-1-phenylethyl]amine (2.73 g) [prepared as described in step (a) above], nickel chloride hexahydrate (3.19 g) and sodium borohydride (1.01 g) were reacted, and the reaction mixture was purified, to afford isomer A (895 mg) as a yellow oil and isomer B (319 mg) as a pale yellow oil of the title compound.

Isomer A

Nuclear Magnetic Resonance Spectrum (CDCl$_3$) δ ppm: 1.36 (3H, doublet, J=6.6 Hz); 3.71 (1H, quartet, J=6.6 Hz); 3.80 (3H, singlet); 3.82 (3H, singlet); 4.42 (1H, singlet); 6.27 (1H, doublet, J=1.9 Hz); 6.34 (1H, doublet, J=1.9 Hz); 6.92 (2H, triplet, J=8.7 Hz); 7.20–7.42 (7H, multiplet).

Isomer B

Nuclear Magnetic Resonance Spectrum (CDCl$_3$) δ ppm: 1.35 (3H, doublet, J=6.6 Hz); 3.60 (1H, quartet, J=6.6 Hz); 3.75 (6H, singlet); 4.44 (1H, singlet); 6.22 (1H, doublet, J=1.7 Hz); 6.28 (1H, doublet, J=1.7 Hz); 7.00 (2H, triplet, J=8.7 Hz); 7.18–7.38 (7H, multiplet).

(17c) 3-Methoxy-4-<2,3-dimethoxy-5-{(4-fluorophenyl)-[(S)-1-phenylethylamino]methyl}phenylamino>-3-cyclobutene-1,2-dione In a similar manner to that described in Example (1c), isomer A of 2,3-dimethoxy-5-{(4-fluorophenyl-[(S)-1-phenylethylamino]methyl}phenylamine (890 mg) [prepared as described in step (b) above] and 3,4-dimethoxy-3-cyclobutene-1,2-dione (343 mg) were reacted, to afford isomer A of the title compound (762 mg) as a white solid.

Isomer A

Nuclear Magnetic Resonance Spectrum (CDCl$_3$) δ ppm: 1.39 (3H, doublet, J=6.6 Hz); 3.60–3.70 (1H, multiplet); 3.83 (3H, singlet); 3.90 (3H, singlet); 4.41 (3H, singlet); 4.53 (1H, singlet); 6.63 (1H, singlet); 6.95 (2H, triplet, J=8.7 Hz); 7.20–7.40 (8H, multiplet).

In a similar manner to that described in Example (1c), isomer B of 2,3-dimethoxy-5-{(4-fluorophenyl )-[(S)-1-phenylethylamino]methyl}phenylamine (1.15 g) and 3,4- dimethoxy-3-cyclobutene-1,2-dione (455 mg) were reacted, to afford isomer B of the title compound (789 mg) as a white foamy solid.
Isomer B Nuclear Magnetic Resonance Spectrum (CDCl₃) δ ppm: 1.38 (3H, doublet, J=6.6 Hz); 3.62 (1H, quartet, J=6.6 Hz); 3.78 (3H, singlet); 3.85 (3H, singlet); 4.42 (3H, singlet); 4.54 (1H, singlet); 6.58 (1H, singlet); 7.04 (2H, triplet, J=8.5 Hz); 7.20–7.40 (8H, multiplet).

(17d) 3-Amino-4-<2,3-dimethoxy-5-{(4-fluorophenyl)-[(S)-1-phenylethylamino]methyl}phenylamino)-3-cyclobutene-1,2-dione In a similar manner to that described in Example (1d), isomer A of 3-methoxy-4-(2,3-dimethoxy-5-{(4-fluorophenyl)-[(S)-1-phenylethylamino]methyl}phenylamino>-3-cyclobutene-1,2-dione (755 mg) [prepared as described in step (c) above] and a solution of ammonia in ethanol (2N, 3.0 ml) were reacted, to give isomer A of the title compound (638 mg) as a yellow solid.
Isomer A Nuclear Magnetic Resonance Spectrum (DMSO-d₆) δ ppm: 1.30 (3H, doublet, J=6.6 Hz); 3.55–3.65 (1H, multiplet); 3.75 (3H, singlet); 3.78 (3H, singlet); 4.41 (1H, singlet); 6.76 (1H, singlet); 7.05 (2H, triplet, J=6.9 Hz); 7.15–7.40 (7H, multiplet); 7.57 (1H, singlet). melting point: 120–122° C.

In a similar manner to that described in Example (1d), isomer B of 3-methoxy-4-<2,3-dimethoxy-5-{(4-fluorophenyl)-[(S)-1-phenylethylamino]methyl}phenylamino>-3-cyclobutene-1,2-dione (785 mg) and a solution of ammonia in ethanol (2N, 3.2 ml) were reacted, to give isomer B of the title compound (680 mg) as a yellow solid.
Isomer B Nuclear Magnetic Resonance Spectrum (DMSO-d₆) δ ppm: 1.29 (3H, doublet, J=6.6 Hz); 3.45–3.55 (1H, multiplet); 3.70 (3H, singlet); 3.74 (3H, singlet); 4.46 (1H, singlet); 6.72 (1H, singlet); 7.05–7.45 (9H, multiplet); 7.54 (1H, singlet). melting point: 132–132° C.

EXAMPLE 18

3-Amino-4-<3-{4-methoxyphenyl-[(R)-1-(3,4-difluorophenyl)ethylamino]methyl}phenylamino>-3-cyclobutene-1,2-dione (Compound No. 2-1359)

(18a) N-[(3-Nitrophenyl)-(4-methoxyphenyl)methyl]-N-[(R)-1-3,4-difluorophenyl)ethylamine In a similar manner to that described in Example (1a), 4-methoxy-3'-nitrobenzophenone (3 g), the mandelic acid salt of (R)-1-(3,4-difluorophenyl)ethylamine (3.96 g) triethylamine (9.75 ml), titanium tetrachloride (1.54 ml), sodium cyanoborohydride (3.26 g) and acetic acid (1.0 ml) were reacted, to afford the title compound (1.27 g) as an orange oil.

Nuclear Magnetic Resonance Spectrum (CDCl₃) δ ppm: 1.35 and 1.36 (total 3H, each doublet, J=6.4, 6.5 Hz); 3.57–3.69 (1H, multiplet); 3.77 and 3.82 (total 3H, each singlet); 4.60 and 4.66 (total 1H, each singlet); 6.82 and 6.89 (total 2H, each doublet, J=8.7, 8.7 Hz); 6.94–7.12 (5H, multiplet); 7.40 and 7.45 (total 1H, each triplet, J=8.0, 8.0 Hz); 7.59 and 7.65 (total 1H, each doublet, J=7.8, 7.6 Hz); 8.03 and 8.10 (total 1H, doublet of doublets, J=2.0, 8.0 and 1.8, 8.0 Hz); 8.23 (1H, doublet, J=8.0 Hz).

(18b) 3-{(4-Methoxyphenyl)-[(R)-1-(3,4-difluorophenyl)ethylamino]methyl}phenylamine In a similar manner to that described in Example (1b), a solution of N-[(3-nitrophenyl)-(4-methoxyphenyl)methyl]-[(R)-1-(3,4-difluorophenyl)ethyl]amine (1.27 g) [prepared as described in step (a) above] in methanol (50 ml), nickel chloride hexahydrate (1.52 g) and sodium borohydride (510 mg) were reacted, and the reaction mixture was purified by chromatography through a silica gel column using a 1:8 by volume mixture of ethynyl acetate and toluene as the eluant, to afford isomer A (235 mg,) as a yellow oil and isomer B (240 mg) as a pale yellow oil of the title compound.
Isomer A Nuclear Magnetic Resonance Spectrum (CDCl₃) δ ppm: 1.31 (3H, doublet J=6.6 Hz); 3.60–3.70 (1H, multiplet); 3.76 (3H, singlet); 4.44 (1H, singlet); 6.56–6.77 (3H, multiplet); 6.79 (2H, doublet, J=8.7 Hz); 6.94–6.97 (1H, multiplet); 7.05–7.20 (5H, multiplet).
Isomer B Nuclear Magnetic Resonance Spectrum (CDCl₃) δ ppm: 1.31 (3H, doublet, J=6.6 Hz); 3.60–3.64 (1H, multiplet); 3.80 (3H, singlet); 4.44 (1H, singlet); 6.49–6.52 (1H, multiplet); 6.61 (2H, doublet, J=8.9 Hz); 6.65 (1H, doublet, J=7.3 Hz); 6.86 (2H, doublet, J=8.7 Hz); 6.92–6.95 (5H, multiplet); 7.02–7.20 (5H, multiplet).

(18c) 3-Methoxy-4-<3-{(4-methoxyphenyl)-[(R)-1-(3,4-difluorophenyl)ethylamino]methyl}phenylamino>-3-cyclobutene-1,2-dione In a similar manner to that described in Example (1c), a solution of isomer A of 3-{(4-methoxyphenyl)-[(R)-1-(3,4-difluorophenyl)ethylamino]methyl}phenylamine (225 mg) [prepared as described in step (b) above] in methanol (5 ml) and 3,4-dimethoxy-3-cyclobutene-1,2-dione (174 mg) were reacted, to afford isomer A of the title compound (293 mg) as a pale yellow oil.
Isomer A Nuclear Magnetic Resonance Spectrum (CDCl₃) δ ppm: 1.35 (3H, doublet, J=6.6 Hz); 3.64 (1H, quartet, J=6.6 Hz); 3.76 (3H, singlet); 4.44 (3H, singlet); 4.55 (1H, singlet); 6.81 (2H, doublet, J=8.7 Hz); 6.92–6.95 (1H, multiplet); 7.06–7.34 (8H, multiplet).

In a similar manner to that described in Example (1c), a solution of isomer B of 3-{(4-methoxyphenyl)-[(R)-1-(3,4-difluorophenyl)ethylamino]methyl}phenylamine (230 mg) in methanol (5 ml) and 3,4-dimethoxy-3-cyclobutene-1,2-dione (177 mg) were reacted, to afford isomer B of the title compound (320 mg) as a yellow oil.
Isomer B Nuclear Magnetic Resonance Spectrum (CDCl₃) δ ppm: 1.33 (3H, doublet, J=6.6 Hz); 3.64 (1H, quartet, J=6.6 Hz); 3.81 (3H, singlet); 4.44 (3H, singlet); 4.52 (1H, singlet); 6.89 (2H, doublet, J=8.7 Hz); 6.91–6.96 (1H, multiplet); 7.06–7.24 (8H, multiplet).

(18d) 3-Amino-4-<3-{(4-methoxyphenyl)-[(R)-1-(3,4-difluorophenyl)ethylamino]methyl}phenylamino>-3-cyclobutene-1,2-dione In a similar manner to that described in Example (1d), a solution of isomer A of 3-methoxy-4-<3-{(4-methoxyphenyl)-[(R)-1-(3,4-difluorophenyl)ethylamino]methyl}phenylamino>-3-cyclobutene-1,2-dione (280 mg) [prepared as described in step (c) above] in ethanol (5 ml) and a solution of ammonia in ethanol (2N, 1.0 ml) were reacted, to give isomer A of the title compound (190 mg) as a yellow solid.
Isomer A Nuclear Magnetic Resonance Spectrum (DMSO-d₆) δ ppm: 1.29 (3H, doublet, J=6.7 Hz); 3.56 (1H, quartet, J=6.7 Hz); 3.69 (3H, singlet); 4.42 (1H, singlet); 6.81 (2H, doublet, J=8.7 Hz); 6.97 (1H, doublet, J=4.7 Hz); 7.06–7.09 (1H, multiplet); 7.21–7.27 (3H, multiplet); 7.30–7.42 (4H, multiplet). melting point: 171–173° C.; optical rotation [α]$_D$: −33.8 (c=1.0, EtOH).

In a similar manner to that described in Example (1d), a solution of isomer B of 3-methoxy-4-<3-{(4-methoxyphenyl)-[(R)-1-(3,4-difluorophenyl)ethylamino]methyl}phenylamino>-3-cyclobutene-1,2-dione (280 mg) in ethanol (5 ml) and a solution of ammonia in ethanol (2N, 1.0 ml) were reacted, to give isomer B of the title compound (180 mg) as a yellow solid.

Isomer B

Nuclear Magnetic Resonance Spectrum (DMSO-$d_6$) δ ppm: 1.26 (3H, doublet J=6.6 Hz); 3.52 (1H, quartet, J=6.6 Hz); 3.73 (3H, singlet); 4.40 (1H, singlet); 6.88 (2H, doublet, J=8.5 Hz); 6.91 (1H, doublet, J=7.8 Hz); 7.06–7.07 (1H, multiplet); 7.18–7.42 (7H, multiplet). melting point: 191–194° C.; optical rotation $[\alpha]_D$: +38.2 (c=1.0, EtOH).

EXAMPLE 19

3-Amino-4-<3-{4-methoxyphenyl-[(S)-1-(3,4-difluorophenyl)ethylamino]methyl}phenylamino>-3-cyclobutene-1,2-dione (Compound No. 2-1359)

(19a) N-[(3-Nitrophenyl)-(4-methoxyphenyl)methyl-N-[(S)-1-(3,4-difluorophenyl)ethy]amine In a similar manner to that described in Example (1a), 4-methoxy-3'-nitrobenzophenone (3 g), the mandelic acid salt of (S)-1-(3,4-difluorophenyl)-ethylamine (5.41 g), triethylamine (9.75 ml), titanium tetrachloride (1.54 ml), sodium cyanoborohydride (3.26 g) and acetic acid (1.0 ml) were reacted, to afford the title compound (1.60 g) as an orange oil.

Nuclear Magnetic Resonance Spectrum (CDCl$_3$) δ ppm: 1.35 and 1.36 (total 3H, each doublet, J=6.4, 6.5 Hz); 3.57–3.69 (1H, multiplet); 3.77 and 3.82 (total 3H, each singlet); 4.60 and 4.66 (total 1H, each singlet); 6.82 and 6.89 (total 2H, each doublet, J=8.7, 8.7 Hz); 6.94–7.12 (5H, multiplet); 7.40 and 7.45 (total 1H, each triplet, J=8.0, 8.0 Hz); 7.59 and 7.65 (total 1H, each doublet, J=7.8, 7.6 Hz); 8.03 and 8.10 (total 1H, doublet of doublets, J=2.0, 8.0 and 1.8, 8.0 Hz); 8.23 (1H, doublet J=8.0 Hz).

(19b) 3-{(4-Methoxyphenyl)-[(S)-1-(3,4-difluorophenyl)ethylamino]methyl}phenylamine In a similar manner to that described in Example (1b), a solution N-[(3-nitrophenyl)-(4-methoxyphenyl)methyl]-[(S)-1-(3,4-difluorophenyl)ethyl]amine (1.50 g) [prepared as described in step (a) above] in methanol (50 ml), nickel chloride hexahydrate (1.79 g) and sodium borohydride (600 mg) were reacted, and the reaction mixture was purified by chromatography through a silica gel column using a 1:8 by volume mixture of ethyl acetate and toluene as the eluant, to afford isomer A (199 mg) as a yellow oil and isomer B (290 mg) as a yellow oil of the title compound.

Isomer A

Nuclear Magnetic Resonance Spectrum (CDCl$_3$) δ ppm: 1.31 (3H, doublet, J=6.6 Hz); 3.60–3.70 (1H, multiplet); 3.76 (3H, singlet); 4.43 (1H, singlet); 6.56–6.61 (2H, multiplet); 6.67 (1H, doublet, J=7.6 Hz); 6.74 (2H, doublet, J=8.7 Hz); 6.92–6.97 (1H, multiplet); 7.05–7.19 (5H, multiplet).

Isomer B

Nuclear Magnetic Resonance Spectrum (CDCl$_3$) δ ppm: 1.31 (3H, doublet, J=6.7 Hz); 3.55–3.65 (1H, multiplet); 3.80 (3H, singlet); 4.44 (1H, singlet); 6.50–6.66 (3H, multiplet); 6.86 (2H, doublet, J=8.6 Hz); 6.92–6.95 (1H, multiplet); 7.02–7.20 (5H, multiplet).

(19c) 3-Methoxy-4-<3-{(4-methoxyphenyl)-[(S)-1-(3,4-difluorophenyl)ethylamino]methyl}phenylamino>-3-cyclobutene-1,2-dione In a similar manner to that described in Example (1c), a solution of isomer A of 3-{(4-methoxyphenyl)-[(S)-1-(3,4-difluorophenyl)ethylamino]methyl}phenylamine (180 mg) [prepared as described in step (b) above] in methanol (10 ml) and 3,4-dimethoxy-3-cyclobutene-1,2-dione (139 mg) were reacted, to afford isomer A of the title compound (220 mg) as a yellow oil.

Isomer A

Nuclear Magnetic Resonance Spectrum (CDCl$_3$) δ ppm: 1.35 (3H, doublet, J=6.7 Hz); 3.64 (1H, quartet, J=6.6 Hz); 3.76 (3H, singlet); 4.44 (3H, singlet); 4.55 (1H, singlet); 6.81 (2H, doublet, J=8.7 Hz); 6.92–6.95 (1H, multiplet); 7.06–7.19 (6H, multiplet); 7.28–7.34 (2H, multiplet).

In a similar manner to that described in Example (1c), a solution of isomer B of 3-{(4-methoxyphenyl)-[(S)-1-(3,4-difluorophenyl)ethylamino]methyl}phenylamine (270 mg) in methanol (10 ml) and 3,4-dimethoxy-3-cyclobutene-1,2-dione (208 mg) were reacted, to afford isomer B of the title compound (160 mg) as a pale yellow oil.

Isomer B

Nuclear Magnetic Resonance Spectrum (CDCl$_3$) δ ppm: 1.33 (3H, doublet, J=6.6 Hz); 3.64 (1H, quartet, J=6.6 Hz); 3.81 (3H, singlet); 4.44 (3H, singlet); 4.52 (1H, singlet); 6.89 (2H, doublet, J=8.5 Hz); 6.91–6.96 (1H, multiplet); 7.06–7.24 (8H, multiplet).

(19d) 3-Amino-4-<3-{(4-methoxyphenyl)-[(S)-1-(3,4-difluorophenyl)ethylaimino]methyl}phenylamino>-3-cyclobutene-1,2-dione In a similar manner to that described in Example (1d), a solution of isomer A of 3-methoxy-4-<3-{(4-methoxyphenyl)-[(S)-1-(3,4-difluorophenyl)ethylamino]methyl}phenylamino>-3-cyclobutene-1,2-dione (220 mg) [prepared as described in step (c) above] in ethanol (5 ml) and a solution of ammonia in ethanol (2N, 1.0 ml) were reacted, to give isomer A of the title compound (210 mg) as a yellow solid.

Isomer A

Nuclear Magnetic Resonance Spectrum (DMSO-$d_6$) δ ppm: 1.29 (3H, doublet, J=6.6 Hz); 3.56 (1H, quartet, J=6.5 Hz); 3.69 (3H, singlet); 4.43 (1H, singlet); 6.81 (2H, doublet, J=8.7 Hz); 6.97 (1H, doublet, J=7.6 Hz); 7.07–7.09 (1H, multiplet); 7.21–7.27 (3H, multiplet); 7.31–7.43 (4H, multiplet). melting point: 171–173° C.; optical rotation $[\alpha]_D$: +32.5 (c=1.0, EtOH).

In a similar manner to that described in Example (1d), a solution of isomer B of 3-methoxy-4-<3-{(4-methoxyphenyl)-[(S)-1-(3,4-difluorophenyl)ethylamino]methyl}phenylamino>-3-cyclobutene-1,2-dione (150 mg) in ethanol (5 ml) and a solution of ammonia in ethanol (2N. 1.0 ml) were reacted, to give isomer B of the title compound (130 mg) as a yellow solid.

Isomer B

Nuclear Magnetic Resonance Spectrum (DMSO-$d_6$) δ ppm: 1.26 (3H, doublet, J=6.6 Hz); 3.52 (1H, quartet, J=6.8 Hz); 3.73 (3H, singlet); 4.40 (1H, singlet); 6.88 (2H, doublet, J=8.5 Hz); 6.91 (1H, doublet, J=7.7 Hz); 7.66 (1H, multiplet); 7.18–7.42 (7H, multiplet). melting point: 195–197° C.; optical rotation $[\alpha]_D$: −41.6 (c=1.0, EtOH).

EXAMPLE 20

3-Amino-4-<3-{4-methoxyphenyl-[(S)-1-(3-fluorophenyl)ethylamino]methyl}phenylamino>-3-cyclobutene-1,2-dione (Compound No. 2-815)

(20a) N-[(3-Nitrophenyl)-(4-methoxyphenyl)methyl-[(S)-1-(3-fluorophenyl)ethyl]amine In a similar manner to that described in Example (1a), 4-methoxy-3'-nitrobenzophenone (2.0 g), (S)-1-(3-fluorophenyl)ethylamine hydrochloride (2.73 g), triethylamine (6.50 ml), titanium tetrachloride (1.03 ml), sodium cyanoborohydride (2.15 g) and acetic acid (0.67 ml) were reacted, to afford the title compound (2.77 g) as a yellow oil.

Nuclear Magnetic Resonance Spectrum (CDCl$_3$) δ ppm: 1.37 and 1.38 (total 3H, each doublet, J=6.5, 6.6 Hz); 3.59–3.69 (1H, multiplet); 3.76 and 3.81 (total 3H, each singlet); 4.63 and 4.68 (total 1H, each singlet); 6.81 and 6.89 (total 2H, each doublet, J=8.6, 8.7 Hz); 6.91–7.03 (3H, multiplet); 7.17 (2H, doublet of doublets, J=8.3, 8.5 Hz); 7.27–7.33 (1H, multiplet); 7.37–7.50 (1H, multiplet); 7.60 and 7.67 (total 1H, each doublet, J=7.9, 7.9 Hz); 8.01–8.11 (1H, multiplet); 8.22 and 8.26 (total 1H, each singlet).

(20b) 3-{(4-Methoxyphenyl)-[(S)-1-(3-fluorophenyl) ethylamino]methyl}phenylamine In a similar manner to that described in Example (1b), a solution N-[(3-nitrophenyl)-(4-methoxyphenyl)methyl]-N-[(S)-1-(3-fluorophenyl)ethyl)amine (2.70 g) [prepared as described in step (a) above] in methanol (100 ml), nickel chloride hexahydrate (3.37 g) and sodium borohydride (1.13 g) were reacted, to afford the title compound (2.32 g) as a yellow oil.

Nuclear Magnetic Resonance Spectrum (CDCl$_3$) δ ppm: 1.33 (3H, doublet, J=6.7 Hz); 3.59–3.71 (1H, multiplet); 3.75 and 3.80 (total 3H, each singlet); 4.47 (1H, singlet); 6.49–6.70 (3H, multiplet); 6.78 and 6.86 (total 2H, each doublet, J=8.6, 8.7 Hz); 6.91–7.30 (7H, multiplet).

(20c) 3-Methoxy-4-<3-{(4-methoxyphenyl)-[(S)-1-(3-fluorophenyl)ethylamino]methyl}phenylamino>-3-cyclobutene-1,2-dione In a similar manner to that described in Example (1c), a solution of 3-{(4-methoxyphenyl)-[(S)-1-(3-fluorophenyl) ethylamino]methyl}phenylamine (2.27 g) [prepared as described in step (b) above] in methanol (50 ml) and 3,4-dimethoxy-3-cyclobutene-1,2-dione (1.84 g) were reacted, and the crude product was purified by reverse phase chromatography using a 40:60 by volume mixture of acetonitrile and an acetic acid buffer solution (water/acetic acid/triethylamine=1000:2:2) as the eluant, to afford isomer A of the title compound (145 mg) as a pale yellow foamy solid and isomer B of the title compound (350 mg) as a yellow foamy solid.

Isomer A

Nuclear Magnetic Resonance Spectrum (CDCl$_3$) δ ppm: 1.37 (3H, doublet, J=6.6 Hz); 3.66 (1H, quartet, J=6.6 Hz); 3.76 (3H, singlet); 4.43 (3H, singlet); 4.58 (1H, singlet); 6.80 (2H, doublet, J=8.7 Hz); 6.93–7.04 (3H, multiplet); 7.10–7.19 (4H, multiplet); 7.29–7.36 (3H, multiplet).

Isomer B

Nuclear Magnetic Resonance Spectrum (CDCl$_3$) δ ppm: 1.35 (3H, doublet, J=6.7 Hz); 3.66 (1H, quartet, J=6.6 Hz); 3.81 (3H, singlet); 4.43 (3H, singlet); 4.55 (1H, singlet); 6.88 (2H, doublet, J=8.5 Hz); 6.90–7.31 (10H, multiplet).

(20d) 3-Amino-4-<3-{(4-methoxyphenyl)-[(S)-1-(3-fluorophenyl)ethylamino]methyl}phenylamino>-3-cyclobutene-1,2-dione In a similar manner to that described in Example (1d), a solution of isomer A of 3-methoxy-4-<3-{(4-methoxyphenyl)-[(S)-1-(3-fluorophenyl)ethylamino] methyl}phenylamino>-3-cyclobutene-1,2-dione (130 mg) [prepared as described in step (c) above] in ethanol (5 ml) and a solution of ammonia in ethanol (2N, 1.0 ml) were reacted, to give isomer A of the title compound (110 mg) as a yellow solid.

Isomer A

Nuclear Magnetic Resonance Spectrum (DMSO-d$_6$) δ ppm: 1.30 (3H, doublet, J=6.6 Hz); 3.58 (1H, multiplet); 3.69 (3H, singlet); 4.45 (1H, doublet, J=4.9 Hz); 6.82 (2H, doublet, J=8.7 Hz); 6.96 (1H, doublet, 7.7 Hz); 7.03–7.09 (2H, multiplet); 7.16–7.41 (7H, multiplet). melting point: 170–172° C.; optical rotation [α]$_D$: +48.1 (c=0.5, EtOH).

In a similar manner to that described in Example (1d), a solution of isomer B of 3-methoxy-4-<3-{(4-methoxyphenyl)-[(S)-1-(3-fluorophenyl)ethylamino] methyl}phenylamino>-3-cyclobutene-1,2-dione (330 mg) in ethanol (5 ml) and a solution of ammonia in ethanol (2N, 2 ml) were reacted, to give isomer B of the title compound (282 mg,) as a yellow solid.

Isomer B

Nuclear Magnetic Resonance Spectrum (DMSO-d$_6$) δ ppm: 1.28 (3H, doublet, J=6.6 Hz); 3.57 (1H, multiplet); 3.73 (3H, singlet); 4.42 (1H, doublet, J=4.7 Hz); 6.88 (2H, doublet, J=8.6 Hz); 6.91 (1H, doublet, J=7.7 Hz); 7.01–7.07 (2H, multiplet); 7.14–7.27 (5H, multiplet); 7.32–7.37 (1H, multiplet); 7.42 (1H, doublet of doublets, J=1.9, 8.0 Hz). melting point: 178–181° C.; optical rotation [α]$_D$: –106.8 (c=0.5, EtOH).

EXAMPLE 21

3-Amino-4-<3-{2-thienyl-[(S)-1-phenylethylamino] methyl}phenylamino>-3-cyclobutene-1,2-dione
(Compound No. 2-646)

(21a) N-[(3-Nitrophenyl)-2-thienylmethyl]-N-[(S)-1-phenylethyl]amine

In a similar manner to that described in Example (1a), (3-nitrophenyl)-2-thienylketone (2.0 g), (S)-1-phenylethylamine (1.94 ml), triethylamine (4.2 ml), and titanium tetrachloride (1.0 ml) were reacted, to afford the imine derivative.

In a similar manner to that described in Example (1a), this imine derivative, sodium cyanoborohydride (1.91 g) and acetic acid (0.65 ml) were reacted, to afford the title compound (2.58 g) as an orange oil.

Nuclear Magnetic Resonance Spectrum (CDCl$_3$) δ ppm: 1.37 and 1.40 (total 3H, each doublet, J=6.6 Hz); 3.59 and 3.83 (total 1H, each quartet, J=6.6 Hz); 4.91 and 4.98 (total 1H, each singlet); 6.65–7.00 (2H, multiplet); 7.18–7.70 (8H, multiplet); 8.05–8.27 (2H, multiplet).

(21b) 3-{[(S)-1-phenylethylamino]-2-thienylmethyl}phenylamine

In a similar manner to that described in Example (15b), N-[(3-nitrophenyl)-2-thienylmethyl]-N-[(S)-1-phenylethyl] amine (4.56 g) [prepared as described in step (a) above], nickel chloride hexahydrate (6.42 g) and sodium borohydride (2.04 g) were reacted and purified, to afford isomer A of the title compound (936 mg) as a pale yellow oil and isomer B of the title compound (380 mg) as a pale yellow oil.

Isomer A

Nuclear Magnetic Resonance Spectrum (CDCl$_3$) δ ppm: 1.33 (3H, doublet, J=6.6 Hz); 3.70 (1H, quartet, J=6.6 Hz); 4.65 (1H, singlet); 6.60–6.72 (4H, multiplet); 6.83–6.88 (1H, multiplet); 7.10–7.43 (7H, multiplet).

Isomer B

Nuclear Magnetic Resonance Spectrum (CDCl$_3$) δ ppm: 1.37 (3H, doublet, J=6.6 Hz); 3.80 (1H, quartet, J=6.6 Hz); 4.80 (1H, singlet); 6.54 (1H, doublet of doublets, J=2.0, 8.2 Hz); 6.65–6.72 (2H, multiplet); 6.82 (1H, doublet, J=3.4 Hz); 6.91–6.95 (1H, multiplet); 7.06 (1H, triplet, J=7.7 Hz); 7.20–7.37 (6H, multiplet).

(21c) 3-Methoxy-4-<3-{2-thienyl-[(S)-1-phenylethylamino] methyl}phenylamino>-3-cyclobutene-1,2-dione In a similar manner to that described in Example (1c), isomer A of 3-{[(S)-1-phenylethylamino]-2-thienylmethyl}phenylamine (930 mg) [prepared as described in step (b) above] and 3,4-dimethoxy-3- cyclobutene-1,2-dione (466 mg) were reacted, to afford isomer A of the title compound (932 mg) as a white foamy solid.

Isomer A

Nuclear Magnetic Resonance Spectrum (CDCl₃) δ ppm: 1.36 (3H, doublet J=6.6 Hz); 3.65 (1H, quartet, J=6.6 Hz); 4.42 (3H, singlet); 4.79 (1H, singlet); 6.67 (1H, doublet, J=3.3 Hz); 6.85–6.90 (1H, multiplet); 7.05–7.40 (10H, multiplet).

In a similar manner to that described in Example (1c), isomer B of 3-{[(S)-1-phenylethylamino]-2-thienylmethyl}phenylamine (375 mg) and 3,4-dimethoxy-3-cyclobutene-1,2-dione (185 mg) were reacted, to afford isomer B of the title compound (471 mg) as a white foamy solid.

Isomer B

Nuclear Magnetic Resonance Spectrum (CDCl₃) δ ppm: 1.39 (3H, doublet, J=6.6 Hz); 3.81 (1H, quartet, J=6.6 Hz); 4.42 (3H, singlet); 4.90 (1H, singlet); 6.83–6.87 (1H, multiplet); 6.95–6.98 (1H, multiplet); 7.05–7.40 (10H, multiplet).

(21d) 3-Amino-4-<3-{2-thienyl-[(S)-1-phenylethylamino]methyl}phenylamino>-3-cyclobutene-1,2-dione In a similar manner to that described in Example (1d), isomer A of 3-methoxy-4-<3-{2-thienyl-[(S)-1-phenylethylamino]methyl}phenylamino)-3-cyclobutene-1,2-dione (927 mg) [prepared as described in step (c) above] and a solution of ammonia in ethanol (2N, 4.4 ml) were reacted, to give isomer A of the title compound (654 mg) as a yellow solid.

Isomer A

Nuclear Magnetic Resonance Spectrum (DMSO-d₆) δ ppm: 1.29 (3H, doublet, J=6.6 Hz); 3.52–3.62 (1H, multiplet); 4.64 (1H, singlet); 6.69 (1H, doublet, J=3.3 Hz); 6.85–6.90 (1H, multiplet); 6.99 (1H, doublet, J=7.6 Hz); 7.20–7.40 (8H, multiplet); 7.51 (1H, doublet, J=7.9 Hz). melting point: 180–182° C.; optical rotation [α]$_D$: −31.7 (c=1.00, EtOH).

In a similar manner to that described in Example (1d), isomer B of 3-methoxy-4-<3-{2-thienyl-[(S)-1-phenylethylamino]methyl}phenylamino)-3-cyclobutene-1,2-dione (465 mg) and a solution of ammonia in ethanol (2N, 2.2 ml) were reacted, to give isomer B of the title compound (391 mg) as a yellow solid.

Isomer B

Nuclear Magnetic Resonance Spectrum (DMSO-d₆,) δ ppm:

1.30 (3H, doublet, J=6.6 Hz); 3.62–3.72 (1H, multiplet); 4.76 (1H, singlet); 6.85–7.00 (3H, multiplet); 7.20–7.55 (9H, multiplet). melting point: 188–190° C. optical rotation [α]$_D$: +23.4 (c=1.00, EtOH).

EXAMPLE 22

3-Amino-4-<3-2-thienyl-[(R)-1-phenylethylamino]methyl}phenylamino)-3-cyclobutene-1,2-dione (Compound No. 2-646)

In a similar manner to that described in Example 21, (3-nitrophenyl)-2-thienylketone (2.0 g) and (R)-1-phenylethylamine (1.94 ml) were reacted, to give isomer A of the title compound (1.25 g) and isomer B of the title compound (762 mg).

Isomer A melting point: 162° C. (dec.); optical rotation [α]$_D$: +32.4 (c=1.00, EtOH).

Isomer B melting point: 190–192° C.; optical rotation [α]$_D$: −18.7 (c=1.00, EtOH).

EXAMPLE 23

3-Amino-4-<3-{4-pyridyl-[(S)-1-phenylethylamino]methyl}phenylamino>-3-cyclobutene-1,2-dione (Compound No. 2-691)

(23a) N-[(3-Nitrophenyl)-4-pyridylmethyl-N-[(S)-1-phenylethyl amine

In a similar manner to that described in Example (1a), (3-nitrophenyl)-4-pyridylketone (2.0 g), (S)-1-phenylethylamine (2.24 ml), triethylamine (4.89 ml), and titanium tetrachloride (1.16 ml) were reacted, to afford the imine derivative.

In a similar manner to that described in Example (1a), this imine derivative, sodium cyanoborohydride (2.21 g) and acetic acid (0.76 ml) were reacted, to afford isomer A of the title compound (1.09 g) as a pale yellow oil and isomer B of the title compound (1.02 g) as a pale yellow oil.

Isomer A

Nuclear Magnetic Resonance Spectrum (CDCl₃) δ ppm: 1.41 (3H, doublet, J=6.6 Hz); 3.64 (1H, quartet, J=6.6 Hz); 4.67 (1H, singlet); 7.19–7.37 (7H, multiplet); 7.42 (1H, triplet, J=8.0 Hz); 7.55 (1H, doublet, J=7.4 Hz); 8.08 (1H, doublet of doublets, J=1.9, 7.9 Hz); 8.19 (1H, doublet, J=1.9 Hz); 8.60–8.61 (2H, multiplet).

Isomer B

Nuclear Magnetic Resonance Spectrum (CDCl₃) δ ppm: 1.40 (3H, doublet, J=6.6 Hz); 3.60 (1H, quartet, J=6.6 Hz); 4.69 (1H, singlet); 7.19–7.38 (7H, multiplet); 7.53 (1H, triplet, J=7.8 Hz); 7.63 (1H, doublet, J=7.5 Hz); 8.14–8.17 (1H, multiplet); 8.20–8.21 (1H, multiplet); 8.50–8.52 (2H, multiplet).

(23b) 3-{[(S)-1-Phenylethylamino]-4-pyridylmethyl}phenylamine

In a similar manner to that described in Example (1b), isomer A of N-[(3-nitrophenyl)-4-pyridylmethyl]-N-[(S)-1-phenylethylamine (1.09 g) [prepared as described in step (a) above], nickel chloride hexahydrate (1.57 g) and sodium borohydride (500 mg) were reacted, to afford isomer A of the title compound (752 mg) as a pale yellow oil.

Isomer A

Nuclear Magnetic Resonance Spectrum (CDCl₃) δ ppm: 1.37 (3H, doublet, J=6.8 Hz); 3.61 (1H, quartet, J=6.8 Hz); 4.49 (1H, singlet); 6.52–6.56 (2H, multiplet); 6.60 (1H, doublet, J=7.9 Hz); 7.04 (1H, triplet, J=7.7 Hz); 7.19–7.36 (7H, multiplet); 8.53–8.54 (2H, multiplet).

In a similar manner to that described in Example (1b), isomer B of N-[(3-nitrophenyl)-4-pyridylmethyl]-[(S)-1-phenylethyl]amine (1.02 g), nickel chloride hexahydrate (1.47 g) and sodium borohydride (470 mg) were reacted, to afford isomer B of the title compound (694 mg) as a pale yellow oil.

Isomer B

Nuclear Magnetic Resonance Spectrum (CDCl₃) δ ppm: 1.36 (3H, doublet, J=6.6 Hz); 3.72 (1H, quartet, J=6.6 Hz); 4.47 (1H, singlet); 6.57–6.64 (3H, multiplet); 7.12 (1H, triplet, J=7.7 Hz); 7.22–7.35 (7H, multiplet); 8.45–8.46 (2H, multiplet).

(23c) 3-Methoxy-4-<3-{4-pyridyl-[(S)-1-phenylethylamino]methyl}phenylamino>-3-cyclobutene-1,2-dione In a similar manner to that described in Example (1c), isomer A of 3-{[(S)-1-phenylethylamine]-4-pyridylmethyl}phenylamine (745 mg) [prepared as described in step (b) above] and 3,4-dimethoxy-3-cyclobutene-1,2-dione (373 mg) were reacted, to afford isomer A of the title compound (805 mg) as a pale yellow solid.

Isomer A

Nuclear Magnetic Resonance Spectrum (CDCl$_3$) δ ppm: 1.40 (3H, doublet, J=6.7 Hz); 3.63 (1H, quartet, J=6.7 Hz); 4.42 (3H, singlet); 4.59 (1H, singlet); 7.03 (1H, doublet, J=7.7 Hz); 7.14–7.37 (10H, multiplet); 8.56–8.57 (2H, multiplet).

In a similar manner to that described in Example (1c), isomer B of 3-{[(S)-1-phenylethylamine]-4-pyridylmethyl}phenylamine (690 mg) and 3,4-dimethoxy-3-cyclobutene-1,2-dione (355 mg) were reacted, to afford isomer B of the title compound (604 mg) as a pale yellow solid.
Isomer B Nuclear Magnetic Resonance Spectrum (CDCl$_3$) δ ppm: 1.40 (3H, doublet, J=6.6 Hz); 3.69 (1H, quartet, J=6.6 Hz); 4.41 (3H, singlet); 4.60 (1H, singlet); 7.05 (1H, doublet, J=7.5 Hz); 7.21–7.36 (10H, multiplet); 8.47–8.48 (2H, multiplet).

(23d) 3-Amino-4-<3-{4-pyridyl-[(S)-1-phenylethylamino]methyl}phenylamino>-3-cyclobutene-1,2-dione In a similar manner to that described in Example (1d), isomer A of 3-methoxy-4-<3-{2-pyridyl-[(S)-1-phenylethylamino]methyl}phenylamino>-3-cyclobutene-1,2-dione (800 mg) [prepared as described in step (c) above] and a solution of ammonia in ethanol (2N, 3.8 ml) were reacted, to give isomer A of the title compound (625 mg) as an orange solid.
Isomer A Nuclear Magnetic Resonance Spectrum (DMSO-d$_6$) δ ppm: 1.30 (3H, doublet, J=6.6 Hz); 3.49 (1H, quartet, J=6.6 Hz); 4.49 (1H, singlet); 6.93 (1H, doublet, J=7.8 Hz); 7.21–7.44 (10H, multiplet); 8.50 (2H, doublet, J=5.3 Hz). melting point: 152–154° C.; optical rotation [α]$_D$: +16.8 (c=1.00, EtOH).

In a similar manner to that described in Example (1d), isomer B of 3-methoxy-4-(3-14-pyridyl-[(S)-1-phenylethylamino]methyl}phenylamino)-3-cyclobutene-1,2-dione (600 mg) and a solution of ammonia in ethanol (2N, 3.0 ml) were reacted, to give isomer B of the title compound (412 mg) as a pale yellow solid.
Isomer B Nuclear Magnetic Resonance Spectrum (DMSO-d$_6$) δ ppm: 1.31 (3H, doublet, J=6.6 Hz); 3.57 (1H, quartet, J=6.6 Hz); 4.49 (1H, singlet); 6.99 (1H, doublet, J=7.5 Hz); 7.20–7.35 (9H, multiplet); 7.42 (1H, doublet, J=8.0 Hz); 8.43 (2H, doublet, J=5.7 Hz). melting point: 168–171° C.; optical rotation [α]$_D$: +23.5 (c=1.00, EtOH).

EXAMPLE 24

3-Amino-4-<3-{4-pyridyl-[(R)-1-phenylethylamino]methyl}phenylamino>-3-cyclobutene-1,2-dione (Compound No. 2-691)

In a similar manner to that described in Example 23, (3-nitrophenyl)-4-pyridylketone (2.0 g) and (R)-1-phenylethylamine were reacted, to give isomer A of the title compound and isomer B of the title compound.
Isomer A melting point: 109° C. (dec); optical rotation [α]$_D$: −16.1 (c=1.0, EtOH).
Isomer B melting point: 141–143° C.; optical rotation [α]$_D$: −3.87 (c=0.1, EtOH).

EXAMPLE 25

3-Amino-4-<3-{(3,4-dimethoxyphenyl)-[1-(3,4-difluorophenyl)ethylamino]methyl}phenylamino>-3-cyclobutene-1,2-dione and the hydrochloride thereof (Compound No. 2-1397)
(25a) 3-{(3,4-dimethoxyphenyl)-[1-(3,4-difluorophenyl)ethylamino]methyl}phenylamine Triethylamine (5.82 ml) was added to a suspension of 3,4-dimethoxy-3'-nitro-benzophenone (2.0 g) and 1-(3,4-difluorophenyl)ethylamine hydrochloride (2.48 g) in anhydrous dichloromethane (60 ml). In an ice bath, a solution of titanium tetrachloride (0.92 ml) in anhydrous dichloromethane (10 ml) was slowly added dropwise to the mixture. This mixture was stirred at ambient temperature for 2 hours. At the end of this time, ethyl acetate and an aqueous solution of sodium hydrogencarbonate were added to the reaction mixture, and the insoluble material was removed by filtration. The filtrate was separated and the aqueous layer was extracted with ethyl acetate. The ethyl acetate layer and extract were combined and washed with a saturated aqueous solution of sodium chloride and dried over anhydrous sodium sulfate. The residue was then concentrated by evaporation under reduced pressure, to afford the imine derivative as an oil.

Nickel chloride hexahydrate (3.31 g,) was added to a solution of this oil in methanol (100 ml). In an ice bath sodium borohydride (1.11 g) was added in several portions to the mixture, and this mixture was stirred at ambient temperature for 3 hours. Water and ethyl acetate were added to the reaction mixture, and the insoluble material was removed by filtration. The filtrate was separated and the aqueous layer was extracted with ethyl acetate. The ethyl acetate layer and extract were combined, washed with a saturated aqueous solution of sodium chloride and dried over anhydrous sodium sulfate. It was then concentrated by evaporation under reduced pressure. The residue was purified by chromatography through a silica gel column using a 5:1 by volume mixture of cyclohexane and ethyl acetate as the eluant, to afford the title compound (1.45 g) as a yellow oil.

Nuclear Magnetic Resonance Spectrum (CDCl$_3$) δ ppm: 1.317 and 1.325 (total, 3H, each doublet, J=6.6, 6.6 Hz); 3.59–3.69 (1H, multiplet); 3.81, 3.83, 3.85 and 3.88 (total 6H, each singlet); 4.42 and 4.44 (total 1H, each singlet); 6.50–7.17 (10H, multiplet).

(25b) 3-Methoxy-4-<3-{(3,4-dimethoxyphenyl)-[1-(3,4-difluorophenyl)ethylamino]methyl}phenylamino>-3-cyclobutene-1,2-dione In a similar manner to that described in Example (1c), a solution A of 3-{(3,4-dimethoxyphenyl-[1-(3,4-difluorophenyl)ethylamino]methyl}phenylamine (500 mg) [prepared as described in step (a) above] in methanol (10 ml) and 3,4-dimethoxy-3-cyclobutene-1,2-dione (357 mg) were reacted, to afford the title compound (450 mg) as a brown foamy solid.

Nuclear Magnetic Resonance Spectrum (CDCl$_3$) δ ppm: 1.33–1.37 (3H, multiplet); 3.63–3.66 (1H, multiplet); 3.82, 3.83, 3.85 and 3.89 (total 6H, each singlet); 4.45 (3H, singlet); 4.50 and 4.55 (total 1H, each singlet); 6.75–7.34 (10H, multiplet).

(25c) 3-Amino-4-<3-{3,4-dimethoxyphenyl)-1-(3,4-difluorophenyl)-ethylamino]methyl}phenylamino>-3-cyclobutene-1,2-dione In a similar manner to that described in Example (1d), a solution of 3-methoxy-4-<3-{(3,4-dimethoxyphenyl)-[1-(3,4-difluorophenyl)ethylamino]methyl}phenylamino>-3-cyclobutene-1,2-dione (450 mg) [prepared as described in step (b) above] in ethanol (5 ml) and a solution of ammonia in ethanol (2N, 1 ml) were reacted, to give the title compound (298 mg) as a yellow solid.

Nuclear Magnetic Resonance Spectrum (DMSO-d$_6$) δ ppm: 1.27–1.30 (3H, multiplet); 3.50–3.60 (1H, multiplet); 3.68, 3.70, 3.72 and 3.73 (total 6H, each singlet); 4.38 and 4.45 (total 1H, each singlet); 6.82–7.01 (4H, multiplet);

7.07–7.10 (1H, multiplet); 7.18–7.43 (5H, multiplet). melting point: 134–136° C.

(25d) 3-Amino-4-<3-{(3,4-dimethoxyphenyl)-[1-(3,4-difluorophenyl)ethylamino]methyl}phenylamino>-3-cyclobutene-1,2-dione hydrochloride Hydrogen chloride in ethyl acetate (4N, 1 ml) was added to a solution of 3-amino-4-<3-{(3,4-dimethoxyphenyl)-[1-(3,4-difluorophenyl)ethylamino]methyl}phenylamino>-3-cyclobutene-1,2-dione (145 mg) [prepared as described in step (c) above] in ethyl acetate (5 ml). The mixture was stirred for 15 minutes. At the end of this time, the precipitate was filtered and washed with diethyl ether to give the title compound (155 mg) as a pale yellow solid.

Nuclear Magnetic Resonance Spectrum (DMSO-$d_6$) δ ppm: 1.65–1.66 (3H, multiplet); 3.73, 3.76, 3.80 and 3.81 (total 6H, each singlet); 4.21–4.30 (1H, multiplet); 5.06–5.21 (1H, multiplet); 6.95–7.00 (total 1H, doublet, J=6.95, 7.00 Hz); 7.07–7.12 (1H, multiplet); 7.23–7.58 (8H, multiplet). melting point: 160–162° C.

EXAMPLE 26

3-Amino-4-<3-{(4-fluorophenyl)-[1-(3,4-difluorophenyl)ethylamino]methyl}phenylamino>-3-cyclobutene-1,2-dione (Compound No. 2-1299)

(26a) N-[(3-Nitrophenyl)-(4-fluorophenyl)methyl]-N-[1-(3,4-difluorophenyl)ethyl]amine In a similar manner to that described in Example (1a), 4-fluoro-3'-nitrobenzophenone (2.0 g), 1-(3,4-difluorophenyl)ethylamine hydrochloride (3.16 g), triethylamine (6.82 ml), titanium tetrachloride (1.08 ml), sodium cyanoborohydride (2.28 g) and acetic acid (0.7 ml) were reacted, to afford the title compound (3.03 g) as a yellow oil.

Nuclear Magnetic Resonance Spectrum (CDCl$_3$) δ ppm: 1.36 and 1.37 (total 3H, each doublet, J=6.6, 6.6 Hz); 3.59 and 3.63 (total 1H, each quartet, J=6.7, 6.8 Hz); 4.65 and 4.69 (total 1H, each singlet); 6.87–7.00 (2H, multiplet); 7.03–7.16 (3H, multiplet); 7.19–7.26 (2H, multiplet); 7.41 and 7.51 (total 1H, each doublet, J=8.0, 8.0 Hz); 7.57 and 7.63 (total 1H, each doublet, J=7.9, 7.9 Hz); 8.04–8.14 (1H, multiplet); 8.20–8.23 (1H multiplet).

(26b) 3-{(4-Fluorophenyl)-[1-(3,4-difluorophenyl)ethylamino]methyl}phenylamine

In a similar manner to that described in Example (15b), a solution of N-[(3-nitrophenyl)-(4-fluorophenyl)methyl]-N-[1-(3,4-difluorophenyl)ethyl]amine (3.0 g) [prepared as described in step (a) above] in methanol (10 ml), nickel chloride hexahydrate (3.69 g) and sodium borohydride (1.24 g) were reacted, and the reaction mixture was purified to afford isomer A of the title compound (630 mg) as a pale yellow oil and isomer B of the title compound (580 mg) as a pale yellow oil.

Isomer A

Nuclear Magnetic Resonance Spectrum (CDCl$_3$) δ ppm: 1.31 (3H, doublet, J=6.6 Hz); 3.67 (1H, quartet, J=6.6 Hz); 4.45 (1H, singlet); 6.56–6.59 (2H, multiplet); 6.64 (1H, doublet, J=7.4 Hz); 6.90–6.97 (3H, multiplet); 7.06–7.14 (3H, multiplet); 7.23 (2H, doublet of doublets, J=3.0, 5.5 Hz).

Isomer B

Nuclear Magnetic Resonance Spectrum (CDCl$_3$) δ ppm: 1.32 (3H, doublet, J=6.6 Hz); 3.63 (1H, quartet, J=6.6 Hz); 4.47 (1H, singlet); 6.52 (1H, doublet, J=10.0 Hz); 6.58 (1H, singlet); 6.63 (1H, doublet, J=7.9 Hz); 6.89–6.93 (1H, multiplet); 6.98–7.13 (5H, multiplet); 7.22–7.28 (2H, multiplet).

(26c) 3-Methoxy-4-<3-{(4-fluorophenyl)-[1-(3,4-difluorophenyl)ethylamino]methyl}phenylamino>-3-cyclobutene-1,2-dione In a similar manner to that described in Example (1c), a solution of isomer A of 3-{(4-fluorophenyl)-[1-(3,4-difluorophenyl)ethylamino]methyl}phenylamine (520 mg) [prepared as described in step (b) above] in methanol (20 ml) and 3,4-dimethoxy-3-cyclobutene-1,2-dione (174 mg) were reacted, to afford isomer A of the title compound (650 mg) as a colorless foamy solid.

Isomer A

Nuclear Magnetic Resonance Spectrum (CDCl$_3$) δ ppm: 1.35 (3H, doublet, J=6.7 Hz); 3.64 (1H, quartet, J=6.6 Hz); 4.44 (3H, singlet); 4.57 (1H, singlet); 6.92–6.98 (3H, multiplet); 7.06–7.15 (3H, multiplet); 7.18–7.35 (5H, multiplet).

In a similar manner to that described in Example (1c), a solution of isomer B of 3-{(4-fluorophenyl)-[1-(3,4-difluorophenyl)ethylamino]methyl}phenylamine (550 mg) in methanol (20 ml) and 3,4-dimethoxy-3-cyclobutene-1,2-dione (439 mg) were reacted, to afford isomer B of the title compound (670 mg) as a colorless foamy solid.

Isomer B

Nuclear Magnetic Resonance Spectrum (CDCl$_3$) δ ppm: 1.34 (3H, doublet, J=6.6 Hz); 3.61 (1H, quartet, J=6.6 Hz); 4.45 (3H, singlet); 4.56 (1H, singlet); 6.91–6.95 (1H, multiplet); 7.02–7.14 (6H, multiplet); 7.24–7.27 (4H, multiplet).

(26d) 3-Amino-4-(3-{(4-fluorophenyl)-[1-(3,4-difluorophenyl)ethylamino]methyl}phenylamino>-3-cyclobutene-1,2-dione In a similar manner to that described in Example (1d), a solution of isomer A of 3-methoxy-4-<3-{(4-fluorophenyl)-[1-(3,4-difluorophenyl)ethylamino]ethyl}phenylamino>-3-cyclobutene-1,2-dione (630 mg) [prepared as described in step (c) above] in ethanol (20 ml) and a solution of ammonia in ethanol (2N, 5 ml) were reacted, to give isomer A of the title compound (366 mg) as a pale yellow solid.

Isomer A

Nuclear Magnetic Resonance Spectrum (DMSO-$d_6$) δ ppm: 1.29 (3H, doublet, J=6.6 Hz); 3.58 (1H, quartet, J=6.5 Hz); 4.49 (1H, singlet); 6.99 (1H, doublet, J=7.6 Hz); 7.05–7.10 (3H, multiplet); 7.27 (1H, doublet of doublets, J=7.7, 7.9 Hz); 7.30–7.42 (6H, multiplet). melting point: 204–206° C.

In a similar manner to that described in Example (1d), a solution of isomer B of 3-methoxy-4-<3-{(4-fluorophenyl)-[1-(3,4-difluorophenyl)ethylamino]methyl}phenylamino>-3-cyclobutene-1,2-dione (630 mg) in ethanol (20 ml) and a solution of ammonia in ethanol (2N, 5 ml) were reacted, to give isomer B of the title compound (362 mg) as a pale yellow solid.

Isomer B

Nuclear Magnetic Resonance Spectrum (DMSO-$d_6$) δ ppm: 1.27 (3H, doublet, J=6.6 Hz); 3.48–3.52 (1H, multiplet); 4.48 (1H, singlet); 6.93 (1H, doublet, J=7.7 Hz); 7.05–7.08 (1H, multiplet); 7.14 (2H, triplet, J=8.8 Hz); 7.21 (1H, doublet of doublets, J=7.7, 7.9 Hz); 7.30 (1H, singlet); 7.33–7.41 (5H, multiplet). melting point: 210–212° C.

EXAMPLE 27

3-Amino-4-<3-{(3-methoxyphenyl)-[(S)-1-(3-fluorophenyl)ethylamino]methyl}phenylamino>-3-cyclobutene-1,2-dione (Compound No. 2-802)

(27a) N-[(3-Nitrophenyl)-(3-methoxyphenyl)methyl]-N-[(S)-1-(3-fluorophenyl)ethyl]amine In a similar manner to that described in Example (1a), 3-methoxy-3'-nitrobenzophenone (2.0 g), (S)-1-(3-fluorophenyl)ethylamine hydrochloride (2.73 g), triethylamine (6.50 ml), titanium tetrachloride (1.03 ml), sodium cyanoborohydride (2.15 g) and acetic acid (0.67 ml) were reacted, to afford the title compound (2.93 g) as a yellow oil.

Nuclear Magnetic Resonance Spectrum (CDCl$_3$) δ ppm: 1.37 and 1.39 (total 3H, each doublet, J=6.6, 6.7 Hz); 3.62 and 3.71 (total 1H, each quartet, J=6.6, 6.6 Hz); 3.76 and 3.80 (total 3H, each singlet); 4.64 and 4.69 (total 1H, each singlet); 6.75–6.86 (3H, multiplet); 6.91–7.04 (3H, multiplet); 7.20–7.33 (2H, multiplet); 7.39 and 7.48 (total 1H, each triplet, J=7.8, 7.9 Hz); 7.61 and 7.68 (total 1H, each triplet, J=7.9, 8.1 Hz); 8.02–8.12 (1H, multiplet); 8.23 and 8.26 (total 1H, each doublet of doublets, J=1.8 and 1.9 Hz).

(27b) 3-{(3-methoxyphenyl)-[(S)-1-(3-fluorophenyl)ethylamino]methyl}phenylamine

In a similar manner to that described in Example (1b), a solution of N-[(3-nitrophenyl)-(4-methoxyphenyl)methyl]-N-[(S)-1-(3-fluorophenyl)ethyl]amine (2.79 g) [prepared as described in step (a) above] in methanol (50 ml), nickel chloride hexahydrate (3.49 g) and sodium borohydride (1.17 g) were reacted, and the residue was purified by chromatography through a silica gel column, using mixtures of toluene and ethyl acetate ranging from 8:1 to 5:1 by volume as the eluant, and reverse phase chromatography through a Lobar column under medium pressure using a 35:65 by volume mixture of acetonitrile and an acetic acid buffer solution (water/acetic acid/triethylamine=1000:2:2) as the eluant, to afford isomer A of the title compound (700 mg) as a yellow oil and isomer B of the title compound (220 mg) as a yellow oil.

Isomer A

Nuclear Magnetic Resonance Spectrum (CDCl$_3$) δ ppm: 1.34 (3H, doublet, J=6.6 Hz); 3.71 (1H, quartet, J=6.6 Hz); 3.75 (3H, singlet); 4.49 (1H, singlet); 6.57 (1H, doublet of doublets, J=1.9, 8.2 Hz); 6.64 (1H, doublet, J=2.0 Hz); 6.69–6.73 (2H, multiplet); 6.85–6.95 (3H, multiplet); 7.00–7.04 (2H, multiplet); 7.06–7.18 (2H, multiplet); 7.24–7.30 (1H, multiplet).

Isomer B

Nuclear Magnetic Resonance Spectrum (CDCl$_3$) δ ppm: 1.34 (3H, doublet, J=6.7 Hz); 3.68 (1H, quartet, J=6.7 Hz); 3.79 (3H, singlet); 4.48 (1H, singlet); 6.51 (1H, doublet of doublets, J=2.2, 7.8 Hz); 6.62 (1H, doublet, J=1.9 Hz); 6.67 (1H, doublet, J=7.7 Hz); 6.78 (1H, doublet of doublets, J=2.1, 8.0 Hz); 6.88–7.05 (6H, multiplet); 7.21–7.30 (2H, multiplet).

(27c) 3-Methoxy-4-<3-{(3-methoxyphenyl)-[(S)-1-(3-fluorophenyl)ethylamino]methyl}phenylamino>-3-cyclobutene-1,2-dione In a similar manner to that described in Example (1c), a solution of isomer A of 3-{(3-methoxyphenyl)-[(S)-1-(3-fluorophenyl)ethylamino]methyl}phenylamine (640 mg) [prepared as described in step (b) above] in methanol (20 ml) and 3,4-dimethoxy-3-cyclobutene-1,2-dione (519 mg) were reacted, to afford isomer A of the title compound (800 mg) as a pale yellow foamy solid.

Isomer A

Nuclear Magnetic Resonance Spectrum (CDCl$_3$) δ ppm: 1.37 (3H, doublet, J=6.6 Hz); 3.67 (1H, quartet, J=6.6 Hz); 3.75 (3H, singlet); 4.43 (3H, singlet); 4.60 (1H, singlet); 6.73–6.76 (1H, multiplet); 6.84–6.86 (2H, multiplet); 6.92–7.01 (3H, multiplet); 7.11–7.33 (6H, multiplet).

In a similar manner to that described in Example (1c), a solution of isomer B of 3-{(3-methoxyphenyl)-[(S)-1-(3-fluorophenyl)ethylamino]methyl}phenylamine (210 mg) in methanol (10 ml) and 3,4-dimethoxy-3-cyclobutene-1,2-dione (170 mg) were reacted, to afford isomer B of the title compound (267 mg) as a pale yellow foamy solid.

Isomer B

Nuclear Magnetic Resonance Spectrum (CDCl$_3$) δ ppm: 1.36 (3H, doublet, J=6.6 Hz); 3.69 (1H, quartet, J=6.6 Hz); 3.80 (3H, singlet); 4.44 (3H, singlet); 4.56 (1H, singlet); 6.80–7.10 (8H, multiplet); 7.22–7.31 (4H, multiplet).

(27d) 3-Amino-4-<3-{(3-methoxyphenyl)-[(S)-1-(3-fluorophenyl)ethylamino]methyl}phenylamino>-3-cyclobutene-1,2-dione In a similar manner to that described in Example (1d), a solution of isomer A of 3-methoxy-4-<3-{(3-methoxyphenyl)-[(S)-1-(3-fluorophenyl)ethylamino]methyl}phenylamino>-3-cyclobutene-1,2-dione (200 mg) [prepared as described in step (c) above] in ethanol (10 ml) and a solution of ammonia in ethanol (2N, 1 ml) were reacted, to give isomer A of the title compound (147 mg) as a yellow solid.

Isomer A

Nuclear Magnetic Resonance Spectrum (DMSO-d$_6$) δ ppm: 1.31 (3H, doublet, J=6.6 Hz); 3.59 (1H, quartet, J=6.5 Hz); 3.70 (3H, singlet); 4.48 (1H, singlet); 6.73–6.75 (1H, multiplet); 6.87–7.43 (11H, multiplet). melting point: 155–156° C.; optical rotation [α]$_D$: −13.2 (c=0.5, EtOH).

In a similar manner to that described in Example (1d), a solution of isomer B of 3-methoxy-4-<3-{(3-methoxyphenyl)-[(S)-1-(3-fluorophenyl)ethylamino]methyl}phenylamino>-3-cyclobutene-1,2-dione (200 mg) in ethanol (10 ml) and a solution of ammonia in ethanol (2N, 1 ml) to give isomer B of the title compound (158 mg) as a yellow solid.

Isomer B

Nuclear Magnetic Resonance Spectrum (DMSO-d$_6$) δ ppm: 1.29 (3H, doublet, J=6.6 Hz); 3.56 (1H, quartet, J=6.6 Hz); 3.73 (3H, singlet); 4.44 (1H, singlet); 6.78–6.80 (1H, multiplet); 6.87–7.43 (11H, multiplet). melting point: 171–173° C.; optical rotation [α]$_D$: −60.3 (c=0.5, EtOH).

EXAMPLE 28

2-{3,4-Dioxo<2-{3-(3-methoxyphenyl)-[(S)-1-(3-fluorophenyl)ethylamino]methyl}phenylamino>-1-cyclobutenylamino}ethanesulfonic acid (Compound No. 2-2918)

A solution of isomer A of 3-methoxy-4-<3-{(3-methoxyphenyl)-[(S)-1-(3-fluorophenyl)ethylamino]methyl}phenylamino>-3-cyclobutene-1,2-dione (200 mg) [prepared as described in Example 27(c)], 2-aminoethanesulfonic acid (109 mg) and triethylamine (0.12 ml) in a mixture of ethanol (5 ml) and water (2 ml) was stirred at ambient temperature for 1 hour. The reaction mixture was then diluted with ethyl acetate and washed with a saturated aqueous solution of sodium hydrogencarbonate and a saturated aqueous solution of sodium chloride. The organic layer was separated, dried over anhydrous sodium sulfate and concentrated by evaporation under reduced pressure. The residue was powdered with diethyl ether and dried to afford the sodium salt (40%) of the title compound (130 mg) as a pale yellow solid.

Nuclear Magnetic Resonance Spectrum (DMSO-d$_6$) δ ppm: 1.30 (3H, doublet, J=6.6 Hz); 2.72 (2H, triplet, J=6.0 Hz); 3.59 (1H, quartet, J=6.5 Hz); 3.70 (3H, singlet); 3.89 (2H, broad); 4.46 (1H, singlet); 6.37 (1H, doublet of doublets, J=2.1, 8.1 Hz); 6.86–7.42 (11H, multiplet). melting point: 240–244° C.

EXAMPLE 29

3-Amino-4-(3-{2-methoxyphenyl-1(S)-1-(3-fluorophenyl)ethylamino]methyl}phenylamino>-3-cyclobutene-1,2-dione (Compound No. 2-797)

(29a) N-[(3-Nitrophenyl)-(2-methoxyphenyl)methyl]-N-[(S)-1-(3-fluorophenyl)ethyl]amine In a similar manner to that described in Example (1a), 2-methoxy-3'-nitrobenzophenone (2.0 g), (S)-1-(3-fluorophenyl)ethylamine hydrochloride (2.73 g), triethylamine (6.50 ml), titanium tetrachloride (1.03 ml), sodium cyanoborohydride (2.15 g) and acetic acid (0.67 ml) were reacted, to afford the title compound (3.10 g) as a yellow oil.

Nuclear Magnetic Resonance Spectrum (CDCl$_3$) δ ppm: 1.35 and 1.37 (total 3H, each doublet, J=6.6, 6.6 Hz); 3.53–3.70 (1H, multiplet); 3.70 and 3.72 (total 3H, each singlet); 4.87 and 5.12 (total 1H, each singlet); 6.81–7.08 (5H, multiplet); 7.20–7.47 (4H, multiplet); 7.60 and 7.70 (total 1H, each doublet, J=8.0, 7.4 Hz); 8.00 and 8.07 (total 1H, each doublet of doublets, J=1.9, 8.2 and 1.8, 7.8 Hz); 8.26 and 8.28 (total 1H, each doublet, J=2.1, 1.9 Hz).

(29b) 3-{(2-Methoxyphenyl)-[(S)-1-(3-fluorophenyl)ethylamino]methyl}phenylamine

In a similar manner to that described in Example (1b), a solution of N-[(3-nitrophenyl)-(2-methoxyphenyl)methyl]-N-[(S)-1-(3-fluorophenyl)ethyl]amine (2.96 g) [prepared as described in step (a) above] in methanol (50 ml), nickel chloride hexahydrate (3.70 g) and sodium borohydride (1.24 g) were reacted, and the crude product was purified by reverse phase HPLC using a 40:60 by volume mixture of acetonitrile and an acetic acid buffer solution (water/acetic acid/triethylamine=1000:2:2) as the eluant, to afford isomer A of the title compound (540 mg) as a yellow oil and isomer B of the title compound (800 mg) as a yellow oil.

Isomer A

Nuclear Magnetic Resonance Spectrum (CDCl$_3$) δ ppm: 1.33 (3H, doublet, J=6.7 Hz); 3.65 (1H, quartet, J=6.7 Hz); 3.67 (3H, singlet); 4.85 (1H, singlet); 6.48–6.50 (1H, multiplet); 6.68–6.70 (2H, multiplet); 6.85–7.06 (6H, multiplet); 7.16–7.35 (3H, multiplet).

Isomer B

Nuclear Magnetic Resonance Spectrum (CDCl$_3$) δ ppm: 1.34 (3H, doublet, J=6.7 Hz); 3.71–3.76 (1H, multiplet); 3.73 (3H, singlet); 4.95 (1H, singlet); 6.55–6.58 (1H, multiplet); 6.73–7.28 (11H, multiplet).

(29c) 3-Methoxy-4-<3-{(2-methoxyphenyl)-[(S)-1-(3-fluorophenyl)ethylamino]methyl}phenylamino>-3-cyclobutene-1,2-dione In a similar manner to that described in Example (1c), a solution of isomer A of 3-{(2-methoxyphenyl)-[(S)-1-(3-fluorophenyl)ethylamino]methyl}phenylamine (400 mg) [prepared as described in step (b) above] in methanol (10 ml) and 3,4-dimethoxy-3-cyclobutene-1,2-dione (324 mg) were reacted, to afford isomer A of the title compound (470 mg) as a pale yellow oil.

Isomer A

Nuclear Magnetic Resonance Spectrum (CDCl$_3$) δ ppm: 1.33 (3H, doublet, J=6.6 Hz); 3.66 (1H, quartet, J=6.6 Hz); 3.68 (3H, singlet); 4.42 (3H, singlet); 4.85 (1H, singlet); 6.89–7.12 (7H, multiplet); 7.18–7.31 (5H, multiplet).

In a similar manner to that described in Example (1c), a solution of isomer B of 3-{(2-methoxyphenyl)-[(S)-1-(3-fluorophenyl)ethylamino]methyl}phenylamine (730 mg) in methanol (10 ml) and 3,4-dimethoxy-3-cyclobutene-1,2-dione (592 mg) were reacted, to afford isomer B of the title compound (850 mg) as a pale yellow foamy solid.

Isomer B

Nuclear Magnetic Resonance Spectrum (CDCl$_3$) δ ppm: 1.37 (3H, doublet, J=6.7 Hz); 3.69 (1H, quartet, J=6.7 Hz); 3.72 (3H, singlet); 4.40 (3H, singlet); 5.05 (1H, singlet); 6.82 (1H, doublet, J=8.1 Hz); 6.86–7.04 (4H, multiplet); 7.15–7.32 (7H, multiplet).

(29d) 3-Amino-4-<3-{(2-methoxyphenyl)-[(S)-1-(3-fluorophenyl)ethylamino]methyl}phenylamino>-3-cyclobutene-1,2-dione In a similar manner to that described in Example (1d), a solution of isomer A of 3-methoxy-4-<3-{(2-methoxyphenyl)-[(S)-1-(3-fluorophenyl)ethylamino]methyl}phenylamino>-3-cyclobutene-1,2-dione (390 mg) [prepared as described in step (c) above] in ethanol (10 ml) and a solution of ammonia in ethanol (2N, 2 ml) were reacted, to give isomer A of the title compound (323 mg) as a yellow solid.

Isomer A

Nuclear Magnetic Resonance Spectrum (DMSO-d$_6$) δ ppm: 1.27 (3H, doublet, J=6.5 Hz); 3.53 (1H, quartet, J=6.5 Hz); 3.62 (3H, singlet); 4.86 (1H, singlet); 6.87 (1H, doublet, J=7.7 Hz); 6.94–7.25 (8H, multiplet); 7.31–7.37 (1H, multiplet); 7.46 (1H, doublet, J=7.9 Hz); 7.55 (1H, doublet J=7.2 Hz). melting point: 187–189° C.; optical rotation [α]$_D$: −32.8 (c=0.5, EtOH).

In a similar manner to that described in Example (1d), a solution of isomer B of 3-methoxy-4-<3-{(2-methoxyphenyl)-[(S)-1-(3-fluorophenyl)ethylamino]methyl}phenylamino>-3-cyclobutene-1,2-dione (300 mg) in ethanol (10 ml) and a solution of ammonia in ethanol (2N, 2 ml) were reacted, to give isomer B of the title compound (235 mg) as a yellow solid.

Isomer B

Nuclear Magnetic Resonance Spectrum (DMSO-d$_6$) δ ppm: 1.28 (3H, doublet, J=6.6 Hz); 3.58–3.62 (1H, multiplet); 3.67 (3H, singlet); 4.90 (1H, singlet); 6.88–6.95 (3H, multiplet); 7.04 (2H, doublet, J=8.1 Hz); 7.15–7.36 (5H, multiplet); 7.40–7.45 (2H, multiplet). melting point: 190–193° C.; optical rotation [α]$_D$: +69.7 (c=0.5, EtOH).

EXAMPLE 30

3-Amino-4-<3-{(4-methoxyphenyl)-[(R)-1-cyclohexylaminoethyl]methyl}phenylamino>-3-cyclobutene-1,2-dione (Compound No. 2-<36)

(30a) N-[(3-Nitrophenyl)-(4-methoxyphenyl)methyl-N-[(R)-1-cyclohexylethyl]amine

In a similar manner to that described in Example (1a), 4-methoxy-3'-nitrobenzophenone (2.0 g), (R)-1-cyclohexylethylamine (2.36 ml), triethylamine (4.33 ml), titanium tetrachloride (1.03 ml), sodium cyanoborohydride (2.15 g) and acetic acid (0.67 ml) were reacted, to afford the title compound (2.68 g) as a yellow oil.

Nuclear Magnetic Resonance Spectrum (CDCl$_3$) δ ppm: 0.97–1.82 (14H, multiplet); 2.30–2.42 (1H, multiplet); 3.77 and 3.78 (total 3H, each singlet); 5.00 and 5.02 (total 1H, each singlet); 6.83–6.87 (2H, multiplet); 7.26–7.29 (2H, multiplet); 7.41–7.46 (1H, multiplet); 7.76 (1H, doublet of doublets, J=8.0, 8.2 Hz); 8.05 (1H, doublet, J=8.0 Hz); 8.30–8.34 (1H, multiplet).

(30b) 3-{(4-Methoxyphenyl)-[(R)-1-cyclohexylethylamino]methyl}phenylamine

In a similar manner to that described in Example (1b), a solution of N-[(3-nitrophenyl)-(4-methoxyphenyl)methyl]-N-[(R)-1-cyclohexylethyl]amine (2.60 g) [prepared as described in step (a) above] in methanol (50 ml), nickel chloride hexahydrate (3.35 g) and sodium borohydride (1.12 g) were reacted, to afford the title compound (1.83 g) as a colorless oil.

Nuclear Magnetic Resonance Spectrum (CDCl$_3$) δ ppm: 0.95–1.74 (14H, multiplet); 2.34–2.44 (1H, multiplet); 3.76 and 3.77 (total 3H, each singlet); 4.82 (1H, singlet); 6.50–6.53 (1H, multiplet); 6.73 (1H, singlet); 6.76–6.84 (3H, multiplet); 7.03–7.09 (1H, multiplet); 7.29–7.31 (2H, multiplet).

(30c) 3-Methoxy-4-(3-{(4-methoxyphenyl)-[(R)-1-cyclohexylethylamino]methyl}phenylamino>-3-cyclobutene-1,2-dione In a similar manner to that described in Example (1c), a solution of 3-{(4-methoxyphenyl)-[(R)-1-cyclohexylethylamino]methyl}phenylamine (1.65 g) [prepared as described in step (b) above] in methanol (50 ml) and 3,4-dimethoxy-3-cyclobutene-1,2-dione (1.39 g) were reacted, to afford the title compound (1.77 g) as a colorless foamy solid.

Nuclear Magnetic Resonance Spectrum (CDCl$_3$) δ ppm: 0.96–1.36 (9H, multiplet); 1.64–1.75 (5H, multiplet); 2.38 (1H, quartet, J=5.9 Hz); 3.77 and 3.78 (total 3H, each singlet); 4.46 (3H, singlet); 4.91 (1H, singlet); 6.82–6.86 (2H, multiplet); 7.11–7.33 (6H, multiplet).

(30d) 3-Amino-4-<3-{(4-methoxyphenyl)-[(R)-1-cyclohexylethylamino]methyl}phenylamino>-3-cyclobutene-1,2-dione In a similar manner to that described in Example (1d), a solution of 3-methoxy-4-<3-{(4-methoxyphenyl)-[(R)-1-cyclohexylethylamino]methyl}phenylamino>-3-cyclobutene-1,2-dione (500 mg) [prepared as described in step (c) above] in ethanol (20 ml) and a solution of ammonia in ethanol (2N, 5 ml) were reacted, to give the title compound (412 mg) as a yellow solid.

Nuclear Magnetic Resonance Spectrum (DMSO-d$_6$) δ ppm: 0.94–1.37 (9H, multiplet); 1.60–1.77 (5H, multiplet); 2.24–2.25 (1H, multiplet); 3.71 (3H, singlet); 4.87 (1H, singlet); 6.85 (2H, doublet, J=7.5 Hz); 7.02–7.39 (6H, multiplet). melting point: 194–196° C.; optical rotation $[\alpha]_D$: −49.5 (c=0.5, EtOH).

EXAMPLE 31

3-Amino-4-<3-{(4-methoxyphenyl)-[(S)-1-cyclohexylethylamino]methyl}phenylamino>-3-cyclobutene-1,2-dione (Compound No. 2-436)

(31a) N-[(3-Nitrophenyl)-(4-methoxyphenyl)methyl-N-[(S)-1-cyclohexylethyl]amine

In a similar manner to that described in Example (1a), 4-methoxy-3'-nitrobenzophenone (2.0 g), (S)-1-cyclohexylethylamine (2.44 g), triethylamine (4.33 ml), titanium tetrachloride (1.03 ml), sodium cyanoborohydride (2.15 g) and acetic acid (0.67 ml) were reacted, to afford the title compound (2.73 g) as a yellow oil.

Nuclear Magnetic Resonance Spectrum (CDCl$_3$) δ ppm: 0.97–1.82 (14H, multiplet); 2.30–2.42 (1H, multiplet); 3.77 and 3.78 (total 3H, each singlet); 5 5.00 and 5.02 (total 1H, each singlet); 6.82–6.87 (2H, multiplet); 7.27–7.29 (2H, multiplet); 7.41–7.46 (1H, multiplet); 7.76 (1H, doublet of doublets, J=7.9, 8.2 Hz); 8.03–8.06 (1H, multiplet); 8.30–8.34 (1H, multiplet).

(31b) 3-{(4-Methoxyphenyl)-[(S)-1-cyclohexylethylamino]methyl}phenylamine

In a similar manner to that described in Example (1b), a solution of N-[(3-nitrophenyl)-(4-methoxyphenyl)methyl]-N-[(S)-1-cyclohexylethyl]amine (2.63 g) [prepared as described in step (a) above] in methanol (50 ml), nickel chloride hexahydrate (3.39 g) and sodium borohydride (1.14 g) were reacted, to afford the title compound (2.42 g) as a yellow oil.

Nuclear Magnetic Resonance Spectrum (CDCl$_3$) δ ppm: 0.93–1.38 (9H, multiplet); 1.64–1.74 (5H, multiplet); 2.34–2.45 (1H, multiplet); 3.76 and 3.77 (total 3H, each singlet); 4.82 (1H, singlet); 6.50–6.53 (1H, multiplet); 6.73 (1H, singlet); 6.76–6.83 (3H, multiplet); 7.04–7.10 (1H, multiplet); 7.30 (2H, doublet of doublets, J=1.3, 8.6 Hz).

(31c) 3-Methoxy-4-<3-{(4-methoxyphenyl)-[(S)-1-cyclohexylethylamino]methyl}phenylamino>-3-cyclobutene-1,2-dione In a similar manner to that described in Example (1c), a solution of 3-{(4-methoxyphenyl)-[(S)-1-cyclohexylethylamino]methyl}phenylamine (1.35 g) [prepared as described in step (b) above] in methanol (50 ml) and 3,4-dimethoxy-3-cyclobutene-1,2-dione (1.13 g) were reacted, to afford the title compound (1.01 g) as a yellow foamy solid.

Nuclear Magnetic Resonance Spectrum (CDCl$_3$) δ ppm: 0.96–1.36 (9H, multiplet); 1.64–1.75 (5H, multiplet); 2.38 (1H, quartet, J=5.6 Hz); 3.77 and 3.78 (total 3H, each singlet); 4.46 (3H, singlet); 4.91 (1H, singlet); 6.82–6.86 (2H, multiplet); 7.18–7.33 (6H, multiplet).

(31d) 3-Amino-4-<3-{(4-methoxyphenyl)-[(S)-1-cyclohexylethylamino]methyl}phenylamino>-3-cyclobutene-1,2-dione In a similar manner to that described in Example (1d), a solution of 3-methoxy-4-<3-{(4-methoxyphenyl)-[(S)-1-cyclohexylethylamino]methyl}phenylamino>-3-cyclobutene-1,2-dione (960 mg) [prepared as described in step (c) above] in ethanol (20 ml) and a solution of ammonia in ethanol (2N, 5 ml) were reacted, to give the title compound (780 mg) as a yellow solid.

Nuclear Magnetic Resonance Spectrum (DMSO-d$_6$) δ ppm: 0.89–1.37 (9H, multiplet); 1.60–1.77 (5H, multiplet); 2.22–2.29 (1H, multiplet); 3.70 (3H, singlet); 4.87 (1H, singlet); 6.85 (2H, doublet, J=8.2 Hz); 7.01–7.39 (6H, multiplet ). melting point: 191–193° C.; optical rotation $[\alpha]_D$: +58.9 (c=0.55, EtOH).

EXAMPLE 32

3-Amino-4-<3-{cyclohexyl-[1-(3,4-difluorophenyl)ethylamino]methyl}phenylamino>-3-cyclobutene-1,2-dione (Compound No. 2-1252)

(32a) 3-{Cyclohexyl-[1-(3,4-difluorophenyl)ethylamino]methyl}phenylamine

In a similar manner to that described in Example (25a), cyclohexyl-3-nitrophenylketone (3.0 g), 1-(3,4-difluorophenyl)ethylamine hydrochloride (4.98 g) triethylamine (10.8 ml), titanium tetrachloride (1.70 ml), nickel chloride hexahydrate (6.11 g), and sodium borohydride (2.05 g) were reacted, to afford the title compound (1.59 g) as a yellow oil.

Nuclear Magnetic Resonance Spectrum (CDCl$_3$) δ ppm: 0.81–1.69 (12H, multiplet); 1.72–1.76 (1H, multiplet); 2.03 (1H, doublet, J=12.7 Hz); 3.31 (1H, doublet, J=7.4 Hz); 3.56 (1H, quartet, J=6.4 Hz); 6.49 (2H, doublet, J=1.9 Hz); 6.55 (2H, doublet of doublets, J=2.5, 7.3 Hz); 6.90–6.93 (6H, multiplet); 6.97–7.12 (3H, multiplet).

(32b) 3-Methoxy-4-<3-{cyclohexyl-[1-(3,4-difluorophenyl)ethylamino]methyl}phenylamino>-3-cyclobutene-1,2-dione In a similar manner to that described in Example (1c), a solution of 3-{cyclohexyl-[1-(3,4-difluorophenyl)ethylamino]methyl}phenylamine (500 mg) [prepared as described in step (a) above] in methanol (50 ml) and 3,4-dimethoxy-3-cyclobutene-1,2-dione (413 mg) were reacted, to afford the title compound (650 mg) as a yellow foamy solid.

Nuclear Magnetic Resonance Spectrum (CDCl$_3$) δ ppm: 0.80–1.65 (12H multiplet); 1.75–1.78 (1H, multiplet); 1.95 (1H, doublet, J=6.5 Hz); 3.43 (1H, doublet, J=7.3 Hz); 3.54 (1H, quartet, J=6.4 Hz); 4.46 (3H, singlet); 6.87–7.14 (6H, multiplet); 7.23–7.26 (1H, multiplet).

(32c) 3-Amino-4-<3-{cyclohexyl-[1-(3,4-difluorophenyl)ethylamino]methyl}phenylamino<-3-cyclobutene-1,2-dione In a similar manner to that described in Example (1d), a solution of 3-methoxy-4-<3-{cyclohexyl-[1-(3,4-difluorophenyl)ethylamino]methyl}phenylamino>-3-cyclobutene-1,2-dione (300 mg) [prepared as described in step (b) above] in ethanol (10 ml) and a solution of ammonia in ethanol (2N, 2 ml) were reacted, to give the title compound (230 mg) as a yellow solid.

Nuclear Magnetic Resonance Spectrum (DMSO-$d_6$) δ ppm: 0.76–1.58 (12H, multiplet); 1.70 (1H, doublet, J=12.4 Hz); 2.02 (1H, doublet, J=11.6 Hz); 3.37 (1H, doublet, J=7.3 Hz); 3.52 (1H, quartet, J=6.4 Hz); 6.86 (1H, doublet, J=7.6 Hz); 7.05–7.08 (1H, multiplet); 7.19–7.37 (5H, multiplet). melting point: 202–205° C.

EXAMPLE 33

3-Amino-4-<3-{(4-methoxyphenyl)-[1-(4-hydroxyphenyl)ethylamino]methyl}phenylamino>-3-cyclobutene-1,2-dione (Compound No. 2-1816)

(33a) N-[(3-Nitrophenyl)-(4-methoxyphenyl)methyl]-N-[1-(4-acetoxyphenyl)-ethyl]amine In a similar manner to that described in Example (1a), 4-methoxy-3'-nitrobenzophenone (500 mg), 4-(1-aminoethyl)phenyl acetate hydrochloride (1.0 g), triethylamine (1.63 ml), titanium tetrachloride (0.26 ml), sodium cyanoborohydride (543 mg) and acetic acid (0.17 ml) were reacted, to afford the title compound (215 mg) as a yellow oil.

Nuclear Magnetic Resonance Spectrum (CDCl$_3$) δ ppm: 1.36 and 1.37 (total 3H, each doublet, J=6.6, 6.6 Hz); 2.30 and 2.32 (total 3H, each singlet); 3.60–3.72 (1H, multiplet); 3.76 and 3.81 (total 3H, each singlet); 4.64 and 4.69 (total 1 H, each singlet); 6.81 and 6.89 (total 2H, each doublet, J=8.7, 8.7 Hz); 7.04 and 7.07 (total 2H, each doublet, J=8.6, 8.6 Hz); 7.14–7.27 (4H, multiplet); 7.38 and 7.47 (total 1H, each triplet, J=8.0 and 8.0 Hz); 7.57 and 7.66 (total 1H, each doublet, J=7.6, 7.9 Hz); 8.01–8.10 (1H, multiplet); 8.23–8.27 (1H, multiplet).

(33b) 3-{(4-Methoxyphenyl)-[1-(4-acetoxyphenyl)ethylamino]methyl}phenylamine

Tin (II) chloride (451 mg) was added to a solution of N-[(3-nitrophenyl)-(4-methoxyphenyl)methyl]-N-[1-(4-acetoxyphenyl)ethyl]amine (200 mg) [prepared as described in step (a) above] in ethanol (10 ml). The mixture was heated under reflux for 1 hour. At the end of this time, ethyl acetate and a saturated aqueous solution of sodium hydrogencarbonate were added to the reaction mixture. The insoluble material was removed by filtration. The filtrate was separated and the aqueous layer was extracted with ethyl acetate. The ethyl acetate layer and extract were combined, washed with a saturated aqueous solution of sodium chloride and dried over magnesium sulfate. It was then concentrated by evaporation under reduced pressure, to afford the title compound (170 mg) as a yellow oil.

Nuclear Magnetic Resonance Spectrum (CDCl$_3$) δ ppm: 1.33 (3H, doublet, J=6.6 Hz); 2.30 (3H, singlet); 3.53–3.73 (1H, multiplet); 3.75 and 3.79 (total 3H, each singlet); 4.47 and, 4.49 (total 1H, each singlet); 6.48–6.87 (6H, multiplet); 7.01–7.28 (6H, multiplet).

(33c) 3-Methoxy-4-<3-{(4-methoxyphenyl)-[1-(4-acetoxyphenyl)ethylamino]methyl}phenylamino>-3-cyclobutene-1,2-dione In a similar manner to that described in Example (1c), a solution of 3-{(4-methoxyphenyl)-[1-(4-acetoxyphenyl)ethylamino]methyl}phenylamine (160 mg) in methanol (5 ml) and 3,4-dimethoxy-3-cyclobutene-1,2-dione (116 mg) were reacted, to afford the title compound (172 mg) as a yellow oil.

Nuclear Magnetic Resonance Spectrum (CDCl$_3$) δ ppm: 1.35 and 1.36 (total 31H, each doublet, J=6.6, 6.7 Hz); 2.31 (3H, singlet); 3.65–3.70 (1H, multiplet); 3.76 and 3.81 (total 3H, each singlet); 4.419 and 4.422 (total 3H, each singlet); 4.58 and 4.59 (total 1H, each singlet); 6.80 and 6.88 (total 2H, each doublet, J=8.5, 8.7 Hz); 7.00–7.33 (10H, multiplet).

(33d) 3-Amino-4-<3-{(4-methoxyphenyl)-[1-(4-hydroxyphenyl)ethylamino]methyl}phenylamino>-3-cyclobutene-1,2-dione A mixture of a solution of 3-methoxy-4-<3-{(4-methoxyphenyl)-[1-(4-acetoxyphenyl)ethylamino]methyl}phenylamino>-3-cyclobutene-1,2-dione (160 mg) [prepared as described in step (c) above] in ethanol (5 ml) and a solution of ammonia in ethanol (2N, 2 ml) was stirred at ambient temperature overnight. The reaction mixture was concentrated by evaporation under reduced pressure. The residue was powdered with a mixture of diethyl ether and ethyl acetate and filtered, to give the title compound (15 mg) as a yellow solid.

Nuclear Magnetic Resonance Spectrum (DMSO-$d_6$) δ ppm: 1.23–1,26 (3H, multiplet); 3.36–3.45 (1H, multiplet); 3.69 and 3.73 (total 3H, each singlet); 4.40 and 4.44 (total 1H, each singlet); 6.70 (2H, doublet, J=8.0 Hz); 6.80–7.45 (10H, multiplet). melting point: 127–129° C.

EXAMPLE 34

3-Amino-4-<3-{(4-methoxyphenyl)-1-(3,4-difluorophenyl)ethylamino]methyl}phenylamino>-3-cyclobutene-1,2-dione (Compound No. 2-1379)

(34a) [(3-Nitrophenyl)-(4-methoxyphenyl)methyl] [1-(3,4-difluorophenyl)ethyl]ether Methyltrioxorhenium (VII) (29 mg) was added to a solution of a mixture of 1-(3,4-difluorophenyl)ethanol (920 mg) and 4-methoxy-3'-nitro-diphenylmethanol (151 mg) in anlydrotis benzene (50 ml). The mixture was stirred at ambient temperature for 3 days and then heated under reflux for 4 hours. At the end of this time, the solvent was evaporated under reduced pressure. The residue was purified by chromatography through a silica gel column using mixtures of cyclohexane and ethyl acetate ranging from 10:1 to 8:1 by volume as the eluant, to afford the title compound (160 mg) as a yellow oil.

Nuclear Magnetic Resonance Spectrum (CDCl$_3$) δ ppm: 1.45 and 1.48 (total 3H, each doublet, J=6.5, 6.5 Hz); 3.77 and 3.82 (total 3H, each singlet); 4.40 (1H, quartet, J=6.5 Hz); 5.18 and 5.33 (total 1H, each singlet); 6.83 and, 6.92 (total 2H, each doublet, J=8.7, 8.7 Hz); 6.96–7.01 (1H, multiplet); 7.09–7.22 (4H, multiplet); 7.41–7.68 (2H, multiplet); 8.06–8.22 (2H, multiplet).

(34b) 3-{(4-Methoxyphenyl)-[1-(3,4-difluorophenyl)ethylamino]methyl}phenylamine

In a similar manner to that described in Example (1b), a solution of [(3-nitrophenyl)-(4-methoxyphenyl)methyl] [1-(3,4-difluorophenyl)ethyl] ether (150 mg) [prepared as described in step (a) above] in methanol (10 ml), nickel chloride hexahydrate (179 mg) and sodium borohydride (60 mg) were reacted, to afford the title compound (125 mg) as a yellow oil.

Nuclear Magnetic Resonance Spectrum (CDCl$_3$) δ ppm: 1.42 and 1.43 (total 3H each doublet, J=6.4, 6.5 Hz); 3.76 and 3.81 (total 3H, each singlet); 4.36–4.46 (1H, multiplet); 5.08 and 5.09 (total 1H, each singlet); 6.52–6.73 (3H, multiplet); 6.80 and 6.88 (total 2H, each doublet, J=8.5, 8.7 Hz); 6.99–7.23 (6H, multiplet).

(34c) 3-Methoxy-4-<3-{(4-methoxyphenyl)-[1-(3,4-difluorophenyl)ethylamino]methyl}phenylamino>-3-cyclobutene-1,2-dione In a similar manner to that described in Example (1c), a solution of 3-{(4-methoxyphenyl)-[1-(3,4-difluorophenyl)ethoxy]methyl}phenylamine (115 mg) [prepared as described in step (b) above] in methanol (10 ml) and 3,4-dimethoxy-3-cyclobutene-1,2-dione (88.5 mg) were reacted, to afford the title compound (135 mg) as a yellow foamy solid.

Nuclear Magnetic Resonance Spectrum (CDCl$_3$) δ ppm: 1.44 and 1.46 (total 3H, each doublet, J=6.5, 6.5 Hz); 3.77 and 3.82 (total 3H, each singlet); 4.38–4.42 (1H, multiplet); 4.436 and 4.441 (total 3H, each singlet); 5.13 and 5.21 (total 1H, each singlet); 6.82 and 6.91 (total 2H, each doublet, J=8.7, 8.7 Hz); 6.98–7.38 (9H, multiplet).

(34d) 3-Amino-4-<3-{(4-methoxyphenyl)-{1-(3,4-difluorophenyl)ethylamino]methyl}phenylamino>-3-cyclobutene-1,2-dione In a similar manner to that described in Example (1d), a solution of 3-methoxy-4-<3-{(4-methoxyphenyl)-[1-(3,4-difluorophenyl)ethoxy]methyl}phenylamino>-3-cyclobutene-1,2-dione (130 mg) [prepared as described in step (c) above] in ethanol (5 ml) and a solution of ammonia in ethanol (2N, 1 ml) were reacted, to give the title compound (104 mg,) as a yellow solid.

Nuclear Magnetic Resonance Spectrum (DMSO-d$_6$) δ ppm: 1.37 and 1.41 (total 3H, each doublet, J=6.4, 6.5 Hz); 3.70 and 3.74 (total 3H, each singlet); 4.42–4.51 (1H, multiplet); 5.21 and 5.25 (total 1H, each singlet); 6.83–6.99 (3H, multiplet); 7.17–7.46 (8H, multiplet). melting point: 170–172° C.

EXAMPLE 35

3-Methoxy-4-<3-{(4-methoxyphenyl)-[1-(3,4-difluorophenyl)ethylamino]methyl}phenylamino>-3-cyclobutene-1,2-dione (Compound No. 2-1359)

(35a) N-[(3-Nitrophenyl)-(4-methoxyphenyl)methyl]-N-[1-(3,4-difluorophenyl)ethyl]amine Triethylamine (17.3 ml) was added to a solution of 3-nitro-4'-methoxybenzophenone (6.40 g) and 1-(3,4-difluorophenyl)ethylamine hydrochloride (8.71 g) in anhydrous dichloromethane (120 ml). A solution of titanium tetrachloride (3.0 ml) in anhydrous dichloromethane (30 ml) was slowly added dropwise to the mixture in an ice bath. This mixture was then stirred at ambient temperature for 1 hour. At the end of this time, ethyl acetate and an aqueous solution of sodium hydrogencarbonate were added to the reaction mixture. This was filtered through a Celite (trade mark) filter aid to remove the insoluble material, and the ethyl acetate layer was separated from the filtrate. The aqueous layer was extracted with ethyl acetate. The ethyl acetate layer and extract were combined and washed with a saturated aqueous solution of sodium chloride. The organic layer was dried over anhydrous sodium sulfate and concentrated by evaporation under reduced pressure, to afford the imine derivative (10.7 g) as a dark brown oil.

Sodium cyanoborohydride (6.28 g) and acetic acid (2.1 ml) were added to a solution of this oil in methanol (80 ml). The mixture was heated under reflux for 1 hour. The reaction mixture was then concentrated by evaporation under reduced pressure. The residue was neutralized with an aqueous solution of sodium hydrogencarbonate and extracted with ethyl acetate three times. The combined ethyl acetate extracts were washed with a saturated aqueous solution of sodium chloride and dried over anhydrous sodium sulfate and concentrated by evaporation under reduced pressure. The residue was purified by chromatography through a silica gel column using an 8:1 by volume mixture of hexane and ethyl acetate as eluant, to afford a mixture of diastereomers of the title compound (7.17 g) as a yellow oil.

Nuclear Magnetic Resonance Spectrum (CDCl$_3$) δ ppm: 1.35 and 1.36 (3H, each doublet, J=6.6 Hz); 3.54–3.67 (1H, multiplet); 3.77 and 3.82 (total 3H, each singlet); 4.60 and 4.66 (total 1H, each singlet); 6.82 and 6.90 (total 2H, each doublet, J=8.7 Hz); 6.80–7.17 (3H, multiplet); 7.15 (2H, each doublet, J=8.7 Hz); 7.40 and 7.49 (total 1H, each triplet, J=8.0 Hz); 7.59 and 7.65 (total 1H, each doublet, J=8.0 Hz); 8.02 and 8.10 (total 1H, each doublet of doublets, J=1.9, 8.0 Hz); 8.22 and 8.24 (total 1H, each doublet, J=1.9 Hz).

(35b) 3-{(4-Methoxyphyenyl)-[1-(3,4-difluorophenyl)ethylamino]methyl}phenylamine In a similar manner to that described in Example (15b), a solution of N-[(3-nitrophenyl)-(4-methoxypheinyl)methyl]-N-[1-(3,4-difluorophenyl)ethyl]amine (6.84 g) [prepared as described in step (a) above] in methanol (140 ml), nickel chloride hexahydrate (8.26 g) and sodium borohydride (2.60 g) were reacted and purified, to afford the less polar isomer A (2.35 g) as a yellow oil and the more polar isomer B (3.16 g) as a yellow, oil of the title compound.

Isomer A

Nuclear Magnetic Resonance Spectrum (CDCl$_3$) δ ppm: 1.31 (3H, doublet, J=6.6 Hz); 3.67 (1H, quartet, J=6.6 Hz); 3.76 (3H, singlet), 4.44 (1H, singlet); 6.58 (1H, doublet, J=8.0 Hz); 6.61 (1H, singlet); 6.67 (1H, doublet, J=7.7 Hz); 6.79 (2H, doublet, J=8.6 Hz); 6.79–7.21 (4H, multiplet); 7.18 (2H, doublet, J=8.6 Hz).

Isomer B

Nuclear Magnetic Resonance Spectrum (CDCl$_3$) δ ppm: 1.31 (3H, doublet, J=6.7 Hz); 3.62 (1H, quartet, J=6.7 Hz); 3.80 (3H, singlet); 4.44 (1H, singlet); 6.51 (1H, doublet of doublets, J=1.7, 7.3 Hz); 6.61 (1H, doublet, J=1.7 Hz); 6.65 (1H, doublet, J=7.3 Hz); 6.86 (2H, doublet, J=8.8 Hz); 6.91–7.23 (4H, multiplet); 7.19 (2H, doublet, J=8.8 Hz).

(35c) 3-Methoxy-4-<3-{(4-methoxyphenyl)-[1-(3,4-difluorophenyl)ethylamino]methyl}phenylamino>-3-cyclobutene-1,2-dione In a similar manner to that described in Example (1c), a solution of isomer A of 3-{(4-methoxyphenyl )-[1-(3,4-difluorophenyl)ethylamino]methyl}phenylamine (252 mg) [prepared as described in step (b) above] in methanol (8 ml) and 3,4-dimethoxy-3-cyclobutene-1,2-dione (194 mg,) were reacted, to afford isomer A of the title compound (301 mg) as a white foamy solid.

Isomer A

Nuclear Magnetic Resonance Spectrum (CDCl$_3$) δ ppm: 1.35 (3H, doublet, J=6.7 Hz); 3.63 (1H, quartet, J=6.7 Hz); 3.76 (3H, singlet); 4.44 (3H, singlet); 4.55 (1H, singlet); 6.81 (2H, doublet, J=8.7 Hz); 6.90–7.34 (7H, multiplet); 7.17 (2H, doublet, J=8.7 Hz).

In a similar manner to that described in Example (1c), a solution of isomer B of 3-{(4-methoxyphenyl)-[1-(3,4-difluorophenyl)ethylamino]methyl}phenylamine (247 mg) in methanol (10 ml) and 3,4-dimethoxy-3-cyclobutene-1,2-dione (190 mg) were reacted, to afford isomer B of the title compound (259 mg) as a white foamy solid.

Isomer B

Nuclear Magnetic Resonance Spectrum (CDCl$_3$) δ ppm: 1.33 (3H, doublet, J=6.6 Hz); 3.64 (1H, quartet, J=6.6 Hz); 3.81 (3H, singlet); 4.44 (3H, singlet); 4.52 (1H, singlet); 6.89 (2H, doublet, J=8.7 Hz); 6.89–7.52 (7H, multiplet); 7.17 (2H, doublet, J=8.7 Hz).

EXAMPLE 36

3-(N-Methylamino)-4-<3-{(4-methoxyphenyl)-[1-(3,4-difluorophenyl)ethylamino]methyl}phenylamino>-3-cyclobutene-1,2-dione (Compound No. 2-2478)

In a similar manner to that described in Example (1d), a solution of isomer B of 3-methoxy-4-<3-{(4-methoxyphenyl)-[1-(3,4-difluorophenyl)ethylamino]methyl}phenylamino>-3-cyclobutene-1,2-dione (178 mg)

[prepared as described in Example 35(c)] in ethanol (7.5 ml) and a solution of methylamine in ethanol (2N, 2.5 ml) were reacted, to give the title compound (130 mg) as a white foamy solid.

Nuclear Magnetic Resonance Spectrum (DMSO-d$_6$) δ ppm: 1.26 (3H, doublet, J=6.5 Hz); 3.21 (3H, singlet); 3.51 (1H, quartet, J=6.5 Hz); 3.73 (3H, singlet); 4.39 (1H, singlet); 6.87 (2H, doublet, J=8.4 Hz); 6.91 (1H, doublet, J=7.8 Hz); 6.94–7.57 (6H, multiplet); 7.25 (2H, doublet, J=8.4 Hz).

EXAMPLE 37

3-(N,N-Dimethylamino)-4-<3-{(4-methoxyphenyl)-[1-(3,4-difluorophenyl)ethylamino]methyl}phenylamino>-3-cyclobutene-1,2-dione (Compound No. 2-2676)

In a similar manner to that described in Example (1d), a solution of isomer B of 3-methoxy-4-<3-{(4-methoxyphenyl)-[1-(3,4-difluorophenyl)ethylamino]methyl}phenylamino]-3-cyclobutene-1,2-dione (181 mg) [prepared as described in Example 35(c)] in ethanol (5 ml) and a solution of dimethylamine in methanol (2N, 2.5 ml) were reacted, to give the title compound (143 mg) as a white solid.

Nuclear Magnetic Resonance Spectrum (DMSO-d$_6$) δ ppm: 1.26 (3H, doublet, J=6.5 Hz); 3.21 (6H, singlet); 3.51 (1H, quartet, J=6.5 Hz); 3.72 (3H, singlet); 4.38 (1H, singlet); 6.87 (2H, doublet, J=8.5 Hz); 6.95 (1H, doublet, J=7.4 Hz); 6.98–7.54 (6H, multiplet); 7.25 (2H, doublet, J=8.5 Hz).

EXAMPLE 38

3-Amino-4-{N-<3-{(4-methoxyphenyl)-[1-(3,4-difluorophenyl)ethylamino]methyl}phenyl>-N-methylamino}-3-cyclobutene-1,2-dione (Compound No. 2-2142)

(38a) <3-{(4-Methoxyphenyl)-[1-(3,4-difluorophenyl)ethylamino]methyl}phenyl>carbamic acid methyl ester Methyl chloroformate (1.1 ml) was added dropwise to a solution of 3-{(4-methoxyphenyl)-[1-(3,4-difluorophenyl)ethylamino]methyl}phenylamine [prepared as described in Example 35(b)] in N,N-dimethylacetamide (10 ml) in an ice bath. The mixture was stirred for 1 hour. At the end of this time, an aqueous solution of sodium hydrogencarbonate was added to the reaction mixture and the aqueous layer was extracted with ethyl acetate three times. The combined ethyl acetate extracts were washed with water and with a saturated aqueous solution of sodium chloride, dried over anhydrous sodium sulfate and then concentrated by evaporation under reduced pressure. The residue was purified by chromatography through a silica gel column using a 4:1 by volume mixture of hexane and ethyl acetate as the eluant, to afford the title compound (563 mg) as a colorless oil.

Nuclear Magnetic Resonance Spectrum (CDCl$_3$) δ ppm: 1.36 (3H, doublet, J=6.3 Hz); 3.62 (1H, quartet, J=6.3 Hz); 3.80 (3H, singlet); 3.85 (3H, singlet); 4.56 (1H, singlet); 6.91 (2H, doublet, J=8.7 Hz); 6.78–7.30 (9H, multiplet).

(38b) N-Methyl-N-<3-{(4-methoxyphenyl)-[1-(3,4-difluorophenyl)ethylamino]methyl}phenyl>amine A mixture of a solution of <3-{(4-methoxyphenyl)-[1-(3,4-difluorophenyl)ethylamino]methyl}phenyl>carbamic acid methyl ester (560 mg) [prepared as described in step (a) above] in tetrahydrofuran (15 ml) and lithium aluminum hydride (250 mg) was heated under reflux for 4 hours. After addition of sodium sulfate decahydrate (4.0 g) in an ice bath, the reaction mixture was filtered using, a Celite (trade mark) filter aid. The filtrate was dried over anhydrous sodium sulfate and concentrated by evaporation under reduced pressure. The residue was purified by chromatography through a silica gel column using a 4:1 by volume mixture of hexane and ethyl acetate as the eluant, to afford the title compound (215 mg) as a yellow oil.

Nuclear Magnetic Resonance Spectrum (CDCl$_3$) δ ppm: 1.31 (3H, doublet, J=6.6 Hz); 2.78 (3H, singlet); 3.64 (1H, quartet, J=6.6 Hz); 3.80 (3H, singlet); 4.47 (1H, singlet); 6.85 (2H, doublet, J=8.7 Hz); 6.80–7.26 (7H, multiplet); 7.21 (2H, doublet, J=8.7 Hz).

(38c) 3-Methoxy-4-{N-methyl-N-<3-{(4-methoxyphenyl)-[1-(3,4-difluorophenyl)ethylamino]methyl}methyl>amino}-3-cyclobutene-1,2-dione In a similar manner to that described in Example (1c), a solution of N-<3-{(4-methoxyphenyl)-[1-(3,4-difluorophenyl)ethylamino]methyl}phenyl>-N-methylamine (210 mg) [prepared as described in step (b) above] in methanol (12 ml) and 3,4-dimethoxy-3-cyclobutene-1,2-dione (117 mg) were reacted, to afford the title compound (192 mg) as a white foamy solid.

Nuclear Magnetic Resonance Spectrum (CDCl$_3$) δ ppm: 1.33 (3H, doublet, J=6.6 Hz); 3.68–3.72 (1H, multiplet); 3.81 (3H, singlet); 4.18–4.32 (3H, broad); 4.53 (1H, singlet); 6.88 (2H, doublet, J=8.6 Hz); 6.90–7.28 (7H, multiplet); 7.18 (2H, doublet, J=8.6 Hz).

(38d) 3-Amino-4-{N-<3-{(4-methoxyphenyl)-[1-(3,4-difluorophenyl)ethylamino]methyl}phenyl>-N-methylamino}-3-cyclobutene-1,2-dione In a similar manner to that described in Example (1d), a solution of 3-methoxy-4-{N-methyl-N-<3-{(4-methoxyphenyl)-[1-(3,4-difluorophenyl)ethylamino]methyl}phenyl>amino}- 3-cyclobutene-1,2-dione (188 mg) [prepared as described in step (c) above] in ethanol (6 ml) and a solution of ammonia in ethanol (2N, 2 ml) were reacted, to give the title compound (140 mg) as a yellow solid.

Nuclear Magnetic Resonance Spectrum (DMSO-d$_6$) δ ppm: 1.26 (3H, doublet, J=6.5 Hz); 3.53 (1H, quartet, J=6.5 Hz); 3.61 (3H, singlet); 3.72 (3H, singlet); 4.44 (1H, singlet); 6.87 (2H, doublet, J=8.5 Hz); 6.98 (1H, doublet, J=8.0 Hz); 7.05–7.48 (6H, multiplet); 7.27 (2H, doublet, J=8.0 Hz). melting point: 164–167° C.

EXAMPLE 39

3-Amino-4-<4-{(4-methoxyphenyl)-[1-(3,4-difluorophenyl)ethylamino]methyl}phenylamino>-3-cyclobutene-1,2-dione (Compound No. 3-208)

(39a) N-[(4-Nitrophenyl)-(4-nethoxyphenyl)methyl]-N-[1-(3,4-difluorophenyl)ethyl]amine In a similar manner to that described in Example (1a), 4-nitro-4'-methoxybenzophenone (2.13 g), 1-(3,4-difluorophenyl)ethylamine hydrochloride (2.90 g), triethylamine (5.8 ml), titanium tetrachloride (1.0 ml), sodium cyanoborohydride (2.09 g) and acetic acid (0.7 ml) were reacted, to afford the title compound (3.21 g) as a pale yellow oil.

Nuclear Magnetic Resonance Spectrum (CDCl$_3$) δ ppm: 1.34 and 1.35 (total 3H, each doublet, J=6.6 Hz); 3.58 and 3.66 (total 1H, each quartet, J=6.6 Hz); 3.76 and 3.81 (total 3H, each singlet); 4.61 and 4.64 (total 1H, each singlet); 6.82 and 6.88 (total 2H, each doublet, J=7.9 Hz); 6.85–7.18 (5H, multiplet); 7.54 and 7.56 (total 2H, each doublet, J=7.8 Hz); 8.09 and 8.19 (total 2H, each doublet, J=7.80 Hz).

(39b) 4-{(4-Methoxyphenyl)-[1-(3,4-difluorophenyl)ethylamino]methyl}phenylamine

In a similar manner to that described in Example (1b), a solution of N-[(4-nitrophenyl)-(4-methoxyphenyl)methyl]-N-[1-(3,4-difluorophenyl)ethyl]amine (3.20 g) [prepared as described in step (a) above] in methanol (60 ml), nickel chloride hexahydrate (3.82 a) and sodium borohydride (1.21 g) were reacted and purified, to afford the less polar isomer A (720 mg) as a pale yellow oil and the more polar isomer B (805 mg) as a pale yellow oil of the title compound.
Isomer A
Nuclear Magnetic Resonance Spectrum (CDCl$_3$) δ ppm: 1.33 (3H, doublet, J=6.6 Hz); 3.61 (1H, quartet, J=6.6 Hz); 3.76 (3H, singlet); 4.51 (3H, singlet); 4.54 (1H, singlet); 6.80 (2H, doublet, J=8.6 Hz); 6.89–7.32 (7H, multiplet); 7.16 (2H, doublet, J=8.6 Hz).
Isomer B
Nuclear Magnetic Resonance Spectrum (CDCl$_3$) δ ppm: 1.30 (3H, doublet, J=6.6 Hz); 3.61 (1H, quartet, J=6.6 Hz); 3.80 (3H, singlet); 4.44 (1H, singlet); 6.58 (2H, doublet. .=S.4 Hz); 6.86 (2H, doublet .1=S.6 Hz); 7.02–7.20 (3H, multiplet); 7.03 (2H, doublet, J=8.4 Hz); 7.18 (2H, doublet, J=8.6 Hz).
(39c) 3-Methoxy-4-<4-{(4-methoxyphenyl)-[1-(3,4-difluorophenyl)ethylamino]methyl}phenylamino>-3-cyclobutene-1,2-dione In a similar manner to that described in Example (1c), a solution of isomer A of 4-{(4-methoxyphenyl)-[1-(3,4-difluorophenyl)ethylamino]methyl}phenylamine (710 mg) [prepared as described in step (b) above] in methanol (15 ml) and 3,4-dimethoxy-3-cyclobutene-1,2-dione (410 mg) were reacted, to afford isomer A of the title compound (597 mg) as a colorless oil.
Isomer A
Nuclear Magnetic Resonance Spectrum (CDCl$_3$) δ ppm: 1.33 (3H, doublet, J=6.6 Hz); 3.61 (1H, quartet, J=6.6 Hz); 3.76 (3H, singlet); 4.51 (3H, singlet); 4.54 (1H, singlet); 6.80 (2H, doublet, J=8.6 Hz); 6.89–7.32 (7H, multiplet); 7.16 (2H, doublet, J=8.6 Hz).

In a similar manner to that described in Example (1c), a solution of isomer B of 4-{(4-methoxyphenyl)-[1-(3,4-difluorophenyl)ethylamino]methyl}phenylamine (790 mg) in methanol (15 ml) and 3,4-dimethoxy-3-cyclobutene-1,2-dione (456 mg) were reacted, to afford isomer B of the title compound (480 mg) as a white solid.
Isomer B
Nuclear Magnetic Resonance Spectrum (CDCl$_3$) δ ppm: 1.32 (3H, doublet, J=6.7 Hz); 3.63 (1H, quartet, J=6.7 Hz); 3.81 (3H, singlet); 4.49 (3H, singlet); 4.51 (1H, singlet); 6.88 (2H, doublet, J=8.5 Hz); 6.85–7.28 (7H, multiplet); 7.17 (2H, doublet, J=8.5 Hz).
(39d) 3-Amino-4-<4-{(4-methoxyphenyl)-[1-(3,4-difluorophenyl)ethylamino]methyl}phenylamino>-3-cyclobutene-1,2-dione In a similar manner to that described in Example (1d), a solution of isomer A of 3-methoxy-4-<4-{(4-methoxyphenyl)-[1-(3,4-difluorophenyl)ethylamino]methyl}phenylamino>-3-cyclobutene-1,2-dione (570 mg) [prepared as described in step (c) above] in ethanol (5 ml) and a solution of ammonia in ethanol (2N, 1.5 ml) were reacted, to give isomer A of the title compound (246 mg) as a pale yellow solid.
Isomer A
Nuclear Magnetic Resonance Spectrum (DMSO-d$_6$) δ ppm: 1.27 (3H, doublet, J=6.6 Hz); 3.52 (1H, quartet, J=6.6 Hz); 3.67 (3H, singlet); 4.40 (1H, singlet); 6.81 (2H, doublet, J=8.6 Hz); 7.02–7.42 (7H, multiplet); 7.20 (2H, doublet, J=8.6 Hz). melting point: 146° C. (dec).

In a similar manner to that described in Example (1d), a solution of isomer B of 3-methoxy-4-<4-{(4-methoxyphenyl)-[1-(3,4-difluorophenyl)ethylamino]methyl}phenylamino>-3-cyclobutene-1,2-dione (390 mg) in ethanol (5 ml) and a solution of ammonia in ethanol (2N, 5 ml) were reacted, to give isomer B of the title compound (298 mg) as a white solid.
Isomer B
Nuclear Magnetic Resonance Spectrum (DMSO-d$_6$) δ ppm: 1.26 (3H, doublet, J=6.6 Hz); 3.51 (1H, quartet, J=6.6 Hz); 3.73 (3H, singlet); 4.39 (1H, singlet); 6.87 (2H, doublet, J=8.6 Hz); 7.03–7.42 (7H, multiplet); 7.23 (2H, doublet, J=8.6 Hz). melting point: 205° C. (dec).

EXAMPLE 40

3-Amino-4-<2-{(4-nethoxyphenyl)-[1-(3,4-difluorophenyl)ethylamino]methyl}phenylamino>-3-cyclobutene-1,2-dione (Compound No. 1-86)

(40a) 2-{(4-Methoxyphenyl)-[1-(3,4-difluorophenyl)ethylamino]methyl}phenylamine

In a similar manner to that described in Example (1a), 2-amino-4'-methoxybenzophenone (2.12 g), 1-(3,4-difluorophenyl)-ethylamine hydrochloride (2.60 g), triethylamine (7.8 ml), titanium tetrachloride (1.1 ml), sodium cyanoborohydride (2.34 g) and acetic acid (0.8 ml) were reacted, to afford a mixture of diastereomers of the title compound (2.05 g) as a colorless oil.
Nuclear Magnetic Resonance Spectrum (CDCl$_3$) δ ppm: 1.34 and 1.36 (total 3H, each doublet, J=6.6 Hz); 3.61–3.74 (1H, multiplet); 3.78 and 3.83 (total 3H, each singlet); 4.11 and 4.14 (total 1H each singlet); 6.59–7.24 (9H, multiplet), 6.84 and 6.92 (total 2H, doublet, J=8.6 Hz).
(40b) 3-Methoxy-4-<2-{(4-methoxyphenyl)-[1-(3,4-difluorophenyl)ethylamino]methyl}phenylamino>-3-cyclobutene-1,2-dione In a similar manner to that described in Example (1c), a solution of 2-{(4-methoxyphonyl)-[1-(3,4-difluorophenyl)ethylamino]methyl}phenylamine (1.30 g) [prepared as described in step (a) above] in methanol (20 ml) and 3,4-dimethoxy-3-cyclobutene-1,2-dione (1.05 g) were reacted, to afford a mixture of diastereoisomers of the title compound (952 mg) as a white solid.
Nuclear Magnetic Resonance Spectrum (CDCl$_3$) δ ppm: 1.51 and 1.53 (total 3H, each doublet, J=6.5 Hz); 3.61–3.73 (1H, multiplet); 3.84 and 3.91 (total 3H, each singlet); 4.55 and 4.57 (total 3H, singlet); 4.71 and 4.84 (total 1H, each singlet); 6.64–7.37 (11H, multiplet).
(40c) 3-Amino-4-<2-{(4-methoxyphenyl)-[1-(3,4-difluorophenyl)ethylamino]methyl}phenylamino>-3-cyclobutene-1,2-dione In a similar manner to that described in Example (1d), a solution of 3-methoxy-4-<2-{(4-methoxyphenyl)-[1-(3,4-difluorophenyl)ethylamino]methyl}phenylamino>-3-cyclobutene-1,2-dione (305 mg) [prepared as described in step (b) above] in methylene chloride (6 ml) and a solution of ammonia in ethanol (2N, 3 ml) were reacted, to give a mixture of diastereoisomers of the title compound (204 mg) as a yellow solid.
Nuclear Magnetic Resonance Spectrum (DMSO-d$_6$) δ ppm: 1.29 and 1.32 (total 3H, each doublet, J=6.5 Hz); 3.45 and 3.59 (total 1H, each quartet, J=6.5 Hz); 3.69 and 3.74 (total 3H, singlet); 4.77 (1H, singlet): 6.84 and 6.91 (total 2H, each doublet, J=8.6 Hz); 6.97–7.34 (9H, multiplet). melting point: 106–111° C. (dec).

EXAMPLE 41

3-Amino-4-<3-{(4-methoxyphenyl)-[1-(3,4-difluorophenyl)ethylamino]methyl}phenylamino>-3-cyclobutene-1,2-dione (Compound No. 2-2027)

(41a) N-[(3-Cyanophenyl)-(4-methoxyphenyl)methyl]-N-[1-(3,4-difluorophenyl)ethyl]amine In a similar manner to that described in Example (1a), 3-cyano-4'-methoxybenzophenone (1.40 g) 1-(3,4-difluorophenyl)ethylamine hydrochloride (1.83 g), triethylamine (4.1 ml), titanium tetrachloride (0.7 ml), sodium cyanoborohydride (1.49 g) and acetic acid (0.5 ml) were reacted, to afford a mixture of diastereoisomers of the title compound (2.16 g) as a pale yellow oil.

Nuclear Magnetic Resonance Spectrum (CDCl$_3$) δ ppm: 1.33 and 1.35 (total 3H, each doublet, J=6.6 Hz); 3.57 and 3.63 (total 1H, each quartet, J=6.6 Hz); 3.77 and 3.82 (total 3H, each singlet); 4.52 and 4.58 (total 1H, each singlet); 6.81 and 6.89 (total 2H, each doublet, J=8.7 Hz); 6.87–7.52 (8H, multiplet); 7.63 and 7.68 (total 1H, each singlet).

(41b) N-[(3-Aminomethylphenyl)-(4-methoxyphenyl) methyl]-N-[1-(3,4-difluorophenyl)ethyl]amine A solution of lithium aluminum hydride in tetrahydrofuran (1N, 15 ml) was added to a solution of N-[(3-cyanophenyl)-(4-methoxyphenyl)methyl]-N-[1-(3,4-difluorophenyl)ethyl]amine (1.65 g) [prepared as described in step (a) above] in anhydrous tetrahydrofuran (20 ml) in an ice bath. The mixture was stirred at ambient temperature for 4 hours. Sodium sulfate decahydrate (15 g) was added to the reaction mixture and the insoluble material was removed by filtration using a Celite (trade mark) filter aid. The filtrate was concentrated by evaporation under reduced pressure. The residue was purified by chromatography through a silica gel column using 20:1 by volume mixture of methylene chloride and methanol as the eluant, to afford a mixture of diastereoisomers of the title compound (1.59 g) as a yellow oil.

Nuclear Magnetic Resonance Spectrum (CDCl$_3$) δ ppm: 1.32 (3H, doublet, J=6.7 Hz); 3.63 (1H, quartet, J=6.7 Hz); 3.76 and 3.81 (total 3H, each singlet); 3.80 and 3.85 (total 2H, singlet); 4.53 and 4.56 (total 1H, each singlet); 6.79 and 6.86 (total 2H, each doublet, J=8.5 Hz); 6.89–7.32 (9H, multiplet).

(41c) 3-Methoxy-4-<3-{(4-methoxyphenyl)-[1-(3,4-difluorophenyl)ethylamino]methyl}phenylamino>-3-cyclobutene-1,2-dione In a similar manner to that described in Example (1c), a solution of N-[(3-aminomethylphenyl)-(4-methoxyphenyl) methyl]-N-[1-(3,4-difluorophenyl)ethyl]amine (290 mg) [prepared as described in step (b) above] in methanol (80 ml) and 3,4-dimethoxy-3-cyclobutene-1,2-dione (216 mg) were reacted, to afford a mixture of diastereoisomers of the title compound (272 mg) as a colorless oil.

Nuclear Magnetic Resonance Spectrum (CDCl$_3$) δ ppm: 1.33 (3H, doublet, J=6.6 Hz); 3.57–3.68 (1H, multiplet); 3.76 and 3.81 (total 3H, each singlet); 4.37 and 4.38 (total 3H, each singlet); 4.47–4.60 (2H, broad); 4.53 and 4.57 (total 1H, each singlet); 6.80 and 6.88 (total 2H, each doublet, J=8.5 Hz); 6.88–7.35 (9H, multiplet).

(41d) 3-Amino-4-<3-{(4-methoxyphenyl)-[1-(3,4-difluorophenyl)ethylamino]methyl}phenylamino>-3-cyclobutene-1,2-dione In a similar manner to that described in Example (1d), a solution of 3-methoxy-4-<3-{(4-methoxyphenyl)-[1-(3,4-difluorophenyl)ethylamino]methyl}benzylamino>-3-cyclobutene-1,2-dione (268 mg) [prepared as described in step (c) above] in ethanol (4 ml) and a solution of ammonia in ethanol (2N, 4 ml) were reacted, to give a mixture of diastereoisomers of the title compound (160 mg) as a white solid.

Nuclear Magnetic Resonance Spectrum (DMSO-d$_6$) δ ppm: 1.26 (3H, doublet, J=6.0 Hz); 3.38–3.51 (1H, multiplet); 3.68 and 3.72 (total 3H, each singlet); 4.41 and 4.42 (total 1H, each singlet); 4.55–4.72 (2H, broad singlet); 6.80 and 6.85 (total 2H, each doublet, J=8.5 Hz); 6.94–7.38 (9H, multiplet). melting point: 191–194° C.

EXAMPLE 42

3-(N-Methylamino)-4-<3-{(4-methoxyphenyl)-[1-(3,4-difluorophenyl)ethylamino]methyl}benzylamino>-3-cyclobutene-1,2-dione (Compound No. 2-2583)

In a similar manner to that described in Example (1d), a solution of 3-methoxy-4-<3-{(4-methoxyphenyl)-[1-(3,4-difluorophenyl)ethylamino]methyl}benzylamino>-3-cyclobutene-1,2-dione (300 mg) [prepared as described in Example 41(c)] in methanol (5 ml) and a solution of methylamine in methanol (2N, 5 ml) were reacted, to give a mixture of diastereoisomer of the title compound (190 mg) as a white solid.

Nuclear Magnetic Resonance Spectrum (DMSO-d$_6$) δ ppm: 1.26 (3H, doublet, J=6.0 Hz); 3.11 (3H, singlet); 3.42–3.53 (1H, multiplet); 3.68 and 3.72 (total 3H, each singlet); 4.41 and 4.43 (total 1H, each singlet); 4.63 and 4.66 (total 2H, each singlet); 6.80 and 6.85 (total 2H, each doublet, J=8.6 Hz); 6.98–7.38 (9H, multiplet). mp 101–103° C.

EXAMPLE 43

3-Amino-4-<4-{(4-methoxyphenyl)-[1-(3,4-difluorophenyl)ethylamino]methyl}benzylamino>-3-cyclobutene-1,2-dione (Compound No. 3-292)

(43) N-[(4-Cyanophenyl)-(4-methoxyphenyl)methyl-N-[1-(3,4-difluorophenyl)ethyl]amine In a similar manner to that described in Example (1a), 4-cyano-4'-methoxybenzophenone (1.18 g), 1-(3,4-difluorophenyl)ethylamine hydrochloride (1.54 g), triethylamine (3.6 ml), titanium tetrachloride (0.4 ml), sodium cyanoborohydride (1.25 g) and acetic acid (0.4 ml) were reacted, to afford a mixture of diastereoisomers of the title compound (1.76 g) as a colorless oil.

Nuclear Magnetic Resonance Spectrum (CDCl$_3$) δ ppm: 1.33 and 1.34 (total 3H, each doublet, J=6.5 Hz); 3.51–3.67 (1H, multiplet); 3.76 and 3.81 (total 3H, each singlet); 4.55 and 4.59 (total 1H, each singlet); 6.80 and 6.88 (total 2H, each doublet, J=8.5 Hz); 6.80–7.18 (3H, multiplet); 7.12 and 7.13 (total 2H, each doublet, J=7.9 Hz); 7.41 and 7.44 (total 2H, each doublet, J=7.9 Hz); 7.54 and 7.62 (total 2H, doublet, J=7.9 Hz).

(43b) N-[(4-Aminomethylphenyl)-(4-methoxyphenyl) methyl]-N-[1-(3,4-difluorophenyl)ethyl)amine dihydrochloride Lithium aluminum hydride (700 mg) was added to a solution of N-[(4-cyanophenyl)-(4-methoxylphenyl) methyl]-N-[1-(3,4-difluorophenyl)ethyl]amine (1.74 g) [prepared as described in step (a) above] in anhydrous tetrahydrofuran (40 ml) in an ice bath. The mixture was stirred at ambient temperature for 2 hours. At the end of this time, sodium sulfate decahydrate (10 g) was added to the reaction mixture and the insoluble material was removed by filtration using a Celite (trade mark) filter aid. The filtrate was concentrated by evaporation under reduced pressure. The residue was dissolved in small amount of diethyl ether, and a solution of hydrochloric acid in ethyl acetate (4N, 3 ml) was added to the solution. The precipitate was filtered, washed with diethyl ether and dried, to afford a mixture of diastereoisomers of the title compound (2.01 g) as a white solid.

Nuclear Magnetic Resonance Spectrum (DMSO-d$_6$) δ ppm: 1.71 (3H, doublet, J=6.3 Hz); 3.73 and 3.75 (total 3H, each singlet); 3.91–4.06 (2H, multiplet); 4.09–4.22 (1H, multiplet); 5.02–5.18 (1H, multiplet); 6.92 and 6.96 (total 2H, each doublet, J=8.2 Hz); 7.09–7.21 (1H, multiplet); 7.45–7.81 (2H, multiplet); 7.47 and 7.52 (total 2H, each doublet, J=8.2 Hz); 7.58 and 7.62 (total 2H, each doublet, J=8.2 Hz); 7.74 and 7.75 (total 2H, each doublet, J=8.2 Hz).

(43c) 3-Methoxy-4-<3-{(4-methoxyphenyl)-[1-(3,4-difluorophenyl)ethylamino]methyl}benzylamino>-3-cyclobutene-1,2-dione Aqueous solution of sodium hydroxide (1N, 5 ml) was added to N-[(4-aminomethylphenyl)-(4-methoxyphenyl)methyl]-N-[1-(3,4-difluorophenyl)ethyl]amine dihydrochloride (790 mg) [prepared as described in step (b) above]. The mixture was extracted with ethyl acetate. The ethyl acetate extract was washed with a saturated aqueous solution of sodium chloride, dried over anhydrous sodium sulfate and concentrated by evaporation under reduced pressure to afford a yellow oil (670 mg).

In a similar manner to that described in Example (1c), a solution of this oil in methanol (15 ml) and 3,4-dimethoxy-3-cyclobutene-1,2-dione (332 mg) were reacted, to afford a mixture of diastereoisomers of the title compound (615 mg) as a white foamy solid.

Nuclear Magnetic Resonance Spectrum (CDCl$_3$) δ ppm: 1.32 (3H, doublet, J=6.6 Hz); 3.54–3.63 (1H, multiplet); 3.76 and 3.80 (total 3H, each singlet); 4.40 and 4.42 (total 3H, each singlet); 4.41–4.60 (2H, broad); 4.54 (1H, singlet); 6.79 and 6.87 (total 2H, doublet, J=8.7 Hz); 6.85–7.35 (9H, multiplet).

(43d) 3-Amino-4-<4-{(4-methoxyphenyl)-[1-(3,4-difluorophenyl)ethylamino]methyl}benzylamino>-3-cyclobutene-1,2-dione In a similar manner to that described in Example (1d), a solution of 3-methoxy-4-<4-{(4-methoxyphenyl)-[1-(3,4-difluorophenyl)ethylamino]methyl}benzylamino>-3-cyclobutene-1,2-dione (608 mg) [prepared as described in step (c) above] in ethanol (6 ml) and a solution of ammonia in ethanol (2N, 4 ml) were reacted, to give a mixture of diastereoisomers of the title compound (450 mg) as a pale yellow solid.

Nuclear Magnetic Resonance Spectrum (DMSO-d$_6$) δ ppm: 1.26 (3H, doublet, J=6.4 Hz); 3.51 (1H, quartet, J=6.4 Hz); 3.68 and 3.71 (total 3H, each singlet); 4.43 (1H, singlet); 4.62 and 4.64 (total 2H, each singlet); 7.19 and 7.23 (total 2H, each doublet, J=8.1 Hz); 6.93–7.82 (9H, multiplet). melting point: 220–225° C.

EXAMPLE 44

N-[3-(2-Amino-3,4-dioxo-1-cyclobutenylamino)phenyl]-N-(4-methoxyphenyl)-2-phenylpropionamide (Compound No. 2-588)

(44a) 3-Methoxy-4-[3-(4-methoxyphenylamino)phenyl]amino-3-cyclobutene-1,2-dione 3,4-Dimethoxy-3-cyclobutene-1,2-dione (531 mg) was added to a solution of 3-amino-4'-methoxybipienylamine (508 mg) in methanol (12 ml) at ambient temperature. The mixture was stirred at 50° C. for 1 hour. The solvent was removed from the reaction mixture by evaporation under reduced pressure. The residue was purified by chromatography through a silica gel column using a 1:1 by volume mixture of methylene chloride and ethyl acetate as the eluant, to afford the title compound (589 mg) as a yellow solid.

Nuclear Magnetic Resonance Spectrum (DMSO-d$_6$) δ ppm: 3.72 (3H, singlet): 4.35 (3H, singlet); 6.62 (1H, doublet, J=8.1 Hz); 6.65–6.80 (1H, multiplet); 6.85–7.18 (2H, multiplet); 6.88 (2H, doublet, J=8.7 Hz); 7.07 (2H, doublet, J=8.7 Hz).

(44b) N-[3-(2-Methoxy-3,4-dioxo-1-cyclobutenylamino)phenyl-N-(4-methoxyphenyl)-2-phenylpropionamide Oxalyl chloride (0.8 ml) and N,N-dimethylformamide (1 drop) were added to a solution of 2-phenylpropionic acid (900 mg) in methylene chloride (10 ml). This mixture was stirred at ambient temperature for 2 hours. The reaction mixture was then concentrated by evaporation under reduced pressure to afford a yellow oil. A solution of 3-methoxy-4-[3-(4-methoxyphenylamino)phenyl]amino-3-cyclobutene-1,2-dione (576 mg) [prepared as described in step (a) above] in N,N-dimethylacetamide (4 ml) was added to a solution of the oil in N,N-dimethylacetamide (4 ml) in an ice bath. The mixture was stirred at ambient temperature for 3 hours. At the end of this time, the reaction mixture was partitioned between a saturated aqueous solution of sodium hydrogencarbonate and ethyl acetate. The ethyl acetate layer was washed with a saturated aqueous solution of sodium chloride, dried over anhydrous sodium sulfate and concentrated by evaporation under reduced pressure. The residue was purified by chromatography through a silica gel column using a 2:1 by volume mixture of methylene chloride and ethyl acetate as the eluant, to afford the title compound (603 mg) as a purple foamy solid.

Nuclear Magnetic Resonance Spectrum (CDCl$_3$) δ ppm: 1.37 (3H, doublet, J=6.6 Hz); 3.66 (1H, quartet, J=6.6 Hz); 4.41 (3H, singlet); 4.61 (3H, singlet); 7.08 (1H, doublet, ==7.6 Hz); 7.22–7.37 (13H, multiplet).

(44c) N-[3-(2-Amino-3,4-dioxo-1-cyclobutenylamino)phenyl]-N-(4-methoxyphenyl)-2-phenylpropionamide In a similar manner to that described in Example (1d), a solution of N-[3-(2-methoxy-3,4-dioxo-1-cyclobutenylamino)phenyl]-N-(4-methoxyphenyl)-2-phenylpropionamide (600 mg) [prepared as described in step (b) above] in ethanol (4 ml) and a solution of ammonia in ethanol (2N, 6 ml) were reacted, to afford the title compound (521 mg) as a yellow solid.

Nuclear Magnetic Resonance Spectrum (CDCl$_3$) δ ppm: 1.31 (3H, doublet, J=6.6 Hz); 3.57 (1H, quartet, J=6.2 Hz); 4.49 (3H, singlet); 6.98 (1H, doublet, J=7.5 Hz); 7.15–7.43 (13H, multiplet). mp 168–170° C.

EXAMPLE 45

3-Amino-4-{3-[(3-fluorobenzyl amino)-(4-methoxyphenyl)methyl]phenylamino}-3-cyclobutene-1,2-dione (Compound No. 2-813)

(45a) N-(3-Fluorobenzyl)-[(4-methoxyphenyl)-3-(nitrophenyl)methyl]amine

In a similar manner to that described in Example (1a), 3-nitro-4'-methoxybenzophenone (2.57 g), 3-fluorobenzylamine (2.35 g) were reacted, to afford the title compound (3.29 g) as a yellow oil.

Nuclear Magnetic Resonance Spectrum (CDCl$_3$) δ ppm: 3.73 (2H, singlet); 3.78 (3H, singlet); 4.89 (1H, singlet); 6.83–7.12 (5H, multiplet); 7.28–7.34 (3H, multiplet); 7.47 (1H, triplet, J=7.9 Hz); 7.77 (1H, doublet, J=7.9 Hz); 8.06–8.09 (1H, multiplet); 8.33 (1H, triplet, J=1.7 Hz).

(45b) 3-[(3-Fluorobenzyl amino)-(4-methoxyphenyl)methyl]phenylamine

In a similar manner to that described in Example (1b), N-(3-fluorobenzyl)-N-[(4-methoxyphenyl)-3-(nitroplenyl)methyl]amine (3.27 g) were reacted, to afford the title compound (2.74 g) as a pale yellow oil.

Nuclear Magnetic Resonance Spectrum (CDCl$_3$) δ ppm: 3.73 (2H, singlet); 3.77 (3H, singlet); 4.71 (1H, singlet); 6.54 (1H, doublet of doublets, J=8.2, 1.9 Hz); 6.74–6.96 (5H, multiplet); 7.06–7.13 (2H, multiplet); 7.23–7.34 (4H, multiplet).

(45c) 3-{3-[(3-Fluorobenzyl amino)-(4-methoxyphenyl) methyl]phenylamino}-4-methoxy-3-cyclobutene-1,2-dione In a similar manner to that described in Example (1c), 3-[(3-fluorobenzyl amino)-(4-methoxyphenyl)methyl] phenylamine (409 mg) [prepared as described in step (b) above] and 3,4-dimethoxy-3-cyclobutene-1,2-dione (173 mg) were reacted, to afford the title compound (490 mg) as a pale yellow oil.

Nuclear Magnetic Resonance Spectrum (CDCl$_3$) δ ppm: 3.73 (2H, singlet); 3.79 (3H, singlet); 4.42 (3H, singlet); 4.80 (1H, singlet); 6.86 (1H, doublet of triplets, J=8.7, 2.3 Hz); 6.94 (1H, doublet of triplets, J=8.6, 2.4 Hz); 7.05–7.33 (8H, multiplet); 7.38 (1H, singlet).

(45d) 3-Amino-4-{3-[(3-fluorobenzyl amino)-(4-methoxyphenyl)methyl]phenylamino}-3-cyclobutene-1,2-dione In a similar manner to that described in Example (1d), 3-{3-[(3-fluorobenzyl amino)-(4-methoxyphenyl)methyl] phenylamino}-4-methoxy-3-cyclobutene-1,2-dione (423 mg) [prepared as described in step (c) above] was reacted, to give the title compound (327 mg) as a pale yellow solid. mp 209–212° C.

Nuclear Magnetic Resonance Spectrum (DMSO-d$_6$) δ ppm: 3.63 (2H, singlet); 3.71 (3H, singlet); 4.69 (1H, singlet), 6.87 (2H, doublet, J=8.5 Hz); 7.00–7.45 (10H, multiplet).

EXAMPLE 46

N-[(3-(2-Amino-3,4-dioxocyclobut-1-enylamino) phenyl)-4-(methoxyphenyl)methyl]benzamide
(Compound No. 2-565)

(46a) α-(4-Methoxyphenyl)-3-nitrobenzyl azide

Sodium azide (26.1 g) was added to a solution of α-(4-methoxyphenyl)-3-nitrobenzyl bromide (25.8 g) in dimethylformamide (200 ml) in an ice bath. The mixture was stirred on the ice bath for 1 hour and then at ambient temperature for 1 hour. The dimethylformamidle was then removed by evaporation under reduced pressure. The residue was partitioned between ethyl acetate and water two times. The ethyl acetate layers were combined and washed with a saturated aqueous solution of sodium chloride, dried over anhydrous magnesium sulfate and concentrated by evaporation under reduced pressure. The residue was purified by chromatography through a silica gel column using a 6:1 by volume mixture of hexane and ethyl acetate as the eluant, to afford the title compound (18.6 g) as a yellow oil.

Nuclear Magnetic Resonance Spectrum (CDCl$_3$) δ ppm: 3.82 (3H, singlet). 5.77 (1H, singlet); 6.90–6.94 (2H, multiplet); 7.21 (2H, doublet, J=8.7 Hz); 7.53 (1H, triplet, J=8.0 Hz); 7.65 (1H, doublet, J=7.1 Hz); 8.15 (1H, doublet of doublets, J=8.0, 1.9 Hz); 8.21 (1H, singlet).

(46b) α-(4-Methoxyphenyl)-3-nitrobenzylamine hydrochloride

Triphenylphosphinie (20.5 g) was added in small portions to a solution of α-(4-methoxyphenyl)-3-nitrobenzyl azide (18.5 g) [prepared as described in step (a) above] in anhydrous tetrahydrofuran (100 ml). When the triphenylphosphine was dissolved and the evolution of nitrogen had ceased, water (20 ml) was added to the reaction mixture and this mixture was heated under reflux for 6 hours. At the end of this time, the tetrahydrofuran of the reaction mixture was removed by evaporation under reduced pressure. The residue was extracted with ethyl acetate. The organic layer was washed with a saturated aqueous solution of sodium chloride, dried over magnesium sulfate and concentrated by evaporation under reduced pressure. The residue was purified by chromatography through a silica gel column using a 2:1 by volume mixture of hexane and ethyl acetate as the eluant, to afford a colorless oil. This oil was dissolved in a solution of hydrogen chloride in ethyl acetate (4N). The ethyl acetate was evaporated to dryness. The residue was suspended in diisopropyl ether and filtered to afford the title compound (13.8 g) as a white solid.

Nuclear Magnetic Resonance Spectrum (CDCl$_3$) δ ppm: 3.75 (3H, singlet); 5.84 (1H, singlet); 7.00 (2H, doublet, J=8.7 Hz); 7.51 (2H, doublet, J=8.8 Hz); 7.74 (1H, triplet, J=8.0 Hz); 8.03 (1H, doublet, J=7.8 Hz); 8.22 (1H, doublet of doublets, J=8.3, 1.8 Hz); 8.47 (1H, triplet, J=1.7 Hz).

(46c) N-[(4-Methoxyphenyl)-(3-nitrophenyl)methyl] benzamide Triethylamine (2.95 ml) was added to a suspension of α-(4-methoxyphenyl)-3-nitrobenzylamine hydrochloride (3.12 g) [prepared as described in step (b) above] in acetonitrile (20 ml). The mixture was stirred at ambient temperature for 20 minutes. A solution of benzoyl chloride (1.49 g) in acetonitrile (20 ml) was then added dropwise to the reaction mixture in an ice bath. This mixture was stirred at ambient temperature for 30 minutes. The reaction mixture was partitioned between ethyl acetate and a saturated aqueous sodium hydrogencarbonate solution. The organic layer was washed with a saturated aqueous solution of sodium chloride, dried over anhydrous magnesium sulfate and concentrated by evaporation under reduced pressure. The residual pale brown solid was suspended in methanol, filtered and washed with diethyl ether, to afford the title compound (3.29 g) as a white solid.

Nuclear Magnetic Resonance Spectrum (CDCl$_3$) δ ppm: 3.81 (3H, singlet); 6.43 (1H, doublet, J=7.0 Hz); 6.66 (1H, doublet, J=6.8 Hz); 6.91 (2H, doublet, J=8.7 Hz); 7.18 (1H, doublet, J=8.7 Hz); 7.44–7.56 (4H, multiplet); 7.67 (1H, doublet, J=7.7 Hz); 7.82 (1H, doublet, J=7.3 Hz); 8.19 (1H, singlet).

(46d) N-[(3-Aminophenyl)-(4-methoxyphenyl)methyl] benzamide hydrochloride

N-[(4-methoxyphenyl)-(3-nitrophenyl)methyl]benzamide (3.24 g) [prepared as described in step (c) above] was added in small portions to a 1:1 by volume mixture of ethanol and concentrated hydrochloric acid at ambient temperature. Tin (II) chloride (6.78 g) was then added in small portions to the mixture in an ice bath. The mixture was stirred at ambient temperature for 20 minutes and then heated under reflux for 2 hours. After cooling, the reaction mixture was neutralized with aqueous solution of sodium hydroxide and the insoluble material was removed by filtration using a Celite (trade mark) filter aid. The filtrate was extracted with ethyl acetate and the organic layer was washed with a saturated aqueous solution of sodium chloride, dried over anhydrous magnesium sulfate and concentrated by evaporation under reduced pressure. The residue was purified by chromatography through a silica gel column using a 2:1 by volume mixture of hexane and ethyl acetate as the eluant, to afford a colorless oil. This oil was dissolved in a solution of hydrogen chloride in ethyl acetate (4N) and the solvent was evaporated to dryness. The residual solid was suspended in diethyl ether and filtered, to afford the title compound (2.68 g) as a white solid.

Nuclear Magnetic Resonance Spectrum (DMSO-d$_6$) δ ppm: 3.74 (3H, singlet); 6.37 (1H, doublet, J=8.5 Hz); 6.93 (2H, doublet, J=8.7 Hz); 7.19–7.57 (9H, multiplet); 7.93 (2H, doublet, J=8.2 Hz).

(46e) N-[(3-(2-Methoxy-3,4-dioxocyclobut-1-enylamino) phenyl)-(4-methoxyphenyl)methyl]benzamide 3,4-dimethoxy-3-cyclobutene-1,2-dione (428 mg) was added to a solution of N-[(3-aminophenyl)-(4-methoxyphenyl)methyl]benzamide hydrochloride (555 mg)

[prepared as described in step (d) above] in methanol (15 ml) at ambient temperature. After stirring for 10 minutes, a solution of triethylamine (153 mg) in methanol (10 ml) was added dropwise to the mixture. This mixture was stirred at ambient temperature for 1 hour. The reaction mixture was then slightly acidified with hydrochloric acid (0.5N) and extracted with ethyl acetate. The organic extract was washed with a saturated aqueous solution of sodium chloride, dried over anhydrous magnesium sulfate and concentrated by evaporation under reduced pressure. The residue was purified by chromatography through a silica gel column using a 1:1 by volume mixture of hexane and ethyl acetate as the eluant, to afford the title compound (505 mg) as a white foamy solid.

Nuclear Magnetic Resonance Spectrum (CDCl$_3$) δ ppm: 3.74 (3H, singlet): 4.31 (3H, singlet); 6.35 (1H, doublet, J=7.3 Hz); 6.75–7.62 (11H, multiplet); 7.86 (2H, doublet, J=7.5 Hz).

(46f) N-{[3-(2-Amino-3,4-(dioxo-1-cyclobutenylamino) phenyl-(4-methoxyphenyl)methyl}benzamide In a similar manner to that described in Example (1d), N-{[3-(2-methoxy-3,4-dioxocyclobut-1-enylamino) phenyl]-4-(methoxyphenyl)methyl}benzamide (489 mg) [prepared as described in step (c) above] was reacted, to give the title compound (301 mg) as a yellow solid.

Nuclear Magnetic Resonance Spectrum (DMSO-d$_6$) δ ppm: 3.74 (3H, singlet); 6.32 (1H, doublet, J=8.5 Hz); 6.92 (2H, doublet, J=8.7 Hz); 6.98 (1H, doublet, J=7.7 Hz); 7.21 (1H, singlet); 7.27–7.56 (7H, multiplet); 7.94 (2H, doublet, J=7.4 Hz).

EXAMPLE 47

N-{[3-(2-Amino-3,4-dioxocyclobut-1-enylamino) phenyl-(4-methoxyphenyl)methyl}-3-fluoro-benzamide (Compound No. 2-826)

(47a) N-[(4-Methoxyphenly)-(3-nitrophenyl)methyl-3-fluorobenzamide

In a similar manner to that described in Example (46c) α-(4-methoxyphenyl)-3-nitrobenzylamine hydrochloride (1.50 g) [prepared as described in Example 46(b) above] and 3-fluorobenzoyl chloride (811 mg) were reacted, to afford the title compound (1.73 g) as a , white solid.

Nuclear Magnetic Resonance Spectrum (CDCl$_3$) δ ppm: 3.81 (3H, singlet); 6.41 (1H, doublet, J=7.0 Hz); 6.64 (1H, doublet, J=6.9 Hz); 6.89–6.98 (2H, multiplet); 7.15–7.63 (7H, multiplet); 7.66 (1H, doublet, J=8.0 Hz); 8.18 (1H, singlet).

(47b) N-[(3-Aminophenyl)-(4-methoxyphenyl)methyl]-3-fluorobenzamide hydrochloride Tin (II) chloride (1.54 g) was added in small portions to a solution of N-[(4-methoxyphenyl)-(3'-nitrophenyl) methyl]-3-fluorobenzamide (617 mg) [prepared as described in step (a) above] in ethanol (20 ml) at ambient temperature. The mixture was heated under reflux for 1 hour. After cooling, a saturated aqueous solution of sodium hydrogencarbonate was added to the reaction mixture. The insoluble material was removed by filtration using,g a Celite (trade mark) filter aid. The filtrate was extracted with ethyl acetate. The organic layer was washed with a saturated aqueous solution of sodium chloride, dried over anhydrous magnesium sulfate and then concentrated by evaporation under reduced pressure. A solution of hydrogen chloride in ethyl acetate (4N) was added to the residue, and the precipitate was filtered to afford the title compound (468 mg) as a white solid.

Nuclear Magnetic Resonance Spectrum (DMSO-d$_6$) δ ppm: 3.74 (3H, singlet); 6.34 (1H, doublet, J=8.2 Hz); 6.93 (2H, doublet, J=8.6 Hz); 7.10–7.35 (5H, multiplet); 7.38–7.43 (2H, multiplet); 7.51–7.57 (1H, multiplet); 7.74–7.80 (2H, multiplet).

(47c) N-{[3-(2-methoxy-3,4-dioxocyclobut-1-enylamino) phenyl]-(4-methoxyphenyl)methyl}-3-fluorobenzamide In a similar manner to that described in Example (46e) N-[(3-aminophenyl)-(4-methoxyphenyl)methyl]-3-fluorobenzamide hydrochloride (244 mg) [prepared as described in step (b) above] and 3,4-dimethoxy-3-cyclobutene-1,2-dione (107 mg) were reacted, to afford the title compound (285 mg) as a white solid.

Nuclear Magnetic Resonance Spectrum (CDCl$_3$) δ ppm: 3.78 (3H, singlet); 4.31 (3H, singlet); 6.31 (1H, doublet, J=7.3 Hz); 6.85–7.66 (12H, multiplet).

(47d) N-{[3-(2-Amino-3,4-dioxocyclobut-1-enylamino) phenyl]-(4-methoxyphenyl)methyl}-3-fluorobenzamide In a similar manner to that described in Example (1d), N-{[3-(2-methoxy-3,4-dioxocyclobut-1-enylamino) phenyl]-(4-methoxyphenyl)methyl}-3-fluorobenzamide (269 mg) [prepared as described in step (c) above] was reacted, to give the title compound (230 mg) as a yellow solid.

Nuclear Magnetic Resonance Spectrum (DMSO-d$_6$) δ ppm: 3.74 (3H, singlet); 6.31 (1H, doublet, J=8.4 Hz); 6.97 (2H, doublet, J=7.7 Hz); 6.93 (2H, doublet, J=8.7 Hz); 7.20–7.39 (5H, multiplet); 7.50–7.54 (2H, multiplet); 7.75–7.81 (2H, multiplet).

EXAMPLE 48

N-{[3-(2-Amino-3,4-dioxocyclobut-1-enylamino) phenyl]-(4-methoxyphenyl)methyl}-4-fluorobenzamide (Compound No. 2-969)

(48a) N-[(4-Methoxyphenyl)-(3-nitrophenyl)methyl]-4-fluorobenzamide

In a similar manner to that described in Example (46c) α-(4-methoxyphenyl)-3-nitrobenzylamine hydrochloride (1.51 g) [prepared as described in Example 46(b) above] and 4-fluorobenzoyl chloride (813 mg) were reacted, to afford the title compound (1.72 g) as a white solid.

Nuclear Magnetic Resonance Spectrum (CDCl$_3$) δ ppm: 3.81 (3H, singlet); 6.41 (1H, doublet, J=7.0 Hz); 6.60 (2H, doublet, J=7.0 Hz); 6.89–6.93 (2H, multiplet ); 7.10–7.25 (4H, multiplet); 7.53 (2H, triplet, J=8.0 Hz); 7.66 (1H, doublet, J=8.0 Hz); 7.81–7.86 (2H, multiplet); 8.14 (1H, singlet).

(48b) N-[(3-Aminophenyl)-(4-methoxyphenyl)methyl[-4-fluorobenzamide hydrochloride In a similar manner to that described in Example (47b), N-[(4-methoxyphenyl)-(3-nitrophenyl)methyl]-4-fluorobenzamide (1.72 g) [prepared as described in step (a) above] and tin (II) chloride (4.30 g) were reacted, to afford the title compound (706 mg) as a white solid.

Nuclear Magnetic Resonance Spectrum (CDCl$_3$) δ ppm: 3.73 (3H, singlet); 6.17 (1H, doublet, J=8.7 Hz); 6.60 (1H, doublet, J=7.0 Hz); 6.89–6.92 (2H, multiplet); 7.10–7.25 (4H, multiplet); 7.53 (1H, triplet, J=7.9 Hz); 7.66 (1H, doublet, J=8.0 Hz); 7.81–7.86 (2H, multiplet); 8.14 (1H, singlet).

(48c) N-{[3-(2-Methoxy-3,4-dioxocyclobut-1-enylamino) phenyl]-(4-methoxyphenyl)methyl}-4-fluorobenzamide In a similar manner to that described in Example (46e) N-[(3-aminophenyl)-(4-methoxyphenyl)methyl]-4-fluorobenzamide hydrochloride (674 mg) [prepared as described in step (b) above] and 3,4-dimethoxy-3-cyclobutene-1,2-dione (250 mg) were reacted, to afford the title compound (399 mg) as a yellow solid.

mp 115–116° C.

Nuclear Magnetic Resonance Spectrum (DMSO-d$_6$) δ ppm: 3.74 (3H, singlet); 4.28 (3H, singlet); 6.30 (1H, doublet, J=8.4 Hz); 6.93 (2H, doublet, J=8.7 Hz); 7.06 (1H, doublet, J=7.7 Hz); 7.26–7.34 (7H, multiplet); 8.00–8.04 (2H, multiplet).

(48d) N-{[3-(2-Amino-3,4-dioxocyclobut-1-enylamino) phenyl]-(4-methoxyphenyl)methyl}-4-fluorobenzamide In a similar manner to that described in Example (1d), N-{[3-(2-methoxy-3,4-dioxocyclobut-1-enylamino) phenyl]-(4-methoxyphenyl)methyl}-4-fluorobenzamide (346 mg) [prepared as described in step (c) above] was reacted, to give the title compound (223 mg) as a yellow solid.

mp 212–213° C. (dec).

Nuclear Magnetic Resonance Spectrum (DMSO-d$_6$) δ ppm: 3.74 (3H, singlet); 6.31 (1H, doublet, J=8.5 Hz); 6.92 (2H, doublet, J=8.7 Hz); 6.97 (1H, doublet, J=7.7 Hz); 7.20 (1H, singlet); 7.23–7.48 (5H, multiplet); 7.50–7.53 (1H, multiplet); 7.96–8.04 (2H, multiplet).

EXAMPLE 49

3-Amino-4-{3-[benzyloxylmino-(4-methoxyphenyl) methyl]phenylamino}-3-cyclobutene-1,2-dione
(Compound No. 5-4)

(49a) 4-Methoxyphenyl 3-nitrophenyl ketone O-benzyloxime

O-Benzylhydroxylamine (3.02 g) and triethylamine (7.9 ml) were added to a solution of 4-methoxyphenyl 3-nitrophenyl ketone (2.44 g) in anhydrous dichloromethane (40 ml). The mixture was stirred in an ice bath for 15 minutes. A solution of titanium tetrachloride (1.51 ml) in anhydrous dichloromethane (30 ml) was then slowly added dropwise to the reaction mixture. This mixture was stirred at ambient temperature for 1 hour. At the end of this time, ethyl acetate and a saturated aqueous solution of sodium hydrogencarbonate were added to the reaction mixture and the insoluble material was removed by filtration using a Celite (trade mark) filter aid. The organic layer was separated from the filtrate and the aqueous layer was extracted with ethyl acetate. The ethyl acetate layer and extract were combined, washed with a saturated aqueous solution of sodium chloride and dried over anhydrous magnesium sulfate. It was then concentrated by evaporation under reduced pressure. The residue was purified by chromatography through a silica gel column using a 9:1 by volume mixture of hexane and ethyl acetate as the eluant, to afford a pale yellow oil (1.81 g). Ethanol was added to the oil and the precipitate was filtered off, to afford isomer A of the title compound (1.54 g) as a white solid. The filtrate was concentrated by evaporation to afford a mixture of isomer A/isomer B=½of the title compound (764 mg) as a pale yellow oil.

Isomer A mp 100–101° C.

Nuclear Magnetic Resonance Spectrum (CDCl$_3$) δ ppm: 3.82 (3H, singlet); 5.21 (2H, singlet); 6.86 (2H, doublet, J=8.9 Hz); 7.27–7.38 (7H, multiplet); 7.59 (1H, triplet, J=7.9 Hz); 7.63–7.66 (1H, multiplet); 8.22–8.27 (2H, multiplet).

Isomer B

Nuclear Magnetic Resonance Spectrum (CDCl$_3$) δ ppm: 3.82 (1H, singlet); 3.86 (2H, singlet); 5.21 (2/3H, singlet); 5.26 (4/3H, singlet); 6.86 (2/3H, doublet, J=8.9 Hz); 6.96 (4/3H, doublet, J=8.7 Hz); 7.27–7.39 (7H, multiplet); 7.49 (2/3H, triplet, J=8.0 Hz); 7.59 (1/3H, triplet, J=7.9 Hz); 7.63–7.66 (1/3H, multiplet); 7.73–7.88 (2/3H, multiplet); 8.22–8.35 (2H, multiplet).

(49b) 3-Aminophenyl 4-methoxyphenyl ketone O-benzyloxime

A mixture of isomer A of 4-methoxyphenyl 3-nitrophenyl ketone O-benzyloxime (974 mg) [prepared as described in step (a) above] and tin (II) chloride (2.55 g) in ethanol (30 ml) was heated under reflux for 1 hour. After removal of the ethanol by evaporation, the residue was diluted with ethyl acetate. The ethyl acetate was washed with a 5N aqueous solution of sodium hydroxide, with water and then with a saturated aqueous solution of sodium chloride. It was then dried over anhydrous magnesium sulfate and evaporated under reduced pressure, to afford isomer A of the title compound (893 mg) as a yellow oil.

Isomer A

Nuclear Magnetic Resonance Spectrum (CDCl$_3$) δ ppm: 3.80 (3H, singlet); 5.20 (2H, singlet); 6.57–6.86 (5H, multiplet); 7.20 (1H, triplet, J=7.87 Hz); 7.22–7.45 (7H, multiplet).

In a similar manner to that described in Example (1b), the mixture (752 mg) of isomer A and B of 4-methoxyphenyl 3-nitrophenyl ketone O-benzyloxime and tin (II) chloride (1.97 g) were reacted, to afford a mixture of isomer A/isomer B=½ of the title compound as a yellow oil.

Isomer B

Nuclear Magnetic Resonance Spectrum (CDCl$_3$) δ ppm: 3.80 (1H, singlet); 3.81 (2H, singlet); 5.20 (2/3H, singlet); 5.23 (4/3H, singlet); 6.55–7.45 (13H, multiplet).

(49c) 3-{3-[Benzyloxylmino-(4-methoxyphenyl)methyl] phenylamino}-4-methoxy-3-cyclobutene-1,2-dione In a similar manner to that described in Example (1c), isomer A of 3-aminophenyl 4-methoxyphenyl ketone O-benzyloxime (886 mg) and 3,4-dimethoxy-3-cyclobutene-1,2-dione (757 mg) were reacted, to afford isomer A of the title compound (1.09 g) as a yellow foamy solid.

Isomer A mp 70–71° C.

Nuclear Magnetic Resonance Spectrum (CDCl$_3$) δ ppm: 3.81 (3H, singlet); 4.35 (3H, singlet); 5.21 (2H, singlet); 6.82–6.86 (2H, multiplet); 7.12–7.15 (2H, multiplet); 7.22–7.45 (9H, multiplet).

In a similar manner to that described in Example (1c), the mixture (593 mg) of isomer A and B of 3-aminophenyl 4-methoxyphenyl ketone O-benzyloxime and 3,4-dimethoxy-3-cyclobutene-1,2-dione (507 mg) were reacted, to afford a mixture (690 mg) of isomer A/isomer B=½ of the title compound as a yellow foamy solid.

Isomer B mp 71–72° C.

Nuclear Magnetic Resonance Spectrum (CDCl$_3$) δ ppm: 3.81 (1H, singlet); 3.85 (2H, singlet); 4.34 (2H, singlet); 4.35 (1H, singlet); 5.21 (2/3H, singlet); 5.25 (4/3H, singlet); 6.82–6.86 (2/3H, multiplet); 6.93–6.97 (4/3H, multiplet); 7.12–7.15 (2/3H, multiplet); 7.22–7.45 (31/3H, multiplet).

(49d) 3-Amino-4-[(3-(benzyloxylmino-(4-methoxyphenyl) methyl)phenylamino]-3-cyclobutene-1,2-dione In a similar manner to that described in Example (1d), isomer A (780 mg) of 3-{3-[benzyloxyimino-(4-methoxyphenyl)methyl]phenylamino}-4-methoxy-3-cyclobutene-1,2-dione [prepared as described in step (c) above] was reacted, to give isomer A (869 mg) of the title compound as a yellow solid.

Isomer A mp 245–248° C. (dec).

Nuclear Magnetic Resonance Spectrum (DMSO-d$_6$) δ ppm: 3.76 (3H, singlet); 5.15 (2H, singlet); 6.90–6.95 (3H, multiplet); 7.22–7.58 (10H, multiplet).

In a similar manner to that described in Example (1d), the mixture (442 mg) of isomer A and B of 3-{3-

[benzyloxyimino-(4-methoxyphenyl)methyl]phenylamino}-4-methoxy-3-cyclobutene-1,2-dione to give a mixture (190 mg) of isomer A/isomer B=½ of the title compound as a yellow foamy solid.
Isomer B
mp 218–220° C. (dec).
Nuclear Magnetic Resonance Spectrum (DMSO-$d_6$) δ ppm: 3.76 (1H, singlet); 3.80 (2H, singlet); 5.15 (2/3H, singlet); 5.18 (4/3H, singlet); 6.90–6.95 (1H, multiplet); 7.00–7.03 (2H, multiplet); 7.22–7.75 (10H, multiplet).

EXAMPLE 50

N-{[3-(2-Amino-3,4-dioxocyclobut-1-enylamino)phenyl]-(4-methoxyphenyl)methyl}-2-phenylpropionamide (Compound No. 2-464)

(50a) N-[(4-Methoxyphenyl)-(3-nitrophenyl)methyl]-2-phenylpropionyl amide

A mixture of a solution of α-(4-methoxyphenyl)-3-nitrobenzylamine hydrochloride (2.58 g) in anhydrous dichloromethane (50 ml) and triethylamine (1.77 ml) was stirred in an ice bath. A solution of 2-phenylpropionic acid (1.32 g) in dichloromethane (20 ml) and anhydrous dimethylformamide (10 ml) was added to the mixture. A suspension of 1-ethyl-3-(3-dimethylaminopropyl)carbodiimide hydrochloride (2.40 g) in dichloromethane (30 ml) was added dropwise, and the mixture was stirred at ambient temperature for 2 hours. The reaction mixture was then partitioned between ethyl acetate and a saturated aqueous solution of sodium chloride. The organic layer was washed with a saturated aqueous solution of sodium chloride, dried over anhydrous magnesium sulfate and then concentrated by evaporation under reduced pressure. The residue was purified by chromatography through a silica gel column using a 2:1 by volume mixture of hexane and ethyl acetate as the eluant, to afford the title compound (2.41 g) as a colorless oil Nuclear Magnetic Resonance Spectrum (CDCl$_3$) δ ppm: 1.53 and 1.56 (total 3H, each doublet, J=7.1 Hz); 3.63 and 3.68 (total 1H, each quartet, J=7.1 Hz); 3.77 and 3.78 (total 3H, each singlet); 5.85 and 5.87 (total 1H, each doublet, J=7.7 Hz); 6.17 and 6.19 (total 1H, each doublet, J=7.3 Hz); 6.69–7.00 (4H, multiplet); 7.25–7.50 (7H, multiplet); 7.87 and 8.02 (total 3H, each singlet).

(50b) N-[(3-Aminophenyl)-(4-methoxyphenyl)methyl]-2-phenylpropionamide hydrochloride In a similar manner to that described in Example (47b), N-[(4-methoxyphenyl)-(3-nitrophenyl)methyl]-2-phenylpropionamide (2.37 g) [prepared as described in step (a) above] and tin (II) chloride (5.76 g) were reacted, to afford the title compound (1.96 g) as a white solid.

Nuclear Magnetic Resonance Spectrum (DMSO-$d_6$) δ ppm: 1.34 and 1.35 (total 3H, each doublet, J=6.9 Hz); 3.35–3.55 (1H, multiplet); 3.70 and 3.74 (total 3H, each singlet); 6.01–6.06 (1H, multiplet); 6.83 (1H, doublet, J=8.7 Hz); 6.92 (1H, doublet, J=8.7 Hz); 7.06–7.55 (11H, multiplet).

(50c) N-{[3-(2-Methoxy-3,4-dioxocyclobut-1-enylamino)phenyl]-(4-methoxyphenyl)methyl}-2-phenylpropionamide In a similar manner to that described in Example (46e) N-[(3-aminophenyl)-(4-methoxyphenyl)methyl]-2-phenylpropionamide hydrochloride (555 mg) [prepared as described in step (b) above] and 3,4-dimethoxy-3-cyclobutene-1,2-dione (398 mg) were reacted, to afford the title compound (425 mg) as a yellow solid.

Nuclear Magnetic Resonance Spectrum (CDCl$_3$) δ ppm: 1.25 and 1.27 (total 3H, each doublet, J=7.3 Hz); 3.63 and 3.71 (total 1H, each quartet, J=7.1 Hz); 3.75 and 3.77 (total 3H, each singlet); 4.39 and 4.38 (total 3H, each singlet); 6.08 and 6.09 (total 1H, each doublet, J=7.5 Hz); 6.72–7.42 (13H, multiplet).

(50d) N-{[3-(2-Amino-3,4-dioxocyclobut-1-enylamino)phenyl]-(4-methoxyphenyl)methyl}-2-phenylpropionamide In a similar manner to that described in Example (1d), N-{[3-(2-methoxy-3,4-dioxocyclobut-1-enylamino)phenyl]-(4-methoxyphenyl)methyl}-2-phenylpropionamide (380 mg) [prepared as described in step (c) above] was reacted, to give the title compound (262 mg) as a yellow solid.

mp 206–209° C.

Nuclear Magnetic Resonance Spectrum (DMSO-$d_6$) δ ppm: 1.34 and 1.36 (total 3H, each doublet, J=7.4 Hz); 3.69 and 3.74 (total 3H, each singlet); 3.818 and 3.824 (total 1H, each quartet, J=7.1 Hz); 5.98 (1H, doublet, J=8.2 Hz); 6.74–7.50 (13H, multiplet).

EXAMPLE 51

3-Amino-4-<3-{(4-methoxyphenyl)-[1-(3,4-difluorophenyl)ethylamino]methyl}phenylamino>-3-cyclobutene-1,2-dione and the hydrochloride thereof (Compound No. 2-237)

(51a) 3-Amino-4-<3-{(4-methoxyphenyl)-[1-(3,4-difluorophenyl)ethylamino]methyl}phenylamino>-3-cyclobutene-1,2-dione In a similar manner to that described in Example (1d), a solution of isomer A (294 mg) of 3-methoxy-4-<3-{(4-methoxyphenyl)-[1-(3,4-difluorophenyl)ethylamino]methyl}phenylamino>-3-cyclobutene-2-1,2-dione [prepared as described in Example 35] in ethanol (8 ml) and a solution of ammonia in ethanol (2N, 1.5 ml) were reacted, to give isomer A (202 mg) of the title compound as a yellow solid.
Isomer A
melting point: 163–165° C.
Nuclear Magnetic Resonance Spectrum (DMSO-$d_6$) δ ppm: 1.29 (3H, doublet, J=6.6 Hz); 3.57 (1H, quartet, J=6.6 Hz); 3.69 (3H, singlet); 4.43 (1H, singlet); 6.82 (2H, doublet, J=8.7 Hz); 6.97 (1H, doublet, J=7.5 Hz); 7.02–7.40 (6H, multiplet); 7.22 (2H, doublet, J=8.7 Hz).

In a similar manner to that described in Example (1d), a solution of isomer B (254 mg) of 3-methoxy-4-<3-{(4-methoxyphenyl)-[1-(3,4-difluorophenyl)ethylamino]methyl}phenylamino>-3-cyclobutene-1,2-dione [prepared as described in Example 35] in ethanol (6 ml) and a solution of ammonia in ethanol (2N, 1 ml) were reacted, to give isomer B (169 mg) of the title compound as a yellow solid.
Isomer B
melting point: 172–174° C.
Nuclear Magnetic Resonance Spectrum (DMSO-$d_6$) δ ppm: 1.26 (3H, doublet, J=6.6 Hz); 3.52 (1H, quartet, J=6.6 Hz); 3.73 (3H, singlet); 4.40 (1H, singlet); 6.88 (2H, doublet, J=8.6 Hz); 6.91 (1H, doublet, J=7.7 Hz); 7.00–7.42 (6H, multiplet); 7.25 (2H, doublet, J=8.6 Hz).

(51b) 3-Amino-4-<3-{(4-methoxyphenyl)-[1-(3,4-difluorophenyl)ethylamino]methyl}phenylamino>-3-cyclobutene-1,2-dione hydrochloride A solution of hydrogen chloride in ethyl acetate (4N, 1 ml) was added to a solution of isomer B (163 mg) of 3-amino-4-<3-{(4-methoxyphenyl)-[1-(3,4-difluorophenyl)ethylamino]methyl}phenylamino>-3-cyclobutene-1,2-dione [prepared as described in step (a) above] in methanol (5 ml). The mixture was concentrated by evaporation under reduced pressure, and methanol and diethyl ether were added to the residue to give a white solid (158 mg).

melting point: 172–175° C.

Nuclear Magnetic Resonance Spectrum (DMSO-$d_6$) δ ppm: 1.64 (3H, doublet, J=6.6 Hz); 3.77 (3H, singlet); 4.23 (1H, quartet, J=6.6 Hz); 5.16 (1H, singlet); 7.00 (2H, doublet, J=8.6 Hz); 7.18–7.62 (7H, multiplet); 7.54 (2H, doublet, J=8.6 Hz).

EXAMPLE 52

3-Amino-4-{3-[(2-hydroxy-2-phenylethylamino)-(4-methoxyphenyl)methyl]phenylamino}-3-cyclobutene-1,2-dione (Compound No. 2-558)

(52a) N-[2-(t-Butyl-dimethylsilyloxy)-2-phenylethyl]-N-[(4-methoxyphenyl)(3-nitrophenyl)methyl]amine Triethylamine (5.1 ml) was added to a solution of 3-nitro-4'-methoxybenzophenone (2.38 g) and 2-(t-butyl-dimethylsilyloxy)-2-phenylethylamine (4.64 g) in anhydrous dichloromethane (40 ml). A solution of titanium tetrachloride (1.2 ml) in anhydrous dichloromethane (12 ml) was slowly added dropwise to the mixture in an ice bath. This mixture was then stirred at ambient temperature for 1 hour. At the end of this time, ethyl acetate and an aqueous solution of sodium hydrogencarbonate were added to the reaction mixture. This was filtered through a Celite (trade mark) filter aid to remove the insoluble material, and the ethyl acetate layer was separated from the filtrate. The aqueous layer was extracted with ethyl acetate. The ethyl acetate layer and extract were combined and washed with a saturated aqueous solution of sodium chloride. The organic layer was dried over anhydrous sodium sulfate and concentrated by evaporation under reduced pressure, to afford the imine derivative (6.88 g) as a yellow oil.

In a similar manner to that described in Example (1a), a solution of this oil in ethanol (70 ml), sodium cyanoborohydride (2.33 g) and acetic acid (0.8 ml) were reacted, to afford the title compound (4.95 g) as a yellow oil Nuclear Magnetic Resonance Spectrum (CDCl$_3$) δ ppm: −0.12 (3H, singlet); 0.03 and 0.04 (total 3H, each singlet); 0.859 and 0.864 (total 9H, each singlet); 2.68–2.77 (2H, multiplet); 3.76 and 3.78 (total 3H, each singlet); 4.83–4.87 (2H, multiplet); 6.82 and 6.84 (2H, each doublet, J=6.6 Hz); 7.23–7.31 (7H, multiplet); 7.38–7.44 (1H, multiplet); 7.66–7.69 (1H, multiplet); 8.02–8.06 (1H, multiplet); 8.27 (1H, doublet, J=7.9 Hz).

(52b) 2-{[(4-Methoxyphenyl)-(3-nitrophenyl)methyl]amino}-1-phenylethanol

A mixture of N-[2-(t-butyl-dimethylsilyloxy)-2-phenylethyl]-N-[(4-methoxyphenyl)-(3-nitrophenyl)methyl]amine (4.95 g) [prepared as described in step (a) above] and a solution of tetrabutylammonium fluoride in tetrahydrofuran (1M, 20 ml) was stirred at ambient temperature for 1 hour. The reaction mixture was diluted with ethyl acetate, and the ethyl acetate was washed with water and with an aqueous solution of sodium chloride, dried over anhydrous magnesium sulfate and then evaporated under reduced pressure. The residue was purified by chromatography through a silica gel column using a 3:1 by volume mixture of cyclohexane and ethyl acetate as the eluant, to afford the title compound (3.26 g) as a pale yellow oil.

Nuclear Magnetic Resonance Spectrum (CDCl$_3$) δ ppm: 2.80–2.90 (2H, multiplet); 3.777 and 3.780 (total 3H, each singlet); 4.76–4.83 (1H, multiplet); 4.91 (1H, singlet); 6.86 (2H, doublet, J=8.6 Hz); 7.24–7.45 (7H, multiplet); 7.46–7.48 (1H, multiplet); 7.71 (1H, doublet, J=7.5 Hz); 8.07 (1H, doublet, J=7.9 Hz); 8.26 (1H, doublet, J=9.2 Hz).

(52c) 2-{[(3-Aminophenyl)-(4-methoxyphenyl)methyl]amino}-1-phenylethanol

In a similar manner to that described in Example (1b), a solution of 2-{[(4-methoxyphenyl)-(3-nitrophenyl)methyl]amino}-1-phenylethanol (3.26 g) [prepared as described in step (b) above] in methanol (60 m), nickel chloride hexahydrate (4.09 g) and sodium borohydride (1.3 g) were reacted, to afford the title compound (2.2 g) as a yellow oil.

Nuclear Magnetic Resonance Spectrum (CDCl$_3$) δ ppm: 2.66–2.75 (1H, multiplet); 2.85–2.90 (1H, multiplet); 3.77 (3H,s), 4.70–4.74 (1H, multiplet); 4.71 (1H, singlet); 6.53 (1H, doublet of doublets, J=2.0, 8.3 Hz); 6.65–6.67 (1H, multiplet); 6.70–6.74 (1H, multiplet); 6.83 (2H, doublet, J=8.4 Hz); 7.08 (1H, triplet, J=5.2 Hz); 7.20–7.36 (7H, multiplet).

(52d) 3-{3-[(2-Hydroxy-2-phenylethyl)amino-(4-methoxyphenyl)methyl]-phenylamino}-4-methoxy-3-cyclobutene-1,2-dione In a similar manner to that described in Example (1c), a solution of 2-{[(3-aminophenyl)-(4-methoxyphenyl)methyl]amino}-1-phenylethanol (2.2 g) [prepared as described in step (c) above] in methanol (40 ml) and 3,4-dimethoxy-3-cyclobutene-1,2-dione (940 mg) were reacted, to afford the title compound (1.32 g) as a white foamy solid.

Nuclear Magnetic Resonance Spectrum (CDCl$_3$) δ ppm: 2.67–2.80 (1H, multiplet); 2.85–2.93 (1H, multiplet); 3.77 (3H, singlet); 4.44 (3H, singlet); 4.74–4.83 (2H, multiplet); 6.84 (2H, doublet, J=8.6 Hz); 7.10–7.12 (2H, multiplet); 7.24–7.37 (9H, multiplet).

(52e) 3-Amino-4-{3-[(2-hydroxy-2-phenylethylamino)-(4-methoxyphenyl)methyl]phenylamino-}3-cyclobutene-1,2-dione In a similar manner to that described in Example (1d), 3-{3-[(2-hydroxy-2-phenylethylamino)-(4-methoxyphenyl)methyl]phenylamino}-4-methoxy-3-cyclobutene-1,2-dione (1.35 g) [prepared as described in step (d) above] and a solution of ammonia in ethanol (2N, 19 ml) were reacted, to give the title compound (1.36 g) as a yellow solid.

melting point: 117° C. (dec).

Nuclear Magnetic Resonance Spectrum (DMSO-d$_6$) δ ppm: 2.57 (2H, doublet, J=6.6 Hz); 3.695 and 3.704 (total 3H, each singlet); 4.76–4.84 (2H, multiplet); 6.84 and 6.86 (total 2H, each doublet, J=8.4 Hz); 7.04 (1H, triplet, J=7.1 Hz); 7.17–7.42 (10H, multiplet).

EXAMPLE 53

3-Amino-4-<3-{[2-(1H-indole-3-yl)ethylaminol-(4-methoxyphenyl)methyl}-phenylamino>-3-cyclobutene-1,2 dione (Compound No. 2-1985)

(53a) N-[2-(1H-Indol-3-yl)ethyl]-N-[(4-methoxyphenyl)-(3-nitrophenyl)methyl]amine Triethylamine (3.22 ml) was added to a solution of 3-nitro-4'-methoxybenzophenone (1.5 g) and tryptamine (1.86 g) in anhydrous dichloromethane (15 ml). A solution of titanium tetrachloride (0.77 ml) in anhydrous dichloromethane (8 ml) was slowly added dropwise to the mixture in an ice bath. This mixture was stirred at ambient temperature for 2 hours. At the end of this time, ethyl acetate and an aqueous solution of sodium hydrogencarbonate were added to the reaction mixture. This was filtered through a Celite (trade mark) filter aid to remove the insoluble material, and the ethyl acetate layer was separated from the filtrate. The aqueous layer was extracted with ethyl acetate. The ethyl acetate layer and extract were combined and washed with a saturated aqueous solution of sodium chloride. The organic layer was dried over anhydrous sodium sulfate and concentrated by evaporation under reduced pressure, to afford the imine derivative (2.63 g) as a yellow oil.

In a similar manner to that described in Example (1a), a solution of this oil in ethanol (30 ml), sodium cyanoborohydride (1.46 g) and acetic acid (0.5 ml) were reacted, to afford the title compound (2.33 g) as a yellow oil Nuclear Magnetic Resonance Spectrum (CDCl$_3$) δ ppm: 2.84–3.04 (4H, multiplet); 3.76 (3H, singlet); 4.86 (1H, singlet); 6.81 (2H, doublet, J=8.7 Hz); 7.03 (1H, doublet, J=2.1 Hz); 7.10 (1H, triplet, J=7.2 Hz); 7.17–7.24 (3H, multiplet); 7.34–7.42 (2H, multiplet); 7.55 (1H, doublet, J=7.6 Hz); 7.68 (1H, doublet, J=7.8 Hz); 8.02 (1H, doublet, J=8.0 Hz); 8.27 (1H, triplet, J=1.9 Hz).

(53b) 3-{[2-(1H-Indol-3-yl)ethylamino]-(4-methoxyphenyl)methyl}phenylamine

In a similar manner to that described in Example (1b), a solution of N-[2-(1H-indol-3-yl)ethyl]-N-[(4-methoxyphenyl)-(3-nitrophenyl)methyl]amine (2.33 g) [prepared as described in step (a) above] in ethanol (50 ml), nickel chloride hexahydrate (2.76 g) and sodium borohydride (878 mg) were reacted, to afford the title compound (484 mg) as a pale yellow oil.

Nuclear Magnetic Resonance Spectrum (CDCl$_3$) δ ppm: 2.86–3.03 (4H, multiplet); 3.75 (3H, singlet); 4.69 (1H, singlet); 6.49 (1H, doublet, J=8.1 Hz); 6.62 (1H, doublet, J=1.9 Hz); 6.71 (1H, doublet, J=7.6 Hz); 6.79 (2H, doublet, J=8.7 Hz); 7.00–7.25 (6H, multiplet); 7.35 (1H, doublet, J=8.1 Hz); 7.58 (1H, doublet, J=7.7 Hz).

(53c) 3-<3-{[2-(1H-Indol-3-yl)ethylamino]-(4-methoxyphenyl)methyl}phenylamino>-4-methoxy-3-cyclobutene-1,2-dione In a similar manner to that described in Example (1c), a solution of 3-{[2-(1H-indol-3-yl)ethylamino]-(4-methoxyphenyl)methyl}phenylamine (480 mg) [prepared as described in step (b) above] in methanol (5 ml) and 3,4-dimethoxy-3-cyclobutene-1,2-dione (193 mg) were reacted, to afford the title compound (342 mg) as a pale yellow foamy solid.

Nuclear Magnetic Resonance Spectrum (CDCl$_3$) δ ppm: 2.28–3.05 (4H, multiplet); 3.75 (3H, singlet); 4.37 (3H, singlet); 4.78 (1H, singlet); 6.79 (2H, doublet, J=8.6 Hz); 7.03–7.24 (9H, multiplet); 7.36 (1H, doublet, J=8.1 Hz); 7.54 (1H, doublet, J=7.8 Hz).

(53d) 3-Amino-4-<3-{[2-(1H-indol-3-yl)ethylamino]-(4-methoxyphenyl)methyl}phenylamino>-3-cyclobutene-1,2-dione In a similar manner to that described in Example (1d), 3-(3-{[2-(1H-indol-3-yl)ethylamino]-(4-methoxyphenyl)methyl}phenylamino>-4-methoxy-3-cyclobutene-1,2-dione (340 mg) [prepared as described in step (c) above] and a solution of ammonia in ethanol (2N, 1.4 ml) were reacted, to give the title compound (257 mg) as a yellow solid.

melting point: 184° C. (dec).

Nuclear Magnetic Resonance Spectrum (DMSO-d$_6$) δ ppm: 2.73–2.76 (2H, multiplet); 2.86–2.91 (2H, multiplet); 3.70 (3H, singlet); 6.82 and 6.85 (total 1H, each singlet); 6.84 (2H, doublet, J=8.6 Hz); 6.92 (1H, triplet, J=7.3 Hz); 7.00–7.46 (10H, multiplet).

EXAMPLE 54

3-Amino-4-{3-[(4-methoxyphenyl)-(2-cyclohexylethylamino)methyl]-phenylamino}-3-cyclobutene-1,2-dione (Compound No. 2-437)

(54a) N-[(4-Methoxyphenyl)-(3-nitrophenyl)methyl-N-[2-(cyclohexen-1-yl)ethyl]amine Triethylamine (4.33 ml) was added to a solution of 3-nitro-4'-methoxybenzophenone (2 g) and 2-(cyclohexen-1-yl)ethylamine (2.17 ml) in anhydrous dichloromethane (20 ml). A solution of titanium tetrachloride (1.03 ml) in anhydrous dichloromethane (10 ml) was slowly added dropwise to the mixture in an ice bath. This mixture was stirred at ambient temperature for 1 hour. At the end of this time, ethyl acetate and an aqueous solution of sodium hydrogencarbonate were added to the reaction mixture. This was filtered through a Celite (trade mark) filter aid to remove the insoluble material, and the ethyl acetate layer was separated from the filtrate. The aqueous layer was extracted with ethyl acetate. The ethyl acetate layer and extract were combined and washed with a saturated aqueous solution of sodium chloride. The organic layer was dried over anhydrous sodium sulfate and concentrated by evaporation under reduced pressure, to afford the imine derivative (2.70 g) as a brown oil.

In a similar manner to that described in Example (1a), a solution of this oil in ethanol (60 ml), sodium cyanoborohydride (1.96 g) and acetic acid (0.67 ml) were reacted, to afford the title compound (2.80 g) as a yellow oil Nuclear Magnetic Resonance Spectrum (CDCl$_3$) δ ppm: 1.50–1.63 (4H, multiplet); 1.86–1.87 (2H, multiplet); 2.16 (2H, triplet, J=6.8 Hz); 2.56–2.67 (2H, multiplet); 3.78 (3H, singlet); 4.86 (1H, singlet); 5.45 (1H, broad singlet); 6.85 (2H, doublet, J=8.7 Hz); 7.25–7.28 (2H, multiplet); 7.45 (1H, triplet, J=7.8 Hz); 7.73 (1H, doublet, J=8.0 Hz); 8.06 (1H, doublet, J=7.8 Hz); 8.28–8.29 (1H, multiplet).

(54b) 3-{(4-Methoxyphenyl)-[2-(cyclohexen-1-yl)ethylamino]methyl}phenylamine

In a similar manner to that described in Example (1b), a solution of N-[(4-methoxyphenyl)-(3-nitrophenyl)methyl]-N-[2-(cyclohexen-1-yl)ethyl]amine (2.80 g) [prepared as described in step (a) above] in methanol (60 m), nickel chloride hexahydrate (3.61 g) and sodium borohydride (1.15 g) were reacted, to afford a mixture (2.15 g) of the title compound and the reduction product of the title compound, that is 3-[(4-methoxyphenyl)-(2-cyclohexylethylamino)methyl]phenylamine, as a yellow oil.

Nuclear Magnetic Resonance Spectrum (CDCl$_3$) δ ppm: 1.37–1.42 (2H, multiplet); 1.50–1.66 (2H, multiplet); 1.87–1.97 (4H, multiplet); 2.13–2.17 (2H, multiplet); 2.54–2.65 (2H, multiplet); 3.77 (3H, singlet); 4.66 (1H, singlet); 5.44–5.47 (1H, multiplet); 6.51–6.53 (1H, multiplet); 6.70–6.84 (4H, multiplet); 7.06 (1H, triplet, J=7.7 Hz); 7.26–7.31 (2H, multiplet).

(54c) 3-Methoxy-4-<3-{4-methoxyphenyl)-[2-(cyclohexen-1-yl)ethylamino]-methyl}phenylamino>-3-cyclobutene-1,2-dione In a similar manner to that described in Example (1c), a solution of the mixture (2.15 g) of 3-{(4-methoxyphenyl)-[2-(cyclohexen-1-yl)ethylamino]methyl}phenylamine and 3-[(4-methoxyphenyl)-(2-cyclohexylethylamino)methyl]phenylamine [prepared as described in step (b) above] in methanol (40 ml) and 3,4-dimethoxy-3-cyclobutene-1,2-dione (953 mg) were reacted, to afford a crude product, which was purified by reverse phase medium pressure chromatography using a 50:50 by volume mixture of acetonitrile and an aqueous acetic acid buffer solution (water/acetic acid/triethylamine=1000/2/2) as the eluant, to afford the title compound (815 mg) as a pale orange foamy solid.

Nuclear Magnetic Resonance Spectrum (CDCl$_3$) δ ppm: 1.48–2.70 (12H, multiplet); 3.77 (3H, singlet); 4.44 (3H, singlet); 4.82 (1H, broad); 5.44 (1H, broad singlet); 6.81–7.30 (8H, multiplet).

Following the same procedure, 3-methoxy-4-{3-[(4-methoxyphenyl)-(2-cyclohexylethylamino)methyl] phenylamino}-3-cyclobutene-1,2-dione (632 mg) was obtained from 3-[(4-methoxyphenyl)-(2-cyclohexylethylamino)methyl]phenylamine as a white foamy solid.

Nuclear Magnetic Resonance Spectrum (CDCl$_3$) δ ppm: 0.81–2.63 (15H, multiplet); 3.77 (3H, singlet); 4.45 (3H, singlet); 4.82 (1H, broad); 6.82–7.38 (8H, multiplet).

(54d) 3-Amino-4-{3-[(4-methoxyphenyl)-(2-cyclohexylethylamino)methyl]phenylamino}-3-cyclobutene-1,2 dione In a similar manner to that described in Example (1d), 3-methoxy-4-{3-[(4-methoxyphenyl)-(2-cyclohexylethylamino)methyl]phenylamino}-3-cyclobutene-1,2-dione (630 mg) [prepared as described in step (c) above] and a solution of ammonia in ethanol (2N, 2.8 ml) were reacted, to give the title compound (536 mg) as a yellow solid.

melting point: 168–171° C.

Nuclear Magnetic Resonance Spectrum (DMSO-$d_6$) δ ppm: 0.77–1.38 (3H, multiplet); 2.43–2.49 (2H, multiplet); 3.70 (3H, singlet); 4.70 (1H, broad singlet); 6.84 (2H, doublet, J=8.6 Hz); 7.03 (1H, doublet, J=7.6 Hz); 7.23 (1H, triplet, J=7.7 Hz); 7.31–7.40 (4H, multiplet).

EXAMPLE 55

3-Hydroxy-4-<3-{phenyl-[(R)-1-phenylethylamino]methyl}phenylamino>-3-cyclobutene-1,2-dione (Compound No. 2-3)

(55a) 3-t-Butoxy-4-<3-{phenyl-[(R)-1-phenylethylamino]methyl}phenylamino>-3-cyclobutene-1,2-dione Following a similar procedure to that described in Example (1c), 1.9 g of isomer A of 3-{phenyl-[(R)-1-phenylethylamino]methyl}phenylamine and 1.25 g of 4-t-butoxy-3-methoxy-3-cyclobutene-1,2-dione were reacted, to obtain 2.3 g of isomer A of the title compound as a white solid.

Isomer A

Nuclear Magnetic Resonance Spectrum (CDCl$_3$) δ ppm: 1.39 (3H, doublet, J=6.6 Hz); 1.62 (9H, singlet); 3.62–3.71 (1H, multiplet); 4.62 (1H, singlet); 7.10–7.36 (14H, multiplet). mp: 129–131° C.

Following a similar procedure to that described in Example (1c), 2.3 g of isomer B of 3-{phenyl-[(R)-1-phenylethylamino]methyl}phenylamine and 1.54 g of 4-t-butoxy-3-methoxy-3-cyclobutene-1,2-dione were reacted, to obtain 2.53 g of isomer B of the title compound as a white solid.

Isomer B

Nuclear Magnetic Resonance Spectrum (CDCl$_3$) δ ppm: 1.37 (3H, doublet, J=6.7 Hz); 1.62 (9H, singlet); 3.66 (1H, quartet, J=6.7 Hz); 4.61 (1H, singlet); 7.00–7.36 (14H, multiplet). mp: 137–139° C.

(55b) 3-Hydroxy-4-<3-{phenyl-[(R)-1-phenylethylamino]methyl}phenylamino>-3-cyclobutene-1,2-dione 1.0 g of isomer A of 3-t-butoxy-4-(3-{phenyl-[(R)-1-phenylethylamino]-methyl}phenylamino>-3-cyclobutene-1,2-dione [prepared as described in step (a) above] was dissolved in 5 ml of dichloromethane, and then 1.5 ml of trifluoroacetic acid were added. The resulting mixture was stirred at room temperature for 3 hours. At the end of this time, the pH was adjusted to a value of 4.5 by the addition of dilute aqueous hydrochloric acid and an aqueous solution of sodium hydroxide. The reaction mixture was then extracted with methylene chloride. The organic extract was washed with a saturated aqueous solution of sodium chloride, dried over anhydrous magnesium sulfate, filtered and then concentrated by evaporation under reduced pressure. The solid thus obtained was suspended in ethyl acetate, and then collected by filtration, to obtain 469 mg of isomer A of the title compound as a gray solid.

Isomer A

Nuclear Magnetic Resonance Spectrum (DMSO-$d_6$) δ ppm: 1.63 (3H, doublet, J=6.5 Hz); 4.27 (1H, broad); 4.97 (1H, broad singlet); 6.90 (1H, doublet, J=7.7 Hz); 7.22–7.67 (13H, multiplet). mp: 205° C. (dec); optical rotation [α]$_D$=−359.9 (c=1.00, AcOH).

Following a procedure similar to that described in relation to isomer A in Example (55b), 1.0 g of isomer B of 3-t-butoxy-4-<3-{phenyl-[(R)- 1-phenylethylamino]methyl}phenylamino>-3-cyclobutene-1,2-dione and 1.5 ml of trifluoroacetic acid were reacted, to obtain 855 mg of isomer B of the title compound as a white solid.

Isomer B

Nuclear Magnetic Resonance Spectrum (DMSO-$d_6$) δ ppm: 1.59 (3H, broad); 4.10–4.17 (1H, broad); 4.98–5.03 (1H, broad); 6.89–6.99 (1H, broad); 7.18–7.59 (12H, multiplet); 7.72 (1H, singlet). mp: 202° C. (dec); optical rotation [α]$_D$=+67.5 (c=1.00, AcOH).

EXAMPLE 56

3-Hydroxy-4-<3-{phenyl-[(S)-1-phenylethylamino]methyl}phenylamino>-3-cyclobutene-1,2-dione (Compound No. 2-3)

(56a) 3-t-Butoxy-4-<3-{phenyl-[(S)-1-phenylethylamino]methyl}phenylamino>-3-cyclobutene-1,2-dione Following a similar procedure to that described in Example 1 (c), 1.9 g of isomer A of 3-{phenyl-[(S)-1-phenylethylamino]methyl}phenylamine and 1.25 g of 4-t-butoxy-3-methoxy-3-cyclobutene-1,2-dione were reacted, to give 2.3 g of isomer A of the title compound as a white solid.

Following a similar procedure to that described in Example 1 (c), 2.3 g of isomer B of 3-{phenyl-[(S)-1-phenylethylamino]methyl}phenylamine and 1.54 g of 4-t-butoxy-3-methoxy-3-cyclobutene-1,2-dione were reacted, to give 2.53 of isomer B of the title compound as a white solid.

(56b) 3-Hydroxy-4-<3-{phenyl-[(S)-1-phenylethylamino]methyl}phenylamino>-3-cyclobutene-1,2-dione Following a similar procedure to that described in Example (55b), 1.0 g of isomer A of 3-t-butoxy-4-(3-{phenyl-[(S)-1-phenylethylamino]methyl}phenylamino>-3-cyclobutene-1,2-dione [prepared as described in step (a) above] and 1.5 ml of trifluoroacetic acid were reacted, to obtain 855 mg of isomer A of the title compound as a white solid.

Isomer A optical rotation [α]$_D$=+359.4 (c=1.00, AcOH).

Following a similar procedure to that described in Example (55b), 1.0 of isomer B of 3-t-butoxy-4-<3-{phenyl-[(S)-1-phenylethylamino]methyl}phenylamino>-3-cyclobutene-1,2-dione [prepared as described in step (a) above] and 1.5 ml of trifluoroacetic acid were reacted, to obtain 855 m of isomer B of the title compound as a white solid.

Isomer B optical rotation [α]$_D$=−56.4 (c=(1.00, AcOH).

EXAMPLE 57

4-<3-{[1-(3,4-Difluorophenyl)ethylamino]-(3-methoxyphenyl)methyl}-4-methoxyphenylamino>-3-hydroxy-3-evelobutene-1,2-dione (Compound No. 2-3390)

(57a) N-[1-(3,4-Difluorophenyl)ethyl]-N-[(2-methoxy-5-nitrophenyl)-(3-methoxyphenyl)methyl]amine Following a similar procedure to that described in Example (1a), 600 mg of 2-methoxy-5-nitrophenyl 3-methoxyphenyl ketone, 809 mg of 1-(3,4-difluorophenyl)ethylamine hydrochloride, 1.75 ml of triethylamine, 0.28 ml of titanium tetrachloride, 583 mg of sodium cyanoborohydride and 0.18 ml of acetic acid were reacted, to obtain 830 mg of the title compound as a yellow foamy solid.

Nuclear Magnetic Resonance Spectrum (CDCl$_3$) δ ppm: 1.31 and 1.35 (total 3H, each doublet, J=6.6 and 6.6 Hz);

3.60 and 3.69 (total 1H, each quartet, J=6.6 and 6.6 Hz); 3.76 and 3.82 (total 3H, each singlet); 3.80 (3H, singlet); 4.91 and 4.92 (total 1H, each singlet); 6.73–6.94 (5H, multiplet); 7.04–7.27 (3H, multiplet); 8.10 and 8.18 (total 1H, each doublet of doublets, J=2.9, 8.9 and 2.9, 9.2 Hz); 8.29 and 8.46 (total 1H, each doublet, J=2.8 and 2.8 Hz).

(57b) 3-{[1-(3,4-Difluorophenyl)ethylamino]-(3-methoxyphenyl)methyl}-4-methoxyphenylamine 810 mg of N-[1-(3,4-difluorophenyl)ethyl]-N-[(2-methoxy-5-nitrophenyl)-(3-methoxyphenyl)methyl]amine [prepared as described in step (a) above] and 1.43 g of tin (II) chloride were added to 20 ml of a 1:1 by volume mixture of concentrated hydrochloric acid and ethanol, and then the mixture was heated under reflux for 2 hours. The reaction mixture was adjusted to a weakly alkaline pH by the addition of excess sodium hydroxide, after which it was extracted with ethyl acetate. The extract was washed with a saturated aqueous solution of sodium chloride, dried over magnesium sulfate and then distilled under reduced pressure to remove the solvent. The residue was separated and purified by reverse phase HPLC [acetonitrile: acetate buffer (water:acetic acid:triethylamine=1000:2:2)=50:50], to obtain 235 mg of isomer A of the title compound as a yellow oil. The isomer mixture was purified further by chromatography through a silica gel column using a 1:1 by volume mixture of cyclohexane and ethyl acetate as the eluant, to obtain 187 mg of isomer B as a yellow oil.

Isomer A

Nuclear Magnetic Resonance Spectrum ($CDCl_3$) δ ppm: 1.32 (3H, doublet, J=6.8 Hz); 3.61–3.69 (1H, multiplet); 3.65 (3H, singlet); 3.80 (3H, singlet); 4.88 (1H, singlet); 6.50–6.51 (2H, multiplet); 6.65 (1H, doublet, J=9.2 Hz); 6.78 (1H, doublet of doublets, J=3.0, 7.9 Hz); 6.88–6.94 (3H, multiplet); 7.03–7.10 (1H, multiplet); 7.12–7.18 (1H, multiplet); 7.22 (1H, triplet, J=7.9 Hz).

Isomer B

Nuclear Magnetic Resonance Spectrum ($CDCl_3$) δ ppm: 1.30 (3H, doublet, J=6.6 Hz); 3.60 (3H, singlet); 3.67 (1H, quartet, J=6.6 Hz); 3.76 (3H, singlet); 4.77 (1H, singlet); 6.57–6.59 (1H, multiplet); 6.64 (1H, doublet, J=2.7 Hz); 6.71 (2H, doublet, J=8.6 Hz); 6.87 (1H, doublet, J=8.0 Hz); 6.93 (1H, doublet, J=1.7 Hz); 6.98–7.19 (4H, multiplet).

(57c) 3-t-Butoxy-4-<3-{[1-(3,4-difluorophenyl)ethylamino]-3-(methoxyphenyl)methyl}-4-methoxyphenylamino>-3-cyclobutene-1,2-dione Following a similar procedure to that described in Example (1c), 220 mg of isomer A of 3-{[1-(3,4-difluorophenyl)ethylamino]-(3-methoxyphenyl)methyl}-4-methoxyphenylamine [prepared as described in step (b) above] and 203 mg of 4-t-butoxy-3-methoxy-3-cyclobutene-1,2-dione were reacted, to obtain 305 mg of isomer A of the title compound as a yellow foamy solid.

Isomer A

Nuclear Magnetic Resonance Spectrum ($CDCl_3$) δ ppm: 1.33 (3H, doublet, J=6.6 Hz); 1.63 (9H, singlet); 3.68 (1H, quartet, J=6.7 Hz); 3.73 (3H, singlet); 3.81 (3H, singlet); 4.92 (1H, singlet); 6.78–6.81 (2H, multiplet); 6.88–6.94 (3H, multiplet); 7.03–7.31 (5H, multiplet).

Following a similar procedure to that described in Example (1c), 180 mg of isomer B of 3-{[1-(3,4-difluorophenyl)ethylamino]-(3-methoxyphenyl)methyl}-4-methoxyphenylamine [prepared as described in step (b) above] and 166 mg of 4-t-butoxy-3-methoxy-3-cyclobutene-1,2-dione were reacted, to obtain 210 mg of isomer B of the title compound as a yellow foamy solid.

Isomer B

Nuclear Magnetic Resonance Spectrum ($CDCl_3$) δ ppm: 1.34 (3H, doublet, J=6.6 Hz); 1.63 (9H, singlet); 3.64 (1H, quartet, J=6.6 Hz); 3.69 (3H, singlet); 3.76 (3H, singlet); 4.90 (1H, singlet); 6.71–6.73 (1H, multiplet); 6.84–6.87 (2H, multiplet); 6.90 (1H, singlet); 6.96–7.00 (1H, multiplet); 7.05–7.18 (3H, multiplet); 7.29–7.37 (2H, multiplet).

(57d) 4-<3-{[1-(3,4-Difluorophenyl)ethyamino]-(3-methoxyphenyl)methyl}-4-methoxyphenylamino>-3-hydroxy-3-cyclobutene-1,2-dione 300 mg of isomer A of 3-t-butoxy-4-<3-{[1-(3,4-difluorophenyl)ethylamino]-(3-methoxyphenyl)methyl}-4-methoxyphenylamino>-3-cyclobutene-1,2-dione [prepared as described in step (c) above] were dissolved in 5 ml of t-butanol, and then 3 ml of 1N aqueous hydrochloric acid were added. The resulting mixture was stirred at room temperature for 30 minutes and then at 100° C. for 30 minutes. At the end of this time, the reaction mixture was neutralized with 3 ml of a 1N aqueous solution of sodium hydroxide and then diluted with water. The insoluble matter precipitated upon dilution was collected by filtration, washed successively with water, diethyl ether and acetone and then dried, to obtain 206 mg of isomer A of the title compound as a pale yellow solid.

Isomer A

Nuclear Magnetic Resonance Spectrum (DMSO-$d_6$) δ ppm: 1.55 (3H, doublet, J=6.7 Hz); 3.72 (3H, singlet); 3.82 (3H, singlet); 4.22 (1H, broad); 5.27 (1H, broad singlet); 6.93–7.00 (3H, multiplet); 7.21–7.24 (2H, multiplet); 7.34 (1H, triplet, J=8.0 Hz); 7.49–7.57 (3H, multiplet); 7.65–7.68 (1H, multiplet). mp: 238–241° C.

200 mg of isomer B of 3-t-butoxy-4-<3-{[1-(3,4-difluorophenyl)ethylamino]-(3-methoxyphenyl)methyl}-4-methoxyphenylamino>-3-cyclobutene-1,2-dione [prepared as described in step (c) above] were dissolved in 5 ml of t-butanol. 2 ml of 1N aqueous hydrochloric acid were added to the resulting solution, which was then stirred at 100° C. for 1 hour. At the end of this time, the reaction mixture was neutralized with 2 ml of a 1N aqueous solution of sodium hydroxide, and then concentrated by evaporation under reduced pressure. The residue was purified by chromatography through a silica gel column using a 10:1 by volume mixture of methylene chloride and methanol as eluant, to obtain 88 mg of isomer B of the title compound as a pale yellow solid.

Isomer B

Nuclear Magnetic Resonance Spectrum (DMSO-$d_6$) δ ppm: 1.31 (3H, broad); 3.24–3.70 (1H, broad); 3.57 (3H, singlet); 3.70 (3H, singlet); 4.78 (1H, broad singlet); 6.74–6.84 (4H, multiplet); 7.10–7.15 (2H, multiplet); 7.33–7.40 (2H, multiplet); 7.48 (1H, doublet, J=8.1 Hz); 7.84 (1H, broad). mp: 235° C. (dec).

EXAMPLE 58

4-<3-{[1-(3,4-Difluorophenyl)ethylamino]-(4-methoxyphenyl)methyl}-4-methoxyphenylamino>-3-hydroxy-3-cyclobutene-1,2-dione (Compound No. 2-3405)

(58a) N-[1-(3,4-Difluorophenyl)ethyl]-N-[(2-methoxy-5-nitrophenyl)-(4-methoxyphenyl)methyl]amine Following a similar procedure to that described in Example (1a), 2.02 of 2-methoxy-5-nitrophenyl 4-methoxyphenyl ketone, 2.02 a of 1-(3,4-difluorophenyl) ethylamine hydrochloride, 4,37 ml of triethylamine, 0.69 ml of titanium tetrachloride, 1.46 g of sodium cyanoborohydride and 0.45 ml of acetic acid were reacted, to obtain 2.10 g of the title compound as a yellow oil.

Nuclear Magnetic Resonance Spectrum ($CDCl_3$) δ ppm: 1.34 and 1.35 (total 3H, each doublet, J=6.6 and 6.5 Hz);

3.59 and 3.65 (total 1H, each quartet, J=6.6 and 6.6 Hz); 3.76, 3.79, 3.80 and 3.82 (total 6H, each singlet); 4.88 and 4.90 (total 1H, each singlet); 6.78–6.93 (4H, multiplet); 7.04–7.22 (4H, multiplet); 8.10 and 8.17 (total 1H, each doublet of doublets, J=2.8, 8.9 and 2.9, 9.3 Hz); 8.30 and 8.49 (total 1H, each doublet, J=2.8 and 2.8 Hz).

(58b) 3-{[1-(3,4-Difluorophenyl)ethylamino]-(4-methoxyphenyl)methyl}-4-methoxyphenylamine Following a reaction and purification procedure similar to those described in Example (57b), 2.0 g of N-[1-(3,4-difluorophenyl)ethyl]-N-[(2-methoxy-5-nitrophenyl)-(4-methoxyphenyl)methyl]amine [prepared as described in step (a) above], 3.54 g of tin (II) chloride and 40 ml of a 1:1 mixture of concentrated aqueous hydrochloric acid and ethanol were reacted, to obtain 370 mg of isomer A and 591 mg of isomer B of the title compound as yellow oils, respectively.

Isomer A

Nuclear Magnetic Resonance Spectrum (CDCl$_3$) δ ppm: 1.30 (3H, doublet, J=6.6 Hz); 3.59 (3H, singlet); 3.65 (1H, quartet, J=6.6 Hz); 3.76 (3H, multiplet); 4.74 (1H, singlet); 6.58 (1H, doublet of doublets, J=2.8, 8.5 Hz); 6.64–6.72 (2H, multiplet); 6.74–6.83 (3H, multiplet); 6.97–7.00 (1H, multiplet); 7.06–7.22 (4H, multiplet).

Isomer B

Nuclear Magnetic Resonance Spectrum (CDCl$_3$) δ ppm: 1.31 (3H, doublet, J=6.7 Hz); 3.61–3.65 (1H, multiplet); 3.65 (3H, singlet); 3.80 (3H, singlet); 4.85 (1H, singlet); 6.49–6.52 (2H, singlet); 6.65 (1H, doublet of doublets, J=1.3, 7.5 Hz); 6.84–6.90 (3H, multiplet); 7.05–7.16 (2H, multiplet); 7.23–7.27 (3H, multiplet).

(58c) 3-t-Butoxy-4-<3-{[1-(3,4-difluorophenyl)ethylamino]-(4-methoxyphenyl)methyl}-4-methoxyphenylamino>-3-cyclobutene-1,2-dione Following a similar procedure to that described in Example (1c), 360 mg of isomer A of 3-{[1-(3,4-difluorophenyl)ethylamino]-(4-methoxyphenyl)methyl}-4-methoxyphenylamine [prepared as described in step (b) above] and 333 mg of 4-t-butoxy-3-methoxy-3-cyclobutene-1,2-dione were reacted, to obtain 260 mg of isomer A of the title compound as a yellow foamy solid.

Isomer A

Nuclear Magnetic Resonance Spectrum (CDCl$_3$) δ ppm: 1.34 (3H, doublet, J=6.6 Hz); 1.63 (9H, singlet); 3.63 (1H, quartet, J=6.6 Hz); 3.68 (3H, singlet); 3.76 (3H, singlet); 4.87 (1H, singlet); 6.78 (2H, doublet, J=8.7 Hz); 6.84 (1H, doublet, J=8.8 Hz); 6.95–7.00 (1H, multiplet); 7.05–7.15 (2H, singlet); 7.20 (2H, doublet, J=8.6 Hz); 7.26–7.40 (2H, multiplet).

Following a similar procedure to that described in Example (1c), 360 mg of isomer B of 3-{[1-(3,4-difluorophenyl)ethylamino]-(4-methoxyphenyl)methyl}-4-methoxyphenylamine [prepared as described in step (b) above] and 333 mg of 4-t-butoxy-3-methoxy-3-cyclobutene-1,2-dione were reacted, to obtain 512 mg of isomer B of the title compound as a yellow foamy solid.

Isomer B

Nuclear Magnetic Resonance Spectrum (CDCl$_3$) δ ppm: 1.32 (3H, doublet, J=6.6 Hz); 1.63 (9H, singlet); 3.64 (1H, quartet, J=6.6 Hz); 3.72 (3H, singlet); 3.81 (3H, singlet); 4.89 (1H, singlet); 6.78 (1H, doublet, J=8.8 Hz); 6.86–6.90 (3H, multiplet); 7.03–7.26 (6H, multiplet).

(58d) 4-<3-{[1-(3,4-Difluorophenyl)ethylamino]-(4-methoxyphenyl)methyl}-4-methoxyphenylamino>-3-hydroxy-3-cyclobutene-1,2-dione Following a reaction and purification procedure similar to those described in Example (57d), 250 mg of isomer A of 3-t-butoxy-4-(3-{[1-(3,4-difluorophenyl)ethylamino]-(4-methoxyphenyl)methyl}-4-methoxyphenylamino>-3-cyclobutene-1,2-dione [prepared as described in step (c) above] were reacted, to obtain 115 mg of isomer A of the title compound as a pale yellow solid.

Isomer A

Nuclear Magnetic Resonance Spectrum (DMSO-d$_6$) δ ppm: 1.62 (3H, doublet, J=6.6 Hz); 3.57 (3H, singlet); 3.73 (3H, singlet); 4.50 (1H, broad); 5.05 (1H, broad singlet); 6.91–6.95 (3H, multiplet); 7.03–7.05 (1H, multiplet); 7.32–7.40 (4H, multiplet); 7.45–7.52 (1H, multiplet); 7.65 (1H, doublet, J=2.3 Hz). mp: 252–255° C.

Following a reaction and purification procedure similar to those described in Example (57d), 400 mg of isomer B of 3-t-butoxy-4-<3-{[1-(3,4-difluorophenyl)ethylamino]-(4-methoxyphenyl)methyl}-4-methoxyphenylamino>-3-cyclobutene-1,2-dione [prepared as described in step (c) above] was reacted, to obtain 230 mg of isomer B of the title compound as a pale yellow solid.

Isomer B

Nuclear Magnetic Resonance Spectrum (DMSO-d$_6$) δ ppm: 1.53 (3H, doublet, J=6.6 Hz); 3.71 (3H, singlet); 3.77 (3H, singlet); 4.11–4.24 (1H, broad); 5.24 (1H, broad singlet); 6.93 (1H, doublet, J=9.0 Hz); 6.99 (2H, doublet, J=8.7 Hz); 7.23–7.25 (1H, multiplet); 7.47 (2H, doublet, J=8.6 Hz); 7.50–7.65 (4H, multiplet). mp: 245–249° C.

EXAMPLE 59

4-<5-{[1-(3,4-Difluorophenyl)ethylamino]-(4-methoxyphenyl)methyl}-2,3-dimethoxyphenylamino>-3-hydroxy-3-cyclobutene-1,2-dione (Compound No. 2-3406)

(59a) N-[1-(3,4-Difluorophenyl)ethyl]-N-[(3,4-dimethoxy-5-nitrophenyl)-(4-methoxyphenyl)methyl]amine Following a similar procedure to that described in Example (1a), 700 mg of 3,4-dimethoxy-5-nitrophenyl 4-methoxyphenyl ketone, 854 mg of 1-(3,4-difluorophenyl)ethylamine hydrochloride, 1.84 ml of triethylamine, 0.29 ml of titanium tetrachloride, 616 mg of sodium cyanoborohydride and 0.19 ml of acetic acid were reacted, to obtain 950 mg of the title compound as a yellow oil.

Nuclear Magnetic Resonance Spectrum (CDCl$_3$) δ ppm: 1.34 and 1.35 (total 3H, each doublet, J=6.4 and 6.4 Hz); 3.59–3.65 (1H, multiplet); 3.77, 3.81, 3.82, 3.73, 3.91 and 3.96 (total 9H, each singlet); 4.49 and 4.52 (total 1H, each singlet); 6.81–6.95 (3H, multiplet); 7.00–7.17 (5H, multiplet); 7.03 and 7.31 (total 1H, each singlet).

(59b) 5-{[1-(3,4-Difluorophenyl)ethylamino]-(4-methoxyphenyl)methyl}-2,3-dimethoxyphenylamine Following a reaction and purification procedure similar to those described in Example (1b), 950 mg of N-[1-(3,4-difluorophenyl)ethyl]-N-[(3,4-dimethoxy-5-nitrophenyl)-(4-methoxyphenyl)methyl]amine [prepared as described in step (a) above], 985 mg of nickel chloride hexahydrate and 330 mg of sodium borohydride were reacted. The crude product was purified by chromatography through a silica gel column using a 10:1 by volume mixture of toluene and ethyl acetate as eluant, to afford isomer A of the title compound (215 mg) as a yellow oil and isomer B of the title compound (370 mg) as a yellow oil, respectively.

Isomer A

Nuclear Magnetic Resonance Spectrum (CDCl$_3$) δ ppm: 1.32 (3H, doublet, J=6.7 Hz); 3.68 (1H, quartet, J=6.6 Hz); 3.76 (3H, singlet); 3.80 (3H, singlet); 3.81 (3H, singlet); 4.36 (1H, singlet); 6.25 (1H, doublet, J=1.9 Hz); 6.33 (1H, doublet, J=1.8 Hz); 6.79 (2H, doublet, J=8.7 Hz); 6.94–6.98 (1H, multiplet); 7.09–7.21 (4H, multiplet).

Isomer B

Nuclear Magnetic Resonance Spectrum (CDCl$_3$) δ ppm: 1.35 (3H, doublet, J=6.8 Hz); 3.61 (1H, quartet, J=6.6 Hz); 3.758 (3H, singlet); 3.764 (1H, singlet ); 3.81 (3H, singlet); 4.38 (1H, singlet); 6.25 (1H, doublet, J=1.8 Hz); 6.30 (3H, doublet, J=1.8 Hz); 6.86 (2H, doublet, J=8.7 Hz); 6.88–6.94 (3H, multiplet); 7.06–7.26 (4H, multiplet).

(59c) 3-t-Butoxy-4-<5-{[1-(3,4-difluorophenyl)ethylamino]-(4-methoxyphenyl)methyl}-2,3-dimethoxyphenylamino>-3-cyclobutene-1,2-dione Following a similar procedure to that described in Example (1c), 360 mg of isomer B of 5-{[1-(3,4-difluorophenyl)ethylamino]-(4-methoxyphenyl)methyl}-2,3-dimethoxyphenylamine [prepared as described in step (b) above] and 310 mgr of 4-t-butoxy-3-methoxy-3-cyclobutene-1,2-dione were reacted, to obtain 150 mg of isomer B of the title compound as a yellow foamy solid.

Isomer B

Nuclear Magnetic Resonance Spectrum (CDCl$_3$) δ ppm: 1.35 (3H, doublet, J=6.7 Hz); 1.65 (9H, singlet); 3.64 (1H, quartet, J=6.6 Hz); 3.78 (3H, singlet); 3.80 (3H, singlet); 3.86 (3H, singlet); 4.49 (1H, singlet); 6.55 (1H, broad); 6.88 (2H, doublet, J=8.7 Hz); 6.97–7.00 (1H, multiplet); 7.05–7.12 (2H, multiplet); 7.25–7.31 (2H, multiplet); 7.52–7.70 (1H, broad).

(59d) 4-<5-{[1-(3,4-difluorophenyl)ethylamino]-(4-methoxyphenyl)methyl}-2,3-dimethoxyphenylamino>-3-hydroxy-3-cyclobutene-1,2-dione Following a reaction and purification procedure similar to those described in Example (57d), 147 mg of isomer B of 3-t-butoxy-4-<5-{[1-(3,4-difluorophenyl)ethylamino]-(4-methoxyphenyl)methyl}-2,3-dimethoxyphenylamino>-3-cyclobutene-1,2-dione [prepared as described in step (c) above] was reacted, to obtain 82 mg of isomer B of the title compound as a yellow solid.

Isomer B

Nuclear Magnetic Resonance Spectrum (DMSO-d$_6$) δ ppm: 1.20–1.45 (3H, broad); 3.35–3.90 (10H, multiplet); 4.25–4.50 (1H, broad); 6.50–6.70 (1H, multiplet); 6.80–7.70 (7H, multiplet); 7.80–8.00 (1H, multiplet). mp: 200–205° C.

EXAMPLE 60

4-<5-{[-(3,5-Difluorophenyl)ethylamino]-(4-methoxyphenyl)methyl}-2,3-dimethoxyphenylamino>-3-hydroxy-3-cyclobutene-1,2-dione (Compound No. 2-3476)

(60a) N-[1-(3,5-Difluorophenyl)ethyl]-N-[(3,4-dimethoxy-5-nitrophenyl)-(4-methoxyphenyl)methyl]amine Following a similar procedure to that described in Example (1a), 750 mg of 3,4-dimethoxy-5-nitrophenyl 4-methoxyphenyl ketone, 915 mg of 1-(3,5-difluorophenyl)ethylamine hydrochloride, 1.98 ml of triethylamine, 0.31 ml of titanium tetrachloride, 660 mg of sodium cyanoborohydride and 0.20 ml of acetic acid were reacted, to obtain 990 mg of the title compound as a yellow oil.

Nuclear Magnetic Resonance Spectrum (CDCl$_3$) δ ppm: 1.34 and 1.36 (total 3H, each doublet, J=6.5 and 6.5 Hz); 3.61–3.66 (1H, multiplet); 3.77, 3.818, 3.82, 3.88, 3.91 and 3.96 (total 9H, each singlet); 4.52 and 4.55 (total 1H, each singlet); 6.66–6.91 (5H, multiplet); 7.03–7.06 (1H, multiplet); 7.14–7.17 (2H, multiplet); 7.30 and 7.37 (total 1H, each doublet, J=2.0 and 1.9 Hz).

(60b) 5-{[1-(3,5-Difluorophenyl)ethylamino]-(4-methoxyphenyl)methyl}-2,3-dimethoxyphenylamine Following a similar procedure to that described in Example (1b), 870 mg of N-[1-(3,5-difluorophenyl)ethyl-N-[(3,4-dimethoxy-5-nitrophenyl)-(4-methoxyphenyl)methyl]amine [prepared as described in step (a) above], 1.04 g of nickel chloride hexahydrate and 302 mg of sodium borohydride were reacted, to obtain 550 mg of the title compound as a colorless oil.

Nuclear Magnetic Resonance Spectrum (CDCl$_3$) δ ppm: 1.32 (3H, doublet, J=6.6 Hz); 3.62 and 3.69 (total 1H, each quartet, J=6.7 and 6.6 Hz); 3.76, 3.765, 3.768, 3.80, 3.807 and 3.814 (total 9H, each singlet); 4.39 and 4.41 (total 1H, each singlet); 6.25–6.27 (1H, multiplet); 6.31–6.35 (1H, multiplet); 6.65–6.71 (1H, multiplet); 6.77–6.89 (4H, multiplet); 7.19–7.22 (2H, multiplet).

(60c) 3-t-Butoxy-4-<5-{[1-(3,5-difluorophenyl)ethylamino]-(4-methoxyphenyl)methyl}-2,3-dimethoxyphenylamino>-3-cyclobutene-1,2-dione Following a similar procedure to that described in Example (1c), 540 mg of 5-{[1-(3,5-difluorophenyl)ethylamino]-(4-methoxyphenyl)methyl}-2,3-dimethoxyphenylamine [prepared as described in step (b) above] and 348 mg of 4-t-butoxy-3-methoxy-3-cyclobutene-1,2-dione were reacted, to obtain 260 mg of the title compound as a colorless foamy solid.

Nuclear Magnetic Resonance Spectrum (CDCl$_3$) δ ppm: 1.35–1.38 (3H, multiplet); 1.63 and 1.65 (total 9H, each singlet); 3.63–3.70 (1H, multiplet); 3.76, 3.79, 3.80, 3.84, 3.87 and 3.93 (total 9H, each singlet); 4.49 and 4.53 (total 1H, each singlet); 6.59–6.71 (2H, multiplet); 6.80–6.90 (4H, multiplet); 7.21–7.28 (2H, multiplet); 7.52–7.71 (1H, broad).

(60d) 4-<5-{[1-(3,5-Difluorophenyl)ethylamino]-(4-methoxyphenyl)methyl}-2,3-dimethoxyphenylamino>-3-hydroxy-3-cyclobutene-1,2-dione Following a reaction and purification procedure similar to those described in Example (57d), 247 mg of 3-t-butoxy-4-<5-{[1-(3,5-difluorophenyl)ethylamino]-(4-methoxyphenyl)methyl}-2,3-dimethoxyphenylamino>-3-cyclobutene-1,2-dione [prepared as described in step (c) above] were reacted, to obtain 137 mg of the isomer mixture of the title compound as a yellow solid.

Nuclear Magnetic Resonance Spectrum (DMSO-d$_6$) δ ppm: 1.48 (3H, doublet, J=6.8 Hz); 3.70–3.77 (9H, multiplet); 4.10–4.50 (1H, broad); 4.80–5.20 (1H, broad); 6.69–7.90 (9H, multiplet). mp: 167–171° C.

EXAMPLE 61

4-<3-{[1-(3,5-Difluorophenyl)ethylamino]-(4-methoxyphenyl)methyl}-4-methoxyphenylamino>-3-hydroxy-3-cyclobutene-1,2-dione (Compound No. 2-3477)

(61a) N-[1-(3,5-Difluorophenyl)ethyl]-N-[(2-methoxy-5-nitrophenyl)-(4-methoxyphenyl)methyl]amine Following a similar procedure to that described in Example (1a), 1.29 g of 2-methoxy-5-nitrophenyl 4-methoxyphenyl ketone, 1.74 g of 1-(3,5-difluorophenyl)ethylamine hydrochloride, 3.76 ml of triethylamine, 0.59 ml of titanium tetrachloride, 1.25 g of sodium cyanoborohydride and 0.39 ml of acetic acid were reacted, to obtain 1.78 g of the title compound as a yellow oil.

Nuclear Magnetic Resonance Spectrum (CDCl$_3$) δ ppm: 1.33–1.37 (3H, multiplet); 3.60 and 3.66 (total 1H, each quartet, J=6.6, 6.7 Hz); 3.76, 3.79, 3.81 and 3.83 (total 6H, each singlet); 4.91 and 4.93 (total 1H, each singlet); 6.65–6.90 (6H, multiplet); 7.17 and 7.22 (total 2H, each doublet, J=8.6 and 8.6 Hz); 8.10 and 8.17 (total 1H, each doublet of doublets, J=2.9, 8.6 and 2.9, 8.8 Hz); 8.27 and 8.50 (total 1H, each doublet, J=2.8 and 2.9 Hz).

(61b) 3-{[1-(3,5-Difluorophenyl)ethylamino]-(4-methoxyphenyl)methyl}-4-methoxyphenylamine Following a reaction and purification procedure similar to those described in Example (59b), 1.75 g of N-[1-(3,5-difluorophenyl)ethyl]-N-[(2-methoxy-5-nitrophenyl)-(4-methoxyphenyl)methyl]amine [prepared as described in step (a) above], 2.24 g of nickel chloride hexahydrate and 651 mg of sodium borohydride were reacted, to obtain 471 mg of isomer A and 650 mg of isomer B of the title compound were obtained as a yellow oil and an orange solid, respectively.
Isomer A Nuclear Magnetic Resonance Spectrum (CDCl$_3$) δ ppm: 1.30 (3H, doublet, J=6.6 Hz); 3.59 (3H, singlet); 3.67 (1H, quartet, J=6.6 Hz); 3.76 (3H, singlet); 4.77 (1H, singlet); 6.58 (1H, J=2.9, 8.6 Hz); 6.63–6.72 (3H, multiplet); 6.78 (2H, doublet, J=8.7 Hz); 6.85 (2H, doublet of doublets, J=2.1, 8.6 Hz); 7.16–7.23 (2H, multiplet).
Isomer B Nuclear Magnetic Resonance Spectrum (CDCl$_3$) δ ppm: 1.32 (3H, doublet, J=6.7 Hz); 3.64 (1H, quartet, J=6.7 Hz); 3.67 (3H, singlet); 3.81 (3H, singlet); 4.88 (1H, singlet); 6.49–6.52 (2H, multiplet); 6.64–6.70 (1H, multiplet); 6.80 (2H, doublet of doublets, J=2.1, 8.6 Hz); 6.86 (2H, doublet, J=8.7 Hz); 7.26 (2H, doublet, J=8.6 Hz). mp: 105–106° C.

(61c) 3-t-Butoxy-4-<3-{[1-(3,5-difluorophenyl)ethylamino]-(4-methoxyphenyl)methyl}-4-methoxyphenylamino>-3-cyclobutene-1,2-dione Following a similar procedure to that described in Example (1c), 450 mg of isomer A of 3-{[1-(3,5-difluorophenyl)ethylamino]-(4-methoxyphenyl)methyl}-4-methoxyphenylamine [prepared as described in step (b) above] and 416 mg of 4-t-butoxy-3-methoxy-3-cyclobutene-1,2-dione were reacted, to obtain 570 mg of isomer A of the title compound as a yellow foamy solid.
Isomer A Nuclear Magnetic Resonance Spectrum (CDCl$_3$) δ ppm: 1.35 (3H, doublet, J=6.6 Hz); 1.63 (9H, singlet); 3.65 (1H, quartet, J=6.6 Hz); 3.68 (3H, singlet); 3.76 (3H, singlet); 4.90 (1H, singlet); 6.64–6.70 (1H, multiplet); 6.77–6.86 (5H, multiplet); 7.21 (2H, doublet, J=8.7 Hz); 7.26–7.31 (1H, broad); 7.40 (1H, broad singlet).

Following a similar procedure to that described in Example (1c), 630 mg of isomer B of 3-{[1-(3,5-difluorophenyl)ethylamino]-(4-methoxyphenyl)methyl}-4-methoxyphenylamine [prepared as described in step (b) above] and 582 mg of 4-t-butoxy-3-methoxy-3-cyclobutene-1,2-dione were reacted, to obtain 880 mg of isomer B of the title compound as a yellow foamy solid.
Isomer B Nuclear Magnetic Resonance Spectrum CDCl$_3$) δ ppm: 1.33 (3H, doublet, J=6.8 Hz); 1.62 (9H, singlet); 3.65 (1H, quartet, J=6.7 Hz); 3.74 (3H, singlet); 3.81 (3H, singlet); 4.92 (1H, singlet); 6.64–6.70 (1H, multiplet); 6.76–6.80 (3H, multiplet); 6.86–6.89 (2H, multiplet); 7.11 (1H, broad); 7.16–7.28 (3H, multiplet).

(61d) 4-<3-{[1-(3,5-Difluorophenyl)ethylamino]-(4-methoxyphenyl)methyl}-4-methoxyphenylamino>-3-hydroxy-3-cyclobutene-1,2-dione Following a reaction and purification procedure similar to those described in Example (57d), 200 mg of isomer A of 3-t-butoxy-4-<3-{[1-(3,5-difluorophenyl)ethylamino]-(4-methoxyphenyl)methyl}-4-methoxyphenylamino>-3-cyclobutene- 1,2-dione [prepared as described in step (c) above] were reacted, to obtain 118 mg of isomer A of the title compound as a pale green solid.
Isomer A Nuclear Magnetic Resonance Spectrum (DMSO-d$_6$) δ ppm: 1.59 (3H, doublet, J=6.4 Hz); 3.56 (3H, singlet); 3.72 (3H, singlet); 4.47 (1H, broad); 5.07 (1H, broad singlet); 6.90–6.99 (5H, multiplet); 7.27–7.42 (4H, multiplet); 7.69 (1H, singlet). mp: 258–263° C.

Following a reaction and purification procedure similar to those described in Example (57d), 200 mg of isomer B of 3-t-butoxy-4-<3-{[1-(3,5-difluorophenyl)ethylamino]-(4-methoxyphenyl)methyl}-4-methoxyphenylamino>-3-cyclobutene-1,2-dione [prepared as described in step (c) above] were reacted, to obtain 122 mg of isomer B of the title compound as a pale yellow solid.
Isomer B Nuclear Magnetic Resonance Spectrum (DMSO-d$_6$) δ ppm: 1.52 (3H, doublet, J=6.6 Hz); 3.71 (3H, singlet); 3.77 (3H, singlet); 4.21 (1H, broad); 5.27 (1H, broad singlet); 6.94 (1H, doublet, J=8.9 Hz); 7.00 (2H, doublet, J=8.7 Hz); 7.17–7.39 (3H, multiplet); 7.47 (2H, doublet, J=8.5 Hz); 7.55 (1H, doublet, J=2.0 Hz); 7.60–7.64 (1H, multiplet). mp: 200–204° C.

EXAMPLE 62

4-<3-{[(S)-1-(3,4-Difluorophenyl)ethylamino]-(4-methoxyphenyl)methyl}phenylamino>-3-hydroxy-3-cyclobutene-1,2-dione (Compound No. 2-42)

(62a) 3-t-Butoxy-4-<3-{[(S)-1-(3,4-difluorophenyl)ethylamino]-(4-methoxyphenyl)methyl}phenylamino>-3-cyclobutene-1,2-dione Following a similar procedure to that described in Example (1c), 500 mg of isomer B of 3-{[(S)-1-(3,4-difluorophenyl)ethylamino]-(4-methoxyphenyl)methyl}phenylamine and 500 mg of 4-t-butoxy-3-methoxy-3-cyclobutene-1,2-dione were reacted, to obtain 605 mg of isomer B of the title compound as a colorless foamy solid.
Isomer B Nuclear Magnetic Resonance Spectrum (CDCl$_3$) δ ppm: 1.33 (3H, doublet, J=6.6 Hz); 1.63 (9H, singlet); 3.64 (1H, quartet, J=6.6 Hz); 3.81 (3H, singlet); 4.52 (1H, singlet); 6.88 (2H, doublet, J=8.5 Hz); 6.94–7.31 (9H, multiplet).

(62b) 4-<3-{[(S)-1-(3,4-Difluorophenyl)ethylamino]-(4-methoxyphenyl)methyl}phenylamino>-3-hydroxy-3-cyclobutene-1,2-dione hydrochloride 3 ml of a 4N solution of hydrogen chloride in ethyl acetate were added to a solution of 570 mg of isomer B of 3-t-butoxy-4-<3-{[(S)-1-(3,4-difluorophenyl)ethylamino[-(4-methoxyphenyl)methyl}phenylamino>-3-cyclobutene-1,2-dione [prepared as described in step (a) above] in 5 ml of ethyl acetate. The mixture was then stirred at room temperature for 1 hour. At the end of this time, the reaction mixture was diluted with diethyl ether. The solid thus precipitated was collected by filtration and then dried, to obtain 472 mg of the hydrochloride of isomer B of the title compound as a pale yellow solid.
Isomer B Nuclear Magnetic Resonance Spectrum (DMSO-d$_6$) δ ppm: 1.64 (3H, doublet, J=6.8 Hz); 3.77 (3H, singlet); 4.21 (1H, quartet, J=6.7 Hz); 5.10 (1H, singlet); 7.00 (2H, doublet, J=8.7 Hz); 7.20–7.21 (1H, multiplet); 7.30–7.59 (8H, multiplet). mp: 192–195° C.; optical rotation [α]$_D$=−0.1° (c=1.00, AcOH).

EXAMPLE 63

4-<3-{[(R)-1-(3,4-Difluorophenyl)ethylamino]-(4-methoxyphenyl)methyl}phenylamino>-3-hydroxy-3-cyclobutene-1,2-dione and the hydrochloride thereof (Compound No. 2-42)

(63a) 3-t-Butoxy-4-<3-{[(R)-1-(3,4-difluorophenyl)ethylamino]-(4-methoxyphenyl)methyl}phenylamino>-3-cyclobutene-1,2-dione Following a similar procedure to that described in Example (1c), 500 mg of isomer B of 3-{[(R)-1-(3,4-difluorophenyl)ethylamino]-(4-methoxyphenyl)methyl}phenylamine and 410 mg of 4-t-butoxy-3-methoxy-3-cyclobutene-1,2-dione were reacted, to obtain 450 mg of isomer B of the title compound as a colorless foamy solid.

Isomer B

Nuclear Magnetic Resonance Spectrum (CDCl$_3$) δ ppm: 1.34 (3H, doublet, J=6.6 Hz); 1.63 (9H, singlet); 3.64 (1H, quartet, J=6.5 Hz); 3.81 (3H, singlet); 4.52 (1H, singlet); 6.88 (2H, doublet, J=8.6 Hz); 6.97–7.38 (9H, multiplet).

(63b) 4-<3-{[(R)-1-(3,4-Difluorophenyl)ethylamino]-(4-methoxyphenyl)methyl}phenylamino>-3-hydroxy-3-cyclobutene-1,2-dione hydrochloride 2 ml of trifluoroacetic acid were added to a solution of 300 mg of isomer B of 3-t-butoxy-4-<3-{[(R)-1-(3,4-difluorophenyl)ethylamino]-(4-methoxyphenyl)methyl}phenylamino>-3-cyclobutene-1,2-dione [prepared as described in step (a) above] in 5 ml of anhydrous methylene chloride. The resulting mixture was then stored at room temperature for 1 hour. At the end of this time, the solvent and excess trifluoroacetic acid were removed by distillation under reduced pressure. The resulting residue was dissolved again in 10 ml of ethyl acetate, and 2 ml of a 4N solution of hydrogen chloride in ethyl acetate were added. The resulting mixture was stirred at room temperature for 15 minutes. The reaction mixture was then diluted with diethyl ether. The solid thus precipitated was collected by filtration and dried, to obtain 260 mg of the hydrochloride of isomer B of the title compound as a pale yellow solid.

Isomer B

Nuclear Magnetic Resonance Spectrum (DMSO-d$_6$) δ ppm: 1.64 (3H, doublet, J=6.7 Hz); 3.77 (3H, singlet); 4.21 (1H, quartet, J=6.6 Hz); 5.09 (1H, singlet); 6.99 (2H, doublet, J=8.7 Hz); 7.20–7.22 (1H, multiplet); 7.34–7.41 (3H, multiplet); 7.47–7.60 (5H, multiplet). mp: 192–196° C.; optical rotation [α]$_D$=+11.1° (c=1.00, AcOH).

(63c) 4-<3-{[(R)-1-(3,4-Difluorophenyl)ethylamino]-(4-methoxyphenyl)methyl}phenylamino>-3-hydroxy-3-cyclobutene-1,2-dione Following a reaction and purification procedure similar to those described in Example (55b), 175 mg of isomer B of 3-t-butoxy-4-<3-{[(R)-1-(3,4-difluorophenyl)ethylamino]-(4-methoxyphenyl)methyl}phenylamino>-3-cyclobutene-1,2-dione [prepared as described in step (b) above] was reacted, to obtain 129 mg of isomer B of the title compound as a yellow solid.

Isomer B

Nuclear Magnetic Resonance Spectrum (DMSO-d$_6$) δ ppm: 1.56 (3H, broad); 3.76 (3H, singlet); 4.19 (1H, broad); 5.00 (1H, broad); 6.91–7.00 (3H, multiplet); 7.20–7.24 (2H, multiplet); 7.45–7.56 (5H, multiplet); 7.69 (1H, singlet). mp: 193–200° C.; optical rotation [α]$_D$=+102.6° (c=0.76, AcOH).

EXAMPLE 64

4-<3-{[(R)-1-(3,5-Difluorophenyl)ethylamino]-(4-methoxyphenyl)methyl}phenylamino>-3-hydroxy-3-cyclobutene-1,2-dione (Compound No. 2-56)

(64a) N-[(R)-1-(3,5-Difluorophenyl)ethyl]-N-[(4-methoxyphenyl)-(3-nitrophenyl)methyl]amine Following a reaction and purification procedure similar to those described in Example (1a), 4.42 g of 4-methoxyphenyl 3-nitrophenyl ketone, 4.42 g of (R)-1-(3,5-difluorophenyl)ethylamine hydrochloride, 11.7 ml of triethylamine, 2.01 ml of titanium tetrachloride, 4.25 g of sodium cyanoborohydride and 1.31 ml of acetic acid were reacted, to obtain 860 mg of the more polar isomer B of the title compound as a yellow oil.

Isomer B

Nuclear Magnetic Resonance Spectrum (CDCl$_3$) δ ppm: 1.35 (3H, doublet, J=6.6 Hz); 3.67 (1H, quartet, J=6.6 Hz); 3.82 (3H, singlet); 4.63 (1H, singlet); 6.66–6.72 (1H, multiplet); 6.76–6.85 (2H, multiplet); 6.90 (2H, doublet, J=8.6 Hz); 7.17 (2H, doublet, J=8.6 Hz); 7.41 (1H, triplet, J=8.0 Hz); 7.61 (1H, doublet, J=7.3 Hz); 8.04 (1H, doublet of doublets, J=2.0, 8.0 Hz); 8.22 (1H, doublet, J=1.9 Hz).

(64b) 3-{[(R)-1-(3,5-Difluorophenyl)ethylamino]-(4-methoxyphenyl)methyl}phenylamine Following a similar procedure to that described in Example (1b), 820 mg of isomer B of N-[(R)-1-(3,5-difluorophenyl)ethyl]-N-[(4-methoxyphenyl)-(3-nitrophenyl)methyl]amine [prepared as described in step (a) above], 1.13 g of nickel chloride hexahydrate and 328 mg of sodium borohydride were reacted, to obtain 480 mg of isomer B of the title compound as a yellow oil.

Isomer B

Nuclear Magnetic Resonance Spectrum (CDCl$_3$) δ ppm: 1.31 (3H, doublet, J=6.6 Hz); 3.64 (1H, quartet, J=6.6 Hz); 3.80 (3H, singlet); 4.47 (1H, singlet); 6.51 (1H, doublet of doublets, J=2.0, 8.2 Hz); 6.62 (1H, doublet, J=1.6 Hz); 6.62–6.71 (2H, multiplet); 6.80 (2H, doublet of doublets, J=2.1, 8.3 Hz); 6.86 (2H, doublet, J=8.6 Hz); 7.04 (1H, triplet, J=7.9 Hz); 7.20 (2H, doublet, J=8.7 Hz).

(64c) 3-t-Butoxy-4-<3-{[(R)-1-(3,5-difluorophenyl)ethylamino]-(4-methoxyphenyl)methyl}phenylamino}-3-cyclobutene-1,2-dione Following a similar procedure to that described in Example (1c), 450 mg of isomer B of 3-{[(R)-1-(3,5-difluorophenyl)ethylamino]-(4-methoxyphenyl)methyl}phenylamine [prepared as described in step (b) above] and 450 mg of 4-t-butoxy-3-methoxy-3-cyclobutene-1,2-dione were reacted, to obtain 610 mg of isomer B of the title compound as a yellow foamy solid.

Isomer B

Nuclear Magnetic Resonance Spectrum (CDCl$_3$) δ ppm: 1.34 (3H, doublet, J=6.7 Hz); 1.63 (9H, singlet); 3.65 (1H, quartet, J=6.6 Hz); 3.81 (3H, singlet); 4.55 (1H, singlet); 6.66–6.70 (1H, multiplet); 6.80 (2H, doublet of doublets, J=1.9, 8.1 Hz); 6.88 (2H, doublet, J=8.7 Hz); 7.19–7.31 (6H, multiplet).

(64d) 4-<3-{[(R)-1-(3,5-Difluorophenyl)ethylamino]-(4-methoxyphenyl)methyl}phenylamino>-3-hydroxy-3-cyclobutene-1,2-dione hydrochloride Following a reaction and purification procedure similar to those described in Example (63b), 200 mg of isomer B of 3-t-butoxy-4-<3-{[(R)-1-(3,5-difluorophenyl)ethylamino]-(4-methoxyphenyl)methyl}phenylamino>-3-cyclobutene-1,2-dione [prepared as described in step (c) above] were reacted, to obtain 175 mg of isomer B of the title compound as a brown solid.

Isomer B

Nuclear Magnetic Resonance Spectrum (DMSO-d$_6$) δ ppm: 1.65 (3H, doublet, J=6.8 Hz); 3.77 (3H, singlet); 4.24 (1H, multiplet); 5.13 (1H, singlet); 6.99 (2H, doublet, J=8.8 Hz); 7.19–7.22 (2H, multiplet); 7.23–7.42 (4H, multiplet); 7.52–7.57 (3H, multiplet). mp: 180–185° C.; optical rotation [α]$_D$=+14.7° (c=0.90, AcOH).

(64e) 4-<3-{[(R)-1-(3,5-Difluorophenyl)ethylamino]-(4-methoxyphenyl)methyl}phenylamino>-3-hydroxy-3-cyclobutene-1,2-dione Following a reaction and purification procedure similar to those described in Example (55b), 340 mg of isomer B of 3-t-butoxy-4-<3-{[(R)-1-(3,5-difluorophenyl)ethylamino]-(4-methoxyphenyl)methyl}phenylamino>-3-cyclobutene-1,2-dione [prepared as described in step (d) above] were reacted, to obtain 202 mg of isomer B of the title compound as a yellow solid.

Isomer B

Nuclear Magnetic Resonance Spectrum (DMSO-$d_6$) δ ppm: 1.55 (3H, broad); 3.76 (3H, singlet); 4.20 (1H, broad); 5.04 (1H, broad); 6.93–7.00 (3H, multiplet); 7.17–7.30 (4H, multiplet); 7.46 (2H, doublet, J=8.2 Hz); 7.55 (1H, doublet, J=8.1 Hz); 7.69 (1H, doublet, J=0.5 Hz). mp: 195–200° C.; optical rotation $[α]_D$=+117.3° (c=1.03, AcOH).

EXAMPLE 65

4-<3-{[1-(3,5-Difluorophenyl)ethylamino]-(4-ethoxyphenyl)-methyl}phenylamino>-3-hydroxy-3-cyclobutene-1,2-dione hydrochloride (Compound No. 2-3485)

(65a) N-[1-(3,5-Difluorophenyl)ethyl]-N-[(4-ethoxyphenyl)-(3-nitrophenyl)methyl]amine Following a similar procedure to that described in Example (1a), 1.0 g of 4-ethoxyphenyl 3-nitrophenyl ketone, 1.16 g of 1-(3,5-difluorophenyl)ethylamine, 2.01 ml of triethylamine, 0.49 ml of titanium tetrachloride, 975 mg of sodium cyanoborohydride and 0.32 ml of acetic acid were reacted, to obtain 1.41 g of the title compound as a yellow oil.

Nuclear Magnetic Resonance Spectrum (CDCl$_3$) δ ppm: 1.34–1.44 (6H, multiplet); 3.61 and 3.67 (total 1H, each quartet, J=6.6 and 6.7 Hz); 3.98 and 4.21 (total 2H, each quartet, J=6.9 and 6.9 Hz); 4.42 and 4.68 (total 1H, each singlet); 6.66–6.89 (5H, multiplet); 7.13–7.16 (2H, multiplet); 7.40 and 7.49 (total 1H, each triplet, J=7.9 and 7.8 Hz); 7.60–7.66 (1H, multiplet); 8.03–8.12 (1H, multiplet); 8.22–8.26 (1H, multiplet).

(65b) 3-{[1-(3,5-Difluorophenyl)ethylamino]-(4-ethoxyphenyl)methyl}phenylamine

Following a reaction and purification procedure similar to those described in Example (59b), 1.39 g of N-[1-(3,5-difluorophenyl)ethyl]-N-[(4-ethoxyphenyl)-(3-nitrophenyl)methyl]amine [prepared as described in step (a) above], 1.84 g of nickel chloride hexahydrate and 537 mg of sodium borohydride were reacted, to obtain 316 mg of isomer A and 531 mg of isomer B of the title compound as yellow oils, respectively.

Isomer A

Nuclear Magnetic Resonance Spectrum (CDCl$_3$) δ ppm: 1.31 (3H, doublet, J=6.8 Hz); 1.38 (3H, triplet, J=6.8 Hz); 3.68 (1H, quartet, J=6.7 Hz); 3.98 (2H, quartet, J=6.9 Hz); 4.46 (1H, singlet); 6.56–6.70 (4H, multiplet); 6.76–6.85 (4H, multiplet); 7.11 (1H, triplet, J=7.6 Hz); 7.18 (2H, doublet, J=8.7 Hz).

Isomer B

Nuclear Magnetic Resonance Spectrum (CDCl) δ ppm: 1.31 (3H, doublet, J=6.7 Hz). 1.41 (3H, triplet, J=6.7 Hz); 3.63 (1H, quartet, J=6.6 Hz); 4.02 (2H, quartet, J=6.9 Hz); 4.46 (1H, singlet); 6.51 (1H, doublet of doublets, J=2.0, 8.1 Hz); 6.62 (1H, singlet); 6.62–6.70 (2H, multiplet); 6.77–6.87 (4H, multiplet); 7.04 (1H, triplet, J=7.7 Hz); 7.18 (2H, doublet, J=8.6 Hz).

(65c) 3-t-Butoxy-4-<3-{[1-(3,5-difluorophenyl) ethylamino]-(4-ethoxyphenyl)methyl}phenylamino>-3-cyclobutene-1,2-dione Following a similar procedure to that described in Example (1c), 288 mg of isomer A of 3-{[1-(3,5-difluorophenyl)ethylamino]-(4-ethoxyphenyl) methyl}phenylamine [prepared as described in step (b) above] and 277 mg of 4-t-butoxy-3-methoxy-3-cyclobutene-1,2-dione were reacted, to obtain 393 mg of isomer A of the title compound as a yellow oil.

Isomer A

Nuclear Magnetic Resonance Spectrum (CDCl$_3$) δ ppm: 1.35–1.40 (6H, multiplet); 1.63 (9H, multiplet); 3.66 (1H, quartet, J=6.6 Hz); 3.98 (2H, quartet, J=6.9 Hz); 4.56 (1H, singlet); 6.66–6.72 (1H, multiplet); 6.79 (4H, doublet of doublets, J32 2.0, 8.6 Hz); 7.07–7.08 (1H, multiplet); 7.17 (2H, doublet, J=8.6 Hz); 7.24–7.39 (3H, multiplet).

Following a similar procedure to that described in Example (1c), 438 mg of isomer B of 3-{[1-(3,5-difluorophenyl)ethylamino]-(4-ethoxyphenyl) methyl}phenylamine [prepared as described in step (b) above] and 422 mg of 4-t-butoxy-3-methoxy-3-cyclobutene-1,2-dione were reacted, to obtain 494 mg of isomer B of the title compound as a yellow foamy solid.

Isomer B

Nuclear Magnetic Resonance Spectrum (CDCl$_3$) δ ppm: 1.33 (3H, doublet, J=6.6 Hz); 1.41 (3H, triplet, J=7.0 Hz); 1.63 (9H, singlet ); 3.65 (1H, quartet, J=6.9 Hz); 4.03 (2H, quartet, J=6.9 Hz); 4.54 (1H, singlet); 6.65–6.70 (1H, multiplet); 6.80 (2H, doublet of doublets, J=2.0, 8.4 Hz); 6.87 (2H, doublet , J=8.6 Hz); 7.04–7.41 (6H, multiplet).

(65d) 4-<3-{[1-(3,5-Difluorophenyl)ethylamino]-(4-ethoxyphenyl)methyl}phenylamino>-3-hydroxy-3-cyclobutene-1,2-dione hydrochloride Following a reaction and purification procedure similar to those described in Example (63b), 352 mg of isomer A of 3-t-butoxy-4-<3-{[1-(3,5-difluorophenyl)ethylamino]-(4-ethoxyphenyl)methyl}phenylamino>-3-cyclobutene-1,2-dione [prepared as described in step (c) above] was reacted, to obtain 299 mg, of isomer A of the title compound as a pale brown solid.

Isomer A

Nuclear Magnetic Resonance Spectrum (DMSO-$d_6$) δ ppm: 1.30 (3H, triplet, J=6.8 Hz); 1.65 (3H, doublet, J=6.7 Hz); 4.01 (2H, quartet, J=6.9 Hz); 4.29 (1H, broad); 5.13 (1H, singlet); 6.93 (2H, doublet, J=8.7 Hz); 7.16 (2H, doublet of doublets, J=1.6, 7.9 Hz); 7.26–7.54 (7H, multiplet). mp: 185–190° C.

Following a reaction and purification procedure similar to those described in Example (63b), 468 mg of isomer B of 3-t-butoxy-4-<3-{[1-(3,5-difluorophenyl)ethylamino]-(4-ethoxyphenyl)methyl}phenylamino>-3-cyclobutene-1,2-dione [prepared as described in step (c) above] were reacted, to obtain 338 mg of isomer B of the title compound as a yellow solid.

Isomer B

Nuclear Magnetic Resonance Spectrum (DMSO-$d_6$) δ ppm: 1.32 (3H, triplet, J=7.1 Hz); 1.65 (3H, doublet, J=6.8 Hz); 4.03 (2H, quartet, J=7.1 Hz); 4.23 (1H, broad); 5.13 (1H, singlet); 6.97 (2H, doublet, J=8.7 Hz); 7.20–7.22 (2H, multiplet); 7.28–7.42 (4H, multiplet); 7.51–7.55 (3H, multiplet). mp: 178–182° C.

EXAMPLE 66

4-<3-{[1-(3,5-Difluorophenyl)ethylamino]-(4-propoxyphenyl)methyl}phenylamino>-3-hydroxy-3-cyclobutene-1,2-dione hydrochloride (Compound No. 2-3489)

(66a) N-[1-(3,5-Difluorophenyl)ethyl]-N-[(3-nitrophenyl)-(4-propoxyphenyl)methyl]amine Following a similar procedure to that described in Example (1a), 790 mg of 3-nitrophenyl 4-propoxyphenyl ketone, 870 mg of 1-(3,5-difluorophenyl)ethylamine, 1.54 ml of triethylamine, 0.37 ml of titanium tetrachloride, 733 mg of sodium cyanoborohydride and 0.24 ml of acetic acid were reacted, to obtain 1.16 g of the title compound as a yellow oil.

Nuclear Magnetic Resonance Spectrum (CDCl$_3$) δ ppm: 1.01 and 1.04 (total 3H, each triplet, J=7.5 and 7.4 Hz); 1.35 and 1.36 (total 3H, each doublet, J=6.5 and 6.5 Hz); 1.73–1.86 (2H, multiplet); 3.61 and 3.67 (total 1H, each quartet, J=6.6 and 6.6 Hz); 3.87 and 3.92 (total 2H, each triplet, J=6.5 and 6.6 Hz); 4.62 and 4.68 (total 1H, each singlet); 6.66–6.91 (5H, multiplet); 7.14 (2H, doublet, J=8.6 Hz); 7.40 and 7.49 (total 1H, each triplet, J=8.0 and 7.8 Hz); 7.61 and 7.66 (total 1H, each doublet, J=8.0 and 7.9 Hz); 8.04 and 8.10 (total 1H, each doublet of doublets, J=1.8, 8.0 and 1.8, 8.0 Hz); 8.23–8.26 (1H, multiplet).

(66b) 3-{[1-(3,5-Difluorophenyl)ethylamino]-(4-propoxyphenyl)methyl}phenylamine

Following a similar procedure to that described in Example (1b), 1.10 g of N-[1-(3,5-difluorophenyl)ethyl]-N-[(3-nitrophenyl)-(4-propoxyphenyl)methyl]amine [prepared as described in step (a) above], 1.41 g of nickel chloride hexahydrate and 411 mg of sodium borohydride were reacted, to obtain 915 mg of the title compound as a yellow oil.

Nuclear Magnetic Resonance Spectrum (CDCl$_3$) δ ppm: 1.00 and 1.03 (total 3H, each triplet, J=7.4 and 7.4 Hz); 1.31 (3H, doublet, J=6.7 Hz); 1.73–1.85 (2H, multiplet); 3.64 and 3.69 (total 1H, each quartet, J=6.6 and 6.7 Hz); 3.87 and 3.91 (total 2H, each triplet, J=6.6 and 6.5 Hz); 4.46 (1H, singlet); 6.50–6.70 (4H, multiplet); 6.77–6.87 (4H, multiplet); 7.04 and 7.11 (total 1H, each doublet of doublets, J=7.7, 7.9 and 7.6, 7.9 Hz); 7.18 (2H, doublet, J=8.6 Hz).

(66c) 3-t-Butoxy-4-<3-{[1-(3,5-difluorophenyl)ethylamino]-(4-propoxyphenyl)methyl}phenylamino>-3-cyclobutene-1,2-dione Following a reaction and purification procedure similar to those described in Example (1c), 860 mg of 3-{[1-(3,5-difluorophenyl)ethylamino]-(4-propoxyphenyl)methyl}phenylamine [prepared as described in step (b) above] and 599 mg of 4-t-butoxy-3-methoxy-3-cyclobutene-1,2-dione were reacted. The crude product was purified by chromatography through a silica gel column using a 10:1 by volume mixture of toluene and ethyl acetate as eluant, to afford isomer A of the title compound (457 mg) and isomer B of the title compound (206 mg) as pale yellow foamy solids, respectively.

Isomer A

Nuclear Magnetic Resonance Spectrum (CDCl$_3$) δ ppm: 1.00 (3H, triplet, J=7.5 Hz); 1.35 (3H, doublet, J=6.7 Hz); 1.63 (9H, singlet); 1.77 (2H, multiplet); 3.66 (1H, quartet, J=6.6 Hz); 3.87 (2H, triplet, J=6.6 Hz); 4.56 (1H, singlet); 6.66–6.71 (1H, multiplet); 6.80 (4H, doublet, J=8.7 Hz); 7.07–7.36 (6H, multiplet).

Isomer B

Nuclear Magnetic Resonance Spectrum (CDCl$_3$) δ ppm: 1.04 (3H, triplet, J=7.5 Hz); 1.33 (3H, doublet, J=6.6 Hz); 1.63 (9H, singlet); 1.81 (2H, multiplet); 3.65 (1H, quartet, J=6.6 Hz); 3.91 (2H, triplet, J=6.5 Hz); 4.54 (1H, singlet); 6.65–6.70 (1H, multiplet); 6.81 (2H, doublet of doublets, J=2.0, 8.4 Hz); 6.88 (2H, doublet, J=8.5 Hz); 7.05–7.29 (6H, multiplet).

(66d) 4-<3-{[1-(3,5-Difluorophenyl)ethylamino]-(4-propoxyphenyl)methyl}phenylamino>-3-hydroxy-3-cyclobutene-1,2-dione hydrochloride Following a reaction and purification procedure similar to those described in Example (63b), 440 mg of isomer A of 3-t-butoxy-4-<3-{[1-(3,5-difluorophenyl)ethylamino]-(4-propoxyphenyl)methyl}phenylamino>-3-cyclobutene-1,2-dione [prepared as described in step (c) above] was reacted, to obtain 381 mg of isomer A of the title compound as a pale yellow solid.

Isomer A

Nuclear Magnetic Resonance Spectrum (DMSO-d$_6$) δ ppm: 0.95 (3H, triplet, J=7.4 Hz); 1.63 (3H, doublet, J=6.8 Hz); 1.70 (2H, multiplet); 3.91 (2H, triplet, J=6.6 Hz); 4.30 (1H, broad); 5.13 (1H, singlet); 6.94 (2H, doublet, J=8.8 Hz); 7.14–7.19 (3H, multiplet); 7.27–7.36 (2H, multiplet); 7.45 (1H, doublet, J=8.1 Hz); 7.51 (2H, doublet, J=8.7 Hz); 7.56 (1H, singlet). mp: 176–180° C.

Following a reaction and purification procedure similar to those described in Example (63b), 195 mg of isomer B of 3-t-butoxy-4-<3-{[1-(3,5-difluorophenyl)ethylamino]-(4-propoxyphenyl)methyl}phenylamino>-3-cyclobutene-1,2-dione [prepared as described in step (c) above] was reacted, to obtain 170 mg of isomer B of the title compound as a white solid.

Isomer B

Nuclear Magnetic Resonance Spectrum (DMSO-d$_6$) δ ppm: 0.97 (3H, triplet, J=7.5 Hz); 1.64 (3H, doublet, J=6.8 Hz); 1.72 (2H, multiplet); 3.93 (2H, triplet, J=6.6 Hz); 4.24 (1H, broad); 5.14 (1H, singlet); 6.98 (2H, doublet, J=8.7 Hz); 7.19–7.21 (2H, multiplet); 7.29–7.42 (4H, multiplet); 7.52–7.54 (3H, multiplet). mp: 167–172° C.

EXAMPLE 67

4-<3-{[1-(3,5-Difluorophenyl)ethylamino]-(4-isopropoxyphenyl)methyl}phenylamino>-3-hydroxy-3-cyclobutene-1,2-dione hydrochloride
(Compound No. 2-3490)

(67a) N-[1-(3,5-Difluorophenyl)ethyl]-N-[(3-nitrophenyl)-(4-isopropoxyphenyl)methyl]amine Following a similar procedure to that described in Example (1a), 850 mg of 3-nitrophenyl 4-isopropoxyphenyl ketone, 936 mg of 1-(3,5-difluorophenyl)ethylamine, 1.66 ml of triethylamine, 0.39 ml of titanium tetrachloride, 788 mg of sodium cyanoborohydride and 0.26 ml of acetic acid were reacted, to obtain 1.20 g of the title compound as a yellow oil.

Nuclear Magnetic Resonance Spectrum (CDCl$_3$) δ ppm: 1.29–1.37 (9H, multiplet); 3.61 and 3.68 (total 1H, each quartet, J=6.6 and 6.6 Hz); 4.46–4.57 (1H, multiplet); 4.62 and 4.67 (total 1H, each singlet); 6.66–6.83 (4H, multiplet); 6.87 (1H, doublet, J=8.5 Hz); 7.11–7.15 (2H, multiplet); 7.40 and 7.49 (total 1H, each triplet, J=8.0 and 8.0 Hz); 7.62 and 7.66 (total 1H, each doublet, J=8.0 and 7.5 Hz); 8.03–8.12 (1H, multiplet); 8.23–8.26 (1H, multiplet).

(67b) 3-{[1-(3,5-Difluorophenyl)ethylamino]-(4-isopropoxyphenyl)methyl}phenylamine Following a similar procedure to that described in Example (1b), 1.17 g of N-[1-(3,5-difluorophenyl)ethyl]-N-[(3-nitrophenyl)-(4-isopropoxyphenyl)methyl]amine [prepared as described in step (a) above], 1.50 g of nickel chloride hexahydrate and 437 mg of sodium borohydride were reacted, to obtain 1.0 g of the title compound as a yellow oil.

Nuclear Magnetic Resonance Spectrum (CDCl$_3$) δ ppm: 1.29–1.34 (9H, multiplet); 3.64 and 3.68 (total 1H, each quartet, J=6.6 and 6.7 Hz); 4.45–4.55 (1H, multiplet); 4.45 and 4.46 (total 1H, each singlet); 6.50–6.70 (4H, multiplet); 6.75–6.85 (4H, multiplet); 7.02–7.18 (3H, multiplet).

(67c) 3-t-Butoxy-4-<3-{[1-(3,5-difluorophenyl)ethylamino]-(4-isopropoxyphenyl)methyl]phenylamino>-3-cyclobutene-1,2-dione Following a reaction and purification procedure similar to those described in Example (66c), 930 mg of 3-{[1-(3,5-difluorophenyl)ethylamino]-(4-isopropoxyphenyl)methyl}phenylamine [prepared as described in step (b) above] and 648 mg of 4-t-butoxy-3-methoxy-3-cyclobutene- 1,2-dione were reacted, to obtain 463 mg of isomer A and 407 mg of isomer B of the title compound as pale yellow foamy solids, respectively.

Isomer A

Nuclear Magnetic Resonance Spectrum (CDCl$_3$) δ ppm: 1.30 (6H, doublet, J=6.1 Hz); 1.35 (3H, doublet, J=6.7 Hz); 1.63 (9H, singlet); 3.66 (1H, quartet, J=6.6 Hz); 4.48 (1H, multiplet); 4.55 (1H, singlet); 6.66–6.71 (1H, multiplet); 6.76–6.82 (4H, multiplet); 7.08–7.37 (6H, multiplet).

Isomer B

Nuclear Magnetic Resonance Spectrum (CDCl$_3$) δ ppm: 1.33–1.35 (9H, multiplet); 1.63 (9H, singlet); 3.66 (1H, quartet, J=6.6 Hz); 4.53 (2H, multiplet); 6.64–6.70 (1H, multiplet); 6.79–6.87 (4H, multiplet); 7.05–7.40 (6H, multiplet).

(67d) 4-<3-{[1-(3,5-Difluorophenyl)ethylamino]-(4-isopropoxyphenyl)methyl}phenylamino>-3-hydroxy-3-cyclobutene-1,2-dione hydrochloride Following a reaction and purification procedure similar to those described in Example (63b), 450 mg of isomer A of 3-t-butoxy-4-<3-{[1-(3,5-difluorophenyl)ethylamino]-(4-isopropoxyphenyl)methyl}phenylamino>-3-cyclobutene-1,2-dione [prepared as described in step (c) above] was reacted, to obtain 369 mg of isomer A of the title compound as a pale brown solid.

Isomer A

Nuclear Magnetic Resonance Spectrum (DMSO-d$_6$) δ ppm: 1.24 (6H, doublet, J=5.9 Hz); 1.64 (3H, doublet, J=6.7 Hz); 4.25–4.38 (1H, broad); 4.60 (1H, multiplet); 5.11 (1H, singlet); 6.91 (2H, doublet, J=8.7 Hz); 7.14–7.37 (5H, multiplet); 7.45 (1H, doublet, J=8.0 Hz); 7.50 (2H, doublet, J=8.7 Hz); 7.55 (1H, singlet). mp: 194–198° C.

Following a reaction and purification procedure similar to those described in Example (63b), 386 mg of isomer B of 3-t-butoxy-4-<3-{[1-(3,5-difluorophenyl)ethylamino]-(4-isopropoxyphenyl)methyl}phenylamino>-3-cyclobutene-1,2-dione [prepared as described in step (c) above] was reacted, to obtain 302 mg of isomer B of the title compound as a white solid.

Isomer B

Nuclear Magnetic Resonance Spectrum (DMSO-d$_6$) δ ppm: 1.26 (6H, doublet of doublets, J=1.9, 6.0 Hz); 1.65 (3H, doublet, J=6.7 Hz); 4.24 (1H, broad); 4.63 (1H, multiplet); 5.13 (1H, singlet); 6.96 (2H, doublet, J=8.7 Hz); 7.21 (2H, doublet of doublets, J=1.7, 8.0 Hz); 7.23–7.43 (4H, multiplet); 7.52–7.54 (3H, multiplet). mp: 176–179° C.

EXAMPLE 68

4->3-{[1-(3,4-Difluorophenyl)ethylamino]-(4-fluorophenyl)methyl}phenylamino>-3-hydroxy-3-cyclobutene-1,2-dione (Compound No. 2-39)

(68a) 3-t-Butoxy-4-<3-{[1-(3,4-difluorophenyl)ethylamino]-(4-fluorophenyl)methyl}phenylamino>-3-cyclobutene-1,2-dione Following a similar procedure to that described in Example (1c), 300 mg of isomer B of 3-{[1-(3,4-difluorophenyl)ethylamino]-(4-fluorophenyl)methyl}phenylamine and 310 mg of 4-t-butoxy-3-methoxy-3-cyclobutene-1,2-dione were reacted, to obtain 267 mg of isomer B of the title compound as a colorless foamy solid.

Isomer B

Nuclear Magnetic Resonance Spectrum (CDCl$_3$) δ ppm: 1.34 (3H, doublet, J=6.6 Hz); 1.64 (9H, singlet); 3.61 (1H, quartet, J=6.7 Hz); 4.56 (1H, singlet); 6.92–7.14 (6H, multiplet); 7.23–7.40 (5H, multiplet).

(68b) 4-<3-{[1-(3,4-Difluorophenyl)ethylamino]-(4-fluorophenyl)methyl}phenylamino>-3-hydroxy-3-cyclobutene-1,2-dione hydrochloride Following a reaction and purification procedure similar to those described in Example (63b), 250 mg of isomer B of 3-t-butoxy-4-<3-{[1-(3,4-difluorophenyl)ethylamino]-(4-fluorophenyl)methyl}phenylamino>-3-cyclobutene-1,2-dione [prepared as described in step (a) above] were reacted, to obtain 158 mg of isomer B of the title compound as a white solid.

Isomer B

Nuclear Magnetic Resonance Spectrum (DMSO-d$_6$) δ ppm: 1.64 (3H, doublet, J=6.7 Hz); 4.24 (1H, quartet, J=6.7 Hz); 5.20 (1H, singlet); 7.20–7.35 (5H, multiplet); 7.39–7.60 (4H, multiplet); 7.69 (2H, doublet of doublets, J=5.3, 8.6 Hz). mp: 180–182° C.

EXAMPLE 69

4-<3-{[(R)-1-(3,5-Difluorophenyl)ethylamino]-(4-fluorophenyl)methyl}phenylamino>-3-hydroxy-3-cyclobutene-1,2-dione (Compound No. 2-53)

(69a) N-[(R)-1-(3,5-Difluorophenyl)ethyl]-N-[(4-fluorophenyl)-(3-nitrophenyl)methyl]amine Following a similar procedure to that described in Example (1a), 3.0 g of 4-fluorophenyl 3-nitrophenyl ketone, 3.55 g of (R)-1-(3,5-difluorophenyl)ethylamine hydrochloride, 9.38 ml of triethylamine, 1.61 ml of titanium tetrachloride, 3.08 g of sodium cyanoborohydride and 1.05 ml of acetic acid were reacted, to obtain 4.48 g of the title compound as a yellow oil.

Nuclear Magnetic Resonance Spectrum (CDCl$_3$) δ ppm: 1.37 and 1.38 (total 3H, each doublet, J=6.7 and 6.6 Hz); 3.59–3.67 (1H, multiplet); 4.68 and 4.72 (total 1H, each, singlet); 6.67–6.81 (3H, multiplet); 6.96–7.08 (2H, multiplet); 7.21–7.27 (2H, multiplet); 7.43 and 7.51 (total 1H, each triplet, J=8.0 and 7.8 Hz); 7.60 and 7.64 (total 1H, each doublet, J=8.0 and 7.8 Hz); 8.06 and 8.13 (total 1H, each doublet of doublets, J=1.8, 7.9 and 1.8, 7.9 Hz); 8.21–8.25 (1H, multiplet).

(69b) 3-{[(R)-1-(3,5-Difluorophenyl)ethylamino]-(4-fluorophenyl)methyl}phenylamine Following a reaction and purification procedure similar to those described in Example (59b), 4.40 g of N-[(R)-1-(3,5-difluorophenyl)ethyl]-N-[(4-fluorophenyl)-(3-nitrophenyl)methyl]amine [prepared as described in step (a) above], 6.54 g of nickel chloride hexahydrate and 1.81 g of sodium borohydride were reacted, to obtain 1.24 g of isomer A and 1.66 g of isomer B of the title compound as yellow oils, respectively.

Isomer A

Nuclear Magnetic Resonance Spectrum (CDCl$_3$) δ ppm: 1.32 (3H, doublet, J=6.6 Hz); 3.69 (1H, quartet, J=6.7 Hz); 4.47 (1H, singlet); 6.59 (2H, doublet of doublets, J=1.9, 4.0 Hz); 6.64–6.71 (2H, multiplet); 6.82 (2H, doublet of doublets, J=2.1, 6.6 Hz); 6.93 (2H, triplet, J=8.6 Hz); 7.12 (1H, doublet of doublets, J=7.7, 8.4 Hz); 7.23–7.52 (2H, multiplet).

Isomer B

Nuclear Magnetic Resonance Spectrum (CDCl$_3$) δ ppm: 1.32 (3H, doublet, J=6.7 Hz); 3.58–3.66 (1H, multiplet); 4.50 (1H, singlet); 6.51–6.83 (6H, multiplet); 6.91–7.10 (3H, multiplet); 7.23–7.29 (2H, multiplet).

(69c) 3-t-Butoxy-4-<3-{[(R)-1-(3,5-difluorophenyl)ethylamino]-(4-fluorophenyl)methyl}phenylamino>-3-cyclobutene-1,2-dione Following a similar procedure to that described in Example (1c), 500 mg of isomer A of 3-{[(R)-1-(3,5-difluorophenyl)ethylamino]-(4-fluorophenyl)methyl}phenylamine [prepared as described in step (b) above] and 517 mg of 4-t-butoxy-3-methoxy-3-cyclobutene- 1,2-dione were reacted, to obtain 681 mg of isomer A of the title compound as a pale yellow foamy solid.

Isomer A

Nuclear Magnetic Resonance Spectrum (CDCl$_3$) δ ppm: 1.36 (3H, doublet, J=6.7 Hz); 1.63 (9H, singlet); 3.67 (1H, quartet, J=6.6 Hz); 4.59 (1H, singlet); 6.66–6.72 (1H, multiplet); 6.77–6.82 (2H, multiplet); 6.95 (2H, triplet, J=8.7 Hz); 7.04–7.07 (1H, multiplet); 7.16–7.41 (5H, multiplet).

Following a similar procedure to that described in Example (1c), 500 mg of isomer B of 3-{[(R)-1-(3,5-difluorophenyl)ethylamino]-(4-fluorophenyl)methyl}phenylamine [prepared as described in step (b) above] and 517 mg of 4-t-butoxy-3-methoxy-3-cyclobutene-1,2-dione were reacted, to obtain 580 mg of isomer B of the title compound as a pale yellow foamy solid.

Isomer B

Nuclear Magnetic Resonance Spectrum (CDCl$_3$) δ ppm: 1.35 (3H, doublet, J=6.6 Hz); 1.64 (9H, singlet); 3.63 (1H, quartet, J=6.6 Hz); 4.59 (1H, singlet); 6.66–6.71 (1H, multiplet); 6.76–6.81 (2H, multiplet); 7.01–7.07 (3H, multiplet); 7.16–7.36 (5H, multiplet).

(69d) 4-<3-{[(R)-1-(3,5-Difluorophenyl)ethylamino]-(4-fluorophenyl)methyl}phenylamino>-3-hydroxy-3-cyclobutene-1,2-dione hydrochloride Following a reaction and purification procedure similar to those described in Example (63b), 627 mg of isomer A of 3-t-butoxy-4-<3-{[(R)-1-(3,5-difluorophenyl)ethylamino]-(4-fluorophenyl)methyl}phenylamino>-3-cyclobutene-1,2-dione [prepared as described in step (c) above] was reacted, to obtain 542 mg of isomer A of the title compound as a white solid.

Isomer A

Nuclear Magnetic Resonance Spectrum (DMSO-d$_6$) δ ppm: 1.66 (3H, doublet, J=6.7 Hz); 4.32 (1H, quartet, J=6.6 Hz); 5.27 (1H, singlet); 7.17–7.32 (6H, multiplet); 7.34–7.43 (2H, multiplet); 7.56 (1H, singlet); 7.71 (2H, doublet of doublets, J=5.4, 8.7 Hz). mp: 183–187° C.; optical rotation [α]$_D$=−68.0° (c=0.89, AcOH).

Following a reaction and purification procedure similar to those described in Example (63b), 551 mg of isomer B of 3-t-butoxy-4-<3-{[(R)-1-(3,5-difluorophenyl)ethylamino]-(4-fluorophenyl)methyl}phenylamino>-3-cyclobutene-1,2-dione [prepared as described in step (c) above] was reacted, to obtain 501 mg of isomer B of the title compound as a yellow solid.

Isomer B

Nuclear Magnetic Resonance Spectrum (DMSO-d$_6$) δ ppm: 1.66 (3H, doublet, J=6.7 Hz); 4.26 (1H, quartet, J=6.7 Hz); 5.28 (1H, singlet); 7.19–7.43 (8H, multiplet); 7.54 (1H, singlet); 7.72 (2H, doublet of doublets, J=5.5, 8.6 Hz). mp: 187–190° C.; optical rotation [α]$_D$=−12.8° (c=1.00, AcOH).

(69e) 4-<3-{[(R)-1-(3,5-Difluorophenyl)ethylamino]-(4-fluorophenyl)methyl}phenylamino>-3-hydroxy-3-cyclobutene-1,2-dione 300 mg of isomer B of 4-<3-{[(R)-1-(3,5-difluorophenyl)ethylamino]-(4-fluorophenyl)methyl}phenylamino>-3-hydroxy-3-cyclobutene-1,2-dione hydrochloride [prepared as described in step (d) above] were dissolved in 5 ml of methanol. The resulting solution was adjusted to a pH value of 4 by the addition of 1N aqueous hydrochloric acid and an aqueous 1N sodium hydroxide solution. It was then diluted with water. The solid thus precipitated was collected by filtration, washed with water and with diethyl ether and then dried, to obtain 164 mg of isomer B of the title compound as a white solid.

Isomer B

Nuclear Magnetic Resonance Spectrum (DMSO-d$_6$) δ ppm: 1.57 (3H, doublet, J=6.7 Hz); 4.23 (1H, broad); 5.20 (1H, broad singlet); 6.98 (1H, doublet, J=7.6 Hz); 7.17–7.30 (6H, multiplet); 7.51–7.53 (1H, multiplet); 7.62 (2H, doublet of doublets, J=5.5, 8.5 Hz); 7.68 (1H, singlet). mp: 188–192° C.; optical rotation [α]$_D$=+38.2° (c=1.09, AcOH).

EXAMPLE 70

4-<3-{(4-Fluorophenyl)-[(R)-1-phenylpropylamino]methyl}phenylamino>-3-hydroxy-3-cyclobutene-1,2-dione hydrochloride (Compound No. 2-3111)

(70a) N-[(4-Fluorophenyl)-(3-nitrophenyl)methyl]-N-[(R)-1-phenylpropyl amine

Following a similar procedure to that described in Example (1a), 2.0 g of 4-fluorophenyl 3-nitrophenyl ketone, 2.11 g of (R)-1-phenylpropylamine, 4.55 ml of triethylamine, 1.08 ml of titanium tetrachloride, 2.16 g of sodium cyanoborohydride and 0.70 ml of acetic acid were reacted, to obtain 2.85 g of the title compound as a yellow oil.

Nuclear Magnetic Resonance Spectrum (CDCl$_3$) δ ppm: 0.83 and 0.87 (total 3H, each triplet, J=7.4 and 7.4 Hz); 1.62–1.86 (2H, multiplet); 3.31 and 3.36 (total 1H, each quartet, J=6.9 and 7.0 Hz); 4.65 and 4.70 (total 1H, each, singlet); 6.94 and 7.05 (total 2H, each triplet, J=8.7 and 8.7 Hz); 7.12–7.67 (8H, multiplet); 8.01–8.13 (2H, multiplet); 8.18–8.26 (1H, multiplet).

(70b) 3-{(4-Fluorophenyl)-[(R)-1-phenylpropylamino]methyl}phenylamine

Following a reaction and purification procedure similar to those described in Example (59b), 2.70 g of N-[(4-fluorophenyl)-(3-nitrophenyl)methyl]-N-[(R)-1-phenylpropyl]amine [prepared as described in step (a) above], 4.06 g of nickel chloride hexahydrate and 1.18 g of sodium borohydride were reacted, to obtain 778 mg of isomer A and 615 mg of isomer B of the title compound as yellow oils, respectively.

Isomer A

Nuclear Magnetic Resonance Spectrum (CDCl$_3$) δ ppm: 0.81 (3H, triplet, J=7.4 Hz); 1.58–1.80 (2H, multiplet); 3.43 (1H, triplet, J=7.0 Hz); 4.46 (1H, singlet); 6.56–6.59 (1H, multiplet); 6.63 (1H, singlet); 6.69 (1H, doublet, J=7.5 Hz); 6.90 (2H, triplet, J=8.7 Hz); 7.09–7.34 (8H, multiplet).

Isomer B

Nuclear Magnetic Resonance Spectrum (CDCl$_3$) δ ppm: 0.83 (3H, triplet, J=7.5 Hz); 1.57–1.81 (2H, multiplet); 3.32 (1H, triplet, J=7.0 Hz); 4.47 (1H, singlet); 6.50 (1H, doublet of doublets, J=2.1, 8.1 Hz); 6.57–6.63 (2H, multiplet); 6.97–7.04 (3H, multiplet); 7.15–7.35 (7H, multiplet).

(70c) 3-t-Butoxy-4-<3-{(4-fluorophenyl)-[(R)-1-phenylpropylamino]methyl}phenylamino>-3-cyclobutene-1,2-dione Following a similar procedure to that described in Example (1c), 625 mg of isomer A of 3-{(4-fluorophenyl)-[(R)- -phenylpropylamino]methyl}phenylamine [prepared as described in step (b) above] and 691 ml of 4-t-butoxy-3-methoxy-3-cyclobutene-1,2-dione were reacted, to obtain 710 mg of isomer A of the title compound as a colorless foamy solid.

Isomer A

Nuclear Magnetic Resonance Spectrum (CDCl$_3$) δ ppm: 0.81 (3H, triplet, J=7.5 Hz); 1.62 (9H, singlet); 1.57–1.88 (2H, multiplet); 3.38 (1H, triplet, J=6.9 Hz); 4.56 (1H, singlet); 6.92 (2H, triplet, J=8.6 Hz); 7.09–7.35 (11H, multiplet).

Following a similar procedure to that described in Example (1c), 534 mg of isomer B of 3-{(4-fluorophenyl)-

[(R)-1-phenylpropylamino]methyl}phenylamine [prepared as described in step (b) above] and 588 mg of 4-t-butoxy-3-methoxy-3-cyclobutene-1,2-dione were reacted, to obtain 760 mg of isomer B of the title compound as a pale yellow foamy solid.

Isomer B

Nuclear Magnetic Resonance Spectrum (CDCl$_3$) δ ppm: 0.83 (3H, triplet, J=7.4 Hz); 1.62 (9H, singlet); 1.62–1.81 (2H, multiplet); 3.34 (1H, triplet, J=7.0 Hz); 4.56 (1H, singlet); 6.99–7.35 (13H, multiplet).

(70d) 4-<3-{(4-Fluorophenyl)-[(R)-1-phenylpropylamino]ethyl}phenylamino>-3-hydroxy-3-cyclobutene-1,2-dione hydrochloride Following a reaction and purification procedure similar to those described in Example (63b), 500 mg of isomer A of 3-t-butoxy-4-<3-{(4-fluorophenyl)-[(R)-1-phenylpropylamino]methyl}phenylamino>-3-cyclobutene-1,2-dione [prepared as described in step (c) above] was reacted, to obtain 436 mg of isomer A of the title compound as a pale yellow solid.

Isomer A

Nuclear Magnetic Resonance Spectrum (DMSO-d$_6$) δ ppm: 0.58 (3H, triplet, J=7.4 Hz); 1.90–2.02 (1H, multiplet); 2.39–2.50 (1H, multiplet); 3.99 (1H, broad); 5.01 (1H, singlet); 7.18–7.25 (3H, multiplet); 7.32–7.37 (3H, multiplet); 7.43–7.45 (4H, multiplet); 7.53 (1H, singlet); 7.61 (2H, doublet of doublets, J=5.3, 8.7 Hz). mp: 190–194° C.; optical rotation $[α]_D$=−131.5° (c=1.13, AcOH).

Following a reaction and purification procedure similar to those described in Example (63b), 500 mg of isomer B of 3-t-butoxy-4-<3-{(4-fluorophenyl)-[(R)-1-phenylpropylamino]methyl}phenylamino>-3-cyclobutene-1,2-dione [prepared as described in step (c) above] was reacted, to obtain 427 mg of isomer B of the title compound as a pale brown solid.

Isomer B

Nuclear Magnetic Resonance Spectrum (DMSO-d$_6$) δ ppm: 0.56 (3H, triplet, J=7.5 Hz); 1.91–2.01 (1H, multiplet); 2.43–2.51 (1H, multiplet); 3.83 (1H, broad); 5.01 (1H, singlet); 7.26–7.49 (11H, multiplet); 7.65 (2H, doublet of doublets, J=5.3, 8.7 Hz). mp: 180–185° C.; optical rotation $[α]_D$=−38.5 (c=0.50, AcOH).

EXAMPLE 71

4-<3-{(4-Chlorophenyl)-[1-(3,5-difluorophenyl)ethylamino]methyl}phenylamino>-3-hydroxy-3-cyclobutene-1,2-dione hydrochloride (Compound No. 2-54)

(71a) N-[(4-Chlorophenyl)-(3-nitrophenyl)methyl]-N-[1-(3,5-difluorophenyl)ethyl]amine Following a similar procedure to that described in Example (1a), 2.0 g of 4-chlorophenyl 3-nitrophenyl ketone, 2.40 g of 1-(3,5-difluorophenyl)ethylamine, 4.26 ml of triethylamine, 1.01 ml of titanium tetrachloride, 3.02 g of sodium cyanoborohydride and 0.66 ml of acetic acid were reacted, to obtain 2.92 g of the title compound as a yellow oil.

Nuclear Magnetic Resonance Spectrum (CDCl$_3$) δ ppm: 1.37 and 1.38 (total 3H, each doublet, J=6.6 and 6.6 Hz); 3.61–3.67 (1H, multiplet); 4.66 and 4.71 (total 1H, each singlet); 6.67–6.80 (3H, multiplet); 7.19–7.28 (3H, multiplet); 7.34 and 7.36 (total 1H, each singlet); 7.43 and 7.51 (total 1H, each triplet, J=8.0 and 8.0 Hz); 7.57–7.64 (1H, multiplet); 8.05–8.14 (1H, multiplet); 8.20–8.23 (1H, multiplet).

(71b) 3-{(4-Chlorophenyl)-[1-(3,5-difluorophenyl)ethylamino]methyl}phenylamine

Following a reaction and purification procedure similar to those described in Example (59b), 2.79 g of N-[(4-chlorophenyl)-(3-nitrophenyl)methyl]-N-[1-(3,5-difluorophenyl)ethyl]amine [prepared as described in step (a) above], 3.79, of nickel chloride hexahydrate and 1.10 g of sodium borohydride were reacted, to obtain 808 mg of isomer A and 572 mg of isomer B of the title compound as colorless oils, respectively.

Isomer A

Nuclear Magnetic Resonance Spectrum (CDCl$_3$) δ ppm: 1.32 (3H, doublet, J=6.6 Hz); 3.69 (1H, quartet, J=6.7 Hz); 4.47 (1H, singlet); 6.57–6.71 (4H, multiplet); 6.78–6.84 (2H, multiplet); 7.10–7.52 (5H, multiplet).

Isomer B

Nuclear Magnetic Resonance Spectrum (CDCl$_3$) δ ppm: 1.32 (3H, doublet, J=6.6 Hz); 3.58–3.63 (1H, multiplet); 4.48 (1H, singlet); 6.51–6.54 (1H, multiplet); 6.57–6.58 (1H, multiplet); 6.62–6.71 (2H, multiplet); 6.74–6.80 (2H, multiplet); 7.05 (1H, doublet of doublets, J=7.6, 7.9 Hz); 7.24–7.30 (4H, multiplet).

(71c) 3-t-Butoxy-4-<3-{(4-chlorophenyl)-[1-(3,5-difluorophenyl)ethylamino]methyl}phenylamino>-3-cyclobutene-1,2-dione Following a similar procedure to that described in Example (1c), 562 mg of isomer A of 3-{(4-chlorophenyl)-[1-(3,5-difluorophenyl)ethylamino]methyl}phenylamine [prepared as described in step (b) above] and 555 mg of 4-t-butoxy-3-methoxy-3-cyclobutene-1,2-dione were reacted, to obtain 731 mg of isomer A of the title compound as a colorless foamy solid.

Isomer A

Nuclear Magnetic Resonance Spectrum (CDCl$_3$) δ ppm: 1.36 (3H, doublet, J=6.6 Hz); 1.63 (9H, singlet); 3.67 (1H, quartet, J=6.6 Hz); 4.58 (1H, singlet); 6.66–6.72 (1H, multiplet); 6.79 (2H, doublet of doublets, J=2.1, 8.4 Hz); 7.03 (1H, doublet, J=6.8 Hz); 7.23–7.40 (7H, multiplet).

Following a similar procedure to that described in Example (1c), 479 mg of isomer B of 3-{(4-chlorophenyl)-[1-(3,5-difluorophenyl)ethylamino]methyl}phenylamine [prepared as described in step (b) above] and 473 mg of 4-t-butoxy-3-methoxy-3-cyclobutene-1,2-dione were reacted, to obtain 644 mg of isomer B of the title compound as a colorless foamy solid.

Isomer B

Nuclear Magnetic Resonance Spectrum (CDCl$_3$) δ ppm: 1.35 (3H, doublet, J=6.8 Hz); 1.63 (9H, singlet); 3.62 (1H, quartet, J=6.6 Hz); 4.57 (1H, singlet); 6.66–6.71 (1H, multiplet); 6.76–6.80 (2H, multiplet); 7.00–7.02 (1H, multiplet); 7.25–7.35 (7H, multiplet).

(71d) 4-<3-{(4-Chlorophenyl)-[1-(3,5-difluorophenyl)ethylamino]methyl}phenylamino>-3-hydroxy-3-cyclobutene-1,2-dione hydrochloride Following a reaction and purification procedure similar to those described in Example (63b), 300 mg of isomer A of 3-t-butoxy-4-<3-{(4-chlorophenyl)-[1-(3,5-difluorophenyl)ethylamino]methyl}phenylamino>-3-cyclobutene-1,2-dione [prepared as described in step (c) above] was reacted, to obtain 245 mg of isomer A of the title compound as a white solid.

Isomer A

Nuclear Magnetic Resonance Spectrum (DMSO-d$_6$) δ ppm: 1.64 (3H, doublet, J=6.7 Hz); 4.32 (1H, broad); 5.25 (1H, singlet); 7.16–7.19 (3H, multiplet); 7.26–7.36 (2H, multiplet); 7.44–7.47 (3H, multiplet); 7.58 (1H, singlet); 7.66 (2H, doublet, J=8.6 Hz). mp: 182–185° C.

Following a reaction and purification procedure similar to those described in Example (63b), 300 mg of isomer B of 3-t-butoxy-4-<3-{(4-chlorophenyl)-[1-(3,5-difluorophenyl)ethylamino]methyl}phenylamino>-3-cyclobutene-1,2-dione [prepared as described in step (c) above] was reacted, to obtain 255 mg of isomer B of the title compound as a brown solid.
Isomer B
Nuclear Magnetic Resonance Spectrum (DMSO-$d_6$) δ ppm: 1.66 (3H, doublet, J=6.7 Hz); 4.27 (1H, broad); 5.26 (1H, singlet); 7.22 (2H, doublet of doublets, J=1.9, 8.2 Hz); 7.28–7.45 (4H, multiplet); 7.51–7.54 (3H, multiplet); 7.69 (2H, doublet, J=8.6 Hz). mp: 180–185° C.

EXAMPLE 72

4-<5-{[1-(3,4-Difluorophenyl)ethylamino]-(4-methoxyphenyl)methyl}-2-fluorophenylamino>-3-hydroxy-3-cyclobutene-1,2-dione hydrochloride
(Compound No. 2-3400)

(72a) N-[1-(3,4-Difluorophenyl)ethyl]-N-[(4-fluoro-3-nitrophenyl)-(4-methoxyphenyl)methyl]amine Following a similar procedure to that described in Example (1a), 2.0 g of 4-fluoro-3-nitrophenyl 4-methoxyphenyl ketone, 2.81 g of 1-(3,4-difluorophenyl)ethylamine hydrochloride, 6.08 ml of triethylamine, 0.96 ml of titanium tetrachloride, 2.03 g of sodium cyanoborohydride and 0.62 ml of acetic acid were reacted, to obtain 2.63 g of the title compound as a yellow oil.

Nuclear Magnetic Resonance Spectrum (CDCl$_3$) δ ppm: 1.33 and 1.36 (total 3H, each doublet, J=6.6 and 6.7 Hz); 3.58 and 3.64 (total 1H, each quartet, J=6.7 and 6.6 Hz); 3.77 and 3.82 (total 3H, each singlet); 4.53 and 4.60 (total 1H, each singlet); 6.77–6.97 (3H, multiplet); 7.02–7.26 (5H, multiplet); 7.49–7.60 (1H, multiplet); 8.04–8.09 (1H, multiplet).

(72b) 5-{[1-(3,4-Difluorophenyl)ethylamino]-(4-methoxyphenyl)methyl}-2-fluorophenylamine Following a similar procedure to that described in Example (1b), 2.5 g of N-[1-(3,4-difluorophenyl)ethyl]-N-[(4-fluoro-3-nitrophenyl)-(4-methoxyphenyl)methyl]amine [prepared as described in step (a) above], 3.29 g of nickel chloride hexahydrate and 957 mg of sodium borohydride were reacted, to obtain 1.82 g of the title compound as a yellow oil.

Nuclear Magnetic Resonance Spectrum (CDCl$_3$) δ ppm: 1.30 and 1.31 (total 3H, each doublet, J=6.6 and 6.6 Hz); 3.58–3.66 (1H, multiplet); 3.76 and 3.80 (total 3H, each singlet); 4.41 (1H, singlet); 6.56–6.61 (1H, multiplet); 6.68–6.72 (1H, multiplet); 6.77–6.94 (4H, multiplet); 7.06–7.18 (4H, multiplet).

(72c) 3-t-Butoxy-4-<5-{[1-(3,4-difluorophenyl)ethylamino]-(4-methoxyphenyl)methyl}-2-fluorophenylamino>-3-cyclobutene-1,2-dione Following a similar procedure to that described in Example (66c), 500 mg of 5-{[1-(3,4-difluorophenyl)ethylamino]-(4-methoxyphenyl)methyl}-2-fluorophenylamine [prepared as described in step (b) above] and 477 mg of 4-t-butoxy-3-methoxy-3-cyclobutene-1,2-dione were reacted and purified, to obtain 225 mg of isomer A and 256 mg of isomer B of the title compound as a yellow oil and a yellow solid, respectively.
Isomer A
Nuclear Magnetic Resonance Spectrum (CDCl$_3$) δ ppm: 1.36 (3H, doublet, J=6.6 Hz); 1.63 (9H, singlet); 3.65 (1H, quartet, J=6.6 Hz); 3.75 (3H, singlet); 4.53 (1H, singlet); 6.80 (2H, doublet, J=8.7 Hz); 6.94–7.28 (8H, multiplet).
Isomer B
Nuclear Magnetic Resonance Spectrum (CDCl$_3$) δ ppm: 1.34 (3H, doublet, J=6.7 Hz); 1.64 (9H, singlet); 3.63 (1H, quartet, J=6.6 Hz); 3.80 (3H, singlet); 4.51 (1H, singlet); 6.87–7.00 (5H, multiplet); 7.06–7.27 (5H, multiplet). mp: 142–145° C.

(72d) 4-<5-{[1-(3,4-Difluorophenyl)ethylamino]-(4-methoxyphenyl)methyl}-2-fluorophenylamino>-3-hydroxy-3-evelobutene-1,2-dione hydrochloride Following a reaction and purification procedure similar to those described in Example (63b), 200 mg, of isomer A of 3-t-butoxy-4-<5-{[1-(3,4-difluorophenyl)ethylamino]-(4-methoxyphenyl)methyl}-2-fluorophenylamino>-3-cyclobutene-1,2-dione [prepared as described in step (c) above] was reacted, to obtain 175 mg, of isomer A of the title compound as a pale gray solid.
Isomer A
Nuclear Magnetic Resonance Spectrum (DMSO-$d_6$) δ ppm: 1.65 (3H, doublet, J=6.7 Hz); 3.74 (3H, singlet); 4.33 (1H, broad); 5.10 (3H, singlet); 6.94 (2H, doublet, J=8.7 Hz); 7.13–7.15 (1H, multiplet); 7.26–7.32 (2H, multiplet); 7.44–7.57 (4H, multiplet); 7.80 (1H, doublet of doublets, J=1.6, 7.7 Hz). mp: 175–177° C.

Following a reaction and purification procedure similar to those described in Example (63b), 225 mg of isomer B of 3-t-butoxy-4-<5-{[1-(3,4-difluorophenyl)ethylamino]-(4-methoxyphenyl)methyl}-2-fluorophenylamino)-3-cyclobutene-1,2-dione [prepared as described in step (c) above] was reacted, to obtain 190 mg of isomer B of the title compound as a white solid.
Isomer B
Nuclear Magnetic Resonance Spectrum (DMSO-$d_6$) δ ppm: 1.64 (3H, doublet, J=6.7 Hz); 3.76 (3H, singlet); 4.23 (1H, broad); 5.19 (1H, singlet); 6.98 (2H, doublet, J=8.7 Hz); 7.21–7.23 (1H, multiplet); 7.27–7.32 (1H, multiplet); 7.44–7.61 (5H, multiplet); 7.76 (1H, doublet of doublets, J=2.0, 7.9 Hz). mp: 175–178° C.

EXAMPLE 73

4-<3-{[1-(3,4-Difluorophenyl)ethylamino]-(4-methoxyphenyl)methyl}-4-fluorophenylamino>-3-hydroxy-3-cyclobutene-1,2-dione hydrochloride
(Compound No. 2-3401)

(73a) N-[1-(3,4-Difluorophenyl)ethyl]-N-[(2-fluoro-5-nitrophenyl)-(4-methoxyphenyl)methyl]amine Following a similar procedure to that described in Example (1a), 828 mg of 2-fluoro-5-nitrophenyl 4-methoxyphenyl ketone, 1.16 g of 1-(3,4-difluorophenyl)ethylamine hydrochloride, 2.52 ml of triethylamine, 0.40 ml of titanium tetrachloride, 840 mg of sodium cyanoborohydride and 0.62 ml of acetic acid were reacted, to obtain 860 mg of the title compound as a yellow oil.

Nuclear Magnetic Resonance Spectrum (CDCl$_3$) δ ppm: 1.36 and 1.37 (total 3H, each doublet, J=6.6 and 6.7 Hz); 3.61 and 3.69 (total 1H, each quartet, J=6.6 and 6.6 Hz); 3.77 and 3.80 (total 3H, each singlet); 4.89 and 4.90 (total 1H, each singlet); 6.80–6.95 (3H, multiplet); 7.02–7.23 (5H, multiplet); 8.05–8.17 (1H, multiplet); 8.45 and 8.59 (total 1H, each doublet of doublets, J=2.9, 6.3 and 2.9, 6.3 Hz).

(73b) 3-{[1-(3,4-Difluorophenyl)ethylamino]-(4-methoxyphenyl)methyl}-4-fluorophenylamine Following a reaction and purification procedure similar to those described in Example (59b), 800 mg of N-[1-(3,4-difluorophenyl)ethyl]-N-[(2-fluoro-5-nitrophenyl)-(4-methoxyphenyl)methyl]amine [prepared as described in step (a) above], 1.05 g of nickel chloride hexahydrate and 306 mg of sodium borohydride were reacted, to obtain 330 mg of isomer A and 350 mg of isomer B of the title compound as yellow oils, respectively.

Isomer A

Nuclear Magnetic Resonance Spectrum (CDCl$_3$) δ ppm: 1.32 (3H, doublet, J=6.7 Hz); 3.68 (1H, quartet, J=6.6 Hz); 3.76 (3H, singlet); 4.73 (1H, singlet); 6.50–6.54 (1H, multiplet); 6.70 (1 H, doublet of doublets, J=2.9, 6.0 Hz); 6.78–6.83 (3H, multiplet); 6.95–6.99 (1H, multiplet); 7.05–7.27 (4H, multiplet).

Isomer B

Nuclear Magnetic Resonance Spectrum (CDCl$_3$) δ ppm: 1.33 (3H, doublet, J=6.7 Hz); 3.66 (1H, quartet, J=6.6 Hz); 3.80 (3H, singlet); 4.83 (1H, singlet); 6.43–6.47 (1H, multiplet); 6.64 (1H, doublet of doublets, J=2.9, 6.1 Hz); 6.70–7.26 (8H, multiplet).

(73c) 3-t-Butoxy-4-<3-{[1-(3,4-difluorophenyl)ethylamino]-(4-methoxyphenyl)methyl}-4-fluorophenylamino>-3-cyclobutene-1,2-dione Following a similar procedure to that described in Example (1c), 268 mg of isomer A of 3-{[1-(3,4-difluorophenyl)ethylamino]-(4-methoxyphenyl)methyl}-4-fluorophenylamine [prepared as described in step (b) above] and 255 mg of 4-t-butoxy-3-methoxy-3-cyclobutene-1,2-dione were reacted, to obtain 348 mg of isomer A of the title compound as a yellow oil.

Isomer A

Nuclear Magnetic Resonance Spectrum (CDCl$_3$) δ ppm: 1.36 (3H, doublet, J=6.6 Hz); 1.64 (9H, singlet); 3.66 (1H, quartet, J=6.6 Hz); 3.76 (3H, singlet); 4.85 (1H, singlet); 6.81 (2H, doublet, J=8.7 Hz); 6.95–7.57 (7H, multiplet); 7.57 (1H, broad).

Following a similar procedure to that described in Example (1c), 316 mg of isomer B of 3-{[1-(3,4-difluorophenyl)ethylamino]-(4-methoxyphenyl)methyl}-4-fluorophenylamine [prepared as described in step (b) above] and 301 mg of 4-t-butoxy-3-methoxy-3-cyclobutene-1,2-dione were reacted, to obtain 476 mg of isomer B of the title compound as a yellow oil.

Isomer B

Nuclear Magnetic Resonance Spectrum (CDCl$_3$) δ ppm: 1.34 (3H, doublet, J=6.6 Hz); 1.64 (9H, singlet); 3.67 (1H, quartet, J=6.6 Hz); 3.80 (3H, singlet); 4.87 (1H, singlet); 6.86–7.27 (9H, multiplet); 7.44 (1H, broad).

(73d) 4-<3-{[1-(3,4-Difluorophenyl)ethylamino]-(4-methoxyphenyl)methyl}-4-fluorophenylamino>-3-hydroxy-3-cyclobutene-1,2-dione hydrochloride Following a reaction and purification procedure similar to those described in Example (63b), 318 mg of isomer A of 3-t-butoxy-4-<3-{[1-(3,4-difluorophenyl)ethylamino]-(4-methoxyphenyl)methyl}-4-fluorophenylamino>-3-cyclobutene-1,2-dione [prepared as described in step (c) above] was reacted, to obtain 258 mg of isomer A of the title compound as a white solid.

Isomer A

Nuclear Magnetic Resonance Spectrum (DMSO-d$_6$) δ ppm: 1.66 (3H, doublet, J=6.7 Hz); 3.74 (3H, singlet); 4.48 (1H, broad); 5.10 (1H, singlet); 6.94 (2H, doublet, J=8.8 Hz); 7.14–7.19 (2H, multiplet); 7.37–7.52 (5H, multiplet); 7.85 (1H, doublet of doublets, J=2.6, 6.3 Hz). mp: 190–193° C.

Following a reaction and purification procedure similar to those described in Example (63b), 444 mg of isomer B of 3-{[1-(3,4-difluorophenyl)ethylamino]-(4-methoxyphenyl)methyl}-4-fluorophenylamine [prepared as described in step (b) above] was reacted, to obtain 325 mg of isomer B of the title compound as a pale yellow solid.

Isomer B

Nuclear Magnetic Resonance Spectrum (DMSO-d$_6$) δ ppm: 1.62 (3H, doublet, J=6.8 Hz); 3.78 (3H, singlet); 4.29 (1H, broad); 5.24 (1H, singlet); 7.01 (2H, doublet, J=8.9 Hz); 7.18–7.27 (2H, multiplet); 7.39–7.63 (5H, multiplet); 7.72–7.74 (1H, multiplet). mp: 185–190° C.

EXAMPLE 74

4-<3-{[(S)-1-Cyclohexylethylamino]-(4-methoxyphenyl)methyl}phenylamino>-3-hydroxy-3-cyclobutene-1,2-dione hydrochloride (Compound No. 2-2)

(74a) 3-t-Butoxy-4-<3-{[(S)-1-cyclohexylethylamino]-(4-methoxyphenyl)methyl}phenylamino>-3-cyclobutene-1,2-dione Following a similar procedure to that described in Example (1c), 1.63 g of 3-{[(S)-1-cyclohexylethylamino]-(4-methoxyphenyl)methyl}phenylamine [prepared as described in Example 31(b) above] and 1.33 g of 4-t-butoxy-3-methoxy-3-cyclobutene-1,2-dione were reacted, to obtain 1.89 g of the title compound as a pale yellow foamy solid.

Nuclear Magnetic Resonance Spectrum (CDCl$_3$) δ ppm: 0.97–1.41 (9H, multiplet); 1.52–1.80 (14H, multiplet); 2.35–2.42 (1H, multiplet); 3.77 and 3.78 (total 3H, each singlet); 4.91 (1H, singlet); 6.82–6.85 (2H, multiplet); 7.16–7.36 (6H, multiplet).

(74b) 4-<3-{[(S)-1-Cyclohexylethylamino]-(4-methoxyphenyl)methyl}phenylamino>-3-hydroxy-3-cyclobutene-1,2-dione hydrochloride Following a reaction and purification procedure similar to those described in Example (63b), 482 mg of 3-t-butoxy-4-<3-{[(S)-1-cyclohexylethylamino]-(4-methoxyphenyl)methyl}phenylamino>-3-cyclobutene-1,2-dione [prepared as described in step (a) above] was reacted, to obtain 415 mg of the title compound as a white solid.

Nuclear Magnetic Resonance Spectrum (DMSO-d$_6$) δ ppm: 0.95–1.37 (9H, multiplet); 1.60–1.76 (4H, multiplet); 1.82–1.92 (1H, multiplet); 2.88 (1H, broad); 3.75 and 3.76 (total 3H, each singlet); 5.53 (1H, broad); 6.98–7.01 (2H, multiplet); 7.36–7.47 (3H, multiplet); 7.60 (1H, doublet, J=7.5 Hz); 7.68 (2H, doublet of doublets, J=5.5, 8.6 Hz). mp: 192–195° C.

EXAMPLE 75

4-<3-{[1-(2,4-Difluorophenyl)ethylamino]-(4-methoxyphenyl)methyl}phenylamino>-3-hydroxy-3-cyclobutene-1,2-dione hydrochloride (Compound No. 2-49)

(75a) N-[1-(2,4-Difluorophenyl)ethyl-N-[(4-methoxyphenyl)-(3-nitrophenyl)methyl]amine Following a similar procedure to that described in Example (1a), 2.0 g of 4-methoxyphenyl 3-nitrophenyl ketone, 3.01 g of 1-(2,4-difluorophenyl)ethylamine hydrochloride, 6.5 ml of triethylamine, 1.03 ml of titanium tetrachloride, 2.06 g of sodium cyanoborohydride and 0.67 ml of acetic acid were reacted, to obtain 2.90 g of the title compound as a yellow oil.

Nuclear Magnetic Resonance Spectrum (CDCl$_3$) δ ppm: 1.39–1.43 (3H, multiplet); 3.76 and 3.80 (total 3H, each singlet); 3.87 and 3.95 (total 1H, each quartet, J=6.8 and 6.7 Hz); 4.65 (1H, singlet); 6.75–6.90 (4H, multiplet); 7.14–7.28 (3H, multiplet); 7.39 and 7.48 (total 1H, each triplet, J=8.0 and 8.0 Hz); 7.61 and 7.69 (total 1H, each doublet, J=7.5 and 7.7 Hz); 8.03 and 8.09 (total 1H, each doublet of doublets, J=2.0, 8.0 and 1.8, 7.8 Hz); 8.23–8.27 (1H, multiplet).

(75b) 3-{[1-(2,4-Difluorophenyl)ethylamino}-(4-methoxyphenyl)methyl]phenylamine

Following a similar procedure to that described in Example (1b), 2.80 g of N-[1-(2,4-difluorophenyl)ethyl]-N-

[(4-methoxyphenyl)-(3-nitrophenyl)methyl]amine [prepared as described in step (a) above], 3.34 g of nickel chloride hexahydrate and 1.12 g of sodium borohydride were reacted, to obtain 2.23 g of the title compound as a yellow oil.

Nuclear Magnetic Resonance Spectrum (CDCl$_3$) δ ppm: 1.37 (3H, doublet, J=6.8 Hz); 3.75 and 3.79 (total 3H, each singlet); 3.91 and 3.96 (total 1H, each quartet, J=6.8 and 6.6 Hz); 4.46 and 4.64 (total 1H, each singlet); 6.50 and 6.56 (total 1H, each doublet of doublets, J=2.0, 8.1 and 2.0, 8.1 Hz); 6.62–6.86 (6H, multiplet); 7.01 and 7.09 (total 1H, each triplet, J=7.8 and 7.9 Hz); 7.18–7.31 (3H, multiplet).

(75c) 3-t-Butoxy-4-<3-{[1-(2,4-difluorophenyl)ethylamino]-(4-methoxyphenyl)methyl}phenylamino>-3-cyclobutene-1,2-dione Following a reaction and purification procedure similar to those described in Example (66c), 2.18 g of 3-{[1-(2,4-difluorophenyl)ethylamino]-(4-methoxyphenyl)methyl}phenylamine [prepared as described in step (b) above] and 1.63 g of 4-t-butoxy-3-methoxy-3-cyclobutene-1,2-dione were reacted, to obtain 812 mg of isomer A, and 754 mg of isomer B of the title compound as a yellow oil and a pale yellow foamy solid, respectively.

Isomer A

Nuclear Magnetic Resonance Spectrum (CDCl$_3$) δ ppm: 1.40 (3H, doublet, J=6.7 Hz); 1.63 (9H, singlet); 3.75 (3H, singlet); 3.93 (1H, quartet, J=6.8 Hz); 4.56 (1H, singlet); 6.74–6.88 (4H, multiplet); 7.07–7.45 (7H, multiplet).

Isomer B

Nuclear Magnetic Resonance Spectrum (CDCl$_3$) δ ppm: 1.38 (3H, doublet, J=6.8 Hz); 1.63 (9H, singlet); 3.80 (3H, singlet); 3.93 (1H, quartet, J=6.8 Hz); 4.55 (1H, singlet); 6.73–6.88 (4H, multiplet); 7.04–7.38 (7H, multiplet).

(75d) 4-<3-{[1-(2,4-Difluorophenyl)ethylamino]-(4-methoxyphenyl)methyl}phenylamino>-3-hydroxy-3-cyclobutene-1,2-dione hydrochloride Following a reaction and purification procedure similar to those described in Example (63b), 395 mg of isomer A of 3-t-butoxy-4-<3-{[1-(2,4-difluorophenyl)ethylamino]-(4-methoxyphenyl)methyl}phenylamino>-3-cyclobutene-1,2-dione [prepared as described in step (c) above] was reacted, to obtain 336 mg of isomer A of the title compound as a pale red solid.

Isomer A

Nuclear Magnetic Resonance Spectrum (DMSO-d$_6$) δ ppm: 1.69 (3H, doublet, J=6.7 Hz); 3.75 (3H, singlet); 4.45 (1H, broad); 5.23 (1H, broad singlet); 6.97 (2H, doublet, J=8.7 Hz); 7.23–7.41 (5H, multiplet); 7.52 (1H, singlet); 7.59 (2H, doublet, J=8.7 Hz); 7.84–7.90 (1H, multiplet). mp: 182–187° C.

Following a reaction and purification procedure similar to those described in Example (63b), 455 mg of isomer B of 3-t-butoxy-4-<3-{[1-(2,4-difluorophenyl)ethylamino]-(4-methoxyphenyl)methyl}phenylamino>-3-cyclobutene-1,2-dione [prepared as described in step (c) above] was reacted, to obtain 314 mg of isomer B of the title compound as a pale red solid.

Isomer B

Nuclear Magnetic Resonance Spectrum (DMSO-d$_6$) δ ppm: 1.69 (3H, doublet, J=6.8 Hz); 3.76 (3H, singlet); 4.39 (1H, broad); 5.19 (1H, broad singlet); 6.97 (2H, doublet, J=8.7 Hz); 7.23–7.43 (5H, multiplet); 7.55–7.60 (3H, multiplet); 7.86–7.92 (1H, multiplet). mp: 178–185° C.

EXAMPLE 76

4-<3-{[1-(3-Chlorophenyl)ethylamino]-(4-methoxyphenyl)methyl}phenylamino>-3-hydroxy-3-cyclobutene-1,2-dione hydrochloride (Compound No. 2-31)

(76a) N-[1-(3-Chlorophenyl)ethyl-N-[(4-methoxyphenyl)-(3-nitrophenyl)methyl]amine Following a similar procedure to that described in Example (1a), 2.0 g of 4-methoxyphenyl 3-nitrophenyl ketone, 2.99 g of 1-(3-chlorophenyl)ethylamine hydrochloride, 6.5 ml of triethylamine, 1.03 ml of titanium tetrachloride, 2.06 g of sodium cyanoborohydride and 0.67 ml of acetic acid were reacted, to obtain 2.69 g of the title compound as a yellow oil.

Nuclear Magnetic Resonance Spectrum (CDCl$_3$) δ ppm: 1.37 and 1.38 (total 3H, each doublet, J=6.6 and 6.6 Hz); 3.60 and 3.67 (total 1H, each quartet, J=6.6 and 6.6 Hz); 3.76 and 3.81 (total 3H, each singlet); 4.63 and 4.67 (total 1H, each singlet); 6.81 and 6.89 (total 2H, each doublet, J=8.7 and 8.7 Hz); 7.05–7.30 (6H, multiplet); 7.39 and 7.48 (total 1H, each triplet, J=8.0 and 7.9 Hz); 7.60 and 7.67 (total 1H, each doublet, J=7.8 and 7.9 Hz); 8.01–8.11 (1H, multiplet); 8.22–8.26 (1H, multiplet).

(76b) 3-{[1-(3-Chlorophenyl)ethylamino]-(4-methoxyphenyl)methyl}phenylamine

Following a similar procedure to that described in Example (1b), 2.60 g of N-[1-(3-chlorophenyl)ethyl]-N-[(4-methoxyphenyl)-(3-nitrophenyl)methyl]amine [prepared as described in step (a) above], 3.11 g of nickel chloride hexahydrate and 1.04 g of sodium borohydride were reacted, to obtain 2.15 g of the title compound as a yellow oil.

Nuclear Magnetic Resonance Spectrum (CDCl$_3$) δ ppm: 1.33 (3H, doublet, J=6.7 Hz); 3.63 and 3.68 (total 1H, each quartet, J=6.7 and 6.6 Hz); 3.76 and 3.80 (total 3H, each singlet); 4.47 (1H, singlet); 6.49–6.70 (3H, multiplet); 6.79 and 6.86 (total 2H, each doublet, J=8.7 and 8.5 Hz); 7.02–7.35 (7H, multiplet).

(76c) 3-t-Butoxy-4-<3-{[1-(3-chlorophenyl)ethylamino]-(4-methoxyphenyl)methyl}phenylamino>-3-cyclobutene-1,2-dione Following a reaction and purification procedure similar to those described in Example (66c), 2.09 g of 3-{[1-(3-chlorophenyl)ethylamino]-(4-methoxyphenyl)methyl}phenylamine [prepared as described in step (b) above] and 1.57 g of 4-t-butoxy-3-methoxy-3-cyclobutene-1,2-dione were reacted, to obtain 481 mg of isomer A and 504 mg of isomer B of the title compound as yellow oils, respectively.

Isomer A

Nuclear Magnetic Resonance Spectrum (CDCl$_3$) δ ppm: 1.37 (3H, doublet, J=6.6 Hz); 1.63 (9H, singlet); 3.65 (1H, quartet, J=6.7 Hz); 3.76 (3H, singlet); 4.56 (1H, singlet); 6.80 (2H, doublet, J=8.6 Hz); 7.09–7.36 (10H, multiplet).

Isomer B

Nuclear Magnetic Resonance Spectrum (CDCl$_3$) δ ppm: 1.35 (3H, doublet, J=6.6 Hz); 1.63 (9H, singlet); 3.65 (1H, quartet, J=6.6 Hz); 3.81 (3H, singlet); 4.55 (1H, singlet); 6.88 (2H, doublet, J=8.7 Hz); 7.03–7.34 (10H, multiplet).

(76d) 4-<3-{[1-(3-Chlorophenyl)ethylamino]-(4-methoxyphenyl)methyl}phenylamino>-3-hydroxy-3-cyclobutene-1,2-dione hydrochloride Following a reaction and purification procedure similar to those described in Example (63b), 441 mg of isomer A of 3-t-butoxy-4-<3-{[1-(3-chlorophenyl)ethylamino]-(4-methoxyphenyl)methyl}phenylamino>-3-cyclobutene-1,2-dione [prepared as described in step (c) above] was reacted, to obtain 250 mg of isomer A of the title compound as a yellow foamy solid.

Isomer A

Nuclear Magnetic Resonance Spectrum (DMSO-d$_6$) δ ppm: 1.65 (3H, doublet, J=6.7 Hz); 3.74 (3H, singlet); 4.24 (1H, broad); 5.09 (1H, broad singlet); 6.96 (2H, doublet, J=8.7 Hz); 7.22 (1H, doublet, J=7.6 Hz); 7.33–7.37 (2H, multiplet); 7.43–7.54 (7H, multiplet). Infrared Absorption Spectrum ν$_{max}$ (cm⁻): 1800.2, 1703.8, 1582.3, 1516.7, 1440.6, 1257.4.

Following a reaction and purification procedure similar to those described in Example (63b), 474 mg of isomer B of 3-t-butoxy-4-<3-{[1-(3-chlorophenyl)ethylamino]-(4-methoxyphenyl)methyl}phenylamino>-3-cyclobutene-1,2-dione [prepared as described in step (c) above] was reacted, to obtain 333 mg of isomer B of the title compound as a pale yellow solid.

Isomer B

Nuclear Magnetic Resonance Spectrum (DMSO-d$_6$) δ ppm: 1.67 (3H, doublet, J=6.7 Hz); 3.77 (3H, singlet); 4.18 (1H, broad); 5.07 (1H, broad singlet); 6.99 (2H, doublet, J=8.7 Hz); 7.35–7.56 (10H, multiplet). mp: 170–173° C.

EXAMPLE 77

3-Hydroxy-4-<3-{[4-methoxyphenyl)-(1-(3-trifluoromethylphenyl)ethylamino]methyl}phenylamino>-3-cyclobutene-1,2-dione hydrochloride (Compound No. 2-3494)

(77a) N-[(4-Methoxyphenyl)-(3-nitrophenyl)methyl]-N-[1-(3-trifluoromethylphenyl)ethyl amine Following a similar procedure to that described in Example (1a), 2.0 g of 4-methoxyphenyl 3-nitrophenyl ketone, 3.51 g of 1-(3-trifluoromethylphenyl)ethylamine hydrochloride, 6.5 ml of triethylamine, 1.03 ml of titanium tetrachloride, 2.06 g of sodium cyanoborohydride and 0.67 ml of acetic acid were reacted, to obtain 2.92 g of the title compound as a yellow oil.

Nuclear Magnetic Resonance Spectrum (CDCl$_3$) δ ppm: 1.40 and 1.41 (total 3H, each doublet, J=6.7 and 6.7 Hz); 3.71 and 3.77 (total 1H, each quartet, J=6.7 and 6.7 Hz); 3.76 and 3.82 (total 3H, each singlet); 4.60 and 4.65 (total 1H, each singlet); 6.81 and 6.90 (total 2H, each doublet, J=8.7 and 8.7 Hz); 7.14 and 7.17 (total 2H, each doublet, J=8.7 and 8.7 Hz); 7.36–7.66 (6H, multiplet); 8.00–8.12 (1H, multiplet); 8.20–8.26 (1H, multiplet).

(77b) 3-{(4-Methoxyphenyl)-[1-(3-trifluoromethylphenyl)ethylamino]methyl}phenylamine Following a similar procedure to that described in Example (1b), 2.85 g of N-[(4-methoxyphenyl)-(3-nitrophenyl)methyl]-N-[1-(3-trifluoromethylphenyl)ethyl] amine [prepared as described in step (a) above], 3.15 g of nickel chloride hexahydrate and 1.05 g of sodium borohydride were reacted, to obtain 2.60 g of the title compound as a yellow oil.

Nuclear Magnetic Resonance Spectrum (CDCl$_3$) δ ppm: 1.36 (3H, doublet, J=6.8 Hz); 3.71–3.84 (1H, multiplet); 3.75 and 3.80 (total 3H, each singlet); 4.43 and 4.44 (total 1H, each singlet); 6.49–6.69 (3H, multiplet); 6.78 and 6.86 (total 2H, each doublet, J=8.7 and 8.7 Hz); 7.03 and 7.11 (total 1H, each triplet, J=7.8 and 7.7 Hz); 7.17–7.21 (2H, multiplet); 7.41–7.53 (4H, multiplet).

(77c) 3-t-Butoxy-4-<3-{4-methoxyphenyl)-1-(3-trifluoromethylphenyl)ethylamino]methyl}phenylamino>-3-cyclobutene-1,2-dione Following a reaction and purification procedure similar to those described in Example (66c), 2.16 g of 3-{(4-methoxyphenyl)-[1-(3-trifluoromethylphenyl)ethylamino]methyl}phenylamine [prepared as described in step (b) above] and 1.49 g of 4-t-butoxy-3-methoxy-3-cyclobutene-1,2-dione were reacted, to obtain 620 mg of isomer A and 650 mg of isomer B of the title compound as pale yellow foamy solids, respectively.

Isomer A

Nuclear Magnetic Resonance Spectrum (CDCl$_3$) δ ppm: 1.40 (3H, doublet, J=6.6 Hz); 1.62 (9H, singlet); 3.75 (3H, singlet); 3.76 (1H, quartet, J=6.7 Hz); 4.54 (1H, singlet); 6.79 (2H, doublet, J=8.7 Hz); 7.07 (1H, multiplet); 7.17 (2H, doublet, J=8.6 Hz); 7.24–7.53 (7H, multiplet).

Isomer B

Nuclear Magnetic Resonance Spectrum (CDCl$_3$) δ ppm: 1.39 (3H, doublet, J=6.6 Hz); 1.63 (9H, singlet); 3.75 (1H, quartet, J=6.6 Hz); 3.81 (3H, singlet); 4.52 (1H, singlet); 6.89 (2H, doublet, J=8.7 Hz); 7.02 (1H, multiplet); 7.16–7.28 (5H, multiplet); 7.41 (4H, multiplet).

(77d) 3-Hydroxy-4-<3-{(4-methoxyphenyl)-[1-(3-trifluoromethylphenyl)ethylamino]methyl}phenylamino>-3-cyclobutene-1,2-dione hydrochloride Following a reaction and purification procedure similar to those described in Example (63b), 610 mg of isomer A of 3-t-butoxy-4-<3-{(4-methoxyphenyl)-[1-(3-trifluoromethylphenyl)ethylamino]methyl}phenylamino>-3-cyclobutene-1,2-dione [prepared as described in step (c) above] was reacted, to obtain 522 mg of isomer A of the title compound as a brown solid.

Isomer A

Nuclear Magnetic Resonance Spectrum (DMSO-d$_6$) δ ppm: 1.69 (3H, doublet, J=6.7 Hz); 3.73 (3H, singlet); 4.37 (1H, broad); 5.09 (1H, broad singlet); 6.94 (2H, doublet, J=8.7 Hz); 7.28 (1H, doublet, J=7.6 Hz); 7.36 (1H, doublet of doublets, J=7.8, 8.0 Hz); 7.43 (1H, doublet, J=8.4 Hz); 7.52–7.54 (3H, multiplet); 7.64–7.68 (1H, multiplet); 7.73–7.77 (3H, multiplet). mp: 183–188° C.

Following a reaction and purification procedure similar to those described in Example (6b), 630 mg of isomer B of 3-t-butoxy-4-<3-{(4-methoxyphenyl)-[1-(3-trifluoromethylphenyl)ethylamino]methyl}phenylamino>-3-cyclobutene-1,2-dione [prepared as described in step (c) above] was reacted, to obtain 457 mg of isomer B of the title compound as a pale yellow solid.

Isomer B

Nuclear Magnetic Resonance Spectrum (DMSO-d$_6$) δ ppm: 1.68 (3H, doublet, J=6.7 Hz); 3.76 (3H, singlet); 4.32 (1H, broad); 5.11 (1H, broad singlet); 6.99 (2H, doublet, J=8.4 Hz); 7.36–7.41 (3H, multiplet); 7.51–7.54 (3H, multiplet); 7.66–7.70 (1H, multiplet); 7.74–7.79 (1H, multiplet). mp: 180–185° C.

EXAMPLE 78

4-<3-{[1-(3,4-Dimethylphenyl)ethylamino]-(4-methoxyphenyl)methyl}phenylamino>-3-hydroxy-3-cyclobutene-1,2-dione hydrochloride (Compound No. 2-3493)

(78a) N-[1-(3,4-Dimethylphenyl)ethyl]-N-[(4-methoxyphenyl)-(3-nitrophenyl)methyl]amine Following a similar procedure to that described in Example (1a), 1.0 g of 4-methoxyphenyl 3-nitrophenyl ketone, 1.44 g of 1-(3,4-dimethylphenyl)ethylamine hydrochloride, 3.25 ml of triethylamine, 0.51 ml of titanium tetrachloride, 1.03 g of sodium cyanoborohydride and 0.33 ml of acetic acid were reacted, to obtain 1.45 g of the title compound as a yellow oil.

Nuclear Magnetic Resonance Spectrum (CDCl$_3$) δ ppm: 1.359 and 1.364 (total 3H, each doublet, J=6.8 and 6.6 Hz); 2.25, 2.26 and 2.27 (total 6H, each singlet); 3.53 and 3.62 (total 1H, each quartet, J=6.7 and 6.7 Hz); 3.76 and 3.81 (total 3H, each singlet); 4.66 and 4.68 (total 1H, each singlet); 6.80–7.22 (7H, multiplet); 7.37 and 7.49 (total 1H, each triplet, J=7.8 and 7.9 Hz); 7.59 and 7.70 (total 1H, each doublet, J=7.8 and 7.5 Hz); 8.00–8.10 (1H, multiplet); 8.21–8.26 (1H, multiplet). (78b) 3-{[1-(3,4-Dimethylphenyl)ethylamino]-(4-methoxyphenyl)methyl}phenylamine Following a similar procedure to that described in Example (1b), 1.32 g of N-[1-(3,4-dimethylphenyl)ethyl]-N-[(4-methoxyphenyl)-(3-nitrophenyl)methyl]amine [prepared as described in step (a) above], 1.61 g of nickel chloride hexahydrate and 539 mg of sodium borohydride were reacted, to obtain 1.10 g of the title compound as a yellow oil.

Nuclear Magnetic Resonance Spectrum (CDCl$_3$) δ ppm: 1.33 (3H, doublet, J=6.7 Hz); 2.26 (6H, singlet); 3.59 and 3.64 (total 1H, each quartet, J=6.7 and 6.7 Hz); 3.75 and 3.80 (total 3H, each singlet); 4.51 (1H, singlet); 6.48–6.57 (1H, multiplet); 6.62–6.72 (2H, multiplet); 6.78 and 6.85 (total 2H, each doublet, J=8.7 and 8.6 Hz); 6.96–7.11 (4H, multiplet); 7.19 and 7.24 (total 2H, each doublet, J=8.6 and 8.7 Hz).

(78c) 3-t-Butoxy-4-<3-{[1-(3,4-dimethylphenyl) ethylamino]-(4-methoxyphenyl)methyl}phenylamino>-3-cyclobutene-1,2-dione Following a similar procedure to that described in Example (66c), 1.06 g of 3-{[1-(3,4-dimethylphenyl) ethylamino]-(4-methoxyphenyl)methyl}phenylamine [prepared as described in step (b) above] and 812 mg of 4-t-butoxy-3-methoxy-3-cyclobutene-1,2-dione were reacted and purified, to obtain 456 mg of isomer A and 428 mg of isomer B of the title compound as a yellow foamy solid and a pale yellow foamy solid, respectively.

Isomer A

Nuclear Magnetic Resonance Spectrum (CDCl$_3$) δ ppm: 1.35 (3H, doublet, J=6.6 Hz); 1.62 (9H, singlet); 2.31 (6H, singlet); 3.60 (1H, quartet, J=6.7 Hz); 3.75 (3H, singlet); 4.60 (1H, singlet); 6.79 (2H, doublet, J=8.7 Hz); 6.81–6.99 (1H, multiplet); 7.09–7.34 (8H, multiplet).

Isomer B

Nuclear Magnetic Resonance Spectrum (CDCl$_3$) δ ppm: 1.35 (3H, doublet, J=6.7 Hz); 1.62 (9H, singlet); 2.25 (6H, singlet); 3.59 (1H, quartet, J=6.7 Hz); 3.80 (3H, singlet); 4.58 (1H, singlet); 6.87 (2H, doublet, J=8.7 Hz); 6.96–7.10 (2H, multiplet); 7.14–7.27 (7H, multiplet).

(78d) 4-<3-{[1-(3,4-Dimethylphenyl)ethylamino]-(4-methoxybiphenyl)methyl}phenylamino>-3-hydroxy-3-cyclobutene-1,2-dione hydrochloride Following a similar procedure to that described in Example (63b), 360 mg of isomer A of 3-t-butoxy-4-<3-{[1-(3,4-dimethylphenyl)ethylamino]-(4-methoxyphenyl) methyl}phenylamino>-3-cyclobutene-1,2-dione [prepared as described in step (c) above] was reacted and purified, to obtain 289 mg of isomer A of the title compound as a white solid.

Isomer A

Nuclear Magnetic Resonance Spectrum (DMSO-d$_6$) δ ppm: 1.64 (3H, doublet, J=6.7 Hz); 2.19 (3H, singlet); 2.23 (3H, singlet); 3.74 (3H, singlet); 4.08 (1H, broad); 4.99 (1H, broad); 6.96 (2H, doublet, J=8.8 Hz); 7.05 (1H, singlet); 7.09 (1H, doublet, J=7.9 Hz); 7.19 (1H, doublet, J=7.9 Hz); 7.29 (1H, doublet, J=7.1 Hz); 7.35–7.42 (2H, multiplet); 7.50–7.52 (3H, multiplet). mp: 200–206° C.

Following a similar procedure to that described in Example (63b), 350 mg of isomer B of 3-t-butoxy-4-<3-{[1-(3,4-dimethylphenyl)ethylamino]-(4-methoxyphenyl) methyl}phenylamino>-3-cyclobutene-1,2-dione [prepared as described in step (c) above] was reacted and purified, to obtain 305 mg of isomer B of the title compound as a white solid.

Isomer B

Nuclear Magnetic Resonance Spectrum (DMSO-d$_6$) δ ppm: 1.63 (3H, doublet, J=6.8 Hz); 2.22 (3H, singlet); 2.25 (3H, singlet); 3.78 (3H, singlet); 4.00–4.06 (1H, broad); 4.96 (1H, broad); 6.99 (2H, doublet, J=8.7 Hz); 7.08–7.10 (2H, multiplet); 7.20 (1H, doublet, J=8.0 Hz); 7.35–7.42 (3H, multiplet); 7.47 (1H, singlet); 7.51 (2H, doublet, J=8.7 Hz). mp: 198–203° C.

EXAMPLE 79

4-<3-{[(S)-1-(3,4-Difluorophenyl)ethylamino]-(4-methoxyphenyl)methyl}phenylamino>-3-hydroxyamino-3-cyclobutene-1,2-dione (Compound No. 2-3514)

Isomer B (500 mg) of 4-<3-{[(S)-1-(3,4-difluorophenyl) ethylamino]-(4-methoxyphenyl)methyl}phenylamino>-3-methoxy-3-cyclobutene-1,2-dione [prepared as described in Example 62(b)] and a solution of 0.064 ml of a 50 wt. % aqueous hydroxylamine solution in 5 ml of methanol were stirred at room temperature for 1 hour. At the end of this time, the reaction mixture was concentrated by evaporation under reduced pressure. The residue was purified by chromatography through a silica gel column using mixtures of methylene chloride and methanol ranging from 50:1 to 20:1 by volume as eluant, to obtain 346 mg of isomer B of the title compound as a brown solid.

Isomer B

Nuclear Magnetic Resonance Spectrum (DMSO-d$_6$) δ ppm: 1.28 (3H, broad); 3.54 (1H, broad); 3.72 (3H, singlet); 4.40 (1H, broad); 6.86–7.46 (11H, multiplet). mp: 115–118° C.; optical rotation $[\alpha]_D$=−32.0° (c=0.505, EtOH).

EXAMPLE 80

4-<3-{[(R)-1-(3,4-Difluorophenyl)ethylamino]-(4-methoxyphenyl)methyl}phenylamino>-3-hydroxyamino-3-cyclobutene-1,2-dione (Compound No. 2-3514)

Following a similar procedure to that described in Example (79), 300 mg of isomer B of 4-<3-{[(R)-1-(3,4-difluorophenyl)ethylamino]-(4-methoxyphenyl) methyl}phenylamino>-3-methoxy-3-cyclobutene-1,2-dione [prepared as described in Example 18(c) above] and 0.038 ml of a 50 wt. % aqueous hydroxylamine solution were reacted, to obtain 270 mg of isomer B as a brown solid.

Isomer B

Nuclear Magnetic Resonance Spectrum (DMSO-d$_6$) δ ppm: 1.27 (3H, doublet, J=6.4 Hz); 3.54 (1H, broad); 3.72 (3H, singlet); 4.40 (1H, broad); 6.87 (2H, doublet, J=8.6 Hz); 6.94 (1H, doublet, J=7.5 Hz); 7.06–7.08 (1H, multiplet); 7.15–7.42 (7H, multiplet). mp: 90° C. (dec.); optical rotation $[\alpha]_D$=+42.8° (c=0.535, EtOH).

EXAMPLE 81

<2-{3-[(R)-1-(3,4-Difluorophenyl)ethylamino]-(4-methoxyphenyl)methyl]phenylamino]-3,4-dioxo-1-cyclobutene-1-ylamino>acetic acid hydrochloride (Compound No. 2-3513)

(81a) t-Butyl <2-{3-[(R)-1-(3,4-difluorophenyl) ethylamino]-(4-methoxyphenyl)methyl]phenylamino}-3,4-dioxo-1-cyclobutene-1-ylamino>acetate 0.13 ml of triethylamine was added to a suspension of 300 mg of isomer B of 4-<3-{[(R)-1-(3,4-difluorophenyl) ethylamino]-(4-methoxyphenyl)methyl}phenylamino>-3-methoxy-3-cyclobutene-1,2-dione (prepared as described in Example 18(c) above] and 116 mg of glycine t-butyl ester hydrochloride in 5 ml of t-butanol, and then the mixture was allowed to react at room temperature for 3 hours. At the end of this time, the reaction mixture was diluted with ethyl acetate, washed with a saturated aqueous solution of sodium chloride, dried over anhydrous magnesium sulfate and concentrated by evaporation. The residue was purified by chromatography through a silica gel column using a 1:1 by volume mixture of cyclohexane and ethyl acetate as eluant, to obtain 380 mg of isomer B of the title compound as a pale yellow foamy solid.

Isomer B

Nuclear Magnetic Resonance Spectrum (CDCl$_3$) δ ppm: 1.32 (3H, doublet, J=6.6 Hz); 1.45 (9H, singlet); 3.63 (1H, quartet, J=6.6 Hz); 3.79 (3H, singlet); 4.33–4.45 (2H, multiplet); 4.54 (1H, singlet); 6.86 (2H, doublet, J=8.5 Hz); 6.95–7.28 (9H, multiplet).

(81b) >2-{3-[(R)-1-(3,4-Difluorophenyl)ethylamino]-(4-methoxyphenyl)methyl]phenylamino}-3,4-dioxo-1-cyclobutene-1-ylamino>acetic acid hydrochloride Following a similar procedure to that described in Example (63b), 280 mg of isomer B of t-butyl >(2-{3-[(R)-1-(3,4-difluorophenyl)ethylamino]-(4-methoxyphenyl)methyl]phenylamino}-3,4-dioxo-1-cyclobutene-1-ylamino>acetate [prepared as described in step (a) above] was reacted, to obtain 250 mg of isomer B of the title compound as a white solid.

Isomer B

Nuclear Magnetic Resonance Spectrum (DMSO-d$_6$) δ ppm: 1.64 (3H, broad); 3.76 (3H, singlet); 4.22–4.24 (1H, broad); 4.35 (2H, broad); 5.14 (1H, broad); 6.99 (2H, doublet, J=8.4 Hz); 7.20–7.56 (8H, multiplet); 8.28 (1H, broad). mp: 168–171° C. optical rotation [α]$_D$=+33.8° (c=1.02, AcOH).

EXAMPLE 82

2-<2-{3-[(R)-1-(3,4-Difluorophenyl)ethylamino]-(4-methoxyphenyl)methyl]phenylamino}-3,4-dioxo-1-cyclobutene-1-ylamino>ethanesulfonic acid
(Compound No. 2-2937)

Isomer B (300 mg) of 4-<3-{[(R)-1-(3,4-difluorophenyl)ethylamino]-(4-methoxyphenyl)methyl}phenylamino>-3-methoxy-3-cyclobutene-1,2-dione [prepared as described in Example 18(c) above], and a solution of 0.26 ml of triethylamine and 157 mg of taurine in 5 ml of methanol were stirred at room temperature for 4 hours. The reaction mixture was neutralized with ??N aqueous hydrochloric acid and then diluted with water and ethyl acetate. The solid thus precipitated was collected by filtration and purified by chromatography through a silica gel column using a 10:1 by volume mixture of methylene chloride and methanol as eluant, to obtain 205 mg of isomer B of the title compound as a white solid.

Isomer B

Nuclear Magnetic Resonance Spectrum (DMSO-d$_6$) δ ppm: 1.64 (3H, broad); 2.79 (2H, broad); 3.77 (3H, singlet); 3.95 (2H, broad); 4.26 (1H, broad); 5.19 (1H, broad); 6.86–7.58 (11H, multiplet). mp: 212–214° C.; optical rotation [α]$_D$=+28.5° (c=1.04, AcOH).

EXAMPLE 83

4-<3-{(4-Fluorophenyl)-[1-(thiophen-2-yl)ethylamino]methyl}phenylamino>-3-hydroxy-3-cyclobutene-1,2-dione hydrochloride (Compound No. 2-81)

(83a) N-[(4-Fluorophenyl)-(3-nitrophenyl)methyl]-N-[1-(thiophen-2-yl)ethyl]amine Following a similar procedure to that described in Example (1a), 1.80 g of 4-fluoro-3'-nitrobenzophenone, 2.05 g of 1-(thiophen-2-yl)ethylamine hydrochloride, 6.1 ml of triethylamine and 0.9 ml of titanium tetrachloride were reacted, to obtain the corresponding imine compound.

Following a similar procedure to that described in Example (1a), the resulting imine compound, 1.84 g of sodium cyanoborohydride and 0.6 ml of acetic acid were reacted, to obtain 2.43 g of the title compound as a yellow oil.

Nuclear Magnetic Resonance Spectrum (CDCl$_3$) δ ppm: 1.50 and 1.51 (total 3H, each doublet, J=6.6 Hz); 3.90 and 3.94 (total 1H, each quartet, J=6.6 Hz); 4.87 and 4.89 (total 1H, each singlet); 6.78 and 6.80 (total 1H, each doublet, J=3.3 Hz); 6.93–7.09 (3H, multiplet); 7.23–7.34 (3H, multiplet); 7.42 and 7.51 (total 1H, each triplet, J=7.9 Hz); 7.65 and 7.72 (total 1H, each doublet, J=7.7 Hz); 8.05 and 8.13 (total 1H, each doublet of doublets, J=2.2, 8.1 Hz); 8.23 and 8.28 (total 1H, each triplet, J=1.9 Hz).

(83b) 3-{(4-Fluorophenyl)-[1-(thiophen-2-yl)ethylamino]methyl}phenylamine

Following a similar reaction, separation and purification procedure to that described in Example (59b), 2.41 of N-[(4-fluorophenyl)-(3-nitrophenyl)methyl]-N-[1-(thiophen-2-yl)ethyl]amine [prepared as described in step (a) above], 3.22 g of nickel chloride hexahydrate and 1.03 g of sodium borohydride were reacted, to obtain 687 mg of isomer A and 552 mg of isomer B of the title compound as pale yellow oils, respectively.

Isomer A

Nuclear Magnetic Resonance Spectrum (CDCl$_3$) δ ppm: 1.46 (3H, doublet, J=6.6 Hz); 3.99 (1H, quartet, J=6.6 Hz); 4.69 (1H, singlet); 6.58 (1H, doublet of doublets, J=1.8, 7.5 Hz); 6.68 (1H, triplet, J=1.8 Hz); 6.73 (1H, doublet of doublets, J=1.8, 7.5 Hz); 6.83 (1H, doublet, J=3.4 Hz); 6.90–6.96 (3H, multiplet); 7.12 (1H, triplet, J=7.7 Hz); 7.21 (1H, doublet of doublets, J=1.1, 5.1 Hz); 7.29 (2H, doublet of doublets, J=5.5, 8.6 Hz).

Isomer B

Nuclear Magnetic Resonance Spectrum (CDCl$_3$) δ ppm: 1.47 (3H, doublet, J=6.6 Hz); 3.92 (1H, quartet, J=6.6 Hz); 4.70 (1H, singlet); 6.51 (1H, doublet of doublets, J=2.0, 7.9 Hz); 6.64 (1H, triplet, J=1.7 Hz); 6.68 (1H, doublet, J=7.7 Hz); 6.79 (1H, doublet, J=3.4 Hz); 6.90–7.06 (4H, multiplet); 7.22 (1H, doublet of doublets, J=1.1, 5.1 Hz); 7.34 (2H, doublet of doublets, J=5.5, 8.6 Hz).

(83c) 3-t-Butoxy-4-<3-{(4-fluorophenyl)-1-(thiophen-2-yl)ethylamino)]methyl}phenylamino>-3-cyclobutene-1,2-dione Following a similar procedure to that described in Example (1c), 320 mg of isomer A of 3-{(4-fluorophenyl)-[1-(thiophen-2-yl)ethylamino]methyl}phenylamine [prepared as described in step (b) above] and 431 mg of 4-t-butoxy-3-methoxy-3-cyclobutene-1,2-dione were reacted, to obtain 431 mg of isomer A of the title compound as a white foamy solid.

Isomer A

Nuclear Magnetic Resonance Spectrum (CDCl$_3$) δ ppm: 1.50 (3H, doublet, J=6.6 Hz); 1.64 (9H, singlet); 3.96 (1H, quartet, J=6.6 Hz); 4.79 (1H, singlet); 6.81 (1H, doublet, J=3.2 Hz); 6.91–6.96 (1H, multiplet); 6.95 (2H, triplet, J=8.3 Hz); 7.12–7.53 (7H, multiplet).

Following a similar procedure to that described in Example (1c), 280 mg of isomer B of 3-{(4-fluorophenyl)-[1-(thiophen-2-yl)ethylamino]methyl}phenylamine [prepared as described in step (b) above] and 190 mg of 4-t-butoxy-3-methoxy-3-cyclobutene-1,2-dione were reacted, to obtain 317 mg of isomer B of the title compound as a white foamy solid.

Isomer B

Nuclear Magnetic Resonance Spectrum (CDCl$_3$) δ ppm: 1.49 (3H, doublet, J=6.6 Hz); 1.63 (9H, singlet); 3.93 (1H, quartet, J=6.6 Hz); 4.79 (1H, singlet); 6.81 (1H, doublet, J=3.3 Hz); 6.95 (1H, doublet of doublets, J=3.4, 5.0 Hz); 7.03 (2H, triplet, J=6.5 Hz); 7.02–7.48 (7H, multiplet).

(83d) 4-<3-{(4-Fluorophenyl)-[1-(thiophen-2-yl)ethylamino]methyl}phenylamino>-3-hydroxy-3-cyclobutene-1,2-dione hydrochloride Following a similar procedure to that described in Example (63b), 351 mg of isomer A of 3-t-butoxy-4-<3-{(4-fluorophenyl)-[1-(thiophen-2-yl)ethylamino]methyl}phenylamino>-3-cyclobutene-1,2-dione [prepared as described in step (c) above] and 1.5 ml of trifluoroacetic acid were reacted, to obtain 282 mg of isomer A of the title compound as a white solid.

Isomer A

Nuclear Magnetic Resonance Spectrum (DMSO-d$_6$) δ ppm: 1.74 (3H, doublet, J=6.7 Hz); 4.59 (1H, quartet, J=6.7 Hz); 5.15 (1H, singlet); 7.10 (1H, doublet of doublets, J=3.7, 5.0 Hz); 7.15 (1H, doublet, J=3.5 Hz); 7.23–7.29 (3H, multiplet); 7.37 (1H, triplet, J=8.0 Hz); 7.45 (1H, doublet, J=8.0 Hz); 7.60–7.66 (2H, multiplet); 7.64 (2H, doublet of doublets, J=5.2, 8.8 Hz). mp: 183–190° C. (dec).

Following a similar procedure to that described in Example (63b), 285 mg of isomer B of 3-t-butoxy-4-<3-{(4-fluorophenyl)-[1-(thiophen-2-yl)ethylamino]methyl}phenylamino>-3-cyclobutene-1,2-dione [prepared as described in step (c) above] and 1.5 ml of trifluoroacetic acid were reacted, to obtain 225 mg of isomer B of the title compound as a white solid.

Isomer B

Nuclear Magnetic Resonance Spectrum (DMSO-d$_6$) δ ppm: 1.72 (3H, doublet, J=6.7 Hz); 4.50 (1H, quartet, J=6.7 Hz); 5.19 (1H, singlet); 7.10–7.16 (2H, multiplet); 7.23–7.43 (4H, multiplet); 7.46 (1H, doublet, J=7.5 Hz); 7.56 (1H, singlet); 7.67 (1H, doublet, J=5.2 Hz); 7.71 (2H, doublet of doublets J=5.5, 8.7 Hz). mp: 195–200° C. (dec).

EXAMPLE 84

4-<3-{[1-(3,5-Dimethoxyphenyl)ethylamino]-(4-fluorophenyl)methyl}phenylamino>-3-hydroxy-3-cyclobutene-1,2-dione hydrochloride (Compound No. 2-3501)

(84a) N-[1-(3,5-Dimethoxyphenyl)ethyl]-N-[(4-fluorophenyl)-(3-nitrophenyl)methyl]amine Following a similar procedure to that described in Example (1a), 1.72 g of 4-fluoro-3'-nitrobenzophenone, 2.73 g of 1-(3,5-dimethoxyphenyl)ethylamine hydrochloride, 5.8 ml of triethylamine and 0.9 ml of titanium tetrachloride were reacted, to obtain the corresponding imine compound.

Following a similar procedure to that described in Example (1a), the resulting imine compound, 1.76 g of sodium cyanoborohydride and 0.6 ml of acetic acid were reacted, to obtain 2.71 g of the title compound as a yellow oil.

Nuclear Magnetic Resonance Spectrum (CDCl$_3$) δ ppm: 1.37 and 1.38 (total 3H, each doublet, J=6.7 Hz); 3.52 and 3.59 (total 1H, each quartet, J=6.7 Hz); 3.78 (6H, singlet); 4.71 and 4.74 (total 1H, each singlet); 6.33 and 6.37 (total 1H, each doublet, J=2.3 Hz); 6.39 (2H, doublet, J=2.2 Hz); 6.96 and 7.04 (total 2H, each triplet, J=8.6 Hz); 7.22–7.33 (2H, multiplet); 7.40 and 7.49 (total 1H, each triplet, J=7.9 Hz); 7.56 and 7.67 (total 1H, each doublet, J=7.7 Hz); 8.10 and 8.12 (total 1H, each doublet, J=7.0 Hz); 8.25 and 8.26 (total 1H, each singlet).

(84b) 3-{[1-(3,5-Dimethoxyphenyl)ethylamino]-(4-fluorophenyl)methyl}phenylamine

Following a similar reaction, separation and purification procedure to that described in Example (59b), 2.70 g of N-[1-(3,5-dimethoxyphenyl)ethyl]-N-[(4-fluorophenyl)-(3-nitrophenyl)methyl]amine [prepared as described in step (a) above], 3.13 g of nickel chloride hexahydrate and 1.00 g of sodium borohydride were reacted, to obtain 892 mg of isomer A and 546 mg of isomer B of the title compound as pale yellow oils, respectively.

Isomer A

Nuclear Magnetic Resonance Spectrum (CDCl$_3$) δ ppm: 1.33 (3H, doublet, J=6.6 Hz); 3.64 (1H, quartet, J=6.6 Hz); 3.77 (6H, singlet); 4.53 (1H, singlet); 6.36 (1H, triplet, J=2.2 Hz); 6.43 (2H, doublet, J=2.2 Hz); 6.57 (1H, doublet, J=8.0 Hz); 6.64 (1H, singlet); 6.69 (1H, doublet, J=7.5 Hz); 6.92 (2H, triplet, J=8.7 Hz); 7.10 (1H, triplet, J=7.7 Hz); 7.24–7.28 (2H, multiplet).

Isomer B

Nuclear Magnetic Resonance Spectrum (CDCl$_3$) δ ppm: 1.34 (3H, doublet, J=6.7 Hz); 3.55 (1H, quartet, J=6.6 Hz); 3.77 (6H, singlet); 4.54 (1H, singlet); 6.36 (1H, triplet, J=1.5 Hz); 6.37 (2H, doublet, J=2.1 Hz); 6.50 (1H, doublet, J=7.5 Hz); 6.59 (1H, singlet); 6.65 (1H, doublet, J=7.7 Hz); 6.96–7.06 (3H, multiplet); 7.28–7.42 (2H, multiplet).

(84c) 3-t-Butoxy-4-<3-{[1-(3,5-dimethoxyphenyl)ethylamino]-(4-fluorophenyl)methyl}phenylamino>-3-cyclobutene-1,2-dione Following a similar procedure to that described in Example (1c), 708 mg of isomer A of 3-{[1-(3,5-dimethoxyphenyl)ethylamino]-(4-fluorophenyl)methyl}phenylamine [prepared as described in step (b) above] and 411 mg of 4-t-butoxy-3-methoxy-3-cyclobutene-1,2-dione were reacted, to obtain 953 mg of isomer A of the title compound as a white foamy solid.

Isomer A

Nuclear Magnetic Resonance Spectrum (CDCl$_3$) δ ppm: 1.36 (3H, doublet, J=6.7 Hz); 1.63 (9H, singlet); 3.60 (1H, quartet, J=6.5 Hz); 3.78 (6H, singlet); 4.63 (1H, singlet); 6.37 (1H, triplet, J=2.2 Hz); 6.40 (2H, doublet, J=2.2 Hz); 6.94 (2H, triplet, J=8.7 Hz); 7.05–7.11 (2H, multiplet); 7.22–7.49 (5H, multiplet).

Following a similar procedure to that described in Example (1c), 526 mg of isomer B of 3-{[1-(3,5-dimethoxyphenyl)ethylamino]-(4-fluorophenyl)methyl}phenylamine [prepared as described in step (b) above] and 306 mg of 4-t-butoxy- 3-methoxy-3-cyclobutene-1,2-dione were reacted, to obtain 673 mg of isomer B of the title compound as a white foamy solid.

Isomer B

Nuclear Magnetic Resonance Spectrum (CDCl$_3$) δ ppm: 1.36 (3H, doublet, J=6.6 Hz); 1.63 (9H, singlet); 3.56 (1H, quartet, J=6.6 Hz); 3.77 (6H, singlet); 4.63 (1H, singlet); 6.36 (1H, triplet, J=2.3 Hz); 6.38 (2H, doublet, J=2.2 Hz); 7.00–7.05 (3H, multiplet); 7.22–7.49 (5H, multiplet).

(84d) 4-<3-{[1-(3,5-Dimethoxyphenyl)ethylamino]-(4-fluorophenyl)methyl}phenylamino>-3-hydroxy-3-cyclobutene-1,2-dione hydrochloride Following a similar procedure to that described in Example (63b), 426 mg of isomer A of 3-t-butoxy-4-<3-{[1-(3,5-dimethoxyphenyl)ethylamino]-(4-fluorophenyl)methyl}phenylamino}-3-cyclobutene-1,2-dione [prepared as described in step (c) above] and 2 ml of trifluoroacetic acid were reacted, to obtain 371 mg of isomer A of the title compound as a white solid.

Isomer A

Nuclear Magnetic Resonance Spectrum (DMSO-d$_6$) δ ppm: 1.63 (3H, doublet, J=6.7 Hz); 3.72 (6H, singlet); 4.13–4.18 (1H, multiplet); 5.11 (1H, singlet); 6.51 (1H, doublet, J=2.0 Hz); 6.55 (2H, doublet, J=2.0 Hz); 7.17 (1H, doublet, J=7.7 Hz); 7.24 (2H, t, J=8.8 Hz); 7.34 (1H, triplet, J=7.8 Hz); 7.46 (1H, doublet, J=7.8 Hz); 7.58 (1H, singlet); 7.64 (2H, doublet of doublets, J=5.6, 8.7 Hz). mp: 191–194° C.

Following a similar procedure to that described in Example (63b), 338 mg of isomer B of 3-t-butoxy-4-<3-{[1-(3,5-dimethoxyphenyl)ethylamino]-(4-fluorophenyl)methyl}phenylamino>-3-cyclobutene-1,2-dione [prepared as described in step (c) above] and 1.5 ml of trifluoroacetic acid were reacted, to obtain 241 mg, of isomer B of the title compound as a white solid.
Isomer B
Nuclear Magnetic Resonance Spectrum (DMSO-$d_6$) δ ppm: 1.64 (3H, doublet, J=6.7 Hz); 3.74 (6H, singlet); 4.05 (1H, quartet, J=6.7 Hz); 5.13 (1H, singlet); 6.53 (1H, doublet, J=2.0 Hz); 6.57 (2H, doublet, J=2.1 Hz); 7.29 (2H, triplet, J=8.8 Hz); 7.29–7.40 (2H, multiplet); 7.41–7.44 (1H, multiplet); 7.52 (1H, singlet); 7.69 (2H, doublet of doublets, J=5.4, 8.6 Hz). mp: 189–192° C.

EXAMPLE 85

4-<3-{(4-Fluorophenyl)-[1-(3,4,5-trifluorophenyl)ethylamino]methyl}phenylamino>-3-hydroxy-3-cyclobutene-1,2-dione hydrochloride (Compound No. 2-3502)

(85a) N-[(4-Fluorophenyl)-(3-nitrophenyl)methyl]-N-[1-(3,4,5-trifluorophenyl)ethyl]amine Following a similar procedure to that described in Example (1a), 2.14 g of 4-fluoro-3'-nitrobenzophenone, 3.33 g of 1-(3,4,5-trifluorophenyl)ethylamine hydrochloride, 7.2 ml of triethylamine and 1.1 ml of titanium tetrachloride were reacted, to obtain the corresponding imine compound.

Following a similar reaction, separation and purification procedure to that described in Example (1a), the resulting imine compound, 2.19 g of sodium cyanoborohydride and 0.7 ml of acetic acid were reacted, to obtain 3.35 g of the title compound as a yellow oil.
Nuclear Magnetic Resonance Spectrum (CDCl$_3$) δ ppm: 1.34 and 1.36 (total 3H, each doublet, J=6.8 Hz); 3.56–3.64 (1H, multiplet); 4.65 and 4.70 (total 1H, each singlet); 6.83–6.91 (2H, multiplet); 6.98 and 7.07 (total 2H, each triplet, J=8.7 Hz); 7.20–7.27 (2H, multiplet); 7.43 and 7.52 (total 1H, each triplet, J=7.9 Hz); 7.56 and 7.62 (total 1H, each doublet, J=7.7 Hz); 8.08 and 8.14 (total 1H, each doublet, J=7.7 Hz); 8.21 and 8.23 (total 1H, each singlet).
(85b) 3-{(4-Fluorophenyl)-[1-(3,4,5-trifluorophenyl)ethylamino]methyl}phenylamine Following a similar reaction, separation and purification procedure to that described in Example (59b), 3.30 g of N-[(4-fluorophenyl)-(3-nitrophenyl)methyl]-N-[1-(3,4,5-trifluorophenyl)ethyl]amine [prepared as described in step (a) above], 3.96 g of nickel chloride hexahydrate and 1.25 g of sodium borohydride were reacted, to obtain 1.25 g of isomer A and 975 mg of isomer B of the title compound as pale yellow oils, respectively.
Isomer A
Nuclear Magnetic Resonance Spectrum (CDCl$_3$) δ ppm: 1.30 (3H, doublet, J=6.7 Hz); 3.65 (1H, quartet, J=6.7 Hz); 4.44 (1H, singlet); 6.65–6.64 (3H, multiplet); 6.90–7.00 (4H, multiplet); 7.13 (1H, triplet, J=7.8 Hz); 7.21–7.42 (2H, multiplet).
Isomer B
Nuclear Magnetic Resonance Spectrum (CDCl$_3$) δ ppm: 1.30 (3H, doublet, J=6.7 Hz); 3.57 (1H, quartet, J=6.7 Hz); 4.47 (1H, singlet); 6.53 (1H, doublet of doublets, J=1.4, 7.9 Hz); 6.58 (1H, doublet, J=1.8 Hz); 6.63 (1H, doublet, J=7.7 Hz); 6.88 (2H, triplet, J=7.5 Hz); 6.98–7.08 (3H, multiplet); 7.22–7.31 (2H, multiplet).
(85c) 3-t-Butoxy-4-<3-{(4-fluorophenyl)-[1-(3,4,5-trifluorophenyl)ethylamino]methyl}phenylamino>-3-cyclobutene-1,2-dione Following a similar procedure to that described in Example (1c), 450 mg of isomer A of 3-{(4-fluorophenyl)-[1-(3,4,5-trifluorophenyl)ethylamino]methyl}phenylamine [prepared as described in step (b) above] and 266 mg of 4-t-butoxy-3-methoxy-3-cyclobutene-1,2-dione were reacted, to obtain 953 mg of isomer A of the title compound as a white foamy solid.
Isomer A
Nuclear Magnetic Resonance Spectrum (CDCl$_3$) δ ppm: 1.34 (3H, doublet, J=6.6 Hz); 1.64 (9H, singlet); 3.63 (1H, quartet, J=6.6 Hz); 4.56 (1H, singlet); 6.91–7.04 (4H, multiplet); 7.22–7.46 (6H, multiplet).

Following a similar procedure to that described in Example (1c), 928 mg of isomer B of 3-{(4-fluorophenyl)-[1-(3,4,5-trifluorophenyl)ethylamino]methyl}phenylamine [prepared as described in step (b) above] and 548 mg of 4-t-butoxy-3-methoxy-3-cyclobutene-1,2-dione were reacted, to obtain 1.25 g of isomer B of the title compound as a white foamy solid.
Isomer B
Nuclear Magnetic Resonance Spectrum (CDCl$_3$) δ ppm: 1.33 (3H, doublet, J=6.6 Hz); 1.64 (9H, singlet); 3.59 (1H, quartet, J=6.6 Hz); 4.56 (1H, singlet); 6.90 (2H, doublet of doublets, J=6.6, 8.3 Hz); 7.04 (2H, triplet, J=8.7 Hz); 7.22–7.48 (6H, multiplet).
(85d) 4-<3-{(4-Fluorophenyl)-[1-(3,4,5-trifluorophenyl)ethylamino]methyl}phenylamino>-3-hydroxy-3-cyclobutene-1,2-dione hydrochloride Following a similar procedure to that described in Example (63b), 473 mg of isomer A of 3-t-butoxy-4-<3-{(4-fluorophenyl)-[1-(3,4,5-trifluorophenyl)ethylamino]methyl}phenylamino>-3-cyclobutene-1,2-dione [prepared as described in step (c) above] and 1 ml of trifluoroacetic acid were reacted, to obtain 350 mg of isomer A of the title compound as a white solid.
Isomer A
Nuclear Magnetic Resonance Spectrum (DMSO-$d_6$) δ ppm: 1.65 (3H, doublet, J=6.7 Hz); 4.32 (1H, quartet, J=6.5 Hz); 5.20 (1H, singlet); 7.20–7.26 (3H, multiplet); 7.34–7.46 (4H, multiplet); 7.56 (1H, singlet); 7.70 (2H, doublet of doublets, J=5.4, 8.5 Hz). mp: 189–193° C.

Following a similar procedure to that described in Example (63b), 509 mg of isomer B of 3-t-butoxy-4-<3-{(4-fluorophenyl)-[1-(3,4,5-trifluorophenyl)ethylamino]methyl}phenylamino>-3-cyclobutene-1,2-dione [prepared as described in step (c) above] and 1 ml of trifluoroacetic acid, 310 mg of isomer B of the title compound as a white solid.
Isomer B
Nuclear Magnetic Resonance Spectrum (DMSO-$d_6$) δ ppm: 1.64 (1H, doublet, J=6.7 Hz); 4.26 (1H, quartet, J=6.7 Hz); 5.26 (1H, singlet); 7.24 (2H, triplet, J=8.8 Hz); 7.32–7.46 (5H, multiplet); 7.53 (1H, singlet); 7.71 (2H, doublet of doublets, J=5.3, 8.6 Hz). mp: 192–197° C.

EXAMPLE 86

4-<3-{[1-(3,5-Dichlorophenyl)ethylamino]-(4-fluorophenyl)methyl}phenylamino>-3-hydroxy-3-cyclobutene-1,2-dione hydrochloride (Compound No. 2-3505)

(86a) N-[1-(3,5-Dichlorophenyl)ethyl]-N-[(4-fluorophenyl)-(3-nitrophenyl)methyl]amine Following a similar procedure to that described in Example (1a), 3.00 g of 4-fluoro-3'-nitrobenzophenone, 3.00 g of (1-(3,5-dichlorophenyl)ethylamine hydrochloride, 6.8 ml of triethylamine and 1.0 ml of titanium tetrachloride were reacted, to obtain the corresponding imine compound.

Following a similar reaction, separation and purification procedure to that described in Example (1a), the resulting imine compound, 2.07 g of sodium cyanoborohydride and 0.7 ml of acetic acid were reacted, to obtain 3.40 g of the title compound as a yellow oil.

Nuclear Magnetic Resonance Spectrum (CDCl$_3$) δ ppm: 1.37 and 1.38 (total 3H, each doublet, J=6.7 Hz); 3.50–3.66 (1H, multiplet); 4.67 and 4.71 (total 1H, each singlet); 6.96–7.17 (5H, multiplet); 7.21–7.42 (2H, multiplet); 7.42 and 7.52 (total 1H, each triplet, J=7.9 Hz); 7.58 and 7.64 (total 1H, each doublet, J=7.7 Hz); 8.06 and 8.13 (total 1H, each doublet, J=8.3 Hz); 8.20 and 8.24 (total 1H, each singlet).

(86b) 3-{[1-(3,5-Dichlorophenyl)ethylamino]-(4-fluorophenyl)methyl}phenylamine

Following, a similar reaction, separation and purification procedure to that described in Example (59b), 3.39 g of N-[1-(3,5-dichlorophenyl)ethyl]-N-[(4-fluorophenyl)-(3-nitrophenyl)methyl]amine [prepared as described in step (a) above], 3.86 g of nickel chloride hexahydrate and 1.23 g of sodium borohydride were reacted, to obtain 970 mg of isomer A and 567 mg of isomer B of the title compound as a pale yellow oil and a white solid, respectively.

Isomer A

Nuclear Magnetic Resonance Spectrum (CDCl$_3$) δ ppm: 1.33 (3H, doublet, J=6.6 Hz); 3.66 (1H, quartet, J=6.5 Hz); 4.47 (1H, singlet); 6.58–6.60 (2H, multiplet); 6.66 (1H, doublet, J=7.6 Hz); 6.93 (2H, triplet, J=8.7 Hz); 7.10–7.15 (2H, multiplet); 7.16 (2H, doublet, J=1.8 Hz); 7.22–7.39 (2H, multiplet).

Isomer B

Nuclear Magnetic Resonance Spectrum (CDCl$_3$) δ ppm: 1.32 (3H, doublet, J=6.7 Hz); 3.58 (1H, quartet, J=6.7 Hz); 4.49 (1H, singlet); 6.52 (1H, doublet of doublets, J=2.4, 8.0 Hz); 6.59 (1H, doublet, J=2.0 Hz); 6.64 (1H, doublet, J=7.6 Hz); 6.90–7.14 (3H, multiplet); 7.21 (2H, doublet, J=1.9 Hz); 7.23–7.31 (3H, multiplet).

(86c) 3-t-Butoxy-4-<3-{[1-(3,5-dichlorophenyl)ethylamino]-(4-fluorophenyl)methyl}phenylamino>-3-cyclobutene-1,2-dione Following a similar procedure to that described in Example (1c), 491 mg of isomer A of 3-{[1-(3,5-dichlorophenyl)ethylamino]-(4-fluorophenyl)methyl}phenylamine [prepared as described in step (b) above] and 279 mg of 4-t-butoxy-3-methoxy-3-cyclobutene-1,2-dione were reacted, to obtain 400 mg of isomer A of the title compound as a white solid.

Isomer A

Nuclear Magnetic Resonance Spectrum (CDCl$_3$) δ ppm: 1.36 (3H, doublet, J=6.6 Hz); 1.64 (9H, singlet); 3.64 (1H, quartet, J=6.8 Hz); 4.58 (1H, singlet); 6.95 (2H, triplet, J=8.6 Hz); 7.04 (1H, doublet, J=7.3 Hz); 7.13 (2H, doublet, J=1.9 Hz); 7.22–7.44 (6H, multiplet).

Following a similar procedure to that described in Example (1c), 535 mg of isomer B of 3-{[1-(3,5-dichlorophenyl)ethylamino]-(4-fluorophenyl)methyl}phenylamine [prepared as described in step (b) above] and 304 mg of 4-t-butoxy-3-methoxy-3-cyclobutene-1,2-dione were reacted, to obtain 646 mg of isomer B of the title compound as a white foamy solid.

Isomer B

Nuclear Magnetic Resonance Spectrum (CDCl$_3$) δ ppm: 1.35 (3H, doublet, J=6.7 Hz); 1.64 (9H, singlet); 3.61 (1H, quartet, J=6.7 Hz); 4.59 (1H, singlet); 7.00–7.06 (1H, multiplet); 7.04 (2H, triplet, J=8.7 Hz); 7.12 (2H, doublet, J=1.8 Hz); 7.21–7.38 (6H, multiplet).

(86d) 4-<3-{[1-(3,5-Dichlorophenyl)ethylamino]-(4-fluorophenyl)methyl}phenylamino>-3-hydroxy-3-cyclobutene-1,2-dione hydrochloride Following a similar procedure to that described in Example (63b), 391 mg of isomer A of 3-t-butoxy-4-<3-{[1-(3,5-dichlorophenyl)ethylamino]-(4-fluorophenyl)methyl}phenylamino>-3-cyclobutene-1,2-dione [prepared as described in step (c) above] and 1 ml of trifluoroacetic acid were reacted, to obtain 326 mg of isomer A of the title compound as a white solid.

Isomer A

Nuclear Magnetic Resonance Spectrum (DMSO-d$_6$) δ ppm: 1.63 (3H, doublet, J=6.7 Hz); 4.32 (1H, quartet, J=6.8 Hz); 5.31 (1H, singlet); 7.21–7.25 (3H, multiplet); 7.35 (1H, doublet, J=7.8 Hz); 7.42–7.45 (1H, multiplet); 7.47 (2H, doublet, J=1.5 Hz); 7.58–7.70 (4H, multiplet). mp: 189–192° C.

Following a similar procedure to that described in Example (63b), 605 mg of isomer B of 3-t-butoxy-4-<3-{[1-(3,5-dichlorophenyl)ethylamino]-(4-fluorophenyl)methyl}phenylamino>-3-cyclobutene-1,2-dione [prepared as described in step (c) above] and 1.5 ml of trifluoroacetic acid were reacted, to obtain 498 mg of isomer B of the title compound as a white solid.

Isomer B

Nuclear Magnetic Resonance Spectrum (DMSO-d$_6$) δ ppm: 1.64 (3H, doublet, J=6.7 Hz); 4.28 (1H, quartet, J=6.7 Hz); 5.34 (1H, singlet); 7.27–7.42 (5H, multiplet); 7.48–7.56 (3H, multiplet); 7.64 (1H, triplet, J=1.9 Hz); 7.70 (2H, doublet of doublets, J=5.3, 8.7 Hz). mp: 193–198° C.

EXAMPLE 87

4-{3-[[1-(3,4-Difluorophenyl)propylamino]-(4-methoxyphenyl)methyl]phenylamino>-3-hydroxy-3-cyclobutene-1,2-dione hydrochloride (Compound No. 2-42)

(87a) N-[1-(3,4-Difluorophenyl)propyl]-N-[(4-methoxyphenyl)-(3-nitrophenyl)methyl]amine Following a similar procedure to that described in Example (1 a), 2.00 g of 4-methoxy-3'-nitrobenzophenone, 2.75 g of 1-(3,4-difluorophenyl)propylamine hydrochloride, 6.5 ml of triethylamine and 1.0 ml of titanium tetrachloride were reacted, to obtain the corresponding imine compound.

Following a similar reaction, separation and purification procedure to that described in Example (1a), the resulting imine compound, 1.97 g of sodium cyanoborohydride and 0.7 ml of acetic acid were reacted, to obtain 3.18 g of the title compound as a yellow oil.

Nuclear Magnetic Resonance Spectrum (CDCl$_3$) δ ppm: 0.80 and 0.86 (total 3H, each triplet, J=7.4 Hz); 1.55–1.82 (2H, multiplet); 3.31 and 3.38 (total 1H, each triplet, J=6.9 Hz); 3.76 and 3.82 (total 3H, each singlet); 4.57 and 4.62 (total 1H, each singlet); 6.80 and 6.90 (total 2H, each doublet, J=8.7 Hz); 6.82–7.17 (5H, multiplet); 7.38 and 7.48 (total 1H, each triplet, J=7.9 Hz); 7.57 and 7.64 (total 1H, each doublet, J=7.8 Hz); 8.03 and 8.09 (total 1H, each doublet, J=8.3 Hz); 8.20 and 8.25 (total 1H, each singlet).

(87b) 3-{[1-(3,4-Difluorophenyl)propylamino]-(4-methoxyphenyl)methyl}phenylamine Following a similar procedure to that described in Example (1b), 3.17 go N-[1-(3,4-difluorophenyl)propyl]-N-[(4-methoxyphenyl)-(3-nitrophenyl)methyl]amine [prepared as described in step (a) above], 3.66 g, of nickel chloride hexahydrate and 1.17 g of sodium borohydride were reacted, to obtain 2.76 of the title compound as a pale yellow oil.

Nuclear Magnetic Resonance Spectrum (CDCl$_3$) δ ppm: 0.89 (3H, triplet, J=6.6 Hz); 1.51–1.76 (2H, multiplet); 3.34 and 3.41 (total 1H, each triplet, J=6.6 Hz); 3.75 and 3.80 (total 3H, each singlet); 4.40 (1H, singlet); 6.48–6.68 (3H, multiplet); 6.77 and 6.86 (total 2H, each doublet, J=8.8 Hz); 6.83–6.94 (5H, multiplet); 7.00–7.19 (5H, multiplet).

(87c) 3-t-Butoxy-4-<3-{[1-(3,4-difluorophenyl)propylamino]-(4-methoxyphenyl)methyl}phenylamino>-3-cyclobutene-1,2-dione Following a similar reaction, separation and purification procedure to that described in Example (66c), 2.70 g of 3-{[1-(3,4-difluorophenyl)propylamino]-(4-methoxyphenyl)methyl}phenylamine [prepared as described in step (b) above] and 1.56 g of 4-t-butoxy-3-methoxy-3-cyclobutene-1,2-dione were reacted, to obtain 652 mg of isomer A and 657 mg of isomer B of the title compound, respectively, each as a white foamy solid.

Isomer A

Nuclear Magnetic Resonance Spectrum (CDCl$_3$) δ ppm: 0.88 (3H, triplet, J=6.8 Hz); 1.51–1.90 (2H, multiplet); 1.63 (9H, singlet); 3.38 (1H, triplet, J=6.7 Hz); 3.75 (3H, singlet); 4.50 (1H, singlet); 6.79 (2H, doublet, J=8.4 Hz); 6.85–7.03 (1H, multiplet); 7.16 (2H, doublet, J=8.5 Hz); 7.03–7.36 (6H, multiplet).

Isomer B

Nuclear Magnetic Resonance Spectrum (CDCl$_3$) δ ppm: 0.86 (3H, triplet, J=7.5 Hz); 1.51–1.83 (2H, multiplet); 1.68 (9H, singlet); 3.41 (1H, triplet, J=6.8 Hz); 3.86 (3H, singlet); 4.53 (1H, singlet); 6.93 (2H, doublet, J=8.7 Hz); 6.90–6.98 (1H, multiplet); 7.24 (2H, doublet, J=8.6 Hz); 7.04–7.37 (6H, multiplet).

(87d) 4-<3-{[1-(3,4-Difluorophenyl)propylamino]-(4-methoxyphenyl)methyl}phenylamino>-3-hydroxy-3-cyclobutene-1,2-dione hydrochloride Following a similar procedure to that described in Example (63b), 622 mg of isomer A of 3-t-butoxy-4-<3-{[1-(3,4-difluorophenyl)propylamino]-(4-methoxyphenyl)methyl}phenylamino>-3-cyclobutene-1,2-dione [prepared as described in step (c) above] and 1.5 ml of trifluoroacetic acid were reacted, to obtain 482 mg of isomer A of the title compound as a white solid.

Isomer A

Nuclear Magnetic Resonance Spectrum (DMSO-d$_6$) δ ppm: 0.60 (3H, triplet, J=7.4 Hz); 1.87–1.99 (1H, multiplet); 2.32–2.38 (1H, multiplet); 3.73 (3H, singlet); 4.03–4.13 (1H, multiplet); 4.98 (1H, singlet); 6.93 (2H, doublet, J=8.7 Hz); 7.07–7.09 (2H, multiplet); 7.31 (1H, triplet, J=7.9 Hz); 7.43–7.54 (4H, multiplet); 7.46 (2H, doublet, J=8.6 Hz). mp: 185–188° C. (dec).

Following a similar procedure to that described in Example (63b), 626 mg of isomer B of 3-t-butoxy-4-<3-{[1-(3,4-difluorophenyl)propylamino]-(4-methoxyphenyl)methyl}phenylamino>-3-cyclobutene-1,2-dione [prepared as described in step (c) above] and 1.5 ml of trifluoroacetic acid were reacted, to obtain 498 mg of isomer B of the title compound as a white solid.

Isomer B

Nuclear Magnetic Resonance Spectrum (DMSO-d$_6$) δ ppm: 0.57 (3H, triplet, J=7.4 Hz); 1.88–1.98 (1H, multiplet); 2.34–2.42 (1H, multiplet); 3.77 (3H, singlet); 3.92 (1H, doublet, J=10.5 Hz); 5.00 (1H, singlet); 6.99 (2H, doublet, J=8.7 Hz); 7.14–7.16 (1H, multiplet); 7.32–7.56 (6H, multiplet); 7.52 (2H, doublet, J=8.9 Hz). mp: 188–192° C. (dec).

EXAMPLE 88

4-<3-{[1-(3,4-Difluorophenyl)ethylamino]-(4-fluorophenyl)methyl}-4-methoxyphenylamino>-3-hydroxy-3-cyclobutene-1,2-dione (Compound No. 2-3376)

(88a) N-[1-(3,4-Difluorophenyl)ethyl]-N-[(4-fluorophenyl)-(2-methoxy-5-nitrophenyl)methyl]amine Following a similar procedure to that described in Example (1a), 3.11 g of 4-fluoro-2'-methoxy-5'-nitrobenzophenone, 2.73 g of 1-(3,4-difluorophenyl)ethylamine hydrochloride, 5.8 ml of triethylamine and 0.9 ml of titanium tetrachloride were reacted, to obtain the corresponding imine compound.

Following a similar reaction, separation and purification procedure to that described in Example (1a), the resulting imine compound, 1.76 g of sodium cyanoborohydride and 0.6 ml of acetic acid were reacted, to obtain 1.62 g of isomer A and 2.19 g of isomer B of the title compound as white solids, respectively.

Isomer A

Nuclear Magnetic Resonance Spectrum (CDCl$_3$) δ ppm: 1.36 (3H, doublet, J=6.7 Hz); 3.60 (1H, quartet, J=6.6 Hz); 3.79 (3H, singlet); 4.89 (1H, singlet); 6.90–6.95 (3H, multiplet); 7.05–7.15 (2H, multiplet); 7.20–7.33 (3H, multiplet); 8.20 (1H, doublet of doublets, J=2.9, 7.8 Hz); 8.48 (1H, doublet, J=2.8 Hz).

Isomer B

Nuclear Magnetic Resonance Spectrum (CDCl$_3$) δ ppm: 1.34 (3H, doublet, J=6.7 Hz); 3.63 (1H, quartet, J=6.6 Hz); 3.81 (3H, singlet); 4.91 (1H, singlet); 6.83 (1H, doublet, J=9.0 Hz); 6.87–6.92 (1H, multiplet); 6.98–7.11 (4H, multiplet); 7.24–7.28 (2H, multiplet); 8.12 (1H, doublet of doublet s, J=2.9, 9.1 Hz); 8.30 (1H, doublet, J=2.8 Hz).

(88b) 3-{[1-(3,4-Difluorophenyl)ethylamino]-(4-fluorophenyl)methyl}-4-methoxyphenylamine Following a similar procedure to that described in Example (1b), 700 mg of isomer A of N-[1-(3,4-difluorophenyl)ethyl]-N-[(4-fluorophenyl)-(2-methoxy- 5 nitrophenyl)methyl]amine [prepared as described in step (a) above], 800 mg of nickel chloride hexahydrate and 258 mg of sodium borohydride were reacted, to obtain 532 mg of isomer A of the title compound as a pale yellow oil.

Isomer A

Nuclear Magnetic Resonance Spectrum (CDCl$_3$) δ ppm: 1.30 (3H, doublet, J=6.6 Hz); 3.58 (3H, singlet); 3.66 (1H, quartet, J=6.6 Hz); 4.72 (1H, singlet); 6.59–6.68 (2H, multiplet); 6.72 (1H, doublet, J=8.4 Hz); 6.91 (2H, triplet, J=8.7 Hz); 6.96–7.18 (3H, multiplet); 7.24–7.38 (2H, multiplet).

Following a similar procedure to that described in Example (1b), 660 mg of isomer B of N-[1-(3,4-difluorophenyl)ethyl]-N-[(4-fluorophenyl)-(2-methoxy-5-nitrophenyl)methyl]amine [prepared as described in step (a) above], 762 mg of nickel chloride hexahydrate and 243 mg of sodium borohydride were reacted, to obtain 332 mg of isomer B of the title compound as a pale yellow oil.

Isomer B

Nuclear Magnetic Resonance Spectrum (CDCl$_3$) δ ppm: 1.32 (3H, doublet, J=6.7 Hz); 3.60–3.71 (1H, multiplet); 3.64 (3H, singlet); 4.88 (1H, singlet); 6.50–6.67 (2H, multiplet); 6.65 (1H, doublet, J=8.0 Hz); 6.85–6.92 (1H, multiplet); 6.95–7.18 (4H, multiplet); 7.28–7.35 (2H, multiplet).

(88c) 3-t-Butoxy-4-<3-{[1-(3,4-difluorophenyl)ethylamino]-(4-fluorophenyl)methyl}-4-methoxyphenylamino>-3-cyclobutene-1,2-dione Following a similar procedure to that described in Example (1c), 526 mg of isomer A of 3-{[1-(3,4-difluorophenyl)ethylamino]-(4-fluorophenyl)methyl}-4-methoxyphenylamine [prepared as described in step (b) above] and 351 mg of 4-t-butoxy-3-methoxy-3-cyclobutene-1,2-dione were reacted, to obtain 588 mg of isomer A of the title compound as a white foamy solid.

Isomer A
Nuclear Magnetic Resonance Spectrum (CDCl$_3$) δ ppm: 1.34 (3H, doublet, J=6.6 Hz); 1.63 (9H, singlet); 3.64 (1H, quartet, J=6.5 Hz); 3.68 (3H, singlet); 4.86 (1H, singlet); 6.85 (1H, doublet, J=8.7 Hz); 6.92 (2H, triplet, J=8.8 Hz); 6.93–6.99 (1H, multiplet); 7.08–7.42 (6H, multiplet).

Following a similar procedure to that described in Example (1c), 324 mg of isomer B of 3-{[1-(3,4-difluorophenyl)ethylamino]-(4-fluorophenyl)methyl}-4-methoxyphenylamine [prepared as described in step (b) above] and 232 mg of 4-t-butoxy-3-methoxy-3-cyclobutene-1,2-dione were reacted, to obtain 407 mg of isomer B of the title compound as a white foamy solid.

Isomer B
Nuclear Magnetic Resonance Spectrum (CDCl$_3$) δ ppm: 1.33 (3H, doublet, J=6.6 Hz); 1.63 (9H, singlet); 3.62 (1H, quartet, J=6.0 Hz); 3.72 (3H, singlet); 4.92 (1H, singlet); 6.79 (1H, doublet, J=8.6 Hz); 6.86–6.93 (1H, multiplet); 7.01 (2H, triplet, J=8.4 Hz); 7.01–7.37 (6H, multiplet).

(88d) 4-<3-{[1-(3,4-Difluorophenyl)ethylamino]-(4-fluorophenyl)methyl}-4-methoxyphenylamino>-3-hydroxy-3-cyclobutene-1,2-dione Following a similar procedure to that described in Example (55b), 560 mg of isomer A of 3-t-butoxy-4-<3-{[1-(3,4-difluorophenyl)ethylamino]-(4-fluorophenyl)methyl}-4-methoxyphenylamino>-3-cyclobutene-1,2-dione [prepared as described in step (c) above] and 1.5 ml of trifluoroacetic acid were reacted, to obtain 425 mg of isomer A of the title compound as a white solid.

Isomer A
Nuclear Magnetic Resonance Spectrum (DMSO-d$_6$) δ ppm: 1.35 (3H, broad); 3.34–3.75 (1H, multiplet); 3.55 (3H, singlet); 4.80 (1H, broad); 6.84 (1H, doublet, J=8.8 Hz); 7.05–7.15 (3H, multiplet); 7.25–7.41 (4H, multiplet); 7.47 (1H, doublet, J=8.8 Hz); 7.83 (1H, singlet). mp: 191° C. (dec).

Following a similar procedure to that described in Example (55b), 402 mg of isomer B of 3-t-butoxy-4-<3-{[1-(3,4-difluorophenyl)ethylamino]-(4-fluorophenyl)methyl}- 4-methoxyphenylamino>-3-cyclobutene-1,2-dione [prepared as described in step (c) above] and 1 ml of trifluoroacetic acid were reacted, to obtain 153 mg of isomer B of the title compound as a white solid.

Isomer B
Nuclear Magnetic Resonance Spectrum (DMSO-d$_6$) δ ppm: 1.31 (3H, broad); 3.34–3.64 (1H, multiplet); 3.62 (3H, singlet); 4.89 (1H, broad); 6.78–6.80 (1H, multiplet); 7.05–7.18 (3H, multiplet); 7.31–7.58 (5H, multiplet); 7.63 (1H, singlet). mp: 230° C. (dec).

EXAMPLE 89

4-<5-{[1-(3,4-Difluorophenyl)ethylamino]-(4-fluorophenyl)methyl}-2,3-dimethoxyphenylamino}>-3-hydroxy-3-cyclobutene-1,2-dione (Compound No. 2-3377)

(89a) N-[1-(3,4-Difluorophenyl)ethyl]-N-[(4-fluorophenyl)-(3,4-dimethoxy-5-nitrophenyl)methyl]amine Following a similar procedure to that described in Example (1a), 2.47 g of 4-fluoro-3',4'-dimethoxy-5'-nitrobenzophenone, 2.83 g of 1-(3,4-difluorophenyl)ethylamine hydrochloride, 5.6 ml of triethylamine and 1.0 ml of titanium tetrachloride were reacted, to obtain the corresponding, imine compound.

Following a similar reaction, separation and purification procedure to that described in Example (1a), the resulting imine compound, 2.04 g of sodium cyanoborohydride and 0.7 ml of acetic acid, were reacted, to obtain 3.42 g of the title compound as a yellow oil.

Nuclear Magnetic Resonance Spectrum (CDCl$_3$) δ ppm: 1.34 and 1.36 (total 3H, each doublet, J=6.7 Hz); 3.58–3.67 (1H, multiplet); 3.82, 3.88, 3.92 and 3.97 (total 6H, each singlet); 4.54 (1H, singlet); 6.85–7.39 (9H, multiplet).

(89b) 5-{[1-(3,4-Difluorophenyl)ethylamino]-(4-fluorophenyl)methyl}-2,3-dimethoxyphenylamine Following a similar reaction, separation and purification procedure to that described in Example (59b), 3.42 g of N-[1-(3,4-difluorophenyl)ethyl]-N-[(4-fluorophenyl)-(3,4-dimethoxy-5-nitrophenyl)methyl]amine [prepared as described in step (a) above], 3.65 g of nickel chloride hexahydrate and 1.17 g of sodium borohydride were reacted, to obtain 1.10 g of isomer A and 1.39 g of isomer B of the title compound as pale yellow oils, respectively.

Isomer A
Nuclear Magnetic Resonance Spectrum (CDCl$_3$) δ ppm: 1.32 (3H, doublet, J=6.7 Hz); 3.68 (1H, quartet, J=6.6 Hz); 3.80 (3H, singlet); 3.82 (3H, singlet); 4.38 (1H, singlet); 6.22 (1H, doublet, J=1.8 Hz); 6.30 (1H, doublet, J=1.9 Hz); 6.93 (2H, triplet, J=8.8 Hz); 6.90–6.97 (1H, multiplet); 7.07–7.18 (2H, multiplet); 7.22–7.28 (2H, multiplet).

Isomer B
Nuclear Magnetic Resonance Spectrum (CDCl$_3$) δ ppm: 1.32 (3H, doublet, J=6.7 Hz); 3.58 (1H, quartet, J=6.7 Hz); 3.76 (6H, singlet); 4.41 (1H, singlet); 6.22 (1H, doublet, J=1.4 Hz); 6.28 (1H, doublet, J=1.4 Hz); 6.88–6.92 (1H, multiplet); 7.01 (2H, triplet, J=8.7 Hz); 7.05–7.11 (2H, multiplet); 7.24–7.28 (2H, multiplet).

(89c) 3-t-Butoxy-4-<5-{[1-(3,4-difluorophenyl)ethylamino]-(4-fluorophenyl)methyl}-2,3-dimethoxyphenylamino>-3-cyclobutene-1,2-dione Following a similar procedure to that described in Example (1c), 637 mg of isomer A of 5-{[1-(3,4-difluorophenyl)ethylamino]-(4-fluorophenyl)methyl}-2,3-dimethoxyphenylamine [prepared as described in step (b) above] and 338 mg of 4-t-butoxy-3-methoxy-3-cyclobutene-1,2-dione were reacted, to obtain 690 mg of isomer A of the title compound as a white foamy solid.

Isomer A
Nuclear Magnetic Resonance Spectrum (CDCl$_3$) δ ppm: 1.37 (3H, doublet, J=4.7 Hz); 1.63 (9H, singlet); 3.65–3.74 (1H, multiplet); 3.84 (3H, singlet); 3.94 (3H, singlet); 4.49 (1H, singlet); 6.73–6.78 (1H, multiplet); 6.92–7.01 (3H, multiplet); 7.08–7.16 (2H, multiplet); 7.21–7.39 (3H, multiplet).

Following a similar procedure to that described in Example (1c), 660 mg of isomer B of 5-{[1-(3,4-difluorophenyl)ethylamino]-(4-fluorophenyl)methyl}-2,3-dimethoxyphenylamine [prepared as described in step (b) above] and 350 mg of 4-t-butoxy-3-methoxy-3-cyclobutene-1,2-dione were reacted, to obtain 602 mg of isomer B of the title compound as a white foamy solid.

Isomer B
Nuclear Magnetic Resonance Spectrum (CDCl$_3$) δ ppm: 1.38 (3H, doublet, J=6.7 Hz); 1.68 (9H, singlet); 3.64 (1H, quartet, J=6.8 Hz); 3.81 (3H, singlet); 3.90 (3H, singlet); 4.55 (1H, singlet); 6.53 (1H, broad); 6.94–7.00 (1H, multiplet); 7.03–7.13 (2H, multiplet); 7.05 (2H, triplet, J=8.7 Hz); 7.31–7.38 (2H, multiplet); 7.60–7.71 (1H, multiplet).

(89d) 4-<5-{[1-(3,4-Difluorophenyl)ethylamino]-(4-fluorophenyl)methyl}-2,3-dimethoxyphenylamino>-3-hydroxy-3-cyclobutene-1,2-dione Following a similar procedure to that described in Example (55b), 688 mg of isomer A of 3-t-butoxy-4-<5-{[1-(3,4-difluorophenyl)ethylamino]-(4-fluorophenyl)methyl}-2,3-dimethoxyphenylamino>-3-cyclobutene-1,2- dione [prepared as described in step (c) above] and 1 ml of trifluoroacetic acid were reacted, to obtain 350 mg of isomer A of the title compound as a white solid.
Isomer A Nuclear Magnetic Resonance Spectrum (DMSO-$d_6$) δ ppm: 1.30 (3H, broad); 3.33 (1H, broad); 3.76 (6H, singlet); 4.38 (1H, broad); 6.63 (1H, singlet); 7.02–7.13 (3H, multiplet); 7.31–7.51 (4H, multiplet); 7.94 (1H, singlet). mp: 188° C. (dec).

Following a similar procedure to that described in Example (55b), 595 mg of isomer B of 3-t-butoxy-4-<5-{[1-(3,4-difluorophenyl)ethylamino]-(4-fluorophenyl) methyl}-2,3-dimethoxyphenylamino>-3-cyclobutene-1,2-dione [prepared as described in step (c) above] and 1 ml of trifluoroacetic acid were reacted, to obtain 360 mg of isomer B of the title compound as a white solid.
Isomer B Nuclear Magnetic Resonance Spectrum (DMSO-$d_6$) δ ppm: 1.30 (3H, broad); 3.33 (1H, broad); 3.71 (6H, singlet); 4.44 (1H, broad); 6.57 (1H, singlet); 7.06–7.18 (3H, multiplet); 7.28–7.51 (4H, multiplet); 7.93 (1H, singlet). mp: 195° C. (dec).

EXAMPLE 90

4-<3-{[1-(3,4-Difluorophenyl)ethylamino]-(4-methoxyphenyl)methyl}benzylamino>-3-hydroxy-3-cyclobutene-1,2-dione (Compound No. 2-117)

(90a) 3-t-Butoxy-4-<3-{[1-(3,4-difluorophenyl) ethylamino]-(4-methoxyphenyl)methyl}benzylamino>-3-cyclobutene-1,2-dione 684 mg of 4-t-butoxy-3-methoxy-3-cyclobutene-1,2-dione were added to 1.47 g of N-[(3-aminomethylphenyl)-(4-methoxyphenyl)methyl]-N-[1-(3,4-difluorophenyl)ethyl] amine dihydrochloride [prepared as described in Example 41(b)], 0.8 ml of triethylamine and 30 ml of methanol were added, and then the mixture was stirred for 2 hours at ambient temperature. After neutralization with hydrochloric acid, the reaction mixture was concentrated by evaporation under reduced pressure. The residue was extracted with ethyl acetate. The organic extract was washed with water and with a saturated aqueous solution of sodium chloride, dried over sodium sulfate and concentrated by evaporation under reduced pressure. The residue was purified by chromatography through a silica gel column using a 2:1 by volume mixture of hexane and ethyl acetate as eluant, to obtain 1.09 g of the title compound as a white foamy solid.

Nuclear Magnetic Resonance Spectrum (CDCl$_3$) δ ppm: 1.32 (3H, doublet, J=6.7 Hz); 1.59 (9H, singlet); 3.54–3.67 (1H, multiplet); 3.76 and 3.81 (total 3H, each singlet); 4.52 and 4.56 (total 1H, each singlet); 4.58, 4.74 and 4.81 (total 2H, each broad); 6.79 and 6.87 (total 2H, each doublet, J=8.7 Hz); 6.85–6.93 (1H, multiplet); 7.05–7.38 (8H, multiplet).

(90b) 4-<3-{[1-(3,4-Difluorophenyl)ethylamino]-(4-methoxyphenyl)methyl}benzylamino>-3-hydroxy-3-cyclobutene-1,2-dione Following a similar procedure to that described in Example (55d), 1.08 g of 3-t-butoxy-4-<3-{[1-(3,4-difluorophenyl)ethylamino]-(4-methoxyphenyl) methyl>benzylamino>-3-cyclobutene-1,2-dione [prepared as described in step (a) above] were reacted, to obtain 889 mg of the title compound as a white solid.

Nuclear Magnetic Resonance Spectrum (DMSO-$d_6$) δ ppm: 1.49 (3H, broad); 3.70–4.08 (1H, multiplet); 3.72 and 3.74 (total 3H, each singlet); 4.59 and 4.61 (total 1H, each singlet); 4.71 and 5.00 (total 2H, each broad); 6.90 and 6.94 (total 2H, each doublet, J=8.7 Hz); 7.04–7.16 (1H, multiplet); 7.23–7.82 (6H, multiplet); 7.41 and 7.45 (total 2H, each doublet, J=8.8 Hz). mp: 180–184° C.

EXAMPLE 91

4-(4-{[1-(3,4-Difluorophenyl)ethylamino]-(4-methoxyphenyl)methyl}benzylamino>-3-hydroxy-3-cyclobutene-1,2-dione (Compound No. 3-47)

(91a) 3-t-Butoxy-4->4-{[1-(3,4-difluorophenyl) ethylamino]-(4-methoxyphenyl)methyl}benzylamino>-3-cyclobutene-1,2-dione Following a similar reaction, separation and purification procedure to that described in Example (90a), 1.88 g of N-[(4-aminomethylphenyl)-(4-methoxyphenyl)methyl]-N-[1-(3,4-difluorophenyl)ethyl]amine dihydrochloride [prepared as described in Example 43(b)], 3.3 ml of triethylamine and 883 mg of 4-t-butoxy- 3-methoxy-3-cyclobutene-1,2-dione were reacted, to obtain 645 mg of isomer A and 712 mg, of isomer B of the title compound as white foamy solids, respectively.
Isomer A Nuclear Magnetic Resonance Spectrum (CDCl$_3$) δ ppm: 1.32 (3H, doublet, J=6.7 Hz); 1.59 (9H, singlet); 3.60 (1H, quartet, J=6.7 Hz); 3.75 (3H, singlet); 4.55 (1H, singlet); 4.62 (1H, broad); 4.82 (1H, broad); 6.79 (2H, doublet, J=8.6 Hz); 6.90–6.97 (1H, multiplet); 7.08–7.36 (8H, multiplet).
Isomer B Nuclear Magnetic Resonance Spectrum (CDCl$_3$) δ ppm: 1.32 (3H, doublet, J=6.7 Hz); 1.57 (9H, singlet); 3.64 (1H, quartet, J=6.6 Hz); 3.80 (3H, singlet); 4.54 (1H, singlet); 4.65 (1H, broad); 4.76 (1H, broad); 6.87 (2H, doublet, J=8.6 Hz); 6.92–6.98 (1H, multiplet); 7.08–7.42 (8H, multiplet).

(91b) 4-<4-{[1-(3,4-Difluorophenyl)ethylamino]-(4-methoxyphenyl)methyl}benzylamino>-3-hydroxy-3-cyclobutene-1,2-dione Following a similar procedure to that described in Example (55b), 622 mg of isomer A of 3-t-butoxy-4-<4-{[1-(3,4-difluorophenyl)ethylamino]-(4-methoxyphenyl) methyl}benzylamino>-3-cyclobutene-1,2-dione [prepared as described in step (a) above] was reacted, to obtain 168 mg of the title compound as a white solid.
Isomer A Nuclear Magnetic Resonance Spectrum (DMSO-$d_6$) δ ppm: 1.43 (3H, broad); 3.53–3.70 (1H, multiplet); 3.80 (3H, singlet); 4.42–4.58 (2H, broad); 4.55 (1H, singlet); 6.82 (2H, doublet, J=7.0 Hz); 7.00–7.08 (1H, multiplet); 7.18–7.48 (8H, multiplet). mp: 188° C. (dec).

Following a similar procedure to that described in Example (55b), 705 mg of isomer B of 3-t-butoxy-4-<4-{[1-(3,4-difluorophenyl)ethylamino]-(4-methoxyphenyl) methyl}benzylamino>-3-cyclobutene-1,2-dione [prepared as described in step (a) above] was reacted, to obtain 266 mg of the title compound as a white solid.
Isomer B Nuclear Magnetic Resonance Spectrum (DMSO-$d_6$) δ ppm: 1.46 (3H, broad); 3.73 (3H, singlet); 3.75–4.03 (1H, multiplet); 4.52 (1H, singlet); 4.60–5.08 (2H, broad); 6.92 (2H, doublet, J=8.3 Hz); 7.08–7.16 (1H, multiplet); 7.21–7.60 (8H, multiplet). mp: 193° C. (dec).

EXAMPLE 92

4-<3-{[1-(3,4-Difluorophenyl)ethylamino]-(4-methoxyphenyl)methyl}phenylamino>-3-hydroxy-3-cyclobutene-1,2-dione and hydrochloride thereof (Compound No. 2-42)

(92a) 3-t-Butoxy-4-<3-{[1-(3,4-difluorophenyl) ethylamino]-(4-methoxyphenyl)methyl}phenylamino>-3-cyclobutene-1,2-dione Following a similar procedure to that described in Example (1c), 396 mg of isomer A of 3-{[1-(3,4- difluorophenyl)ethylamino]-(4-methoxyphenyl)methyl}phenylamine [prepared as described in Example 35(b) above] and 237 mg of 4-t-butoxy-3-methoxy-3-cyclobutene-1,2-dione were reacted, to obtain 525 mg of isomer A of the title compound as a white foamy solid.
Isomer A Nuclear Magnetic Resonance Spectrum (CDCl$_3$) δ ppm: 1.35 (3H, triplet, J=6.6 Hz); 1.63 (9H, singlet); 3.65 (1H, quartet, J=6.6 Hz); 3.76 (3H, singlet); 4.54 (1H, singlet); 6.80 (2H, doublet, J=8.8 Hz); 6.92–6.97 (1H, multiplet); 7.05–7.14 (1H, multiplet); 7.17 (2H, doublet, J=8.7 Hz); 7.31–7.40 (3H, multiplet).

Following a similar procedure to that described in Example (1c), 340 mg of isomer B of 3-{[1-(3,4-difluorophenyl)ethylamino]-(4-methoxyphenyl)methyl}-phenylamine [prepared as described in Example 35(b) above] and 339 mg of 4-t-butoxy-3-methoxy-3-cyclobutene-1,2-dione were reacted, to obtain 464 mg of isomer B of the title compound as a white foamy solid.
Isomer B Nuclear Magnetic Resonance Spectrum (CDCl$_3$) δ ppm: 1.33 (3H, triplet, J=6.6 Hz); 1.63 (9H, singlet); 3.64 (1H, quartet, J=6.7 Hz); 3.81 (3H, singlet); 4.52 (1H, singlet); 6.88 (2H, doublet, J=8.6 Hz); 6.92–6.97 (1H, multiplet); 7.06–7.17 (3H, multiplet); 7.19 (2H, doublet, J=8.7 Hz); 7.17–7.32 (3H, multiplet).

(92b) 4<3-{[1-(3,4-Difluorophenyl)ethylamino]-(4-methoxyphenyl)methyl}-phenylamino>-3-hydroxy-3-cyclobutene-1,2-dione Following a similar procedure to that described in Example (55b), 511 mg of isomer A of 3-t-butoxy-4-<3-{[1-(3,4-difluorophenyl)ethylamino]-(4-methoxyphenyl)methyl}phenylamino>-3-cyclobutene-1,2-dione [prepared as described in step (a) above] was reacted, to obtain 257 mg of isomer A of the title compound as a white solid.
Isomer A Nuclear Magnetic Resonance Spectrum (DMSO-d$_6$) δ ppm: 1.29 (3H, broad); 3.58 (1H, broad); 3.70 (3H, singlet); 4.35 (1H, broad); 6.74–6.93 (3H, multiplet); 7.10–7.55 (7H, multiplet); 7.64 (1H, singlet). mp: 198° C. (dec).

Following a similar procedure to that described in Example (55b), 774 mg of isomer B of 3-t-butoxy-4-<3-{[1-(3,4-difluorophenyl)ethylamino]-(4-methoxyphenyl)methyl}phenylamino>-3-cyclobutene-1,2-dione [prepared as described in step (a) above] and 4 ml of trifluoroacetic acid were reacted, to obtain 642 mg of isomer B of the title compound as a white solid.
Isomer B Nuclear Magnetic Resonance Spectrum (DMSO-d$_6$) δ ppm: 1.29 (3H, broad); 3.30–3.61 (1H, multiplet); 3.73 (3H, singlet); 4.35 (1H, broad); 6.63–7.48 (8H, multiplet); 7.51 (2H, doublet, J=7.4 Hz); 7.64 (1H, singlet). mp: 183° C. (dec).

(92c) 4-<3-{[1-(3,4-Difluorophenylethylamino]-(4-methoxyphenyl)methyl}-phenylamino>-3-hydroxy-3-cyclobutene-1,2-dione hydrochloride 2 ml of a 4N solution of hydrogen chloride in ethyl acetate were added to 462 mg of isomer B of 3-t-butoxy-4-<3-{[1-(3,4-difluorophenyl)ethylamino]-(4-methoxyphenyl)methyl}phenylamino>-3-cyclobutene-1,2-dione [prepared as described in step (b) above] and 2 ml of ethyl acetate, and then the mixture was stirred for 1.5 hours. The solid thus precipitated was collected and washed with a mixture of ethyl acetate and diethyl ether, to obtain 120 mg of isomer B of the title compound as a white solid.
Isomer B Nuclear Magnetic Resonance Spectrum (DMSO-d$_6$) δ ppm: 1.63 (3H, doublet, J=6.7 Hz); 3.76 (3H, singlet); 4.23 (1H, quartet, J=6.8 Hz); 5.03 (1H, singlet); 6.98 (2H, doublet, J=8.7 Hz); 7.18 (1H, doublet, J=7.6 Hz); 7.21–7.24 (1H, multiplet); 7.28 (1H, triplet, J=7.7 Hz); 7.48–7.58 (5H, multiplet); 7.61 (1H, doublet, J=1.4 Hz). mp: 193–195° C.

EXAMPLE 93

4-<3-{[1-(3,5-Difluorophenyl)ethylamino]-(4-methoxyphenyl)methyl}-phenylamino>-3-hydroxy-3-cyclobutene-1,2-dione (Compound No. 2-56)

(93a) 3-{[-(3,5-Difluorophenyl)ethylamino]-(4-methoxyphenyl)methyl}-phenylamine

Following a similar reaction, separation and purification procedure to that described in Example (59b), 7.59 g of N-[1-(3,5-difluorophenyl)ethyl]-N-[(4-methoxyphenyl)-(3-nitrophenyl)methyl]amine [prepared as described in Example 9(a) above], 9.05 g of nickel chloride hexahydrate and 2.89 g of sodium borohydride were reacted, to obtain 1.18 g of isomer A and 1.17 g of isomer B of the title compound as pale yellow oils, respectively.
Isomer A Nuclear Magnetic Resonance Spectrum (CDCl$_3$) δ ppm: 1.34 (3H, doublet, J=6.7 Hz); 3.71 (1H, quartet, J=6.7 Hz); 3.79 (3H, singlet); 4.49 (1H, singlet); 6.60 (1H, doublet, J=7.9 Hz); 6.64 (1H, singlet); 6.57–6.68 (2H, multiplet); 6.75–6.86 (2H, multiplet); 6.82 (2H, doublet, J=8.7 Hz); 7.14 (1H, triplet, J=7.7 Hz); 7.22 (2H, doublet, J=8.7 Hz).
Isomer B Nuclear Magnetic Resonance Spectrum (CDCl$_3$) δ ppm: 1.31 (3H, doublet, J=6.6 Hz); 3.63 (1H, quartet, J=6.6 Hz); 3.80 (3H, singlet); 4.47 (1H, singlet); 6.51 (1H, doublet of doublets, J=2.3, 8.0 Hz); 6.62 (1H, doublet, J=1.9 Hz); 6.65–6.71 (2H, multiplet); 6.79 (2H, doublet of doublets, J=2.0, 8.4 Hz); 6.86 (2H, doublet, J=8.7 Hz); 7.04 (1H, triplet, J=7.8 Hz); 7.20 (2H, doublet, J=8.6 Hz).

(93b) 3-t-Butoxy-4-<3-{[1-(3,5-difluorophenyl)ethylamino]-(4-methoxyphenyl)methyl}phenylamino>-3-cyclobutene-1,2-dione Following a similar procedure to that described in Example (1c), 552 mg of isomer A of 3-{[(1-(3,5-difluorophenyl)ethylamino]-(4-methoxyphenyl)methyl}-phenylamine [prepared as described in step (a) above] and 331 mg of 4-t-butoxy-3-methoxy-3-cyclobutene-1,2-dione were reacted, to obtain 740 mg of isomer A of the title compound as a white foamy solid.
Isomer A Nuclear Magnetic Resonance Spectrum (CDCl$_3$) δ ppm: 1.37 (3H, doublet, J=6.7 Hz); 1.64 (9H, singlet); 3.67 (1H, quartet, J=6.5 Hz); 3.77 (3H, singlet); 4.58 (1H, singlet); 6.67–6.73 (1H, multiplet); 6.79–6.84 (2H, multiplet); 6.82 (2H, doublet, J=8.8 Hz); 6.96–7.01 (1H, multiplet); 7.20 (2H, doublet, J=8.6 Hz); 7.29–7.40 (3H, multiplet).

Following a similar procedure to that described in Example (1c), 570 mg of isomer B of 3-{[(1-(3,5-difluorophenyl)ethylamino]-(4-methoxyphenyl)methyl}-phenylamine [prepared as described in step (a) above] and 342 mg of 4-t-butoxy-3-methoxy-3-cyclobutene-1,2-dione were reacted, to obtain 808 mg of isomer B of the title compound as a white foamy solid.
Isomer B Nuclear Magnetic Resonance Spectrum (CDCl) δ ppm: 1.34 (3H, doublet, J=6.8 Hz); 1.64 (9H, singlet); 3.65 (1H, quartet, J=6.7 Hz); 3.81 (3H, singlet); 4.54 (1H, singlet); 6.66–6.71 (1H, multiplet); 6.80 (2H, doublet, J=7.1 Hz); 6.88 (2H, doublet, J=8.6 Hz); 7.01–7.08 (1H, multiplet); 7.20 (2H, doublet, J=8.7 Hz); 7.23–7.33 (3H, multiplet).

(93c) 4-<(3-{[1-(3,5-Difluorophenyl)ethylamino]-(4-methoxyphenyl)methyl}phenylamino>-3-hydroxy-3-cyclobutene-1,2-dione Following a similar procedure to that described in Example (55b), 738 mg of isomer A of 3-t-butoxy-4-<3-{[1-(3,5-difluorophenyl)ethylamino]-(4-methoxyphenyl) methyl}phenylamino>-3-cyclobutene-1,2-dione [prepared as described in step (b) above] was reacted, to obtain 489 mg of isomer A of the title compound as a white solid.
Isomer A Nuclear Magnetic Resonance Spectrum (DMSO-$d_6$) δ ppm: 1.48 (3H, broad); 3.33–3.70 (1H, broad); 3.70 (3H, singlet); 4.40 (1H, broad); 6.82–7.35 (8H, multiplet); 7.53 (2H, doublet, J=8.0 Hz); 7.65 (1H, singlet). mp: 183° C. (dec).

Following a similar procedure to that described in Example (55b), 807 mg of isomer B of 3-t-butoxy-4-<3-{[1-(3,5-difluorophenyl)ethylamino]-( 4-methoxyphenyl) methyl}phenylamino>-3-cyclobutene-1,2-dione [prepared as described in step (b) above] was reacted, to obtain 510 mg of isomer B of the title compound as a white solid.
Isomer B Nuclear Magnetic Resonance Spectrum (DMSO-$d_6$) δ ppm: 1.53 (3H, broad); 3.76 (3H, singlet); 4.17 (1H, broad); 5.01 (1H, broad); 6.91 (1H, doublet, J=7.3 Hz); 6.98 (2H, doublet, J=8.3 Hz); 7.12–7.32 (4H, multiplet); 7.44 (2H, doublet, J=8.0 Hz); 7.55 (1H, doublet, J=8.1 Hz); 7.68 (1H, singlet). mp: 195° C. (dec).

EXAMPLE 94

3-Hydroxy-4-<3-{4-methoxyphenyl)-[(R)-1-(p-tolyl) ethylamino]methyl}-phenylamino>-3-cyclobutene-1, 2-dione hydrochloride (Compound No. 2-3491)

(94a) N-[{(4-Methoxyphenyl)-(3-nitrophenyl)methyl]-N-[(R)-1-(p-tolyl)ethyl]amine Following a similar procedure to that described in Example (1a), 10.79 g of 4-methoxyphenyl 3-nitrophenyl ketone and 5.67 g of (R)-1-(p-tolyl)ethylamine were reacted, to obtain 7.78 g of the title compound as a pale yellow oil.

Nuclear Magnetic Resonance Spectrum (CDCl$_3$) δ ppm: 1.38 (3H, doublet, J=6.7 Hz); 2.35 and 2.37 (total 3H, each singlet); 3.58 and 3.66 (total 1H, each quartet, J=6.7 and 6.8 Hz); 3.76 and 3.81 (total 3H, each singlet); 4.64 and 4.67 (total 1H, each singlet); 6.80 and 6.89 (total 2H, each doublet, J=8.7 and 8.6 Hz); 7.06–7.21 (6H, multiplet): 7.38 and 7.47 (total 1H, each triplet, J=7.9 and 8.0 Hz); 7.61 and 7.70 (total 1H, each doublet, J=7.7 and 7.8 Hz); 8.00–8.10 (1H, multiplet); 8.21 and 8.25 (total 1H, each singlet).

(94b) 3-{(4-Methoxyphenyl)-[(R)-1-p-tolylethylamino] methyl}phenylamine 7.72 g of N-[(4-methoxyphenyl)-(3-nitrophenyl)methyl]-N-[(R)-1-p-tolylethyl]amine [prepared as described in step (a) above] were dissolved in 150 ml of ethanol. Tin (II) chloride (15.6 g) was added to the resulting solution, which was then heated under reflux for 3 hours. The reaction mixture was allowed to cool, and the ethanol was distilled off. The residue was dissolved in ethyl acetate. The organic solution was washed with a 1N aqueous solution of sodium hydroxide and a saturated aqueous solution of sodium chloride, dried over anhydrous magnesium sulfate and then distilled under reduced pressure to remove the solvent. The yellow oil thus obtained was purified by chromatography through a silica gel column using an 8:1 by volume mixture of toluene and tetrahydrofuran as eluant, to obtain 1.43 g and 0.78 g of isomer A and isomer B of the title compound, respectively, each as a pale yellow oil.
Isomer A Nuclear Magnetic Resonance Spectrum (CDCl$_3$) δ ppm: 1.33 (3H, doublet, J=6.7 Hz); 2.35 (3H, singlet); 3.66 (1H, quartet, J=6.7 Hz); 3.74 (3H, singlet); 4.48 (1H, singlet); 6.56 (1H, doublet of doublets, J=2.0, 8.2 Hz); 6.65–6.88 (4H, multiplet); 7.07–7.30 (7H, multiplet).
Isomer B Nuclear Magnetic Resonance Spectrum (CDCl$_3$) δ ppm: 1.33 (3H, doublet, J=6.8 Hz); 2.35 (3H, singlet); 3.61 (1H, quartet, J=6.8 Hz), 3.80 (3H, singlet); 4.48 (1H, singlet); 6.49 (1H, doublet of triplets, J=1.1, 7.0 Hz); 6.61–6.62 (1H, multiplet); 6.65 (1H, doublet, J=7.6 Hz); 6.85 (2H, doublet, J=8.7 Hz); 7.02 (1H, triplet, J=7.8 Hz); 7.10–7.30 (6H, multiplet).

(94c) 3-t-Butoxy-4-<3- [(4-methoxyphenyl)-[(R)-1-p-tolylethylamino]methyl}-phenylamino>-3-cyclobutenle-1, 2-dione 1.41 g of isomer A of 3-{(4-methoxypoenyl)-[(R)-1-p-tolylethylamino]-methyl}phenylamine [prepared as described in step (b) above] was dissolved in 25 ml of methanol. 1.12 g of 3-t-butoxy-4-methoxy-3-cyclobutene-1, 2-dione was added to the resulting solution, which was then stirred at room temperature for 1 hour. At the end of this time, the solvent was removed by distillation under reduced pressure. The resulting pale yellow foamy solid was purified by chromatography through a silica el column using a 10:1 by volume mixture of toluene and tetrahydrofuran as eluant, to obtain 780 mg, of isomer A of the title compound as a pale yellow foamy solid.
Isomer A Nuclear Magnetic Resonance Spectrum (CDCl$_3$) δ ppm: 1.36 (3H, doublet, J=6.6 Hz); 1.61 (9H, singlet); 2.35 (3H, singlet); 3.63 (1H, quartet, J=6.7 Hz); 3.74 (3H, singlet); 4.57 (1H, singlet); 6.58 (2H, doublet, J=8.7 Hz); 7.05–7.40 (10H, multiplet).

Following a similar procedure to that described in the preparation of isomer A of the title compound, 750 mu of isomer B of 3-{(4-methoxyphenyl)-[(R)-1-p-tolylethylamino]methyl}phenylamine [prepared as described in step (b) above], 598 mg of 3-t-butoxy-4-methoxy-3-cyclobutene-1,2-dione and 10 ml of methanol were reacted, to obtain 990 mg of isomer B of the title compound as a pale yellow oil.
Isomer B Nuclear Magnetic Resonance Spectrum (CDCl$_3$) δ ppm: 1.36 (3H, doublet, J=6.7 Hz); 1.61 (9H, singlet); 2.35 (3H, singlet); 3.63 (1H, quartet, J=6.7 Hz); 3.74 (3H, singlet); 4.57 (1H, singlet); 6.78 (2H, doublet, J=8.7 Hz); 7.05–7.40 (10H, multiplet).

(94d) 3-Hydroxy-4-<3-{(4-methoxyphenyl)-[(R)-1-p-tolylethylamino]methyl}-phenylamino>-3-cyclobutene-1,2-dione hydrochloride Following a similar procedure to that described in Example (63b), 768 mg of isomer A of 3-t-butoxy-4-<3-{(4-methoxyphenyl)-[(R)-1-p-tolylethylamino]methyl}-phenylamino>-3-cyclobutene-1,2-dione [prepared as described in step (c) above] was reacted, to obtain 584 mg of isomer A of the title compound as a pale yellowish white solid.
Isomer A Nuclear Magnetic Resonance Spectrum (DMSO-$d_6$) δ ppm: 1.67 (3H, broad); 2.33 (3H, broad); 3.74 (3H, broad); 4.14 (1H, broad); 4.95 (1H, broad singlet); 6.95 (2H, doublet, J=8.8 Hz); 7.19–7.29 (4H, broad); 7.34–7.42 (3H, broad); 7.48 (1H, broad); 7.51–7.54 (2H, broad). mp: 196–202° C. (dec.); optical rotation [α]$_D$=−42.4 (c=1.00, AcOH).

Following a similar procedure to that described in Example (63b), 970 m) of isomer B of 3-t-butoxy-4-<3-{(4-methoxyphenyl)-[(R)-1-p-tolylethylamino]methyl}-phenylamino>-3-cyclobutene-1,2-dione [prepared as described in step (c) above] was reacted, to obtain 652 mg of isomer B of the title compound as a pale yellowish white solid.
Isomer B
Nuclear Magnetic Resonance Spectrum (DMSO-$d_6$) δ ppm: 1.65 (3H, doublet, J=6.6 Hz); 2.34 (3H, singlet); 3.77 (3H, singlet); 4.06 (1H, broad); 4.92 (1H, broad singlet); 6.99 (2H, doublet, J=8.8 Hz); 7.08–7.26 (4H, broad); 7.30–7.41 (4H, multiplet); 7.47 ((H, broad); 7.53 (1H, doublet, J=8.1 Hz). mp: 199–203° C. (dec.); optical rotation $[α]_D$=−16.9 (c=1.00, AcOH).

EXAMPLE 95

3-Hydroxy-4-<3-{4-methoxyphenyl)-[(R)-1-(4-methozyphenyl)ethylamino]methyl}-phenylamino>-3-cyclobutene-1,2-dione hydrochloride (Compound No. 2-74)

(95a) N-[(R)-1-(4-Methoxyphenyl)-ethyl]-N-[(4-methoxyphenyl)-(3-nitrophenyl)methyl]amine Following a similar procedure to that described in Example (1a), 6.00 g of 4-methoxyphenyl 3-nitrophenyl ketone and 5.32 g of (R)-1-(4-methoxyphenyl)ethylamine were reacted, to obtain 8.83 of the title compound as a pale yellow oil.
Nuclear Magnetic Resonance Spectrum (CDCl$_3$) δ ppm: 1.36 and 1.37 (total 3H, each doublet, J=6.61 and 6.62 Hz); 3.55 and 3.64 (total 1H, each quartet, J=6.61 and 6.63 Hz); 3.76, 3.81 and 3.83 (total 6H, each singlet); 4.63 and 4.66 (total 1H, each singlet); 6.77–6.93 (4H, multiplet); 7.09–7.24 (4H, multiplet); 7.37 and 7.47 (total 1H, each triplet, J=7.90 and 7.91 Hz); 7.58 and 7.68 (total 1H, each doublet, J=7.93 and 7.94 Hz); 8.01 and 8.08 (total 1H, each doublet of doublets, J=2.0, 7.9 and 2.0, 8.0 Hz); 8.22 and 8.27 (total 1H, each doublet, J=1.86 and 1.91 Hz).

(95b) 3-{(4-Methoxyphenyl)-[(R)-1-(4-methoxyphenyl)ethylamino]methy}phenylaminle Following a similar procedure to that described in Example (94b), 8.83 g of N-[(R)-1-(4-methoxyphenyl)ethyl]-N-[(4-methoxyphenyl)-(3-nitrophenyl)methyl]amine [prepared as described in step (a) above], 17.6 g of anhydrous (II) tin chloride and 50 ml of ethanol were reacted, to obtain 1.02 g and 1.06 g of isomer A and isomer B of the title compound, respectively, each as a pale yellow oil.
Isomer A
Nuclear Magnetic Resonance Spectrum (CDCl$_3$) δ ppm: 1.33 (3H, doublet, J=6.6 Hz); 3.61 (1H, quartet, J=6.6 Hz); 3.75 (3H, singlet); 3.81 (3H, singlet); 4.47 (1H, singlet); 6.51 (1H, doublet of doublets, J=2.0, 7.1 Hz); 6.66 (1H, doublet, J=2.0 Hz); 6.70 (1H, doublet, J=7.5 Hz); 6.78 (2H, doublet, J=8.7 Hz); 6.87 (2H, doublet, J=8.7 Hz); 7.10 (1H, triplet, J=7.9 Hz); 7.13–7.20 (4H, multiplet).
Isomer B
Nuclear Magnetic Resonance Spectrum (CDCl$_3$) δ ppm: 1.32 (3H, doublet, J=6.6 Hz); 3.60 (1H, quartet, J=6.6 Hz); 3.80 (3H, singlet); 3.81 (3H, singlet); 4.47 (1H, singlet); 6.49 (1H, doublet of doublets, J=2.0, 8.1 Hz); 6.61 (1H, doublet, J=2.0 Hz); 6.65 (1H, doublet, J=2.0 Hz); 6.82–6.88 (4H, multiplet); 7.02 (1H, triplet, J=7.8 Hz); 7.15–7.35 (4H multiplet).

(95c) 3-t-Butoxy-4-<3-{(4-methoxyphenyl)-[(R)-1-(4-methoxyphenyl)ethylamino]-methyl}phenylamino>-3-cyclobutene-1,2-dione Following a similar procedure to that described in Example (1c), 990 mg of isomer A of 3-{(4-methoxyphenyl)-[(R)-1-(4-methoxyphenyl)ethylamino]methyl}-phenylamine [prepared as described in step (b) above], 655 mg of 3-t-butoxy-4-methoxy-3-cyclobutene-1,2-dione and 25 ml of methanol were reacted, to obtain 1.29 g of isomer A of the title compound as a pale yellow foamy solid.
Isomer A
Nuclear Magnetic Resonance Spectrum (CDCl$_3$) δ ppm: 1.36 (31H, doublet, J=6.6 Hz); 1.62 (9H, singlet); 3.62 (1H, quartet, J=6.6 Hz); 3.75 (3H, singlet); 3.82 (3H, singlet); 4.57 (1H, singlet); 6.79 (2H, doublet, J=8.7 Hz); 6.88 (2H, doublet, J=8.4 Hz); 7.05–7.20 (4H, multiplet); 7.25–7.40 (4H, multiplet).

Following a similar procedure to that described in Example (1c), 1.03 g of isomer B of 3-{(4-methoxyphenyl)-[(R)-1-(4-methoxyphenyl)ethylamino]methyl}-phenylamine [prepared as described in step (b) above], 787 mg of 3-t-butoxy-4-methoxy-3-cyclobutene-1,2-dione and 25 ml of methanol were reacted, to obtain 1.17 g of isomer B of the title compound as a pale yellow foamy solid.
Isomer B
Nuclear Magnetic Resonance Spectrum (CDCl$_3$) δ ppm: 1.34 (3H, doublet, J=6.6 Hz); 1.62 (9H, singlet); 3.61 (1H, quartet, J=6.6 Hz); 3.80 (3H, singlet); 3.81 (3H, singlet); 4.55 (1H, singlet); 6.86–6.89 (4H, multiplet); 7.03 (1H, doublet, J=7.5 Hz); 7.10–7.35 (7H, multiplet).

(95d) 3-Hydroxy-4-<3-{(4-methoxyphenyl)-[(R)-1-(4-methoxyphenyl)ethylamino]methyl}phenylamino>-3-cyclobutene-1,2-dione Hydrochloride Following a similar procedure to that described in Example (63b), 1.25 g of isomer A of 3-t-butoxy-4-<3-{(4-methoxyphenyl)-[(R)-1-(4-methoxyphenyl)ethylamino]methyl}phenylamino>-3-cyclobutene-1,2-dione [prepared as described in step (c) above] was reacted, to obtain 831 mg of isomer A of the title compound as a pale yellowish white solid.
Isomer A
Nuclear Magnetic Resonance Spectrum (DMSO-$d_6$) δ ppm: 1.65 (3H, doublet, J=6.6 Hz); 3.74 (3H, singlet); 3.78 (3H, singlet); 4.14 (1H, broad); 4.94 (1H, broad singlet); 6.94–6.99 (4H, doublet, J=8.8 Hz); 7.20–7.30 (3H, multiplet); 7.36 (1H, triplet, J=8.1 Hz); 7.43 (1H, doublet, J=8.1 Hz); 7.49–7.51 (3H, multiplet) mp: 191–195 (dec.); optical rotation $[α]_D$=−82.6 (c=1.00, AcOH).

Following a similar procedure to that described in Example (63b), 1.11 g of isomer B of 3-t-butoxy-4-<3-{(4-methoxyphenyl)-[(R)-1-(4-methoxyphenyl)ethylamino]methyl}phenylamino>-3-cyclobutene-1,2-dione [prepared as described in step (c) above] was reacted, to obtain 911 mg of isomer B of the title compound as a pale yellowish white solid.
Isomer B
Nuclear Magnetic Resonance Spectrum (DMSO-$d_6$) δ ppm: 1.65 (3H, doublet, J=6.6 Hz); 3.77 (3H, singlet); 3.79 (3H, singlet); 4.06 (1H, broad); 4.92 (1H, broad singlet); 6.99 (4H, doublet of doublets, J=2.9, 8.8 Hz); 7.39 (2H, doublet, J=8.8 Hz); 7.34–7.42 (3H, multiplet); 7.47 (1H, singlet); 7.58 (1H, doublet, J=8.8 Hz). mp: 194–198° C. (dec.); optical rotation $[α]_D$=−1.79 (c=1.01, AcOH).

EXAMPLE 96

3-<3-{[(R)-1-(3,4-Difluorophenyl)ethylamino]-(4-fluorophenyl)methyl}phenylamino>-4-hydroxy-3-cyclobutene-1,2-dione and Hydrochloride Thereof (Compound No. 2-39)

(96a) N-[(R)-1-(3,4-Difluorophenyl)ethyl]-N-[(4-fluorophenyl)-(3-nitrophenyl)methyl]amine Following a similar procedure to that described in Example (1a), 12.91 g of 4-fluorophenyl 3-nitrophenyl ketone and 10.19 g of (R)-1-(3,4-difluorophenyl)ethylamine hydrochloride were reacted, to obtain 18.47 g of the title compound as a pale yellow oil.

Nuclear Magnetic Resonance Spectrum (CDCl$_3$) δ ppm: 1.36 and 1.37 (total 3H, each doublet, J=6.60 and 6.64 Hz); 3.60 and 3.64 (total 1H, each quartet, J=6.69 and 6.60 Hz); 4.65 and 4.69 (total 1H, each singlet); 6.85–7.30 (7H, multiplet); 7.41 and 7.51 (total 1H, each triplet, J=7.99 and 7.94 Hz); 7.57 and 7.63 (total 1H, each doublet, J=7.82 and 7.84 Hz); 8.05 and 8.12 (total 1H, each doublet of doublets, J=1.6, 8.0 and 1.8, 8.0 Hz); 8.21 and 8.23 (total 1H, each triplet, J=1.87 and 1.90 Hz)

(96b) 3-{[(R)-1-(3,4-Difluorophenyl)ethylamino]-(4-fluorophenyl)methyl}-phenylamine Following a similar reaction, separation and purification procedure to that described in Example (59b), 18.44 g of N-[(R)-1-(3,4-difluorophenyl)ethyl]-N-[(4-fluorophenyl)-(3-nitrophenyl)methyl]amine, 22.69 g of nickel chloride hexahydrate, 7.22 g of sodium borohydride and 150 ml of methanol were reacted, to obtain 1.27 g of isomer A and 2.79 g of isomer B of the title compound, respectively, each as a pale yellow oil.

Isomer A

Nuclear Magnetic Resonance Spectrum (CDCl$_3$) δ ppm: 1.31 (3H, doublet, J=6.6 Hz); 3.67 (1H, quartet, J=6.6 Hz); 4.45 (1H, singlet); 6.57–6.65 (3H, multiplet); 6.89–6.97 (3H, multiplet); 7.00–7.27 (5H, multiplet).

Isomer B

Nuclear Magnetic Resonance Spectrum (CDCl$_3$) δ ppm: 1.32 (3H, doublet, J=6.7 Hz); 3.68 (1H, quartet, J=6.6 Hz); 4.47 (1H, singlet); 6.50–6.53 (1H, multiplet); 6.57 (1H, doublet of doublets, J=1.6, 1.9 Hz); 6.63 (1H, doublet, J=7.3 Hz); 6.87–6.95 (1H, multiplet); 6.97–7.15 (5H, multiplet); 7.23–7.30 (2H, multiplet).

(96c) 3-t-Butoxy-4-<3-{[(R)-1-(3,4-difluorophenyl) ethylamino]-(4-fluorophenyl)methyl}phenylamino>-3-cyclobutene-1,2-dione Following a similar procedure to that described in Example (94c), 1.24 g of isomer A of 3-{[(R)-1-(3,4-difluorophenyl)ethylamino]-(4-fluorophenyl) methyl}phenylamine [prepared as described in step (b) above], 963 mg of 3-t-butoxy-4-methoxy-3-cyclobutene-1,2-dione and 15 ml of methanol were reacted, to obtain 597 mg of isomer A of the title compound as a white foamy solid.

Isomer A

Nuclear Magnetic Resonance Spectrum (CDCl$_3$) δ ppm: 1.36 (3H, doublet, J=6.6 Hz); 1.63 (9H, singlet); 3.66 (1H, quartet, J=6.6 Hz); 4.56 (1H, singlet); 6.91–6.96 (3H, multiplet); 6.98–7.14 (3H, multiplet); 7.20–7.41 (5H, multiplet).

Following a similar procedure to that described in Example (1c), 1.31 g of isomer B of 3-{[(R)-1-(3,4-difluorophenyl)ethylamino]-(4-fluorophenyl)methyl}-phenylamine [prepared as described in step (b) above], 1.01 g of 3-t-butoxy-4-methoxy-3-cyclobutene-1,2-dione and 16 ml of methanol were reacted, to obtain 997 mg of isomer B of the title compound as a white foamy solid.

Isomer B

Nuclear Magnetic Resonance Spectrum (CDCl$_3$) δ ppm: 1.34 (3H, doublet, J=6.7 Hz); 1.63 (9H, singlet); 3.61 (1H, quartet, J=6.6 Hz); 4.56 (1H, singlet); 6.90–7.15 (6H, multiplet); 7.20–7.45 (5H, multiplet).

(96d) 3-<3-{[(R)-1-(3,4-difluoroplenyl)ethylamino]-(4-fluorophenyl)methyl}phenylamino>-4-hydroxy-3-cyclobutene-1,2-dione Following a similar procedure to that described in Example (55b), 585 mg of isomer A of 3-t-butoxy-4-<3-{[(R)-1-(3,4-difluorophenyl)ethylamino]-(4-fluorophenyl) methyl}phenylamino>-3-cyclobutene-1,2-dione [prepared as described in step (c) above] was reacted, to obtain 516 mg of isomer A of the title compound as a pale yellowish white solid.

Isomer A

Nuclear Magnetic Resonance Spectrum (DMSO-d$_6$) δ ppm: 1.59 (3H, doublet, J=5.7 Hz); 4.30 (1H, broad); 5.05 (1H, broad singlet); 6.98–7.00 (3H, doublet, J=7.5 Hz); 7.25–7.35 (2H, multiplet); 7.42–7.65 (5H, multiplet); 7.77 (1H, doublet, J=1.7 Hz). mp: 195–198° C. (dec.); optical rotation [α]$_D$=−398.8 (c=1.00□AcOH).

Following a similar procedure to that described in Example (55b), 979 mg of isomer B of 3-t-butoxy-4-<3-{[(R)-1-(3,4-difluorophenyl)ethylamino]-(4-fluorophenyl) methyl}phenylamino>-3-cyclobutene-1,2-dione [prepared as described in step (c) above] was reacted, to obtain 868 mg of isomer B of the title compound as a pale yellowish white solid.

Isomer B

Nuclear Magnetic Resonance Spectrum (DMSO-d$_6$) δ ppm: 1.38 (3H, doublet, J=6.7 Hz); 3.50 (1H, broad); 4.41 (1H, broad singlet); 6.71 (1H, doublet, J=7.48 Hz); 7.03–7.14 (4H, multiplet); 7.28–7.43 (4H, multiplet); 7.51 (1H, doublet, J=1.8 Hz); 7.63 (1H, singlet). mp: 130–132° C. (dec.); optical rotation [α]$_D$=−33.8 (c=0.10, DMSO).

(96e) 3-<3-{[(R)-1-(3,4-Difluorophenyl)ethylamino]-(4-fluorophenyl)methyl}phenylamino>-4-hydroxy-3-cyclobutene-1,2-dione Hydrochloride 337 mg of isomer A of 3-<3-{[(R)-1-(3,4-difluorophenyl) ethylamino]-(4-fluorophenyl)methyl}phenylamino>-4-hydroxy-3-cyclobutene-1,2-dione [prepared as described in step (d) above] were suspended in 5 ml of methanol. 3 ml of a 4N solution of hydrogen chloride in ethyl acetate were added to the resulting suspension to dissolve the suspension. The solvent was then distilled off under reduced pressure. The pale yellowish foamy solid thus obtained was suspended in diethyl ether, and the resulting precipitate was collected by filtration, to obtain 337 mg of isomer A of the title compound as a pale yellowish white solid.

Isomer A

Nuclear Magnetic Resonance Spectrum (DMSO-d$_6$) δ ppm: 1.70 (3H, doublet, J=6.8 Hz); 4.31 (1H, quartet, J=6.4 Hz); 5.07 (1H, singlet); 7.10–7.25 (3H, multiplet); 7.34 (1H, doublet of doublets, J=7.9, 8.1 Hz); 7.42 (2H, doublet, J=7.3 Hz); 7.46–7.55 (2H, multiplet); 7.57–7.66 (1H, multiplet); 7.72 (2H, doublet of doublets, J=5.4, 8.4 Hz). mp: 195–200° C. (dec.); optical rotation [α]$_D$=−50.6 (c=1.00, AcOH).

Following a similar procedure to that employed in the preparation of isomer A of the title compound, but using 404 mg of isomer B of 3-<3-{[(R)-1-(3,4-difluorophenyl) ethylamino]-(4-fluorophenyl)methyl}phenylamino>-4-hydroxy-3-cyclobutene-1,2-dione [prepared as described in step (d) above], 4 ml of methanol and 3 ml of a 4N solution of hydrogen chloride in ethyl acetate, to obtain 338 mg of isomer B of the title compound as a pale yellowish white solid.

Isomer B

Nuclear Magnetic Resonance Spectrum (DMSO-d$_6$) δ ppm: 1.71 (3H, doublet, J=6.7 Hz); 4.03 (1H, broad); 5.12 (1H, singlet); 7.18–7.30 (3H, multiplet); 7.32–7.51 (4H, multiplet); 7.56 (1H, doublet, J=7.5 Hz); 7.63–7.68 (1H, multiplet); 7.76 (2H, doublet of doublets, J=5.3, 8.7 Hz). mp: 172–180° C. (dec.); optical rotation [α]$_D$=−17.2 (c=1.00, AcOH).

EXAMPLE 97

3-<3-{[(R)-1-(3-Fluorophenyl)ethylamino]-(4-methoxyphenyl)methyl}phenylamino>-4-hydroxy-3-cyclobutene-1,2-dione and Hydrochloride Thereof (Compound No. 2-21)

(97a) N-[(R)-1-(3-Fluorophenyl)ethyl]-N-[(4-methoxyphenyl)-(3-nitrophenyl)methyl]amine Following a similar procedure to that described in Example (1a), 11.16 g of 4-methoxyphenyl 3-nitrophenyl ketone and 7.62 g of (R)-1-(3-fluorophenyl)ethylamine hydrochloride were reacted, to obtain 15.11 of the title compound as a pale yellow oil.

Nuclear Magnetic Resonance Spectrum (CDCl$_3$) δ ppm: 1.36 and 1.38 (total 3H, each doublet, J=6.7 and 6.6 Hz); 3.61 and 3.69 (total 1H, each quartet, J=6.6 and 6.7 Hz); 3.76 and 3.81 (total 3H, each singlet); 4.63 and 4.68 (total 1H, each singlet); 6.78–7.05 (5H, multiplet); 7.13–7.33 (3H, multiplet); 7.39 and 7.48 (total 1H, each triplet, J=8.0 and 7.8 Hz); 7.60–7.67 (total 1H, each doublet, J=7.3, 7.9 Hz); 8.07–8.11 (1H, multiplet); 8.22–8.26 (1H, multiplet).

(97b) 3-{[(R)-1-(3-Fluorophenyl)ethylamino]-(4-methoxyphenyl)methyl}phenylamine

Following a similar procedure to that described in Example (59b), 15.08 g of N-[(R)-1-(3-fluorophenyl)ethyl]-N-[(4-methoxyphenyl)-(3-nitrophenyl)methyl]amine [prepared as described in step (a) above], 18.84 g of nickel chloride hexahydrate, 6.0 g of sodium borohydride and 150 ml of methanol were reacted, to obtain 787 mg and 605 mg of isomer A and isomer B of the title compound, respectively, each as a pale yellowish oil.

Isomer A

Nuclear Magnetic Resonance Spectrum (CDCl$_3$) δ ppm: 1.33 (3H, doublet, J=6.6 Hz); 3.70 (1H, quartet, J=6.6 Hz); 3.75 (3H, singlet); 4.47 (1H, singlet); 6.55–6.58 (1H, multiplet); 6.63–6.64 (1H, multiplet); 6.69 (1H, doublet, J=7.5 Hz); 6.78 (2H, doublet, J=8.7 Hz); 6.91–6.98 (1H, multiplet); 6.97–7.30 (6H, multiplet).

Isomer B

Nuclear Magnetic Resonance Spectrum (CDCl$_3$) δ ppm: 1.33 (3H, doublet, J=6.6 Hz); 3.65 (1H, quartet, J=6.6 Hz); 3.80 (3H, singlet); 4.47 (1H, singlet); 6.50 (1H, doublet of doublets, J=2.1, 8.1 Hz); 6.61–6.62 (1H, multiplet); 6.66 (1H, doublet, J=7.5 Hz); 6.86 (2H, doublet, J=8.7 Hz); 6.94–7.05 (3H, multiplet); 7.15–7.30 (4H, multiplet).

(97c) 3-t-Butoxy-4-<3-{[(R)-1-(3-fluorophenyl)ethylamino]-(4-methoxyphenyl)methyl}phenylamino>cyclobut-3-ene-1,2-dione Following a similar procedure to that described in Example (94c), 765 mg of isomer A of 3-{[(R)-1-(3-fluorophenyl)ethylamino]-(4-methoxyphenyl)methyl}phenylamine [prepared as described in step (b) above], 603 mg of 3-t-butoxy-4-methoxy-3-cyclobutene-1,2-dione and 10 ml of methanol were reacted, to obtain 767 mg of isomer A of the title compound as a white foamy solid.

Isomer A

Nuclear Magnetic Resonance Spectrum (CDCl$_3$) δ ppm: 1.37 (3H, doublet, J=6.7 Hz); 1.63 (9H, singlet); 3.67 (1H, quartet, J=6.7 Hz); 3.76 (3H, singlet); 4.57 (1H, singlet); 6.80 (2H, doublet, J=8.7 Hz); 6.92–7.04 (2H, multiplet); 7.06–7.40 (8H, multiplet).

Following a similar procedure to that described in Example (94c), 582 mg of isomer B of 3-{[(R)-1-(3-fluorophenyl)ethylamino]-(4-methoxyphenyl)methyl}-phenylamine [prepared as described in step (b) above], 459 mg of 3-t-butoxy-4-methoxy-3-cyclobutene-1,2-dione and 8 ml of methanol were reacted, to obtain 792 mg of isomer B of the title compound as a pale yellowish foamy solid.

Isomer B

Nuclear Magnetic Resonance Spectrum (CDCl$_3$) δ ppm: 1.35 (3H, doublet, J=6.6 Hz); 1.63 (9H, singlet); 3.66 (1H, quartet, J=6.6 Hz); 3.81 (3H, singlet); 4.55 (1H, singlet); 6.75–7.10 (4H, multiplet); 7.13–7.40 (8H, multiplet).

(97d) 3-<3-{[(R)-1-(3-Fluoropheny)ethylamino]-(4-methoxyphenyl)methyl}phenylamino>-4-hydroxy-3-cyclobutene-1,2-dione Following a similar procedure to that described in Example (55b), 476 mg of isomer B of 3-t-butoxy-4-<3-{[(R)-1-(3-fluorophenyl)ethylamino]-(4-methoxyphenyl)methyl}phenylamino>-3-cyclobutene-1,2-dione [prepared as described in step (c) above], 3 ml of trifluoroacetic acid and 10 ml of dichloromethane were reacted, to obtain 232 mg of isomer B of the title compound as a white solid.

Isomer B

Nuclear Magnetic Resonance Spectrum (DMSO-d$_6$) δ ppm: 1.30 (3H, broad); 3.74 (3H, singlet); 3.74 (1H, quartet, J=6.7 Hz); 3.60–3.80 (1H, broad); 4.00–4.20 (1H, broad); 6.80–7.75 (12H, multiplet). mp: 114–117° C. (dec.); optical rotation [α]$_D$=+44.7 (c=1.01, AcOH).

Following a similar procedure to that described in Example (55b), 772 mg of isomer A of 3-t-butoxy-4-<3-{[(R)-1-(3-fluorophenyl)ethylamino]-(4-methoxyphenyl)methyl}phenylamino>-3-cyclobutene-1,2-dione [prepared as described in step (c) above], 3 ml of trifluoroacetic acid and 10 ml of dichloromethane were reacted, to obtain 635 mg of isomer A of the title compound as a white solid.

Isomer A

Nuclear Magnetic Resonance Spectrum (DMSO-d$_6$) δ ppm: 1.29 (3H, doublet, J=6.6 Hz); 3.57–3.62 (1H, broad); 3.68 (3H, singlet); 4.35 (1H, broad singlet); 6.75–6.81 (3H, multiplet); 7.02 (1H, doublet of triplets, J=2.5, 8.5 Hz); 7.08–7.23 (5H, multiplet); 7.30–7.38 (1H, multiplet); 7.54 (1H, doublet, J=8.0 Hz); 7.63 (1H, singlet). mp: 114–117° C. (dec.); optical rotation [α]$_D$=−196 (c=1.00, AcOH).

(97e) 3-<3-{[(R)-1-(3-Fluorophenyl)ethylamino]-(4-methoxyphenyl)methyl}-phenylamino>-4-hydroxy-3-cyclobutene-1,2-dione Hydrochloride Following a similar procedure to that described in Example (96e), 133 mg of isomer A of 3-(3-{[(R)-1-(3-fluorophenyl)ethylamino]-(4-methoxyphenyl)methyl}-phenylamino>-4-hydroxy-3-cyclobutene-1,2-dione [prepared as described in step (d) above], 3 ml of methanol and 3 ml of a 4N solution of hydrogen chloride in ethyl acetate were reacted, to obtain 122 mg of isomer A of the title compound as a pale yellow solid.

Isomer A

Nuclear Magnetic Resonance Spectrum (DMSO-d$_6$) δ ppm: 1.67 (3H, doublet, J=6.8 Hz); 3.74 (3H, singlet); 4.15–4.30 (1H, broad); 5.03 (1H, broad singlet); 6.94–6.96 (2H, multiplet); 7.12–7.60 (10H, multiplet). mp: 175–180 (dec.); optical rotation [α]$_D$=−112 (c=0.46, AcOH).

Following a similar procedure to that described in Example (96e), 404 mg of isomer B of 3-<3-{[(R)-1-(3-fluorophenyl)ethylamino]-(4-methoxyphenyl)methyl}phenylamino>-4-hydroxy-3-cyclobutene-1,2-dione [prepared as described in step (d) above], 4 ml of methanol and 2 ml of a 4N solution of hydrogen chloride in ethyl acetate were reacted, to obtain 146 mg of isomer B of the title compound as a pale yellowish white solid.

Isomer B

Nuclear Magnetic Resonance Spectrum (DMSO-d$_6$) δ ppm: 1.70 (3H, doublet, J=6.9 Hz); 3.73 (3H, singlet); 4.16–4.25 (1H, broad); 4.96 (1H, broad); 6.92 (2H, doublet, J=7.6 Hz); 7.13–7.26 (3H, multiplet); 7.31–7.47 (5H, multiplet); 7.56–7.62 (2H, multiplet). mp: 164–168° C. (dec.); optical rotation [α]$_D$=−3.8 (c=0.42, AcOH).

EXAMPLE 98

3-(3-{(4-Fluorophenyl)-[(R)-1-(3-fluorophenyl)ethylamino]methyl}phenylamino)-4-hydroxy-3-cyclobutene-1,2-dione and Trifluoroacetate and Hydrochloride Thereof (Compound No. 2-18)

(98a) N-[(R)-1-(3-Fluorophenyl)ethyl]-N-[(4-fluorophenyl)-(3-nitrophenyl)methyl]amine Following a similar procedure to that described in Example (1a), 8.03 g of 4-fluorophenyl 3-nitrophenyl ketone and 5.75 g of (R)-1-(3-difluorophenyl)ethylamine hydrochloride were reacted, to obtain 2.85 g of isomer A and 1.67 g of isomer B of the title compound as pale yellow oils, respectively.

Isomer A
Nuclear Magnetic Resonance Spectrum (CDCl$_3$) δ ppm: 1.39 (3H, doublet, J=6.8 Hz); 3.61 (1H, quartet, J=6.7 Hz); 4.70 (1H, singlet); 6.91–7.00 (5H, multiplet); 7.19–7.33 (3H, multiplet); 7.51 (1H, triplet, J=7.9 Hz); 7.65 (1H, doublet, J=7.5 Hz); 8.12 (1H, doublet of doublets, J=1.9, 8.0 Hz); 8.24 (1H, doublet of doublets, J=1.3, 1.9 Hz).

Isomer B
Nuclear Magnetic Resonance Spectrum (CDCl$_3$) δ ppm: 1.37 (3H, doublet, J=6.6 Hz); 3.66 (1H, quartet, J=6.7 Hz); 4.68 (1H, singlet); 6.90–7.09 (5H, multiplet); 7.18–7.32 (3H, multiplet); 7.41 (1H, triplet, J=8.0 Hz); 7.58 (1H, doublet, J=8.0 Hz); 8.03–8.06 (1H, multiplet); 8.24 (1H, doublet of doublets, J=1.6, 1.9 Hz).

(98b) 3-{(4-Fluorophenyl)-[(R)-1-(3-fluorophenyl)ethylamino]methyl}phenylamine

Following a similar procedure to that described in Example (1b), 2.82 g of isomer A of N-[(R)-1-(3-fluorophenyl)ethyl]-N-[(4-fluorophenyl)-(3-nitrophenyl)methyl]amine [prepared as described in step (a) above], 3.64 g of nickel chloride hexahydrate, 1.16 g of sodium borolydride and 30 ml of methanol were reacted, to obtain 2.52 g of isomer A of the title compound as a colorless oil.

Isomer A
Nuclear Magnetic Resonance Spectrum (CDCl$_3$) δ ppm: 1.34 (3H, doublet, J=6.7 Hz); 3.70 (1H, quartet, J=6.6 Hz); 4.48 (1H, singlet); 6.59–6.61 (2H, multiplet); 6.67 (1H, doublet J=7.4 Hz); 6.89–6.96 (3H, multiplet); 7.00–7.03 (2H, multiplet); 7.14 (1H, triplet, J=7.7 Hz); 7.23–7.30 (3H, multiplet).

Following a similar procedure to that described in Example (1b), 1.63 g of isomer B of N-[(R)-1-(3-fluorophenyl)ethyl]-N-[(4-fluorophenyl)-(3-nitrophenyl)methyl]amine [prepared as described in step (a) above], 2.11 g of nickel chloride hexahydrate, 6.74 g of sodium borohydride and 20 ml of methanol were reacted, to obtain 1.45 g of isomer B of the title compound as a colorless oil.

Isomer B
Nuclear Magnetic Resonance Spectrum (CDCl$_3$) δ ppm: 1.34 (3H, doublet, J=6.6 Hz); 3.62 (1H, quartet, J=6.7 Hz); 4.50 (1H, singlet); 6.50–6.53 (1H, multiplet); 6.59 (1H, doublet of doublets, J=1.5, 1.9 Hz); 6.64 (1H, doublet, J=8.0 Hz); 6.90–7.06 (6H, multiplet); 7.26–7.33 (3H, multiplet).

(98c) 3-t-Butoxy-4-<3-{(4-fluorophenyl)-[(R)-1-(3-fluorophenyl)ethylamino]methyl}phenylamino>-3-cyclobutene-1,2-dione Following a similar procedure to that described in Example (94c), 2.48 g of isomer A of 3-{(4-fluorophenyl)-[(R)1-(3-fluorophenyl)ethylamino]methyl}phenylamine [prepared as described in step (b) above], 2.02 g of 3-t-butoxy-4-methoxy-3-cyclobutene-1,2-dione and 35 ml of methanol were reacted, to obtain 3.49 g of isomer A of the title compound as a white foamy solid.

Isomer A
Nuclear Magnetic Resonance Spectrum (CDCl$_3$) δ ppm: 1.37 (3H, doublet, J=6.6 Hz); 1.63 (9H, singlet); 3.68 (1H, quartet, J=6.6 Hz); 4.59 (1H, singlet); 6.91–7.10 (6H, multiplet), 7.22–7.39 (6H, multiplet).

Following a similar procediure to that described in Example (94c), 1.46 g, of isomer B of 3-{(4-fluorophenyl)-[(R)1-(3-fluorophenyl)ethylamino]methyl}phenylamine [prepared as described in step (b) above], 1.19 of 3-t-butoxy-4-methoxy-3-cyclobutene-1,2-dione and 30 ml of methanol were reacted, to obtain 2.04 g of isomer B of the title compound as a white foamy solid.

Isomer B
Nuclear Magnetic Resonance Spectrum (CDCl$_3$) δ ppm: 1.36 (3H, doublet, J=6.6 Hz); 1.63 (9H, singlet); 3.64 (1H, quartet, J=6.6 Hz); 4.59 (1H, singlet); 6.92–7.06 (6H, multiplet); 7.21–7.32 (6H, multiplet).

(98) 3-<3-{(4-Fluorophenyl)-[(R)-1-(3-fluorophenyl)ethylamino]methyl}phenylamino>-4-hydroxy-3-cyclobutene-1,2-dione Trifluoroacetate 1.29 g of isomer A of 3-t-betoxy-4-<3-{(4-fluorophenyl)-[(R)-1-(3-fluorophenyl)ethylamino]methyl}phenylamino>-3-cyclobutene-1,2-dione [prepared as described in step (c) above] was dissolved in 13 ml of dichloromethane, and then 1 ml of trifluoroacetic acid was added. The mixture was stirred at room temperature for 30 minutes, after which the solvent Was distilled off under reduced pressure. Toluene was added to the residue followed by azeotropic removal of the solvent twice. The resulting white solid was mixed with diethyl ether and collected by filtration, to obtain 1.34 g of the title compound as a white solid.

Isomer A
Nuclear Magnetic Resonance Spectrum (DMSO-d$_6$) δ ppm: 1.62 (3H, doublet, J=6.7 Hz); 4.31 (1H, quartet, J=6.7 Hz); 5.25 (1H, singlet); 7.05 (1H, doublet, J=7.7 Hz); 7.17 (1H, doublet, J=7.6 Hz); 7.24–7.28 (4H, multiplet); 7.34 (1H, triplet, J=7.9 Hz); 7.44–7.48 (2H, multiplet); 7.60–7.65 (3H, multiplet). mp: 190–194° C. (dec.); optical rotation $[\alpha]_D$=−56.2 (c=1.07, AcOH).

Following a similar procedure to that employed in the preparation of isomer A, 2.00 g of isomer B of 3-t-butoxy-4-<3-{(4-fluorophenyl)-[(R)-1-(3-fluorophenyl)ethylamino]methyl}phenylamino>-3-cyclobutene-1,2-dione [prepared as described in step (c) above], 4 ml of trifluoroacctic acid and 8 ml of dichloromethane were reacted, to obtain 1.68 g of isomer B of the title compound as a pale yellowish solid.

Isomer B
Nuclear Magnetic Resonance Spectrum (DMSO-d$_6$) δ ppm: 1.62 (3H, doublet, J=6.7 Hz); 4.24 (1H, quartet, J=6.7 Hz); 5.25 (1H, singlet); 7.06 (1H, doublet, J=7.7 Hz); 7.21 (1H, doublet, J=7.8 Hz); 7.25–7.33 (5H, multiplet); 7.45–7.54 (2H, multiplet); 7.61–7.66 (3H, multiplet). mp: 187–189° C. (dec.); optical rotation $[\alpha]_D$=+37.1 (c=1.01, AcOH).

(98e) 3-<3-{(4-Fluorophenyl)-[(R)-1-(3-fluorophenyl)ethylamino]metbyl}phenylamino)4-hydroxy-3-cyclobutene-1,2-dione 513 mg of isomer B of 3-<3-{(4-fluorophenyl)-[(R)-1-(3-fluorophenyl)ethylamino]methyl}phenylamino>-4-hydroxy-3-cyclobutene-1,2-dione trifluoroacetate [prepared as described in step (d) above] were dissolved in 5 ml of methanol, after which 80 ml of a phthalic acid standard solution (pH 4.01) was added. The white precipitate thus obtained was collected by filtration and washed sufficiently with water, to obtain 453 mg of the title compound as a white solid.

Nuclear Magnetic Resonance Spectrum (CDCl$_3$) δ ppm: 1.59 (3H, doublet, J=6.6 Hz); 4.10–4.30 (1H, broad); 5.16 (1H, singlet); 6.97 (1H, doublet, J=7.7 Hz); 7.20–7.31 (6H, multiplet); 7.44–7.66 (4H, multiplet); 7.70 (1H, singlet). mp: 186° C. (dec.); optical rotation: $[\alpha]_D$=+39.4 (c1.01, AcOH).

(98f) 3-<3-{(4-Fluorophenyl)-[(R)-1-(3-fluorophenyl)ethylamino]methyl}phenylamino>-4-hydroxy-3-cyclobutene-1,2-dione Hydrochloride Following a similar procedure to that described in Example (63b), 500 mg of 3-(3-{(4-fluorophenyl)-[(R)-1-(3-fluorophenyl)ethylamino]methyl}phenylamino>-4-hydroxy-3-cyclobutene-1,2-dione trifluoroacetate [prepared as described in step (d) above] was reacted, to obtain 410 mg of the title compound as a pale yellow solid.

Nuclear Magnetic Resonance Spectrum (CDCl$_3$) δ ppm: 1.68 (3H, doublet, J=6.6 Hz); 4.13–4.28 (1H, broad); 5.17 (1H, singlet); 7.20 (1H, doublet, J=7.5 Hz); 7.24–7.51 (8H, multiplet); 7.53 (1H, singlet); 7.71 (2H, doublet of doublets, J=5.3, 8.5 Hz). mp: 180° C. (dec.); optical rotation: [α]$_D$=−22.3 (c=0.99, AcOH).

EXAMPLE 99

3-(3-{[1-(3,4-Difluorophenyl)ethylamino]-(thiophen-2-yl)methyl}phenylamino>-4-hydroxy-3-cyclobutene-1,2-dione Trifluoroacetate (Compound No. 2-45)

(99a) N-[1-(3,4-Difluorophenyl)ethyl]-N-[(3-nitrophenyl)-(thiophen-2-yl)methyl}amine Following a similar procedure to that described in Example (1a), 3.03 g of 3-nitrophenyl thiophen-2-yl ketone and 2.52 g of 1-(3,4-difluorophenyl)ethylamine were reacted, to obtain 4.62 g of the title compound as a reddish orange oil.

Nuclear Magnetic Resonance Spectrum (CDCl$_3$) δ ppm: 1.34 and 1.37 (total 3H, each doublet, J=6.61 and 6.63 Hz); 3.59 and 38.1 (total 1H, each quartet, J=6.58 and 6.60 Hz); 4.88 and 4.95 (total 1H, each singlet); 6.63–7.03 (3H, multiplet); 7.05–7.37 (3H, multiplet); 7.44 and 7.54 (total 1H, each triplet, J=7.97 and 7.93 Hz); 7.64–7.97 (1H, multiplet); 8.07–8.19 (1H, multiplet); 8.21–8.27 (1H, multiplet).

(99b) 3-{[1-(3,4-Difluorophenyl)enthylamino]-(thiophen-2-yl)methyl}phenylamine

Following a similar reaction, separation and purification procedure to that described in Example (59b), 4.60 of N-[1-(3,4-difluorophenyl)ethyl]-N-[(3-nitrophenyl)-(thiophen-2-yl)methyl]amine [prepared as described in step (a) above], 5.84 g of nickel chloride hexahydrate, 1.86 g of sodium borohydride and 100 ml of methanol were reacted, to obtain 1.025 g and 495 mg of isomer A and isomer B of the title compound, respectively, each as a pale yellowish oil.

Isomer A

Nuclear Magnetic Resonance Spectrum (CDCl$_3$) δ ppm: 1.29 (3H, doublet, J=6.6 Hz); 3.67 (1H, quartet, J=6.5 Hz); 4.59 (1H, singlet); 6.60–6.66 (4H, multiplet); 6.89 (1H, doublet of doublets, J=3.7, 5.1 Hz); 7.02–7.26 (5H, multiplet).

Isomer B

Nuclear Magnetic Resonance Spectrum (CDCl$_3$) δ ppm: 1.33 (3H, doublet, J=6.6 Hz); 3.77 (1H, quartet, J6.6 Hz); 4.77 (1H, singlet); 6.54–6.56 (I1H, multiplet); 6.60 (1H, triplet, J=2.0 Hz); 6.70 (1H, doublet, J=7.5 Hz); 6.82 (1H, doublet, J=3.7 Hz); 6.87–6.99 (2H, multiplet); 7.05–7.16 (3H, multiplet); 7.23 (1H, doublet of doublets, J=1.2, 5.1 Hz).

(99c) 3-t-Butoxy-4-<3-{[1-(3,4-difluorophenyl)ethylamino]-(thiophen-2-yl)methyl}phenylamino>-3-cyclobutene-1,2-dione Following a similar procedure to that described in Example (94c), 1.03 g of isomer A of 3-{[1-(3,4-difluorophenyl)ethylamino]-(thiophen-2-yl)methyl}phenylamine [prepared as described in step (b) above], 809 mg of 3-t-butoxy-4-methoxy-3-cyclobutene-1,2-dione and 15 ml of methanol were reacted, to obtain 932 mg of isomer A of the title compound as a white foamy solid.

Isomer A

Nuclear Magnetic Resonance Spectrum (CDCl$_3$) δ ppm: 1.33 (3H, doublet, J=6.6 Hz); 1.63 (9H, singlet); 3.65 (1H, quartet, J=6.6 Hz); 4.72 (1H, singlet); 6.63 (1H, doublet, J=3.6 Hz); 6.87 (1H, doublet of doublets, J=3.4, 5.0 Hz); 7.01–7.27 (5H, multiplet); 7.34–7.37 (3H, multiplet).

Following a similar procedure to that described in Example (94c), 495 mg of isomer B of 3-{[1-(3,4-difluorophenyl)ethylamino]-(thiophen-2-yl)methyl}phenylamine [prepared as described in step (b) above], 391 mg of 3-t-butoxy-4-methoxy-3-cyclobutene-1,2-dione and 10 ml of methanol were reacted, to obtain 709 mg of isomer B of the title compound as a white foamy solid.

Isomer B

Nuclear Magnetic Resonance Spectrum (CDCl$_3$) δ ppm: 1.36 (3H, doublet, J=6.6 Hz); 1.63 (9H, singlet); 3.79 (1H, quartet, J=6.6 Hz); 4.86 (1H, singlet); 6.87 (1H, doublet, J=3.3 Hz); 6.97 (1H, doublet of doublets, J=3.5, 5.0 Hz); 6.99–7.01 (1H, multiplet); 7.07–7.16 (3H, multiplet); 7.25–7.35 (4H, multiplet).

(99d) 3-<3-{[1-(3,4-Difluorophenyl)ethylamino]-(thiophen-2-yl)methyl}phenylamino>-4-hydroxy-3-cyclobutene-1,2-dione trifluoroacetate Following a similar procedure to that described in Example (98d), 906 mg of isomer A of 3-t-butoxy-4-<3-{[1-(3,4-difluorophenyl)ethylamino]-(thiophen-2-yl)methyl}phenylamino>-3-cyclobuLtelle-1,2-dione [prepared as described in step (c) above], 3 ml of trifluoroacetic acicl and 10 ml of dichloromethane were reacted, to obtain 851 mg of isomer A of the title compound as a white solid.

Isomer A

Nuclear Magnetic Resonance SI)cctrurn (DMSO-d$_6$) δ ppm: 1.59 (3H, doublet, J=6.6 Hz); 4.27 (1H, broad); 5.37 (1H, broad singlet); 7.05–7.18 (3H, multiplet); 7.32–7.38 (2H, multiplet); 7.43–7.52 (2H, multiplet); 7.55–7.60 (3H, multiplet). mp: 177–181° C. (dec.).

Following a similar procedure to that described in Example (98d), 699 mg of isomer B of 3-t-butoxy-4-<3-{[-(3,4-difluorophenyl)ethylamino]-(thiophen-2-yl)methyl}phenylamino>-3-cyclobutene-1,2-dione [prepared as described in step (c) above], 3 ml of trifluoroacetic acid and 10 ml of dichloromethane were reacted, to obtain 666 mg of isomer B of the title compound as a white solid.

Isomer B

Nuclear Magnetic Resonance Spectrum (DMSO-d$_6$) δ ppm: 1.57 (3H, doublet, J=6.7 Hz); 4.27 (1H, quartet, J=4.2 Hz); 5.49 (1H, singlet); 7.12 (1H, doublet of doublets, J=3.7, 5.0 Hz); 7.16 (1H, doublet, J=7.7 Hz); 7.26–7.36 (2H, multiplet); 7.44 (1H, doublet, J=3.7, 5.0 Hz); 7.48–7.87 (5H, multiplet). mp: 181–182° C. (dec.).

EXAMPLE 100

3-(5{[(R)-1-(3,5-Difluoropheyl)ethylamino]-(4-methoxyphenyl)methyl}-2-fluorophenylamino>-4-hydroxy-3-cyclobutene-1,2-dione trifluoroacetate (Compound No. 2-3400)

(100a) N-[(R)-1-(3,5-Difluoophenyl)ethyl]-N-[(4-fluoro-3-nitrophenyl)-(4-methoxyphenyl)methy]amine Following a similar procedure to that described in Example (1a), 2.53 g of 4-fluoro-3-nitrophenyl 4-methoxyphelnyl ketone and 1.78 g of (R)-1-(3,5-difluorophenyl)ethylamine hydrochloride vere reacted, to obtain 3.62 g of the title compound as a yellow oil.

Nuclear Magnetic Resonance Spectrum (CDCl$_3$) δ ppm: 1.34 and 1.37 (total 3H, each doublet, J=6.64 and 6.65 Hz); 3.65 and 3.66 (total 1H, each quartet, J=6.6 and 6.5 Hz); 3.77 and 3.82 (total 3H, each singlet); 4.55 and 4.63 (total 1H, each singlet); 6.66–6.92 (5H, multiplet); 7.11–7.24 (3H, multiplet); 7.53 and 7.59 (total 1H, each doubled doublet of doublets, J=2.4, 4.2, 8.5 and 2.3, 4.3, 8.6 Hz); 8.05 and 8.19 (total 1H, each doublet of doublets, J=2.3, 7.1 and 2.2, 7.2 Hz).

(100b) 5-{[(R)-1-(3,5-Difluorophenyl)ethylamino]-(4-methoxypbenyl)methyl-2-fluorophenylamine Following a similar procedure to that described in Example (1b), 3.60 g of N-[(R)-1-(3,5-difluorophenyl)ethyl]-N-[(4-fluoro-3-nitrophenyl)-(4-methoxyphenyl)methyl]amine [prepared as described in step (a) above], 4.11 g of nickel chloride hexahydrate, 1.30 g of sodium borohydride and 50 ml of methanol were reacted, to obtain 3.27 g of the title compound as a yellow oil.

Nuclear Magnetic Resonance Spectrum (CDCl$_3$) δ ppm: 1.31 and 1.32 (total 3H, each doublet, J=6.67 and 6.62 Hz); 3.55–3.75 (1H, multiplet); 3.76 and 3.81 (total 3H, each singlet); 4.44 (1H, singlet); 6.55–6.97 (8H, multiplet); 7.17 (2H, doublet, J=8.6 Hz).

(100c) 3-t-Butoxy-4-<5-{[(R)-1-(3,5-difluorophenyl)ethylamino]-(4-methoxyphenyl)methyl}-2-fluorophenylamino>-3-cyclobutene-1,2-dione Following a similar reaction, separation and purification procedure to that described in Example (66c), 3.24 g of 5-{[(R)-1-(3,5-difluorophenyl)ethylamino]-(4-methoxyphenyl)methyl}-2-fluorophenylamine [prepared as described in step (b) above], 2.32 g of 3-t-butoxy-4-methoxy-3-cyclobutene-1,2-dione and 30 ml of methanol were reacted, to obtain 1.01 g of isomer A and 817 mg of isomer B of the title compound as pale yellow foamy solids, respectively.

Isomer A

Nuclear Magnetic Resonance Spectrum (CDCl$_3$) δ ppm: 1.37 (3H, doublet, J=6.7 Hz); 1.63 (9H, singlet); 3.66 (1H, quartet, J=6.6 Hz); 3.76 (3H, singlet); 4.56 (1H, singlet); 6.66–6.71 (1H, multiplet); 6.78–6.82 (4H, multiplet); 7.00 (1H, broad); 7.04–7.09 (1H, multiplet); 7.15–7.30 (3H, multiplet).

Isomer B

Nuclear Magnetic Resonance Spectrum (CDCl$_3$) δ ppm: 1.35 (3H, doublet, J=6.7 Hz); 1.64 (9H, singlet); 3.65 (1H, quartet, J=6.7 Hz); 3.80 (3H, singlet); 4.54 (1H, singlet); 6.64–6.69 (1H, multiplet); 6.81 (2H, doublet of doublets, J=2.0, 8.1 Hz); 6.88 (2H, doublet, J=8.5 Hz); 6.92–7.02 (2H, multiplet); 7.10–7.30 (3H, multiplet).

(100d) 3-<5-{[(R)-1-(3,5-Difluorophenyl)ethylamino]-(4-methoxyphenyl)methyl}-2-fluorophenylamino>-4-hydroxy-3-cyclobutene-1,2-dione trifluoroacetate Following a similar procedure to that described in Example (98d), 539 mg of isomer A of 3-t-butoxy-4-<5-{[(R)-1-(3,5-difluorophenyl)ethylamino]-(4-methoxyphenyl)methyl}-2-fluorophenylamino>-3-cyclobutene-1,2-dione [prepared as described in step (c) above], 3 ml of trifluoroacetic acid and 10 ml of dichloromethane were reacted, to obtain 358 mg of isomer A of the title compound as a white solid.

Isomer A

Nuclear Magnetic Resonance Spectrum (DMSO-d$_6$) δ ppm: 1.60 (3H, doublet, J=6.7 Hz); 3.76 (3H, singlet); 4.39–4.47 (1H, broad); 5.15 (1H, broad singlet); 6.94–6.99 (3H, multiplet); 7.11 (2H, doublet, J=6.3 Hz); 7.21–7.35 (2H, multiplet); 7.54 (2H, doublet, J=7.6 Hz); 7.57–7.85 (1H, multiplet). mp: 184–186° C. (dec.); optical rotation [α]$_D$=−373 (c=1.00, AcOH).

Following a similar procedure to that described in Example (98d), 360 mg of isomer B of 3-t-butoxy-4-<5-{[(R)-1-(3,5-difluorophenyl)ethylamino]-(4-methoxyphenyl)methyl}-2-fluorophenylamino>-3-cyclobutene-1,2-dione [prepared as described in step (c) above], 3 ml of trifluoroacetic acid and 10 ml of dichloromethane were reacted, to obtain 320 mg of isomer B of the title compound as a white solid.

Isomer B

Nuclear Magnetic Resonance Spectrum (DMSO-d$_6$) δ ppm: 1.59 (3H, doublet, J=6.7 Hz); 3.78 (3H, singlet); 4.37 (1H, quartet, J=6.6 Hz); 5.30 (1H, singlet); 6.99 (2H, doublet, J=8.8 Hz); 7.10–7.33 (5H, multiplet); 7.54 (2H, doublet, J=8.7 Hz); 7.85 (1H, doublet of doublets, J=2.0, 8.0 Hz). mp: 180–182° C. (dec.); optical rotation [α]$_D$=+56.0 (c=104, DMSO).

EXAMPLE 101

3-<3-{[1-(3,4-Difluorophenyl)ethylamino]-(4-methylthiophenyl)methyl}phenylamino>-4-hydroxy-3-cyclobutene-1,2-dione trifluoroacetate (Compound No. 2-3486)

(101a) N-[1-(3,4-Difluorophenyl)ethyl-N-[(4-methylthiophenyl)-(3-nitrophenyl)methyl]amine Following a similar procedure to that described in Example (1a), 2.73 g of 4-methylthiophenyl 3-nitrophenyl ketone and 1.94 g of 1-(3,4-difluorophenyl)ethylamine hydrochloride were reacted, to obtain 3.77 g of the title compound as a yellow oil.

Nuclear Magnetic Resonance Spectrum (CDCl$_3$) δ ppm: 1.32 and 1.36 (total 3H, each doublet, J=6.4 and 6.0 Hz); 2.44 and 2.49 (total 3H, each singlet); 3.60 and 3.66 (total 1H, each quartet, J=6.63 and 6.60 Hz); 4.61 and 4.67 (total 1H, each singlet); 6.88–6.91 (1H, multiplet); 7.03–7.18 (5H, multiplet); 7.23–7.26 (1H, multiplet); 7.40 and 7.48 (total 1H, each triplet, J=8.01 and 7.98 Hz); 7.58 and 7.64 (total 1H, each doublet, J=8.2 and 7.7 Hz); 8.04 and 8.11 (total 1H, each doublet of doublets, J=1.9, 7.9 and 2.0, 8.0 Hz); 8.22–8.24 (1H, multiplet).

(101 b) 3-{[1-(3,4-Difluorophenyl)ethylamino]-(4-methylthiophenyl)methyl}phenylamine Following a similar reaction, separation and purification procedure to that described in Example (59b), 3.74 g of N-[1-(3,4-difluorophenyl)ethyl]-N-[(4-methylthiophenyl)-(3-nitrophenyl)methyl]amine [prepared as described in step (a) above], 4.29 g of nickel chloride lhexahydrate, 1.37 g of sodium borohydride and 80 ml of methanol were reacted, to obtain 796 mg of isomer A and 400 mg of isomer B of the title compound as colorless oils, respectively.

Isomer A

Nuclear Magnetic Resonance Spectrum (CDCl$_3$) δ ppm: 1.31 (3H, doublet, J=6.6 Hz); 2.43 (3H, singlet); 3.68 (1H, quartet, J=6.5 Hz); 4.48 (1H, singlet); 6.56–6.59 (2H, multiplet); 6.65 (1H, doublet, J=7.5 Hz); 6.94–6.97 (1H, multiplet); 7.05–7.29 (7H, multiplet).

Isomer B

Nuclear Magnetic Resonance Spectrum (CDCl$_3$) δ ppm: 1.31 (3H, doublet, J=6.7 Hz); 2.48 (3H, singlet); 3.62 (1H, quartet, J=6.7 Hz); 4.44 (1H, singlet); 6.51 (1H, doublet of doublets, J=2.1, 8.1 Hz); 6.59 (1H, doublet of doublets, J=1.6, 1.8 Hz); 6.65 (1H, doublet, J=7.4 Hz); 6.91–6.95 (1H, multiplet); 7.00–7.13 (3H, multiplet); 7.19–7.34 (4H, multiplet).

(101c) 3-t-Butoxy-4-<3-{1-(3,4-difluorophenyl)ethylamino]-(4-methylthiophenyl)methyl}phenylamino>-3-cyclobutene-1,2-dione Following a similar procedure to that described in Example (94c), 775 mg of isomer A of 3-{[1-(3,4-difluorophenyl)ethylamino]-(4-methylthiophenyl)methyl}phenylamine [prepared as described in step (b)

above], 549 mg of 3-t-butoxy-4-methoxy-3-cyclobutene-1,2-dione and 20 ml of methanol were reacted, to obtain 1.04 g of isomer A of the title compound as a white foamy solid.
Isomer A Nuclear Magnetic Resonance Spectrum (CDCl$_3$) δ ppm: 1.36 (3H, doublet, J=6.6 Hz); 1.64 (9H, singlet); 2.43 (3H, singlet); 3.67 (1H, quartet, J=6.6 Hz); 4.56 (1H, singlet); 6.92–6.98 (1H, multiplet); 7.03–7.43 (10H, multiplet).

Following a similar procedure to that described in Example (94c), 387 mg of isomer B of 3-{[1-(3,4-difluorophenyl)ethylamino]-(4-methylthiophenyl)methyl}phenylamine [prepared as described in step (b) above], 272 mg of 3-t-butoxy-4-methoxy-3-cyclobutene-1,2-dione and 15 ml of methanol were reacted, to obtain 516 mg of isomer B of the title compound as a white foamy solid.
Isomer B Nuclear Magnetic Resonance Spectrum (CDCl$_3$) δ ppm: 1.33 (3H, doublet, J=6.6 Hz); 1.63 (9H, singlet); 2.49 (3H, singlet); 3.64 (1H, quartet, J=6.6 Hz); 4.52 (1H, singlet); 6.93–7.14 (4H, multiplet); 7.16–7.37 (7H, multiplet).

(101d) 3-<3-{[1-(3,4-Difluorophenyl)ethylamino]-(4-methylthiophenyl)methyl}phenylamino>-4-hydroxy-3-cyclobutene-1,2-dione trifluoroacetate Following a similar procedure to that described in Example (98d), 614 mg, of isomer A of 3-t-butoxy-4-<3-{[1-(3,4-difluorophenyl)ethylamino]-(4-methylthiophenyl)methyl}phenylamino>-3-cyclobutene-1,2-dione [prepared as described in step (c) above], 3 ml of trifluoroacetic acid and 15 ml of dichloromethane were reacted, to obtain 543 mg of isomer A of the title compound as a white solid.
Isomer A Nuclear Magnetic Resonance Spectrum (DMSO-d$_6$) δ ppm: 1.61 (3H, doublet, J=6.7 Hz); 2.46 (3H, singlet); 4.34 (1H, quartet, J=6.6 Hz); 5.10 (1H, singlet); 6.99 (1H, doublet, J=7.5 Hz); 7.17–7.19 (1H, multiplet); 7.24–7.62 (9H, multiplet). mp: 191–192° C. (dec.).

Following a similar procedure to that described in Example (98d), 472 mg of isomer B of 3-t-butoxy-4-<3-{[1-(3,4-difluorophenyl)ethylamino]-( 4-methylthiophenyl)methyl}phenylamino>-3-cyclobutene-1,2-dione [prepared as described in step (c) above], 3 ml of trifluoroacetic acid and 12 ml of dichloromethane were reacted, to obtain 435 mg of isomer B of the title compound as a white solid.
Isomer B Nuclear Magnetic Resonance Spectrum (DMSO-d$_6$) δ ppm: 1.60 (3H, doublet, J=6.6 Hz); 2.48 (3H, singlet); 4.26 (1H, quartet, J=6.6 Hz); 5.12 (1H, singlet); 7.06 (1H, doublet, J=7.9 Hz); 7.21–7.37 (4H, multiplet); 7.40–7.62 (5H, multiplet); 7.64 (1H, singlet). mp: 194–196° C. (dec.).

EXAMPLE 102

3-<3-{[1-(3,4-Difluorophenyl)ethylamino]-(2,4-dimethoxyphenyl)methyl}-phenylamino>-4-hydroxy-3-cyclobutene-1,2-dione (Compound No. 2-3439)

(102a) N-[1-(3,4-Difluorophen)ethyl]-N-[(2,4-dimethoxyphenyl)-(3-nitrophenyl)methyl]amine Following a similar reaction, separation and purification procedure to that described in Example (1a), 3.32 g of 2,4-dimethoxyphenyl 3-nitrophenyl ketone and 2.24 g of 1-(3,4-difluorophenyl)etliylamine were reacted, to obtain 940 mg of isomer A and 740 mg of isomer B of the title compound as yellow oils, respectively.
Isomer A Nuclear Magnetic Resonance Spectmim (CDCl$_3$) δ ppm: 1.32 (3H, doublet, J=6.6 Hz); 3.62–6.72 (4H, multiplet), 3.83 (3H, sindlet); 4.75 (3H, singlet); 6.48–6.54 (2H, multiplet): 6.95–7.23 (4H, multiplet): 7.36 (1H, triplet, J=8.0 Hz), 7.59 (1H, doublet, J=7.4 Hz); 8.00 (1H, doublet, J=8.3 Hz); 8.24 (1H, singlet).
Isomer B Nuclear Magnetic Resonance Spectrum (CDCl$_3$) δ ppm: 1.34 (3H, doublet, J=6.6 Hz); 3.61 (1H, quartet, J=6.6 Hz); 3.71 (3H, singlet); 3.77 (1H, singlet); 5.01 (1H, singlet); 6.40–6.43 (2H, multiplet); 6.86–6.89 (1H, multiplet); 7.03–7.14 (3H, multiplet); 7.45 (1H, doublet of doublets, J=7.3, 8.1 Hz); 7.67 (1H, doublet, J=7.3 Hz); 8.07 (1H, doublet of doublets, J=1.5, 8.1 Hz); 8.26 (1H, singlet).

(102b) 3-{[1-(3,4-Difluorophenyl)ethylamino]-(2,4-dimethoxyphenyl)methyl}phenylamine Following a similar procedure to that described in Example (1b), 920 mg of isomer A of N-[1-(3,4-difluorophenyl)ethyl]-N-[(2,4-dimethoxyphenyl)-(3-nitrophenyl)methyl]amine [prepared as described in step (a) above], 1.02 g of nickel chloride hexahydrate, 325 mg of sodium borohydride and 50 ml of methanol were reacted, to obtain 543 mg of isomerci A of the title compound as a colorless oil.
Isomer A Nuclear Magnetic Resonance Spectrum (CDCl$_3$) δ ppm: 1.29 (3H, doublet, J=6.6 Hz); 3.61 (1H, quartet, J=6.6 Hz); 3.66 (3H, singlet); 3.81 (3H, singlet); 4.72 (1H, singlet); 6.45 (1H, doublet, J=2.3 Hz); 6.47–6.50 (2H, multiplet), 6.60–6.69 (2H, multiplet); 6.96–7.20 (5H, multiplet).

Following a similar procedure to that described in Example (1b), 720 mg of isorner B of N-[1-(3,4-difluorophenyl)ethyl]-N-[(2,4-dimethoxyphenyl)-(3-nitrophenyl)methyl]amine [prepared as described in step (a) above], 799 mg of nickel chloride hexahydrate, 254 mg of sodium borohydride and 80 ml of methanol were reacted, to obtain 580 mg of isomer B of the title compound as a colorless oil.
Isomer B Nuclear Magnetic Resonance Spectrum (CDCl$_3$) δ ppm: 1.31 (3H, doublet, J=6.6 Hz); 3.68 (1H, quartet, J=6.6 Hz); 3.72 (3H, singlet); 3.75 (3H, singlet); 4.82 (1H, singlet); 6.35–6.40 (2H, multiplet); 6.56 (1H, doublet of doublets, J=2.0, 8.1 Hz); 6.68 (1H, triplet, J=1.7 Hz); 6.71 (1H, doublet, J=7.9 Hz); 6.89–6.92 (1H, multiplet); 7.00 (1H, doublet, J=8.3, 8.1 Hz); 7.03–7.20 (3H, muitiplet).

(102c) 3-t-Butoxy-4-<3-{[1-(3,4-difluorophenyl)ethylamino]-(2,4-dimethoxyphenyl)methylyhenylamino>-3-cyclobutene-1,2-dione Following a similar procedure to that described in Example (94c), 522 mg of isomer A of 3-{[1-(3,4-difluoroplenyl)ethylamino]-(2,4-dimethoxyphenyl)methyl}phenylamine [prepared as described in step (b) above], 362 mg of 3-t-butoxy-4-methoxy-3-cyclobutene-1,2-dione and 25 ml of methanol were reacted, to obtain 727 mg of isomer A of the title compound as a white foamy solid.
Isomer A Nuclear Magnetic Resonance Spectrum (CDCl$_3$) δ ppm: 1.31 (3H, doublet, J=6.6 Hz); 1.63 (9H, singlet); 3.63 (1H, quartet, J=6.6 Hz); 3.67 (3H, singlet); 3.82 (3H, singlet); 4.75 (1H, singlet); 6.46 (1H, doublet, J=2.3 Hz); 6.51 (1H, doublet of doublets, J=2.4, 8.5 Hz); 6.98–7.37 Hz(8H, multiplet).

Following a similar procedure to that described in Example (94c), 549 mg of isomer B of 3-{[1-(3,4-difluorophenyl)ethylamino]-(2,4-dimethoxyphenyl)methyl}-phenylamine [prepared as described in step (b) above], 380 mg of 3-t-butoxy-4-methoxy-3-cyclobutene-1,2-dione and 25 ml of methanol were reacted, to obtain 682 mg of isomer B of the title compound as a white foamy solid.

Isomer B

Nuclear Magnetic Resonance Spectrum (CDCl$_3$) δ ppm: 1.33 (3H, doublet, J=6.6 Hz); 1.62 (9H, singlet); 3.67 (1H, quartet, J=6.7 Hz); 3.72 (3H, singlet); 3.76 (3H, singlet); 4.93 (1H, singlet); 6.37–6.40 (2H, multiplet); 6.89–6.92 (1H, multiplet), 7.00–7.18 (4H, multiplet); 7.21–7.35 (3H, multiplet).

(102d) 3-(3-{[1-(3,4-Difluorophenyl)ethylamino]-(2,4-dimethoxyphenyl)methyl}phenylamino>-4-hydroxy-3-cyclobutene-1,2-dione Following a similar procedure to that described in Example (55b), 707 mg of isomer A of 3-t-butoxy-4-<3-{[1-(3,4-difluorophenyl)ethylamino]-(2,4-dimethoxyphenyl)methyl}phenylamino>-3-cyclobutene-1,2-dione [prepared as described in step (c) above], 4 ml of trifluoroacetic acid and 12 ml of dichloromethane were reacted, to obtain 543 mg of isomer A of the title compound as a white solid.

Isomer A

Nuclear Magnetic Resonance Spectrum (DMSO-d$_6$) δ ppm: 1.05–1.70 (3H, broad); 3.65 (3H, singlet); 3.77 (3H, singlet); 4.22 (1H, broad); 4.60–5.25 (1H, broad); 6.30–7.20 (5H, broad); 7.30–7.75 (5H, broad). mp: 195–215° C. (dec.).

Following a similar procedure to that described in Example (55b), 659 mg of isomer B of 3-t-butoxy-4-<3-{[1-(3,4-difluorophenyl)ethylamino]-(2,4-dimethoxyphenyl)methyl}phenylamino>-3-cyclobutene-1,2-dione [prepared as described in step (c) above], 4 ml of trifluoroacetic acid and 12 ml of dichloromethane were reacted, to obtain 276 mg of isomer A of the title compound as a white solid.

Isomer B

Nuclear Magnetic Resonance Spectrum (DMSO-d$_6$) δ ppm: 1.10–1.75 (3H, broad); 3.45–4.45 (7H, broad); 4.60–5.30 (1H, broad); 6.35–7.70 (10H, multiplet). mp: 200–220° C. (dec.)

EXAMPLE 103

4-<3-{(4-Chlorophenyl)-[(R)-1-(3-fluorophenyl)ethylamino]methyl}phenylamino>-3-hydroxy-3-cyclobutene-1,2-dione hydrochloride (Compound No. 2-19)

(103a) N-[(4-Chlorophenyl)-(3-nitrophenyl)methyl]-N-[(R)-1-(3-fluorophenyl)ethyl]amine Following a similar procedure to that described in Example (1a), 880 mg of 4-chlorophenyl 3-nitrophenyl ketone, 886 mg of (R)-1-(3-fluorophenyl)ethylamine hydrochloride, 2.58 ml of triethylamine, 0.44 ml of titanium tetrachloride, 890 mg of sodium cyanoborohydride and 0.29 ml of acetic acid were reacted, to obtain 1.25 g of the title compound as a yellow oil.

Nuclear Magnetic Resonance Spectrum (CDCl$_3$) δ ppm: 1.38 and 1.39 (total 3H, each doublet, J=6.6 and 6.8 Hz); 3.61 and 3.65 (total 1H, each quartet, J=6.9 and 6.7 Hz); 4.66 and 4.69 (total 1H, each singlet); 6.91–7.00 (3H, multiplet); 7.18–7.35 (5H, multiplet); 7.41 and 7.50 (total 1H, each triplet, J=8.0 and 7.9 Hz); 7.58 and 7.64 (total 1H, each doublet, J=8.0 and 7.6 Hz); 8.04–8.14 (1H, multiplet); 8.20–8.23 (1H, multiplet).

(103b) 3-{(4-Chlorophenyl)-[(R)-1-(3-fluorophenyl)ethylamino]methyl}phenylamine

Following a similar procedure to that described in Example (1b), 1.23 g of N-[(4-chlorophenyl)-(3-nitrophenyl)methyl]-N-[(R)-1-(3-fluorophenyl)ethyl]amine [prepared as described in step (a) above], 1.52 g of nickel chloride hexahydrate and 509 mg of sodium borohydride were reacted, to obtain 1.12 g of the title compound as a pale yellow oil.

Nuclear Magnetic Resonance Spectrum (CDCl$_3$) δ ppm: 1.34 (3H, doublet, J=6.7 Hz); 3.62 and 3.70 (total 1H, each quartet, J=6.7 and 6.6 Hz); 4.47 and 4.48 (total 1H, each singlet); 6.50–6.66 (3H, multiplet); 6.91–7.06 (4H, multiplet); 7.09–7.32 (5H, multiplet).

(103c) 3-t-Butoxy-4-<3-{(4-cholorophenyl)-1(R)-1-(3-fluorophenyl)ethylamino]methyl}phenylamino>-3-cyclobutene-1,2-dione Following a reaction and purification procedure similar to those described in Example (66c), 1.0 g of 3-{(4-chlorophenyl)-[(R)-1-(3-fluorophenyl)ethylamino]methyl}phenylamine [prepared as described in step (b) above] and 779 mg of 4-t-butoxy-3-methoxy-3-cyclobutene-1,2-dione were reacted, to obtain 566 mg of isomer A and 732 mg of isomer B of the title compound, each as a pale yellow foamy solid.

Isomer A

Nuclear Magnetic Resonance Spectrum (CDCl$_3$) δ ppm: 1.37 (3H, doublet, J=6.6 Hz); 1.63 (9H, singlet); 3.68 (1H, quartet, J=6.6 Hz); 4.58 (1H, singlet); 6.93–7.06 (4H, multiplet); 7.10–7.46 (8H, multiplet).

Isomer B

Nuclear Magnetic Resonance Spectrum (CDCl$_3$) δ ppm: 1.36 (3H, doublet, J=6.6 Hz); 1.63 (9H, singlet); 3.63 (1H, quartet, J=6.7 Hz); 4.57 (1H, singlet); 6.92–7.00 (4H, multiplet); 7.14–7.39 (8H, multiplet).

(103d) 4-<3-{4-Cholorophenyl)-[(R)-1-(3-fluoropbenyl)ethylamino]methyl}phenylamino>-3-hydroxy-3-cyclobutene-1,2-dione hydrochloride Following a reaction and purification procedure similar to those described in Example (63b), 410 mg of isomer A of 3-t-butoxy-4-<3-{(4-chlorophenyl)-[(R)-1-(3-fluorophenyl)ethylamino]methyl}phenylamino>-3-cyclobutene-1,2-dione [prepared as described in step (c) above] was reacted and purified, to obtain 166 mg of isomer A of the title compound as a white solid.

Isomer A

Nuclear Magnetic Resonance Spectrum (DMSO-d$_6$) δ ppm: 1.65 (3H, doublet, J=6.7 Hz); 4.30 (1H, broad); 5.18 (1H, singlet); 7.17–7.36 (5H, multiplet); 7.43–7.48 (4H, multiplet); 7.57 (1H, singlet); 7.64 (2H, doublet, J=8.5 Hz). mp: 191–196° C. optical rotation $[\alpha]_D$=+154.0° (c=0.50, AcOH).

Following a reaction and purification procedure similar to those described in Example (63b), 470 mg of isomer B of 3-t-butoxy-4-<3-{(4-chlorophenyl)-[(R)-1-(3-fluorophenyl)ethylamino]methyl}plenylamino>-3-cyclobutene-1,2-dione [prepared as described in step (c) above] was reacted, to obtain 362 mg of isomer B of the title compound as a pale yellow solid.

Isomer B

Nuclear Magnetic Resonance Spectrum (DMSO-d$_6$) δ ppm: 1.67 (3H, doublet, J=6.7 Hz); 4.22 (1H, broad); 5.19 (1H, singlet); 7.20 (1H, doublet J=7.7 Hz); 7.24–7.29 (1H, multiplet); 7.33–7.54 (8H, multiplet); 7.66 (2H, doublet, J=8.5 Hz). mp: 169° C. (dec.); optical rotation $[\alpha]_D$=−0.7° (c=0.50, AcOH).

EXAMPLE 104

4-<3-{(4-Chlorophenyl)-[(R)-1-(3,5-difluorophenyl)ethylamino]methyl phenylamino>-3-hydroxy-3-cyclobutene-1,2-dione hydrochloride (Compound No. 2-54)

(104a) N-[(4-Chlorophenyl)-(3-nitrophenyl)methyl]-N-[(R)-1-(3,5-difluorophenyl)ethyl]amine Following a similar procedure to that described in Example (1a), 1.0 g of 4-chlorophenyl 3-nitrophenyl ketone, 1.11 g of (R)-1-(3,5-difluorophenyl)ethylamine hydrochloride, 2.93 ml of triethylamine, 0.50 ml of titanium tetrachloride, 1.01 g of sodium cyanoborohydride and 0.33 ml of acetic acid were reacted, to obtain 1.45 g of the title compound as a yellow oil.

Nuclear Magnetic Resonance Spectrum (CDCl₃) δ ppm: 1.36 and 1.37 (total 3H, each doublet, J=6.7 and 6.6 Hz); 3.60–3.66 (1H, multiplet); 4.66 and 4.71 (total 1H, each singlet); 6.67–6.81 (3H, multiplet); 7.19–7.28 (3H, multiplet); 7.34 and 7.36 (total 1H, each, singlet); 7.43 and 7.51 (total 1H, each triplet, J=7.9 and 7.9 Hz); 7.59 and 7.63 (total 1H, each doublet, J=7.6 and 7.9 Hz); 8.05–8.14 (1H, multiplet); 8.20–8.23 (1H multiplet).

(104b) 3-{(4-Chlorophenyl)-[(R)-1-(3,5-difluoropbenyl)ethylamino]methyl}phenylamine Following a similar procedure to that described in Example (1b), 1.41 g of N-[(4-chlorophenyl)-(3-nitrophenyl)methyl]-N-[(R)-1-(3,5-difluorophenyl)ethyl]amine [prepared as described in step (a) above], 1.66 g of nickel chloride hexahydrate and 558 mg of sodium borohydride were reacted, to obtain 1.29 g of the title compound as a pale yellow oil.

Nuclear Magnetic Resonance Spectrum (CDCl₃) δ ppm: 1.32 (3H, doublet, J=6.6 Hz); 3.60 and 3.69 (total 1H, each quartet, J=6.6 and 6.6 Hz); 4.47 and 4.48 (total 1H, each singlet); 6.51–6.84 (6H, multiplet); 7.05 and 7.12 (total 1H, each triplet, J=7.8 and 7.7 Hz); 7.20–7.31 (4H, multiplet).

(104c) 3-t-Butoxy-4-<3-{(4-chlorophlenyl)-[(R)-1-(3,5-difluorophenyl)ethylamino]methyl}phenylamino>-3-cyclobutene-1,2-dione Following a reaction and purification procedure similar to those described in Example (66c), 1.17 g of 3-{(4-chlorophenyl)-[(R)-1-(3,5-difluorophenyl)ethylamino]methyl}phenylamine [prepared as described in step (b) above] and 867 mg of 4-t-butoxy-3-methoxy-3-cyclobutene-1,2-dione were reacted, to obtain 241 mg of isomer A and 365 mg of isomer B of the title compound were obtained, each as a pale yellow oil.

Isomer A

Nuclear Magnetic Resonance Spectrum (CDCl₃) δ ppm: 1.36 (3H, doublet, J=6.6 Hz); 1.63 (9H, singlet); 3.67 (1H, quartet, J=6.6 Hz); 4.58 (1H, singlet); 6.67–6.72 (1H, multiplet); 6.79 (2H, doublet of doublets, J=2.1, 8.5 Hz); 7.03 (1H, doublet, J=6.9 Hz); 7.14–7.40 (7H, multiplet).

Isomer B

Nuclear Magnetic Resonance Spectrum (CDCl₃) δ ppm: 1.35 (3H, doublet, J=6.7 Hz); 1.64 (9H, singlet); 3.61 (1H, quartet, J=6.7 Hz); 4.57 (1H, singlet); 6.66–6.72 (1H, multiplet); 6.76–6.81 (2H, multiplet); 7.00–7.02 (1H, multiplet); 7.14–7.35 (7H, multiplet).

(104d) 4-<3-{(4-Chlorophenyl)-[(R)-1-(3,5-difluorophenyl)ethylamino]methyl}phenylamino>-3-hydroxy-3-cyclobutene-1,2-dione hydrochloride Following a reaction and purification procedure similar to those described in Example (63b), 230 mg of isomer A of 3-t-butoxy-4-<3-{(4-chlorophenyl)-[(R)-1-(3,5-difluorophenyl)ethylamino]methyl}phenylamino>-3-cyclobutene-1,2-dione [prepared as described in step (c) above] was reacted, to obtain 176 mg of isomer A of the title compound as a pale brown solid.

Isomer A

Nuclear Magnetic Resonance Spectrum (DMSO-d₆) δ ppm: 1.64 (3H, doublet, J=6.7 Hz); 4.32 (1H, broad); 5.25 (1H, singlet); 7.17–7.21 (3H, multiplet); 7.26–7.37 (2H, multiplet); 7.43–7.47 (3H, multiplet); 7.58 (1H, singlet); 7.66 (2H, doublet, J=8.6 Hz). mp: 184–187° C.; optical rotation [α]_D=−130.7° (c=0.56, AcOH).

Following a reaction and purification procedure similar to those described in Example (63b), 351 mg of isomer B of 3-t-butoxy-4-<3-{(4-chlorophenyl)-[(R)-1-(3,5-difluorophenyl)ethylamino]methyl}phenylamino>-3-cyclobutene-1,2-dione [prepared as described in step (c) above] was reacted, to obtain 262 mg of isomer B of the title compound as a pale yellow solid.

Isomer B

Nuclear Magnetic Resonance Spectrum (DMSO-d₆) δ ppm: 1.65 (3H, doublet, J=6.7 Hz); 4.27 (1H, broad); 5.26 (1H, singlet); 7.22 (2H, doublet of doublets, J=1.7, 8.0 Hz); 7.28–7.42 (4H, multiplet); 7.51–7.55 (3H, multiplet); 7.68 (2H, doublet, J=8.4 Hz). mp: 182–189° C.; optical rotation [α]_D=+11.1° (c=0.52, AcOH).

EXAMPLE 105

4-<3-{(4-Chlorophenyl)-[(R)-1-(3,4-difluorophenyl)ethylamino]methyl}phenylamino>-3-hydroxy-3-cyclobutene-1,2-dione (Compound No. 2-40)

(105a) N-[(4-Chlorophenyl)-(3-nitrophenyl)methyl]-N-[(R)-1-(3,4-difluorophenyl)ethyl]amine Following a similar procedure to that described in Example (1a), 1.0 g of 4-chlorophenyl 3-nitrophenyl ketone, 1.11 g of (R)-1-(3,4-difluorophenyl)ethylamine hydrochloride, 2.93 ml of trietlaylamine, 0.50 ml of titanium tetrachloride, 1.01 g of sodium cyanoborohydride and 0.33 ml of acetic acid were reacted, to obtain 1.42 g of the title compound as a yellow oil.

Nuclear Magnetic Resonance Spectrum (CDCl₃) δ ppm: 1.36 and 1.37 (total 3H, each doublet, J=6.8 and 6.8 Hz); 3.59 and 3.63 (total 1H, each quartet, J=6.6 and 6.7 Hz); 4.63 and 4.68 (total 1H, each singlet); 6.87–6.95 (1H, multiplet); 7.03–7.22 (4H, multiplet); 7.24–7.27 (1H, multiplet); 7.33 and 7.35 (total 1H, each, singlet); 7.42 and 7.51 (total 1H, each triplet, J=8.0 and 8.0 Hz); 7.56 and 7.62 (total 1H, each doublet, J=8.0 and 7.9 Hz); 8.05–8.14 (1H, multiplet); 8.20–8.22 (1H, multiplet).

(105b) 3-{(4-Chlorophenyl)-[(R)-1-(3,4-difluorophenyl)ethylamino]methyl}-phenylamine Following a similar procedure to that described in Example (1b), 1.30 g of N-[(4-chlorophenyl)-(3-nitrophenyl)methyl]-N-[(R)-1-(3,4-difluorophenyl)ethyl]amine [prepared as described in step (a) above], 1.53 g of nickel chloride hexahydrate and 514 mg of sodium borohydride were reacted, to obtain 1.20 g of the title compound as a yellow oil.

Nuclear Magnetic Resonance Spectrum (CDCl₃) δ ppm: 1.31 (3H, doublet, J=6.7 Hz); 3.59 and 3.67 (total 1H, each quartet, J=6.6 and 6.7 Hz); 4.44 and 4.45 (total 1H, each singlet); 6.51–6.67 (3H, multiplet); 6.89–6.97 (1H, multiplet); 7.02–7.15 (3H, multiplet); 7.19–7.32 (4H, multiplet).

(105c) 3-t-Butoxy-4-<3-{(4-chlorophenyl)-[(R)-1-(3,4-difluorophenyl)ethylamino]methyl}phenylamino>-3-cyclobutene-1,2-dione Following a similar procedure to that described in Example (66c), 1.15 g 3-{(4-chlorophenyl)-[(R)-1-(3,4-difluorophenyl)ethylamino]methyl}phenylamine [prepared as described in step (b) above] and 852 mg of 4-t-butoxy-3-methoxy-3-cyclobutene-1,2-dione were reacted, to obtain 308 mg of isomer A and 800 mg of isomer B of the title compound, each as a pale yellow oil.

Isomer A

Nuclear Magnetic Resonance Spectruim (CDCl₃) δ ppm: 1.35 (3H, doublet, J=6.6 Hz); 1.63 (9H, singlet); 3.65 (1H, quartet, J=6.6 Hz); 4.55 (1H, singlet); 6.93–6.96 (1H, multiplet); 7.02 (1H, doublet, J=6.8 Hz); 7.07–7.40 (9H, multiplet).

Isomer B

Nuclear Magnetic Resonance Spectrum (CDCl$_3$) δ ppm: 1.34 (3H, doublet, J=6.6 Hz); 1.64 (9H, singlet); 3.61 (1H, quartets J=6.6 Hz); 4.54 (1H, singlet); 6.92–7.00 (2H, multiplet); 7.06–7.35 (9H, multiplet).

(105d) 4-<3-{(4-Chlorophlenyl)-[(R)-1-(3,4-difluorophenyl)ethylamino]methyl}phenylamino>-3-hydroxy-3-cyclobutene-1,2-dione hydrochloride Following a reaction and purification procedure similar to those described in Example (63b), 280 mg of isomer A of 3-t-butoxy-4-<3-{(4-chlorophenyl)-[(R)-1-(3,4-difluorophenyl)ethylamino]methyl}phenylamino>-3-cyclobutene-1,2-dione [prepared as described in step (c) above] was reacted, to obtain 229 mg of isomer A of the title compound as a white solid.

Isomer A

Nuclear Magnetic Resonance Spectrum (DMSO-d$_6$) ppm: 1.65 (3H, doublet, J=6.7 Hz); 4.31 (1H, broad); 5.19 (1H, singlet); 7.18–7.25 (2H, multiplet); 7.34–7.59 (7H, multiplet); 7.65 (2H, doublet, J=8.6 Hz). mp: 190–196° C.; optical rotation [α]$_D$=−58.6° (c=0.575, AcOH).

Following a reaction and purification procedure similar to those described in Example (63b), 340 mg of isomer B of 3-t-butoxy-4-<3-{(4-chlorophenyl)-[(R)-1-(3,4-difluorophenyl)ethylamino]methyl}phenylamino>-3-cyclobutene-1,2-dione [prepared as described in step (c) above] was reacted, to obtain 258 mg of isomer B of the title compound as a pale yellow solid.

Isomer B

Nuclear Magnetic Resonance Spectrum (DMSO-d$_6$) δ ppm: 1.66 (3H, doublet, J=6.8 Hz); 4.24 (1H, broad); 5.20 (1H, singlet); 7.20–7.22 (1H, multiplet); 7.30–7.63 (SH, multiplet); 7.68 (2H, doublet, J=8.5 Hz). mp: 190° C. (dec.); optical rotation [α]$_D$=−4.6° (c=0.49, AcOH).

EXAMPLE 106

4-<3-{[1-(3,5-Dinitiophenyl)ethylamino]-(4-fluorophenyl)methyl}phenylamino>-3-hydroxy-3-cyclobutene-1,2-dione hydrochloride (Compound No. 2-3506)

(106a) N-(3-{[1-(3,5-Dinitrophenyl)ethylamino]-(4-fluorophenyl)methyl}phenyl>acetamide Following a similar procedure to that described in Example (1a), 830 mg of N-[3-(4-fluorobenzoyl)phenyl]acetamide, 1.19 g of 1-(3,5-dinitrophenyl)ethylamine hydrochloride, 2.7 ml of trietlylamiie and 0.4 ml of titanium tetrachloride were reacted, to obtain the corresponding imine compound.

Following a similar reaction and purification procedure to that described in Example (1a), the resulting imine compound, 806 mg of sodium cyanoborohydride and 0.3 ml of acetic acid were reacted, to obtain 1.16 g of the title compound as a pale brown foamy solid.

Nuclear Magnetic Resonance Spectrum (CDCl$_3$) δ ppm: 1.46 and 1.47 (total 3H, each doublet, J=6.7 Hz); 2.14 and 2.18 (total 3H, each singlet); 3).95–4.01 (1H multiplet), 4.59 and 4.68 (total 1H, each singlet); 6.90–7.35 (7H, multiplet); 7.51 and 7.56 (total 1H, each singlet); 8.44 and 8.48 (total 2H, each doublet, J=2.8 Hz); 8.84 and 8.91 (total 1H, each triplet, J=2.1 Hz).

(106b) 3-{[1-(3,5-Dinitrophenyl)ethylamino]-(4-fluorophenyl)methyl}phenyl>acetamide 1.15 g of N-<3-{[1-(3,5-dinitrophenyl)ethylamino]-(4-fluorophenyl)methyl}phenyl>acetamide [prepared as described in step (a) above] was dissolved in 16 ml of methanol, and then 4 m l of concentrated hydrochloric acid was added to the resulting solution. The resulting mixture was stirred at 70° C. for 3 hours. At the end of this time, a saturated aqueous solution of sodium hydrogencarbonate was added, and the mixture was concentrated by evaporation uinder reduced pressure. The residue was extracted with ethyl acetate. The extract was washed with water and with a saturated aqueous solution of sodium chloride, dried over anhydrous sodium sulfate and concentrated by evaporation under reduced pressure. The residue was separated and purified by chromatography through a silica gel column using a 2:1 by volume mixture of hexane and ethyl acetate as eluant, to obtain 442 mg of isomer A and 235 mg of isomer B of the title compound as red crystals and a yellow foamy solid, respectively.

Isomner A

Nuclear Magnetic Resonance Spectrum (CDCl$_3$) δ ppm: 1.45 (3 H, doublet, J6.7 Hz); 3.96 (1H, quartet J=6.7 Hz); 4.57 (1H, singlet); 6.43 (1H, doublet of doublets, J=2.4, 8.0 Hz); 6.52 (1H, triplet, J=2.0 Hz); 6.58 (1H, doublet, J=7.6 Hz); 6.97 (1H, triplet, J=7.8 Hz); 7.04 (2H, triplet, J=8.6 Hz); 7.30 (2H, doublet of doublets, J=5.4, 8.7 Hz); 8.45 (2H, doublet, J=2.1 Hz); 8.87 (1H, triplet, J=2.1 Hz).

Isomer B

Nuclear Magnetic Resonance Spectrum (CDCl$_3$) δ ppm: 1.44 (3H, doublet, J=6.7 Hz); 3.99 (1H, quartet, J=6.6 Hz); 4.48 (1H, singlet); 6.56 (1H, triplet, J=2.0 Hz); 6.60–6.65 (2H, multiplet); 6.91 (2H, triplet, J=8.7 Hz); 7.15 (1H, triplet, J=7.7 Hz); 7.24 (2H, doublet of doublets, J=5.6, 8.5 Hz); 8.50 (2H, doublet, J=2.1 Hz); 8.90 (1H, triplet, J=2.1Hz).

(106c) 3-t-Butoxy-4-<3-{[-(3,5-dinitrophenyl)ethylamino]-(4-fluorophenyl)methyl}phenylamino>-3-cyclobutene-1,2-dione Following a similar procedure to that described in Example (1c), 414 mg of isomer A of 3-{[1-(3,5-dinitrophenyl)ethyl amino]-(4-fluorophenyl) methyl}phenylamine [prepared as described in step (b) above] and 221 mg of 4-t-butoxy-3-methoxy-3-cyclobutene-1,2-dione were reacted, to obtain 394 mg of isomer A of the title compound as a yellow foamy solid.

Isomer A

Nuclear Magnetic Resonance Spectrum (CDCl$_3$) δ ppm: 1.48 (3H, doublet, J=6.7 Hz); 1.66 (9H, singlet); 4.01 (1H, quartet, J=6.6 Hz); 4.67 (1H, singlet); 6.90 (1H, doublet, J=7.2 Hz); 7.04–7.10 (3H, multiplet); 7.14 (1H, triplet, J=7.8 Hz); 7.33 (2H, doublet of doublets, J=5.4, 8.6 Hz); 7.48–7.60 (1H, broad); 8.46 (2H, doublet, J=2.1 Hz); 8.84 (1H, triplet, J=2.0 Hz).

Following a similar procedure to that described in Example (1c), 230 mg of isomer B of 3-{[1-(3,5-dinitrophenyl)ethylamino]-(4-fluorophenyl) methyl}phenylamine [prepared as described in step (b) above] and 124 mg of 4-t-butoxy-3-methoxy-3-cyclobutene-1,2-dione were reacted, to obtain 284 mg of isomer B of the title compound as a yellow foamy solid.

Isomer B

Nuclear Magnetic Resonance Spectrum (CDCl$_3$) δ ppm: 1.49 (3H, doublet, J=6.6 Hz); 1.65 (9H, singlet); 3.99 (1H, quartet, J=6.6 Hz); 4.61 (1H, singlet); 6.93 (2H, triplet, J=8.7 Hz); 7.00 (1H, doublet, J=7.8 Hz); 7.21–7.26 (3H, multiplet); 7.35 (1H, triplet, J=7.7 Hz); 7.50–7.60 (1H, broad); 8.49 (2H, doublet, J=2.0 Hz); 8.91 (1H, triplet, J=2.0 Hz).

(106d) 4-(3-{[1-(3,5-Dinitrophenyl)ethylamino]-(4-fluorophenyl)methyl}phenylamino)-3-hydroxy-3-cyclobutene-1,2-dione Hydrochloride Following a similar procedure to that described in Example (63b), 378 mg of isomer A of 3-t-butoxy-4-<3-{[1-(3,5-dinitrophenyl)ethylamino]-(4-fluorophenyl)

methyl}phenylamino>-3-cyclobutene-1,2-dione [prepared as described in step (c) above] and 2 ml of trifluoroacetic acid were reacted, to obtain 338 mu of isomer A of the title compound as a pale yellow solid.

Isomer A

Nuclear Magnetic Resonance Spectrum (DMSO-d$_6$) δ ppm: 1.70 (3H, doublet, J=6.6 Hz); 4.66 (1H, quartet, J=6.6 Hz); 5.36 (1H, singlet); 7.26–7.31 (5H, multiplet); 7.47 (1H, singlet); 7.67 (2H, doublet of doublets, J=5.3, 8.6 Hz); 8.73 (2H, doublet, J=2.0 Hz); 8.80 (1H, triplet, J=2.0 Hz). mp: 188° C.(dec).

Following a similar procedure to that described in Example (63b), 277 mg of isomer B of 3-t-butoxy-4-<3-{[1-(3,5-dinitrophenyl)ethylamino]-(4-fluorophenyl)methyl}phenylamino>-3-cyclobutene-1,2-dione [prepared as described in step (c) above] and 2 ml of trifluoroacetic acid were reacted, to obtain 220 mg of isomer B of the title compound as a light yellow solid.

Isomer B p Nuclear Magnetic Resonance Spectrum (DMSO-d$_6$) δ ppm: 1.76 (3H, doublet, J=6.6 Hz); 4.65 (1H, broad); 5.21 (1H, singlet); 7.18–7.26 (1H, multiplet); 7.21 (2H, triplet, J=8.8 Hz); 7.36 (1H, triplet, J=8.9 Hz); 7.44 (1H, doublet, J=8.3 Hz); 7.50 (1H, singlet); 7.66 (2H, doublet of doublets, J=5.5, 8.2 Hz); 8.69 (2H, doublet, J=1.9 Hz); 8.83 (1H, triplet, J=1.9 Hz). mp: 190° C.(dec).

EXAMPLE 107

4-<3-{(4-Methoxphenyl)-[1-(3,4,5-trifluorophenyl)ethylamino]methyl}phenylamino>-3-hydroxy-3-cyclobutene-1,2-dione Hydrochloride (Compound No. 2-3504)

(107a) N-[(4-Methoxyphenyl)-(3-nitrophenyl)methyl]-N-[1l-(3,4,5-trifluorophenyl)ethyl]amine Following a similar procedure to that described in Example (1a), 2.19 g of 4-methoxy-3'-nitrobenzophenone, 3.25 g of 1-(3,4,5-trifluorophenyl)ethylamine hydrochloride, 7.1 ml of triethylamne and 1.0 ml of titanium tetrachloride were reacted, to obtain the corresponding imine compound.

Following a similar reaction and purification procedure to that described in Example (1a), the resulting imine compound, 214 g, of sodium cyanoborohydride and 0.7 ml of acetic acid were reacted, to obtain 3.35 of the title compound as a yellow oil.

Nuclear Magnetic Resonance Spectrum (CDCl$_3$) δ ppm: 1.36 and 1.35 (total 9H, each doublet, J=6.5 Hz); 3.58 and 3.63 (total 1H, each quartet, J=6.6 Hz); 3.77 and 3.82 (total 3H, each singlet); 4.59 and 4.67 (total 1H, each singlet); 6.81–6.95 (2H, multiplet); 6.82 and 6.90 (total 2H, each doublet, J=8.8 Hz); 7.14 and 7.15 (total 2H, each doublet, J=8.7 Hz); 7.41 and 7.50 (total 1H each triplet, J=7.9 Hz); 7.59 and 7.63 (total 1H, each doublet of doublets, J=1.8, 7.8 Hz); 8.05 and 8.11 (total 1H, each doublet of doublets, J=1.8, 7.7 Hz); 8.23 and 8.24 (total 1H, each triplet, J=1.8 Hz).

(107b) 3-{(4-Methoxyphenyl)-[1-(3,4,5-trifluorophenyl)ethylamino]methyl}phenylamine Following a similar procedure to that described in Example (1b), 3.34 g of N-[(4-methoxyphenyl)-(3-nitrophenyl)methyl]-N-[1-(3,4,5-trifluorophenyl)ethyl]amine [prepared as described in step (a) above], 3.81 g of nickel chloride hexahydrate and 1.22 g of sodium borohydride were reacted, to obtain 2.83 g of the title compound as a pale yellow oil.

Nuclear Magnetic Resonance Spectrum (CDCl$_3$) δ ppm: 1.29 (3H, doublet, J=6.6 Hz); 3.60 and 3.64 (total 1H, each quartet, J=6.6 Hz); 3.76 and 3.80 (total 3H, each singlet); 4.43 and 4.44 (total 1H, each singlet); 6.50–6.67 (3H, multiplet); 6.79 and 6.86 (total 2H, each doublet, J=8.8 Hz); 6.83–6.95 (2H, multiplet); 7.04 and 7.11 (total 1H, each triplet, J=7.6 Hz); 7.18 and 7.19 (total 2H, each doublet, J=8.7 Hz).

(107c) 3-t-Butoxy-4-<3-{(4-methoxyphenyl)-[1-(3,4,5-trifluorophenyl)ethylamino]methyl}phenylamino>-3-cyclobutene-1,2-dione Following a similar reaction, separation and purification procedure to that described in Example (66c), 2.81 g of 3-{(4-methoxyphenyl)-[1-(3,4,5-trifluorophenyl)ethylamino]methyl}phenylamine [prepared as described in step (b) above] and 1.61 g of 4-t-butoxy-3-methoxy-3-cyclobutene-1,2-dione were reacted, to obtain 913 mg of isomer A and 403 mg of isomer B of the title compound, each as a white foamy solid.

Isomer A

Nuclear Magnetic Resonance Spectrum (CDCl$_3$) δ ppm: 1.34 (3H, doublet, J=6.6 Hz); 1.64 (9H, singlet); 3.63 (1H, quartet, J=6.5 Hz); 3.76 (3H, singlet); 4.54 (1H, singlet); 6.81 (2H, doublet, J=8.6 Hz); 6.90 (2H, doublet of doublets, J=6.7,8.3 Hz); 7.04 (1H, doublet, J=7.0 Hz); 7.18 (2H, doublet, J=8.6 Hz); 7.23–7.42 (3H, multiplet).

Isomer B

Nuclear Magnetic Resonance Spectrum (CDCl$_3$) δ ppm: 1.33 (3H, doublet, J=6.6 Hz); 1.65 (9H, singlet); 3.63 (1H, quartet, J=6.7 Hz); 3.82 (3H, singlet); 4.52 (1H, singlet); 6.88–6.96 (2H, multiplet); 6.90 (2H, doublet, J=8.6 Hz); 7.02–7.08 (1H, broad); 7.20 (2H, doublet, J=8.7 Hz); 7.17–7.42 (3H, multiplet).

(107d) 4-<3-{(4-Methoxyphenyl)-[1-(3,4,5-trifluorophenyl)ethylamino]methyl}phenylamino>-3-hydroxy-3-cyclobutene-1,2-dione Hydrochloride Following a similar procedure to that described in Example (63b), 828 mg of isomer A of 3-t-butoxy-4-<3-{(4-methoxyphenyl)-[1-(3,4,5-trifluorophenyl)ethylamino]methyl}phenylamino>-3-cyclobutene-1,2-dione [prepared as described in step (c) above] and 2 ml of trifluoroacetic acid were reacted, to obtain 699 mg of isomer A of the title compound as a white solid.

Isomer A

Nuclear Magnetic Resonance Spectrum (DMSO-d$_6$) δ ppm: 1.62 (3H, doublet, J=6.7 Hz); 3.74 (3H, singlet); 4.31 (1H, quartet, J=6.2 Hz); 5.12 (1H, singlet); 6.94 (2H, doublet, J=8.9 Hz); 7.15 (1H, doublet, J=7.5 Hz); 7.32–7.40 (3H, multiplet); 7.44 (1H, doublet, J=8.0 Hz); 7.52 (2H, doublet, J=8.8 Hz); 7.56 (1H, singlet). mp: 185° C.(dec).

Following a similar procedure to that described in Example (63b), 392 mg of isomer B of 3-t-butoxy-4-<3-{(4-metihoxyphenyl)-[1-(3,4,5-trifluorophenyl)ethylamino]methyl}phenylamino>-3-cyclobutene-1,2-dione [prepared as described in step (c) above] and 1.5 ml of trifluoroacetic acid were reacted, to obtain 265 mg of isomer B of the title compound as a white solid.

Isomer B

Nuclear Magnetic Resonance Spectrum (DMSO-d$_6$) δ ppm: 1.63 (3H, doublet, J=6.7 Hz); 3.77 (3H, singlet); 4.24 (1H, quartet, J=6.7 Hz); 5.15 (1H, singlet); 7.00 (2H, doublet, J=8.9 Hz); 7.33 (1H, doublet, J=7.0 Hz); 7.36–7.44 (4H, multiplet); 7.52 (1H, singlet); 7.55 (2H, doublet, J=8.7 Hz). mp: 188° C.(dec).

EXAMPLE 108

4-<3-{(4-Chlorophenyl)-[1-(3,4.5-trifluorophenyl)ethylamino]methyl}phenylamino>-3-hydroxy-3-cyclobutene-1,2-dione Hydrochloride (Compound No. 2-3503)

(108a) N-[(4-Chlorophenyl)-(3-nitrophenyl)methyl]-N-[1-(3,4,5-trifluorophenyl)ethyl]amine Following a similar procedure to that described in Example (1a), 1.82 g of 4-chloro-3'-nitrobenzophenone, 2.65 g of 1-(3,4,5-trifluorophenyl)ethylamine hydrochloride, 5.7 ml of triethylamine and 0.9 ml of titanium tetrachloride were reacted, to obtain the corresponding imine compound.

Following a similar reaction and purification procedure to that described in Example (1a), the resulting imine compound, 1.74 g of sodium cyanoborohydride and 0.7 ml of acetic acid were reacted, to obtain 2.74 g of the title compound as a yellow oil.

Nuclear Magnetic Resonance Spectrum (CDCl$_3$) δ ppm: 1.35 and 1.36 (total 3H, each doublet, J=6.6 Hz); 3.56–3.63 (1H, multiplet); 4.63 and 4.69 (total 1H, each singlet); 6.82–6.91 (2H, multiplet); 7.20 (2H, doublet J=7.4 Hz); 7.27 and 7.35 (total 2H, each doublet, J=8.4 Hz); 7.43 and 7.52 (total 1H, each triplet, J=7.9 Hz); 7.57 and 7.61 (total 1H, each doublet, J=7.7 Hz); 8.07 and 8.14 (total 1H, each doublet, J=8.1 Hz); 8.21 (1H, singlet).

(108b) 3-{(4-chlorophenyl)-[1-(3,4,5-trifluorophenyl)ethylamino]methyl}-phenylamine Following a similar reaction, separation and purification procedure to that described in Example (59b), 2.71 g of N-[(4-chlorophenyl)-(3-nitrophenyl)methyl]-N-[1-(3,4,5-trifluorophenyl)ethyl]amine [prepared as described in step (a) above], 3.06 g of nickel chloride hexahydrate and 973 mg of sodium borohydride were reacted, to obtain 946 mg of isomer A and 691 mg of isomer B of the title compound as a colorless oil and white solid, respectively.

Isomer A

Nuclear Magnetic Resonance Spectrum (CDCl$_3$) δ ppm: 1.30 (3H, doublet, J=6.6 Hz); 3.65 (1H, quartet, J=6.6 Hz); 4.43 (1H, singlet); 6.58 (1H, triplet, J=1.5 Hz); 6.59–6.64 (2H, multiplet); 6.89–6.95 (2H, multiplet); 7.12 (1H, triplet, J=7.7 Hz); 7.22 (4H, singlet).

Isomer B

Nuclear Magnetic Resonance Spectrum CDCl$_3$) δ ppm: 1.30 (3H, doublet, J=6.6 Hz); 3.59 (1H, quartet, J=6.7 Hz); 4.45 (1H, singlet); 6.52–6.56 (2H, multiplet); 6.62 (1H, doublet, J=7.9 Hz); 6.85–6.92 (2H, multiplet); 7.05 (1H, triplet, J=7.8 Hz); 7.23 (2H, doublet, J=8.4 Hz); 7.30 (2H, doublet, J=8.4 Hz).

(108c) 3-t-Butoxy-4-<3-{(4-clorophenyl)-[1-(3,4,5-trifluorophenyl)ethylamino]methyl}phenylamino>-3-cyclobutene-1,2-dione Following a similar procedure to that described in Example (1c), 923 mg of isomer A of 3-{(4-chlorophenyl)-[1-(3,4,5-trifluorophenyl)ethylamino]methyl}phenylamine [prepared as described in step (b) above] and 521 mg of 4-t-butoxy-3-methoxy-3-cyclobutene-1,2-dione were reacted, to obtain 834 mg of isomer A of the title compound as a white foamy solid.

Isomer A

Nuclear Magnetic Resonance Spectrum (CDCl$_3$) δ ppm: 1.34 (3H, doublet, J=6.6 Hz); 1.64 (9H, singlet); 3.63 (1H, quartet, J=6.5 Hz); 4.55 (1H, singlet); 6.89–6.94 (2H, multiplet); 7.00 (1H, doublet, J=7.3 Hz); 7.20–7.44 (7H, multiplet).

Following a similar procedure to that described in Example (1c), 595 mg of isomer B of 3-{(4-chlorophenyl)-[1-(3,4,5-trifluorophenyl)ethylamino]methyl}phenylamine [prepared as described in step (b) above] and 336 mg of 4-t-butoxy-3-methoxy-3-cyclobutene-1,2-dione were reacted, to obtain 583 mg of isomer B of the title compound as a white foamy solid.

Isomer B

Nuclear Magnetic Resonance Spectrum (CDCl$_3$) δ ppm: 1.33 (3H, doublet, J=6.6 Hz); 1.64 (9H, singlet); 3.59 (1H, quartet, J=6.6 Hz); 4.55 (1H, singlet); 6.87–6.92 (2H, multiplet); 6.98 (1H, doublet, J=6.9 Hz); 7.16–7.42 (3H, multiplet); 7.24 (2H, doublet, J=8.6 Hz); 7.33 (2H, doublet, J=8.5 Hz).

(108d) 4-<3-{(4-Chlorophenyl)-[1-(3,4,5-trifluorophenyl)ethylamino]methyl}phenylamino>-3-hydroxy-3-cyclobutene-1,2-dione Hydrochloride Following a similar procedure to that described in Example (63b), 774 mg of isomer A of 3-t-butoxy-4-<3-{(4-chlorophenyl)-[1-(3,4,5-trifluorophenyl)ethylamino]methyl}phenylamino>-3-cyclobutene-1,2-dione [(prepared as described in step (c) above] and 1.5 ml of trifluoroacetic acid were reacted, to obtain 637 mg, of isomer A of the title compound as a white solid.

Isomer A

Nuclear Magnetic Resonance Spectrum (DMSO-d$_6$) δ ppm: 1.61 (3H, doublet, J=6.6 Hz); 4.31 (1H, quartet, J=5.4 Hz); 5.19 (1H, singlet); 7.11 (1H, doublet, J=7.6 Hz); 7.30–7.39 (3H, multiplet); 7.43–7.47 (1H, multiplet); 7.46 (2H, doublet, J=8.4 Hz); 7.59 (1H, singlet); 7.62 (2H, doublet, J=8.8SHz). mp: 187° C.(dec).

Following a similar procedure to that described in Example (63b), 510 mg of isomer B of 3-t-butoxy-4-<3-{(4-chlorophenyl)-[1-(3,4,5-trifluorophenyl)ethylamino]methyl}phenylamino>-3-cyclobutene-1,2-dione [prepared as described in step (c) above] and 1.5 ml of trifluoroacetic acid were reacted, to obtain 354 mg of isomer B of the title compound as a white solid.

Isomer B

Nuclear Magnetic Resonance Spectrum (DMSO-d$_6$) δ ppm: 1.64 (3H, doublet, J=6.7 Hz); 4.26 (1H, quartet, J=6.6 Hz); 5.25 (1H, singlet); 7.33–7.53 (6H, multiplet); 7.52 (2H, doublet, J=8.5 Hz); 7.69 (2H, doublet, J=8.6 Hz). mp: 190° C.(dec).

EXAMPLE 109

3-Hydroxy-4-{3-[(4-methoxyphenyl)-(1-methyl-1-phenylethylamino)-methyl]phenylamino}-3-cyclobutene-1,2-dione (Compound No. 2-3136)

(109a) N-[(4-Methoxyphenyl)-(3-nitrophenyl)methyl]-N-(1-methyl-1-phenylethyl)amine 2.57 g of 4-methoxyphenyl 3-nitrophenyl ketone, 1.35 g of cumyl amine and 1.35 g of triethylamine were dissolved in 50 ml of dichloromethane, and then 30 ml of a solution of 1.65 ml of titanium tetrachloride in dichloromethane was added dropwise whilst ice cooling. The reaction mixture was stirred at room temperature for 2 hours and was then heated under reflux for 3 hours. The reaction mixture was allowed to cool, after which it was diluted with 150 ml of ethyl acetate. The insoluble matter was then filtered off. The filtrate was washed with a saturated solution of sodium hydrogencarbonate and with a saturated aqueous solution of sodium chloride, dried over anhydrous magnesium sulfate and distilled under reduced pressure to remove the solvent. Following a similar reaction, separation and purification procedure to that described in Example (1a), the resulting brown oil, 100 ml of ethanol 2.51 g of sodium cyanoborohydride and 2.58 ml of acetic acid were reacted, to obtain 1.43 g of the title compound as a yellow oil.

Nuclear Magnetic Resonance Spectrum; (CDCl$_3$) δ ppm: 1.34 (3H, singlet), 1.40 (3H, singlet); 3.75 (3H, singlet); 4.64 (1H, singlet); 6.77 (2H, doublet, J=8.8 Hz); 7.03 (2H, doublet, J=8.8 Hz); 7.21–7.40 (6H, multiplet); 7.66 (1H, doublet, J=7.3 Hz); 7.99 (1H, doublet of doublets, J=1.5, 8.1 Hz); 8.27 (1H, singlet).

(109b) 3-[(4-Methoxyphenyl)-(1-methyl-1-phenylethylamino)methyl]phenylamine

Following a similar procedure to that described in Example (94b), 1.39 g of N-[(4-methoxyphenyl)-(3-nitrophenyl)methyl]-N-(1-methyl-1-phenylethyl)amine [prepared as described in step (a) above], 1.76 g of nickel chloride hexahydrate, 559 mg of sodium borohydride and 100 ml of methanol were reacted, to obtain 1.21 g of the title compound as a yellow oil.

Nuclear Magnetic Resonance Spectrum (CDCl$_3$) δ ppm: 1.34 (3H, singlet); 1.35 (3H, singlet); 3.80 (3H, singlet); 4.46 (1H, singlet); 6.65 (1H, doublet, J=2.2, 7.3 Hz); 6.60 (1H, singlet); 6.65 (1H, doublet, J=8.1 Hz); 6.76 (2H, doublet, J=8.8 Hz); 7.00 (1H, doublet of doublets, J=7.3, 8.1 Hz); 7.17 (2H, doublet, J=8.8 Hz); 7.21–7.26 (1H, multiplet); 7.33 (1H, doublet of doublets, J=7.3, 8.1 Hz); 7.41 (2H, doublet, J=7.4 Hz).

(109c) 3-t-Butoxy-4-{3-[(4-methoxyphenyl)-(1-methyl-1-phenylethylamino)methyl]phenylamino}-3-cyclobutene-1,2-dione Following a similar procedure to that described in Example (94c), 1.19 g of 3-[(4-methoxyphenyl)-(1-methyl-1-phenylethylamino)methyl]phenylamine [prepared as described in step (b) above], 886 mg of 3-t-butoxy-4-methoxy-3-cyclobutene-1,2-dione and 40 ml of methanol were reacted, to obtain 1.42 g of the title compound as a white foamy solid.

Nuclear Magnetic Resonance Spectrum (CDCl$_3$) δ ppm: 1.35 (3H, singlet); 1.37 (3H, singlet); 1.63 (9H, singlet); 3.75 (3H, singlet); 4.56 (1H, singlet); 6.77 (2H, doubled doublet of doublets, J=2.2, 2.9, 8.8 Hz); 7.07–7.12 (3H, multiplet); 7.20–7.34 (6H, multiplet); 7.40 (2H, doublet, J=7.3 Hz).

(109d) 3-Hydroxy-4-{3-[(4-methoxyphenyl)-(1-methyl-1-phenylethylamino)methyl]phenylamino}-3-cyclobutene-1,2-dione Following a similar procedure to that described in Example (55b), 1.40 g of 3-t-butoxy-4-{3-[(4-methoxyphenyl )-(1-methyl-1-phenylethylamino)methyl]phenylamino}-3-cyclobutene-1,2-dione [prepared as described in step (c) above], 10 ml of trifluoroacetic acid and 35 ml of dichloromethane were reacted, to obtain 1.24 g of the title compound as a white solid.

Nuclear Magnetic Resonance Spectrum (DMSO-d$_6$) δ ppm: 1.61 (3H, singlet); 1.67 (3H, singlet); 3.76 (3H, singlet); 4.78 (1H, singlet); 6.81 (1H, doublet, J=8.1 Hz); 6.86 (2H, doublet, J=8.8 Hz); 7.15 (1H, triplet, J=8.1 Hz); 7.32–7.46 (6H, multiplet); 7.49–7.54 (2H, multiplet); 7.65–7.68 (1H, multiplet). mp: 197° C.(dec.).

EXAMPLE 110

3-<3-{(4-Chlorophenyl)-[1-(2,3,4-trifluorophenyl) ethylamino]-methyl}phenylamino>-4-hydroxy-3-cyclobutene-1,2-dione Hydrochloride (Compound No. 2-3507)

(110a) N-[(4-Chlorophenyl)-(3-nitrophenyl)methyl]-N-[1-(2,3,4-trifluorophenyl)ethyl]amine Following a similar procedure to that described in Example (1a), 2.62 g of 4-chlorophenyl 3-nitrophenyl ketone, 2.12 g of 1-(2,3,4-trifluorophenyl)ethylamine hydrochloride, 6.97 ml of triethylamine and 1.6 ml of titanium tetrachloride were reacted, to obtain the corresponding imine compound.

Following a similar reaction and purification procedure to that described in Example (1a), the resulting imine compound, 2.51 g of sodium cyanoborohydride and 2.6 ml of acetic acid were reacted, to obtain 4.06 g of the title compound as a yellow oil.

Nuclear Magnetic Resonance Spectrum (CDCl$_3$) δ ppm: 1.43 and 1.44 (total 3H, each doublet, J=6.6 Hz); 3.90 and 3.94 (total 1H, each quartet, J=6.6 Hz); 4.67 and 4.69 (total 1H, each singlet); 6.91–7.05 (2H, multiplet); 7.19–7.26 (3H, multiplet); 7.32 and 7.34 (total 1H, each triplet, J=2.2 Hz); 7.41 and 7.49 (total 1H, each doublet, J=8.1 Hz); 8.06 and 8.21 (total 1H, each doublet of doublets, J=2.2, 8.1 Hz); 8.21–8.28 (1H, multiplet).

(110b) 3-{(4-Chlorophenyl)-[1-(2,3,4-trifluorophenyl) ethylamino]methyl}phenylamine Following a similar reaction, separation and purification procedure to that described in Example (59b), 3.96 g of N-[(4-chlorophenyl)-(3-nitrophenyl)methyl]-N-[1-(2,3,4-trifluorophenyl)ethyl]amine [prepared as described in step (a) above], 4.47 g of nickel chloride hexahydrate and 1.42g of sodium borohydride were reacted, to obtain 1.05 g of isomer A and 720 mg, of isomer B of the title compound, each as a pale yellow oil.

Isomer A

Nuclear Magnetic Resonance Spectrum (CDCl$_3$) δ ppm: 1.38 (3H, doublet, J=6.6 Hz); 3.99 (1H, quartet, J=6.6 Hz); 4.47 (1H, singlet); 6.56–6.60 (2H, multiplet); 6.65 (1H, doublet, J=S. 1Hz); 6.89–6.95 (1H, multiplet); 7.01–7.29 (6H, multiplet).

Isomer B

Nuclear Magnetic Resonance Spectrum (CDCl$_3$) δ ppm: 1.38 (3H, doublet, J=6.6 Hz); 3.90 (1H, quartet, J=6.6 Hz); 4.46 (1H, singlet); 6.51 (1H, doublet of doublets, J=1.5, 7.3 Hz); 6.57 (1H, singlet); 6.63 (1H, doublet, J=7.3 Hz); 6.90–7.18 (3H, multiplet); 7.20–7.34 (4H, multiplet).

(110c) 3-t-Butoxy-4-<3-{(4-chlorophenyl)-[1-(2,3,4-trifluorophenyl)ethylamino]methyl}phenylamino>-3-cyclobutene-1,2-dione Following a similar procedure to that described in Example (1c), 1.01 g of isomer A of 3-{(4-chlorophenyl)-[1-(2,3,4-trifluorophenyl)ethylamino]methyl}phenylamine [prepared as described in step (b) above] and 668 mg of 4-t-butoxy-3-methoxy-3-cyclobutene-1,2-dione were reacted, to obtain 560 mg of isomer A of the title compound as a white foamy solid.

Isomer A

Nuclear Magnetic Resonance Spectrum (CDCl$_3$) δ ppm: 1.42 (3H, doublet, J=6.6 Hz); 1.63 (9H, singlet); 3.97 (1H, quartet, J=6.0 Hz); 4.58 (1H, singlet); 6.91–7.09 (3H, multiplet); 7.12–7.47 (7H, multiplet).

Following a similar procedure to that described in Example (1c), 700 mg of isomer B of 3-{(4-chlorophenyl)-[1-(2,3,4-trifluorophenyl)ethylamino]methyl}phenylamine [prepared as described in step (b) above] and 462 mg of 4-t-butoxy-3-methoxy-3-cyclobutene-1,2-dione were reacted, to obtain 500 mg of isomer B of the title compound as a white foamy solid.

Isomer B

Nuclear Magnetic Resonance Spectrum (CDCl$_3$) δ ppm: 1.41 (3H, doublet, J=6.6 Hz); 1.64 (9H, singlet); 3.90–3.98 (1H, multiplet); 4.57 (1H, singlet); 6.90–7.08 (3H, multiplet); 7.20–7.42 (7H, multiplet).

(110d) 3-<3-{(4-Chlorophenyl)-[1-(2,3,4-trifluorophenyl) ethylamino]methyl}phenylamino>-4-hydroxy-3-cyclobutene-1,2-dione Hydrochloride Following a similar procedure to that described in Example (63b), 520 mg of isomer A of 3-t-butoxy-4-<3-{(4-chlorophenyl)-[1-(2,3,4-trifluorophenyl)ethylamino]-methyl}phenylamino>-3-cyclobutene-1,2-dione [prepared as described in step (c) above] and 6 ml of trifluoroacetic acid were reacted, to obtain 225 mg of isomer A of the title compound as a white solid.

Isomer A

Nuclear Magnetic Resonance Spectrum (DMSO-d$_6$) δ ppm: 1.68 (3H, doublet, J=6.6 Hz); 4.49 (1H, quartet, J=6.6

Hz); 5.31 (1H, singlet); 7.24 (1H, doublet, J=7.3 Hz); 7.34 (1H, triplet, J=8.1 Hz); 7.41 (1H, doublet, J=8.1 Hz); 7.43–7.52 (3H, multiplet); 7.56–7.59 (1H, multiplet); 7.60–7.69 (3H, multiplet). mp: 176° C.(dec).

Following a similar procedure to that described in Example (63b), 460 mg of isomer B of 3-t-butoxy-4-<3-{(4-chlorophenyl)-[1-(2,3,4-trifluorophenyl)ethylamino]methyl}phenylamino>-3-cyclobutene-1,2-dione [prepared as described in step (c) above] and 5 ml of trifluoroacetic acid were reacted, to obtain 337 mg of isomer B of the title compound as a white solid.

Isomer B

Nuclear Magnetic Resonance Spectrum (DMSO-$d_6$) δ ppm: 1.62–1.75 (3H, broad); 4.41 (1H, quartet, J=6.0 Hz); 5.36 (1H, singlet); 7.25–7.74 (10H, multiplet). mp: 191° C.(dec).

EXAMPLE 111

3-<3-{[(R)-1-(4-Fluorophenyl)ethylamino]-(4-methoxyphenyl)methyl}phenylamino>-4-hydroxy-3-cyclobutene-1,2-dione Hydrochloride (Compound No. 2-28)

(111a) N-[(R)-1-(4-Fluorophenyl)ethyl]-N-[(4-methoxyphenyl)-(3-nitrophenyl)methyl]amine Following a similar procedure to that described in Example (1a), 5.14 g of 4-methoxyphenyl 3-nitrophenyl ketone 4.24 g of (R)-1-(4-fluorophenyl)ethylamine hydrochloride, 13.9 ml of triethylamine and 3.3 ml of titanium tetrachloride were reacted, to obtain the corresponding imine compound. Following a similar reaction, separation and purification procedure to that described in Example (1a), the resulting imine compound, 5.03 g of sodium cyanoborohydride and 5.15 ml of acetic acid were then reacted, to obtain 7.60 g of the title compound as a yellow oil.

Nuclear Magnetic Resonance Spectrum (CDCl$_3$) δ ppm: 1.36 and 1.39 (total 31H, each doublet, J=6.6 Hz); 3.56–3.72 (1H, multiplet); 3.76 and 3.81 (total 3H, each singlet); 4.60 and 4.64 (total 1H, each singlet); 6.81 and 6.89 (total 2H, each doublet, J=8.7 Hz); 7.00 and 7.04 (total 2H, each doublet, J=8.7 Hz); 7.12–7.25 (4H, multiplet); 7.38 and 7.48 (total 1H, each triplet, J=8.0 Hz); 7.57 and 7.66 (total 1H, each doublet, J=7.6 Hz); 8.02–8.10 (total 1H, multiplet); 8.22–8.28 (total 1H, multiplet).

(111b) 3-{[(R)-1-(4-Fluorophenyl)ethylamino]-(4-methoxyphenyl)methyl}phenylamine Following a similar reaction, separation and purification procedure to that described in Example (59b), 7.60 g of N-[(R)-1-(4-fluorophenyl)ethyl]-N-[(4-methoxyphenyl)-(3-nitrophenyl)methyl]amine [prepared as described in step (a) above], 9.51 g of nickel chloride hexahydrate and 3.03 g of sodium borohydride were reacted, to obtain 1.52 g of isomer A and 1.39 g of isomer B of the title compound, each as a pale yellow oil.

Isomer A

Nuclear Magnetic Resonance Spectrum (CDCl$_3$) δ ppm: 1.33 (3H, doublet, J=6.6 Hz); 3.69 (1H, quartet, J=6.6 Hz); 3.75 (3H, singlet); 4.44 (1H, singlet); 6.57 (1H, doublet of doublets, J=2.2, 8.1 Hz); 6.63 (1H, singlet); 6.68 (1H, doublet, J=7.3 Hz); 6.77–6.80 (2H, multiplet); 6.98–7.02 (2H, multiplet); 7.08–7.12 (1H. multiplet); 7.17–7.29 (4H, multiplet).

Isomer B

Nuclear Magnetic Resonance Spectrum (CDCl$_3$) δ ppm: 1.32 (3H, doublet, J=6.6 Hz); 3.65 (1H, quartet, J=6.6 Hz); 3.80 (3H, singlet); 4.44 (1H, singlet); 6.49–6.51 (1H, multiplet); 6.61 (1H, singlet); 6.65 (1H, doublet, J=7.3 Hz); 6.86 (2H, doublet, J=8.8 Hz); 6.98–7.05 (3H, multiplet); 7.19–7.22 (4H, multiplet).

(111c) 3-t-Butoxy-4-<3-{[(R)-1-(4-fluorophenyl)ethylamino]-(4-methoxyphenyl)methyl}phenylamino>-3-cyclobutene-1,2-dione Following a similar procedure to that described in Example (1c), 1.50 g of isomer A of 3-{[(R)-1-(4-fluorophenyl)ethylamino]-(4-methoxyphenyl)methyl}phenylamine [prepared as described in step (b) above] and 1.10 g of 4-t-butoxy-3-methoxy-3-cyclobutene-1,2-dione were reacted, to obtain 1.95 g of isomer A of the title compound as a white foamy solid.

Isomer A

Nuclear Magnetic Resonance Spectrum (CDCl$_3$) δ ppm: 1.36 (3H, doublet, J=6.6 Hz); 1.63 (9H, singlet); 3.67 (1H, quartet, J=6.6 Hz); 3.75 (3H, singlet); 4.54 (1H, singlet); 6.77–6.81 (2H, multiplet); 6.99–7.08 (3H, multiplet); 7.15–7.23 (4H. multiplet); 7.29–7.36 (3H, multiplet).

Following a similar procedure to that described in Example (1c), 1.35 g of isomer B of 3-{[(R)-1-(4-fluorophenyl)ethylamino]-(4-methoxyphenyl)methyl}phenylamine [prepared as described in step (b) above] and 993 mg of 4-t-butoxy-3-methoxy-3-cyclobutene-1,2-dione were reacted, to obtain 2.14 g of isomer B of the title compound as a white foamy solid.

Isomer B

Nuclear Magnetic Resonance Spectrum (CDCl$_3$) δ ppm: 1.35 (3H, doublet, J=6.6 Hz); 1.64 (9H, singlet); 3.66 (1H, quartet, J=6.6 Hz); 3.81 (3H, singlet); 4.53 (1H, singlet); 6.89 (2H, doublet, J=8.1 Hz); 6.99–7.04 (3H, multiplet); 7.20–7.27 (7H, multiplet).

(111d) 3-<3-{[(R)-1-(4-Fluorophenyl)ethylamino]-(4-methoxyphenyl)methyl}-phenylamino>-4-hydroxy-3-cyclobutene-1,2-dione Hydrochloride Following a similar procedure to that described in Example (63b), 1.92 g of isomer A of 3-t-butoxy-4-<3-{[(R)-1-(4-fluorophenyl)ethylamino]-(4-methoxyphenyl)-methyl}phenylamino>-3-cyclobutene-1,2-dione [prepared as described in step (c) above] and 8 ml of trifluoroacetic acid were reacted, to obtain 1.85 g of isomer A of the title compound as a white solid.

Isomer A

Nuclear Magnetic Resonance Spectrum (DMSO-$d_6$) δ ppm: 1.65–1.68 (3H, multiplet); 3.74 (3H, singlet); 4.15–4.33 (1H, broad); 5.00 (1H, singlet); 6.95–6.98 (2H, multiplet); 7.25–7.57 (10H, multiplet). mp: 176° C.(dec); optical rotation [α]$_D$=−44.5 (c=1.00, AcOH).

Following a similar procedure to that described in Example (63b), 2.12 g of isomer B of 3-t-butoxy-4-<3-{[(R)-1-(4-fluorophenyl)ethylamino]-(4-methoxyphenyl)methyl}phenylamino>-3-cyclobutene-1,2-dione [prepared as described in step (c) above] and 10 ml of trifluoroacetic acid were reacted, to obtain 1.81 g of isomer B of the title compound as a white solid.

Isomer B

Nuclear Magnetic Resonance Spectrum (DMSO-$d_6$) δ ppm: 1.65–1.69 (3H, multiplet); 3.77 (3H, singlet); 4.10–4.22 (1H, broad); 4.90–5.05 (1H, broad); 6.97–7.00 (2H, multiplet); 7.26–7.56 (10H, multiplet). mp: 173° C.(dec); optical rotation [α]$_D$=−16.0 (c=100, AcOH).

EXAMPLE 112

3-<3-{[(R)-1-(3,4-Difluorophenylamino)ethylamino]-(p-tolyl)methyl}-phenylamino>-4-hydroxy-3-cyclobutene-1,2-dione (Compound No. 2-3386)

(112a) N-[(R)-1-(3,4-Difluorophenyl)ethyl]-N-[(3-nitrophenyl)-p-tolylmethyl]-amine Following a similar procedure to that described in Example (1a), 4.23 g of 3-nitrophenyl p-tolyl ketone, 3.39 g of (R)-1-(3,4-difluorophenyl)ethylamine hydrochloride, 12.2 ml of triethylamine and 2.8 ml of titanium tetrachloride were reacted, to obtain the corresponding imine compound.

Following a similar reaction and purification procedure to that described in Example (1a), the resulting imine compound, 4.41 g of sodium cyanoborohydride and 4.52 ml of acetic acid were reacted, to obtain 5.92 g of the title compound as a yellow oil.

Nuclear Magnetic Resonance Spectrum (CDCl$_3$) δ ppm: 1.34 and 1.36 (total 3H, each doublet, J=6.6 Hz); 2.23 and 2.35 (total 3H, each singlet); 3.60 and 3.66 (total 1H, each quartet, J=6.6 Hz); 4.11 and 4.13 (total 1H, each singlet); 6.87–6.90 (1H, multiplet); 7.02–7.20 (7H, multiplet); 7.39 and 7.48 (total 1H, each doublet of doublets, J=7.3, 8.1 Hz); 7.58 and 7.65 (total 1H, each doublet, J=7.3 and 8.1 Hz); 8.02–8.04 (total 1H, multiplet); 8.21–8.27 (total 1H, multiplet).

(112b) 3-{[(R)-1-(3,4-Difluorophenyl)ethylamino]-(p-tolyl)methyl}phenylamine

Following a similar reaction, separation and purification procedure to that described in Example (59b), 5.88 g of N-[(R)-1-(3 4-difluorophenyl)ethyl]-N-[(3-nitrophenyl)-(p-tolyl)methyl]amine [prepared as described in step (a) above], 7.31 g of nickel chloride hexahydrate and 2.33 g of sodium borohydride were reacted, to obtain 0.91 g of isomer A and 335 mg of isomer B of the title compound, each as a colorless oil.

Isomer A

Nuclear Magnetic Resonance Spectrum (CDCl$_3$) δ ppm: 1.31 (3H, doublet, J=7.3 Hz); 2.29 (3H, singlet); 3.65–3.80 (1H, multiplet); 4.45 (1H, singlet); 6.55–6.72 (3H, multiplet); 6.93–7.00 (1H, singlet); 7.04–7.20 (7H, multiplet).

Isomer B

Nuclear Magnetic Resonance Spectrum (CDCl$_3$) δ ppm: 1.31 (3H, doublet, J=6.6 Hz); 2.34 (3H, singlet); 3.63 (1H, quartet, J=6.6 Hz); 4.45 (1H, singlet); 6.50 (1H, doublet of doublets, J=2.2, 8.1 Hz); 6.61 (1H, singlet); 6.66 (1H, doublet, J=8.1 Hz); 6.91–6.97 (1H, multiplet); 6.98–7.22 (7H, multiplet).

(112c) 3-t-Butoxy-4-<3-{[(R)-1-(3,4-difluorophenyl)ethylamino]-p-tolylmethyl}phenylamino>-3-cyclobutene-1,2-dione Following a similar procedure to that described in Example (1c), 0.90 g of isomer A of 3-{[(R)-1-(3,4-difluorophenyl)ethylamino]-(p-tolyl)methyl}phenylamine [prepared as described in step (b) above] and 658 mg of 4-t-butoxy-3-methoxy-3-cyclobutene-1,2-dione were reacted, to obtain 230 ml of isomer A of the title compound as a white foamy solid.

Isomer A

Nuclear Magnetic Resonance Spectrum (CDCl$_3$) δ ppm: 1.35 (3H, doublet, J=6.6 Hz); 1.63 (9H, singlet); 2.29 (3H, singlet); 3.66 (1H, quartet, J=6.6 Hz); 4.56 (1H, singlet); 6.92–6.98 (1H, multiplet); 7.03–7.18 (7H, multiplet); 7.28–7.40 (3H, multiplet).

Following a similar procedure to that described in Example (1c), 305 mg of isomer B of 3-{[(R)-1-(3,4-difluorophenyl)ethylamino]-(p-tolyl)methyl}phenylamine [prepared as described in step (b) above] and 224 ml of 4-t-butoxy-3-methoxy-3-cyclobutene-1,2-dione were reacted, to obtain 460 mg of isomer B of the title compound as a white foamy solid.

Isomer B

Nuclear Magnetic Resonance Spectrum (CDCl$_3$) δ ppm: 1.33 (3H, doublet, J=6.6 Hz); 1.63 (9H, singlet); 2.34 (3H, singlet); 3.64 (1H, quartet J=6.6 Hz); 4.53 (1H, singlet); 6.92–6.99 (1H, multiplet); 7.00–7.38 (10H, multiplet).

(112d) 3-<3-{[(R)-1-(3,4-Difluorophenylamino)ethylamino]-(p-tolyl)methyl}-phenylamino>-4-hydroxy-3-cyclobutene-1,2-dione Following a similar procedure to that described in Example (63b), 220 mg of isomer A of 3-t-butoxy-4-<3-{[(R)-1-(3,4-difluorophenylamino)ethylamino]-(p-tolyl)methyl}phenylamino>-3-cyclobutene-1,2-dione [prepared as described in step (c) above] and 3 ml of trifluoroacetic acid were reacted, to obtain 207 mg of isomer A of the title compound as a white solid.

Isomer A

Nuclear Magnetic Resonance Spectrum (DMSO-d$_6$) δ ppm: 1.64 (3H, doublet, J=6.6 Hz); 2.28 (3H, singlet); 4.25–4.35 (1H, broad); 5.09 (1H, singlet); 7.12–7.24 (4H, multiplet); 7.31–7.38 (1H, multiplet); 7.41–7.57 (6H, multiplet). mp: 187° C.(dec); optical rotation [α]$_D$=−93.5 (c=1.01 AcOH).

Following a similar procedure to that described in Example (63b), 509 mg of isomer B of 3-t-butoxy-4-<3-{[(R)-1-(3,4-difluorophenylamino)ethylamino]-(p-tolyl)methyl}-phenylamino>-3-cyclobutene-1,2-dione [prepared as described in step (c) above] and 3 ml of trifluoroacetic acid were reacted, to obtain 402 mg of isomer B of the title compound as a white solid.

Isomer B

Nuclear Magnetic Resonance Spectrum (DMSO-d$_6$) δ ppm: 1.64 (3H, doublet, J=6.6 Hz); 2.31 (3H, singlet); 4.15–4.24 (1H. broad); 5.08 (1H, singlet); 7.16–7.23 (1H, multiplet); 7.25 (2H,d, J=8.1 Hz); 7.28–7.62 (8H, multiplet). mp: 185° C.(dec); optical rotation [α]$_D$=−12.5 (c=1.01, AcOH).

EXAMPLE 113

4-<3-{(4-Methoxyphenyl)-[(R)-1-(3,4,5-trifluorophenyl)ethylamino]methyl}phenylamino>-3-hydroxy-3-cyclobutene-1,2-dione Hydrochloride (Compound No. 2-3504)

(113a) N-[(4-Methoxyphenyl)-(3-nitrophenyl)methyl]-N-[(R)-1-(3,4,5-trifluorophenyl)ethyl]amine Following a similar procedure to that described in Example (1a), 1.73 g of 4-methoxy-3'-nitrobenzophenone, 2.28 g of (R)-1-(3,4,5-trifluorophenyl)ethylamine hydrochloride, 5.6 ml of triethylamine and 0.8 ml of titanium tetrachloride were reacted, to obtain the corresponding imine compound.

Following a similar reaction and purification procedure to that described in Example (1a), the resulting imine compound, 1.69 g of sodium cyanoborohydride and 0.6 ml of acetic acid were reacted, to obtain 2.63 g of the title compound as a yellow oil.

Nuclear Magnetic Resonance Spectrum (CDCl$_3$) δ ppm: 1.33 and 1.35 (total 3H, each doublet, J=6.6 Hz); 3.58 and 3.63 (total 1H, each quartet, J=6.6 Hz); 3.77 and 3.82 (total 3H, each singlet); 4.59 and 4.67 (total 1H, each singlet); 6.81–6.94 (2H, multiplet); 6.82 and 6.90 (total 2H, each doublet, J=8.8 Hz); 7.14 and 7.15 (total 2H, each doublet, J=8.7 Hz); 7.41 and 7.56 (total 1H, each triplet, J=7.8 Hz); 7.59 and 7.63 (total 1H, each doublet, J=7.7 Hz); 8.05 and 8.11 (total 1H, each doublet of doublets, J=1.2, 7.4 Hz); 8.23 and 8.24 (total 1H, each triplet, J=1.9 Hz).

(113b) 3-{(4-Methoxyphenyl)-[(R)-1-(3,4,5-trifluorophenyl)ethylamino]methyl}phenylamine Following a similar procedure to that described in Example (1b), 2.61 g of N-[(4-methoxyphenyl)-(3-nitrophenyl)methyl]-N-[(R)-1-(3,4,5-trifluorophenyl)ethyl]

amine [prepared as described in step (a) above], 3.00 g of nickel chloride hexahydrate and 958 mg of sodium borohydride were reacted, to obtain 2.33 g of the title compound as a colorless oil.

Nuclear Magnetic Resonance Spectrum (CDCl$_3$) δ ppm: 1.29 (3H, doublet, J=6.6 Hz); 3.60 and 3.65 (total 1H, each quartet, J=6.6 Hz); 3.76 and 3.80 (total 3H, each singlet); 4.43 and 4.44 (total 1H, each singlet); 6.50–6.61 (9H, multiplet); 6.66 (1H, doublet, J=7.5 Hz); 6.79 and 6.86 (total 2H, each doublet, J=8.7 Hz); 6.89–6.96 (2H, multiplet); 7.04 and 7.1 (total 1H, each triplet, J=7.8 Hz); 7.18 and 7.9 (total 2H, each doublet, J=8.8 Hz).

(113c) 3-t-Butoxy-4-<3-{(4-methoxyphenyl)-[(R)-1-(3,4,5-trifluorophenyl)ethyl-amino]methyl}phenylamino>-3-cyclobutene-1,2-dione Following a similar reaction, separation and purification procedure to that described in Example (66c), 2.31 g of 3-{(4-methoxyphenyl)-[(R)-1-(3,4,5-trifluorophenyl) ethylamino]methyl}phenylamine [prepared as described in step (b) above] and 1.32 g of 4-t-butoxy-3-methoxy-3-cyclobutene-1,2-dione were reacted, to obtain 950 mg of isomer A and 793 mg of isomer B of the title compound, each as a white foamy solid.

Isomer A

Nuclear Magnetic Resonance Spectrum (CDCl$_3$) δ ppm: 1.34 (3H, doublet. T=6.6 Hz); 1.63 (9H, singlet); 3.64 (1H, quartet, J=6.6 Hz); 3.76 (3H, singlet); 4.54 (1H, singlet); 6.81 (2H, doublet, J=8.7 Hz); 6.90 (2H, doublet of doublets, J=6.7, 8.3 Hz); 7.04 (1H, doublet, J=6.9 Hz); 7.18 (2H, doublet, J=8.7 Hz); 7.23–7.40 (3H, multiplet).

Isomer B

Nuclear Magnetic Resonance Spectrum (CDCl$_3$) δ ppm: 1.32 (3H, doublet, J=6.6 Hz); 1.64 (9H, singlet); 3.62 (1H, quartet, J=6.7 Hz); 3.81 (3H, singlet); 4.51 (1H, singlet); 6.88–6.94 (2H, multiplet); 6.89 (2H, doublet, J=8.7 Hz); 7.00–7.06 (1H, broad); 7.19 (2H, doublet, J=8.6 Hz); 7.20–7.40 (3H, multiplet).

(113d) 4-<3-{(4-Methoxyphenyl)-[(R)-1-(3,4,5-trifluorophenyl)ethylamino]methyl}phenylamino>-3-hydroxy-3-cyclobutene-1,2-dione Hydrochloride Following a similar procedure to that described in Example (63b), 916 mg of isomer A of 3-t-butoxy-4-<3-{(4-methoxyphenyl)-[(R)-1-(3,4,5-trifluorophenyl) ethylamino]methyl}phenylamino>-3-cyclobutene-1,2-dione [prepared as described in step (c) above] and 2 ml of trifluoroacetic acid were reacted, to obtain 628 mg of isomer A of the title compound as a white solid.

Isomer A

Nuclear Magnetic Resonance Spectrum (DMSO-d$_6$) δ ppm: 1.64 (3H, doublet, J=6.7 Hz); 3.73 (3H, singlet); 4.30 (1H, quartet, J=5.8 Hz); 5.12 (1H, singlet); 6.94 (2H, doublet, J=8.7 Hz); 7.24 (1H, doublet, J=7.5 Hz); 7.34–7.43 (4H, multiplet); 7.53 (1H, singlet); 7.54 (2H, doublet, J=8.6 Hz). mp: 188° C.(dec); optical rotation [α]$_D$=−154 (c=0.91, AcOH).

Following a similar procedure to that described in Example (63b), 689 mg of isomer B of 3-t-butoxy-4-<3-{(4-methoxyphenyl)-[(R)-1-(3,4,5-trifluorophenyl) ethylamino]methyl}phenylamino>-3-cyclobutene-1,2-dione [prepared as described in step (c) above] and 2 ml of trifluoroacetic acid were reacted, to obtain 616 mg of isomer B of the title compound as a white solid.

Isomer B

Nuclear Magnetic Resonance Spectrum (DMSO-d$_6$) δ ppm: 1.63 (3H, doublet, J=6.8 Hz); 3.77 (3H, singlet); 4.25 (1H, quartet, J=6.8 Hz); 5.15 (1H, singlet), 7.00 (2H, doublet, J=8.8 Hz); 7.33 (1H, doublets J=7.0 Hz); 7.36–7.44 (4H, multiplet); 7.52 (1H, singlet); 7.55 (2H. doublet, J=8.8 Hz). mp: 183° C.(dec); optical rotation [α]$_D$=+23.6 (c= (0.82, AcOH).

EXAMPLE 114

4-<3-{(4-Chlorophenyl)-[(R)-1-(3,4,5-trifluorophenyl)ethylamino]methyl}phenylamino>-3-hydroxy-3-cyclobutene-1,2-dione Hydrochloride (Compound No. 2-3503)

(114a) N-[(4-Chlorophenyl)-(3-nitrophenyl)methyl]-N-[(R)-1-(3,4,5-trifluorophenyl)ethyl]amine Following a similar procedure to that described in Example (1a), 1.68 g of 4-chloro-3'-nitrobenzophenone, 2,21 of (R)-1-(3,4,5-trifluorophenyl)ethylamine hydrochloride, 5.3 ml of triethylamine and 0.8 ml of titanium tetrachloride were reacted, to obtain the corresponding imine compound.

Following a similar reaction and purification procedure to that described in Example (1a), the resulting imine compound, 1.61 g of sodium cyanoborohydride and 0.5 ml of acetic acid were reacted, to obtain 2.44 g of the title compound as a yellow oil.

Nuclear Magnetic Resonance Spectrum CDCl$_3$) δ ppm: 1.35 and 1.36 (total 3H, each doublet, J=6.6 Hz); 3.56–3.64 (1H, multiplet); 4.63 and 4.69 (total 1H, each singlet); 6.83–6.91 (2H, multiplet); 7.20 (2H, doublet, J=8.3 Hz); 7.27 and 7.35 (total 2H, each doublet, J=7.7 Hz); 7.43 and 7.52 (total 1H, each triplet, J=8.0 Hz); 7.57 and 7.61 (total 1H, each doublet, J=7.8 Hz); 8.07 and 8.14 (total 1H, each doubled doublet of doublets, J=1.0, 2.2, 8.1 Hz); 8.21 (1H, triplet, J=1.8 Hz).

(114b) 3-{(4-Chlorophenyl)-[(R)-1-(3,4,5-trifluorophenyl) ethylamino]methyl}phenylamine Following a similar reaction, separation and purification procedure to that described in Example (59b), 2.38 g of N-[(4-clorophenyl)-(3-nitrophenyl)methyl]-N-[(R)-1-(3,4, 5-trifluorophenyl)ethyl]amine [prepared as described in step (a) above], 2.69 g of nickel chloride hexahydrate and 866 mg of sodium borohydride were reacted, to obtain 942 mg of isomer A and 663 mg of isomer B of the title compound, each as a colorless oil.

Isomer A

Nuclear Magnetic Resonance Spectrum (CDCl$_3$) δ ppm: 1.30 (3H, doublet, J=6.6 Hz); 3.65 (1H, quartet, J=6.6 Hz); 4.43 (1H, singlet); 6.54 (1H, triplet, J=1.9 Hz); 6.58–6.63 (2H, multiplet); 6.92 (2H, doublet, J=6.6, 8.5 Hz); 7.12 (1H, triplet, J=7.7 Hz); 7.22 (4H, singlet).

Isomer B

Nuclear Magnetic Resonance Spectrum (CDCl$_3$) δ ppm: 1.30 (3H, doublet, J=6.6 Hz); 3.57 (1H, quartet, J=6.6 Hz); 4.45 (1H, singlet); 6.52–6.60 (2H, multiplet); 6.62 (1H, doublet, J=7.9 Hz); 6.87 (2H, doublet of doublets, J=6.8, 8.1 Hz); 7.05 (1H, triplet, J=7.8 Hz); 7.23 (2H, doublet, J=8.4 Hz); 7.30 (2H, doublet, J=8.4 Hz).

(114c) 3-t-Butoxy-4-<3-{(4-chlorophenyl)-[(R)-1-(3,4,5-trifluorophenyl)ethyl-amino]methyl}phenylamino)-3-cyclobutene-1,2-dione Following a similar procedure to that described in Example (1c), 865 mg of isomer A of 3-{(4-chlorophenyl)-[(R )-1-(3,4,5-trifluorophenyl)ethylamino] methyl}phenylamine [prepared as described in step (b) above] and 488 mg of 4-t-butoxy-3-methoxy-3-cyclobutene-1,2-dione were reacted, to obtain 947 mg of isomer A of the title compound as a white foamy solid.

Isomer A

Nuclear Magnetic Resonance Spectrum (CDCl$_3$) δ ppm: 1.34 (3H, doublet, J=6.6 Hz); 1.64 (9H, singlet); 3.63 (1H, quartet, J=6.5 Hz); 4.55 (1H, singlet); 6.90 (2H, doublet of doublets, J=6.7, 8.1 Hz); 7.00 (1H, doublet, J=7.2 Hz); 7.21–7.42 (7H, multiplet).

Following a similar procedure to that described in Example (1c), 624 mg of isomer B of 3-{(4-chlorophenyl)-[(R)-1-(3,4,5-trifluorophenyl)ethylamino]methyl}phenylamine [prepared as described in step (b) above] and 353 mg of 4-t-butoxy-3-methoxy-3-cyclobutene-1,2-dione were reacted, to obtain 797 mg, of isomer B of the title compound as a white foamy solid.

Isomer B

Nuclear Magnetic Resonance Spectrum (CDCl$_3$) δ ppm: 1.33 (3H, doublet, J=6.6 Hz); 1.64 (9H, singlet); 3.59 (1H, quartet, J=6.6 Hz); 4.55 (1H, singlet); 6.89 (2H, doublet of doublets, J=6.7, 8.1 Hz); 6.98 (1H, doublet, J=6.9 Hz); 7.16–7.42 (3H, multiplet); 7.24 (2H, doublet, J=8.3 Hz); 7.33 (2H, doublet, J=S.4 Hz).

(114d) 4-<3-{(4-Chlorophenyl)-[(R)-1-(3,4,5-trifluorophenyl)ethylamino]methyl}-phenylamino>-3-hydroxy-3-cyclobutene-1,2-dione Hydrochloride Following a similar procedure to that described in Example (63b), 840 mg of isomer A of 3-t-butoxy-4-<3-{(4-chlorophenyl)-[(R)-1-(3,4,5-trifluorophenyl)ethyl-amino]methyl}phenylamino>-3-cyclobutene-1,2-dione [prepared as described in step (c) above] and 2 ml of trifluoroacetic acid were reacted, to obtain 744 mg of isomer A of the title compound as a white solid.

Isomer A

Nuclear Magnetic Resonance Spectrum (DMSO-d$_6$) δ ppm: 1.64 (3H, doublet, J=6.6 Hz); 4.32 (1H, quartet, J=6.5 Hz); 5.23 (1H, singlet); 7.25 (1H, doublet, J=7.2 Hz); 7.26–7.44 (4H, multiplet); 7.46 (2H, doublet, J=8.6 Hz); 7.55 (1H, singlet); 7.67 (2H, doublet, J=8.4 Hz). mp: 188° C.(dec); optical rotation [α]$_D$=−117 (c=0.82, AcOH).

Following a similar procedure to that described in Example (63b), 757 mg of isomer B of 3-t-butoxy-4-<3-{(4-chlorophenyl)-[(R)-1-(3,4,5-trifluorophenyl)ethyl-amino]methyl}phenylamino>-3-cyclobutene-1,2-dione [prepared as described in step (c) above] and 2 ml of trifluoroacetic acid were reacted, to obtain 662 mg of isomer B of the title compound as a white solid.

Isomer B

Nuclear Magnetic Resonance Spectrum (DMSO-d$_6$) δ ppm: 1.63 (3H, doublet, J=6.7 Hz); 4.26 (1H, quartet, J=6.7 Hz); 5.24 (1H, singlet); 7.33–7.53 (5H, multiplet); 7.52 (2H, doublet, J=8.5 Hz); 7.54 (1H, singlet); 7.68 (2H, doublet, J=8.5 Hz). mp: 190° C.(dec); optical rotation [α]$_D$=+17.6 (c=0.92, AcOH).

EXAMPLE 115

4-<3-{(4-Fluorophenyl)-[(R)-1-(3,4,5-trifluorophenyl)ethylamino]methyl}phenylamino>-3-hydroxy-3-cyclobutene-1,2-dione Hydrochloride
(Compound No. 2-3502)

(115a) N-[(4-Fluorophenyl)-(3-nitrophenyl)methyl]-N-[(R)-1-(3,4,5-trifluorophenyl)ethyl]amine Following a similar procedure to that described in Example (1a), 1.59 g of 4-fluoro-3'-nitrobenzophenone, 2.20 of (R)-1-(3,4,5-trifluorophenyl)ethylamine hydrochloride, 5.4 ml of triethylamine and 0.8 ml of titanium tetrachloride were reacted, to obtain the corresponding imine compound.

Following a similar reaction and purification procedure to that described in Example (1a), the resulting imine compound, 1.64 of sodium cyanoborohydride and 0.6 ml of acetic acid were related, to obtain 2.50 g of the title compound as a yellow oil.

Nuclear Magnetic Resonance Spectrum (CDCl$_3$) δ ppm: 1.35 and 1.36 (total 3H, each doublet, J=6.6 Hz); 3.56–3.63 (1H, multiplet); 4.65 and 4.70 (total 1H, each singlet); 6.83–6.91 (2H, multiplet); 6.98 and 7.07 (total 2H, each triplet, J=8.6 Hz); 7.20–7.26 (2H, multiplet); 7.43 and 7.52 (total 1H, each triplet, J=7.8 Hz); 7.58 and 7.62 (total 1H, each doublet, J=7.7 Hz); 8.07 and 8.14 (total 1H, each doublet of doublets, J=2.0, 8.0 Hz); 8.21 and 8.23 (total 1H, each doublet, J=1.9 Hz).

(115b) 3-{(4-Fluorophenyl)-[(R)-1-(3,4,5-trifluorophenyl)ethylamino]methyl}-phenylamine Following a similar reaction, separation and purification procedure to that described in Example (59b), 2.46 g of N-[(4-fluorophenyl)-(3-nitrophenyl)methyl]-N-[(R)-1-(3,4,5-trifluorophenyl)ethyl]amine [prepared as described in step (a) above], 2.90 g of nickel chloride hexahydrate and 927 mg of sodium borohydride were reacted, to obtain 760 mg of isomer A and 716 mg of isomer B of the title compound, each as a colorless oil.

Isomer A

Nuclear Magnetic Resonance Spectrum (CDCl$_3$) δ ppm: 1.30 (3H, doublet, J=6.6 Hz); 3.65 (1H, quartet, J=6.6 Hz); 4.44 (1H, singlet); 6.56 (1H, doublet, J=1.8 Hz); 6.58–6.64 (2H, multiplet); 6.89–6.98 (4H, multiplet); 7.12 (1H, triplet, J=7.8 Hz); 7.21–7.26 (2H, multiplet).

Isomer B

Nuclear Magnetic Resonance Spectrum (CDCl$_3$) δ ppm: 1.30 (3H doublet, J=6.6 Hz); 3.58 (1H. quartet, J=6.6 Hz); 4.47 (1H, singlet); 6.53 (1H, doublet of doublets, J=1.6, 8.0 Hz); 6.58 (1H, singlet: 6.63 (1H, doublet of doublets, J=0.6, 7.7 Hz); 6.86–6.89 (2H, multiplet); 7.01 (2H, triplet, J=8.6 Hz); 7.05 (1H, triplet, J=7.8 Hz); 7.24–7.27 (2H, multiplet).

(115c) 3-t-Butoxy-4-<3-{(4-fluorophenyl)-[(R)-1-(3,4,5-trifluorophenyl)ethylamino]methyl}phenylamino>-3-cyclobutene-1,2-dione Following a similar procedure to that described in Example (1c), 738 mg of isomer A of 3-{(4-fluorophenyl)-[(R)-1-(3,4,5-trifluorophenyl)ethylamino]methyl}phenylamine [prepared as described in step (b) above] and 434 g of 4-t-butoxy-3-methoxy-3-cyclobutene-1,2-dione were reacted, to obtain 800 mg of isomer A of the title compound as a white foamy solid.

Isomer A

Nuclear Magnetic Resonance Spectrum (CDCl$_3$) δ ppm: 1.34 (3H, doublet, J=6.6 Hz); 1.63 (9H, singlet); 3.64 (1H, quartet, J=6.6 Hz); 4.56 (1H, singlet); 6.90 (2H, doublet of doublets, J=6.7, 8.2 Hz); 6.95 (2H, triplet, J=8.7 Hz); 7.22–7.36 (5H, multiplet); 7.43 (1H, broad).

Following a similar procedure to that described in Example (1c), 677 mg of isomer B of 3-{(4-fluorophenyl)-[(R)-1-(3,4,5-trifluorophenyl)ethylamino]methyl}phenylamine [prepared as described in step (b)) above] and 400 mg of 4-t-butoxy-3-methoxy-3-cyclobutene-1,2-dione were reacted, to obtain 824 mg of isomer B of the title compound as a white foamy solid.

Isomer B

Nuclear Magnetic Resonance Spectrum (CDCl$_3$) δ ppm: 1.33 (3H, doublet, J=6.7 Hz); 1.64 (9H, singlet); 3.60 (1H, quartet, J=6.6 Hz); 4.56 (1H, singlet); 6.89 (2H, doublet of doublets, J=6.6, 8.4 Hz); 7.04 (2H, triplet, J=8.6 Hz); 7.21–7.35 (5H, multiplet); 7.40 (1H, broad).

(115d) 4-<3-{(4-Fluorophenyl)-[(R)-1-(3,4,5-trifluorophenyl)ethylamino]methyl}-phenylamino>-3-hydroxy-3-cyclobutene-1,2-dione Hydrochloride Following a similar procedure to that described in Example (63b), 759 mg of isomer A of 3-t-butoxy-4-<3-{(4-fluorophenyl)-[(R)-1-(3,4,5-trifluorophenyl)ethyl-amino]methyl}phenylamino>-3-cyclobutene-1,2-dione [prepared as described in step (c) above] and 3 ml of trifluoroacetic acid were reacted, to obtain 635 mg of isomer A of the title compound as a white solid.

Isomer A

Nuclear Magnetic Resonance Spectrum (DMSO-d$_6$) δ ppm: 1.64 (3H, doublet, J=6.7 Hz); 4.32 (1H, quartet, J=6.7 Hz); 5.22 (1H, singlet); 7.21–7.25 (1H, multiplet); 7.23 (2H, triplet, J=8.7 Hz); 7.34–7.44 (4H, multiplet); 7.56 (1H, singlet); 7.68 (2H, doublet of doublets, J=5.3, 8.6 Hz). mp: 186° C.(dec); optical rotation [α]$_D$=−66.5 (c=0.09, AcOH).

Following a similar procedure to that described in Example (63b), 740 mg of isomer B of 3-t-butoxy-4-<3-{(4-fluorophenyl)-[(R)-1-(3,4,5-trifluorophenyl)ethylamino]-methyl}phenylamino>-3-cyclobutene-1,2-dione [prepared as described in step (c) above] and 3 ml of trifluoroacetic acid were reacted, to obtain 590 mg of isomer B of the title compound as a white solid.

Isomer B

Nuclear Magnetic Resonance Spectrum (DMSO-d$_6$) δ ppm: 1.64 (3H, doublet, J=6.7 Hz); 4.26 (1H, quartet, J=6.7 Hz); 5.26 (1H, singlet); 7.29 (2H, triplet, J=8.8 Hz); 7.34–7.46 (5H, multiplet); 7.53 (1H, singlet); 7.71 (2H, doublet of doublets, J=5.3, 8.6 Hz). mp: 191° C.(dec); optical rotation [α]$_D$=+19.1 (c=0.36, AcOH).

EXAMPLE 116

4-<3-{[(R)-1-(3,5-Difluorophenyl)ethylamino]-(4-methylphenyl)methyl}phenylamino>-3-hydroxy-3-cyclobutene-1,2-dione Hydrochloride (Compound No. 2-3457)

(116a) N-[(R)-1-(3,5-Difluorophenyl)ethyl]-N-[(4-methylphenyl)-(3-nitrophenyl)-methyl]amine Following a similar procedure to that described in Example (1a), 1.69 g of 4-methyl-3'-nitrobenzophenone, 2.19 g of (R)-1-(3,5-difluorophenyl)ethylamine hydrochloride, 5.9 ml of triethylamine and 0.9 ml of titanium tetrachloride were reacted, to obtain the corresponding imine compound.

Following a similar reaction and purification procedure to that described in Example (1a), the resulting imine compound. 1.79 g of sodium cyanoborohydride and 0.6 ml of acetic acid were reacted, to obtain 2.62 g of the title compound as a yellow oil.

Nuclear Magnetic Resonance Spectrum (CDCl$_3$) δ ppm: 1.35 and 1.37 (total 3H, each doublet, J=6.7 Hz); 2.30 and 2.35 (total 3H, each singlet); 3.62 and 3.68 (total 1H, each quartet, J=6.7 Hz); 4.64 and 4.70 (total 1H, each singlet); 6.66–6.81 (3H, multiplet); 7.09–7.19 (4H, multiplet); 7.40 and 7.49 (total 1H, each triplet, J=8.0 Hz); 7.61 and 7.66 (total 1H, each doublet, J=7.7 Hz); 8.04 and 8.10 (total 1H, each doublet, J=8.1 Hz); 8.23 and 8.26 (total 1H, each singlet).

(116b) 3-{[(R)-1-(3,5-Difluorophenyl)ethylamino]-(4-methylphenyl)methyl}phenylamine Following a similar reaction, separation and purification procedure to that described in Example (59b), 2.59 g of N-[(R)-1-(3,5-difluorophenyl)ethyl]-N-[(4-methylphenyl)-(3-nitrophenyl)methyl]amine [prepared as described in step (a) above], 3.23 g of nickel chloride hexahydrate and 1.03 g of sodium borohydride were reacted, to obtain 1.02 g of isomer A and 1.08 g of isomer B of the title compound, each as a colorless oil.

Isomer A

Nuclear Magnetic Resonance Spectrum (CDCl$_3$) δ ppm: 1.32 (3H, doublet, J=6.7 Hz); 2.29 (3H, singlet); 3.69 (1H, quartet, J=6.6 Hz); 4.48 (1H, singlet); 6.57 (1H, doubled doublet of doublets, J=0.9, 2.4, 7.9 Hz); 6.62 (1H, triplet, J=2.0 Hz); 6.64–6.70 (2H, multiplet); 6.82 (2H, doublet of doublets, J=2.2, 8.5 Hz); 7.06 (2H, doublet, J=8.0 Hz); 7.10 (1H, triplet, J=7.7 Hz); 7.17 (2H, doublet, J=8.1 Hz).

Isomer B

Nuclear Magnetic Resonance Spectrum (CDCl$_3$) δ ppm: 1.32 (3H, doublet, J=6.7 Hz); 2.34 (3H, singlet); 3.64 (1H, quartet, J=6.6 Hz); 4.48 (1H, singlet); 6.51 (1H, doubled doublet of doublets, J=0.9, 2.4, 8.0 Hz); 6.62 (1H, triplet, J=2.0 Hz); 6.65–6.70 (2H, multiplet); 6.80 (2H, doublet of doublets, J=2.2, 8.5 Hz); 7.04 (1H1, triplet, J=7.8 Hz); 7.13 (2H, doublet, J=8.0 Hz); 7.17 (2H, doublet, J=8.2 Hz).

(116c) 3-t-Butoxy-4-<3-{[(R)-1-(3,5-difluorophenyl)ethylamino]-(4-methylphenyl)methyl}phenylamino>-3-cyclobutene-1,2-dione Following a similar procedure to that described in Example (1c), 940 mg of isomer A of 3-{[(R)-1-(3,5-difluorophenyl)etlhylamino]-(4-methylphenyl)methyl}phenylamine [prepared as described in step (b) above] and 590 mg of 4-t-butoxy-3-methoxy-3-cyclobutene-1,2-dione were reacted, to obtain 1.20 g of isomer A of the title compound as a white foamy solid.

Isomer A

Nuclear Magnetic Resonance Spectrum (CDCl$_3$) δ ppm: 1.36 (3H, doublet, J=6.6 Hz); 1.63 (9H, singlet); 2.29 (3H, singlet); 3.67 (1H, quartet, J=6.6 Hz); 4.58 (1H, singlet); 6.66–6.72 (1H, multiplet); 6.79 (2H, doublet of doublets, J=2.0, 8.5 Hz); 7.06–7.12 (1H, multiplet); 7.08 (2H, doublet, J=8.0 Hz); 7.16 (2H, doublet, J=8.0 Hz); 7.26–7.38 (3H, multiplet).

Following a similar procedure to that described in Example (1c), 990 mg of isomer B of 3-{[(R)-1-(3,5-difluorophenl)ethylamino]-(4-methylphenyl)methyl}phenylamine [prepared as described in step (b) above] and 618 mg of 4-t-butoxy-3-methoxy-3-cyclobutene-1,2-dione were reacted, to obtain 1.09 g of isomer B of the title compound as a white foamy solid.

Isomer B

Nuclear Magnetic Resonance Spectrum (CDCl$_3$) δ ppm: 1.34 (3H, doublet, J=6.7 Hz); 1.63 (9H, singlet); 2.35 (3H, singlet); 3.66 (1H, quartet, J=6.6 Hz); 4.55 (1H, singlet); 6.65–6.70 (1H, multiplet); 6.81 (2H, doublet of doublets, J=1.9, 8.0 Hz); 7.04–7.07 (1H, multiplet); 7.15 (2H, doublet, J=8.9 Hz); 7.17 (2H, doublet, J=8.8 Hz); 7.22–7.36 (3H, multiplet).

(116d) 4-<3-{[(R)-1-(3,5-Difluorophenyl)ethylamino]-(4-methylphenyl)methyl}phenylamino>-3-hydroxy-3-cyclobutene-1,2-dione hydrochloride Following a similar procedure to that described in Example (63b), 1.10 g of isomer A of 3-t-butoxy-4-<3-[(R)-1-(3,5-difluorophenyl)ethylamino]-(4-methylphenyl)methyl}phenylamino>-3-cyclobutene-1,2-dione [prepared as described in step (c) above] and 3 ml of trifluoroacetic acid were reacted, to obtain 712 mg of isomer A of the title compound as a white solid.

Isomer A

Nuclear Magnetic Resonance Spectrum (DMSO-d$_6$) δ ppm: 1.65 (3H, doublet, J=6.7 Hz); 2.28 (3H, singlet); 4.30 (1H, broad); 5.15 (1H, singlet); 7.17 (2H, doublet of doublets, J=1.8, 8.0 Hz); 7.21 (2H, doublet, J=8.1 Hz); 7.27–7.43 (4H, multiplet); 7.51 (2H, doublet, J=8.2 Hz); 7.53 (1H, singlet). mp: 193° C. (dec); optical rotation [α]$_D$=−25.9 (c=0.55, AcOH).

Following a similar procedure to that described in Example (63b), 990 mg of isomer B of 3-t-butoxy-4-<3-[(R)-1-(3,5-difluorophenyl)ethylamino]-(4-methylphenyl)methyl}phenylamino>-3-cyclobutene-1,2-dione [prepared as described in step (c) above] and 3 ml of trifluoroacetic acid were reacted, to obtain 708 mg of isomer B of the title compound as a white solid.

Isomer B
Nuclear Magnetic Resonance Spectrum (DMSO-$d_6$) δ ppm: 1.64 (3H, doublet, J=(0.7 Hz); 2.31 (3H, singlet); 4.25 (1H, quartet, J=6.7 Hz); 5.14 (1H, singlet); 7.19 (2H, doublet of doublets, J=1.9, 8.3 Hz); 7.25 (2H, doublet, J=8.0 Hz); 7.28–7.37 (3H, multiplet); 7.40–7.42 (1H, multiplet); 7.51 (2H, doublet, J=8.1 Hz); 7.54 (1H, singlet). mp: 190° C. (dec); optical rotation $[α]_D$=+2.1 (c=0.65. AcOH).

EXAMPLE 117

3-<3-{[1-(3,4-Difluorophenylamino)ethylamino]-(p-tolyl)methyl}phenylamino>-4-hydroxy-3-cyclobutene-1,2-(dione, and triethylammonium salt and sodium salt thereof. (Compound No. 2-3386)

(117a) N-[1-(3,4-Difluorophenyl)ethyl]-N-[(3-nitrophenyl)-(p-tolyl)methyl]amine

Following a similar procedure to that described in Example (1a), 6.02 g of 3-nitrophenyl p-tolyl ketone, 3.92 g of 1-(3,4-difluorophenyl)ethylamine, 13.9 ml of triethylamine and 4.0 ml of titanium tetrachloride were reacted, to obtain the corresponding imine compound. Following a similar reaction and purification procedure to that described in Example (1a), the resulting imine compound, 6.27 g of sodium cyanoborohydride and 6.5 ml of acetic acid were reacted, to obtain 7.79 g of the title compound as a yellow oil.

Nuclear Magnetic Resonance Spectrum (CDCl$_3$) δ ppm: 1.34 and 1.30 (total 3H, each doublet, J=6.6 Hz); 2.23 and 2.35 (total 3H, each singlet); 3.60 and 3.66 (total 1H, each quartet, J=6.6 Hz); 4.11 and 4.13 (total 1H, each singlet); 6.87–6.90 (1H, multiplet); 7.02–7.20 (7H, multiplet); 7.39 and 7.48 (total 1H, each doublet of doublets, J=7.3, 8.1 Hz); 7.58 and 7.65 (total 1H each doublet, J=7.3 and 8.1 Hz); 8.02–8.04 (total 1H, multiplet); 8.21–8.27 (total 1H, multiplet).

(117b) 3-{[1-(3,4-Difluorophenyl)ethylamino]-(p-tolyl)methyl}phenylamine

Following a similar reaction, separation and purification procedure to that described in Example (59b), 7.76 g of N-[1-(3,4-difluorophenyl)ethyl]-N-[(3-nitrophenyl)-(p-tolyl)methyl]amine [prepared as described in step (a) above], 9.65 g of nickel chloride hexahydrate and 3.07 g of sodium borohydride were reacted, to obtain 1.67 g of isomer A and 2.37 g of isomer B of the title compound, each as a pale yellow oil.

Isomer A
Nuclear Magnetic Resonance Spectrum (CDCl$_3$) δ ppm: 1.31 (3H, doublet, J=7.3 Hz); 2.29 (3H, singlet); 3.65–3.80 (1H, multiplet); 4.45 (1H, singlet); 6.55–6.72 (3H, multiplet); 6.93–7.00 (1H, multiplet); 7.04–7.20 (7H, multiplet).

Isomer B
Nuclear Magnetic Resonance Spectrum (CDCl$_3$) δ ppm: 1.31 (3H, doublet, J=6.6 Hz); 2.34 (3H, singlet); 3.63 (1H, quartet, J=6.6 Hz); 4.45 (1H singlet); 6.50 (1H, doublet of doublets, J=2.2, 8.1 Hz); 6.61 (1H, multiplet); 6.66 (1H, doublet, J=8.1 Hz); 6.91–6.97 (1H, multiplet); 6.98–7.22 (7H, multiplet).

(117c) 3-t-Butoxy-4-<3-{[1-(3,4-difluorophenyl) ethylamino]-(p-tolyl)methyl}phenylamino>-3-cyclobutene-1,2-dione Following a similar procedure to that described in Example (1c), 1.64 g of isomer A of 3-{[1-(3,4-difluorophenyl)ethylamino]-(p-tolyl)methyl}phenylamine [prepared as described in step (b) above] and 1.29 g of 4-t-butoxy-3-methoxy-3-cyclobutene-1,2-dione were reacted, to obtain 1.98 g of isomer A of the title compound as a white foamy solid.

Isomer A
Nuclear Magnetic Resonance Spectrum (CDCl$_3$) δ ppm: 1.35 (3H, doublet, J=6.6 Hz); 1.63 (9H, singlet); 2.29 (3H, singlet); 3.66 (1H, quartet, J=6.6 Hz); 4.56 (1H, singlet); 6.92–6.98 (1H, multiplet); 7.03–7.18 (7H, multiplet); 7.28–7.40 (3H, multiplet).

Following a similar procedure to that described in Example (1c), 2.34 g of isomer B of 3-{[1-(3,4-difluorophenyl)ethylamino]-(p-tolyl)methyl}phenylamine [prepared as described in step (b) above] and 1.83 g of 4-t-butoxy-3-methoxy-3-cyclobutene-1,2-dione were reacted, to obtain 1.98 g, of isomer B of the title compound as a white foamy solid.

Isomer B
Nuclear Magnetic Resonance Spectrum (CDCl$_3$) δ ppm: 1.33 (3H, doublet, J=(6.6 Hz); 1.63 (9H, singlet); 2.34 (3H, singlet); 3.64 (1H, quartet, J=6.6 Hz); 4.53 (1H, singlet); 6.92–6.99 (1H, multiplet); 7.00–7.38 (10H, multiplet).

(117d) 3-<3-{[1-(3,4-Difluorophenylamino)ethylamino]-(p-tolyl)methyl}phenylamino>-4-hydroxy-3-cyclobutene-1,2-dione Following a similar procedure to that described in Example (55b), 1.95 g of isomer A of 3-t-butoxy-4-<3-{[1-(3,4-difluorophenyl)ethylamino]-(p-tolyl) methyl}phenylamino>-3-cyclobutene-1,2-dione [prepared as described in step (c) above] and 4 ml of trifluoroacetic acid were reacted, to obtain 1.50 g of isomer A of the title compound as a white solid.

Isomer A
Nuclear Magnetic Resonance Spectrum (DMSO-$d_6$) δ ppm: 1.60 (3H, doublet, J=6.6 Hz); 2.28 (3H, singlet); 4.27–4.40 (1H, broad); 5.02 (1H, singlet); 6.91 (1H, doublet, J=7.7 Hz); 7.16–7.26 (4H, multiplet); 7.41–7.57 (5H, multiplet); 7.65 (1H, singlet). mp: 240° C.(dec).

Following a similar procedure to that described in Example (55b), 1.96 g of isomer B of 3-t-butoxy-4-<3-{[1-(3,4-difluorophenyl)ethylamino]-(p-tolyl) methyl}phenylamino>-3-cyclobutene-1,2-dione [prepared as described in step (c) above] and 4 ml of trifluoroacetic acid were reacted, to obtain 402 mg of isomer B of the title compound as a white solid.

Isomer B
Nuclear Magnetic Resonance Spectrum (DMSO-$d_6$) δ ppm: 1.58 (3H, doublet, J=6.7 Hz); 2.31 (3H, singlet); 4.15–4.30 (1H, broad); 5.05 (1H, singlet); 6.95 (1H, doublet, J=7.7 Hz); 7.20–7.26 (4H, multiplet); 7.43 (1H, doublet, J=8.1 Hz); 7.45–7.57 (3H, multiplet); 7.70 (1H, singlet). mp: 216° C.(dec).

(117e) 3-Hydroxy-4-<3-{[1-(3,4-difluorophenyl) ethylamino]-(p-tolyl)-methyl}phenylamino>-3-cyclobutene-1,2-dione triethylammonium salt 418 mg of isomer B of 3-hydroxy-4-<3-{[1-(3,4-difluorophenyl)ethylamino]-(p-tolyl) methyl}phenylamino>-3-cyclobutene-1,2-dione [prepared as described in step (d) above] were suspended in 5 ml of acetone. Sufficient triethylamine to thoroughly dissolve the solids was added to the resulting suspension. The solvent and excess triethylamine were distilled off under reduced pressure. The resulting white solid was suspended in diisopropyl ether, collected by filtration and dried, to obtain 463 mg of isomer B of the title compound as a white solid.

Nuclear Magnetic Resonance Spectrum (DMSO-$d_6$) δ ppm: 1.19 (9H, triplet, J=7.2 Hz); 1.33 (3H, doublet, J=6.6 Hz); 2.27 (3H, singlet); 3.11 (6H, quartet, J=7.3 Hz); 3.60–3.75 (1H, broad); 4.52 (1H, singlet); 6.72 (1H, doublet, J=7.6 Hz); 7.03–7.13 (4H, multiplet); 7.25 (2H, doublet, J=7.9 Hz); 7.30–7.39 (2H, multiplet); 7.48 (1H, doublet of doublets, J=1.8, 8.0 Hz); 7.65 (1H, singlet). mp: 106° C.(dec).

(117f) 3-Hydroxy-4-<3-{[1-(3,4-difluorophenyl) ethylamino]-(p-tolyl)methyl}phenylamino>-3-cyclobutene-1,2-dione sodium salt 888 mg of isomer B of 3-hydroxy-4-<3-{[1-(3,4-difluorophenyl)ethylamino]-(p-tolyl) methyl}phenylamino>-3-cyclobutene-1,2-dione [prepared as described in step (d) above] were suspended in 5 nil of acetone. 185 mg of sodium hydrogencarbonate and 3 ml of distilled water were added to the resulting suspension. The solvent was distilled off under reduced pressure. Ethyl acetate was added to the residue to dissolve it. Insoluble matter was filtered off. The filtrate was distilled off under reduced pressure. The resulting white powder was dissolved in ethyl acetate, and then the insoluble matter was removed by filtration. This procedure was repeated three times. The resulting white powder was suspended in hexane, and then collected by filtration, to obtain 652 mg of the title compound.

Nuclear Magnetic Resonance Spectrum (DMSO-$d_6$) δ ppm: 1.26 (3H, doublet, J=6.6 Hz); 2.26 (3H, singlet); 3.51 (1H, quartet, 6.6 Hz); 4.34 (1H, doublet, J=5.9 Hz); 6.70 (1H, doublet, J=7.3 Hz); 7.01–7.11 (4H, multiplet); 7.21 (2H, doublet, J=8.1 Hz); 7.30–7.41 (2H, multiplet); 7.50 (1H, doublet of doublets, J=2.2, 8.1 Hz); 7.62 (1H, singlet). mp: 156° C.(dec).

EXAMPLE 118

3-Hydroxy-4-<3-{(4-methoxyphenyl)-[(R)-1-(naphthalen-1-yl)ethylamino]methyl}phenylamino>-3-cyclobutene-1,2-dione (Compound No. 2-13)

(118a) N-[(4-Methoxyphenyl)-(3-nitrophenyl)methyl]-N-[(R)-1-(naphthalen-1-yl)ethyl]amine Following a similar procedure to that described in Example (1a), 5.32 g of 4-methoxyphenyl 3-nitrophenyl ketone. 3.54 g of (R)-1-(1-naphthyl)ethylamine, 11.5 ml of triethylamine and 3.4 ml of titanium tetrachloride were reacted, to obtain the corresponding imine compound. Following a similar reaction and purification procedure to that described in Example (1a), the resulting imine compound, 5.20 g of sodium cyanoborohydride and 5.53 ml of acetic acid were reacted, to obtain 8.34 g of the title compound as a yellow oil.

Nuclear Magnetic Resonance Spectrum (CDCl$_3$) δ ppm: 1.526 and 1.534 (total 3H, each doublet, J=6.6 Hz); 3.77 and 3.81 (total 3H, each singlet); 4.53 and 4.58 (total 1H, each quartet, J=6.6 Hz); 4.74 and 4.78 (total 1H, each singlet); 6.82 and 6.85 (total 2H, each doublet, J=8.8 Hz); 7.12 and 7.20 (total 2H, each doublet, J=8.8 Hz); 7.32–7.85 (9H, multiplet); 8.01 and 8.08 (total 1H, each doublet of doublets, J=2.2 and 8.1 Hz); 8.22 and 8.28 (total 1H, each singlet).

(118b) 3-{(4-Methoxyphenyl)-[(R)-1-(naphthalen-1-yl) ethylamino]methyl}phenylamine Following a similar reaction, separation and purification procedure to that described in Example (59b), 8.32 g of N-[(4-methoxyphenyl)-(3-nitrophenyl)methyl]-N-[(R)-1-(naphthalen-1-yl)ethyl]amine [prepared as described in step (a) above], 9.51 g of nickel chloride hexahydrate and 3.03 g of sodium borohydride were reacted, to obtain 1.15 g of isomer A and 462 mg of isomer B of the title compound, each as a colorless oil.

Isomer A

Nuclear Magnetic Resonance Spectrum (CDCl$_3$) δ ppm: 1.47 (3H, doublet, J=6.6 Hz); 3.76 (3H), singlet); 4.57–4.60 (2H, multiplet); 6.54–6.66 (2H, multiplet); 6.65 (1H, doublet, J=7.6 Hz); 6.80 (2H, doublet, J=8.7 Hz); 7.05–7.30 (3H, multiplet); 7.36–7.55 (3H, multiplet); 7.69 (1H, doublet, J=7.0 Hz); 7.76 (1H, doublet, J=8.1 Hz); 7.86 (1H, doublet, J=7.9 Hz); 7.94 (1H, doublet, J=8.4 Hz).

Isomer B

Nuclear Magnetic Resonance Spectrum (CDCl$_3$) δ ppm: 1.47 (3H, doublet, J=6.6 Hz); 3.80 (3H, singlet); 4.54 (1H, quartet, J=6.6 Hz); 4.60 (1H, singlet); 6.52–6.54 (1H, multiplet); 6.70 (1H, doublet, J=1.5 Hz); 6.71 (1H, doublet, J=7.3 Hz); 6.82 (2H, doublet, J=8.8 Hz); 7.05 (1H, triplet, J=8.1 Hz); 7.17 (2H, doublet, J=8.8 Hz); 7.37–7.52 (3H, multiplet); 7.67 (1H, doublet, J=7.3 Hz); 7.76 (1H, doublet, J=8.1 Hz); 7.87 (1H, doublet, J=8.1 Hz); 7.90 (1H, doublet, J=8.8 Hz).

(118c) 3-t-Butoxy-4-<3-{(4-methoxyphenyl)-[(R)-1-(naphthalen-1-yl)ethylamino]methyl}phenylamino>-3-cyclobutene-1,2-dione Following a similar procedure to that described in Example (1c), 1.11 g of isomer A of 3-{(4-methoxyphenyl)-[(R)-1-(naphthalen-1-yl)ethylamino]methyl}phenylamine [prepared as described in step (b) above] and 748 mg of 4-t-butoxy-3-methoxy-3-cyclobutene-1,2-dione were reacted, to obtain 1.30 g of isomer A of the title compound as a white foamy solid.

Isomer A

Nuclear Magnetic Resonance Spectrum (CDCl$_3$) δ ppm: 1.51 (3H, doublet, J=6.6 Hz); 1.58 (9H, singlet); 3.78 (3H, singlet); 4.56 (1H, quartet, J=6.6 Hz); 4.68 (1H, singlet); 6.83 (2H, doublet, J=8.8 Hz); 7.01–7.10 (1H, multiplet); 7.20–7.54 (8H, multiplet); 7.66 (1H, doublet, J=7.7 Hz); 7.78 (1H, doublet, J=7.8 Hz); 7.84–7.90 (2H, multiplet).

Following a similar procedure to that described in Example (1c), 449 mg of isomer B of 3-{(4-methoxyphenyl)-[(R)-1-(naphthalen-1-yl)ethylamino] methyl}phenylamine [prepared as described in step (b) above] and 324 mg of 4-t-butoxy-3-methoxy-3-cyclobutene-1,2-dione were reacted, to obtain 452 mg of isomer B of the title compound as a white foamy solid.

Isomer B

Nuclear Magnetic Resonance Spectrum (CDCl$_3$) δ ppm: 1.49 (3H, doublet, J=6.6 Hz); 1.59 (9H, singlet); 3.79 (3H, singlet); 4.55 (1H, quartet, J=6.6 Hz); 4.67 (1H, singlet); 6.85 (2H, doublet, J=8.8 Hz); 7.07–7.52 (9H, multiplet); 7.67 (1H, doublet, J=7.7 Hz); 7.76 (1H, doublet, J=8.3 Hz); 7.87 (1H, doublet, J=8.1 Hz); 7.91 (1H, doublet, J=8.1 Hz).

(118d) 3-Hydroxy-4-<3-{(4-methoxyphenyl)-[(R)-1-(naphthalen-1-yl)ethylamino]methyl}phenylamino>-3-cyclobutene-1,2-dione Following a similar procedure to that described in Example (55b), 1.24 g of isomer A of 3-t-butoxy-4-<3-{(4-methoxyphenyl)-[(R)-1-(naphthalen-1-yl)ethylamino] methyl}phenylamino>-3-cyclobutene-1,2-dione [prepared as described in step (c) above] and 5 ml of trifluoroacetic acid were reacted, to obtain 1.07 g of isomer A of the title compound as a white solid.

Isomer A

Nuclear Magnetic Resonance Spectrum (DMSO-$d_6$) δ ppm: 1.76 (3H, doublet, J=6.6 Hz); 3.77 (3H, singlet); 5.23 (1H, singlet); 5.25–5.38 (1H, broad); 6.71 (1H, doublet, J=7.3 Hz); 7.00 (2H, doublet, J=8.8 Hz); 7.08–7.12 (1H, multiplet); 7.32–7.56 (6H, multiplet); 7.60–7.72 (2H, multiplet); 7.90–8.05 (3H, multiplet). optical rotation $[\alpha]_D$=−311.5 (c=1.07, AcOH).

Following a similar procedure to that described in Example (63b), 434 mg of isomer B of 3-t-butoxy-4-<3-{(4-methoxyphenyl)-[(R)-1-(naphthalen-1-yl)ethylamino] methyl}phenylamino>-3-cyclobutene-1,2-dione [prepared as described in step (c) above] and 3 ml of trifluoroacetic acid were reacted, to obtain 317 mg of the hydrochloride of isomer B of the title compound as a white solid.

Isomer B

Nuclear Magnetic Resonance Spectrum (DMSO-$d_6$) δ ppm: 1.80 (3H doublet, J=6.6 Hz); 3.74 (3H, singlet); 4.95–5.10 (1H, broad); 5.30 (1H, singlet); 6.89 (2H, doublet, J=8.8 Hz); 7.28–7.48 (7H, multiplet); 7.50–7.55 (1H, multiplet); 7.59 (1H, singlet); 7.65–7.69 (1H, multiplet); 7.90–8.17 (3H, multiplet). mp: 179° C.(dec); optical rotation $[\alpha]_D$=−83.1 (c=1.01, AcOH).

EXAMPLE 119

3-Hydroxy-4-<3-{(4-methoxyphenyl)-[(R)-1-(naphthalen-2-yl)ethylamino]methyl}phenylamino>-3-cyclobutene-1,2-dione (Compound No. 2-14)

(119a) N-[(4-Methoxyphenyl)-(3-nitrophenyl)methyl]-N-[(R)-1-(naphthalen-2-yl)ethyl]amine Following a similar procedure to that described in Example (1a), 4.45 g of 4-methoxyphenyl 3-nitrophenyl ketone, 2.96 of (R)-1-(2-naphthyl)ethylamine, 9.6 ml of triethylamine and 2.9 ml of titanium tetrachloride were reacted, to obtain the corresponding imine compound. Following a similar reaction and purification procedure to that described in Example (1a), the resulting imine compound, 4.34 g of sodium cyanoborohydride and 4.45 ml of acetic acid were reacted, to obtain 6.15 g of the title compound as a yellow oil.

Nuclear Magnetic Resonance Spectrum (CDCl$_3$) δ ppm: 1.52 and 1.53 (total 3H, each doublet, J=6.6 Hz); 3.77 and 3.79 (total 3H, each singlet); 4.52–4.60 (2H, multiplet); 6.51–6.72 (3H, multiplet); 6.79–6.87 (2H, multiplet); 7.03–7.09 (1H, multiplet); 7.16–7.19 (1H, multiplet); 7.23–7.29 (1H, multiplet); 7.35–7.53 (3H, multiplet); 7.66–7.70 (1H, multiplet); 7.74 and 7.68 (total 1H, each singlet); 7.85–7.95 (2H, multiplet).

(119b) 3-{(4-Methoxyphenyl)-[(R)-1-(naphthalen-2-yl)ethylamino]methyl}phenylamine Following a similar procedure to that described in Example (1b), 6.13 g of N-[(4-methoxyphenyl)-(3-nitrophenyl)methyl]-N-[(R)-1-(naphthalen-2-yl)ethyl]amine [prepared as described in step (a) above], 7.06 g of nickel chloride hexahydrate and 2.25 g of sodium borohydride were reacted, to obtain 5.23 g of the title compound as a pale yellow oil.

Nuclear Magnetic Resonance Spectrum (CDCl$_3$) δ ppm: 1.46 and 1.48 (total 3H, each doublet, J=6.6 Hz); 3.77 and 3.81 (total 3H, each singlet); 4.51 and 4.56 (total 1H, each quartet, J=6.6 Hz); 4.73 and 4.77 (total 1H, each singlet); 6.83 and 6.86 (total 2H, each doublet, J=8.8 Hz); 7.12 and 7.20 (total 2H, each doublet, J=8.6 Hz); 7.33–8.09 (10H, multiplet); 8.02 and 8.28 (total 1H, each singlet).

(119c) 3-t-Butoxy-4-<3-{(4-methoxyphenyl)-[(R)-1-(naphthalen-2-yl)ethylamino]methyl}phenylamino>-3-cyclobutene-1,2-dione Following a similar reaction, separation and purification procedure to that described in Example (66c), 5.21 g of 3-{(4-methoxyphenyl)-[(R)-1-(naphthalen-2-yl)ethylamino]methyl}phenylamine [prepared as described in step (b) above] and 3.53 g of 4-t-butoxy-3-methoxy-3-cyclobutene-1,2-dione were reacted, to obtain 170 mg of isomer A and 176 mg of isomer B of the title compound, each as a white foamy solid.

Isomer A

Nuclear Magnetic Resonance Spectrum (CDCl$_3$) δ ppm: 1.495 (31H, doublet, J=6.6 Hz); 1.58 (9H, singlet); 3.77 (3H, singlet); 4.55 (1H, quartet, J=6.6 Hz); 4.67 (1H, singlet); 6.79 (2H, doublet, J=1.5, 7.3 Hz); 7.02–7.06 (1H, multiplet); 7.17–7.31 (5H, multiplet); 7.35–7.52 (3H, multiplet); 7.65 (1H, doublet, J=6.6 Hz); 7.77 (1H, doublet, J=8.1 Hz); 7.84–7.88 (2H, multiplet).

Isomer B

Nuclear Magnetic Resonance Spectrum (CDCl$_3$) δ ppm: 1.502 (3H, doublet, J=6.6 Hz); 1.61 (9H, singlet); 4.55 (1H, quartet, J=6.6 Hz); 4.68 (1H, singlet); 6.85 (2H, doublet of doublets, J=1.5, 7.3 Hz); 7.08 (1H, doublet, J=7.3 Hz); 7.17 (2H, doublet, J=7.3 Hz); 7.23–7.30 (3H, multiplet); 7.36–7.51 (3H, multiplet); 7.67 (1H, doublet, J=6.6 Hz); 7.76 (1H, doublet, J=8.1 Hz); 7.87 (1H, doublet, J=8.1 Hz); 7.91 (1H, doublet, J=8.8 Hz).

(119d) 3-Hydroxy-4-<3-{(4-methoxyphenyl)-[(R)-1-(naphthalen-2-yl)ethylamino]methyl}phenylamino>-3-cyclobutene-1,2-dione Following a similar procedure to that described in Example (55b), 155 mg of isomer A of 3-t-butoxy-4-<3-{(4-methoxyphenyl)-[(R)-1-(naphthalen-2-yl)ethylamino]methyl}phenylamino>-3-cyclobutene-1,2-dione [prepared as described in step (c) above] and 2.5 ml of trifluoroacetic acid were reacted, to obtain 113 mg of isomer A of the title compound as a white solid.

Isomer A

Nuclear Magnetic Resonance Spectrum (DMSO-$d_6$) δ ppm: 1.75 (3H, doublet, J=5.9 Hz); 3.77 (3H, singlet); 5.20 (1H, broad singlet); 5.32 (1H, singlet); 6.67 (1H, doublet, J=7.3 Hz); 6.99 (2H, doublet, J=8.8 Hz); 7.08 (1H, doublet of doublets. J=7.3, 8.1 Hz); 7.33–7.68 (8H, multiplet); 7.95–7.80 (3H, multiplet). mp: 194° C.(dec); optical rotation $[\alpha]_D$=−324.5 (c=0.57, AcOH).

Following a similar procedure to that described in Example (55b), 170 mg of isomer B of 3-t-butoxy-4-<3-{(4-methoxyphenyl)-[(R)-1-(naphthalen-2-yl)ethylamino]methyl}phenylamino>-3-cyclobutene-1,2-dione [prepared as described in step (c) above] and 2.5 ml of trifluoroacetic acid were reacted, to obtain 141 mg of isomer B of the title compound as a white solid.

Isomer B

Nuclear Magnetic Resonance Spectrum (DMSO-$d_6$) δ ppm: 1.77 (3H, doublet, J=5.9 Hz); 3.75 (3H, singlet); 5.00–5.12 (1H, multiplet); 5.28 (1H, broad singlet); 6.99 (2H, doublet, J=7.3 Hz); 7.01 (1H, doublet, J=7.3 Hz); 7.29 (1H, doublet of doublets, J=7.3, 8.8 Hz); 7.36–7.46 (4H, multiplet); 7.50–7.71 (3H, multiplet); 7.82 (1H, singlet); 7.93 (1H , doublet, J=7.3 Hz); 7.99–8.01 (2H, multiplet). mp: 195° C.(dec); optical rotation $[\alpha]_D$=+85.3 (c=1.03, AcOH).

EXAMPLE 120

3-<3-{[1-(3,4-Difluorophenyl)ethylamino]-(pyridin-4-yl)methyl}phenylamino>-4-hydroxy-3-cyclobutene-1,2-dione dihydrochloride (Compound No. 2-46)

(120a) N-[1-(3,4-Difluorophenyl)ethyl]-N-[(3-nitrophenyl)-(pyridin-4-yl)methylamine Following a similar procedure to that described in Example (1a), 2.81 g of 3-nitrophenyl pyridin-4-yl ketone. 1.94 g of 1-(3,4-difluorophenyl)ethylamine, 6.9 ml of triethylamine and 2.0 ml of titanium tetrachloride were reacted, to obtain the corresponding imine compound. Following a similar reaction and purification procedure to that described in Example (1a), the resulting imine compound, 3.19 g of sodium cyanoborohydride and 3.2 ml of acetic acid were reacted, to obtain 2.10 g of the title compound as a yellow oil.

Nuclear Magnetic Resonance Spectrum (CDCl$_3$) δ ppm: 1.376 and 1.382 (total 3H, each doublet, J=6.6 Hz); 3.60 and 3.63 (total 1H, each quartet, J=6.6 Hz); 4.65 and 4.68 (total 1H, each singlet); 6.88–6.95 (1H, multiplet); 7.04–7.17 (2H, multiplet); 7.19 and 7.25 (2H, multiplet); 7.42 and 7.62 (2H, multiplet); 8.07–8.21 (2H, multiplet); 8.52–8.69 (2H, multiplet).

(120b) 3{[1-(3,4-Difluorophenyl)ethylamino]-(pyridin-4-yl)methyl}phenylamine

Following a similar reaction, separation and purification procedure to that described in Example (1b). 2.07 g of N-[1-(3,4-difluorophenyl)ethyl]-N-[(3-nitrophenyl)(pyridin-4-yl)methyl]amine [prepared as described in step (a) above], 2.66 g of nickel chloride hexahydrate and 848 mg of sodium borohydride were reacted, to obtain 684 mg of the title compound as a colorless oil.

Nuclear Magnetic Resonance Spectrum (CDCl$_3$) δ ppm: 1.32 and 1.34 (total 3H, each doublet, J=6.6 Hz); 3.59–3.69 (total 1H, multiplet); 4.42 and 4.46 (total 1H, each singlet); 6.51–6.63 (3H, multiplet); 6.88–7.00 (1H, multiplet); 7.04–7.17 (3H, multiplet); 7.21–7.27 (2H, multiplet); 8.47 and 8.55 (total 2H, each doublet of doublets, J=1.5, 4.4 Hz).

(120c) 3-t-Butoxy-4-<3-{[1-(3,4-difluorophenyl)ethylamino]-(pyridin-4-yl)methyl}phenylamino>-3-cyclobutene-1,2-dione Following a similar procedure to that described in Example (1c), 280 mg of 3-{[1-(3,4-difluorophenyl)ethylamino]-(pyridin-4-yl)methyl}phenylamine [prepared as described in step (b) above] and 213 mg of 4-t-butoxy-3-methoxy-3-cyclobutene-1,2-dione were reacted, to obtain 292 mg of the title compound as a white foamy solid.

Nuclear Magnetic Resonance Spectrum (CDCl$_3$) δ ppm: 1.37 (3H, doublet, J=6.6 Hz); 1.63 (9H, singlet); 3.61 and 3.67 (total 1H, each quartet, J=6.6 Hz); 4.54 and 4.56 (total 1H, each singlet); 6.90–7.02 (2H, multiplet); 7.05–7.16 (2H, multiplet); 7.22–7.46 (5H, multiplet); 8.48 and 8.57 (total 2H, each doublet of doublets, J=2.2, 4.4 Hz).

(120d) 3-<3-{[1-(3,4-Difluorophenyl)ethylamino]-(pyridin-4-yl)methyl}phenylamino>-4-hydroxy-3-cyclobutene-1,2-dione dihydrochloride Following a similar procedure to that described in Example (63b), 270 mg of 3-t-butoxy-4-<3-{[1-(3,4-difluorophenyl)ethylamino]-(pyridin-4-yl)methyl}phenylamino>-3-cyclobutene-1,2-dione [prepared as described in step (c) above] and 3 ml of trifluoroacetic acid were reacted, to obtain 143 mg of the title compound as a pale yellow solid.

Nuclear Magnetic Resonance Spectrum (DMSO-d$_6$) δ ppm: 1.65 (3H, multiplet); 4.10–4.35 (1H, broad); 5.32 (1H, singlet); 7.24–7.74 (7H, multiplet); 8.04 and 8.08 (total 2H, each singlet); 8.75 and 8.83 (total 2H, each doublet, J=5.1 Hz). mp: 182° C.(dec).

EXAMPLE 121

3-{3-[(3,4-Difluorophenylamino)-(4-methoxyphenyl)methyl]phenylamino}-4-hydroxy-3-cyclobutene-1,2-dione (Compound No. 2-42)

(121a) N-(3,4-Difluorobenzyl)-N-[(4-methoxyphenyl)-(3-nitrophenyl)methyl]amine

Following a similar procedure to that described in Example (1a), 8.91 g of 4-methoxyphenyl 3-nitrophenyl ketone and 4.96 g of 3,4-difluorobenzylamine were reacted, to obtain 12.72 g of the title compound as a pale yellow oil.

Nuclear Magnetic Resonance Spectrum (CDCl$_3$) δ ppm: 3.69 (2H, doublet, J=3.8 Hz); 3.79 (3H, singlet); 4.88 (1H, singlet); 6.87 (2H, doublet, J=8.6 Hz); 6.96–7.32 (5H, multiplet); 7.47 (1H, triplet, J=7.9 Hz); 7.76 (1H, doublet, J=8.7 Hz); 8.07–8.09 (1H, multiplet); 8.32 (1H, doublet of doublets, J=1.6, 1.9 Hz).

(121b) 3-[(3,4-Difluorobenzylamino)-(4-methoxyphenyl)methyl]phenylamine

Following a similar procedure to that described in Example (94b), 12.68 g of N-(3,4-difluorobenzyl)-N-[(4-methoxyphenyl)-(3-nitrophenyl)methyl]amine [prepared as described in step (a) above]. 25.03 g of tin (II) chloride and 120 ml of ethanol were reacted, to obtain 13.32 g of the title compound as a pale yellow oil.

Nuclear Magnetic Resonance Spectrum (CDCl$_3$) δ ppm: 3.67 (2H, singlet); 3.88 (3H, singlet); 4.67 (1H, singlet); 6.52–6.55 (1H, multiplet); 6.715–6.724 (1H, multiplet); 6.77–6.79 (1H, multiplet); 6.82–6.87 (2H, multiplet); 6.93–7.11 (3H, multiplet); 7.15–7.22 (2H, multiplet); 7.30 (2H, doublet, J=8.1 Hz).

(121c) 3-t-Butoxy-4-{3-[(3,4-(difluorobenzylamino)-(4-methoxyphenyl)methyl]phenylamino}-3-cyclobutene-1,2-dione Following a similar procedure to that described in Example (1c), 1.32 g of 3-[(3,4-difluorobenzylamino)-(4-methylphenyl)methyl]phenylamine [prepared as described in step (b) above], 1.11 g of 3-t-butoxy-4-methoxy-3-cyclobutene-1,2-dione and 30 ml of methanol were reacted, to obtain 1.11 g of the title compound as a pale yellow foamy solid.

Nuclear Magnetic Resonance Spectrum (CDCl$_3$) δ ppm: 1.63 (9H, singlet); 3.69 (2H, singlet); 3.78 (3H, singlet); 4.78 (1H, singlet); 6.85 (2H, doublet, J=8.6 Hz); 7.00–7.55 (10H, multiplet).

121d) 3-{3-[(3,4-Difluorobenzylamino)-(4-methoxyphenyl)methyl]phenylamino}-4-hydroxy-3-cyclobutene-1,2-dione trifluoroacetate 1.09 g of 3-t-butoxy-4-{3-[(3,4-difluorobenzylamino)-(4-methoxyphenyl)methyl]phenylamino}-3-cyclobutene-1,2-dione [prepared as described in step (c) above] was dissolved in 30 ml of dichloromethane. 2 ml of trifluoroacetic acid were added to the resulting solution. The mixture was stirred at room temperature for 30 minutes, and then the solvent was distilled off under reduced pressure. Toluene was added to the residue, followed by azeotropic distillation twice. The resulting white solid was suspended in diethyl ether and collected by filtration, to obtain 830 mg of the title compound as a white solid.

Nuclear Magnetic Resonance Spectrum (DMSO-d$_6$) δ ppm: 3.75 (3H, singlet); 4.02–4.23 (2H, multiplet); 5.42 (1H, singlet); 6.99 (2H, doublet, J=8.8 Hz); 7.13–7.30 (4H, multiplet); 7.40–7.70 (6H, multiplet). mp: 206–208° C.

EXAMPLE 122

3-Hydroxy-4-<3-{[(R)-1-(3-methoxyphenyl)ethylamino]-(4-methoxyphenyl)methyl}phenylamino>-3-cyclobutene-1,2-dione hydrochloride (Compound 2-3497)

(122a) N-[(R)-1-(3-Methoxphenyl)ethyl]-N-[(4-methoxyphenyl)-(3-nitrophenyl)methyl]amine Following a similar procedure to that described in Example (1a), 9.91 g of 4-methoxyphenyl 3-nitrophenyl ketone, 5.83 g of (R)-1-(3-methoxyphenyl)ethylamine, 21.5 ml of triethylamine and 6.15 ml of titanium tetrachloride were reacted, to obtain the corresponding imine compound. Following a similar reaction and purification procedure to that described in Example (1a), the resulting imine compound, 9.68 g of sodium cyanoborohydride and 10 ml acetic acid were reacted, to obtain 9.07 g of the title compound as a yellow oil.

Nuclear Magnetic Resonance Spectrum (CDCl$_3$) δ ppm: 1.37 and 1.38 (total 3H, each doublet, J=6.6 Hz); 3.57 and 3.66 (total 1H, each quartet, J=6.7 and 6.6 Hz); 3.76, 3.80 and 3.81 (total 6H, each singlet); 4.66 and 4.69 (total 1H, each singlet); 6.72–6.79 (5H, multiplet); 7.25–7.32 (3H, multiplet); 7.38 and 7.47 (1H, each triplet, J=7.9 Hz); 7.59 and 7.62 (1H, each doublet, J=7.6 and 7.5 Hz); 8.00–8.10 (1H, multiplet); 8.23–8.27 (1H, multiplet).

(122b) 3-{(4-Methoxyphenyl)-[(R)-1-(3-methoxyphenyl)ethylamino]methyl}phenylamine Following a similar reaction, separation and purification procedure to that described in Example (94b), 9.04 g of N-[(R)-1-(3-methoxyphenyl)ethyl]-N-[(4-methoxyphenyl)-(3-nitrophenyl)methyl]amine [prepared as described in step (a) above], 17.5 g of anhydrous tin chloride and 150 ml of ethanol were reacted, to obtain 1.48 g of isomer A and 1.28 g of isomer B of the title compound as a pale yellow oil.

Isomer A

Nuclear Magnetic Resonance Spectrum (CDCl$_3$) δ ppm: 1.34 (3H, doublet, J=6.6 Hz); 3.68 (1H, quartet, J=6.6 Hz); 3.75 (3H, singlet); 3.80 (3H, singlet); 4.50 (1H, singlet); 6.55–6.57 (1H, multiplet); 6.67–6.86 (6H, multiplet); 7.07–7.14 (1H, multiplet); 7.16–7.28 (4H, multiplet).

Isomer B

Nuclear Magnetic Resonance Spectrum (CDCl$_3$) δ ppm: 1.34 (3H, doublet, J=6.7 Hz); 3.62 (1H, quartet, J=6.7 Hz); 3.80 (6H, singlet); 4.50 (1H, singlet); 6.50–6.51 (1H, multiplet); 6.62 (1H, singlet); 6.67 (1H, doublet, J=7.6 Hz); 6.75–6.89 (5H, multiplet); 7.03 (1H, triplet, J=7.9 Hz); 7.15–7.28 (3H, multiplet).

(122c) 3-t-Butoxy-4-<3-{[(R)-1-(3-methoxyphenyl)ethylamino]-(4-methoxyphenyl)methyl}phenylamino>-3-cyclobutene-1,2-dione Following a similar procedure to that described in Example (1c), 180 mg of isomer B of 3-{[(R)-1-(3-methoxyphenyl)ethylamino]-(4-methoxyphenyl)methyl}phenylamine [prepared as described in step (b) above] and 183 mg of 4-t-butoxy-3-methoxy-3-cyclobutene-1,2-dione were reacted, to obtain 185 mg of isomer B of the title compound as a colorless foamy solid.

Isomer B

Nuclear Magnetic Resonance Spectrum (CDCl$_3$) δ ppm: 1.37 (3H, doublet, J=6.7 Hz); 1.63 (9H, singlet); 3.64 (1H, quartet, J=6.5 Hz); 3.80 (3H, singlet); 3.81 (3H, singlet); 4.58 (1H, singlet); 6.78–6.89 (6H, multiplet); 7.05 (1H, doublet, J=7.7 Hz); 7.17–7.36 (5H, multiplet).

(122d) 3-Hydroxy-4-<3-{[(R)-1-(3-methoxyphenyl)ethylamino]-(4-methoxyphenyl)methyl}phenylamino>-3-cyclobtutene-1,2-dione hydrochloride Following a reaction and purification procedure similar to those described in Example (63b), 180 mg of isomer B of 3-t-butoxy-4-(3-{[(R)-1-(3-methoxyphenyl)-ethylamino]-(4-methoxyphenyl)methyl}phenylamino)-3-cyclobutene-1,2-dione [prepared as described in step (c) above] was reacted, to obtain 149 mg of isomer B of the title compound as a pale brown solid.

Isomer B

Nuclear Magnetic Resonance Spectrum (DMSO-d$_6$) δ ppm: 1.64 (3H, doublet, J=6.7 Hz); 3.76 (3H, singlet); 3.77 (3H, singlet); 4.09 (1H, broad); 5.01 (1H, singlet); 6.90–7.02 (5H, multiplet); 7.31–7.44 (4H, multiplet); 7.50–7.52 (3H, multiplet). mp: 180–183° C. optical rotation [α]$_D$=+16.0 (c=0.60 AcOH).

EXAMPLE 123

3-<3-{(4–Chlorophenyl)-[(R)-1-phenylethylamino]methyl}phenylamino>-4-hydroxy-3-cyclobutene-1,2-dione (Compound No. 2-6)

(1:23a) N-[(4-chlorophenyl)-(3-nitrophenyl)methyl]-N-[(R)-1-phenylethyl]amine

Following a procedure similar to that described in Example (1a), 2.00 g of 3-nitrophenyl 4-chlorophenyl ketone, 1.16 ml of (R)-1-phenylethylamine, 4.24 ml of triethylamine and 1.26 ml of titanium tetrachloride were reacted, to obtain the corresponding imine compound. Then following a procedure similar to that described in Example (1a), the resulting imine compound, 1.92 g of sodium cyanoborohydride and 0.66 ml of acetic acid were reacted, to obtain 760 mg of isomer A and 720 mg of isomer B of the title compound, each as a yellow oil.

Isomer A

Nuclear Magnetic Resonance Spectrum (CDCl$_3$) δ ppm: 1.38 (3H, doublet, J=6.7 Hz); 3.65 (1H, quartet, J=6.6 Hz); 4.66 (1H, singlet); 7.20–7.41 (10H, multiplet); 7.56 (1H, doublet, J=7.49 Hz); 8.02–8.05 (1H, multiplet); 8.19–8.21 (1H, multiplet).

Isomer B

Nuclear Magnetic Resonance Spectrum (CDCl$_3$) δ ppm: 1.40 (3H, doublet, J=6.6 Hz); 3.60 (1H, quartet, J=6.7 Hz); 4.69 (1H, singlet); 7.15–7.39 (9H, multiplet); 7.49 (1H triplet, J=8.0 Hz); 7.65 (1H, doublet, J=7.8 Hz); 8.05–8.13 (1H, multiplet); 8.22–8.24 (1H, multiplet).

(123b) 3-{(4-Chlorophenyl)-[(R)-1-phenylethylamino]methyl}phenylamine

Following a procedure similar to that described in Example (1b), 750 mg of isomer A of N-[(4-chlorophenyl)-(3-nitrophenyl)methyl]-N-[(R)-1-phenylethyl]amine [prepared as described in step (a) above], 972 mg of nickel chloride hexahydrate and 309 mg of sodium borohydride were reacted and purified, to obtain 640 mg of isomer A of the title compound as a colorless oil.

Isomer A

Nuclear Magnetic Resonance Spectrum (CDCl$_3$) δ ppm: 1.35 (3H, doublet, J=6.6 Hz); 3.69 (1H, quartet, J=6.7 Hz); 4.48 (1H, singlet); 6.50–6.70 (3H, multiplet); 7.11 (1H, triplet, J=7.7 Hz); 7.13–7.40 (9H, multiplet).

Following a procedure similar to that described in Example (1b), 710 mg of isomer B of N-[(4-chlorophenyl)-(3-nitrophenyl)methyl]-N-[(R)-1-phenylethyl]amine [prepared as described in step (a) above], 920 mg of nickel chloride hexahydrate and 293 mg of sodium borohydride were reacted and purified, to obtain 620 mg of isomer B of the title compound as a colorless oil.

Isomer B

Nuclear Magnetic Resonance Spectrum (CDCl$_3$) δ ppm: 1.35 (3H, doublet, J=6.6 Hz); 3.61 (1H, quartet, J=6.7 Hz); 4.48 (1H, singlet); 6.45–6.65 (3H, multiplet); 7.03 (1H, triplet, J=7.7 Hz); 7.16–7.40 (9H, multiplet).

(123c) 3-t-Butoxy-4-<3-{(4-chlorophenyl)-[(R)-1-phenylethylamino]methyl}phenylamino>-3-cyclobutene-1,2-dione Following a procedure similar to that described in Example (1c), 630 mg of isomer A of 3-{(4-chlorophenyl)-[(R)-1-phenylethylaminio]methyl}phenylamine [prepared as described in step (b) above] and 689 mg of 4-t-butoxy-3-methoxy-3-cyclobutene-1,2-dione were reacted, to obtain 430 mg of isomer A as a white foamy solid.

Isomer A

Nuclear Magnetic Resonance Spectrum (CDCl$_3$) δ ppm: 1.39 (3H, doublet, J=(6.6 Hz); 1.62 (9H, singlet); 3.67 (1H, quartet, J=6.6 Hz), 4.59 (1H, singlet); 7.03–7.07 (1H, multiplet); 7.20–7.37 (12H, multiplet).

Following a procedure similar to that described in Example (1c), 610 mg of isomer B of 3-{(4-chlorophenyl)-[(R)-1-phenylethylamino]methyl}phenylamine [prepared as described in step (b) above] and 667 mg of 4-t-butoxy-3-methoxy-3-cyclobutene-1,2-dione were reacted, to obtain 794 mg of isomer B as a white foamy solid.

Isomer B

Nuclear Magnetic Resonance Spectrum (CDCl$_3$) δ ppm: 1.37 (3H, doublet, J=(6.7 Hz); 1.63 (9H, singlet); 3.62 (1H, quartet, J=6.7 Hz); 4.57 (1H, singlet); 6.98–7.03 (1H, multiplet); 7.15–7.38 (12H, multiplet).

(123d) 3-<3-{(4–Chlorophenyl)-[(R)-1-phenylethylamino]methyl}phenylamino>-4-hydroxy-3-cyclobutene-1,2-dione Following a procedure similar to that described in Example (55b), 430 mg of isomer A of 3-t-butoxy-4-<3-{4-chlorophenyl)-[(R)-1-phenylethylamino]methyl}phenylamino >-3-cyclobutene-1,2-dione [prepared as described in step (c) above] and 2 ml of trifluoroacetic acid were reacted, to obtain 292 mg of isomer A of the title compound as a white solid.

Isomer A

Nuclear Magnetic Resonance Spectrum (DMSO-$d_6$) δ ppm: 1.63 (3H, doublet, J=6.7 Hz); 4.27 (1H, quartet, J=6.7 Hz); 5.13 (1H, singlet); 6.94 (1H, doublet, J=7.7 Hz); 7.28 (1H, triplet, J=8.1 Hz); 7.35–7.68 (11H, multiplet). mp: 205° C.(dec); optical rotation $[α]_D$=−275 (c=1.00 AcOH).

Following a procedure similar to that described in Example (55b), 324 mg of isomer B of 3-t-butoxy-4-<3-{(4-chlorophenyl)-[(R)-1-phenylethylamino]methyl}phenylamino>-3-cyclobutene-1,2-dione [prepared as described in step (c) above] and 2 ml of trifluoroacetic acid were reacted, to obtain 210 mg of isomer B of the title compound as a white solid.

Isomer B

Nuclear Magnetic Resonance Spectrum (DMSO-$d_6$) δ ppm: 1.62 (3H, doublet, J=6.7 Hz); 4.18 (1H, quartet, J=6.7 Hz); 5.14 (1H, singlet); 7.02 (1H, doublet, J=7.7 Hz); 7.30 (1H, triplet, J=7.9 Hz); 7.32–7.65 (10H, multiplet); 7.67 (1H, singlet). mp: 208° C.(dec); optical rotation $[α]_D$=−27.0 (c=1.00, DMSO).

EXAMPLE 124

3-Hydroxy-4-<3-{[(R)-1-phenylethylamino]-(4-methoxyphenyl)methyl}-phenylamino>-3-cyclobutene-1,2-dione (Compound No. 2–8)

(124a) N-[(R)-1-Phenylethyl]-N-[(3-nitrophenyl)-(4-methoxyphenyl)methyl]amine

Following a procedure similar to that described ix Example (1a), 2.00 g of 3-nitrophenyl 4-methoxyphenyl ketone, 1.18 ml of (R)-1-phenylethylamine, 4.31 ml of triethylamine and 1.28 ml of titanium tetrachloride were reacted, to obtain the corresponding imine compound. Then following a procedure similar to that described in Example (1a), the resulting imine compound, 1.95 g of sodium cyanoborohydride and 0.67 ml of acetic acid were reacted, to obtain 2.08 g of the title compound as a yellow oil.

Nuclear Magnetic Resonance Spectrum (CDCl$_3$) δ ppm: 1.38 and 1.39 (total 3H, each doublet, J=6.6 Hz); 3.60 and 3.68 (total 1H, each quartet, J=6.7 Hz); 3.76 and 3.81 (total 3H, each singlet); 4.64 and 4.67 (total 1H, each singlet); 6.80 and 6.89 (total 2H, each doublet, J=8.7 Hz); 7.10–7.50 (8H, multiplet); 7.59 and 7.68 (total 1H, each doublet, J=7.8 Hz); 7.95–8.13 (1H, multiplet); 8.20–8.30 (1H, multiplet).

(124b) 3-{(4-Methoxyphenyl)-[(R)-1-phenylethylamino]methyl}phenylamine

Following a procedure similar to that described in Example (59b), 2.06 g of N-[(4-methoxyphenyl)-(3-nitrophenyl)methyl]-N-[(R)-1-phenylethyl]amine [prepared as described in step (a) above], 2.70 g of nickel chloride hexahydrate and 860 mg of sodium borohydride were reacted, separated and purified, to obtain 510 mg of isomer A and 672 mg of isomer B of the title compound, each as a yellow oil.

isomer A

Nuclear Magnetic Resonance Spectrum (CDCl$_3$) δ ppm: 1.35 (3H, doublet, J=6.7 Hz); 3.70 (1H, quartet, J=6.6 Hz); 3.75 (3H, singlet); 4.48 (1H, singlet); 6.53–6.60 (1H, multiplet); 6.65–6.70 (1H, multiplet); 6.70 (1H, doublet, J=7.4 Hz); 6.75–6.80 (2H, multiplet); 7.10 (1H, triplet, J=7.7 Hz); 7.15–7.38 (7H, multiplet).

isomer B

Nuclear Magnetic Resonance Spectrum (CDCl$_3$) δ ppm: 1.35 (3H, doublet, J=6.6 Hz); 3.65 (1H, quartet, J=6.6 Hz); 3.80 (3H, singlet); 4.48 (1H, singlet); 6.45–6.51 (1H, multiplet); 6.52–6.62 (1H, multiplet); 6.66 (1H, doublet, J=7.9 Hz); 6.82–6.87 (2H, multiplet); 7.03 (1H, triplet, J=7.8 Hz); 7.15–7.36 (7H, multiplet).

(124c) 3-t-Butoxy-4-<3-{(4-methoxyphenyl)-[(R)-1-phenylethylamino]methyl}-phenylamino>-3-cyclobutene-1,2-dione Following a procedure similar to that described in Example (1c), 500 mg of isomer A of 3-{(4-methoxyphenyl)-[(R)-1-phenylethylamino]methyl}phenylamine [prepared as described in step (b) above] and 554 mg of 4-t-butoxy-3-methoxy-3-cyclobutene-1,2-dione were reacted, to obtain 633 mg of isomer A of the title compound as a white foamy solid.

isomer A

Nuclear Magnetic Resonance Spectrum (CDCl$_3$) δ ppm: 1.41 (3H, doublet, J=6.3 Hz); 1.62 (9H, singlet); 3.71 (4H, broad); 4.60 (1H, singlet); 6.77 (2H, doublet, J=8.7 Hz); 7.05–7.56 (11H, multiplet).

Following a procedure similar to that described in Example (1c), 660 mg of isomer B of 3-{(4-methoxyphenyl)-[(R)-1-phenylethylamino]methyl}phenylamine [prepared as described in step (b) above] and 731 mg 4-t-butoxy-3-methoxy-3-cyclobutene-1,2-dione were reacted, to obtain 389 mg of isomer B of the title compound as a white foamy solid.

isomer B

Nuclear Magnetic Resonance Spectrum (CDCl$_3$) δ ppm: 1.45 (3H, broad); 1.61 (9H, singlet); 3.65–3.80 (1H, multiplet); 3.81 (3H, singlet); 4.59 (1H, singlet); 6.90 (2H, doublet, J=8.5 Hz); 7.00 (1H, doublet, J=6.4 Hz); 7.13–7.50 (10H, multiplet).

(124d) 3-Hydroxy-4-<3-{(4-methoxyphenyl)-[(R)-1-phenylethylamino]methyl}-phenylamino>-3-cyclobutene-1,2-dione Following a procedure similar to that described in Example (55b), 620 mg of isomer A of 3-t-butoxy-4-<3-{(4-methoxyphenyl)-[(R)-1-phenylethylamino]-methyl}phenylamino>-3-cyclobutene-1,2-dione [prepared as described in step (c) above] and 3 ml of trifluoroacetic acid were reacted, to obtain 181 mg of isomer A of the title compound as a pale green solid.

isomer A

Nuclear Magnetic Resonance Spectrum (DMSO-$d_6$) δ ppm: 1.64 (3H, doublet, J=6.7 Hz); 3.74 (3H, singlet); 4.24 (1H, quartet, J=6.7 Hz); 4.97 (1H, singlet); 6.97 (2H, doublet, J=8.7 Hz); 7.00 (1H, doublet, J=8.2 Hz); 7.27 (1H, triplet, J=7.9 Hz); 7.33–7.52 (7H, multiplet); 7.53 (1H, doublet, J=8.1 Hz); 7.59 (1H, singlet). mp: 195° C.(dec); optical rotation $[α]_D$=−52.0(c=1.00, DMSO).

Following a procedure similar to that described in Example (55b), 324 mg of isomer B of 3-t-butoxy-4-<3-{(4-methoxyphenyl)-[(R)-1-phenylethylamino]-methyl}phenylamino>-3-cyclobutene-1,2-dione [prepared as described in step (c) above] and 2 ml of trifluoroacetic acid were reacted, to obtain 164 mg of isomer B of the title compound as a pale yellow solid.

isomer B

Nuclear Magnetic Resonance Spectrum (DMSO-$d_6$) δ ppm: 1.62 (3H, doublet, J=6.8 Hz); 3.77 (3H, singlet); 4.13 (1H, quartet, J=6.6 Hz); 4.96 (1H, singlet); 6.95–7.05 (3H, multiplet); 7.27 (1H, triplet, J=7.9 Hz); 7.35–7.50 (7H, doublet of doublets, J=1.6 Hz, 8.1 Hz); 7.67 (1H, singlet). mp: 195° C.(dec); optical rotation [α]$_D$=−40.3 (c=1.00, DMSO).

EXAMPLE 125

3-<3-{[4-(p-Tolyl)-[(R)-1-(3-fluorophenyl) ethylamino]methyl}phenylamino>-4-hydroxy-3-cyclobutene-1,2-dione hydrochloride (Compound No. 2-3197)

(125a) N-[(p-Tolyl)-(3-nitrophenyl)methyl]-N-[(R)-1-(3-fluorophenyl)ethyl]amine

Following a procedure similar to that described in Example (1a), 3.00 g of 3-nitrophenyl p-tolyl ketone, 2.62 g of (R)-1-(3-fluorophenyl)ethylamine, 8.6 ml of triethylamine and 2.1 ml of titanium tetrachloride were reacted, to obtain the corresponding imine compound. Then following a procedure similar to that described in Example (1a), the resulting imine compound, 3.13 g of sodium cyanoborohydride and 1.1 ml of acetic acid were reacted, to obtain 3.59 g of the title compound as a brown oil.

Nuclear Magnetic Resonance Spectrum (CDCl$_3$) δ ppm: 1.36 and 1.38 (total 3H, each doublet, J=6.7 Hz); 2.29 and 2.36 (total 3H, each singlet); 3.60–3.77 (1H, multiplet); 4.66 and 4.70 (total 1H, each singlet); 6.90–7.75 (10H, multiplet); 8.00–8.13 (1H, multiplet); 8.22 and 8.26 (total 1H, each singlet).

(125b) 3-{(p-Tolyl)-[(R)-1-(3-fluorophenyl)ethylamino] methyl}phenylamine

Following a procedure similar to that described in Example (59b), 3.59 g of N-[(p-tolyl)-(3-nitrophenyl) methyl]-N-[(R)-1-(3-fluorophenyl)ethyl]amine [prepared as described in step (a) above], 4.68 g of nickel chloride hexahydrate and 1.49 g of sodium borohydride were reacted, separated and purified, to obtain 955 mg of isomer A and 649 mg of isomer B of the title compound, each as a yellow oil.

isomer A

Nuclear Magnetic Resonance Spectrum (CDCl$_3$) δ ppm: 1.33 (3H, doublet, J=6.7 Hz); 2.28 (3H, singlet); 3.71 (1H, quartet, J=6.7 Hz); 4.49 (1H, singlet); 6.56 (1H, doublet of doublets, J=2.0, 8.1 Hz); 6.64 (1H, doublet, J=2.0 Hz); 6.69 (1H, doublet, J=7.5 Hz); 6.88–6.98 (1H, multiplet); 7.00–7.30 (8H, multiplet).

isomer B

Nuclear Magnetic Resonance Spectrum (CDCl$_3$) δ ppm: 1.33 (3H, doublet, J=6.6 Hz); 2.33 (3H, singlet); 3.66 (1H, quartet, J=6.7 Hz); 4.48 (1H, singlet); 6.50 (1H, doublet of doublets, J=2.0, 8.2 Hz); 6.62 (1H, doublet, J=1.9 Hz); 6.66 (1H, doublet, J=7.5 Hz); 6.90–7.35 (9H, multiplet).

(125c) 3-t-Butoxy-4-<3-{(p-tolyl)-[(R)-1-(3-fluorophenyl) ethylamino]methyl}-phenylamino>-3-cyclobutene-1,2-dione Following a procedure similar to that described in Example (1c), 500 mg of isomer A of 3-{(p-tolyl)-[(R)-1-(3-fluorophenyl)ethylamino]methyl}phenylamine [prepared as described in step (b) above] and 554 mg of 4-t-butoxy-3-methoxy-3-cyclobutene-1,2-dione were reacted, to obtain 633 mg of isomer A of the title compound as a white foamy solid.

isomer A

Nuclear Magnetic Resonance Spectrum (CDCl$_3$) δ ppm: 1.37 (3H, doublet, J=6.6 Hz); 1.62 (9H, singlet); 2.29 (3H, singlet); 3.68 (1H, quartet, J=6.6 Hz); 4.59 (1H, singlet); 6.90–7.40 (12H, multiplet).

Following a procedure similar to that described in Example (1c), 660 mg of isomer B of 3-{(p-tolyl)-[(R)-1-(3-fluorophenyl)ethylamino]methyl}phenylamine [prepared as described in step (b) above] and 731 mg of 4-t-butoxy-3-methoxy-3-cyclobutene-1,2-dione were reacted, to obtain 389 mg of isomer B of the title compound as a white foamy solid.

isomer B

Nuclear Magnetic Resonance Spectrum (CDCl$_3$) δ ppm: 1.35 (3H, doublet, J=6.6 Hz); 1.62 (9H, singlet); 2.34 (3H, singlet); 3.67 (1H, quartet, J=6.6 Hz); 4.56 (1H, singlet): 6.90–7.35 (12H, multiplet).

(125d) 3-<3-{(p-Tolyl)-[(R)-1-(3-fluorophenyl)ethylamino] methyl}phenylamino>-4-hydroxy-3-cyclobutene-1,2-dione Following a procedure similar to that described in Example (55b), 620 mg of isomer A of 3-t-butoxy-4-<3-{(p-tolyl)-[(R)-1-(3-fluorophenyl)ethylamino] methyl}phenylamino>-3-cyclobutene-1,2-dione [prepared as described in step (c) above] and 3 ml of trifluoroacetic acid were reacted, to obtain 181 mg of isomer A of the title compound as a pale green solid.

isomer A

Nuclear Magnetic Resonance Spectrum (DMSO-d$_6$) δ ppm: 1.62 (3H, doublet, J=6.7 Hz); 2.28 (3H, singlet); 4.31 (1H, quartet, J=6.6 Hz); 5.04 (1H, singlet); 6.93 (1H, doublet, J=7.7 Hz); 7.17 (1H, doublet, J=7.8 Hz); 7.18–7.30 (8H, multiplet); 7.55 (1H, doublet of doublets, J=1.5, 8.1 Hz); 7.65 (1H, singlet). mp: 200° C.(dec); optical rotation [α]$_D$=−392.2 (c=1.00, AcOH).

Following a procedure similar to that described in Example (55b), 324 mg of isomer B of 3-t-butoxy-4-<3-{(p-tolyl)-[(R)-1-(3-fluorophenyl)ethylamino] methyl}phenylamino>-3-cyclobutene-1,2-dione [prepared as described in step (c) above] and 2 ml of trifluoroacetic acid were reacted, to obtain 164 mg of isomer B of the title compound as a pale yellow solid.

isomer B

Nuclear Magnetic Resonance Spectrum (DMSO-d$_6$) δ ppm: 1.61 (3H, doublet, J=6.8 Hz); 2.31 (3H, singlet); 4.22 (1H, quartet, J=6.7 Hz); 5.04 (1H, singlet); 6.99 (1H, doublet, J=7.7 Hz); 7.20 (1H, doublet, J=7.6 Hz); 7.23–7.35 (5H, multiplet); 7.42 (1H, singlet); 7.44 (1H, singlet); 7.45–7.55 (1H, multiplet); 7.56 (1H, doublet of doublets, J=1.7, 8.1 Hz); 7.69 (1H, singlet). mp: 198° C.(dec); optical rotation [α]$_D$=+74.9 (c=1.00, DMSO).

EXAMPLE 126

3-Hydroxy-4-<3-{[(R)-1-(3-fluorophenyl) ethylamino]-phenylmethyl}-phenylamino>-3-cyclobutene-1,2-dione hydrochloride (Compound No. 2-16)

(126a) N-[(R)-1-(3-Fluorophenyl)ethyl]-N-[(3-nitrophenyl) phenylmethyl]amine

Following a procedure similar to that described in Example (1a), 1.0 g of 3-nitrophenyl phenyl ketone, 1.12 g of (R)-1-(3-fluorophenyl)ethylamine, 3.27 ml of triethylamine, 0.56 ml of titanium tetrachloride, 1.13 g of sodium cyanoborohydride and 0.37 ml of acetic acid were reacted, to obtain 1.45 g of the title compound as a yellow oil.

Nuclear Magnetic Resonance Spectrum (CDCl$_3$) δ ppm: 1.37 and 1.39 (total 3H, each doublet, J=6.5 and 6.5 Hz); 3.63 and 3.69 (total 1H, each quartet, J=6.7 and 6.6 Hz); 4.68 and 4.72 (total 1H, each singlet); 6.92–7.03 (3H, multiplet); 7.20–7.51 (7H, multiplet); 7.60 and 7.68 (total 1H, each doublet, J=8.0 and 8.0 Hz); 8.02–8.12 (1H, multiplet); 8.23–8.28 (1H, multiplet).

(126b) 3-{Phenyl-[(R)-1-(3-fluorophenyl)ethylamino] methyl}phenylamine

Following a procedure similar to that described in Example (1b), 1.37 g of N-[phenyl-(3-nitrophenyl)methyl]-

N-[(R)-1-(3-fluorophenyl)ethyl]amine [prepared as described in step (a) above], 2.14 g of nickel chloride hexahydrate and 623 mg of sodium borohydride were reacted, to obtain 1.16 g of the title compound as a yellow oil.

Nuclear Magnetic Resonance Spectrum (CDCl$_3$) δ ppm: 1.34 and 1.34 (total 3H, each doublet, J=6.6 and 6.6 Hz); 3.66 and 3.72 (total 1H, each quartet, J=6.7 and 6.7 Hz); 4.52 (1H, singlet); 6.51 and 6.57 (total 1H, each doublet of doublets, J=2.0, 8.1 and 2.0, 8.2 Hz); 6.63–6.71 (2H, multiplet); 6.91–7.34 (10H, multiplet).

(126c) 3-t-Butoxy-4-<3-{phenyl-[(R)-1-(3-fluorophenyl)ethylamino]methyl}-phenylamino>-3-cyclobutene-1,2-dione Following a procedure similar to that described in Example (66c), 1.14 g of 3-{phenyl-[(R)-1-(3-fluorophenyl)ethylamino]methyl}phenylamine [prepared as described in step (b) above] and 983 mg of 4-t-butoxy-3-methoxy-3-cyclobutene-1,2-dione were reacted, to obtain 591 mg of isomer A and 660 mg of isomer B of the title compound, each as a yellow foamy solid.

isomer A

Nuclear Magnetic Resonance Spectrum (CDCl$_3$) δ ppm: 1.38 (3H, doublet, J=6.6 Hz); 1.62 (9H, singlet); 3.69 (1H, quarted, J=6.7 Hz); 4.62 (1H, singlet); 6.92–7.02 (3H, multiplet); 7.06–7.37 (10H, multiplet).

isomer B

Nuclear Magnetic Resonance Spectrum (CDCl$_3$) δ ppm: 1.36 (3H, doublet, J=6.7 Hz); 1.63 (9H, singlet); 3.67 (1H, quartet, J=6.6 Hz); 4.60 (1H, singlet); 6.91–7.06 (4H, multiplet); 7.14–7.37 (9H, multiplet).

(126d) 3-Hydroxy-4-<3-{phenyl-[(R)-1-(3-fluorophenyl)ethylamino]methyl}phenylamino>-3-cyclobutene-1,2-dione hydrochloride Following a reaction and purification procedure similar to that described in Example (63b), 360 mg of isomer A of 3-t-butoxy-4-<3-{phenyl-[(R)-1-(3-fluorophenyl)ehtylamino]methyl}phenylamino>-3-cyclobutene-1,2-dione [prepared as described in step(c) above] was reacted, to obtain 301 mg of isomer A of the title compound as a pale brown solid.

isomer A

Nuclear Magnetic Resonance Spectrum (DMSO-d$_6$) δ ppm: 1.68 (3H, doublet, J=6.7 Hz); 4.28 (1H, broad); 5.09 (1H, singlet); 7.18 (1H, doublet, J=7.8 Hz); 7.24–7.50 (9H, multiplet); 7.53 (1H, singlet); 7.63–7.65 (2H, multiplet). mp: 255° C.(dec) optical rotation [α]$_D$=–51.0 (c=0.53, AcOH).

Following a reaction and purification procedure similar to that described in Example (63b), 340 mg of isomer B of 3-t-butoxy-4-<3-{phenyl-[(R)-1-(3-fluorophenyl)ethylamino]phenylamino>-3-cyclobutene-1,2-dione [prepared as described in step (c) above] were reacted, to obtain 301 mg of isomer B of the title compound as a pale yellow solid.

isomer B

Nuclear Magnetic Resonance Spectrum (DMSO-d$_6$) δ ppm: 1.68 (3H, doublet, J=6.7 Hz); 4.21 (1H, broad); 5.14 (1H, singlet); 7.18 (1H, doublet, J=7.8 Hz); 7.24–7.51 (9H, multiplet); 7.55 (1H, singlet); 7.63 (2H, doublet, J=7.0 Hz). mp: 177–182° C.(dec); optical rotation [α]$_D$=–31.7 (c=0.59, AcOH).

EXAMPLE 127

3-Hydroxy-4-<3-{[(R)-1-(3,4-difluorophenyl)ethylamino]-phenylmethyl]-phenylamino>-3-cyclobutene-1,2-dione hydrochloride (Compound No. 2-37)

(127a) N-[(R)-1-(3,4-difluorophenyl)ethyl]-N-[(3-nitrophenyl)phenylmethyl]amine

Following a procedure similar to that described in Example (1a), 1.0 g of 3-nitrophenyl phenyl ketone, 1.24 g of (R)-1-(3,4-difluorophenyl)ethylamine hydrochloride, 3.27 ml of triethylamine, 0.56 ml of titanium tetrachloride, 1.13 g of sodium cyanoborohydride and 0.37 ml of acetic acid were reacted, to obtain 1.41 g of the title compound as a yellow oil.

Nuclear Magnetic Resonance Spectrum (CDCl$_3$) δ ppm: 1.35 and 1.37 (total 3H, each doublet, J=6.5 and 6.5 Hz); 3.61 and 3.67 (total 1H, each quartet, J=6.6 and 6.9 Hz); 4.65 and 4.71 (total 1H, each singlet); 6.88–6.98 (1H, multiplet); 7.04–7.16 (2H, multiplet); 7.21–7.52 (6H, multiplet); 7.59 and 7.66 (total 1H, each, doublet, J=7.4 and 7.9 Hz); 8.03–8.13 (1H, multiplet); 8.24 8.26 (total 1H, each triplet, J=1.7 and 1.8 Hz).

(127b) 3-{Phenyl-[(R)-1-(3,4-difluorophenyl)ethylamino]methyl}phenylamine

Following a procedure similar to that described in Example (1b), 1.36 g of N-[phenyl-(3-nitrophenyl)methyl]-N-(R)-1-(3,4-difluorophenyl)ethyl]amine [prepared as described in step (a) above], 2.02 g of nickel chloride hexahydrate and 588 mg of sodium borohydride were reacted, to obtain 1.17 g of the title compound a sa orange oil.

Nuclear Magnetic Resonance Spectrum (CDCl$_3$) δ ppm: 1.31 (3H, doublet, J=6.6 Hz); 3.63 and 3.69 (total 1H, each quartet, J=6.6 and 6.6 Hz); 4.48 and 4.49 (total 1H, each singlet); 6.50–6.69 (3H, multiplet); 6.92–7.34 (9H, multiplet).

(127c) 3-t-Butoxy-4-<3-{phenyl-[(R)-1-(3,4-difluorophenyl)ethylamino]methyl}-phenylamino>-3-cyclobutene-1,2-dione Following a procedure similar to that described in Example (66c), 1.15 g of 3-{phenyl-[(R)-1-(3,4-difluorophenyl)ethylamino]methyl}phenylamine [prepared as described in step (b) above] and 939 mg of 4-t-butoxy-3-methoxy-3-cyclobutene-1,2-dione were reacted, to obtain 442 mg of isomer A and 207 mg of isomer B of the title compound, each as a yellow oil.

isomer A

Nuclear Magnetic Resonance Spectrum (CDCl$_3$) δ ppm: 1.36 (3H, doublet, J=6.6 Hz); 1.63 (9H, singlet); 3.67 (1H, quartet, J=6.6 Hz); 4.59 (1H, singlet); 6.94–6.97 (1H, multiplet); 7.07–7.38 (11H, multiplet);

isomer B

Nuclear Magnetic Resonance Spectrum (CDCl$_3$) δ ppm: 1.34 (3H, doublet, J=6.6 Hz); 1.63 (9H, singlet); 3.64 (1H, quartet, J=6.6 Hz); 4.57 (1H, singlet); 6.94–6.97 (1H, multiplet); 7.02–7.37 (11H, multiplet).

(127d) 3-Hydroxy-4-<3-{phenyl-[(R)-1-(3,4-difluorophenyl)ethylamino]methyl}phenylamino>-3-cyclobutene-1,2-dione hydrochloride Following a reaction and purification procedure similar to that described in Example (63b), 300 mg of isomer A of 3-t-butoxy-4-<3-{phenyl-[(R)-1-(3,4-difluorophenyl)ethylamino]methyl}phenylamino>-3-cyclobutene-1,2-dione [prepared as described in step (c) above] was reacted, to obtain 174 mg of isomer A of the title compound as a pale yellow solid.

isomer A

Nuclear Magnetic Resonance Spectrum (DMSO-d$_6$) δ ppm: 1.66 (3H, doublet, J=6.8 Hz); 4.32 (1H, broad); 5.10 (1H, singlet); 7.17–7.19 (1H, multiplet); 7.27 (1H, doublet, J=7.6 Hz); 7.33–7.56 (8H, multiplet); 7.62 (2H, doublet, J=7.0 Hz). mp: 184–187° C.; optical rotation [α]$_D$=–70.9 (c=0.59, AcOH).

Following a reaction and purification procedure similar to that described in Example (63b), 195 mg of isomer B of 3-t-butoxy-4-<3-{phenyl-[(R)-1-(3,4-difluorophenyl)ethylamino]methyl}phenylamino>-3-cyclobutene-1,2-dione [prepared as described in step (c) above] was reacted, to obtain 152 mg of isomer B of the title compound as a pale yellow solid.
isomer B Nuclear Magnetic Resonance Spectrum (DMSO-$d_6$) δ ppm: 1.66 (3H, doublet, J=6.7 Hz); 4.24 (1H, broad); 5.16 (1H, singlet); 7.18–7.20 (1H, multiplet); 7.32–7.57 (9H, multiplet); 7.64 (2H, doublet, J=7.4 Hz). mp: 180° C.(dec); optical rotation $[\alpha]_D$=−22.7 (c=0.49, AcOH).

EXAMPLE 128

3-Hydroxy-4-<3-{[(R)-1-(3,5-difluorophenyl)ethylamino]-phenylmethyl}phenylamino>-3-cyclobutene-1,2-dione hydrochloride (Compound No. 2-51)

(128a) N-[(R)-1-(3,5-difluorophenyl)ethyl]-N-[(3-nitrophenyl)phenylmethyl]amine

Following a procedure similar to that described in Example (1a), 1.0 g of 3-nitrophenyl phenyl ketone, 1.24 g of (R)-1-(3,4-difluorophenyl)ethylamine hydrochloride, 3.27 ml of triethylamine, 0.56 ml of titanium tetrachloride, 1.13 g of sodium cyanoborohydride and 0.37 ml of acetic acid were reacted, to obtain 1.51 g of the title compound as a yellow oil.

Nuclear Magnetic Resonance Spectrum (CDCl$_3$) δ ppm: 1.36 and 1.38 (total 3H, each doublet, J=6.6 and 6.7 Hz); 3.63 and 3.68 (total 1H, each quartet, J=6.6 and 6.6 Hz); 4.68 and 4.74 (total 1H, each singlet); 6.66–6.83 (3H, multiplet); 7.22–7.52 (6H, multiplet); 7.61 and 7.67 (total 1H, each doublet, J=7.3 and 7.8 Hz); 8.03–8.13 (1H, multiplet); 8.24 and 8.27 (total 1H, each triplet, J=1.9 and 1.8 Hz).

(128b) 3-{Phenyl-[(R)-1-(3,5-difluorophenyl)ethylamino]methyl}phenylene

Following a procedure similar to that described in Example (1b), 1.36 g of N-[phenyl-(3-nitrophenyl)methyl]-N-[(R)-1-(3,5-difluorophenyl)ethyl]amine [prepared as described in step(a) above], 2.02 g of nickel chloride hexahydrate and 588 mg of sodium borohydride were reacted, to obtain 1.25 g of the title compound as a colorless oil.

Nuclear Magnetic Resonance Spectrum (CDCl$_3$) δ ppm: 1.322 and 1.325 (total 3H, each doublet, J=6.6 and 6.6 Hz); 3.64 and 3.71 (total 1H, each quartet, J=6.7 and 6.7 Hz); 4.51 and 4.52 (total 1H, each singlet); 6.52 and 6.58 (total 1H, each doublet of doublets, J=2.0, 8.0 and 2.1, 7.2 Hz); 6.63 (1H, singlet); 6.65–6.71 (2H, multiplet); 6.76–7.85 (2H, multiplet); 7.05 and 7.12 (total 1H, each triplet, J=7.8 and 7.8 Hz); 7.17–7.35 (5H, multiplet).

(128c) 3-t-Butoxy-4-<3-{phenyl-[(R)-1-(3,5-difluorophenyl)ethylamino]methyl}phenylamino>-3-cyclobutene-1,2-dione Following a procedure similar to that described in Example (66c), 1.25 g of 3-{phenyl-[(R)-1-(3,5-difluorophenyl)ethylamino]methyl}phenylamine [prepared as described in step (b) above] and 1.02 g of 4-t-butoxy-3-methoxy-3-cyclobutene-1,2-dione were reacted, to obtain 733 mg of isomer A and 715 mg of isomer B of the title compound, each as a pale yellow foamy solid.
isomer A Nuclear Magnetic Resonanace Spectrum (CDCl$_3$) δ ppm: 1.36 (3H, doublet, J=6.7 Hz); 1.63 (9H, singlet); 3.69 (1H, quartet, J=6.6 Hz); 4.62 (1H, singlet); 6.66–6.72 (1H, multiplet); 6.80 (2H, doublet of doublets, J=2.0, 8.1 Hz); 7.07–7.39 (9H, multiplet).

isomer B

Nuclear Magnetic Resonance Spectrum (CDCl$_3$) δ ppm: 1.35 (3H, doublet, J=6.6 Hz); 1.63 (9H, singlet); 3.66 (1H, quartet, J=6.6 Hz); 4.60 (1H, singlet); 6.65–6.71 (1H, multiplet); 6.80 (2H, doublet of doublets, J=2.1, 8.4 Hz); 7.05–7.38 (9H, multiplet).

(128d) 3-Hydroxy-4-<3-{phenyl-[(R)-1-(3,5-difluorophenyl)ethylamino]methyl}phenylamino>-3-cyclobutene-1,2-dione hydrochloride Following a reaction and purification procedure similar to that described in Example (63b), 325 mg of isomer A of 3-t-butoxy-4-<3-{phenyl-[(R)-1-(3,5-difluorophenyl)ethylamino]methyl}phenylamino>-3-cyclobutene-1,2-dione [prepared as described in step (c) above] was reacted, to obtain 251 mg of isomer A of the title compound as a pale yellow solid.
isomer A Nuclear Magnetic Resonance Spectrum (DMSO-$d_6$) δ ppm: 1.66 (3H, doublet, J=6.7 Hz); 4.32 (1H, broad); 5.18 (1H, singlet); 7.17 (2H, doublet of doublets, J=1.8, 8.0 Hz); 7.26–7.43 (7H, multiplet); 7.56 (1H, singlet); 7.65 (2H, doublet, J=7.1 Hz). mp: 184–187° C.(dec); optical rotation $[\alpha]_d$=−47.2 (c=0.475, AcOH).

Following a reaction and purification procedure similar to that described in Example (63b), 353 mg of isomer B of 3-t-butoxy-4-<3-{phenyl-[(R)-1-(3,5-difluorophenyl)ethylamino]methyl}phenylamino>-3-cyclobutene-1,2-dione [prepared as described in step (c) above] was reacted, to obtain 158 mg of isomer B of the title compound as a white solid.
isomer B Nuclear Magnetic Resonance Spectrum (DMSO-$d_6$) δ ppm: 1.66 (3H, doublet, J=6.7 Hz); 4.27 (1H, broad); 5.22 (1H, singlet); 7.17–7.19 (2H, multiplet); 7.28–7.47 (7H, multiplet); 7.57 (1H, singlet); 7.65 (2H, doublet, J=7.3 Hz). mp: 180–185° C.(dec); optical rotation $[\alpha]_D$=−10.2 (c=0.59, AcOH).

EXAMPLE 129

3-<3-{(4-Fluorophenyl)-[(R)-1-(naphthalen-1-yl)ethylamino]methyl}phenylamino>-4-hydroxy-3-cyclobutene-1,2-dione hydrocyloride (Compound No. 2-3162)

(129a) N-[(4-Fluorophenyl)-(3-nitrophenyl)methyl]-N-[(R)-1-(naphthalen-1-yl)ethyl]amine Following a procedure similar to that described in Example (1a), 3.68 g of 3-nitrophenyl 4-fluorophenyl ketone, 2.57 g of (R)-1-(1-naphthyl)ethylamine, 8.36 ml of triethylamine and 2.47 ml of titanium tetrachloride were reacted, to obtain the corresponding imine compound. Then following a procedure similar to that described in Example (1a), the resulting imine compound, 3.77 g of sodium cyanoborohydride and 3.86 ml of acetic acid were reacted, to obtain 5.41 g of the title compound as a yellow oil.

Nuclear Magnetic Resonance Spectrum (CDCl$_3$) δ ppm: 1.52 and 1.53 (total 3H, each doublet, J=6.6 Hz); 4.51 and 4.54 (total 1H, each quartet, J=6.6 Hz); 4.76 and 4.79 (total 1H, each singlet); 6.95–7.04 (2H, multiplet); 7.16–7.27 (2H, multiplet); 7.36–7.64 (6H, multiplet); 7.75–7.93 (3H, multiplet); 8.03 and 8.10 (total 1H, each doublet of doublets, J=2.2 and 8.1 Hz); 8.21 and 8.26 (total 1H, each singlet).

(129b) 3-{(4-Fluorophenyl)-[(R)-1-(naphthalen-1-yl)ethylamino]methyl}phenylamine Following a procedure similar to that described in Example (1b), 5.38 g of N-[(4-fluorophenyl)-(3-nitrophenyl)methyl]-N-[(R)-1-(napthalen-1-yl)ethyl]amine [prepared as described in step (a) above], 6.39 g of nickel chloride hexahydrate and 2.03 g of sodium bobohydride were reacted and purified, to obtain 4.46 g of the title compound as a pale yellow oil.

Nuclear Magnetic Resonance Spectrum (CDCl$_3$) δ ppm: 1.48 (3H, doublet, J=6.6 Hz); 4.52 and 4.58 (total 1H, each quartet, J=6.6 Hz); 4.59 and 4.62 (total 1H, each singlet); 6.52–6.69 (3H, multiplet); 6.91–7.10 (3H, multiplet); 7.22–7.31 (2H, multiplet); 7.37–7.51 (3H, multiplet); 7.62–7.69 (1H, multiplet); 7.75 and 7.77 (total 1H, each singlet); 7.83–7.95 (2H, multiplet).

(129c) 3-t-Butoxy-4-<3-{(4-fluorophenyl)-[(R)-1-(naphthalen-1-yl)ethylamino]-methyl}phenylamino>-3-cyclobutene-1,2-dione Following a reaction and purification procedure similar to that described in Example (66c), 2.43 g of 3-{(4-fluorophenyl)-[(R)-1-(napthalen-1-yl)ethylamino]methyl}phenylamine [prepared as described in step (b) above] and 1.64 g of 4-t-butoxy-3-methoxy-3-cyclobutene-1,2-dione were reacted, to obtain 0.62 g of isomer A and 0.20 g of isomer B of the title compound, each as a white foamy solid.

isomer A

Nuclear Magnetic Resonance Spectrum (CDCl$_3$) δ ppm: 1.51 (3H, doublet, J=6.6 Hz); 1.58 (9H, singlet); 4.55 (1H, quartet, J=6.6 Hz); 4.68 (1H, singlet); 6.92–7.03 (3H, multiplet); 7.13–7.22 (3H, multiplet); 7.23–7.42 (3H, multiplet); 7.42–7.53 (2H, multiplet); 7.65 (1H, doublet, J=7.3 Hz); 7.77 (1H, doublet, J=8.1 Hz); 7.84–7.88 (2H, multiplet).

isomer B

Nuclear Magnetic Resonance Spectrum (CDCl$_3$) δ ppm: 1.51 (3H, doublet, J=6.6 Hz); 1.62 (9H, singlet); 4.53 (1H, quartet, J=6.6 Hz); 4.71 (1H, singlet); 6.96–7.08 (3H, multiplet); 7.13–7.35 (5H, multiplet); 7.37–7.54 (3H, multiplet); 7.65 (1H, doublet, J=8 Hz); 7.77 (1H, doublet, J=8.1 Hz); 7.84–7.90 (2H, doublet, J=8.1 Hz).

(129d) 3-<3-{(4-Fluorophenyl)-[(R)-1-(napthalen-1-yl)ethylamino]methyl}phenylamino>-4-hydroxy-3-cyclobutene-1,2-dione hydrochloride Following a procedure similar to that described in Example (63b), 0.61 g of isomer A of 3-t-butoxy-4-<3-{(4-fluorophenyl)-[(R)-1-(naphthalen-1-yl)ethylamino]methyl}phenylamino}-3-cyclobutene-1,2-dione [prepared as described in step (c) above] and 4 ml of trifluoroacetic acid were reacted to obtain 285 mg of isomer A of the title compound as a white solid.

isomer A

Nuclear Magnetic Resonance Spectrum (DMSO-d$_6$) δ ppm: 1.81 (3H, doublet, J=6.6 Hz); 5.10–5.30 (2H, broad); 7.09 (1H, doublet, J=8.1 Hz); 7.17–7.43 (7H, multiplet); 7.47 (1H, doublet of doublets, J=7.3, 8.1 Hz); 7.66 (1H, doublet of doublets, J=7.3, 8.1 Hz); 7.70 (1H, doublet, J=5.1 Hz); 7.72 (1H, doublet, J=5.9 Hz); 7.95 (1H, doublet, J=8.8 Hz); 7.98 (1H, doublet, J=8.1 Hz); 8.05–8.18 (1H, broad). mp: 173° C.(dec); optical rotation [α]$_D$=−48.0 (c=1.04, DMSO).

Following a procedure similar to that described in Example (63b), 0.19 g of isomer B of 3-t-butoxy-4-<3-{(4-fluorophenyl)-[(R)-1-(naphthalen-1-yl)ethylamino]methyl}phenylamino}-3-cyclobutene-1,2-dione [prepared as described in step (c) above] and 2 ml of trifluoroacetic acid were reacted, to obtain 147 mg of isomer B of the title compound as a white solid.

isomer B

Nuclear Magnetic Resonance Spectrum (DMSO-d$_6$) δ ppm: 1.81 (3H, doublet, J=6.6 Hz); 5.00–5.10 (1H, broad); 5.45 (1H, singlet); 7.16–7.24 (2H, multiplet); 7.29–7.71 (10H, multiplet); 7.97–8.04 (3H, multiplet). mp: 178° C.(dec); optical rotation [α]$_D$=−92.9 (c=1.01, DMSO).

EXAMPLE 130

3-<3-{(4-Chlorophenyl)-[(R)-1-(naphthalen-1yl)ethylamino]methyl}phenylamino>-4-hydroxy-3-cyclobutene-1,2-dione hydrochloride (Compound No. 2-3136)

(130a) N-[(4-Chlorophenyl)-(3-nitrophenyl)methyl]-N-[(R)-1-(naphthalen-1-yl)ethyl]amine Following a procedure similar to that described in Example (1a), 3.93 g of 3-nitrophenyl 4-chlorophenyl ketone, 2.57 g of (R)-1-(1-naphthyl)ethylamine, 8.36 ml of triethylamine and 2.47 ml of titanium tetrachloride were reacted, to obtain the corresponding imine compound. Then following a procedure similar to that described in Example (1a), the resulting imine compound, 3.77 g of sodium cyanoborohydride and 3.86 ml of acetic acid were reacted, to obtain 5.42 g of the title compound as a yellow oil.

Nuclear Magnetic Resonance Spectrum (CDCl$_3$) δ ppm: 1.52 and 1.53 (total 3H, each doublet, J=6.6 Hz); 4.48–4.56 (1H, multiplet); 4.75 and 4.78 (total 1H, each singlet); 7.15–7.31 (4H, multiplet); 7.36–7.63 (6H, multiplet); 7.75–7.94 (3H, multiplet); 8.02–8.12 (1H, multiplet); 8.20 and 8.26 (total 1H, each singlet).

(130b) 3-{(4-Chlorophenyl)-(R)-1-(naphthalen-1-yl)ethylamino]methyl}phenylamine

Following a procedure similar to that described in Example (1b), 5.38 g of N-[(4-chlorophenyl)-(3-nitrophenyl)methyl]-N-[(R)-1-(naphthalen-1-yl)ethyl]amine [prepared as described in step (a) above], 6.15 g of nickel chloride hexahydrate and 1.98 g of sodium borohydride were reacted, separated and purified, to obtain 4.30 g of the title compound as a pale yellow oil.

Nuclear Magnetic Resonance Spectrum (CDCl$_3$) δ ppm: 1.48 (3H, doublet, J=6.6 Hz); 4.49–4.60 (2H, multiplet); 6.52–6.70 (3H, multiplet); 7.03–7.10 (1H, multiplet); 7.20–7.29 (4H, multiplet); 7.37–7.51 (3H, multiplet); 7.62–7.68 (1H, multiplet); 7.76 and 7.77 (total 1H, each singlet); 7.84–7.96 (2H, multiplet).

(130c) 3-t-Butoxy-4-<3-{(4-chlorophenyl)-[(R)-1-(naphthalen-1-yl)ethylamino]methyl}phenylamino>-3-cyclobutene-1,2-dione Following a reaction and purification procedure similar to that described in Example (66c), 4.29 g of 3-{(4-chlorophenyl)-[(R)-1-(naphthalen-1-yl)ethylamino}methyl}-phenylamine [prepared as described in step (b) above] and 2.45 g of 4-t-butoxy-3-methoxy-3-cyclobutene-1,2-dione were reacted, to obtain 1.49 g of isomer A and 1.81 g of isomer B os the title compound, each as a white foamy solid.

isomer A

Nuclear Magnetic Resonance Spectrum (CDCl$_3$) δ ppm: 1.52 (3H, doublet, J=6.6 Hz); 1.58 (9H, singlet); 4.55 (1H, quartet, J=6.6 Hz); 4.68 (1H, singlet); 6.99 (1H, doublet, J=6.6 Hz); 7.13–7.20 (2H, multiplet); 7.22–7.42 (6H, multiplet); 7.43–7.53 (2H, multiplet); 7.65 (1H, doublet, J=7.3 Hz); 7.78 (1H, doublet, J=8.8 Hz); 7.87 (2H, doublet, J=8.1 Hz).

isomer B

Nuclear Magnetic Resonance Spectrum (CDCl$_3$) δ ppm: 1.50 (3H, doublet, J=6.6 Hz); 1.77 (9H, singlet); 4.52 (1H, quartet, J=6.6 Hz); 4.67 (1H, singlet); 7.03 (1H, doublet, J=7.3 Hz); 7.13–7.34 (7H, multiplet); 7.37–7.51 (3H, multiplet); 7.64 (1H, doublet, J=6.6 Hz); 7.77 (1H, doublet, J=8.1 Hz); 7.87 (2H, doublet, J=8.1 Hz).

(130d) 3-<3-{(4-Chlorophenyl)-[(R)-1-(naphthalen-1-yl)ethylamino]methyl}phenyhlamino>-4-hydroxy-3-cyclobutene-1,2-dione hydrochloride Following a procedure similar to that described in Example (63b), 0.80 g of isomer A of 3-t-butoxy-4-<3-{(4- chlorophenyl)-[(R)-1-(naphthalen-1-yl)ethylamino]methyl}phenylamino>-3-cyclobutene-1,2-dione [prepared as described in step (c) above] and 5 ml of trifluoroacetic acid were reacted, to obtain 470 mg of isomer A of the title compound as a white solid.
isomer A Nuclear Magnetic Resonance Spectrum (DMSO-$d_6$) δ ppm: 1.79 (3H, doublet, J=5.9 Hz); 5.18–5.24 (1H, broad); 5.33 (1H, singlet); 6.98 (1H, doublet, J=7.3 Hz); 7.21 (1H, triplet, J=8.1 Hz); 7.28–7.44 (3H, multiplet); 7.45–7.55 (4H, multiplet); 7.59–7.70 (3H, multiplet); 7.92–8.04 (3H, multiplet). mp: 167° C.(dec); optical rotation $[\alpha]_D$=−71.9 (c=1.02, DMSO).

Following a procedure similar to that described in Example (63b), 0.68 g of isomer B of 3-t-butoxy-4-<3-{(4-chlorophenyl)-[(R)-1-(naphthalen-1-yl)ethylamino]methyl}phenylamino>-3-cyclobutene-1,2-dione [prepared as described in step (c) above] and 5 ml of trifluoroacetic acid were reacted, to obtain 477 mg of isomer B of the title compound as a white solid.
isomer B Nuclear Magnetic Resonance Spectrum (DMSO-$d_6$) δ ppm: 1.82 (3H, doublet, J=6.6 Hz); 5.00–5.12 (1H, broad); 5.43 (1H, singlet); 7.26–7.61 (10H, multiplet); 7.63–7.71 (2H, multiplet); 7.97–8.09 (3H, multiplet). mp: 176° C.(dec); optical rotation $[\alpha]_D$=−93.7 (c=1.01, DMSO).

EXAMPLE 131

3-<3-{(4-Fluorophenyl)-[(R)-1-phenylethylamino]methyl}phenylamino>-4-hydroxy-3-cyclobutene-1,2-dione hydrochloride (Compound No. 2-5)

(131a) N-[(4-Fluorophenyl)-(3-nitrophenyl)methyl]-N-[(R)-1-phenylethyl]amine

Following a procedure similar to that described in Example (1a), 3.00 g of 3-nitrophenyl 4-fluorophenyl ketone, 1.85 ml of (R)-1-phenylethylamine, 6.78 ml of triethylamine and 2.02 ml of titanium tetrachloride were reacted, to obtain the corresponding imine compound. Then following a procedure similar to that described in Example (1a), the resulting imine compound, 3.08 g of sodium cyanoborohydride and 1.05 ml of acetic acid were reacted, to obtain 3.93 g of the title compound as a yellow oil.

Nuclear Magnetic Resonance Spectrum (CDCl$_3$) δ ppm: 1.39 and 1.40 (total 3H, each doublet, J=6.6 Hz); 3.60 and 3.65 (total 1H, each quartet, J=6.6 Hz); 4.67 and 4.69 (total 1H, each singlet); 6.96 and 7.04 (total 2H, each triplet, J=8.7 Hz); 7.10–7.41 (7H, multiplet); 7.39 and 7.49 (total 1H, each triplet, J=7.8 Hz); 7.57 and 7.67 (total 1H, each doublet, J=7.8 Hz); 8.00–8.15 (1H, multiplet); 8.20 and 8.24 (total 1H, each triplet, J=1.9 Hz);

(131b) 3-{(4-Fluorophenyl)-[(R)-1-phenylethylamino]methyl}phenylamine

Following a procedure similar to that described in Example (59b), 3.90 g of N-[(4-fluorophenyl)-(3-nitrophenyl)methyl]-N-[(R)-1phenylethyl]amine [prepared as described in step (a) above], 5.29 g of nickel chloride hexahydrate and 1.68 g of sodium borohydride were reacted, separated and purified, to obtain 1.24 g of isomer A and 848 mg of isomer B of the title compound, each as a colorless oil.
isomer A Nuclear Magnetic Resonance Spectrum (CDCl$_3$) δ ppm: 1.35 (3H, doublet, J=6.6 Hz); 3.70 (1H, quartet, J=6.7 Hz); 4.49 (1H, singlet); 6.57 (1H, doublet of doublets, J=2.0 Hz, 7.8 Hz); 6.63 (1H, triplet, J=1.8 Hz); 6.68 (1H, doublet, J=7.8 Hz); 6.91 (2H, triplet, J=8.7 Hz); 7.11 (1H, triplet, J=7.8 Hz); 7.20–7.30 (5H, multiplet); 7.33 (2H, triplet, J=7.8 Hz);

isomer B

Nuclear Magnetic Resonance Spectrum (CDCl$_3$) δ ppm: 1.35 (3H, doublet, J=6.6 Hz); 3.61 (1H, quartet, J=6.7 Hz); 4.50 (1H, singlet); 6.50 (1H, doublet of doublets, J=2.0 Hz, 8.0 Hz); 6.59 (1H, triplet, J=1.7 Hz); 6.63 (1H, doublet, J=7.9 Hz); 6.95–7.07 (3H, multiplet); 7.15–7.40 (7H, multiplet).

(131c) 3-t-Butoxy-4-<3-{(4-fluorophenyl)-[(R)-1-phenylethylamino]methyl}phenylamino>-3-cyclobutene-1,2-dione Following a procedure similar to that described in Example (1c), 1.24 g of isomer A of 3-{(4-fluorophenyl)-[(R)-1-phenylethylamino]methyl}phenylamine [prepared as described in step (b) above] and 1.43 g of 4-t-butoxy-3-methoxy-3-cyclobutene-1,2-dione were reacted, to obtain 1.22 g of isomer A of the title compound as a white foamy solid.
isomer A Nuclear Magnetic Resonance Spectrum (CDCl$_3$) δ ppm: 1.39 (3H, doublet, J=6.6 Hz); 1.62 (9H, singlet); 3.67 (1H, quartet, J=6.6 Hz); 4.60 (1H, singlet); 6.93 (2H, triplet, J=8.8 Hz); 7.04–7.40 (11H, multiplet).

Following a procedure similar to that described in Example (1c), 848 mg of isomer B of 3-{(4-fluorophenyl)-[(R)-1-phenylethylamino]methyl}phenylamine [prepared as described in step (b) above] and 975 mg of 4-t-butoxy-3-methoxy-3-cyclobutene-1,2-dione were reacted, to obtain 1.03 g of isomer B of the title compound as a white foamy solid.
isomer B Nuclear Magnetic Resonance Spectrum (CDCl$_3$) δ ppm: 1.37 (3H, doublet, J=6.6 Hz); 1.62 (9H, singlet); 3.63 (1H, quartet, J=6.6 Hz); 4.59 (1H, singlet); 7.02 (3H, triplet, J=8.8 Hz); 7.12–7.37 (10H, multiplet).

(131d) 3-<3-{(4-Fluorophenyl)-[(R)-1-phenylethylamino]methyl}phenylamino>-4-hydroxy-3-cyclobutene-1,2-dione hydrochloride Following a procedure similar to that described in Example (63b), 830 mg of isomer A of 3-t-butoxy-4-<3-{(4-fluorophenyl)-[(R)-1-phenylethylamino]methyl}phenylamino>-3-cyclobutene-1,2-dione [prepared as described in step (c) above] and 4 ml of trifluoroacetic acid were reacted, to obtain 610 mg of isomer A of the title compound as a pale green solid.
isomer A Nuclear Magnetic Resonance Spectrum (DMSO-$d_6$) δ ppm: 1.63 (3H, doublet, J=6.8 Hz); 4.28 (1H, broad); 5.10 (1H, singlet); 6.91 (1H, doublet, J=7.8 Hz); 7.22–7.46 (8H, multiplet); 7.53 (1H, doublet, J=7.8 Hz); 7.56–7.62 (2H, multiplet); 7.65 (1H, singlet). mp: 198° C.(dec); optical rotation $[\alpha]_D$=−62.6 (c=1.00, DMSO).

Following a procedure similar to that described in Example (63b), 618 mg of isomer B of 3-t-butoxy-4-<3-{(4-fluorophenyl)-[(R)-1-phenylethylamino]methyl}phenylamino>-3-cyclobutene-1,2-dione [prepared as described in step (c) above] and 3 ml of trifluoroacetic acid were reacted to obtain 484 mg of isomer B of the title compound as a white solid.
isomer B Nuclear Magnetic Resonance Spectrum (DMSO-$d_6$) δ ppm: 1.60 (3H, doublet, J=5.9 Hz); 4.14 (1H, broad); 5.09 (1H, singlet); 6.95 (1H, doublet, J=7.8 Hz); 7.23–7.63 (11H, multiplet); 7.70 (1H, singlet). mp: 209° C.(dec); optical rotation $[\alpha]_D$=−20.5 (c=1.00. DMSO).

EXAMPLE 132

3-<3-{[(R)-1-(3,4-Difluorophenyl)ethylamino]-(p-tolyl)methyl}phenylamino>-4-hydroxy-3-cyclobutene-1,2-dione hydrochloride (Compound No. 2-3386)

Following a reaction and purification procedure similar to that described in Example 117, 4.23 g of 3-nitrophenyl p-tolyl ketone and 3.39 mg of (R)-1-(3,4-difluorophenyl)-ethylamine were reacted, to obtain 207 mg of isomer A and 403 mg of isomer B of the title compound.

isomer A
optical rotation $[\alpha]_D=-93.5$ (c=1.01, AcOH)

isomer B
optical rotation $[\alpha]_d=-12.5$ (c=1.01, AcOH)

EXAMPLE 133

3-Hydroxy-4-<3-{[(R)-1-(1-naphthyl)ethylamino]-phenylmethyl}phenylamino>-3-cyclobutene-1,2-dione hydrochloride (Compound No. 2-3161)

(133a) N-[(R)-1-(1-Naphthyl)ethyl]-N-[(3-nitrophenyl)phenylmethyl]amine

Following a procedure similar to that described in Example (1a), 1.09 g of 3-nitrophenyl phenyl ketone, 1.09 g of (R)-1-(1-naphthyl)ethylamine, 2.68 ml of triethylamine and 0.56 ml of titanium tetrachloride were reacted, to obtain the corresponding imine compound. Then following a procedure similar to that described in Example (1a), the resulting imine compound, 1.13 g of sodium cyanoborohydride and 0.37 ml of acetic acid were reacted, to obtain 1.63 g of the title compound as a yellow oil.

Nuclear Magnetic Resonance Spectrum (CDCl$_3$) δ ppm: 1.52 and 1.53 (total 3H, each doublet, J=6.6 and 6.8 Hz); 4.50–4.59 (1H, multiplet); 4.78 and 4.82 (total 1H, each singlet); 7.21–7.97 (14H, multiplet); 8.00–8.10 (1H, multiplet); 8.25–8.30 (1H, multiplet).

(133b) 3-{Phenyl-[(R)-1-(napthalen-1-yl)ethylamino]methyl}phenylamine

Following a procedure similar to that described in Example (1b), 1.56 g of N-[phenyl-(3-nitrophenyl)methyl]-N-[(R)-1-(napthalen-1-yl)ethyl]amine [prepared as described in step (a) above], 2.23 g of nickel chloride hexahydrate and 650 mg of sodium borohydride were reacted, to obtain 1.35 g of the title compound as a yellow oil.

Nuclear Magnetic Resonance Spectrum (CDCl$_3$) δ ppm: 1.479 and 1.482 (total 3H, each doublet, J=6.6 and 6.6 Hz); 4.55 and 4.60 (total 1H, each quartet, J=6.7 and 6.6 Hz); 4.63 and 4.65 (total 1H, each singlet); 6.51–6.73 (3H, multiplet); 7.04–7.09 (1H, multiplet); 7.17–7.51 (8H, multiplet); 7.69 (1H, triplet, J=7.5 Hz); 7.75–7.95 (3H, multiplet).

(133c) 3-t-Butoxy-4-<3-{phenyl-[(R)-1-(naphthalen-1-yl)ethylamino]methyl}phenylamino>-3-cyclobutene-1,2-dione Following a reaction and purification procedure similar to that described in Example (66c), 1.28 g of 3-{phenyl-[(R)-1-(naphthalen-1-yl)ethylamino]methyl}phenylamine [prepared as described in step (b) above] and 1.0 g of 4-t-butoxy-3-methoxy-3-cyclobutene-1,2-dione were reacted, to obtain 680 mg of isomer A as a yellow foamy solid and 670 mg of isomer B as a pale yellow foamy solid of the title compound.

isomer A
Nuclear Magnetic Resonance Spectrum (CDCl$_3$) δ ppm: 1.51 (3H, doublet, J=6.6 Hz); 1.57 (9H, singlet); 4.57 (1H, quartet, J=6.6 Hz); 4.72 (1H, singlet); 6.99–7.08 (1H, multiplet); 7.14–7.53 (11H, multiplet); 7.67 (1H, doublet, J=7.0 Hz); 7.77 (1H, doublet, J=8.1 Hz); 7.82–7.88 (2H, multiplet).

isomer B
Nuclear Magnetic Resonance Spectrum (CDCl$_3$) δ ppm: 1.50 (3H, doublet, J=6.6 Hz); 1.61 (9H, singlet); 4.55 (1H, quartet, J=6.6 Hz); 4.73 (1H, singlet); 7.08 (1H, doublet, J=7.4 Hz); 7.12–7.51 (11H, multiplet); 7.68 (1H, doublet, J=7.1 Hz); 7.76 (1H, doublet, J=8.2 Hz); 7.86–7.90 (2H, multiplet).

(133d) 3-Hydroxy-4-<3-{phenyl-[(R)-1-(naphthalen-1-yl)ethylamino]methyl}phenylamino>-3-cyclobutene-1,2-dione hydrochloride Following a reaction and purification procedure similar to that described in Example (63b), 400 mg of isomer A of 3-t-butoxy-4-<3-{phenyl-[(R)-1-(naphthalen-1-yl)ethylamino]methyl}phenylamino>-3-cyclobutene-1,2-dione [prepared as described in step (c) above] was reacted, to obtain 315 mg of isomer A of the title compound as a pale yellow solid.

isomer A
Nuclear Magnetic Resonance Spectrum (DMSO-d$_6$) δ ppm: 1.81 (3H, doublet, J=6.6 Hz); 5.19 (1H, broad); 5.25 (1H, broad); 7.09 (1H, doublet, J=7.7 Hz); 7.21–7.25 (1H, multiplet); 7.32–7.50 (8H, multiplet); 7.65–7.69 (3H, multiplet); 7.95–8.05 (3H, multiplet). mp: 202–206° C.; optical rotation $[\alpha]_D=-122.9$ (c=0.5, AcOH).

Following a reaction and purification procedure similar to that described in Example (63b), 240 mg of isomer B of 3-t-butoxy-4-<3-{phenyl-[(R)-1-(napthalen-1-yl)ethylamino]methyl}phenylamino>-3-cyclobutene-1,2-dione [prepared as described in step (c) above] was reacted, to obtain 195 mg of isomer B of the title compound as a yellow solid.

isomer B
Nuclear Magnetic Resonance Spectrum (DMSO-d$_6$) δ ppm: 1.83 (3H, doublet, J=6.7 Hz); 5.06 (1H, broad); 5.36 (1H, singlet); 7.22–7.46 (8H, multiplet); 7.49–7.55 (3H, multiplet); 7.62 (1H, singlet); 7.67 (1H, doublet of doublets, J=7.7, 7.8 Hz); 7.97–8.04 (3H, multiplet). mp: 206° C.; optical rotation $[\alpha]_D=-117.6$ (c=0.5, AcOH).

EXAMPLE 134

3-Hydroxy-4-<3-{[(R)-1-(1-naphthyl)ethylamino]-p-tolylmethyl}phenylamino>-3-cyclobutene-1,2-dione hydrochloride (Compound No. 2-3164)

(134a) N-[(R)-1-(1-Naphthyl)ethyl]-N-[(3-nitrophenyl)-p-tolymethyl]amine

Following a procedure similar to that described in Example (1a), 1.0 g of 3-nitrophenyl p-tolyl ketone, 1.06 g of (R)-1-(1-naphthyl)ethylamine, 2.60 ml of triethylamine, 0.55 ml of titanium tetrachloride, 1.10 g of sodium cyanoborohydride and 0.36 ml of acetic acid were reacted, to obtain 1.60 g of the title compound as a yellow oil.

Nuclear Magnetic Resonance Spectrum (CDCl$_3$) δ ppm: 1.51 and 1.52 (total 3H, each doublet, J=6.6 and 6.8 Hz); 2.31 and 2.35 (total 3H, each singlet); 4.52 and 4.57 (total 1H, each quartet, J=6.7 and 6.6 Hz); 4.74 and 4.79 (total 1H, each singlet); 7.09–7.19 (4H, multiplet); 7.33–8.09 (10H, multiplet); 8.25 and 8.30 (1H, multiplet).

(134b) 3-{p-Tolyl-[(R)-1-(naphthalen-1-yl)ethylamino]methyl}phenylamine

Following a procedure similar to that described in Example (1B), 1.51 g of N-[p-tolyl-(3-nitrophenyl)methyl]-N-[(R)-1-(naphthalen-1-yl)ethyl]amine [prepared as described in step (a) above], 2.08 g of nickel chloride hexahydrate and 607 mg of sodium borohydride were reacted, separated and purified, to obtain 1.40 g of the title compound as a yellow oil.

Nuclear Magnetic Resonance Spectrum (CDCl$_3$) δ ppm: 1.47 (3H, doublet, J=6.6 Hz); 2.30 and 2.33 (total 3H, each singlet); 4.53 and 4.61 (1H, multiplet); 4.60 and 4.61 (total 1H, each singlet); 6.50–6.72 (3H, multiplet); 7.03–7.10 (3H, multiplet); 7.15 (1H, doublet, J=8.0 Hz); 7.22 (1H, doublet, J=8.0 Hz); 7.35–7.51 (3H, multiplet); 7.69 (1H, doublet of doublets, J=4.3, 6.2 Hz); 7.76 (1H, doublet, J=8.2 Hz); 7.86 (1H, doublet, J=8.0 Hz); 7.90–7.95 (1H, multiplet).

(134c) 3-t-Butoxy-4-<3-{p-tolyl-[(R)-1-(naphthalen-1-yl)ethylamino]methyl}phenylamino>-3-cyclobutene-1,2-dione Following a reaction and purification procedure similar to that described in Example (66c), 1.40 g of 3-{p-tolyl-[(R)-1-(naphthalen-1-yl)ethylamino]methyl}phenylamine [prepared as described in step (b) above] and 1.06 g of 4-t-butoxy-3-methoxy-3-cyclobutene-1,2-dione were reacted, to obtain 780 mg of isomer A and 790 mg of isomer B of the title compound, each as a yellow foamy solid.

isomer A

Nuclear Magnetic Resonance Spectrum (CDCl$_3$) δ ppm: 1.50 (3H, doublet, J=6.6 Hz); 1.57 (9H, singlet); 2.31 (3H, singlet); 4.56 (1H, quartet, J=6.6 Hz); 4.68 (1H, singlet); 7.00–7.52 (11H, multiplet); 7.66 (1H, doublet, J=7.1 Hz); 7.77 (1H, doublet, J=8.4 Hz); 7.82–7.88 (2H, multiplet).

isomer B

Nuclear Magnetic Resonance Spectrum (CDCl$_3$) δ ppm: 1.49 (3H, doublet, J=6.7 Hz); 1.60 (9H, singlet); 2.34 (3H, singlet); 4.55 (1H, quartet, J=6.6 Hz); 4.69 (1H, singlet); 7.07–7.27 (8H, multiplet); 7.37–7.50 (3H, multiplet); 7.68 (1H, doublet, J=7.1 Hz); 7.75 (1H, doublet, J=8.1 Hz); 7.86 (1H, doublet, J=8.0 Hz); 7.92 (1H, doublet, J=8.5 Hz).

(134d) 3-Hydroxy-4-<3-{p-tolyl-[(R)-1-(naphthalen-1-yl)ethylamino]methyl}phenylamino>-3-cyclobutene-1,2-dione hydrochloride Following a reaction and purification procedure similar to that described in Example (63b), 400 mg of isomer A of 3-t-butoxy-4-<3-{p-tolyl-[(R)-1-(naphthalen-1-yl)ethylamino]methyl}phenylamino>-3-cyclobutene-1,2-dione [prepared as described in step (c) above] was reacted, to obtain 343 mg of isomer A of the title compound as a pale yellow solid.

isomer A

Nuclear Magnetic Resonance Spectrum (DMSO-d$_6$) δ ppm: 1.80 (3H, doublet, J=6.6 Hz); 2.31 (3H, singlet); 5.16 (1H, broad); 5.23 (1H, broad); 7.08 (1H, doublet, J=7.7 Hz); 7.22–7.35 (6H, multiplet); 7.40 (1H, singlet); 7.46–7.53 (3H, multiplet); 7.67 (1H, triplet, J=7.7 Hz); 7.95–8.03 (3H, multiplet). mp: 203° C.(dec); optical rotation [α]$_D$=−84.2 (c=0.5, AcOH).

Following a reaction and purification procedure similar to that described in Example (63b), 300 mg of isomer B of 3-t-butoxy-4-<3-{p-tolyl-[(R)-1-(naphthalen-1-yl)ethylamino]methyl}phenylamino>-3-cyclobutene-1,2-dione [prepared as described in step (c) above] was reacted, to obtain 218 mg of isomer B of the title compound as a yellow solid.

isomer B

Nuclear Magnetic Resonance Spectrum (DMSO-d$_6$) δ ppm: 1.81 (3H, doublet, J=6.6 Hz); 2.28 (3H, singlet); 5.05 (1H, broad); 5.31 (1H, singlet); 7.15 (2H, doublet, J=8.1 Hz); 7.29–7.47 (7H, multiplet); 7.52 (1H, doublet of doublets, J=7.7, 7.9 Hz); 7.61 (1H, singlet); 7.67 (1H, doublet of doublets, J=7.7, 7.8 Hz); 7.98–8.02 (3H, multiplet). mp: 210–215° C.; optical rotation [α]$_D$=−96.0 (c=0.54, AcOH).

EXAMPLE 135

3-Hydroxy-4-<3-{[(R)-1-(2,3-difluorophenyl)ethylamino]phenylmethyl}phenylamino>-3-cyclobutene-1,2-dione (Compound No. 2-3508)

By carrying out reaction and purification procedures in a similar manner to that described in Example 55, 3-nitrobenzophenone and (R)-1-(2,3-difluorophenyl)ethylamine may be reacted, to obtain the title compound.

EXAMPLE 136

3-Hydroxy-4-<3-{[(R)-1-(2,3-difluorophenyl)ethylamino]-p-tolylmethyl}phenylamino>-3-cyclobutene-1,2-dione (Compound No. 2-3511)

By carrying out reaction and purification procedures in a similar manner to that described in Example 55, 3-nitrophenyl p-tolyl ketone and (R)-1-(2,3-difluorophenyl)ethylamine may be reacted, to obtain the title compound.

EXAMPLE 137

3-Hydroxy-4-<3-{[(R)-1-(2,3-difluorophenyl)ethylamino]-(4-fluorophenyl)methyl}phenylamino>-3-cyclobutene-1,2-dione (Compound No. 2-3509)

By carrying out reaction and purification procedures in a similar manner to that described in Example 55, 3-nitrophenyl 4-fluorophenyl ketone and (R)-1-(2,3-difluorophenyl)ethylamine may be reacted, to obtain the title compound.

EXAMPLE 138

3-Hydroxy-4-<3-{[(R)-1-(2,3-difluorophenyl)ethylamino]-(4-chlorophenyl)methyl}phenylamino>-3-cyclobutene-1,2-dione (Compound No. 2-3510)

By carrying out reaction and purification procedures in a similar manner to that described in Example 55, 3-nitrophenyl 4-chlorophenyl ketone and (R)-1-(2,3-difluorophenyl)ethylamine may be reacted, to obtain the title compound.

EXAMPLE 139

3-Hydroxy-4-<3-{[(R)-1-(2,3-difluorophenyl)ethylamino]-(4-methoxyphenyl)methyl}phenylamino>-3-cyclobutene-1,2-dione (Compound No. 2-3512)

By carrying out reaction and purification procedures in a similar manner to that described in Example 55, 3-nitrophenyl 4-methoxyphenyl ketone and (R)-1-(2,3-difluorophenyl)ethylamine may be reacted, to obtain the title compound.

TEST EXAMPLE 1

Measurement of Bile Acid Transporter Inhibitory Activity in vitro

1) Insertion of human ileal bile acid transporter cDNA into a mammalian expression vector Human ileal bile acid transporter cDNA (GenBank accession number U10417, hereinafter abbreviated as "hIBAT") was amplified by PCR using a human kidney cDNA library ("Marathon-Ready"™, Clontech Laboratories) as a template. The sense oligonucleotide primer used was 5'-AACGTTGCTTAACTCAACCAGC-3' (corresponding to residues 512–533 of hIBAT cDNA: Sequence ID No. 1) while the antisense oligonucleotide primer used was 5'-CTCGTCTGTTTTGTCCACTTGA-3' (corresponding to residues 1649–1670 of hIBAT cDNA: Sequence ID NO. 2).

The PCR reaction product was subjected to agarose gel electrophoresis, and the target cDNA was collected from a single band of the resulting gel corresponding to 1159 bases. This cDNA was inserted into a mannalian expression vector using the "Eukaryotic TA Cloning Kit" (trade name; product of Invitrogen Corp).

2) Construction of human ileal bile acid transporter expression cells

The hIBAT expression vector obtained in 1) carries a G418 resistance marker. Vectors obtained in 1) were transfected into Caco-2 cells (ATCC accession no. HTB-37, a cell line derived from human bowel cancer) using a lipid reagent ("LIPOFECTAMINE PLUS", trade name; Gibco BRL).

Resulting cells were cultured in the presence of the antibiotic Gp418 ("Geneticin", trade name: Gibco, BRL) in order to select cells having G418 resistance and which, therefore, stably expressed the target vector.

3) Measurement of bile acid transporter inhibitory activity

The hIBAT-expressing Caco-2 cells obtained in 2) were cultured for seven days in a collagen-coated, 96-well microtiter plate ("Viewplate", trade name; product of Packard Instrument Company), each well containing 200 µl of a 4×10$^4$ cell/ml culture of the hIBAT-expressing Caco-2 cells. After this time, either nothing (control) or a selected amount of the test sample (the compound of Example 2) was added to each well of the plate, and then 0.1 µCi of radioactive taurocholic acid ([$^3$H]-taurocholic acid: NEN Corp) was added to each well. The plate was then further incubated at 37° C. for 1 hour under 5% $CO_2$, in order to allow uptake of the radioactive taurocholic acid into cells via ileal bile acid transporter.

After incubation, the cells were washed 5 times with ice cooled PBS (phosphate buffered saline) containing 0.2% bovine serum albumin and 1 mM non-radioactive taurocholic acid. The plate was then allowed to stand overnight for drying, after which time, 250 µl of a liquid scintillation cocktail ("Microscint 20", trade name; product of Packard Instrument Company) were added to each well. Radioactivity was measured using a "Top Count" (Packard) liquid scintillation counter.

By measuring the radioactivity of the control (no text compound) and comparing this with the radioactivity obtained from the cells exposed to test compound at various, predetermined concentrations, it was possible to determine a percentage inhibition (%) and to obtain an $IC_{50}$ for the test compound against the ileal bile acid transporter activity. The results are shown in Table 7.

TABLE 7

| Example Compound No. | $IC_{50}$ (µg/ml) |
|---|---|
| 2 (isomer B) | 5.5 |

It can be seen, from the above results, that the compound of the present invention exhibits excellent ileal bile acid transporter inhibitory activity.

TEST EXAMPLE 2

Measurement of Bile Acid Transporter Inhibitory Activity in vivo

Male Syrian golden hamsters were used. The hamsters were reared in cages and fed food and water ad libitum. Test compound was orally administered by gavage (100 mg/10 ml/kg) as a suspension in 0.5% w/v carboxymethyl cellulose aqueous solution. Each hamster was given orally 1 µCi of [$^3$H]-taurocholic acid (2 µCi/mol) in physiological saline 1.5 hours after administration of the test compound. Twenty four hours after the oral administration of [$^3$H]-taurocholic acid, each of the hamsters was sacrificed and the gall bladder bile was collected. The total radioactivity in the bladder bile was determined and compared to a vehicle-treated group.

Percentage inhibition (%) was determined by the following formula:

Inhibition percentage=100−(radioactivity in the treated group)/(radioactivity in the control group)×100

The result is shown in Table 8.

TABLE 8

| Example Compound No. | Percentage inhibition (%) |
|---|---|
| 2 (isomer B) | 61.87 |
| 64(e) | 80.0 |

From the result shown above, it can be seen that the compound of the present invention exhibits potent inhibitory activity against the ileal bile acid transporter in hamsters.

We claim:
1. A compound of formula (I):

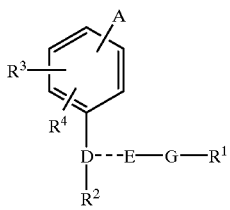

(I)

wherein:
R$^1$ represents an unsubstituted cycloalkyl group, an unsubstituted aryl group, an unsubstituted heterocyclic group, a cycloalkyl group substituted by at least one of substituents α and β defined below, an aryl group substituted by at least one of substituents α and β defined below, or a heterocyclic group substituted by at least one of substituents α and β defined below;

R$^2$ represents an unsubstituted cycloalkyl group, an unsubstituted aryl group, an unsubstituted heterocyclic group, a cycloalkyl group substituted by at least one of substituents α defined below, an aryl group substituted by at least one of substituents α defined below, or a heterocyclic group substituted by at least one of substituents α defined below;

R$^3$ and R$^4$ are the same as or different from each other and each represents a hydrogen atom or one of substituents α defined below;

A represents a group of formula (A-1):

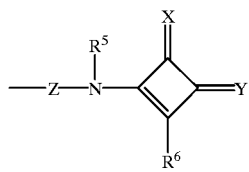

(A-1)

wherein:
R$^5$ represents a hydrogen atom, a hydroxy group or a lower alkyl group, R$^6$ represents a hydroxy group, a lower alkoxy group, a lower alkylthio group or an amine residue, X and Y are the same as or different from each other and each represents an oxygen atom or a sulfur atom, and Z represents a direct single bond between the nitrogen atom and the benzene ring in formula (I), or an alkylene group having from 1 to 6 carbon atoms, G represents a single bond, an alkylene group having from 1 to 6 carbon atoms or an alkylene group having from 1 to 6 carbon atoms and substituted by at least one of substituents γ defined below; the broken line represents a single or double bond; when the broken line represents a double bond,
D represents a carbon atom; and
E represents an =N—O— group;

when the broken line represents a single bond,
D represents a CH group or a nitrogen atom, and
E represents an oxygen atom, a sulfur atom, an —NH— group or a —CO— group;

said substituents α are selected from the group consisting of halogen atoms, hydroxy groups, cyano groups, nitro groups, lower alkyl groups, lower haloalkyl groups, lower alkoxy groups, lower alkylthio groups, amino groups, lower monoalkylamino groups and di(lower alkyl)amino groups;

said substituents β are selected from the group consisting of carboxy groups, lower alkoxycarbonyl groups, carbamoyl groups, lower monoalkylcarbamoyl groups, di(lower alkyl)carbamoyl groups, nitro groups, unsubstituted cycloalkyl groups, unsubstituted aryl groups, unsubstituted aryloxy groups, unsubstituted aralkyloxy groups, unsubstituted arylthio groups and cycloalkyl, aryl, aryloxy, aralkyloxy and arylthio groups, each substituted by at least one of said substituents α;

said substituents γ are selected from the group consisting of hydroxy groups, oxo groups, unsubstituted cycloalkyl groups, unsubstituted aryl groups, unsubstituted heterocyclic groups, cycloalkyl groups substituted by at least one of said substituents α and β, aryl groups substituted by at least one of said substituents α and β, and heterocyclic groups substituted by at least one of said substituents α and β;

said cycloalkyl groups are optionally fused to an aryl group;

said heterocyclic groups are optionally fused to an aryl group;

or a pharmaceutically acceptable salt, ester or other derivative thereof.

2. A compound of claim 1, having the formula (Ia):

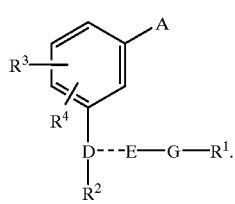

(Ia)

3. A compound of claim 1, having the formula (Ib):

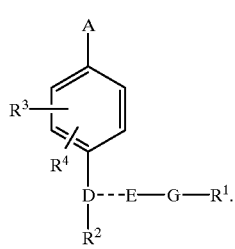

(Ib)

4. A compound of claim 1, wherein R$^5$ represents a hydrogen atom or a lower alkyl group.

5. A compound of claim 1, wherein R$^6$ represents a hydroxy group or an amine residue.

6. A compound of claim 1, wherein X and Y each represent an oxygen atom.

7. A compound of claim 1, wherein D represents a CH group or a nitrogen atom.

8. A compound of claim 1, wherein E represents an oxygen atom, a sulfur atom or an —NH— group.

9. A compound of claim 1, wherein G represents a substituted or unsubstituted alkylene group having from 1 to 6 carbon atoms.

10. A compound of claim 1, wherein R$^1$ represents a cycloalkyl group, an unsubstituted aryl group, an unsubstituted heterocyclic group, an aryl group substituted by from 1 to 3 substituents selected from said substituents α and β, or a heterocyclic group substituted by from 1 to 3 substituents selected from said substituents α and β.

11. A compound of claim 1, wherein $R^2$ represents a cycloalkyl group, an unsubstituted aryl group, an unsubstituted heterocyclic group, an aryl group substituted by from 1 to 3 substituents selected from said substituents α, or a heterocyclic group substituted by from 1 to 3 of said substituents α.

12. A compound of claim 1, wherein $R^3$ and $R^4$ are the same as or different from each other and each represents a hydrogen atom, a hydroxy group, a halogen atom, a lower alkoxy group, an amino group or a di(lower alkyl)amino group.

13. A compound of claim 1, wherein:

Z represents a single bond or an alkylene group having 1 to 2 carbon atoms;

$R^5$ represents a hydrogen atom or a lower alkyl group;

$R^6$ represents a hydroxy group or an amine residue;

X and Y each represents an oxygen atom;

D represents a CH group or a nitrogen atom;

E represents an oxygen atom, a sulfur atom or an —NH— group;

G represents a substituted or unsubstituted alkylene group having from 1 to 6 carbon atoms;

$R^1$ represents a cycloalkyl group, an unsubstituted aryl group, an unsubstituted heterocyclic group, an aryl group substituted by from 1 to 3 substituents selected from said substituents α and β, or a heterocyclic group substituted by from 1 to 3 substituents selected from said substituents α and β;

$R^2$ represents a cycloalkyl group, an unsubstituted aryl group, an unsubstituted heterocyclic group, an aryl group substituted by from 1 to 3 of said substituents α, or a heterocyclic group substituted by from 1 to 3 of said substituents α; and $R^3$ and $R^4$ are the same as or different from each other and each represents a hydrogen atom, a hydroxy group, a halogen atom, a lower alkoxy group, an amino group or a di(lower alkyl)amino group.

14. A compound of claim 13, having the formula (Ia):

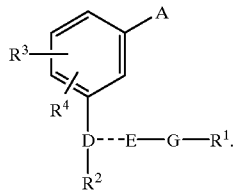

(Ia)

15. A compound of claim 1, wherein Z represents a single bond or a methylene group.

16. A compound of claim 1, wherein $R^5$ represents a hydrogen atom or a methyl group.

17. A compound of claim 1, wherein $R^6$ represents a hydroxy group, an amino group or a hydroxyamino group.

18. A compound of claim 1, wherein D represents a CH group.

19. A compound of claim 1, wherein E represents an —NH— group.

20. A compound of claim 1, wherein G represents an unsubstituted alkylene group having from 1 to 6 carbon atoms or an alkylene group having from 1 to 6 carbon atoms which is substituted with a hydroxy group, an oxo group, an unsubstituted aryl group or an aryl group substituted by from 1 to 3 of said substituents α.

21. A compound of claim 1, wherein $R^1$ represents an unsubstituted aryl group, an unsubstituted 5- or 6-membered aromatic heterocyclic group which is unfused or fused with a benzene ring, an aryl group substituted by from 1 to 3 substituents selected from said substituents α and β, a 5- or 6-membered aromatic heterocyclic group which is substituted by from 1 to 3 substituents selected from said substituents α and β, and which is unfused or fused with a benzene ring.

22. A compound of claim 1, wherein $R^2$ represents an aryl group, an unsubstituted 5- or 6-membered aromatic heterocyclic group which is unfused or fused with a benzene ring, or a 5- or 6-membered aromatic heterocyclic group which is unfused or fused with an aryl group substituted by from 1 to 3 substituents or a benzene ring, said substituent being a halogen atom, a hydroxy group, a lower alkyl group, a lower haloalkyl group or a lower alkoxy group.

23. A compound of claim 1, wherein $R^3$ and $R^4$ are the same as or different from each other and each represents a hydrogen atom, a hydroxy group or a lower alkoxy group.

24. A compound of claim 1, wherein:

Z represents a single bond or a methylene group;

$R^5$ represents a hydrogen atom or a methyl group;

$R^6$ represents a hydroxy group, an amino group or a hydroxyamino group;

X and Y each represents an oxygen atom;

D represents a CH group;

E represents an —NH— group;

G represents an unsubstituted alkylene group having from 1 to 6 carbon atoms, or an alkylene group having from 1 to 6 carbon atoms which is substituted with a hydroxy group, an oxy group, an unsubstituted aryl group or an aryl group substituted by from 1 to 3 substituents selected from said substituents α;

$R^1$ represents an unsubstituted aryl group, an unsubstituted 5- or 6-membered aromatic heterocyclic group which is unfused or fused with a benzene ring, an aryl group substituted by from 1 to 3 substituents selected from said substituents α and β, or a 5- or 6-membered aromatic heterocyclic group which is substituted by from 1 to 3 substituents selected from said substituents α and β, and which is unfused or fused with a benzene ring;

$R^2$ represents an aryl group, an unsubstituted 5- or 6-membered aromatic heterocyclic group which is unfused or fused with a benzene ring, or a 5- or 6-membered aromatic heterocyclic group which is unfused or fused with an aryl group substituted by from 1 to 3 substituents or a benzene ring, said substituent being a halogen atom, a hydroxy group, a lower alkyl group, a lower haloalkyl group or a lower alkoxy group; and $R^3$ and $R^4$ are the same as or different from each other and each represents a hydrogen atom, a hydroxy group or a lower alkoxy group.

25. A compound of claim 24, having the formula (Ia):

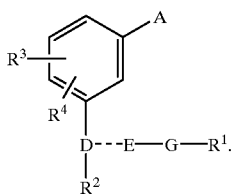

(Ia)

26. A compound of claim 1, wherein Z represents a single bond.

27. A compound of claim 1, wherein $R^5$ represents a hydrogen atom.

28. A compound of claim 1, wherein $R^1$ represents a hydroxy group.

29. A compound of claim 1, wherein G represents an alkylene group having from 1 to 6 carbon atoms.

30. A compound of claim 1, wherein $R^1$ represents an aryl group, an unsubstituted 5- or 6-membered aromatic heterocyclic group which is unfused or fused with a benzene ring, or a 5- or 6-membered aromatic heterocyclic group which is substituted by an aryl group substituted by from 1 to 3 substituents and which is unfused or fused with a benzene ring, the substituent being selected from said substituents α, nitro groups, unsubstituted cycloalkyl groups, unsubstituted aryl groups, unsubstituted aryloxy groups, unsubstituted aralkyloxy groups or unsubstituted arylthio groups, or cycloalkyl, aryl, aryloxy, aralkyloxy and arylthio groups each substituted by from 1 to 3 substituents selected from said substituents α.

31. A compound of claim 1, wherein $R^2$ represents an aryl group, a thienyl group, a furyl group, a pyrrolyl group, a thiazolyl group, an oxazolyl group, an imidazolyl group or a pyridyl group, or a thienyl, furyl, pyrrolyl, thiazolyl, oxazolyl, imidazolyl or pyridyl group fused with a benzene ring or an aryl group substituted by a substituent selected from the group consisting of a halogen atom, a hydroxy group, a lower alkyl group, a lower haloalkyl group and a lower alkoxy group.

32. A compound of claim 1, wherein $R^3$ and $R^4$ each represents a hydrogen atom.

33. A compound of claim 1, wherein:

Z represents a single bond;

$R^5$ represents a hydrogen atom;

$R^6$ represents a hydroxy group;

X and Y each represents an oxygen atom;

D represents a CH group;

E represents an —NH— group;

G represents an alkylene group having from 1 to 6 carbon atoms;

$R^1$ represents an aryl group, an unsubstituted 5- or 6-membered aromatic heterocyclic group which is unfused or fused with a benzene ring, or a 5- or 6-membered aromatic heterocyclic group which is substituted by an aryl group substituted by from 1 to 3 substituents and which is unfused or fused with a benzene ring, the substituent being selected from said substituents α, nitro groups, unsubstituted cycloalkyl groups, unsubstituted aryl groups, unsubstituted aryloxy groups, unsubstituted aralkyloxy groups or unsubstituted arylthio groups, or cycloalkyl, aryl, aryloxy, aralkyloxy and arylthio groups each substituted by from 1 to 3 substituents selected from said substituents α;

$R^2$ represents an aryl group, a thienyl group, a furyl group, a pyrrolyl group, a thiazolyl group, an oxazolyl group, an imidazolyl group or a pyridyl group, or a thienyl, furyl, pyrrolyl, thiazolyl, oxazolyl, imidazolyl or pyridyl group fused with a benzene ring or an aryl group substituted by a substituent selected from the group consisting of a halogen atom, a hydroxy group, a lower alkyl group, a lower haloalkyl group and a lower alkoxy group; and $R^3$ and $R^4$ each represents a hydrogen atom.

34. A compound of claim 33, having the formula (Ia):

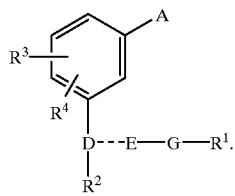

(Ia)

35. A compound of claim 1, wherein $R^1$ represents a hydroxy group.

36. A compound of claim 1, wherein G represents an alkylene group having from 1 to 4 carbon atoms.

37. A compound of claim 1, wherein $R^1$ represents an aryl group, an unsubstituted 5- or 6-membered aromatic heterocyclic group which is unfused or fused with a benzene ring, or a 5- or 6-membered aromatic heterocyclic group which is substituted by an aryl group substituted from 1 to 3 substituents and which is unfused or fused with a benzene ring, the substituent being selected from the group consisting of halogen atoms, hydroxy groups, lower alkyl groups, lower haloalkyl groups, lower alkoxy groups, nitro groups, cycloalkyl groups, aryl groups, aryloxy groups and arylthio groups.

38. A compound of claim 1, wherein $R^2$ represents an unsubstituted aryl group having from 6 to 10 carbon atoms, a 2-thienyl group, a 4-pyridyl group or an aryl group having from 6 to 10 carbon atoms substituted by a substituent selected from the group consisting of a halogen atom, a hydroxy group, a lower alkyl group, a lower haloalkyl group or a lower alkoxy group.

39. A compound of claim 1, wherein:

Z represents a single bond;

$R^5$ represents a hydrogen atom;

$R^6$ represents a hydroxy group;

X and Y each represents an oxygen atom;

D represents a CH group;

E represents an —NH— group;

G represents an alkylene group having from 1 to 4 carbon atoms;

$R^1$ represents an aryl group, an unsubstituted 5- or 6-membered aromatic heterocyclic group which is unfused or fused with a benzene ring, or a 5- or 6-membered aromatic heterocyclic group which is substituted by an aryl group substituted by from 1 to 3 substituents and which is unfused or fused with a benzene ring, the substituent being selected from the group consisting of halogen atoms, hydroxy groups, lower alkyl groups, lower haloalkyl groups, lower alkoxy groups, nitro groups, cycloalkyl groups, aryl groups, aryloxy groups and arylthio groups;

$R^2$ represents an aryl group having from 6 to 10 carbon atoms, a 2-thienyl group, a 4-pyridyl group or an aryl group having from 6 to 10 carbon atoms substituted by a substituent selected from the group consisting of a halogen atom, a hydroxy group, a lower alkyl group, a lower haloalkyl group and a lower alkoxy group; and $R^3$ and $R^4$ each represents a hydrogen atom.

40. A compound of claim 39, having the formula (Ia):

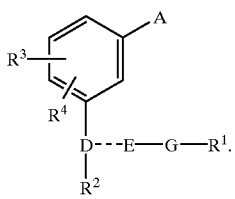

(Ia)

41. A compound of claim 1, wherein G represents a methylene, methylmethylene or ethylmethylene group.

42. A compound of claim 1, wherein $R^1$ represents an aryl group having from 6 to 10 carbon atoms, a thienyl group, a furyl group, a pyrrolyl group, a thiazolyl group, an oxazolyl group, an imidazolyl group or a pyridyl group, or a thienyl, furyl, pyrrolyl, thiazolyl, oxazolyl, imidazolyl or a pyridyl group fused with a benzene ring, or an aryl group having from 6 to 10 carbon atoms and substituted by from 1 to 3 substituents selected from the group consisting of halogen atoms, hydroxy groups, lower alkyl groups, lower haloalkyl groups, lower alkoxy groups and nitro groups.

43. A compound of claim 1, wherein $R^2$ represents an unsubstituted phenyl group or a phenyl group substituted by a substituent selected from the group consisting of a halogen atom, a hydroxy group, a lower alkyl group, a lower haloalkyl group and a lower alkoxy group.

44. A compound of claim 1, wherein:

Z represents a single bond;

$R^5$ represents a hydrogen atom;

$R^6$ represents a hydroxy group;

X and Y each represents an oxygen atom;

D represents a CH group;

E represents an —NH— group;

G represents a methylene, methylmethylene or ethylmethylene group;

$R^1$ represents an aryl group having from 6 to 10 carbon atoms, a thienyl group, a furyl group, a pyrrolyl group, a thiazolyl group, an oxazolyl group, an imidazolyl group or a pyridyl group, or a thienyl, furyl, pyrrolyl, thiazolyl, oxazolyl, imidazolyl or a pyridyl group fused with a benzene ring, or an aryl group having from 6 to 10 carbon atoms and substituted by from 1 to 3 substituents selected from the group consisting of halogen atoms, hydroxy groups, lower alkyl groups, lower haloalkyl groups, lower alkoxy groups and nitro groups;

$R^2$ represents an unsubstituted phenyl group or a phenyl group substituted by a substituent selected from the group consisting of a halogen atom, a hydroxy group, a lower alkyl group, a lower haloalkyl group and a lower alkoxy group; and $R^3$ and $R^4$ each represents a hydrogen atom.

45. A compound of claim 44, having the formula (Ia):

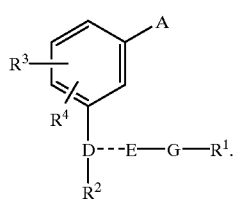

(Ia)

46. A compound of claim 1, wherein G represents a methylmethylene group.

47. A compound of claim 1, wherein $R^1$ represents a phenyl, 1-naphthyl, 2-naphthyl, 3-fluorophenyl, 4-fluorophenyl, 3-chlorophenyl, 4-chlorophenyl, 3,4-difluorophenyl, 3,5-difluorophenyl, 3,4-dichlorophenyl, 3,5-dichlorophenyl, 3-hydroxyphenyl, 4-hydroxyphenyl, 3-methylphenyl, 4-methylphenyl, 3,4-dimethylphenyl, 3-methoxyphenyl, 4-methoxyphenyl, 3,4-dimethoxyphenyl, 3,4,5-trimethoxyphenyl, 3,4,5-trifluorophenyl, thienyl or pyridyl group.

48. A compound of claim 1, wherein $R^1$ represents a phenyl, 4-fluorophenyl, 4-chlorophenyl, 4-methylphenyl or 4-methoxyphenyl group.

49. A compound of claim 1, wherein:

Z represents a single bond;

$R^5$ represents a hydrogen atom;

$R^6$ represents a hydroxy group;

X and Y each represents an oxygen atom;

D represents a CH group;

E represents an —NH— group;

G represents a methylmethylene group;

$R^1$ represents a phenyl, 1-naphthyl, 2-naphthyl, 3-fluorophenyl, 4-fluorophenyl, 3-chlorophenyl, 4-chlorophenyl, 3,4-difluorophenyl, 3,5-difluorophenyl, 3,4-dichlorophenyl, 3,5-dichlorophenyl, 3-hydroxyphenyl, 4-hydroxyphenyl, 3-methylphenyl, 4-methylphenyl, 3,4-dimethylphenyl, 3-methoxyphenyl, 4-methoxyphenyl, 3,4-dimethoxyphenyl, 3,4,5-trimethoxyphenyl, 3,4,5-trifluorophenyl, thienyl or pyridyl group;

$R^2$ represents a phenyl, 4-fluorophenyl, 4-chlorophenyl, 4-methylphenyl or 4-methoxyphenyl group; and $R^3$ and $R^4$ each represents a hydrogen atom.

50. A compound of claim 49, having the formula (Ia):

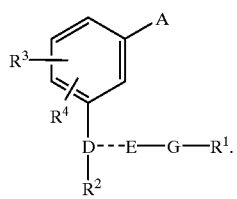

(Ia)

51. A compound of claim 1, wherein $R^1$ represents a phenyl, 3-fluorophenyl, 3-chlorophenyl, 3,4-difluorophenyl, 3,5-difluorophenyl, 3,4-dichlorophenyl, 3,5-dichlorophenyl, 1-naphthyl, 2-thienyl or 4-pyridyl group.

52. A compound of claim 1, wherein:

Z represents a single bond;

$R^5$ represents a hydrogen atom;

R⁶ represents a hydroxy group;

X and Y each represents an oxygen atom;

D represents a CH group;

E represents an —NH— group;

G represents a methylmethylene group;

R¹ represents a phenyl, 3-fluorophenyl, 3-chlorophenyl, 3,4-difluorophenyl, 3,5-difluorophenyl, 3,4-dichlorophenyl, 3,5-dichlorophenyl, 1-naphthyl, 2-thienyl or 4-pyridyl group;

R² represents a phenyl, 4-fluorophenyl, 4-chlorophenyl, 4-methylphenyl or 4-methoxyphenyl group; and R³ and R⁴ each represents a hydrogen atom.

53. A compound of claim 52, having the formula (Ia):

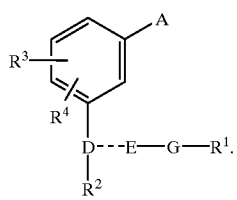

(Ia)

54. A compound of claim 1, wherein the compound is selected from the group consisting of:

3-amino-4-(3-{(4-methoxyphenyl)-[1-(3,4-difluorophenyl)ethyl-amino]methyl} phenyl-amino)-3-cyclobutene-1,2-dione, 3-amino-4-{3-[(4-fluorophenyl)-(1-phenylethylamino)methyl]phenylamino}-3-cyclobutene-1,2-dione, 3-amino-4-{3-[(4-methoxyphenyl)-(1-phenylethylamino)methyl]phenylamino}-3-cyclobutene-1,2-dione, 3-amino-4-{3-[4-pyridyl-(1-phenylethylamino)methyl]phenylamino}-3-cyclobutene-1,2-dione, 3-amino-4-(3-{(4-methoxyphenyl)-[1-(3-fluorophenyl)ethylamino]methyl}phenylamino)-3-cyclobutene-1,2-dione, 3-amino-4-(3-{(4-fluorophenyl)-[1-(3,4-difluorophenyl)ethylamino]methyl}phenylamino)-3-cyclobutene-1,2-dione, 3-amino-4-(3-{(4-methoxyphenyl)-[1-(3,4-difluorophenyl)ethylamino]methyl}phenylamino)-3-cyclobutene-1,2-dione, 3-amino-4-(3-{4-pyridyl-[1-(3,4-difluorophenyl)ethylamino]methyl}phenylamino)-3-cyclobutene-1,2-dione, 3-amino-4-(3-{phenyl-[1-(3,5-difluorophenyl)ethylamino]methyl}phenylamino)-3-cyclobutene-1,2-dione, 3-amino-4-(3-{(4-fluorophenyl)-[1-(3,5-difluorophenyl)ethylamino]methyl}phenylamino)-3-cyclobutene-1,2-dione, 3-amino-4-(3-{(4-methoxyphenyl)-[1-(3,5-difluorophenyl)ethylamino]methyl}phenylamino)-3-cyclobutene-1,2-dione, 3-amino-4-(3-{(4-methoxyphenyl)-[1-(4-pyridyl)ethylamino]methyl}phenylamino)-3-cyclobutene-1,2-dione, and 3-amino-4-(3-{(4-methoxyphenyl)-[1-(3,4-difluorophenyl)ethylamino]methyl}phenylamino)-3-cyclobutene-1,2-dione, or a pharmaceutically acceptable salt, ester or other derivative thereof.

55. A compound of claim 1, wherein the compound is selected from the group consisting of:

4-(3-{[1-(3,4-difluorophenyl)ethylamino]-(4-methoxyphenyl)methyl}phenylamino)-3-hydroxy-3-cyclobutene-1,2-dione, 4-(3-{[1-(3,5-difluorophenyl)ethylamino]-(4-methoxyphenyl)methyl}phenylamino)-3-hydroxy-3-cyclobutene-1,2-dione, 4-(3-{[1-(3,5-difluorophenyl)ethylamino]-(4-fluorophenyl)methyl}phenylamino)-3-hydroxy-3-cyclobutene-1,2-dione, 3-(3-{[1-(3,4-difluorophenyl)ethylamino]-(4-fluorophenyl)methyl}phenylamino)-4-hydroxy-3-cyclobutene-1,2-dione, 3-(3-{[1-(3-fluorophenyl)ethylamino]-(4-methoxyphenyl)methyl}phenylamino)-4-hydroxy-3-cyclobutene-1,2-dione, 3-(3-{(4-fluorophenyl)-[1-(3-fluorophenyl)ethylamino]methyl}phenylamino)-4-hydroxy-3-cyclobutene-1,2-dione, 4-(3-{(4-chlorophenyl)-[1-(3-fluorophenyl)ethylamino]methyl}phenylamino)-3-hydroxy-3-cyclobutene-1,2-dione, 4-(3-{(4-chlorophenyl)-[1-(3,5-difluorophenyl)ethylamino]methyl}phenylamino)-3-hydroxy-3-cyclobutene-1,2-dione, 4-(3-{(4-chlorophenyl)-[1-(3,4-difluorophenyl)ethylamino]methyl}phenylamino)-3-hydroxy-3-cyclobutene-1,2-dione, 3-(3-{[1-(3,4-difluorophenylamino)ethylamino]-(p-tolyl)methyl}phenylamino)-4-hydroxy-3-cyclobutene-1,2-dione, 4-(3-{[1-(3,5-difluorophenyl)ethylamino]-(4-methylphenyl)methyl}phenylamino)-3-hydroxy-3-cyclobutene-1,2-dione, 3-hydroxy-4-(3-{(4-methoxyphenyl)-[1-(naphthalen-1-yl)ethylamino]methyl}phenylamino)-cycylobut-3-ene-1,2-dione, 3-(3-{(4-chlorophenyl)-[1-phenylethylamino]methyl)phenylamino)-4-hydroxy-3-cyclobutene-1,2-dione, 3-(3-{[4-(p-tolyl)-[1-(3-fluorophenyl)ethylamino]methyl)phenylamino)-4-hydroxy-3-cyclobutene-1,2-dione hydrochloride, 3-hydroxy-4-(3-{[1-(3-fluorophenyl)ethylamino]phenylmethyl}phenylamino)-3-cyclobutene-1,2-dione, 3-hydroxy-4-(3-{[1-(3,4-difluorophenyl)ethylamino]phenylmethyl]phenylamino)-3-cyclobutene-1,2-dione, 3-hydroxy-4-(3-{[1-(3,5-difluorophenyl)ethylamino]phenylmethyl}phenylamino)-3-cyclobutene-1,2-dione, 3-(3-{(4-fluorophenyl)-[1-(naphthalen-1-yl)ethylamino]methyl)phenylamino)-4-hydroxy-3-cyclobutene-1,2-dione, 3-(3-{(4-chlorophenyl)-[1-(naphthalen-1-yl)ethylamino]methyl]phenylamino)-4-hydroxy-3-cyclobutene-1,2-dione, 3-(3-{(4-fluorophenyl)-[1-phenylethylamino]methyl}phenylamino)-4-hydroxy-3-cyclobutene-1,2dione, 3-hydroxy-4-(3-{[1-(1-naphthyl)ethylamino]phenylmethyl}phenylamino)-3-cyclobutene-1,2-dione, 3-hydroxy-4-(3-{[1-(1-naphthyl)ethylamino]-p-tolymethyl}phenylamino)-3-cyclobutene-1,2-dione, and 3-hydroxy-4-(3-{[1-phenylethylamino]-(4-methoxyphenyl)methyl}phenylamino)-3-cyclobutene-1,2-dione, or a pharmaceutically acceptable salt thereof.

56. A method of reducing the cholesterol level in a human having or susceptible to a high blood cholesterol level, which comprises administering to said human an effective dose of an inhibitor or an ileal bile acid transporter selected from the group consisting of compounds of formula (I):

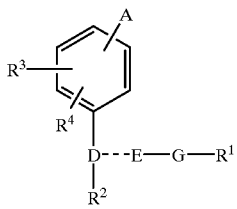

(I)

wherein:
- $R^1$ represents an unsubstituted cycloalkyl group, an unsubstituted aryl group, an unsubstituted heterocyclic group, a cycloalkyl group substituted by at least one of substituents α and β defined below, an aryl group substituted by at least one of substituents α and β defined below, or a heterocyclic group substituted by at least one of substituents α and β defined below;
- $R^2$ represents an unsubstituted cycloalkyl group, an unsubstituted aryl group, an unsubstituted heterocyclic group, a cycloalkyl group substituted by at least one of substituents α defined below, an aryl group substituted by at least one of substituents α defined below, or a heterocyclic group substituted by at least one of substituents α defined below;
- $R^3$ and $R^4$ are the same as or different from each other and each represents a hydrogen atom or one of substituents α defined below;
- A represents a group of formula (A-1):

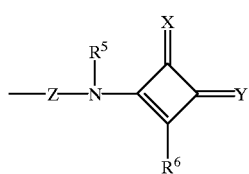

(A-1)

wherein:
- $R^5$ represents a hydrogen atom, a hydroxy group or a lower alkyl group,
- $R^6$ represents a hydroxy group, a lower alkoxy group, a lower alkylthio group or an amine residue,
- X and Y are the same as or different from each other and each represents an oxygen atom or a sulfur atom, and
- Z represents a direct single bond between the nitrogen atom and the benzene ring in formula (I), or an alkylene group having from 1 to 6 carbon atoms,
- G represents a single bond, an unsubstituted alkylene group having from 1 to 6 carbon atoms or an alkylene group having from 1 to 6 carbon atoms and substituted by at least one of substituents γ, defined below;
- the broken line represents a single or double bond;
- when the broken line represents a double bond, D represents a carbon atom; and
E represents an =N—O— group;

when the broken line represents a single bond,
D represents a CH group or a nitrogen atom, and
E represents an oxygen atom, a sulfur atom, an —NH— group or a —CO— group;

said substituents α are selected from the groups consisting of halogen atoms, hydroxy groups, cyano groups, nitro groups, lower alkyl groups, lower haloalkyl groups, lower alkoxy groups, lower alkylthio groups, amino groups, lower monoalkylamino groups and di(lower alkyl)amino groups;

said substituents β are selected from the group consisting of carboxy groups, lower alkoxycarbonyl groups, carbamoyl groups, lower monoalkylcarbamoyl groups, di(lower alkyl)carbamoyl groups, nitro groups, unsubstituted cycloalkyl groups, unsubstituted aryl groups, unsubstituted aryloxy groups, unsubstituted aralkyloxy groups, unsubstituted arylthio groups and cycloalkyl, aryl, aryloxy, aralkyloxy and arylthio groups each substituted by at least one of said substituents α;

said substituents γ are selected from the group consisting of hydroxy groups, oxo groups, unsubstituted cycloalkyl groups, unsubstituted aryl groups, unsubstituted heterocyclic groups, cycloalkyl groups substituted by at least one of said substituents α and β, aryl groups substituted by at least one of said substituents α and β, and heterocyclic groups substituted by at least one of said substituents α and β;

said cycloalkyl groups are optionally fused to an aryl group;

said heterocyclic groups and are optionally fused to an aryl group;

or a pharmaceutically acceptable salt, ester or other derivative thereof.

57. A method of claim 56, wherein said inhibitor is selected from the group consisting of:

3-amino-4-(3-{(4-methoxyphenyl)-[1-(3,4-difluorophenyl)ethylamino]methyl}phenylamino)-3-cyclobutene-1,2-dione, 3-amino-4-{3-[(4-fluorophenyl)-(1-phenylethylamino)methyl]phenylamino}-3-cyclobutene-1,2-dione, 3-amino-4-{3-[(4-methoxyphenyl)-(1-phenylethylamino)methyl]phenylamino}-3-cyclobutene-1,2-dione, 3-amino-4-{3-[4-pyridyl-(1-phenylethylamino)methyl]phenylamino}-3-cyclobutene-1,2-dione, 3-amino-4-(3-{(4-methoxyphenyl)-[1-(3-fluorophenyl)ethylamino]methyl}phenylamino)-3-cyclobutene-1,2-dione, 3-amino-4-(3-{(4-fluorophenyl)-[1-(3,4-difluorophenyl)ethylamino]methyl}phenylamino)-3-cyclobutene-1,2-dione, 3-amino-4-(3-{(4-methoxyphenyl)-[1-(3,4-difluorophenyl)ethylamino]methyl}phenylamino)-3-cyclobutene-1,2-dione, 3-amino-4-(3-{4-pyridyl-[1-(3,4-difluorophenyl)ethylamino]methyl}phenylamino)-3-cyclobutene-1,2-dione, 3-amino-4-(3-{phenyl-[1-(3,5-difluorophenyl)ethylamino]methyl}phenylamino)-3-cyclobutene-1,2-dione, 3-amino-4-(3-{(4-fluorophenyl)-[1-(3,5-difluorophenyl)ethylamino]methyl}phenylamino)-3-cyclobutene-1,2-dione, 3-amino-4-(3-{(4-methoxyphenyl)-[1-(3,5-difluorophenyl)ethylamino]methyl}phenylamino)-3-cyclobutene-1,2-dione, 3-amino-4-(3-{(4-methoxyphenyl)-[1-(4-pyridyl)ethylamino]methyl}phenylamino)-3-cyclobutene-1,2-dione, and 3-amino-4-(3-{(4-methoxyphenyl)-[1-(3,4-difluorophenyl)ethylamino]methyl}phenylamino)-3-cyclobutene-1,2-dione, or a pharmaceutically acceptable salt or ester thereof.

58. A method of claim 56, wherein said inhibitor is selected from the group consisting of:

4-(3-{[1-(3,4-difluorophenyl)ethylamino]-(4-methoxyphenyl)methyl}phenylamino)-3-hydroxy-3-cyclobutene-1,2-dione, 4-(3-{[1-(3,5-difluorophenyl)ethylamino]-(4-methoxyphenyl)methyl}phenylamino)-3-hydroxy-3-cyclobutene-1,2-dione, 4-(3-{[1-(3,5-difluorophenyl)ethylamino]-(4-fluorophenyl)methyl}phenylamino)-3-hydroxy-3-cyclobutene-1,2-dione, 3-(3-{[1-(3,4-difluorophenyl)ethylamino]-(4-fluorophenyl)methyl}phenylamino)-4-hydroxy-3-cyclobutene-1,2-dione, 3-(3-{[1-(3-fluorophenyl)ethylamino]-(4-methoxyphenyl)methyl}phenylamino)-4-hydroxy-3-cyclobutene-1,2-dione, 3-(3-{(4-fluorophenyl)-[1-(3-fluorophenyl)ethylamino]methyl}phenylamino)-4-hydroxy-3-cyclobutene-1,2-dione, 4-(3-{(4-chlorophenyl)-[1-(3-fluorophenyl)ethylamino]methyl}phenylamino)-3-hydroxy-3-cyclobutene-1,2-dione, 4-(3-{(4-chlorophenyl)[1-(3,5-difluorophenyl)ethylamino]methyl}phenylamino)-3-hydroxy-3-cyclobutene-1,2-dione, 4-(3-{(4-chlorophenyl)-[1-(3,4-difluorophenyl)ethylamino]methyl}phenylamino)-3-hydroxy-3-cyclobutene-1,2-dione, 3-(3-{[1-(3,4-difluorophenylamino)ethylamino]-(p-tolyl)methyl)phenylamino)-4-hydroxy-3-cyclobutene-1,2-dione, 4-(3-{[1-(3,5-difluorophenyl)ethylamino]-(4-methylphenyl)methyl}phenylamino)-3-hydroxy-3-cyclobutene-1,2-dione, 3-hydroxy-4-(3-{(4-methoxyphenyl)-[1-(naphthalen-1-yl)ethylamino]methyl}phenylamino)-cycylobut-3-ene-1,2-dione, 3-(3-{(4-chlorophenyl)-[1-phenylethylamino]methyl}phenylamino)-4-hydroxy-3-cyclobutene-1,2-dione, 3-(3-{[4-(p-tolyl)-[1-(3-fluorophenyl)ethylamino]methyl}phenylamino)-4-hydroxy-3-cyclobutene-1,2-dione hydrochloride, 3-hydroxy-4-(3-{[1-(3-fluorophenyl)ethylamino]phenylmethyl}phenylamino)-3-cyclobutene-1,2-dione, 3-hydroxy-4-(3-{[1-(3,4-difluorophenyl)ethylamino]phenylmethyl]phenylamino)-3-cyclobutene-1,2-dione, 3-hydroxy-4-(3-{[1-(3,5-difluorophenyl)ethylamino]phenylmethylphenylamino)-3-cyclobutene-1,2-dione, 3-(3-{(4-fluorophenyl)-[1-(naphthalen-1-yl)ethylamino]methyl}phenylamino)-4-hydroxy-3-cyclobutene-1,2-dione, 3-(3-{(4-chlorophenyl)-[1-(naphthalen-1-yl)ethylamino]methyl}phenylamino)-4-hydroxy-3-cyclobutene-1,2-dione, 3-(3-{(4-fluorophenyl)-[1-phenylethylamino]methyl}phenylamino)-4-hydroxy-3-cyclobutene-1,2-dione, 3-hydroxy-4-(3-{[1-(1-naphthyl)ethylamino]phenylmethyl}phenylamino)-3-cyclobutene-1,2-dione, 3-hydroxy-4-(3-{[1-(1-naphthyl)ethylamino]-p-tolymethyl}phenylamino)-3-cyclobutene-1,2-dione, and 3-hydroxy-4-(3-{[1-phenylethylamino]-(4-methoxyphenyl)methyl}phenylamino)-3-cyclobutene-1,2-dione, or a pharmaceutically acceptable salt or ester thereof.

59. A pharmaceutical composition comprising an active ingredient together with a carrier, said active ingredient being a compound according to claim 1 or a pharmaceutically acceptable salt or ester thereof.

60. A compound of claim 1, wherein Z represents a single bond or an alkylene group having 1 or 2 carbon atoms.

61. A compound of claim 1, wherein the compound is 4-(3{[(R)-1-(3,5-difluorophenyl)ethylamino]-(4-methoxyphenyl)-methyl}phenylamino)-3-hydroxy-3-cyclobutene-1,2-dione or a pharmaceutically acceptable salt thereof.

62. A compound of claim 1, wherein said cycloalkyl groups have 3 to 10 ring carbon atoms; said aryl groups are aromatic carbocyclic groups having 6 to 10 ring carbon atoms; and said heterocyclic groups have 5 to 7 ring atoms, wherein 1 to 3 of said ring atoms are selected from the group consisting of a sulfur atom, an oxygen atom and a nitrogen atom.

63. A method of claim 56, wherein said cycloalkyl groups have 3 to 10 ring carbon atoms; said aryl groups are aromatic carbocyclic groups having 6 to 10 ring carbon atoms; and said heterocyclic groups have 5 to 7 ring atoms, wherein 1 to 3 of said ring atoms are selected from the group consisting of a sulfur atom, an oxygen atom and a nitrogen atom.

* * * * *

SEQUENCE LISTING

<160> NUMBER OF SEQ ID NOS: 2

<210> SEQ ID NO 1
<211> LENGTH: 22
<212> TYPE: DNA
<213> ORGANISM: Homo Sapiens

<400> SEQUENCE: 1
aacgttgctt aactcaacca gc                    22

<210> SEQ ID NO 2
<211> LENGTH: 22
<212> TYPE: DNA
<213> ORGANISM: Homo Sapiens

<400> SEQUENCE: 2
ctcgtctgtt ttgtccactt ga                    22